(12) United States Patent
Ju et al.

(10) Patent No.: US 12,337,009 B2
(45) Date of Patent: Jun. 24, 2025

(54) NUCLEOTIDE DERIVATIVES AND METHODS OF USE THEREOF

(71) Applicant: The Trustees of Columbia University in the City of New York, New York, NY (US)

(72) Inventors: Jingyue Ju, Englewwod Cliffs, NJ (US); Xin Chen, Changsha (CN); Xiaoxu Li, New York, NY (US); Zengmin Li, Flushing, NY (US); Min-Kang Hsieh, Radford, VA (US); Minchen Chien, Tenafly, NJ (US); Shundi Shi, Ozone Park, NY (US); Jianyi Ren, Rosemead, CA (US); Cheng Guo, Brooklyn, NY (US); Shiv Kumar, Belle Mead, NJ (US); James Russo, New York, NY (US); Chuanjuan Tao, Fort Lee, NJ (US); Steffen Jockusch, New York, NY (US); Sergey Kalachikov, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 133 days.

(21) Appl. No.: 17/688,752

(22) Filed: Mar. 7, 2022

(65) Prior Publication Data
US 2023/0028321 A1 Jan. 26, 2023

Related U.S. Application Data

(62) Division of application No. 16/303,715, filed as application No. PCT/US2017/033939 on May 23, 2017, now Pat. No. 11,266,673.

(Continued)

(51) Int. Cl.
C07H 19/20 (2006.01)
A61K 31/7052 (2006.01)
(Continued)

(52) U.S. Cl.
CPC ......... A61K 31/7052 (2013.01); C07H 21/04 (2013.01); C07H 19/20 (2013.01); C12Q 1/6869 (2013.01)

(58) Field of Classification Search
CPC ....... C12Q 1/6869; C07H 19/20; C07H 21/04
See application file for complete search history.

(56) References Cited

U.S. PATENT DOCUMENTS 5,034,036 A 7/1991 Summerton
5,235,033 A 8/1993 Summerton
(Continued)

FOREIGN PATENT DOCUMENTS

CN 109476694 A 3/2019
EP 2876166 5/2015
(Continued)

OTHER PUBLICATIONS

Cherkasov et al. Abstract US9035035 (Year: 2015).*
(Continued)

Primary Examiner — Jezia Riley
(74) Attorney, Agent, or Firm — Gary J. Gershik

(57) ABSTRACT

Disclosed herein, inter alia, are compounds, compositions, and methods of use thereof in the sequencing a nucleic acid.

20 Claims, 133 Drawing Sheets
Specification includes a Sequence Listing.

Related U.S. Application Data

(60) Provisional application No. 62/477,945, filed on Mar. 28, 2017, provisional application No. 62/365,321, filed on Jul. 21, 2016, provisional application No. 62/340,419, filed on May 23, 2016.

(51) Int. Cl.
  *C07H 21/04* (2006.01)
  *C12Q 1/6869* (2018.01)

(56) References Cited

U.S. PATENT DOCUMENTS

| | | | |
|---|---|---|---|
| 5,804,386 A | 9/1998 | Ju | |
| 5,814,454 A | 9/1998 | Ju | |
| 5,876,936 A | 3/1999 | Ju | |
| 5,952,180 A | 9/1999 | Ju | |
| 6,046,005 A | 4/2000 | Ju et al. | |
| 6,485,944 B1 | 11/2002 | Church | |
| 6,627,748 B1 | 9/2003 | Ju et al. | |
| 6,664,079 B2 | 12/2003 | Ju et al. | |
| 7,074,597 B2 | 7/2006 | Ju | |
| 7,279,563 B2 | 10/2007 | Kwiatkowski | |
| 7,345,159 B2 | 3/2008 | Ju et al. | |
| 7,414,116 B2 | 8/2008 | Milton | |
| 7,541,444 B2 | 6/2009 | Milton | |
| 7,566,537 B2 | 7/2009 | Barnes | |
| 7,622,279 B2 | 11/2009 | Ju | |
| 7,635,578 B2 | 12/2009 | Ju et al. | |
| 7,713,698 B2 | 5/2010 | Ju et al. | |
| 7,771,973 B2 | 8/2010 | Milton | |
| 7,790,869 B2 | 9/2010 | Ju et al. | |
| 7,883,869 B2 | 2/2011 | Ju et al. | |
| 7,982,029 B2 | 7/2011 | Ju et al. | |
| 8,071,739 B2 | 12/2011 | Milton | |
| 8,088,575 B2 | 1/2012 | Ju et al. | |
| 8,114,973 B2 | 2/2012 | Siddiqi | |
| 8,298,792 B2 | 10/2012 | Ju et al. | |
| 8,399,188 B2 | 3/2013 | Zhao | |
| 8,597,881 B2 | 12/2013 | Milton | |
| 8,796,432 B2 | 8/2014 | Ju et al. | |
| 8,889,348 B2 | 11/2014 | Ju | |
| 8,900,810 B2 | 12/2014 | Gordon et al. | |
| 9,035,035 B2 * | 5/2015 | Cherkasov | C07H 19/06 536/25.5 |
| 9,115,163 B2 | 8/2015 | Ju et al. | |
| 9,121,060 B2 | 9/2015 | Milton | |
| 9,121,062 B2 | 9/2015 | Balasubramanian | |
| 9,133,511 B2 | 9/2015 | Ju et al. | |
| 9,169,510 B2 | 10/2015 | Ju et al. | |
| 9,175,342 B2 | 11/2015 | Ju et al. | |
| 9,255,292 B2 | 2/2016 | Ju et al. | |
| 9,297,042 B2 | 3/2016 | Ju et al. | |
| 9,388,464 B2 | 7/2016 | Milton | |
| 9,410,200 B2 | 8/2016 | Balasubramanian | |
| 9,453,258 B2 | 9/2016 | Kain et al. | |
| 9,528,151 B2 | 12/2016 | Ju et al. | |
| 9,593,373 B2 | 3/2017 | Liu | |
| 9,624,539 B2 | 4/2017 | Ju et al. | |
| 9,670,539 B2 | 6/2017 | Ju et al. | |
| 9,708,358 B2 | 7/2017 | Ju et al. | |
| 9,718,852 B2 | 8/2017 | Ju et al. | |
| 9,719,139 B2 | 8/2017 | Ju et al. | |
| 9,725,480 B2 | 8/2017 | Ju et al. | |
| 9,868,985 B2 | 1/2018 | Ju et al. | |
| 9,890,426 B2 | 2/2018 | Ju et al. | |
| 10,000,801 B2 | 6/2018 | Ju et al. | |
| 10,144,961 B2 | 12/2018 | Ju et al. | |
| 10,190,157 B2 | 1/2019 | Wu | |
| 10,240,195 B2 | 3/2019 | Fuller et al. | |
| 10,246,479 B2 | 4/2019 | Ju et al. | |
| 10,260,094 B2 | 4/2019 | Ju et al. | |
| 10,273,539 B2 | 4/2019 | Marma et al. | |
| 10,301,346 B2 | 5/2019 | Marma et al. | |
| 10,336,785 B2 | 7/2019 | Marma et al. | |
| 11,085,076 B2 | 8/2021 | Ju et al. | |
| 11,089,353 B1 | 8/2021 | Ju et al. | |
| 2002/0015961 A1 | 2/2002 | Kwiatkowski et al. | |
| 2003/0027140 A1 | 2/2003 | Ju et al. | |
| 2006/0003383 A1 | 1/2006 | Graham | |
| 2006/0057565 A1 | 3/2006 | Ju et al. | |
| 2006/0188901 A1 | 8/2006 | Barnes et al. | |
| 2006/0252038 A1 | 11/2006 | Ju | |
| 2007/0009980 A1 | 1/2007 | Graham | |
| 2007/0219367 A1 | 9/2007 | Shchepinov | |
| 2008/0103058 A1 | 5/2008 | Sidiqi | |
| 2009/0047699 A1 | 2/2009 | Graham | |
| 2010/0304368 A1 | 12/2010 | Cherkasov et al. | |
| 2011/0014611 A1 | 1/2011 | Ju | |
| 2011/0300534 A1 | 12/2011 | Chiou et al. | |
| 2012/0142006 A1 | 6/2012 | Ju et al. | |
| 2012/0156671 A1 | 6/2012 | Liu | |
| 2012/0156680 A1 | 6/2012 | Ju et al. | |
| 2013/0053252 A1 | 2/2013 | Xie et al. | |
| 2013/0264207 A1 | 10/2013 | Ju et al. | |
| 2013/0280700 A1 | 10/2013 | Ju et al. | |
| 2015/0037788 A1 | 2/2015 | Ju | |
| 2015/0050697 A1 | 2/2015 | Kim | |
| 2015/0080232 A1 | 3/2015 | Ju | |
| 2015/0140561 A1 | 5/2015 | Bergmann et al. | |
| 2015/0197800 A1 | 7/2015 | Ju et al. | |
| 2015/0368710 A1 | 12/2015 | Fuller | |
| 2016/0002721 A1 | 1/2016 | Liu | |
| 2016/0024570 A1 | 1/2016 | Ju et al. | |
| 2016/0041179 A1 | 2/2016 | Ju et al. | |
| 2016/0108382 A1 | 4/2016 | Efcavitch | |
| 2016/0208313 A1 | 7/2016 | Ju et al. | |
| 2016/0264612 A1 | 9/2016 | Ju et al. | |
| 2016/0265048 A1 | 9/2016 | Ju et al. | |
| 2016/0355541 A1 | 12/2016 | Jain et al. | |
| 2016/0369336 A1 | 12/2016 | Stupi et al. | |
| 2017/0002407 A1 | 1/2017 | Balasubramanian et al. | |
| 2017/0058335 A1 | 3/2017 | Tao et al. | |
| 2017/0137869 A1 | 5/2017 | Marma et al. | |
| 2017/0166961 A1 | 6/2017 | Liu et al. | |
| 2017/0211134 A1 | 7/2017 | Marma et al. | |
| 2017/0283451 A1 | 10/2017 | Ju et al. | |
| 2018/0073071 A1 | 4/2018 | Ju et al. | |
| 2018/0112257 A1 | 7/2018 | Ju et al. | |
| 2018/0201642 A1 | 7/2018 | Ju et al. | |
| 2018/0208774 A1 | 9/2018 | Marma et al. | |
| 2018/0274024 A1 | 9/2018 | Ju et al. | |
| 2018/0274025 A1 | 11/2018 | Marma et al. | |
| 2018/0327828 A1 | 11/2018 | Ju et al. | |
| 2019/0031704 A1 | 1/2019 | Ju et al. | |
| 2019/0031705 A1 | 1/2019 | Ju et al. | |
| 2019/0031706 A1 | 1/2019 | Ju et al. | |
| 2019/0085014 A1 | 3/2019 | Ju et al. | |
| 2019/0085015 A1 | 3/2019 | Ju et al. | |
| 2019/0085016 A1 | 3/2019 | Ju et al. | |
| 2019/0085388 A1 | 3/2019 | Ju et al. | |
| 2019/0092805 A1 | 3/2019 | Ju et al. | |
| 2019/0092806 A1 | 3/2019 | Ju et al. | |
| 2019/0112650 A1 | 4/2019 | Ju et al. | |
| 2019/0135850 A1 | 5/2019 | Ju et al. | |
| 2019/0135851 A1 | 5/2019 | Ju et al. | |
| 2019/0136308 A1 | 5/2019 | Ju et al. | |
| 2019/0153527 A1 | 5/2019 | Ju et al. | |
| 2019/0330693 A1 | 10/2019 | Liu et al. | |
| 2020/0069717 A1 | 3/2020 | Ju et al. | |
| 2021/0072234 A1 | 3/2021 | Arslan | |
| 2021/0381043 A1 | 12/2021 | Ju et al. | |

FOREIGN PATENT DOCUMENTS

| | | |
|---|---|---|
| EP | 3356381 | 8/2018 |
| EP | 3356381 A4 | 5/2019 |
| WO | WO 2001/025247 A1 | 4/2001 |
| WO | WO 2002/022883 | 3/2002 |
| WO | WO 2002/029003 | 4/2002 |
| WO | WO 2008/037568 A2 | 3/2008 |
| WO | WO 2008/144315 A1 | 11/2008 |
| WO | WO 2009/054922 | 4/2009 |
| WO | WO 2012/083249 | 6/2012 |

(56) References Cited

FOREIGN PATENT DOCUMENTS

| | | |
|---|---|---|
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2016/063059 A1 | 4/2016 |
| WO | WO 2016/144973 | 9/2016 |
| WO | WO 2016/154215 | 9/2016 |
| WO | WO 2017/058593 | 4/2017 |
| WO | WO 2017/058953 A1 | 4/2017 |
| WO | WO 2017/079498 | 5/2017 |
| WO | WO 2017/079498 A2 | 5/2017 |
| WO | WO 2017/087887 | 5/2017 |
| WO | WO 2017/176677 | 10/2017 |
| WO | WO 2017/176679 | 10/2017 |
| WO | WO 2017/205336 | 11/2017 |
| WO | WO 2018/183538 | 10/2018 |
| WO | WO 2019/105421 A1 | 6/2019 |

OTHER PUBLICATIONS

International Search Report issued in connection with PCT International Application No. PCT/US2017/033939.
Written Opinion of the International Searching Authority issued in connection with the PCT International Application No. PCT/US2017/033939.
Apr. 8, 2021 Non-Final Rejection issued in connection with U.S. Appl. No. 16/303,715.
Dec. 28, 2020 Restriction Requirement issued in connection with U.S. Appl. No. 16/303,715.
Feb. 26, 2021 Response to Dec. 28, 2020 Restriction Requirement issued in connection with U.S. Appl. No. 16/303,715.
Oct. 28, 2021 Notice of Allowance issued in connection with U.S. Appl. No. 16/303,715.
Sep. 8, 2021 Amendment in Response to Apr. 8, 2021 Non-Final Rejection issued in connection with U.S. Appl. No. 16/303,715.
Sep. 20, 2021 Notice of Non-compliant Amendment issued in connection with U.S. Appl. No. 16/303,715.
Sep. 23, 2021 Communication in Response to Sep. 20, 2021 Notice of Non-compliant Amendment issued in connection with U.S. Appl. No. 16/303,715.
Communication forwarding an Extended European Search Report, issued by the European Patent Office on Nov. 28, 2019, concerning counterpart European Patent Application No. 17803398.1.
Svagera, Z., Hanzlikova, D., Simek, P., and Husek, P. (2012) Study of disulfide reduction and alkyl chloroformate derivatization of plasma sulfur amino acids using gas chromatography-mass spectrometry. Anal. Bioanal. Chem. 402: 2953-2963.
Communication pursuant to Article 94(3) EPC issued Feb. 10, 2021 by the European Patent Office in connection with EP 16852516.0.
Dec. 30, 2020 Office Action issued in connection with Chinese Application No. 201680069556.3.
International Search Report issued Dec. 29, 2016 in connection with PCT International Application No. PCT/US2016/054236.
May 10, 2019 Extended European Search Report issued in connection with European Patent Application No. EP16852516.0, which is a foreign counterpart of the subject application.
PubChem Compound Summary for CID 121486816 (Aug. 16, 2016). Located at <https://pubchem.ncbi.nlm.nih.gov/compound/121486816> last visited Apr. 22, 2019, 7 pages.
PubChem Compound Summary for CID 69188114 (Nov. 30, 2012). Located at <https://pubchem.ncbi.nlm.nih.gov/compound/69188114> last visited Apr. 22, 2019, 7 pages.
Written Opinion (form PCT/ISA/237) issued Dec. 29, 2016 in connection with PCT International Application No. PCT/US2016/054236.

Bentley, D.R. et al. (Nov. 6, 2008). "Accurate whole human genome sequencing using reversible terminator chemistry," Nature 456(7218):53-59.
Bergen, K. et al. (Jun. 17, 2013, e-published Jun. 3, 2013). "Structures of KOD and 9° N DNA polymerases complexed with primer template duplex," Chembiochem 14(9):1058-1062.
Bergseid, M. et al. (Nov. 2000). "Small molecule-based chemical affinity system for the purification of proteins," BioTechniques 29(5):1126-1133.
Binauld, S. et al. (Mar. 14, 2013). "Acid-degradable polymers for drug delivery: a decade of innovation," Chem Commun 49(21):2082-2102.
Blackman, M.L. et al. (Oct. 15, 2008, e-published Sep. 18, 2008). "The Tetrazine ligation: fast bioconjugation based on inverse-electron-demand Diels-Alder reactivity," J Am Chem Soc 130(41):13518-13519.
Debets, M.F. et al. (Oct. 14, 2013, e-published Aug. 23, 2013). "Bioorthogonal labelling of biomolecules: new functional handles and ligation methods," Org Biomol Chem 11(38):6439-6455.
Fuller, C.W. et al. (May 10, 2016, e-published Apr. 18, 2016). "Real-time single-molecule electronic DNA sequencing by synthesis using polymer-tagged nucleotides on a nanopore array," PNAS USA 113(19):5233-5238.
Guillier, F. et al. (Jun. 14, 2000). "Linkers and cleavage strategies in solid-phase organic synthesis and combinatorial chemistry," Chem Rev 100(6):2091-2158.
Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," PNAS USA 105(27):9145-9150.
Hutter, D. et al. (Nov. 2010). "Labeled nucleoside triphosphates with reversibly terminating aminoalkoxyl groups," Nucleosides Nucleotides Nucleic Acids 29(11):879-895.
Inoue, T. et al. (Nov. 2015). "Synthesis of trifluoromethyl ethers and difluoro(methylthio)methyl ethers by the reaction of dithiocarbonates with IF5-pyridine-HF," Journal of Fluorine Chemistry 179:48-52.
Jewett, J.C. et al. (Mar. 24, 2010). "Rapid Cu-free click chemistry with readily synthesized biarylazacyclooctynones," J Am Chem Soc 132(11):3688-3690.
Ju, J. et al. (Dec. 26, 2006, e-published Dec. 14, 2006). "Four-color DNA sequencing by synthesis using cleavable fluorescent nucleotide reversible terminators," PNAS USA 103(52):19635-19640.
Kumar, S. et al. (2012, e-published Sep. 21, 2012). "PEG-labeled nucleotides and nanopore detection for single molecule DNA sequencing by synthesis," Sci Rep 2:684.
Leicher, T. et al. (Dec. 25, 1998). "Coexpression of the KCNA3B gene product with Kv1.5 leads to a novel A-type potassium channel," J Biol Chem 273(52):35095-35101.
Leriche, G. et al. (Jul. 2010). "Optimization of the Azobenzene Scaffold for Reductive Cleavage by Dithionite; Development of an Azobenzene Cleavable Linker for Proteomic Applications," Eur J Org Chem 2010(23):4360-4364.
Marcus-Sekura, C.J. et al. (Aug. 1, 1988). "Techniques for using antisense oligodeoxyribonucleotides to study gene expression," Anal Biochem 172(2):289-295.
Needleman, S.B. et al. (Mar. 1970). "A general method applicable to the search for similarities in the amino acid sequence of two proteins," J Mol Biol 48(3):443-453.
Pearson, W.R. et al. (Apr. 1988). "Improved tools for biological sequence comparison," PNAS USA 85(8):2444-2448.
Rathod, K.M. et al. (2013). "Synthesis and Antimicrobial Activity of Azo Compounds Containing m-Cresol Moiety," Chem Sci Trans 2(1):25-28.
Rosenblum, B.B. et al. (Nov. 15, 1997). "New dye-labeled terminators for improved DNA sequencing patterns," Nucleic Acids Res 25(22):4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," PNAS USA 102(17):5932-5937.
Shenoi, R.A. et al. (Sep. 12, 2012, e-published Aug. 30, 2012). "Branched multifunctional polyether polyketals: variation of ketal

(56) References Cited

OTHER PUBLICATIONS group structure enables unprecedented control over polymer degradation in solution and within cells," J Am Chem Soc 134(36):14945-14957.

Smith T.F. et al. (Dec. 1981). "Comparison of biosequences," Adv Appl Math 2(4):482-489.

Southworth, M.W. et al. (May 28, 1996). "Cloning of thermostable DNA polymerases from hyperthermophilic marine Archaea with emphasis on *Thermococcus* sp. 9° N-7 and mutations affecting 3'-5' exonuclease activity," PNAS USA 93(11):5281-5285.

Tang et al. Synthesis and Application of Four Fluorescence Labeled Nucleotides Through Disulfide as Reversible Terminators in DNA Sequencing by Synthesis. Chem. J. Chinese U. Nov. 2014; 35(11):2346-52, including an English language abstract.

Uhlmann, E. (Jun. 1990). "Antisense oligonucleotides: a new therapeutic principle," Chemical Reviews 90(4):543-584.

Weintraub, H.M. (Jan. 1990). "Antisense RNA and DNA," Sci Am 262(1):40-46.

Wolfram Schumacher, Christof Holliger, Alexander J.B Zehnder, Wilfred R Hagen, Redox chemistry of cobalamin and iron-sulfur cofactors in the tetrachloroethene reductase of Dehalobacter restrictus, FEBS Letters, vol. 409, Issue 3, 1997, pp. 421-425, ISSN 0014-5793.

Wu, J. et al. (Oct. 16, 2007, e-published Oct. 8, 2007). "3'-O-modified nucleotides as reversible terminators for pyrosequencing," PNAS USA 104(42):16462-16467.

Zhu, Z. et al. (Aug. 25, 1994). "Directly labeled DNA probes using fluorescent nucleotides with different length linkers," Nucleic Acids Res 22(16):3418-3422.

Response to Dec. 30, 2020 Office Action, filed May 14, 2021 in connection with counterpart Chinese Application No. 201680069556.3, including English language draft thereof.

Sep. 24, 2021 Office Action issued in connection with counterpart Chinese Application No. 201680069556.3, including English Summary thereof.

Response to Sep. 24, 2021 Office Action, filed Dec. 9, 2021 in connection with counterpart Chinese Application No. 201680069556.3, including English language draft thereof.

Response to Feb. 10, 2021 Communication pursuant to Article 94(3) EPC, filed Aug. 20, 2021 in connection with counterpart European Patent Application No. EP 16852516.0.

Qiu C, Kumar S, Guo J, Yu L, Guo W, Shi S, Russo JJ, Ju J. Design and synthesis of cleavable biotinylated dideoxynucleotides for DNA sequencing by matrix-assisted laser desorption/ionization time-of-flight mass spectrometry. Anal Biochem. Aug. 15, 2012;427(2):193-201. doi: 10.1016/j.ab.2012.04.021. Epub Apr. 25, 2012. PMID: 22543091.

Arslan, S., Garcia, F.J., Guo, M. et al. Sequencing by avidity enables high accuracy with low reagent consumption. *Nat Biotechnol* 42, 132-138 (2024).

* cited by examiner

3'-*O*-Biotin-*t*-Butyldithiomethyl-dATP

3'-O-Biotin-*t*-Butyldithiomethyl-dCTP

3'-O-Biotin-*t*-Butyldithiomethyl-dGTP

3'-O-Biotin-t-Butyldithiomethyl-dTTP

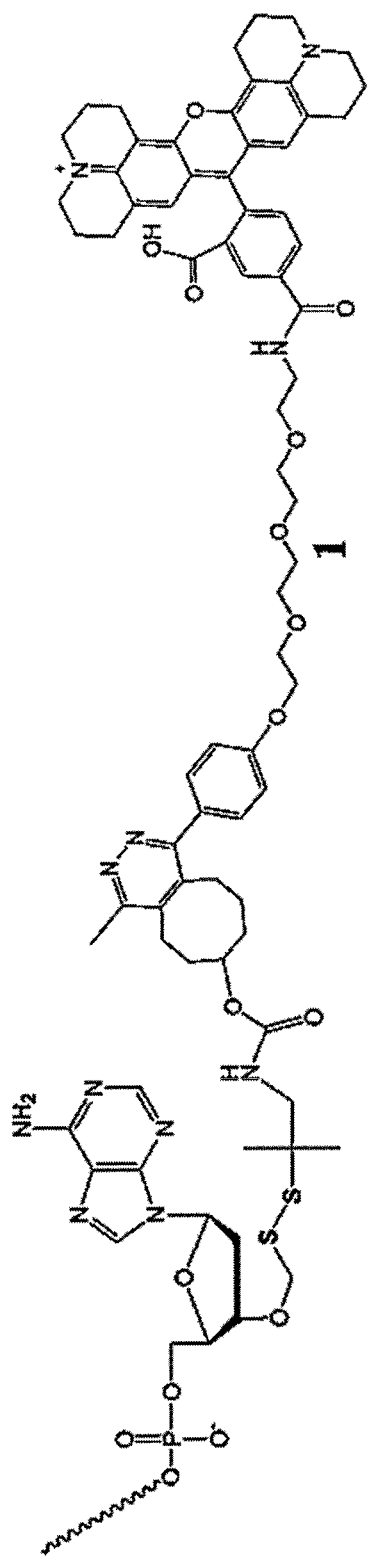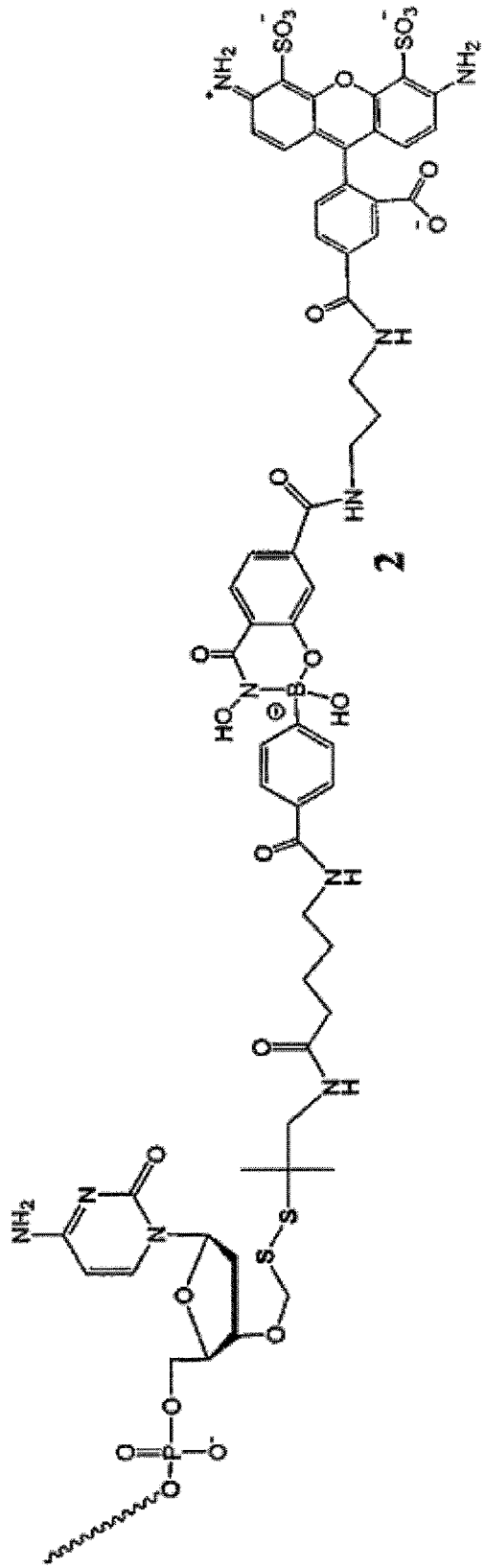
FIG. 6A
FIG. 6B

3'-O-TCO-t-Butyldithiomethyl-dNTP

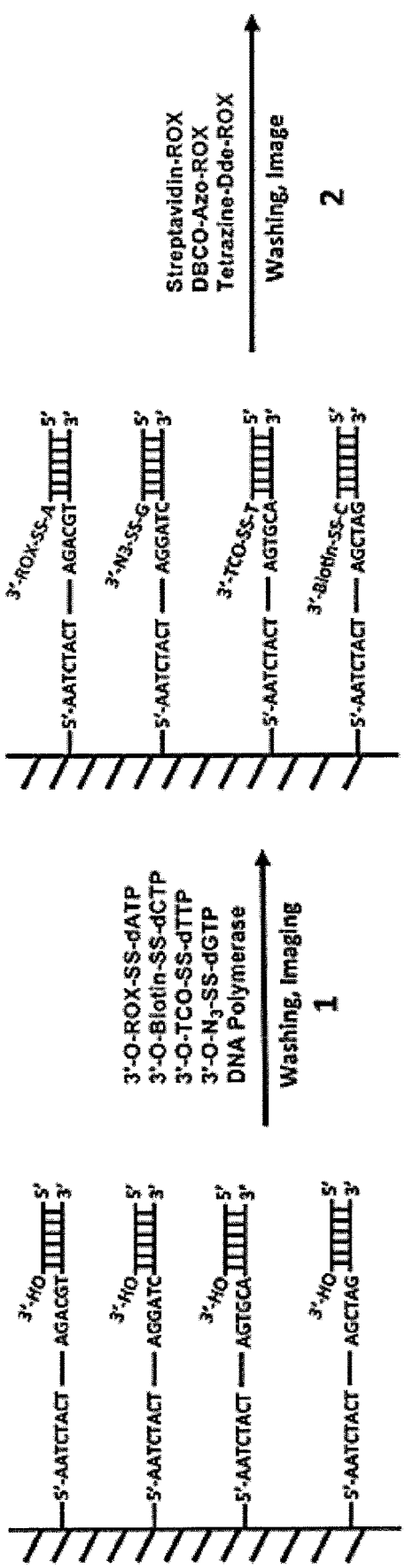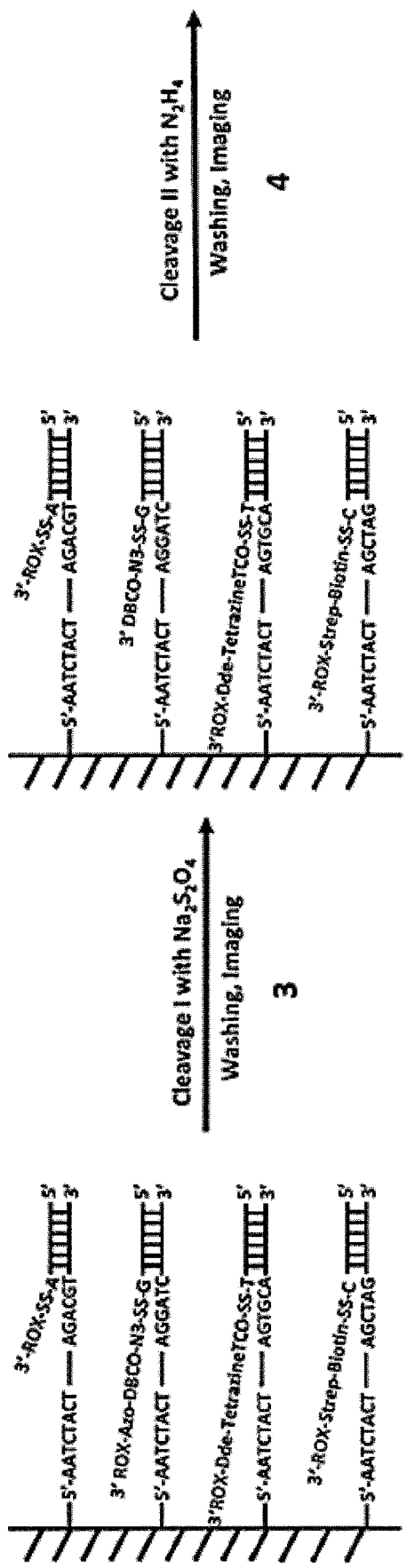
FIG. 20A
FIG. 20B

M.W. 1157

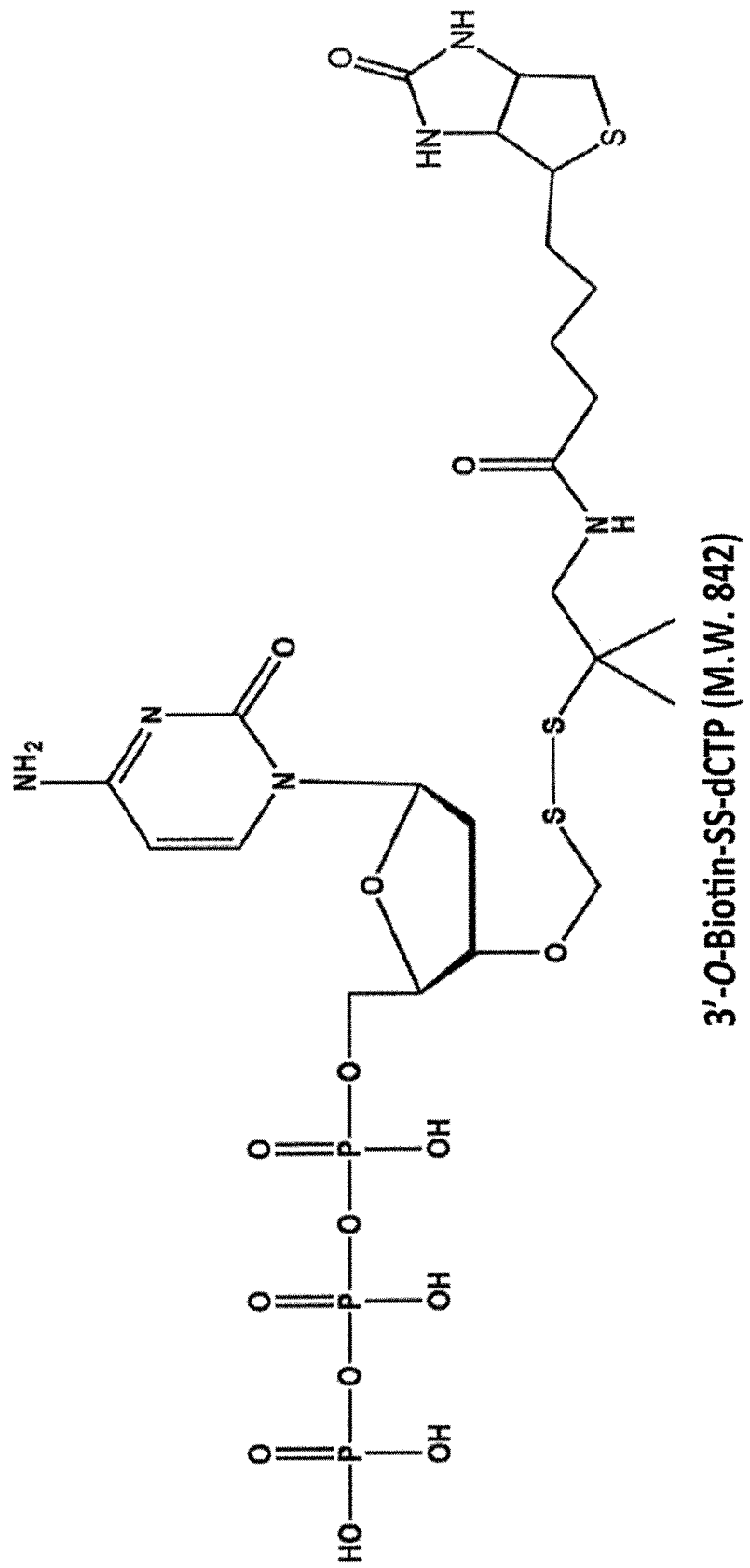
FIG. 27B 3'-O-Biotin-SS-dCTP (M.W. 842)

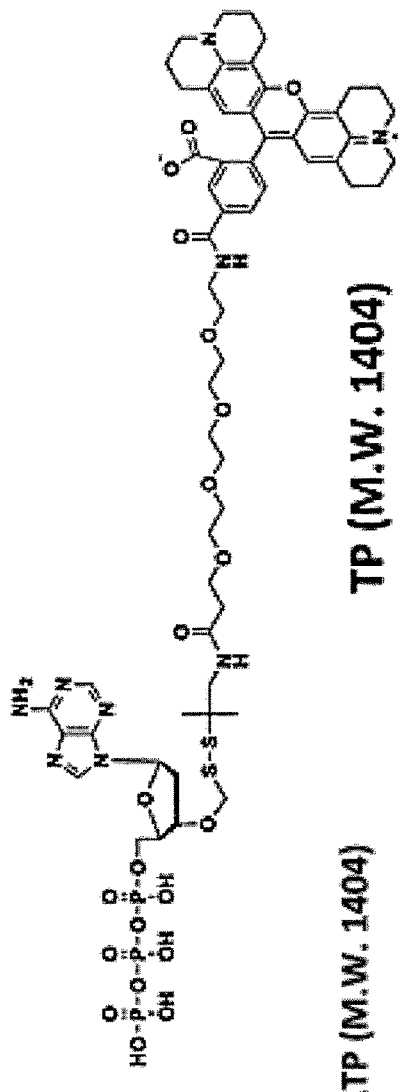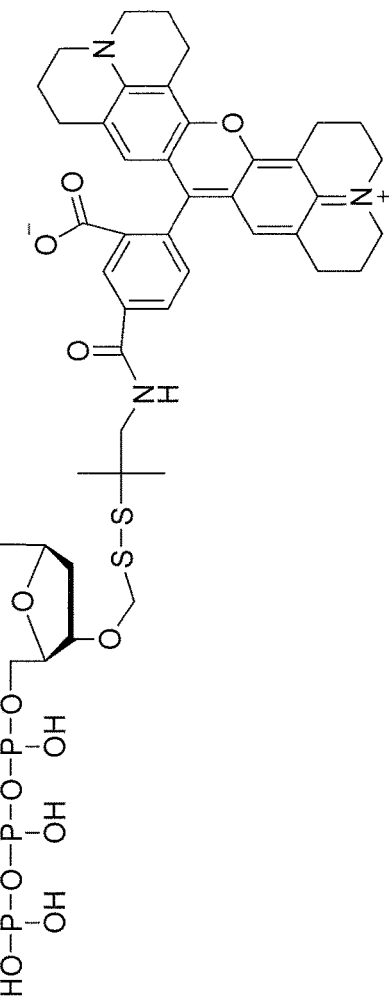
FIG. 28B 3'-O-Rox-PEG₄-SS-dATP (M.W. 1404) TP (M.W. 1404)
FIG. 28C 3'-O-Rox-SS-dATP (M.W. 1157)

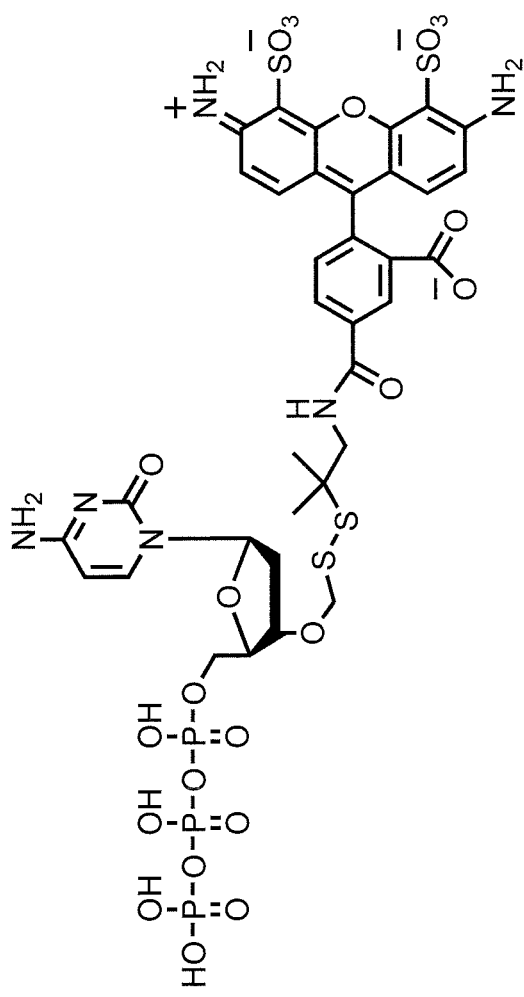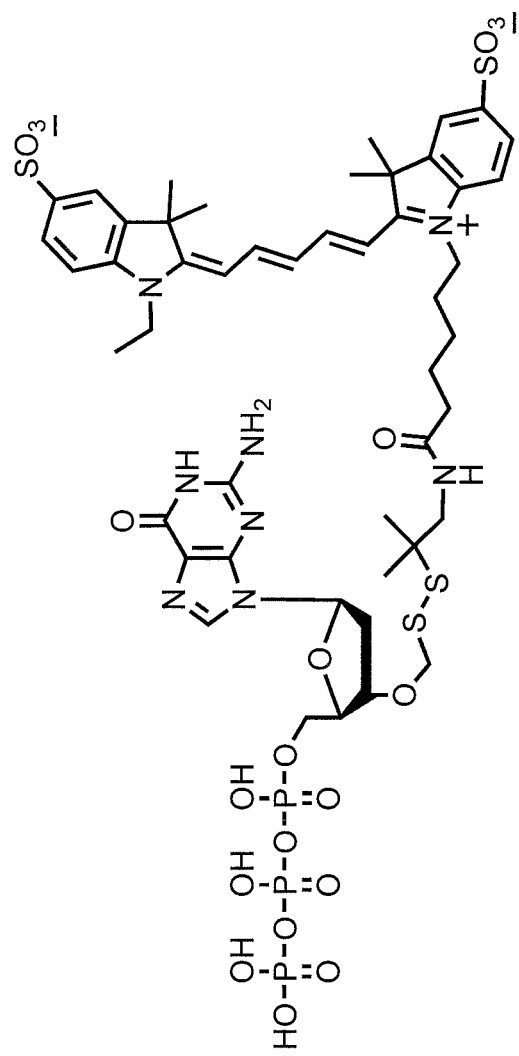
FIG. 30A
FIG. 30B

3'-O-Rox-SS-dATP
M.W. 1157

Tris(hydroxypropyl)phosphine (THP)

First Extension (Product 1)

First Cleavage (Product 2)

Extension Product
Calc. M.W. 7314

M.W. 905.52

Extension Product
Calc. M.W. 5894

Extension Product
Calc. M.W. 6141

3'-O-Rox-DTM(SS)-dATP

3'-O-BodipyFl-DTM(SS)-dTTP

3'-O-DTM(SS)-dCTP-5-SS-R6G

3'-O-DTM(SS)-dGTP-7-SS-Cy5

3'-O-Anchor-SS-dNTPs                    3'-O-Anchor-Allyl-dNTPs

3'-O-Anchor-2NB-dNTPs

BASE = A, T, G, C or derivatives thereof

Anchor = $N_3$, TCO, PBA, Quadricyclane, Biotin

SEQUENCE LISTING

<160> NUMBER OF SEQ ID NOS: 27

<210> SEQ ID NO 1
<211> LENGTH: 109
<212> TYPE: DNA
<213> ORGANISM: Homo sapiens

<400> SEQUENCE: 1
gaaggagaca cgcggccaga gagggtcctg tccgtgtttg tgcgtggagt tcgacaaggc      60
agggtcatct aatggtgatg agtcctatcc ttttctcttc gttctccgt              109

```
<210> SEQ ID NO 2
<211> LENGTH: 20
<212> TYPE: DNA
<213> ORGANISM: Homo sapiens

<400> SEQUENCE: 2
tagatgaccc tgccttgtcg                                                   20

<210> SEQ ID NO 3
<211> LENGTH: 109
<212> TYPE: DNA
<213> ORGANISM: Homo sapiens

<400> SEQUENCE: 3
gaaggagaca cgcggccaga gagggtcctg tccgtgtttg tgcgtggagt tcgacaaggc       60
agggtcatct aatggtgatg agtcctatcc ttttctcttc gttctccgt                  109

<210> SEQ ID NO 4
<211> LENGTH: 17
<212> TYPE: DNA
<213> ORGANISM: Homo sapiens

<400> SEQUENCE: 4
gataggactc atcacca                                                      17

<210> SEQ ID NO 5
<211> LENGTH: 109
<212> TYPE: DNA
<213> ORGANISM: Homo sapiens

<400> SEQUENCE: 5
gaaggagaca cgcggccaga gagggtcctg tccgtgtttg tgcgtggagt tcgacaaggc       60
agggtcatct aatggtgatg agtcctatcc ttttctcttc gttctccgt                  109

<210> SEQ ID NO 6
<211> LENGTH: 109
<212> TYPE: DNA
<213> ORGANISM: Homo sapiens

<400> SEQUENCE: 6
gaaggagaca cgcggccaga gagggtcctg tccgtgtttg tccgtggagt tcgacaaggc       60
agggtcatct aatggtgatg agtcctatcc ttttctcttc gttctccgt                  109

<210> SEQ ID NO 7
<211> LENGTH: 20
<212> TYPE: DNA
<213> ORGANISM: Homo sapiens

<400> SEQUENCE: 7
tagatgaccc tgccttgtcg                                                   20

<210> SEQ ID NO 8
<211> LENGTH: 109
<212> TYPE: DNA
<213> ORGANISM: Homo sapiens

<400> SEQUENCE: 8
gaaggagaca cgcggccaga gagggtcctg tccgtgtttg tccgtggagt tcgacaaggc       60
agggtcatct aatggtgatg agtcctatcc ttttctcttc gttctccgt                  109
```

```
<210> SEQ ID NO 9
<211> LENGTH: 20
<212> TYPE: DNA
<213> ORGANISM: Homo sapiens

<400> SEQUENCE: 9
tagatgaccc tgccttgtcg                                              20

<210> SEQ ID NO 10
<211> LENGTH: 109
<212> TYPE: DNA
<213> ORGANISM: Homo sapiens

<400> SEQUENCE: 10
gaaggagaca cgcggccaga gagggtcctg tccgtgtttg tccgtggagt tcgacaaggc    60
agggtcatct aatggtgatg agtcctatcc ttttctcttc gttctccgt              109

<210> SEQ ID NO 11
<211> LENGTH: 20
<212> TYPE: DNA
<213> ORGANISM: Homo sapiens

<400> SEQUENCE: 11
tagatgaccc tgccttgtcg                                              20

<210> SEQ ID NO 12
<211> LENGTH: 109
<212> TYPE: DNA
<213> ORGANISM: Homo sapiens

<400> SEQUENCE: 12
gaaggagaca cgcggccaga gagggtcctg tccgtgtttg tccgtggagt tcgacaaggc    60
agggtcatct aatggtgatg agtcctatcc ttttctcttc gttctccgt              109

<210> SEQ ID NO 13
<211> LENGTH: 17
<212> TYPE: DNA
<213> ORGANISM: Homo sapiens

<400> SEQUENCE: 13
gataggactc atcacca                                                 17

<210> SEQ ID NO 14
<211> LENGTH: 100
<212> TYPE: DNA
<213> ORGANISM: Homo sapiens

<400> SEQUENCE: 14
tacccggagg ccaagtacgg cgggtacgtc cttgacaatg tgtacatcaa catcacctac    60
caccatgtca gtctcggttg gatcctctat tgtgtccggg                        100

<210> SEQ ID NO 15
<211> LENGTH: 20
<212> TYPE: DNA
<213> ORGANISM: Homo sapiens

<400> SEQUENCE: 15
gttgatgtac acattgtcaa                                              20

<210> SEQ ID NO 16
<211> LENGTH: 109
```

```
<212> TYPE: DNA
<213> ORGANISM: Homo sapiens

<400> SEQUENCE: 16
gaaggagaca cgcggccaga gagggtcctg tccgtgtttg tccgtggagt tcgacaaggc    60
agggtcatct aatggtgatg agtcctatcc ttttctcttc gttctccgt              109

<210> SEQ ID NO 17
<211> LENGTH: 20
<212> TYPE: DNA
<213> ORGANISM: Homo sapiens

<400> SEQUENCE: 17
tagatgaccc tgccttgtcg                                               20

<210> SEQ ID NO 18
<211> LENGTH: 20
<212> TYPE: DNA
<213> ORGANISM: Homo sapiens

<400> SEQUENCE: 18
tagatgaccc tgccttgtcg                                               20

<210> SEQ ID NO 19
<211> LENGTH: 109
<212> TYPE: DNA
<213> ORGANISM: Homo sapiens

<400> SEQUENCE: 19
gaaggagaca cgcggccaga gagggtcctg tccgtgtttg tgcgtggagt tcgacaaggc    60
agggtcatct aatggtgatg agtcctatcc ttttctcttc gttctccgt              109

<210> SEQ ID NO 20
<211> LENGTH: 20
<212> TYPE: DNA
<213> ORGANISM: Homo sapiens

<400> SEQUENCE: 20
tagatgaccc tgccttgtcg                                               20

<210> SEQ ID NO 21
<211> LENGTH: 109
<212> TYPE: DNA
<213> ORGANISM: Homo sapiens

<400> SEQUENCE: 21
gaaggagaca cgcggccaga gagggtcctg tccgtgtttg tgcgtggagt tcgacaaggc    60
agggtcatct aatggtgatg agtcctatcc ttttctcttc gttctccgt              109

<210> SEQ ID NO 22
<211> LENGTH: 17
<212> TYPE: DNA
<213> ORGANISM: Homo sapiens

<400> SEQUENCE: 22
gataggactc atcacca                                                  17
```

```
<210> SEQ ID NO 23
<211> LENGTH: 109
<212> TYPE: DNA
<213> ORGANISM: Homo sapiens

<400> SEQUENCE: 23
gaaggagaca cgcggccaga gagggtcctg tccgtgtttg tgcgtggagt tcgacaaggc    60
agggtcatct aatggtgatg agtcctatcc ttttctcttc gttctccgt              109

<210> SEQ ID NO 24
<211> LENGTH: 51
<212> TYPE: DNA
<213> ORGANISM: Homo sapiens

<400> SEQUENCE: 24
tacatcaact acccggaggc caagtacggc gggtacgtcc ttgacaatgt g             51

<210> SEQ ID NO 25
<211> LENGTH: 13
<212> TYPE: DNA
<213> ORGANISM: Homo sapiens

<400> SEQUENCE: 25
cacattgtca agg                                                       13

<210> SEQ ID NO 26
<211> LENGTH: 80
<212> TYPE: DNA
<213> ORGANISM: Homo sapiens

<400> SEQUENCE: 26
gaggaagtat cctgtcgttt agcatacccA aacttgatgc tctactgacc tcagctgcac    60
gtaagtgcag ctgaggtcag                                                80

<210> SEQ ID NO 27
<211> LENGTH: 80
<212> TYPE: DNA
<213> ORGANISM: Homo sapiens

<400> SEQUENCE: 27
tcacagagga agtatcctgt cgtttagcat acccaaactt gatgctgacc tcagctgcac    60
gtaagtgcag ctgaggtcag                                                80
```

NUCLEOTIDE DERIVATIVES AND METHODS OF USE THEREOF

CROSS-REFERENCES TO RELATED APPLICATIONS

This application is a divisional of U.S. application Ser. No. 16/303,715, filed Nov. 21, 2018, now U.S. Pat. No. 11,266,673, issued Mar. 8, 2022, which is a § 371 national stage of PCT International Application No. PCT/US2017/033,939, filed May 23, 2017, claiming the benefit of U.S. Provisional Applications Nos. 62/477,945, filed Mar. 28, 2017; 62/365,321, filed Jul. 21, 2016; and 62/340,419, filed May 23, 2016, the contents of each of which are incorporated herein by reference in its entirety.

REFERENCE TO A "SEQUENCE LISTING," A TABLE, OR A COMPUTER PROGRAM LISTING APPENDIX SUBMITTED AS AN ASCII FILE

This application incorporates-by reference nucleotide and/or amino acid sequences which are present in the file named "220307_88662-AA-PCT-US_Seq_Listing_JMP.txt", which is 6.0 kilobytes in size, and which was created Mar. 4, 2022 in the IBM-PC machine format, having an operating system capacity with MS-Windows, which is contained in the text file being filed Mar. 7, 2022 as part of this application.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Currently, the widely used high-throughput SBS technology (Bentley D R, et al. Nature, 2008, 456, 53-59) determines DNA sequences during the polymerase reaction using cleavable fluorescently labeled nucleotide reversible terminator (NRT) sequencing chemistry that has been previously developed (Ju J et al. 2003, U.S. Pat. No. 6,664,079; Ju J et al. Proc Natl Acad Sci USA, 2006, 103, 19635-19640). These cleavable fluorescent NRTs were designed based on the rationale that each of the nucleotides is modified by attaching a unique cleavable fluorophore to the specific location of the base and capping the 3'-OH group with a small reversible-blocking moiety so they are still recognized by DNA polymerase as substrates. A disadvantage of the abovementioned SBS approach is the production of a small molecular "scar" (e.g., a propargylamine or a modified propargylamino moiety) at the nucleotide base after cleavage of the fluorescent dye from the incorporated nucleotide in the polymerase reaction. The growing DNA chain accumulates these scars through each successive round of SBS. At some point, the residual scars may be significant enough to interfere with the DNA double helix structure, thereby negatively affecting DNA polymerase recognition and consequently limiting the read length. Accumulated research efforts indicated that the major challenge for this approach is that DNA polymerase has difficulty accepting 3'-O bulky-dye-modified nucleotides as substrates, because the 3' position on the deoxyribose of the nucleotides is very close to the amino acid residues in the active site of the DNA polymerase while in the ternary complex formed by the polymerase with the complementary nucleotide and the primed template. Accordingly, there is a need for the use in scarless SBS, and synthesis of, 3'-O modified nucleotides and nucleosides that are effectively recognized as substrates by DNA polymerases, are efficiently and accurately incorporated into growing DNA chains during SBS, have a 3'-O blocking group that is cleavable under mild conditions wherein cleavage results in a 3'-OH, and permit long SBS read-lengths. Disclosed herein, inter alia, are solutions to these and other problems in the art.

BRIEF SUMMARY OF THE INVENTION

In an aspect is provided a nucleotide analogue having the formula:

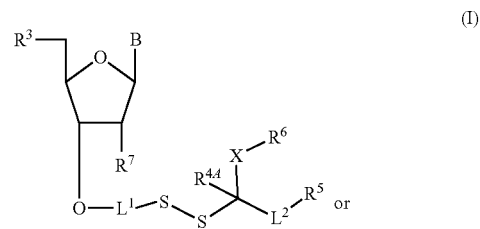

(I)

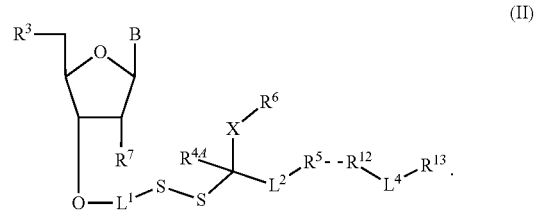

(II)

B is a base or analogue thereof. $L^1$ is covalent linker. $L^2$ is covalent linker. $L^4$ is covalent linker. X is a bond, O, $NR^{6A}$, or S. $R^3$ is —OH, monophosphate, polyphosphate or a nucleic acid. $R^{4A}$ and $R^{6A}$ are independently hydrogen, —OH, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, anchor moiety, or affinity anchor moiety. $R^6$ is hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —OR$^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In an aspect is provided a thermophilic nucleic acid polymerase complex, wherein the thermophilic nucleic acid polymerase is bound to a nucleotide analogue having the formula:

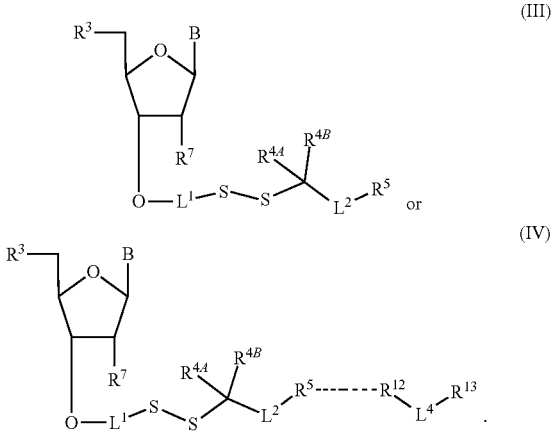

(III)

(IV)

B is a base or analogue thereof. $L^1$ is covalent linker. $L^2$ is covalent linker. $L^4$ is covalent linker. $R^3$ is —OH, monophosphate, polyphosphate or a nucleic acid. $R^{4A}$ and $R^{6A}$ are independently is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4B}$ is hydrogen, —OH, —$CF_3$, —$CCl_3$, ~$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —X—$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is a bond, O, $NR^{6A}$, or S. $R^5$ is a detectable label, anchor moiety, or affinity anchor moiety. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In another aspect is provided a thermophilic nucleic acid polymerase complex (e.g., 9° N nucleic acid polymerase complex), wherein the nucleic acid polymerase (e.g., thermophilic) is bound to a nucleotide analogue, wherein the nucleotide analogue includes a fluorescent dye with a molecular weight of at least about 140 Daltons, and wherein the fluorescent dye is covalently bound at the 3' position of the nucleotide analogue.

In an aspect is provided a method of incorporating a nucleotide analogue into a nucleic acid sequence including combining a thermophilic nucleic acid polymerase, a primer hybridized to nucleic acid template, and a nucleotide analogue including a detectable label, within a reaction vessel and allowing the thermophilic nucleic acid polymerase to incorporate the nucleotide analogue into the primer thereby incorporating a nucleotide analogue into a nucleic acid sequence.

In an aspect is provided a method for sequencing a nucleic acid, including: (i) incorporating in series with a thermophilic nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues are of the structure formula:

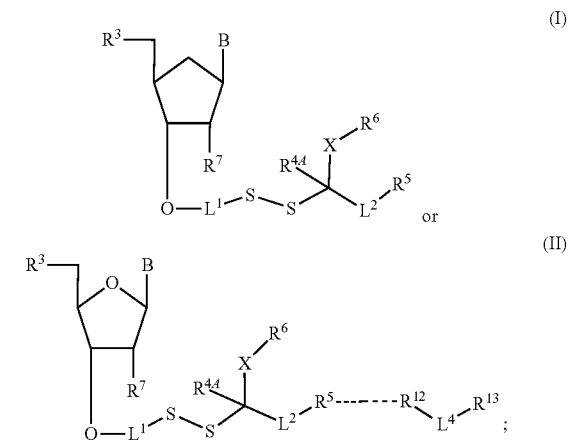

(I)

(II)

wherein the first of the four different labeled nucleotide analogues, B is a thymine or uracil hybridizing base; in the second of the four different labeled nucleotide analogues, B is an adenine hybridizing base; in the third of the four different labeled nucleotide analogues, B is an guanine hybridizing base; and in the fourth of the four different labeled nucleotide analogues, B is an cytosine hybridizing base. B is a base or analogue thereof. $L^1$ is covalent linker. $L^2$ is covalent linker. $L^4$ is covalent linker. X is a bond, O, $NR^{6A}$, or S. $R^3$ is —OH, monophosphate, polyphosphate or a nucleic acid. $R^{4A}$ and $R^{6A}$ are independently hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, anchor moiety, or affinity anchor moiety. $R^6$ is hydrogen, —$CF_3$, —$CCl_3$, ~$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In another aspect is provided a method of incorporating a nucleotide analogue into a nucleic acid sequence including combining a thermophilic nucleic acid polymerase, a primer hybridized to nucleic acid template, and a nucleotide analogue, within a reaction vessel and allowing the thermophilic nucleic acid polymerase to incorporate the nucleotide analogue into the primer thereby incorporating a nucleotide analogue into a nucleic acid sequence, wherein the nucleotide analogue includes a fluorescent dye with a molecular weight of at least about 140 Daltons, and wherein the fluorescent dye is covalently bound at the 3' position of the nucleotide analogue.

BRIEF DESCRIPTION OF THE DRAWINGS

FIG. 2A: Cy5 Labeled Streptavidin. FIG. 2B: 3'-O-Biotin-t-Butyldithiomethyl-dATP. FIG. 2C: 3'-O-Biotin-t-Butyldithiomethyl-dCTP. FIG. 2D: 3'-O-Biotin-t-Butyldithiomethyl-dGTP. FIG. 2E: 3'-O-Biotin-t-Butyldithiomethyl-dTTP FIGS. 3A-3B. Scarless one-color SBS using 3'-O-Biotin-SS(DTM)-dNTPs and Cy5 labeled streptavidin. DNA polymerase incorporation reaction is conducted by using one of the four 3'-O-Biotin-SS-dNTPs, followed by the addition of the Cy5 labeled streptavidin and imaging to determine DNA sequences as described in STEP 1 through STEP 4 (as shown in as 3.1 and repeated in 3.2, 3.3 and 3.4). Each step consists of three parts: (PART a) Add polymerase and one of the four 3'-O-Biotin-SS-dNTPs followed by washing; if the added nucleotide is complementary to the nucleotide on the template immediately next to the 3' end of the primer, then the added nucleotide will incorporate into the primer to produce a DNA extension product that has a Biotin at the 3' end. (PART b) Add Cy5 labeled streptavidin, which will bond to the Biotin at the 3' end of the DNA extension product. (PART c) After washing away the unbound Cy5 labeled streptavidin, perform imaging to detect the Cy5 signal for the identification of the incorporated nucleotide. Following STEP 4, addition of THP to the DNA extension products will cleave the disulfide bond and regenerate a free 3'-OH group on the 3' end of the DNA extension products. Sequentially repeat the process, consisting of STEP 1 through STEP 4, followed by THP cleavage, for continuing sequence determination. The text over the arrows is as follows: 3.1: 1. (a) Add 3'-O-Biotin-SS-dATP and DNA polymerase; (b) add Cy5-streptavidin; (c) imaging; 2. (a) Add 3'-O-Biotin-SS-dTTP and DNA polymerase; (b) add Cy5-streptavidin; (c) imaging; 3. (a) Add 3'-O-Biotin-SS-dGTP and DNA polymerase; (b) add Cy5 labeled streptavidin; (c) imaging; 4. (a) Add 3'-O-Biotin-SS-dCTP and DNA polymerase; (b) add Cy5 labeled streptavidin; (c) imaging. 3.2: Repeat steps 1, 2, 3 and 4. 3.3: Repeat steps 1, 2, 3 and 4. 3.4: Repeat steps 1, 2, 3 and 4.

FIGS. 6A-6D. Conjugates or complexes between DNA products produced by incorporating 3'-O "anchor" labeled nucleotides (3'-O-TCO-t-Butyldithiomethyl-dATP, 3'-O-PBA-t-Butyldithiomethyl-dCTP, 3'-O-Biotin-t-Butyldithiomethyl-dGTP, 3'-O-Azido-t-Butyldithiomethyl-dTTP) with four correspondingly-matched labeled binding molecules (Rox-Labeled Tetrazine, Alexa488-Labeled SHA, Cy5-Labeled Streptavidin, and R6G-Labeled Dibenzocyclooctyne). The reaction of the DNA extension product containing four "anchor" moieties at the 3'-end with four correspondingly-matched labeled binding molecules leads to each incorporated nucleotide in the DNA extension product being labeled with a unique dye. Thus, Rox will be tethered to the 3'-end of a DNA extension product through a specific Tetrazine TCO ligation to form PRODUCT 1; Alexa488 will be tethered to the 3'-end of a DNA extension product through a stable PBA-SHA complex to form PRODUCT 2; Cy5 will be tethered to the 3'-end of a DNA extension product through a Biotin Streptavidin complex to form PRODUCT 3; and R6G will be tethered to the 3'-end of a DNA extension product through triazole formation via a click reaction between Dibenzocyclooctyne and an azido group to form PRODUCT 4.

FIG. 16A: 1. 3'-O—$N_3$-SS-dATP, 3'-O-TCO-SS-dTTP, 3'-O-Biotin-SS-dCTP, 3'-O-SS-dGTP, DNA Polymerase. 2. DBCO-Azo-ATT0647N, Tetrazinc-Dde-ATT0647N, Streptavidin-ATT0647N, Washing, Imaging. FIG. 16B: 3. Cleavage 1 with $Na_2S204$; Washing, Imaging. 4. Cleavage II with $N_2H_4$ Washing, Imaging. FIG. 16C: Cleavage III with THP Washing, Imaging.

FIG. 18A: 1. 3'-O-Rox-SS-dATP, 3'-O-Biotin-SS-dCTP, 3'-O—$N_3$-SS-dTTP, 3'-O-SS-dGTP, DNA Polymerase, Washing, Imaging. 2. Streptavidin-Rox, DBCO-Azo-Rox, Washing, Imaging. FIG. 18B: 3. Cleavage 1 with $Na_2S_2O_4$ Washing, Imaging. 4. Cleavage II with THP Washing, Imaging. FIG. 18C: Repeat steps 1, 2, 3, 4 For Subsequent cycles of Sequencing.

FIGS. 20A-20C. (1) In presence of DNA polymerase, three 3'-anchor nucleotides [3'-O—$N_3$-SS(DTM)-dGTP, 3'-O-Biotin-SS(DTM)-dCTP, 3'-O-TCO-SS(DTM)-dTTP)] and 3'-O-Rox-SS(DTM)-dATP, as shown in FIGS. 19A-19B] are added to the primed DNA templates to allow incorporation into the primer; (2) After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals; (3) Attach the fluorescent label (Rox, for example) by adding DBCO-Azo-(-N=N-Linker)-Rox, Tetrazine-Dde-Rox and Streptavidin-Rox (as shown in FIGS. 19A-19B) to the DNA extension products that contain the incorporated 3'-anchor nucleotide analogues, which leads to the labeling of all the incorporated nucleotides at their 3'-end due to specific anchor-binding molecule interaction; (4) After washing, the second round of imaging is performed, and the DNA products terminated with A, G, T, C all display the same Rox signal. Subtraction of the Rox signals from the DNA products determined in the first round of imaging as terminated at an A nucleotide reveals the DNA products terminated at G, T, C; (5) The first cleavage (I) is conducted by treatment with sodium dithionite ($Na_2S_2O_4$), which only cleaves the azo linkage to remove the fluorescent dye Rox from the DNA products terminated with the G nucleotide. The second round of imaging is performed. If the Rox fluorescent signal disappears after the cleavage I, the DNA products are determined as having incorporated a G nucleotide; (6) The second cleavage (II) is conducted with hydrazine ($N_2H_4$), which will cleave the Dde linkage to remove the fluorescent dye Rox from the DNA products terminated with the T nucleotide. The third round of imaging is performed. If the Rox fluorescent signal disappears after the cleavage II, the DNA products are determined as having incorporated a T nucleotide. If the Rox fluorescent signal stays after the cleavage II, the DNA products are determined as having incorporated a C nucleotide; (7) The third cleavage (III) is conducted with THP to cleave the disulfide bond and remove the Rox dye from the DNA extension products terminated with nucleotides A and C, so the change of the signal after the THP treatment also determines the DNA products as being terminated by a C nucleotide, because DNA products as being terminated by an A nucleotide have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Repeat steps 1 to 7 to continue subsequent cycles of single-color DNA SBS. The text under the arrows is as follows: FIG. 20A: 1. 3'-O-Rox-SS-dATP, 3'-O-Biotin-SS-dCTP, 3'-O-TCO-dTTP, 3'-O—$N_3$-SS-dGTP, DNA Polymerase, Washing, Imaging. 2. Streptavidin-Rox, DBCO-Azo-Rox, Tetrazine-Dde-ROX, Washing, Imaging. FIG. 20B: 3. Cleavage 1 with $Na_2S_2O_4$ Washing, Imaging. 4. Cleavage II with THP Washing, Imaging. FIG. 20C: 5. Cleavage III with THP, Washing, Imaging. Repeat steps 1, 2, 3, 4, 5 For Subsequent cycles of Sequencing.

FIG. 25B: 3'-O-tButyl-SS-dATP (M.W. 625). FIG. 25C: 3'-O-Rox-SS-dATP (M.W. 1157).

FIGS. 27A-27B. MALDI-TOF mass spectrum of a DNA extension product from polymerase reaction using 3'-O-Biotin-dCTP. The majority of the primer (M.W. 5136) was extended to produce a single extension product detected at 5801 Daltons (calculated M.W. 5811).

FIGS. 28A-28C. MALDI-TOF mass spectrum of DNA extension products from polymerase reaction using with a mixture of 3'-O-Rox-SS-dATP and 3'-O-Rox-PEG4-SS-dATP at a 1:1 ratio. The peak of the extension product 2 with 3'-O-Rox-PEG$_4$-SS-dATP at 7311 Daltons (calculated M.W. 7314) is much higher than that of the extension product 1 with 3'-O-Rox-SS-dATP at 7063 Daltons (calculated M.W. 7064). This result indicates the nucleotide analogue modified by a Rox through a PEG4 linker is a better substrate for the DNA polymerase than the nucleotide analogue modified by Rox without a PEG linker.

FIGS. 30A-30D. Structures of four 3'-O-Dye-DTM-dNTPs. FIG. 30A: 3'-O-Alexa488-t-Butyldithiomethyl-dCTP. FIG. 30B: 3'-O-Cy5-t-Butyldithiomethyl-dGTP. FIG. 30C: 3'-O-Rox-t-Butyldithiomethyl-dATP. FIG. 30D: 3'-O-R6G-t-Butyldithiomethyl-dTTP.

```
51 mer template:
5'-TACATCAACTACCCGGAGGCCAAGTACGGCGGGTACGTCCTTGACA
ATGTG-3'

13 mer primer:
5'-CACATTGTCAAGG-3' MW:3959
```

After each incorporation, the expected size of the product should be the sum of the starting primer plus the incoming nucleotide minus the MW (175) of the pyrophosphate group, yielding MWs of 5188 Da, 4939 Da, 5194 Da and 5620 Da.

Figure 54:
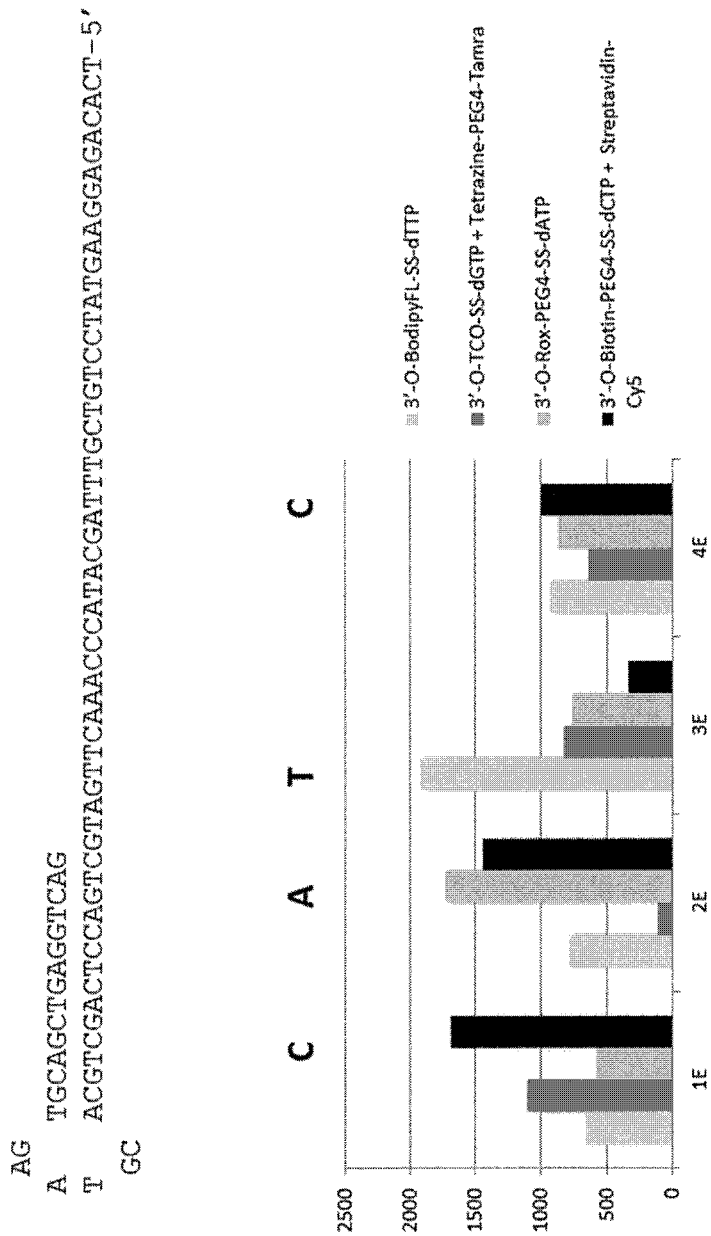

FIG. 54: Four base read obtained using four-color approach. Using the looped priming template shown at the top of the figure, in which the next four bases to be added are C, A, T, C, reactions were carried out as in the protocol for FIG. 70. 5'-NH$_2$-modified template was immobilized on NHS ester-modified slides from Surmodics (as described previously in the patent). Each cycle was carried out as follows: (1) extension with 60 µl of 0.02 µM 3'-O-Rox-SS-dATP, 0.05 µM 3'-O-BodipyFL-SS-dTTP, 0.5 µM 3'-O-Biotin-SS-dCTP, 0.5 µM 3'-O-TCO-SS-dGTP, 1X Thermo Pol Reaction Buffer (NEB), 2 mM MnCl$_2$, 2-10 U Therminator IX DNA polymerase for 15 min at 65° C.; (2) washing with 1X Thermo Pol Reaction Buffer; (3) chase with 60 µl of 4 µM each of the four 3'-O-SS(DTM)-dNTPs, 1X Thermo Pol Reaction Buffer, 2 mM MnCl$_2$, 2-10 U Therminator IX DNA polymerase for 10 min at 65° C.; (4) washing with 1X Thermo Pol Reaction Buffer; (5) labeling with 60 µl of 10 µM Tetrazine-PEG4-TAMRA (used as an alternative to Tetrazine-Cy3 in this specific experiment), 4 M Streptavidin-Cy5, 1X PBS, pH 7.4 for 15 min at 37° C.; (6) washing with 1X Thermo Pol Reaction Buffer, 1X SPSC buffer and water; (7) scanning air dried slides at 488 nm, 543 nm, 594 nm and 633 nm emission settings to record fluorescence intensity of spots; (8) cleavage with 10 mM THP for 10 min at 65° C.; (9) washing with water, 1X SPSC, and water again; (9) scanning air dried slides to determine background (repeating washes as necessary to minimize the background). The above was carried out 4 times to obtain the raw image intensity readings shown in the bar graph at the bottom for the first four bases of the extended primer.

Figure 55:
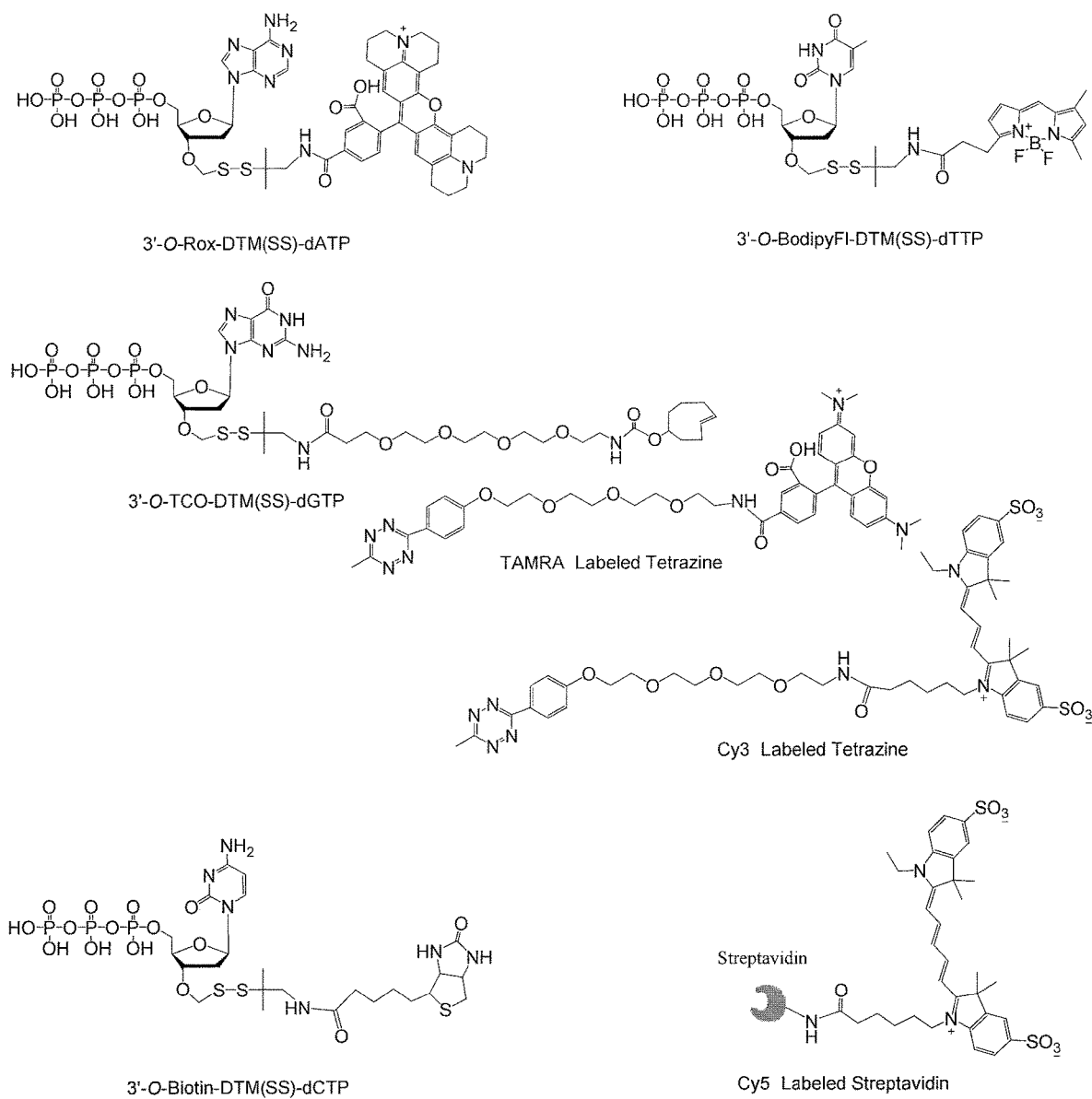

FIG. 55: Structures of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG4-SS-dGTP and 3'-O-Biotin-SS-dCTP) with their corresponding Dye Labeled Binding Molecules (TAMRA Labeled Tetrazine and Cy5 Labeled Streptavidin) to perform 4-color DNA SBS using approach delineated in FIG. 70.

Figure 56:
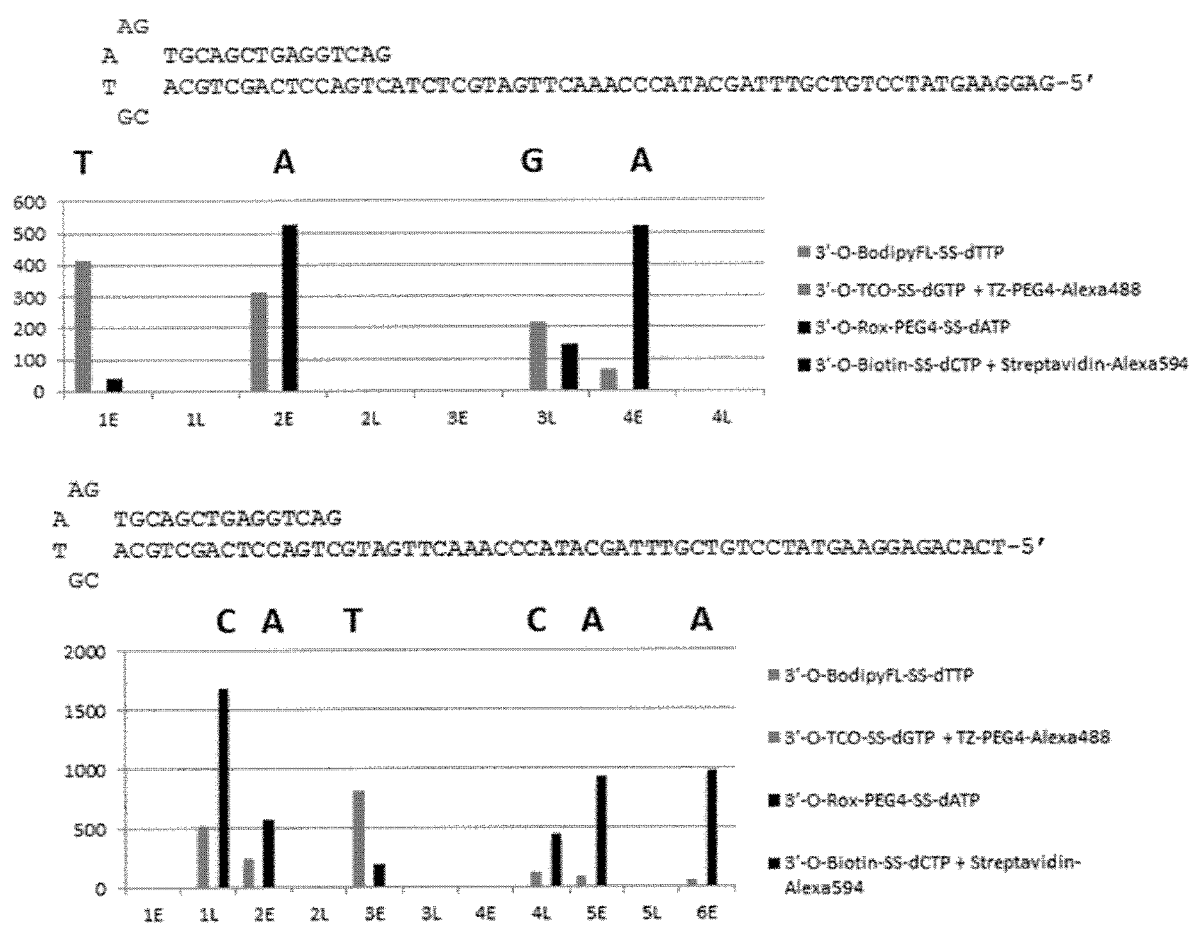

FIG. 56: Four and six base reads obtained using two-color approach. Using the looped priming template shown at the top of the figure, in which the next four bases to be added are T, A, G, A, or the looped priming template shown in the middle of the figure, in which the next six bases are C, A, T, C, A, A, reactions were carried out as in the protocol for FIG. 71. 5'-NH$_2$-modified template was immobilized on NHS ester-modified slides from Surmodics (as described previously in the patent). Each cycle was carried out as follows: (1) extension with 60 µl of 0.02 µM 3'-O-Rox-PEG4-SS-dATP, 0.05 µM 3'-O-BodipyFL-SS-dTTP, 0.5 M 3'-O-Biotin-SS-dCTP, 0.2 M 3'-O-TCO-SS-dGTP, 1X Thermo Pol Reaction Buffer (NEB), 2 mM MnCl$_2$, 2-10 U Therminator IX DNA polymerase for 15 min at 65° C.; (2) washing with 1X Thermo Pol Reaction Buffer; (3) chase with 60 µl of 4 µM each of the four 3'-O-SS(DTM)-dNTPs, 1X Thermo Pol Reaction Buffer, 2 mM MnCl$_2$, 2-10 U Terminator IX DNA polymerase for 10 min at 65° C.; (4) washing with 1X Thermo Pol Reaction Buffer; (5) scanning air dried slides at 488 nm and 594 nm emission settings to record fluorescence intensity of spots; (6) labeling with 60 µl of 10 µM Tetrazine-PEG4-Alexa488, 4 µM Streptavidin-Alexa594, 1X PBS, pH 7.4 for 10 min at 37° C.; (7) washing with 1X Thermo Pol Reaction Buffer, 1X SPSC buffer and water; (8) scanning air dried slides at 488 nm and 594 nm emission settings to record fluorescence intensity of spots; (9) cleavage with 10 mM THP for 10 min at 65° C.; (10) washing with water, 1X SPSC, and water again; (11) scanning air dried slides to determine background (repeating washes as necessary to obtain minimal background). The above was carried out 4-6 times to obtain the raw image intensity readings shown in the bar graphs below the template structures. In each cycle, E represents the imaging results after the extension and L represents the imaging results after the labeling. So in the top graph, the T is determined after the initial extension due to the presence of the BodipyFL dye directly attached to the 3'-O- of the dTTP, as are the A's in the second and fourth cycle; however the G in the third cycle is not seen until the labeling reaction in which the Alexa488-tetrazine is conjugated to the anchoring molecule (TCO) on the 3'-O- of the dGTP. Similarly in the lower bar graph, the A's and T's are visualized immediately after extension, but the C's are not observed until the labeling reaction is performed.

Figure 57:
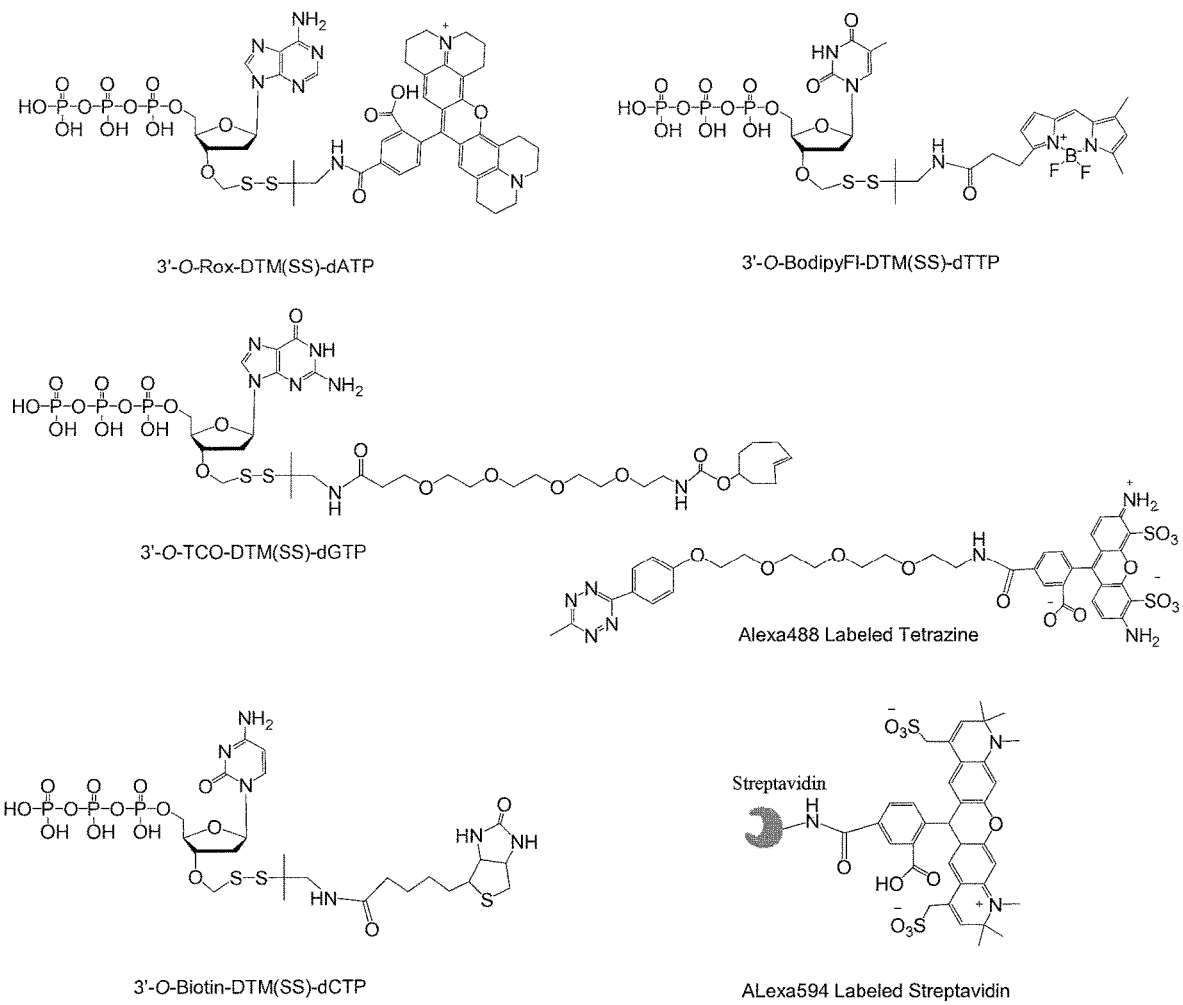

FIG. 57: Structures of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG4-SS-dGTP and 3'-O-Biotin-SS-dCTP) with their corresponding Dye Labeled Binding Molecules (Alexa488 Labeled Tetrazine and Alexa594 Labeled Streptavidin) to perform 2-color DNA SBS using approach delineated in FIG. 71.

Figure 58:
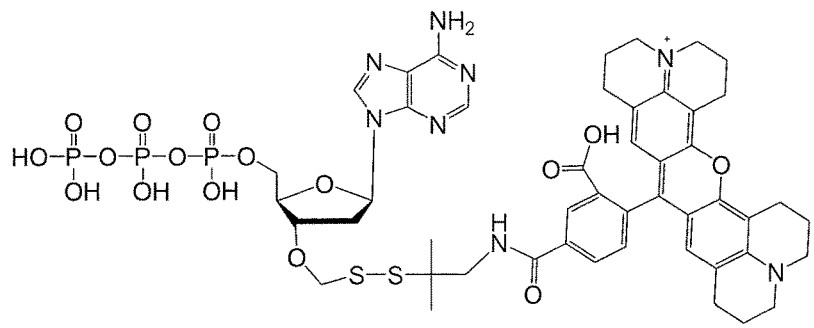
Figure 58:
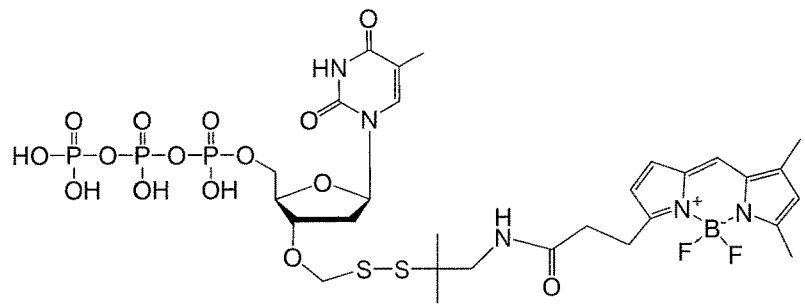
Figure 58:
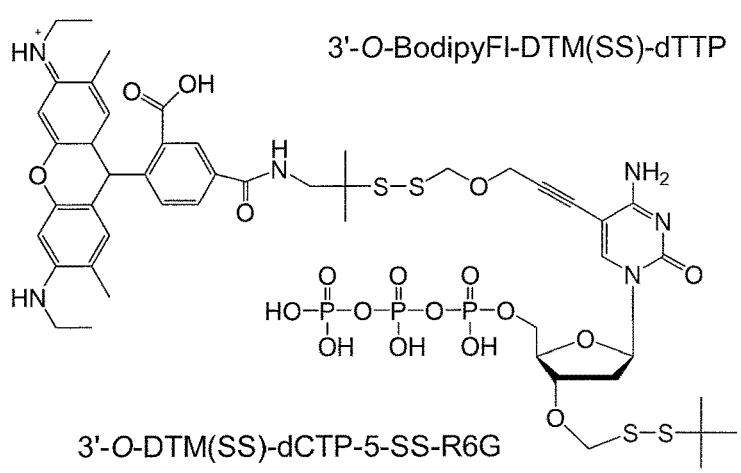
Figure 58:
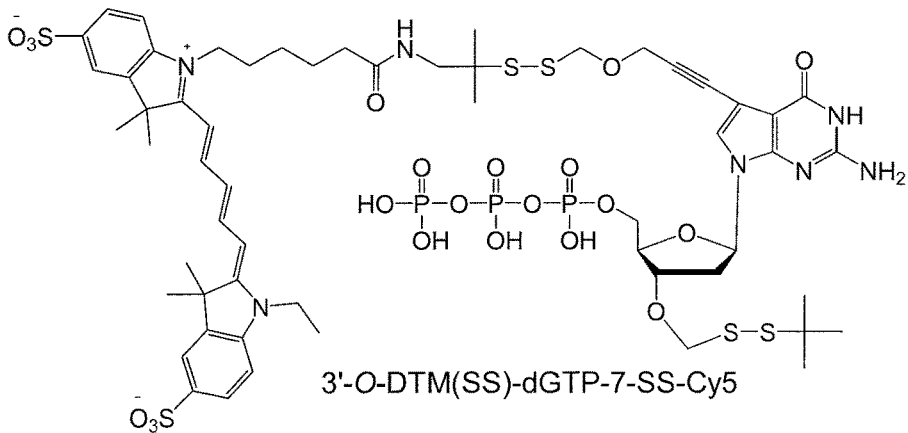

FIG. 58: Structures of 3'-O-Dye-SS(DTM)-dNTPs (3'-O-Rox-SS-dATP and 3'-O-BodipyFL-SS-dTTP) and 3'-O-SS (DTM)-dNTP-SS-Dyes (3'-O-SS-dGTP-7-SS-Cy5 and 3'-O-SS-dCTP-5-SS-R6G) for 4-color sequencing using approach delineated in FIG. 72.

Figure 59:
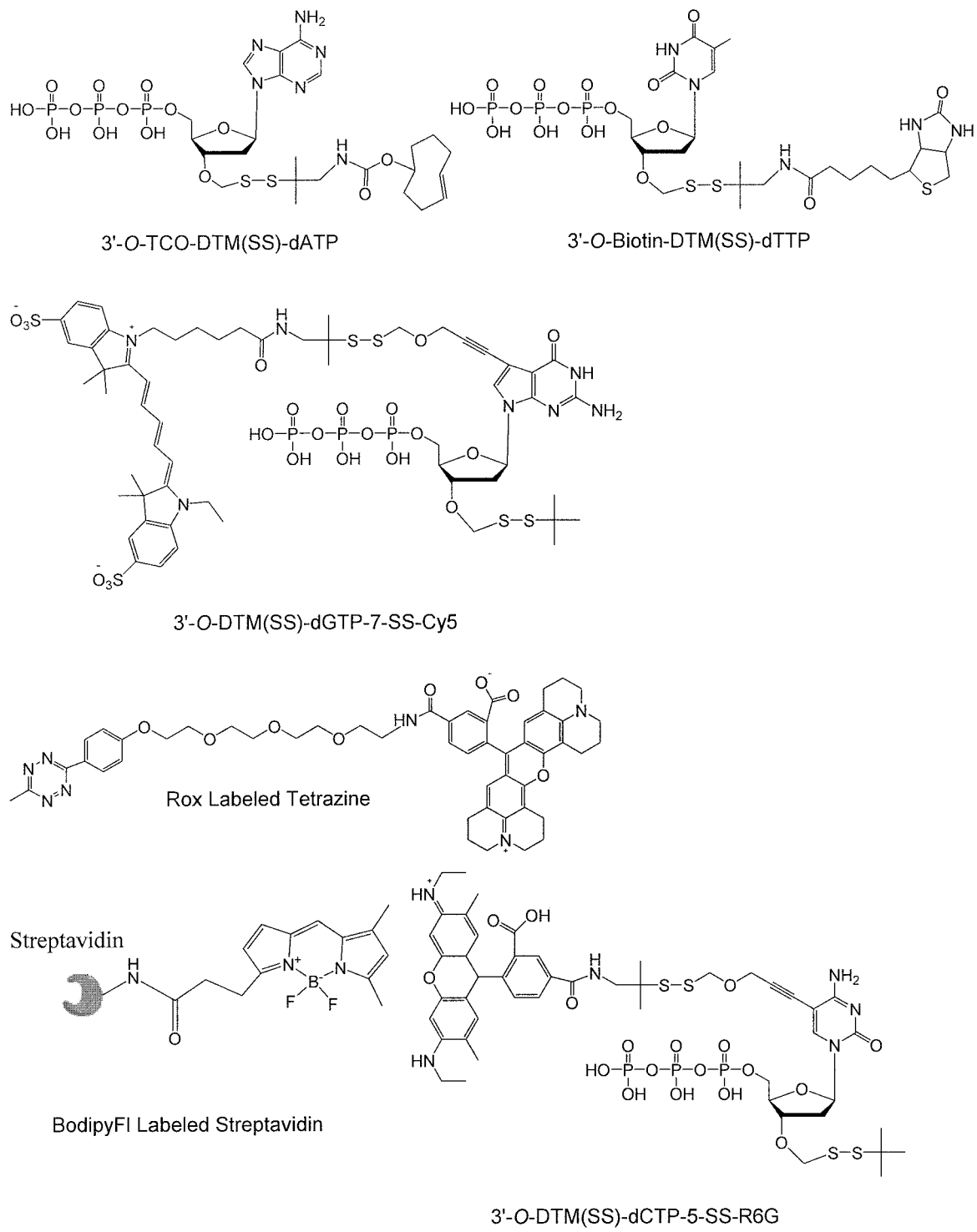

FIG. 59: Structures of 3'-O-Anchor-SS(DTM)-dNTPs (3'-O-TCO-SS-dATP and 3'-O-Biotin-SS-dTTP), 3'-O-SS (DTM)-dNTP-SS-Dyes (3'-O-SS-dGTP-7-SS-Cy5 and 3'-O-SS-dCTP-5-SS-R6G) and the corresponding Dye Labeled Binding Molecules (Rox Labeled Tetrazine and BodipyFL Labeled Streptavidin) to perform 4-color DNA SBS using approach delineated in FIG. 73.

Figure 60:
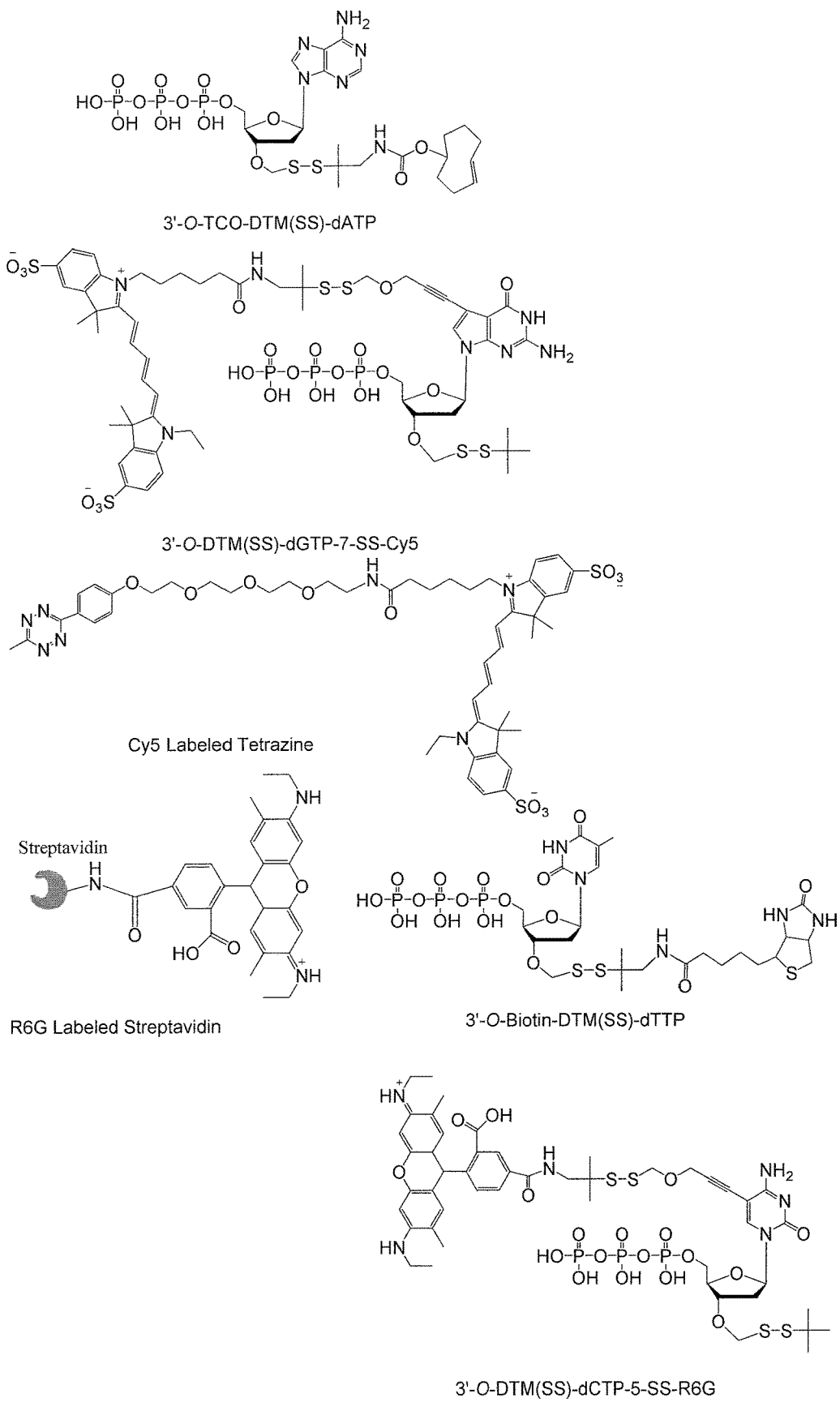

FIG. 60: Structures of 3'-O-Anchor-SS(DTM)-dNTPs (3'-O-TCO-SS-dATP and 3'-O-Biotin-SS-dTTP), 3'-O-SS (DTM)-dNTP-SS-Dyes (3'-O-SS-dGTP-7-SS-Cy5 and 3'-O-SS-dCTP-5-SS-R6G) and the corresponding Dye Labeled Binding Molecules (Cy5 Labeled Tetrazine and R6G Labeled Streptavidin) to perform 2-color DNA SBS using approach delineated in FIG. 74.

Figure 61:
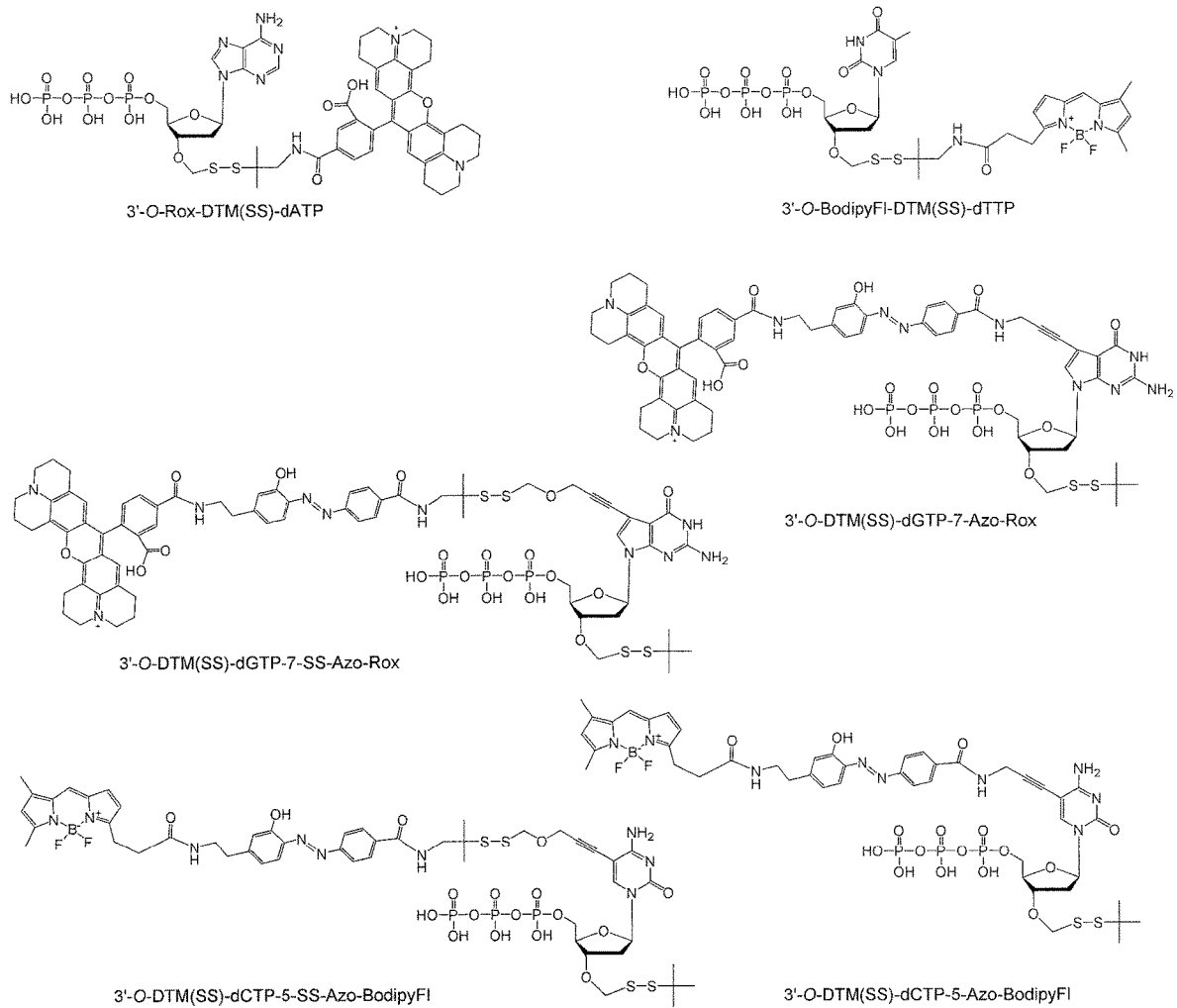

FIG. 61: Structures of 3'-O-Dye-SS(DTM)-dNTPs (3'-O-Rox-SS-dATP and 3'-O-BodipyFL-SS-dTTP) and 3'-O-DTM(SS)-dNTP-Azo-Dyes (3'-O-SS-dGTP-7-Azo-Rox or 3'-O-SS-dGTP-7-SS-Azo-Rox and 3'-O-SS-dCTP-5-Azo-BodipyFL or 3'-O-SS-dCTP-5-SS-Azo-BodipyFL) for 2-color DNA SBS using approach delineated in FIG. 75.

Figure 62:
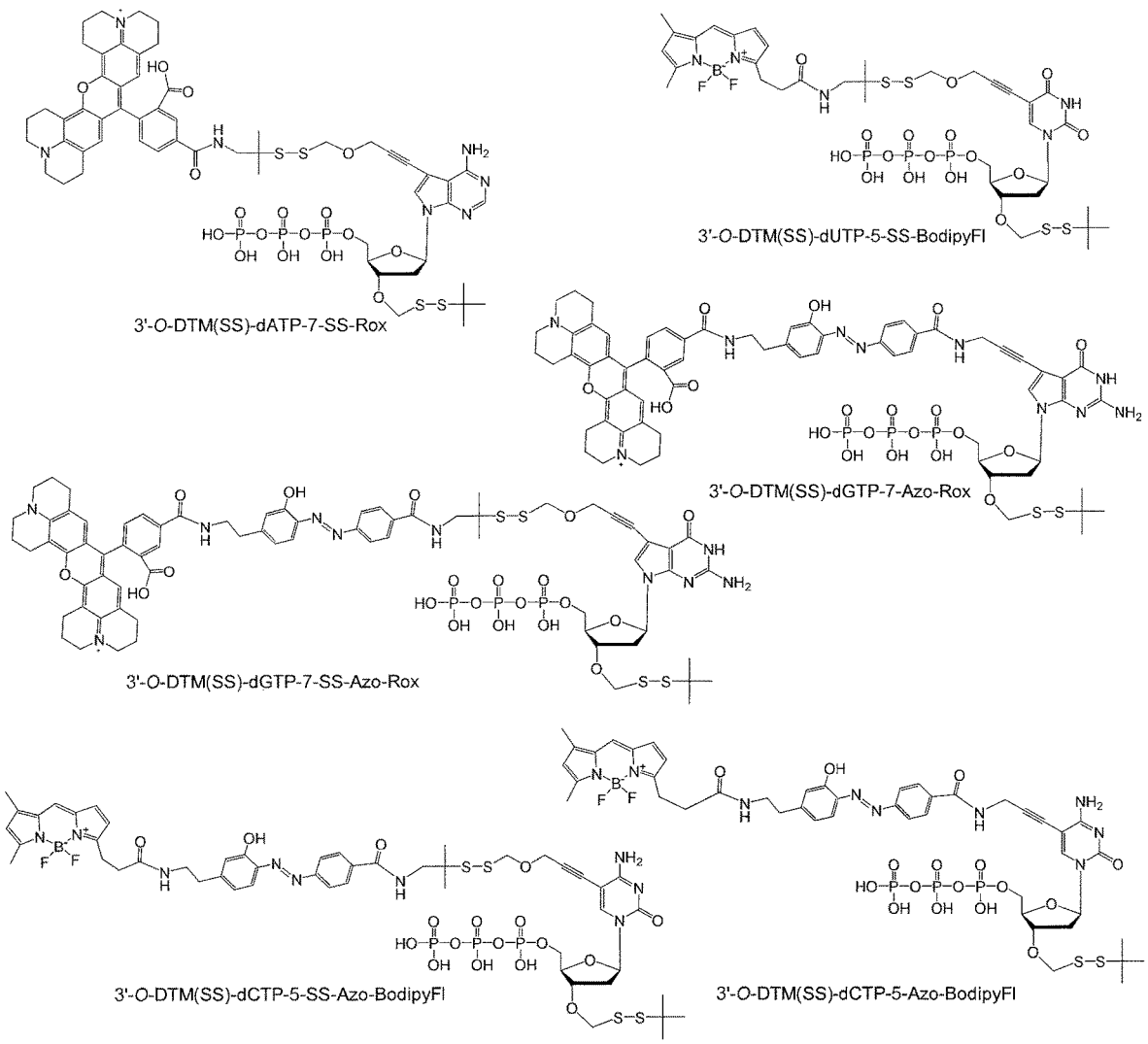

FIG. 62: 3'-O-SS(DTM)-dNTP-SS-Dyes (3'-O-SS-dATP-7-SS-Rox and 3'-O-SS-dUTP-5-SS-BodipyFL) and 3'-O-SS (DTM)-dNTP-SS-Azo-Dyes (3'-O-SS-dGTP-7-Azo-Rox or 3'-O-SS-dGTP-7-SS-Azo-Rox and 3'-O-SS-dCTP-5-SS-Azo-BodipyFL or 3'-O-SS-dCTP-5-SS-Azo-BodipyFL) for 2-color DNA SBS.

Figure 63:
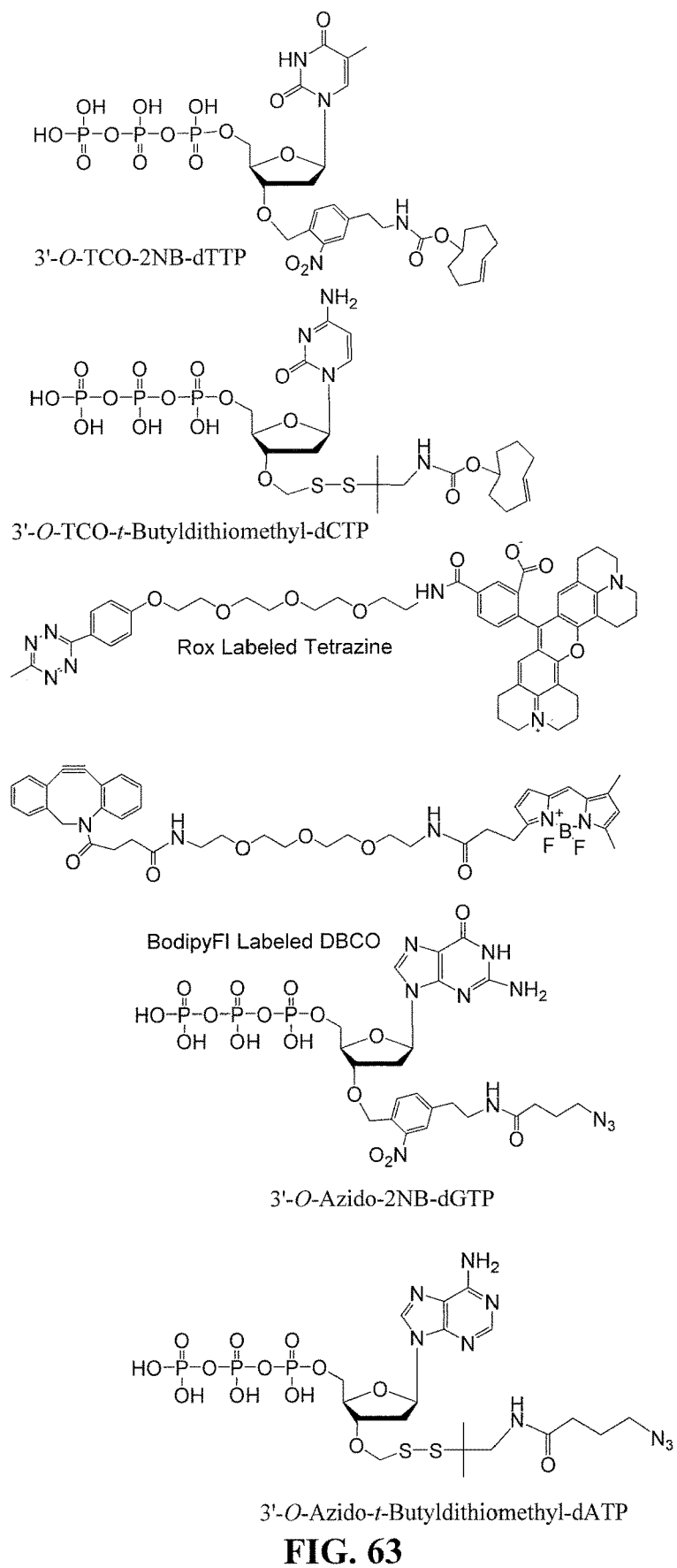
Figure 76:
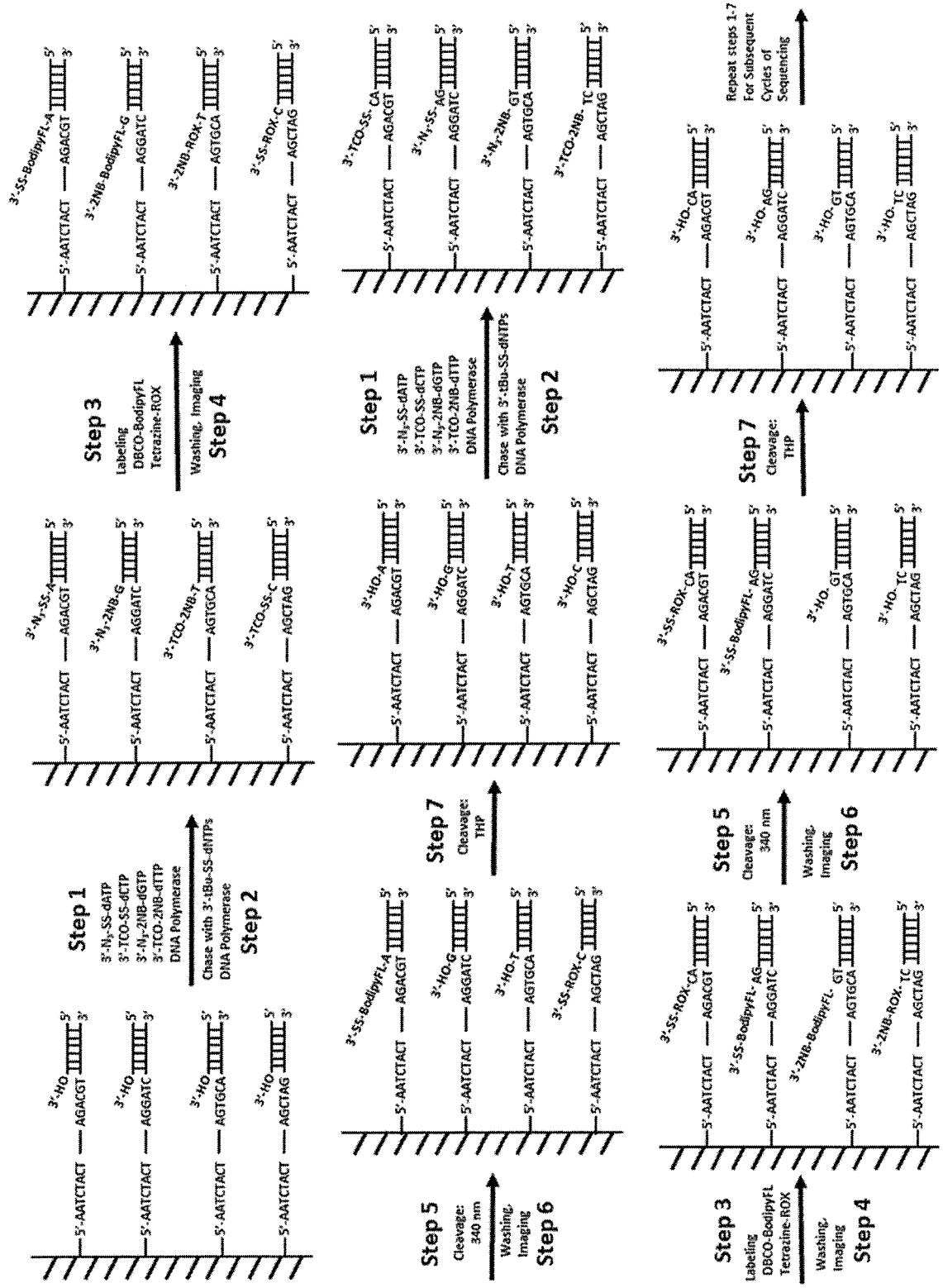

FIG. 63: 3'-O-Anchor-SS(DTM)-dNTP (3'-O-TCO-SS-dCTP and 3'-O-N3-SS-dATP), 3'-O-Anchor-2NB-dNTPs (3'-O-TCO-2NB-dTTP and 3'-O-N3-2NB-dGTP) and their corresponding Dye-labeled binding molecules (Rox labeled tetrazine and BodipyFl labeled DBCO) for 2-color DNA SBS using approach delineated in FIG. 76.

Figure 64:
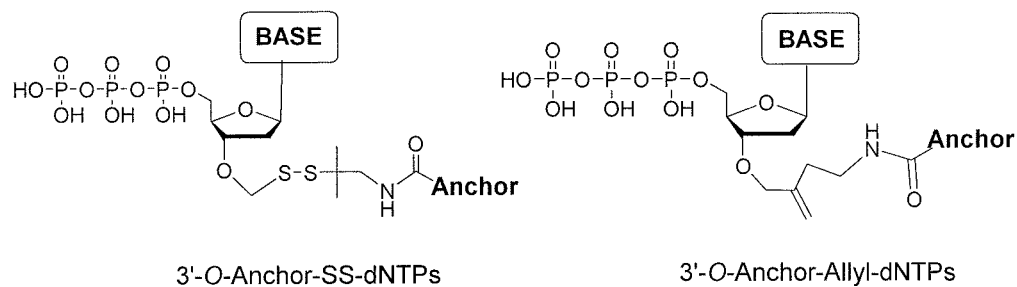
Figure 64:
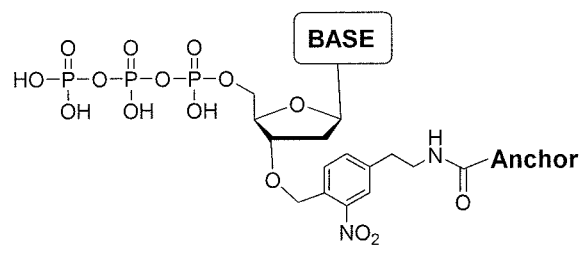
Figure 71:
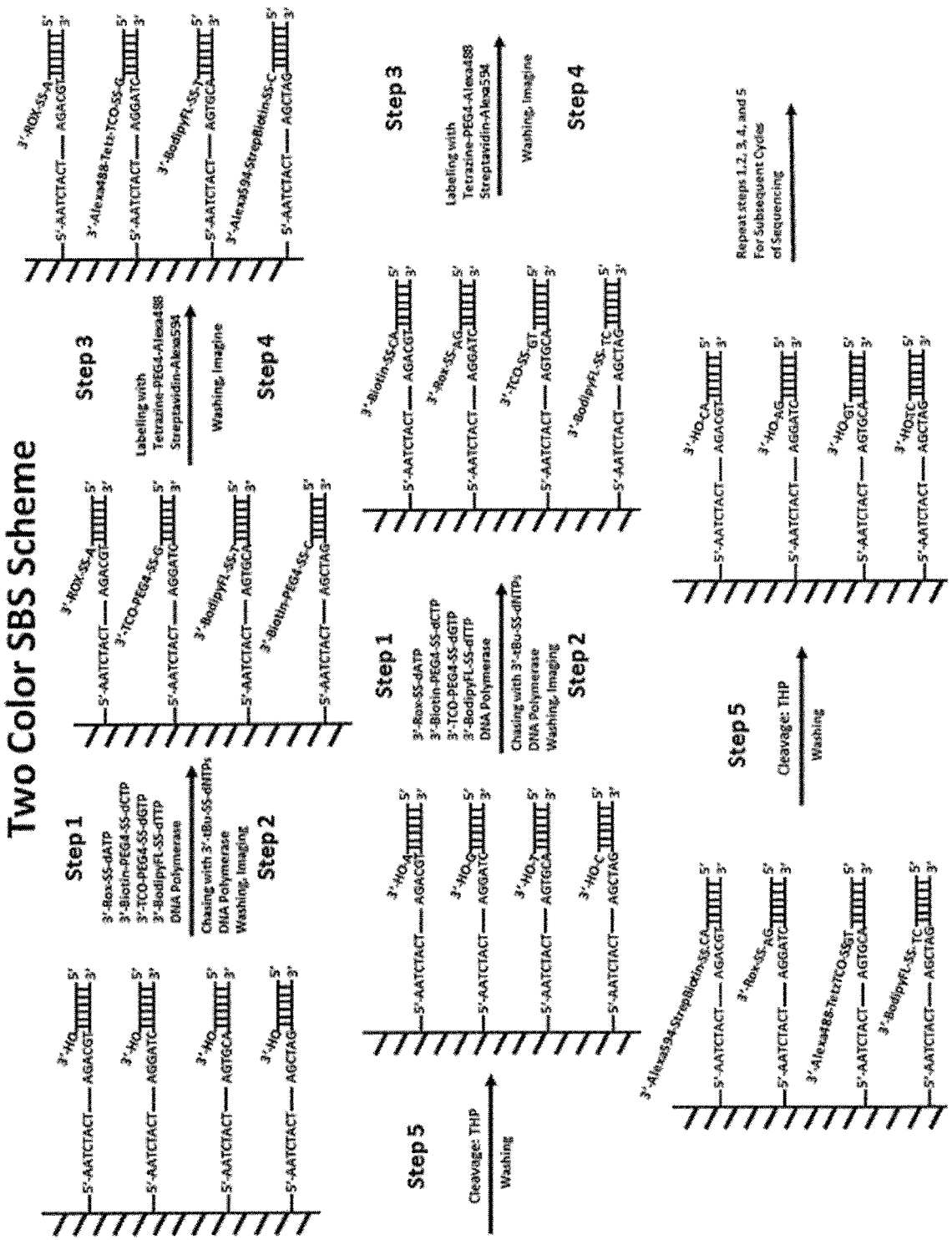

FIG. 64: Structures of 3'-O-Anchor-SS(DTM)-dNTP, 3'-O-Anchor-Allyl-dNTPs, and 3'-O-Anchor-2NB-dNTPs. Combinatorial use of two from one category with the same anchor, two from another category with another anchor and their corresponding two Dye-labeled binding molecules results in 2-color DNA SBS. One specific approach is shown in FIG. 71 as an example.

Figure 65:
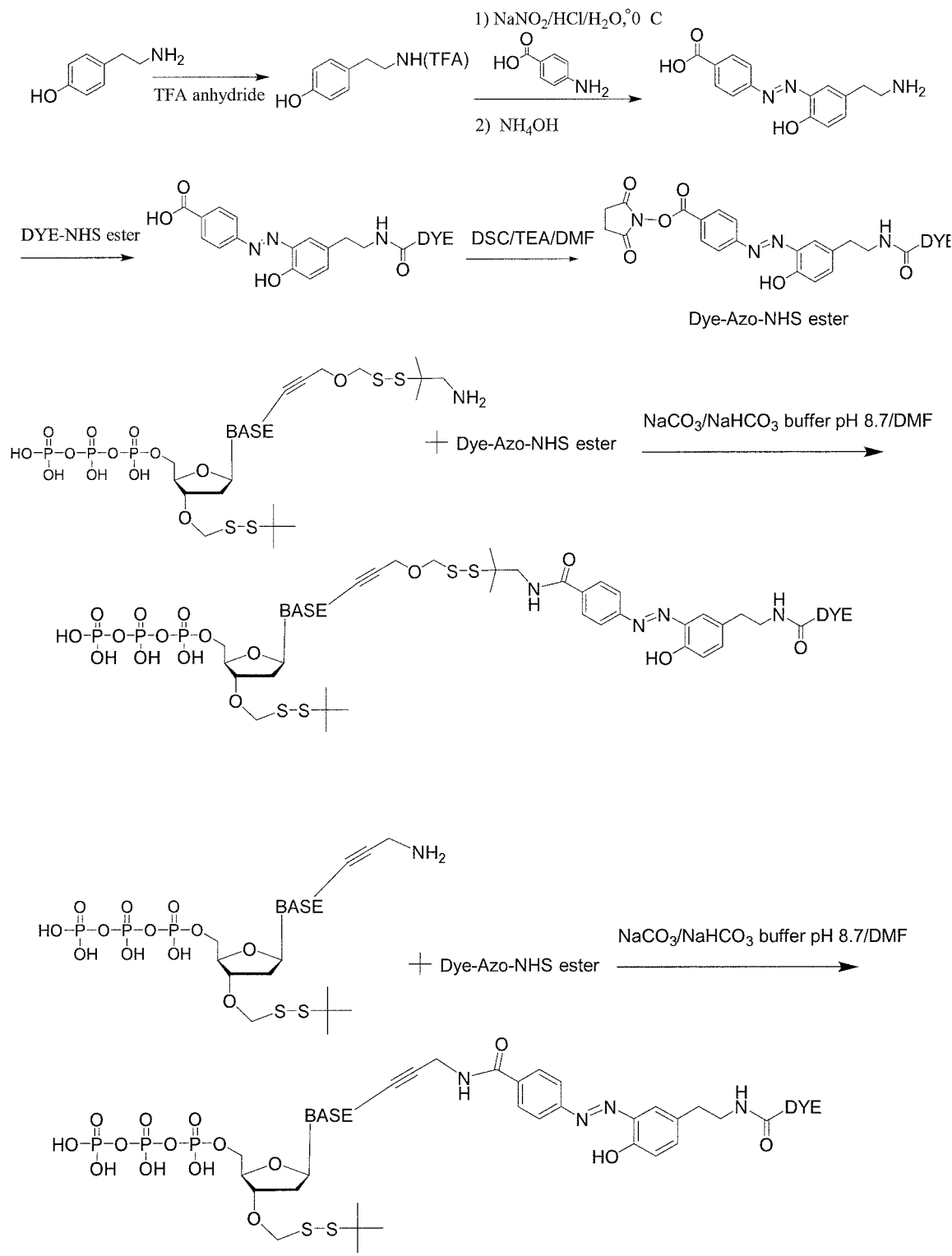

FIG. 65: Synthesis of Azo Linker and general method to synthesize 3'-O-SS(DTM)-dNTP-SS-Azo-Dye. The amino acid derivative of the Azo linker molecule is synthesized using the well-established diazonium coupling reaction. The resulting compound is coupled with Dye NHS ester giving the dye labeled acid derivative of the Azo linker, which can be further converted to the NHS ester by treatment with DSC and TEA. The product is then coupled to the amino group of 3'-O-SS(DTM)-dNTP-SS-NH$_2$ yielding 3'-O-SS(DTM)-dNTP-SS-Azo-Dye.

Figure 66:
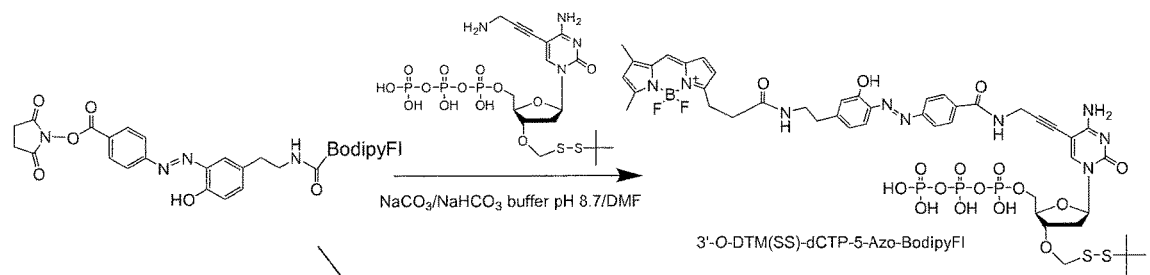
Figure 66:
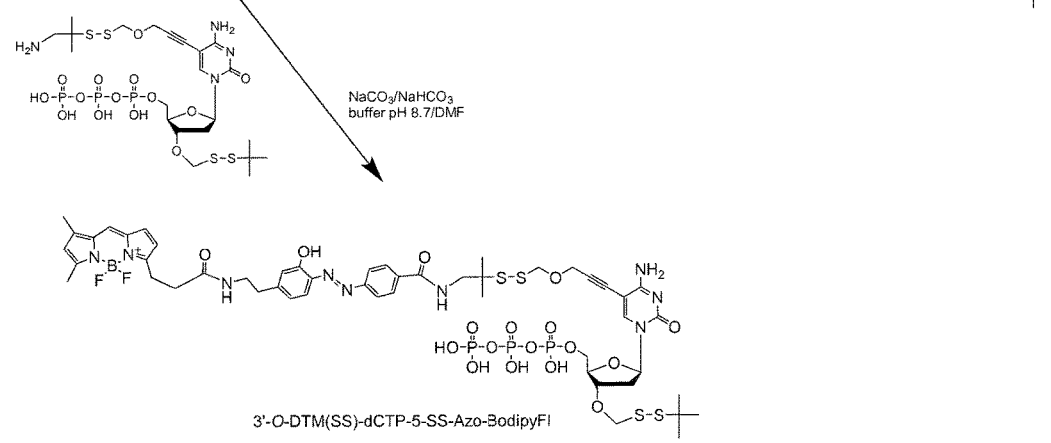
Figure 66:
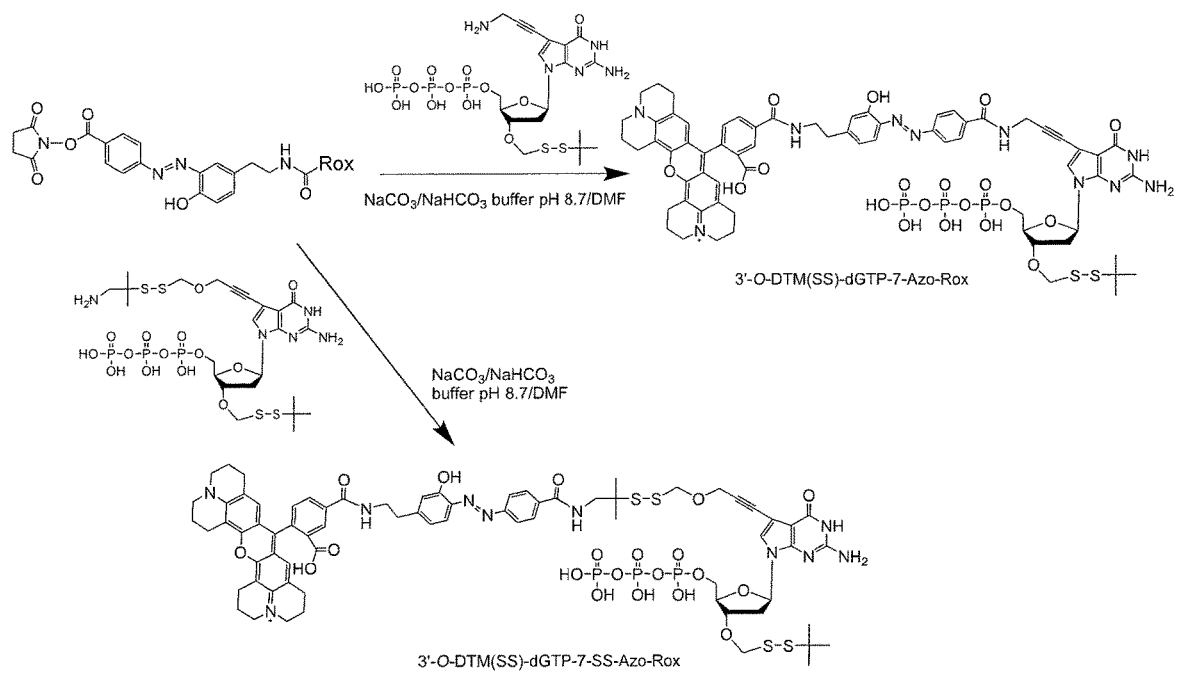

FIG. 66: Example synthesis 3'-O-SS(DTM)-dGTP-SS-Azo-Rox and 3'-O-SS(DTM)-dTTP-SS-Azo-BodipyFL. Rox and BodipyFL labeled Azo Linker NHS esters are coupled with 3'-O-SS(DTM)-dGTP-SS-NH$_2$ and 3'-O-SS (DTM)-dTTP-SS-NH2 giving 3'-O-SS(DTM)-dGTP-SS-Azo-Rox and 3'-O-SS(DTM)-dTTP-SS-Azo-BodipyFL.

Figure 67:
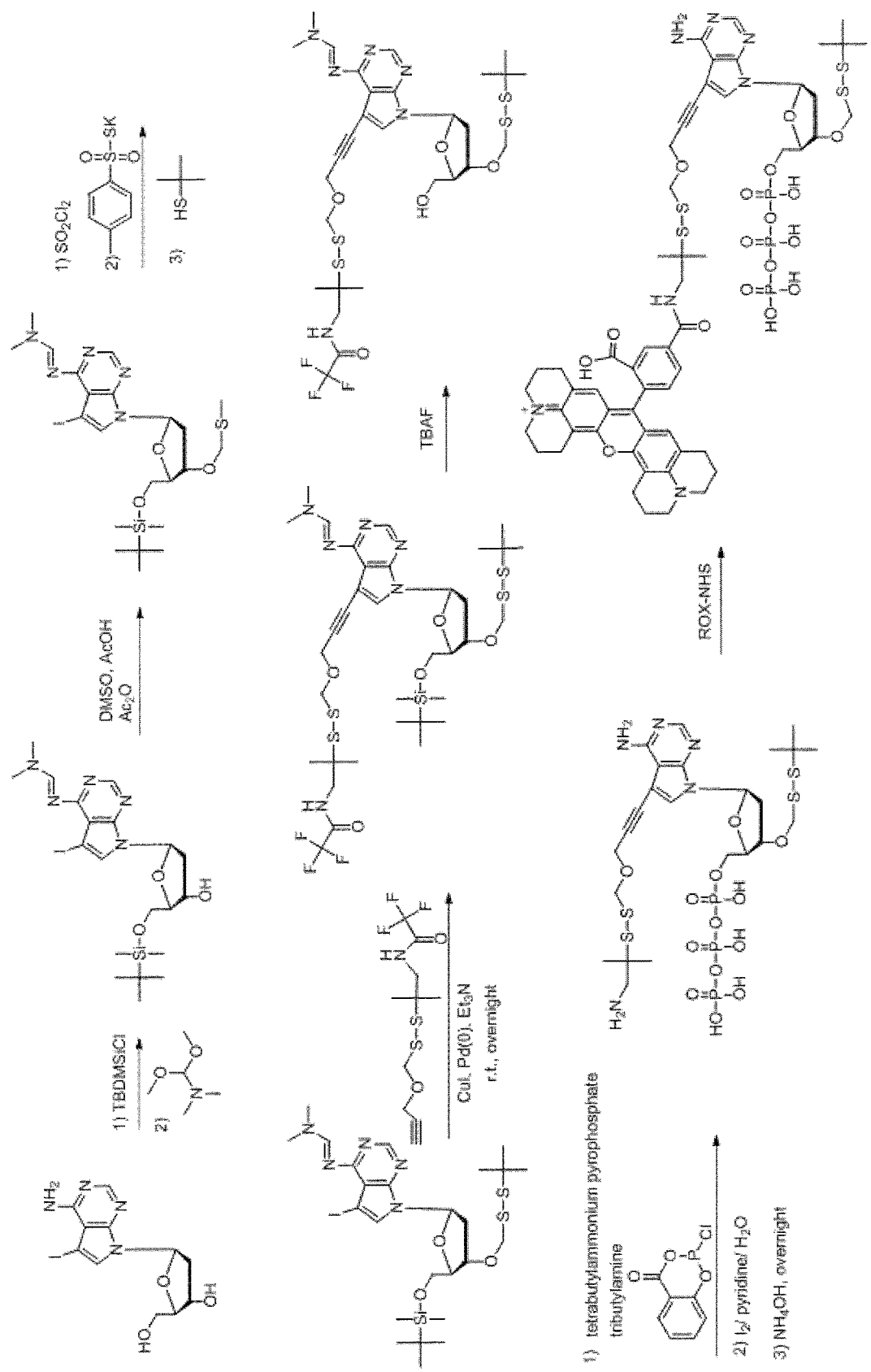

FIG. 67: Synthesis of 3'-O-SS(DTM)-dATP-SS-Rox.

Figure 68:
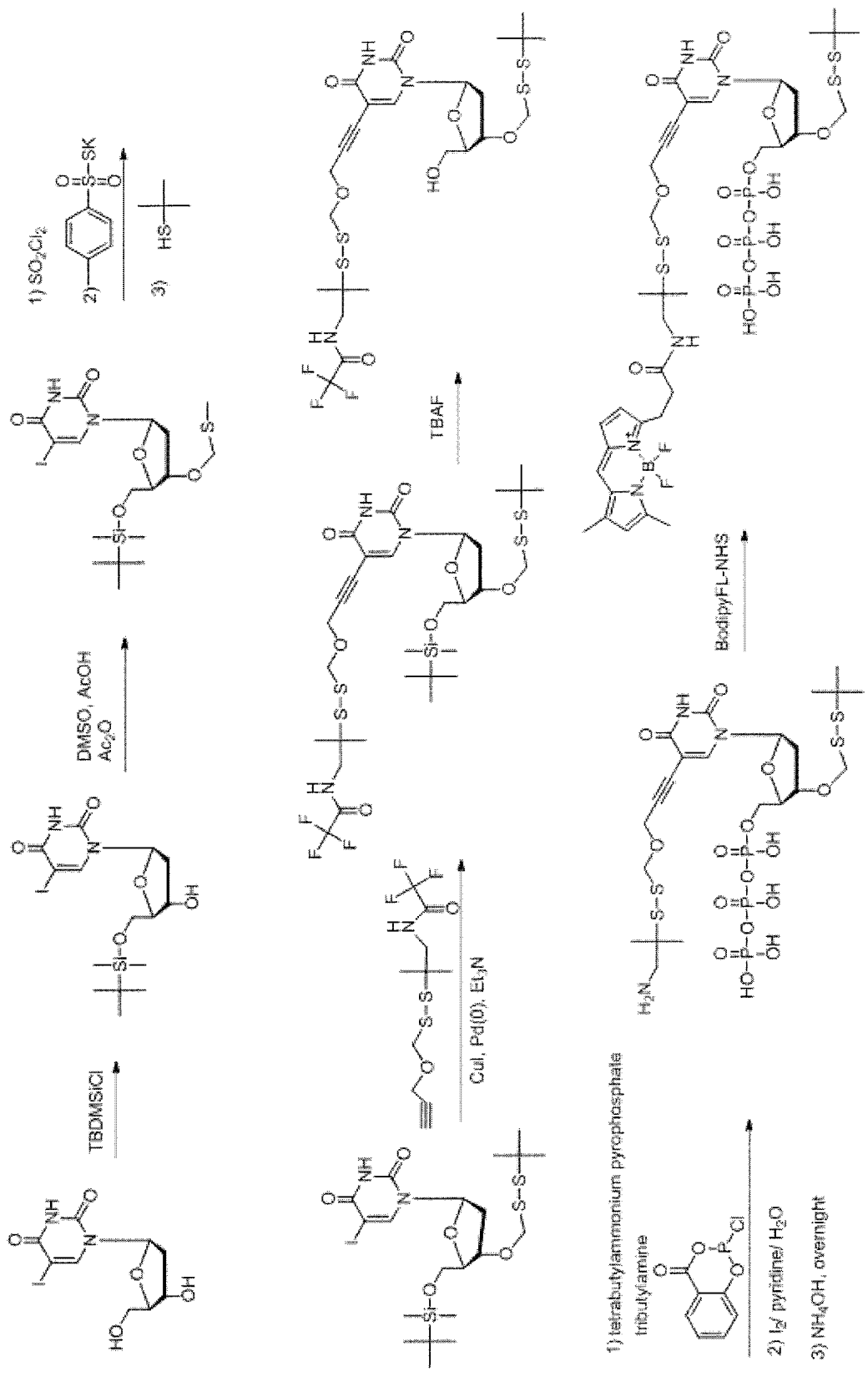

FIG. 68: Synthesis of 3'-O-SS(DTM)-dUTP-SS-BodipyFL.

Figure 69:
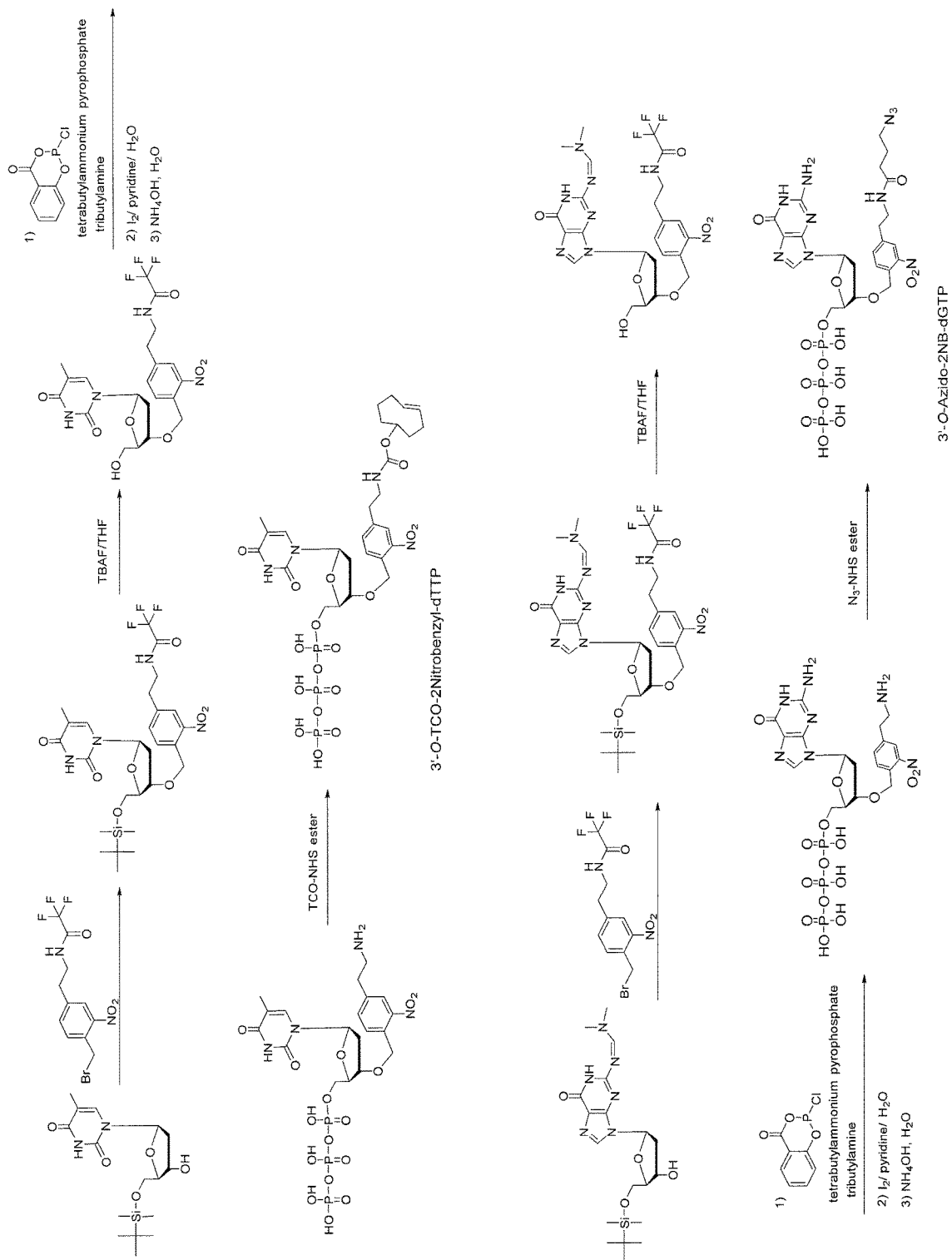

FIG. 69: Example syntheses of 3'-O-Anchor-2NB-dNTP (3'-O-TCO-2-Nitrobenzyl-dTTP and 3'-O-Azido-2-Nitrobenzyl-dGTP).

Figure 70:
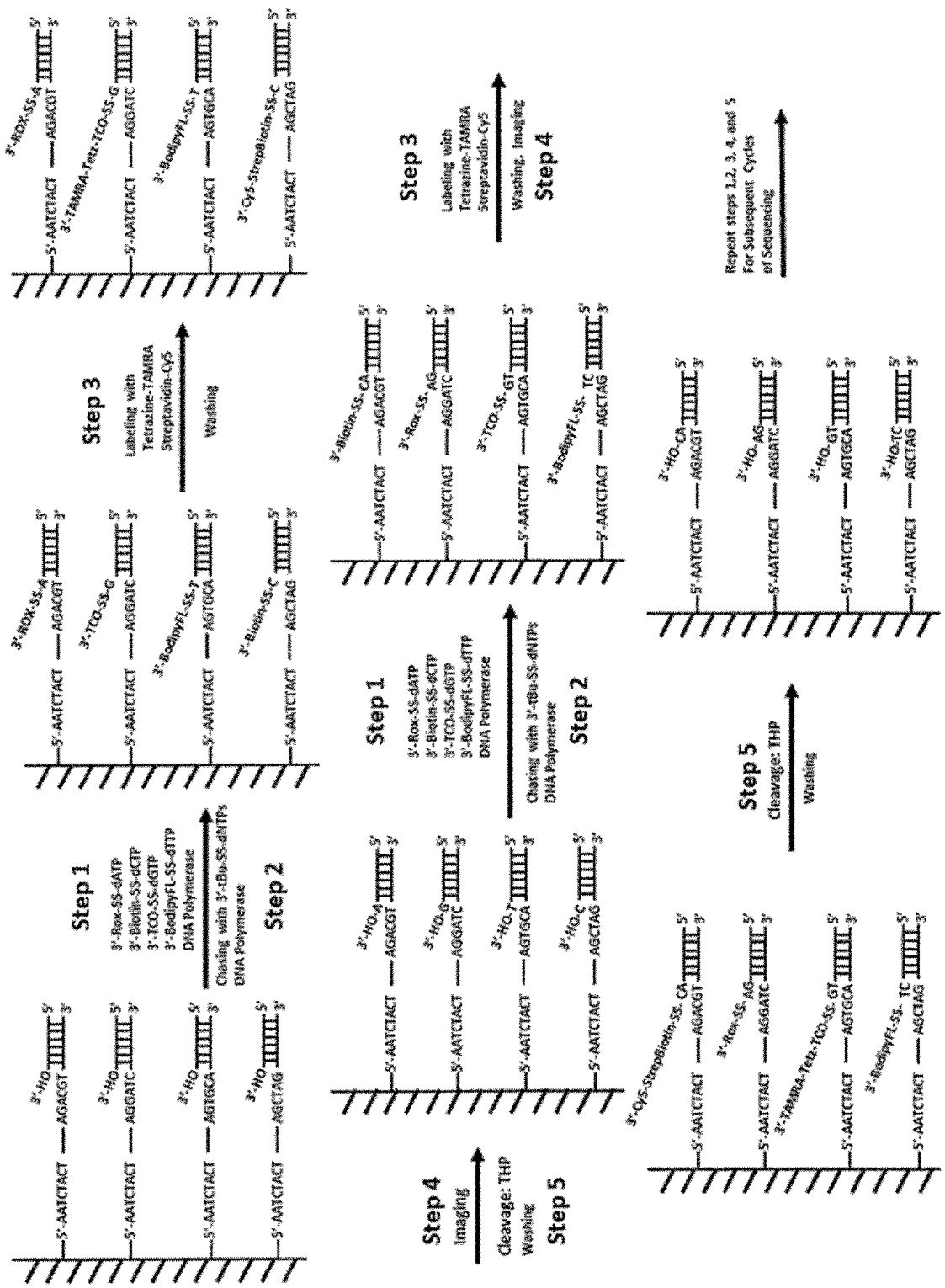

FIG. 70. Use of 3'-O-Dye-SS(DTM)-dNTPs (3'-O-Rox-PEG4-SS-dATP and 3'-O-BodipyFL-SS-dTTP), 3'-O-Anchor-SS(DTM)-dNTPs (3'-O-TCO-SS-dGTP and 3'-O-Biotin-SS-dCTP) with their corresponding Dye Labeled Binding Molecules (TAMRA Labeled Tetrazine and Cy5 Labeled Streptavidin) to perform 4-color DNA SBS. Step 1, addition of DNA polymerase and the four nucleotide analogues (3'-O-Rox-PEG$_4$-SS-dATP, 3'-O-BodipyFL-SS-dTTP, 3'-O-TCO-SS-dGTP and 3'-O-Biotin-SS-dCTP) to the immobilized primed DNA template enables the incorporation of the complementary nucleotide analogue to the growing DNA strand to terminate DNA synthesis. Step 2, Chase: addition of the DNA polymerase and four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl (SS)-dTTP and 3'-O-t-Butyldithiomethyl(SS)-dGTP) to the immobilized primed DNA template enables the incorporation of the complementary 3'-O-SS(DTM)-nucleotide analogue to the growing DNA strands that were not extended with one of the dye or anchor labeled dNTPs in step 1. The growing DNA strands are terminated with one of the four dye or anchor labeled nucleotide analogues (A, C, G, T) or the same one of the four nucleotide analogues (A, C, G, T) without dye or anchor. Step 3, Next, the dye labeled binding molecules (TAMRA labeled tetrazine and Cy5 labeled streptavidin) are added to the DNA extension products, which will specifically connect with the two unique "anchor" moieties (TCO and biotin) on each DNA extension product, to enable the labeling of each DNA product terminated with each of the two nucleotide analogues (G and C) with two distinct fluorescent dyes (labeled with TAMRA for G and labeled with Cy5 for C). Step 4, after washing away the unbound dye labeled binding molecules, detection of the unique fluorescence signal from each of the fluorescent dyes on the DNA products allows the identification of the incorporated nucleotide for sequence determination. Next, in Step 5, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 55

FIG. 71. Use of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG4-SS-dGTP and 3'-O-Biotin-PEG4-SS-dCTP) with their corresponding Dye Labeled Binding Molecules (Alexa488-PEG4 Labeled Tetrazine and Alexa594 Labeled Streptavidin) to perform 2-color DNA SBS. Demonstration of Successful 2-Color Continuous Sequencing Using a Combination of 3'-O-Dye-SS(DTM)-dNTPs and 3'-O-Anchor-SS(DTM)-dNTPs with their Corresponding Dye Labeled Binding Molecules on Immobilized DNA Templates (Scheme Z2 and FIG. 56). Use of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG4-SS-dGTP and 3'-O-Biotin-PEG4-SS-dCTP) with their corresponding Dye Labeled Binding Molecules (Alexa488-PEG4 Labeled Tetrazine and Alexa594 Labeled Streptavidin) to perform 2-color DNA SBS. Although 4 different dyes have been used in this experiment, Rox and Alexa594 have very similar absorption and emission spectra, as do BodipyFL and Alexa488. Hence this is described as a 2-color experiment. Step 1, addition of DNA polymerase and the four nucleotide analogues (3'-O-Rox-SS-dATP, 3'-O-BodipyFL-SS-dTTP, 3'-O-TCO-PEG4-SS-dGTP and 3'-O-Biotin-PEG4-SS-dCTP) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the growing DNA strands that were not extended with one of the dye or anchor labeled dNTPs in step 1. The growing DNA strands are terminated with one of the four dye or anchor labeled nucleotide analogues (A, C, G, T) or the same one of the four nucleotide analogues (A, C, G, T) without dye or anchor. Step 3, Next, the dye labeled binding molecules (Alexa488-PEG labeled tetrazine and Alexa594 labeled streptavidin) are added to the DNA extension products, which will specifically connect with the two unique "anchor" moieties (TCO and biotin) on each DNA extension product, to enable the labeling of each DNA product terminated with each of the two nucleotide analogues (G and C) with two distinct fluorescent dyes (labeled with Alexa488 for G and labeled with Alexa594 for C). Step 4, after washing away the unbound dye labeled binding molecules, detection of the unique fluorescence signal from each of the fluorescent dyes on the DNA products allows the identification of the incorporated nucleotide for sequence determination. Next, in Step 5, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 57.

Figure 72:
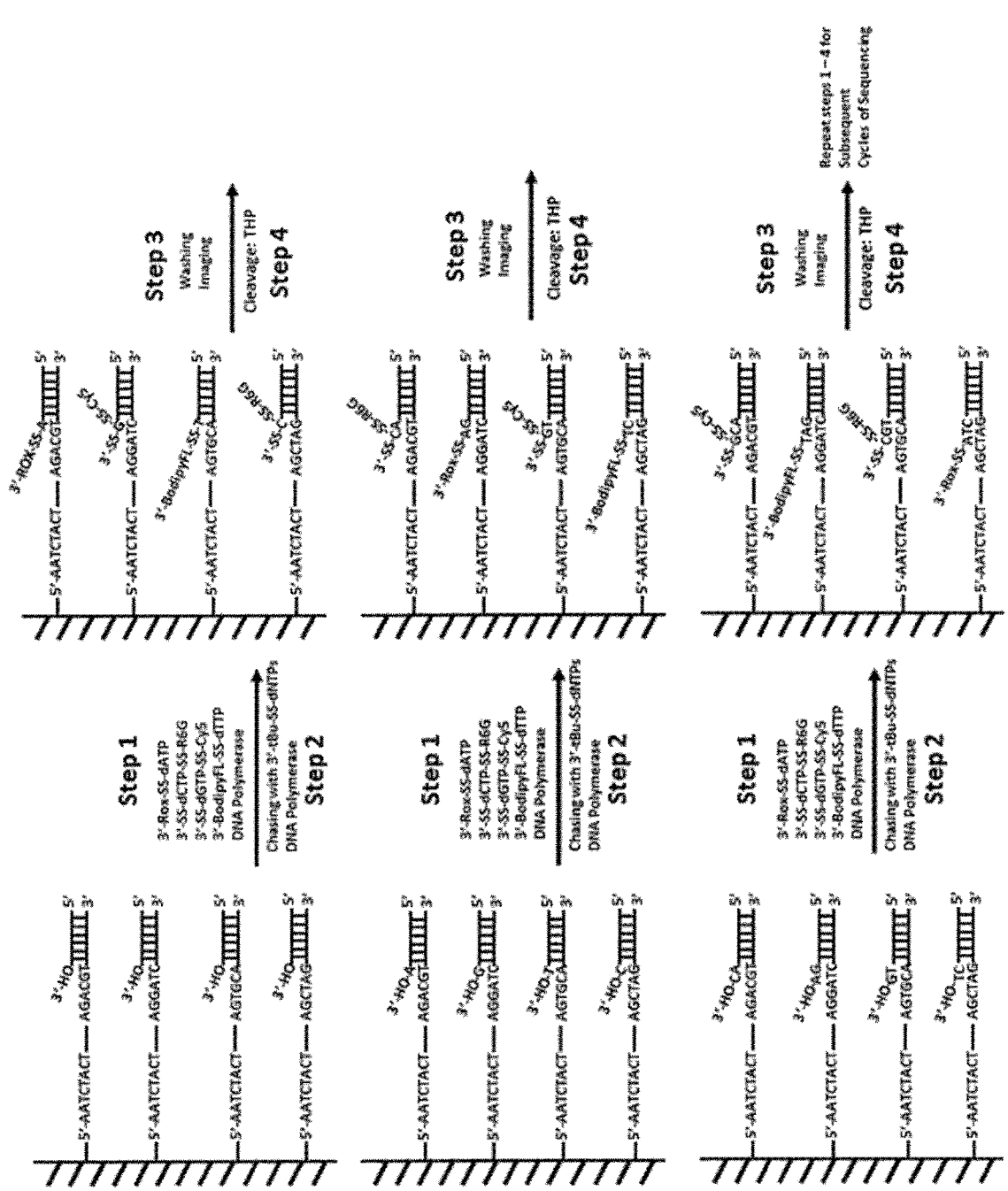

FIG. 72. Use of 3'-O-SS(DTM)-dNTP-SS-Dyes (3'-O-SS-dGTP-7-SS-Cy5, 3'-O-SS-dCTP-5-SS-R6G); 3'-O-Dye-SS(DTM)-dNTPs (3'-O-Rox-PEG4-SS-dATP and 3'-O-BodipyFL-SS-dTTP) for 4-color DNA SBS. Use of 3'-O-SS(DTM)-dNTP-SS-Dyes (3'-O-SS-dGTP-7-SS-Cy5, 3'-O-SS-dCTP-5-SS-R6G); 3'-O-Dye-SS(DTM)-dNTPs (3'-O-Rox-PEG4-SS-dATP and 3'-O-BodipyFL-SS-dTTP) for 4-color DNA SBS. Step 1, Addition of DNA polymerase and the four nucleotide analogues (3'-O-SS-dGTP-7-SS-Cy5, 3'-O-SS-dCTP-5-SS-R6G, 3'-O-Rox-PEG$_4$-SS-dATP and 3'-O-BodipyFL-SS-dTTP) to the immobilized primed DNA template enables the incorporation of the complementary dye labeled nucleotide analogue to the growing DNA strand. The growing DNA strand is terminated with each of the four nucleotide analogues (A, C, G, T) with the four distinct fluorescent dyes. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four nucleotide analogues (A, C, G, T) with the four distinct fluorescent dyes or the same one of the four nucleotide analogues (A, C, G, T) without dye. Step 3, after washing away the unincorporated nucleotide analogues, detection of the unique fluorescence signal from each of the fluorescent dyes on the DNA products allows the identification of the incorporated nucleotide for sequence determination. Next, in Step 4, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 58.

Figure 73:
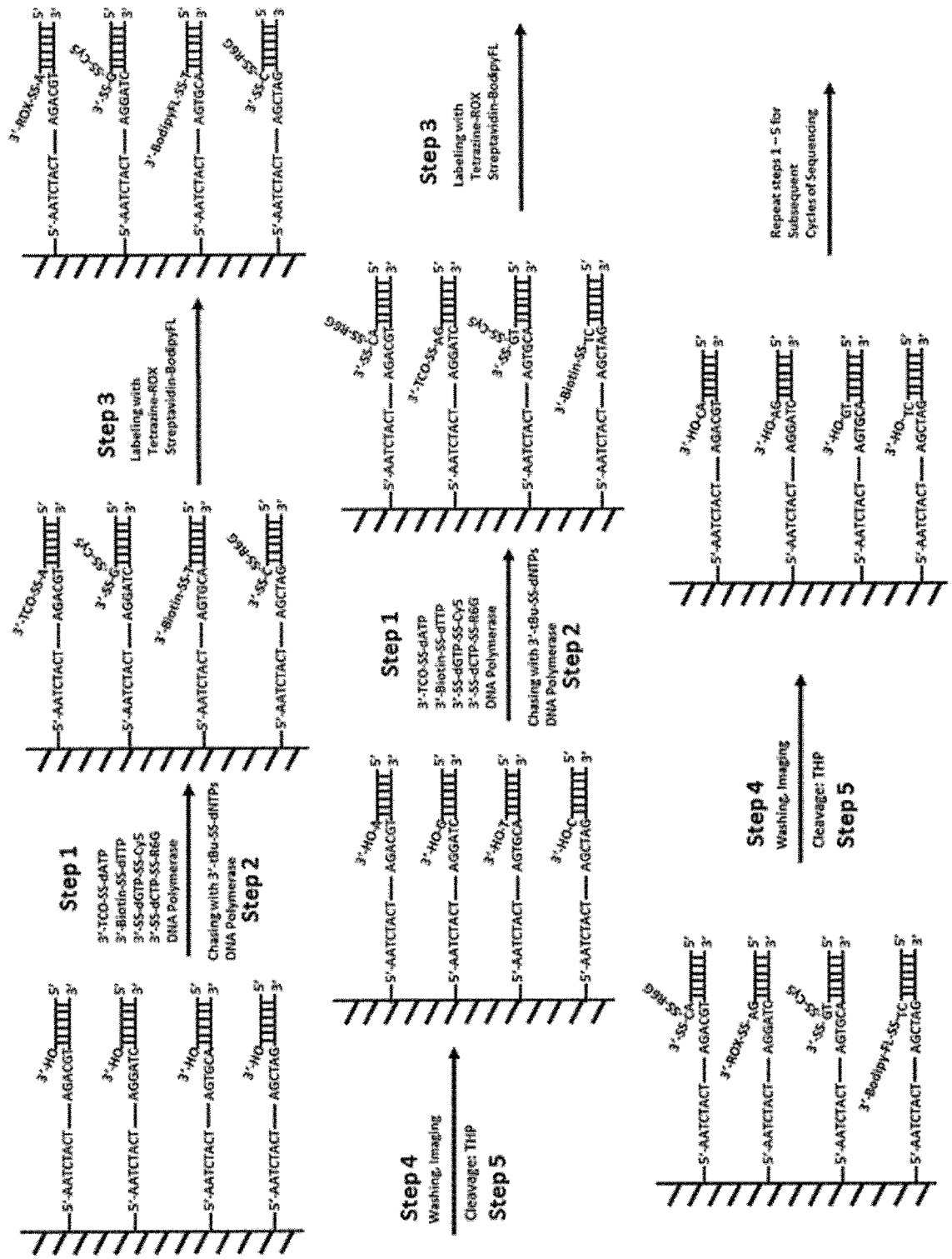

FIG. 73. Use of 3'-O-SS(DTM)-dNTP-SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Rox Labeled Tetrazine and BodipyFL Labeled Streptavidin) to perform 4-color DNA SBS. Use of 3'-O-SS(DTM)-dNTP—SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Rox Labeled Tetrazine and BodipyFL Labeled Streptavidin) to perform 4-color DNA SBS. Step 1, addition of DNA polymerase and the four nucleotide analogues (3'-O-SS-dGTP-7-SS-Cy5, 3'-O-SS-dCTP-5-SS-R6G, 3'-O-TCO-SS-dATP and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to the subset of growing DNA strands in the ensemble that were not extended with any of the dye labeled dNTPs in step 1. The growing DNA strands are terminated with one of the four dye or anchor labeled nucleotide analogues (A, C, G, T) or the same one of the four nucleotide analogues (A, C, G, T) without dye or anchor.

Step 3, next, the dye labeled binding molecules (Rox labeled tetrazine and BodipyFL labeled streptavidin) are added to the DNA extension products, which will specifically connect with the two unique "anchor" moieties (TCO and biotin) on each DNA extension product, to enable the labeling of each DNA product terminated with each of the two nucleotide analogues (A and T) with two distinct fluorescent dyes (labeled with Rox for A and labeled with BodipyFL for T). Step 4, after washing away the unbound dye-labeled binding molecules, detection of the unique fluorescence signal from each of the fluorescent dyes on the DNA products allows identification of the incorporated nucleotides for sequence determination. A Rox signal indicates incorporation of A, a BodipyFL signal indicates incorporation of T, a Cy5 signal indicates incorporation of G and an R6G signal indicates incorporation of C. Next, in Step 5, treatment of the DNA products with THP cleaves the SS linker, leading to the removal of the remaining fluorescent dye and the regeneration of a free 3'-OH group on the DNA extension product, which is ready for the next cycle of the DNA sequencing reaction. Structures of modified nucleotides used in this scheme are shown in FIG. 59.

Figure 74:
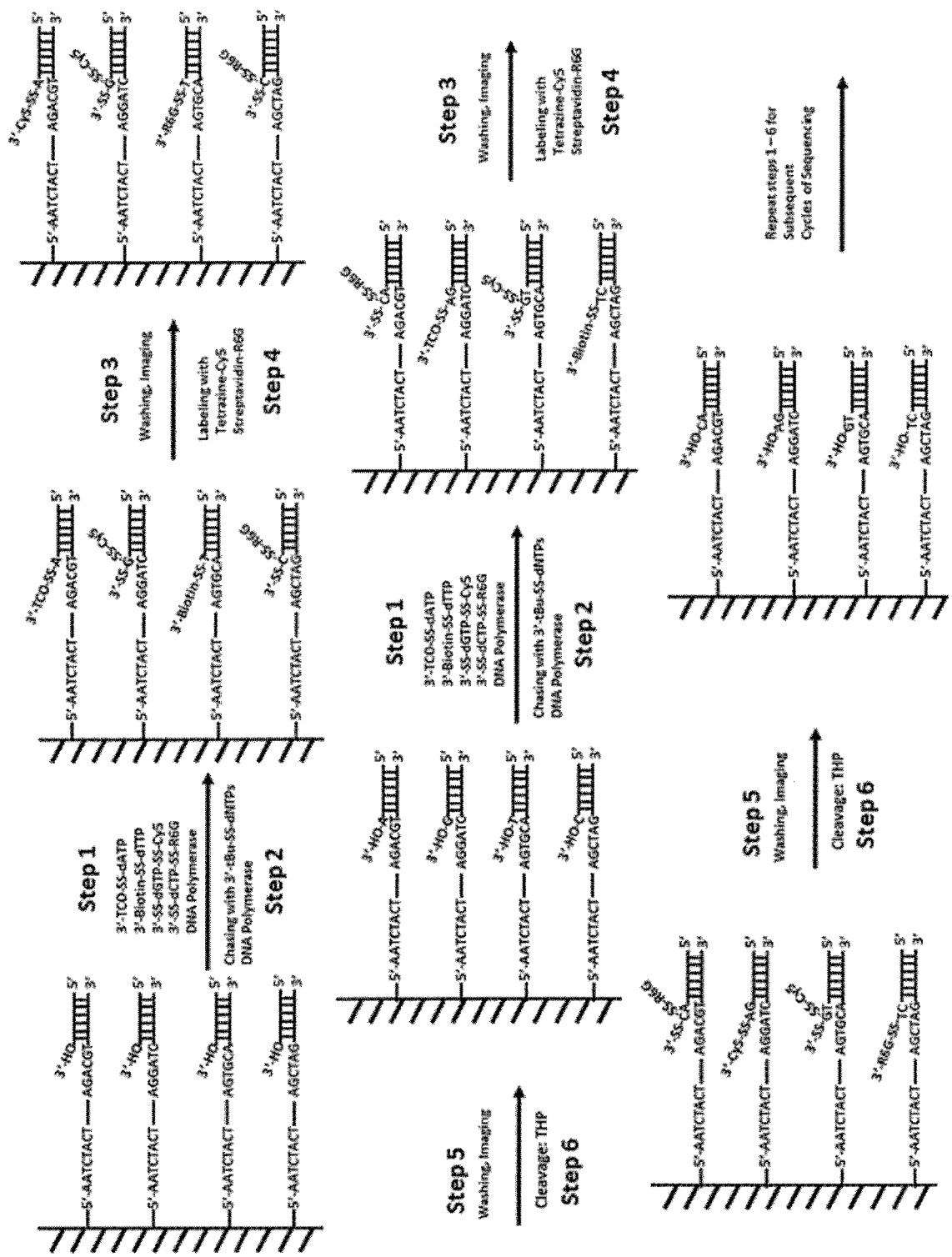

FIG. 74. Use of 3'-O-SS(DTM)-dNTP-SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Cy5 Labeled Tetrazine and R6G Labeled Streptavidin) to perform 2-color DNA SBS. Use of 3'-O-SS(DTM)-dNTP-SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Cy5 Labeled Tetrazine and R6G Labeled Streptavidin) to perform 2-color DNA SBS. Step 1, addition of DNA polymerase and the four nucleotide analogues (3'-O-SS-dGTP-7-SS-Cy5, 3'-O-SS-dCTP-5-SS-R6G, 3'-O-TCO-SS-dATP and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows identification of the incorporated nucleotide for sequence determination, Cy5 signal indicates incorporation of G, R6G signal indicates incorporation of C. Step 4, next, the dye labeled binding molecules (Cy5 labeled tetrazine and R6G labeled streptavidin) are added to the DNA extension products, which will specifically connect with the two unique "anchor" moieties (TCO and biotin) on each DNA extension product, to enable the labeling of each DNA product terminated with each of the two nucleotide analogues (A and T) with two distinct fluorescent dyes (labeled with Cy5 for A and labeled with R6G for T). Step 5, after washing away the unattached labels, a second round of detection of the unique fluorescence signal from each of the fluorescent dyes on the DNA products allows the identification of the incorporated nucleotide for sequence determination. Appearance of a Cy5 signal indicates incorporation of A, R6G signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. Structures of modified nucleotides used in this scheme are shown in FIG. 60.

Figure 75:
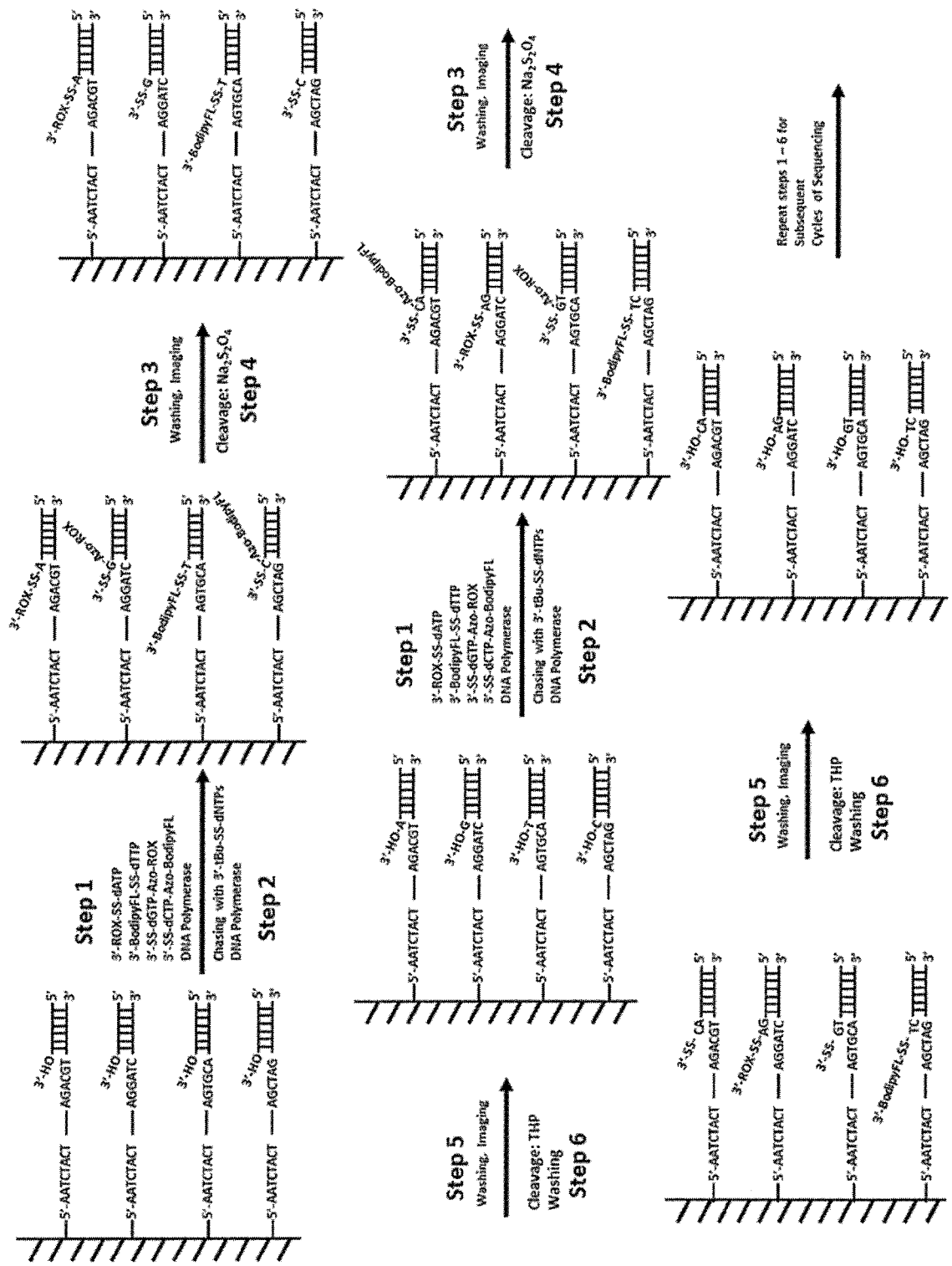

FIG. 75. Use of 3'-O-SS(DTM)-dNTP-Azo-Dyes (3'-O-SS-dGTP-7-Azo-Rox, 3'-O-SS-dCTP-5-Azo-BodipyFL); 3'-O-Dye-SS(DTM)-dNTPs (3'-O-Rox-SS-dATP, 3'-O-BodipyFL-SS-dTTP) to perform 2-color DNA SBS. Use of 3'-O-SS(DTM)-dNTP-Azo-Dyes (3'-O-SS-dGTP-7-Azo-Rox, 3'-O-SS-dCTP-5-Azo-BodipyFL); 3'-O-Dye-SS(DTM)-dNTPs (3'-O-Rox-SS-dATP, 3'-O-BodipyFL-SS-dTTP) to perform 2-color DNA SBS. Step 1, addition of DNA polymerase and the four nucleotide analogues (3'-O-SS-dGTP-7-Azo-Rox, 3'-O-SS-dCTP-5-Azo-BodipyFL, 3'-O-Rox-SS-dATP and 3'-O-BodipyFL-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows the identification of the incorporated nucleotide for sequence determination. Rox signal indicates incorporation of A or G, BodipyFL signal indicates incorporation of C or T. Step 4, cleavage of Azo linker by adding sodium dithionite ($Na_2S_2O_4$) to the elongated DNA strands results in removal of Rox from incorporated G and BodipyFL from incorporated C. Step 5, after washing away the cleaved dyes, a second round of detection of the unique fluorescence signal from each of the fluorescent dyes on the DNA products allows the identification of the incorporated nucleotide for sequence determination. Disappearance of Rox signal indicates incorporation of G, and disappearance of BodipyFL signal indicates incorporation of C. Remaining Rox signal indicates incorporation of A, and remaining BodipyFL signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. The presence of an additional SS linkage between the Azo group and the base results in the production of a shorter scar on the incorporated nucleotide after THP treatment which should result in longer reads. Structures of modified nucleotides used in this scheme are shown in FIG. 61.

FIG. 76. Use of 3'-O-Anchor-SS(DTM)-dNTPs (3'-O—$N_3$-SS-dATP and 3'-O-TCO-SS-dCTP) and 3'-O-Anchor-2-Nitrobenzyl-dNTPs (3'-O—$N_3$-2-Nitrobenzyl-dGTP and 3'-O-TCO-2-Nitrobenzyl-dTTP) with their corresponding Dye Labeled Binding Molecules (BodipyFL Labeled DBCO and Rox labeled Tetrazine) to perform 2-color DNA SBS. Use of 3'-O-Anchor-SS(DTM)-dNTPs (3'-O—$N_3$-SS-dATP and 3'-O-TCO-SS-dCTP) and 3'-O-Anchor-2-Nitrobenzyl-dNTPs (3'-O—$N_3$-2-Nitrobenzyl-dGTP and 3'-O-TCO-2-Nitrobenzyl-dTTP) with their corresponding Dye Labeled Binding Molecules (BodipyFL Labeled DBCO and Rox labeled Tetrazine) to perform 2-color DNA SBS. Step 1, addition of DNA polymerase and the four nucleotide analogues (3'-O—$N_3$-SS-dATP, 3'-O-TCO-SS-dCTP, 3'-O—$N_3$-2-Nitrobenzyl-dGTP and 3'-O-TCO-2-Nitrobenzyl-dTTP) to the immobilized primed DNA template enables the incorporation of the complementary nucleotide analogue to the growing DNA strand to terminate DNA synthesis. Step 2, Chase: addition of DNA polymerase and four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to the subset of growing DNA strands in the ensemble that were not extended with any of the dye labeled dNTPs in step 1. The growing DNA strands are terminated with one of the four anchor labeled nucleotide analogues (A, C, G, T) or the same one of the four nucleotide analogues (A, C, G, T) without dye or anchor. Step3, next, the dye labeled binding molecules (Rox labeled Tetrazine and BodipyFL labeled DBCO) are added to the DNA extension products, which will specifically connect with the two unique "anchor" moieties (TCO and $N_3$) on each DNA extension product, to enable the labeling of each DNA product terminated with each of the four nucleotide analogues with one of the two dyes (A and G with BodipyFL and C and T with Rox). Step 4, after washing away the unbound dye-labeled binding molecules, detection of the fluorescence signals from each of the fluorescent dyes on the DNA products allows partial identification of the incorporated nucleotides for sequence determination. A BodipyFL signal indicates incorporation of A or G, a Rox signal indicates incorporation of T or C. Next, in Step 5, treatment of the DNA products with 340 nm light cleaves the 2-Nitrobenzyl linker, leading to the removal of the fluorescent dye and the regeneration of a free 3'-OH group on the DNA extension products extended with either a G or T. After washing, in Step 6 imaging is carried out a second time to detect remaining fluorescent signals. Loss of a BodipyFL signal indicates that the incorporated nucleotide was a G, a remaining Bodipy FL signal indicates that the incorporated nucleotide was an A; similarly loss of a Rox signal indicates that the incorporated nucleotide was a T, a remaining Rox signal indicates that the incorporated nucleotide was a C. Finally, in Step 7, treatment with THP cleaves any dye remaining on incorporated A or C, and restores the 3'-OH on those nucleotides as well. At this point, the extension products are ready for the next cycle of the DNA sequencing reaction. Structures of modified nucleotides used in this scheme are shown in FIG. 63.

Figure 77:
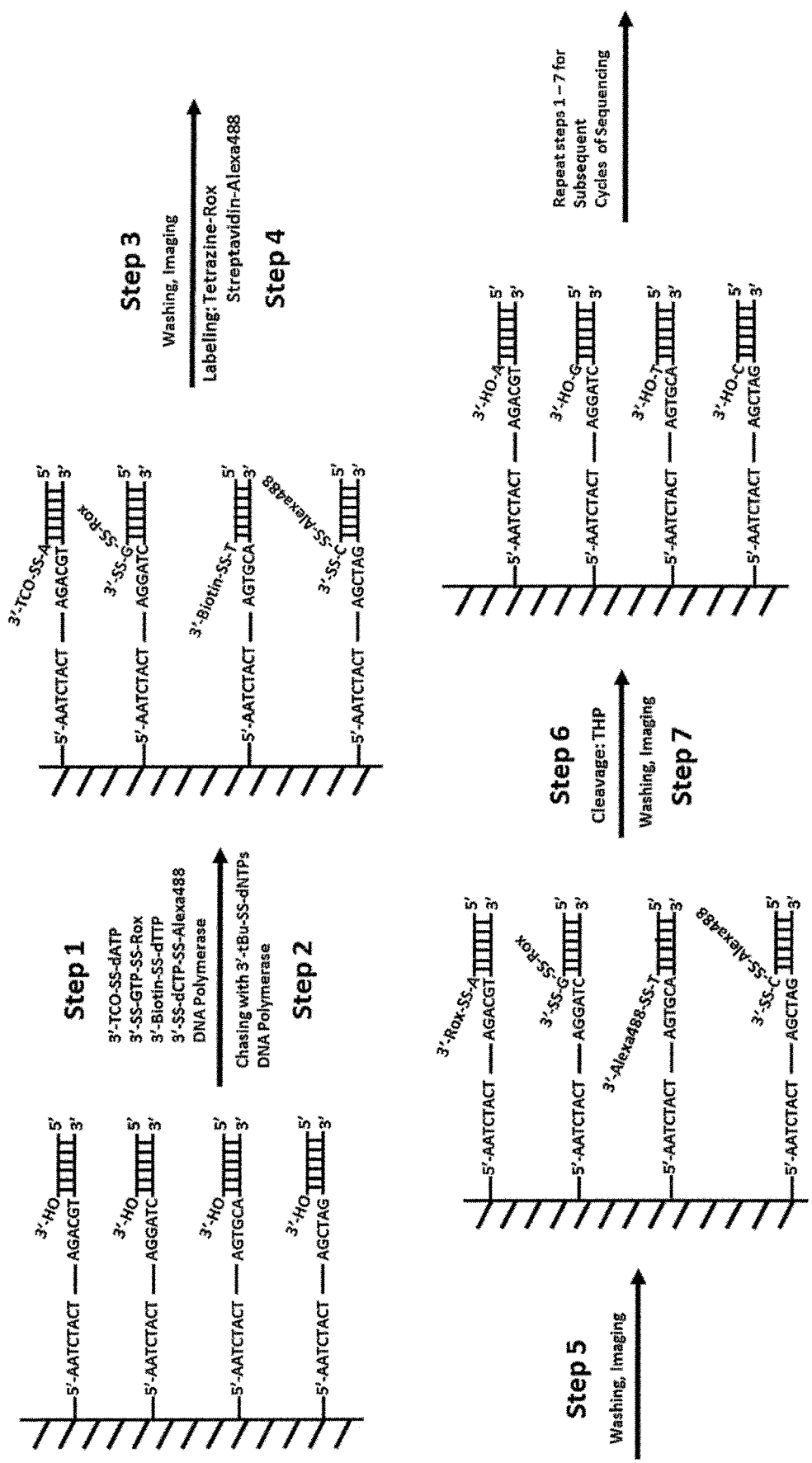

FIG. 77: (Scheme A) Use of 3'-O-SS(DTM)-dNTP-SS-Dyes (3'-O-SS-dGTP-7-SS-Rox, 3'-O-SS-dCTP-5-SS-Alexa488); 3'-O-Anchor-SS(DTM)-dNTPs (3'-O-TCO-SS-dATP, 3'-O-Biotin-SS-dTTP) and appropriate dye labeled anchor binding molecules (Tetrazine-Rox, Streptavidin-Alexa488) to perform 2-color DNA SBS. Step 1, addition of DNA polymerase and the four nucleotide analogues (3'-O-SS-dGTP-7-SS-Rox, 3'-O-SS-dCTP-5-SS-Alexa488, 3'—O-TCO-SS-dATP and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. Step 3, after washing away the unincorporated dye labeled nucleotide analogues, detection of the unique fluorescence signal from each of the fluorescent dyes on the DNA products allows the precise identification of two of the incorporated nucleotide analogues for sequence determination. Rox signal indicates incorporation of G, Alexa488 signal indicates incorporation of C. Step 4, addition of Tetrazine-Rox and Streptavidin-Alexa488 leads to labeling of the two nucleotide analogues with 3' anchors. Step 5, after washing away the excess labeling molecules, a second round of detection of the unique fluorescence signal from each of the fluorescent dyes on the DNA products allows the identification of the incorporated nucleotide for sequence determination. Appearance of a previously undetected Rox signal indicates incorporation of A, and appearance of a previously undetected Alexa488 signal indicates incorporation of T. Next, in Step 6, treatment of the DNA products with THP cleaves the SS linker, leading to the removal of the remaining fluorescent dye and the regeneration of a free 3'-OH group on the DNA extension product. Step 7, after washing away the THP, an optional imaging step allows confirmation of absence of any remaining fluorescent label indicating readiness for the next cycle of the DNA sequencing reaction. Although Scheme A is presented here as an ensemble SBS approach, it can also be used for single molecule SBS sequencing with an appropriate imaging setup. Structures of modified nucleotide analogues used in this scheme are shown in FIG. 78.

Figure 78:
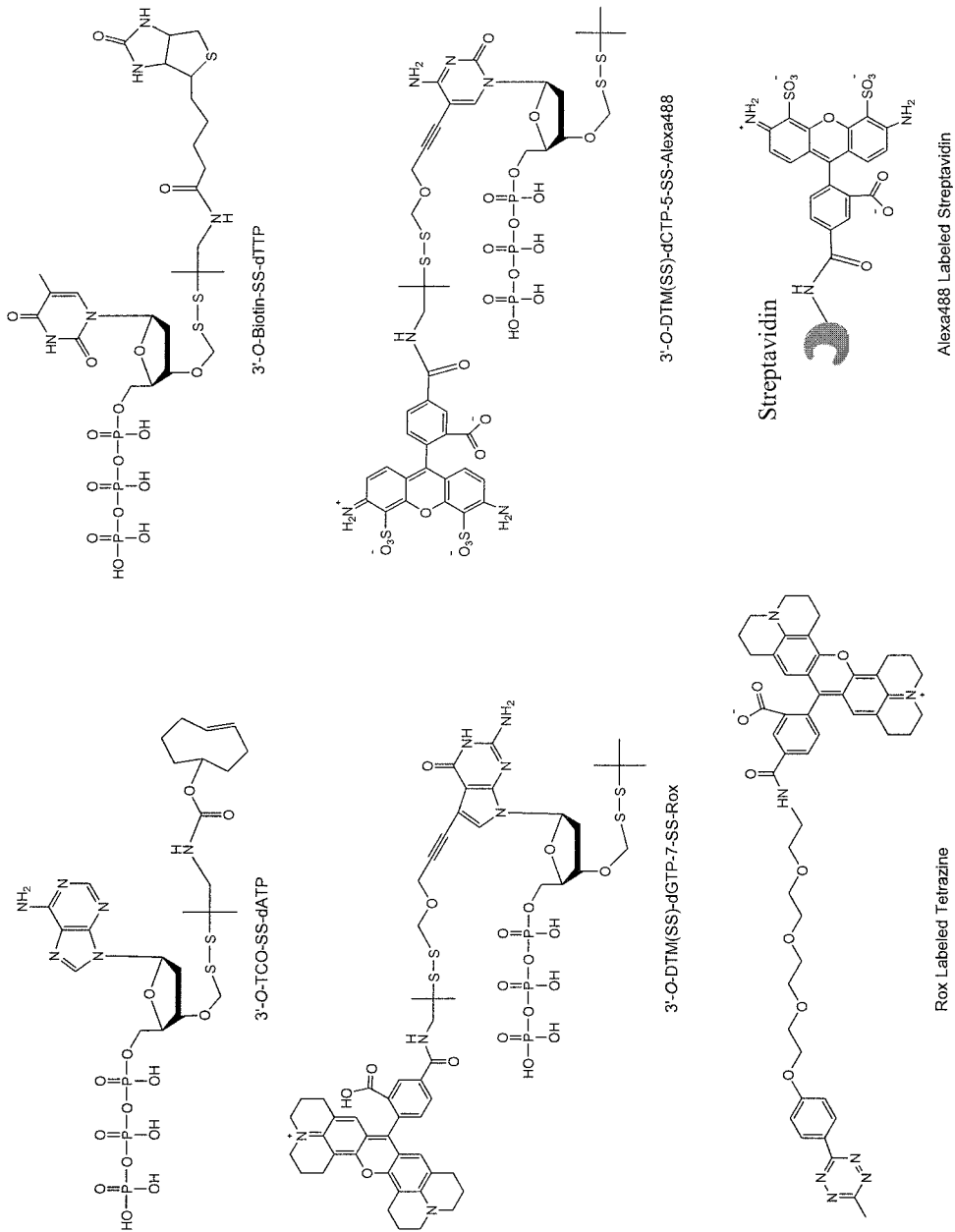

FIG. 78: Structures of 3'-O-DTM(SS)-dNTP-SS-Dye (3'-O-SS-dGTP-7-SS-Rox, 3'-O-SS-dCTP-5-SS-Alexa488), 3'-O-Anchor-SS-dNTP (3'-O-TCO-SS-dATP, 3'-O-Biotin-SS-dTTP) and the labeled binding molecules (Rox Labeled Tetrazine and Alexa 488 labeled Straptavidin) for 2-color DNA SBS as in Scheme A.

Figure 79:
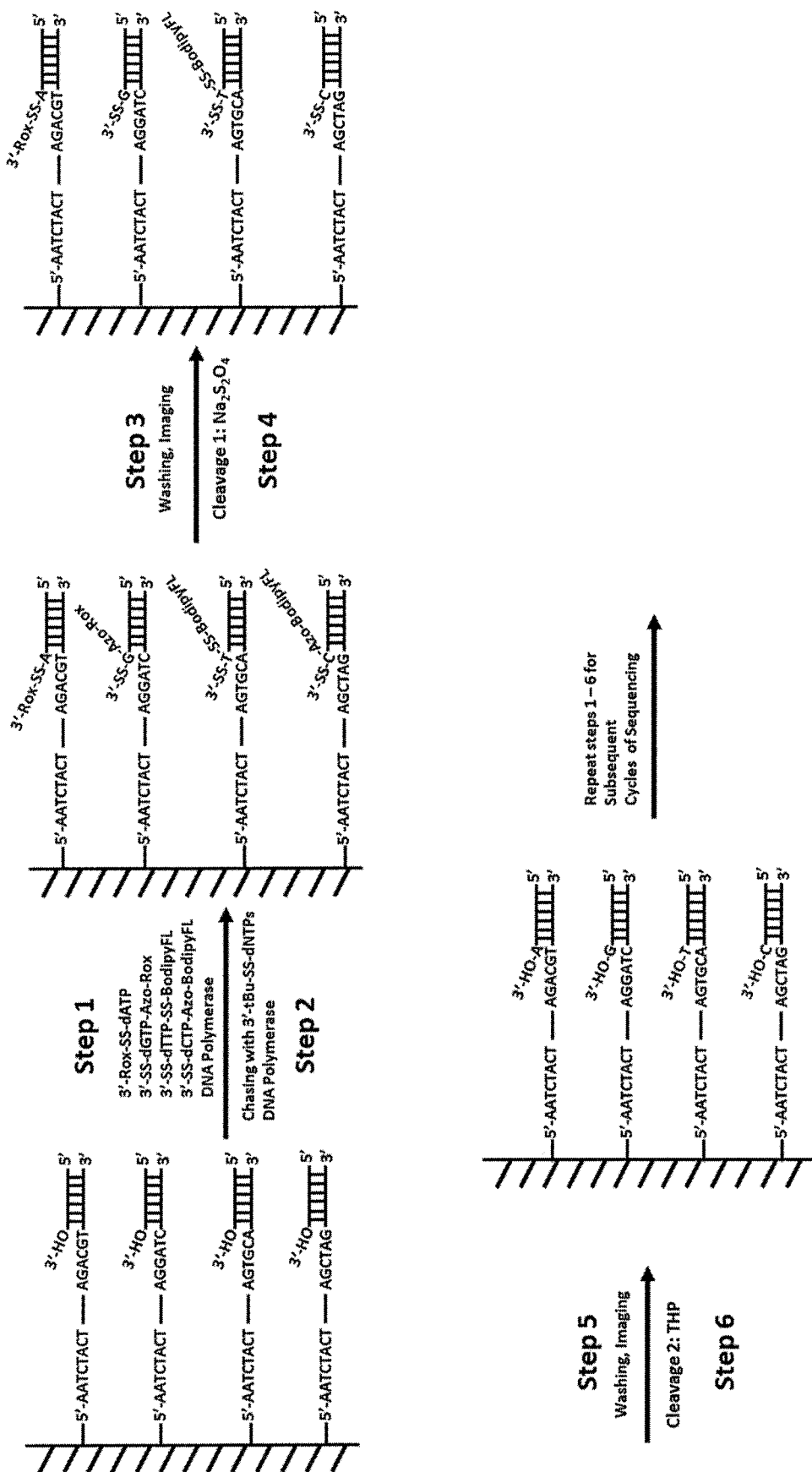

FIG. 79: (Scheme B) Use of 3'-O-SS(DTM)-dNTP-SS-Dye (3'-O-SS-dTTP-5-SS-BodipyFL), 3'-O-SS(DTM)-dNTP-Azo-Dyes (3'-O-SS-dCTP-5-Azo-BodipyFL, 3'-O-SS-dGTP-7-Azo-Rox), and 3'-O-Dye-SS(DTM)-dNTP (3'-O-Rox-SS-dATP) to perform 2-color DNA SBS. Step 1, addition of DNA polymerase and the four nucleotide analogues (3'-O-SS-dTTP-5-SS-BodipyFL, 3'-O-SS-dCTP-5-Azo-BodipyFL, 3'-O-SS-dGTP-7-Azo-Rox and 3'-0-Rox-SS-dATP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the equivalent nucleotide analogues (A, C, G, T) without dye. Step 3, after washing away the unincorporated dye labeled nucleotide analogues, detection of the fluorescence signal from the fluorescent dyes on the DNA products allows the identification of two of the incorporated nucleotide analogues for sequence determination. Rox signal indicates incorporation of A or G, BodipyFL signal indicates incorporation of either C or T. Step 4, treatment with sodium dithionite cleaves the Azo linker. Step 5, after washing away the cleaved dyes, a second round of detection of any remaining fluorescence signal allows the identification of the incorporated nucleotide for sequence determination. Loss of a BodipyFL signal indicates incorporation of C, remaining BodipyFL signal indicates incorporation of T. Loss of Rox signal indicates incorporation of G, remaining Rox signal indicates incorporation of A. Next, in Step 6, treatment of the DNA products with THP cleaves the SS linker, leading to the removal of the remaining fluorescent dye and the regeneration of a free 3'-OH group on the DNA extension product. Although Scheme B is presented here as an ensemble SBS approach, it can also be used for single molecule SBS sequencing with an appropriate imaging setup. Structures of modified nucleotide analogues used in this scheme are shown in FIG. 80.

Figure 80:
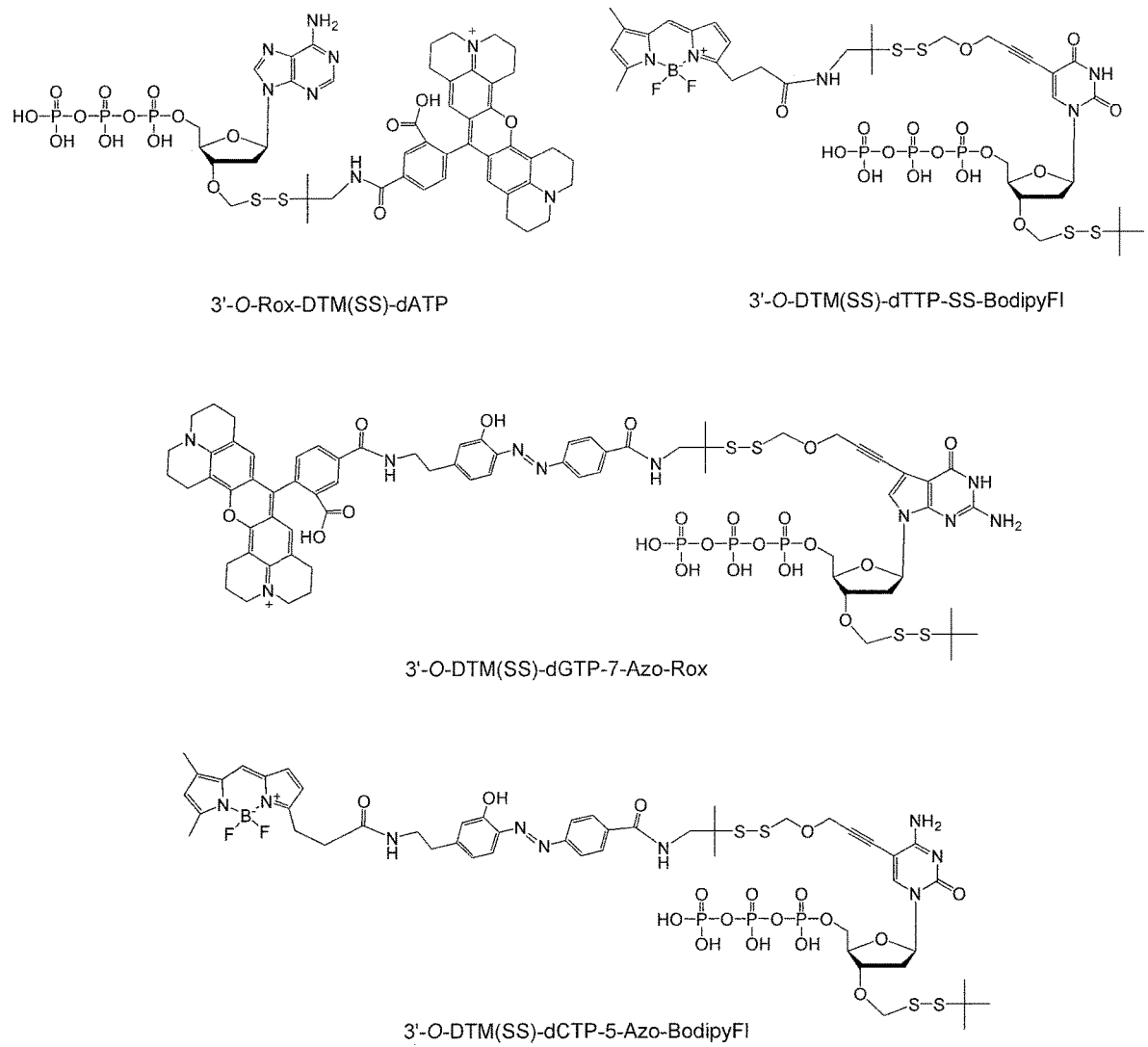

FIG. 80: Structures of 3'-O-Dye-DTM(SS)-dNTPs (3'-O-Rox-SS-dATP), 3'-O-DTM(SS)-dNTP-SS-Dye (3'-O-SS-dTTP-5-SS-BodipyFL) and 3'-O-DTM(SS)-dNTP-SS-Azo-Dyes (3'-O-SS-dGTP-7-Azo-Rox and 3'-O-SS-dCTP-5-Azo-BodipyFL) for 2-color DNA SBS as in Scheme B.

Figure 81:
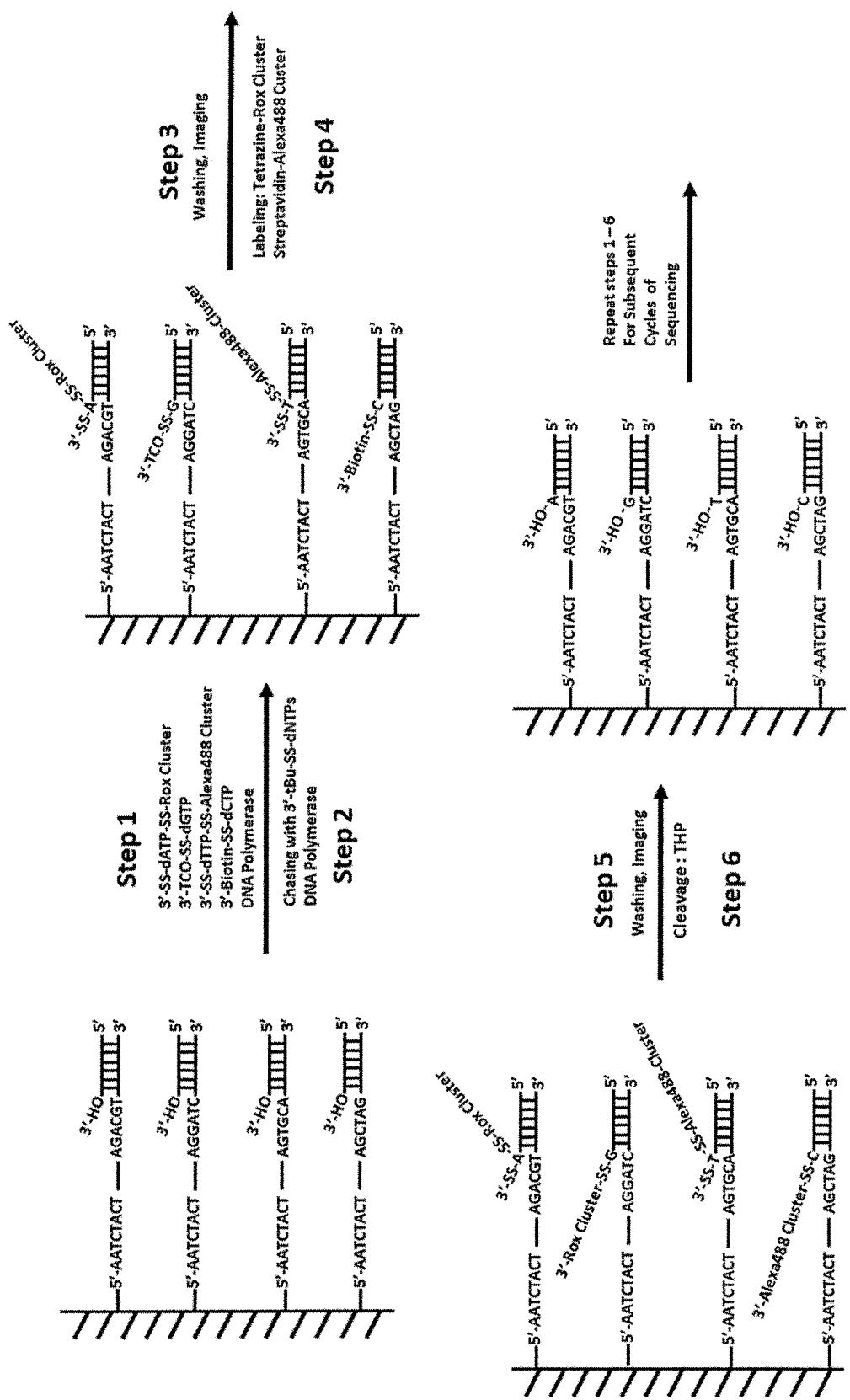

FIG. 81: (Scheme C) Use of 3'-O-Anchor-SS(DTM)-dNTPs (3'-O-TCO-SS-dGTP, 3'-O-Biotin-SS-dCTP), 3'-O-SS(DTM)-dNTP-SS-Dye Clusters (3'-O-SS-dATP-7-SS-Rox Cluster, 3'-O-SS-dTTP-5-SS-Alexa488 Cluster), and appropriate dye labeled anchor binding molecules (Tetrazine-Rox Cluster, Streptavidin-Alexa488 Cluster) to perform 2-color DNA SBS. Step 1, addition of DNA polymerase and the four nucleotide analogues (3'-O-TCO-SS-dGTP, 3'-O-Biotin-SS-dCTP, 3'-O-SS-dATP-7-SS-Rox Cluster and 3'-O-SS-dTTP-5-SS-Alexa488 Cluster) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue in case the primer was not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. In the case of single molecule sequencing, the base at this position in the growing DNA strand would not be called, but because the 3'-OH will be restored in step 6, sequencing can still be carried out beyond this point. Step 3, after washing away the unincorporated dye labeled nucleotide analogues, detection of the fluorescence signal from the fluorescent dyes on the DNA products allows the identification of two of the incorporated nucleotide analogues for sequence determination. Rox signal indicates incorporation of A, Alexa488 signal indicates incorporation of T. Step 4, addition of Rox cluster-labeled tetrazine and Alexa488 cluster-labeled streptavidin which bind to the TCO and biotin anchors respectively. Step 5, after washing away the excess labeling molecules, a second round of detection of any new fluorescence signal allows the identification of the incorporation of the remaining two nucleotide analogues for sequence determination. Appearance of a Rox signal indicates incorporation of G, appearance of an Alexa488 signal indicates incorporation of C. Next, in Step 6, treatment of the DNA products with THP cleaves the SS linker, leading to the removal of the remaining fluorescent dye and the regeneration of a free 3'-OH group on the DNA extension product. Although Scheme C is presented here as a single molecule SBS method, it can also be used for ensemble sequencing without any design changes. Structures of modified nucleotide analogues used in this scheme are shown in FIG. 82 (1-3).

Figure 1:
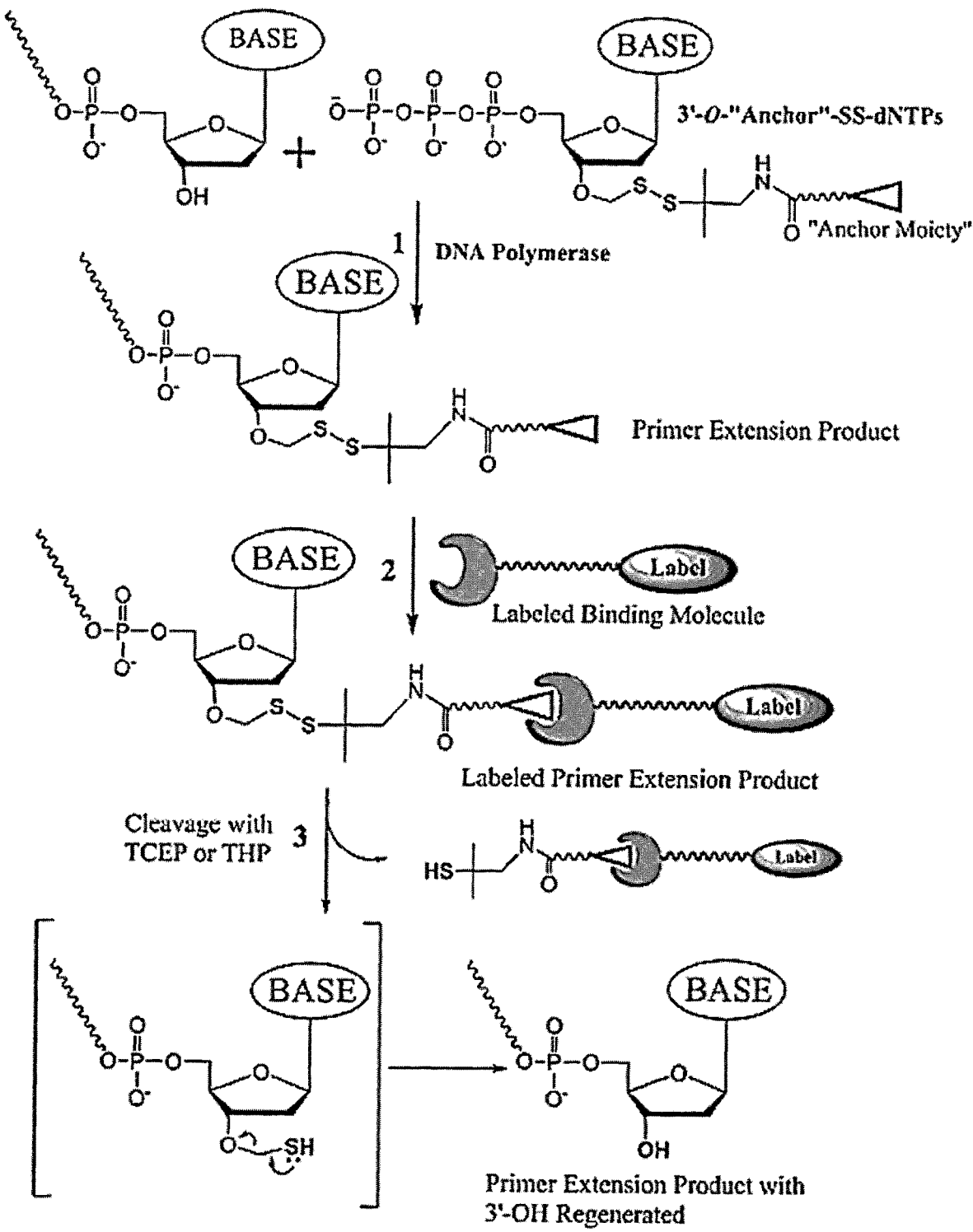
FIG. 1. Scarless SBS using 3'-O-"anchor"-SS(DTM)-dNTPs and corresponding labeled binding molecules (where "DTM" refers to the Dithiomethyl group). (STEP 1) Addition of a DNA polymerase to the primed template moiety (only the primer strand is shown above) leads to the incorporation of a complementary 3'-O-"anchor"-SS(DTM)-dNTP to the 3' end of a primer with high efficiency and specificity. (STEP 2) Addition of labeled binding molecules to the corresponding primer extension product leads to orthogonal binding of the labeled binding molecules with the corresponding "anchor" moiety in the 3' end of the primer extension product; after washing away the unbound labeled molecule, the detection of the unique label attached to the 3' end of the primer extension product determines the identity of the incorporated nucleotide. (STEP 3) Addition of TCEP or THP results in the cleavage of the disulfide bond, and therefore to the removal of the label on the primer extension product and the regeneration of the 3'-OH on the primer extension product. The repetition of STEP 1 through STEP 3 allows for continuous DNA sequence determination. The "Anchor" moiety and the labeled binding molecule include any specifically reactive pair that can form a covalent bond or a stable noncovalent bond. The label can be a fluorescent molecule, a FRET cassette or a fluorescent dendrimers.
Figure 2A:
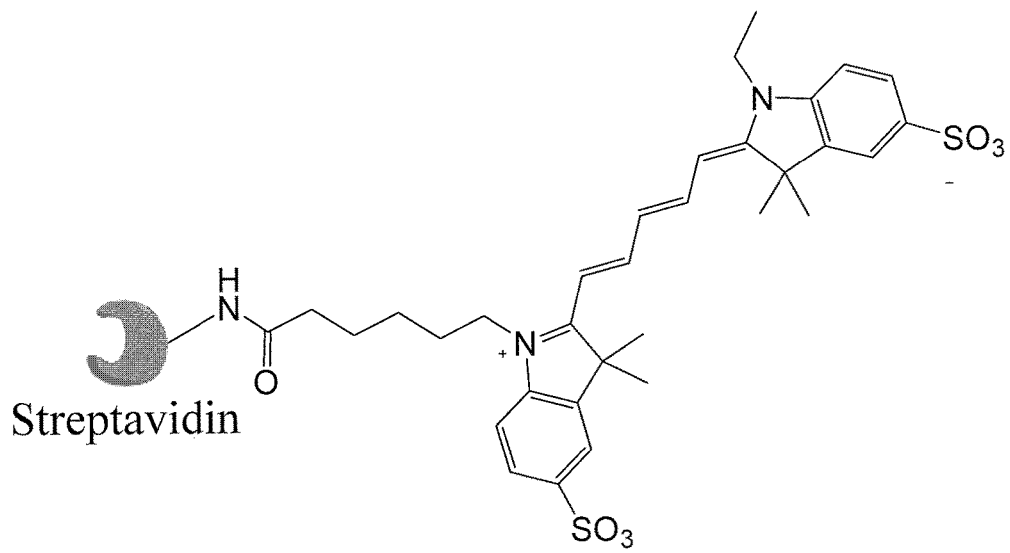
FIGS. 2A-2E. Structures of 3'-O-Biotin-DTM-dNTPs (3'-O-Biotin-t-Butyldithiomethyl-dATP, 3'-O-Biotin-t-Butyldithiomethyl-dCTP, 3'-O-Biotin-t-Butyldithiomethyl-dGTP, 3'-O-Biotin-t-Butyldithiomethyl-dTTP) and with Cy5 dye labeled streptavidin as an example (wherein "DTM" refers to the Dithiomethyl group).
Figure 2B:
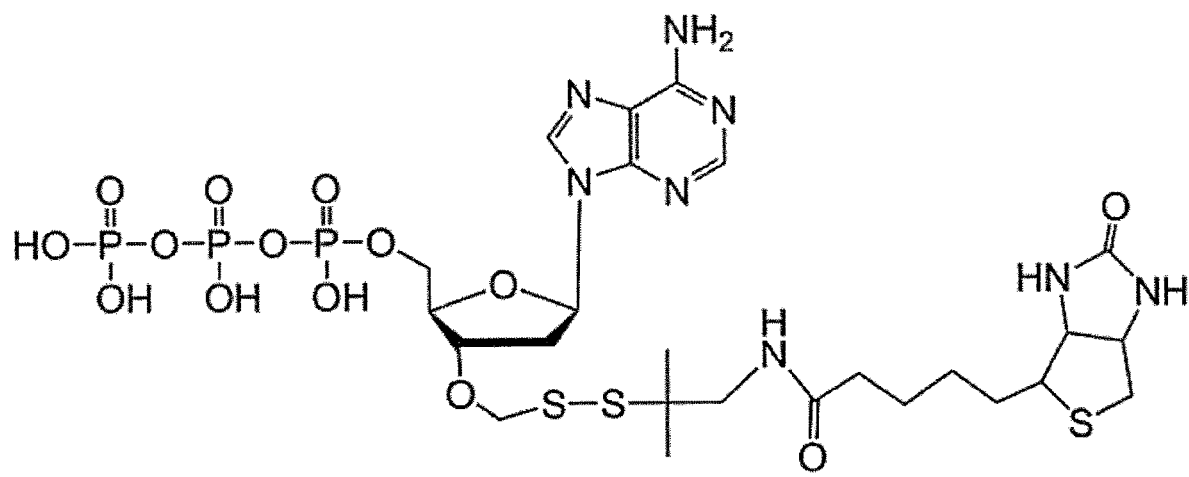
Figure 2C:
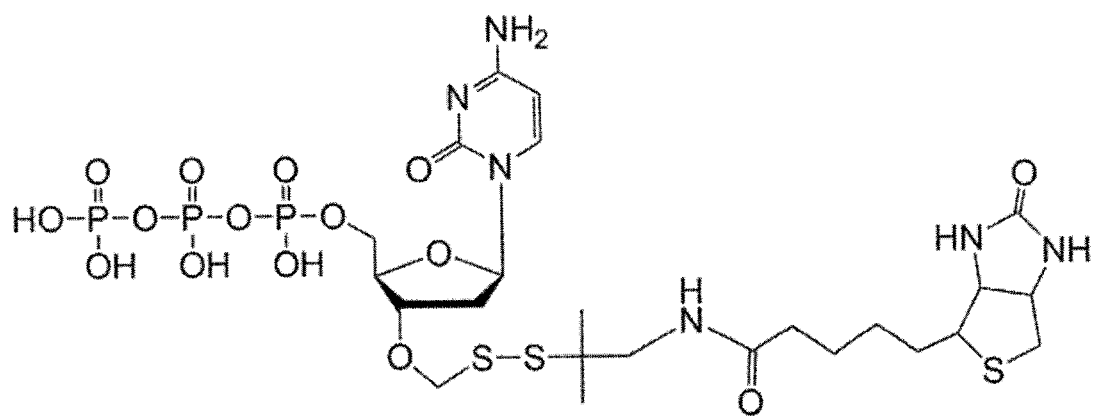
Figure 2D:
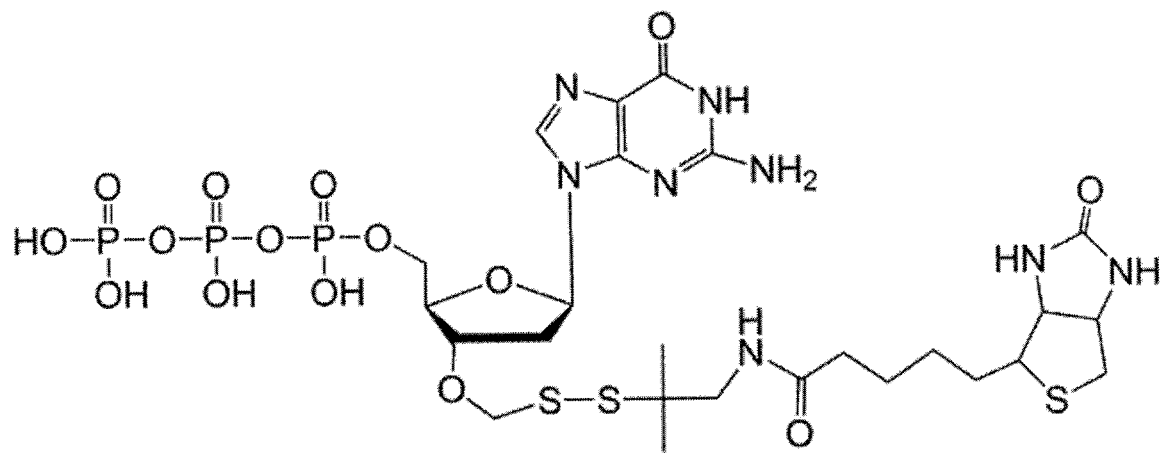
Figure 2E:
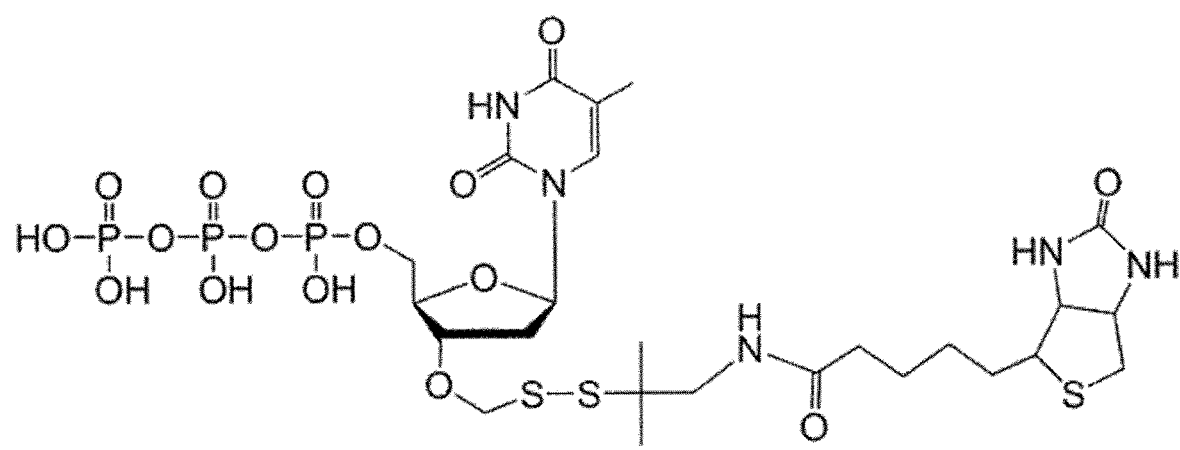
Figures 1, 82:
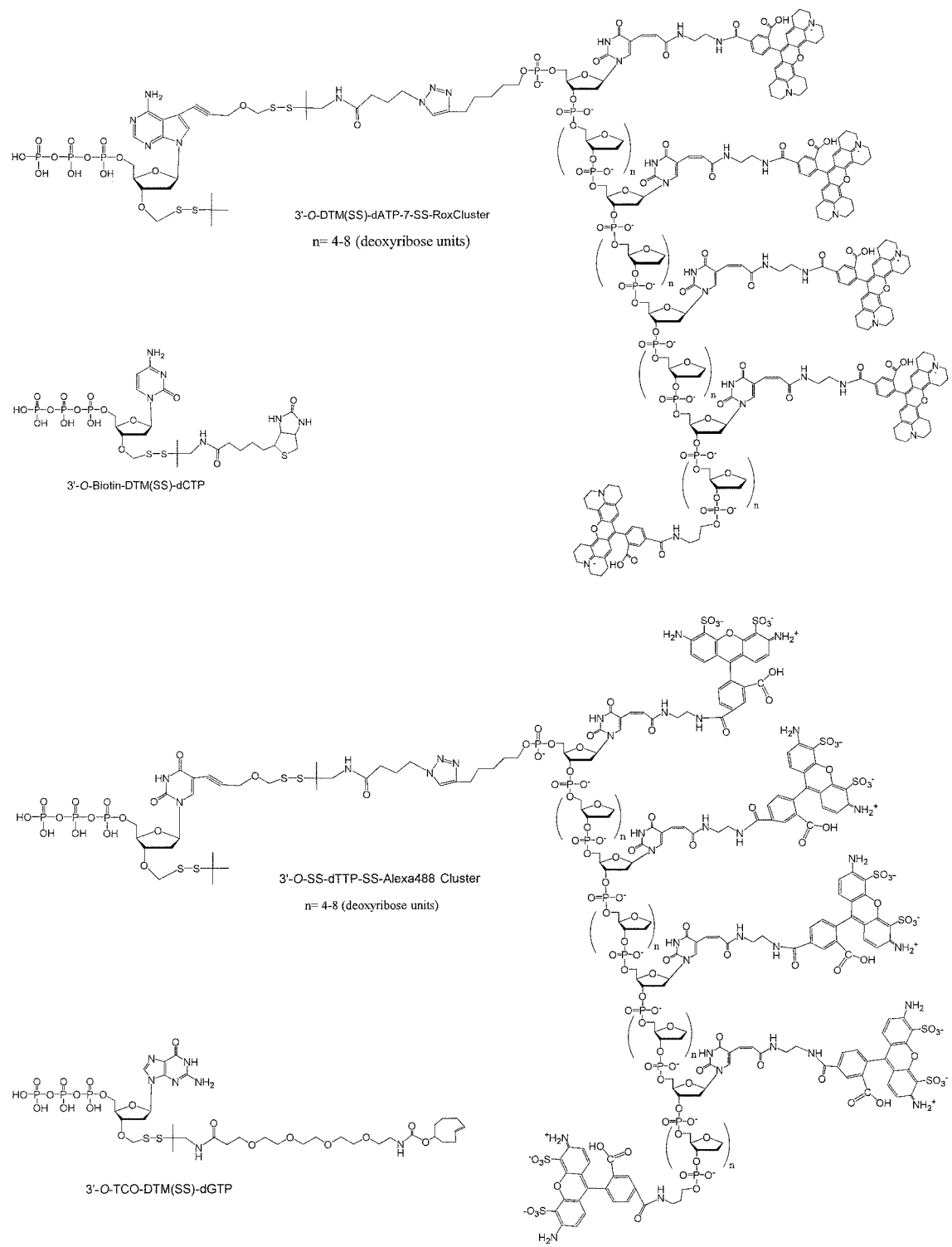
Figures 2, 82:
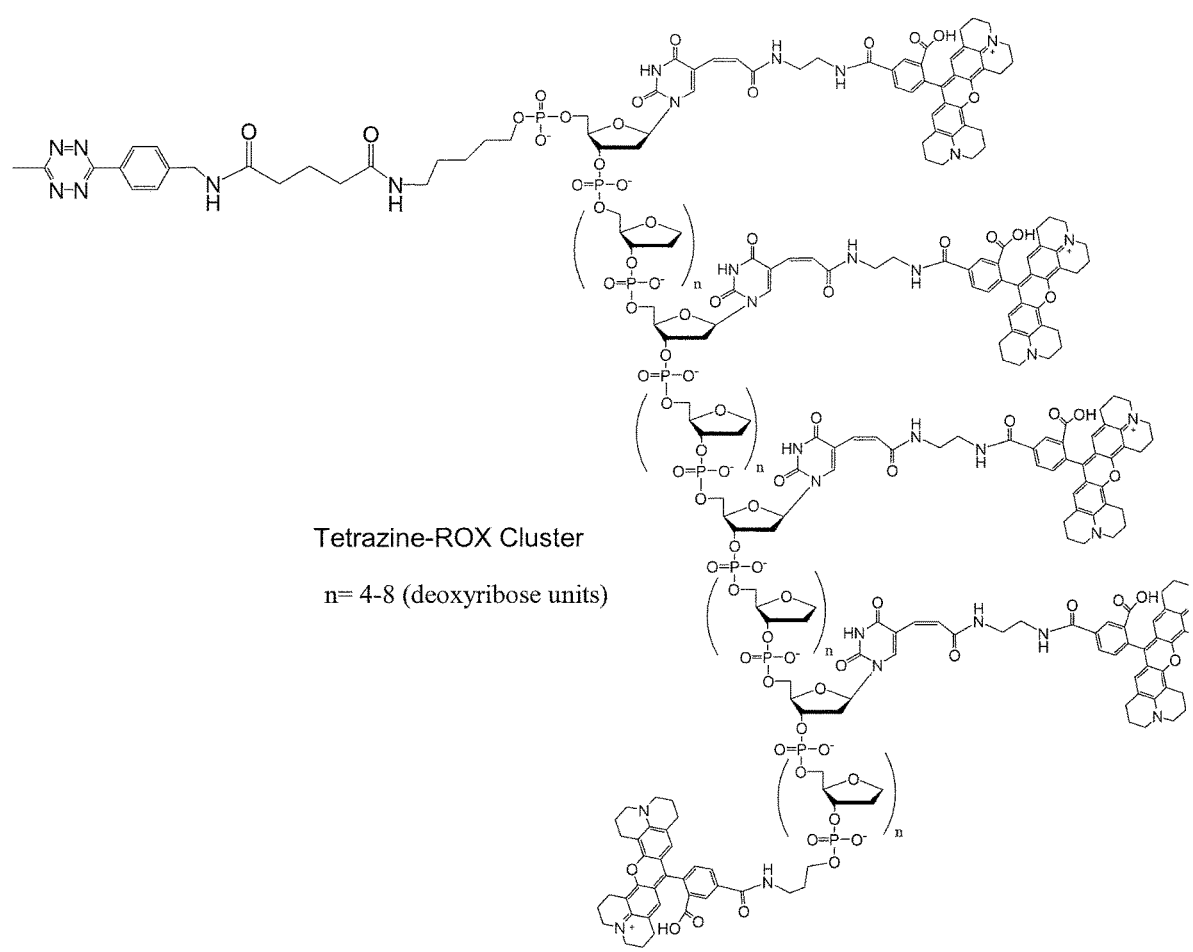
Figures 3, 82:
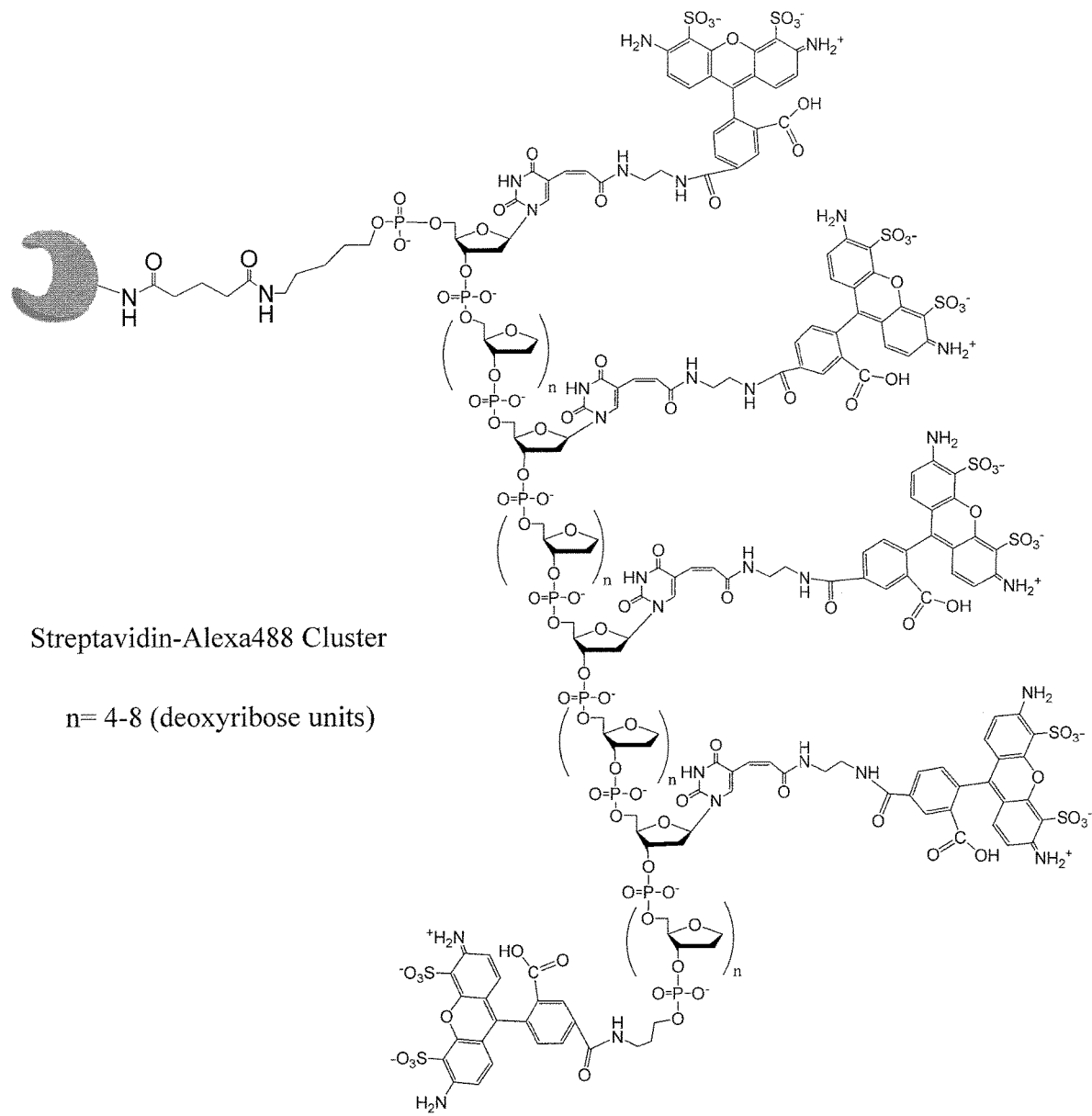

FIG. 82: FIG. 82-1 Structures of 3'-O-Anchor-SS(DTM)-dNTPs (3'-O-TCO-SS-dGTP and 3'-O-Biotin-SS-dCTP), 3'-O-DTM(SS)-dNTP-SS-DyeCluster (3'-O-SS-dATP-7-SS-Rox Cluster and 3'-O-SS-dTTP-5-SS-Alexa488 Cluster) for 2-color DNA SBS as in Scheme C. FIG. 82-2: Structure of the corresponding Dye Labeled Binding Molecules (Rox Cluster Labeled Tetrazine) for 2-color DNA SBS as in Scheme C. FIG. 82-3: The structure of Alexa488 Cluster Labeled Streptavidin for 2-color DNA SBS as in Scheme C.

Figure 83:
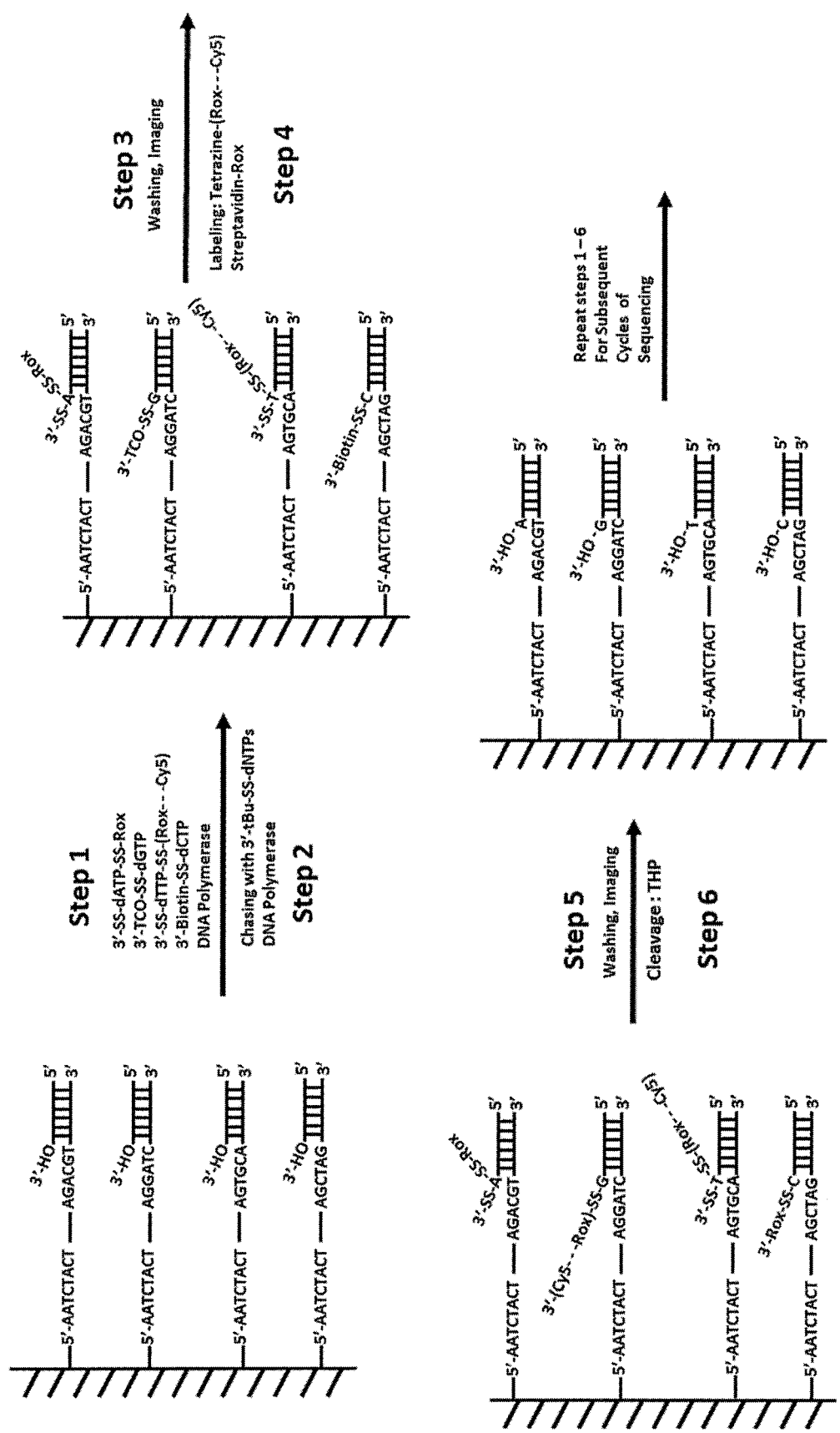
Figure 84:
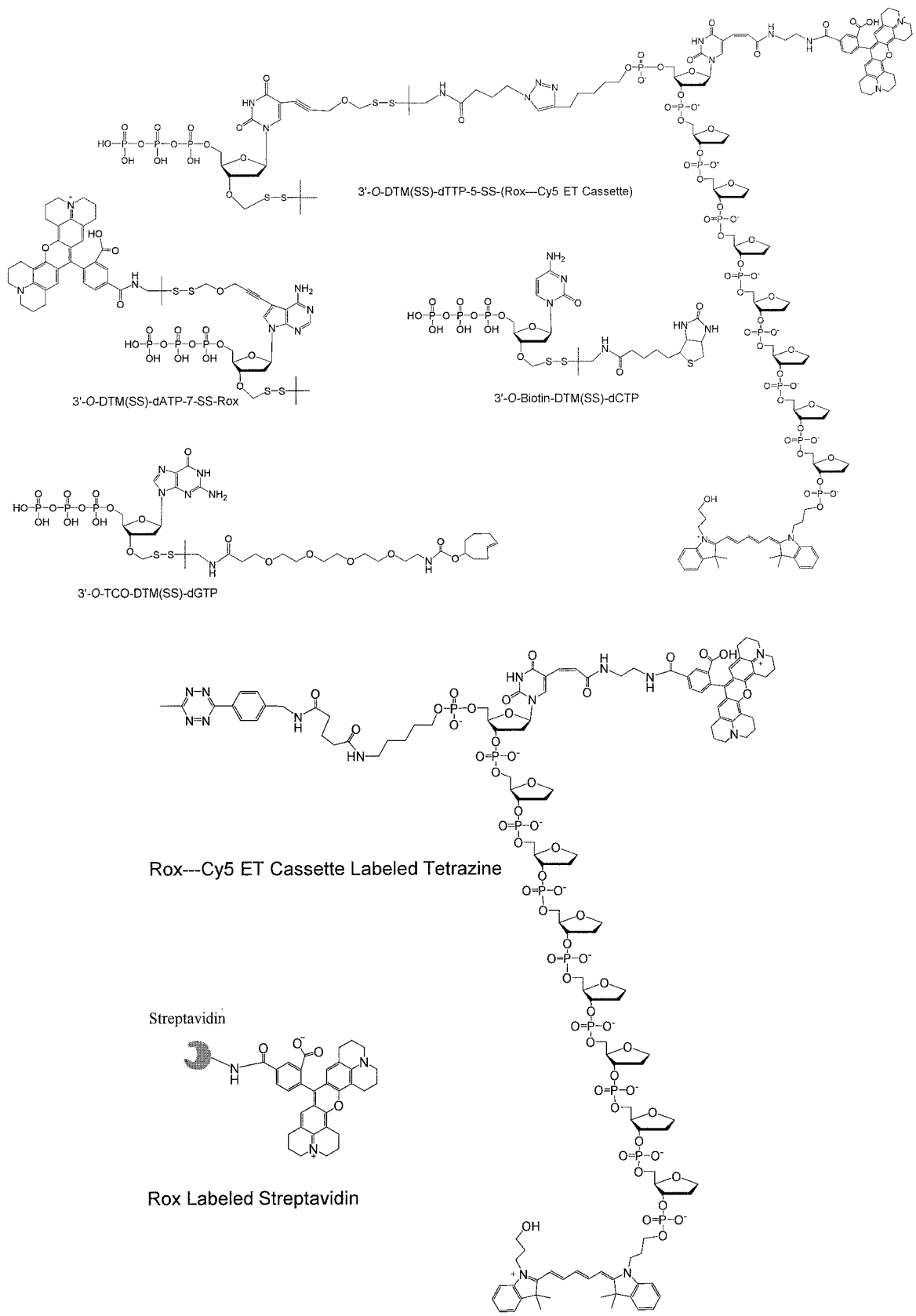

FIG. 83: Scheme D Use of 3'-O-Anchor-SS(DTM)-dNTPs (3'-O-TCO-SS-dGTP, 3'-O-Biotin-SS-dCTP), 3'-O-SS(DTM)-dNTP-SS(DTM)-Dye (3'-O-SS-dATP-7-SS-Rox), 3'-O-SS(DTM)-dNTP-SS-ET Cassette (3'-O-SS-dTTP-5-SS-[Rox---Cy5]) and appropriate dye labeled anchor binding molecules (Streptavidin-Rox, Tetrazine-[Rox---Cy5]) to perform 2-color DNA SBS. Step 1, addition of DNA polymerase and the four nucleotide analogues (3'-0-TCO-SS-dGTP, 3'-O-Biotin-SS-dCTP, 3'-O-SS-dATP-7-SS-Rox and 3'-O-SS-dTTP-5-SS-[Rox---Cy5]) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. Step 3, after washing away the unincorporated dye labeled nucleotide analogues, detection of the fluorescence signal from the fluorescent dyes on the DNA products allows the identification of two of the incorporated nucleotide analogues for sequence determination. Rox signal indicates incorporation of A, Cy5 signal indicates incorporation of T. Step 4, addition of Rox-labeled streptavidin and [Rox . . . Cy5] cassette-labeled tetrazine which bind to the biotin and TCO anchors respectively. Step 5, after washing away the excess labeling molecules, a second round of detection of any new fluorescence signal allows the identification of the incorporation of the remaining two nucleotide analogues for sequence determination. Appearance of a Rox signal indicates incorporation of C, appearance of a Cy5 signal indicates incorporation of G. Note that specific excitation of the donor dye, Rox, will result in emission of light at wavelengths that overlap the absorbance spectrum of the acceptor dye, Cy5. As shown in FIG. 84, the position of Rox and Cy5 on the polymeric molecule attached to the base is chosen to produce optimal energy transfer. Next, in Step 6, treatment of the DNA products with THP cleaves the SS linker, leading to the removal of the remaining fluorescent dye and the regeneration of a free 3'-OH group on the DNA extension product. Although Scheme D is presented here as an ensemble SBS approach, it can also be used for single molecule SBS sequencing with an appropriate imaging setup. Structures of modified nucleotide analogues used in this scheme are shown in FIG. 84.

FIG. 84: Structures of 3'-O-Anchor-SS(DTM)-dNTPs (3'-O-TCO-SS-dGTP and 3'-O-Biotin-SS-dCTP), 3'-O-DTM(SS)-dNTP-SS-ET Cassette (3'-O-SS-dATP-7-SS-Rox and 3'-O-SS-dTTP-5-SS-Rox----Cy5 ET Cassette) and the corresponding Dye Labeled Binding Molecules (Rox Labeled Streptavidin and Rox----Cy5 ET Cassette Labeled Tetrazine) for 2-color DNA SBS as in Scheme D.

Figure 85:
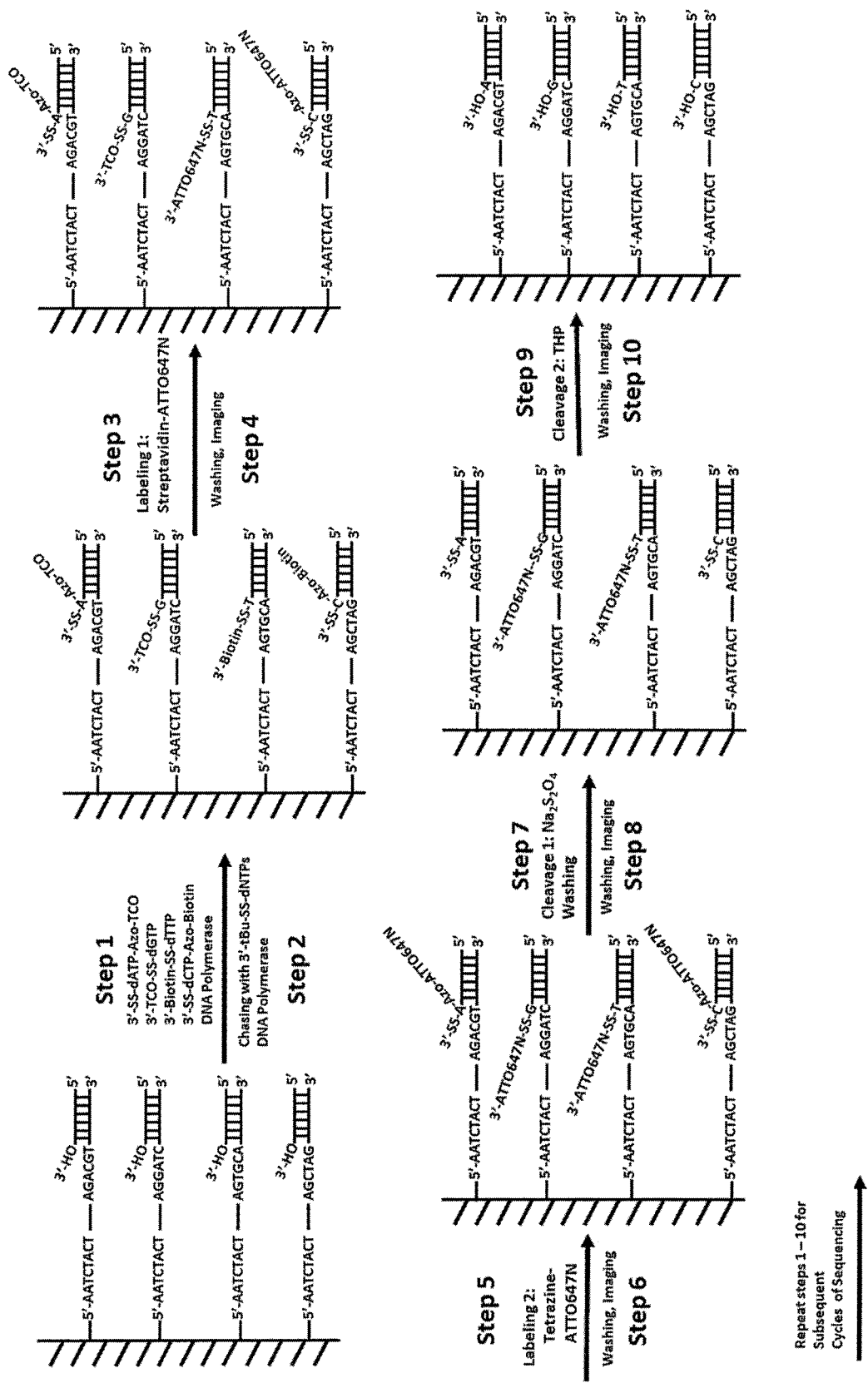

FIG. 85: (Scheme E) Use of 3'-O-SS(DTM)-dNTP-Azo-Anchors (3'-O-SS-dATP-7-Azo-TCO, 3'-O-SS-dCTP-5-Azo-Biotin); 3'-O-Anchor-SS(DTM)-dNTPs (3'-O-TCO-SS-dGTP, 3'-O-Biotin-SS-dTTP) and appropriate dye labeled anchor binding molecule (Tetrazine-ATTO647N, Streptavidin-ATTO647N) to perform 1-color DNA SBS. Step 1, addition of DNA polymerase and the four nucleotide analogues (3'-O-SS-dATP-7-Azo-TCO, 3'-O-SS-dCTP-5-Azo-Biotin, 3'-O-TCO-SS-dGTP, and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. Step 3, addition of ATTO647N-labeled streptavidin which binds to nucleotide analogues with biotin anchors. Step 4, after washing away the remaining labeling molecules, detection of a fluorescence signal indicates incorporation of either T or C. Step 5, addition of ATTO647N-labeled tetrazine which binds to nucleotide analogues with TCO anchors. Step 6, after washing away the excess labeling molecules, appearance of a previously absent fluorescence signal confirms the incorporation of either A or G. Step 7, treatment with sodium dithionite to cleave the Azo linkers on A and C nucleotide analogues. After washing, in Step 8 imaging is carried out a third time to detect remaining fluorescent signals. If we have already determined that the incorporated nucleotide could be T or C, loss of fluorescence would reveal it to be C, while remaining fluorescence would reveal it to be T. Similarly, for signals previously determined as A or G, loss of fluorescence would indicate incorporation of A specifically while remaining fluorescence would indicate incorporation of G. Next, in Step 9, treatment of the DNA products with THP cleaves the SS linker, leading to the removal of the remaining fluorescent dye and the regeneration of a free 3'-OH group on the DNA extension product. Step 10, after washing away the THP, optional imaging to confirm absence of any remaining fluorescent label indicates readiness for the next cycle of the DNA sequencing reaction. Although Scheme E is presented here as an ensemble SBS approach, it can also be used for single molecule SBS sequencing with an appropriate imaging setup. Structures of modified nucleotide analogues used in this scheme are shown in FIG. 86.

Figure 86:
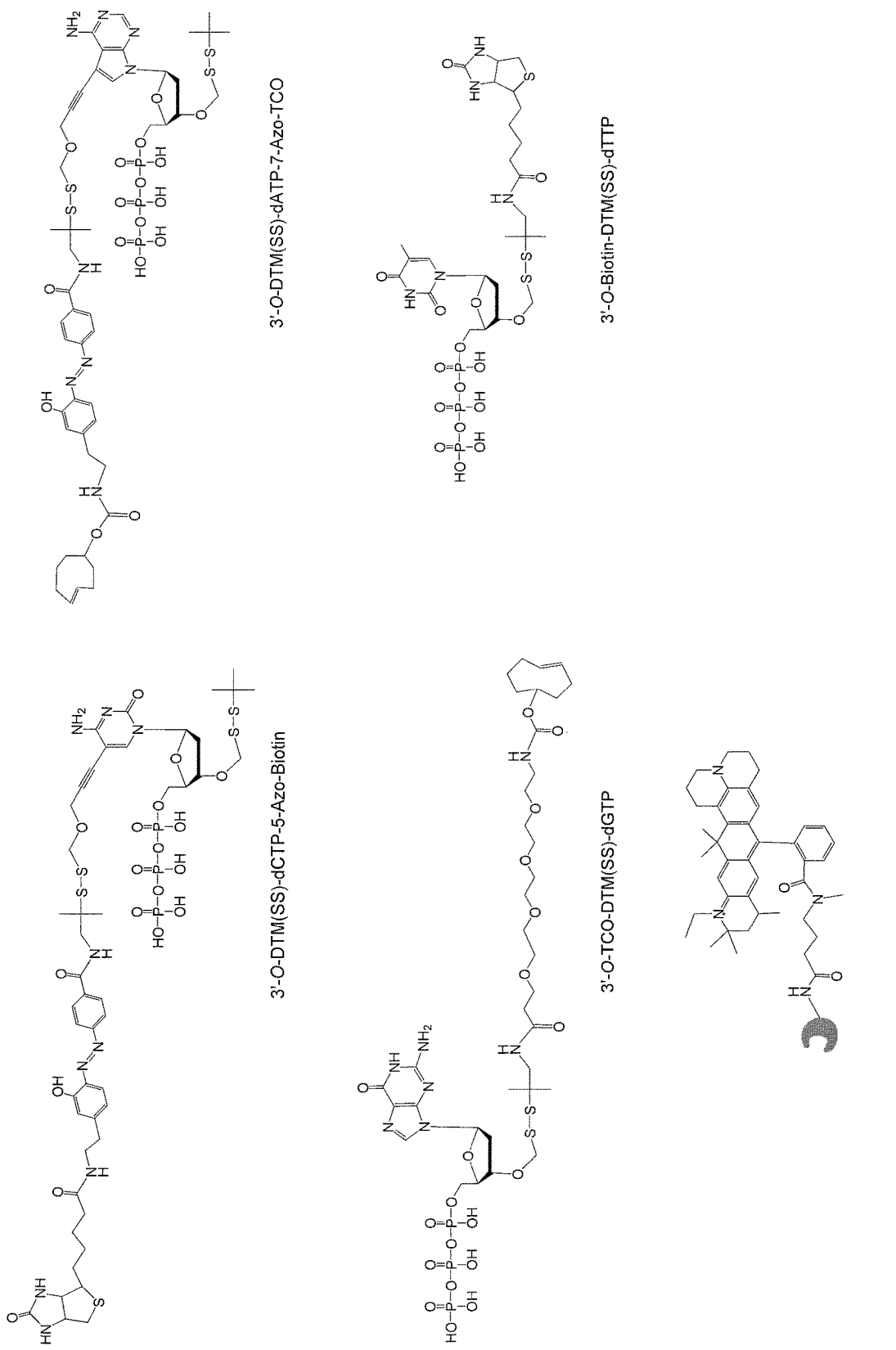

FIG. 86: 3'-O-DTM(SS)-dNTP-Azo-Anchors (3'-O-SS-dATP-7-Azo-TCO and 3'-O-SS-dCTP-5-Azo-Biotin), 3'-O-Anchor-DTM(SS)-dNTP (3'-O-TCO-SS-dGTP and 3'-O-Biotin-SS-dTTP) and the dye labeled anchor binding molecule (ATTO647N labeled streptavidin) for 1-color DNA SBS as in Scheme E.

Figure 87:
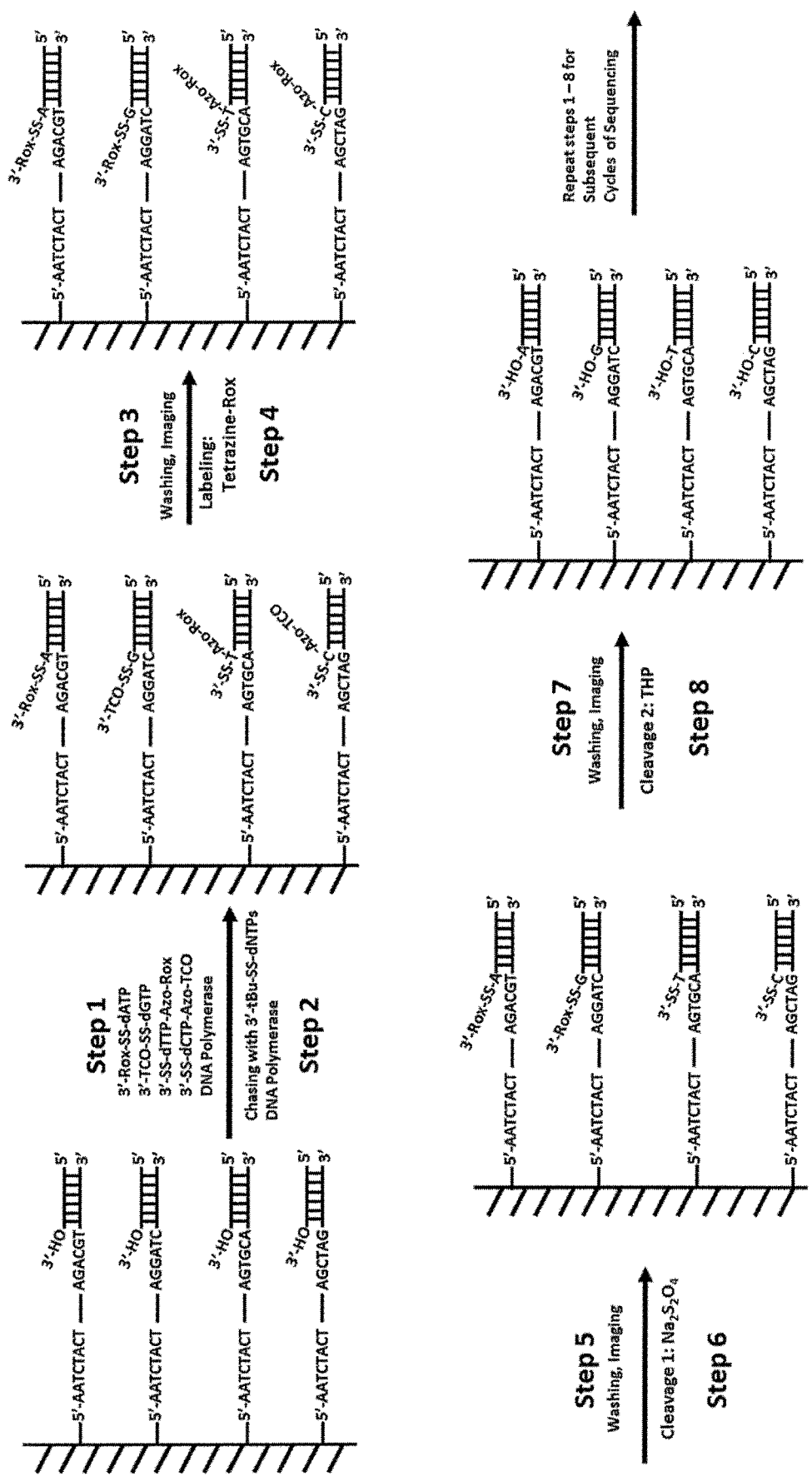

FIG. 87: (Scheme F) Use of 3'-O-SS(DTM)-dNTP-Azo-Anchor (3'-O-SS-dCTP-5-Azo-TCO), 3'-O-Anchor-SS(DTM)-dNTP (3'-O-TCO-SS-dGTP), 3'-O-SS(DTM)-dNTP-Azo-Dye (3'-O-SS-dTTP-5-Azo-Rox), 3'-O-Dye-SS(DTM)-dNTP (3'-O-Rox-SS-dATP) and appropriate dye labeled anchor binding molecule (Tetrazine-Rox) to perform 1-color DNA SBS. Step 1, addition of DNA polymerase and the four nucleotide analogues (3'-O-SS-dCTP-5-Azo-TCO, 3'-O-TCO-SS-dGTP, 3'-O-SS-dTTP-5-Azo-Rox, and 3'-O-Rox-SS-dATP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. Step 3, after washing away unincorporated nucleotide analogues, imaging is performed to detect fluorescence of incorporated nucleotide analogues. Rox fluorescence indicates incorporation of either A or T. Step 4, addition of Rox-labeled tetrazine which binds to nucleotide analogues with TCO anchors. Step 5, after washing away the remaining labeling molecules, detection of a previously missing Rox signal confirms incorporation of either C or G. Step 6, treatment with sodium dithionite to cleave Azo linkers on T and C nucleotide analogues. After washing, in Step 7 imaging is carried out a third time to detect remaining fluorescent signals. If we have already determined that the incorporated nucleotide could be A or T, loss of fluorescence would reveal it to be T, while remaining fluorescence would reveal it to be A. Similarly, for signals previously determined as C or G, loss of fluorescence would indicate incorporation of C specifically while remaining fluorescence would indicate incorporation of G. Next, in Step 8, treatment of the DNA products with THP cleaves the SS linker, leading to the removal of the remaining fluorescent dye and the regeneration of a free 3'-OH group on the DNA extension product in readiness for the next cycle of the DNA sequencing reaction. Although Scheme F is presented here as an ensemble SBS approach, it can also be used for single molecule SBS sequencing with an appropriate imaging setup. Structures of modified nucleotide analogues used in this scheme are shown in FIG. 88.

Figure 88:
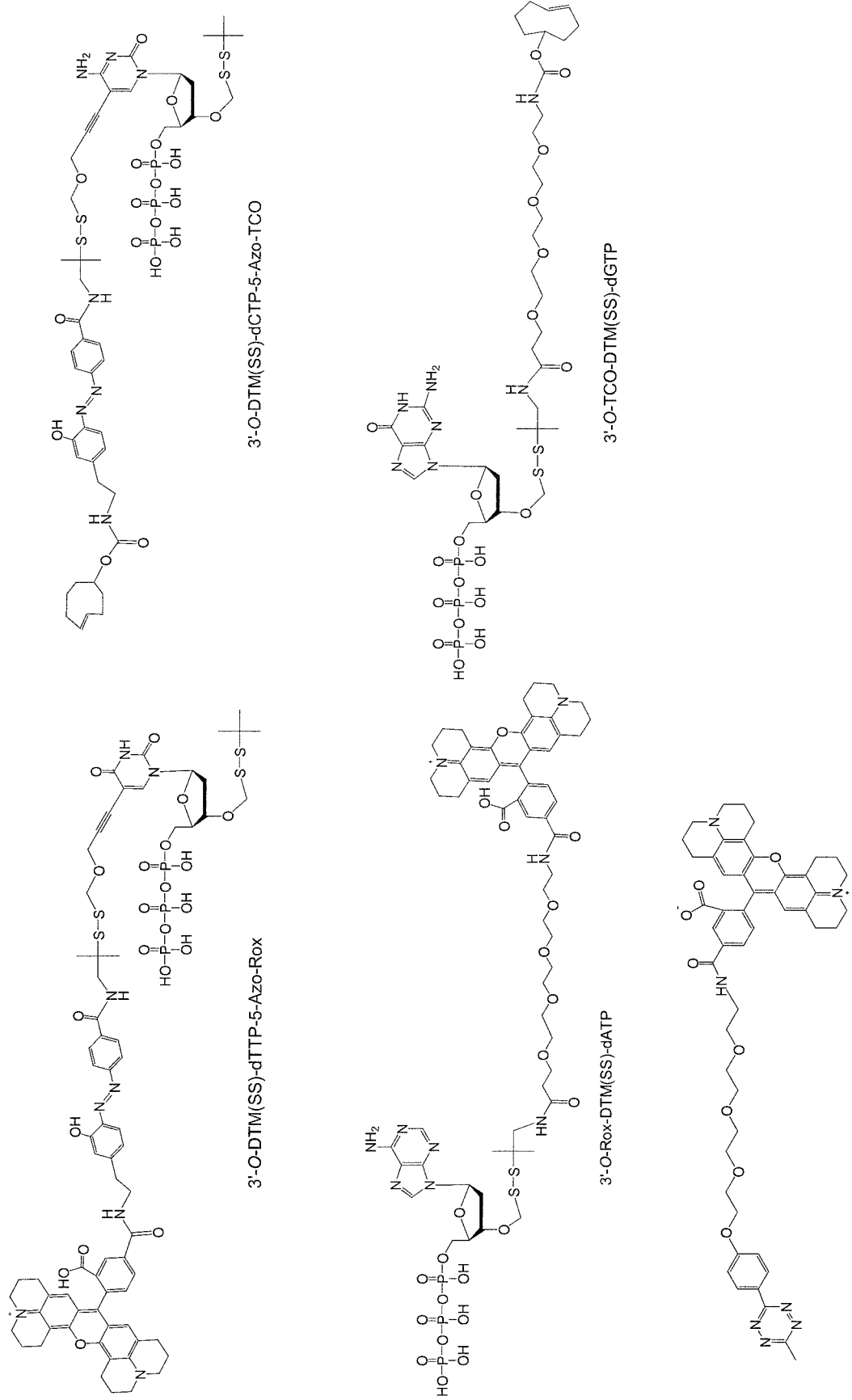

FIG. 88: Structures of 3'-O-Dye-DTM(SS)-dNTPs (3'-O-Rox-SS-dATP), 3'-O-DTM(SS)-dNTP-Azo-Dye (3'-O-SS-dTTP-5-Azo-Rox), 3'-O-DTM(SS)-dNTP-Azo-Anchor (3'-O-SS-dCTP-5-Azo-TCO) and 3'-O-Anchor-SS-dNTP (3'-O-TCO-SS-dGTP) as well as the dye labeled binding molecule (Rox Labeled Tetrazine) for 1-color DNA SBS as in Scheme F.

Figure 89:
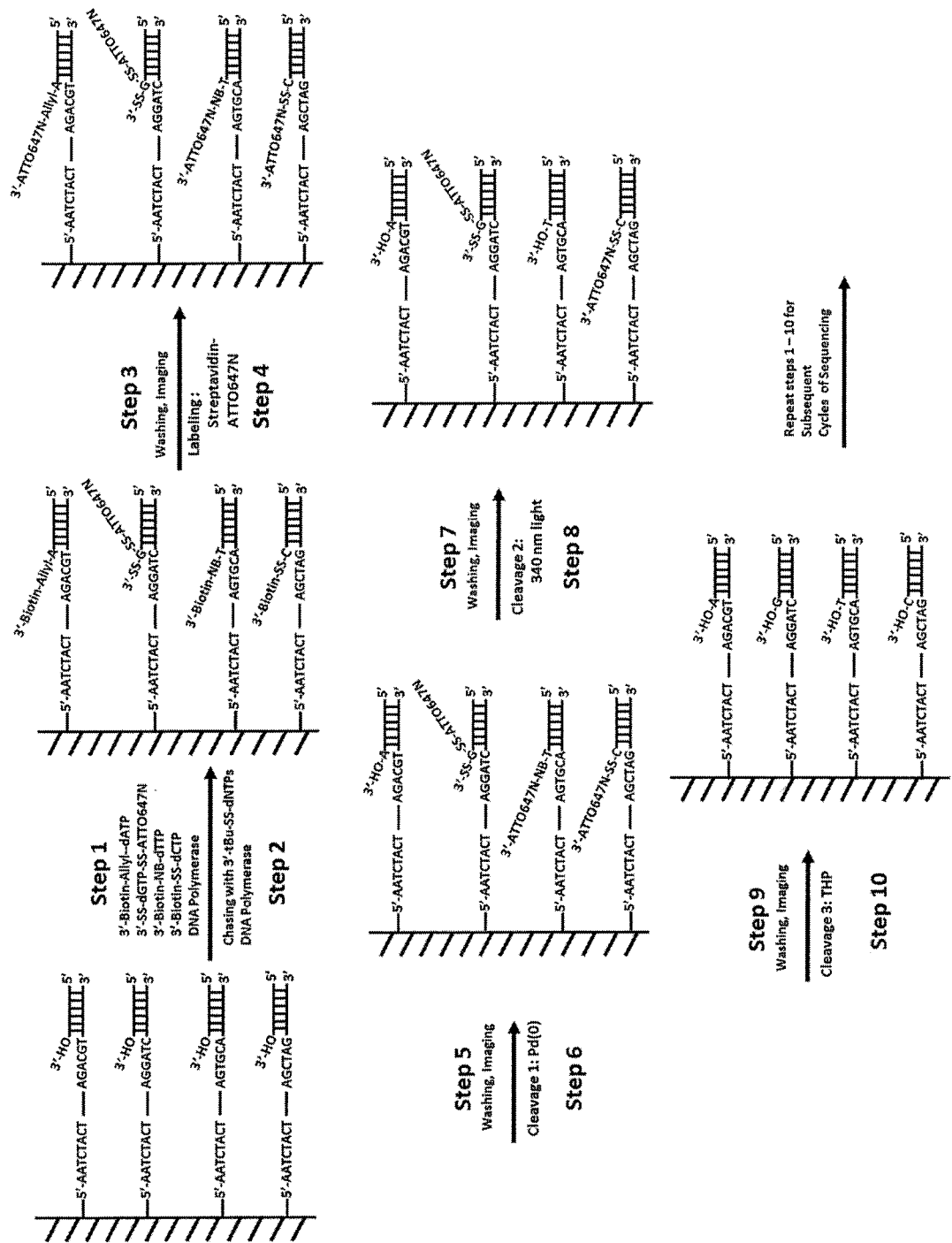

FIG. 89: Scheme G Use of 3'-O-SS(DTM)-dNTP-SS-Dye (3'-O-SS-dGTP-7-SS-ATTO647N), 3'-O-Anchor-SS(DTM)-dNTP (3'-O-Biotin-SS-dCTP), 3'-O-Anchor-AllyldNTP (3'-O-Biotin-Allyl-dATP) and 3'-O-Anchor-2NB-dNTP (3'-O-Biotin-2NB-dTTP) and appropriate dye labeled anchor binding molecule (Streptavidin-ATTO647N) to perform 1-color ensemble DNA SBS. Step 1, addition of DNA polymerase and the four nucleotide analogues (3'-O-SS-dGTP-7-SS-ATTO647N, 3'-O-Biotin-SS-dCTP, 3'-O-Biotin-Allyl-dATP, and 3'-O-Biotin-2NB-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. Step 3, after washing away unincorporated nucleotide analogues, imaging is performed to detect fluorescence of incorporated nucleotide analogues. ATTO647N fluorescence indicates incorporation of G. Step 4, addition of ATTO647N-labeled streptavidin which binds to nucleotide analogues with biotin anchors. Step 5, after washing away the remaining labeling molecules, an optional imaging step is carried out. Detection of a new ATTO647N signal confirms incorporation of any one of A, C or T. Step 6, treatment with Pd(0) to cleave allyl linker on A. After washing, in Step 7 imaging is carried out to detect remaining fluorescent signals. Loss of ATTO647N signal indicates an A was incorporated. Step 8, treatment with 340 nm light to cleave 2-nitrobenzyl linker on T. After washing, in Step 7 imaging is carried out to detect remaining fluorescent signals. Loss of ATTO647N signal indicates a T was incorporated. Remaining signal after the two cleavage steps indicates incorporation of C, since a G would have been seen in the first imaging step. Next, in Step 9, treatment of the DNA products with THP cleaves the SS linker, leading to the removal of the remaining fluorescent dye and the regeneration of a free 3'-OH group on the DNA extension product in readiness for the next cycle of the DNA sequencing reaction. An optional imaging step showing absence of fluorescence would confirm C incorporation. Although Scheme G is presented here as an ensemble SBS approach, it can also be used for single molecule SBS sequencing with an appropriate imaging setup. Structures of modified nucleotide analogues used in this scheme are shown in FIG. 90.

Figure 90:
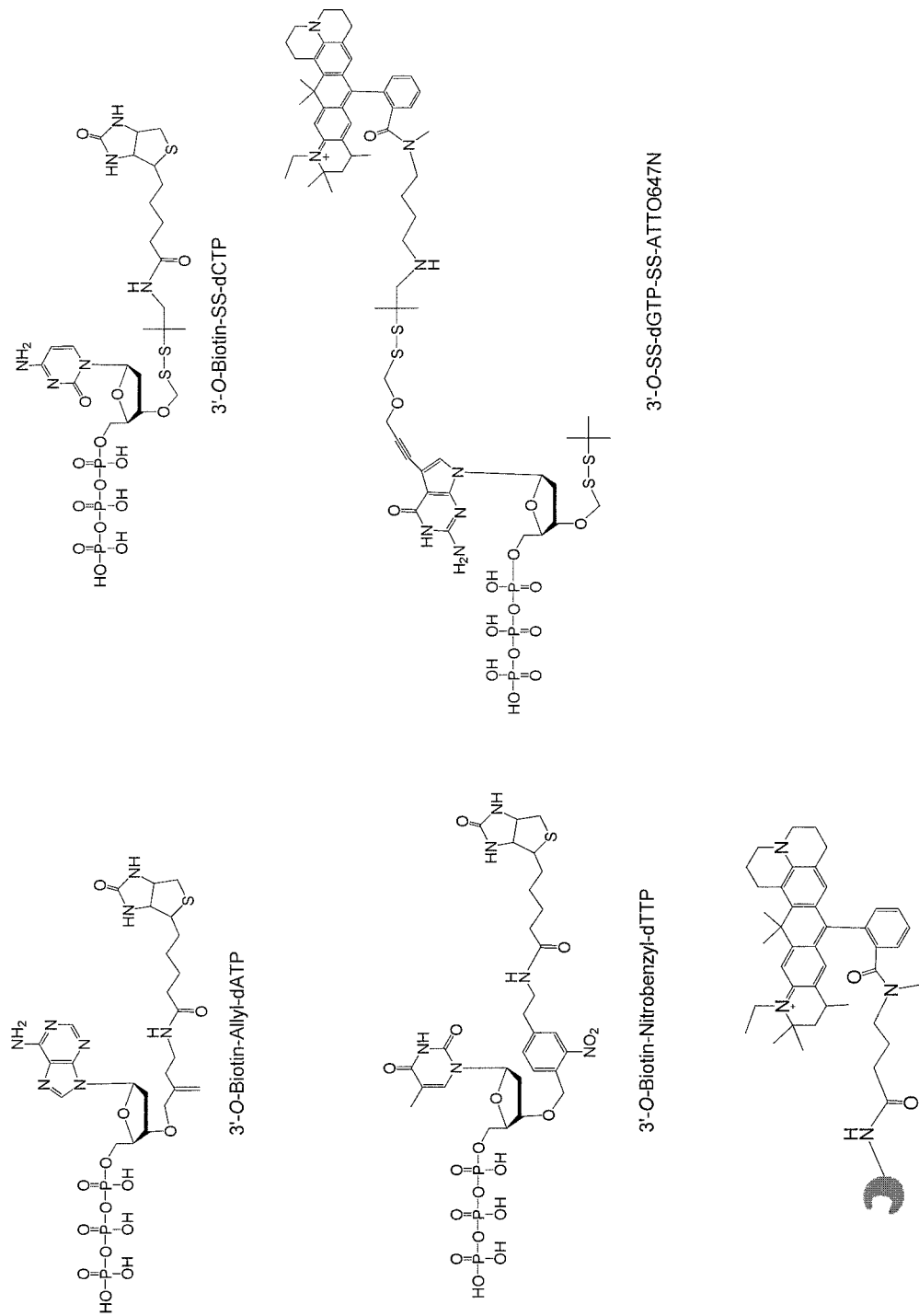

FIG. 90: Structures of 3'-O-Anchor-CleavableLinker-dNTPs (3'-O-Biotin-Allyl-dATP, 3'-O-Biotin-SS-dCTP, 3'-O-Biotin-NB-dTTP), 3'-O-DTM(SS)-dNTP-SS-Dye (3'-O-SS-dGTP-7-SS-ATTO647N) and the corresponding Dye Labeled Binding Molecules (ATTO647N Labeled Streptavidin) for 1-color DNA SBS as in Scheme G.

Figure 91:
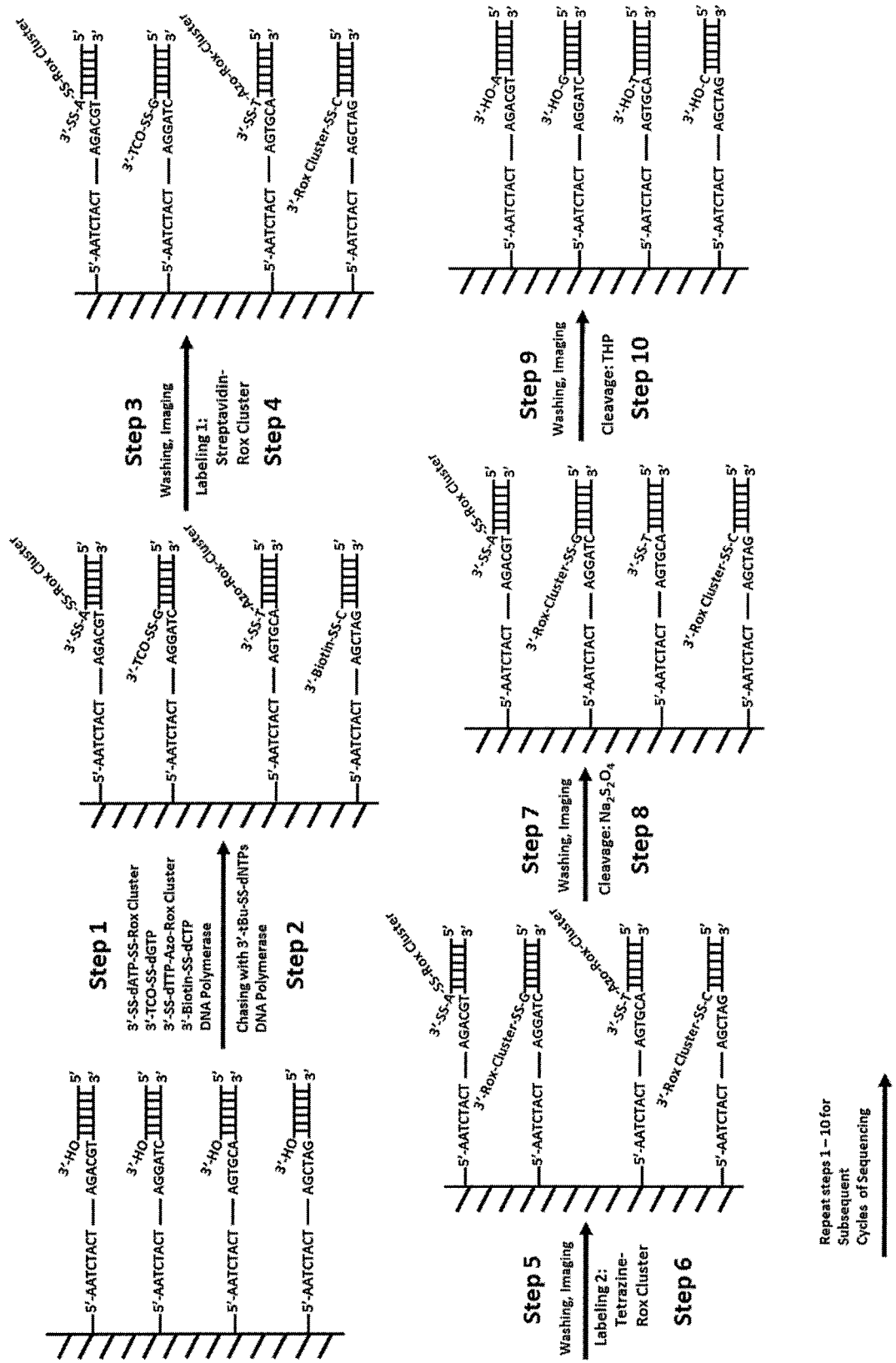

FIG. 91: (Scheme H) Use of 3'-O-Anchor-SS(DTM)-dNTPs (3'-O-TCO-SS-dGTP, 3'-O-Biotin-SS-dCTP), 3'-O-SS(DTM)-dNTP-SS-Dye Clusters (3'-O-SS-dATP-7-SS-Rox Cluster), 3'-O-SS(DTM)-dNTP-Azo-Dye Clusters (3'-O-SS-dTTP-5-Azo-Rox Cluster), and appropriate dye labeled anchor binding molecules (Tetrazine-Rox Cluster, Streptavidin-Rox Cluster) to perform 1-color DNA SBS. Step 1, addition of DNA polymerase and the four nucleotide analogues (3'-O-TCO-SS-dGTP, 3'-O-Biotin-SS-dCTP, 3'-O-SS-dATP-7-SS-Rox Cluster and 3'-O-SS-dTTP-5-Azo-Rox Cluster) to the immobilized primed DNA template enables the incorporation of the complementary nucleotide analogue to the growing DNA strand to terminate DNA synthesis. Step 2, Chase: addition of DNA polymerase and four 3'-0-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue in case the primer was not extended with any of the dye or anchor labeled dNTPs in step 1. The growing DNA strands are terminated with one of the four dye or anchor labeled nucleotide analogues (A, C, G, T) or the equivalent nucleotide analogues (A, C, G, T) without dye. In the case of single molecule sequencing, the base at this position in the growing DNA strand would not be called, but because the 3'-OH will be restored in step 10, sequencing can still be carried out beyond this point. Step 3, after washing away the unincorporated dye labeled nucleotide analogues, detection of the fluorescence signal from the fluorescent dyes on the DNA products allows the identification of either of two of the incorporated nucleotide analogues for sequence determination. Rox signal indicates incorporation of A or T. Step 4, addition of Rox cluster-labeled streptavidin to bind to the biotin anchors. Step 5, after washing away the excess labeling molecules, a second round of detection is performed. Appearance of a new Rox signal confirms incorporation of C. Step 6, addition of Rox cluster-labeled tetrazine to bind to the TCO anchors. Step 7, after washing away the excess labeling molecules, a third round of detection is performed. Appearance of a new Rox signal confirms incorporation of G. Step 8, treatment with sodium dithionite cleaves the Azo linkers on T nucleotide analogues. Step 9, after washing, loss of Rox signal indicates incorporation of T; remaining Rox signal indicates incorporation of A. Finally, in Step 10, treatment of the DNA products with THP cleaves the DTM linker, removing the fluorescent dye from the T nucleotide analogue and regenerating a free 3'-OH group on the DNA extension product. At this point, the DNA is ready for the next sequencing cycle. Although Scheme H is presented here as a single molecule SBS methods, it can also be used for ensemble sequencing without any design changes. Structures of modified nucleotide analogues used in this scheme are shown in FIGS. 92-1 and 92-2).

Figures 1, 92:
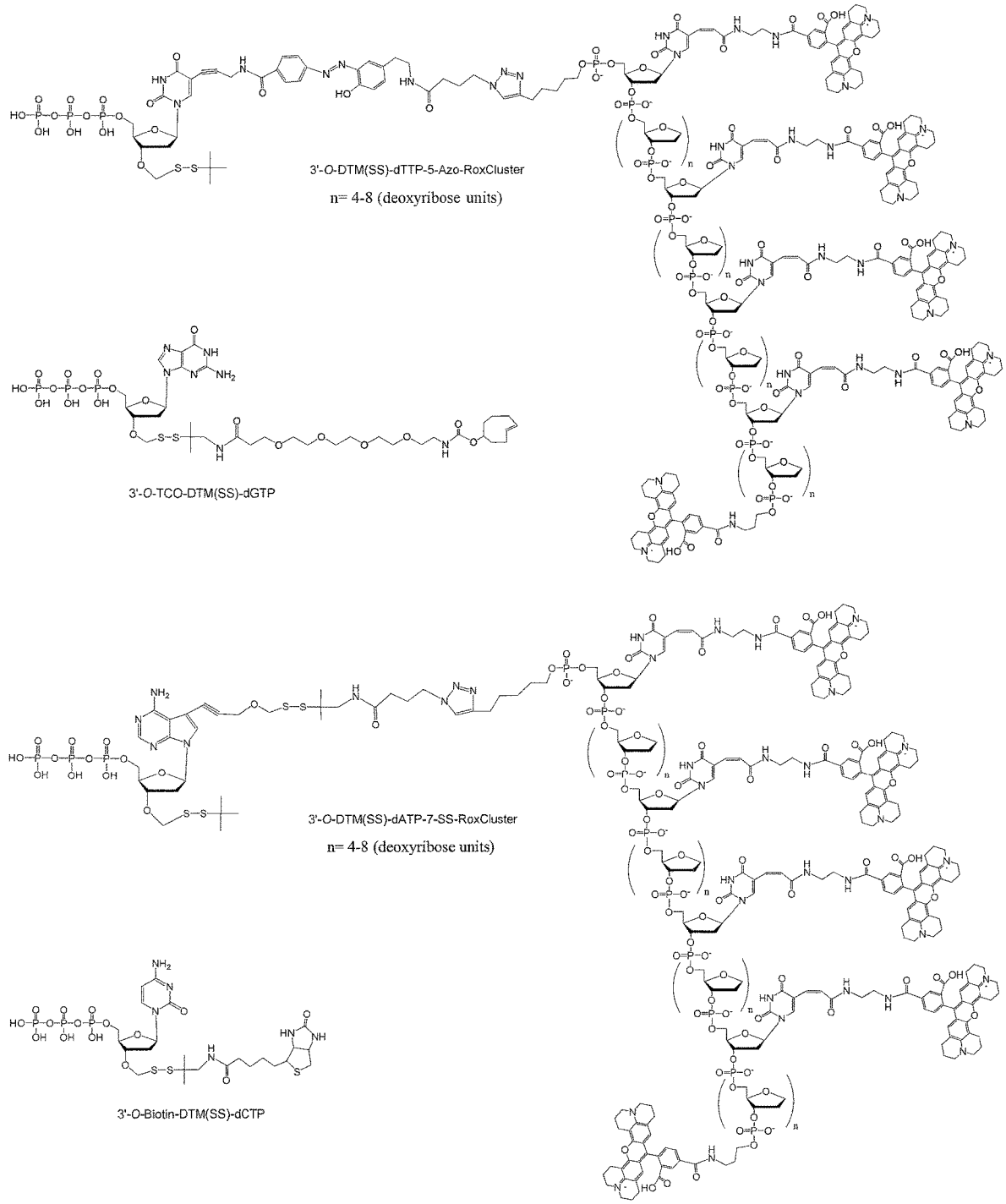
Figures 2, 92:
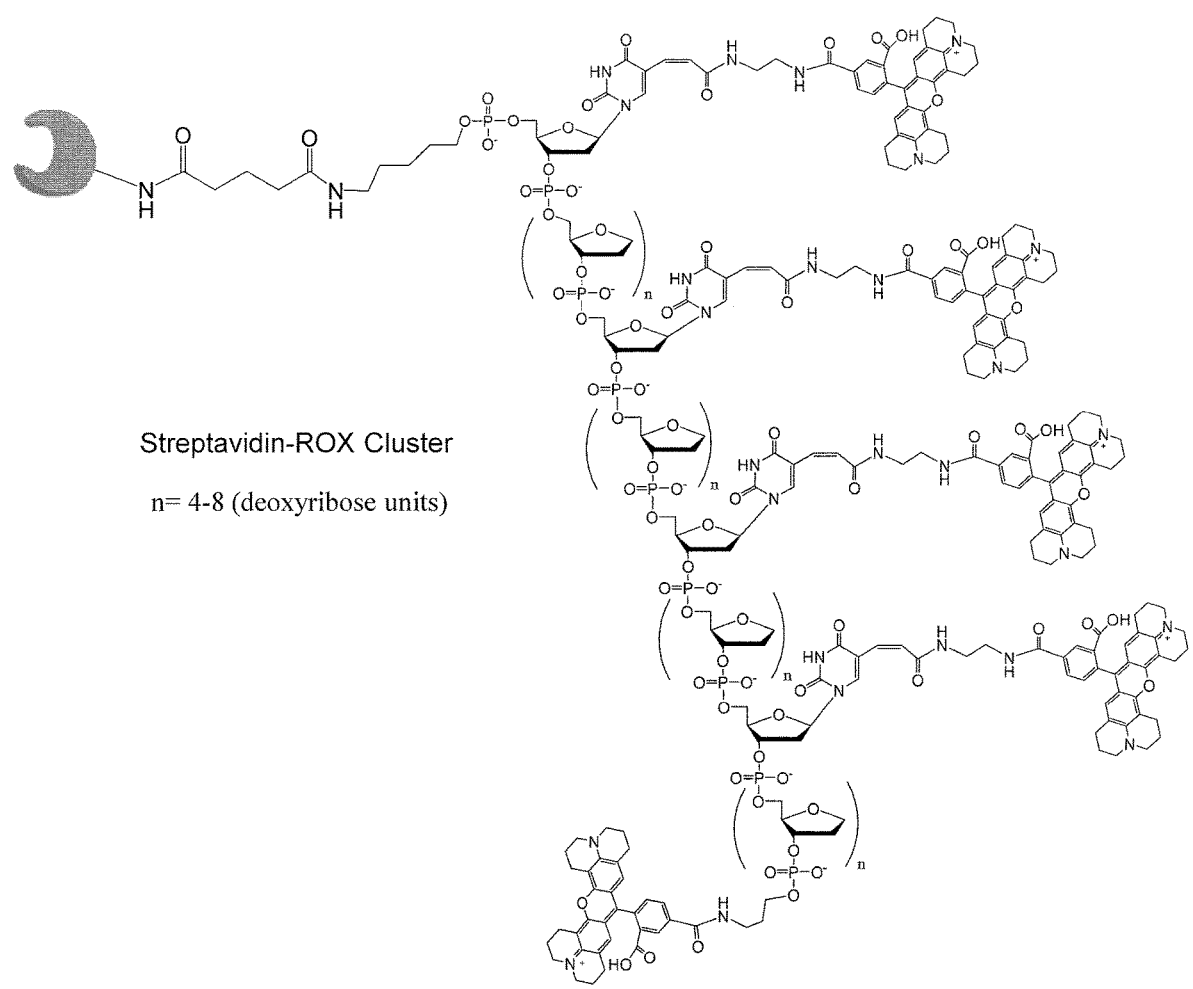

FIG. 92: FIG. 92-1: Structures of 3'-O-Anchor-SS(DTM)-dNTPs (3'-O-TCO-SS-dGTP and 3'-O-Biotin-SS-dCTP), 3'-O-DTM(SS)-dNTP-SS-DyeCluster (3'-O-SS-dATP-7-SS-Rox Cluster), 3'-O-DTM(SS)-dNTP-Azo-DyeCluster (3'-O-SS-dTTP-5-Azo-Rox Cluster) and the corresponding Dye Labeled Binding Molecules (Rox Cluster Labeled Streptavidin (FIG. 92-2) and Rox Cluster Labeled Tetrazine (FIG. 82-2)) for 1-color DNA SBS as in Scheme H. FIG. 92-2: The structure of Rox Cluster Labeled Streptavidin for 1-color DNA SBS as in Scheme H.

Figure 93:
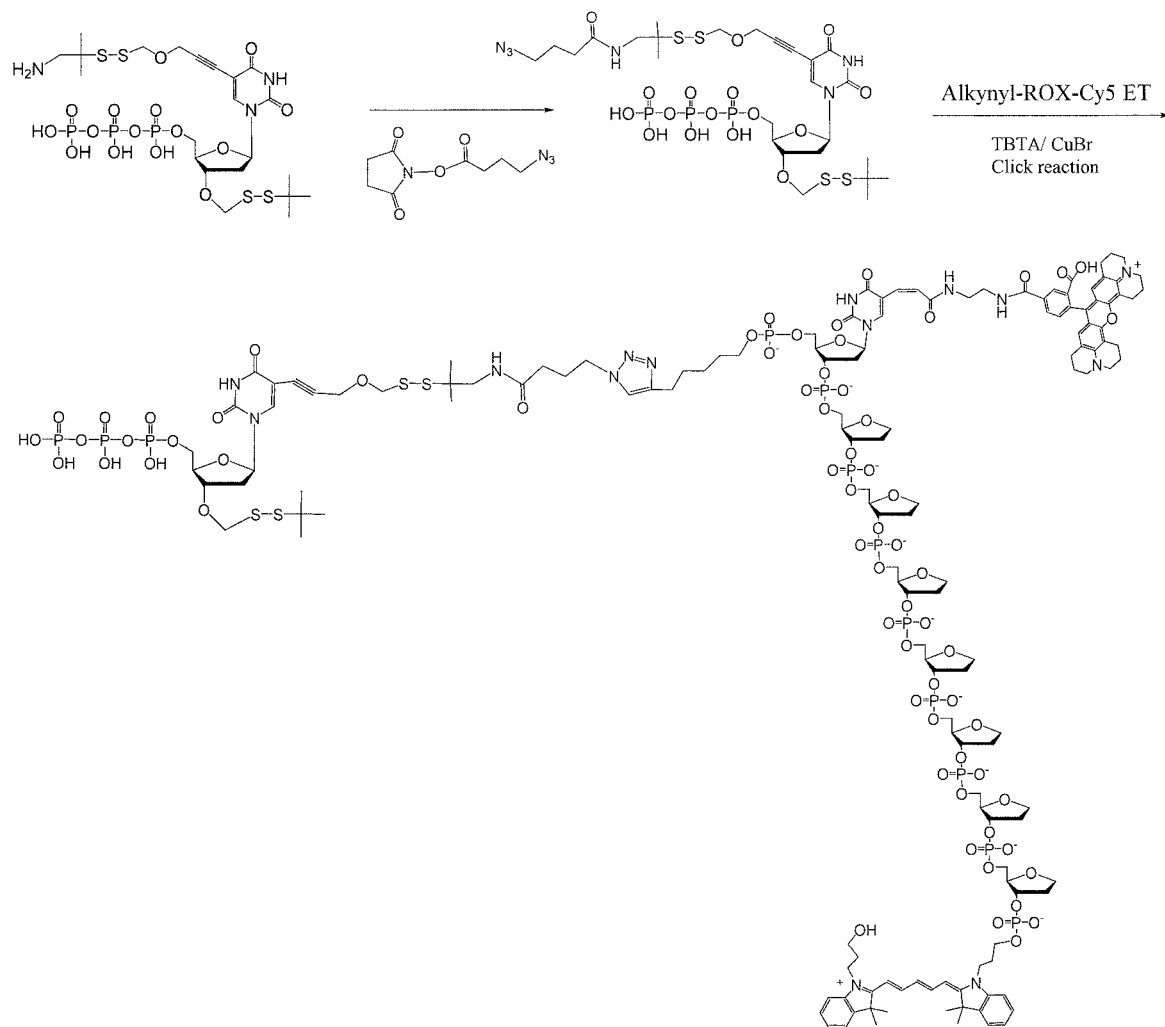

FIG. 93: Synthesis of 3'-O-SS-dTTP-SS-(Rox---Cy5 ET Cassette). The Alkynyl-Rox-Cy5 ET Cassette can be routinely synthesized by using the standard oligonucleotide synthesis approach.

Figure 94:
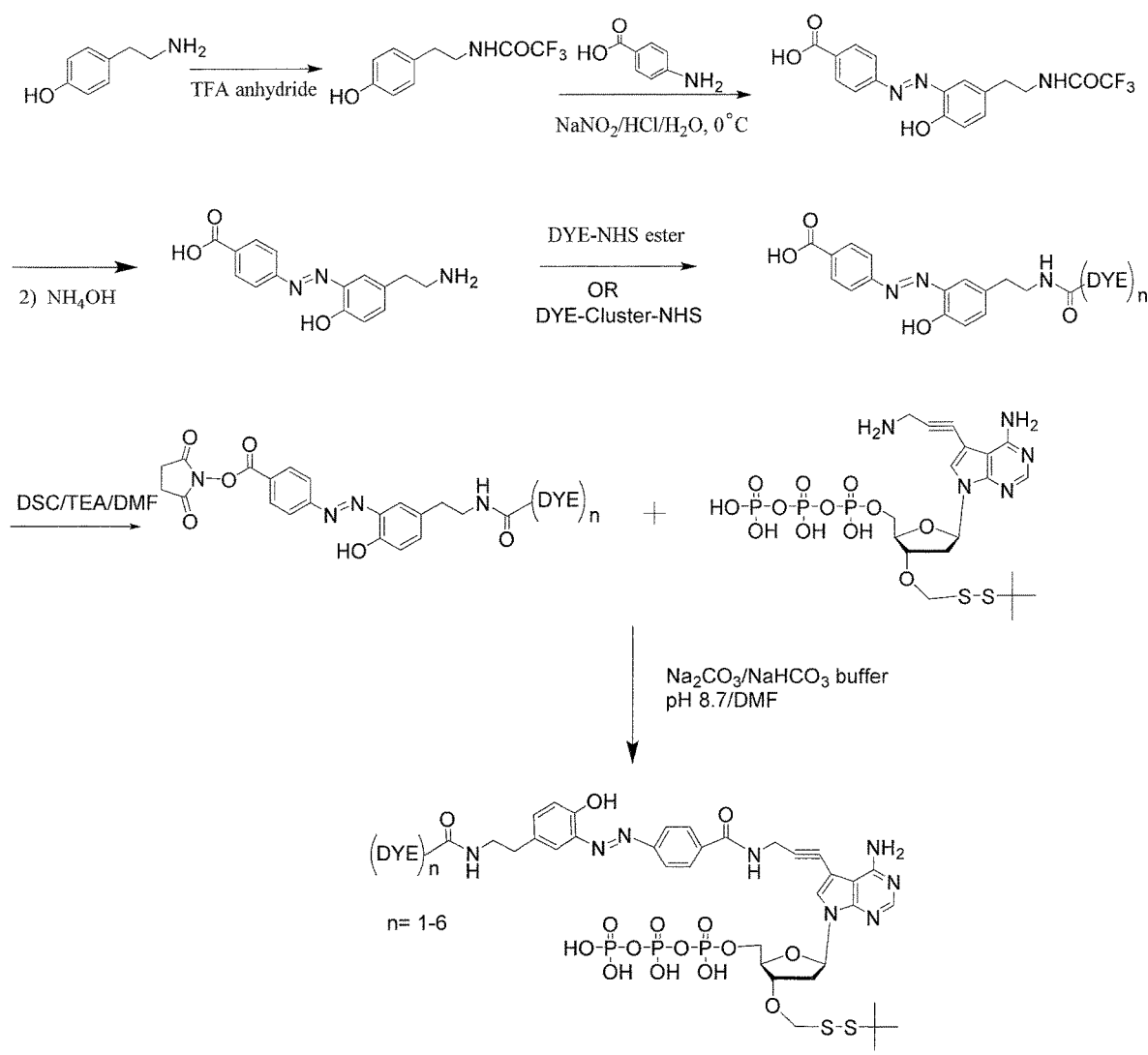

FIG. 94: General synthesis of 3'-SS-dNTP-Azo-Dye Cluster (dATP as an example).

Figure 95:
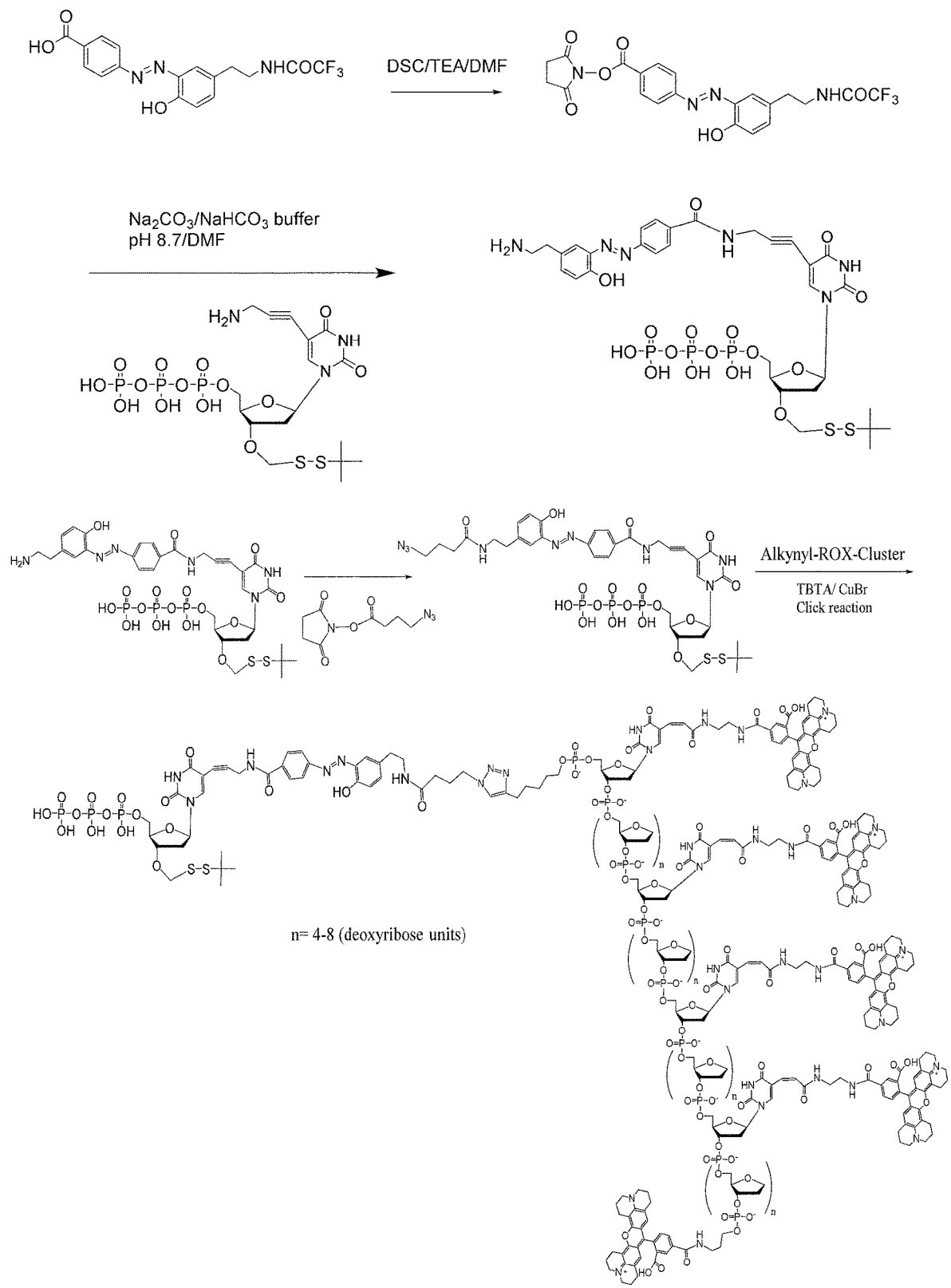

FIG. 95: Synthesis of 3'-O-SS-dTTP-Azo-(Rox Cluster). The Alkynyl-Rox Cluster can be routinely synthesized by using the standard oligonucleotide synthesis approach.

Figure 96:
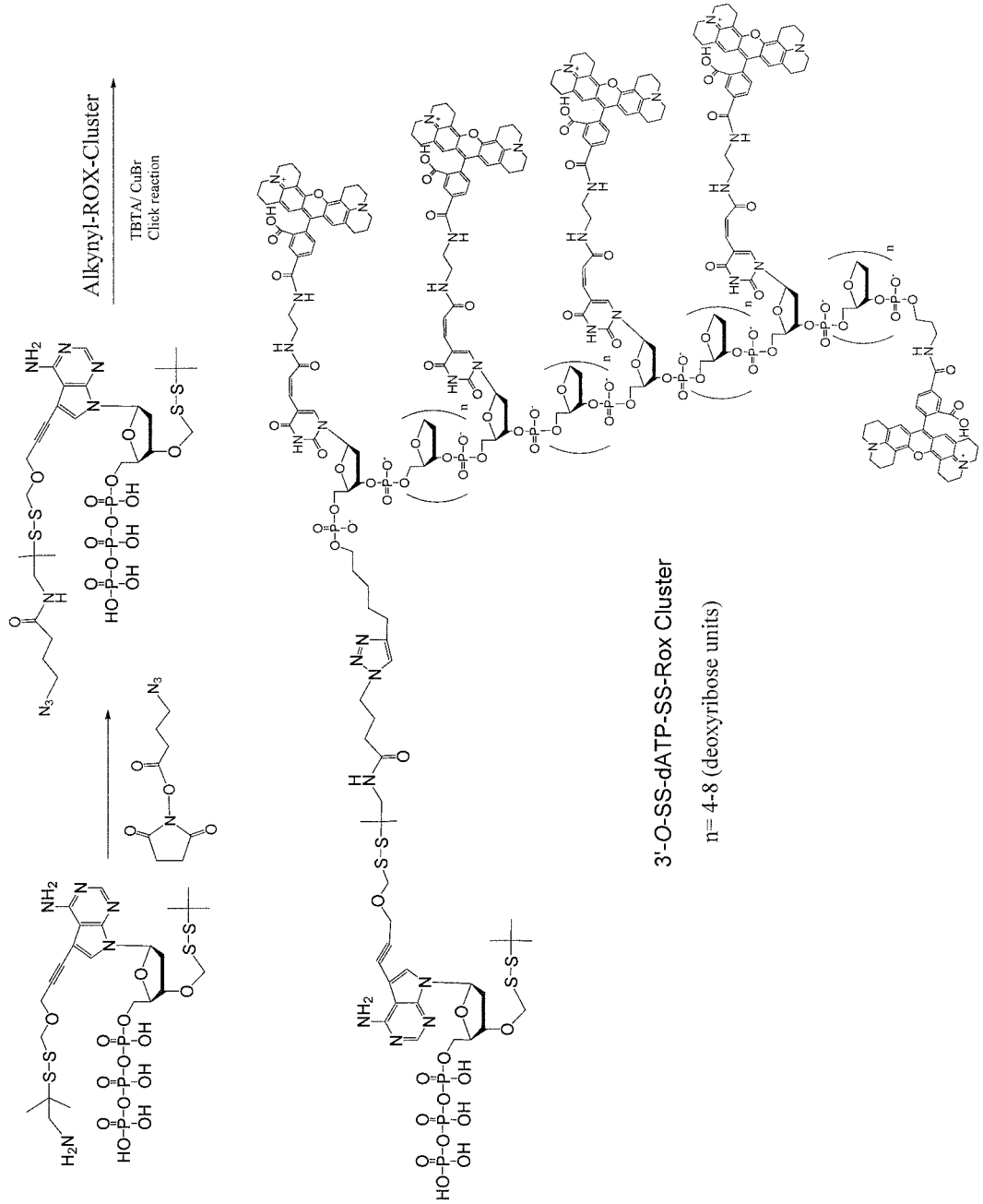

FIG. 96: Synthesis of 3'-O-SS-dATP-SS-(Rox Cluster). The Alkynyl-Rox Cluster can be routinely synthesized by using the standard oligonucleotide synthesis approach.

Figure 97:
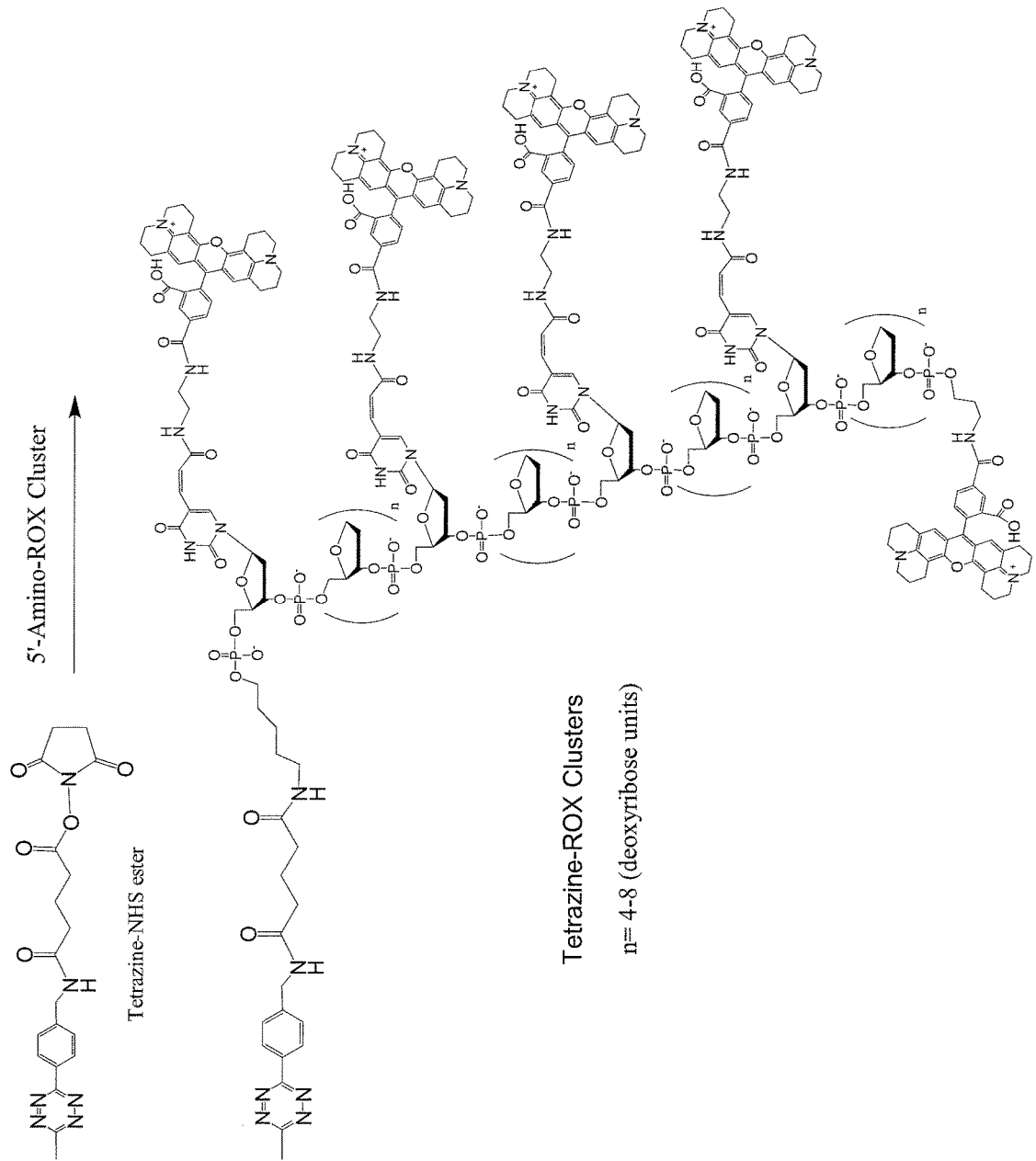

FIG. 97: Synthesis of Rox Cluster labeled tetrazine. The 5'-Amino-Rox Cluster can be routinely synthesized by using the standard oligonucleotide synthesis approach.

Figure 98:
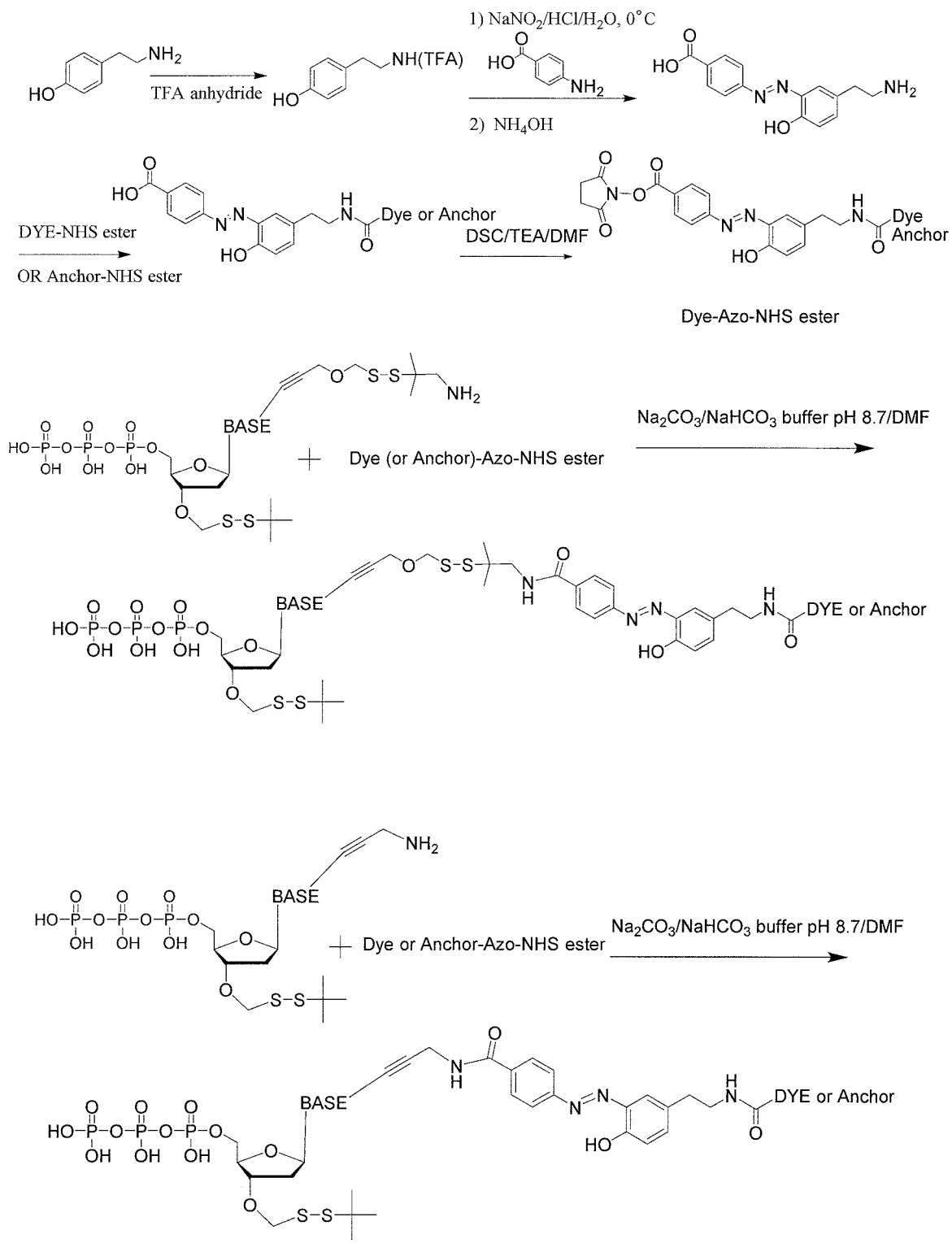

FIG. 98: General Synthesis of 3'-O-SS-dNTP-Azo-Dye (Anchor).

Figure 99:
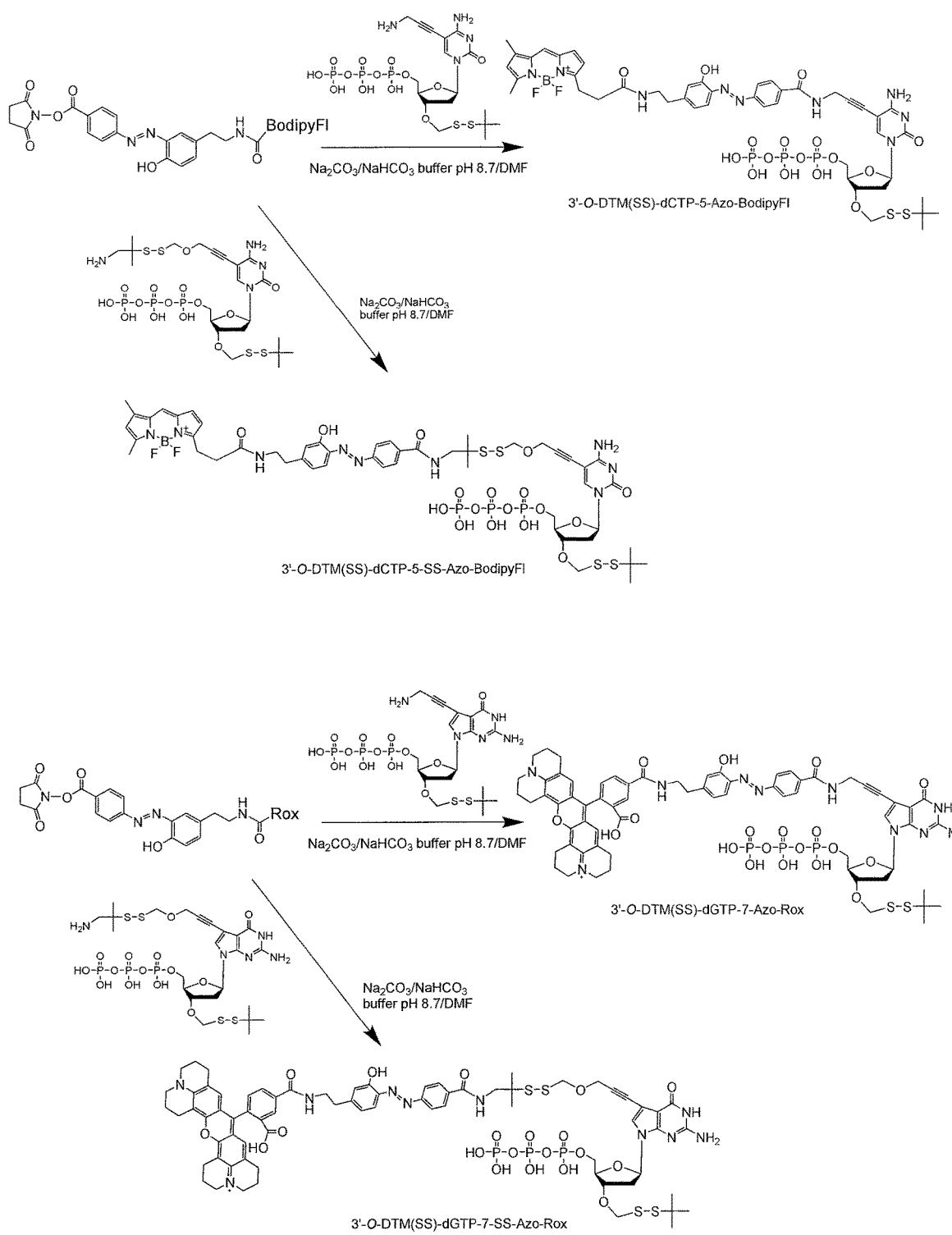

FIG. 99: Synthesis of 3'-O-SS-dTTP-5-Azo-BodipyFL and 3'-O-SS-dGTP-7-Azo-Rox.

Figure 100:
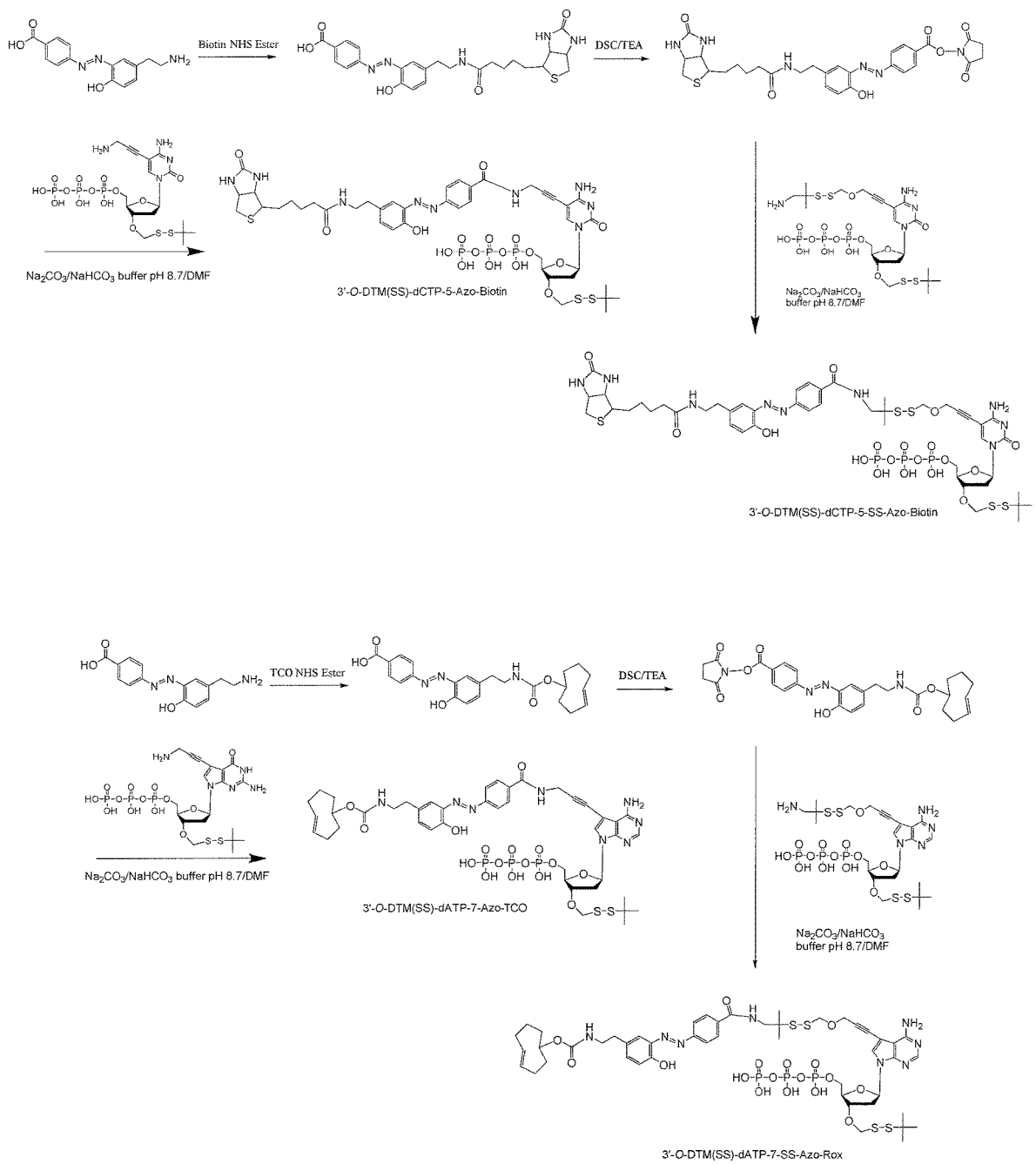

FIG. 100: Synthesis of 3'-O-SS-dCTP-5-Azo-Biotin and 3'-O-SS-dATP-7-Azo-TCO.

DETAILED DESCRIPTION

This invention provides novel nucleotide analogs containing a 3'-O-labled reversibly removable moiety that are efficiently incorporated by DNA polymerases into the growing DNA strand to temporarily terminate the reaction and produce a DNA extension product carrying the fluorescent label. By detecting the signal from the fluorophore, the identity of the incorporated nucleotide is determined (e.g., by the process of sequencing by synthesis (SBS)). Then the Dye-DTM moiety on the 3' of the DNA extension product is removed by treatment with Tris(3-hydroxypropyl)phosphine (THP) in an aqueous buffer solution to regenerate the 3'-OH group, which allows the re-initiation of the polymerase reaction for incorporation of the next incoming 3'-O-Dye-DTM-dNTP with high efficiency. Consecutive SBS using 3'-O-Dye-DTM-dNTP as reversible terminator generates a natural DNA strand, allowing the generation of accurate DNA sequencing data with long read length.

This invention provides novel nucleotide analogues containing a 3'-O-modification that can be efficiently incorporated by DNA polymerases into the growing DNA strand to temporarily terminate the reaction and produce a DNA extension product carrying a detectable label. The invention further provides novel nucleotide analogues comprising a 3'-O-labeled reversibly removable moiety and an anchor moiety, which is a predetermined small chemical group correlated to the identity of the base and that orthogonally and rapidly reacts with a complementary binding molecule thereby joining the anchor and binding molecule so as to form a conjugate. The complementary binding molecule comprises a detectable label and a binder that binds to the anchor on the nucleotide and a detectable label. By detecting the signal from the detectable label, whether attached to an incorporated nucleotide analogue, or attached to a binding molecule that has formed a conjugate with a nucleotide analogue, the identity of the incorporated nucleotide is determined. Then the 3'-O moiety of the DNA extension product is removed by treatment with a water soluble phosphine in an aqueous buffer solution to regenerate the 3'-OH group, which allows the re-initiation of the polymerase reaction for incorporation of the next incoming nucleotide analogue. The use of the following nucleotide analogues in various combinations to perform SBS are described: (a) those with fluorophores attached at the 3'-O position via a cleavable linker, (b) those with cleavable anchors at the 3'-O position for subsequent attachment of fluorophores, and (c) those with cleavable fluorophores on the base and a reversible blocking group on the 3'-OH. Consecutive SBS using the disclosed nucleotide analogues as reversible terminators generates a natural DNA strand, allowing the generation of accurate DNA sequencing data with long read length.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkelyene (e.g., alkylene, alkenylene, or alkynylene) group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, B, and S), and wherein the nitrogen and sulfur atoms may optionally be oxidized, and the nitrogen heteroatom may optionally be quaternized. The heteroatom(s) (e.g., O, N, S, Si, B, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si (CH₃)₃. A heteroalkyl moiety may include one heteroatom (e.g., O, N, S, Si, B, or P). A heteroalkyl moiety may include two optionally different heteroatoms (e.g., O, N, S, Si, B, or P). A heteroalkyl moiety may include three optionally different heteroatoms (e.g., O, N, S, Si, B, or P). A heteroalkyl moiety may include four optionally different heteroatoms (e.g., O, N, S, Si, B, or P). A heteroalkyl moiety may include five optionally different heteroatoms (e.g., O, N, S, Si, B, or P). A heteroalkyl moiety may include up to 8 optionally different heteroatoms (e.g., O, N, S, Si, B, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl" by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkelyene groups, heteroatoms can also occupy either or both of the chain termini (e.g., alkyleneoxy, alkylenedioxy, alkyleneamino, alkylenediamino, and the like). Still further, for alkelyene (e.g., alkylene, alkenylene, or alkynylene) and heteroalkelyene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C₁-C₄) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkelyene and individual rings within a spirocyclic ring group may be any of the immediately previous list, including having all rings of one type (e.g. all rings being substituted heterocycloalkelyene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkelyene (e.g., alkylene, alkenylene, or alkynylene) moiety (also referred to herein as an alkelyene). In embodiments, the alkylarylene group has the formula:

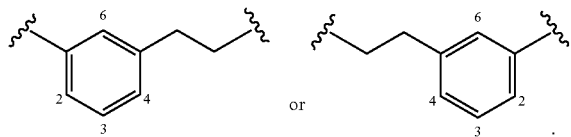

An alkylarylene moiety may be substituted (e.g., with a substituent group) on the alkelyene (e.g., alkylene, alkenylene, or alkynylene) moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, JNHNH$_2$, UONH$_2$, _NHC(O) NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', CNR'NR"R", QONR'R", LNR'C(O) NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR', —S(O)R', —S(O)$_2$R', —S(O)$_2$NR'R", —NRSO$_2$R', □NR'NR"R'", □ONR'R", □NR'C(O) NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include boron (B), oxygen (O), nitrogen (N), sulfur (S), phosphorus (P), and silicon (Si).

A "substituent" or "substituent group," as used herein, means a group selected from the following moieties:

(A) oxo, halogen, —CF$_3$, —CHF$_2$, —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, ☐NHNH$_2$, ☐ONH$_2$, ☐NHC(O)NHNH$_2$, ☐NHC(O)NH$_2$, —NHSO$_2$H, —NHC(O)H, —NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl (e.g., C$_1$-C$_{20}$, C$_1$-C$_8$, C$_1$-C$_6$, C$_1$-C$_4$, or C$_1$-C$_2$), unsubstituted heteroalkyl (e.g., 2 to 20 membered, 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), unsubstituted heteroaryl (e.g., 5 to 10 membered, 5 to 9 membered, or 5 to 6 membered); and (B) alkyl (e.g., C$_1$-C$_{20}$, C$_1$-C$_8$, C$_1$-C$_6$, C$_1$-C$_4$, or C$_1$-C$_2$), heteroalkyl (e.g., 2 to 20 membered, 2 to 8 membered, 2 to 6 membered, 4 to 6 membered, 2 to 3 membered, or 4 to 5 membered), cycloalkyl (e.g., C$_3$-C$_8$, C$_3$-C$_6$, C$_4$-C$_6$, or C$_5$-C$_6$), heterocycloalkyl (e.g., 3 to 8 membered, 3 to 6 membered, 4 to 6 membered, 4 to 5 membered, or 5 to 6 membered), aryl (e.g., C$_6$-C$_{10}$ or phenyl), heteroaryl (e.g., 5 to 10 membered, 5 to 9 membered, or 5 to 6 membered), substituted with at least one substituent selected from:

(i) oxo, halogen, —CF$_3$, —CHF$_2$, —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH2(halogen), unsubstituted alkyl (e.g., C$_1$-C$_{20}$, C$_1$-C$_8$, C$_1$-C$_6$, C$_1$-C$_4$, or C$_1$-C$_2$), unsubstituted heteroalkyl (e.g., 2 to 20 membered, 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), unsubstituted heteroaryl (e.g., 5 to 10 membered, 5 to 9 membered, or 5 to 6 membered), and (ii) alkyl (e.g., C$_1$-C$_{20}$, C$_1$-C$_5$, C$_1$-C$_6$, C$_1$-C$_4$, or C$_1$-C$_2$), heteroalkyl (e.g., 2 to 20 membered, 2 to 8 membered, 2 to 6 membered, 4 to 6 membered, 2 to 3 membered, or 4 to 5 membered), cycloalkyl (e.g., C$_3$-C$_8$, C$_3$-C$_6$, C$_4$-C$_6$, or C$_5$-C$_6$), heterocycloalkyl (e.g., 3 to 8 membered, 3 to 6 membered, 4 to 6 membered, 4 to 5 membered, or 5 to 6 membered), aryl (e.g., C$_6$-C$_{10}$ or phenyl), heteroaryl (e.g., 5 to 10 membered, 5 to 9 membered, or 5 to 6 membered), substituted with at least one substituent selected from:

(a) oxo, halogen, —CF$_3$, —CHF$_2$, —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, ☐NHNH$_2$, ☐ONH$_2$, ☐NHC(O)NHNH2, ☐NHC(O)NH2, —NHSO$_2$H, —NHC(O)H, —NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl (e.g., C$_1$-C$_{20}$, C$_1$-C$_8$, C$_1$-C$_6$, C$_1$-C$_4$, or C$_1$-C$_2$), unsubstituted heteroalkyl (e.g., 2 to 20 membered, 2 to 8 membered, 2 to 6 membered, 4 to 6 membered, 2 to 3 membered, or 4 to 5 membered), unsubstituted cycloalkyl (e.g., C$_3$-C$_5$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), unsubstituted heteroaryl (e.g., 5 to 10 membered, 5 to 9 membered, or 5 to 6 membered), and (b) alkyl (e.g., C$_1$-C$_{20}$, C$_1$-C$_8$, C$_1$-C$_6$, C$_1$-C$_4$, or C$_1$-C$_2$), heteroalkyl (e.g., 2 to 20 membered, 2 to 8 membered, 2 to 6 membered, 4 to 6 membered, 2 to 3 membered, or 4 to 5 membered), cycloalkyl (e.g., $C_3$-$C_8$, $C_3$-$C_6$, $C_4$-$C_6$, or $C_5$-$C_6$), heterocycloalkyl (e.g., 3 to 8 membered, 3 to 6 membered, 4 to 6 membered, 4 to 5 membered, or 5 to 6 membered), aryl (e.g., $C_6$-$C_{10}$ or phenyl), heteroaryl (e.g., 5 to 10 membered, 5 to 9 membered, or 5 to 6 membered), substituted with at least one substituent selected from:

oxo, halogen, —$CF_3$, —$CHF_2$, —$CH_2F$, —C(halogen)$_3$, —CH(halogen)$_2$, —$CH_2$(halogen), —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$OCH_2F$, —$OCF_3$, —$OCHF_2$, —$OCH_2F$, —OC(halogen)$_3$, —OCH(halogen)$_2$, —$OCH_2$(halogen), unsubstituted alkyl (e.g., $C_1$-$C_{20}$, $C_1$-$C_8$, $C_1$-$C_6$, $C_1$-$C_4$, or $C_1$-$C_2$), unsubstituted heteroalkyl (e.g., 2 to 20 membered, 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), unsubstituted heteroaryl (e.g., 5 to 10 membered, 5 to 9 membered, or 5 to 6 membered).

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkelyene (e.g., alkylene, alkenylene, or alkynylene) is a substituted or unsubstituted $C_1$-$C_{20}$ alkylene, each substituted or unsubstituted heteroalkelyene is a substituted or unsubstituted 2 to 20 membered heteroalkylene, each substituted or unsubstituted cycloalkelyene is a substituted or unsubstituted $C_3$-$C_8$ cycloalkylene, each substituted or unsubstituted heterocycloalkelyene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkelyene (e.g., alkylene, alkenylene, or alkynylene) is a substituted or unsubstituted $C_1$-$C_8$ alkylene, each substituted or unsubstituted heteroalkelyene is a substituted or unsubstituted 2 to 8 membered heteroalkylene, each substituted or unsubstituted cycloalkelyene is a substituted or unsubstituted $C_3$-$C_7$ cycloalkylene, each substituted or unsubstituted heterocycloalkelyene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable compound" or "detectable label" or "detectable moiety" is a composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

Radioactive substances (e.g., radioisotopes) that may be used as detectable, imaging and/or labeling agents in accordance with the embodiments described herein include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y $^{89}$Sr, $^{89}$Zr, $^{94}$Tc, $^{94}$Tc, $^{99m}$Tc, 99Mo, $^{105}$Pd, $^{105}$Rh, $^{111}$Ag, $^{111}$In, 123I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5- (and 6)-isothiocyanate moiety, Cy2 moeity, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO—PRO-1 moiety, PO—PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO—PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO—PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2', 7-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO—PRO-3-DNA moiety, PO—PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO—PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO—PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein., 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(p-C1)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO—PRO-1, BO—PRO-3, BOBO-1, BOBO-3, BODIPY 630 650—X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, C1OH butoxy aza-BODIPY, C1OH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kitzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, *Diversa* Cyan-FP, *Diversa* Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta)3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluoro1 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRedl, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO—C1, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoney-Dew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO—PRO-1, PO—PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH—CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styry18 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride. Tris(4,4-diphenyl-2,2-bipyridine) ruthenium(II) chloride., Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO—PRO-1, YO—PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a compound containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e. cyanine 7 or Cy7).

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "streptavidin" and "  " refer to a tetrameric protein (including homologs, isoforms, and functional fragments thereof) capable of binding biotin. The term includes any recombinant or naturally-occurring form of streptavidin variants thereof that maintain streptavidin activity (e.g. within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide).

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments a bioconjugate is a click chemistry reactant moiety when the association between atoms or molecules of bioconjugate reactive groups is direct (e.g., covalent bond, linker).

In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

The terms "monophosphate" is used in accordance with its ordinary meaning in the arts and refers to a moiety having the formula:

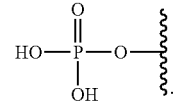

The term "polyphosphate" refers to at least two phosphate groups, having the formula:

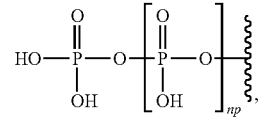

wherein np is an integer of 1 or greater. In embodiments, np is an integer from 0 to 5. In embodiments, np is an integer from 0 to 2. In embodiments, np is 2.

The term "base" as used herein refers to a divalent purine or pyrimidine compound or a derivative therof, that may be a constituent of nucleic acid (i.e. DNA or RNA, or a derivative thereof). In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g,. hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, hypoxanthine, xanthine, theobromine, caffeine, uric acid, or isoguanine. In embodiments, the base is

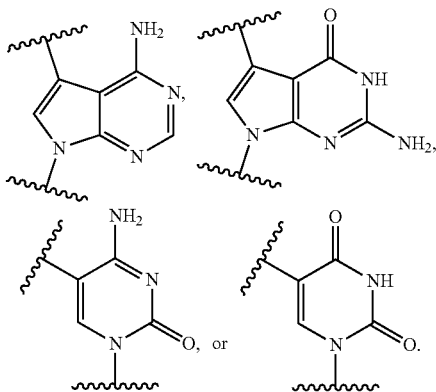

The term "non-covalent linker" is used in accordance with its ordinary meaning and refers to a divalent moiety which includes at least two molecules that are not covalently linked to each other but do interact with each other via a non-covalent bond (e.g. electrostatic interactions (e.g. ionic bond, hydrogen bond, halogen bond) or van der Waals interactions (e.g. dipole-dipole, dipole-induced dipole, London dispersion).

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) and phenyl boric acid (PBA). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety, tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation).

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally is a cleavable linker that following cleavage the two separated entities (e.g., fluorescent dye, bioconjugate reactive group) do not further react and form a new orthogonally cleavable linker.

The term "orthogonal binding group" or "orthogonal binding molecule" as used herein refer to a binding group (e.g. anchor moiety or complementary anchor moiety binder) that is capable of binding a first complementary binding group (e.g., complementary anchor moiety binder or anchor moiety) in a mixture of two or more different complementary binding groups and is unable to bind any other different complementary binding group in the mixture of two or more complementary binding groups. For example, two different binding groups are both orthogonal binding groups when a mixture of the two different binding groups are reacted with two complementary binding groups and each binding group binds only one of the complementary binding groups and not the other complementary binding group. An example of a set of four orthogonal binding groups and a set of orthogonal complementary binding groups are the binding groups biotin, azide, trans-cyclooctene (TCO) and phenyl boric acid (PBA), which specifically and efficiently bind or react with the complementary binding groups streptavidin, dibenzocyclooctyne (DBCO), tetrazine (TZ) and salicylhydroxamic acid (SHA) respectively.

The term "orthogonal detectable label" or "orthogonal detectable moiety" as used herein refer to a detectable label (e.g. fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N3. In embodiments, the polymerase-compatible cleavable moiety is:

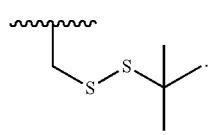 [SMILES: *CSSC(C)(C)C]

The term "allyl" as described herein refers to an unsubstituted methylene attached to a vinyl group (i.e. —CH=CH$_2$), having the formula

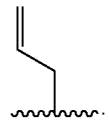 [SMILES: *CC=C]

An "allyl linker" refers to a divalent unsubstituted methylene attached to a vinyl group, having the formula

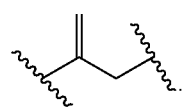 [SMILES: *CC(*)=C]

The term "polymerase-compatible moiety" as used herein refers a moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218):53-59; or Hutter D. et al. (2010) *Nucleosides Nucleotides & Nucleic Acids* 29:879-895, which are incorporated herein by reference in their entirety for all purposes.

The term "thermophilic nucleic acid polymerase" as used herein refers to a family of DNA polymerases (e.g., $_9°$ N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS*. 1996; 93(11):5281-5285). A thermophilic nucleic acid polymerase is a member of the family B DNA polymerases. Site-directed mutagenesis of the 3'-5' exo motif I (Asp-Ile-Glu) to Asp-Ile-Asp resulted in reduction of 3'-5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Terminator IX DNA polymerase), or γ-phosphate labeled nucleotides (e.g., Terminator γ: D141A/E143A/W355A/ L408W/R460A/Q461S/K464E/D480V/R484W/A485L). Typically these enzymes do not have 5'-3' exonuclease activity. Additional information about thermophilic nucleic acid polymerases may be found in (Southworth M W, et al. *PNAS.* 1996; 93(11):5281-5285; Bergen K, et al. *ChemBioChem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27): 9145-9150), which are incorporated herein in their entirety for all purposes.

The term "primer", as used herein, is defined to be one or more nucleic acid fragments that specifically hybridize to a nucleic acid template. A primer can be of any length depending on the particular technique it will be used for. For example, PCR primers are generally between 10 and 40 nucleotides in length. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

II. Compositions

In an aspect is provided a nucleotide analogue having the formula:

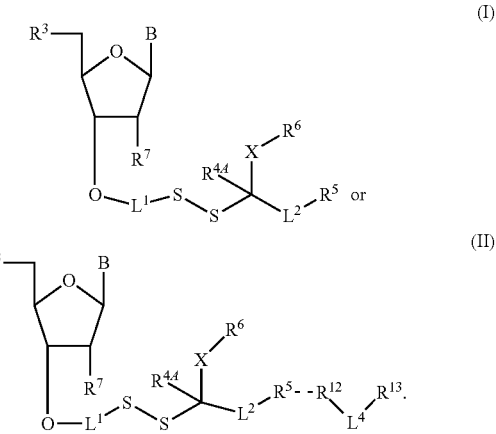

B is a base or analogue thereof. $L^1$ is covalent linker. $L^2$ is covalent linker. $L^4$ is covalent linker. X is a bond, O, $NR^{6A}$, or S. $R^3$ is —OH, monophosphate, polyphosphate or a nucleic acid. $R^{4A}$ and $R^{6A}$ are independently hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, anchor moiety, or affinity anchor moiety. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In embodiments, the nucleotide analogue has the formula:

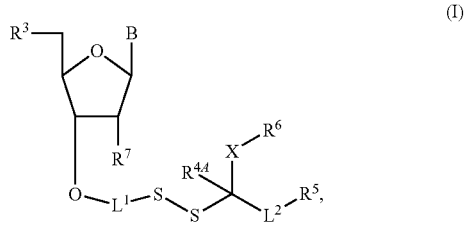

wherein $R^3$, B, $R^7$, $L^1$, $R^{4A}$, X, $R^6$, $L^2$, and $R^5$ are as described herein. In embodiments, $R^5$ is a detectable label or anchor moiety.

In embodiments, the nucleotide analogue has the formula:

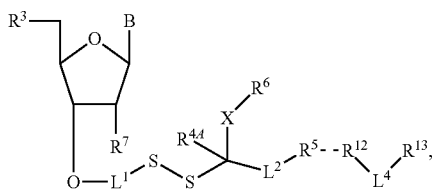
(II)

wherein $R^3$, B, $R^7$, $L^1$, $R^{4A}$, X, $R^6$, $L^2$, $R^5$, $R^{12}$, $L^4$, and $R^{13}$ are as described herein. In embodiments, $R^5$ is an affinity anchor moiety. The symbol "----" is a non-covalent bond.

In an aspect is provided a nucleotide analogue having the formula:

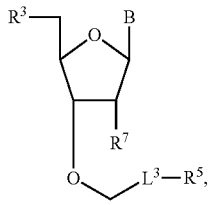
(IA)

wherein $L^3$ is a cleavable linker; $R^3$ is —OH, monophosphate, polyphosphate or a nucleic acid; B is a base or analogue thereof; $R^5$ is a detectable label or anchor moiety; and $R^7$ is hydrogen or —$OR^{7A}$, wherein $R^{7A}$ is hydrogen or a polymerase-compatible moiety.

In an aspect is provided a nucleotide analogue having the formula:

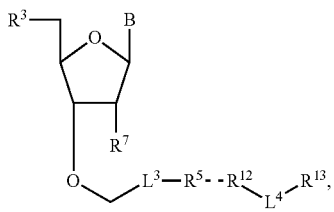
(IIA)

wherein $L^3$ is a cleavable linker; $R^3$ is —OH, monophosphate, polyphosphate or a nucleic acid; B is a base or analogue thereof; $R^5$ is a detectable label or anchor moiety; and $R^7$ is hydrogen or —$OR^{7A}$, wherein $R^{7A}$ is hydrogen or a polymerase-compatible moiety. $L^4$ is covalent linker. $R^{12}$ is a complementary affinity anchor moiety binder. $R^{13}$ is a detectable label. The symbol "----" is a non-covalent bond.

In an aspect is provided a nucleic acid polymerase comprising non-thermophilic or thermophilic polymerase that forms a ternary complex with the primed template and the nucleotide analogue, wherein the nucleic acid polymerase is bound to a nucleotide analogue having the formula:

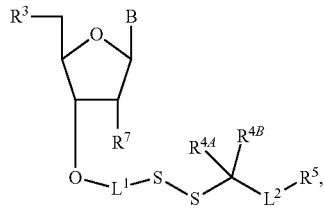
(III)

wherein $R^3$, B, $R^7$, $L^1$, $R^{4A}$, X, $R^6$, $L^2$, and $R^5$ are as described herein, or

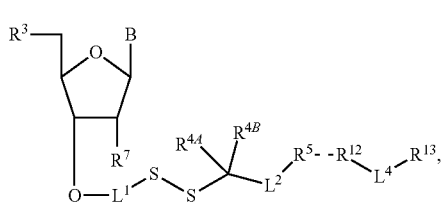
(IV)

wherein $R^3$, B, $R^7$, $L^1$, $R^{4A}$, $R^6$, $L^2$, $R^5$, $R^{12}$, $L^4$, and $R^{13}$ are as described herein.

In embodiments, the nucleotide analogue has the formula:

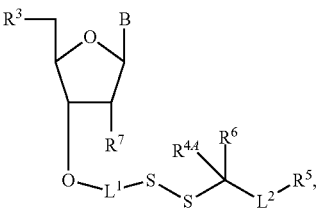
(IIIA)

wherein $R^3$, B, $R^7$, $L^1$, $R^{4A}$, $R^6$, $L^2$, and $R^5$ are as described herein. In embodiments, $R^5$ is a detectable label or anchor moiety. In embodiments, $R^{4A}$ is not hydrogen. In embodiments, $R^{4B}$ is not hydrogen. In embodiments, $R^{4A}$ and $R^{4B}$ are not hydrogen.

In embodiments, the nucleotide analogue has the formula:

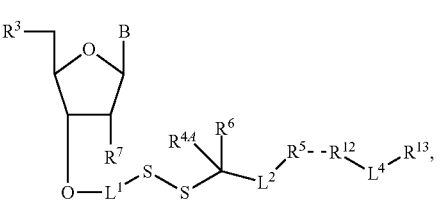
(IVA)

wherein $R^3$, B, $R^7$, $L^1$, $R^{4A}$, $R^6$, $L^2$, $R^5$, $R^{12}$, $L^4$, and $R^{13}$ are as described herein. In embodiments, $R^5$ is an affinity anchor moiety. The symbol "----" is a non-covalent bond. In embodiments, $R^{4A}$ is not hydrogen. In embodiments, $R^6$ is not hydrogen. In embodiments, $R^{4A}$ and $R^6$ are not hydrogen.

In an aspect is provided a nucleic acid polymerase (e.g., thermophilic, 9° N and mutants thereof, Phi29 and mutants thereof) complex, wherein the thermophilic nucleic acid polymerase is bound to a nucleotide analogue having the formula:

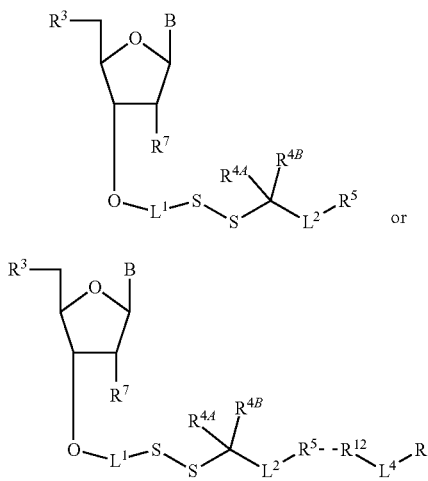
(III)

or (IV)

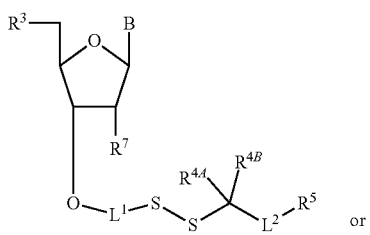

B is a base or analogue thereof. $L^1$ is covalent linker. $L^2$ is covalent linker. $L^4$ is covalent linker. $R^3$ is —OH, monophosphate, polyphosphate or a nucleic acid. $R^{4A}$ and $R^{6A}$ are independently is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4B}$ is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —X—$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is a bond, O, $NR^{6A}$, or S. $R^5$ is a detectable label, anchor moiety, or affinity anchor moiety. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In an aspect is provided a thermophilic nucleic acid polymerase complex, wherein the thermophilic nucleic acid polymerase is bound to a nucleotide analogue having the formula:

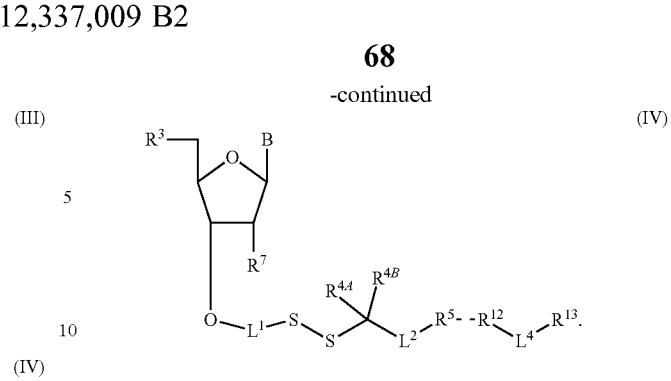

(III)

or (IV)

B is a base or analogue thereof. $L^1$ is covalent linker. $L^2$ is covalent linker. $L^4$ is covalent linker. $R^3$ is —OH, monophosphate, polyphosphate or a nucleic acid. $R^{4A}$ and $R^{6A}$ are independently is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4B}$ is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —X—$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is a bond, O, $NR^{6A}$, or S. $R^5$ is a detectable label, anchor moiety, or affinity anchor moiety. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{7A}$, wherein $R^{7A}$ is hydrogen or a polymerase-compatible moiety. $R^{12}$ is a complementary affinity anchor moiety binder. $R^{13}$ is a detectable label. The symbol "----" is a non-covalent bond.

In embodiments, the thermophilic nucleic acid polymerase is bound to a nucleotide analogue having the formula:

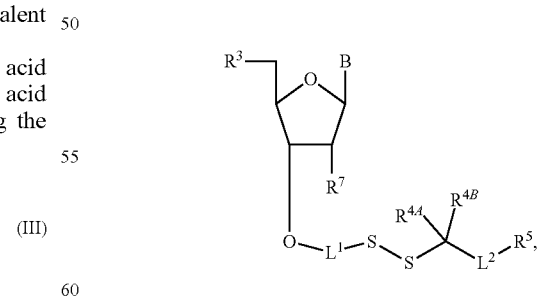

wherein $R^3$, B, $R^7$, $L^1$, $R^{4A}$, $R^{4B}$, $L^2$, and $R^5$ are as described herein. In embodiments, $R^5$ is a detectable label or anchor moiety.

In embodiments, the thermophilic nucleic acid polymerase is bound to a nucleotide analogue having the formula:

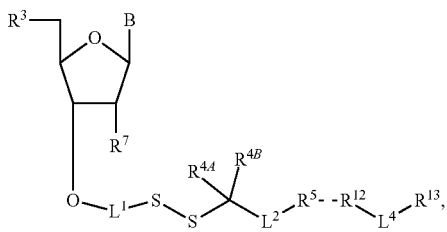

wherein $R^3$, B, $R^7$, $L^1$, $R^{4A}$, $R^{4B}$, $L^2$, $R^5$, $R^{12}$, $L^4$, and $R^{13}$ are as described herein. In embodiments, $R^5$ is an affinity anchor moiety. The symbol "----" is a non-covalent bond.

In another aspect is provided a thermophilic nucleic acid polymerase complex (e.g., 9° N nucleic acid polymerase complex), wherein the thermophilic nucleic acid polymerase is bound to a nucleotide analogue, wherein the nucleotide analogue includes a fluorescent dye with a molecular weight of at least about 140 Daltons, and wherein the fluorescent dye is covalently bound at the 3' position of the nucleotide analogue. In embodiments, the fluorescent dye is covalently bound at the 3' position of the nucleotide analogue via a linker (e.g., —S(O)$_2$—, —NH—, —O—, —S—, —C(O)—, —C(O)NH—, —NHC(O)—, —NHC(O)NH—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene).

In embodiments, B is cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, deaza-adenine or a derivative thereof, deaza-guanine or a derivative thereof, deaza-hypoxanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

In embodiments, B is cytosine or a derivative thereof. In embodiments, B is guanine or a derivative thereof. In embodiments, B is adenine or a derivative thereof. In embodiments, B is thymine or a derivative thereof. In embodiments, B is uracil or a derivative thereof. In embodiments, B is hypoxanthine or a derivative thereof. In embodiments, B is xanthine or a derivative thereof. In embodiments, B is deaza-adenine or a derivative thereof. In embodiments, B is deaza-guanine or a derivative thereof. In embodiments, B is deaza-hypoxanthine or a derivative thereof. In embodiments, B is 7-methylguanine or a derivative thereof. In embodiments, B is 5,6-dihydrouracil or a derivative thereof. In embodiments, B is 5-methylcytosine or a derivative thereof. In embodiments, B is or 5-hydroxymethylcytosine or a derivative thereof.

In embodiments, B is cytosine, guanine, adenine, thymine, uracil, hypoxanthine, xanthine, deaza-adenine, deaza-guanine, deaza-hypoxanthine or a derivative thereof, 7-methylguanine, 5,6-dihydrouracil, 5-methylcytosine, or 5-hydroxymethylcytosine. In embodiments, B is cytosine. In embodiments, B is guanine. In embodiments, B is adenine. In embodiments, B is thymine. In embodiments, B is uracil. In embodiments, B is hypoxanthine. In embodiments, B is xanthine. In embodiments, B is deaza-adenine. In embodiments, B is deaza-guanine. In embodiments, B is deaza-hypoxanthine. In embodiments, B is 7-methylguanine. In embodiments, B is 5,6-dihydrouracil. In embodiments, B is 5-methylcytosine. In embodiments, B is or 5-hydroxymethylcytosine.

In embodiments, B is

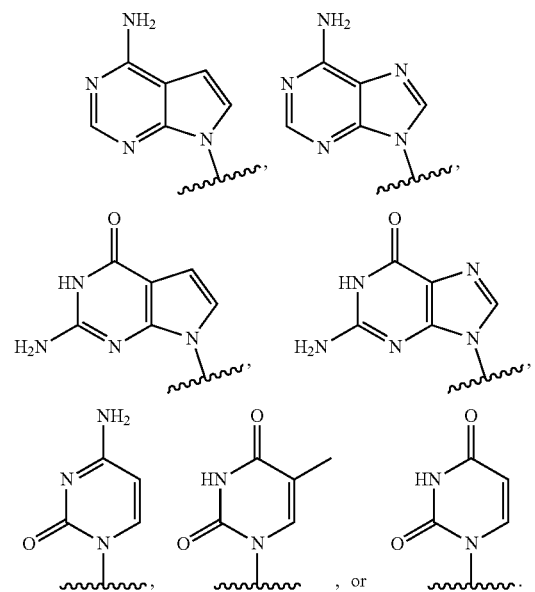

In embodiments, B is

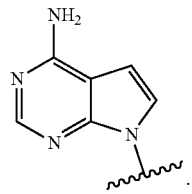 [SMILES: *n1ccc2c(N)ncnc21]

In embodiments, B is

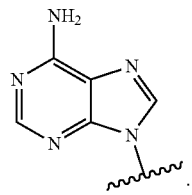 [SMILES: *n1cnc2c(N)ncnc21]

In embodiments, B is

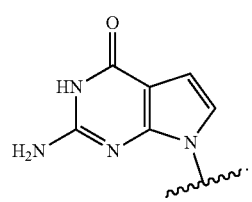 [SMILES: *n1ccc2c(=O)[nH]c(N)nc21]

In embodiments, B is

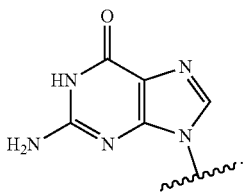

In embodiments, B is

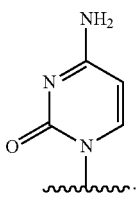

In embodiments, B is

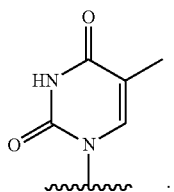 [SMILES: *n1cc(C)c(=O)[nH]c1=O]

In embodiments, B is

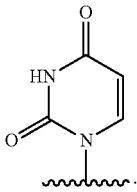 [SMILES: *n1ccc(=O)[nH]c1=O]

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{1A}$, $L^{1B}$, $L^{1C}$, $L^{1D}$ and $L^{1E}$ is not a bond.

In embodiments, $L^1$ is a substituted or unsubstituted methylene, wherein $L^1$ is substituted with a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene. In embodiments, $L^1$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

In embodiments, $L^1$ is a substituted or unsubstituted methylene, wherein $L^1$ is substituted with a substituted or unsubstituted $C_1$-$C_6$ alkylene or substituted or unsubstituted 2 to 6 membered heteroalkylene. In embodiments, $L^1$ is a substituted or unsubstituted $C_1$-$C_6$ alkylene or substituted or unsubstituted 2 to 6 membered heteroalkylene. In embodiments, $L^1$ is a substituted or unsubstituted methylene, wherein $L^1$ is substituted with a substituted or unsubstituted $C_1$-$C_6$ alkylene. In embodiments, $L^1$ is an unsubstituted methylene.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_5$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_5$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^1$ is a bond, substituted (e.g., substituted with a substituent group, size-limited substituent group, or lower substituent group) or unsubstituted $C_1$-$C_5$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^1$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ or $L^{1E}$ are independently a bond, substituted (e.g., substituted with a substituent group, size-limited substituent group, or lower substituent group) or unsubstituted alkenylene (e.g., substituted with a substituent group, or substituted with size-limited substituent group), substituted (e.g., substituted with a substituent group, size-limited substituent group, or lower substituent group) or unsubstituted heteroalkenylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ or $L^{1E}$ are independently a bond, substituted (e.g., substituted with a substituent group, size-limited substituent group, or lower substituent group) or unsubstituted $C_1$-$C_5$ alkenylene, or substituted (e.g., substituted with a substituent group, size-limited substituent group, or lower substituent group) or unsubstituted 2 to 8 membered heteroalkenylene; wherein at least one of $L^{1A}$, $L^{1B}$ $L^{1C}$, $L^{1D}$ and $L^{1E}$ is not a bond. In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ or $L^{1E}$ are independently a bond, substituted (e.g., substituted with a substituent group, size-limited substituent group, or lower substituent group) or unsubstituted $C_1$-$C_6$ alkenylene, or substituted (e.g., substituted with a substituent group, size-limited substituent group, or lower substituent group) or unsubstituted 2 to 6 membered heteroalkenylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkenylene, or substituted (e.g., substituted with a substituent group, size-limited substituent group, or lower substituent group) or unsubstituted heteroalkenylene. In embodiments, $L^1$ is a bond, substituted (e.g., substituted with a substituent group, size-limited substituent group, or lower substituent group) or unsubstituted $C_2$-$C_8$ alkenylene, or substituted (e.g., substituted with a substituent group, size-limited substituent group, or lower substituent group) or unsubstituted 3 to 8 membered heteroalkenylene. In embodiments, $L^1$ is a bond, substituted (e.g., substituted with a substituent group, size-limited substituent group, or lower substituent group) or unsubstituted $C_2$-$C_6$ alkenylene, or substituted (e.g., substituted with a substituent group, size-limited substituent group, or lower substituent group) or unsubstituted 3 to 6 membered heteroalkenylene.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ or $L^{1E}$ are independently a bond, substituted (e.g., substituted with a substituent group, size-limited substituent group, or lower substituent group) or unsubstituted alkynylene, substituted (e.g., substituted with a substituent group, size-limited substituent group, or lower substituent group) or unsubstituted heteroalkynylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ or $L^{1E}$ are independently a bond, substituted (e.g., substituted with a substituent group, size-limited substituent group, or lower substituent group) or unsubstituted $C_1$-$C_8$alkynylene, or substituted (e.g., substituted with a substituent group, size-limited substituent group, or lower substituent group) or unsubstituted 2 to 8 membered heteroalkynylene; wherein at least one of $L^{1A}$, $L^{1B}$, $L^{1C}$, $L^{1D}$ and $L^{1E}$ is not a bond. In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and LIE are independently a bond, substituted (e.g., substituted with a substituent group, size-limited substituent group, or lower substituent group) or unsubstituted $C_1$-$C_6$ alkynylene, or substituted (e.g., substituted with a substituent group, size-limited substituent group, or lower substituent group) or unsubstituted 2 to 6 membered heteroalkynylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkynylene, or substituted (e.g., substituted with a substituent group, size-limited substituent group, or lower substituent group) or unsubstituted heteroalkynylene. In embodiments, $L^1$ is a bond, substituted (e.g., substituted with a substituent group, size-limited substituent group, or lower substituent group) or unsubstituted $C_2$-$C_8$ alkynylene, or substituted (e.g., substituted with a substituent group, size-limited substituent group, or lower substituent group) or unsubstituted 3 to 8 membered heteroalkynylene. In embodiments, $L^1$ is a bond, substituted (e.g., substituted with a substituent group, size-limited substituent group, or lower substituent group) or unsubstituted $C_2$-$C_6$ alkynylene, or substituted (e.g., substituted with a substituent group, size-limited substituent group, or lower substituent group) or unsubstituted 3 to 6 membered heteroalkynylene.

In embodiments, $L^1$ is a substituted (e.g., substituted with a substituent group, size-limited substituent group, or lower substituent group) or unsubstituted $C_1$-$C_6$ alkelyene (e.g., alkylene (e.g., alkylene, alkenylene, or alkynylene), alkenylene, or alkynylene) or substituted (e.g., substituted with a substituent group, size-limited substituent group, or lower substituent group) or unsubstituted 2 to 6 membered heteroalkylene (e.g., heteroalkylene, heteroalkenylene, or heteroalkynylene). In embodiments, $L^1$ is an unsubstituted $C_1$-$C_4$ alkylene (e.g., alkylene, alkenylene, or alkynylene). In embodiments, $L^1$ is not substituted with a cleavable moiety. In embodiments, $L^1$ is not substituted with a monovalent cleavable moiety.

In embodiments, $L^1$ is a polymer. In embodiments, $L^2$ is a polymer. In embodiments, $L^2$ includes a polymer. In embodiments, $L^2$ includes PEG. In embodiments, $L^4$ is a polymer. In embodiments, $L^4$ includes a polymer. In embodiments, $L^4$ includes PEG. The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

In embodiments, $L^2$ is a cleavable linker. In embodiments, $L^2$ is a non-cleavable linker. In embodiments, $L^2$ is a chemically cleavable linker. In embodiments, $L^2$ is a photocleavable linker, an acid-cleavable linker, a base-cleavable linker, an oxidant-cleavable linker, a reductant-cleavable linker, or a fluoride-cleavable linker. In embodiments, $L^2$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^2c$, $L^{2D}$, and $L^{2E}$ is not a bond.

In embodiments, $L^2$ is $L^{2A}$-$L^{2B}$-$L^{2C}$-$L^{2D}$-$L^{2E}$; $L^{2A}$ is a bond, substituted or unsubstituted alkylene, substituted or unsubstituted heteroalkylene; $L^{2B}$ is a bond, substituted or unsubstituted cycloalkylene, substituted or unsubstituted heterocycloalkylene, substituted or unsubstituted arylene, substituted or unsubstituted heteroarylene; $L^{2C}$ is a bond, substituted or unsubstituted cycloalkylene, substituted or unsubstituted heterocycloalkylene, substituted or unsubstituted arylene, substituted or unsubstituted heteroarylene; $L^{2D}$ is a bond, substituted or unsubstituted alkylene, substituted or unsubstituted heteroalkylene; and $L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$, and $L^{2E}$ is not a bond.

In embodiments, $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ is a bond, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene.

In embodiments, $L^2$ is a bond, substituted or unsubstituted $C_1$-$C_8$ alkylene, substituted or unsubstituted 2 to 8 membered heteroalkylene, substituted or unsubstituted $C_3$-$C_5$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

In embodiments, $L^2$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

In embodiments, $L^2$ is a substituted or unsubstituted 4 to 10 membered heteroalkylene. In embodiments, $L^2$ is a substituted or unsubstituted 4 to 8 membered heteroalkylene.

In embodiments, $L^2$ is

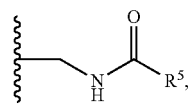

wherein $R^5$ is as described herein. In embodiments, $L^2$ is

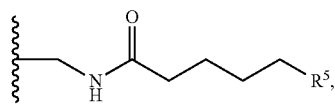

wherein $R^5$ is as described herein. In embodiments, $L^2$ is

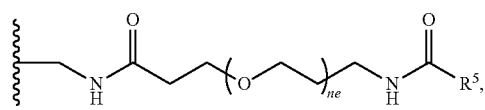

wherein $R^5$ is as described herein and ne is an integer from 0 to 20.

In embodiments, $L^2$ is

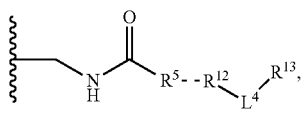

wherein $R^5$ is as described herein. In embodiments, $L^2$ is

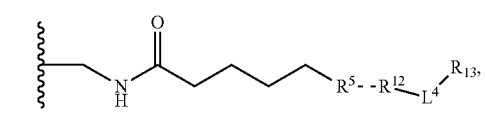

wherein $R^5$ is as described herein. In embodiments, $L^2$ is

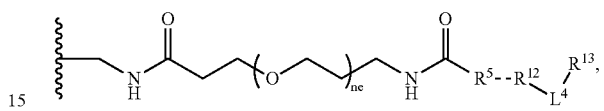

wherein $R^5$ is as described herein and ne is an integer from 0 to 20.

In embodiments, ne is an integer from 0 to 18. In embodiments, ne is an integer from 0 to 12. In embodiments, ne is an integer from 0 to 10. In embodiments, ne is an integer from 0 to 8. In embodiments, ne is an integer from 0 to 4. In embodiments, ne is an integer from 1 to 18. In embodiments, ne is an integer from 1 to 12. In embodiments, ne is an integer from 1 to 10. In embodiments, ne is an integer from 1 to 8. In embodiments, ne is an integer from 1 to 4. In embodiments, ne is an integer from 2 to 18. In embodiments, ne is an integer from 2 to 12. In embodiments, ne is an integer from 2 to 10. In embodiments, ne is an integer from 2 to 8. In embodiments, ne is an integer from 0 to 4. In embodiments, ne is 0. In embodiments, ne is 1. In embodiments, ne is 2. In embodiments, ne is 3. In embodiments, ne is 4. In embodiments, ne is 5. In embodiments, ne is 6. In embodiments, ne is 7. In embodiments, ne is 8. In embodiments, ne is 9. In embodiments, ne is 10. In embodiments, ne is 11. In embodiments, ne is 12. In embodiments, ne is 13. In embodiments, ne is 14. In embodiments, ne is 15. In embodiments, ne is 16. In embodiments, ne is 17. In embodiments, ne is 18. In embodiments, ne is 19. In embodiments, ne is 20.

In embodiments, $L^2$ is —C(CH$_3$)$_2$CH$_2$NHC(O)—. In embodiments, $L^2$ is

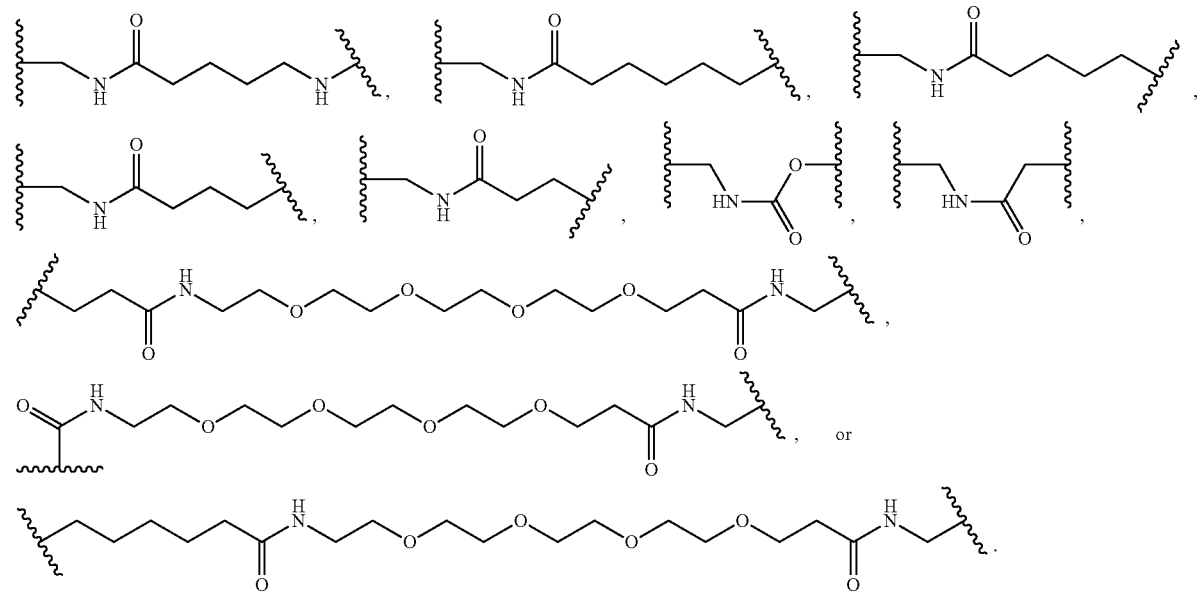

In embodiments, $L^2$ includes

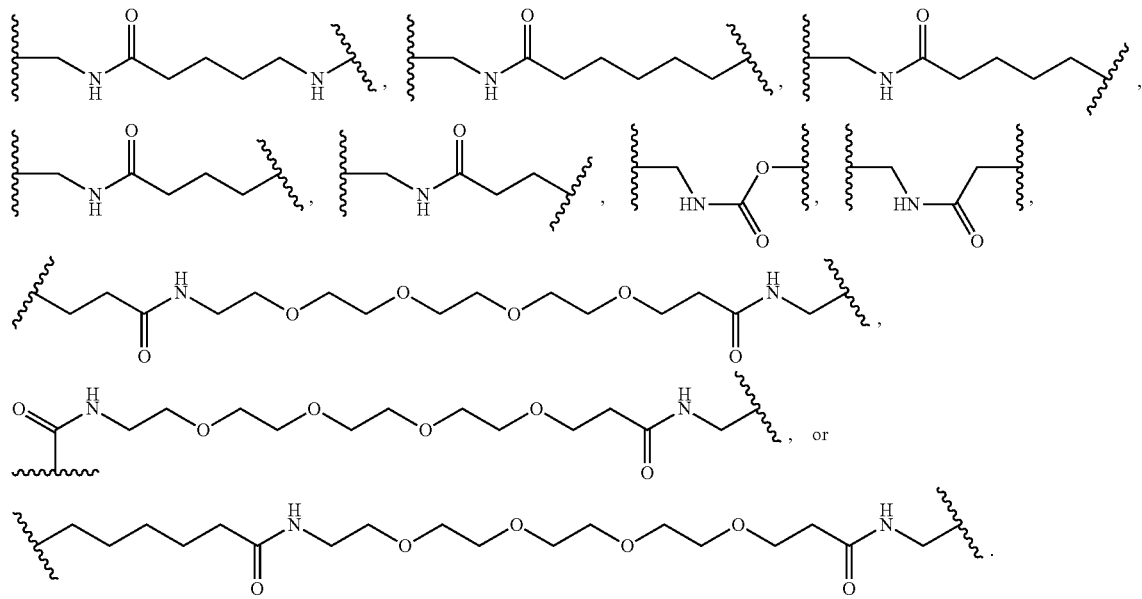

In embodiments, $L^2$ is a cleavable linker. In embodiments, $L^2$ is a chemically cleavable linker. In embodiments, $L^2$ is a photocleavable linker, an acid-cleavable linker, a base-cleavable linker, an oxidant-cleavable linker, a reductant-cleavable linker, or a fluoride-cleavable linker. In embodiments, $L^2$ is a photocleavable linker. In embodiments, $L^2$ is an acid-cleavable linker. In embodiments, $L^2$ is a base-cleavable linker. In embodiments, $L^2$ is an oxidant-cleavable linker. In embodiments, $L^2$ is a reductant-cleavable linker. In embodiments, $L^2$ is a fluoride-cleavable linker.

In embodiments, $L^2$ includes a cleavable linker. In embodiments, $L^2$ includes a chemically cleavable linker. In embodiments, $L^2$ includes a photocleavable linker, an acid-cleavable linker, a base-cleavable linker, an oxidant-cleavable linker, a reductant-cleavable linker, or a fluoride-cleavable linker. In embodiments, $L^2$ includes a photocleavable linker. In embodiments, $L^2$ includes an acid-cleavable linker. In embodiments, $L^2$ includes a base-cleavable linker. In embodiments, $L^2$ includes an oxidant-cleavable linker. In embodiments, $L^2$ includes a reductant-cleavable linker. In embodiments, $L^2$ includes a fluoride-cleavable linker.

In embodiments, $L^2$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^2$ is a cleavable linker including a dialkylketal linker. In embodiments, $L^2$ is a cleavable linker including an azo linker. In embodiments, $L^2$ is a cleavable linker including an allyl linker. In embodiments, $L^2$ is a cleavable linker including a cyanoethyl linker. In embodiments, $L^2$ is a cleavable linker including a 1-(4,4-dimethyl-2,6-dioxocyclohex-1-ylidene)ethyl linker. In embodiments, $L^2$ is a cleavable linker including a nitrobenzyl linker.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, and $L^{2E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; $L^{2A}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene). $L^{2B}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2C}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2D}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{2E}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, $L^2$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene. In embodiments, $L^2$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene. In embodiments, $L^2$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_5$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 4 to 8 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 4 to 6 membered heteroalkylene (e.g., heteroalkylene, heteroalkenylene, or heteroalkynylene).

In embodiments, $L^2$ is an orthogonally cleavable linker or a non-covalent linker. In embodiments, $L^2$ includes an orthogonally cleavable linker or a non-covalent linker. In embodiments, $L^2$ is an orthogonally cleavable linker. In embodiments, $L^2$ is a non-covalent linker.

In embodiments, $L^{2A}$, $L^{2B}$, $L^{2C}$, $L^{2D}$, and $L^{2E}$ are each independently

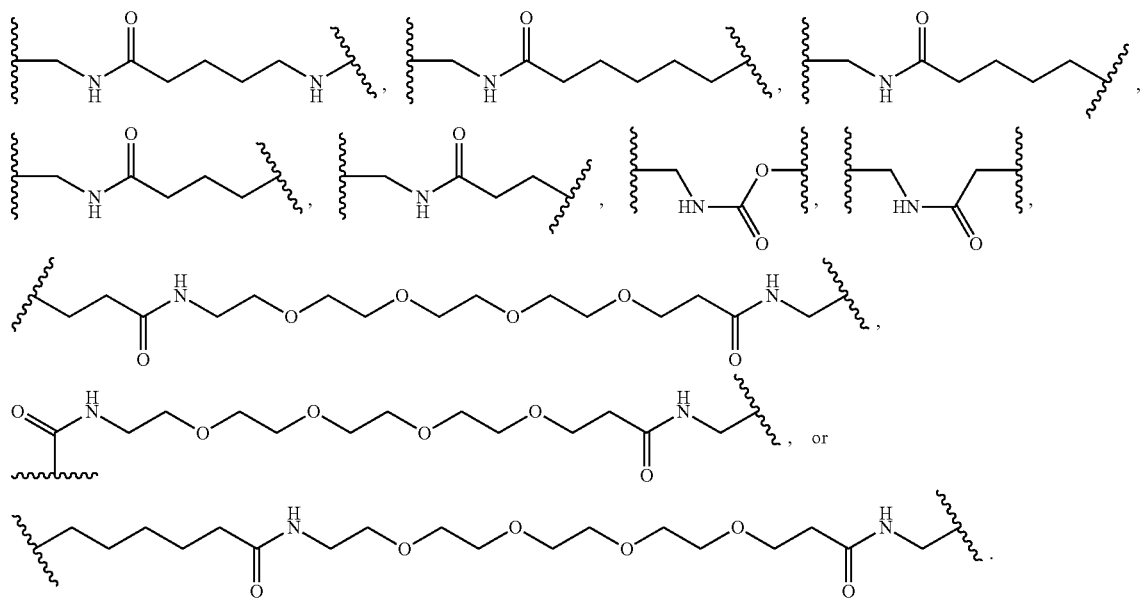

group, or lower substituent group) or unsubstituted 5 to 10 membered heteroarylene. In embodiments, $L^2$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^2$ is a substituted (e.g., substituted with a substituent group, size-limited substituent group, or lower substituent group) or unsubstituted 4 to 10 membered heteroalkylene (e.g., heteroalkylene, heteroalkenylene, or heteroalkynylene). In embodiments, $L^2$ is a substituted (e.g., substituted with a substituent group, size-limited substituent embodiments, -$L^2$- is

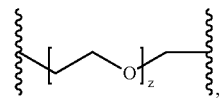

wherein z is an integer from 0 to 10. In embodiments z is an integer from 1 to 8. In embodiments z is an integer from 2 to 4. In embodiments z is 0. In embodiments z is 1. In embodiments z is 2. In embodiments z is 3. In embodiments z is 4. In embodiments z is 5. In embodiments z is 6. In embodiments z is 7. In embodiments z is 8. In embodiments z is 9. In embodiments z is 10.

In embodiments, $L^{2A}$, $L^{2B}$, $L^{2C}$, $L^{2D}$, and $L^{2E}$ are each independently

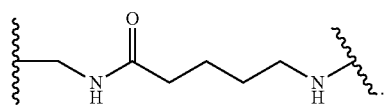 [SMILES: *CNC(=O)CCCCN*]

In embodiments, $L^{2A}$, $L^{2B}$, $L^{2C}$, $L^{2D}$, and $L^{2E}$ are each independently

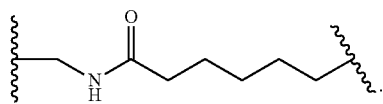 [SMILES: *CCCCCC(=O)NC*]

In embodiments, $L^{2A}$, $L^{2B}$, $L^2c$, $L^{2D}$, and $L^{2E}$ are each independently

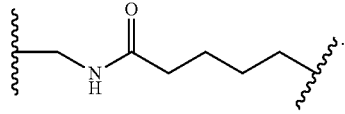 [SMILES: *CCCCC(=O)NC*]

In embodiments, $L^{2A}$, $L^{2B}$, $L^{2C}$, $L^{2D}$, and $L^{2E}$ are each independently

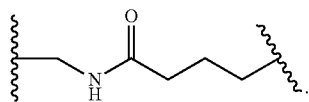 [SMILES: *CCCC(=O)NC*]

In embodiments, $L^{2A}$, $L^{2B}$, $L^{2C}$, $L^{2D}$, and $L^{2E}$ are each independently

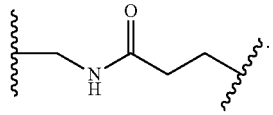 [SMILES: *CCC(=O)NC*]

In embodiments, $L^{2A}$, $L^{2B}$, $L^2c$, $L^{2D}$, and $L^{2E}$ are each independently

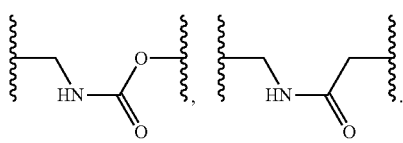

In embodiments, $L^{2A}$, $L^{2B}$, $L^{2C}$, $L^{2D}$, and $L^{2E}$ are each independently

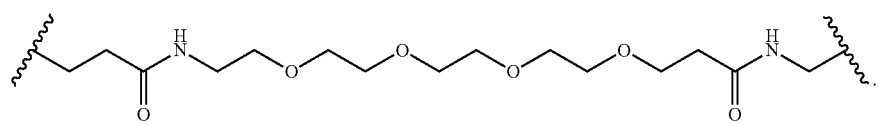 [SMILES: *CCC(=O)NCCOCCOCCOCCOCCC(=O)NC*]

In embodiments, $L^{2A}$, $L^{2B}$, $L^{2C}$, $L^{2D}$, and $L^{2E}$ are each independently

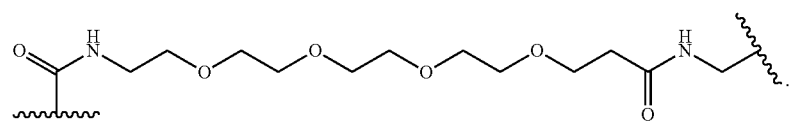 [SMILES: *CNC(=O)CCOCCOCCOCCOCCNC(*)=O]

In embodiments, $L^{2A}$, $L^{2B}$, $L^{2C}$, $L^{2D}$, and $L^{2E}$ are each independently

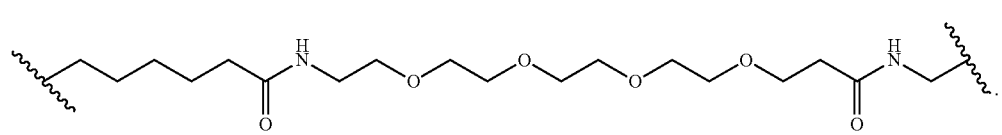 [SMILES: *CCCCCC(=O)NCCOCCOCCOCCOCCC(=O)NC*]

In embodiments, -L²-R⁵ is

-continued
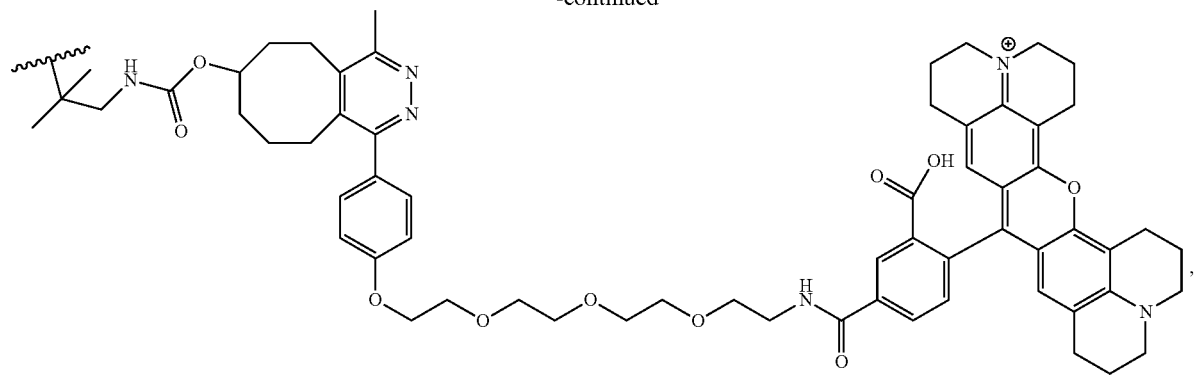
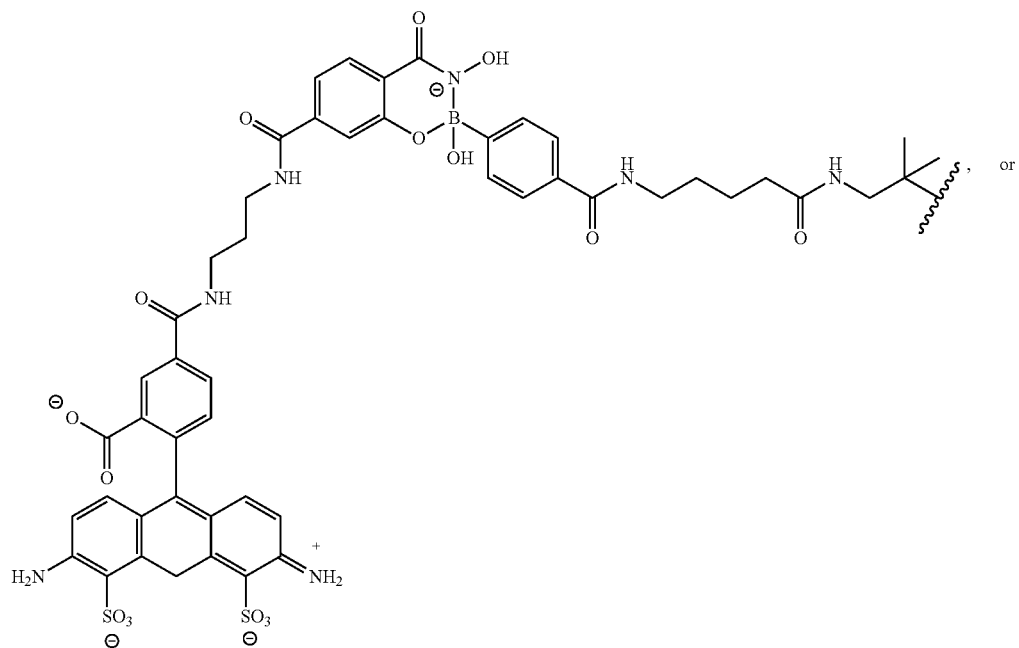
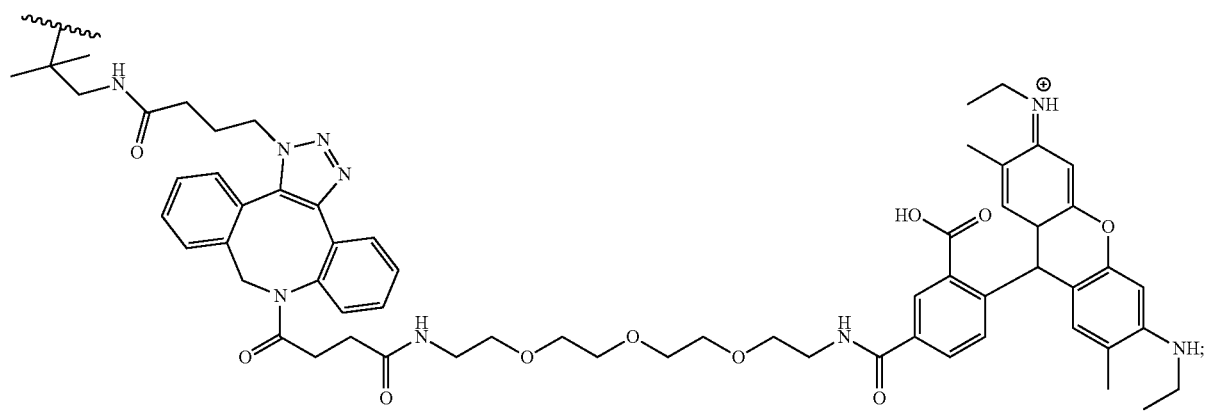
and z is an integer from 0 to 10.

In embodiments, -L²-R⁵ is
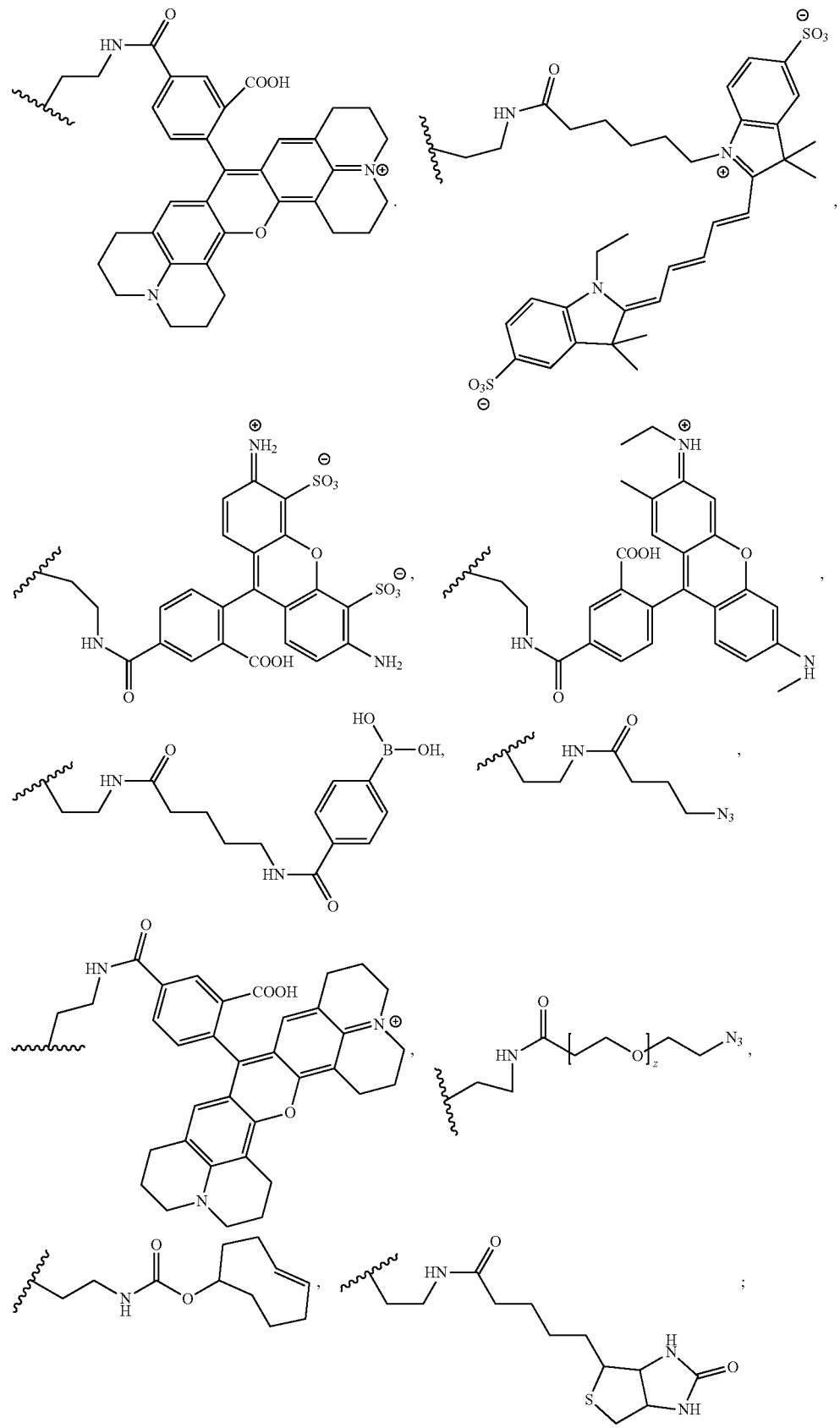

93
-continued
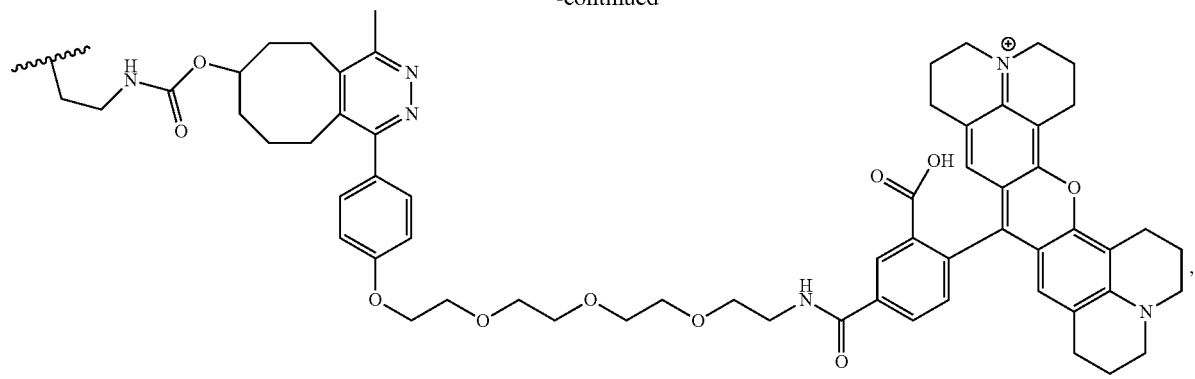
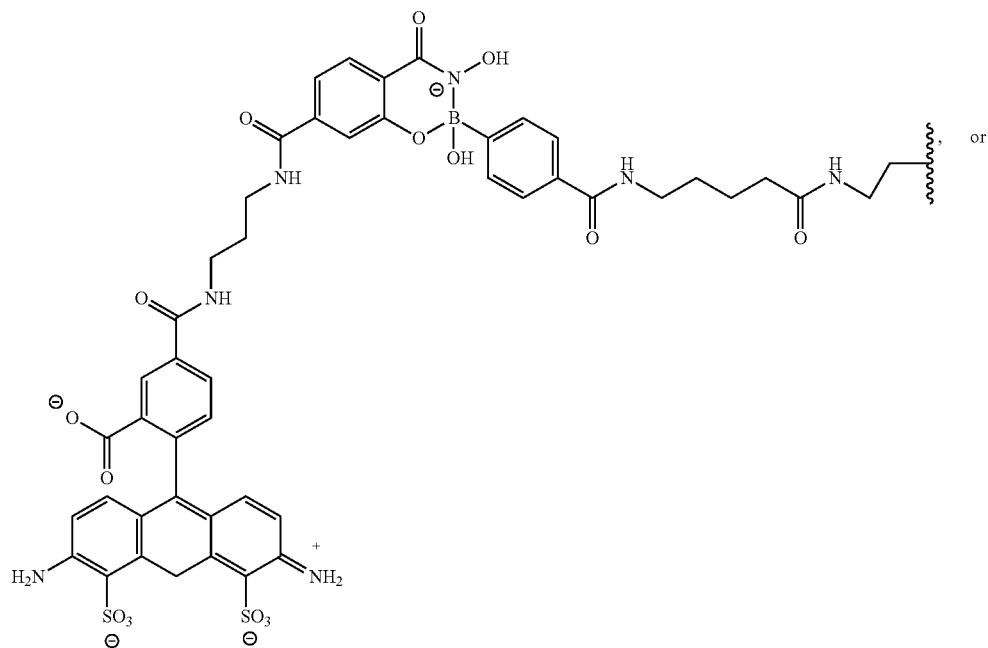
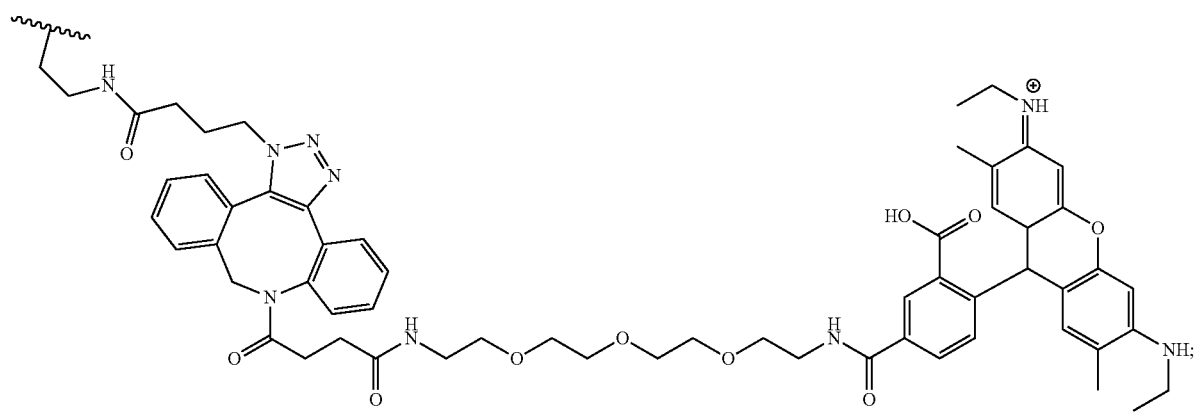
and z is an integer from 0 to 10.

In embodiments, -L²-R⁵ is
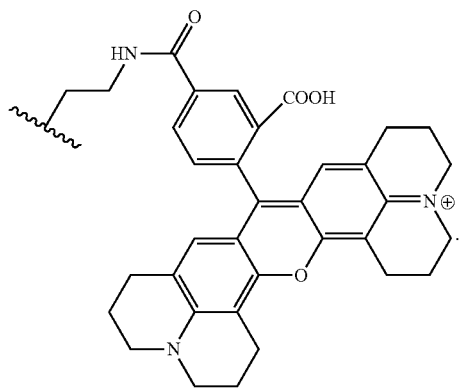
In embodiments, -L²-R⁵ is
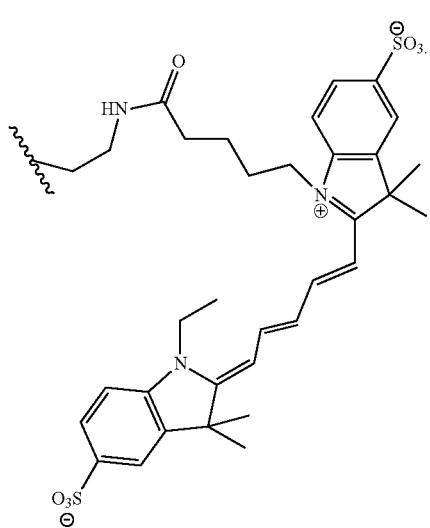
In embodiments, -L²-R⁵ is
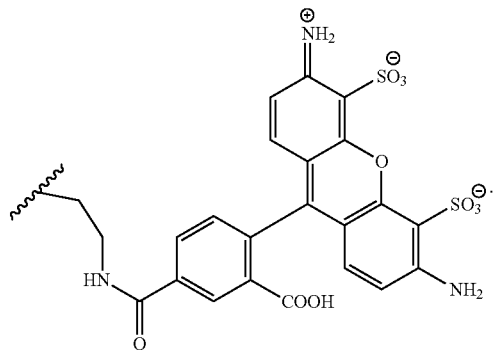
In embodiments, -L²-R⁵ is
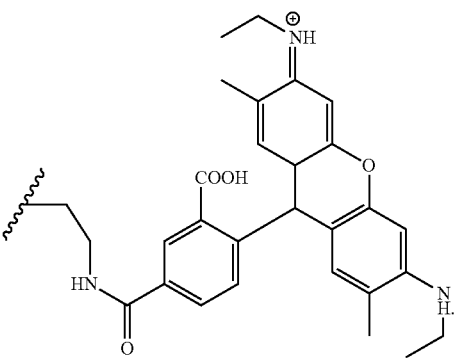 [SMILES: *CCNC(=O)c1ccc(C2c3cc(C)c(NCC)cc3OC3=C/C(=[NH+]/CC)C(C)=CC32)c(C(=O)O)c1]
In embodiments, -L²-R⁵ is
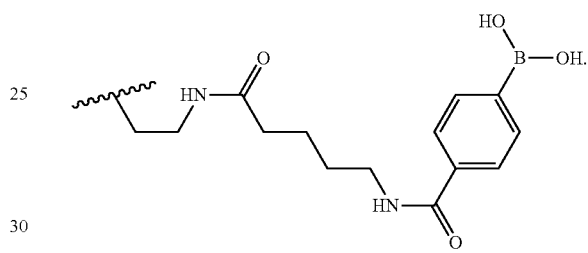
In embodiments, -L²-R⁵ is
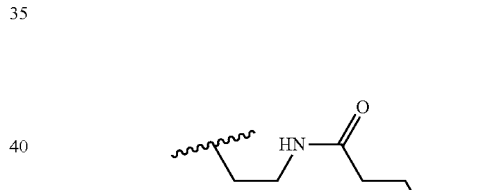
In embodiments, -L²-R⁵ is
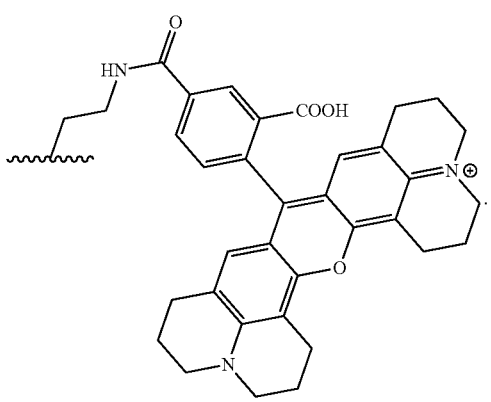 [SMILES: *CCNC(=O)c1ccc(C2=c3cc4c5c(c3Oc3c2cc2c6c3CCCN6CCC2)CCC[N+]=5CCC4)c(C(=O)O)c1]

In embodiments, -L²-R⁵ is

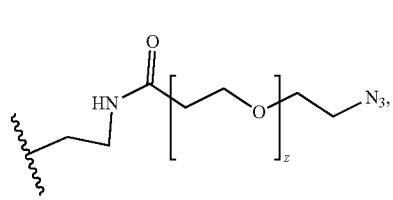

wherein z is an integer from 0 to 10. In embodiments z is an integer from 1 to 8. In embodiments z is an integer from 2 to 4. In embodiments z is 0. In embodiments z is 1. In embodiments z is 2. In embodiments z is 3. In embodiments z is 4. In embodiments z is 5. In embodiments z is 6. In embodiments z is 7. In embodiments z is 8. In embodiments z is 9. In embodiments z is 10. In embodiments, -L²-R⁵ is

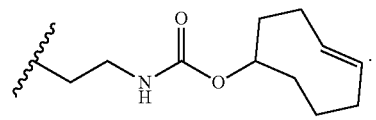 [SMILES: *CCNC(=O)OC1CC/C=C/CCC1]

In embodiments, -L²-R⁵ is

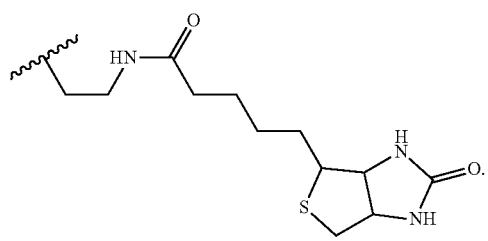 [SMILES: *CCNC(=O)CCCCC1SCC2NC(=O)NC21]

In embodiments, -L²-R⁵ is

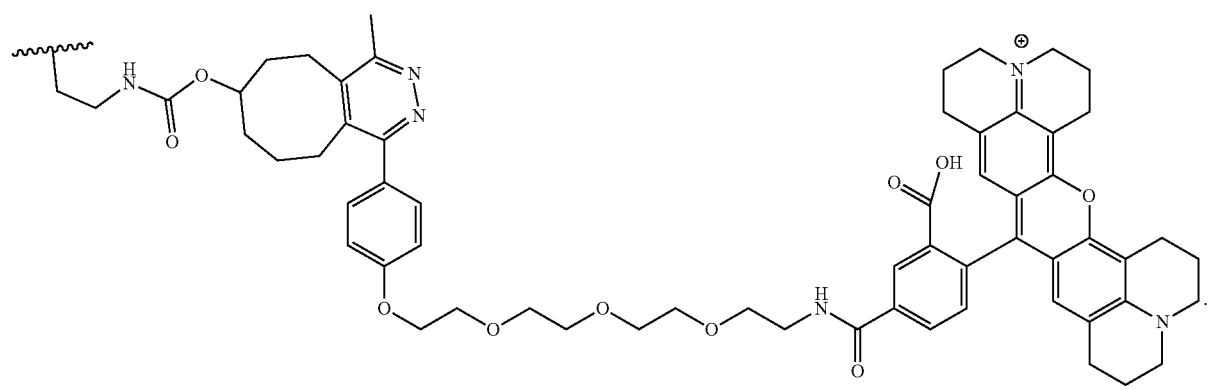 [SMILES: *CCNC(=O)OC1CCCc2c(-c3ccc(OCCOCCOCCOCCNC(=O)c4ccc(C5=c6cc7c8c(c6Oc6c5cc5c9c6CCCN9CCC5)CCC[N+]=8CCC7)c(C(=O)O)c4)cc3)nnc(C)c2CC1]

In embodiments, -L²-R⁵ is

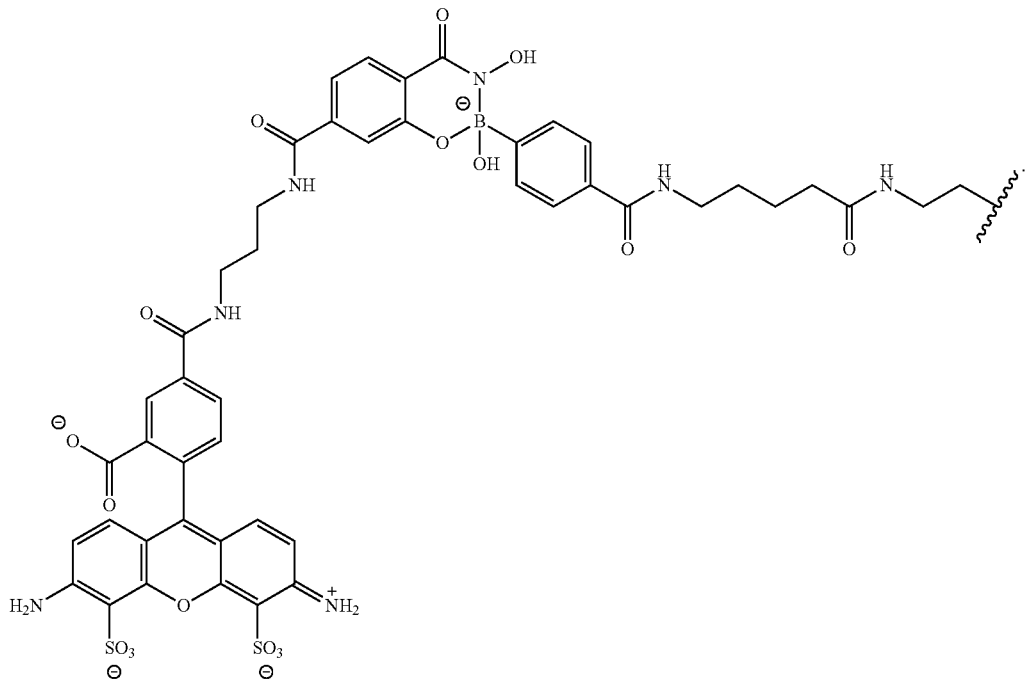

30

In embodiments, -L²-R⁵ is

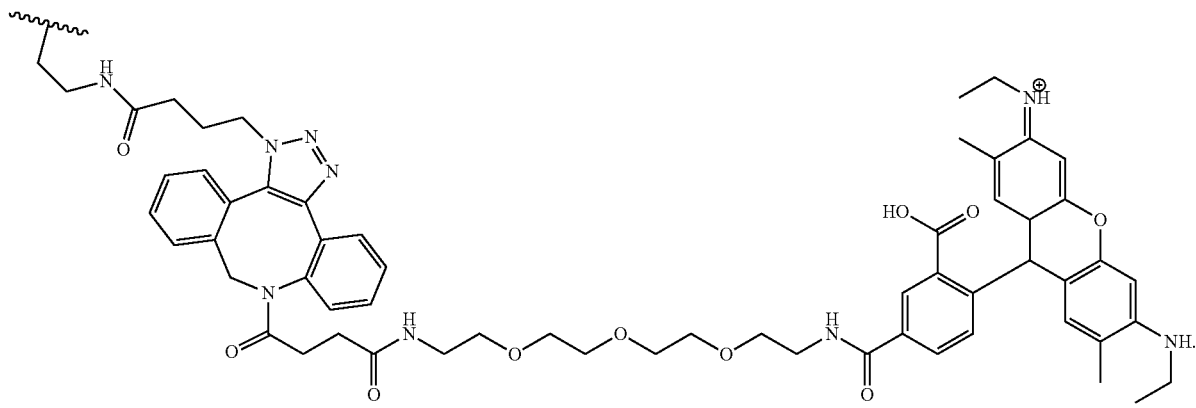 [SMILES: *CCNC(=O)CCCn1nnc2c1-c1ccccc1CN(C(=O)CCC(=O)NCCOCCOCCOCCNC(=O)c1ccc(C3c4cc(C)c(NCC)cc4OC4=C/C(=[NH+]/CC)C(C)=CC43)c(C(=O)O)c1)c1ccccc1-2]

50

In embodiments, L³ is

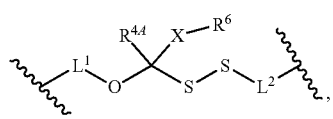

wherein L¹ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene. L² is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene, a cleavable linker, an orthogonally cleavable linker, non-covalent linker, or -$L^{2A}$-$L^{2B}$-$L^{2C}$-$L^{2D}$-, wherein $L^{2A}$ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene). $L^{2B}$ is a bond substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene. $L^{2C}$ is a bond substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene. $L^{2D}$ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), wherein at least one of $L^{2A}$, $L^{2B}$, $L^{2C}$, $L^{2D}$ is not a bond. $R^{4A}$ and $R^{6A}$ are independently hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. X is a bond, O, $N^{6A}$, or S.

In embodiments, $L^3$ is

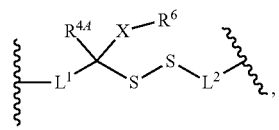

wherein $L^1$, $R^{4A}$, X, $R^6$, and $L^2$ are as described herein. In embodiments, $L^3$ is

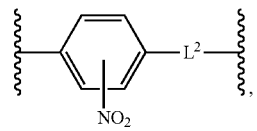

wherein $L^2$ is as described herein. In embodiments, $L^3$ is

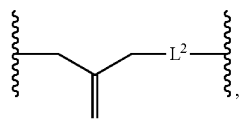

wherein $L^2$ is as described herein.

In embodiments, $L^4$ is an orthogonally cleavable linker. In embodiments, $L^4$ is a photocleavable linker, an acid-cleavable linker, a base-cleavable linker, an oxidant-cleavable linker, a reductant-cleavable linker, or a fluoride-cleavable linker. In embodiments, $L^4$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$, and $L^{4E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{4A}$, $L^{4B}$, $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; $L^{4A}$ is a bond, —NN—, —NHC(O)—, —C(O)NH—, substituted or unsubstituted alkylene, substituted or unsubstituted heteroalkylene; $L^{4B}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene; $L^{4C}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene; $L^{4D}$ is a bond, —NN—, —NHC(O)—, —C(O)NH—, substituted or unsubstituted alkylene, substituted or unsubstituted heteroalkylene; and $L^{4E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{4A}$, $L^{4B}$m $L^{4C}$, $L^{4D}$, and $L^{4E}$ is not a bond.

In embodiments, $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^4$ is a substituted or unsubstituted 3 to 10 membered heteroalkylene.

In embodiments, $L^4$ is an orthogonally cleavable linker. In embodiments, $L^4$ is a cleavable linker. In embodiments, $L^4$ is a chemically cleavable linker. In embodiments, $L^4$ is a photocleavable linker, an acid-cleavable linker, a base-cleavable linker, an oxidant-cleavable linker, a reductant-cleavable linker, or a fluoride-cleavable linker. In embodiments, $L^4$ is a photocleavable linker. In embodiments, $L^4$ is an acid-cleavable linker. In embodiments, $L^4$ is a base-cleavable linker. In embodiments, $L^4$ is an oxidant-cleavable linker. In embodiments, $L^4$ is a reductant-cleavable linker. In embodiments, $L^4$ is a fluoride-cleavable linker. In embodiments, $L^4$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^4$ is a cleavable linker including a dialkylketal linker. In embodiments, $L^4$ is an azo linker. In embodiments, $L^4$ is an allyl linker. In embodiments, $L^4$ is a cyanoethyl linker. In embodiments, $L^4$ is a 1-(4,4-dimethyl-2,6-dioxocyclohex-1-ylidene)ethyl linker, or a nitrobenzyl linker.

In embodiments, $L^4$ includes an orthogonally cleavable linker. In embodiments, $L^4$ includes a cleavable linker. In embodiments, $L^4$ includes a chemically cleavable linker. In embodiments, $L^4$ includes a photocleavable linker, an acid-cleavable linker, a base-cleavable linker, an oxidant-cleavable linker, a reductant-cleavable linker, or a fluoride-cleavable linker. In embodiments, $L^4$ includes a photocleavable linker. In embodiments, $L^4$ includes an acid-cleavable linker. In embodiments, $L^4$ includes a base-cleavable linker. In embodiments, $L^4$ includes an oxidant-cleavable linker. In embodiments, $L^4$ includes a reductant-cleavable linker. In embodiments, $L^4$ includes a fluoride-cleavable linker. In embodiments, $L^4$ includes a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^4$ includes a dialkylketal linker. In embodiments, $L^4$ includes an azo linker. In embodiments, $L^4$ includes an allyl linker. In embodiments, $L^4$ includes a cyanoethyl linker. In embodiments, $L^4$ includes a 1-(4,4-dimethyl-2,6-dioxocyclohex-1-ylidene)ethyl linker. In embodiments, $L^4$ includes a nitrobenzyl linker.

In embodiments, $L^4$ is $L^{4A}$-$L^{4B}$-$L^{4C}$-$L^{4D}$-$L^{4E}$. $L^{4A}$, $L^{4B}$, $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}$, $L^{4B}$, $L^{4C}$, $L^4D$, and $L^{4E}$ is not a bond.

In embodiments, $L^4$ is $L^{4A}$-$L^{4B}$-$L^{4C}$-$L^{4D}$-$L^{4E}$; and $L^{4A}$ $L^{4B}$ $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{4A}$, $L^{4B}$, $L^{4C}$, $L^4D$, and $L^{4E}$ is not a bond.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{4A}$, $L^{4B}$, $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{4A}$, $L^{4B}$, $L^{4C}$, $L^{4D}$, and $L^4E$ is not a bond.

In embodiments, $L^4$ is $L^{4A}$-$L^{4B}$-$L^{4C}$-$L^{4D}$-$L^{4E}$; wherein $L^{4A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{4B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{4E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}A$, $L^{4B}$, $L^{4C}$, $L^{4D}$, and $L^{4E}$ is not a bond.

In embodiments, $L^4$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^4$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_2$0 cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^4$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^4$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^4$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^{4z}$ is an orthogonally cleavable linker. In embodiments, $L^{4z}$ is a cleavable linker. In embodiments, $L^{4z}$ is a chemically cleavable linker. In embodiments, $L^{4z}$ is a photocleavable linker, an acid-cleavable linker, a base-cleavable linker, an oxidant-cleavable linker, a reductant-cleavable linker, or a fluoride-cleavable linker. In embodiments, $L^{4z}$ is a photocleavable linker. In embodiments, $L^{4z}$ is an acid-cleavable linker. In embodiments, $L^{4z}$ is a base-cleavable linker. In embodiments, $L^{4z}$ is an oxidant-cleavable linker. In embodiments, $L^{4z}$ is a reductant-cleavable linker. In embodiments, $L^{4z}$ is a cleavable linker including a dialkylketal linker, an azo linker, an allyl linker, a cyanoethyl linker, a 1-(4,4-dimethyl-2,6-dioxocyclohex-v-ylidene)ethyl linker, or a nitrobenzyl linker.

In embodiments, $L^{4z}$ includes an orthogonally cleavable linker. In embodiments, $L^{4z}$ includes a cleavable linker. In embodiments, $L^{4z}$ includes a chemically cleavable linker. In embodiments, $L^{4z}$ includes a photocleavable linker, an acid-cleavable linker, a base-cleavable linker, an oxidant-cleavable linker, a reductant-cleavable linker, or a fluoride-cleavable linker. In embodiments, $L^{4z}$ includes a photocleavable linker. In embodiments, $L^{4z}$ includes an acid-cleavable linker. In embodiments, $L^{4z}$ includes a base-cleavable linker. In embodiments, $L^{4z}$ includes an oxidant-cleavable linker. In embodiments, $L^{4z}$ includes a reductant-cleavable linker. In embodiments, $L^{4z}$ includes a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^{4z}$ is $L^{4zA}$-$L^{4zB}$-$L^{4zC}$-$L^{4zD}$-$L^{4zE}$. $L^{4zA}$, $L^{4zB}$, $L^{4zC}$, $L^{4zD}$, and $L^{4zE}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4zA}$, $L^{4zB}$, $L^{4zC}$, $L^{4zD}$, and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$, and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{4zA}$, $L^{4zB}$, $L^{4zC}$, $L^{4z}$D, and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$, and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{4zA}$, $L^{4zB}$, $L^{4zC}$, $L^{4zD}$, and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$, and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{4zA}$, $L^{4zB}$, $L^{4zC}$, $L^{4zD}$, and $L^{4zE}$ is not a bond.

In embodiments, $L^{4z}$ is $L^{4zA}$-$L^{4zB}$-$L^{4zC}$-$L^{4zD}$-$L^{4zE}$; wherein $L^{4zA}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{4zB}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4zC}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4zD}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{4zE}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4zA}$, $L^{4zB}$, $L^{4zC}$, $L^{4zD}$, and $L^{4zE}$ is not a bond.

In embodiments, $L^{4z}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^{4z}$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^{4z}$ is a bond, substituted (e.g., substituted with a substituent group, size-limited substituent group, or lower substituent group) or unsubstituted $C_1$-$C_5$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, L$^{4z}$ is a bond, substituted (e.g., substituted with a substituent group, size-limited substituent group, or lower substituent group) or unsubstituted C$_1$-C$_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted C$_3$-C$_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, L$^{4z}$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, L$^{4z}$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, L$^{4z}$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, L$^4$ is —C(CH$_3$)$_2$CH$_2$NHC(O)—,

In embodiments, R$^3$ is diphosphate, triphosphate, tetraphosphate, pentaphosphate, or hexaphosphate. In embodiments, R$^3$ is diphosphate. In embodiments, R$^3$ is triphosphate. In embodiments, R$^3$ is tetraphosphate. In embodiments, R$^3$ is pentaphosphate. In embodiments, R$^3$ is hexaphosphate. In embodiments, R$^3$ is triphosphate or higher polyphosphate (e.g., tetraphosphate, pentaphosphate, or hexaphosphate).

In embodiments, R$^{4A}$ is hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, substituted or unsubstituted alkyl, or substituted or unsubstituted heteroalkyl. In embodiments, R$^{4A}$ is substituted or unsubstituted C$_1$-C$_6$ alkyl, or substituted or unsubstituted 2 to 6 membered heteroalkyl. In embodiments, R$^{4A}$ is substituted or unsubstituted C$_1$-C$_6$ alkyl. In embodiments, R$^{4A}$ is unsubstituted C$_1$-C$_6$ alkyl. In embodiments, R$^{4A}$ is unsubstituted methyl.

In embodiments, R$^{4A}$ is hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{4A}$ is hydrogen, CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted

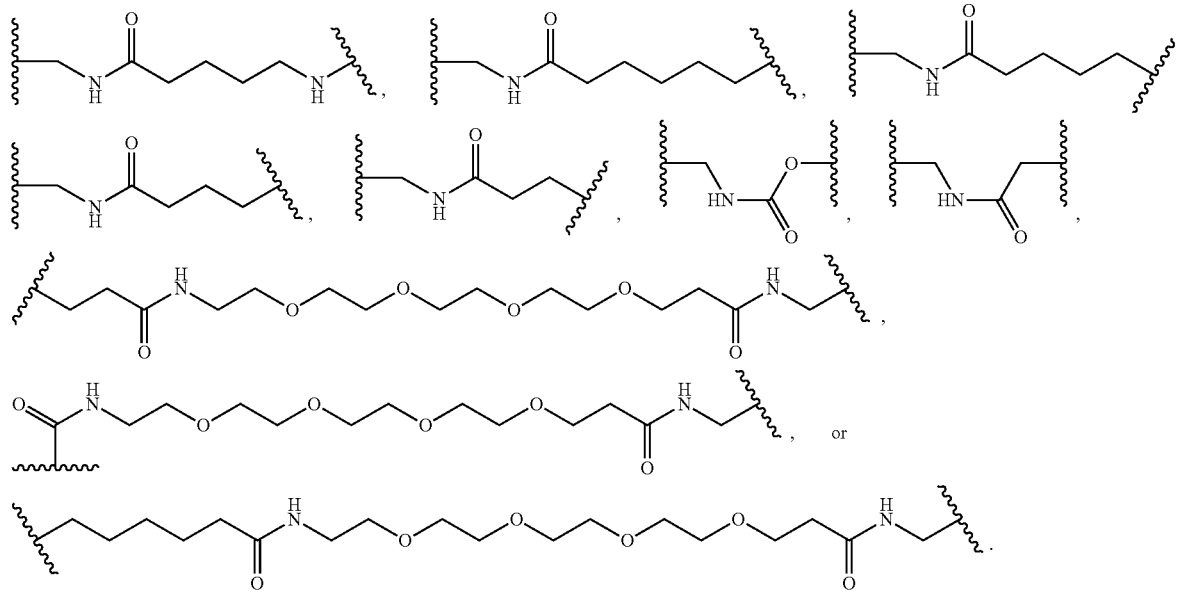

In embodiments, X is O, NR$^{6A}$, or S. In embodiments, X is a bond. In embodiments, X is O. In embodiments, X is NR$^{6A}$. In embodiments, X is NH. In embodiments, X is S. In embodiments, X is O, NH, or S. In embodiments, X is not a bond.

In embodiments, R$^3$ is —OH, monophosphate, or polyphosphate. In embodiments, R$^3$ is —OH. In embodiments, R$^3$ is monophosphate. In embodiments, R$^3$ is polyphosphate.

(e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, R$^{4A}$ is hydrogen, CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, substituted (e.g., substituted with a substituent group, size-limited substituent group, or lower substituent group) or unsubstituted C$_1$-C$_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted C$_3$-C$_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, R$^{4A}$ is hydrogen. In embodiments, when X is a bond, R$^{4A}$ is not hydrogen. In embodiments, when X is a bond, R$^{4B}$ is not hydrogen. In embodiments, when X is a bond, R$^{4A}$ and R$^{4B}$ are not hydrogen.

In embodiments, R$^{4A}$ is hydrogen, —CH$_3$, CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, R$^{4A}$ is hydrogen, —CH$_3$, —CF$_3$, —CCl$_3$, ~CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, R$^{4A}$ is hydrogen, —CH$_3$, —CF$_3$, —CCl$_3$, ~CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted C$_1$-C$_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted (e.g., substituted with a substituent group, size-limited substituent group, or lower substituent group) C$_3$-C$_6$ cycloalkyl, substituted (e.g., substituted with a substituent group, size-limited substituent group, or lower substituent group) or unsubstituted (e.g., substituted with a substituent group, size-limited substituent group, or lower substituent group) 3 to 6 membered heterocycloalkyl, substituted (e.g., substituted with a substituent group, size-limited substituent group, or lower substituent group) or unsubstituted (e.g., substituted with a substituent group, size-limited substituent group, or lower substituent group) phenyl, or substituted (e.g., substituted with a substituent group, size-limited substituent group, or lower substituent group) or unsubstituted (e.g., substituted with a substituent group, size-limited substituent group, or lower substituent group) 5 to 6 membered heteroaryl.

In embodiments, R$^{4A}$ is substituted (e.g., substituted with a substituent group, a size-limited substituent group, or lower substituent group) or unsubstituted alkyl. In embodiments, R$^{4A}$ is substituted (e.g., substituted with a substituent group, a size-limited substituent group, or lower substituent group) alkyl. In embodiments, R$^{4A}$ is unsubstituted alkyl. In embodiments, R$^{4A}$ is substituted or unsubstituted alkyl (e.g., C$_1$-C$_8$, C$_1$-C$_6$, C$_1$-C$_4$, or C$_1$-C$_2$). In embodiments, R$^{4A}$ is substituted alkyl (e.g., C$_1$-C$_5$, C$_1$-C$_6$, C1-C$_4$, or C$_1$-C$_2$). In embodiments, R$^{4A}$ is unsubstituted alkyl (e.g., C$_1$-C$_8$, C$_1$-C$_6$, C$_1$-C$_4$, or C$_1$-C$_2$).

In embodiments, R$^{4A}$ is substituted (e.g., substituted with a substituent group, a size-limited substituent group, or lower substituent group) or unsubstituted heteroalkyl. In embodiments, R$^{4A}$ is substituted (e.g., substituted with a substituent group, a size-limited substituent group, or lower substituent group) heteroalkyl. In embodiments, R$^{4A}$ is unsubstituted heteroalkyl. In embodiments, R$^{4A}$ is substituted or unsubstituted heteroalkyl (e.g., 2 to 8 membered, 2 to 6 membered, 4 to 6 membered, 2 to 3 membered, or 4 to 5 membered). In embodiments, R$^{4A}$ is substituted heteroalkyl (e.g., 2 to 8 membered, 2 to 6 membered, 4 to 6 membered, 2 to 3 membered, or 4 to 5 membered). In embodiments, R$^{4A}$ is an unsubstituted heteroalkyl (e.g., 2 to 8 membered, 2 to 6 membered, 4 to 6 membered, 2 to 3 membered, or 4 to 5 membered).

In embodiments, R$^{4A}$ is substituted (e.g., substituted with a substituent group, a size-limited substituent group, or lower substituent group) or unsubstituted cycloalkyl. In embodiments, R$^{4A}$ is substituted (e.g., substituted with a substituent group, a size-limited substituent group, or lower substituent group) cycloalkyl. In embodiments, R$^{4A}$ is an unsubstituted cycloalkyl. In embodiments, R$^{4A}$ is substituted or unsubstituted cycloalkyl (e.g., C$_3$-C$_8$, C$_3$-C$_6$, C$_4$-C$_6$, or C$_5$-C$_6$). In embodiments, R$^{4A}$ is substituted cycloalkyl (e.g., C$_3$-C$_8$, C$_3$-C$_6$, C$_4$-C$_6$, or C$_5$-C$_6$). In embodiments, R$^{4A}$ is unsubstituted cycloalkyl (e.g., C$_3$-C$_8$, C$_3$-C$_6$, C$_4$-C$_6$, or C$_5$-C$_6$).

In embodiments, R$^{4A}$ is substituted (e.g., substituted with a substituent group, a size-limited substituent group, or lower substituent group) or unsubstituted heterocycloalkyl. In embodiments, R$^{4A}$ is substituted (e.g., substituted with a substituent group, a size-limited substituent group, or lower substituent group) heterocycloalkyl. In embodiments, R$^{4A}$ is an unsubstituted heterocycloalkyl. In embodiments, R$^{4A}$ is substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ is substituted heterocycloalkyl (e.g., 3 to 8 membered, 3 to 6 membered, 4 to 6 membered, 4 to 5 membered, or 5 to 6 membered). In embodiments, $R^{4A}$ an unsubstituted heterocycloalkyl (e.g., 3 to 8 membered, 3 to 6 membered, 4 to 6 membered, 4 to 5 membered, or 5 to 6 membered).

In embodiments, $R^{4A}$ is substituted (e.g., substituted with a substituent group, a size-limited substituent group, or lower substituent group) or unsubstituted aryl. In embodiments, $R^{4A}$ is substituted (e.g., substituted with a substituent group, a size-limited substituent group, or lower substituent group) aryl. In embodiments, $R^{4A}$ is an unsubstituted aryl. In embodiments, $R^{4A}$ is substituted or unsubstituted aryl (e.g., $C_6$-$C_{10}$ or phenyl). In embodiments, $R^{4A}$ is substituted aryl (e.g., $C_6$-$C_{10}$ or phenyl). In embodiments, $R^{4A}$ is an unsubstituted aryl (e.g., $C_6$-$C_{10}$ or phenyl).

In embodiments, $R^{4A}$ is substituted (e.g., substituted with a substituent group, a size-limited substituent group, or lower substituent group) or unsubstituted heteroaryl. In embodiments, $R^{4A}$ is substituted (e.g., substituted with a substituent group, a size-limited substituent group, or lower substituent group) heteroaryl. In embodiments, $R^{4A}$ is an unsubstituted heteroaryl. In embodiments, $R^{4A}$ is substituted or unsubstituted heteroaryl (e.g., 5 to 10 membered, 5 to 9 membered, or 5 to 6 membered). In embodiments, $R^{4A}$ is substituted heteroaryl (e.g., 5 to 10 membered, 5 to 9 membered, or 5 to 6 membered). In embodiments, $R^{4A}$ is an unsubstituted heteroaryl (e.g., 5 to 10 membered, 5 to 9 membered, or 5 to 6 membered).

In embodiments, $R^{4B}$ is hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{4B}$ is —X—$R^6$. In embodiments, $R^{4B}$ is hydrogen.

In embodiments, $R^{4B}$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, or substituted or unsubstituted heteroalkyl. In embodiments, $R^{4B}$ is substituted or unsubstituted $C_1$-$C_6$ alkyl, or substituted or unsubstituted 2 to 6 membered heteroalkyl. In embodiments, $R^{4B}$ is substituted or unsubstituted $C_1$-$C_6$ alkyl. In embodiments, $R^{4B}$ is unsubstituted $C_1$-$C_6$ alkyl. In embodiments, $R^{4B}$ is unsubstituted methyl.

In embodiments, $R^{4B}$ is hydrogen, $CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{4B}$ is hydrogen, $CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{4B}$ is hydrogen.

In embodiments, $R^{4B}$ is hydrogen, —$CH_3$, $CF_3$, —$CCl_3$, ~$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4B}$ is hydrogen, —$CH_3$, —$CF_3$, —$CCl_3$, ~$CBr_3$, —C13, —$CHF_2$, —$CHCl_2$, —$CHBr_2$, —$CHI_2$, —$CH_2F$, —$CH_2Cl$, —$CH_2Br$, —$CH_2I$, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4B}$ is hydrogen, —$CH_3$, —$CF_3$, —$CCl_3$, ~$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —CN, -Ph, substituted (e.g., substituted with a substituent group, size-limited substituent group, or lower substituent group) or unsubstituted (e.g., substituted with a substituent group, size-limited substituent group, or lower substituent group) $C_1$-$C_6$ alkyl, substituted (e.g., substituted with a substituent group, size-limited substituent group, or lower substituent group) or unsubstituted (e.g., substituted with a substituent group, size-limited substituent group, or lower substituent group) 2 to 6 membered heteroalkyl, substituted (e.g., substituted with a substituent group, size-limited substituent group, or lower substituent group) or unsubstituted (e.g., substituted with a substituent group, size-limited substituent group, or lower substituent group) $C_3$-$C_6$ cycloalkyl, substituted (e.g., substituted with a substituent group, size-limited substituent group, or lower substituent group) or unsubstituted (e.g., substituted with a substituent group, size-limited substituent group, or lower substituent group) 3 to 6 membered heterocycloalkyl, substituted (e.g., substituted with a substituent group, size-limited substituent group, or lower substituent group) or unsubstituted (e.g., substituted with a substituent group, size-limited substituent group, or lower substituent group) phenyl, or substituted (e.g., substituted with a substituent group, size-limited substituent group, or lower substituent group) or unsubstituted (e.g., substituted with a substituent group, size-limited substituent group, or lower substituent group) 5 to 6 membered heteroaryl.

In embodiments, $R^{4B}$ is substituted (e.g., substituted with a substituent group, a size-limited substituent group, or lower substituent group) or unsubstituted alkyl. In embodiments, $R^{4B}$ is substituted (e.g., substituted with a substituent group, a size-limited substituent group, or lower substituent group) alkyl. In embodiments, $R^{4B}$ is unsubstituted alkyl. In embodiments, $R^{4B}$ is substituted or unsubstituted alkyl (e.g., $C_1$-$C_8$, $C_1$-$C_6$, $C_1$-$C_4$, or $C_1$-$C_2$). In embodiments, $R^{4B}$ is substituted alkyl (e.g., $C_1$-$C_8$, $C_1$-$C_6$, $C_1$-$C_4$, or $C_1$-$C_2$). In embodiments, $R^{4B}$ is unsubstituted alkyl (e.g., $C_1$-$C_8$, $C_1$-$C_6$, $C_1$-$C_4$, or $C_1$-$C_2$).

In embodiments, $R^{4B}$ is substituted (e.g., substituted with a substituent group, a size-limited substituent group, or lower substituent group) or unsubstituted heteroalkyl. In embodiments, $R^{4B}$ is substituted (e.g., substituted with a substituent group, a size-limited substituent group, or lower substituent group) heteroalkyl. In embodiments, $R^{4B}$ is unsubstituted heteroalkyl. In embodiments, $R^{4B}$ is substituted or unsubstituted heteroalkyl (e.g., 2 to 8 membered, 2 to 6 membered, 4 to 6 membered, 2 to 3 membered, or 4 to 5 membered). In embodiments, $R^{4B}$ is substituted heteroalkyl (e.g., 2 to 8 membered, 2 to 6 membered, 4 to 6 membered, 2 to 3 membered, or 4 to 5 membered). In embodiments, $R^{4B}$ is an unsubstituted heteroalkyl (e.g., 2 to 8 membered, 2 to 6 membered, 4 to 6 membered, 2 to 3 membered, or 4 to 5 membered).

In embodiments, $R^{4B}$ is substituted (e.g., substituted with a substituent group, a size-limited substituent group, or lower substituent group) or unsubstituted cycloalkyl. In embodiments, $R^{4B}$ is substituted (e.g., substituted with a substituent group, a size-limited substituent group, or lower substituent group) cycloalkyl. In embodiments, $R^{4B}$ is an unsubstituted cycloalkyl. In embodiments, $R^{4B}$ is substituted or unsubstituted cycloalkyl (e.g., $C_3$-$C_5$, $C_3$-$C_6$, $C_4$-$C_6$, or $C_5$-$C_6$). In embodiments, $R^{4B}$ is substituted cycloalkyl (e.g., $C_3$-$C_8$, $C_3$-$C_6$, $C_4$-$C_6$, or $C_5$-$C_6$). In embodiments, $R^{4B}$ is unsubstituted cycloalkyl (e.g., $C_3$-$C_8$, $C_3$-$C_6$, $C_4$-$C_6$, or $C_5$-$C_6$).

In embodiments, $R^{4B}$ is substituted (e.g., substituted with a substituent group, a size-limited substituent group, or lower substituent group) or unsubstituted heterocycloalkyl. In embodiments, $R^{4B}$ is substituted (e.g., substituted with a substituent group, a size-limited substituent group, or lower substituent group) heterocycloalkyl. In embodiments, $R^{4B}$ is an unsubstituted heterocycloalkyl. In embodiments, $R^{4B}$ is substituted or unsubstituted heterocycloalkyl (e.g., 3 to 8 membered, 3 to 6 membered, 4 to 6 membered, 4 to 5 membered, or 5 to 6 membered). In embodiments, $R^{4B}$ is substituted heterocycloalkyl (e.g., 3 to 8 membered, 3 to 6 membered, 4 to 6 membered, 4 to 5 membered, or 5 to 6 membered). In embodiments, $R^{4B}$ an unsubstituted heterocycloalkyl (e.g., 3 to 8 membered, 3 to 6 membered, 4 to 6 membered, 4 to 5 membered, or 5 to 6 membered).

In embodiments, $R^{4B}$ is substituted (e.g., substituted with a substituent group, a size-limited substituent group, or lower substituent group) or unsubstituted aryl. In embodiments, $R^{4B}$ is substituted (e.g., substituted with a substituent group, a size-limited substituent group, or lower substituent group) aryl. In embodiments, $R^{4B}$ is an unsubstituted aryl. In embodiments, $R^{4B}$ is substituted or unsubstituted aryl (e.g., $C_6$-$C_{10}$ or phenyl). In embodiments, $R^{4B}$ is substituted aryl (e.g., $C_6$-$C_{10}$ or phenyl). In embodiments, $R^{4B}$ is an unsubstituted aryl (e.g., $C_6$-$C_{10}$ or phenyl).

In embodiments, $R^{4B}$ is substituted (e.g., substituted with a substituent group, a size-limited substituent group, or lower substituent group) or unsubstituted heteroaryl. In embodiments, $R^{4B}$ is substituted (e.g., substituted with a substituent group, a size-limited substituent group, or lower substituent group) heteroaryl. In embodiments, $R^{4B}$ is an unsubstituted heteroaryl. In embodiments, $R^{4B}$ is substituted or unsubstituted heteroaryl (e.g., 5 to 10 membered, 5 to 9 membered, or 5 to 6 membered). In embodiments, $R^{4B}$ is substituted heteroaryl (e.g., 5 to 10 membered, 5 to 9 membered, or 5 to 6 membered). In embodiments, $R^{4B}$ is an unsubstituted heteroaryl (e.g., 5 to 10 membered, 5 to 9 membered, or 5 to 6 membered).

In embodiments, $R^5$ is a detectable label. In embodiments, $R^5$ is a fluorescent dye.

In embodiments, $R^5$ is biotin, azide, trans-cyclooctene (TCO), or phenyl boric acid (PBA). In embodiments, $R^5$ is biotin, azide, trans-cyclooctene (TCO), phenylboronic acid (PBA), quadricyclane, or norbornene.

In embodiments, $R^5$ is fluorescent dye with a molecular weight of at least about 130 Daltons. In embodiments, $R^5$ is fluorescent dye with a molecular weight of at least about 135 Daltons. In embodiments, $R^5$ is fluorescent dye with a molecular weight of at least about 140 Daltons. In embodiments, $R^5$ is fluorescent dye with a molecular weight of at least about 145 Daltons. In embodiments, $R^5$ is fluorescent dye with a molecular weight of at least about 150 Daltons. In embodiments, $R^5$ is fluorescent dye with a molecular weight of about 130 Daltons. In embodiments, $R^5$ is fluorescent dye with a molecular weight of about 135 Daltons. In embodiments, $R^5$ is fluorescent dye with a molecular weight of about 140 Daltons. In embodiments, $R^5$ is fluorescent dye with a molecular weight of about 145 Daltons. In embodiments, $R^5$ is fluorescent dye with a molecular weight of about 150 Daltons. In embodiments, $R^5$ is fluorescent dye with a molecular weight of about 146 Daltons.

In embodiments, $R^5$ is fluorescent dye with a molecular weight of about 140 to about 3000 Daltons. In embodiments, $R^5$ is fluorescent dye with a molecular weight of about 140 to about 2500 Daltons. In embodiments, $R^5$ is fluorescent dye with a molecular weight of about 140 to about 2000 Daltons. In embodiments, $R^5$ is fluorescent dye with a molecular weight of about 140 to about 1000 Daltons. In embodiments, $R^5$ is fluorescent dye with a molecular weight of about 140 to about 900 Daltons. In embodiments, $R^5$ is fluorescent dye with a molecular weight of about 140 to about 800 Daltons. In embodiments, $R^5$ is fluorescent dye with a molecular weight of about 140 to about 700 Daltons. In embodiments, $R^5$ is fluorescent dye with a molecular weight of about 140 to about 600 Daltons. In embodiments, $R^5$ is fluorescent dye with a molecular weight of about 140 to about 500 Daltons. In embodiments, $R^5$ is fluorescent dye with a molecular weight of about 140 to about 400 Daltons. In embodiments, $R^5$ is fluorescent dye with a molecular weight of about 140 to about 300 Daltons. In embodiments, $R^5$ is fluorescent dye with a molecular weight of about 140 to about 200 Daltons.

In embodiments, $R^5$ is fluorescent dye with a molecular weight of about 200 to about 3000 Daltons. In embodiments, $R^5$ is fluorescent dye with a molecular weight of about 200 to about 2500 Daltons. In embodiments, $R^5$ is fluorescent dye with a molecular weight of about 200 to about 2000 Daltons. In embodiments, $R^5$ is fluorescent dye with a molecular weight of about 200 to about 1000 Daltons. In embodiments, $R^5$ is fluorescent dye with a molecular weight of about 200 to about 900 Daltons. In embodiments, $R^5$ is fluorescent dye with a molecular weight of about 200 to about 800 Daltons. In embodiments, $R^5$ is fluorescent dye with a molecular weight of about 200 to about 700 Daltons. In embodiments, $R^5$ is fluorescent dye with a molecular weight of about 200 to about 600 Daltons. In embodiments, $R^5$ is fluorescent dye with a molecular weight of about 200 to about 500 Daltons. In embodiments, $R^5$ is fluorescent dye with a molecular weight of about 200 to about 400 Daltons. In embodiments, $R^5$ is fluorescent dye with a molecular weight of about 200 to about 300 Daltons.

In embodiments, $R^5$ is fluorescent dye with a molecular weight of about 300 to about 3000 Daltons. In embodiments, $R^5$ is fluorescent dye with a molecular weight of about 300 to about 2500 Daltons. In embodiments, $R^5$ is fluorescent dye with a molecular weight of about 300 to about 2000 Daltons. In embodiments, $R^5$ is fluorescent dye with a molecular weight of about 300 to about 1000 Daltons. In embodiments, $R^5$ is fluorescent dye with a molecular weight of about 300 to about 900 Daltons. In embodiments, $R^5$ is fluorescent dye with a molecular weight of about 300 to about 800 Daltons. In embodiments, $R^5$ is fluorescent dye with a molecular weight of about 300 to about 700 Daltons. In embodiments, $R^5$ is fluorescent dye with a molecular weight of about 300 to about 600 Daltons. In embodiments, $R^5$ is fluorescent dye with a molecular weight of about 300 to about 500 Daltons. In embodiments, $R^5$ is fluorescent dye with a molecular weight of about 300 to about 400 Daltons.

In embodiments, $R^5$ is fluorescent dye with a molecular weight of about 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800, 2810, 2820, 2830, 2840, 2850, 2860, 2870, 2880, 2890, 2900, 2910, 2920, 2930, 2940, 2950, 2960, 2970, 2980, 2990, or about 3000 Daltons.

In embodiments, $R^5$ is

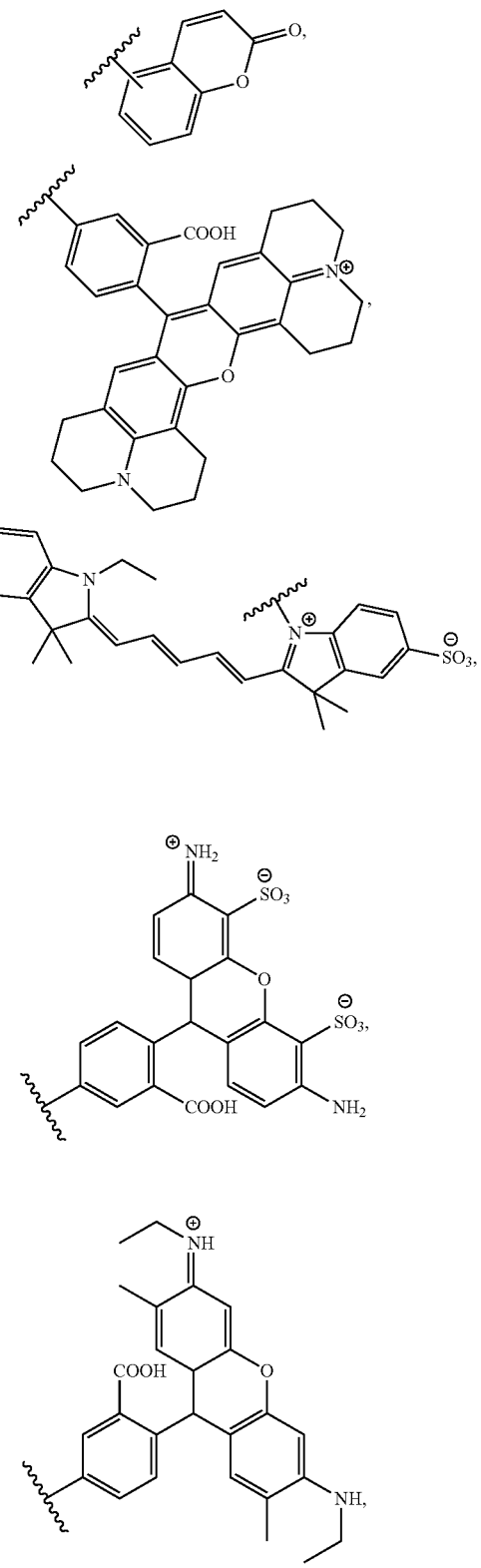

-continued

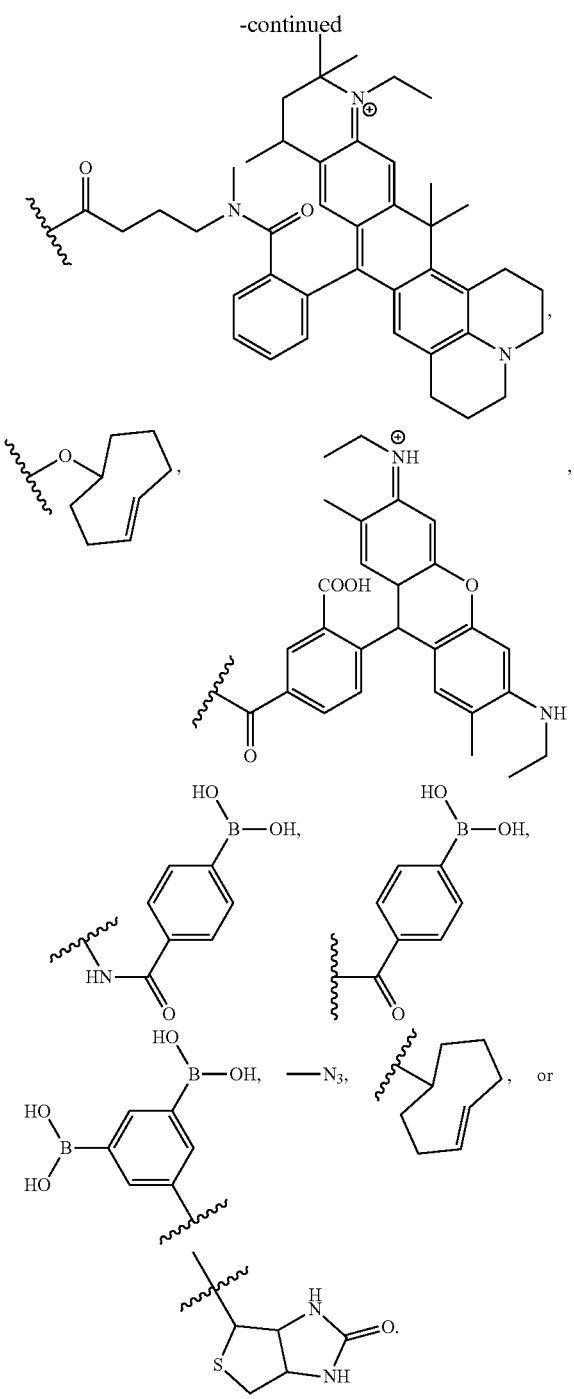

In embodiments, R⁵ is a detectable label. In embodiments, R⁵ is a fluorescent dye. In embodiments, R⁵ is an anchor moiety. In embodiments, R⁵ is a click chemistry reactant moiety. In embodiments, R⁵ is a trans-cyclooctene moiety or azide moiety. In embodiments, R⁵ is an affinity anchor moiety. In embodiments, R⁵ is a biotin moiety. In embodiments, R⁵ is a reactant for a bioconjugate reaction that forms a covalent bond between R⁵ and a second bioconjugate reaction reactant.

In embodiments, R⁵ is a fluorescent dye. In embodiments R⁵ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R⁶G) moiety, ROX Reference Dye (ROX) moiety, or Cy5 moiety.

In embodiments R⁵ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R⁶G) moiety, ROX Reference Dye (ROX) moiety, Sulfo-Cy5, or Cy5 moiety. In embodiments R⁵ is a Rhodamine 6G (R⁶G) moiety, ROX Reference Dye (ROX) moiety, Sulfo-Cy5, or Cy5 moiety.

In embodiments R⁵ is a FAM™ moiety. In embodiments R⁵ is a TET™ moiety. In embodiments R⁵ is a JOE™ moiety. In embodiments R⁵ is a VIC® moiety. In embodiments R⁵ is a HEX™ moiety. In embodiments R⁵ is a NED™ moiety. In embodiments R⁵ is a PET® moiety. In embodiments R⁵ is a ROX™ moiety. In embodiments R⁵ is a TAMRA™ moiety. In embodiments R⁵ is a TET™ moiety. In embodiments R⁵ is a Texas Red® moiety. In embodiments R⁵ is an Alexa Fluor® 488 moiety. In embodiments R⁵ is a Rhodamine 6G (R⁶G) moiety. In embodiments R⁵ is a ROX Reference Dye (ROX) moiety. In embodiments R⁵ is a Sulfo-Cy5. In embodiments R⁵ is a Cy5 moiety.

In embodiments, R⁵ is a biotin moiety. In embodiments, R⁵ is a biotin moiety and R¹² is a streptavidin moiety.

In embodiments, R⁵ is

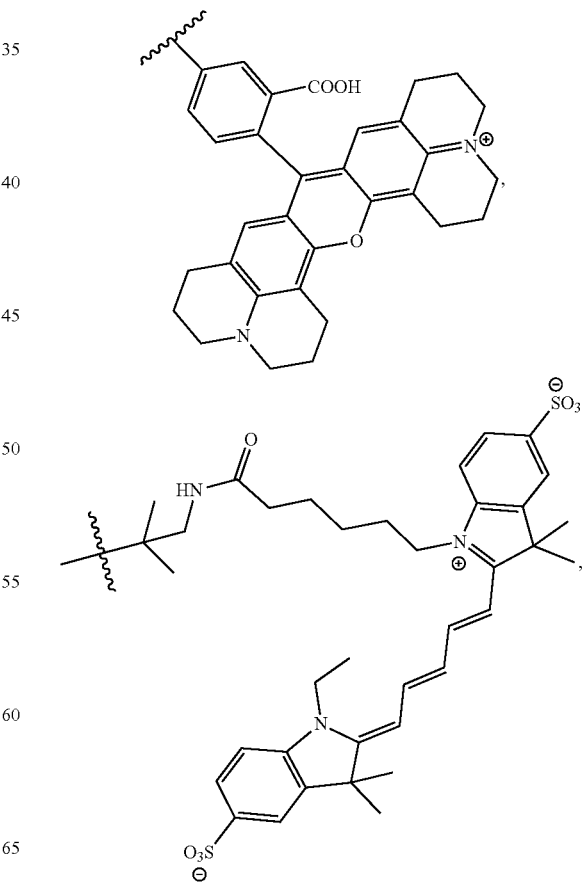

123
-continued
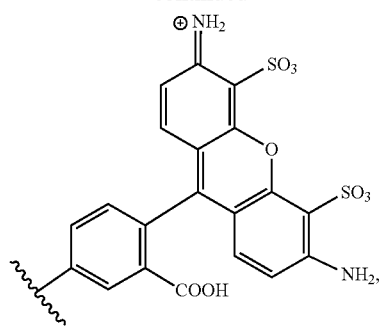
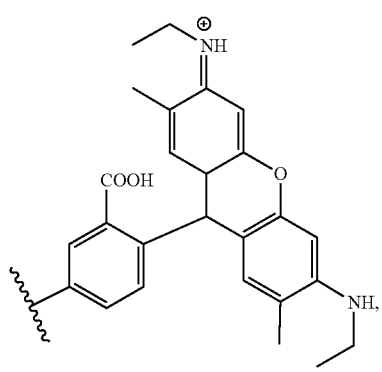
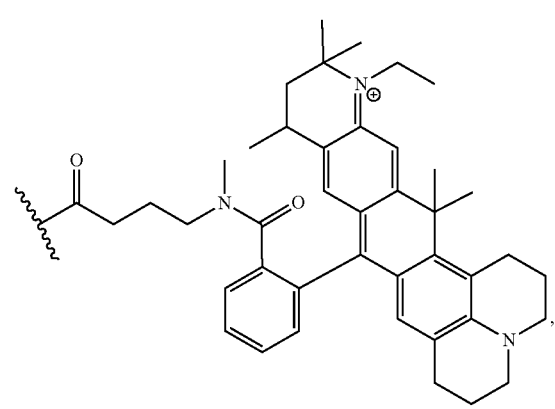
124
-continued
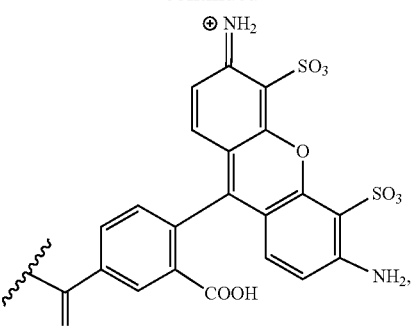
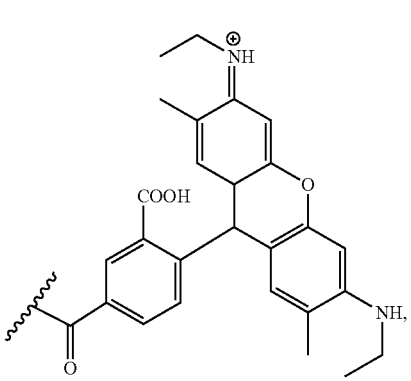
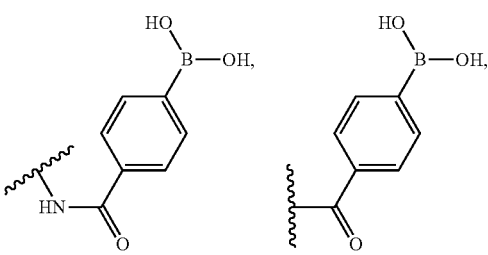
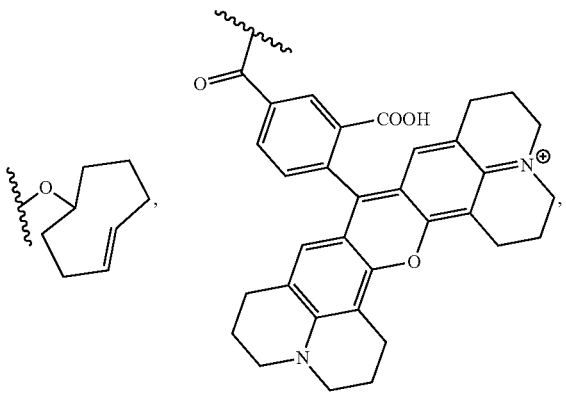
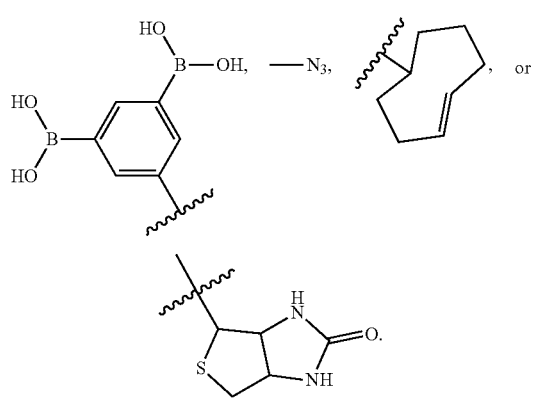

125
In embodiments, $R^5$ is
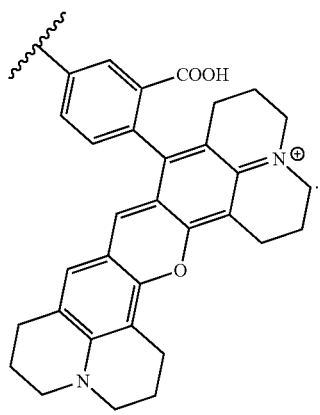 [SMILES: *c1ccc(-c2c3c4c(c5c2=Cc2cc6c7c(c2O5)CCCN7CCC6)CCC[N+]=4CCC3)c(C(=O)O)c1]
In embodiments, $R^5$ is
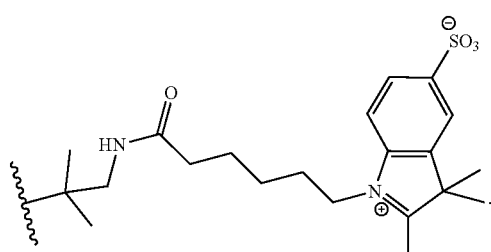
In embodiments, $R^5$ is
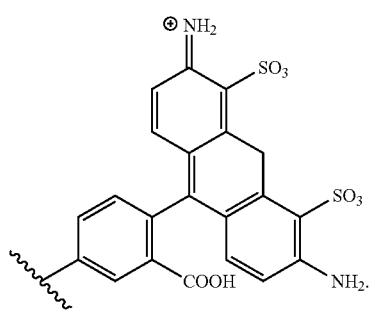
126
In embodiments, $R^5$ is
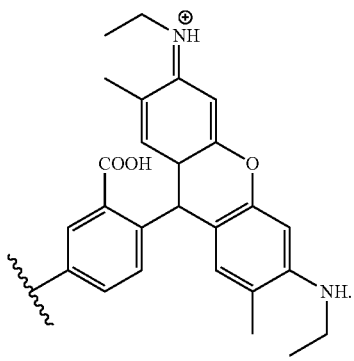 [SMILES: *c1ccc(C2c3cc(C)c(NCC)cc3OC3=C/C(=[NH+]/CC)C(C)=CC32)c(C(=O)O)c1]
In embodiments, $R^5$ is
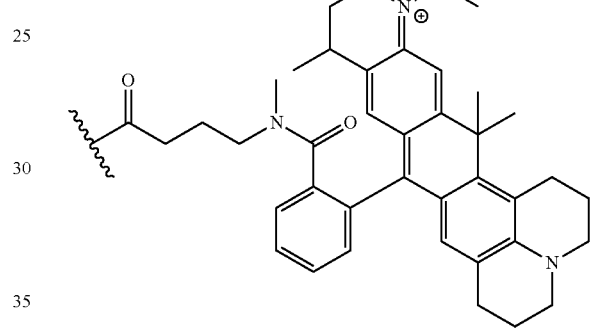
In embodiments, $R^5$ is
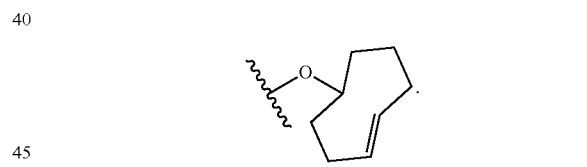
In embodiments, $R^5$ is
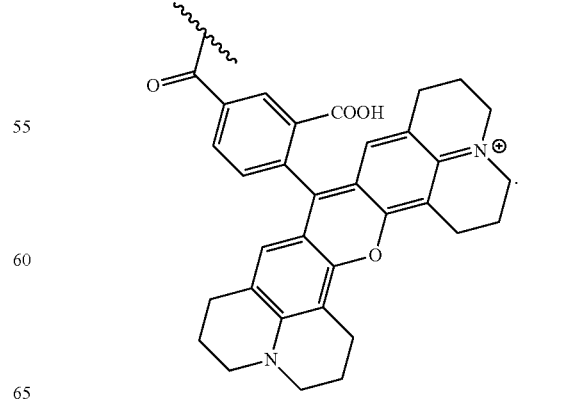

In embodiments, $R^5$ is
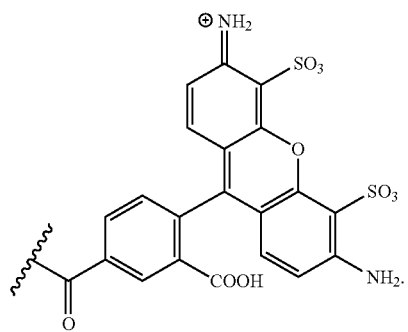
In embodiments, $R^5$ is
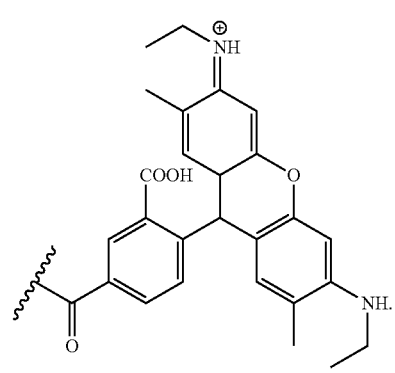 [SMILES: *C(=O)c1ccc(C2c3cc(C)c(NCC)cc3OC3=C/C(=[NH+]/CC)C(C)=CC32)c(C(=O)O)c1]
In embodiments, $R^5$ is
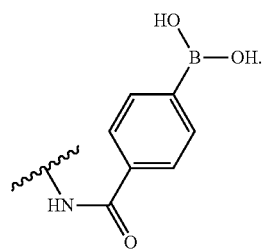 [SMILES: *NC(=O)c1ccc(B(O)O)cc1]
In embodiments, $R^5$ is
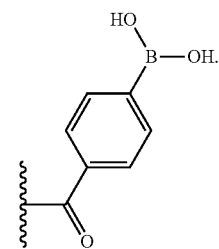 [SMILES: *C(=O)c1ccc(B(O)O)cc1]
In embodiments, $R^5$ is —$N_3$. In embodiments, $R^5$ is
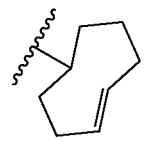
In embodiments, $R^5$ is
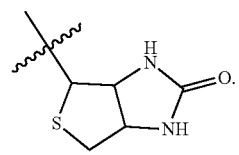 [SMILES: *C1SCC2NC(=O)NC21]
In embodiments, $R^5$ is unsubstituted ethynyl,
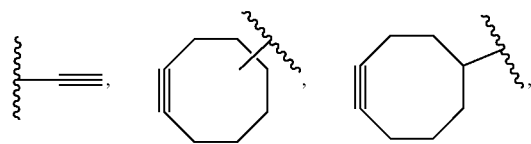
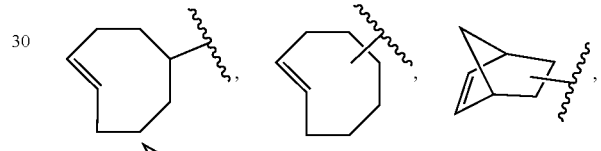
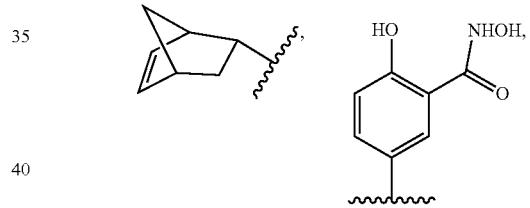
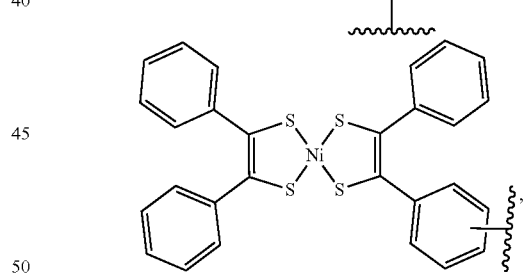
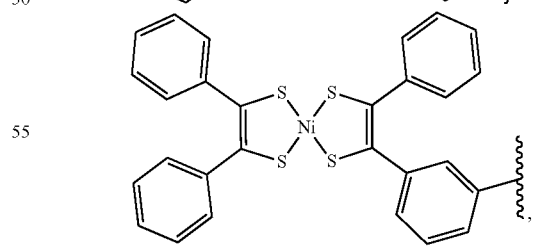
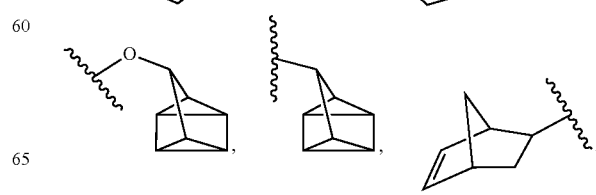

-continued
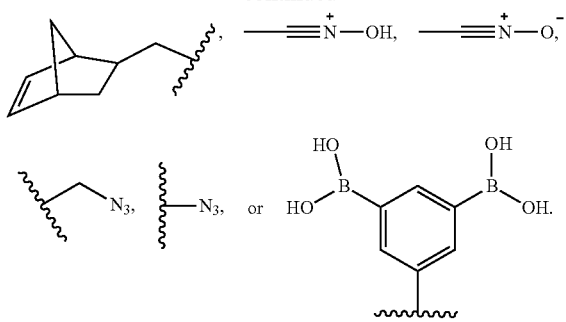
In embodiments, $R^5$ is unsubstituted ethynyl.
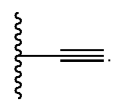
In embodiments, $R^5$ is
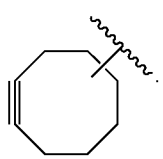
In embodiments, $R^5$ is
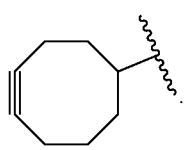 [SMILES: *C1CCC#CCCC1]
In embodiments, $R^5$ is
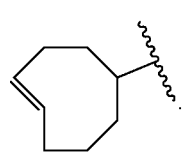 [SMILES: *C1CC/C=C/CCC1]
In embodiments, $R^5$ is
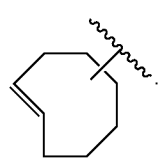
In embodiments, $R^5$ is
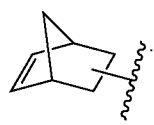
In embodiments, $R^5$ is
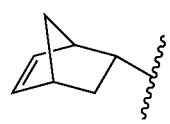
In embodiments, $R^5$ is
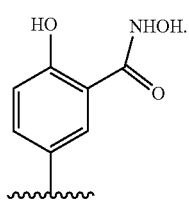
In embodiments, $R^5$ is
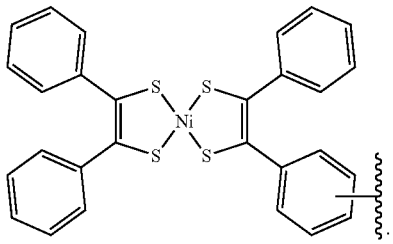
In embodiments, $R^5$ is
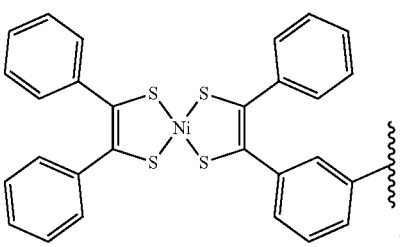

In embodiments, $R^5$ is

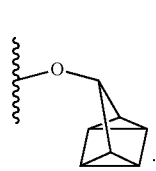 [SMILES: *OC1C2C3C2C2C1C32]

In embodiments, $R^5$ is

In embodiments, $R^5$ is

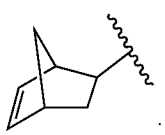

In embodiments, $R^5$ is

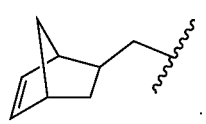 [SMILES: *CC1CC2C=CC1C2]

In embodiments, $R^5$ is

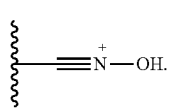

In embodiments, $R^5$ is

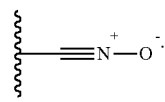

In embodiments, $R^5$ is

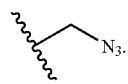

In embodiments, $R^5$ is

In embodiments, $R^5$ is or

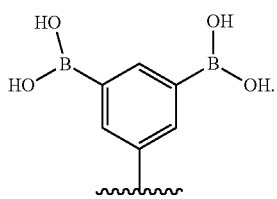 [SMILES: *c1cc(B(O)O)cc(B(O)O)c1]

In embodiments, $R^5$ is a modified oliogonucelotide. In embodiments, $R^5$ is a modified oliogonucelotide as described in Kumar et al Scientific Reports (2012) 2, 684; Fuller et al, PNAS USA (2016) 113, 5233-5238; US Patent Application US20150368710, which are incorporated herein by reference for all purposes. In embodiments, $R^5$ is a modified oliogonucelotide as observed in Example 3. In embodiments, $R^5$ is a modified oliogonucleotide as observed in FIG. 40, and FIGS. 43-46.

In embodiments, $R^5$ is
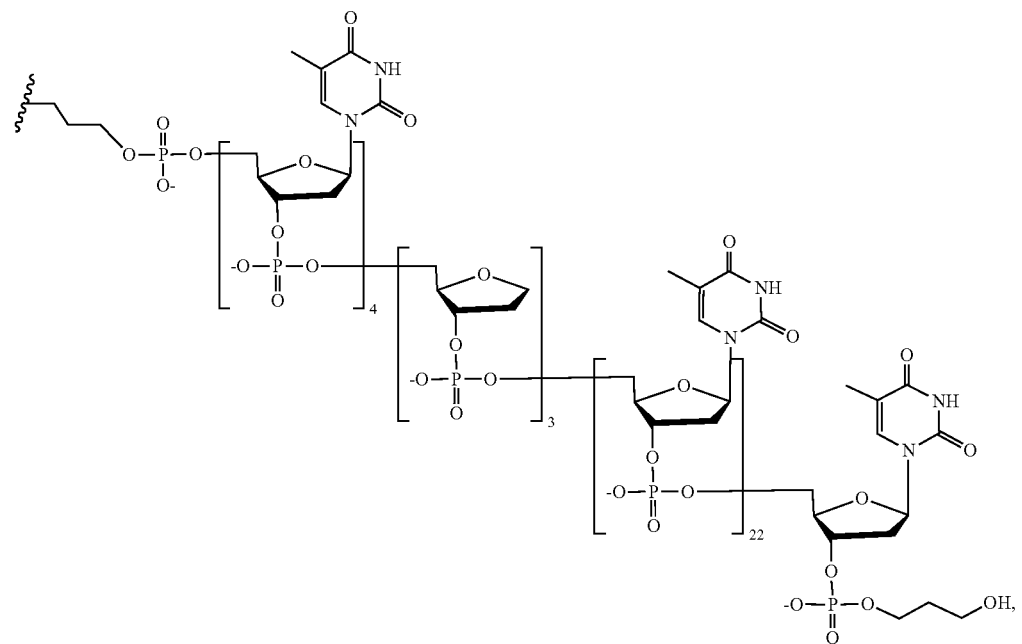
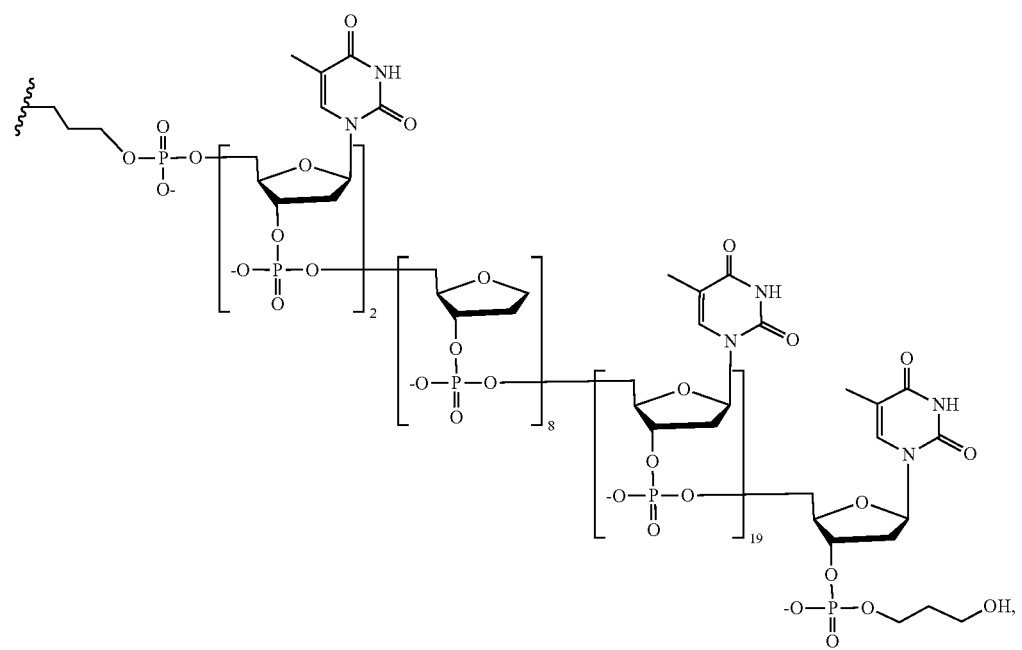

-continued
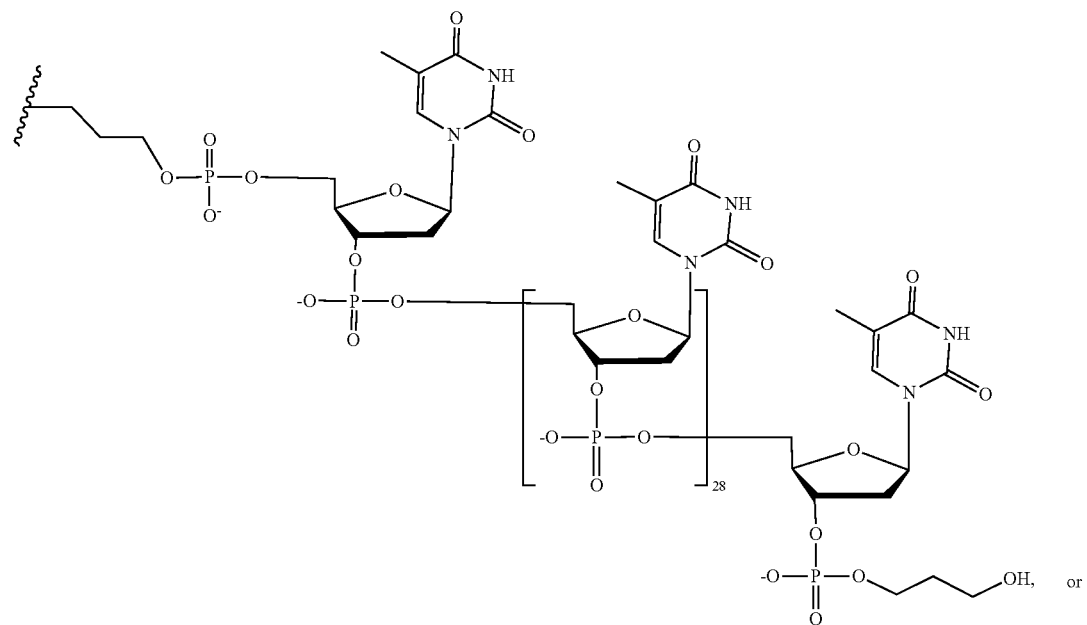
or
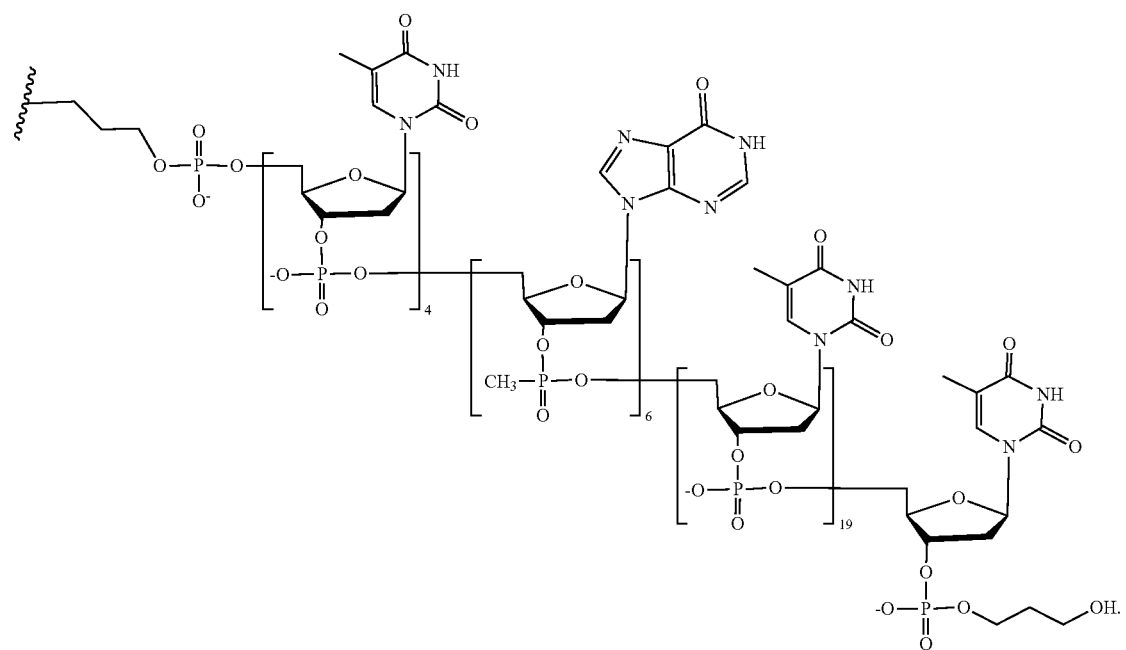

In embodiments, R⁵ is
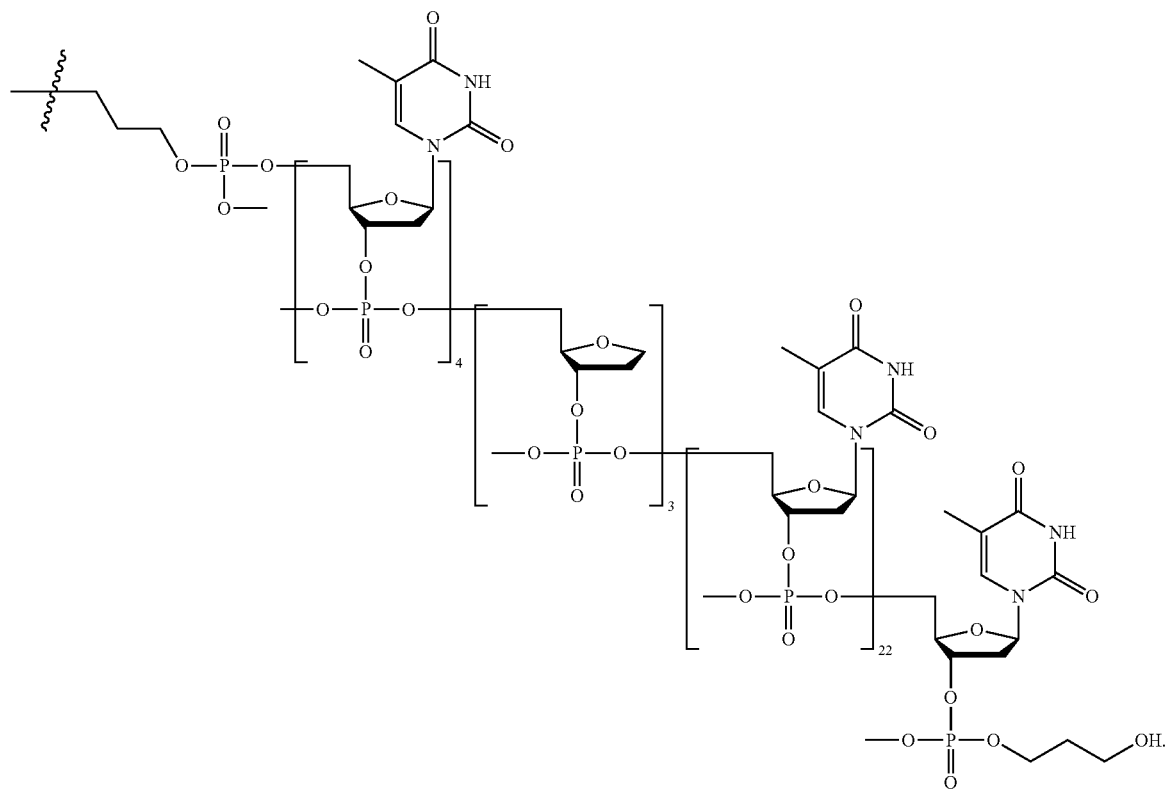
In embodiments, R⁵ is
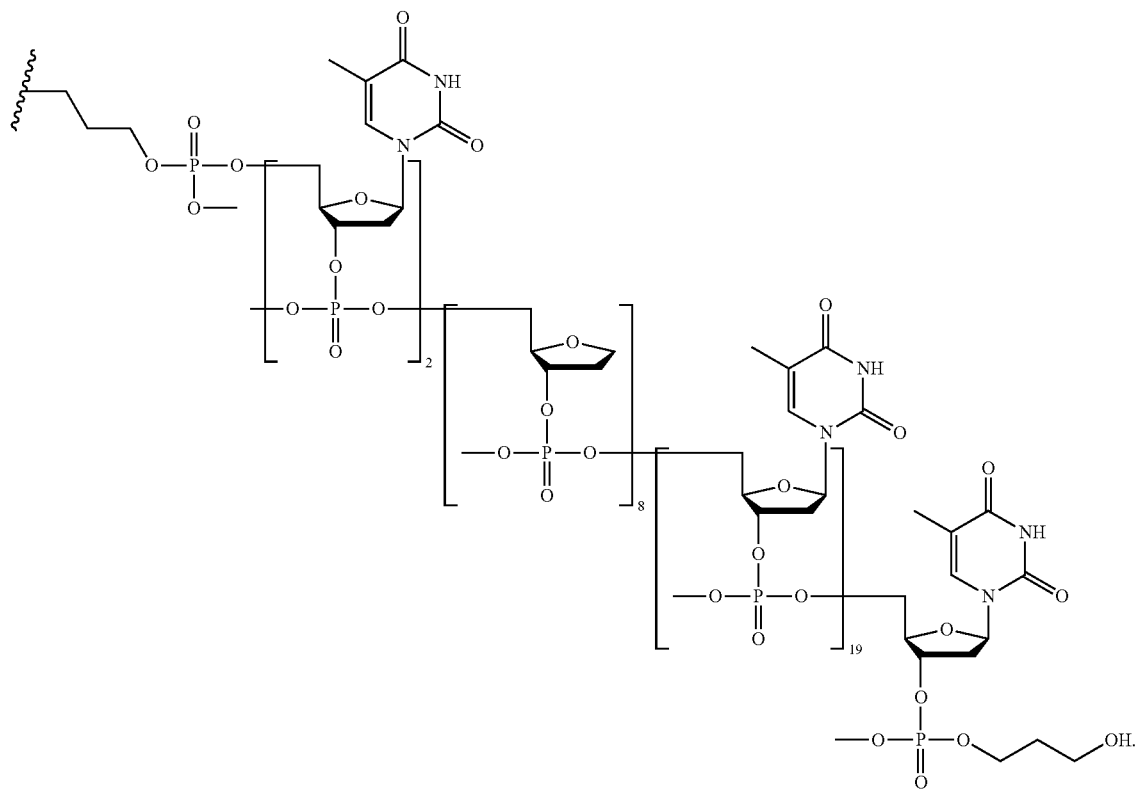

In embodiments, R⁵ is
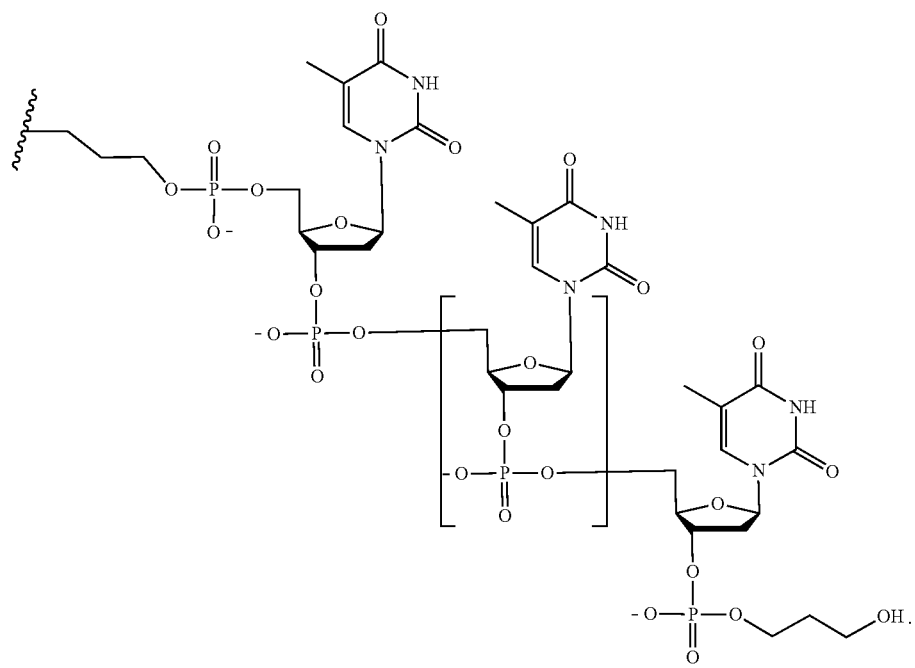
In embodiments, R⁵ is
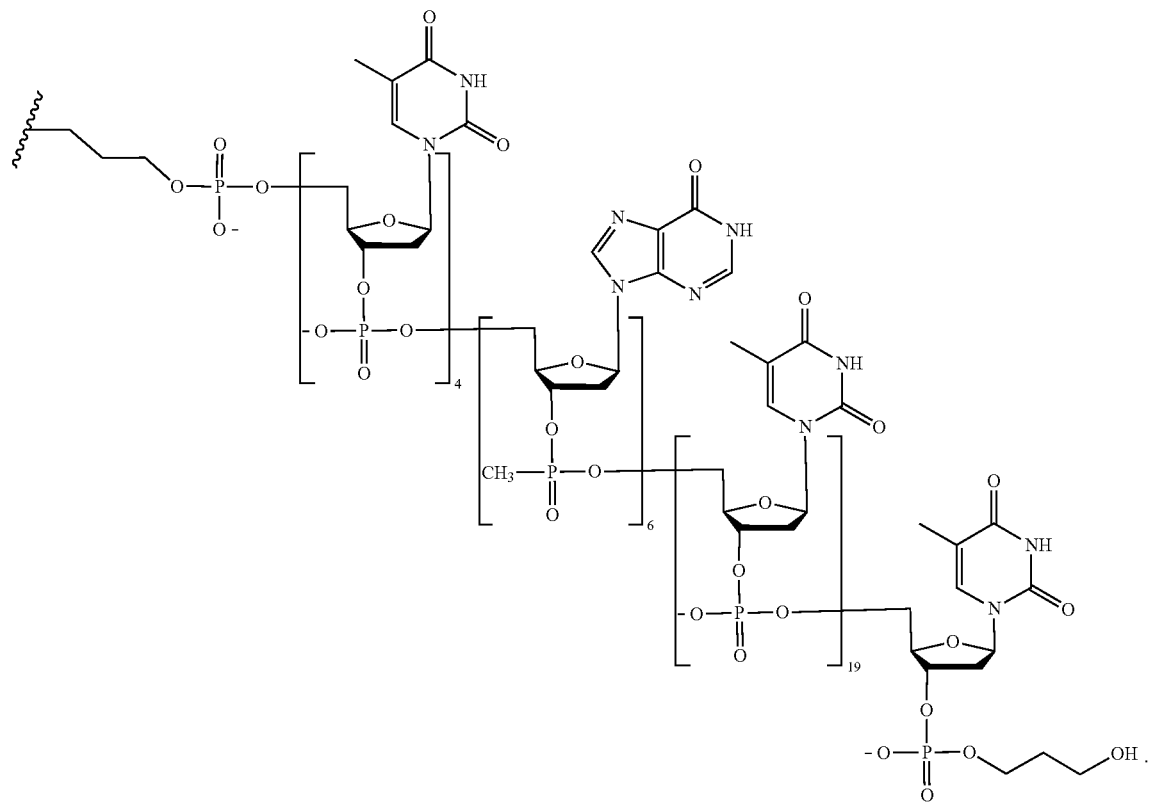

In embodiments, R⁵ is
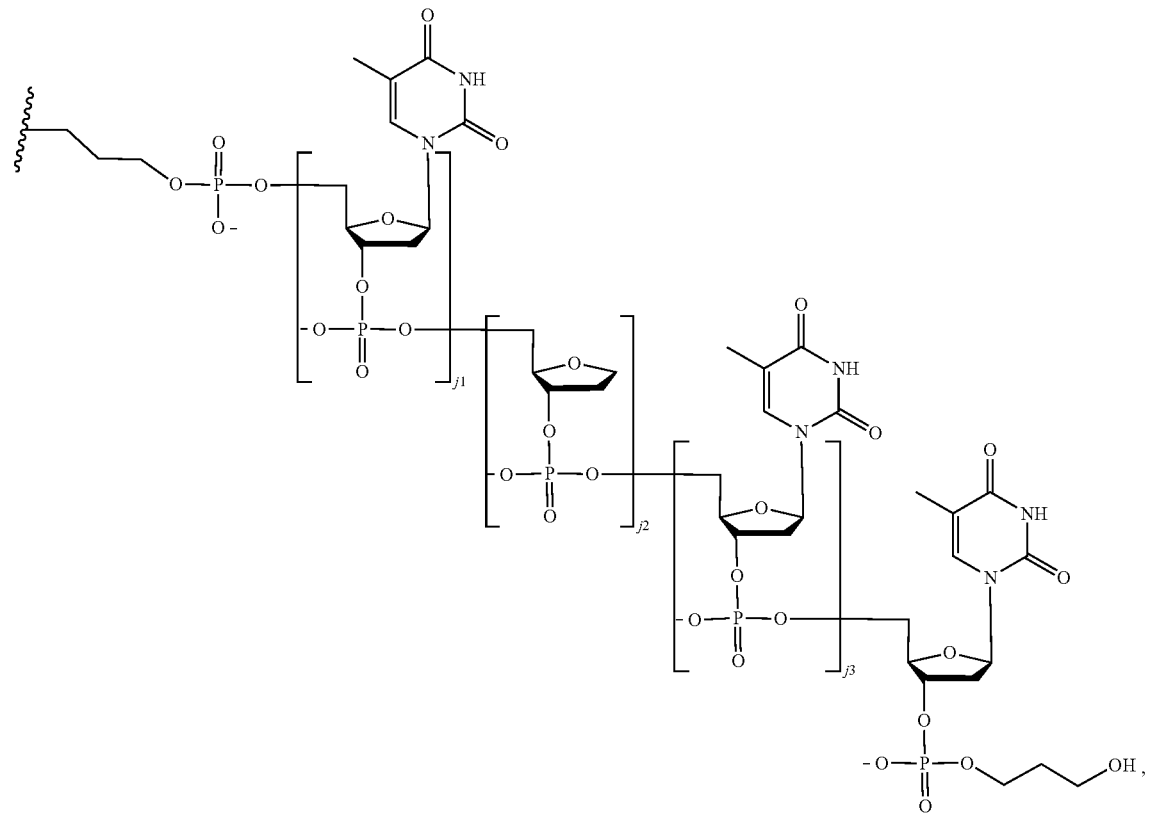
wherein j1, j2, and j3 are independently an integer from 0 to 30.

In embodiments, R⁵ is
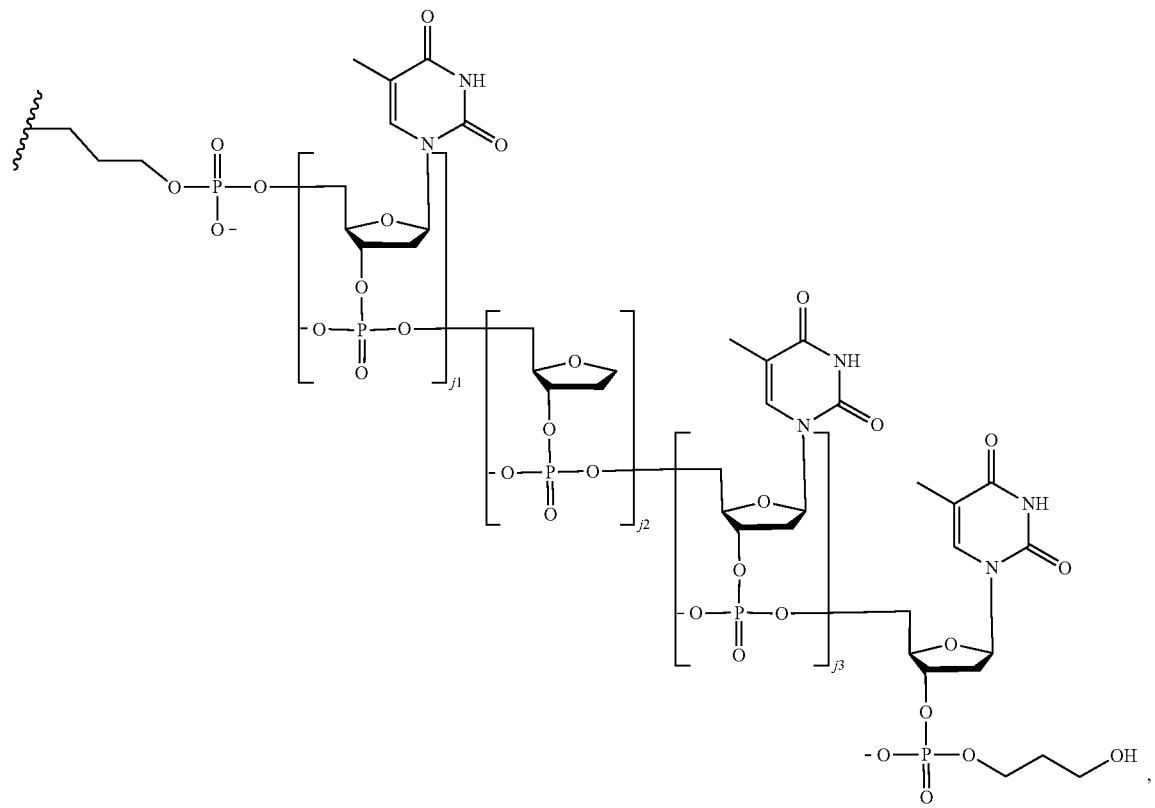
j1, j2, and j3 are independently an integer from 0 to 30.
In embodiments, R⁵ is:
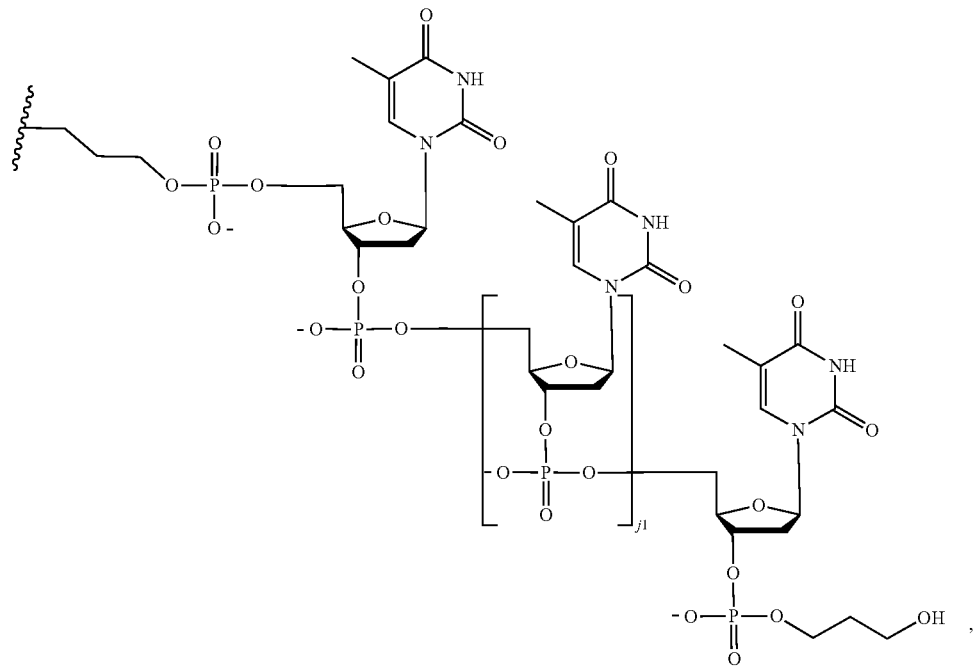
wherein j1 is an integer from 0 to 30.

In embodiments, R⁵ is

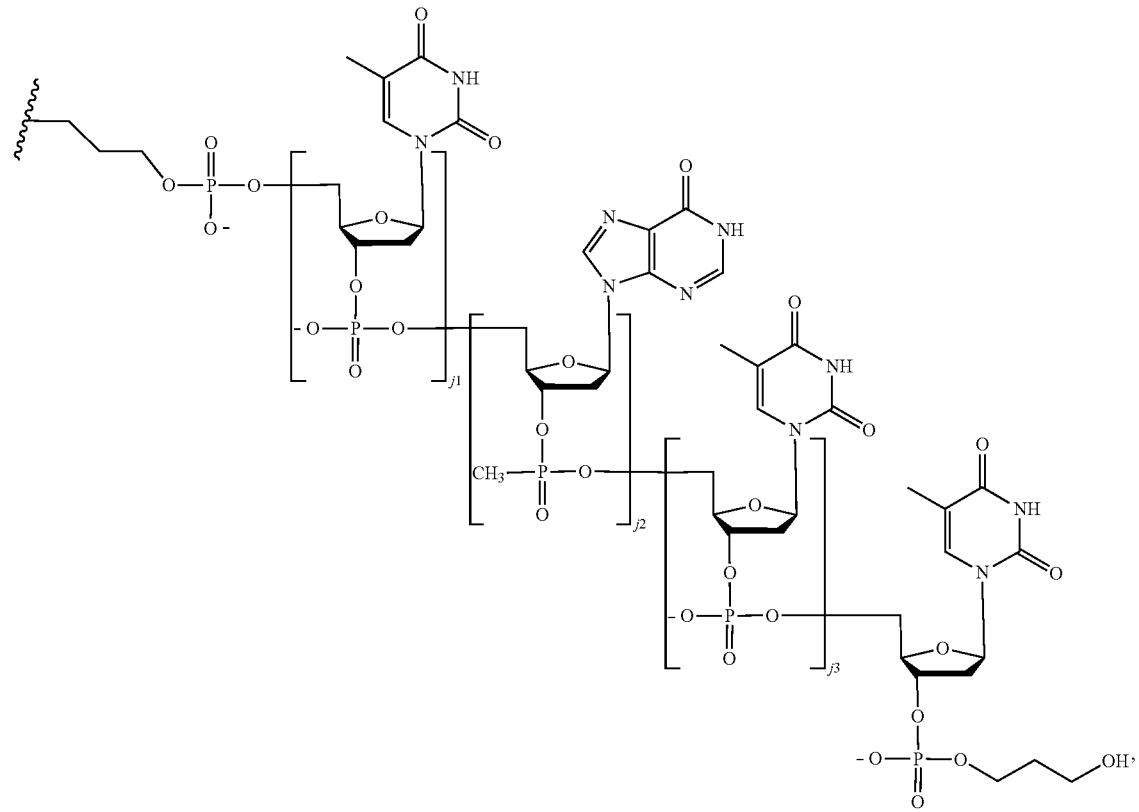

wherein j1, j2, and j3 are independently an integer from 0 to 30.

In embodiments, $R^6$ is hydrogen, —CF₃, —CCl₃, ~CBr₃, —CI₃, —CHF₂, —CHCl₂, —CHBr₂, —CHI₂, —CH₂F, —CH₂Cl, —CH₂Br, —CH₂I, —CN, substituted or unsubstituted alkyl, or substituted or unsubstituted heteroalkyl. In embodiments, $R^6$ is substituted or unsubstituted $C_1$-$C_6$ alkyl, or substituted or unsubstituted 2 to 6 membered heteroalkyl. In embodiments, $R^6$ is substituted or unsubstituted $C_1$-$C_6$ alkyl. In embodiments, $R^6$ is unsubstituted $C_1$-$C_6$ alkyl. In embodiments, $R^6$ is unsubstituted methyl. In embodiments, $R^6$ is hydrogen. In embodiments, $R^6$ is —CF₃. In embodiments, $R^6$ is —CCl₃. In embodiments, $R^6$ is —CBr₃. In embodiments, $R^6$ is —CI₃. In embodiments, $R^6$ is —CHF₂. In embodiments, $R^6$ is —CHCl₂. In embodiments, $R^6$ is —CHBr₂. In embodiments, $R^6$ is —CHI₂. In embodiments, $R^6$ is —CH₂F. In embodiments, $R^6$ is —CH₂Cl. In embodiments, $R^6$ is —CH₂Br. In embodiments, $R^6$ is —CH₂I. In embodiments, $R^6$ is —CN.

In embodiments, $R^6$ is hydrogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^6$ is hydrogen, CF₃, —CCl₃, ~CBr₃, —CI₃, —CHF₂, —CHCl₂, —CHBr₂, —CHI₂, —CH₂F, —CH₂Cl, —CH₂Br, —CH₂I, —CN, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^6$ is hydrogen.

In embodiments, $R^6$ is hydrogen, —CH₃, CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^6$ is hydrogen, —$CH_3$, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^6$ is hydrogen, —$CH_3$, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —CN, -Ph, substituted (e.g., substituted with a substituent group, size-limited substituent group, or lower substituent group) or unsubstituted (e.g., substituted with a substituent group, size-limited substituent group, or lower substituent group) $C_1$-$C_6$ alkyl, substituted (e.g., substituted with a substituent group, size-limited substituent group, or lower substituent group) or unsubstituted (e.g., substituted with a substituent group, size-limited substituent group, or lower substituent group) 2 to 6 membered heteroalkyl, substituted (e.g., substituted with a substituent group, size-limited substituent group, or lower substituent group) or unsubstituted (e.g., substituted with a substituent group, size-limited substituent group, or lower substituent group) $C_3$-$C_6$ cycloalkyl, substituted (e.g., substituted with a substituent group, size-limited substituent group, or lower substituent group) or unsubstituted (e.g., substituted with a substituent group, size-limited substituent group, or lower substituent group) 3 to 6 membered heterocycloalkyl, substituted (e.g., substituted with a substituent group, size-limited substituent group, or lower substituent group) or unsubstituted (e.g., substituted with a substituent group, size-limited substituent group, or lower substituent group) phenyl, or substituted (e.g., substituted with a substituent group, size-limited substituent group, or lower substituent group) or unsubstituted (e.g., substituted with a substituent group, size-limited substituent group, or lower substituent group) 5 to 6 membered heteroaryl.

In embodiments, $R^6$ is substituted (e.g., substituted with a substituent group, a size-limited substituent group, or lower substituent group) or unsubstituted alkyl. In embodiments, $R^6$ is substituted (e.g., substituted with a substituent group, a size-limited substituent group, or lower substituent group) alkyl. In embodiments, $R^6$ is unsubstituted alkyl. In embodiments, $R^6$ is substituted or unsubstituted alkyl (e.g., $C_1$-$C_8$, $C_1$-$C_6$, $C_1$-$C_4$, or $C_1$-$C_2$). In embodiments, $R^6$ is substituted alkyl (e.g., $C_1$-$C_8$, $C_1$-$C_6$, $C_1$-$C_4$, or $C_1$-$C_2$). In embodiments, $R^6$ is unsubstituted alkyl (e.g., $C_1$-$C_8$, $C_1$-$C_6$, $C_1$-$C_4$, or $C_1$-$C_2$).

In embodiments, $R^6$ is substituted (e.g., substituted with a substituent group, a size-limited substituent group, or lower substituent group) or unsubstituted heteroalkyl. In embodiments, $R^6$ is substituted (e.g., substituted with a substituent group, a size-limited substituent group, or lower substituent group) heteroalkyl. In embodiments, $R^6$ is unsubstituted heteroalkyl. In embodiments, $R^6$ is substituted or unsubstituted heteroalkyl (e.g., 2 to 8 membered, 2 to 6 membered, 4 to 6 membered, 2 to 3 membered, or 4 to 5 membered). In embodiments, $R^6$ is substituted heteroalkyl (e.g., 2 to 8 membered, 2 to 6 membered, 4 to 6 membered, 2 to 3 membered, or 4 to 5 membered). In embodiments, $R^6$ is an unsubstituted heteroalkyl (e.g., 2 to 8 membered, 2 to 6 membered, 4 to 6 membered, 2 to 3 membered, or 4 to 5 membered).

In embodiments, $R^6$ is substituted (e.g., substituted with a substituent group, a size-limited substituent group, or lower substituent group) or unsubstituted cycloalkyl. In embodiments, $R^6$ is substituted (e.g., substituted with a substituent group, a size-limited substituent group, or lower substituent group) cycloalkyl. In embodiments, $R^6$ is an unsubstituted cycloalkyl. In embodiments, $R^6$ is substituted or unsubstituted cycloalkyl (e.g., $C_3$-$C_8$, $C_3$-$C_6$, $C_4$-$C_6$, or $C_5$-$C_6$). In embodiments, $R^6$ is substituted cycloalkyl (e.g., $C_3$-$C_8$, $C_3$-$C_6$, $C_4$-$C_6$, or $C_5$-$C_6$). In embodiments, $R^6$ is unsubstituted cycloalkyl (e.g., $C_3$-$C_5$, $C_3$-$C_6$, $C_4$-$C_6$, or $C_5$-$C_6$).

In embodiments, $R^6$ is substituted (e.g., substituted with a substituent group, a size-limited substituent group, or lower substituent group) or unsubstituted heterocycloalkyl. In embodiments, $R^6$ is substituted (e.g., substituted with a substituent group, a size-limited substituent group, or lower substituent group) heterocycloalkyl. In embodiments, $R^6$ is an unsubstituted heterocycloalkyl. In embodiments, $R^6$ is substituted or unsubstituted heterocycloalkyl (e.g., 3 to 8 membered, 3 to 6 membered, 4 to 6 membered, 4 to 5 membered, or 5 to 6 membered). In embodiments, $R^6$ is substituted heterocycloalkyl (e.g., 3 to 8 membered, 3 to 6 membered, 4 to 6 membered, 4 to 5 membered, or 5 to 6 membered). In embodiments, $R^6$ an unsubstituted heterocycloalkyl (e.g., 3 to 8 membered, 3 to 6 membered, 4 to 6 membered, 4 to 5 membered, or 5 to 6 membered).

In embodiments, $R^6$ is substituted (e.g., substituted with a substituent group, a size-limited substituent group, or lower substituent group) or unsubstituted aryl. In embodiments, $R^6$ is substituted (e.g., substituted with a substituent group, a size-limited substituent group, or lower substituent group) aryl. In embodiments, $R^6$ is an unsubstituted aryl. In embodiments, $R^6$ is substituted or unsubstituted aryl (e.g., $C_6$-$C_{10}$ or phenyl). In embodiments, $R^6$ is substituted aryl (e.g., $C_6$-$C_{10}$ or phenyl). In embodiments, $R^6$ is an unsubstituted aryl (e.g., $C_6$-$C_{10}$ or phenyl).

In embodiments, $R^6$ is substituted (e.g., substituted with a substituent group, a size-limited substituent group, or lower substituent group) or unsubstituted heteroaryl. In embodiments, $R^6$ is substituted (e.g., substituted with a substituent group, a size-limited substituent group, or lower substituent group) heteroaryl. In embodiments, $R^6$ is an unsubstituted heteroaryl. In embodiments, $R^6$ is substituted or unsubstituted heteroaryl (e.g., 5 to 10 membered, 5 to 9 membered, or 5 to 6 membered). In embodiments, $R^6$ is substituted heteroaryl (e.g., 5 to 10 membered, 5 to 9 membered, or 5 to 6 membered). In embodiments, $R^6$ is an unsubstituted heteroaryl (e.g., 5 to 10 membered, 5 to 9 membered, or 5 to 6 membered).

In embodiments, $R^{64}$ is hydrogen, —OH, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, substituted or unsubstituted alkyl, or substituted or unsubstituted heteroalkyl. In embodiments, $R^{64}$ is substituted or unsubstituted C$_1$-C$_6$ alkyl, or substituted or unsubstituted 2 to 6 membered heteroalkyl. In embodiments, $R^{64}$ is substituted or unsubstituted C$_1$-C$_6$ alkyl. In embodiments, $R^{64}$ is unsubstituted C$_1$-C$_6$ alkyl. In embodiments, $R^{64}$ is unsubstituted methyl. In embodiments, $R^{64}$ is hydrogen. In embodiments, $R^{64}$ is —OH.

In embodiments, $R^{64}$ is hydrogen, CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{64}$ is hydrogen, CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, substituted (e.g., substituted with a substituent group, size-limited substituent group, or lower substituent group) or unsubstituted C$_1$-C$_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted C$_3$-C$_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{64}$ is hydrogen.

In embodiments, $R^{64}$ is hydrogen, —CH$_3$, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{64}$ is hydrogen, —CH$_3$, —CF$_3$, —CCl$_3$, ~CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{64}$ is hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —CN, -Ph, substituted (e.g., substituted with a substituent group, size-limited substituent group, or lower substituent group) or unsubstituted (e.g., substituted with a substituent group, size-limited substituent group, or lower substituent group) C$_1$-C$_6$ alkyl, substituted (e.g., substituted with a substituent group, size-limited substituent group, or lower substituent group) or unsubstituted (e.g., substituted with a substituent group, size-limited substituent group, or lower substituent group) 2 to 6 membered heteroalkyl, substituted (e.g., substituted with a substituent group, size-limited substituent group, or lower substituent group) or unsubstituted (e.g., substituted with a substituent group, size-limited substituent group, or lower substituent group) C$_3$-C$_6$ cycloalkyl, substituted (e.g., substituted with a substituent group, size-limited substituent group, or lower substituent group) or unsubstituted (e.g., substituted with a substituent group, size-limited substituent group, or lower substituent group) 3 to 6 membered heterocycloalkyl, substituted (e.g., substituted with a substituent group, size-limited substituent group, or lower substituent group) or unsubstituted (e.g., substituted with a substituent group, size-limited substituent group, or lower substituent group) phenyl, or substituted (e.g., substituted with a substituent group, size-limited substituent group, or lower substituent group) or unsubstituted (e.g., substituted with a substituent group, size-limited substituent group, or lower substituent group) 5 to 6 membered heteroaryl.

In embodiments, $R^7$ is hydrogen. In embodiments, $R^7$ is —OH. In embodiments, $R^7$ is —OR$^{7A}$; and $R^{7A}$ is hydrogen. In embodiments, $R^7$ is —OR$^{7A}$; and $R^{7A}$ is a polymerase-compatible moiety. In embodiments, $R^7$ is —OR$^{7A}$; and $R^{7A}$ is a polymerase-compatible cleavable moiety.

In embodiments, $R^7$ is —OR$^{7A}$; and $R^{7A}$ is a polymerase-compatible moiety including an azido moiety.

In embodiments, $R^7$ is —OR$^{7A}$; and $R^{7A}$ is a polymerase-compatible moiety including a dithiol linker, an allyl group, an azo group, or a 2-nitrobenzyl group.

In embodiments, $R^7$ is —OR$^{7A}$; and $R^{7A}$ is a polymerase-compatible cleavable moiety. In embodiments, $R^7$ is —OR$^{7A}$; and $R^{7A}$ is a polymerase-compatible cleavable moiety including an azido moiety. In embodiments, $R^7$ is —OR$^{7A}$; and $R^{7A}$ is a polymerase-compatible cleavable moiety including a dithiol linker, an allyl group, an azo group, or a 2-nitrobenzyl group.

In embodiments, $R^{7A}$ is hydrogen, polymerase-compatible moiety, or polymerase-compatible cleavable moiety. In embodiments, $R^{7A}$ is hydrogen. In embodiments, $R^{7A}$ is polymerase-compatible moiety. In embodiments, $R^{7A}$ is a polymerase-compatible cleavable moiety. In embodiments, $R^{7A}$ is a polymerase-compatible cleavable moiety including an azido moiety. In embodiments, $R^{7A}$ is a polymerase-compatible cleavable moiety including a dithiol linker, an allyl group, an azo group, or a 2-nitrobenzyl group. In embodiments, $R^{7A}$ is a polymerase-compatible cleavable moiety including a dithiol linker. In embodiments, $R^{7A}$ is a polymerase-compatible cleavable moiety including an allyl group. In embodiments, $R^{7A}$ is a polymerase-compatible cleavable moiety including an azo group. In embodiments, $R^{7A}$ is a polymerase-compatible cleavable moiety including a 2-nitrobenzyl group.

In embodiments, $R^7$ is hydrogen. In embodiments, $R^7$ is $-OR^{7A}$; and $R^{7A}$ is hydrogen. In embodiments, $R^7$ is $-OR^{7A}$; and $R^{7A}$ is a polymerase-compatible cleavable moiety. In embodiments, $R^7$ is $-OR^{7A}$; and $R^{7A}$ is a polymerase-compatible cleavable moiety including an azido moiety. In embodiments, $R^7$ is $-OR^{7A}$; and $R^{7A}$ is a polymerase-compatible cleavable moiety including a dithiol linker. In embodiments, $R^7$ is $-OR^{7A}$; $R^{7A}$ is a polymerase-compatible cleavable moiety; and the polymerase-compatible cleavable moiety is $-CH_2N_3$. In embodiments, $R^7$ is $-OR^{7A}$; and $R^{7A}$ is a polymerase-compatible cleavable moiety comprising a dithiol linker, an allyl group, or a 2-nitrobenzyl group. In embodiments, $R^7$ is $-NH_2$, $-CH_2N_3$,

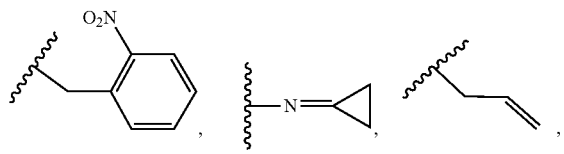

or $-CH_2-O-CH_3$.

In embodiments, $R^7$ is $-OR^{7A}$; $R^{7A}$ is a polymerase-compatible cleavable moiety; and the polymerase-compatible cleavable moiety is:

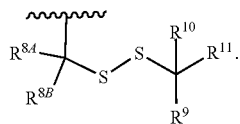

In embodiments, $R^{7A}$ is

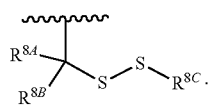

$R^{8C}$ is hydrogen, $-CX^{8C}_3$, $-CHX^{8C}_2$, $-CH_2X^{8C}$, $-OCX^{8C}_3$, $-OCH_2X^{8C}$, $-OCHX^{8C}_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol $X^{8C}$ is independently halogen. In embodiments, $R^{8C}$ is independently unsubstituted phenyl. In embodiments, $R^{8C}$ is $-CX^{8C}_3$, $-CHX^{8C}_2$, $-CH_2X^{8C}$, $-CH_2OCX^{8C}_3$, $-CH_2OCH_2X^{8C}$, $-CH_2OCHX^{8C}_2$, $-CN$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{8A}$ is independently hydrogen, $-CX^3_3$, $-CHX^3_2$, $-CH_2X^3$, $-OCX^3_3$, $-OCH_2X^3$, $-OCHX^3_2$, $-CH_2OCX^{8C}_3$, $-CH_2OCH_2X^{8C}$, $-CH_2OCHX^{8C}_2$, $-CN$, $-OH$, $-SH$, $-NH_2$, substituted (e.g., substituted with a -substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments $R^{8A}$ is independently hydrogen, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{8A}$ is independently hydrogen, deuterium, $-C(CH_3)_3$, $-CH(CH_3)_2$, $-CH_2CH_2CH_3$, $-CH_2CH_3$, $-CH_3$, $-CX^3_3$, $-CHX^3_2$, $-CH_2X^3$, $-CN$, or -Ph. In embodiments, $R^{8B}$ is independently hydrogen, deuterium, $-C(CH_3)_3$, $-CH(CH_3)_2$, $-CH_2CH_2CH_3$, $-CH_2CH_3$, $-CH_3$, $-CX^4_3$, $-CHX^4_2$, $-CH_2X^4$, $-CN$, or -Ph. In embodiments, $R^{8A}$ is independently hydrogen, $-CX^3_3$, $-CHX^3_2$, $-CH_2X^3$, $-OCX^3_3$, $-OCH_2X^3$, $-OCHX^3_2$, $-CN$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

$R^{8B}$ is independently hydrogen, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8B}$ is independently hydrogen, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{8B}$ is independently hydrogen, $-CX^4_3$, $-CHX^4_2$, $-CH_2X^4$, $-OCX^4_3$, $-OCH_2X^4$, $-OCHX^4_2$, $-CN$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8A}$ is independently hydrogen, $-CH_3$, $-CX^3_3$, $-CHX^3_2$, $-CH_2X^3$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8B}$ is independently hydrogen, $-CH_3$, $-CX^4_3$, $-CHX^4_2$, $-CH_2X^4$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8A}$ and $R^{8B}$ are independently hydrogen or unsubstituted alkyl. In embodiments, $R^{8A}$ and $R^{8B}$ are independently hydrogen or unsubstituted $C_1$-$C_4$ alkyl. In embodiments, $R^{8A}$ and $R^{8B}$ are independently hydrogen.

In embodiments, $R^9$ is independently hydrogen, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^9$ is independently hydrogen, $-CX^5_3$, $-CHX^5$, $-CH_2X^5$, $-OCX^5_3$, $-OCH_2X^5$, $-OCHX_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^9$ is independently hydrogen, $-CX^5_3$, $-CHX^5_2$, $-CH_2X^5$, $-OCX^5_3$, $-OCH_2X^5$, $-OCHX^5_2$, $-CN$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{10}$ is independently hydrogen, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{10}$ is independently hydrogen, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{10}$ is independently hydrogen, $-CX^6_3$, $-CHX^6_2$, $-CH_2X^6$, $-OCX^6_3$, $-OCH_2X^6$, $-OCHX^6_2$, $-CN$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^9$ is independently hydrogen, $-CX^5_3$, $-CHX^5_2$, $-CH_2X^5$, $-OCH_3$, $-SCH_3$, $-NHCH_3$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; $R^{10}$ is independently hydrogen, $-CX^6_3$, $-CHX^6_2$, $-CH_2X^6$, $-OCH_3$, $-SCH_3$, $-NHCH_3$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments $R^{11}$ is independently hydrogen, $-CX^7_3$, $-CHX^7_2$, $-CH_2X^7$, $-OCX^{73}$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{11}$ is independently hydrogen, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. The symbols $X^3$, $X^4$, $X^5$, $X^6$ and $X^7$ are independently halogen. In embodiments $R^{11}$ is independently hydrogen, $-CX^7_3$, $-CHX^7_2$, $-CH_2X^7$, $-OCX^7_3$, $-OCH_2X^7$, $-OCHX^7_2$, $-CN$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{11}$ is independently hydrogen, $-CX^7{}_3$, $-CHX^7{}_2$, $-CH_2X^7$, $-OCH_3$, $-SCH_3$, $-NHCH_3$, $-CN$, -Ph substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^9$, $R^{10}$, and $R^{11}$ are independently unsubstituted alkyl or unsubstituted heteroalkyl. In embodiments, $R^9$, $R^{10}$, and $R^{11}$ are independently unsubstituted $C_1$-$C_6$ alkyl or unsubstituted 2 to 4 membered heteroalkyl. In embodiments, $R^9$, $R^{10}$, and $R^{11}$ are independently unsubstituted $C_1$-$C_6$ alkyl or unsubstituted 2 to 4 membered heteroalkyl. In embodiments, $R^9$, $R^{10}$, and $R^{11}$ are independently unsubstituted methyl or unsubstituted methoxy. In embodiments, $R^{8A}$, $R^{8B}$, $R^9$, $R^{10}$, and $R^{11}$ are independently hydrogen or unsubstituted methyl. In embodiments, $R^{8A}$ and $R^{8B}$ are hydrogen and $R^9$, $R^{10}$, and $R^{11}$ are unsubstituted methyl.

In embodiments, $R^7$ is $-OR^{7A}$; $R^{7A}$ is a polymerase-compatible cleavable moiety; and the polymerase-compatible cleavable moiety is:

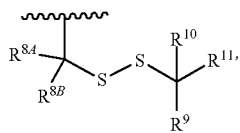

wherein $R^{8A}$ is hydrogen, $-CX^3{}_3$, $-CHX^3{}_2$, $-CH_2X^3$, $-OCX^3{}_3$, $-OCH_2X^3$, $-OCHX^3{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{8B}$ is independently hydrogen, $-CX^4{}_3$, $-CHX^4{}_2$, $-CH_2X^4$, $-OCX^4{}_3$, $-OCH_2X^4$, $-OCHX^{42}$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^9$ is independently hydrogen, $-CX^5{}_3$, $-CHX^5{}_2$, $-CH_2X^5$, $-OCX^5{}_3$, $-OCH_2X^5$, $-OCHX^5$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{10}$ is independently hydrogen, $-CX^6{}_3$, $-CHX^6{}_2$, $-CH_2X^6$, $-OCX^6{}_3$, $-OCH_2X^6$, $-OCHX^6{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{11}$ is independently hydrogen, $-CX^7{}_3$, $-CHX^7{}_2$, $-CH_2X^7$, $-OCX^7{}_3$, $-OCH_2X^7$, $-OCHX^7{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; and $X^3$, $X^4$, $X^5$, $X^6$ and $X^7$ are independently halogen.

In embodiments, $R^7$ is —$OR^{7A}$; $R^{7A}$ is a polymerase-compatible cleavable moiety; and the polymerase-compatible cleavable moiety is:

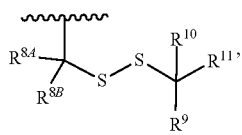

wherein $R^{8A}$, $R^{8B}$, $R^9$, $R^{10}$, and $R^{11}$ are independently hydrogen or unsubstituted methyl. In embodiments, $R^7$ is —$OR^{7A}$; $R^{7A}$ is a polymerase-compatible cleavable moiety; and the polymerase-compatible cleavable moiety is

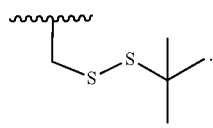 [SMILES: *CSSC(C)(C)C]

In embodiments, $R^{7A}$ is hydrogen. In embodiments, $R^{7A}$ is

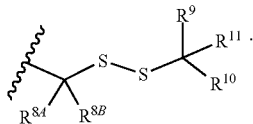

In embodiments, $R^{7A}$ is

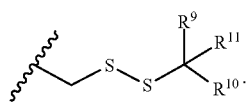

In embodiments, $R^{7A}$ is

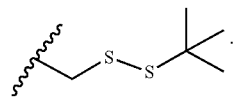 [SMILES: *CSSC(C)(C)C]

In embodiments, $R^{8A}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^{8A}$ is independently hydrogen, —CH$_3$, —CX$^3_3$, —CHX$^3_2$, —CH$_2$X$^3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8A}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

In embodiments, $R^{8B}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^{8B}$ is hydrogen, —CH$_3$, —CX$^4_3$, —CHX$^4_2$, —CH$_2$X$^4$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8B}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

In embodiments, $R^9$ is independently hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^9$ is hydrogen, —CX$^5_3$, —CHX$^5_2$, —CH$_2$X$^5$, —OCH$_3$, —SCH$_3$, —NHCH$_3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{10}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. $R^{10}$ is hydrogen, —CX$^6_3$, —CHX$^6_2$, —CH$_2$X$^6$, —OCH$_3$, —SCH$_3$, —NHCH$_3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl;

In embodiments, $R^{11}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^{11}$ is hydrogen, —CX$^7_3$, —CHX$^7_2$, —CH$_2$X$^7$, —OCH$_3$, —SCH$_3$, —NHCH$_3$, —CN, -Ph substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^2$ is selected from the group consisting of:

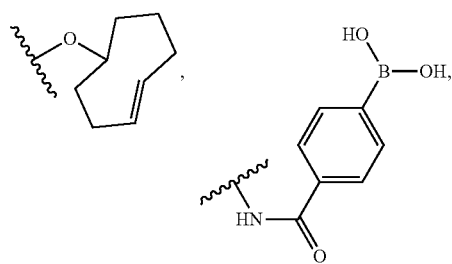

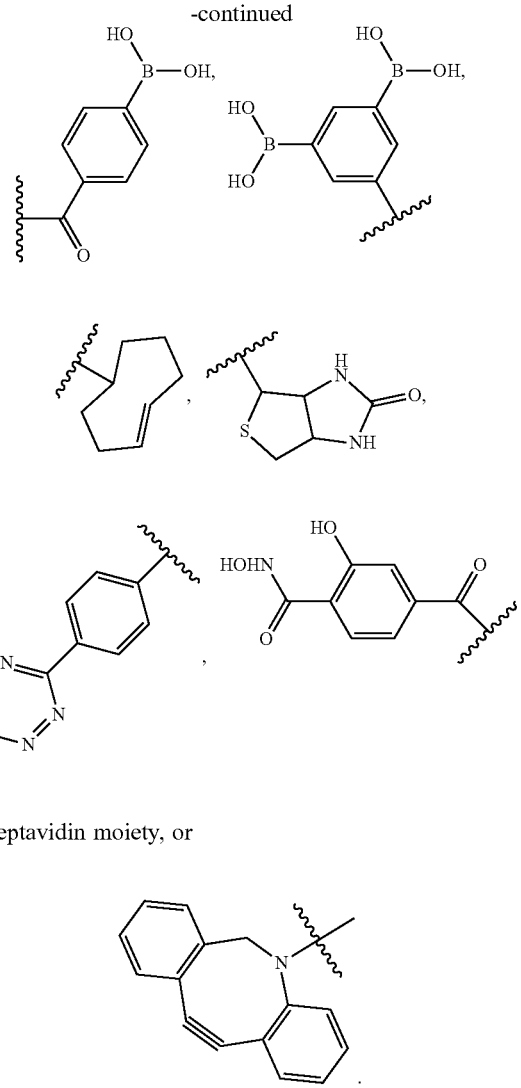

a streptavidin moiety, or

In embodiments, $R^{12}$ is

In embodiments, $R^{12}$ is

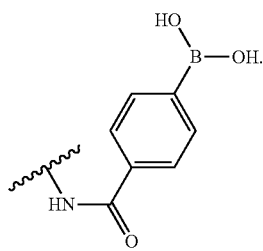 [SMILES: *NC(=O)c1ccc(B(O)O)cc1]

In embodiments, $R^{12}$ is
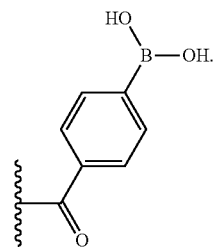 [SMILES: *C(=O)c1ccc(B(O)O)cc1]
In embodiments, $R^{12}$ is
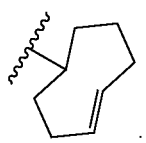 [SMILES: *C1CC/C=C/CCC1]
In embodiments, $R^{12}$ is
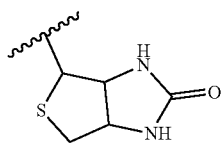
In embodiments, $R^{12}$ is
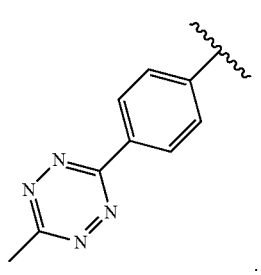 [SMILES: *c1ccc(-c2nnc(C)nn2)cc1]
In embodiments, $R^2$ is
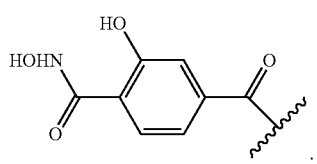
In embodiments, $R^{12}$ is a streptavidin moiety. In embodiments, $R^{12}$ is or
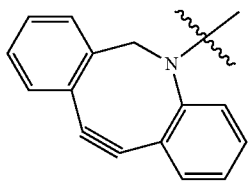
In embodiments, $R^{12}$ streptavidin, dibenzocyclooctyne (DBCO), tetrazine (TZ), or salicylhydroxamic acid (SHA).
In embodiments, $R^{12}$ is unsubstituted ethynyl,
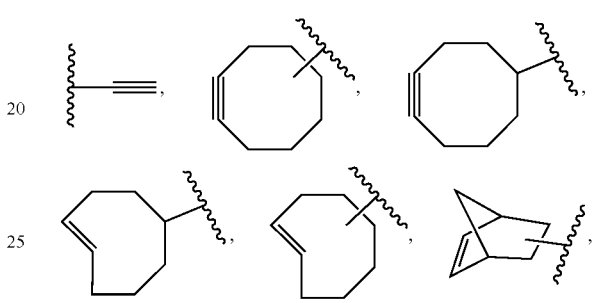
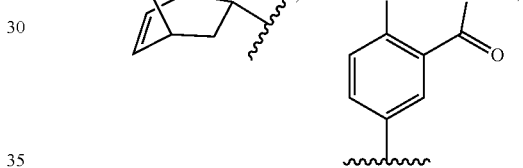
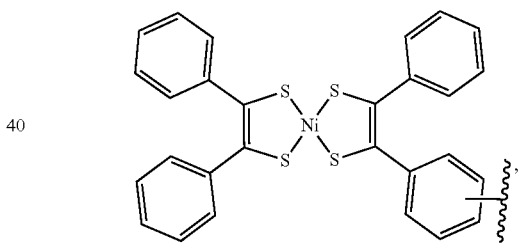
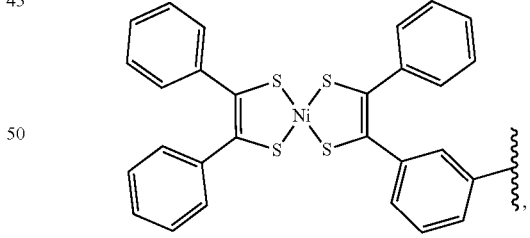
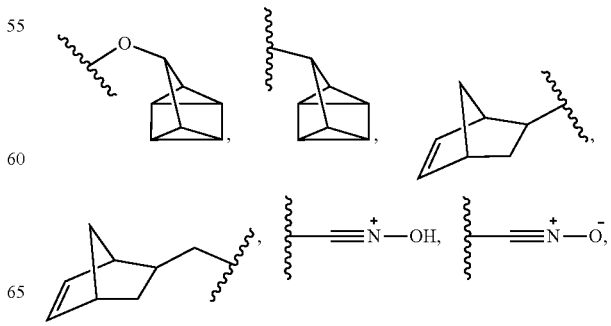

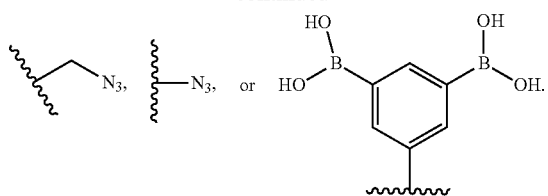
In embodiments, $R^{12}$ is
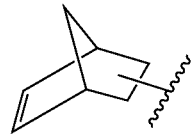
In embodiments, $R^{12}$ is unsubstituted ethynyl. In embodiments, $R^{12}$ is
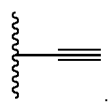 [SMILES: *C#C]
In embodiments, $R^{12}$ is
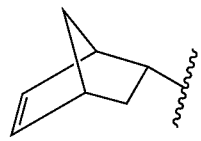
In embodiments, $R^{12}$ is
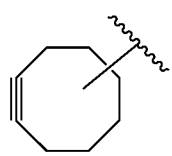
In embodiments, $R^{12}$ is
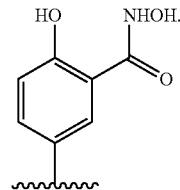
In embodiments, $R^{12}$ is
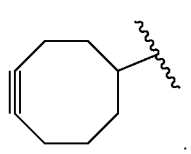
In embodiments, $R^{12}$ is
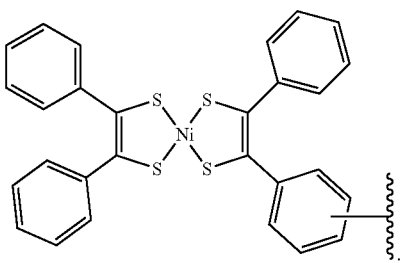
In embodiments, $R^{12}$ is
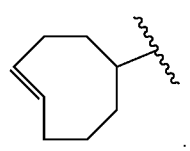
In embodiments, $R^{12}$ is
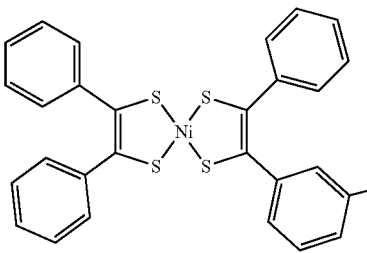
In embodiments, $R^{12}$ is
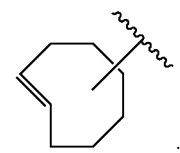
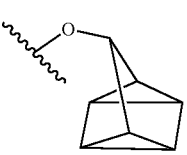

In embodiments, $R^{12}$ is

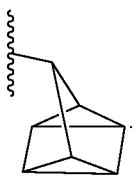 [SMILES: *C1C2C3C2C2C1C32]

In embodiments, $R^{12}$ is

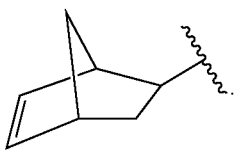 [SMILES: *C1CC2C=CC1C2]

In embodiments, $R^{12}$ is

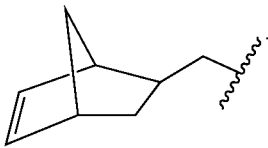 [SMILES: *CC1CC2C=CC1C2]

In embodiments, $R^{12}$ is

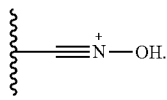

In embodiments, $R^{12}$ is

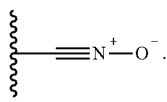

In embodiments, $R^{12}$ is

In embodiments, $R^{12}$ is

In embodiments, $R^{12}$ is or

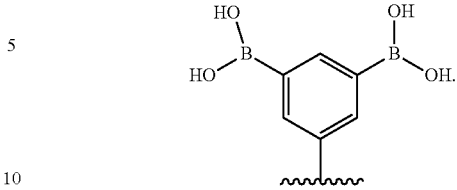

In embodiments, $R^{12}$ is streptavidin, dibenzylcyclooctene (DBCO), tetrazine, salicylhydroxamic acid (SHA), bis(dithiobenzil)nickel(II), or nitrile oxide.

In embodiments, $R^{13}$ is a fluorescent dye. In embodiments $R^{13}$ is a Alexa Fluor®350 moiety, Alexa Fluor®405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor®700 moiety, Alexa Fluor® 750 moiety, or Alexa Fluor® 790 moiety. In embodiments the detectable moiety is a Alexa Fluor®488 moiety, Rhodamine 6G ($R^6G$) moiety, ROX Reference Dye (ROX) moiety, or Cy5 moiety.

In embodiments $R^{13}$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G ($R^6G$) moiety, ROX Reference Dye (ROX) moiety, Sulfo-Cy5, or Cy5 moiety. In embodiments $R^{13}$ is a Rhodamine 6G ($R^6G$) moiety, ROX Reference Dye (ROX) moiety, Sulfo-Cy5, or Cy5 moiety.

In embodiments, $R^{13}$ is a detectable label. In embodiments, $R^{13}$ is a fluorescent dye.

In embodiments, $R^{13}$ is fluorescent dye with a molecular weight of at least about 130 Daltons. In embodiments, $R^{13}$ is fluorescent dye with a molecular weight of at least about 135 Daltons. In embodiments, $R^{13}$ is fluorescent dye with a molecular weight of at least about 140 Daltons. In embodiments, $R^{13}$ is fluorescent dye with a molecular weight of at least about 145 Daltons. In embodiments, $R^{13}$ is fluorescent dye with a molecular weight of at least about 150 Daltons. In embodiments, $R^{13}$ is fluorescent dye with a molecular weight of about 130 Daltons. In embodiments, $R^{13}$ is fluorescent dye with a molecular weight of about 135 Daltons. In embodiments, $R^{13}$ is fluorescent dye with a molecular weight of about 140 Daltons. In embodiments, $R^{13}$ is fluorescent dye with a molecular weight of about 145 Daltons. In embodiments, $R^3$ is fluorescent dye with a molecular weight of about 150 Daltons. In embodiments, $R^{13}$ is fluorescent dye with a molecular weight of about 146 Daltons.

In embodiments, $R^{13}$ is fluorescent dye with a molecular weight of about 140 to about 3000 Daltons. In embodiments, $R^{13}$ is fluorescent dye with a molecular weight of about 140 to about 2500 Daltons. In embodiments, $R^{13}$ is fluorescent dye with a molecular weight of about 140 to about 2000 Daltons. In embodiments, $R^{13}$ is fluorescent dye with a molecular weight of about 140 to about 1000 Daltons. In embodiments, $R^{13}$ is fluorescent dye with a molecular weight of about 140 to about 900 Daltons. In embodiments, $R^{13}$ is fluorescent dye with a molecular weight of about 140 to about 800 Daltons. In embodiments, $R^{13}$ is fluorescent dye with a molecular weight of about 140 to about 700 Daltons. In embodiments, $R^{13}$ is fluorescent dye with a molecular weight of about 140 to about 600 Daltons. In embodiments, $R^{13}$ is fluorescent dye with a molecular weight of about 140 to about 500 Daltons. In embodiments, $R^{13}$ is fluorescent dye with a molecular weight of about 140 to about 400 Daltons. In embodiments, $R^{13}$ is fluorescent dye with a molecular weight of about 140 to about 300 Daltons. In embodiments, $R^{13}$ is fluorescent dye with a molecular weight of about 140 to about 200 Daltons.

In embodiments, $R^{13}$ is fluorescent dye with a molecular weight of about 200 to about 3000 Daltons. In embodiments, $R^{13}$ is fluorescent dye with a molecular weight of about 200 to about 2500 Daltons. In embodiments, $R^{13}$ is fluorescent dye with a molecular weight of about 200 to about 2000 Daltons. In embodiments, $R^{13}$ is fluorescent dye with a molecular weight of about 200 to about 1000 Daltons. In embodiments, $R^{13}$ is fluorescent dye with a molecular weight of about 200 to about 900 Daltons. In embodiments, $R^3$ is fluorescent dye with a molecular weight of about 200 to about 800 Daltons. In embodiments, $R^{13}$ is fluorescent dye with a molecular weight of about 200 to about 700 Daltons. In embodiments, $R^{13}$ is fluorescent dye with a molecular weight of about 200 to about 600 Daltons. In embodiments, $R^{13}$ is fluorescent dye with a molecular weight of about 200 to about 500 Daltons. In embodiments, $R^{13}$ is fluorescent dye with a molecular weight of about 200 to about 400 Daltons. In embodiments, $R^{13}$ is fluorescent dye with a molecular weight of about 200 to about 300 Daltons.

In embodiments, $R^{13}$ is fluorescent dye with a molecular weight of about 300 to about 3000 Daltons. In embodiments, $R^{13}$ is fluorescent dye with a molecular weight of about 300 to about 2500 Daltons. In embodiments, $R^{13}$ is fluorescent dye with a molecular weight of about 300 to about 2000 Daltons. In embodiments, $R^{13}$ is fluorescent dye with a molecular weight of about 300 to about 1000 Daltons. In embodiments, $R^{13}$ is fluorescent dye with a molecular weight of about 300 to about 900 Daltons. In embodiments, $R^{13}$ is fluorescent dye with a molecular weight of about 300 to about 800 Daltons. In embodiments, $R^{13}$ is fluorescent dye with a molecular weight of about 300 to about 700 Daltons. In embodiments, $R^3$ is fluorescent dye with a molecular weight of about 300 to about 600 Daltons. In embodiments, $R^{13}$ is fluorescent dye with a molecular weight of about 300 to about 500 Daltons. In embodiments, $R^{13}$ is fluorescent dye with a molecular weight of about 300 to about 400 Daltons.

In embodiments, $R^{13}$ is fluorescent dye with a molecular weight of about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800, 2810, 2820, 2830, 2840, 2850, 2860, 2870, 2880, 2890, 2900, 2910, 2920, 2930, 2940, 2950, 2960, 2970, 2980, 2990, or about 3000 Daltons.

In embodiments, $R^{13}$ is

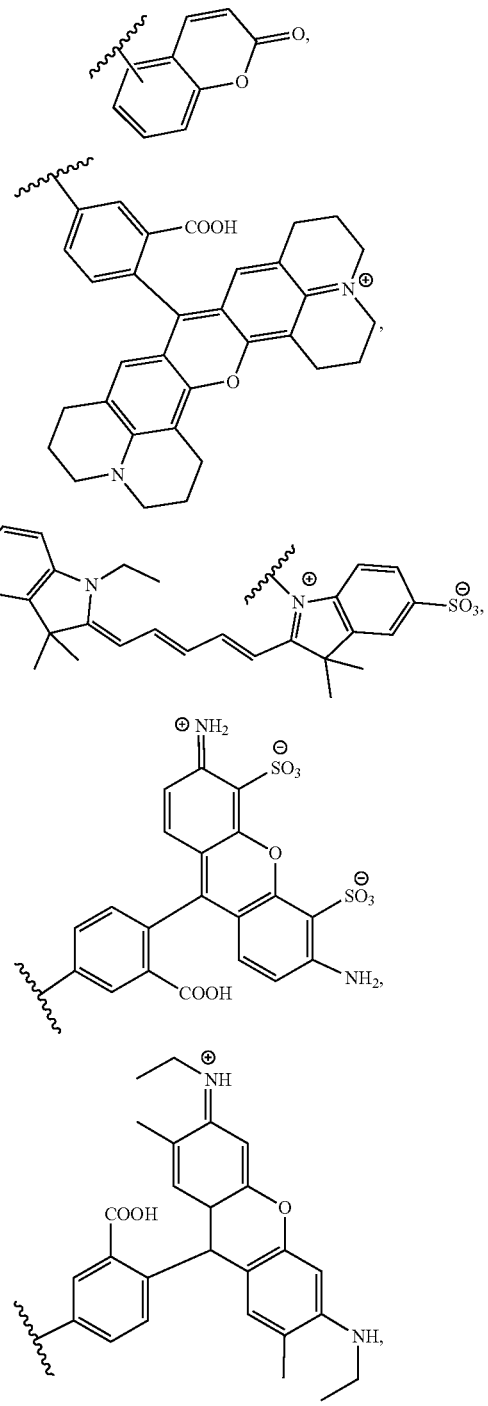

-continued

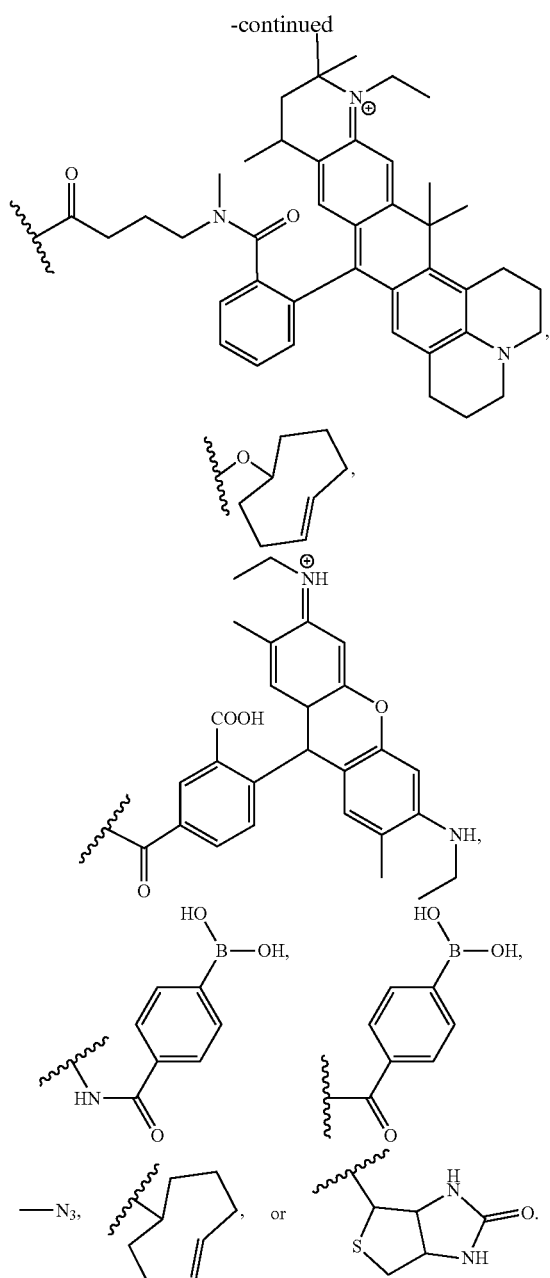

In embodiments, $R^{13}$ is a detectable label. In embodiments, $R^{13}$ is a fluorescent dye. In embodiments, $R^{13}$ is an anchor moiety. In embodiments, $R^{13}$ is a click chemistry reactant moiety. In embodiments, $R^{13}$ is a trans-cyclooctene moiety or azide moiety. In embodiments, $R^{13}$ is an affinity anchor moiety. In embodiments, $R^{13}$ is a biotin moiety. In embodiments, $R^{13}$ is a reactant for a bioconjugate reaction that forms a covalent bond between $R^{13}$ and a second bioconjugate reaction reactant.

In embodiments $R^{13}$ is a FAM™ moiety. In embodiments $R^{13}$ is a TET™ moiety. In embodiments $R^{13}$ is a JOE™ moiety. In embodiments $R^{13}$ is a VIC® moiety. In embodiments $R^{13}$ is a HEX™ moiety. In embodiments $R^{13}$ is a NED™ moiety. In embodiments $R^{13}$ is a PET® moiety. In embodiments $R^{13}$ is a ROX™ moiety. In embodiments $R^{13}$ is a TAMRA™ moiety. In embodiments $R^{13}$ is a TET™ moiety. In embodiments $R^{13}$ is a Texas Red® moiety. In embodiments $R^{13}$ is an Alexa Fluor® 488 moiety. In embodiments $R^{13}$ is a Rhodamine 6G ($R^6G$) moiety. In embodiments $R^{13}$ is a ROX Reference Dye (ROX) moiety. In embodiments $R^{13}$ is a Sulfo-Cy. In embodiments $R^{13}$ is a Cy5 moiety.

In embodiments, $R^{13}$ is

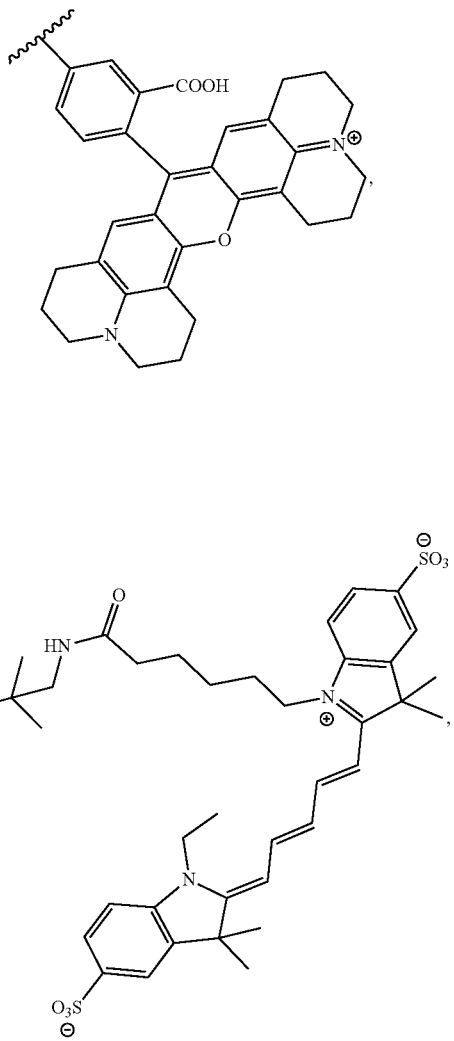

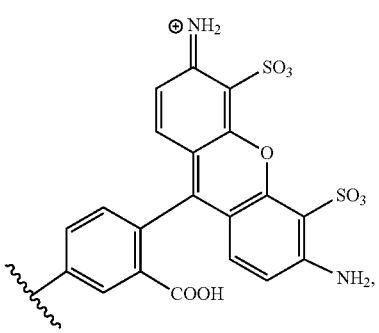

173
-continued
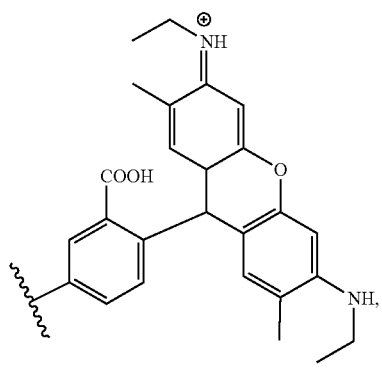
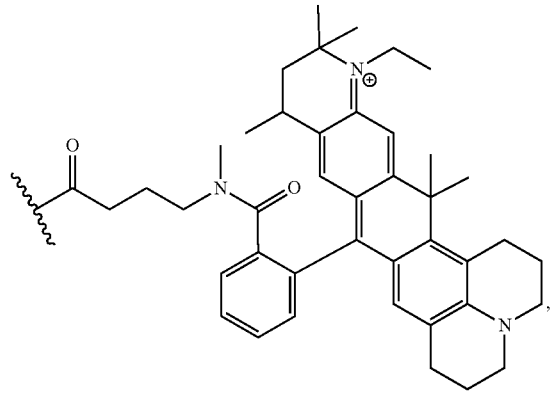
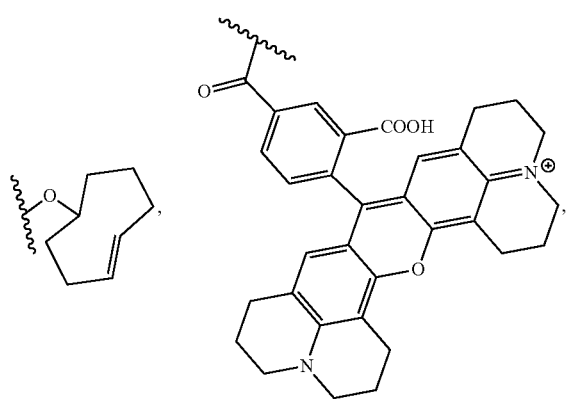
174
-continued
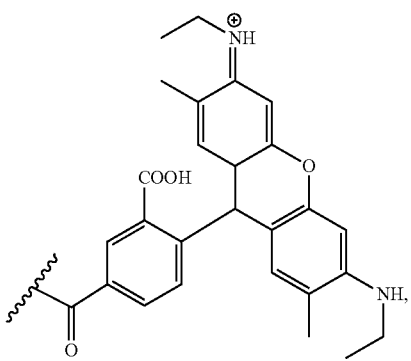
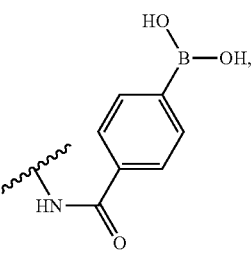, 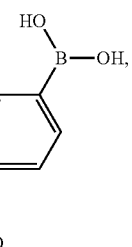
In embodiments, R¹³ is
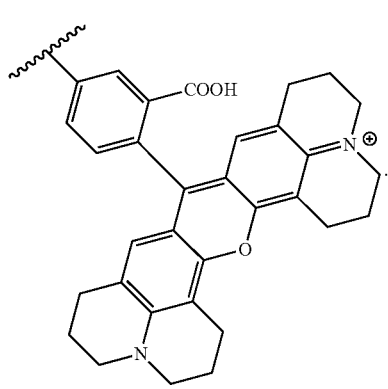 [SMILES: *c1ccc(C2=c3cc4c5c(c3Oc3c2cc2c6c3CCCN6CCC2)CCC[N+]=5CCC4)c(C(=O)O)c1]

In embodiments, R¹³ is
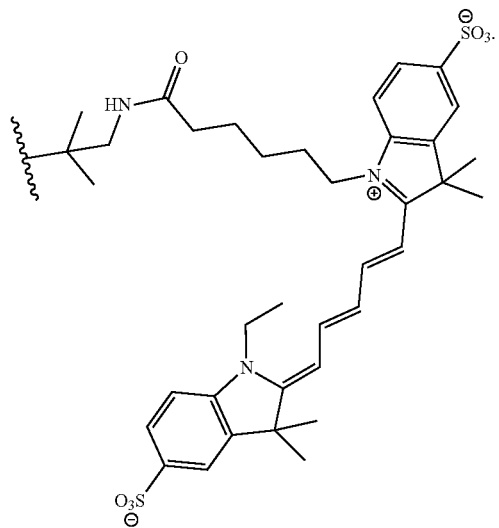
In embodiments, R¹³ is
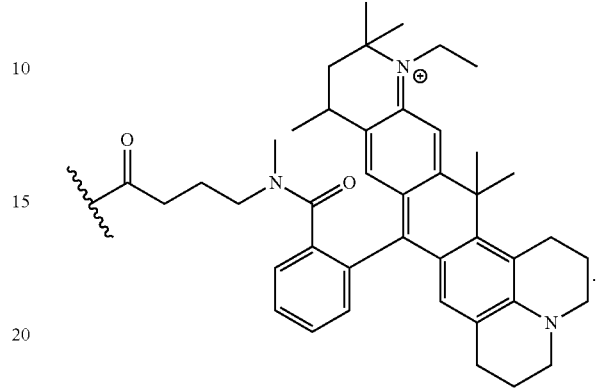
In embodiments, R¹³ is
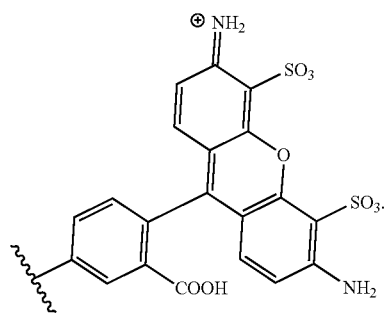
In embodiments, R¹³ is
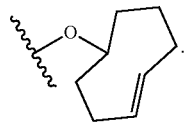
In embodiments, R¹³ is
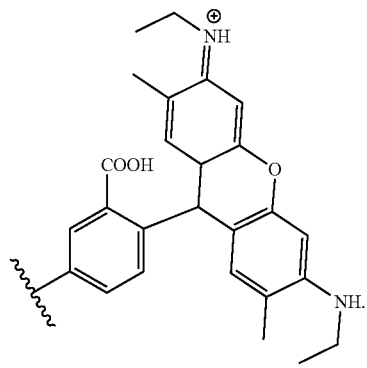 [SMILES: *c1ccc(C2c3cc(C)c(NCC)cc3OC3=C/C(=[NH+]/CC)C(C)=CC32)c(C(=O)O)c1]
In embodiments, R¹³ is
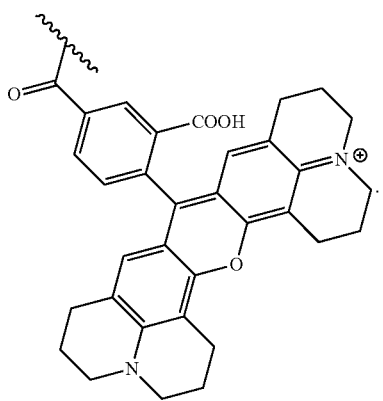 [SMILES: *C(=O)c1ccc(C2=c3cc4c5c(c3Oc3c2cc2c6c3CCCN6CCC2)CCC[N+]=5CCC4)c(C(=O)O)c1]

In embodiments, R¹³ is

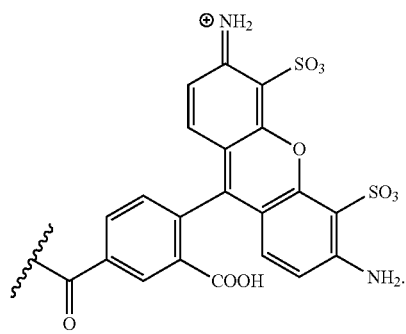

In embodiments, R¹³ is

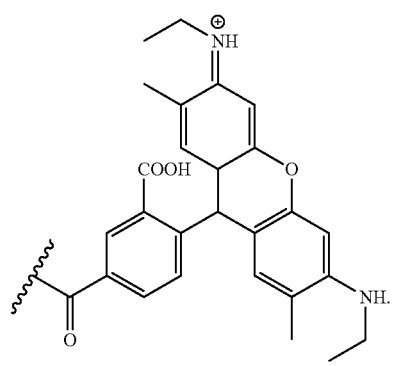 [SMILES: *C(=O)c1ccc(C2c3cc(C)c(NCC)cc3OC3=C/C(=[NH+]/CC)C(C)=CC32)c(C(=O)O)c1]

In embodiments, R¹³ is

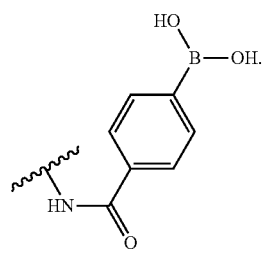 [SMILES: *NC(=O)c1ccc(B(O)O)cc1]

In embodiments, R¹³ is

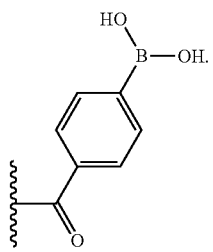

In embodiments, R¹³ is —N₃. In embodiments, R¹³ is

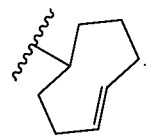 [SMILES: *C1CC/C=C/CCC1]

In embodiments, R¹³ is

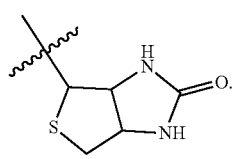 [SMILES: *C1SCC2NC(=O)NC21]

In embodiments, R¹³ is a modified oliogonucelotide. In embodiments, R¹³ is a modified oliogonucelotide as described in Kumar et al Scientific Reports (2012) 2, 684; Fuller et al, PNAS USA (2016) 113, 5233-5238; US Patent Application US20150368710, which are incorporated herein by reference for all purposes. In embodiments, R¹³ is a modified oliogonucelotide as observed in Example 3. In embodiments, R¹³ is a modified oliogonucelotide as observed in FIG. 40 and FIGS. 43-46.

In embodiments, $R^{13}$ is
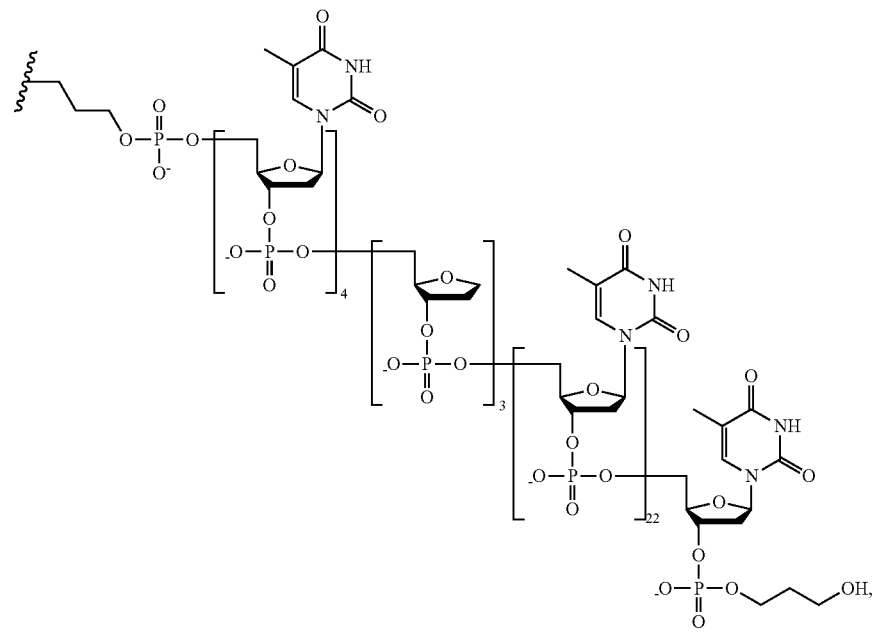
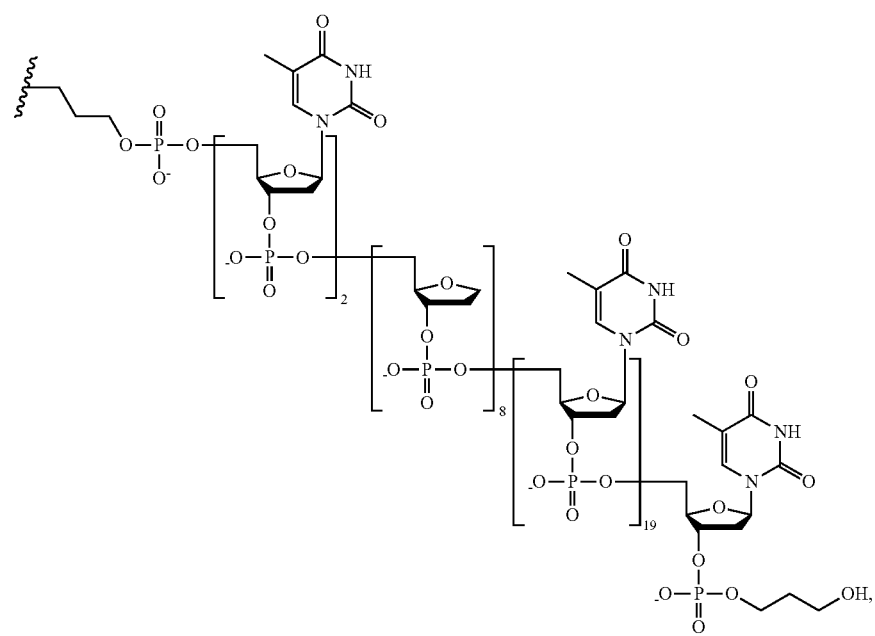

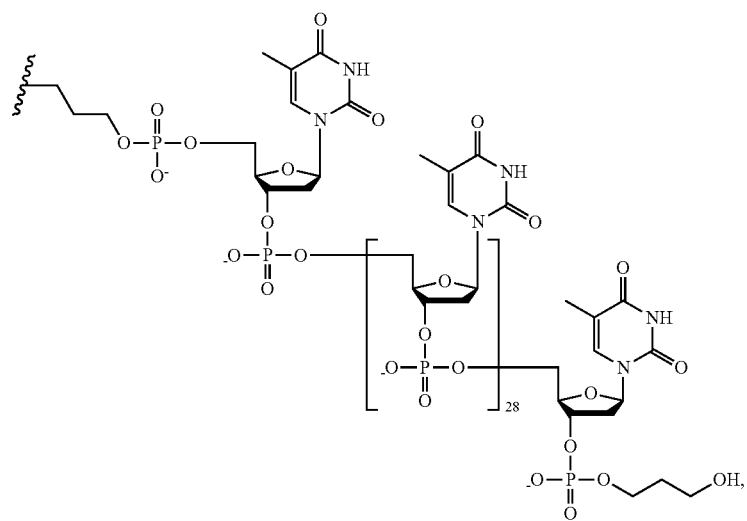
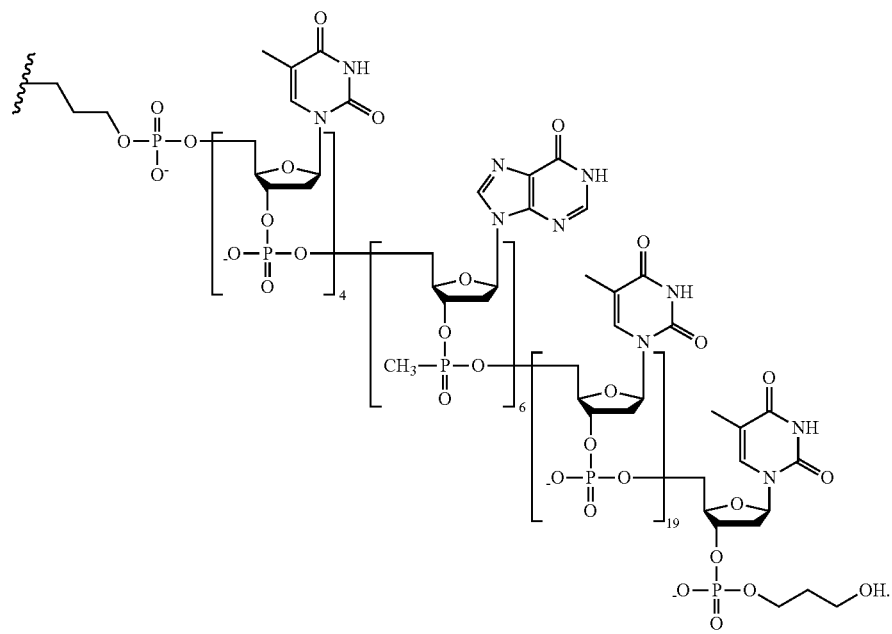

In embodiments, $R^{13}$ is
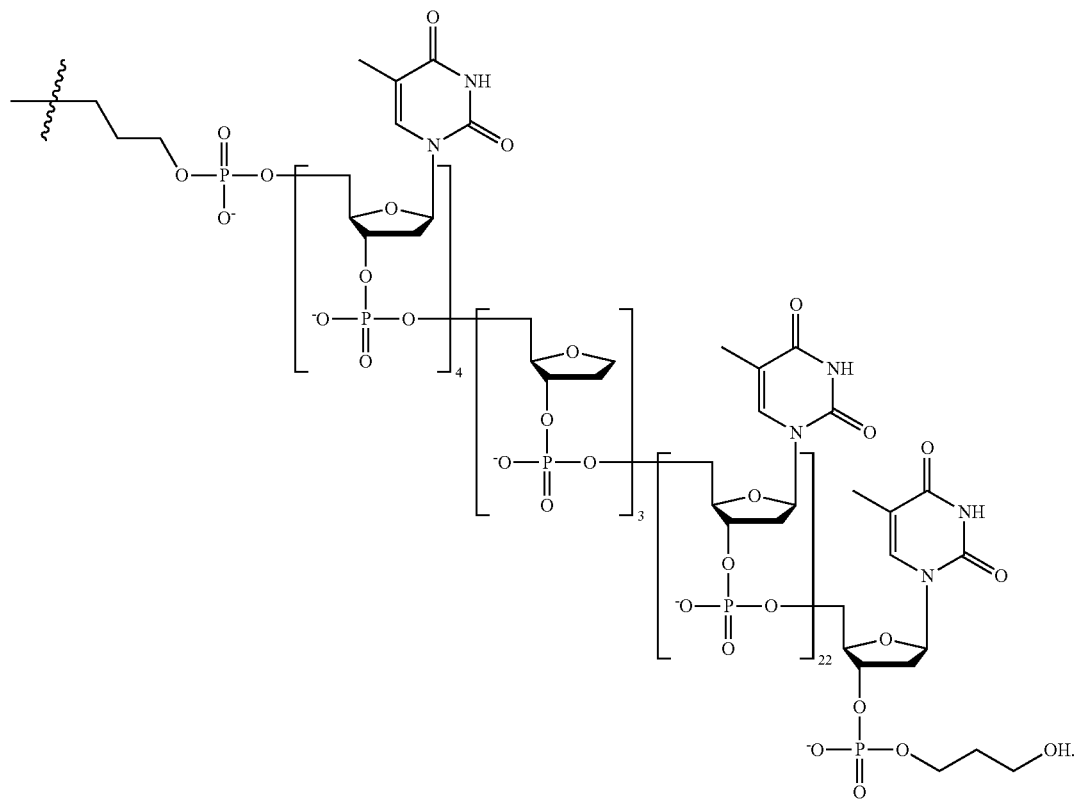
In embodiments, $R^{13}$ is
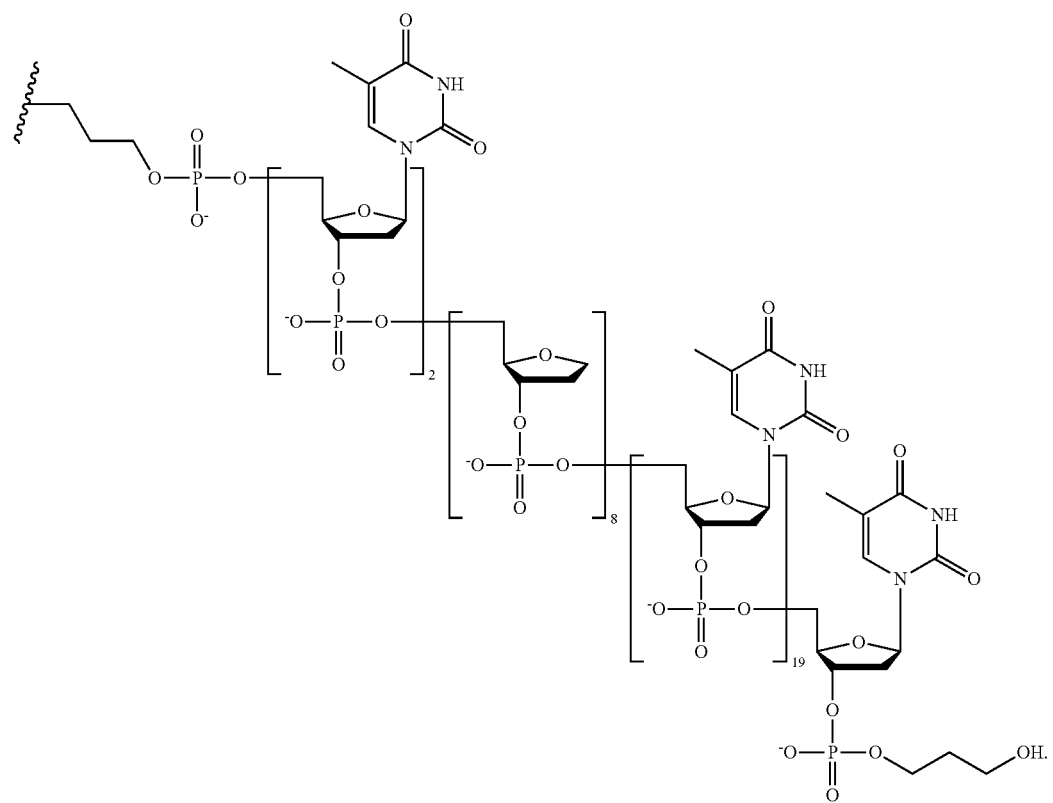

In embodiments, $R^{13}$ is
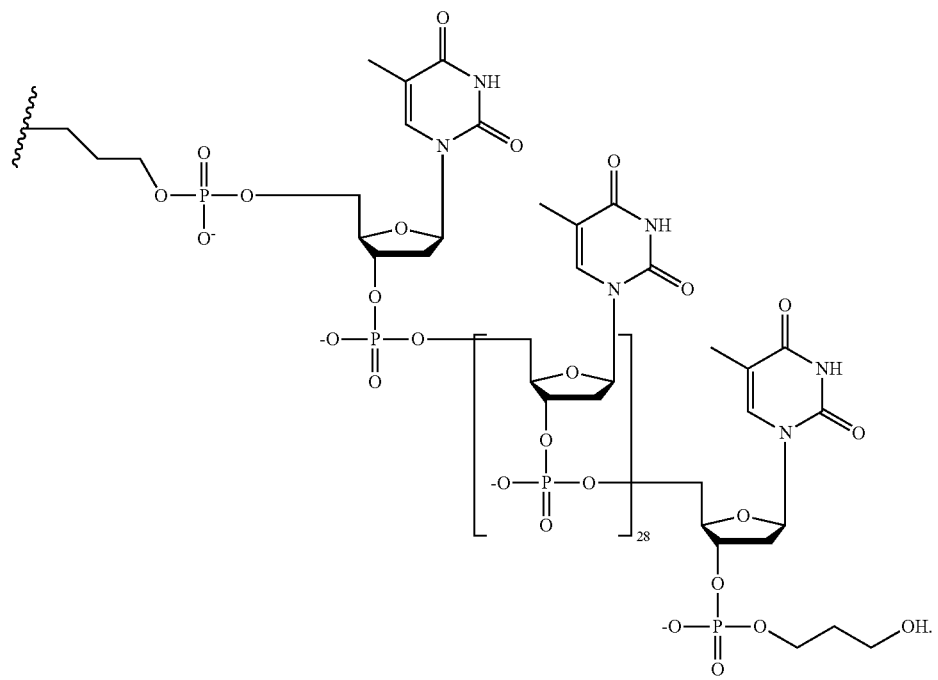
In embodiments, $R^{13}$ is
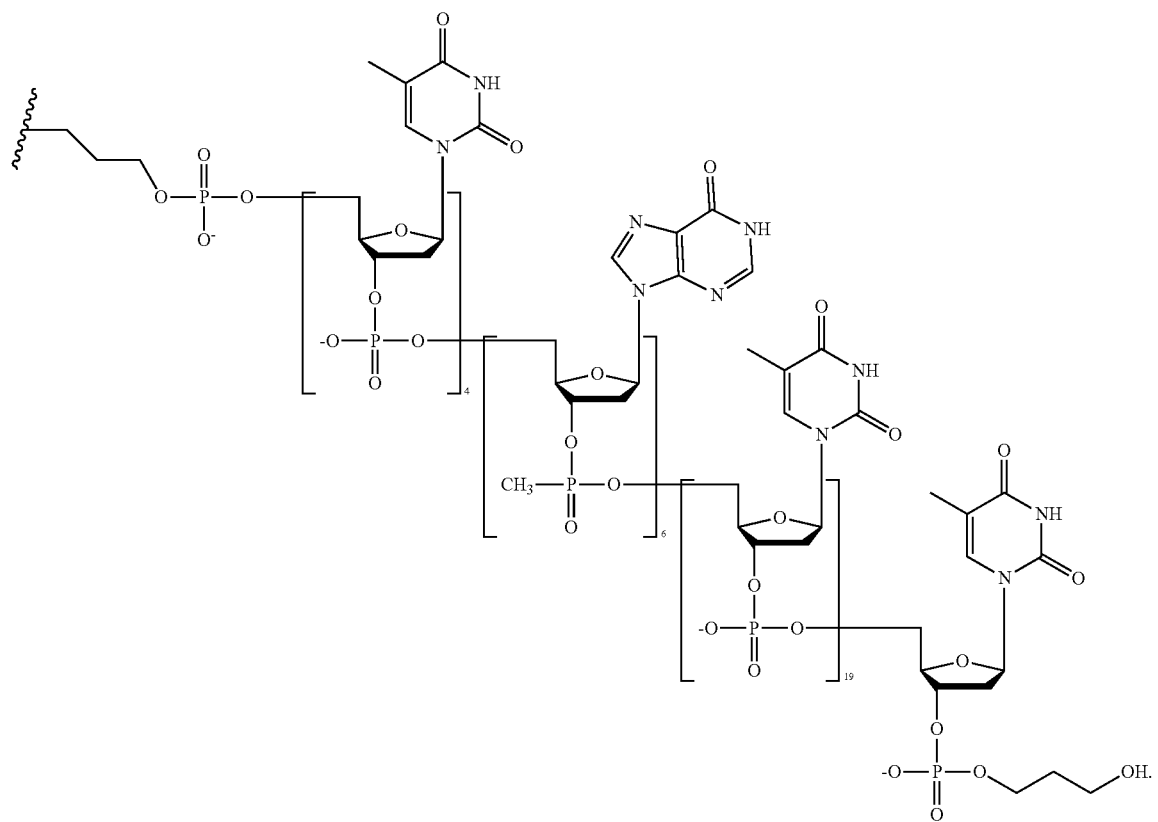

In embodiments, $R^{13}$ is
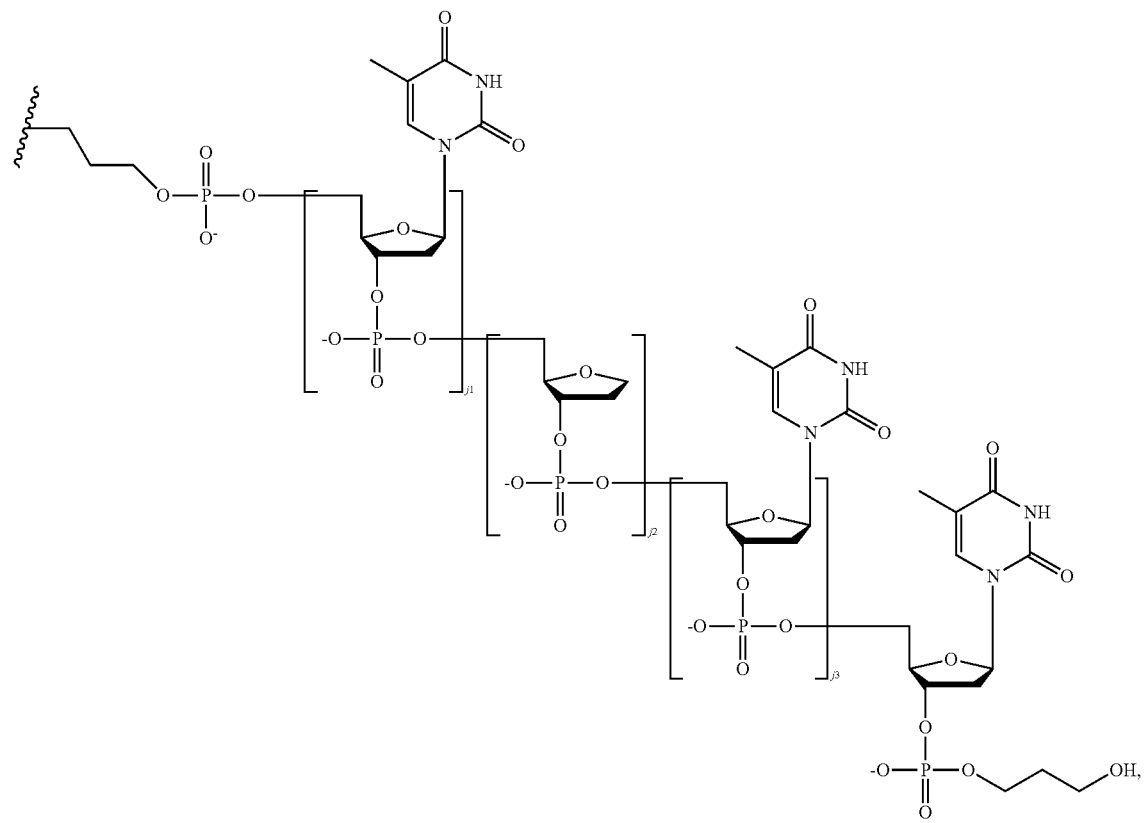
wherein j1, j2, and j3 are independently an integer from 0 to 30.

In embodiments, $R^{13}$ is
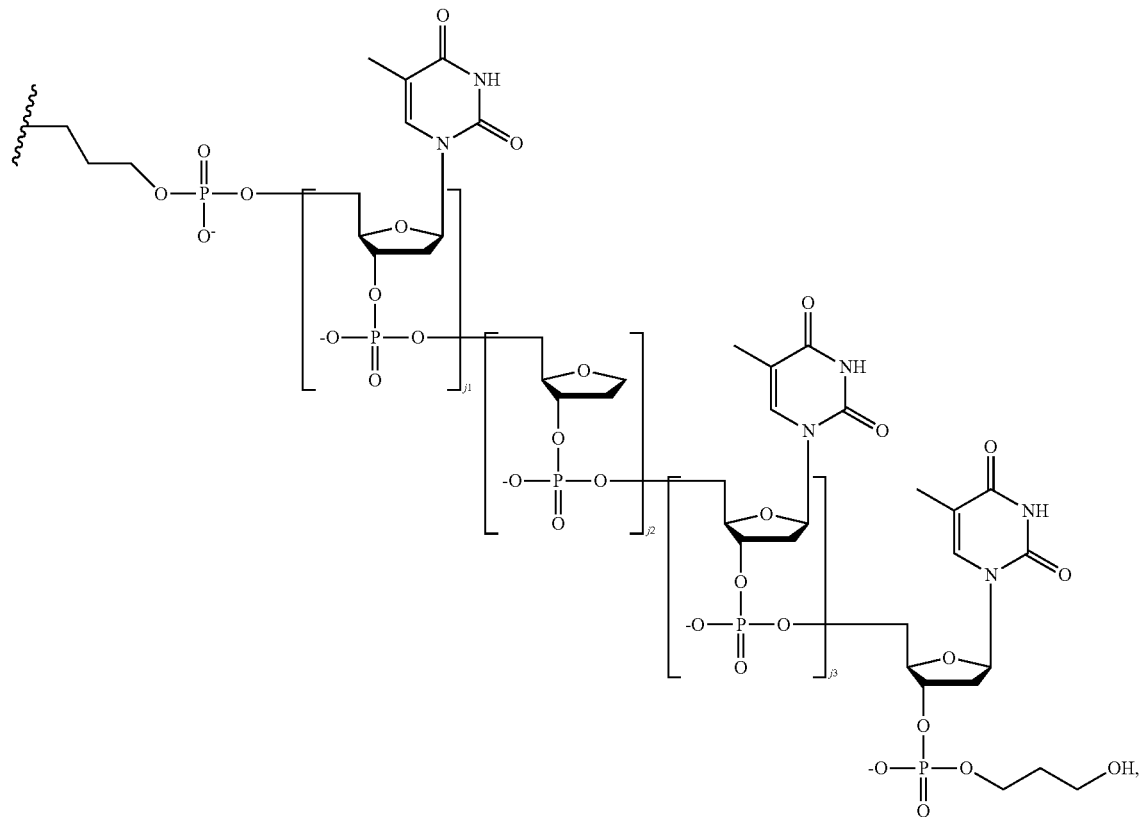
wherein j1, j2, and j3 are independently an interger from 0 to 30.
In embodiments, $R^{13}$ is:
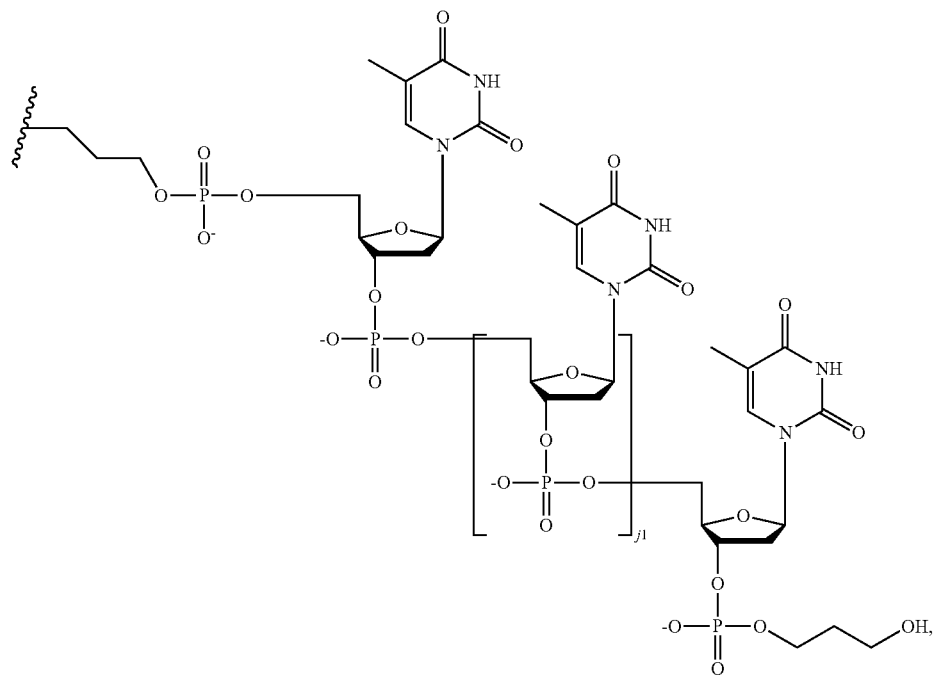
wherein j1 is an integer from 0 to 30.

In embodiments, $R^{13}$ is

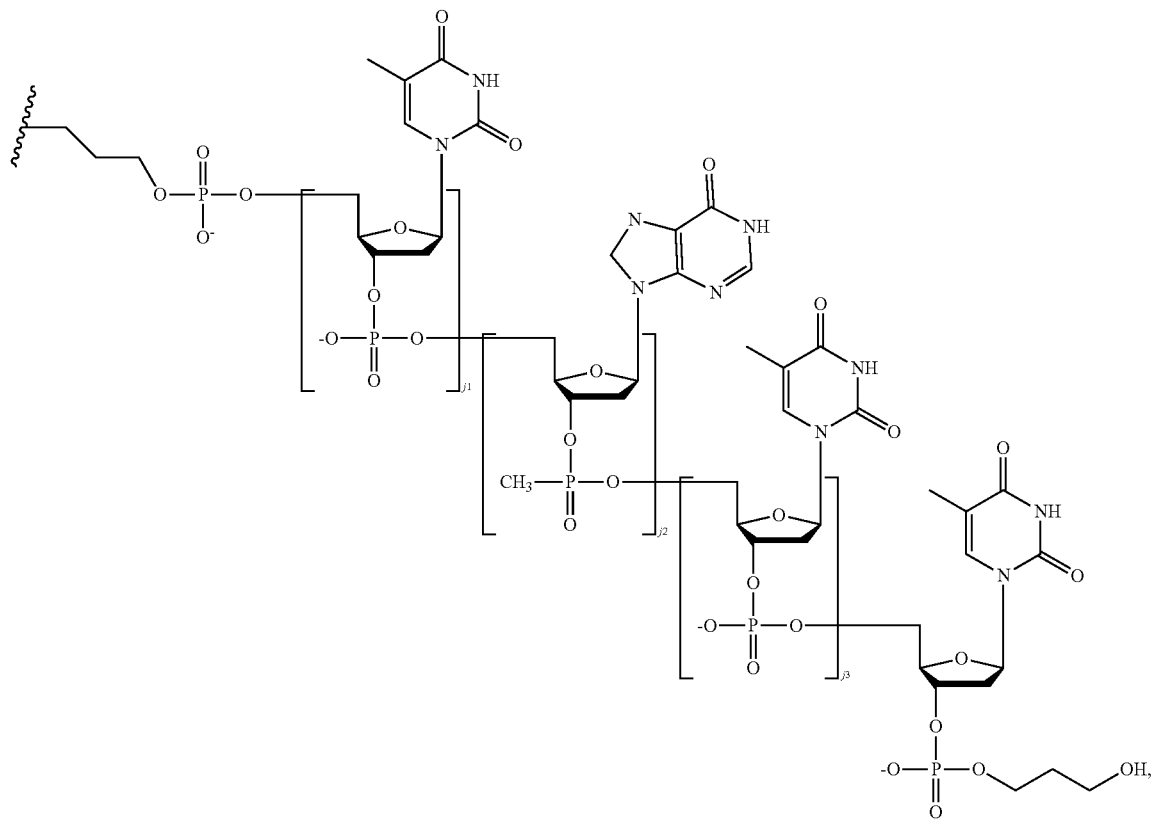

wherein j1, j2, and j3 are independently an integer from 0 to 30.

In embodiments, j1 is in an integer from 10 to 30. In embodiments, j1 is in an integer from 15 to 30. In embodiments, j2 is in an integer from 10 to 30. In embodiments, j2 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In embodiments, j2 is in an integer from 10 to 30. In embodiments, j2 is in an integer from 15 to 30. In embodiments, j2 is in an integer from 10 to 30. In embodiments, j2 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In embodiments, j3 is in an integer from 10 to 30. In embodiments, j3 is in an integer from 15 to 30. In embodiments, j3 is in an integer from 10 to 30. In embodiments, j3 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In embodiments, $X^3$ is independently —F. In embodiments, $X^3$ is independently —Cl. In embodiments, $X^3$ is independently —Br. In embodiments, $X^3$ is independently —I. In embodiments, $X^4$ is independently —F. In embodiments, $X^4$ is independently —Cl. In embodiments, $X^4$ is independently —Br. In embodiments, $X^4$ is independently —I. In embodiments, $X^5$ is independently —F. In embodiments, $X^5$ is independently —Cl. In embodiments, $X^5$ is independently —Br. In embodiments, $X^5$ is independently —I. In embodiments, $X^6$ is independently —F. In embodiments, $X^6$ is independently —Cl. In embodiments, $X^6$ is independently —Br. In embodiments, $X^6$ is independently —I. In embodiments, $X^7$ is independently —F. In embodiments, $X^7$ is independently —Cl. In embodiments, $X^7$ is independently —Br. In embodiments, $X^7$ is independently —I. In embodiments, $X^{8C}$ is independently —F. In embodiments, $X^{8}c$ is independently —Cl. In embodiments, $X^{8C}$ is independently —Br. In embodiments, $X^{8C}$ is independently —I.

In embodiments, z is an integer from 0 to 20. In embodiments, z is an integer from 0 to 10. In embodiments, z is an integer from 0 to 15. In embodiments, z is an integer from 5 to 10. In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, z is 11. In embodiments, z is 12. In embodiments, z is 13. In embodiments, z is 14. In embodiments, z is 15. In embodiments, z is 16. In embodiments, z is 17. In embodiments, z is 18. In embodiments, z is 19. In embodiments, z is 20. In embodiments, m is an integer from 1 to 4. In embodiments, m is 1. In embodiments, m is 2. In embodiments, m is 3. In embodiments, m is 4.

In embodiments, $R^{12}$-$L^4$-$R^{13}$ has the formula:

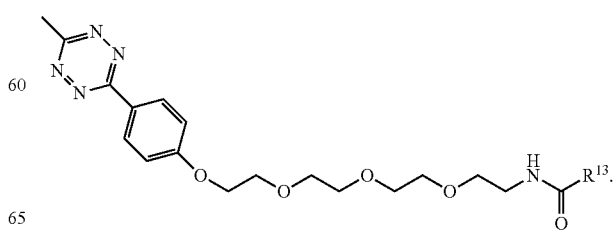

In embodiments, $R^{12}$-$L^4$-$R^3$ has the formula:
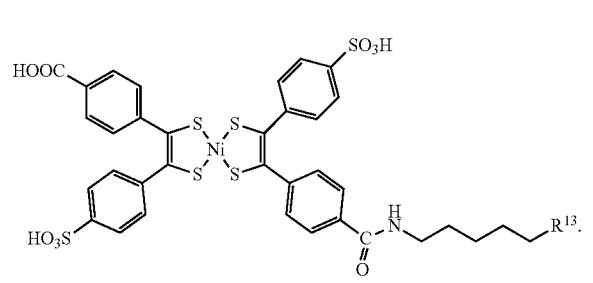
In embodiments, $R^{12}$-$L^4$-$R^{13}$ has the formula:
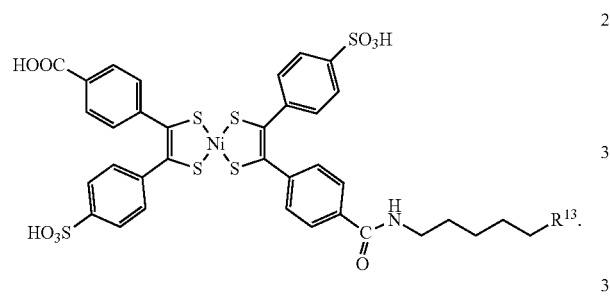
In embodiments, $R^{12}$-$L^4$-$R^{13}$ has the formula:
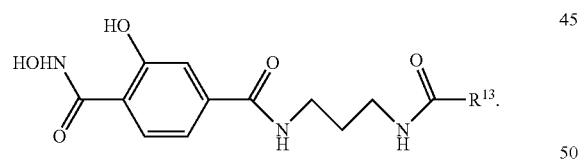
In embodiments, $R^{12}$-$L^4$-$R^{13}$ has the formula:
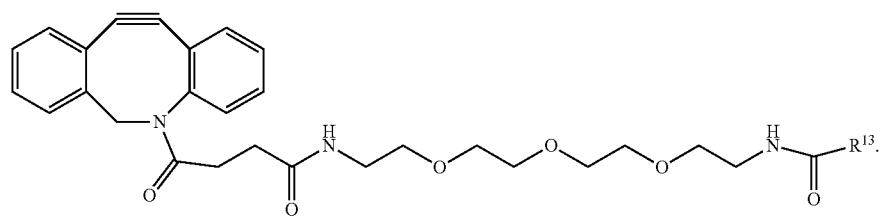

In embodiments, $R^{12}$-$L^4$-$R^{13}$ has the formula:
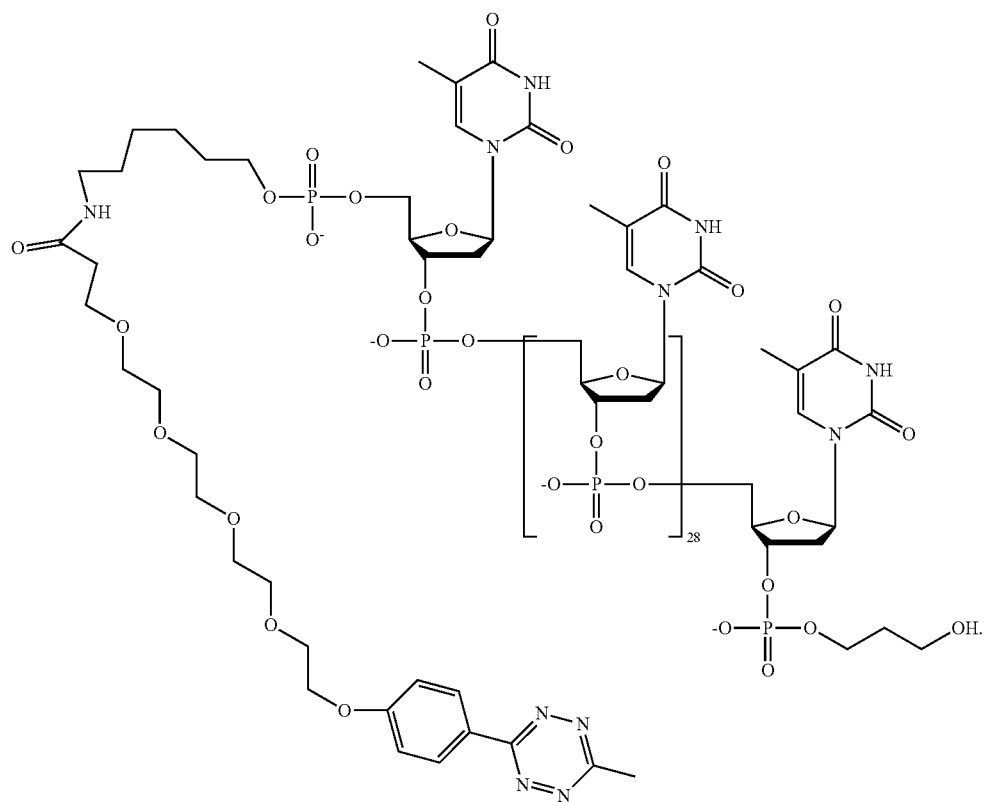
In embodiments, $R^{12}$-$L^4$-$R^{13}$ has the formula:
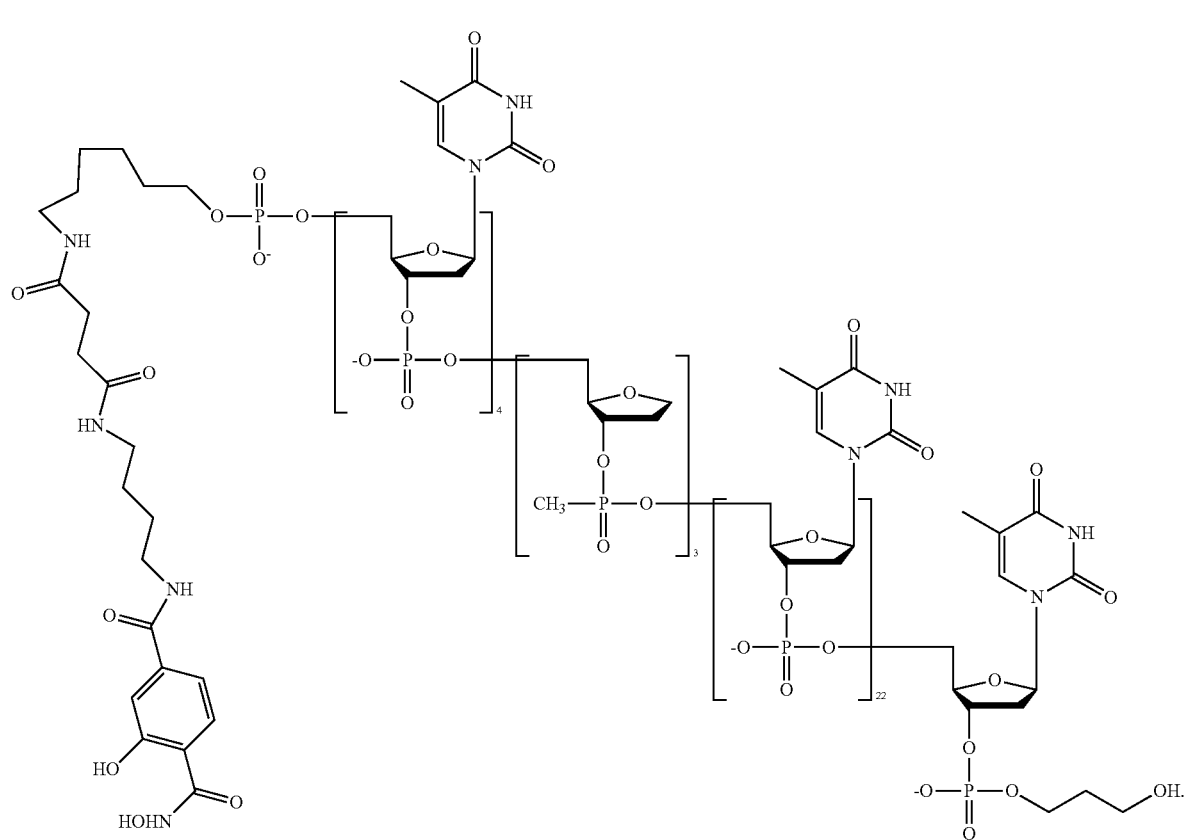

In embodiments, $R^{12}$-$L^4$-$R^{13}$ has the formula:
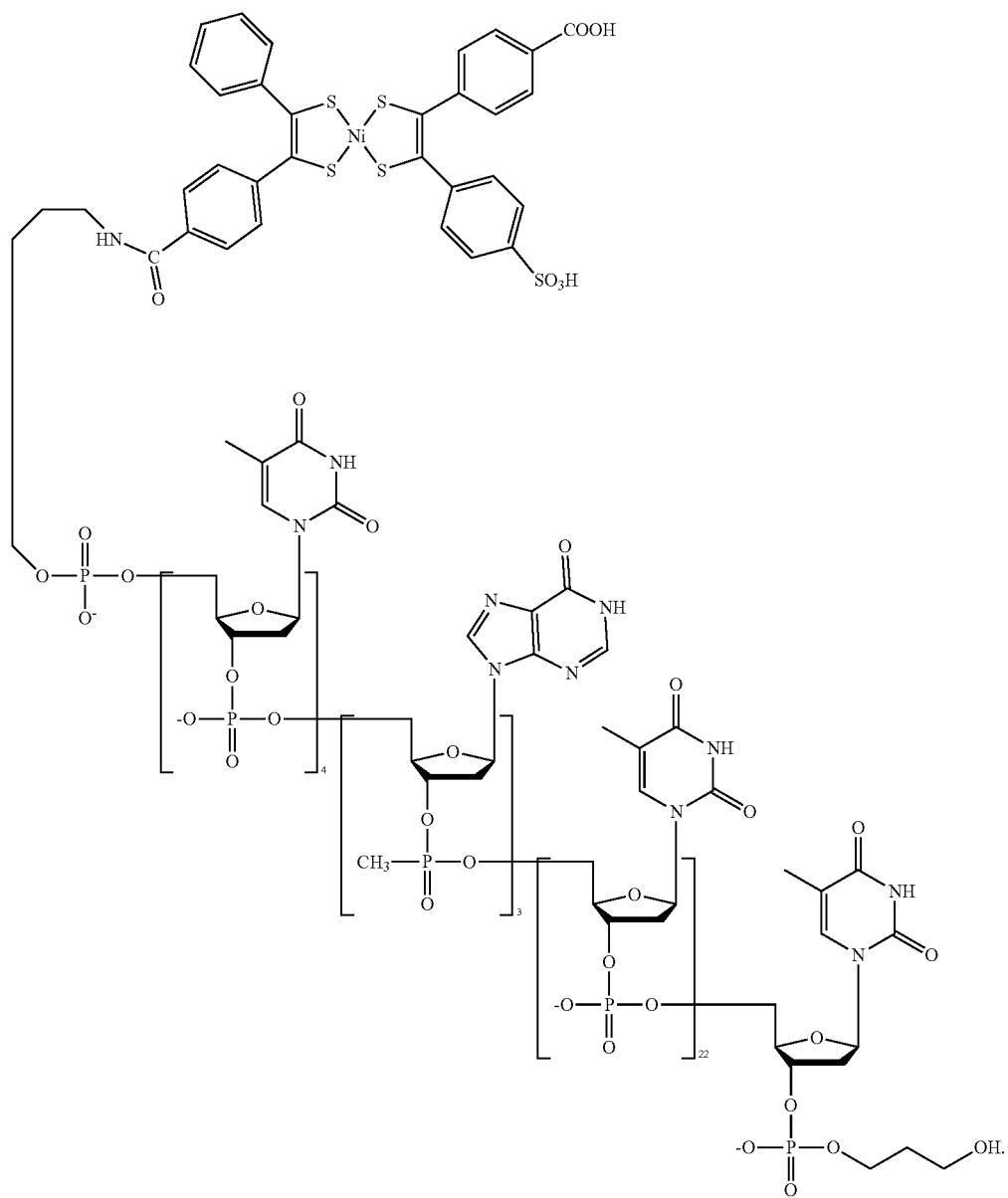

In embodiments, $R^{12}$-$L^4$-$R^{13}$ has the formula:
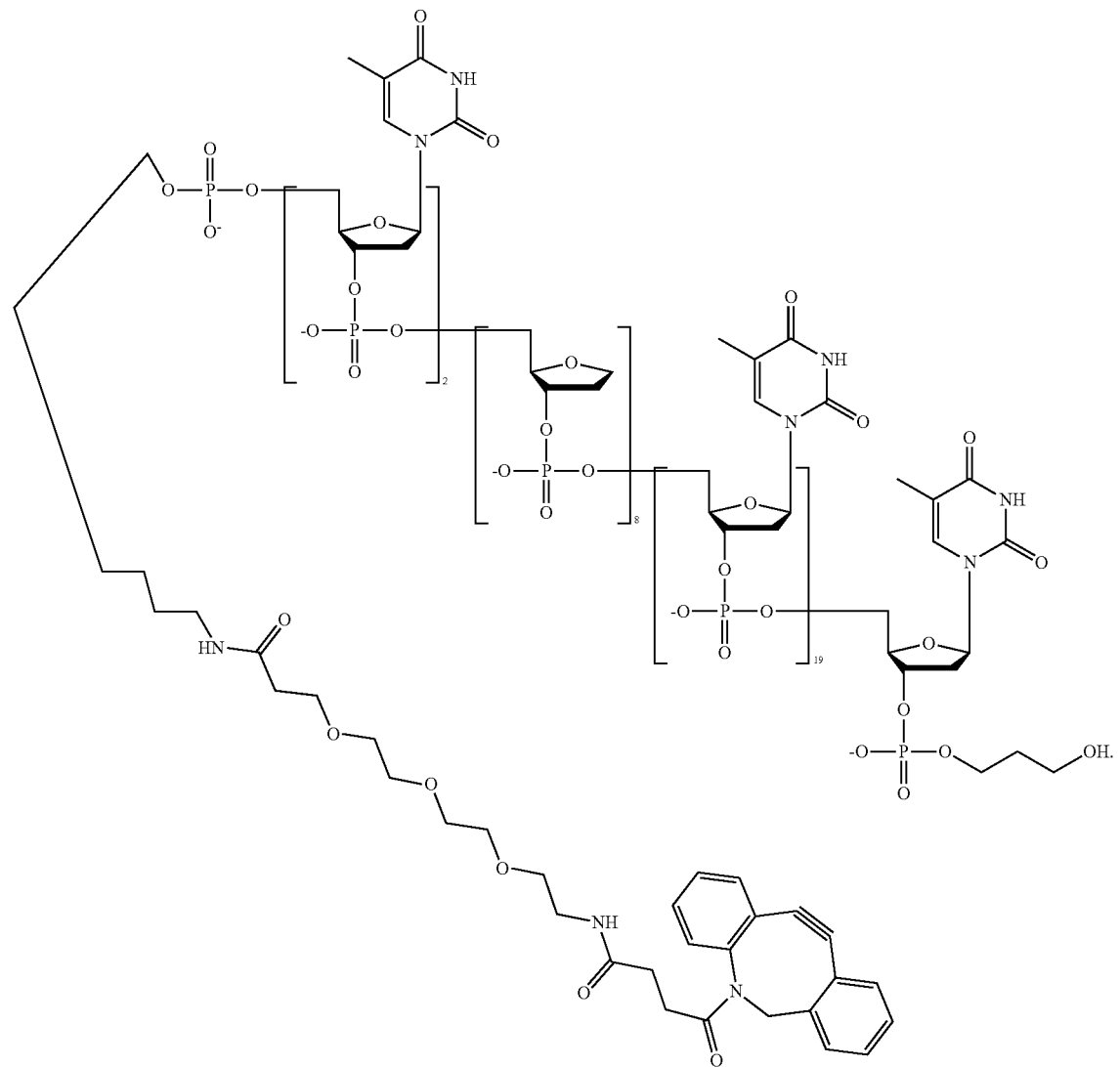
In embodiments, $R^{12}$-$L^4$-$R^{13}$ has the formula:
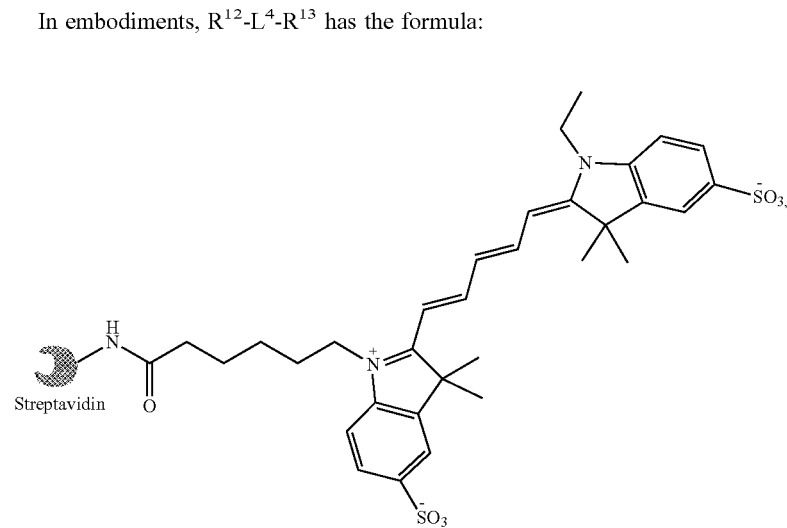

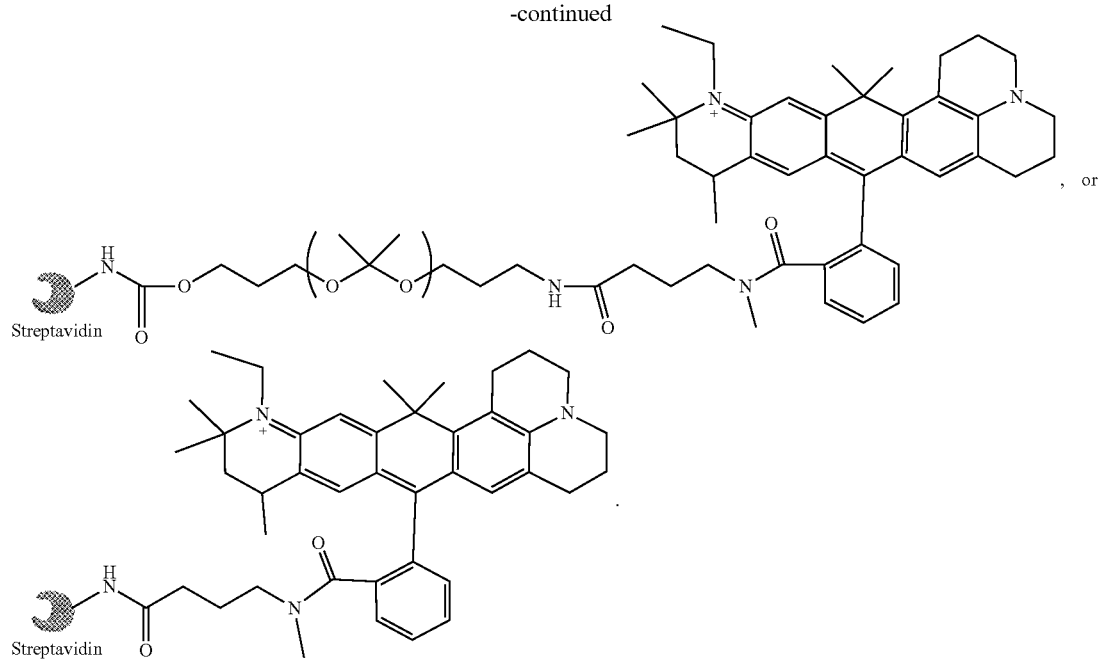
, or
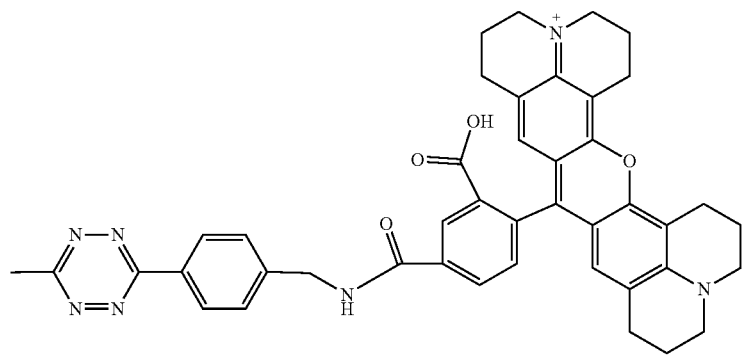
In embodiments, $R^{12}$-$L^4$-$R^{13}$ has the formula:
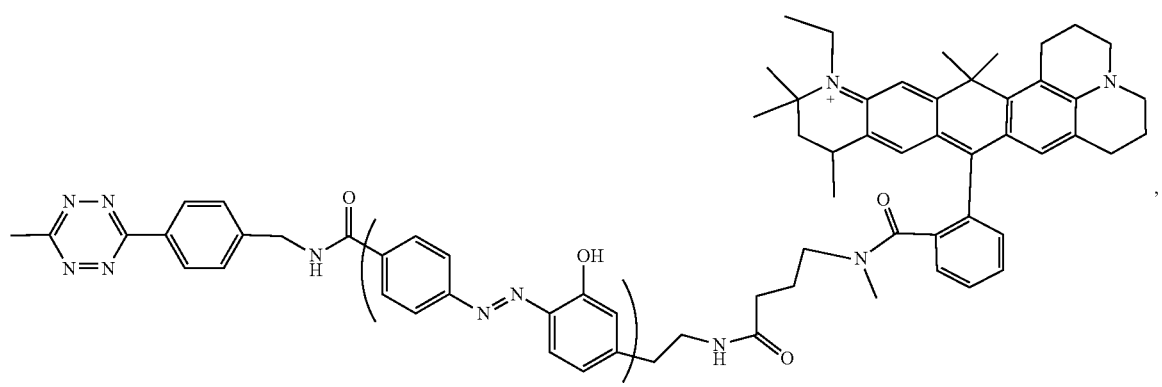

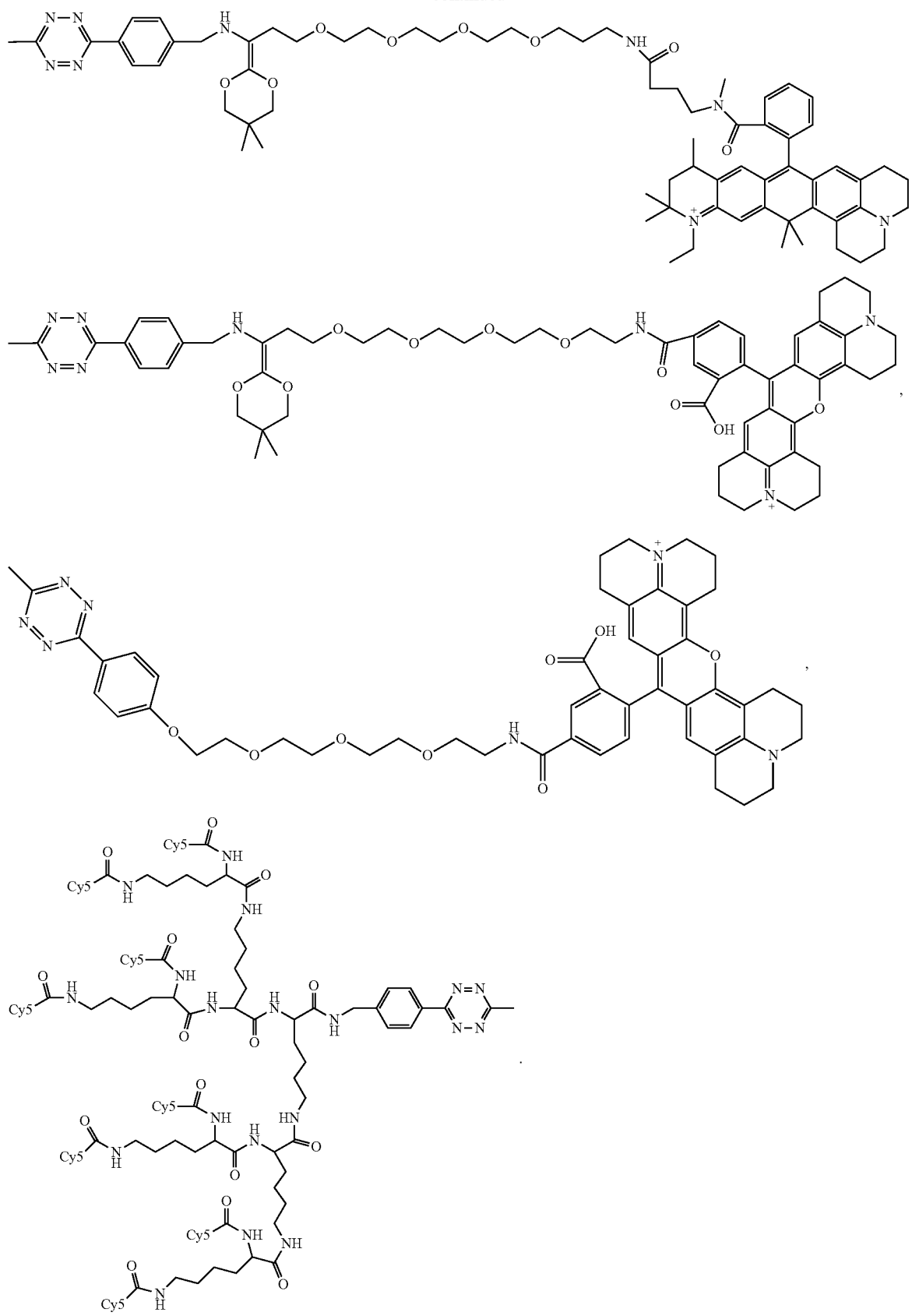

In embodiments, $R^{12}$-$L^4$-$R^{13}$ has the formula:
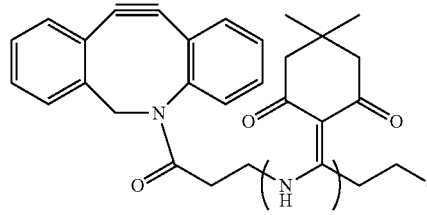 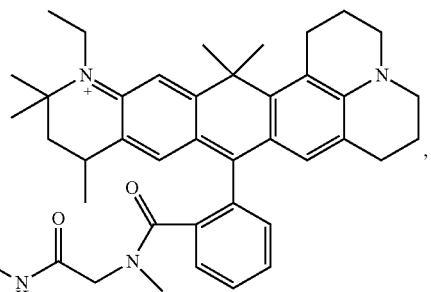,
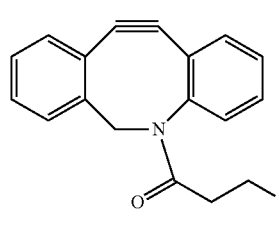 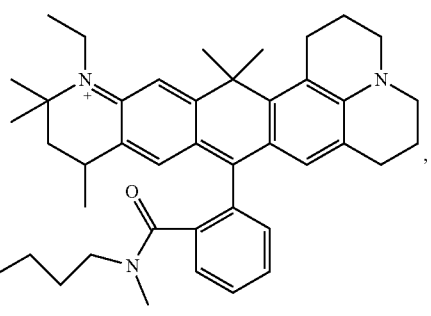,
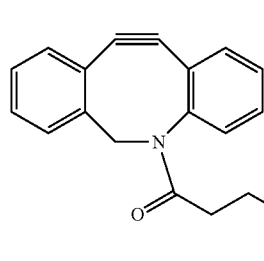 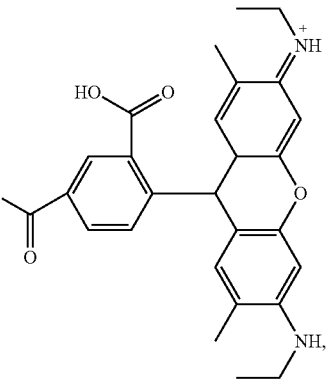,
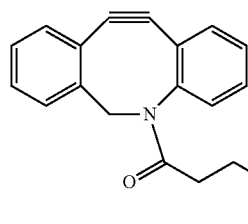 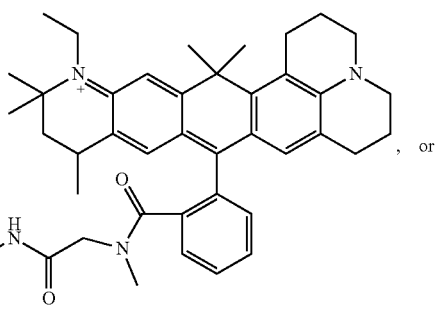, or

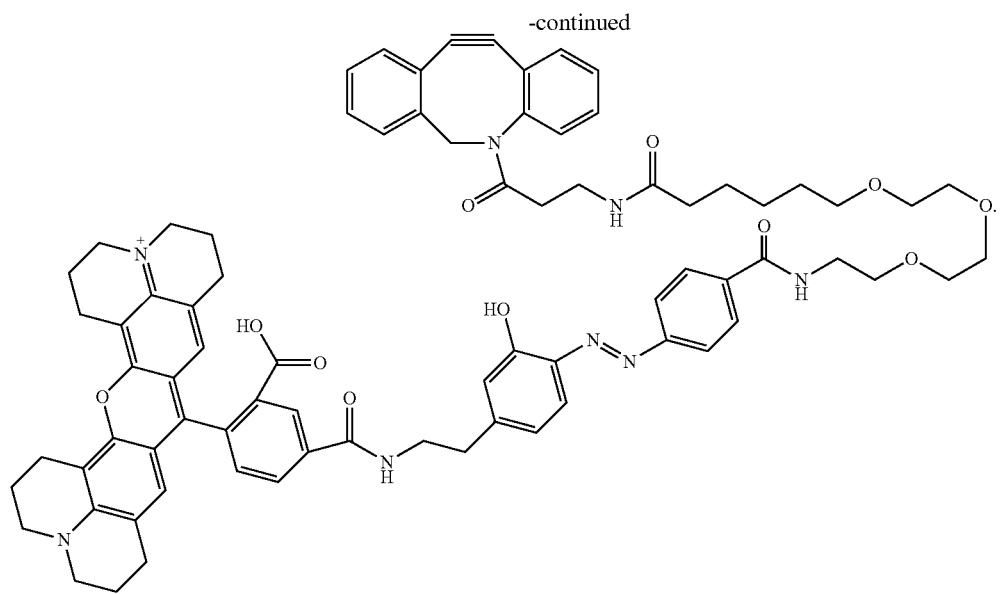
In embodiments, $R^{12}$-$L^4$-$R^{13}$ has the formula:
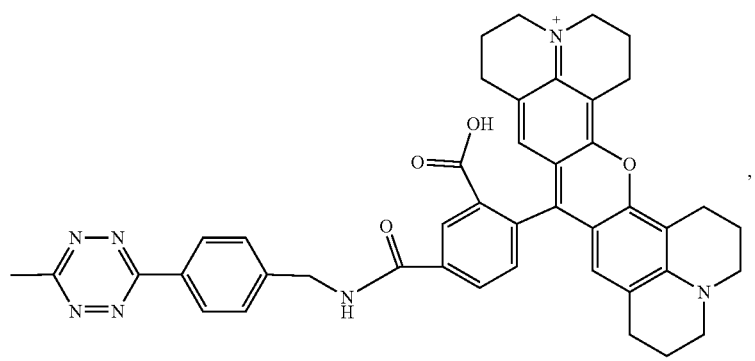
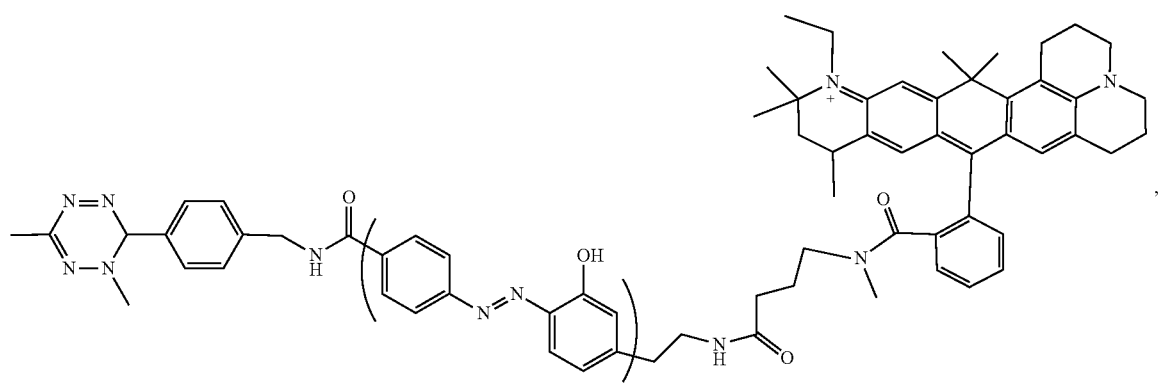

-continued
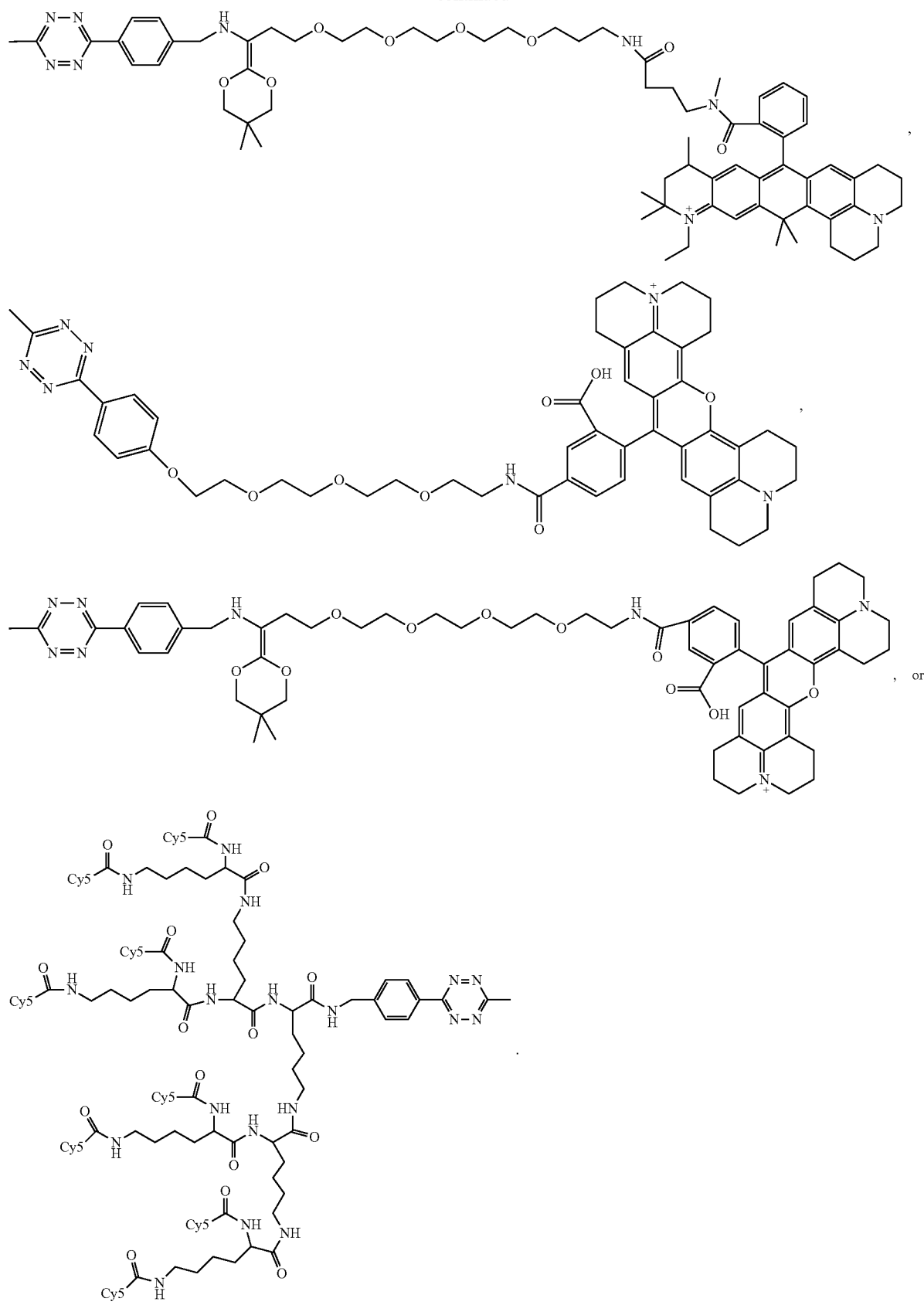

In embodiments, the nucleotide analogue has the formula:
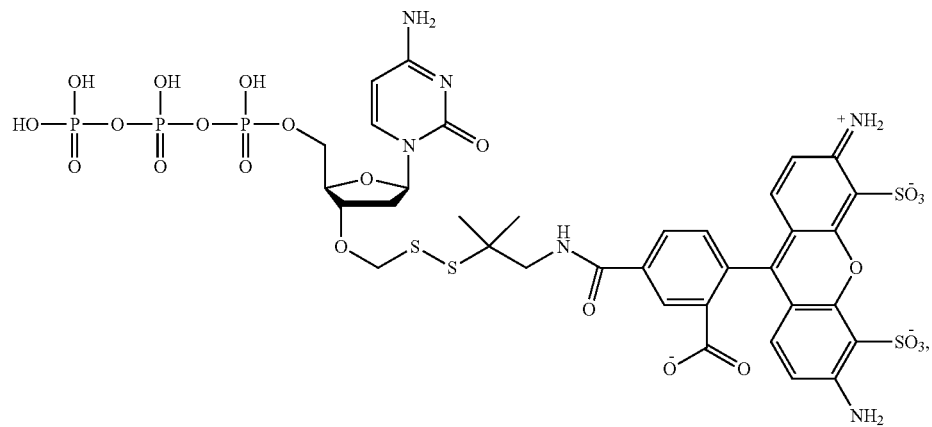
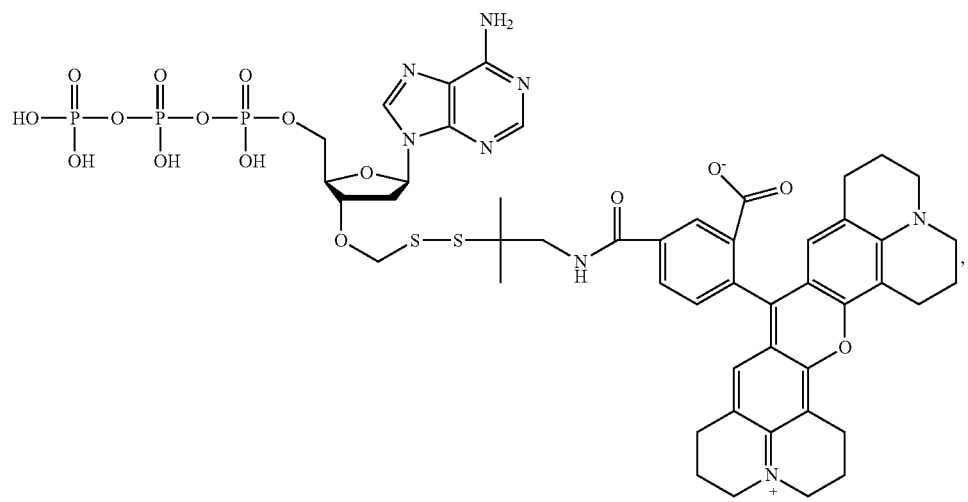
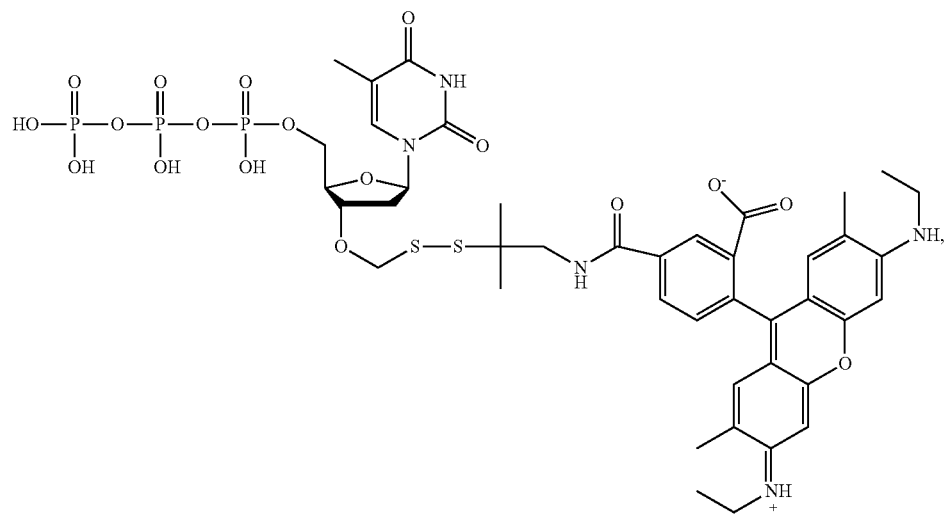

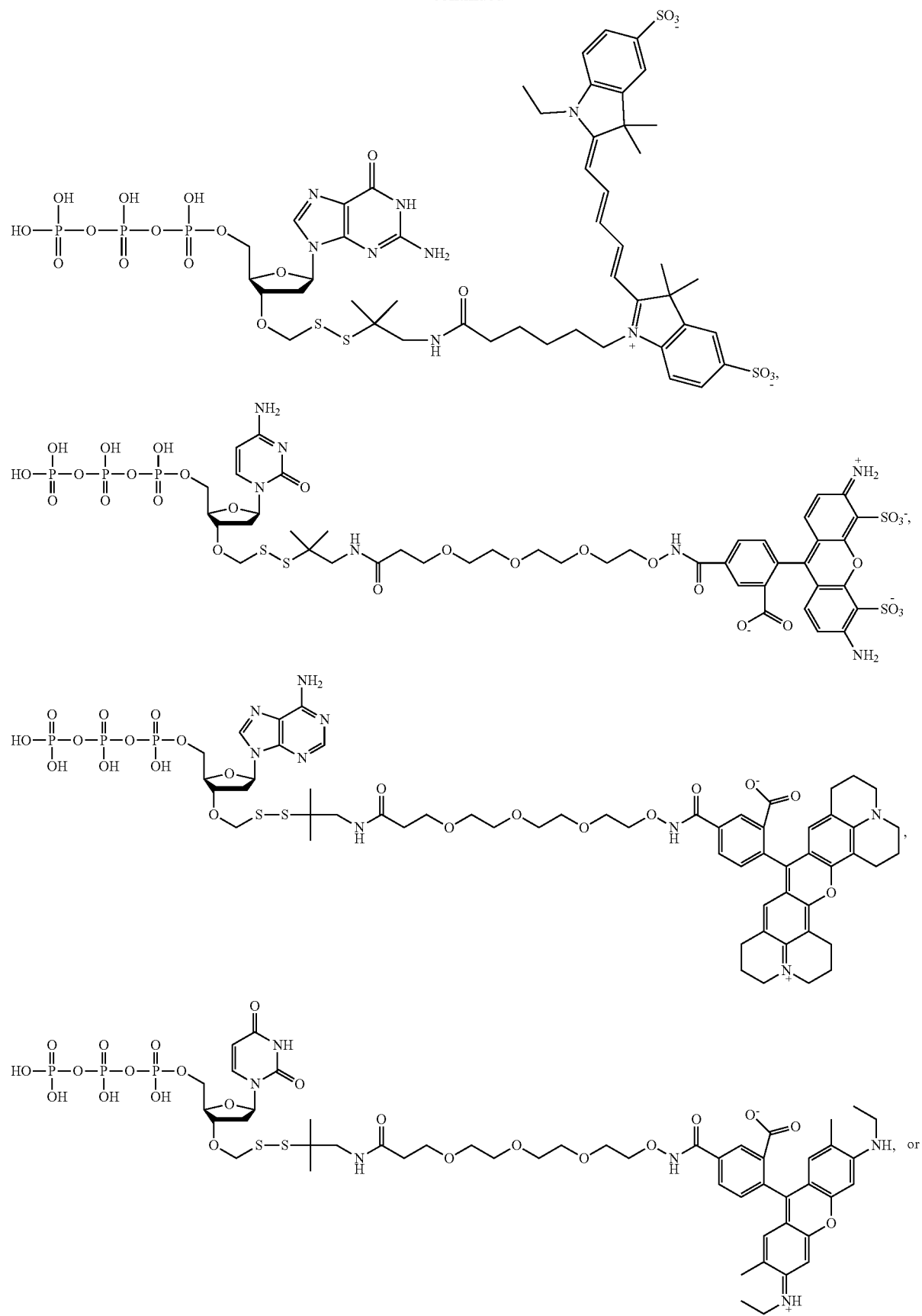

-continued

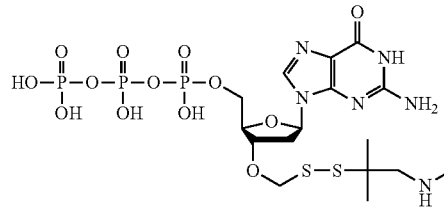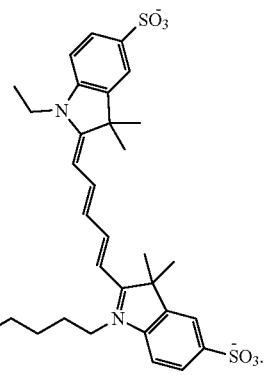

In an aspect is provided a compound of the formula: $R^{12z}—R^{14}$. $R^{12z}$ is a complementary anchor moiety reactive group. $R^{14}$ is $R^{15}$-substituted alkyl, $R^{15}$-substituted heteroalkyl, $R^{15}$-substituted cycloalkyl, $R^{15}$-substituted heterocycloalkyl, $R^{15}$-substituted aryl, or $R^{15}$-substituted heteroaryl. $R^{15}$ is independently $R^{16}$-substituted alkyl, $R^{16}$-substituted heteroalkyl, $R^{16}$-substituted cycloalkyl, $R^{16}$-substituted heterocycloalkyl, $R^{16}$-substituted aryl, $R^{16}$-substituted heteroaryl, or a detectable dye. $R^{16}$ is independently $R^{7}$-substituted alkyl, $R^{17}$-substituted heteroalkyl, $R^{17}$-substituted cycloalkyl, $R^{17}$-substituted heterocycloalkyl, $R^{17}$-substituted aryl, $R^{17}$-substituted heteroaryl, or a detectable dye. $R^{17}$ is independently $R^{18}$-substituted alkyl, $R^{18}$-substituted heteroalkyl, $R^{18}$-substituted cycloalkyl, $R^{18}$-substituted heterocycloalkyl, $R^{18}$-substituted aryl, $R^{18}$-substituted heteroaryl, or a detectable dye. $R^{18}$ is a detectable dye. In embodiments, $R^{14}$ is substituted with a plurality of $R^{5}$ moieties, $R^{15}$ is substituted with a plurality of $R^{16}$ moieties, and $R^{16}$ is substituted with a plurality of $R^{17}$ moieties.

In embodiments, $R^{12z}$ is

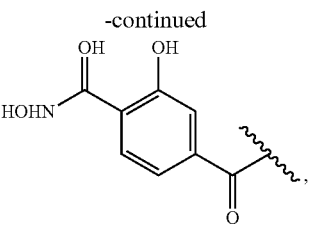

-continued

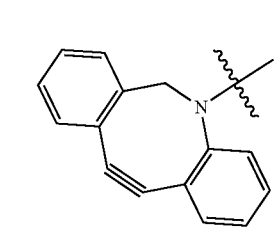

streptavidin moiety, or

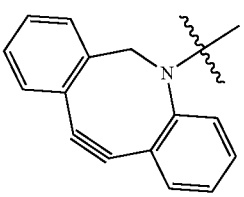

In embodiments, $R^{12z}$ is

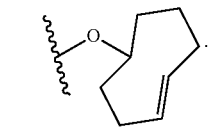

In embodiments, $R^{12z}$ is

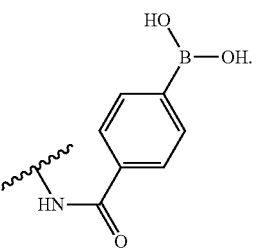 [SMILES: *NC(=O)c1ccc(B(O)O)cc1]

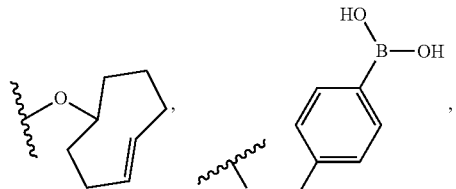

In embodiments, $R^{12z}$ is

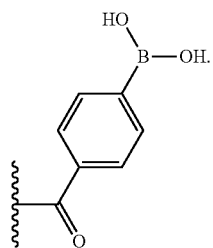 [SMILES: *C(=O)c1ccc(B(O)O)cc1]

In embodiments, $R^{12z}$ is

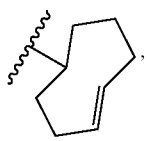 [SMILES: *C1CC/C=C/CCC1]

In embodiments, $R^{12z}$ is

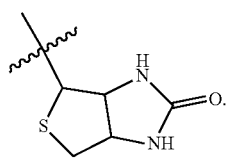 [SMILES: *C1SCC2NC(=O)NC21]

In embodiments, $R^{12z}$ is

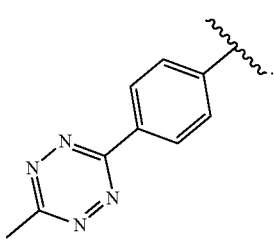 [SMILES: *c1ccc(-c2nnc(C)nn2)cc1]

In embodiments, $R^{12z}$ is

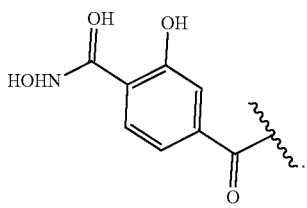

In embodiments, $R^{12z}$ is a streptavidin moiety. In embodiments, $R^{12z}$ is

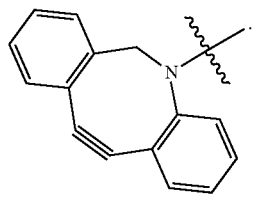 [SMILES: *N1Cc2ccccc2C#Cc2ccccc21]

In embodiments, the detectable dye is a fluorescent dye. In embodiments, the detectable dye includes a fluorescence resonance energy transfer donor fluorescent dye. In embodiments, the detectable dye includes a fluorescence resonance energy transfer acceptor fluorescent dye. In embodiments, the detectable dye includes a fluorescence resonance energy transfer donor and acceptor fluorescent dye pair connected by a linker. In embodiments, the detectable dye includes a fluorescence resonance energy transfer donor and acceptor fluorescent dye pair connected by a linker and separated by 0.1 nm to 10 nm.

In embodiments, the detectable dye is

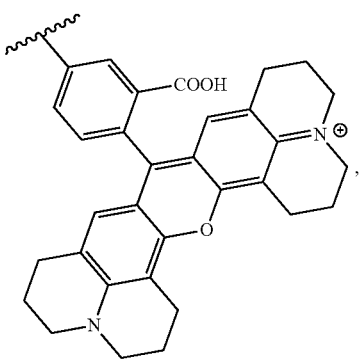

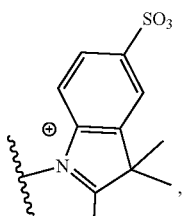

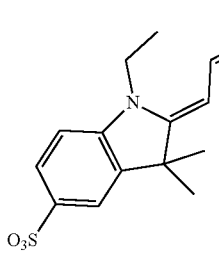

221
-continued
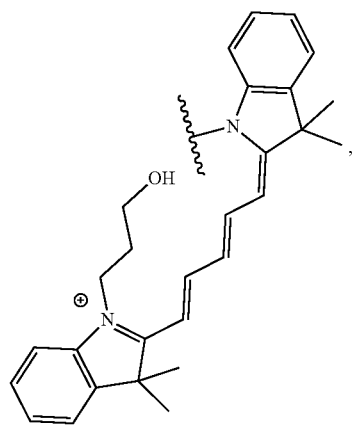
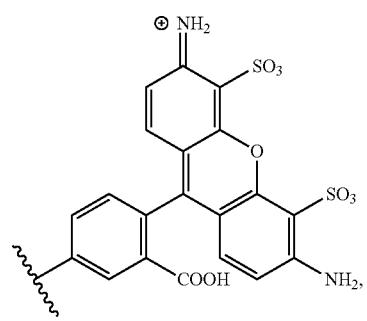
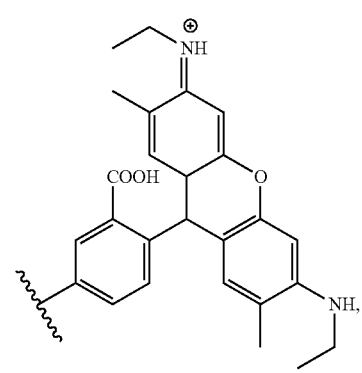
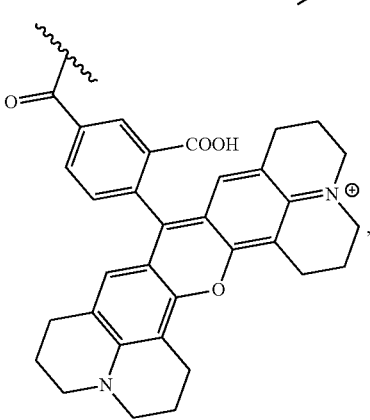
222
-continued
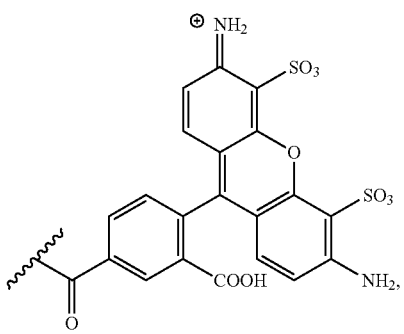
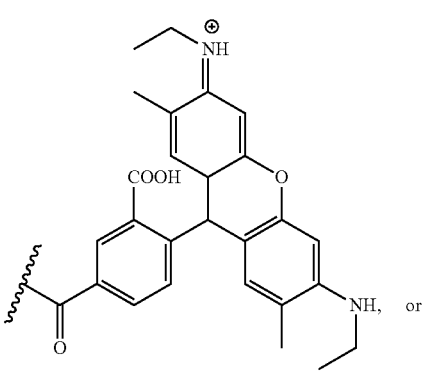
or
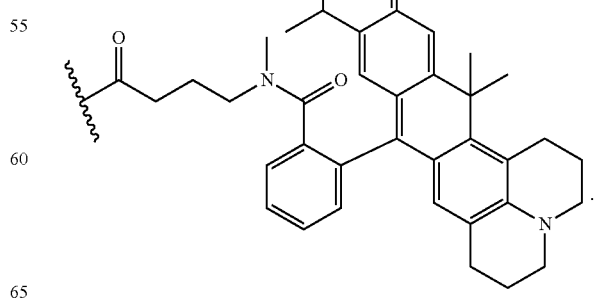

In embodiments, the compound has the formula:
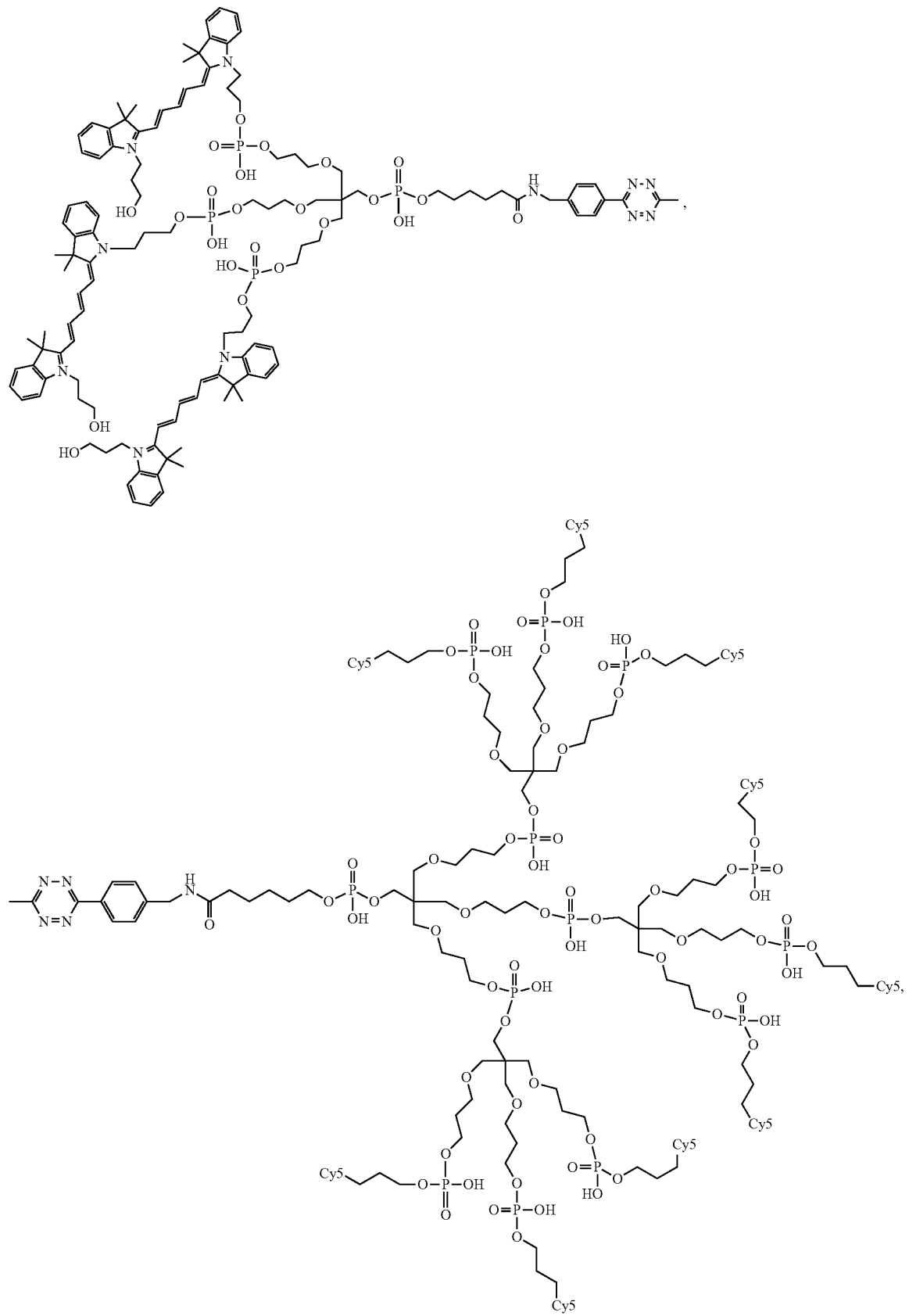

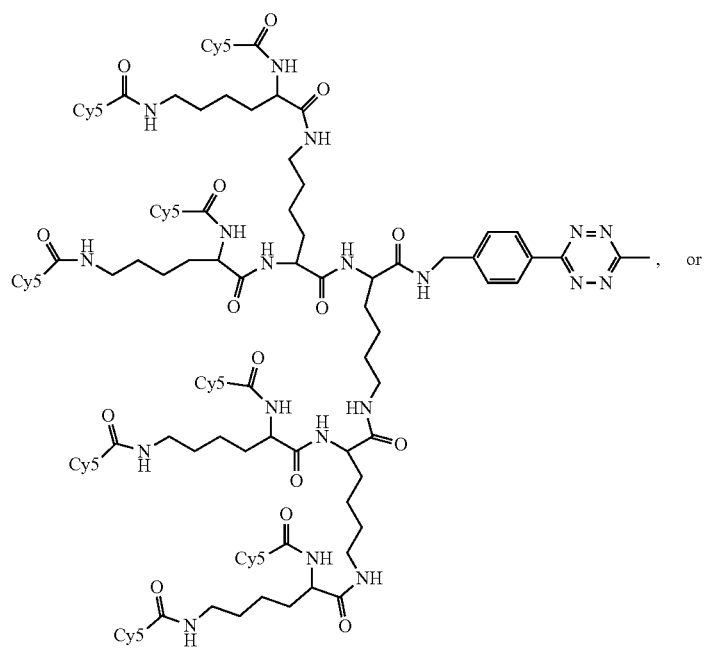
, or
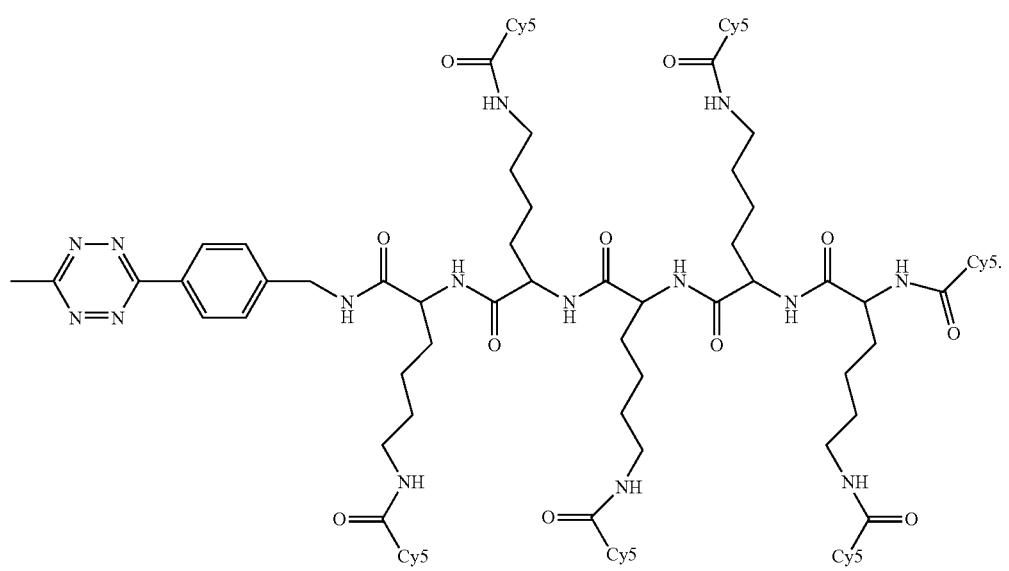

In embodiments, the compound has the formula:
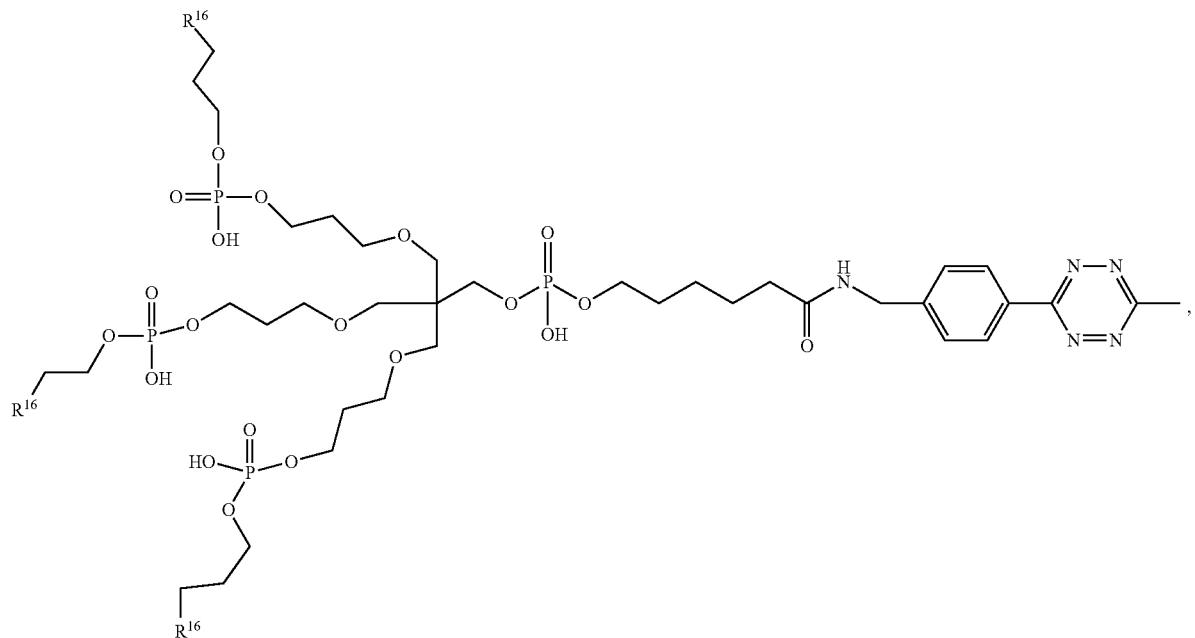
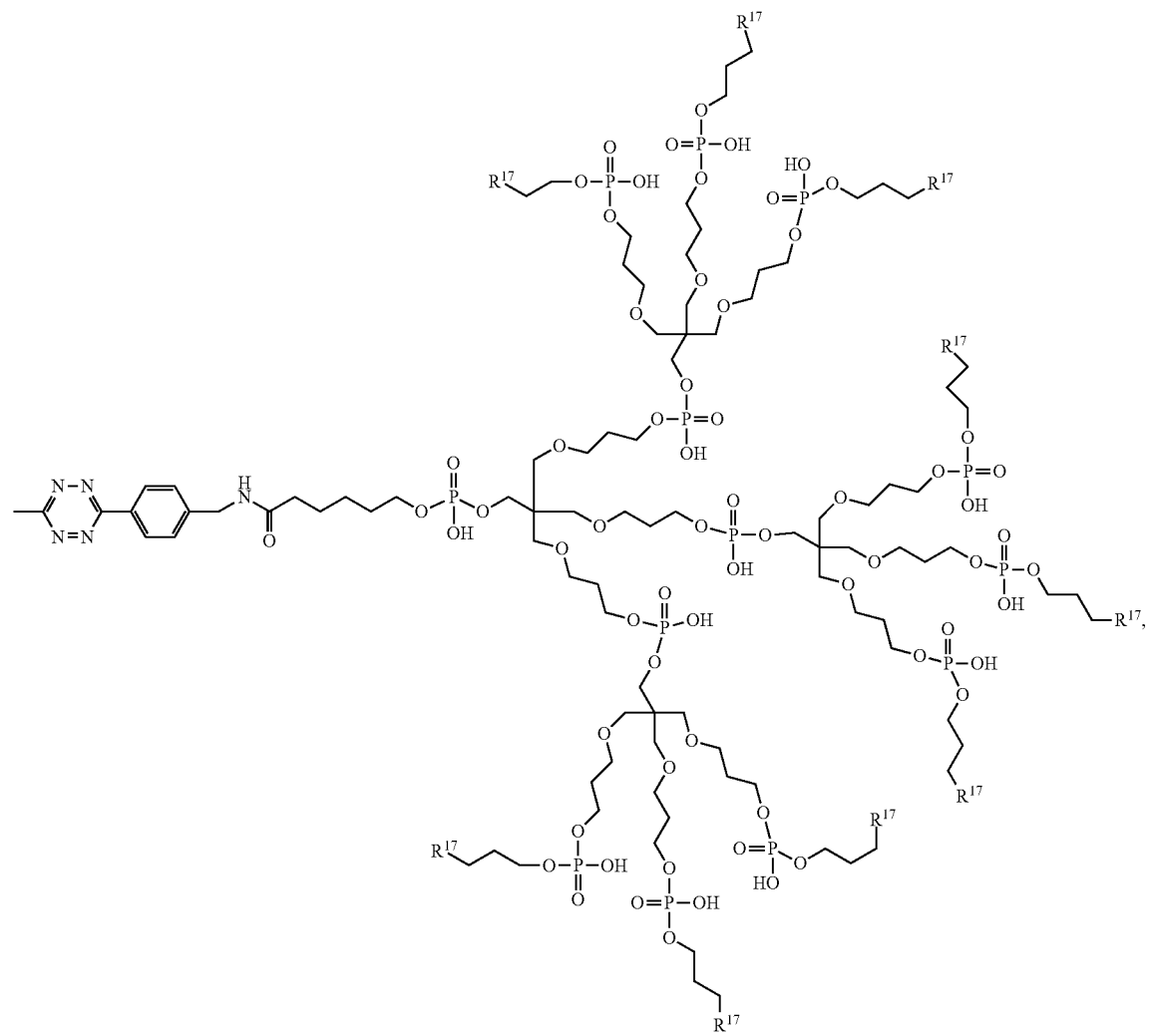

-continued
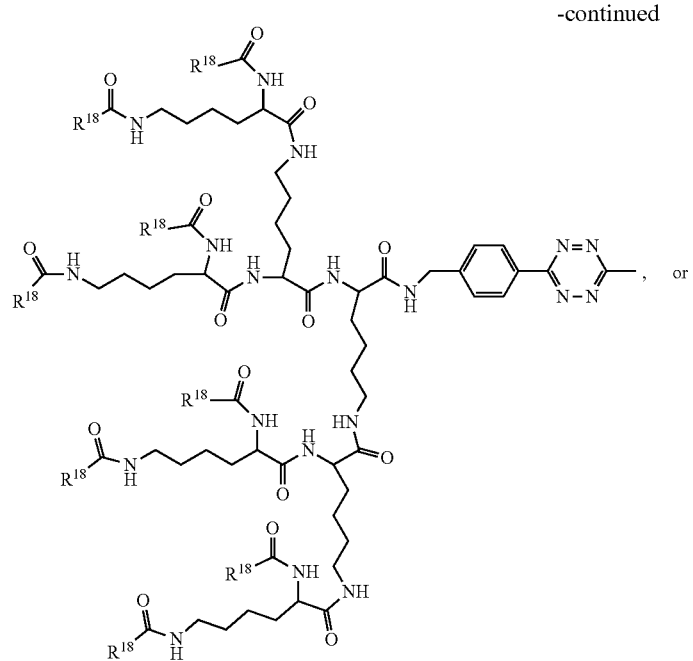
, or
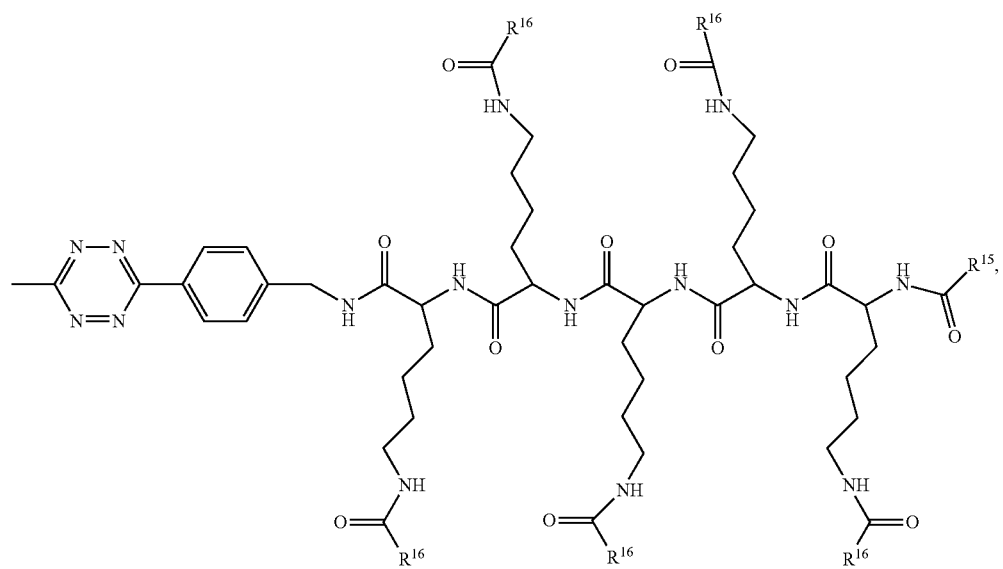
wherein $R^{12z}$, is as described herein.

In embodiments, $R^{13}$ is a modified oligonucleotide, peptide, PEG, carbohydrate or a combination thereof.

In embodiments, the nucleotide analogue has the formula:

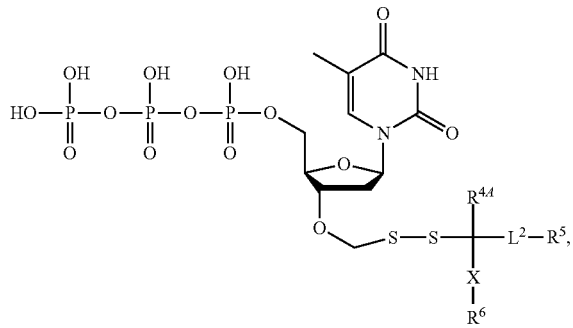

wherein $R^{4A}$, $L^2$, $R^5$, and $R^6$ are as described herein.

In embodiments, the nucleotide analogue has the formula:

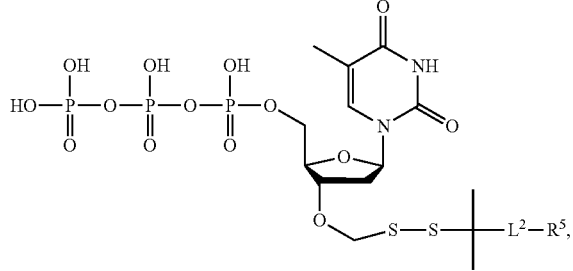

wherein $L^2$ and $R^5$ are as described herein.

In embodiments, the nucleotide analogue has the formula:

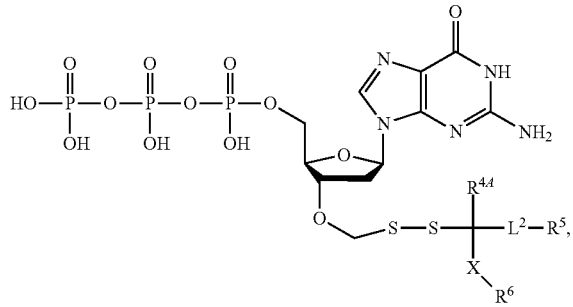

wherein $R^{4A}$, $L^2$, $R^5$, and $R^6$ are as described herein.

In embodiments, the nucleotide analogue has the formula:

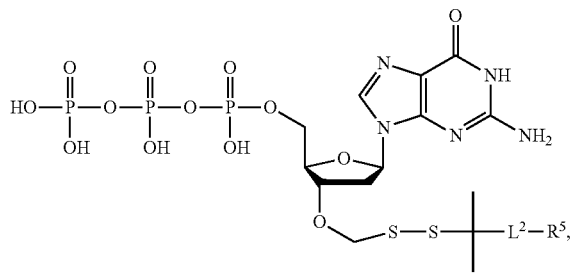

wherein $L^2$ and $R^5$ are as described herein.

In embodiments, the nucleotide analogue has the formula:

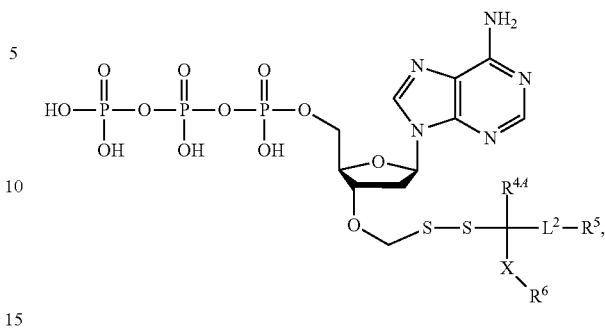

wherein $R^{4A}$, $L^2$, $R^5$, and $R^6$ are as described herein.

In embodiments, the nucleotide analogue has the formula:

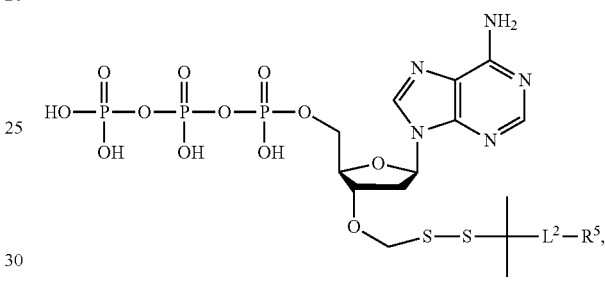

wherein $L^2$ and $R^5$ are as described herein.

In embodiments, the nucleotide analogue has the formula:

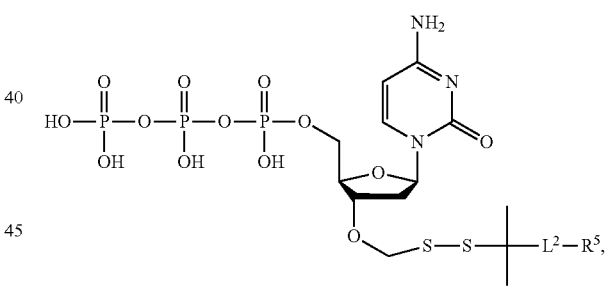

wherein $L^2$ and $R^5$ are as described herein.

In embodiments, the nucleotide analogue has the formula:

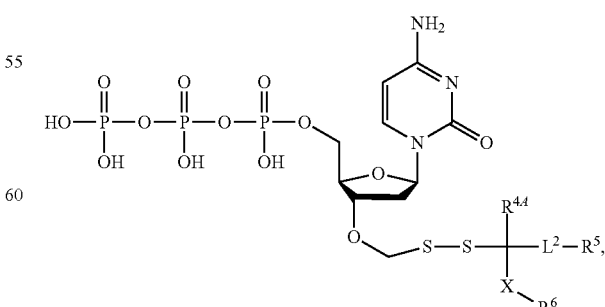

wherein $R^{4A}$, $L^2$, $R^5$, and $R^6$ are as described herein.

In embodiments, the nucleotide analogue has the formula:

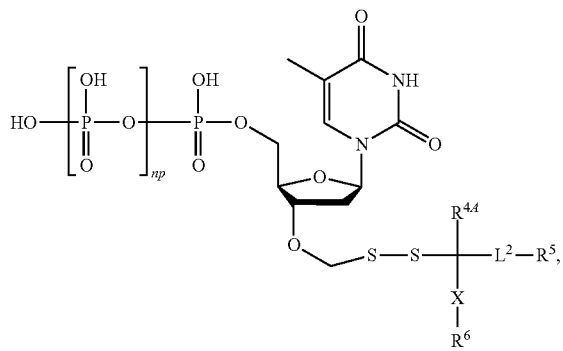

wherein np, $R^{4A}$, $L^2$, $R^5$, and $R^6$ are as described herein.

In embodiments, the nucleotide analogue has the formula:

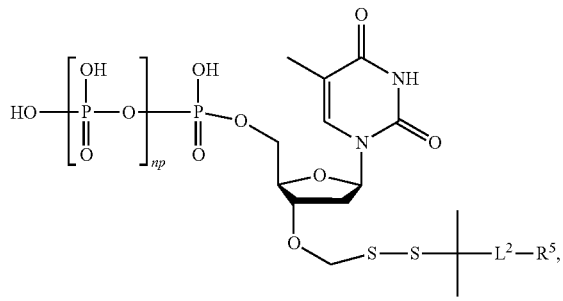

wherein np, $L^2$, and $R^5$ are as described herein.

In embodiments, the nucleotide analogue has the formula:

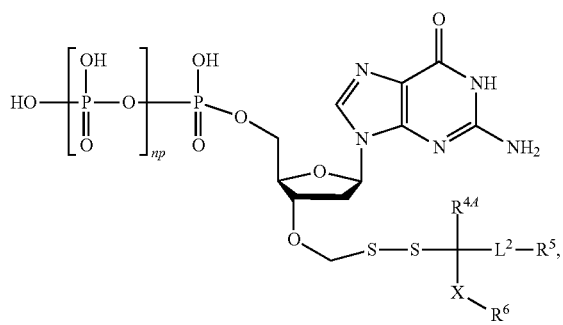

wherein np, $R^{4A}$, $L^2$, $R^5$, and $R^6$ are as described herein.

In embodiments, the nucleotide analogue has the formula:

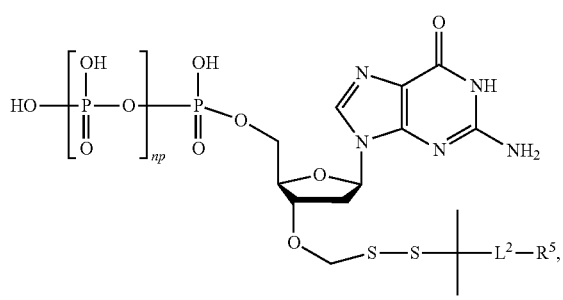

wherein np, $L^2$, and $R^5$ are as described herein.

In embodiments, the nucleotide analogue has the formula:

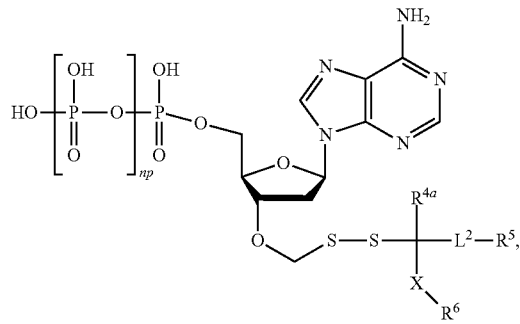

wherein np, $R^{4a}$, $L^2$, $R^5$, and $R^6$ are as described herein.

In embodiments, the nucleotide analogue has the formula:

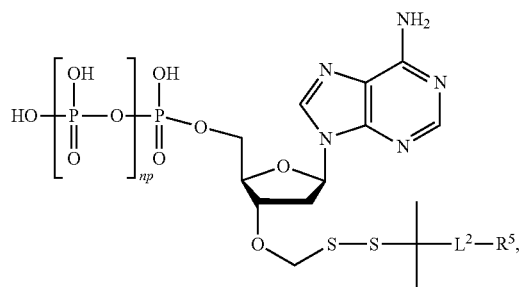

wherein np, $L^2$, and $R^5$ are as described herein.

In embodiments, the nucleotide analogue has the formula:

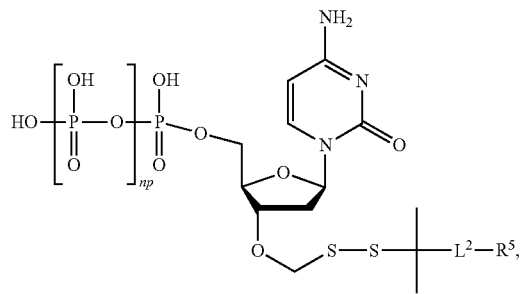

wherein np, $L^2$, and $R^5$ are as described herein.

In embodiments, the nucleotide analogue has the formula:

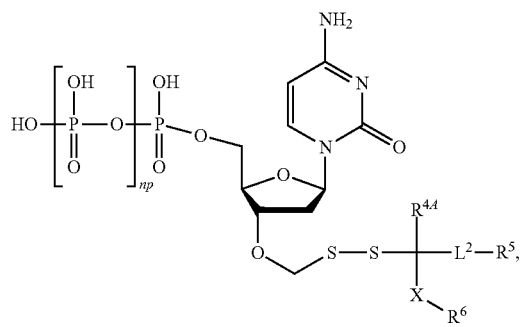

wherein np, $R^{4A}$, $L^2$, $R^5$, and $R^6$ are as described herein.

In embodiments, the nucleotide analogue has the formula:

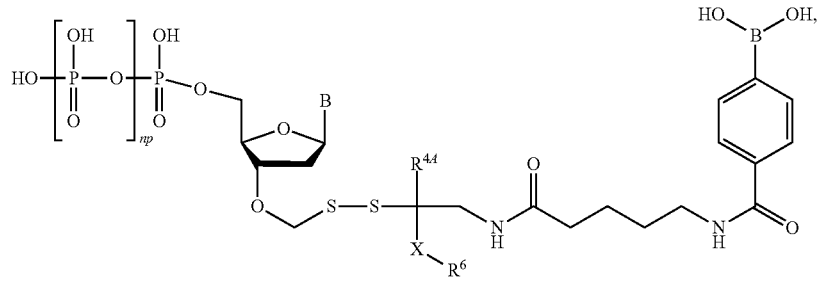

15 wherein np, B, $R^4$, X, and $R^6$ are as described herein.

In embodiments, the nucleotide analogue has the formula:

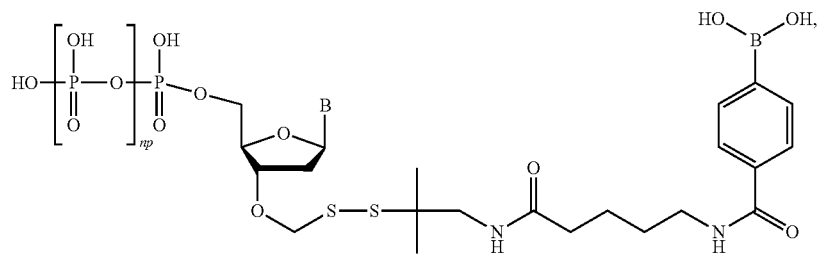

30 wherein np and B are as described herein.

In embodiments, the nucleotide analogue has the formula:

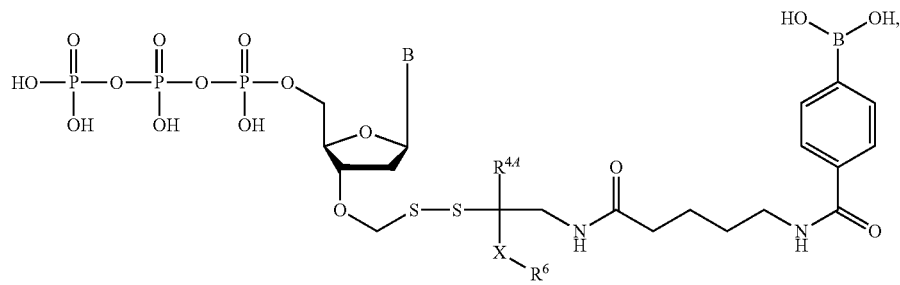

wherein B, $R^{4A}$, X, and $R^6$ are as described herein.

In embodiments, the nucleotide analogue has the formula:

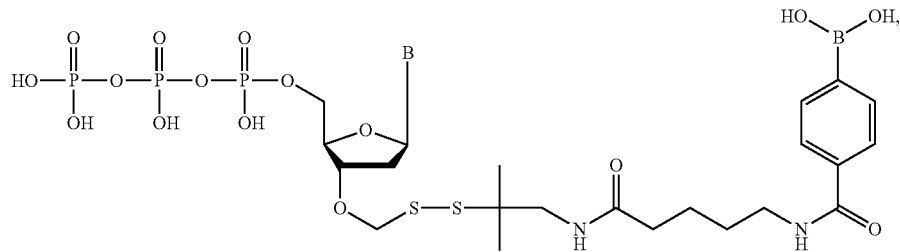

wherein B is as described herein.

In embodiments, the nucleotide analogue has the formula:
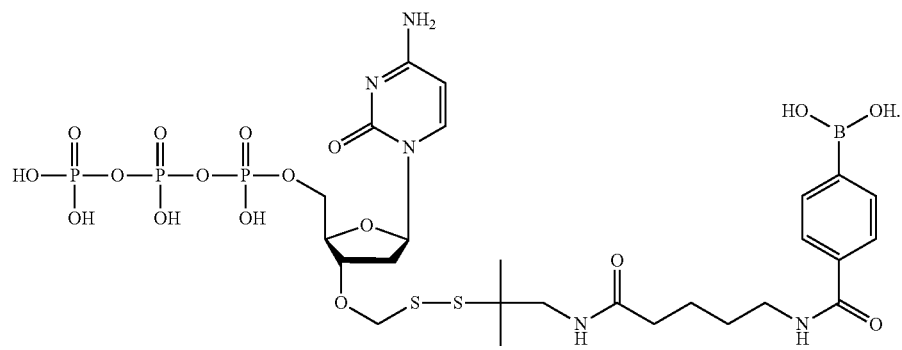
In embodiments, the nucleotide analogue has the formula:
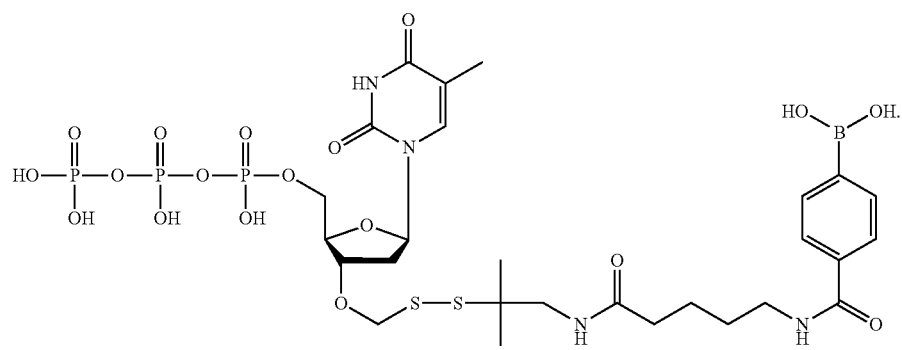
In embodiments, the nucleotide analogue has the formula:
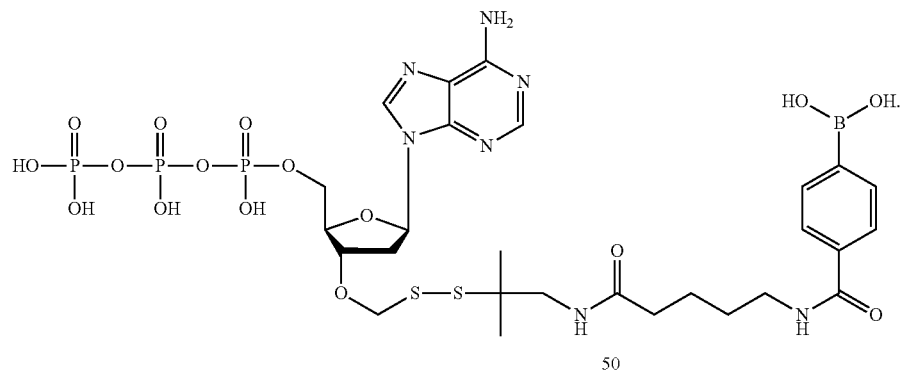
In embodiments, the nucleotide analogue has the formula:
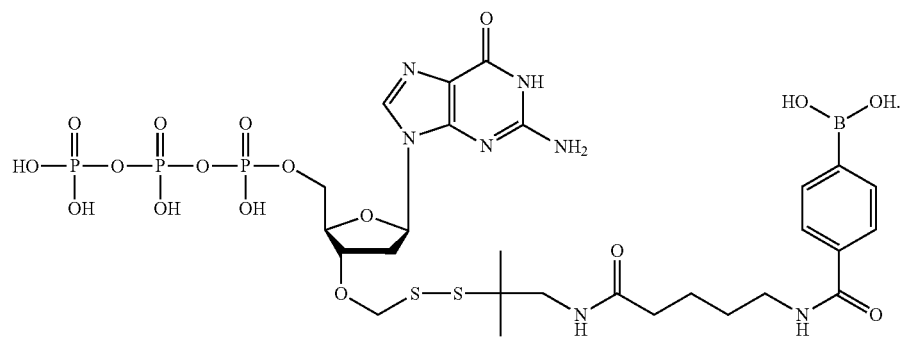

In embodiments, the nucleotide analogue has the formula:
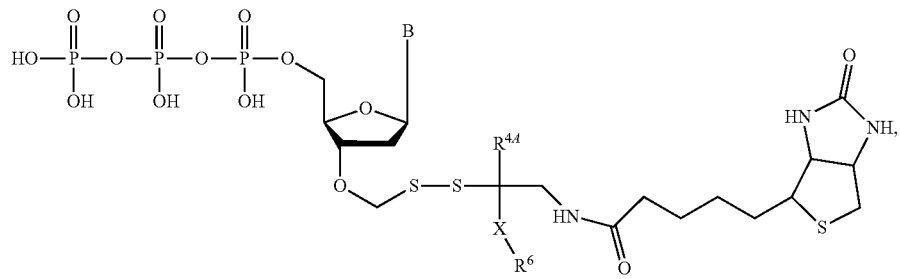
wherein B, $R^{4A}$, X, and $R^6$ are as described herein.
In embodiments, the nucleotide analogue has the formula:
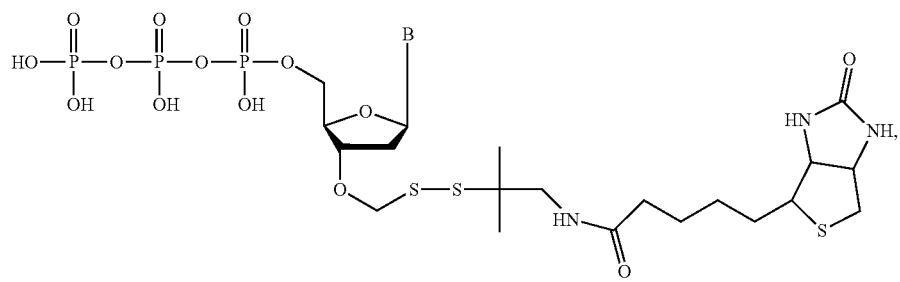
wherein B is as described herein.
In embodiments, the nucleotide analogue has the formula:
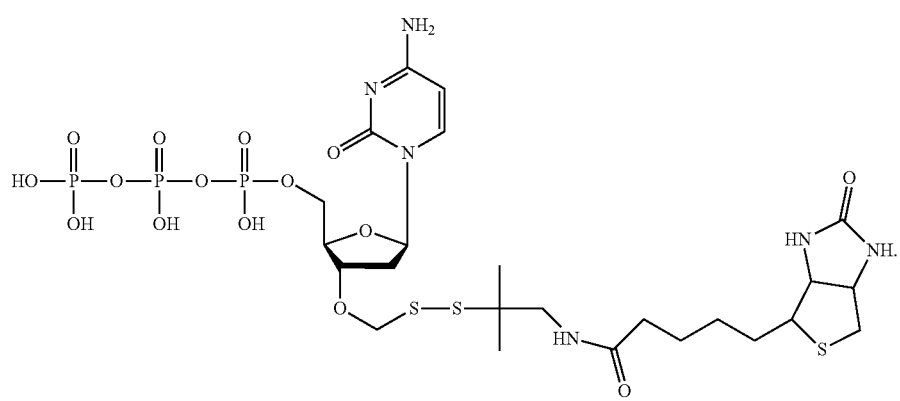
In embodiments, the nucleotide analogue has the formula:
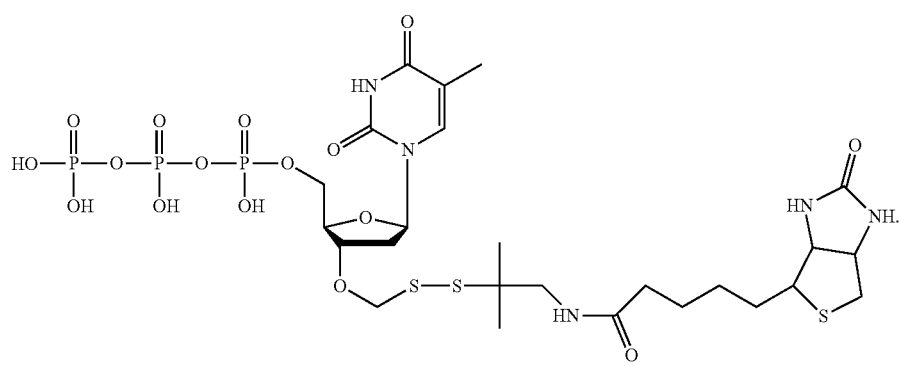

In embodiments, the nucleotide analogue has the formula:

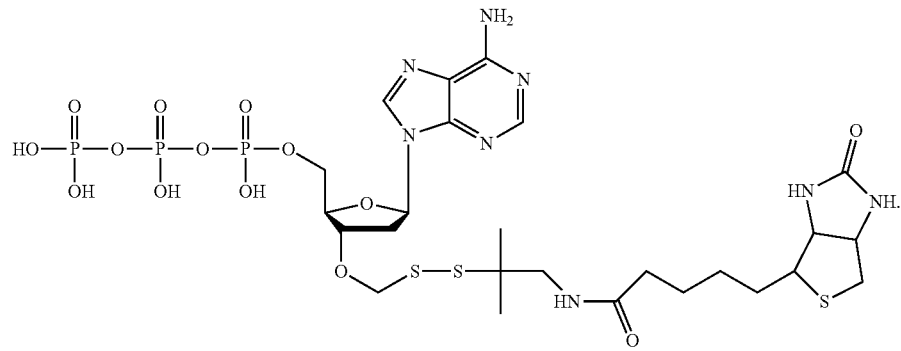

In embodiments, the nucleotide analogue has the formula:

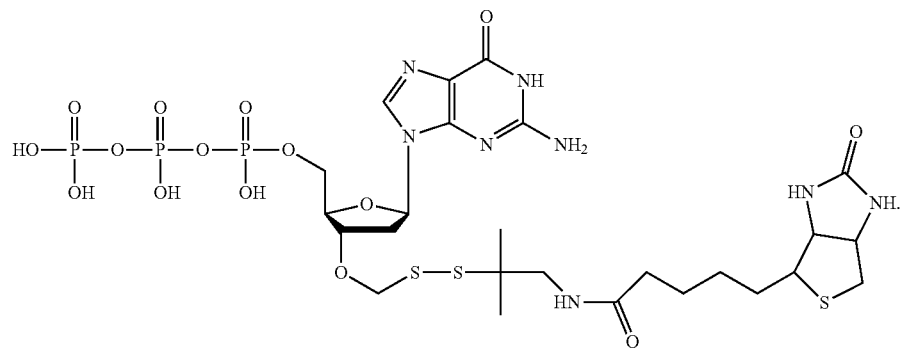

In embodiments, the nucleotide analogue has the formula:

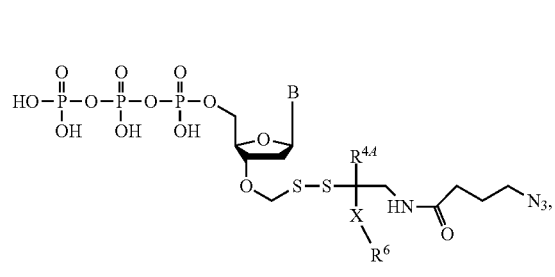

wherein B, $R^{4A}$, X, and $R^6$ are as described herein.

In embodiments, the nucleotide analogue has the formula:

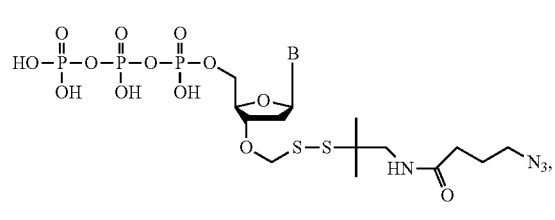

wherein B is as described herein.

In embodiments, the nucleotide analogue has the formula:

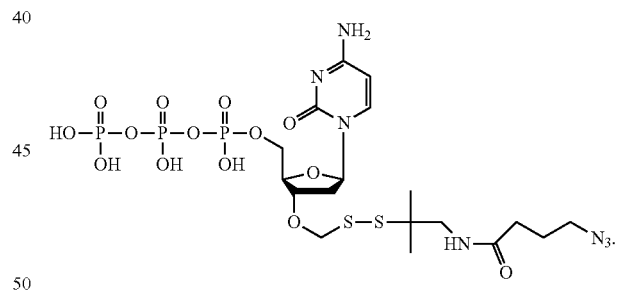

In embodiments, the nucleotide analogue has the formula:

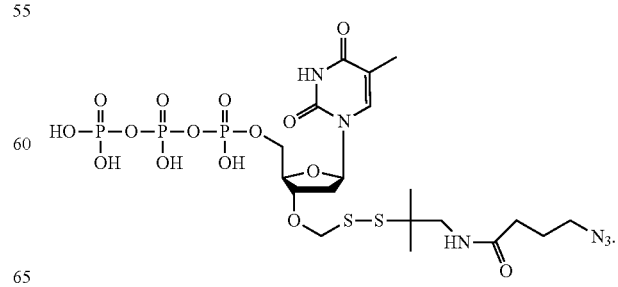

In embodiments, the nucleotide analogue has the formula:

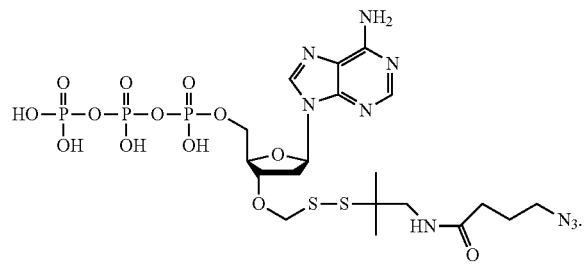

In embodiments, the nucleotide analogue has the formula:

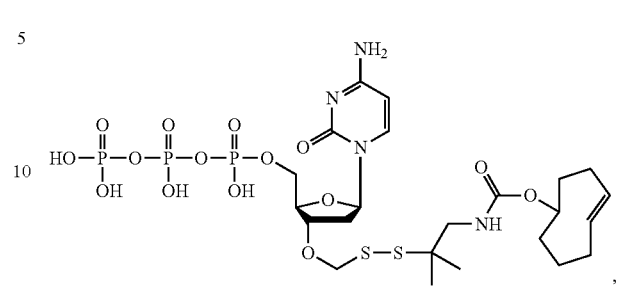

In embodiments, the nucleotide analogue has the formula:

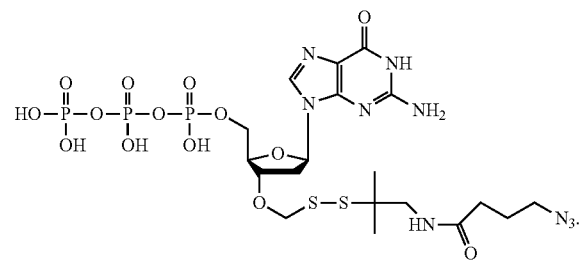

In embodiments, the nucleotide analogue has the formula:

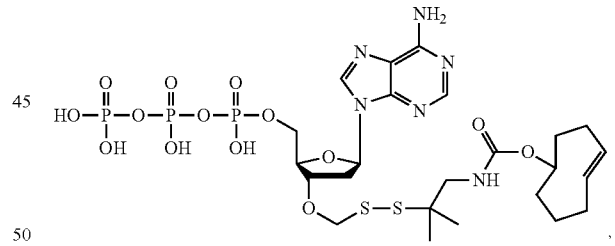

In embodiments, the nucleotide analogue has the formula:

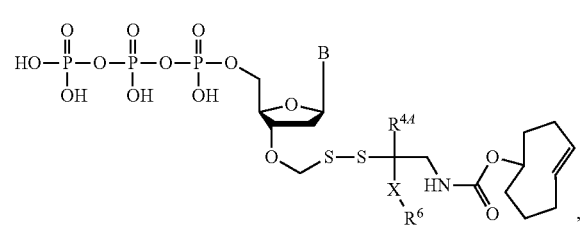

wherein B, $R^{4A}$, X, and $R^6$ are as described herein.

In embodiments, the nucleotide analogue has the formula:

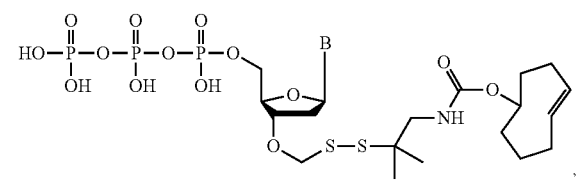

wherein B is as described herein.

In embodiments, the nucleotide analogue has the formula:

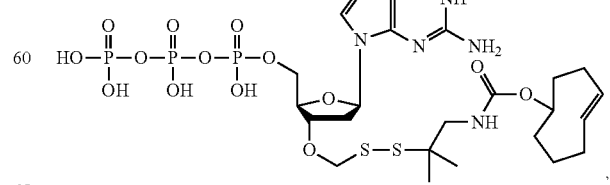

In embodiments, the nucleotide analogue has the formula:

In embodiments, the nucleotide analogue has the formula:
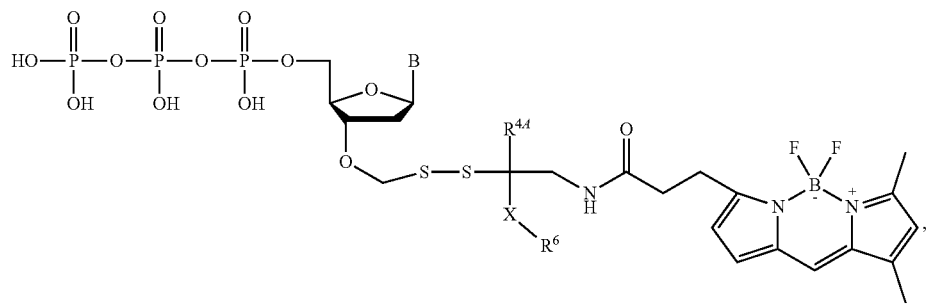
wherein B, $R^{4A}$, X, and $R^6$ are as described herein.
In embodiments, the nucleotide analogue has the formula:
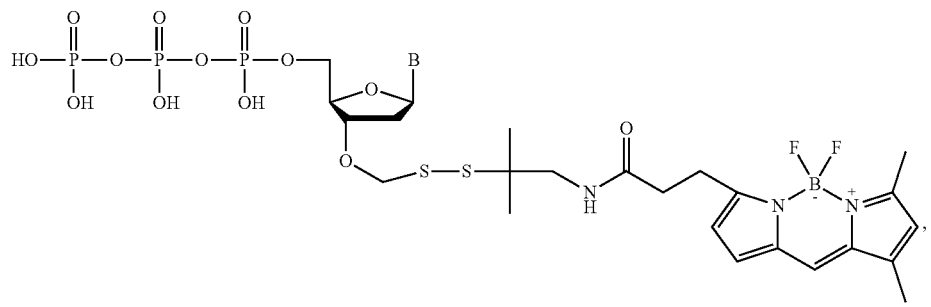
45
wherein B is as described herein.
In embodiments, the nucleotide analogue has the formula:
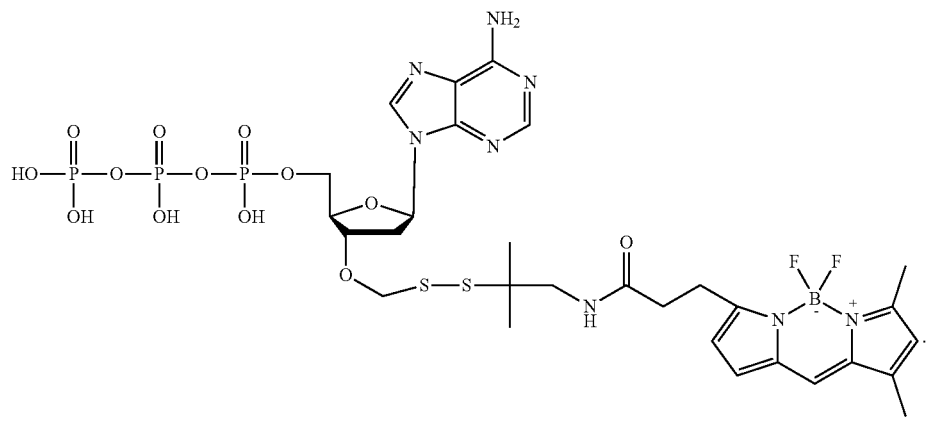

In embodiments, the nucleotide analogue has the formula:
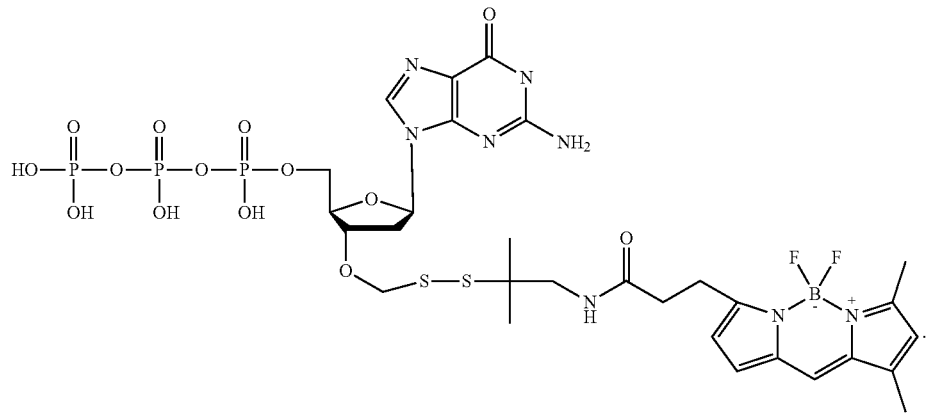
In embodiments, the nucleotide analogue has the formula:
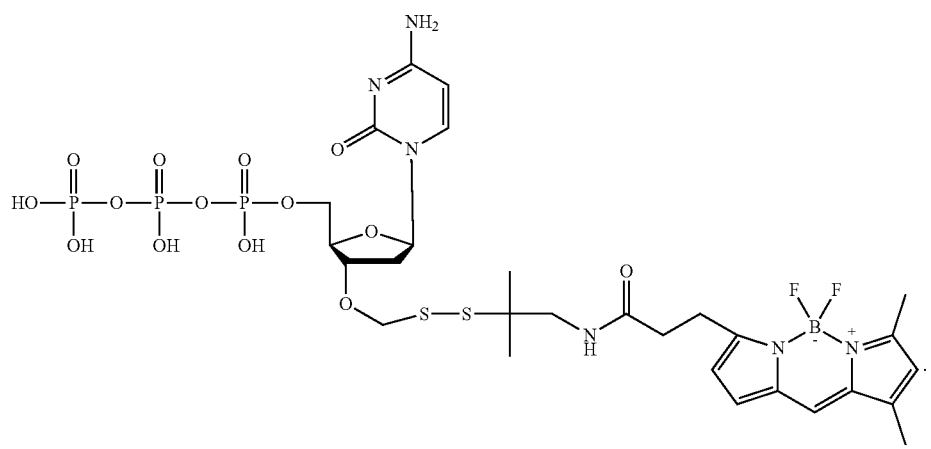
In embodiments, the nucleotide analogue has the formula:
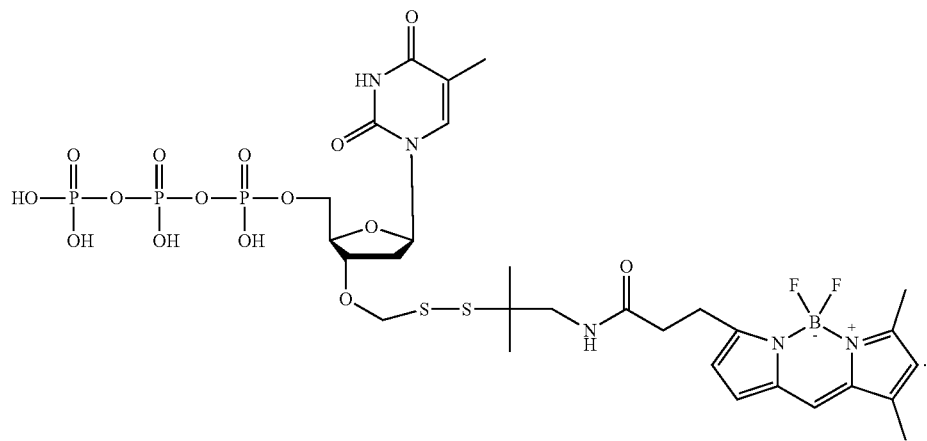

In embodiments, the nucleotide analogue has the formula:
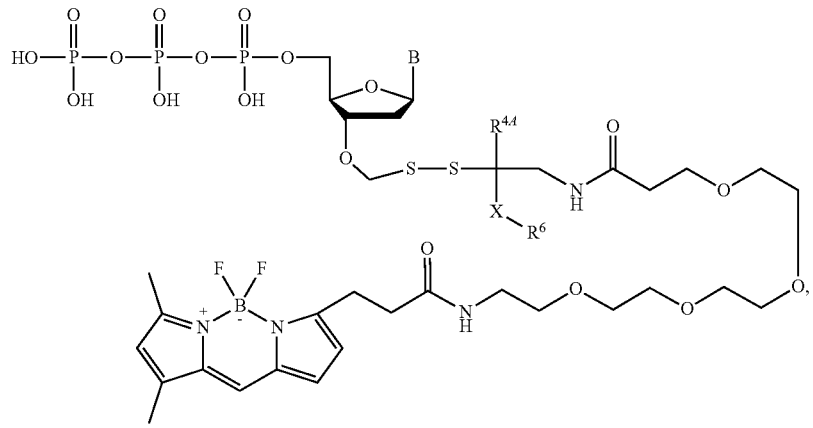
wherein B, $R^{4A}$, X, and $R^6$ are as described herein.
In embodiments, the nucleotide analogue has the formula:
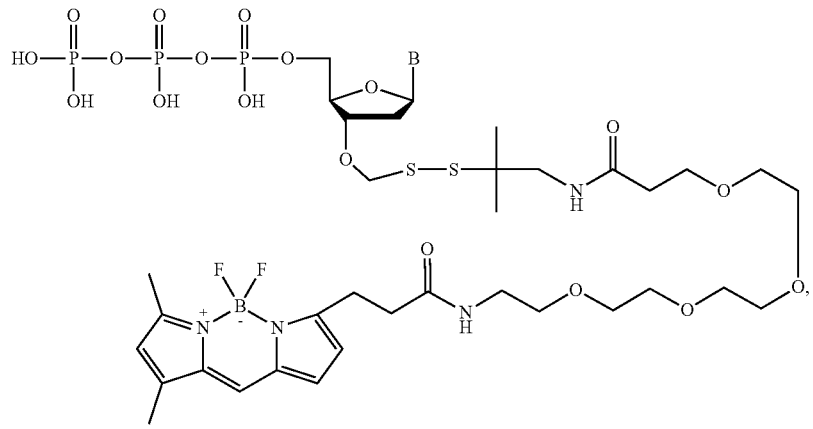
wherein B is as described herein.
In embodiments, the nucleotide analogue has the formula:
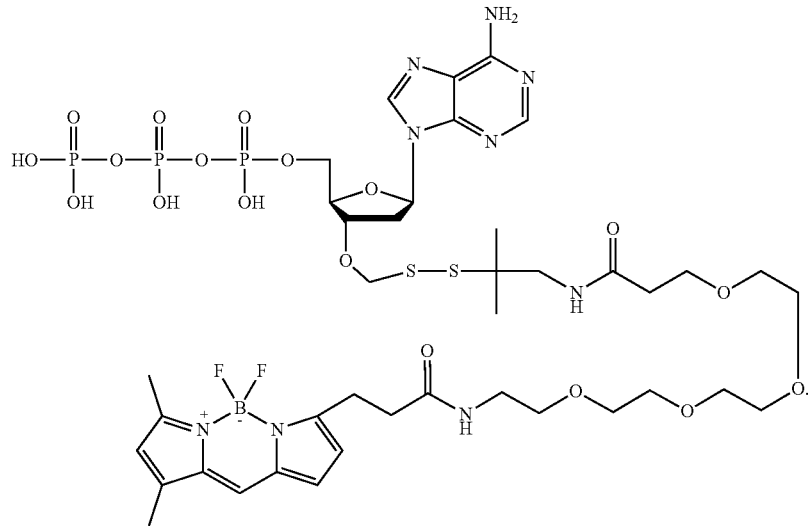

In embodiments, the nucleotide analogue has the formula:
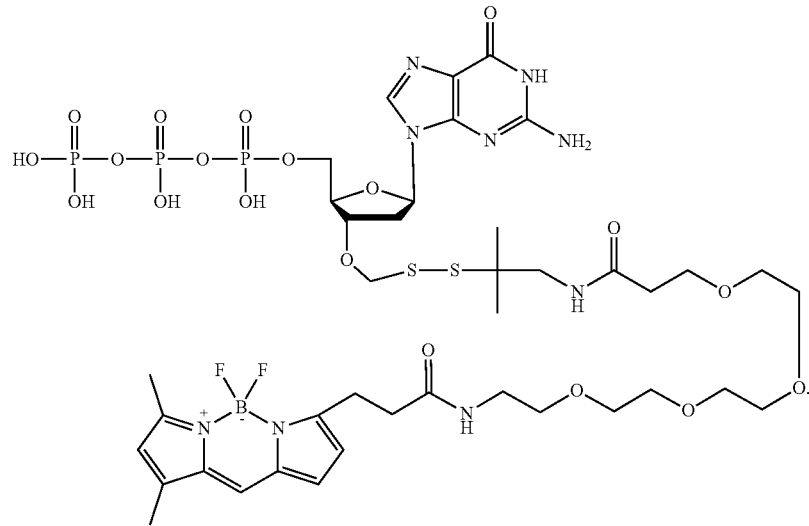
In embodiments, the nucleotide analogue has the formula:
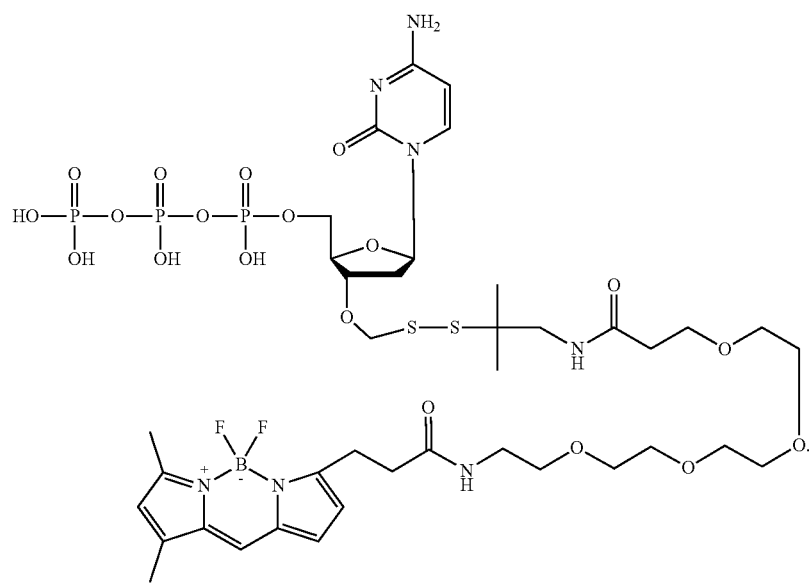

In embodiments, the nucleotide analogue has the formula:
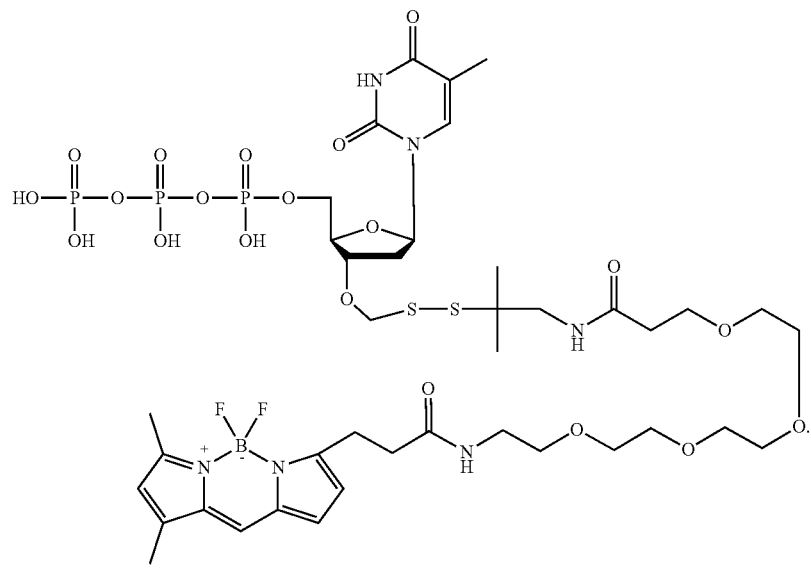
In embodiments, the nucleotide analogue has the formula:
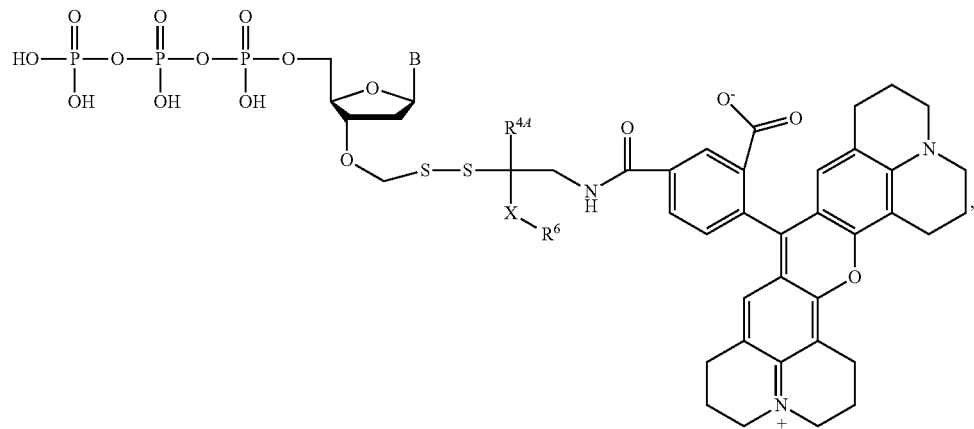
wherein B, $R^{4.4}$, X, and $R^6$ are as described herein.
In embodiments, the nucleotide analogue has the formula:
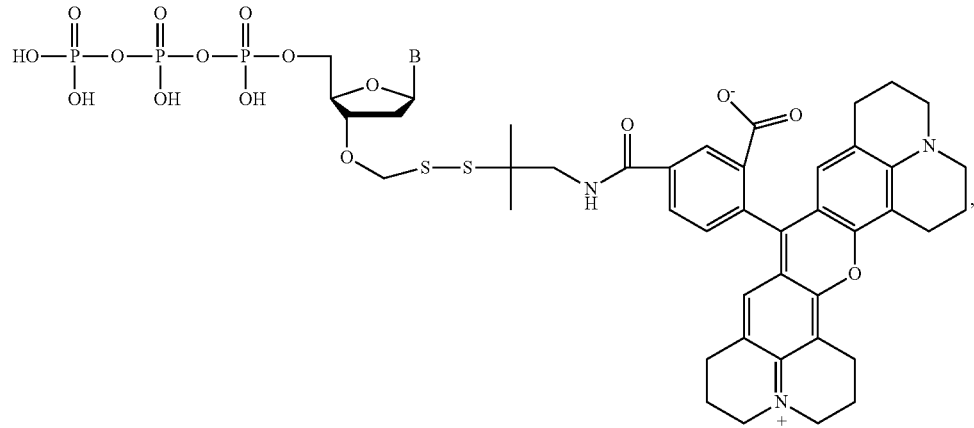
wherein B is as described herein.

In embodiments, the nucleotide analogue has the formula:
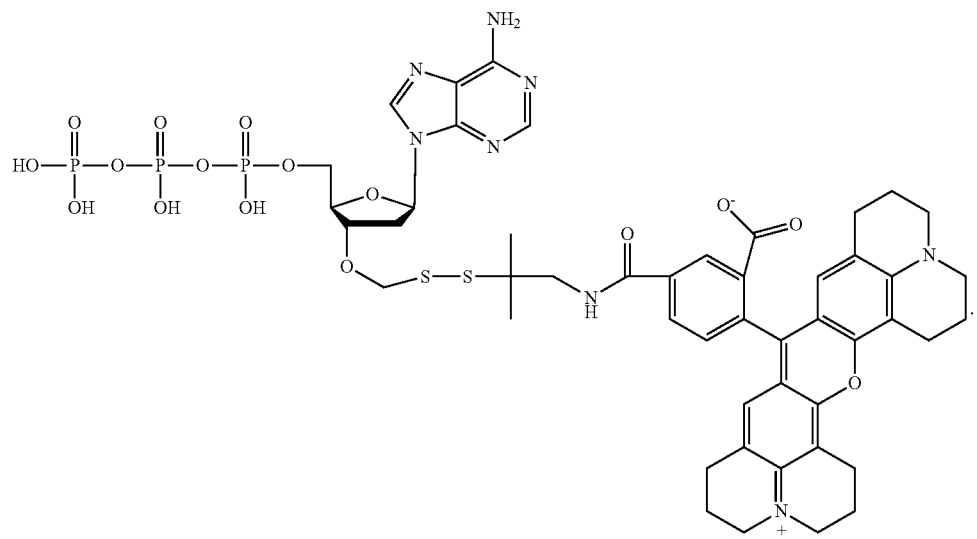
In embodiments, the nucleotide analogue has the formula:
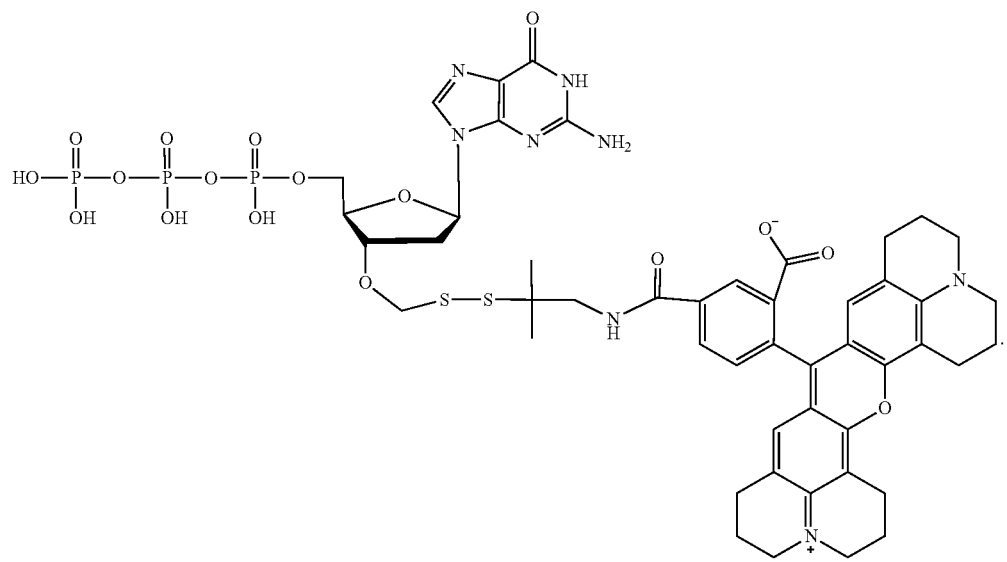 [SMILES: CC(C)(CNC(=O)c1ccc(C2=c3cc4c5c(c3Oc3c2cc2c6c3CCCN6CCC2)CCC[N+]=5CCC4)c(C(=O)[O-])c1)SSCO[C@@H]1C[C@H](n2cnc3c(=O)[nH]c(N)nc32)O[C@@H]1COP(=O)(O)OP(=O)(O)OP(=O)(O)O]

In embodiments, the nucleotide analogue has the formula:
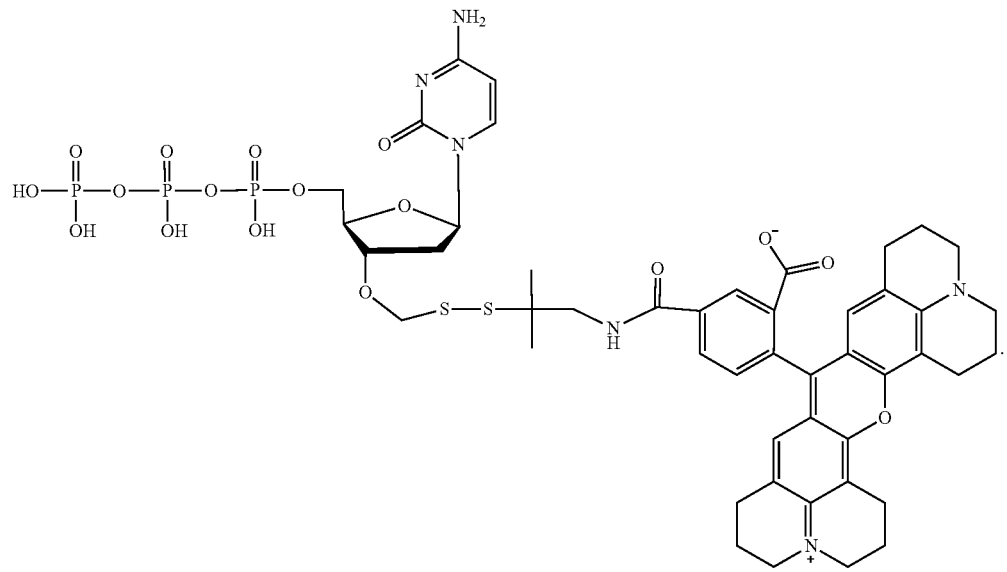 [SMILES: CC(C)(CNC(=O)c1ccc(C2=c3cc4c5c(c3Oc3c2cc2c6c3CCCN6CCC2)CCC[N+]=5CCC4)c(C(=O)[O-])c1)SSCO[C@@H]1C[C@H](n2ccc(N)nc2=O)O[C@@H]1COP(=O)(O)OP(=O)(O)OP(=O)(O)O]
In embodiments, the nucleotide analogue has the formula:
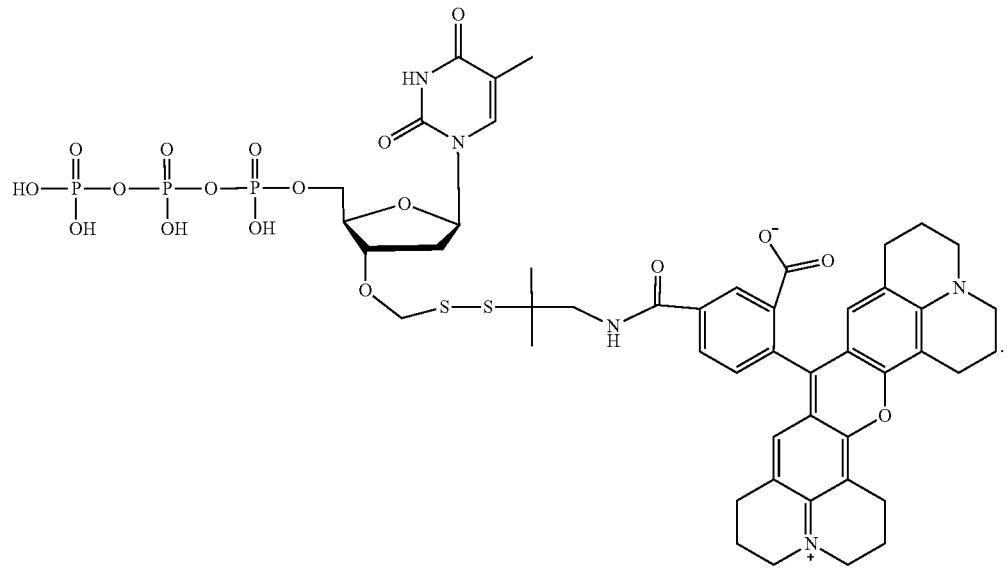 [SMILES: Cc1cn([C@H]2C[C@@H](OCSSC(C)(C)CNC(=O)c3ccc(C4=c5cc6c7c(c5Oc5c4cc4c8c5CCCN8CCC4)CCC[N+]=7CCC6)c(C(=O)[O-])c3)[C@@H](COP(=O)(O)OP(=O)(O)OP(=O)(O)O)O2)c(=O)[nH]c1=O]

In embodiments, the nucleotide analogue has the formula:
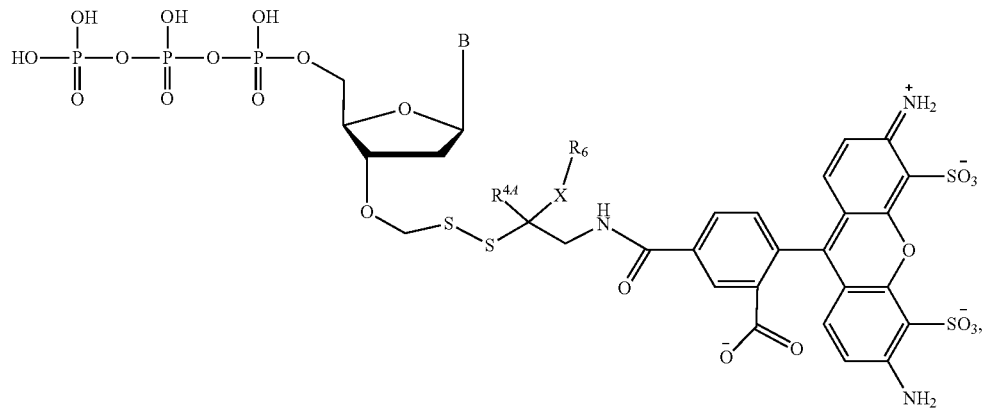
wherein B, $R^{4A}$, X, and $R^6$ are as described herein.
In embodiments, the nucleotide analogue has the formula:
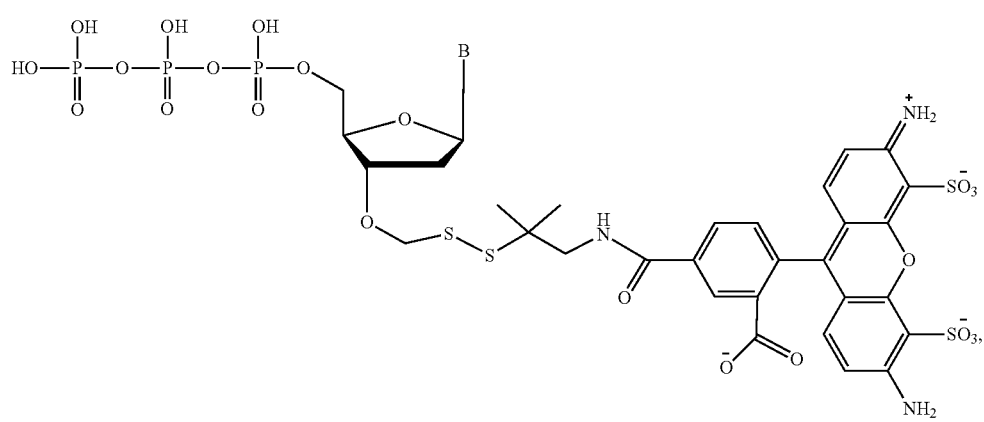
wherein B is as described herein.
In embodiments, the nucleotide analogue has the formula:
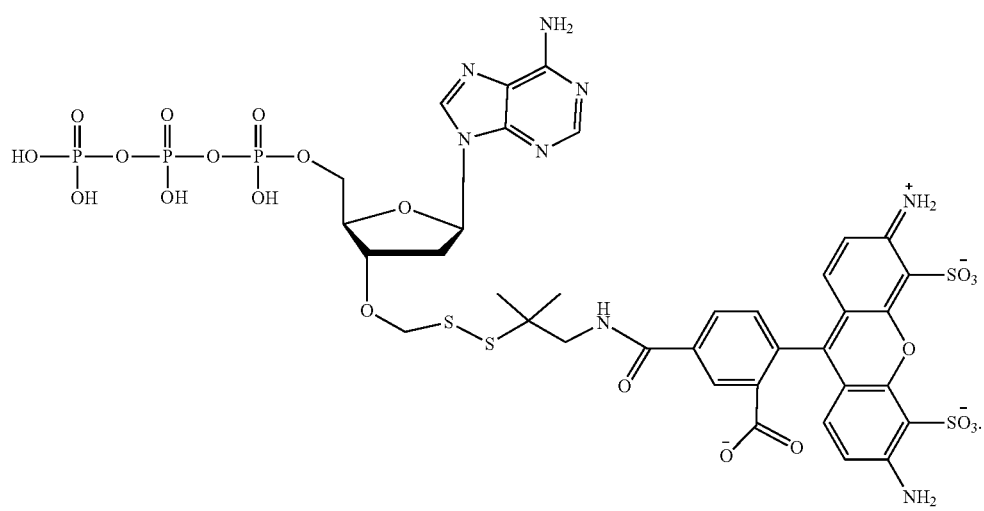

In embodiments, the nucleotide analogue has the formula:
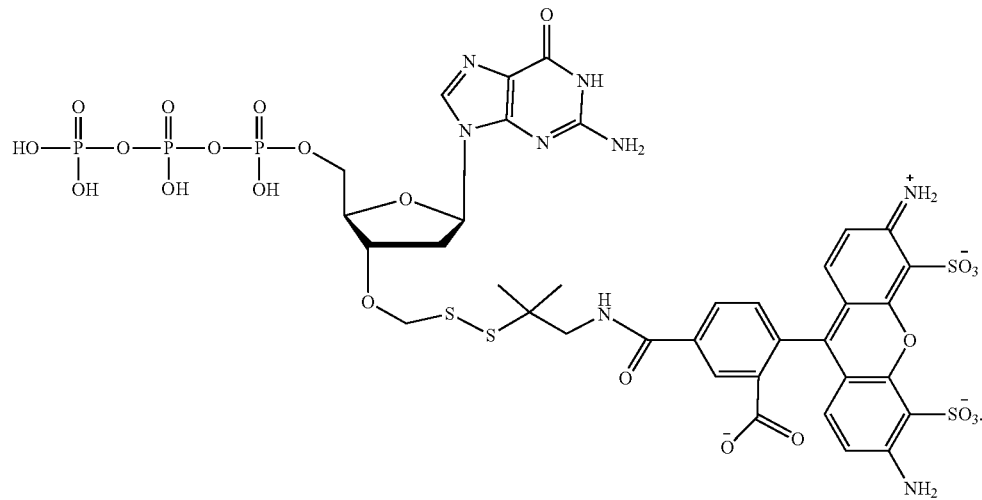
In embodiments, the nucleotide analogue has the formula:
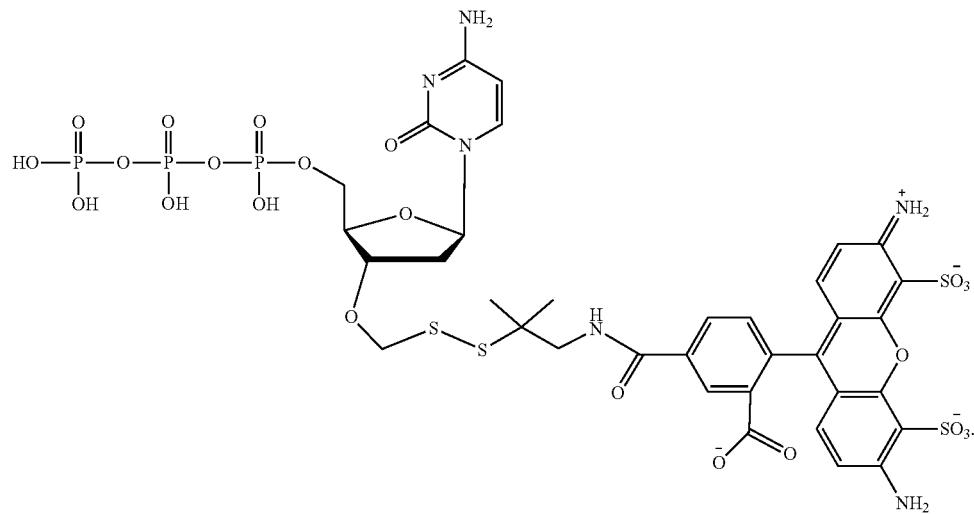

In embodiments, the nucleotide analogue has the formula:
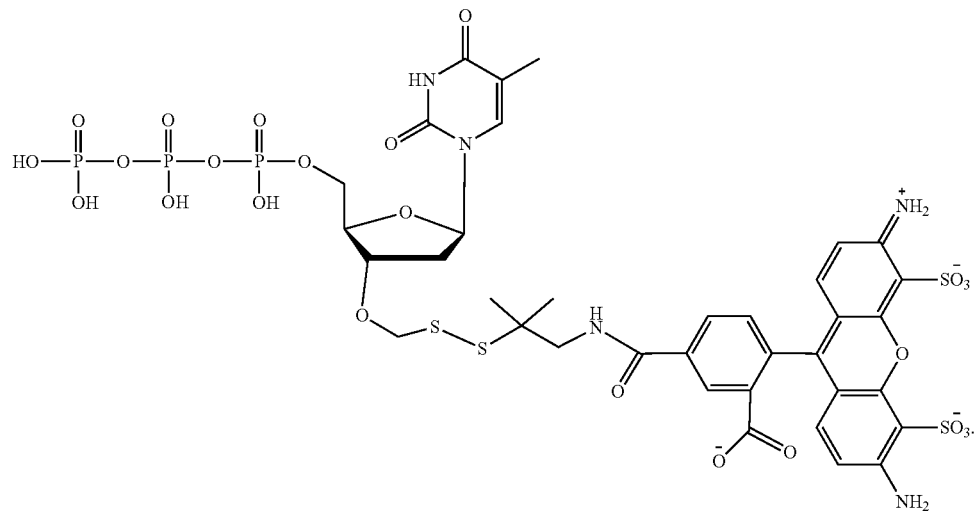
In embodiments, the nucleotide analogue has the formula:
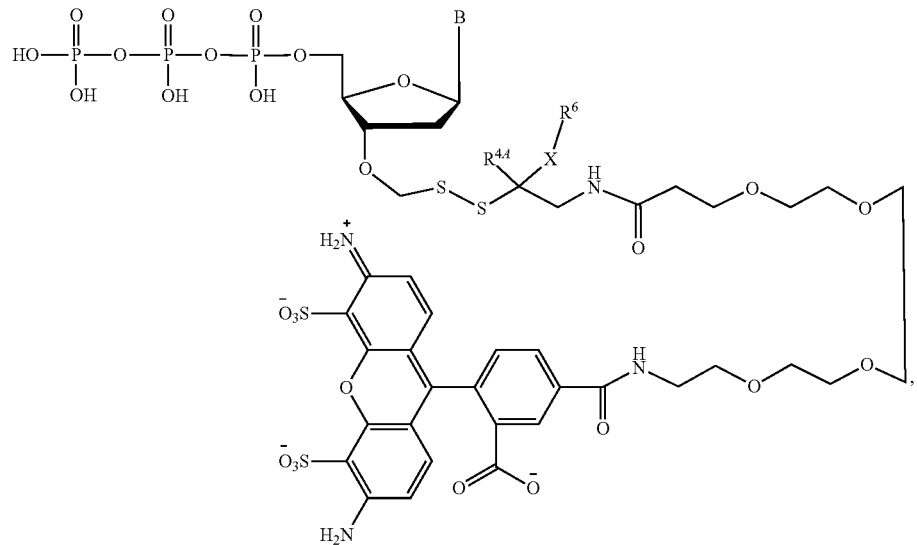
wherein B, $R^{4A}$, X, and $R^6$ are as described herein.

In embodiments, the nucleotide analogue has the formula:
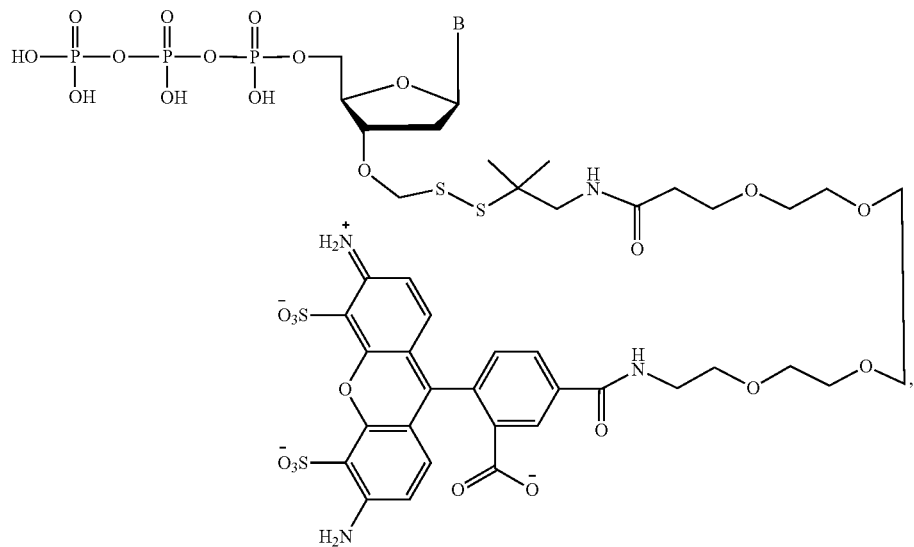
wherein B is as described herein.
In embodiments, the nucleotide analogue has the formula:
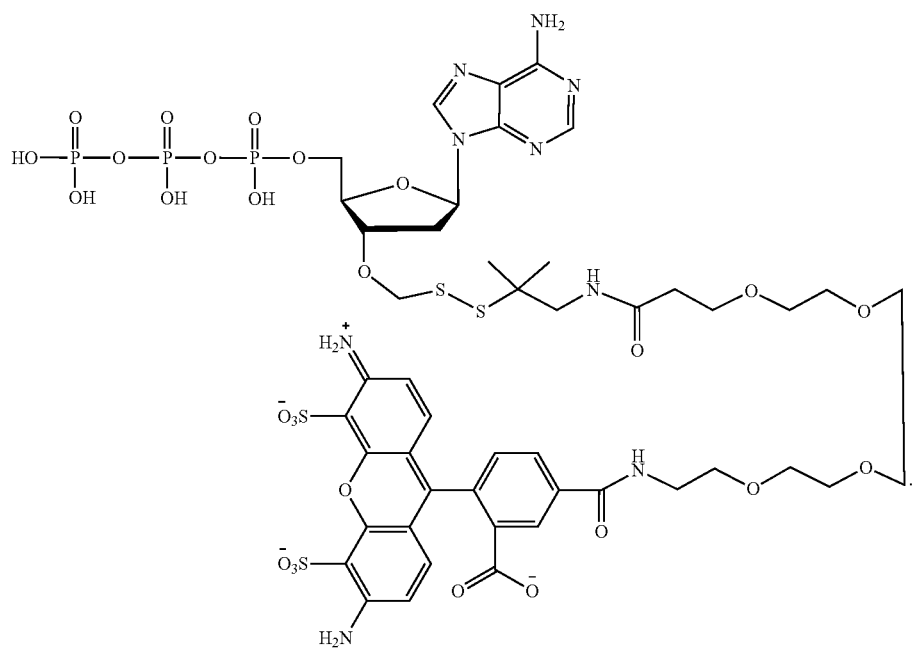

In embodiments, the nucleotide analogue has the formula:
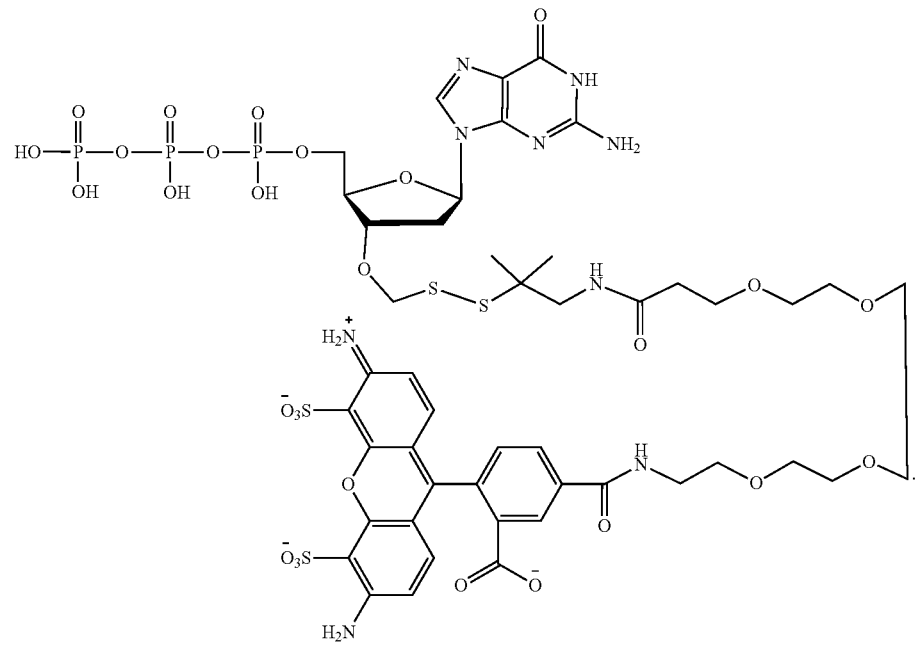
In embodiments, the nucleotide analogue has the formula:
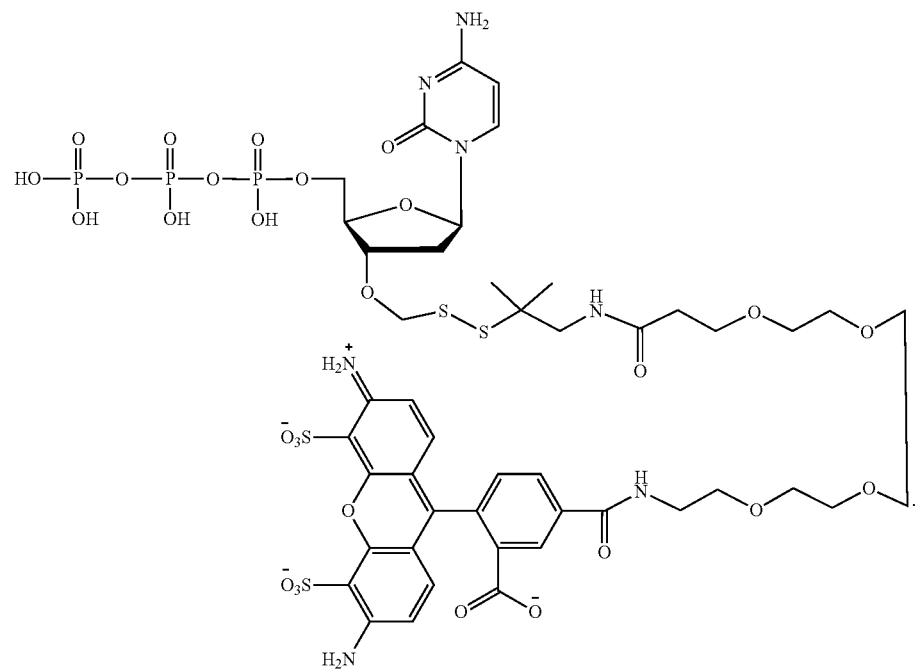

In embodiments, the nucleotide analogue has the formula:
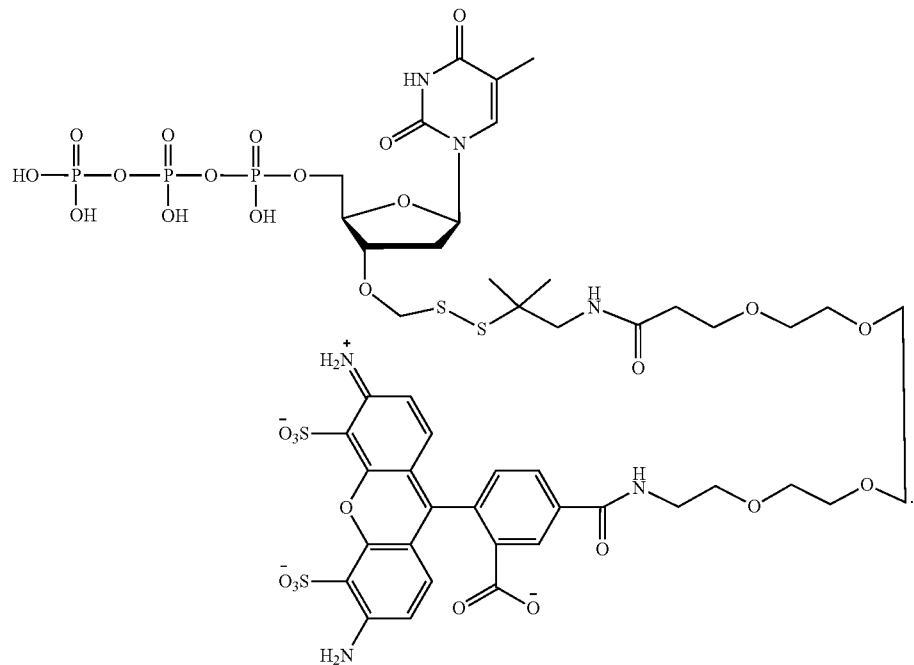
In embodiments, the nucleotide analogue has the formula:
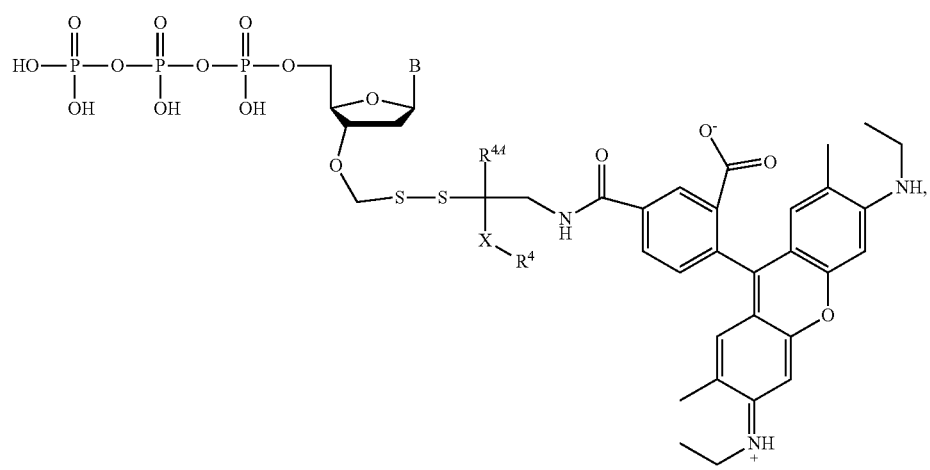
wherein B, $R^{4.4}$, X, and $R^6$ are as described herein.

In embodiments, the nucleotide analogue has the formula:
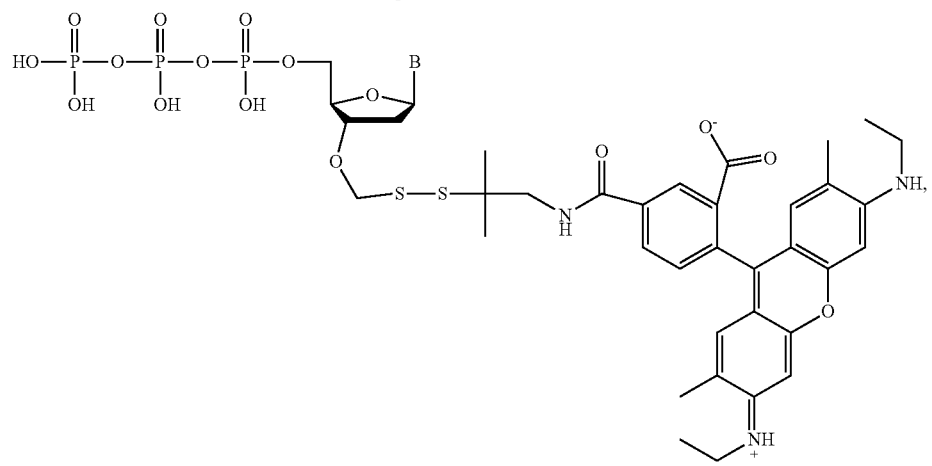
wherein B is as described herein.
In embodiments, the nucleotide analogue has the formula:
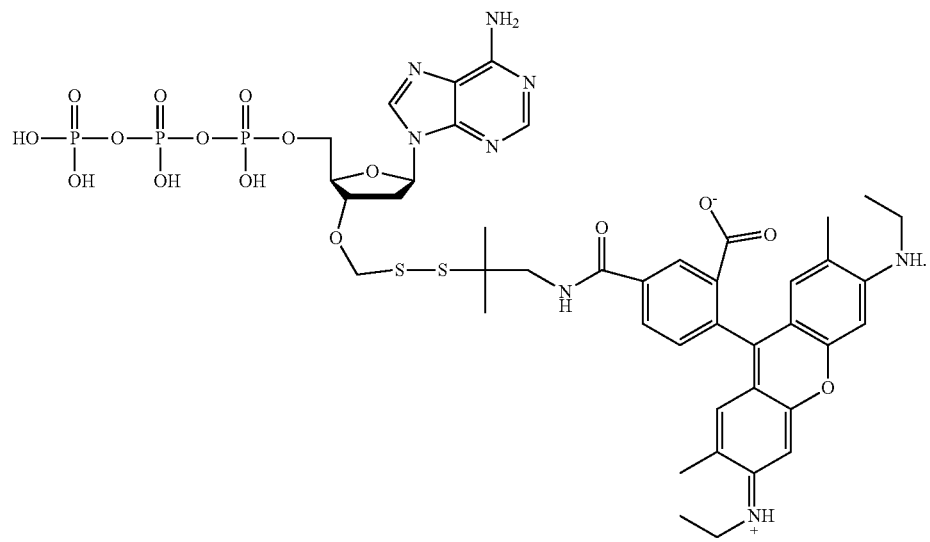
In embodiments, the nucleotide analogue has the formula:
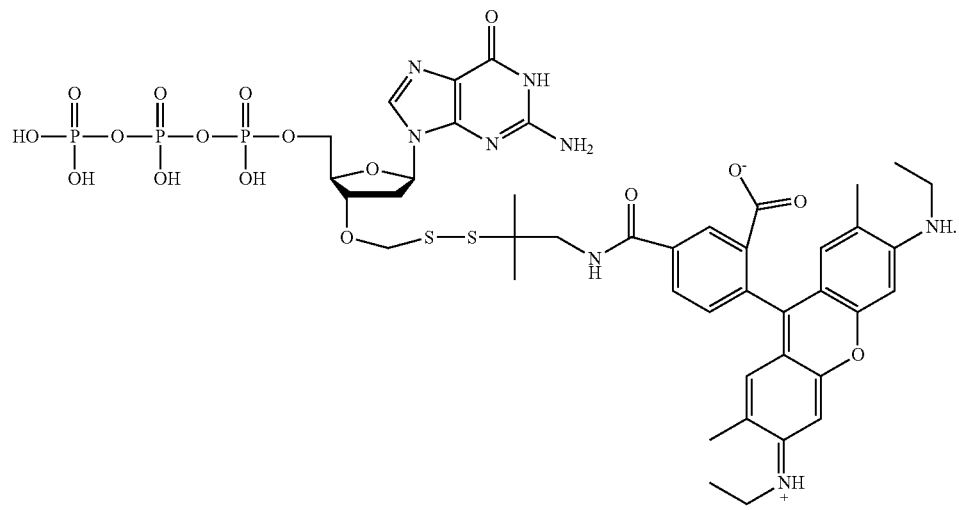

In embodiments, the nucleotide analogue has the formula:
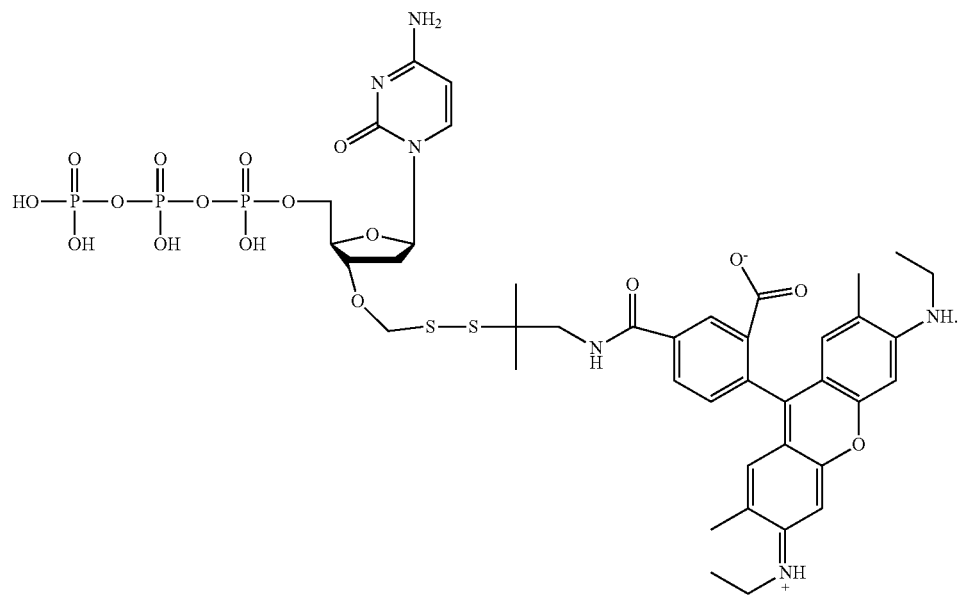
In embodiments, the nucleotide analogue has the formula:
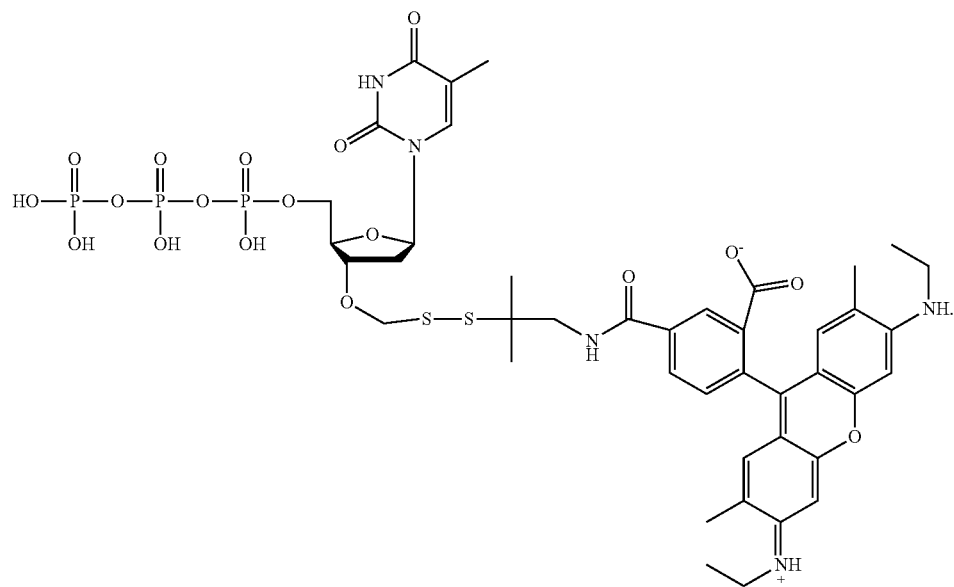

In embodiments, the nucleotide analogue has the formula:
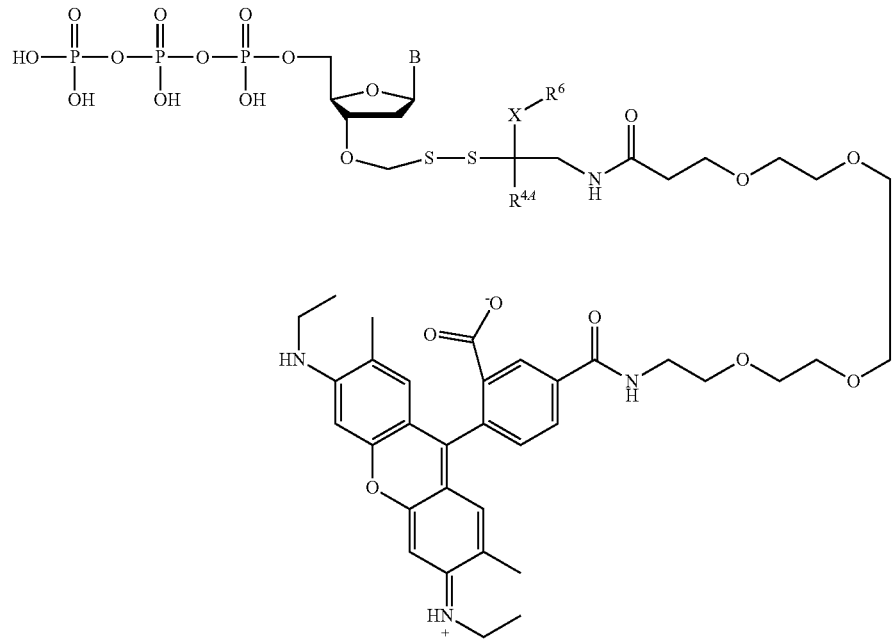
wherein B, $R^{4A}$, X, and $R^6$ are as described herein.
In embodiments, the nucleotide analogue has the formula:
wherein B is as described herein.

In embodiments, the nucleotide analogue has the formula:
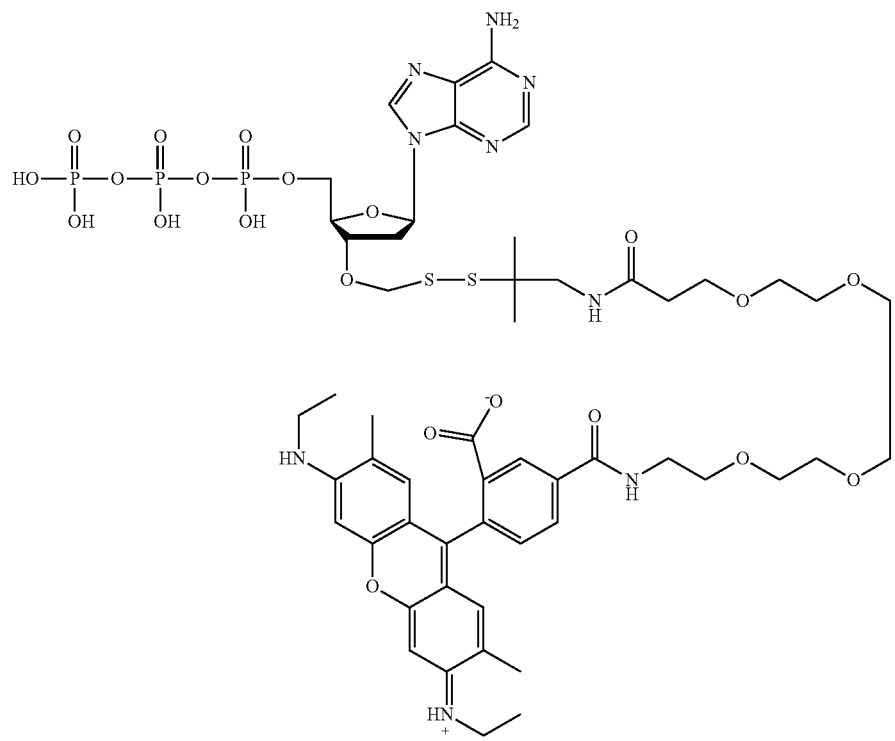
In embodiments, the nucleotide analogue has the formula:
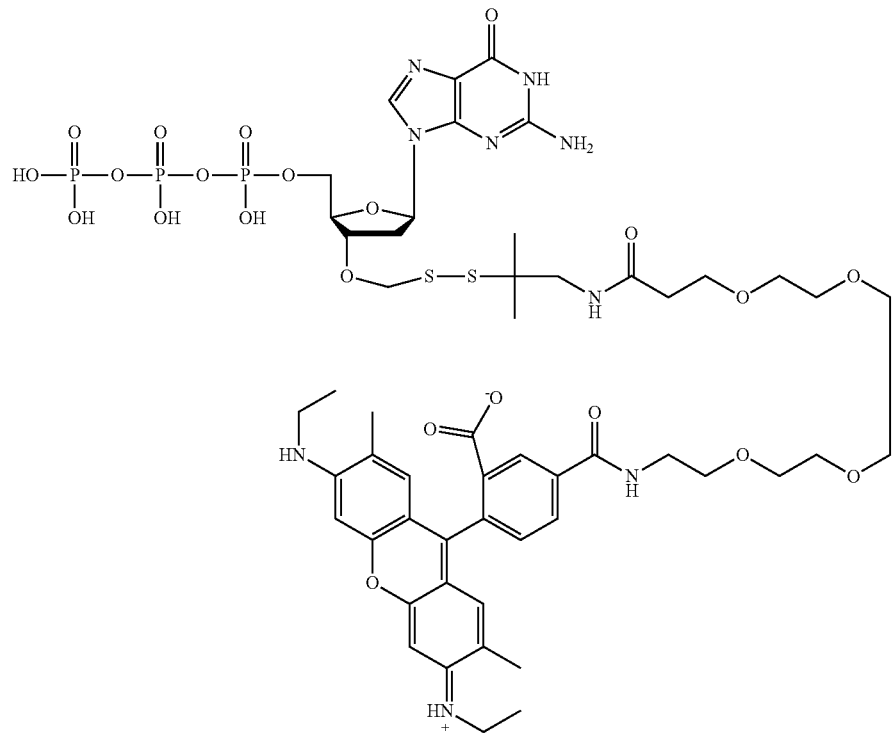

In embodiments, the nucleotide analogue has the formula:
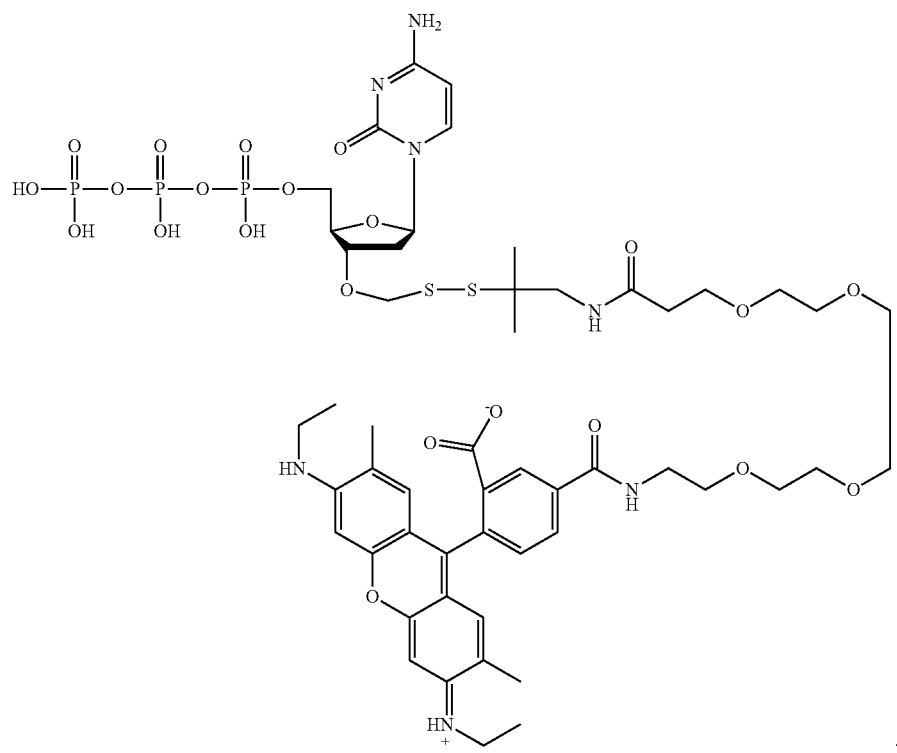
In embodiments, the nucleotide analogue has the formula:
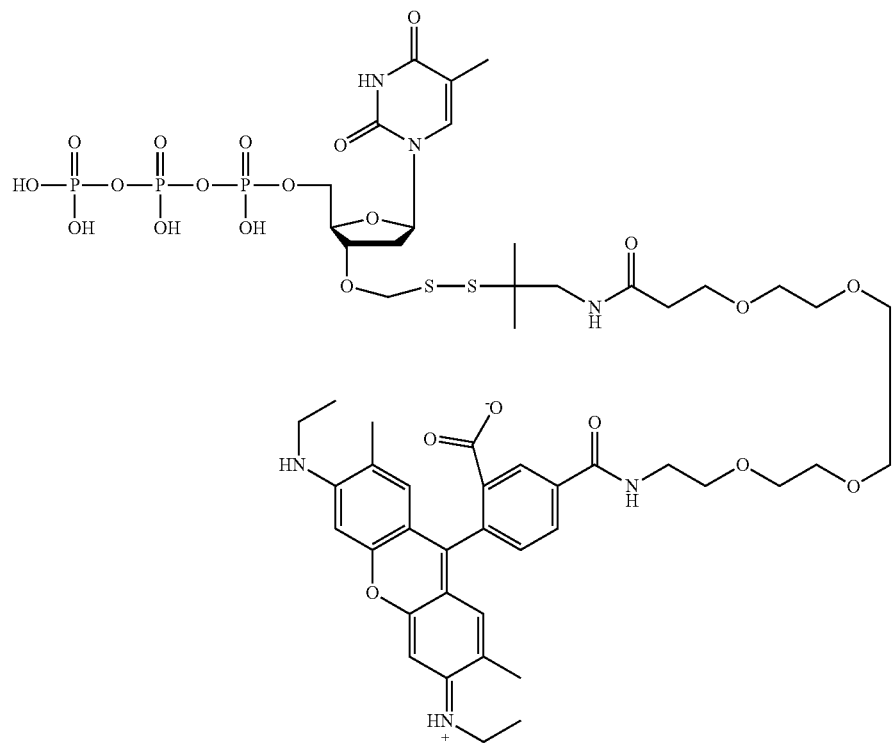

In embodiments, the nucleotide analogue has the formula:
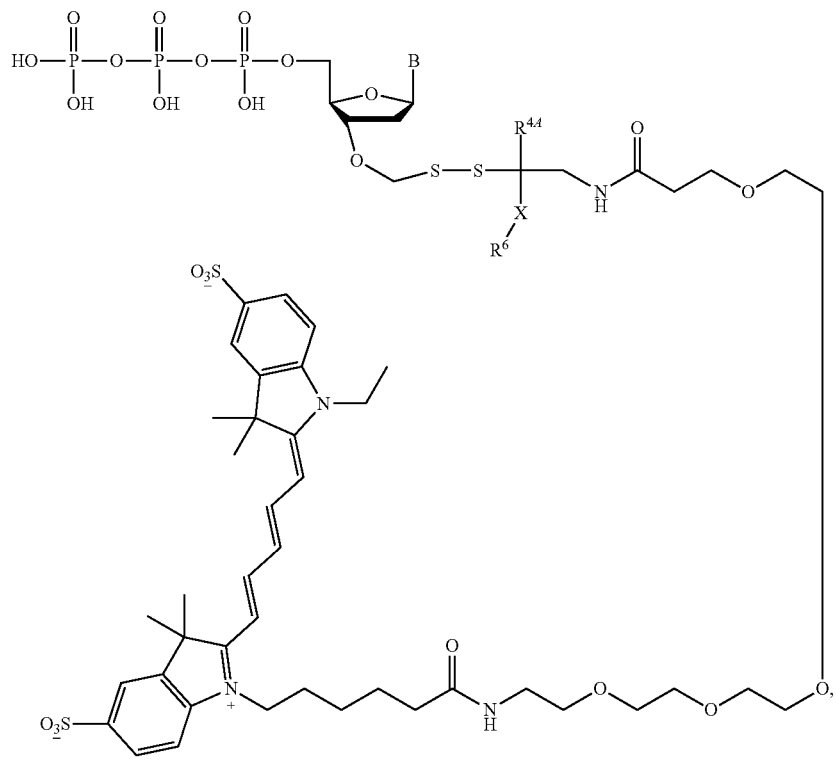
wherein B, $R^{4A}$, X, and $R^6$ are as described herein.
In embodiments, the nucleotide analogue has the formula:
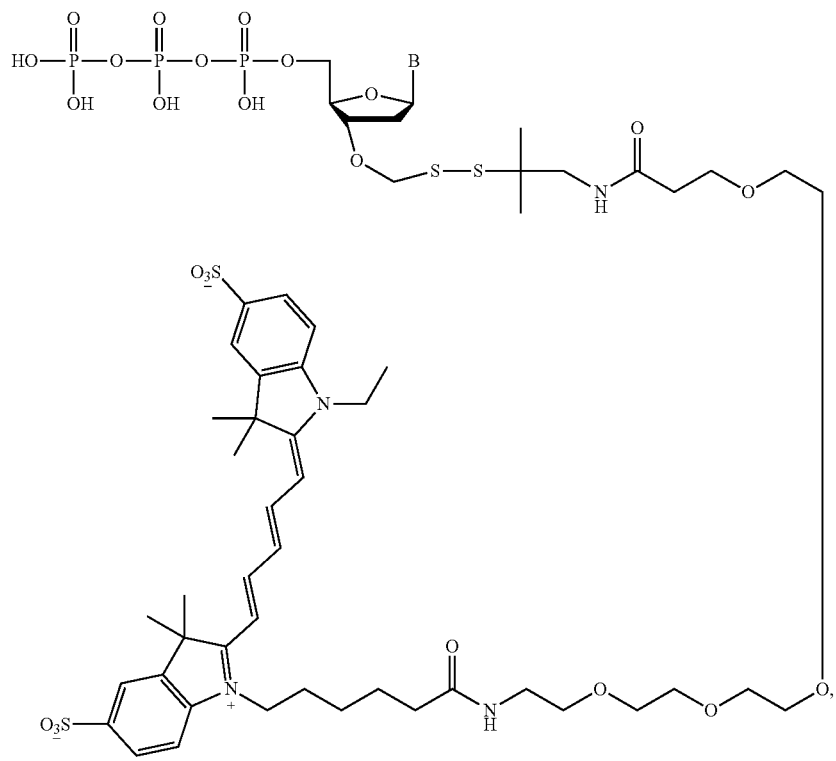
wherein B is as described herein.

In embodiments, the nucleotide analogue has the formula:
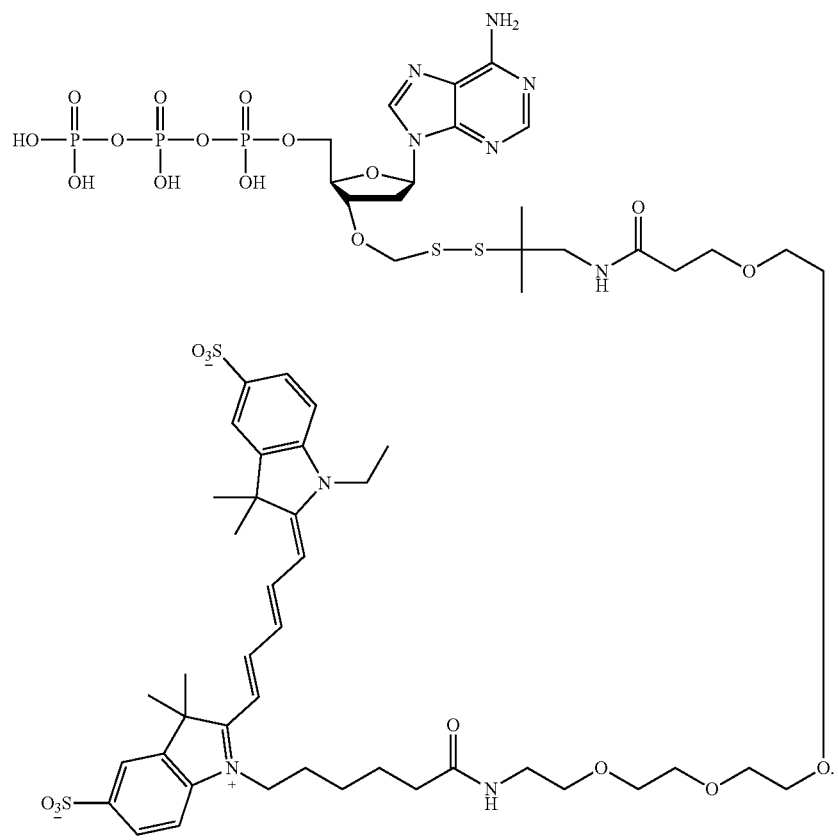
In embodiments, the nucleotide analogue has the formula:
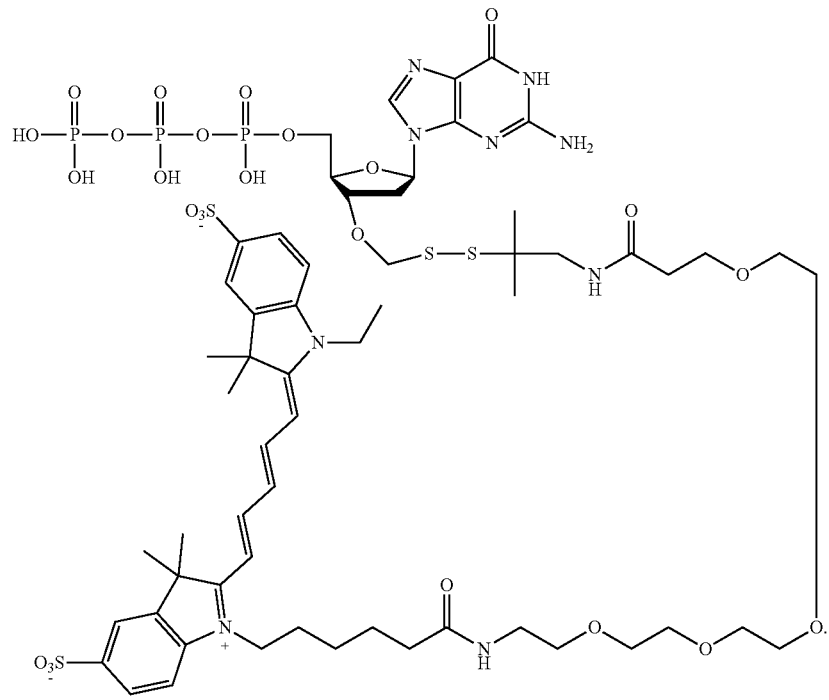

In embodiments, the nucleotide analogue has the formula:
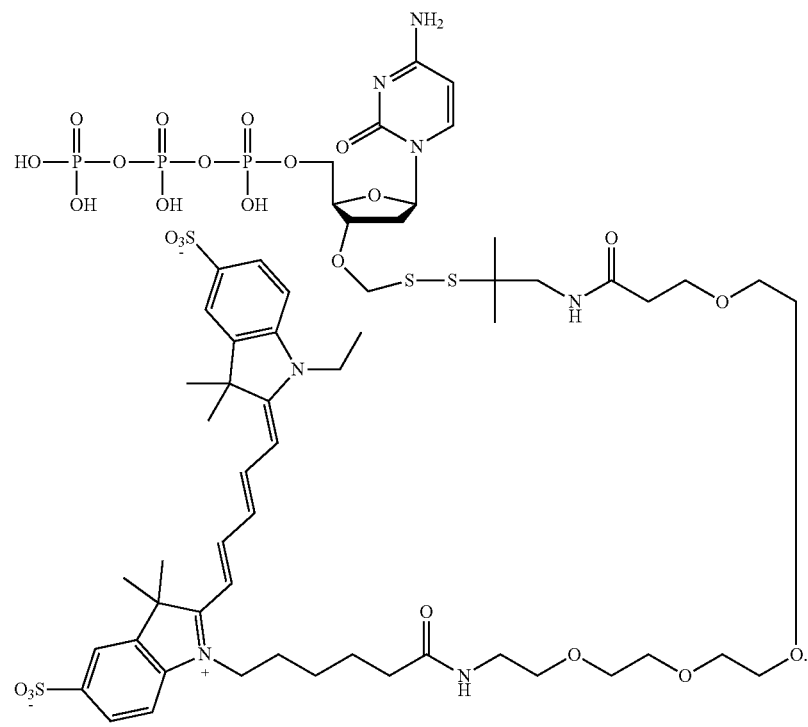
35
In embodiments, the nucleotide analogue has the formula:
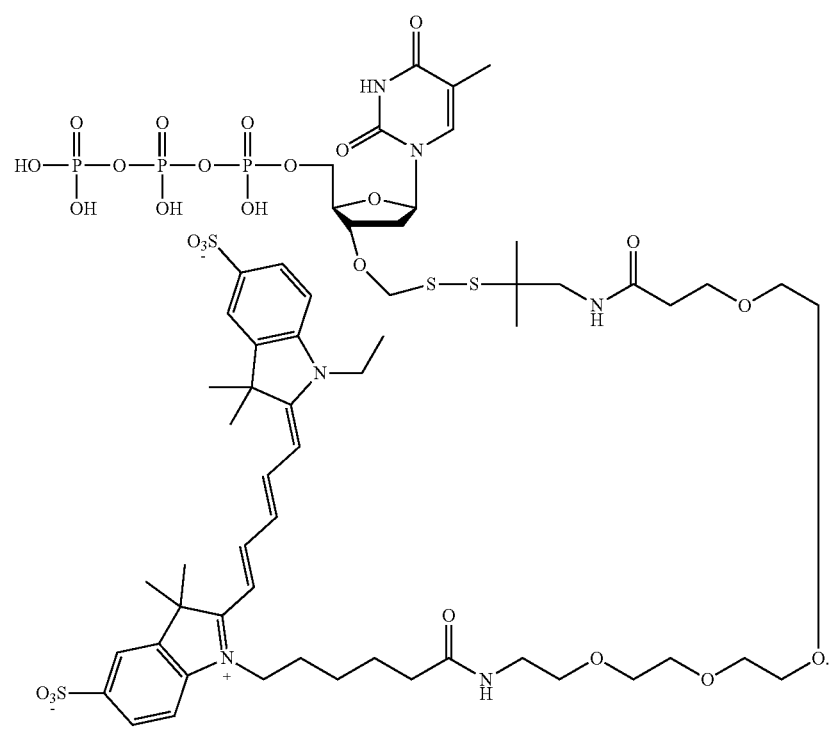

In embodiments, the nucleotide analogue has the formula:
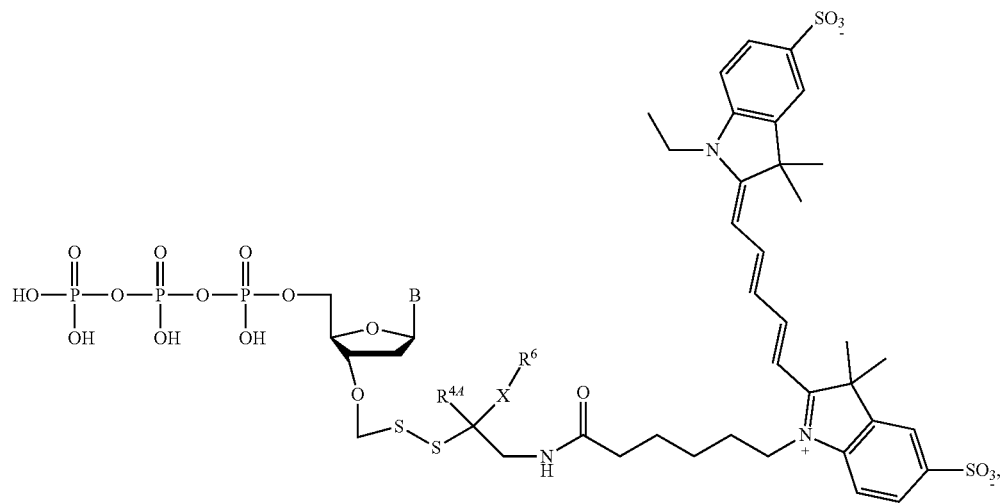
wherein B, $R^{4A}$, X, and $R^6$ are as described herein.
In embodiments, the nucleotide analogue has the formula:
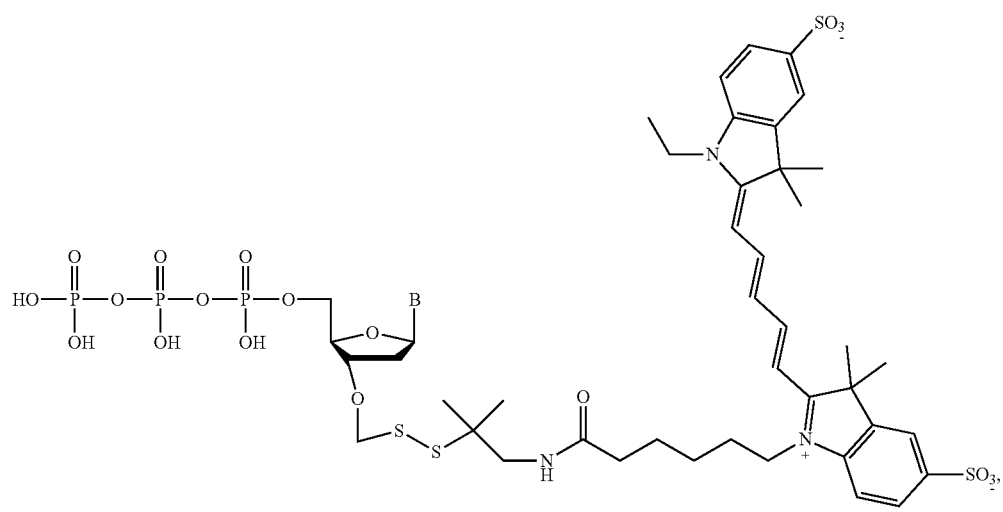
wherein B is as described herein.

In embodiments, the nucleotide analogue has the formula:
In embodiments, the nucleotide analogue has the formula:
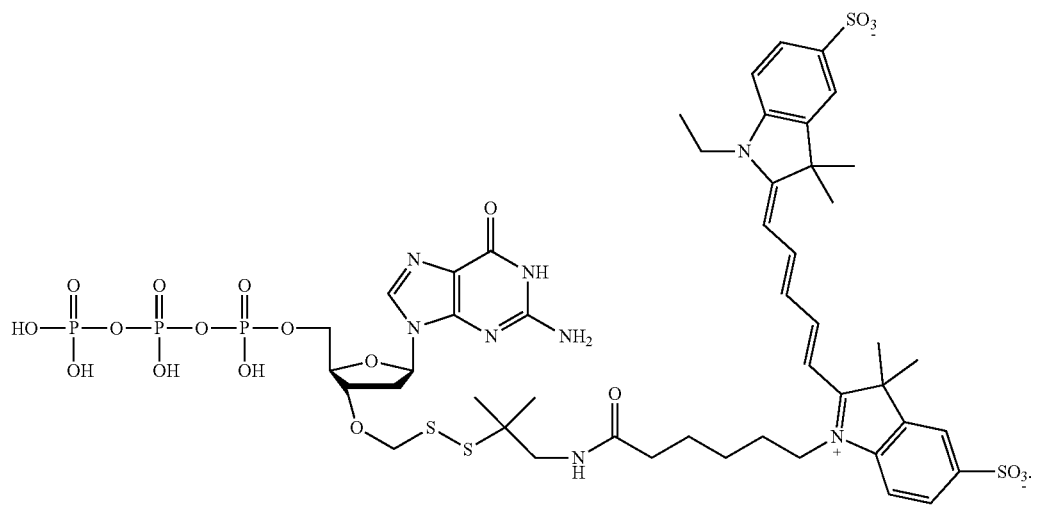
In embodiments, the nucleotide analogue has the formula:
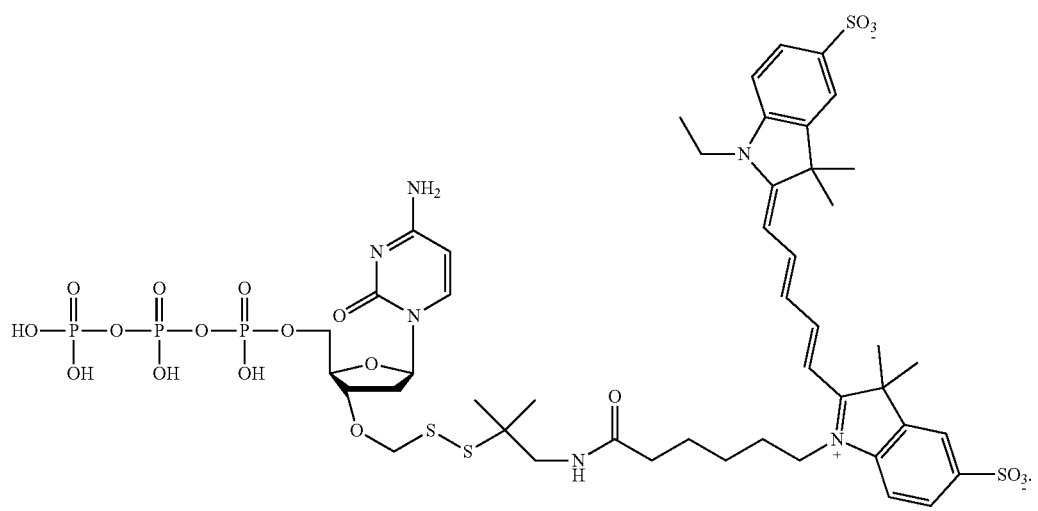

In embodiments, the nucleotide analogue has the formula:

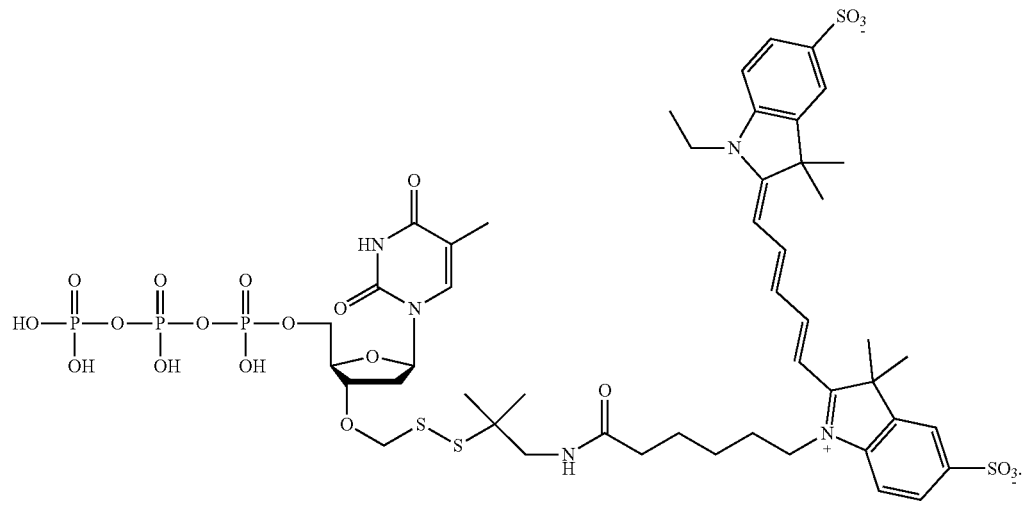

In embodiments, the nucleotide analogue has the formula:

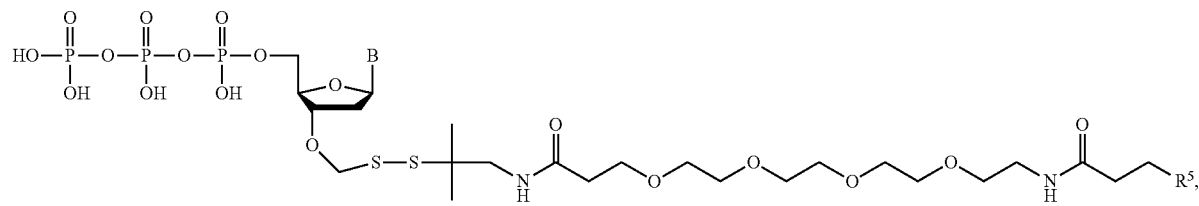

wherein B and R⁵ are as described herein.

In embodiments, the nucleotide analogue has the formula:

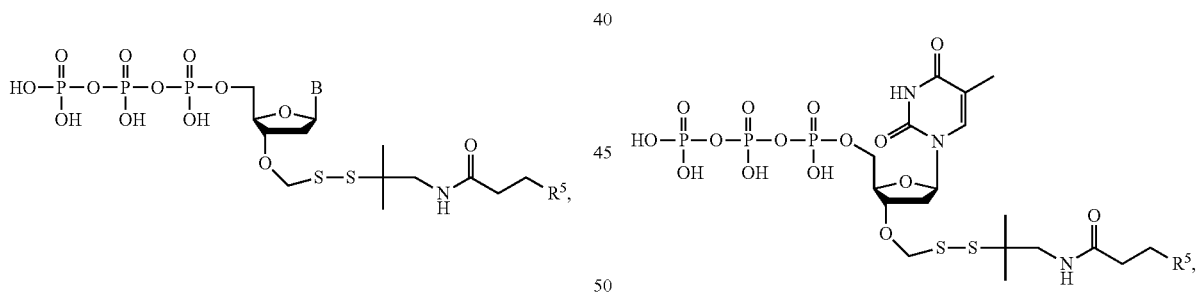

wherein B and R⁵ are as described herein.

In embodiments, the nucleotide analogue has the formula:

wherein R⁵ is as described herein.

In embodiments, the nucleotide analogue has the formula:

wherein R⁵ is as described herein.

In embodiments, the nucleotide analogue has the formula:

wherein R⁵ is as described herein.

In embodiments, the nucleotide analogue has the formula:

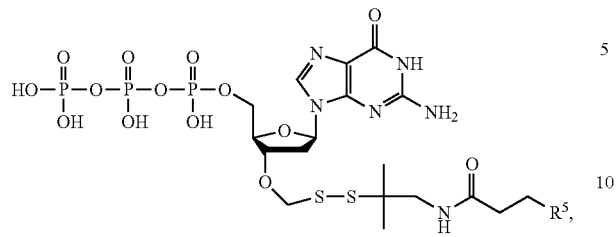

wherein R⁵ is as described herein.

In embodiments, the nucleotide analogue has the formula:

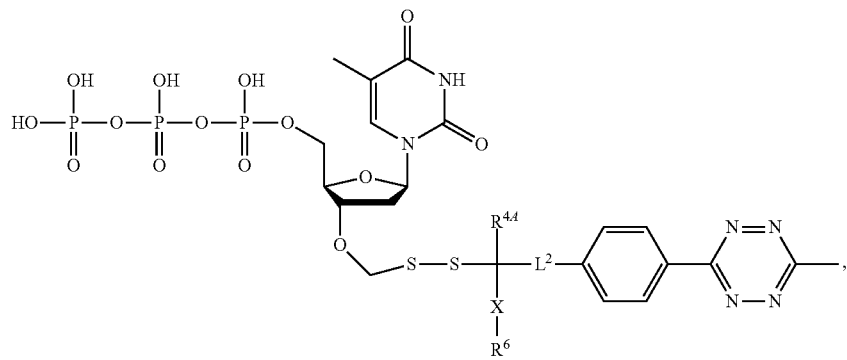

wherein $R^{4A}$, $L^2$, $R^5$, and $R^6$ are as described herein.

In embodiments, the nucleotide analogue has the formula:

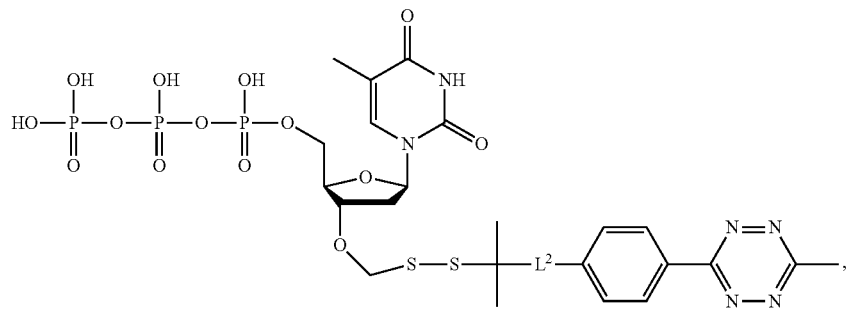

wherein $L^2$ and $R^5$ are as described herein.

In embodiments, the nucleotide analogue has the formula:

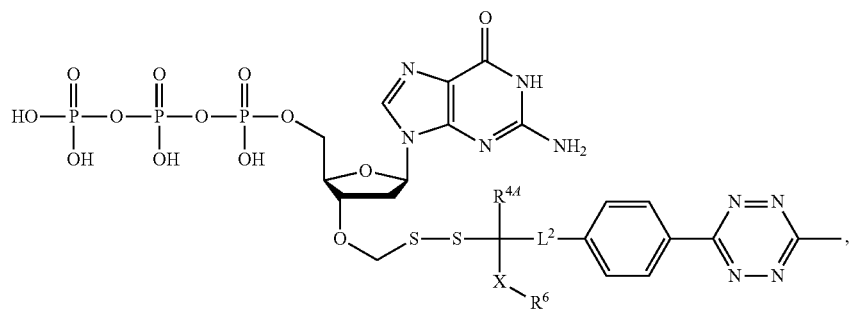

wherein $R^{4A}$, $L^2$, $R^5$, and $R^6$ are as described herein.

In embodiments, the nucleotide analogue has the formula:

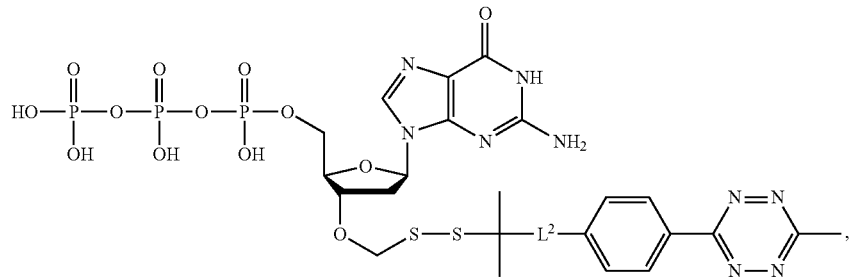

wherein $L^2$ and $R^5$ are as described herein.

In embodiments, the nucleotide analogue has the formula:

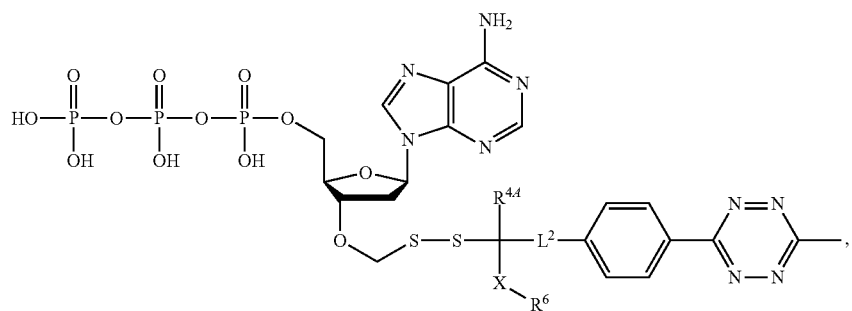

wherein $R^{4A}$, $L^2$, $R^5$, and $R^6$ are as described herein.

In embodiments, the nucleotide analogue has the formula:

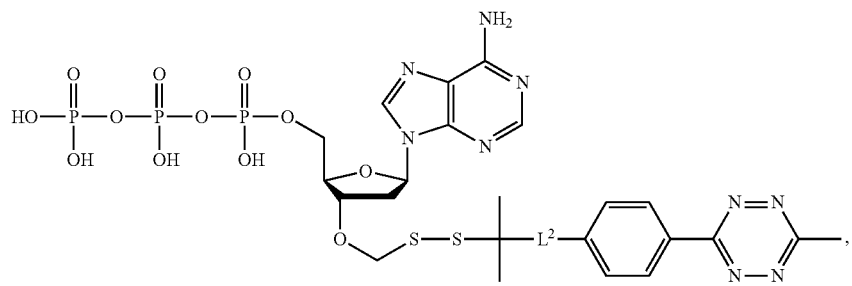

wherein $L^2$ and $R^5$ are as described herein.

In embodiments, the nucleotide analogue has the formula:

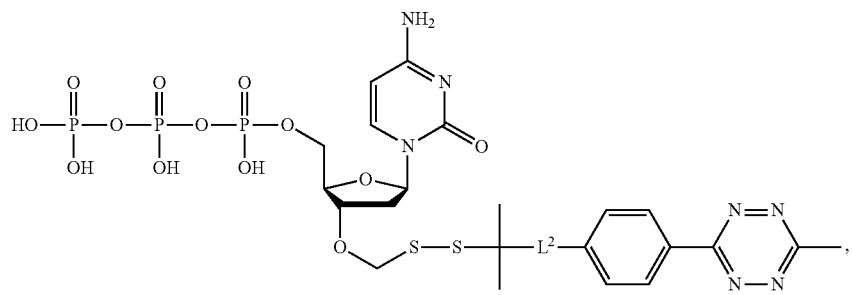

wherein $L^2$ and $R^5$ are as described herein.

In embodiments, the nucleotide analogue has the formula:

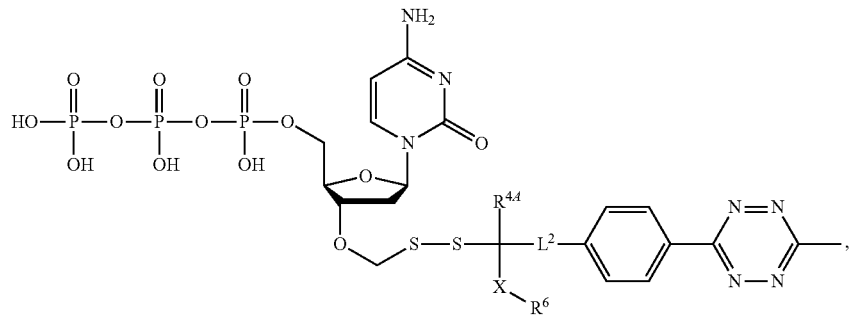

wherein $R^{4A}$, $L^2$, $R^5$, and $R^6$ are as described herein.

In embodiments, the nucleotide analogue has the formula:

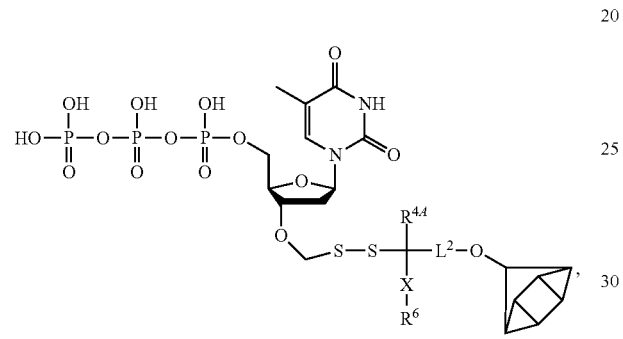

wherein $R^{4A}$, $L^2$, $R^5$, and $R^6$ are as described herein.

In embodiments, the nucleotide analogue has the formula:

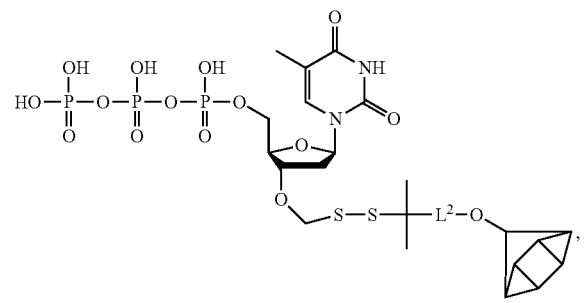

wherein $L^2$ and $R^5$ are as described herein.

In embodiments, the nucleotide analogue has the formula:

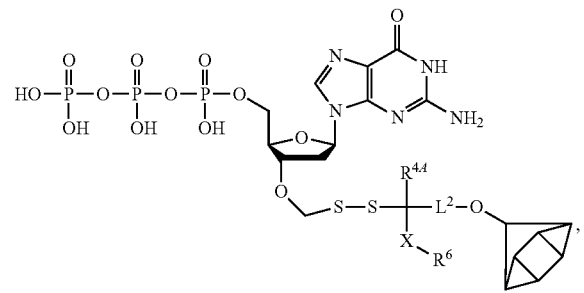

wherein $R^{4A}$, $L^2$, $R^5$, and $R^6$ are as described herein.

In embodiments, the nucleotide analogue has the formula:

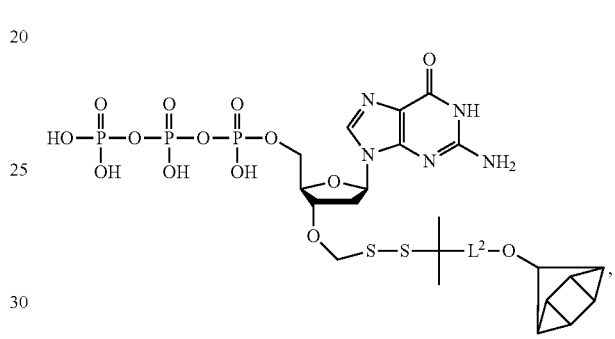

wherein $L^2$ and $R^5$ are as described herein.

In embodiments, the nucleotide analogue has the formula:

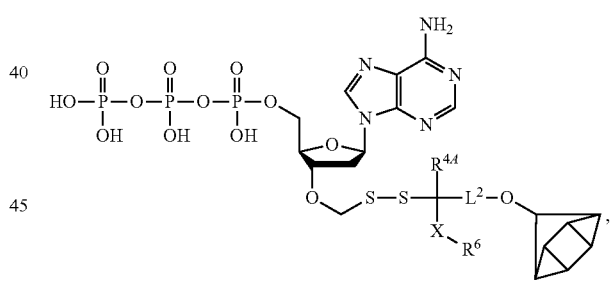

wherein $R^{4A}$, $L^2$, $R^5$, and $R^6$ are as described herein.

In embodiments, the nucleotide analogue has the formula:

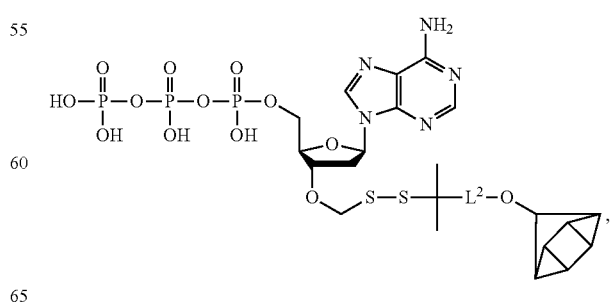

wherein $L^2$ and $R^5$ are as described herein.

In embodiments, the nucleotide analogue has the formula:

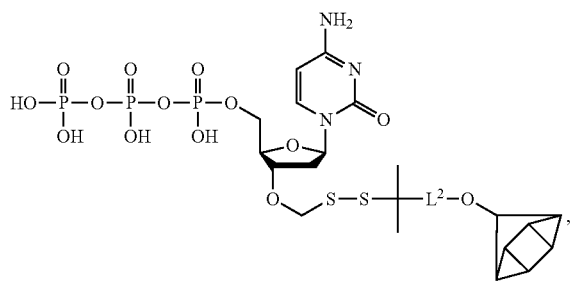

wherein $L^2$ and $R^5$ are as described herein.

In embodiments, the nucleotide analogue has the formula:

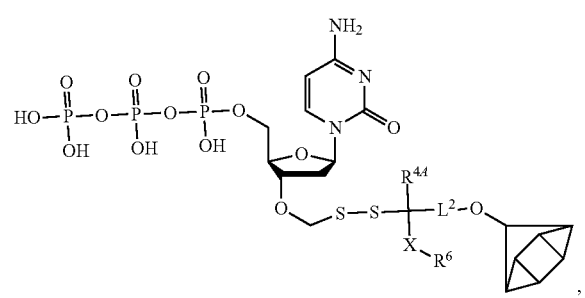

wherein $R^{4A}$, $L^2$, $R^5$, and $R^6$ are as described herein.

In embodiments, the nucleotide analogue has the formula:

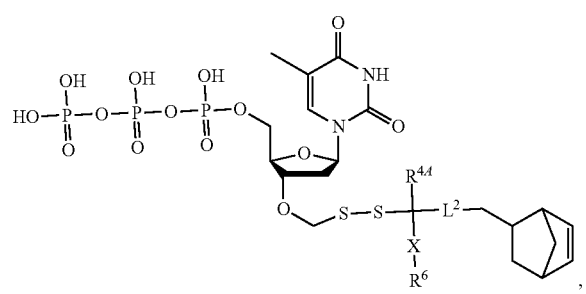

wherein $R^{4A}$, $L^2$, $R^5$, and $R^6$ are as described herein.

In embodiments, the nucleotide analogue has the formula:

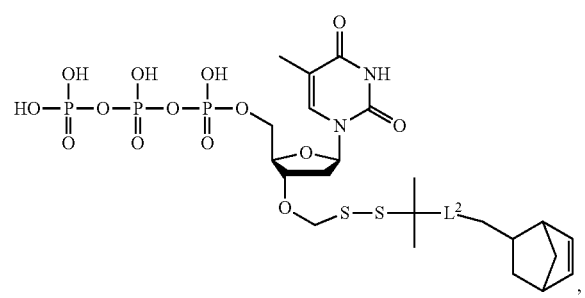

wherein $L^2$ and $R^5$ are as described herein.

In embodiments, the nucleotide analogue has the formula:

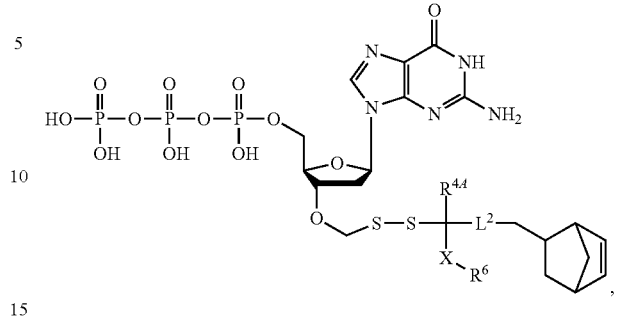

wherein $R^{4A}$, $L^2$, $R^5$, and $R^6$ are as described herein.

In embodiments, the nucleotide analogue has the formula:

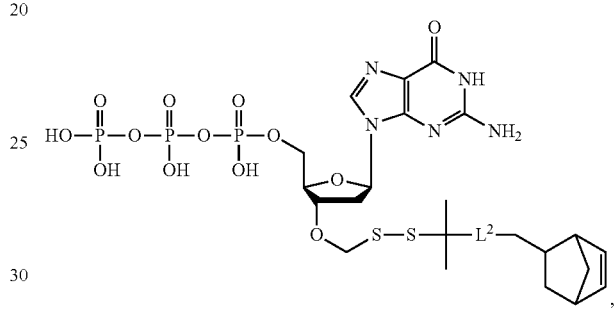

wherein $L^2$ and $R^5$ are as described herein.

In embodiments, the nucleotide analogue has the formula:

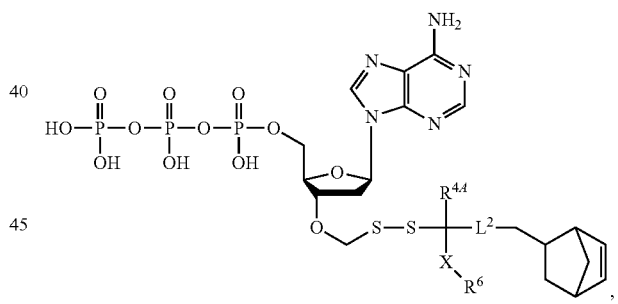

wherein $R^{4A}$, $L^2$, $R^5$, and $R^6$ are as described herein.

In embodiments, the nucleotide analogue has the formula:

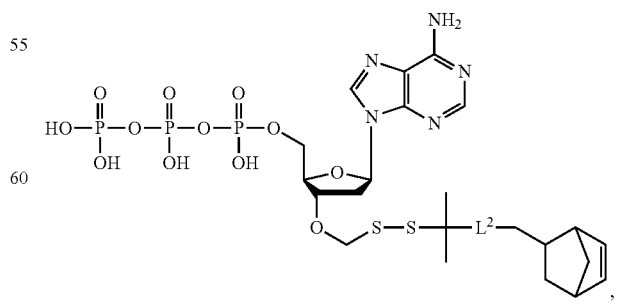

wherein $L^2$ and $R^5$ are as described herein.

In embodiments, the nucleotide analogue has the formula:

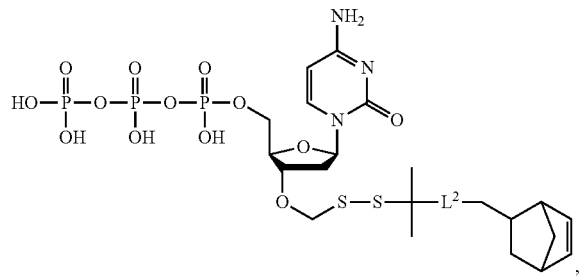

wherein $L^2$ and $R^5$ are as described herein.

In embodiments, the nucleotide analogue has the formula:

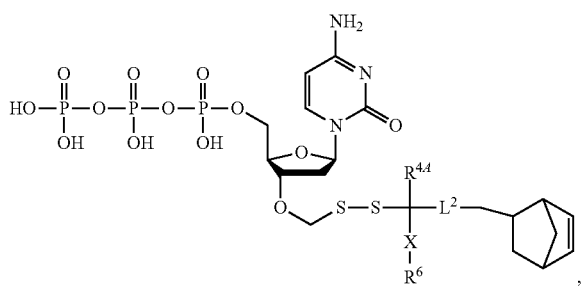

wherein $R^{4A}$, $L^2$, $R^5$, and $R^6$ are as described herein.

In embodiments, the nucleotide analogue has the formula:

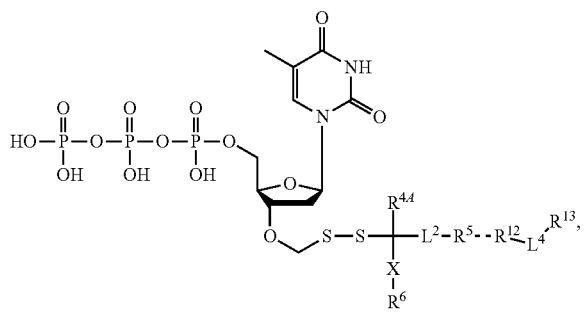

wherein $R^{4A}$, $R^{12}$, $L^4$, $R^{13}$, $L^2$, $R^5$, and $R^6$ are as described herein.

In embodiments, the nucleotide analogue has the formula:

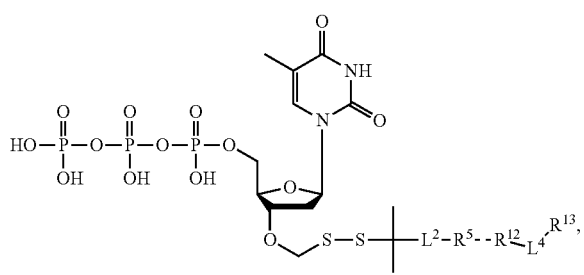

wherein $R^{12}$, $L^4$, $R^{13}$, $L^2$, and $R^5$ are as described herein.

In embodiments, the nucleotide analogue has the formula:

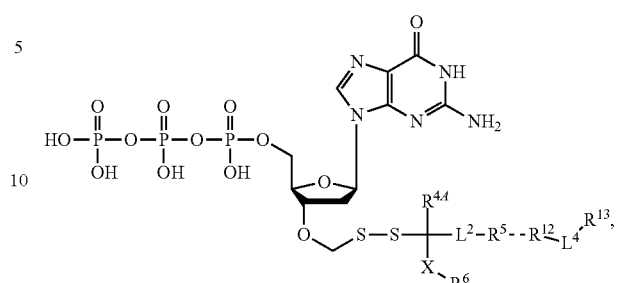

wherein $R^{4A}$, $R^{12}$, $L^4$, $R^{13}$, $L^2$, $R^5$, and $R^6$ are as described herein.

In embodiments, the nucleotide analogue has the formula:

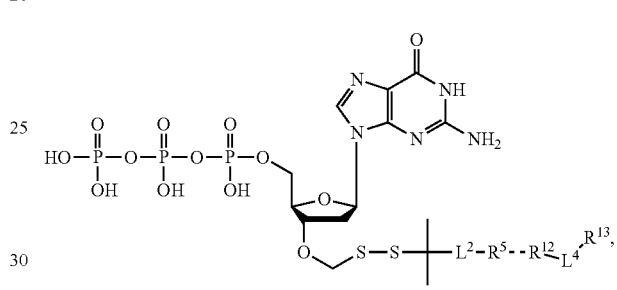

wherein $R^{12}$, $L^4$, $R^{13}$, $L^2$, and $R^5$ are as described herein.

In embodiments, the nucleotide analogue has the formula:

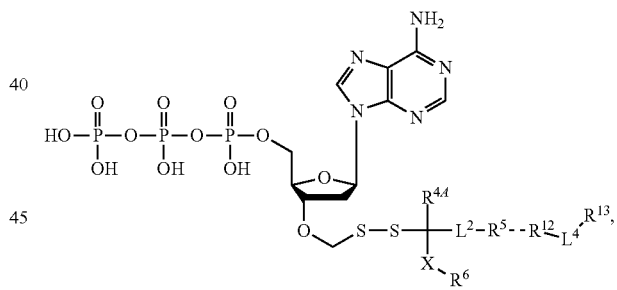

wherein $R^{4A}$, $R^{12}$, $L^4$, $R^{13}$, $L$, $R^5$, and $R^6$ are as described herein.

In embodiments, the nucleotide analogue has the formula:

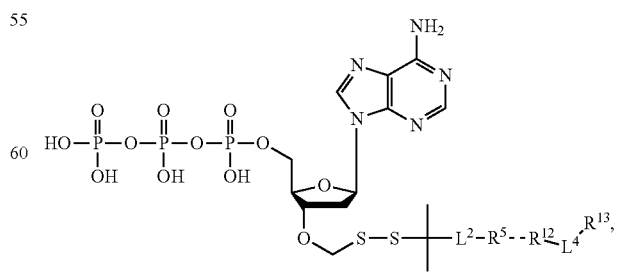

wherein $R^{12}$, $L^4$, $R^{13}$, $L^2$, and $R^5$ are as described herein.

In embodiments, the nucleotide analogue has the formula:

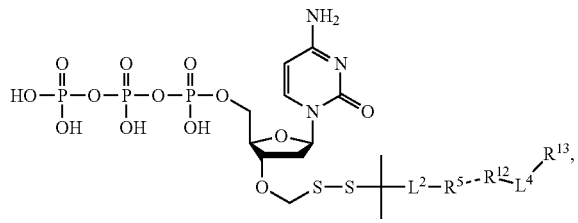

wherein $R^{12}$, $L^4$, $R^{13}$, $L^2$, and $R^5$ are as described herein.

In embodiments, the nucleotide analogue has the formula:

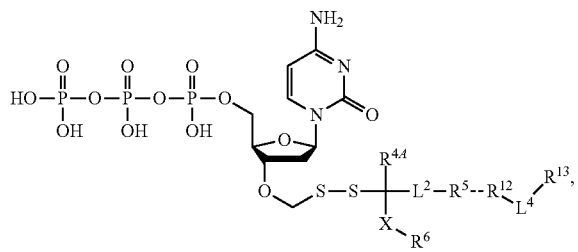

wherein $R^{4A}$, $R^{12}$, $L^4$, $R^{13}$, $L^2$, $R^5$, and $R^6$ are as described herein.

In embodiments, the nucleotide analogue has the formula:

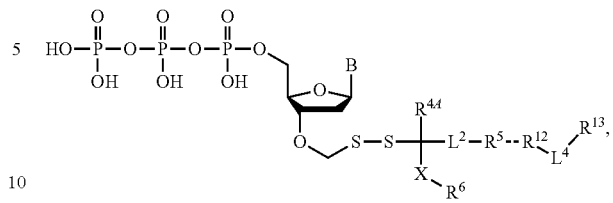

wherein B, $R^4$, $R_{12}$, $L^4$, $R^{13}$, X, and $R^6$ are as described herein.

In embodiments, the nucleotide analogue has the formula:

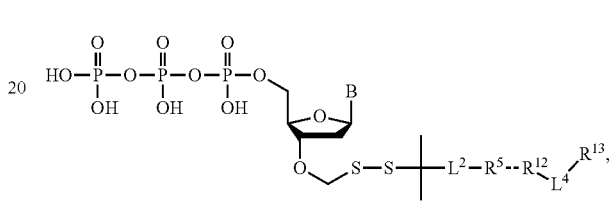

wherein B, $R^4$, X, $R^{12}$, $L^4$, $R^{13}$, and $R^6$ are as described herein.

In embodiments, the nucleotide analogue has the formula:

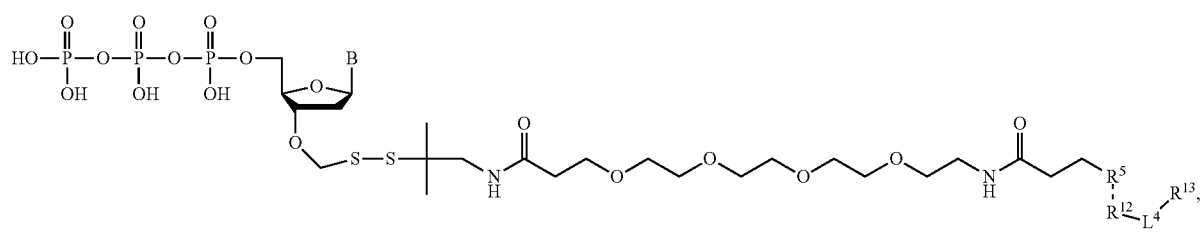

wherein $R^{12}$, $L^4$, $R^{13}$, B, and $R^5$ are as described herein.

In embodiments, the nucleotide analogue has the formula:

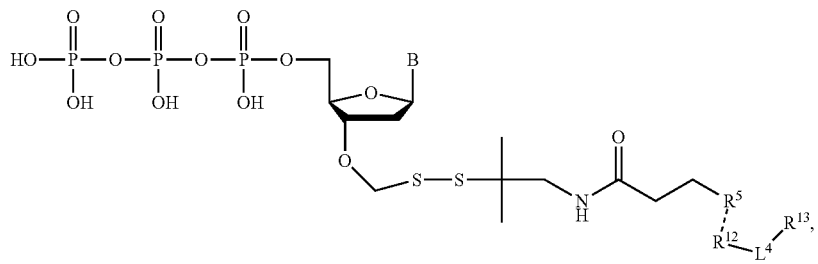

wherein $R^{12}$, $L^4$, $R^{13}$, B, and $R^5$ are as described herein.

In embodiments, the nucleotide analogue has the formula:

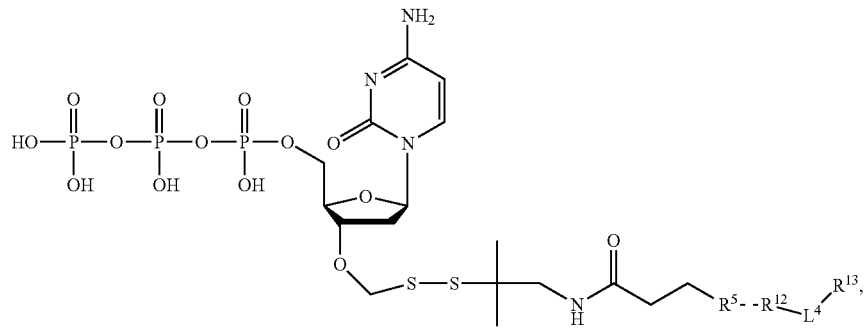

wherein $R^{12}$, $L^4$, $R^{13}$, and $R^5$ are as described herein.

In embodiments, the nucleotide analogue has the formula:

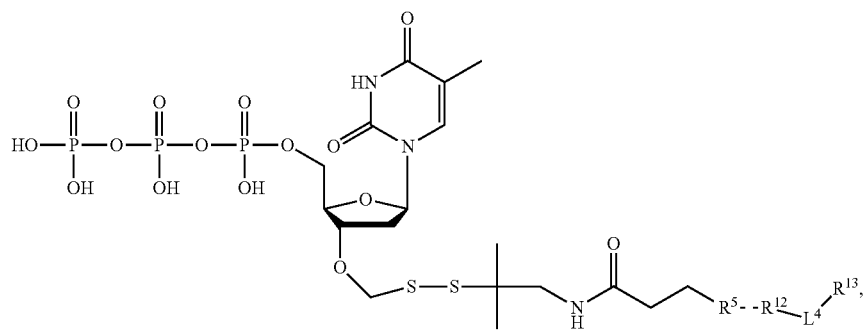

wherein $R^{12}$, $L^4$, $R^{13}$, and $R^5$ are as described herein.

In embodiments, the nucleotide analogue has the formula:

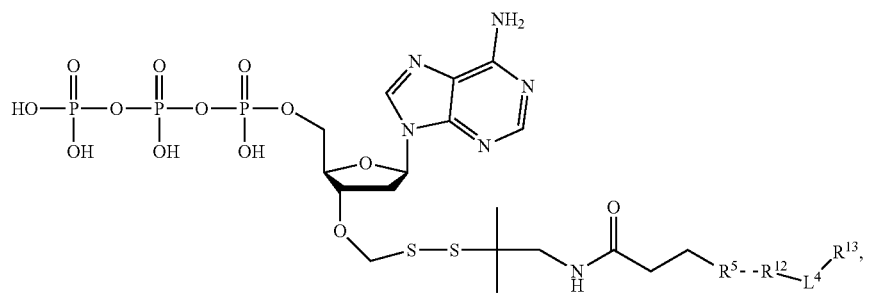

wherein $R^{12}$, $L^4$, $R^{13}$, and $R^5$ are as described herein.

In embodiments, the nucleotide analogue has the formula:

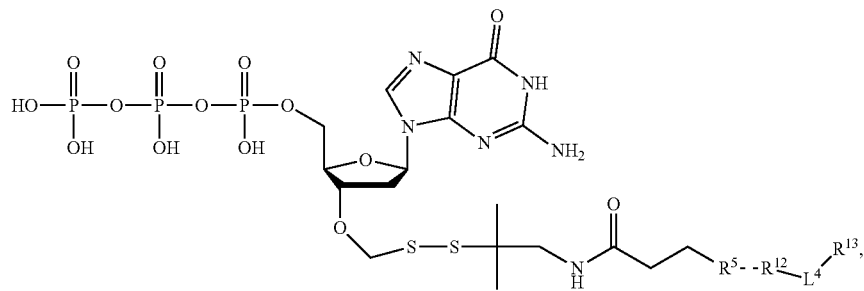

wherein $R^{12}$, $L^4$, $R^{13}$, and $R^5$ are as described herein.

In embodiments, the nucleotide analogue has the formula:

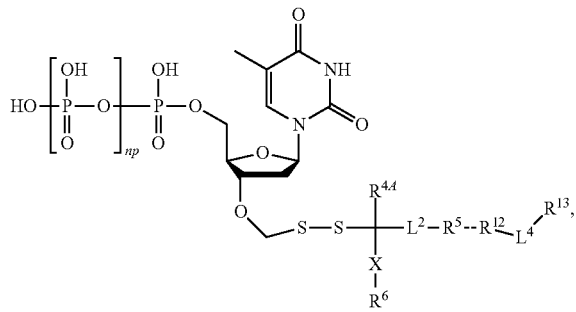

wherein $R^{12}$, $L^4$, $R^{13}$, np, $R^{4A}$, $L^2$, $R^5$, and $R^6$ are as described herein.

In embodiments, the nucleotide analogue has the formula:

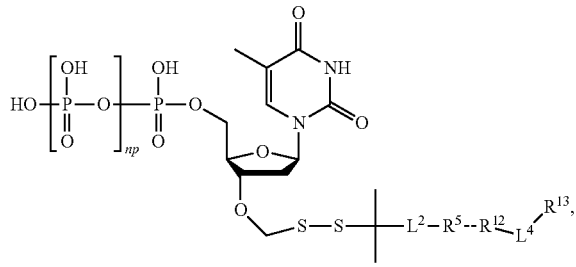

wherein $R^{12}$, $L^4$, $R^{13}$, np, $L^2$, and $R^5$ are as described herein.

In embodiments, the nucleotide analogue has the formula:

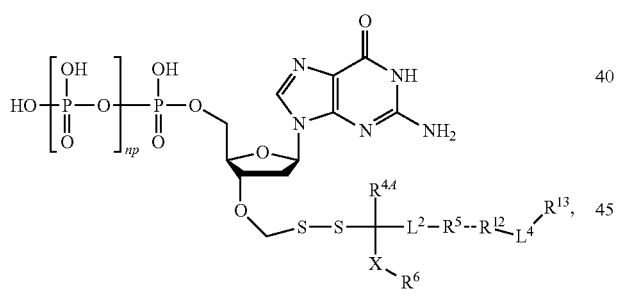

wherein $R^{12}$, $L^4$, $R^{13}$, np, $R^{4A}$, $L^2$, $R^5$, and $R^6$ are as described herein.

In embodiments, the nucleotide analogue has the formula:

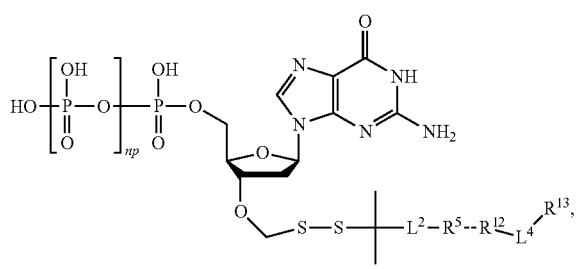

wherein $R^{12}$, $L^4$, $R^{13}$, np, $L^2$, and $R^5$ are as described herein.

In embodiments, the nucleotide analogue has the formula:

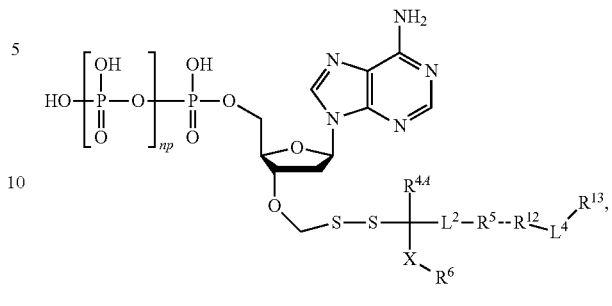

wherein $R^{12}$, $L^4$, $R^{13}$, np, $R^{4A}$, $L^2$, $R^5$, and $R^6$ are as described herein.

In embodiments, the nucleotide analogue has the formula:

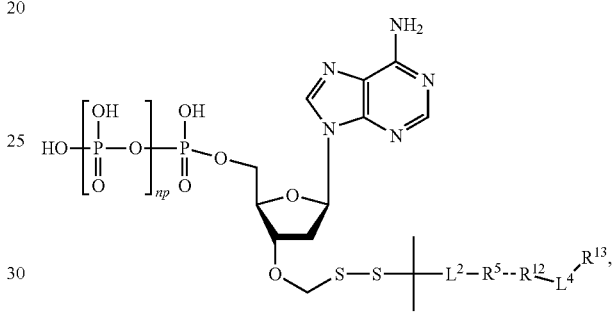

wherein $R^{12}$, $L^4$, $R^{13}$, np, $L^2$, and $R^5$ are as described herein.

In embodiments, the nucleotide analogue has the formula:

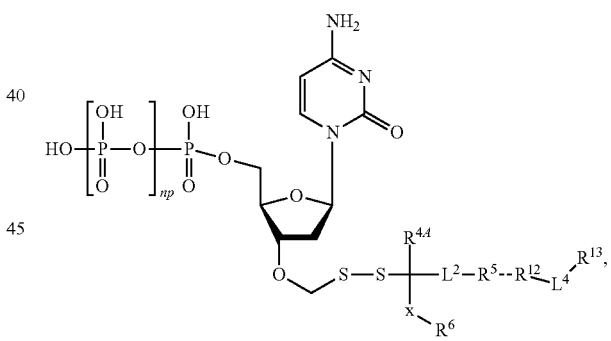

wherein $R^{12}$, $L^4$, $R^{13}$, np, $L^2$, and $R^5$ are as described herein.

In embodiments, the nucleotide analogue has the formula:

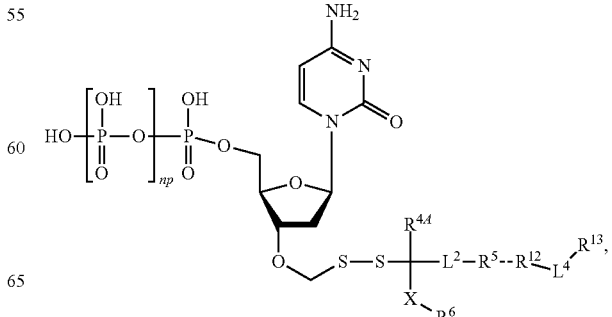

wherein $R^{12}$, $L^4$, $R^{13}$, np, $R^{4A}$, $L^2$, $R^5$, and $R^6$ are as described herein.

In embodiments, the nucleotide analogue has the formula:

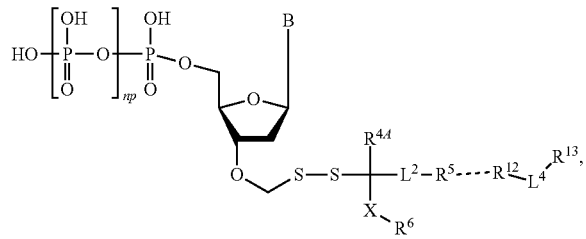

wherein $R^{12}$, $L^4$, $R^{13}$, np, B, $R^4$, X, and $R^6$ are as described herein.

In embodiments, the nucleotide analogue has the formula:

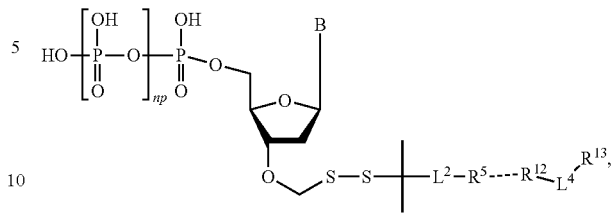

wherein $R^{12}$, $L^4$, $R^{13}$, np, B, $R^4$, X, and $R^6$ are as described herein.

In embodiments, the nucleotide analogue has the formula:

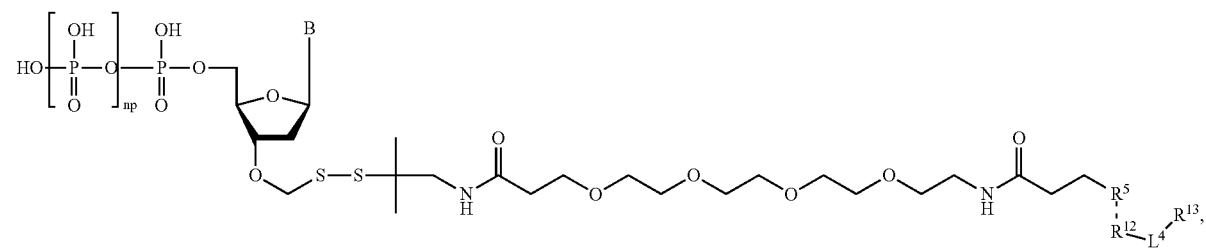

wherein $R^{12}$, $L^4$, $R^{13}$, np, B, and $R^5$ are as described herein.

In embodiments, the nucleotide analogue has the formula:

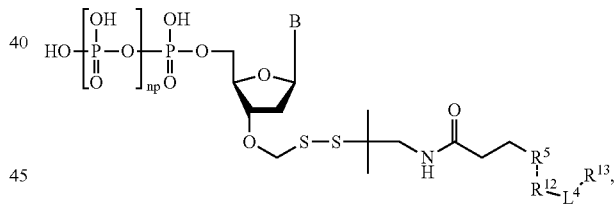

wherein $R^{12}$, $L^4$, $R^{13}$, np, B, and $R^5$ are as described herein.

In embodiments, the nucleotide analogue has the formula:

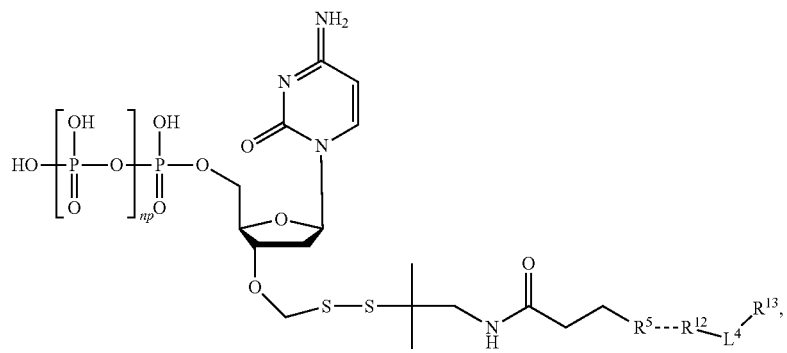

wherein $R^{12}$, $L^4$, $R^{13}$, np, and $R^5$ are as described herein.

In embodiments, the nucleotide analogue has the formula:

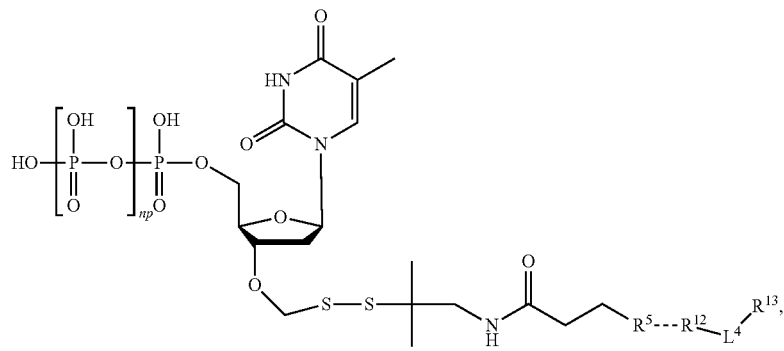

wherein $R^{12}$, $L^4$, $R^{13}$, np, and $R^5$ are as described herein.

In embodiments, the nucleotide analogue has the formula:

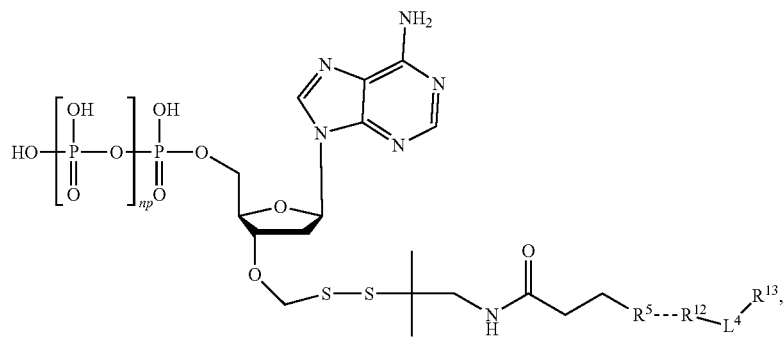

wherein $R^{12}$, $L^4$, $R^{13}$, np, and $R^5$ are as described herein.

In embodiments, the nucleotide analogue has the formula:

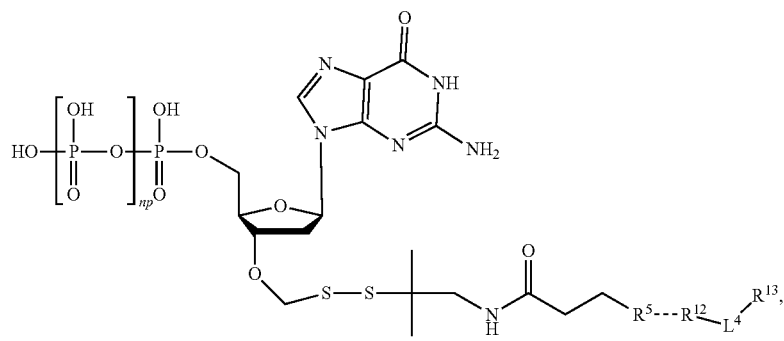

wherein $R^{12}$, $L^4$, $R^{13}$, np, $R^5$ are as described herein.

In embodiments, the nucleotide analogue is a nucleotide analogue described herein (e.g., in an aspect, embodiment, example, figure, table, scheme, or claim).

III. Methods of use

In an aspect is provided a method of incorporating a nucleotide analogue into a nucleic acid sequence including combining a thermophilic nucleic acid polymerase, a primer hybridized to nucleic acid template, and a nucleotide analogue including a detectable label, within a reaction vessel and allowing the thermophilic nucleic acid polymerase to incorporate the nucleotide analogue into the primer thereby incorporating a nucleotide analogue into a nucleic acid sequence.

In an aspect is provided a method of incorporating a nucleotide analogue into a nucleic acid sequence including combining a nucleic acid polymerase (e.g., thermophilic, 9° N and mutants thereof, Phi29 and mutants thereof), a primer hybridized to nucleic acid template, and a nucleotide analogue including a detectable label, within a reaction vessel and allowing the thermophilic nucleic acid polymerase to incorporate the nucleotide analogue into the primer thereby incorporating a nucleotide analogue into a nucleic acid sequence.

In an aspect is provided a method for sequencing a nucleic acid, including: (i) incorporating in series with a nucleic acid polymerase (e.g., thermophilic, 9° N and mutants thereof, Phi29 and mutants thereof), within a reaction vessel, one of four different labeled nucleotide analogues into a primer to create an extension strand, wherein the primer is hybridized to the nucleic acid and wherein each of the four different labeled nucleotide analogues include a unique detectable label; (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues are of the structure formula:

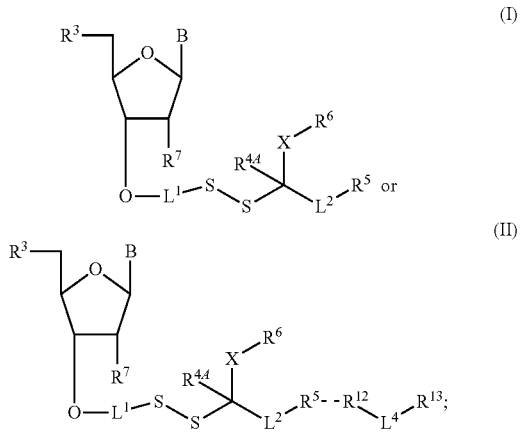

wherein the first of the four different labeled nucleotide analogues, B is a thymine or uracil hybridizing base; in the second of the four different labeled nucleotide analogues, B is an adenine hybridizing base; in the third of the four different labeled nucleotide analogues, B is an guanine hybridizing base; and in the fourth of the four different labeled nucleotide analogues, B is an cytosine hybridizing base. B is a base or analogue thereof. $L^1$ is covalent linker. $L^2$ is covalent linker. $L^4$ is covalent linker. X is a bond, O, $NR^{64}$, or S. $R^3$ is —OH, monophosphate, polyphosphate or a nucleic acid. In embodiments, $R^3$ is a triphosphate or higher polyphosphate. $R^{44}$ and $R^{64}$ are independently hydrogen, —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, anchor moiety, or affinity anchor moiety. $R^6$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen or —$OR^{74}$, wherein $R^{74}$ is hydrogen or a polymerase-compatible moiety. $R^{12}$ is a complementary affinity anchor moiety binder. $R^{13}$ is a detectable label. The symbol "----" is a non-covalent bond. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof.

In another aspect is provided a method of incorporating a nucleotide analogue into a nucleic acid sequence including combining a thermophilic nucleic acid polymerase, a primer hybridized to nucleic acid template, and a nucleotide analogue, within a reaction vessel and allowing the thermophilic nucleic acid polymerase to incorporate the nucleotide analogue into the primer thereby incorporating a nucleotide analogue into a nucleic acid sequence, wherein the nucleotide analogue includes a fluorescent dye with a molecular weight of at least about 140 Daltons, and wherein the fluorescent dye is covalently bound at the 3' position of the nucleotide analogue.

In an aspect is provided a method of incorporating a nucleotide analogue into a nucleic acid sequence comprising combining a nucleic acid polymerase, a primer hybridized to nucleic acid template, and a nucleotide analogue, within a reaction vessel and allowing said nucleic acid polymerase to incorporate said nucleotide analogue into said primer thereby incorporating a nucleotide analogue into a nucleic acid sequence, wherein said nucleotide analogue comprises a fluorescent dye with a molecular weight of at least about 140 Daltons, wherein the fluorescent dye is covalently bound at the 3' position of said nucleotide analogue for sequence determination, and wherein after removal of the fluorescent dye by cleaving the 3'-O linker to regenerate the 3'-OH on the DNA extension product allows continuous nucleotide analogue incorporation and detection of multiple bases.

In embodiments, at least one of the four different labeled nucleotide analogues is an orthogonally cleavable labeled nucleotide analogue including a cleavable linker (e.g., DTM), the orthogonally cleavable labeled nucleotide analogue having the structure as described herein, and wherein the method further includes, after each of the incorporating steps, adding to the reaction vessel a cleaving reagent capable of cleaving the cleavable linker (e.g., DTM). In embodiments, the cleaving reagent is an acid, base, oxidizing agent, reducing agent, Pd(0), tris-(2-carboxyethyl)phosphine, dilute nitrous acid, fluoride, tris(3-hydroxypropyl) phosphine), sodium dithionite ($Na_2S_2O_4$), or hydrazine ($N_2H_4$). In embodiments the nucleic acid sequence is single-stranded DNA.

In embodiments, the method includes contacting the single-stranded DNA, wherein the single-stranded DNA is bound to a polymerase which is in turn attached to a membrane-embedded nanopore in an electrolyte solution, wherein the single-stranded DNA has a primer hybridized to a portion thereof, and determining the sequence of the single stranded DNA template, following the steps of: (a) addition of four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O-being blocked by a cleavable linker and anchor moiety, preventing further incorporation in this step; (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a); (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide; (d) cleavage of the 3'-O-cleavable linker-attached tag by treatment with an appropriate cleaving agent, thus generating a free 3'-OH ready for the next extension reaction; and (e) Iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

In embodiments, the method includes contacting the single-stranded DNA template, wherein the single-strand DNA to be sequenced hybridizes to the primer, wherein the single-stranded primer is conjugated to a membrane-embedded nanopore in an electrolyte solution, and determining the sequence of the single stranded DNA template, following the steps of: (a) addition of polymerase and four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O-being blocked by a cleavable linker and anchor moiety, preventing further incorporation in this step; (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a); (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide; (d) cleavage of the 3'-O-cleavable linker-attached tag by treatment with an appropriate cleaving agent, thus generating a free 3'-OH ready for the next extension reaction; and (e) Iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

In embodiments, the method includes sequencing nucleic acid including: a) providing a nucleic acid template hybridized to a primer; b) extending the primer hybridized to the nucleic acid template with a labeled nucleotide or nucleotide analog, wherein the labeled nucleotide or nucleotide analog includes nucleotide analogs with a label linked to the base and a blocking group on the 3'-hydroxyl group, and nucleotides or nucleotide analogs with a cleavable label blocking the 3' OH; and c) identifying the labeled nucleotide, so as to sequence the nucleic acid. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof.

In embodiments, at least four of the nucleotide analogues (e.g., 3'-O-Anchor-Cleavable Linker nucleotides) include a triphosphate or a polyphosphate, a base which is adenine, guanine, cytosine, thymine, or uracil, or a derivative of each thereof, and an anchor molecule covalently coupled to the 3'-O-position of the nucleotide sugar moiety including a cleavable linker at the 3'-O-position.

In embodiments, the method includes simultaneously sequencing a plurality of different nucleic acids, including: a) extending a plurality of priming DNA strands hybridized to template DNAs, each of which includes one of the priming DNA strands, by incorporating a labeled nucleotide; and b) identifying each labeled nucleotide, so as to simultaneously sequence the plurality of different nucleic acids.

In embodiments, $R^5$ is anchor moiety, the method further including, after the incorporating, labeling the nucleotide analog with a detectable label. In embodiments, $R^5$ is an affinity anchor moiety. In embodiments, the labeling includes adding to the reaction vessel a compound having the formula $R^{12}$-$L^4$-$R^{13}$, wherein $R^{12}$ is a complementary affinity anchor moiety binder; $R^{13}$ is a detectable label; and $L^4$ is a covalent linker.

In embodiments, $R^5$ is a chemically reactive anchor moiety. In embodiments, $R^5$ is a bioconjugate reactive group.

In embodiments, the labeling includes adding to the reaction vessel a compound having the formula $R^{12z}$-$L^{4z}$-$R^{13}$, wherein $R^{12z}$ is a complementary anchor moiety reactive group; $R^{13}$ is a detectable label; and $L^{4Z}$ is a covalent linker. In embodiments, $R^{12z}$-$L^{4z}$-$R^{13}$ has the structure as described herein. In embodiments, $L^{4z}$ is a cleavable linker.

In embodiments, the method further including, after the incorporating, cleaving the cleavable linker (e.g., DTM) with a cleaving reagent. In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$).

In embodiments, the method forms part of a sequencing by synthesis method. In embodiments, the nucleotide analogue is 3'-O-Alexa488-t-Butyldithiomethyl-dCTP, 3'-O-Cy5-t-Butyldithiomethyl-dGTP, 3'-O-Rox-t-Butyldithiomethyl-dATP, 3'-O-RG6-t-Butyldithiomethyl-dTTP, 3'-O-Alexa488-PEG$_4$-t-Butyldithiomethyl-dCTP, 3'-O-RG6-PEG$_4$-t-Butyldithiomethyl-dTTP, 3'-O-Rox-PEG$_4$-t-Butyldithiomethyl-dATP, or 3'-O-Cy5-PEG4-t-Butyldithiomethyl-dGTP.

In embodiments, the thermophilic nucleic acid polymerase is a Taq polymerase, Terminator γ, 9° N polymerase (exo-), Terminator IL, Terminator III, or Terminator IX. In embodiments, the thermophilic nucleic acid polymerase is Terminator γ. In embodiments, the thermophilic nucleic acid polymerase is 9° N polymerase (exo-). In embodiments, the thermophilic nucleic acid polymerase is Terminator II. In embodiments, the thermophilic nucleic acid polymerase is Terminator III. In embodiments, the thermophilic nucleic acid polymerase is Therminator IX. In embodiments, the thermophilic nucleic acid polymerase is a Taq polymerase. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof. In embodiments, the polymerase is a non-thermophilic nucleic acid polymerase.

In embodiments, the method is a method described in a figure and corresponding figure description (e.g., FIGS. 3A-3B, FIGS. 13A-13B, FIGS. 16A-16C, FIGS. 18A-18C, FIGS. 20A-20C, FIG. 22, FIG. 47, FIGS. 48A-48B, FIGS. 49A-49B, FIGS. 50A-50B, FIGS. 51A-51B, FIGS. 52A-52C, FIG. 74, FIG. 75, FIG. 76, FIG. 77, FIG. 78, FIG. 79, or FIG. 80).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Terms defined herein refer only to aspects and embodiments within this "Embodiments" section.

For the embodiments below, each embodiment disclosed herein is contemplated as being applicable to each of the other disclosed embodiments. In addition, the elements recited in the compound embodiments can be used in the composition and method embodiments described herein and vice versa.

As used herein, and unless stated otherwise, each of the following terms shall have the definition set forth below. A=Adenine; C=Cytosine; G=Guanine; T=Thymine; U=Uracil; DNA=Deoxyribonucleic acid; RNA=Ribonucleic acid; "Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives or analogs (also referred to herein as analogues) of these bases are well known in the art, and are exemplified in PCR Systems, Reagents and Consumables (Perkin Elmer Catalogue 1996-1997, Roche Molecular Systems, Inc., Branchburg, New Jersey, USA).

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

"Substrate" or "Surface" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

As used herein, unless otherwise specified, a base which is "unique" or "different from" another base or a recited list of bases shall mean that the base has a different structure from the other base or bases. For example, a base that is "unique" or "different from" adenine, thymine, and cytosine would include a base that is guanine or a base that is uracil.

As used herein, unless otherwise specified, "primer" means an oligonucleotide that upon forming a duplex with a polynucleotide template, is capable of acting as a point of polymerase incorporation and extension from its 3' end along the template, thereby resulting in an extended duplex.

As used herein, unless otherwise specified, a label or tag moiety which is different from the label or tag moiety of a referenced molecule means that the label or tag moiety has a different chemical structure from the chemical structure of the other/referenced label or tag moiety.

In some embodiments of the invention, vibrational spectroscopy is used to detect the presence of incorporated nucleotide analogs. Vibrational spectroscopy is a spectrographic analysis where the sample is illuminated with incident radiation in order to excite molecular vibrations. Vibrational excitation, caused by molecules of the sample absorbing, reflecting or scattering a particular discrete amount of energy, is detected and can be measured. The two major types of vibrational spectroscopy are infrared (usually FTIR) and Raman. If FTIR is employed, then the IR spectra of the nucleotide analogs are measured. If Raman is employed, then the Raman spectra of the nucleotide analogs is measured (for example of the nucleotide analogs and in the methods described herein). These methods are disclosed in Patent Applications 20150080232 and 20160024570 (Ju et al).

In certain embodiments, the polymerase, single-stranded polynucleotide, RNA, or primer is bound to a solid substrate via 1,3-dipolar azide-alkyne cycloaddition chemistry. In an embodiment the polymerase, DNA, RNA, or primer, is bound to the solid substrate via a polyethylene glycol molecule. In an embodiment the polymerase, DNA, RNA, primer, or probe is alkyne-labeled. In an embodiment the polymerase, DNA, RNA, primer, or probe is bound to the solid substrate via a polyethylene glycol molecule and the solid substrate is azide-functionalized. In an embodiment the polymerase, DNA, RNA, or primer, is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded polynucleotide. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In one embodiment, the surface or substrate is a SERS-prepared surface or substrate designed specifically for detection of a label nucleotide. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may include DNA functionalized sites, and may have a gap size range from 50 nm to 1 nm. In another embodiment, a nucleotide polymerase is immobilized within the gap.

In another embodiment the nucleotide polymerase SERS-prepared and designed specifically for detection of a labeled nucleotide and/or nucleoside. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may have a gap size range from 12 nm to 1 nm. In another embodiment, a nucleotide polymerase is immobilized within on a surface, substrate, or nanoplasmonic antenna on a surface.

In another embodiment, the surface comprises a DNA origami scaffold or an array of DNA origami scaffolds. It is also contemplated that the DNA origami scaffold further comprising a primer molecules positioned between Au and Ag nanoparticles and nanorods located at specified binding sites.

In a further embodiment, the surface comprises plasmonic crystals or an array of plasmonic structures. For example, the plasmonic structures may be periodic TiO—Au—TiO structures.

In various embodiments the polymerase, nucleic acid samples, DNA, RNA, primer, or probe are separated in discrete compartments, wells or depressions on a surface.

In this invention methods are provided wherein about 1000 or fewer copies of the polymerase, nucleic acid sample, DNA, RNA, or primer are bound to the substrate. This invention also provides the instant methods wherein $2 \times 10^7$, $1 \times 10^7$, $1 \times 10^6$ or $1 \times 10^4$ or fewer copies of the polymerase, nucleic acid sample, DNA, RNA, or primer are bound to the substrate or surface.

In some embodiments, the immobilized polymerase, nucleic acid sample, DNA, RNA, or primer, is immobilized at a high density. This invention also provides the instant methods wherein over or up to $1 \times 10^7$, $1 \times 10^8$, $1 \times 10^9$ copies of the polymerase, nucleic acid sample, DNA, RNA, or primer are bound to the substrate or surface.

In other embodiments of the methods and/or compositions of this invention, the DNA is single-stranded. In other embodiments of the methods or of the compositions described herein, the single-stranded polynucleotide is replaced with an RNA that is single-stranded.

Because of well-understood base-pairing rules, determining the wavenumber of the Raman spectroscopy peak of a dNTP analog incorporated into a primer or DNA extension product, and thereby the identity of the dNTP analog that was incorporated, permits identification of the complementary nucleotide residue in the single-stranded polynucleotide that the primer or DNA extension product is hybridized to. Thus, if the dNTP analog that was incorporated has a unique wavenumber in the Raman spectroscopy peak identifying it as comprising an adenine, a thymine, a cytosine, or a guanine, then the complementary nucleotide residue in the single-stranded polynucleotide is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analog that was incorporated comprises an adenine, a uracil, a cytosine, or a guanine, then the complementary nucleotide residue in the single-stranded RNA is identified as a uracil, an adenine, a guanine or a cytosine, respectively.

Incorporation into an oligonucleotide or polynucleotide (such as a primer or DNA extension strand) of a nucleotide and/or nucleoside analog means the formation of a phosphodiester bond between the 3' carbon atom of the 3' terminal nucleotide residue of the polynucleotide and the 5' carbon atom of the dNTP analog resulting in the loss of pyrophosphate from the dNTP analog.

A Raman spectroscopy system, as can be used in the methods described herein, typically comprises an excitation source (such as a laser, including a laser diode in appropriate configuration, or two or more lasers), a sample illumination system and light collection optics, a wavelength selector (such as a filter or spectrophotometer), and a detection apparatus (such as a CCD, a photodiode array, or a photomultiplier). Interference (notch) filters with cut-off spectral range of $\pm 80$-$120$ cm$^{-1}$ from the laser line can be used for stray light elimination. Holographic gratings can be used. Double and triple spectrometers allow taking Raman spectra without use of notch filters. Photodiode Arrays (PDA) or a Charge-Coupled Devices (CCD) can be used to detect Raman scattered light.

In an embodiment, surface enhanced Raman spectroscopy (SERS) is used which employs a surface treated with one or more of certain metals known in the art to cause SERS effects. In an embodiment the surface is a surface to which the polymerase, polynucleotide, single-stranded polynucleotide, single-stranded DNA polynucleotide, single-stranded RNA, primer, DNA extension strand, or oligonucleotide probe of the methods described herein is attached. Many suitable metals are known in the art. In an embodiment the surface is electrochemically etched silver or treated with/comprises silver and/or gold colloids with average particle size below 20 nm. The wavenumber of the Raman spectroscopy peak of an entity is identified by irradiating the entity with the excitation source, such as a laser, and collecting the resulting Raman spectrum using a detection apparatus. The wavenumber of the Raman spectroscopy peak is determined from the Raman spectrum. In an embodiment, the spectrum measured is from 2000 cm$^{-1}$ to 2300 cm$^{-1}$ and the wavenumber of the Raman spectroscopy peak is the peak wavenumber within that spectrum. In an embodiment the spectrum measured is a sub-range of 2000 cm$^{-1}$ to 2300 cm$^{-1}$ and the Raman spectroscopy peak wavenumber is the peak wavenumber within that spectrum sub-range.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

Unless otherwise defined, all technical and scientific terms used herein have the same meaning as commonly understood by a one of ordinary skill in the art to which this invention belongs.

As used herein, unless otherwise stated, the singular forms 'a', 'an', and 'the' include plural referents unless the context clearly dictates otherwise. It is further noted that the claims may be drafted to exclude any optional element. As such, this statement is intended to serve as antecedent basis for use of such exclusive terminology as 'solely', 'only' and the like in connection with the recitation of claim elements, or use of a 'negative limitation'.

As used herein "anchor" refers to a small chemical moiety that orthogonally and rapidly reacts with another chemical group that carries a detectable label. As used herein, unless otherwise specified, the "cleavable group" refers to a small chemical moiety that can be cleaved by either chemical or photochemical means.

As used herein, unless otherwise specified, a label or tag moiety which is "different" from the label or tag moiety of a referenced molecule means that the label or tag moiety has a different chemical structure from the chemical structure of the other/referenced label or tag moiety.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

The invention provides for a nucleotide analog consisting of (i) a base, (ii) a sugar which may be a deoxyribose or a ribose, (iii) a t-butyldithiomethyl linker bound to the 3'-oxygen of the deoxyribose or ribose, and (iv) a detectable label bound to the t-butyldithiomethyl linker.

The invention also provides for a method for determining the identity of a nucleotide at a predetermined position in a nucleic acid of interest, comprising:
a) providing
  1) the nucleic acid of interest,
  2) a nucleic acid polymerase,
  3) a primer capable of hybridizing to said nucleic acid immediately 3' of such predetermined position,
  4) four different nucleotide analogs of claim 1, each of which consists of one of adenine or an analog of adenine, guanine or an analog of guanine, cytosine or an analog of cytosine, thiamine or an analog of thiamine, and a unique detectable label;

b) incorporating one of said nucleotide analogs onto the end of said primer to form an extension strand;
c) detecting the unique detectable label of the incorporated nucleotide analog so as to thereby identify the incorporated nucleotide analog on the end of said extension strand; and
d) based on the identity of the incorporated nucleotide, determining the identity of the nucleotide at the predetermined position.

The invention also provides for A process for producing a 3'-O-Bodipy-t-Butyldithiomethyl-dNTP, comprising:
a) reacting,
 1) a 5'-O-tert-Butyldimethylsilyl-nucleoside,
 2) acetic acid,
 3) acetic anhydride, and
 4) DMSO under conditions permitting the production of a 3'-O-methylthiomethyl-5'-O-tert-butyldimerthylsilyl-nucleoside;
b) contacting the 3'-O-methylthiomethyl-5'-O-tert-butyldimerthylsilyl-nucleoside produced in step a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

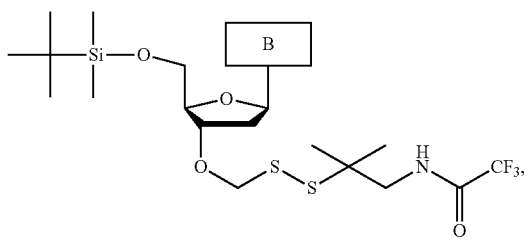

wherein B is a nucleobase;
c) contacting the product produced in step b) with tetrabutylammonium fluoride THF solution under conditions permitting the production of a product having the structure:

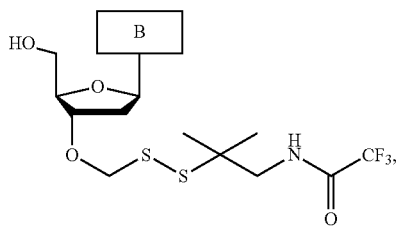

wherein B is a nucleobase;
d) contacting the product produced in step c) with tetrabutylammonium pyrophosphate, 2-chloro-4-H-1,3,2-benzodioxaphosphorin-4-one, iodine solution and ammonium hydroxide under conditions permitting the production of a 3-O—NH$_2$-t-Butyldithiomethyl-dNTP;
e) contacting the 3-O—NH$_2$-t-Butyldithiomethyl-dNTP of step d) with Bodipy FL-NHS ester under conditions permitting the production of the 3'-O-Bodipy-t-Butyldithiomethyl-dNTP.

The invention also provides for a process for producing a 3'-O-Bodipy-PEG4-t-Butyldithiomethyl-dNTP, comprising:

a) reacting,
 1) a 5'-O-tert-Butyldimethylsilyl-nucleoside,
 2) acetic acid,
 3) acetic anhydride, and
 4) DMSO under conditions permitting the production of a 3'-O-methylthiomethyl-5'-O-tert-butyldimerthylsilyl-nucleoside;
b) contacting the 3'-O-methylthiomethyl-5'-O-tert-butyldimerthylsilyl-nucleoside produced in part a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

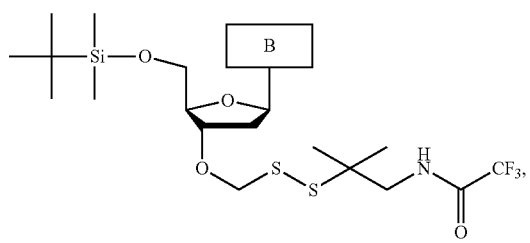

wherein B is a nucleobase;
c) contacting the product produced in step b) with tetrabutylammonium fluoride THF solution under conditions permitting the production of a product having the structure:

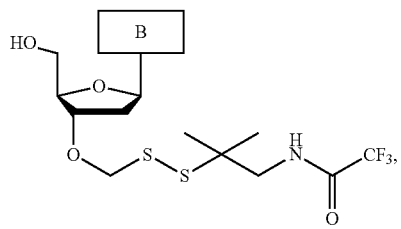

wherein B is a nucleobase;
d) contacting the product produced in step c) with tetrabutylammonium pyrophosphate, 2-chloro-4-H-1,3,2-benzodioxaphosphorin-4-one, iodine solution and ammonium hydroxide under conditions permitting the production of a 3-O—NH$_2$-t-Butyldithiomethyl-dNTP;
e) contacting the 3-O—NH$_2$-t-Butyldithiomethyl-dNTP of step d) with Bodipy-PEG4-Acid, N,N-disuccinimidyl carbonate, and 4-dimethylaminopyridine under conditions permitting the production of the 3'-O-PEG$_4$-Bodipy-t-Butyldithiomethyl-dNTP.

The invention also provides for a process for producing a 3'-O-Rox-t-Butyldithiomethyl-dATP, comprising:
a) reacting,
 1) a N$^4$-Benzoyl-5'-O-tert-butyldimethylsilyl-2'-deoxyadenosine, and
 2) acetic acid and acetic anhydride, and
 3) DMSO under conditions permitting the formation of a N$^4$-Benzoyl-3'-O-methylthiomethyl-5'-O-tert-butyldimethylsilyl-2'-deoxyadenosine;
b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor- N-(2-mercapto-2-methylpropyl)acetamide under conditions permitting the production of a product having the structure:

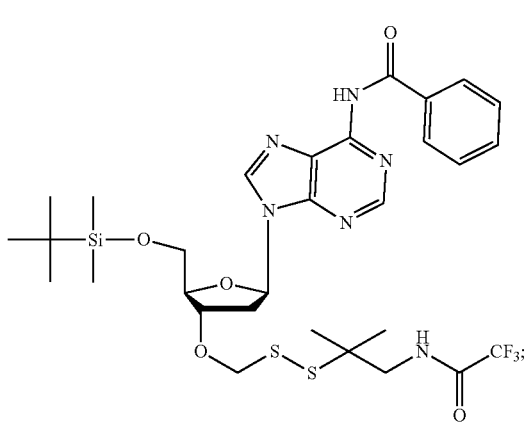

c) contacting the product of step b) with tetrabutylammonium fluoride THF solution under conditions permitting the production of a product having the structure:

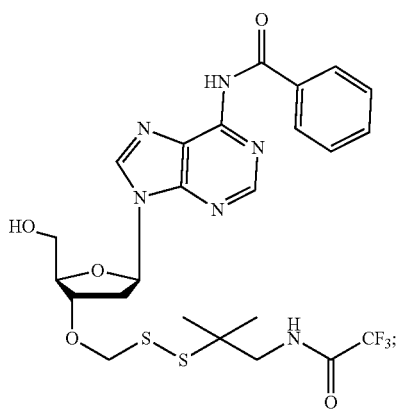

d) contacting product of step c) with tetrabutylammonium pyrophosphate, 1-chloro-4-H-1,3,2-benzodioxaphosphorin-4-one, tributylamine, iodine solution, and ammonium hydroxide under conditions permitting the production of 3'-O-NH2-t-Butyldithiomethyl-dATP;
e) contacting the 3'-O—NH$_2$-t-Butyldithiomethyl-dATP produced in step d) with ROX—NHS ester under conditions permitting the production of the 3'-O-Rox-t-Butyldithiomethyl-dATP.

The invention also provides for a process for producing a 3'-O-Rox-PEG$_4$-t-Butyldithiomethyl-dATP, comprising:
a) reacting,
1) a N$^4$-Benzoyl-5'-O-tert-butyldimethylsilyl-2'-deoxyadenosine, and
2) acetic acid and acetic anhydride; and
3) DMSO under conditions permitting the formation of a N$^4$-Benzoyl-3'-O-methylthiomethyl-5'-O-tert-butyldimethylsilyl-2'-deoxyadenosine;
b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor- N-(2-mercapto-2-methylpropyl)acetamide under conditions permitting the production of a product having the structure:

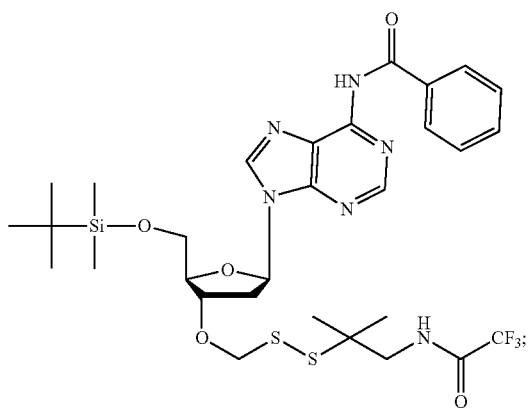

c) contacting the product of step b) with tetrabutylammonium fluoride THF solution under conditions permitting the production of a product having the structure:

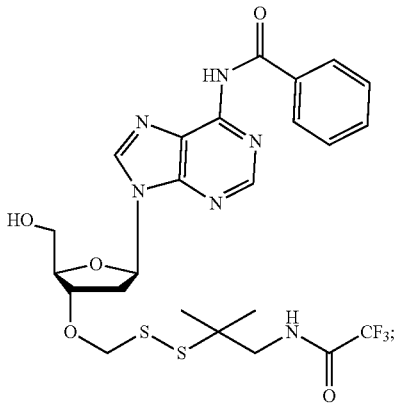

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dATP;
e) contacting the 3'-O—NH$_2$-t-Butyldithiomethyl-dATP produced in step d) with ROX-PEG$_4$-Acid, N,N-disuccinimidyl carbonate, and 4-dimethylaminopyridine under conditions permitting the production of the 3'-O-Rox-PEG$_4$t-Butyldithiomethyl-dATP.

The invention also provides for a process for producing a 3'-O-Alexa488-t-Butyldithiomethyl-dCTP, comprising:
a) reacting
1) a N$^4$-Benzoyl-5'-O-tert-butyldimethylsilyl-2'-deoxycytidine, and
2) acetic acid and acetic anhydride, and
3) DMSO under conditions permitting the formation of a N$^4$-Benzoyl-3'-O-methylthiomethyl-5'-O-tert-butyldimethylsilyl-2'-deoxycytidine;
b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-

(2-mercapto-2-methylpropyl)acetamide under conditions permitting the production of a product having the structure:

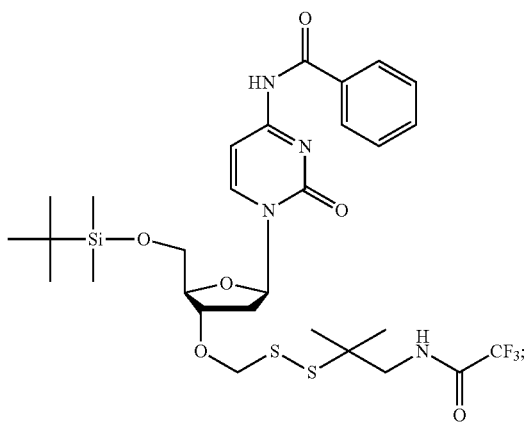

c) contacting the product of step b) with tetrabutylammonium fluoride THF solution under conditions permitting the production of a product having the structure:

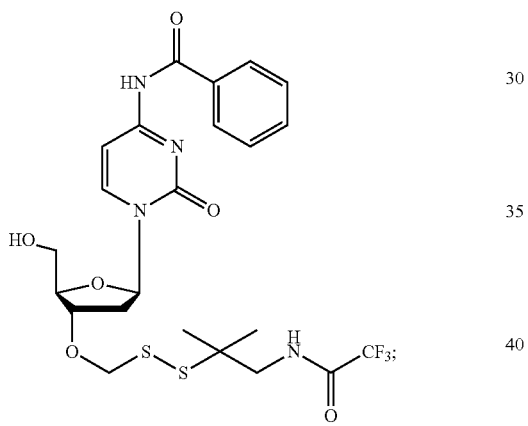

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-NHS ester under conditions permitting the production of the 3'-O-Alexa488-t-Butyldithiomethyl-dCTP.

The invention also provides for a process for producing a 3'-O-Alexa488-PEG4-t-Butyldithiomethyl-dCTP, comprising:

a) reacting
1) a N$^4$-Benzoyl-5'-O-tert-butyldimethylsilyl-2'-deoxycytidine, and
2) acetic acid and acetic anhydride, and
3) DMSO under conditions permitting the formation of a N$^4$-Benzoyl-3'-O-methylthiomethyl-5'-O-tert-butyldimethylsilyl-2'-deoxycytidine;

b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

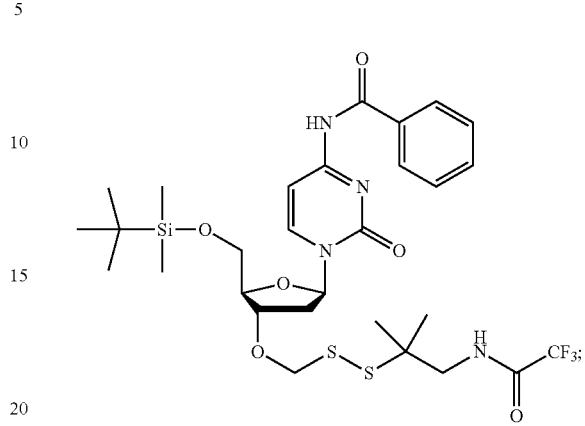

c) contacting the product of step b) with tetrabutylammonium fluoride THF solution under conditions permitting the production of a product having the structure:

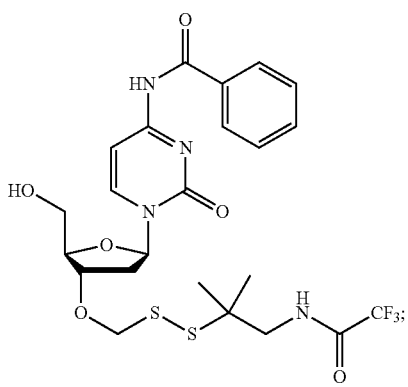

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-PEG$_4$-NHS ester, N,N-disuccinimidyl carbonate, and 4-dimethylaminopyridine under conditions permitting the production of the 3'-O-Alexa488-PEG$_4$-t-Butyldithiomethyl-dCTP.

The invention also provides for a process for producing a 3'-O-Cy5-t-Butyldithiomethyl-dGTP, comprising:

a) reacting
1) a 2'-deoxyguanosine, and
2) tert-butyldimethylsilyl chloride, imidazole, and N,N-dimethylformamide dimethyl acetal, under conditions permitting the formation of a N-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid, acetic anhydride, and DMSO under conditions permitting the production of a product having the structure:

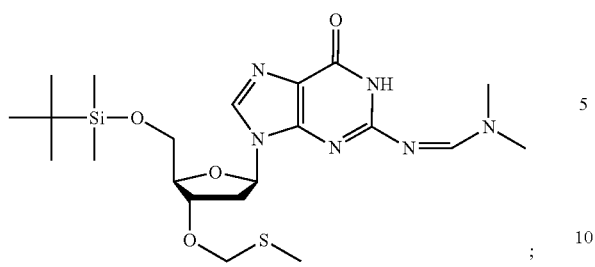

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

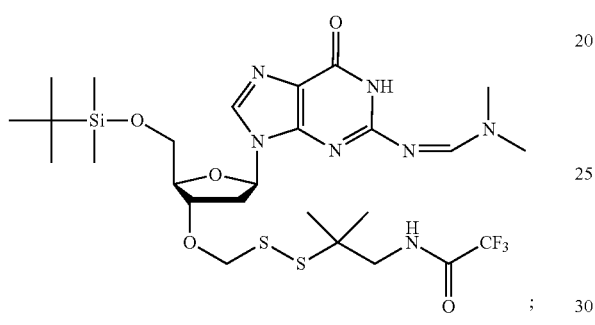

d) contacting the product of step c) with tetrabutylammonium fluoride THF solution under conditions permitting the production of a product having the structure:

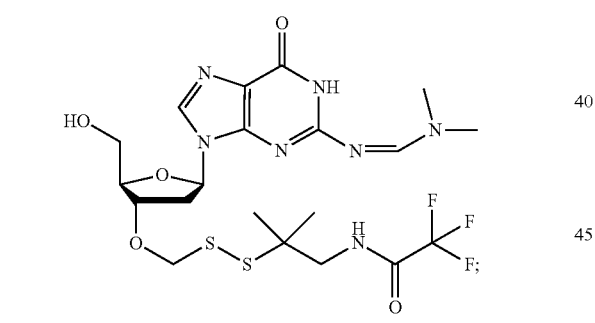

e) contacting product of step d) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dGTP;

f) contacting the 3'-O—NH$_2$-t-Butyldithiomethyl-dGTP produced in step e) with Cy5-NHS under conditions permitting the production of the 3'-O-Cy5-t-Butyldithiomethyl-dGTP.

The invention also provides for a process for producing a 3'-O-Cy5-PEG$_4$-t-Butyldithiomethyl-dGTP, comprising:

a) reacting
1) a 2'-deoxyguanosine, and
2) tert-butyldimethylsilyl chloride, imidazole, and N,N-dimethylformamide dimethyl acetal, under conditions permitting the formation of a N$^4$-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid, acetic anhydride, and DMSO under conditions permitting the production of a product having the structure:

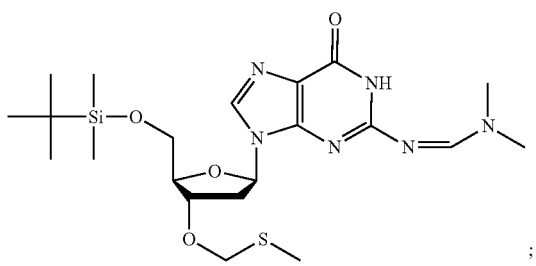

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

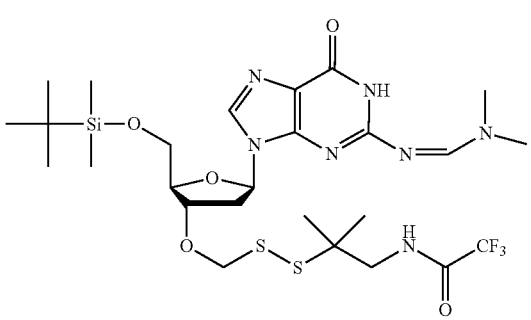

d) contacting the product of step c) with tetrabutylammonium fluoride THF solution under conditions permitting the production of a product having the structure:

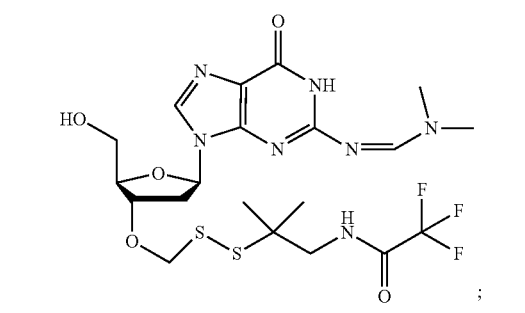

e) contacting product of step d) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dGTP;

contacting the 3'-O—NH$_2$-t-Butyldithiomethyl-dGTP produced in step e) with Cy5-PEG$_4$-NHS under conditions permitting the production of the 3'-O-Cy5-PEG$_4$-t-Butyldithiomethyl-dGTP.

The invention provides for a nucleotide analog consisting of (i) a base, (ii) a sugar which may be a deoxyribose or a ribose, (iii) a t-butyldithiomethyl linker bound to the 3'-oxygen of the deoxyribose or ribose, and (iv) a detectable label bound to the t-butyldithiomethyl linker.

In an embodiment, the sugar is a deoxyribose. In an embodiment, the sugar is a ribose. In an embodiment, the nucleotide analog is a nucleotide monophosphate, a nucleotide diphosphate, a nucleotide triphosphate, a nucleotide tetraphosphate, a nucleotide pentaphosphate, or a nucleotide hexaphosphate. In an embodiment, the base is adenine or an analog of adenine, guanine or an analog of guanine, cytosine or an analog of cytosine, thymine or an analog of thymine or uracil or an analog of uracil.

In an embodiment, the t-butyldithiomethyl linker has the structure:

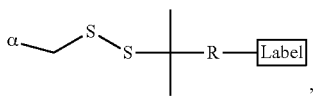

wherein α represents the point of connection to the 3'-oxygen; wherein R represents a structure consisting of one or more atoms one of which is covalently bound to the detectable label; and wherein Label represents the detectable label.

In an embodiment, the t-butyldithiomethyl linker has the structure:

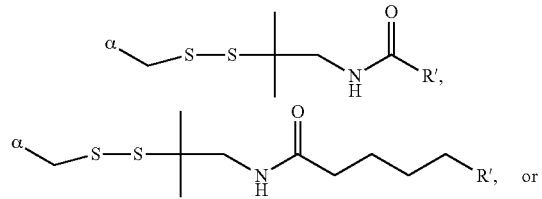

-continued

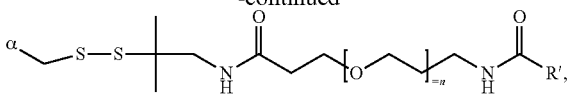

wherein α represents the point of connection to the 3'-oxygen; wherein n is an integer which may be 1, 2, 3, 4, or 5; and wherein R' represents a structure covalently attached to the detectable label.

In an embodiment, the detectable label is a dye, a fluorophore, a fluorescence energy transfer tag, a chemiluminescent compound, a chromophore, a mass tag, an electrophore, a mononucleotide, an oligonucleotide, or a combination thereof. In a further embodiment, the detectable label is a fluorophore. In a further embodiment, the fluorophore is BodipyFL, $R^6G$, ROX, Cy5, or Alexa488.

In an embodiment, the nucleotide analog is 3'-O-Alexa488-t-butyldithiomethyl-dCTP, 3'-O-Cy5-t-butyldithiomethyl-dGTP, 3'-O-Rox-t-butyldithiomethyl-dATP, 3'-O-RG6-t-butyldithiomethyl-dTTP, 3'-O-Alexa488-$PEG_4$-t-butyldithiomethyl-dCTP, 3'-O-RG6-$PEG_4$-t-butyldithiomethyl-dTTP, 3'-O-Rox-$PEG_4$-t-butyldithiomethyl-dATP, or 3'-O-Cy5-$PEG_4$-t-butyldithiomethyl-dGTP.

In an embodiment, the nucleotide analog has the structure:

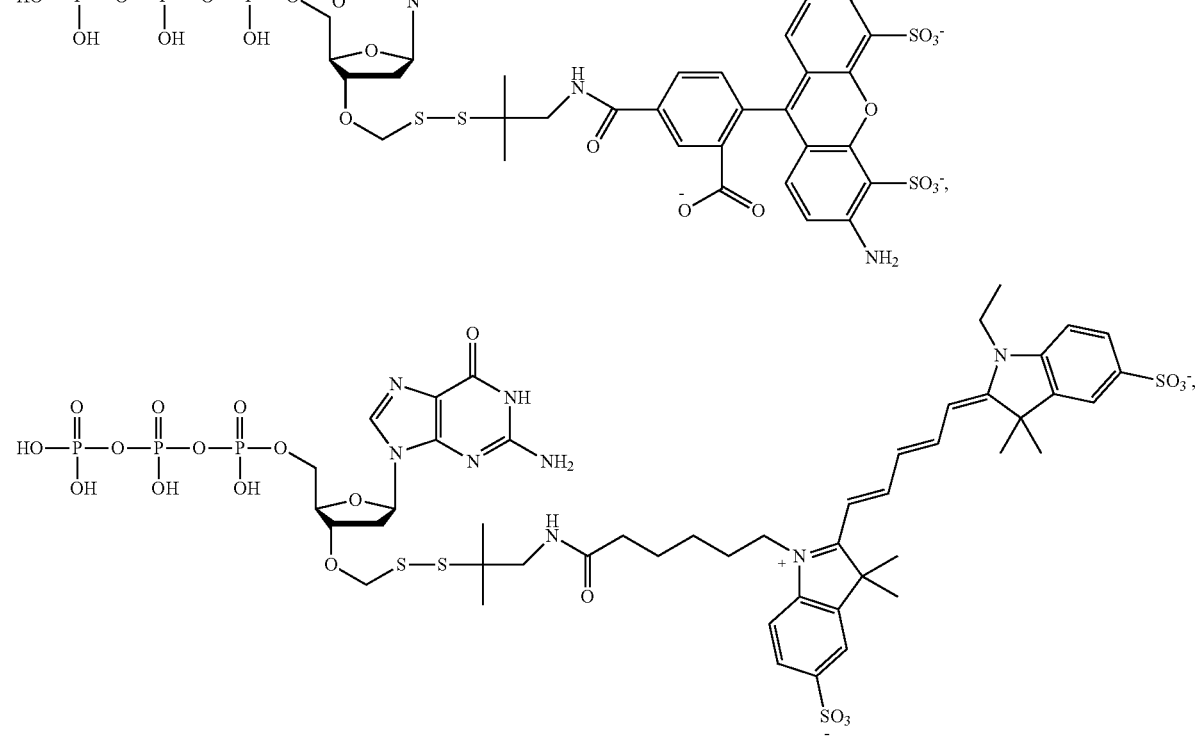

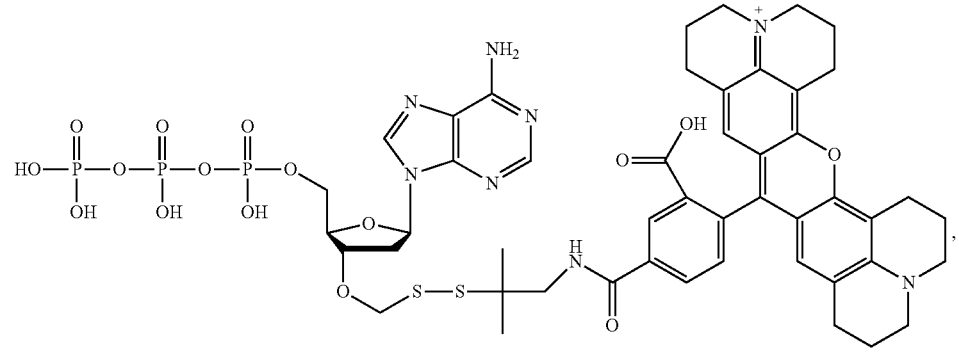
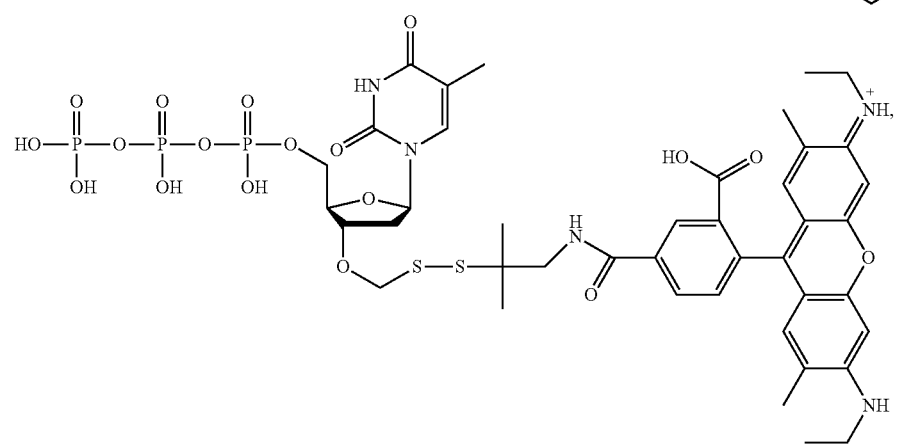
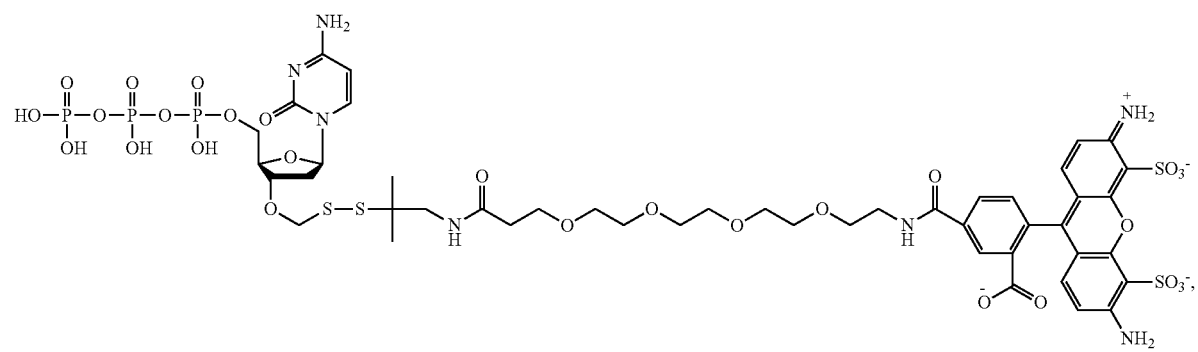
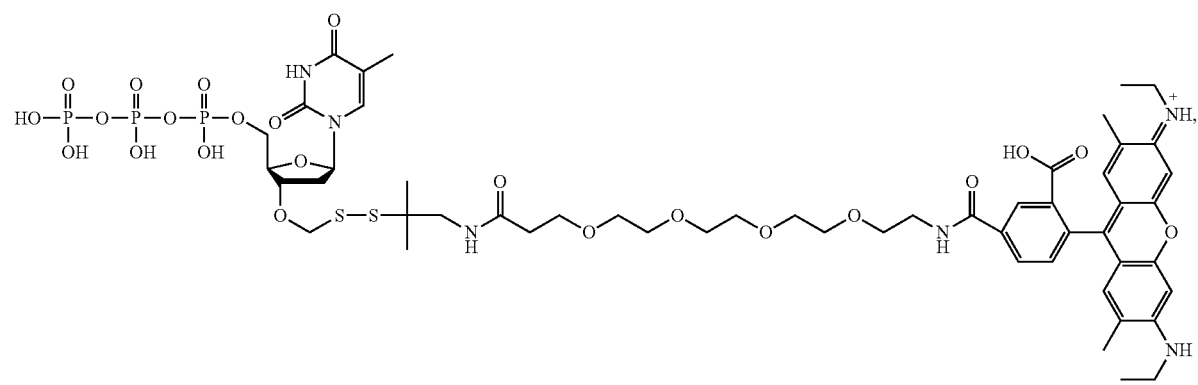

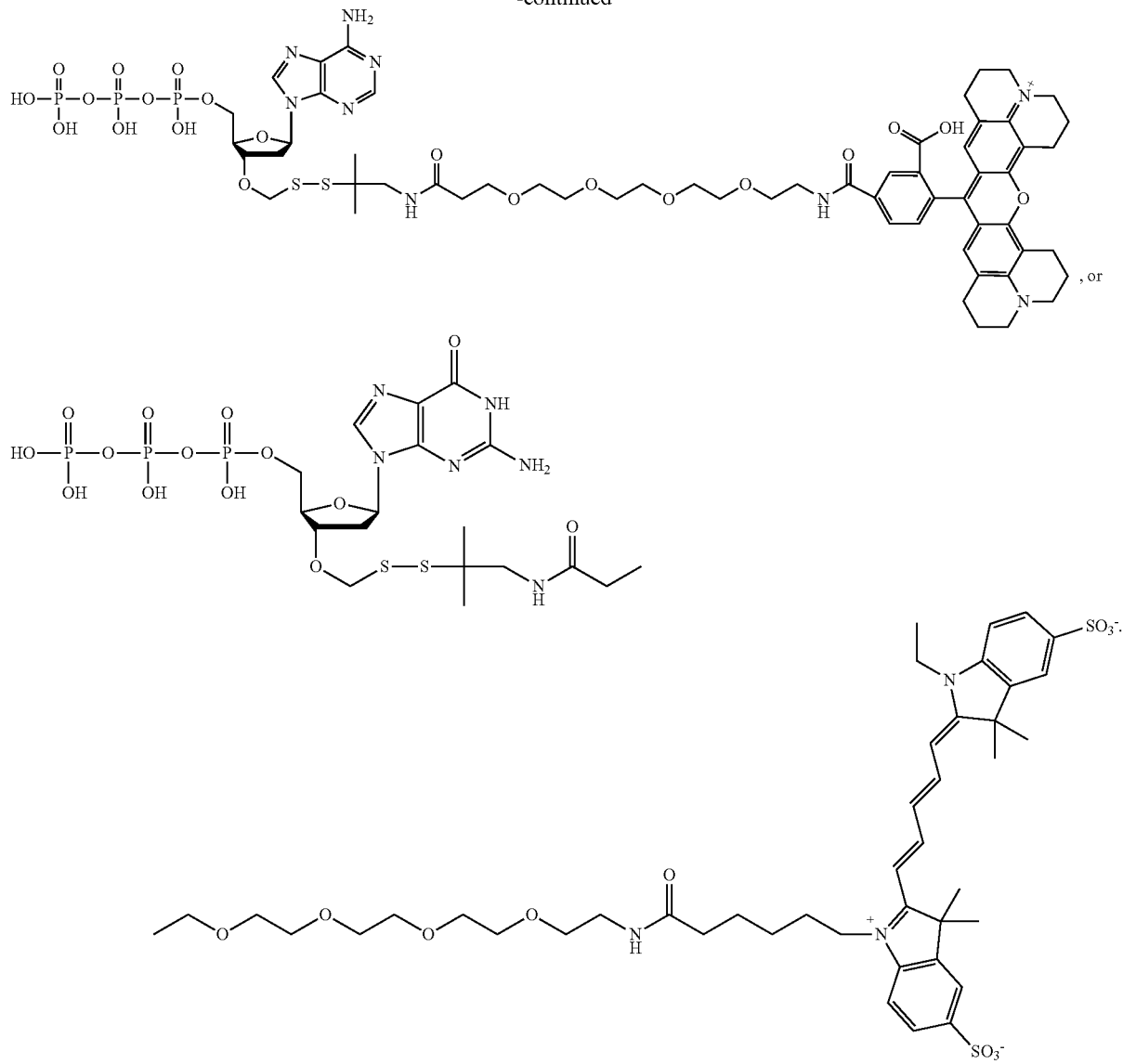

, or

In an embodiment, the invention comprises a composition comprising at least two different nucleotide analogs, wherein each nucleotide analog consists of a different base and a different detectable label from each other nucleotide analog present in the composition.

The invention also provides for a method for determining the identity of a nucleotide at a predetermined position in a nucleic acid of interest, comprising:
a) providing
  1) the nucleic acid of interest,
  2) a nucleic acid polymerase,
  3) a primer capable of hybridizing to said nucleic acid immediately 3' of such predetermined position,
  4) four different nucleotide analogs of claim 1, each of which consists of one of adenine or an analog of adenine, guanine or an analog of guanine, cytosine or an analog of cytosine, thiamine or an analog of thiamine, and a unique detectable label;
b) incorporating one of said nucleotide analogs onto the end of said primer to form an extension strand;
c) detecting the unique detectable label of the incorporated nucleotide analog so as to thereby identify the incorporated nucleotide analog on the end of said extension strand; and
d) based on the identity of the incorporated nucleotide, determining the identity of the nucleotide at the predetermined position.

In an embodiment, the method further comprises treating the extension strand of step (b) so as to cleave the t-butyl-dithiomethyl linker bound to the 3'-oxygen of the sugar and so as to produce a 3'-OH on the sugar and for producing an extension, remove the label from the extension strand to which another nucleotide analog may be added.

In an embodiment, treatment further comprises contacting the extension strand with tris-(2-carboxyethyl)phosphine (TCEP) or tris(hydroxypropyl)phosphine (THP).

In an embodiment, each nucleotide analog is a nucleotide triphosphate, a nucleotide tetraphosphate, a nucleotide pentaphosphate, or a nucleotide hexaphosphate. In an embodiment, the nucleotide analog comprises a deoxyribose. In an embodiment, the polymerase is a DNA polymerase and the nucleic acid is DNA. In an embodiment, the polymerase is a reverse transcriptase and the nucleic acid is RNA. In an embodiment, the nucleotide analog comprises a ribose. In an embodiment, the polymerase is a DNA-based RNA polymerase and the nucleic acid is DNA. In an embodiment, the polymerase is an RNA-based RNA polymerase and the nucleic acid is RNA.

In an embodiment, the t-Butyldithiomethyl linker has the structure:

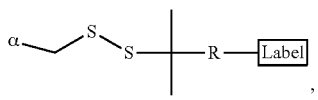

wherein α represents the point of connection to the 3'-oxygen; wherein R represents one or more atoms through which a covalent connection is established to the detectable label; and wherein Label is the detectable label.

In an embodiment, the t-Butyldithiomethyl linker has the structure:

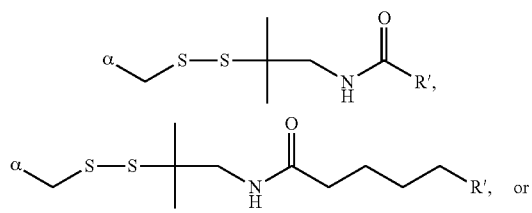

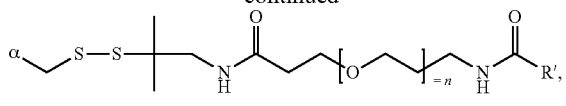

wherein α represents the point of connection to the 3'-oxygen; wherein n is 1, 2, 3, 4, or 5; and wherein R' represents one or more atoms through which a covalent connection is established to the detectable label.

In an embodiment, the detectable label is selected from the group consisting of a dye, a fluorophore, a combinatorial fluorescence energy transfer tag, a chemiluminescent compound, a chromophore, a mass tag, an electrophore, a mononucleotide, an oligonucleotide, or a combination thereof. In a further embodiment, the detectable label is a fluorophore. In a further embodiment, the fluorophore is selected from the group consisting of BodipyFL, R6G, ROX, Cy5, and Alexa488.

In an embodiment, each nucleotide analog is selected from the group consisting of 3'-O-Alexa488-t-Butyldithiomethyl-dCTP, 3'-O-Cy5-t-Butyldithiomethyl-dGTP, 3'-O-Rox-t-Butyldithiomethyl-dATP, 3'-O-RG6-t-Butyldithiomethyl-dTTP, 3'-O-Alexa488-PEG4-t-Butyldithiomethyl-dCTP, 3'-O-RG6-PEG$_4$-t-Butyldithiomethyl-dTTP, 3'-O-Rox-PEG$_4$-t-Butyldithiomethyl-dATP, 3'-O-Cy5-PEG$_4$-t-Butyldithiomethyl-dGTP.

In an embodiment, the structure of each labeled nucleotide analog is selected from:

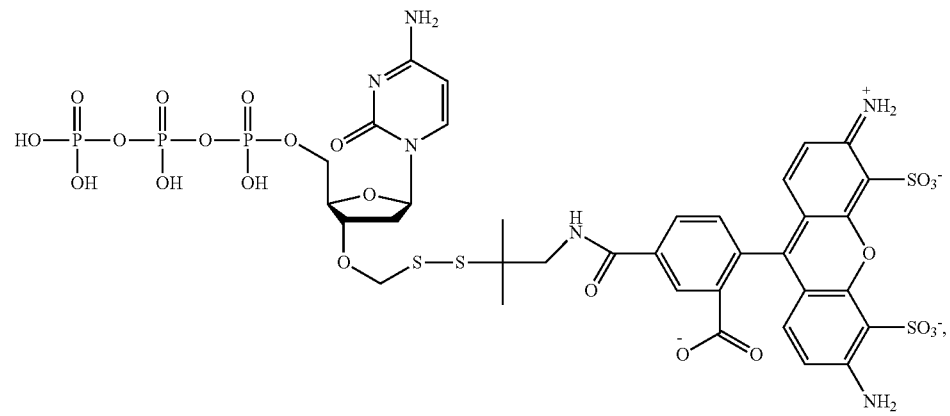

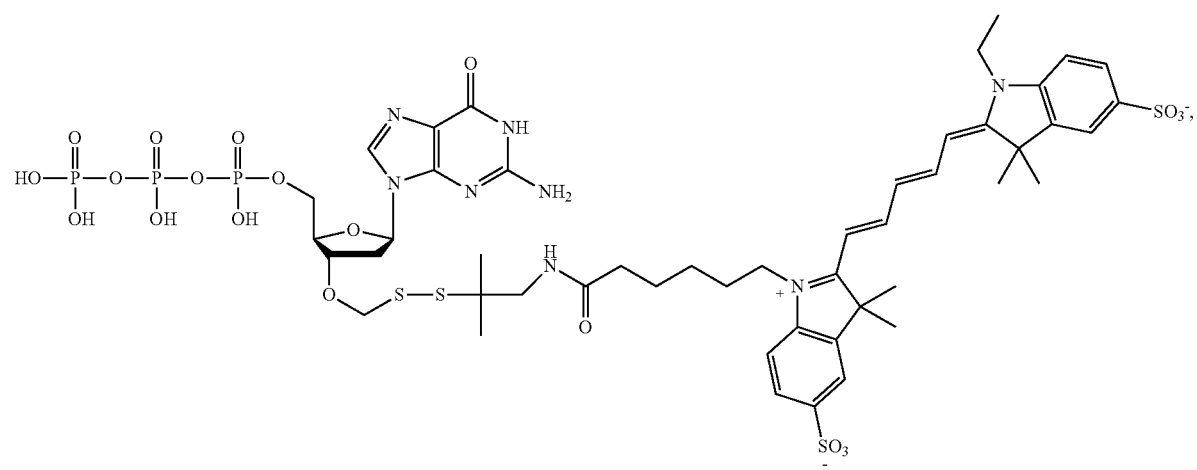

-continued
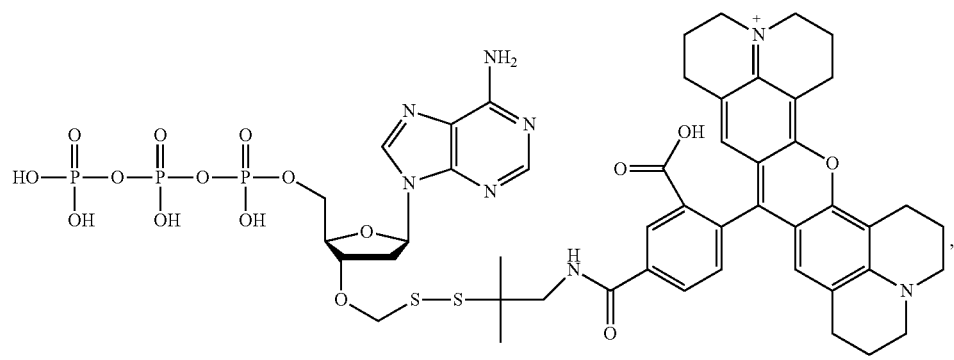
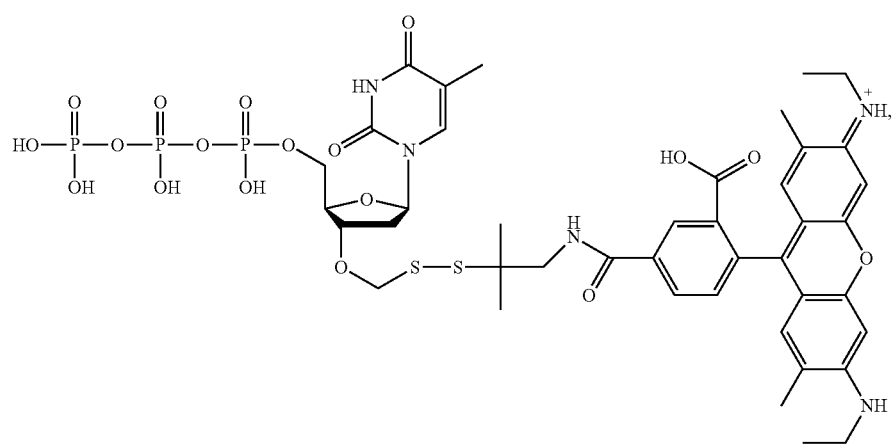
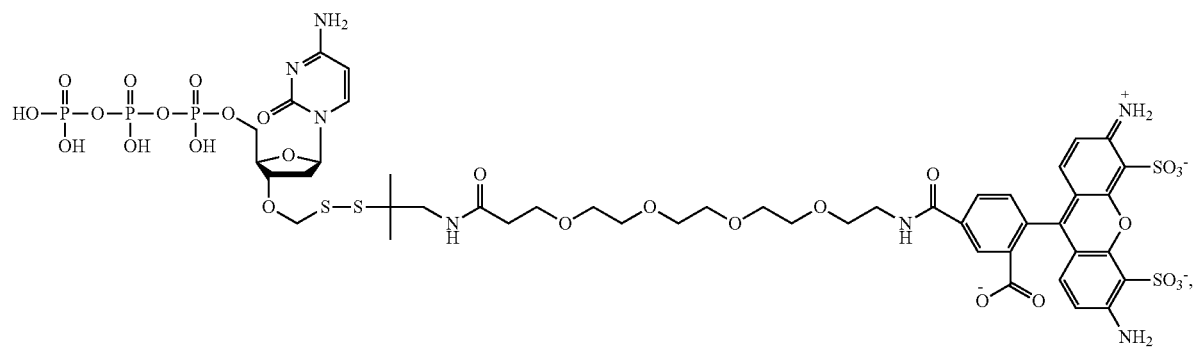
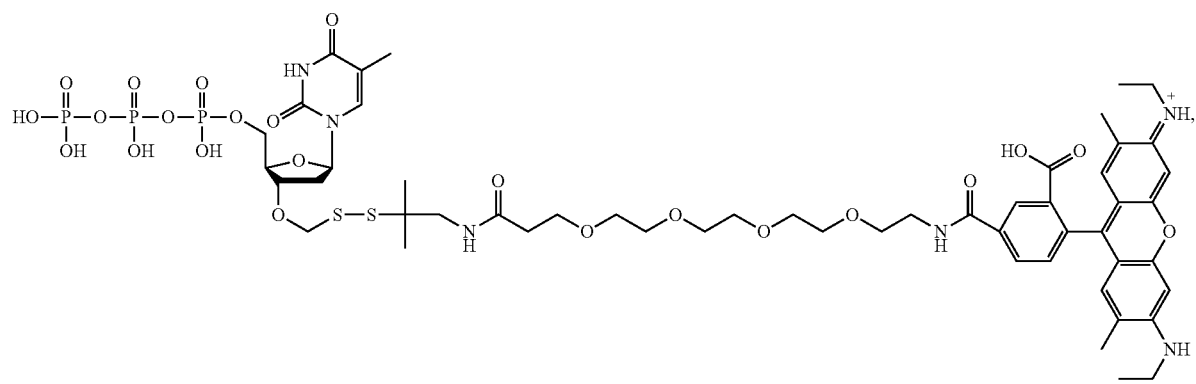

-continued

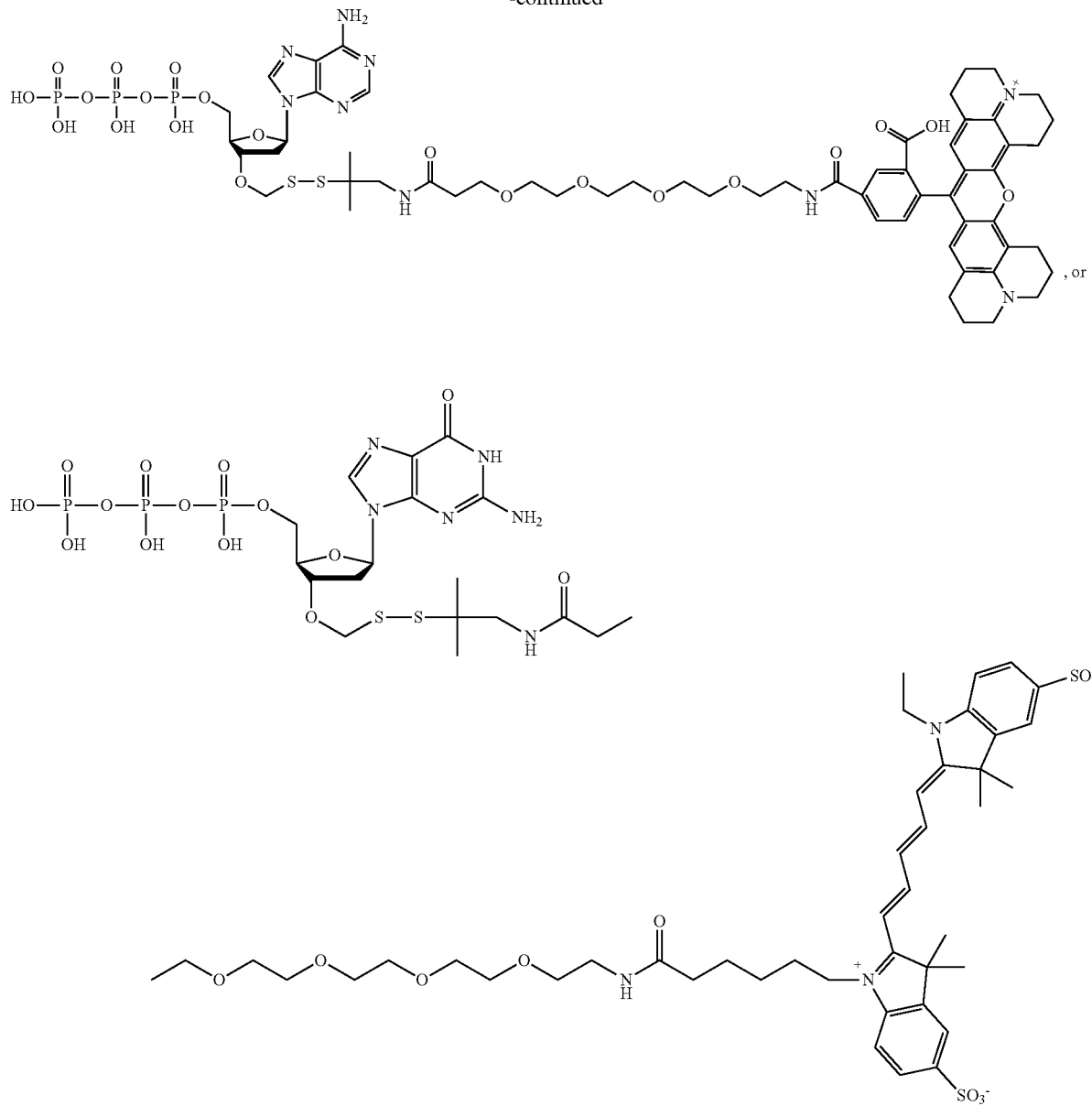

In an embodiment, the nucleic acid of interest is immobilized on a solid support.

In a further embodiment, the nucleic acid of interest is immobilized on the solid support via an azido linkage, an alkynyl linkage, a 1,3-dipolar cycloaddition linkage, or a biotin-streptavidin interaction.

In a further embodiment, the solid support is in the form of a chip, a bead, a well, a capillary tube, or a slide. In a further embodiment, the solid support comprises gold, quartz, silica, or a plastic. In a further embodiment, the solid support is porous.

In an embodiment, the invention comprises a method of sequencing a nucleic acid of interest which comprises repeatedly determining the identity of each nucleotide present in the nucleic acid of interest.

In a further embodiment, the invention comprises a method of simultaneously sequencing a plurality of different nucleic acids of interest which comprises simultaneously sequencing each such nucleic acid.

The invention also provides for a process for producing a 3'-O-Bodipy-t-Butyldithiomethyl-dNTP, comprising:

a) reacting, 1) a 5'-O-tert-Butyldimethylsilyl-nucleoside, 2) acetic acid, 3) acetic anhydride, and

4) DMSO under conditions permitting the production of a 3'-O-methylthiomethyl-5'-O-tert-butyldimerthylsilyl-nucleoside;

b) contacting the 3'-O-methylthiomethyl-5'-O-tert-butyldimethylsilyl-nucleoside produced in step a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

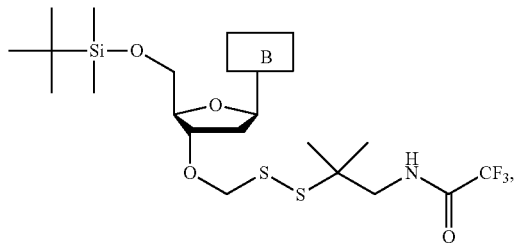

wherein B is a nucleobase;
c) contacting the product produced in step b) with tetra-butylammonium fluoride THF solution under conditions permitting the production of a product having the structure:

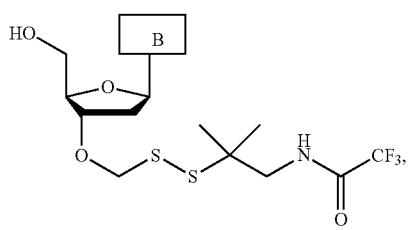

wherein B is a nucleobase;
d) contacting the product produced in step c) with tetrabutylammonium pyrophosphate, 2-chloro-4-H-1,3,2-benzodioxaphosphorin-4-one, iodine solution and ammonium hydroxide under conditions permitting the production of a 3-O—NH$_2$-t-Butyldithiomethyl-dNTP;
e) contacting the 3-O—NH$_2$-t-Butyldithiomethyl-dNTP of step d) with Bodipy FL-NHS ester under conditions permitting the production of the 3'-O-Bodipy-t-Butyldithiomethyl-dNTP.

In an embodiment, the 3'-O-Bodipy-t-Butyldithiomethyl-dNTP is a 3'-O-Bodipy-t-Butyldithiomethyl-dATP or an analog thereof, 3'-O-Bodipy-t-Butyldithiomethyl-dTTP or an analog thereof, 3'-O-Bodipy-t-Butyldithiomethyl-dGTP or an analog thereof, or 3'-O-Bodipy-t-Butyldithiomethyl-dCTP.

In a further embodiment, the 3'-O-Bodipy-t-Butyldithiomethyl-dNTP is 3'-O-Bodipy-t-Butyldithiomethyl-dTTP.

The invention also provides for a process for producing a 3'-O-Bodipy-PEG4-t-Butyldithiomethyl-dNTP, comprising:
a) reacting,
1) a 5'-O-tert-Butyldimethylsilyl-nucleoside,
2) acetic acid,
3) acetic anhydride, and
4) DMSO
under conditions permitting the production of a 3'-O-methylthiomethyl-5'-O-tert-butyldimerthylsilyl-nucleoside;
b) contacting the 3'-O-methylthiomethyl-5'-O-tert-butyldimerthylsilyl-nucleoside produced in part a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

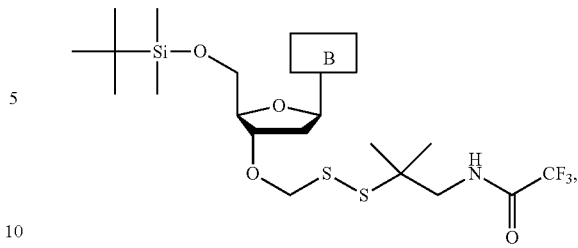

wherein B is a nucleobase;
c) contacting the product produced in step b) with tetrabutylammonium fluoride THF solution under conditions permitting the production of a product having the

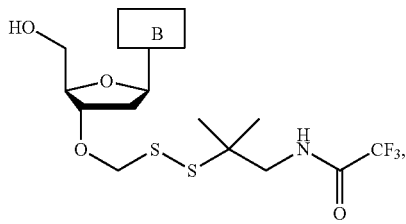

wherein B is a nucleobase;
d) contacting the product produced in step c) with tetrabutylammonium pyrophosphate, 2-chloro-4-H-1,3,2-benzodioxaphosphorin-4-one, iodine solution and ammonium hydroxide under conditions permitting the production of a 3-O—NH$_2$-t-Butyldithiomethyl-dNTP;
e) contacting the 3-O—NH$_2$-t-Butyldithiomethyl-dNTP of step d) with Bodipy-PEG4-Acid, N,N-disuccinimidyl carbonate, and 4-dimethylaminopyridine under conditions permitting the production of the 3'-O-PEG4-Bodipy-t-Butyldithiomethyl-dNTP.

In an embodiment, the 3'-O-PEG$_4$-Bodipy-t-Butyldithiomethyl-dNTP is a 3'-O-PEG$_4$-Bodipy-t-Butyldithiomethyl-dATP or an analog thereof, 3'-O-PEG$_4$-Bodipy-t-Butyldithiomethyl-dTTP or an analog thereof, 3'-O-PEG$_4$-Bodipy-t-Butyldithiomethyl-dGTP or an analog thereof, or 3'-O-PEG$_4$-Bodipy-t-Butyldithiomethyl-dCTP.

In a further embodiment, the 3'-O-PEG$_4$-Bodipy-t-Butyldithiomethyl-dNTP is 3'-O-PEG$_4$-Bodipy-t-Butyldithiomethyl-dTTP.

The invention also provides for a process for producing a 3'-O-Rox-t-Butyldithiomethyl-dATP, comprising:
a) reacting,
1) a N$^4$-Benzoyl-5'-O-tert-butyldimethylsilyl-2'-deoxyadenosine, and
2) acetic acid, acetic anhydride and DMSO
under conditions permitting the formation of a N$^4$-Benzoyl-3'-O-methylthiomethyl-5'-O-tert-butyldimethylsilyl-2'-deoxyadenosine;
b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

345

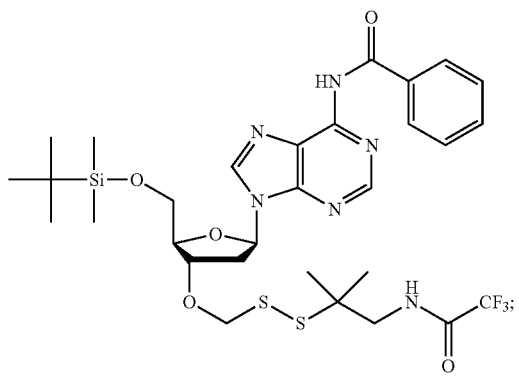

c) contacting the product of step b) with tetrabutylammonium fluoride THF solution under conditions permitting the production of a product having the structure:

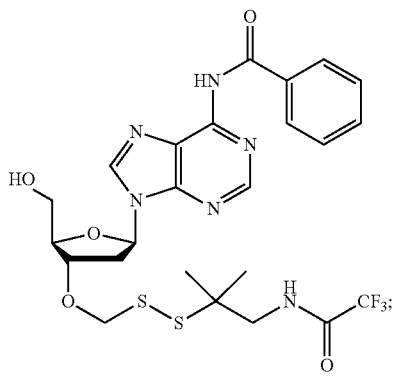

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH2-t-Butyldithiomethyl-dATP;

e) contacting the 3'-O—NH$_2$-t-Butyldithiomethyl-dATP produced in step d) with ROX—NHS ester under conditions permitting the production of the 3'-O-Rox-t-Butyldithiomethyl-dATP.

The invention also provides for a process for producing a 3'-O-Rox-PEG$_4$-t-Butyldithiomethyl-dATP, comprising:

a) reacting,
1) a N$^4$-Benzoyl-5'-O-tert-butyldimethylsilyl-2'-deoxyadenosine, and
2) acetic acid, acetic anhydride and DMSO under conditions permitting the formation of a N$^4$-Benzoyl-3'-O-methylthiomethyl-5'-O-tert-butyldimethylsilyl-2'-deoxyadenosine;

b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

346

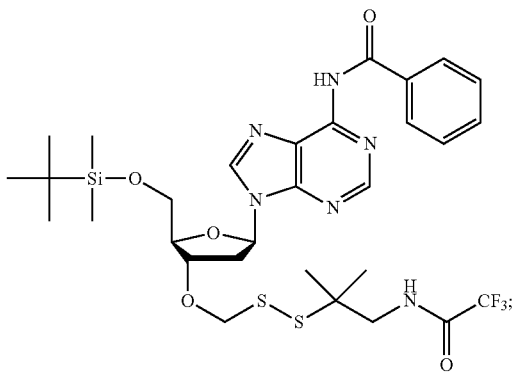

c) contacting the product of step b) with tetrabutylammonium fluoride THF solution under conditions permitting the production of a product having the structure:

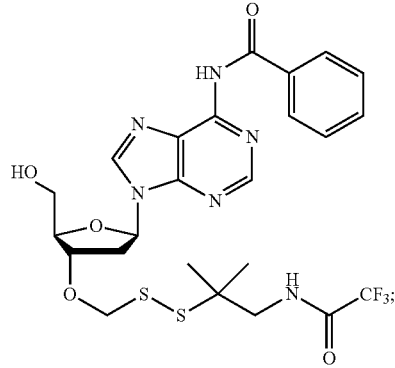

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dATP;

e) contacting the 3'-O—NH$_2$-t-Butyldithiomethyl-dATP produced in step d) with ROX-PEG$_4$-Acid, N,N-disuccinimidyl carbonate, and 4-dimethylaminopyridine under conditions permitting the production of the 3'-O-Rox-PEG$_4$t-Butyldithiomethyl-dATP.

The invention also provides for a process for producing a 3'-O-Alexa488-t-Butyldithiomethyl-dCTP, comprising:

a) reacting
1) a N$^4$-Benzoyl-5'-O-tert-butyldimethylsilyl-2'-deoxycytidine, and
2) acetic acid, acetic anhydride and DMSO under conditions permitting the formation of a N$^4$-Benzoyl-3'-O-methylthiomethyl-5'-O-tert-butyldimethylsilyl-2'-deoxycytidine;

b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

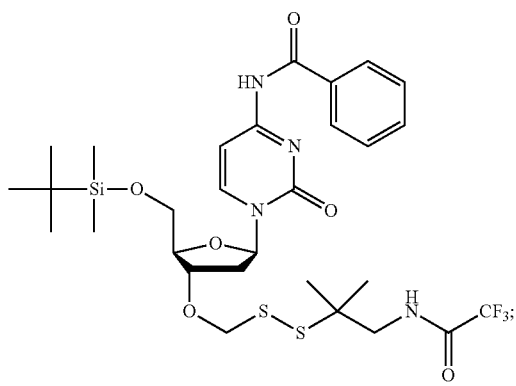

c) contacting the product of step b) with tetrabutylammonium fluoride THF solution under conditions permitting the production of a product having the structure:

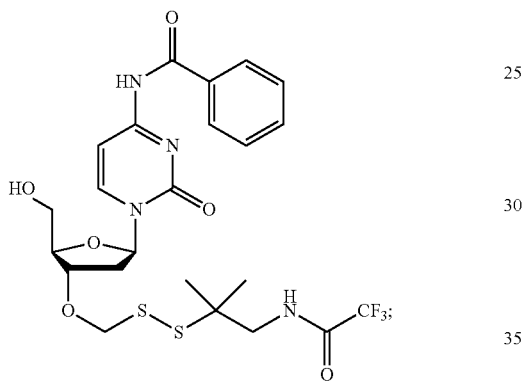

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-NHS ester under conditions permitting the production of the 3'-O-Alexa488-t-Butyldithiomethyl-dCTP.

The invention also provides for a process for producing a 3'-O-Alexa488-PEG$_4$-t-Butyldithiomethyl-dCTP, comprising:

a) reacting 1) a N$^4$-Benzoyl-5'-O-tert-butyldimethylsilyl-2'-deoxycytidine, and 2) acetic acid, acetic anhydride and DMSO under conditions permitting the formation of a N$^4$-Benzoyl-3'-O-methylthiomethyl-5'-O-tert-butyldimethylsilyl-2'-deoxycytidine;

b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

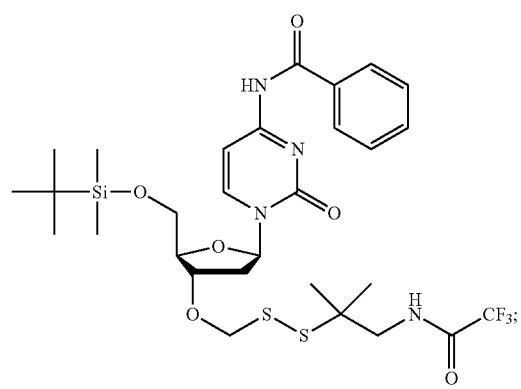

c) contacting the product of step b) with tetrabutylammonium fluoride THF solution under conditions permitting the production of a product having the structure:

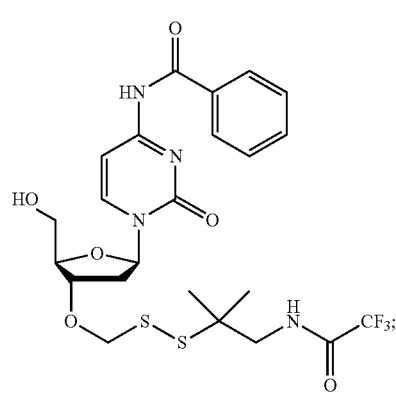

d) contacting product of step c) with tetrabutylammonium pyrophosphate, 1-chloro-4-H-1,3,2-benzodioxaphosphorin-4-one, tributylamine, iodine solution and ammonium hydroxide under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-PEG$_4$-NHS ester, N,N-disuccinimidyl carbonate, and 4-dimethylaminopyridine under conditions permitting the production of the 3'-O-Alexa488-PEG$_4$-t-Butyldithiomethyl-dCTP.

The invention also provides for a process for producing a 3'-O-Cy5-t-Butyldithiomethyl-dGTP, comprising:

a) reacting 1) a 2'-deoxyguanosine, and 2) tert-butyldimethylsilyl chloride, imidazole, and N,N-dimethylformamide dimethyl acetal, under conditions permitting the formation of a N$^4$-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid acetic anhydride and DMSO under conditions permitting the production of a product having the structure:

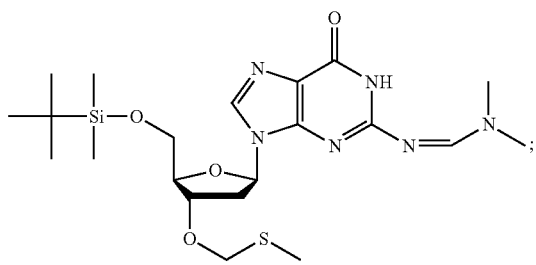

c) contacting the product of step b) with trimethylamine, molecular sieves, sufuryl chloride, p-toluenethiosulfonate, and 2,2,2,-trifluor-N-(2-mercapto-2-methyl-propyl)acetamide under conditions permitting the production of a product having the structure:

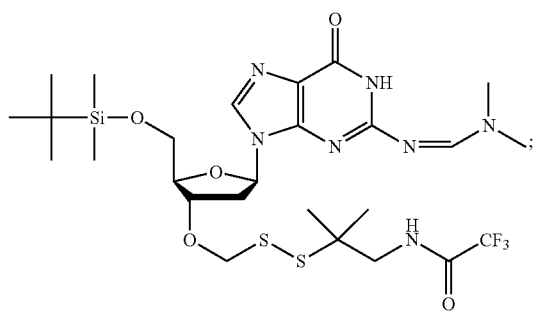

d) contacting the product of step c) with tetrabutylammonium fluoride THF solution under conditions permitting the production of a product having the structure:

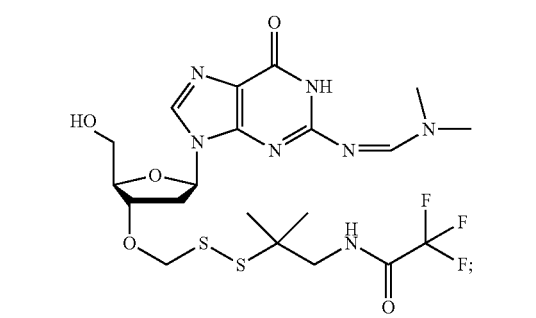

e) contacting product of step d) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dGTP;
f) contacting the 3'-O—NH$_2$-t-Butyldithiomethyl-dGTP produced in step e) with Cy5-NHS under conditions permitting the production of the 3'-O-Cy5-t-Butyldithiomethyl-dGTP.

The invention also provides for a process for producing a 3'-O-Cy5-PEG$_4$-t-Butyldithiomethyl-dGTP, comprising:
a) reacting
  1) a 2'-deoxyguanosine, and
  2) tert-butyldimethylsilyl chloride, imidazole, and N,N-dimethylformamide dimethyl acetal,
under conditions permitting the formation of a N$^4$-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid acetic anhydride and DMSO under conditions permitting the production of a product having the structure:

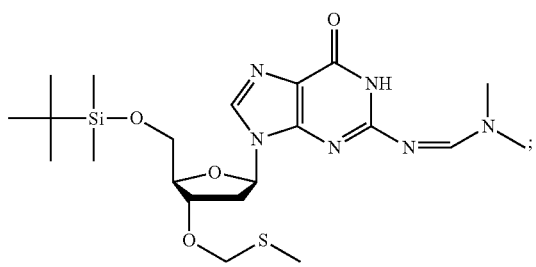

c) contacting the product of step b) with trimethylamine, molecular sieves, sufuryl chloride, p-toluenethiosulfonate, and 2,2,2,-trifluor-N-(2-mercapto-2-methyl-propyl)acetamide under conditions permitting the production of a product having the structure:

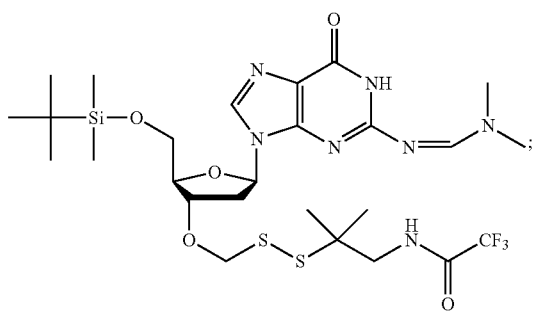

d) contacting the product of step c) with tetrabutylammonium fluoride THF solution under conditions permitting the production of a product having the structure:

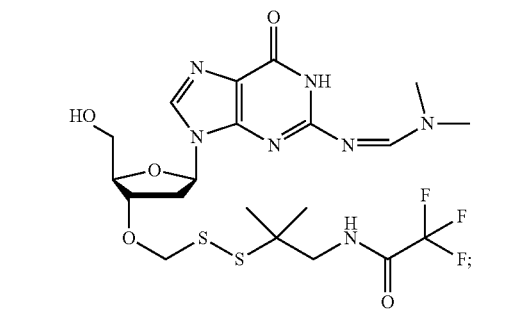

e) contacting product of step d) with tetrabutylammonium pyrophosphate, 1-chloro-4-H-1,3,2-benzodioxaphosphorin-4-one, tributylamine, iodine solution and ammonium hydroxide under conditions permitting the production of 3'-O—NH$_2$-t-Butyldithiomethyl-dGTP;
f) contacting the 3'-O—NH$_2$-t-Butyldithiomethyl-dGTP produced in step e) with Cy5-PEG$_4$-NHS under conditions permitting the production of the 3'-O-Cy5-PEG$_4$-t-Butyldithiomethyl-dGTP.

In certain embodiments of the invention, the label comprises a plurality of identical Raman-scattering moieties. In other embodiments, the tag comprises a plurality of different Raman-scattering moieties. In certain specific embodiments, the tag comprises 3, 9, or 27 Raman-scattering moieties. In an embodiment, the plurality of Raman-scattering moieties forms a linear tag. In another embodiment, the plurality of Raman-scattering moieties forms a non-linear tag. In a preferred embodiment, the non-linear tag is a dendrimer tag. In an embodiment, the tag has a Raman spectroscopy peak with wavenumber from 2125 cm$^{-1}$ to 2260 cm$^{-1}$.

In another embodiment the polymerase or polymerases are tethered to the noble metal nanoparticles. In another embodiment the noble metal nanoparticles are silver and/or gold nanoparticles. In another embodiment the polymerase or polymerases have 1 or more attached and/or conjugated noble metal nanoparticles, wherein the noble metal nanoparticles are a surface-enhanced Raman spectroscopy (SERS) substrates. In another embodiment the noble metal nanoparticles are either gold or silver nanoparticles. In another embodiment the metal nanoparticles of the polymerase or polymerases are between 3 nm and 10 nm. In another embodiment the polymerase or polymerases have 2, 3, 4, or 5 metal nanoparticles. In another embodiment the metal nanoparticles of the polymerase or polymerases are attached and/or conjugated to the polymerase 1 nm-3 nm from the active site of the polymerase. In another embodiment the metal nanoparticles of the polymerase or polymerases are attached and/or conjugated to the polymerase or polymerases 1 nm-3 nm from the active site of the polymerase, thereby creating a region of enhanced sensitivity for surface enhanced Raman spectroscopy (SERS) at the active site. In another embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule. In another embodiment the attached and/or conjugated metal nanoparticles of the polymerase create a region of enhanced sensitivity for surface enhanced Raman spectroscopy (SERS) at the location of the Raman active molecule.

The invention provides for a nucleotide analog consisting of (i) a base, (ii) a sugar, and (iii) a t-butyldithiomethyl linker bound to the 3'-oxygen of the deoxyribose of the sugar.

Herein is further disclosed a method for determining the nucleotide sequence of a single-stranded DNA, the method comprising:
  a) contacting the single-stranded DNA having a primer hybridized to a portion thereof, with a nucleotide polymerase and a first type of nucleotide analogue under conditions permitting the nucleotide polymerase to catalyze incorporation of the nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the nucleotide analogue has the structure:

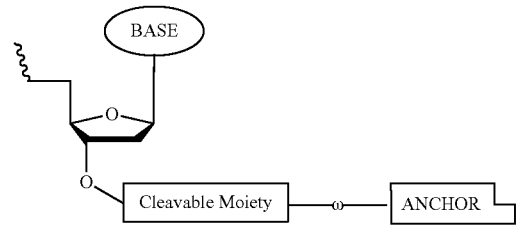

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein w represents a structure consisting of one or more atoms of which is covalently bound to both the cleavable t-butyl-dithiomethyl moiety and the anchor moiety, wherein the identity of the anchor is predetermined and is correlated to the identity of the base,
  b) contacting the single-stranded DNA of step a) with a binding molecule complementary to the anchor of the nucleotide analogue of step a), wherein the binding molecule has the structure:

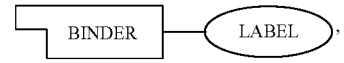

wherein binder is a chemical group that orthogonally and rapidly reacts with the anchor moiety, thereby forming a conjugate of the binding molecule and the anchor moiety, and Label is a detectable label,
  c) removing any nucleotide analogue not incorporated into the primer in step a);
  d) detecting the presence of any detectable label so as to thereby determine whether the nucleotide analogue of step a) was incorporated so as to thereby determine the identity of the complementary nucleotide residue in the single-stranded DNA, and
    wherein if the base of the nucleotide analogue a) is not complementary to the nucleotide residue of the single-stranded DNA which is immediately 5' to the nucleotide residue of the single-stranded DNA hybridized to the 3' terminal nucleotide residue of the primer, then iteratively repeating steps a) through c) with a second, third, and then fourth type of nucleotide analogue, wherein each different type of nucleotide analogue has a different base from each other type of nucleotide analogue, until the nucleotide analogue has a base that is complementary,
  e) cleaving the cleavable t-butyldithiomethyl moiety, so as to thereby create a 3'-OH; and
  f) iteratively performing steps a) through e) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein each type of nucleotide analogue has the structure:

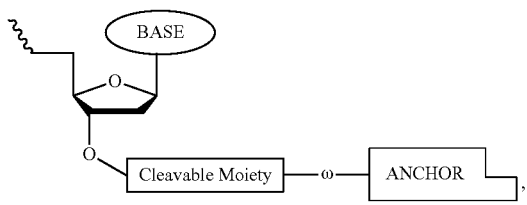

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety,
wherein the base of each type of nucleotide analogue is independently different from the base of the remaining three types of nucleotide analogue, wherein the anchor of each type of nucleotide analogue is independently different from the anchor of the remaining three types of nucleotide analogue, wherein the anchor of each type of nucleotide analogue orthogonally and rapidly reacts with a different binding molecule from each of the remaining three types of nucleotide analogue;
b) contacting the single-stranded DNA of step a) with a first, second, third, and fourth type of binding molecule, under conditions permitting the anchor of the nucleotide analogue incorporated in step a) to orthogonally and rapidly react with a complementary binding molecule thereby binding the binding molecule to the anchor,
wherein the first, second, third, and fourth type of binding molecule each have the structure:

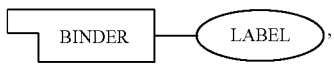

wherein binder is a small chemical group that orthogonally and rapidly reacts with an anchor, and wherein Label is a predetermined detectable label correlated to the identity of the type of binding molecule, wherein the binder of each type of binding molecule is different from the binder of the remaining three types of binding molecule, wherein the first type of binding molecule and the first type of nucleotide analogue, the second type of binding molecule and second type of nucleotide analogue, the third type of binding molecule and third type of nucleotide analogue, and the fourth type of binding molecule and the fourth type of nucleotide analogue are respectively complementary and thereby orthogonally and rapidly react thereby forming a conjugate of each individual type of binding molecule an individual type of nucleotide analogue;
c) determining the identity of the detectable label of the nucleotide analogue incorporated in step a) so as to thereby determine the identity of the incorporated nucleotide analogue and the identity of the complementary nucleotide residue in the single-stranded DNA;
d) cleaving the cleavable t-butyldithiomethyl moiety, so as to thereby create a 3'-OH; and
e) iteratively performing steps a) through d) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:
a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product,
wherein the first and second types of nucleotide analogue have the structure:

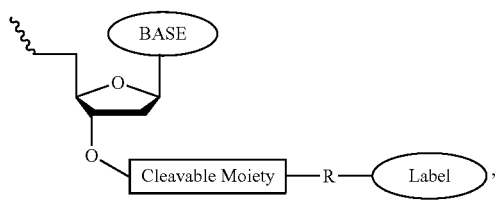

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label,
wherein the label of the first type of nucleotide analogue is different form the label of the second type of nucleotide analogue, wherein the base of each of the first and second type of nucleotide analogue is independently different from the base of each of the three remaining types of nucleotide analogue, wherein the third and fourth type of nucleotide analogue has the structure:

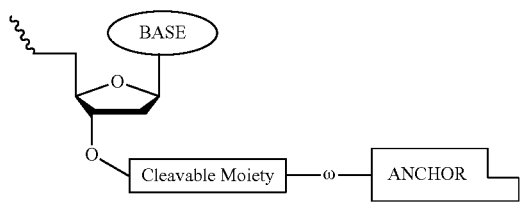

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein (o represents a structure consisting of one or more atoms of which is covalently bound to both the cleavable t-butyldithiomethyl moiety and the anchor moiety, wherein the base of the third and fourth type of nucleotide analogue is independently different from the base of each of the three remaining types of nucleotide analogue, wherein the anchor of the third type of nucleotide analogue is different from the anchor of the fourth type of nucleotide analogue;

b) removing any nucleotide analogues not incorporated in step a);

c) detecting the presence of either the detectable label of the first or second type of nucleotide analogue incorporated in step a) so as to thereby determine the identity of the incorporated nucleotide analogue and the identity of the complementary nucleotide residue in the single-stranded DNA, wherein if the base of the first and second type of nucleotide is not complementary, contacting the single-stranded DNA with a first and second type of binding molecule, wherein the first and second type of binding molecule have the structure:

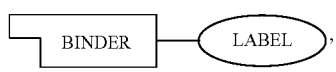

wherein binder is a small chemical group that orthogonally and rapidly reacts with an anchor, and wherein Label is a predetermined detectable label correlated to the identity of the binding molecule, wherein the detectable label of the first type of binding molecule is the same as the detectable label of the first type of nucleotide analogue, wherein the detectable label of the second type of binding molecule is the same as the detectable label of the second type of nucleotide analogue, wherein the binder of the first type of binding molecule orthogonally and rapidly reacts with the anchor of the third type of nucleotide analogue, and wherein the second type of binding molecule orthogonally and rapidly reacts with the anchor of the fourth type of nucleotide analogue, and removing any unbound binding molecule, and detecting the presence of either the first or second binding molecule so as to thereby determine the identity of the nucleotide analogue incorporated in step a) and the identity of the complementary nucleotide residue in the single-stranded DNA;

d) cleaving the cleavable t-butyldithiomethyl moiety so as to thereby create a 3'-OH; and e) iteratively performing steps a) through d) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the structure:

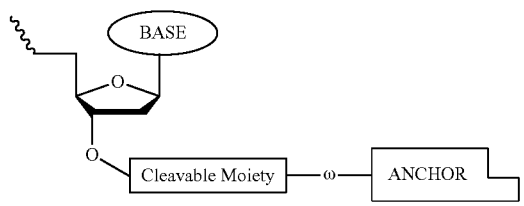

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein o represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

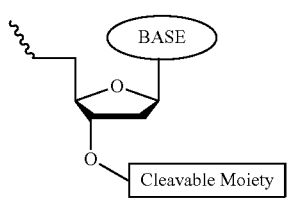

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) contact the single-stranded DNA of step a) with a first, second, and third type of binding molecule, each type of binding molecule having the structure:

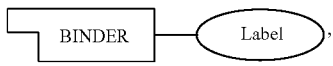

wherein binder is a small chemical group correlated to the identity of the type of binding molecule and that orthogonally and rapidly reacts with an anchor, and wherein Label is a detectable label, wherein the binder of each type of binding molecule is different from the binder of the remaining two types of binding molecule, wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue;

c) removing any nucleotide analogues from step a) not incorporated into the primer;

d) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

e) if a detectable label is detected in step d), contacting the single-stranded DNA with a means of cleaving the detectable label and/or the binding molecule from the first type of nucleotide analogue;

f) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

g) if a detectable label is detected in step f), contacting the single-stranded DNA with a means of cleaving the detectable label and/or the binding molecule from the second type of nucleotide analogue;

h) detecting whether there is an absence of detectable label bound to the incorporated nucleotide of step a), thereby determining the identity of the incorporated nucleotide analogue, and thereby the identity of the complementary nucleotide residue in the single-stranded DNA;

i) cleaving the cleavable t-butyldithiomethyl moiety so as to thereby create a 3'-OH; and j) iteratively performing steps a) through i) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first and second types of nucleotide analogue have the structure:

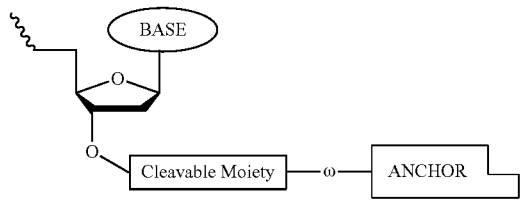

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first and second type of nucleotide analogue is independently different from the base of each of the three remaining types of nucleotide analogue, wherein the anchor of the first type of nucleotide analogue is different from the anchor of the second type of nucleotide analogue, wherein the third type of nucleotide analogue has the structure:

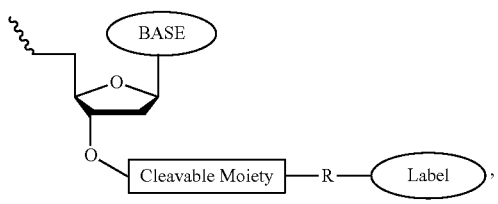

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the third type of nucleotide analogue is independently different from the base of each of the three remaining types of nucleotide analogue, wherein the fourth type of nucleotide analogue has the structure:

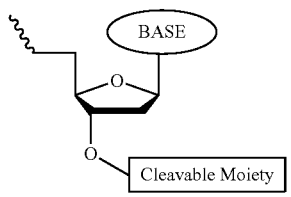

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing any nucleotide analogues from step a) not incorporated into the primer;

c) detecting whether there is a presence of detectable label bound to the incorporated nucleotide of step a), thereby determining that identity of the incorporated nucleotide is of the third type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first and second type of binding molecule, wherein the first and second type of binding molecule have the structure:

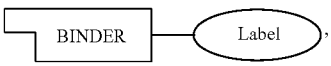

wherein binder is a small chemical group correlated to the identity of the type of binding molecule and that orthogonally and rapidly reacts with an anchor, and wherein Label is a detectable label, wherein the binder of each type of binding molecule is different one another, wherein the first type of binding molecule and the first type of nucleotide analogue, and the second type of binding molecule and second type of nucleotide analogue, respectively complementary and thereby orthogonally and rapidly react thereby binding each individual type of binding molecule with an individual type of nucleotide analogue;

e) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

f) if a detectable label is detected in step e), contacting the single-stranded DNA with a means of cleaving the detectable label and/or the binding molecule from the first type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the structure:

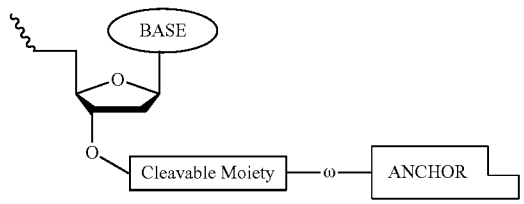

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein w represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

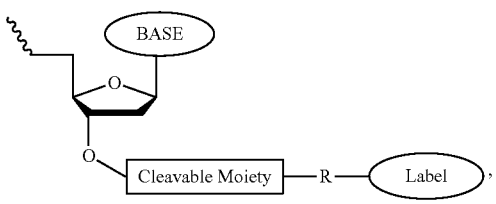

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the fourth type of nucleotide analogue is independently different from the base of each of the three remaining types of nucleotide analogue;

b) removing all unincorporated nucleotide analogues from step a);

c) detecting whether there is a presence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first, second, and third type of binding molecule, wherein the first, second, and third type of binding molecule have the structure:

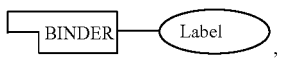

wherein binder is a small chemical group correlated to the identity of the type of binding molecule and that orthogonally and rapidly reacts with an anchor, and wherein Label is a detectable label, wherein the binder of each type of binding molecule is different from one another, wherein the first type of binding molecule and wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue;

e) detecting whether there is a presence of detectable label bound to the incorporated nucleotide of step a);

f) contacting the single-stranded DNA with a means of cleaving the detectable label and/or the binding molecule from the first type of nucleotide analogue;

g) detecting whether there is an absence of detectable label bound to the incorporated nucleotide of step a), thereby determining that the identity of the incorporated nucleotide is of the first type of nucleotide analogue, and thereby the identity of the complementary nucleotide residue in the single-stranded DNA;

h) if a detectable label is detected in step f), contacting the single-stranded DNA with a means of cleaving the detectable label and/or the binding molecule from the second type of nucleotide analogue;

i) detecting whether there is an absence of detectable label bound to the incorporated nucleotide of step a), thereby determining the identity of the incorporated nucleotide analogue, and thereby the identity of the complementary nucleotide residue in the single-stranded DNA;

j) cleaving the cleavable t-butyldithiomethyl moiety so as to thereby create a 3'-OH; and k) iteratively performing steps a) through j) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third types of nucleotide analogue have the structure:

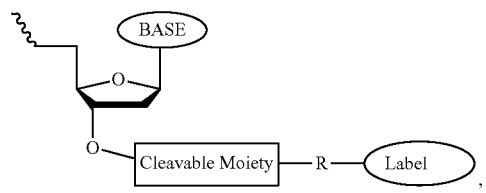

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the first, second, and third type of nucleotide analogue is independently different from the base of each of the three remaining types of nucleotide analogue, wherein the fourth type of nucleotide analogue has the structure:

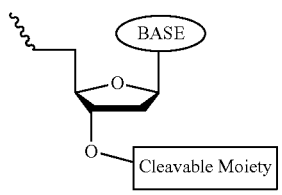

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing all unincorporated nucleotide analogues from step a);

c) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if a detectable label is detected in step c), contacting the single-stranded DNA with a means of cleaving the detectable label from the first type of nucleotide analogue;

e) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

f) if a detectable label is detected in step e), contacting the single-stranded DNA with a means of cleaving the detectable label from the second type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

A further embodiment of the subject invention is a method for determining the identity of a nucleotide at a predetermined position in a nucleic acid of interest, comprising:

a) providing
 1) the nucleic acid of interest,
 2) a nucleic acid polymerase,
 3) a primer capable of hybridizing to said nucleic acid immediately 3' of such predetermined position,
 4) four different nucleotide analogues, wherein each nucleotide analogue comprises (i) a base (ii) a sugar, and (iii) a cleavable t-butyldithiomethyl moiety covalently attached to a 3'-oxygen of the sugar, and wherein the base of each analogue consists of one of adenine or an analogue of adenine, guanine or an analogue of guanine, cytosine or an analogue of cytosine, thiamine or an analogue of thiamine, and a unique detectable label;

b) incorporating one of said nucleotide analogues onto the end of said primer to form an extension strand;

c) detecting the unique detectable label of the incorporated nucleotide analogue so as to thereby identify the incorporated nucleotide analogue on the end of said extension strand; and d) based on the identity of the incorporated nucleotide, determining the identity of the nucleotide at the predetermined position.

3'-O Modified Nucleotides and Sequencing Methods:

Herein described are various approaches for DNA Sequencing by Synthesis (SBS) using 3'-O-reversibly-blocked nucleotide analogues. These nucleotide analogues include molecules with the following structures: 3'-O-CleavableLinker-Label-dNTPs, 3'-O-CleavableLinker-Anchor-dNTPs and 3'-O-CleavableGroup-dNTPs. The Cleavable Linker includes chemically cleavable and photocleavable linkers. The "Anchor" refers to a small chemical moiety that orthogonally and rapidly reacts with another chemical group that carries a detectable label. The Cleavable Group refers to a small chemical moiety that can be cleaved by either chemical or photochemical means. Numerous schemes are provided to perform SBS using the molecules comprising the three classes of nucleotide analogues (described above) in 1-color, 2-color, or 4-color formats.

Also herein disclosed are the design, synthesis, and use of novel 3' reversibly labeled nucleotides having various 3'-O-t-butyldithiomethyl (3'-O-DTM) modifications serving as the linkage to attach a reporter to the nucleotides, thereby permitting the nucleotides to be "scarless" nucleotide reversible terminators (NRT) for DNA sequencing by synthesis (SBS). The 3' attached reporter may be fluorescent. Such novel NRTs may be employed in a set for use in SBS, wherein each NRT is 3'-O reversibly blocked with a DTM group that is labeled with a fluorescent dye that has a unique fluorescence emission corresponding to the type of base of each nucleotide (e.g. a separate emission for A, T, G, and C respectively), thereby installing dual functions (serving as both a reversible blocker and a cleavable fluorescence reporter) to the 3'-O-modified nucleotide analogues. During SBS, after a nucleotide is incorporated, and the fluorescent reporter imaged, the 3'-O-DTM-dye will be cleaved (cleaving agents may include THP or TCEP) to generate a 3'-OH group that is ready for subsequent extension reactions. Many fluorescent dye species (several of which are identified herein) are suitable for polymerase incorporation when attached to the 3'-O of these nucleotide analogues via DTM linkage.

Also described herein are, the three classes of nucleotide analogues previously mentioned (3'-O-CleavableLinker-Label-dNTPs, 3'-O-CleavableLinker-Anchor-dNTPs and 3'-O-CleavableGroup-dNTPs), wherein the analogues are designed and synthesized based on the structure of the nucleotide analogue 3'-O-t-butyldithiomethyl-2'-deoxynucleoside-5'-triphosphates [3'-O-SS(DTM)-dNTPs]. More specifically, attachment of a fluorescent dye to the DTM group at the 3'-end of the nucleotide analogue 3'-O-SS(DTM)-dNTPs yields 3'-O-DTM-Dye-dNTPs; attachment of an "anchor" moiety to the DTM group at the 3'-end of the nucleotide analogue 3'-O-SS(DTM)-dNTPs yields 3'-O-DTM-Anchor-dNTPs; when the cleavable group is the DTM itself at the 3'-end of the nucleotide analogue, the nucleotide analogue bears the parent structure itself [3'-O-SS(DTM)-dNTPs]without further Treatment of the DNA extension products (described above) with tris (3-hydroxypropyl)phosphine (THP) in an aqueous buffer solution cleaves the DTM (SS) bond therefore removing the blocking group at the 3'-O position of the nucleotide, allowing the regeneration of a free OH group that is ready for subsequent polymerase extension reactions to continually sequence DNA. DNA templates with homopolymer regions can be accurately sequenced using these nucleotide analogues.

Additionally, disclosed herein are the design, use, and synthesis of nucleotide analogues that are attached with small "anchor" moieties to the 3'-O position of the nucleotide analogues via a DTM linker. Since attaching smaller groups to the 3'-O position of the nucleotide analogue does not substantially interfere with the polymerase recognition of these molecules as substrates, these NRTs are more efficiently incorporated to the growing DNA strand in SBS. After nucleotide incorporation, a corresponding labeled binding molecule tethered with a fluorescent dye will orthogonally react with the anchor at the 3'-O end of the DNA extension product. Imaging of the fluorescent dye on this DNA extension product will identify the incorporated nucleotide for sequence determination. A general scheme to use these molecules for SBS is shown in FIG. 1.

The anchor moieties include a variety of orthogonally reactive or affinitive functionalities with high efficiency and specificity, such as biotin, azide, trans-cyclooctene (TCO) and phenyl boric acid (PBA), which will efficiently bind or react with streptavidin, dibenzocyclooctyne (DBCO) (John (2010); Shieha (2014)), tetrazine (TZ)(Marjoke (2013); Bergseid (2000)), and salicylhydroxamic acid (SHA) (Bergseid (2000)) respectively. The DNA polymerase will readily incorporate these 3'-O-anchor-modified nucleotides to the growing DNA strand to terminate DNA synthesis. Addition of the labeled binding molecules (such as different fluorophore-labeled streptavidin, DBCO, TZ and SHA) to the corresponding primer extension product leads to orthogonal binding of the labeled binding molecules with the corresponding "anchor" moiety in the 3' end of the primer extension product; after washing away the unbound labeled molecule, the detection of the unique label attached to the 3' end of the primer extension product determines the identity of the incorporated nucleotide.

In addition to performing four-color SBS using the above-mentioned nucleotide analogues, these molecules also allow a wide spectrum of new DNA sequencing methods including one-color or two-color SBS at the single-molecule level or at an ensemble level. Instead of attaching a single dye to the labeled binding molecules, multiple dyes can also be attached to the incorporated nucleotide through conjugation with the labeled binding molecules that carry multiple-dyes (or dendrimers labeled with multiple dyes), so that the amplification of fluorescent signals can be achieved to facilitate single-molecule detection of the DNA extension product via SBS. Two-color SBS can be achieved by connecting a binding molecule to a Fluorescence Resonance Energy Transfer (FRET) cassette formed by two different fluorescent dyes, with distinct emissions, which generate four different FRET signal signatures to identify the four DNA bases (A, C, G, T) (Anthony (2001), Ju (1999)). If each labeled binding molecule is constructed by conjugation with a dye reporter using a uniquely-cleavable linker for labeling the DNA extension product, different cleavage methods can be used for the selective removal of the dye from the DNA extension product; the detected signal changes will therefore determine the incorporated nucleotide at the single-molecule level, or at the ensemble level, to perform SBS. A well-established cleavable linker toolbox [Azo (Leriche (2010), Budin (2010)), Dimethylketal (Bindaulda (2013)) Dde (4,4-dimethyl-2,6-dioxocyclohexylidene)ethyl (Ellis (2003)), ally and nitrobenzyl (Ju (2003), Li (2003), Ju (2006), Wu (2007))] is available to develop the linkage between the labeled binding molecules and the reporting dye. These linkers can be readily cleaved under specific conditions by mild treatment with sodium dithionite ($Na_2S2O_4$), weak acid, hydrazine ($N_2H_4$), Pd(0) and light-irradiation, respectively.

The invention provides for a nucleotide analogue comprised of (i) a base, (ii) a sugar, and (iii) a cleavable t-butyldithiomethyl moiety bound to the 3'-oxygen of the deoxyribose of the sugar. In an embodiment, the sugar is a deoxyribose. In an embodiment, the sugar is a ribose.

In an embodiment, the nucleotide analogue is a nucleotide monophosphate, a nucleotide diphosphate, a nucleotide triphosphate, a nucleotide tetraphosphate, a nucleotide pentaphosphate, or a nucleotide hexaphosphate.

In a further embodiment, the base of the analogue is adenine or an analogue of adenine, guanine or an analogue of guanine, cytosine or an analogue of cytosine, thymine or an analogue of thymine, or uracil or an analogue of uracil.

In a further embodiment, the cleavable moiety may be cleaved by a water soluble phosphine, thereby resulting in a 3'-OH. In a further embodiment, the water soluble phosphine is tris-(2-carboxyethyl)phosphine (TCEP) or tris(hydroxypropyl)phosphine (THP).

In a further embodiment, the cleavable t-butyldithiomethyl moiety has the structure:

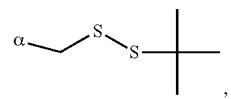

wherein α represents the point of connection to the 3'-oxygen.

In a further embodiment the cleavable t-butyldithiomethyl moiety has the structure:

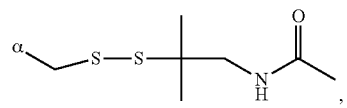

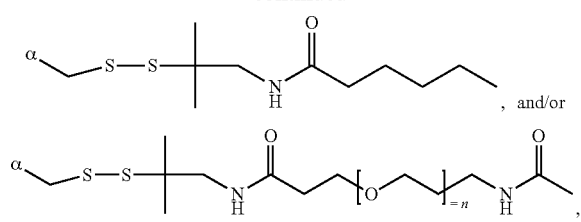

wherein α represents the point of connection to the 3'-oxygen and wherein n is an integer which may be 1, 2, 3, 4, or 5.

In another embodiment the nucleotide analogue has the structure:

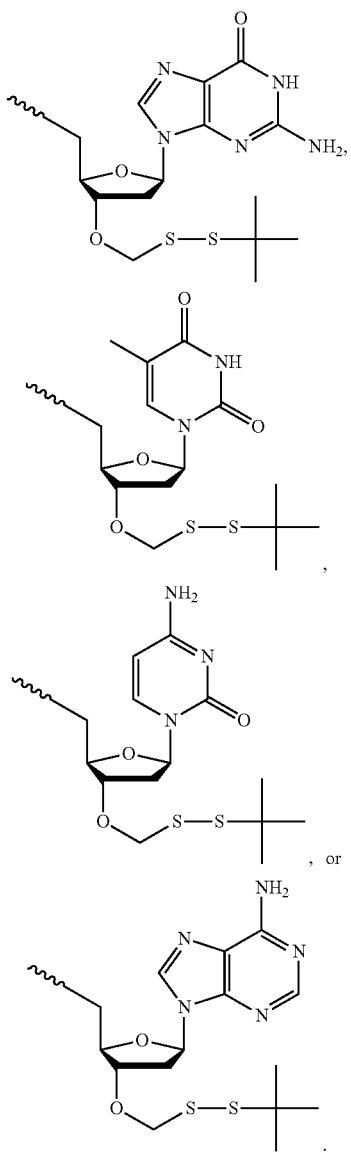

In another embodiment, the nucleotide analogue may further comprise a detectable label. In a further embodiment the cleavable t-butyldithiomethyl moiety has the structure:

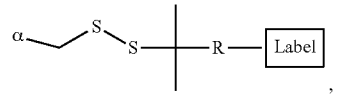

wherein α represents the point of connection to the 3'-oxygen; wherein R represents a structure consisting of one or more atoms one of which is covalently bound to the detectable label; and wherein Label represents the detectable label.

In a further embodiment the cleavable t-butyldithiomethyl moiety has the structure:

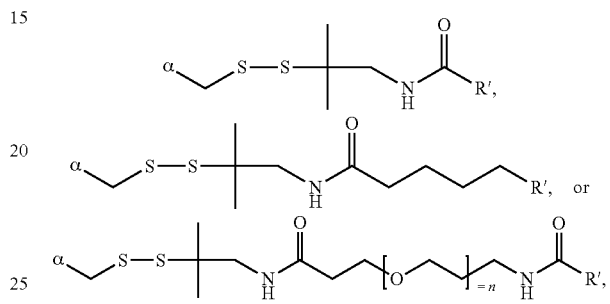

wherein α represents the point of connection to the 3'-oxygen; wherein n is an integer which may be 1, 2, 3, 4, or 5; and wherein R' represents one or more atoms through which a covalent connection is established to the detectable label.

In a further embodiment, the nucleotide analogue has the structure:

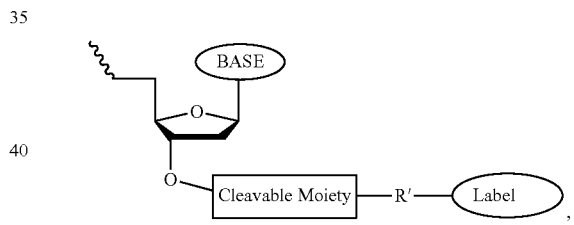

wherein Cleavable Moiety is the cleavable t-butyldithiomethyl moiety, wherein Label represents the detectable label, and wherein R' represents one or more atoms through which a covalent connection is established to the detectable label.

In a further embodiment, the detectable label is one or more of a dye, a fluorophore, a fluorescence energy transfer tag, a chemiluminescent compound, a chromophore, a mass tag, an electrophore, a mononucleotide, an oligonucleotide, or a combination thereof.

In another embodiment, the detectable label is a fluorophore. In yet a further embodiment, the fluorophore is BodipyFL, $R^6G$, ROX, Cy5, or Alexa488.

In a further embodiment, the nucleotide analog is 3'-O-Alexa488-t-butyldithiomethyl-dCTP, 3'-O-Cy5-t-butyldithiomethyl-dGTP, 3'-O-Rox-t-butyldithiomethyl-dATP, 3'-O-RG6-t-butyldithiomethyl-dTTP, 3'-O-Alexa488-PEG$_4$-t-butyldithiomethyl-dCTP, 3'-O-RG6-PEG$_4$-t-butyldithiomethyl-dTTP, 3'-O-Rox-PEG$_4$-t-butyldithiomethyl-dATP, or 3'-O-Cy5-PEG$_4$-t-butyldithiomethyl-dGTP.

In a further embodiment, the nucleotide analogue has the structure:

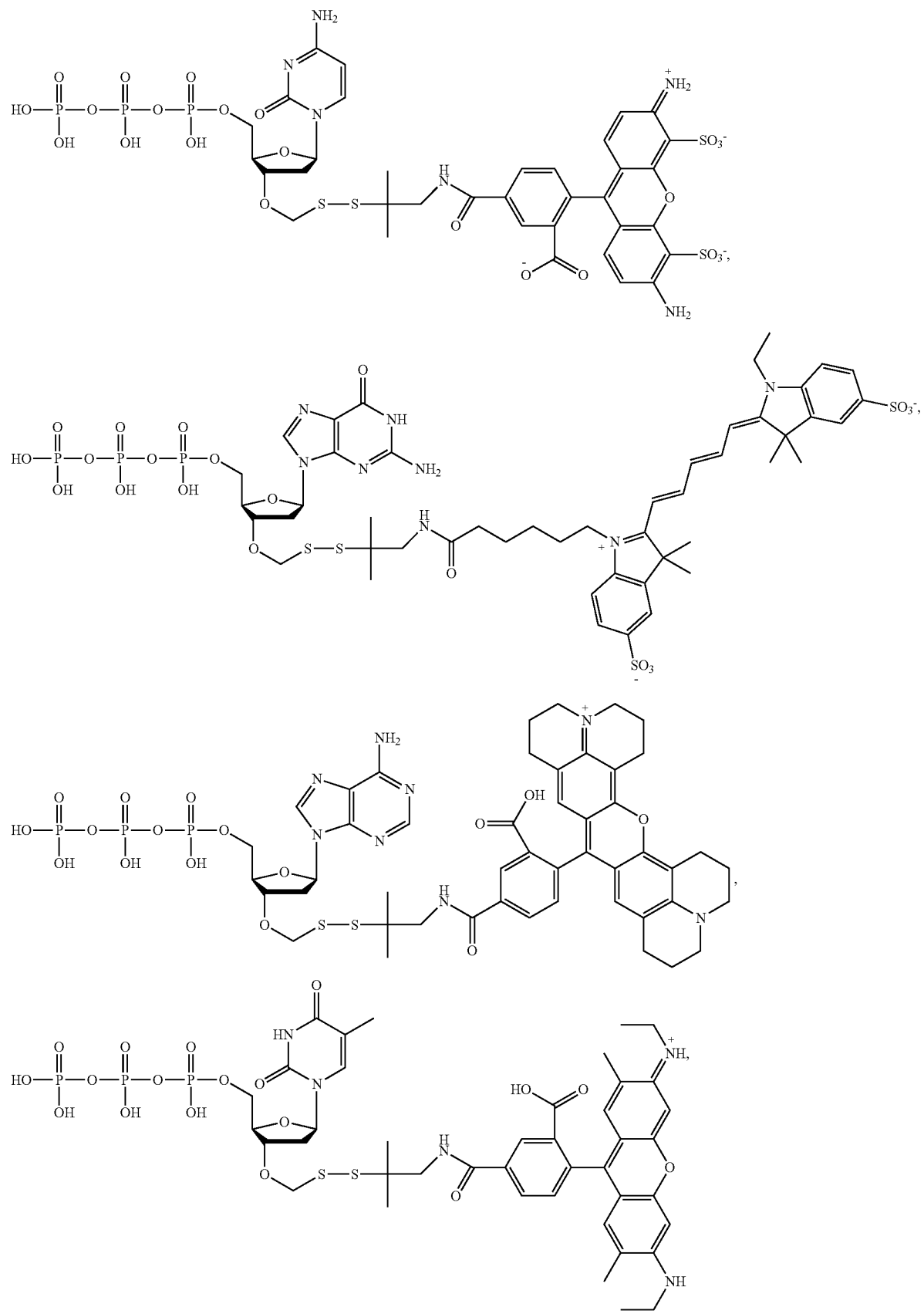

-continued
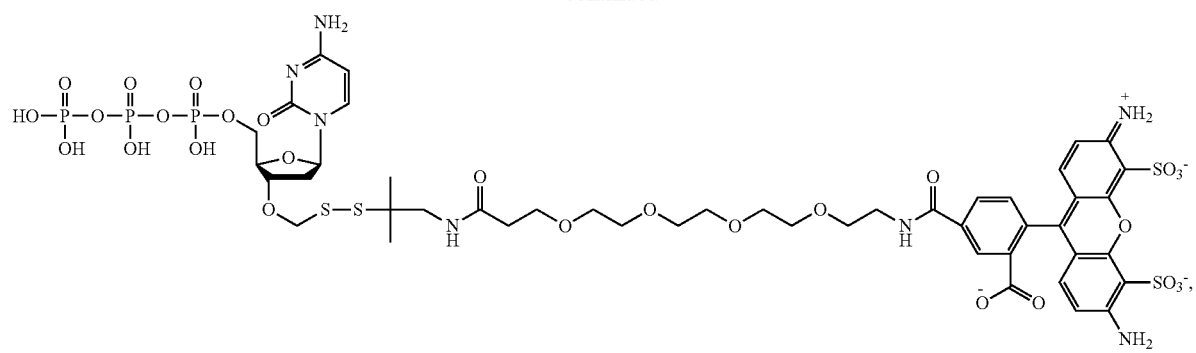
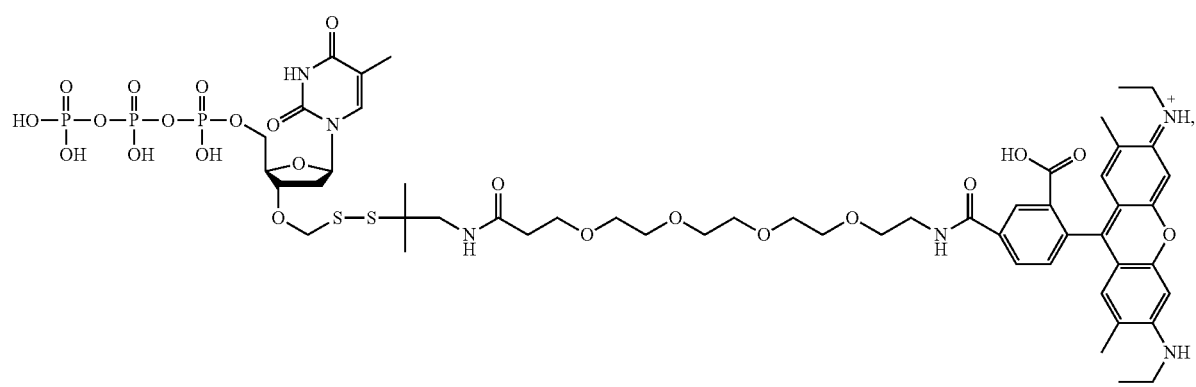
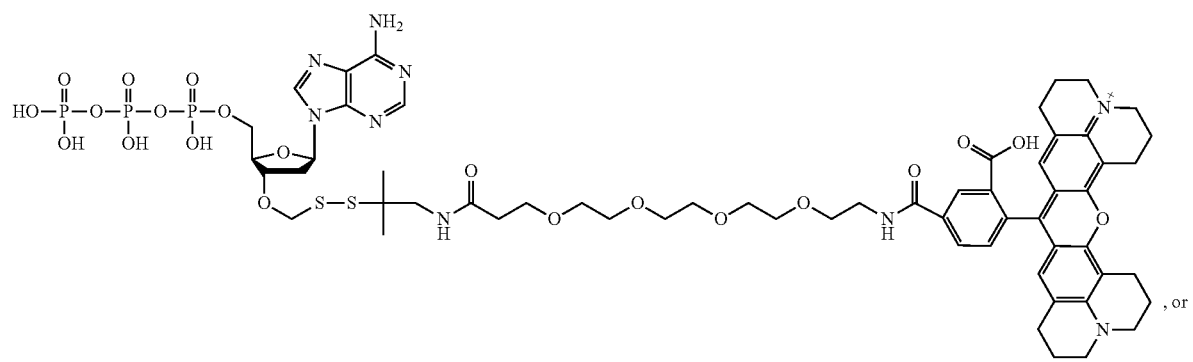
, or
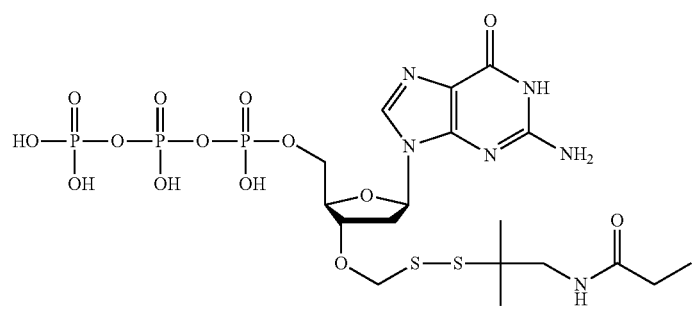

-continued

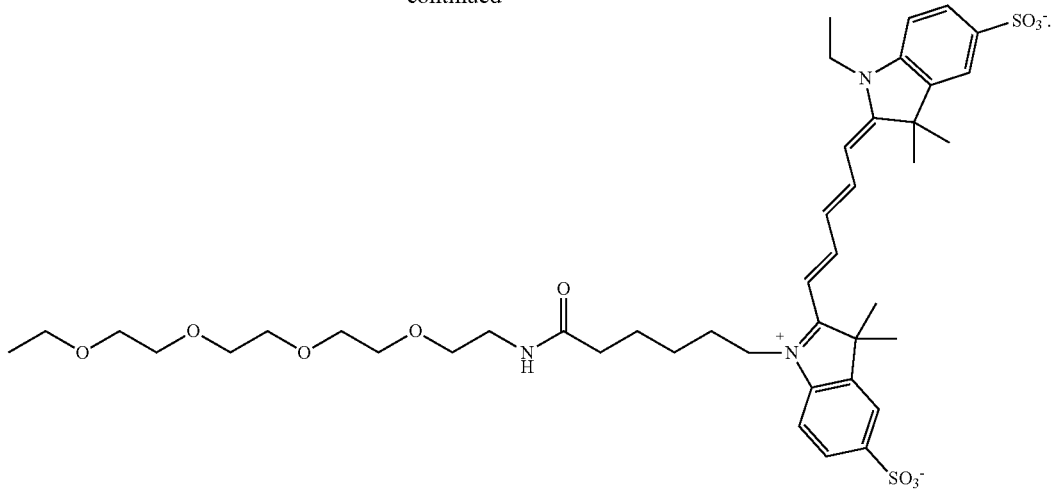

In yet another embodiment, the nucleotide analogue may further comprise an anchor, wherein the anchor is a predetermined small chemical moiety correlated to the identity of the base and that orthogonally and rapidly reacts with a complementary binding molecule thereby binding the anchor and binding molecule.

In a further embodiment, the nucleotide analogue has the structure:

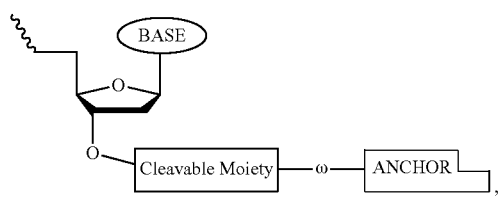

wherein base is one of adenine, guanine, thymine, cytosine, uracil, or an analogue thereof, wherein Cleavable Moiety is the cleavable t-butyldithiomethyl moiety, wherein Anchor is the anchor moiety, and wherein co represents a structure consisting of one or more atoms of which is covalently bound to both the t-butyldithiomethyl cleavable moiety and the anchor moiety.

In a further embodiment of the nucleotide analogue, the anchor has the structure:

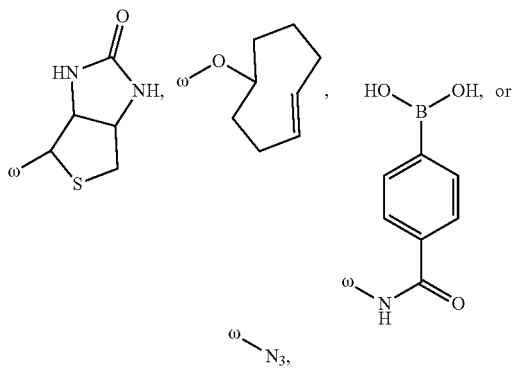

wherein ω represents one or more atoms through which a covalent connection is established to the cleavable t-butyldithiomethyl moiety.

In yet a further embodiment, the anchor of the nucleotide analogue orthogonally and rapidly reacts with a complementary binding molecule thereby forming a conjugate of the anchor and binding molecule, wherein the binding molecule has the structure:

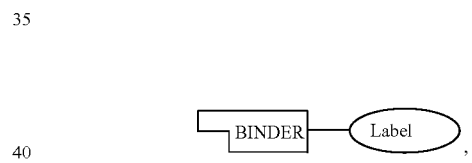

wherein binder is a small chemical group correlated to the identity of the type of binding molecule and that orthogonally and rapidly reacts with an anchor, and wherein Label is a detectable label.

In a further embodiment, the detectable label of the complementary binding molecule is selected from the group consisting of one or more dyes, fluorophores, combinatorial fluorescence energy transfer tags, chemiluminescent compounds, chromophores, mass tags, electrophores, mononucleotides, oligonucleotides, or combinations thereof.

In a further embodiment the detectable label of the complementary binding molecule comprises one or more fluorescence energy transfer tags. In a further embodiment the complementary binding molecule further comprises one or more FRET cassettes. In yet a further embodiment the FRET cassettes comprise one or more dSpacer monomers. In yet a further embodiment, the complementary binding molecule has the structure:

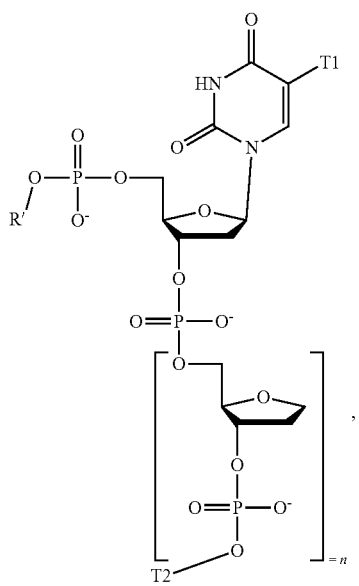

wherein T1 is a point of attachment for one or more fluorescent energy donor or acceptor, and T2 is a point of attachment for one or more of the complementary energy donor or acceptor to that in Ti, wherein n is an integer between 1 and 20, and R represents the point of attachment to the binder of the binding molecule.

In another embodiment, the detectable label of the complementary binding molecule is one or more fluorophore. In a further embodiment, the fluorophore of the detectable label of the complementary binding molecule is selected from the group consisting of BodipyFL, R⁶G, ROX, Cy5, and Alexa488.

In certain embodiments of the invention, the label comprises a plurality of identical Raman-scattering moieties. In other embodiments, the tag comprises a plurality of different Raman-scattering moieties. In certain specific embodiments, the tag comprises 3, 9, or 27 Raman-scattering moieties. In an embodiment, the plurality of Raman-scattering moieties forms a linear tag. In another embodiment, the plurality of Raman-scattering moieties forms a non-linear tag. In a another embodiment, the non-linear tag is a dendrimer tag. In an embodiment, the tag has a Raman spectroscopy peak with wavenumber from 2125 cm$^{-1}$ to 2260 cm$^{-1}$.

In another embodiment the nucleotide analogues are use in conjunction with a nucleotide polymerase or polymerases that are tethered to noble metal nanoparticles. In another embodiment the noble metal nanoparticles are silver and/or gold nanoparticles. In another embodiment the polymerase or polymerases have 1 or more attached and/or conjugated noble metal nanoparticles, wherein the noble metal nanoparticles are a surface-enhanced Raman spectroscopy (SERS) substrates. In another embodiment the noble metal nanoparticles are either gold or silver nanoparticles. In another embodiment the metal nanoparticles of the polymerase or polymerases are between 3 nm and 10 nm. In another embodiment the polymerase or polymerases have 2, 3, 4, or 5 metal nanoparticles. In another embodiment the metal nanoparticles of the polymerase or polymerases are attached and/or conjugated to the polymerase 1 nm-3 nm from the active site of the polymerase. In another embodiment the metal nanoparticles of the polymerase or polymerases are attached and/or conjugated to the polymerase or polymerases 1 nm-3 nm from the active site of the polymerase, thereby creating a region of enhanced sensitivity for surface enhanced Raman spectroscopy (SERS) at the active site. In another embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule. In another embodiment the attached and/or conjugated metal nanoparticles of the polymerase create a region of enhanced sensitivity for surface enhanced Raman spectroscopy (SERS) at the location of the Raman active molecule.

In a further embodiment, the binder of the complementary binding molecule comprises:

a) a compound comprising streptavidin having the structure:

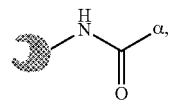

b) a compound comprising the structure:

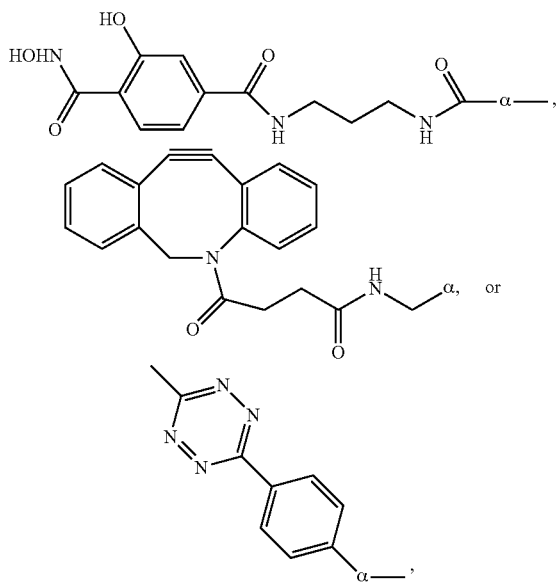

wherein α represents one or more atoms through which a covalent connection is established to the detectable label.

In a further embodiment, if the anchor of the nucleotide analogue has the structure:

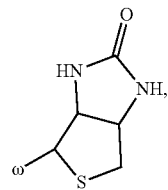

wherein ω represents one or more atoms through which a covalent connection is established to the cleavable t-butyldithiomethyl moiety, then the anchor can orthogonally and rapidly react with a binder of a complimentary binding molecule, wherein said binder comprises streptavidin, and has the structure:

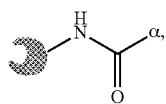

wherein α is one or more atoms through which a covalent connection is established to a detectable label, thereby forming a conjugate having the structure:

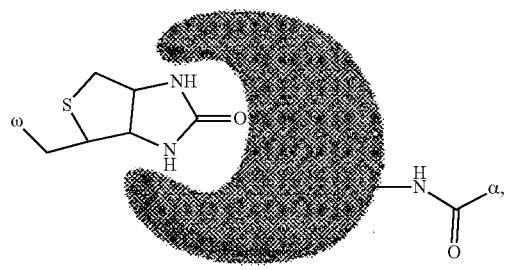

wherein α is one or more atoms through which a covalent connection is established to detectable label, and wherein ω is one or more atoms through which a covalent connection is established to the cleavable t-butyldithiomethyl moiety.

In a further embodiment, the nucleotide analogue has the structure:

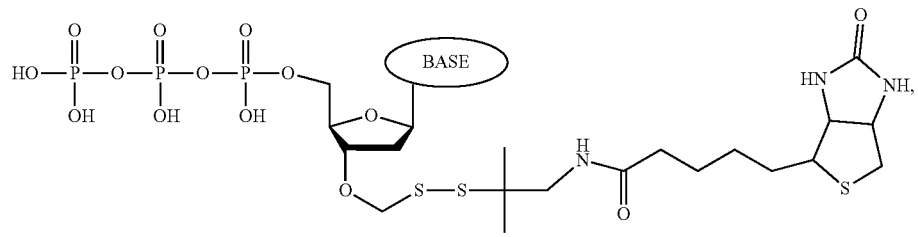

wherein base is one of adenine, guanine, thymine, cytosine, uracil, or an analogue thereof.

In a further embodiment the complementary binding molecule to the nucleotide analogue comprises streptavidin, and wherein the complementary binding molecule has the structure:

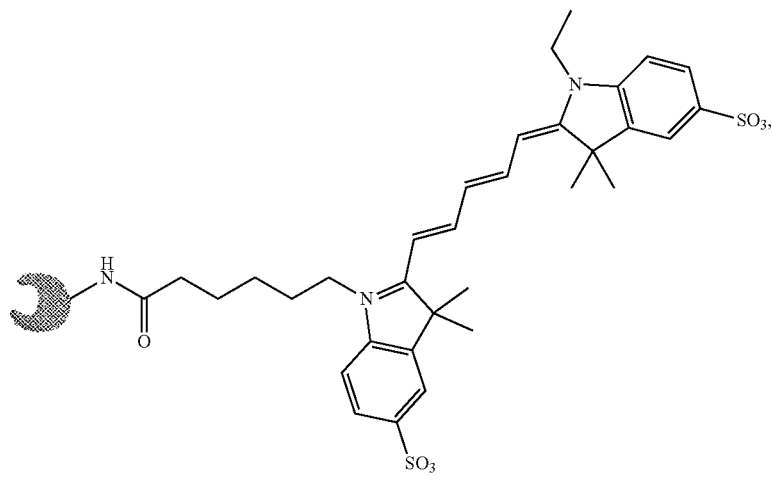

-continued

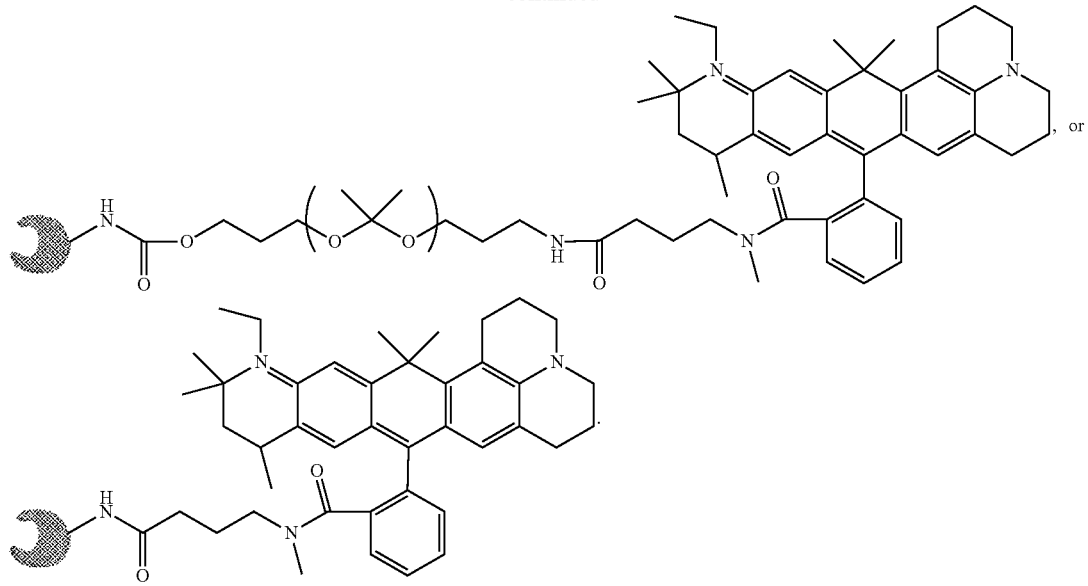

In another embodiment, if the anchor of the nucleotide analogue has the structure:

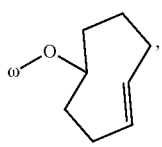

wherein ω represents one or more atoms through which a covalent connection is established to the cleavable t-butyl-dithiomethyl moiety, then the anchor can orthogonally and rapidly react with a binder of a complimentary binding molecule, wherein said binder has the structure:

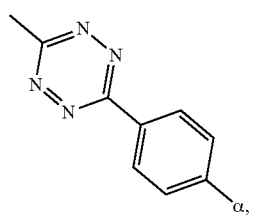

wherein α is one or more atoms through which a covalent connection is established to a detectable label, thereby forming a conjugate having the structure:

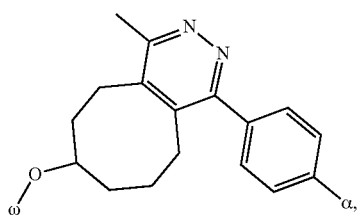

wherein α is one or more atoms through which a covalent connection is established to detectable label, and wherein w is one or more atoms through which a covalent connection is established to the cleavable t-butyldithiomethyl moiety.

In a further embodiment, the nucleotide analogue has the structure:

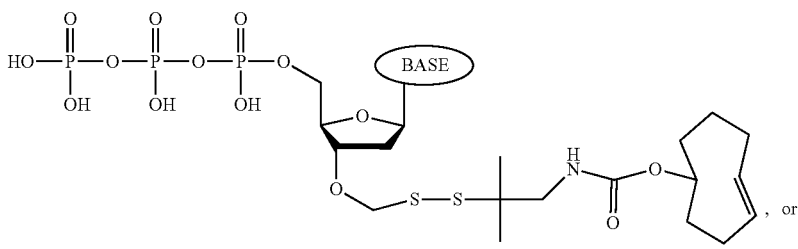

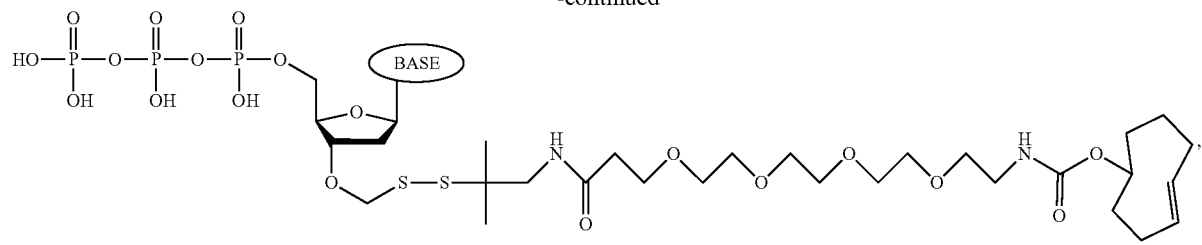
wherein base is one of adenine, guanine, thymine, cytosine, uracil, or an analogue thereof.
In a further embodiment, the complementary binding molecule to the nucleotide analogue has the structure:
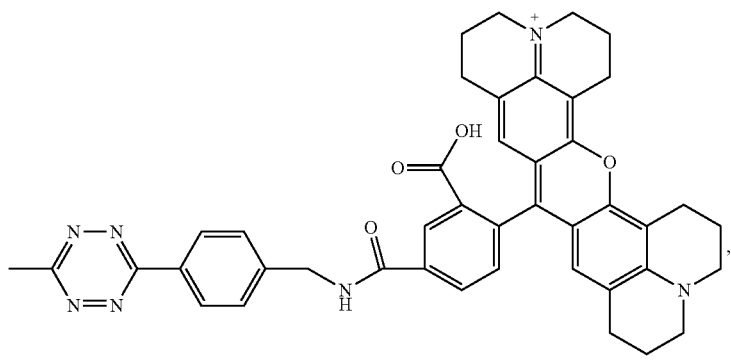
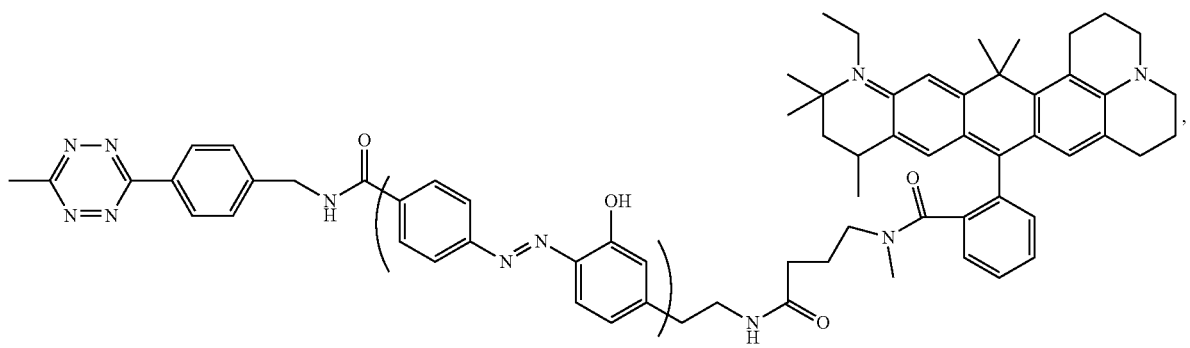
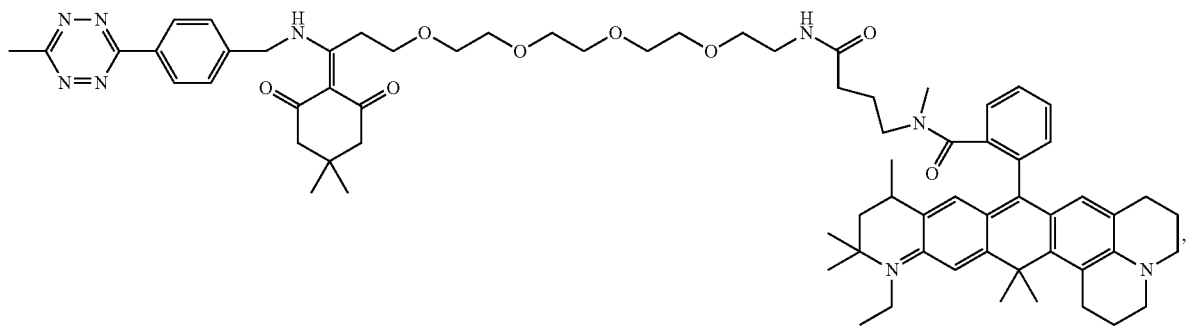

383
384
-continued
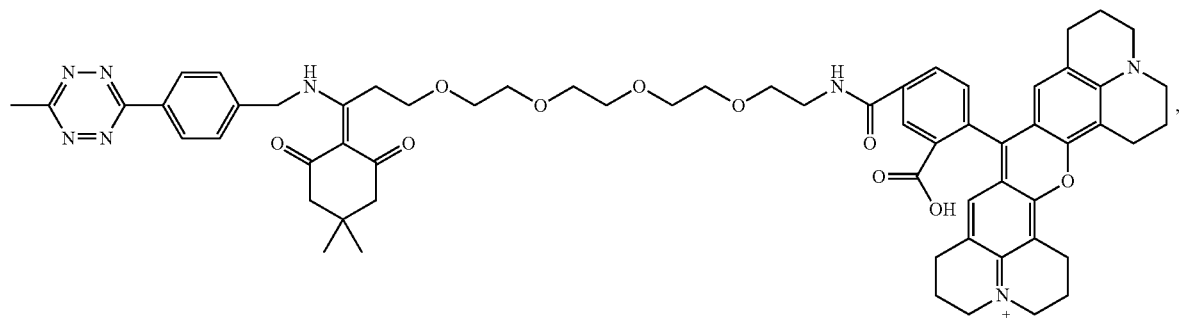
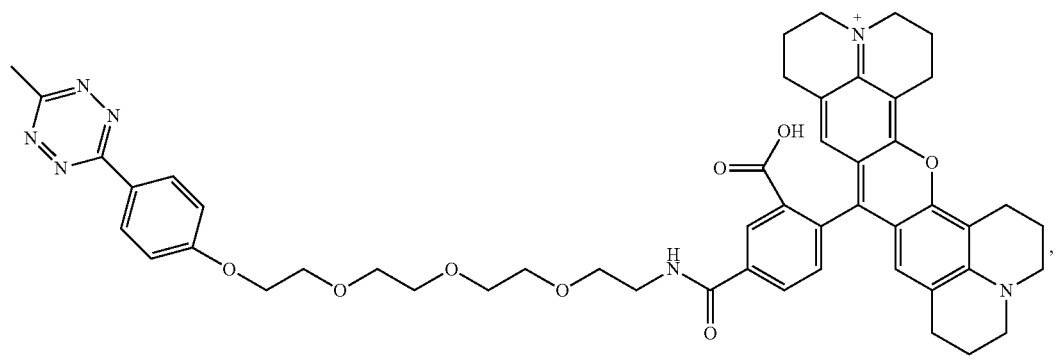
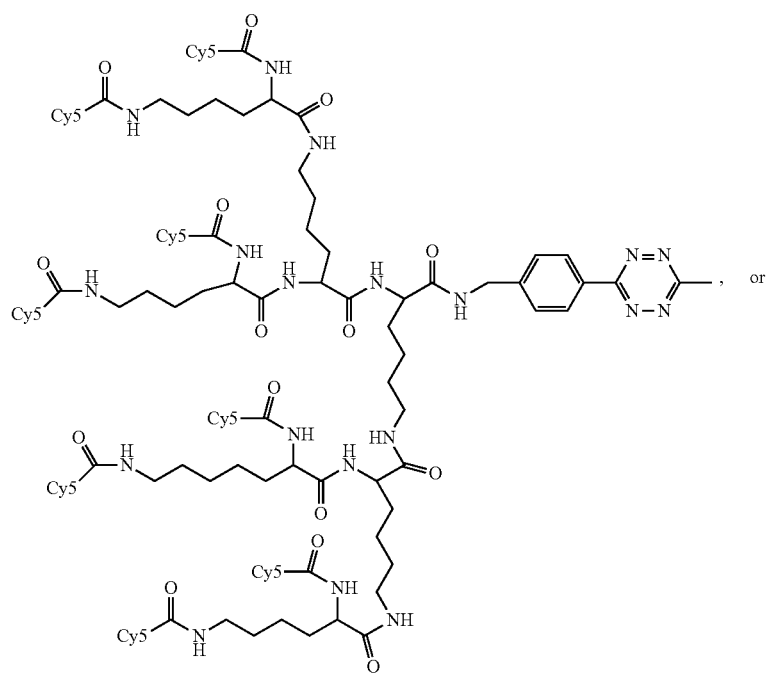

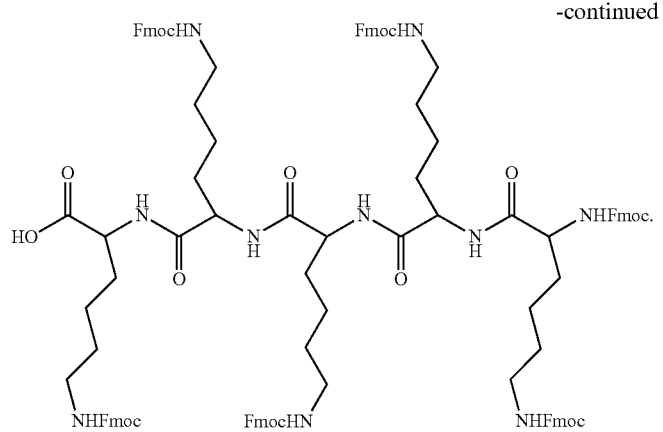

In another embodiment, wherein if the anchor has the structure:

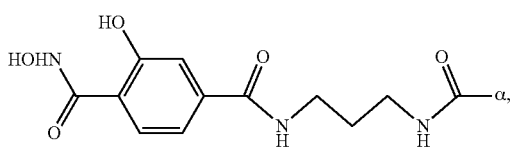

wherein ω represents one or more atoms through which a covalent connection is established to the cleavable t-butyl-dithiomethyl moiety, then the anchor orthogonally and rapidly reacts with a binder of a complimentary binding molecule, wherein said binder has the structure:

wherein α is one or more atoms through which a covalent connection is established to a detectable label, thereby forming a conjugate having the structure:

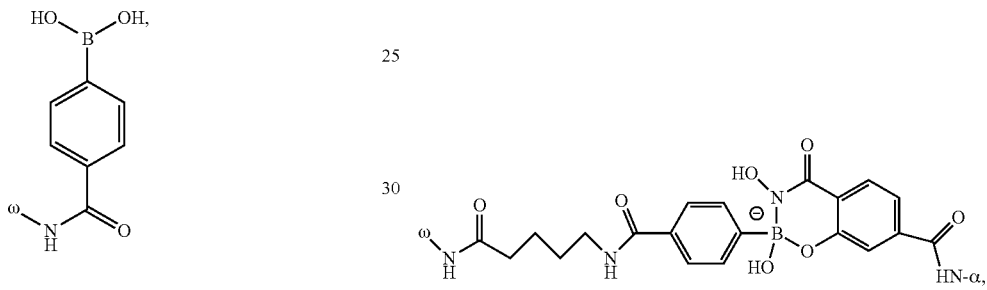

wherein α is one or more atoms through which a covalent connection is established to detectable label, and wherein ω is one or more atoms through which a covalent connection is established to the cleavable t-butyldithiomethyl moiety.

In further embodiment of the nucleotide analogue, the nucleotide analogue has the structure:

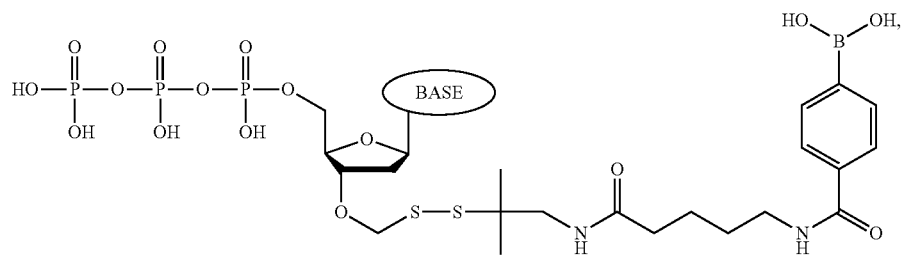

wherein base is one of adenine, guanine, thymine, cytosine, uracil, or an analogue thereof.

In further embodiment the complementary binding to the nucleotide analogue has the structure:

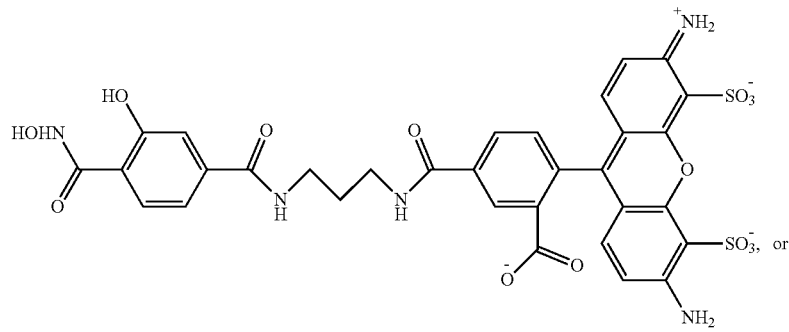

or

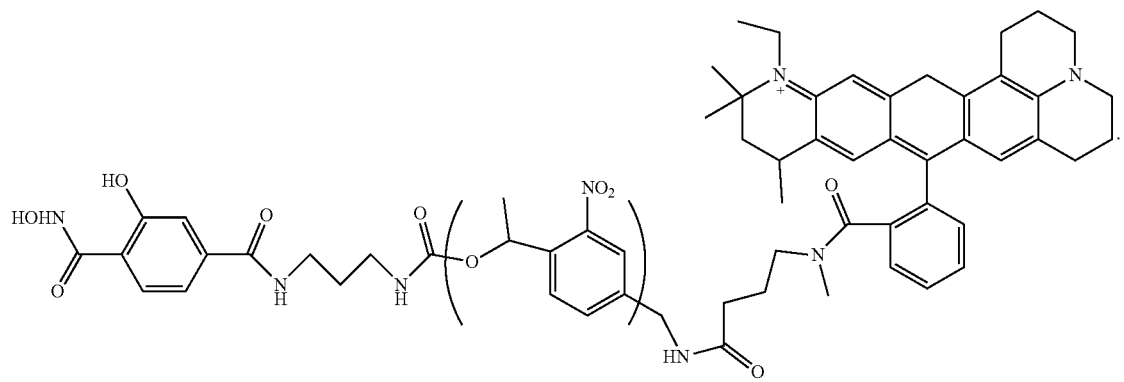

In a further embodiment, if the anchor has the structure:

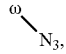

wherein ω represents one or more atoms through which a covalent connection is established to the cleavable t-butyldithiomethyl moiety, then the anchor can orthogonally and rapidly react with a binder of a complimentary binding molecule, wherein said binder has the structure:

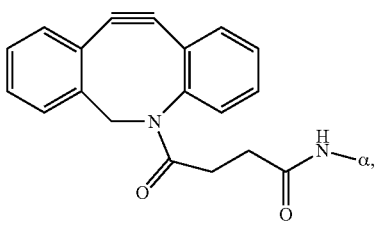

wherein α is one or more atoms through which a covalent connection is established to a detectable label, thereby forming a conjugate having the structure:

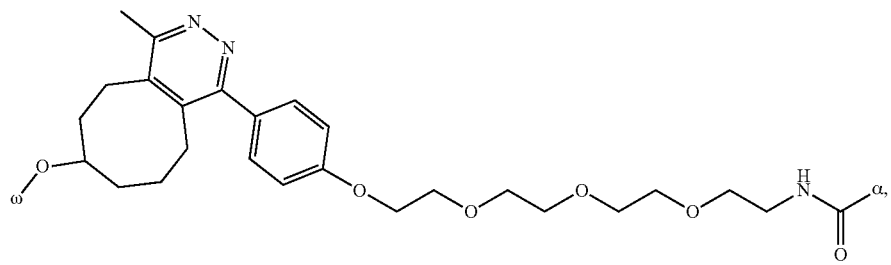

wherein α is one or more atoms through which a covalent connection is established to detectable label, and wherein ω is one or more atoms through which a covalent connection is established to the cleavable t-butyldithiomethyl moiety.

In further embodiment, the nucleotide analogue has the structure:
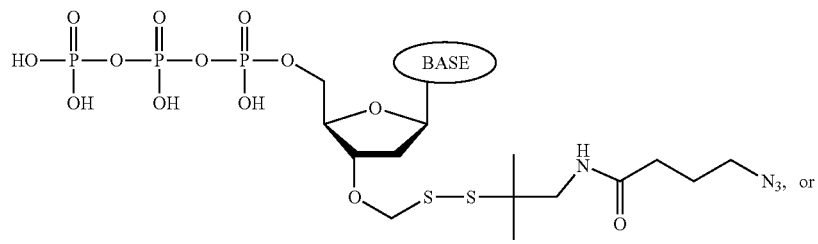
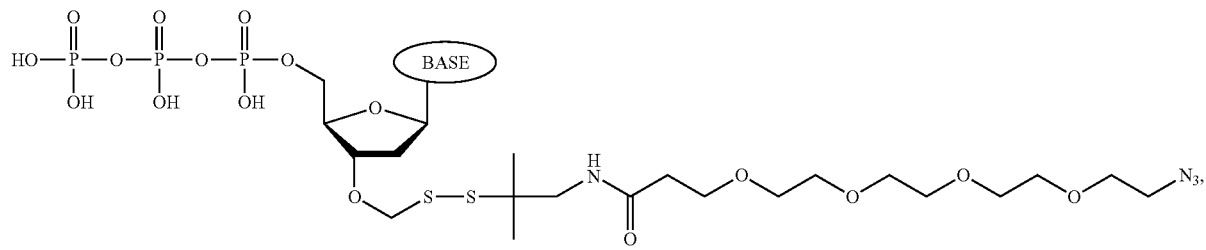
wherein base is one of adenine, guanine, thymine, cytosine, uracil, or an analogue thereof.
In further embodiment, the complementary binding molecule to the nucleotide analogue has the structure:
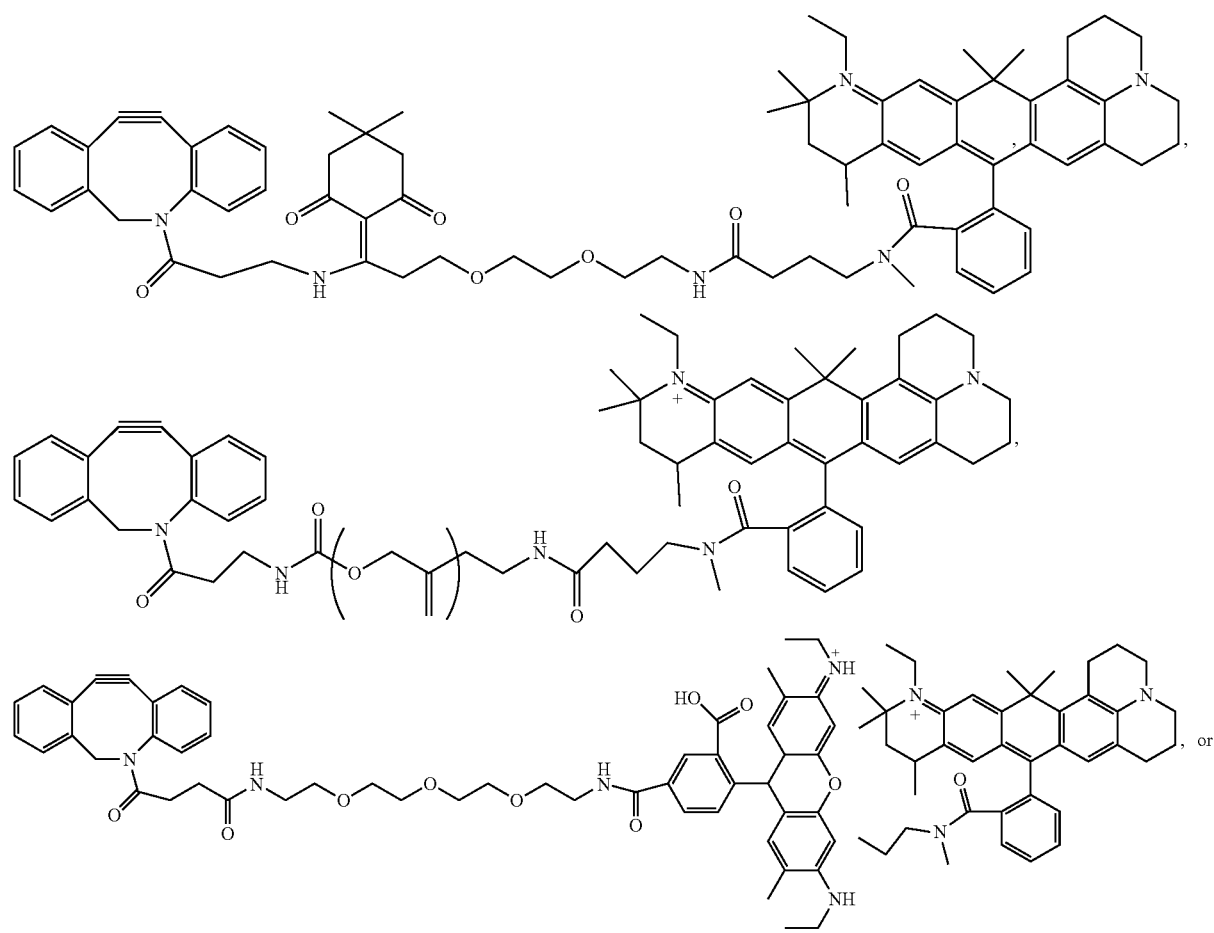

-continued

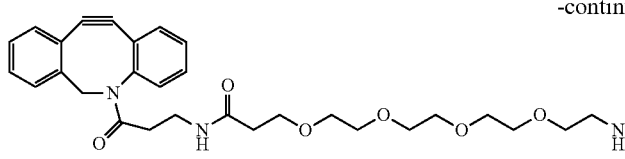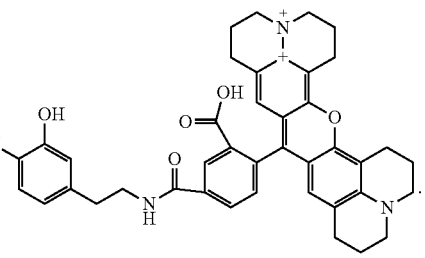

Herein is further disclosed a method for determining the nucleotide sequence of a single-stranded DNA, the method comprising:

a) contacting the single-stranded DNA having a primer hybridized to a portion thereof, with a nucleotide polymerase and a first type of nucleotide analogue under conditions permitting the nucleotide polymerase to catalyze incorporation of the nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the nucleotide analogue has the structure:

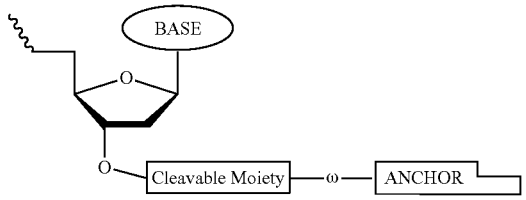

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the identity of the anchor is predetermined and is correlated to the identity of the base, b) contacting the single-stranded DNA of step a) with a binding molecule complementary to the anchor of the nucleotide analogue of step a), wherein the binding molecule has the structure:

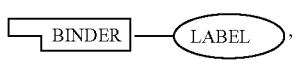

wherein binder is a chemical group that orthogonally and rapidly reacts with the anchor moiety, thereby forming a conjugate of the binding molecule and the anchor moiety, and Label is a detectable label, c) removing any nucleotide analogue not incorporated into the primer in step a);

d) detecting the presence of any detectable label so as to thereby determine whether the nucleotide analogue of step a) was incorporated so as to thereby determine the identity of the complementary nucleotide residue in the single-stranded DNA, and wherein if the base of the nucleotide analogue a) is not complementary to the nucleotide residue of the single-stranded DNA which is immediately 5' to the nucleotide residue of the single-stranded DNA hybridized to the 3' terminal nucleotide residue of the primer, then iteratively repeating steps a) through c) with a second, third, and then fourth type of nucleotide analogue, wherein each different type of nucleotide analogue has a different base from each other type of nucleotide analogue, until the nucleotide analogue has a base that is complementary, e) cleaving the cleavable t-butyldithiomethyl moiety, so as to thereby create a 3'-OH; and f) iteratively performing steps a) through e) for each nucleotide residue of the single-stranded DNA to be sequenced so as to thereby determine the sequence of the single-stranded DNA.

In a further embodiment of the method, steps b) and c) are performed simultaneously, or in the order step b) then step c) or in the order step c) then step b).

In a further embodiment of the method, different nucleotide analogues have different anchors, and each different anchor is complementary to a different binding molecule.

In a further embodiment of the method the different binding molecules each have a different detectable label.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein each type of nucleotide analogue has the structure:

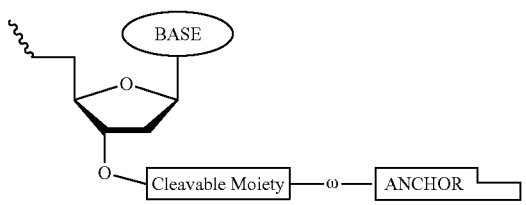

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of each type of nucleotide analogue is independently different from the base of the remaining three types of nucleotide analogue, wherein the anchor of each type of nucleotide analogue is independently different from the anchor of the remaining three types of nucleotide analogue, wherein the anchor of each type of nucleotide analogue orthogonally and rapidly reacts with a different binding molecule from each of the remaining three types of nucleotide analogue;

b) contacting the single-stranded DNA of step a) with a first, second, third, and fourth type of binding molecule, under conditions permitting the anchor of the nucleotide analogue incorporated in step a) to orthogonally and rapidly react with a complementary binding molecule thereby binding the binding molecule to the anchor, wherein the first, second, third, and fourth type of binding molecule each have the structure:

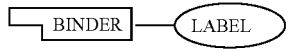

wherein binder is a small chemical group that orthogonally and rapidly reacts with an anchor, and wherein Label is a predetermined detectable label correlated to the identity of the type of binding molecule, wherein the binder of each type of binding molecule is different from the binder of the remaining three types of binding molecule, wherein the first type of binding molecule and the first type of nucleotide analogue, the second type of binding molecule and second type of nucleotide analogue, the third type of binding molecule and third type of nucleotide analogue, and the fourth type of binding molecule and the fourth type of nucleotide analogue are respectively complementary and thereby orthogonally and rapidly react thereby forming a conjugate of each individual type of binding molecule an an individual type of nucleotide analogue;

c) determining the identity of the detectable label of the nucleotide analogue incorporated in step a) so as to thereby determine the identity of the incorporated nucleotide analogue and the identity of the complementary nucleotide residue in the single-stranded DNA;

d) cleaving the cleavable t-butyldithiomethyl moiety, so as to thereby create a 3'-OH; and
  e) iteratively performing steps a) through d) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product,
    wherein the first and second types of nucleotide analogue have the structure:

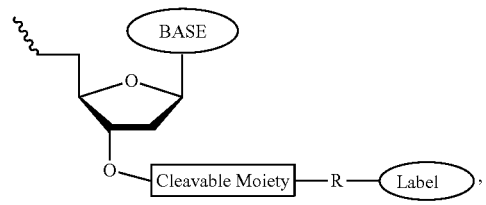

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label,
    wherein the label of the first type of nucleotide analogue is different form the label of the second type of nucleotide analogue, wherein the base of each of the first and second type of nucleotide analogue is independently different from the base of each of the three remaining types of nucleotide analogue,
    wherein the third and fourth type of nucleotide analogue has the structure:

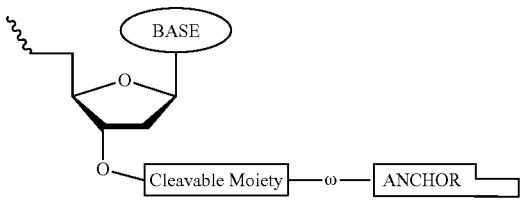

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the third and fourth type of nucleotide analogue is independently different from the base of each of the three remaining types of nucleotide analogue, wherein the anchor of the third type of nucleotide analogue is different from the anchor of the fourth type of nucleotide analogue;

b) removing any nucleotide analogues not incorporated in step a);

c) detecting the presence of either the detectable label of the first or second type of nucleotide analogue incorporated in step a) so as to thereby determine the identity of the incorporated nucleotide analogue and the identity of the complementary nucleotide residue in the single-stranded DNA, wherein if the base of the first and second type of nucleotide is not complementary, contacting the single-stranded DNA with a first and second type of binding molecule, wherein the first and second type of binding molecule have the structure:

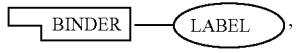

wherein binder is a small chemical group that orthogonally and rapidly reacts with an anchor, and wherein Label is a predetermined detectable label correlated to the identity of the binding molecule, wherein the detectable label of the first type of binding molecule is the same as the detectable label of the first type of nucleotide analogue, wherein the detectable label of the second type of binding molecule is the same as the detectable label of the second type of nucleotide analogue, wherein the binder of the first type of binding molecule orthogonally and rapidly reacts with the anchor of the third type of nucleotide analogue, and wherein the second type of binding molecule orthogonally and rapidly reacts with the anchor of the fourth type of nucleotide analogue, removing any unbound binding molecule, and detecting the presence of either the first or second binding molecule so as to thereby determine the identity of the nucleotide analogue incorporated in step a) and the identity of the complementary nucleotide residue in the single-stranded DNA;

d) cleaving the cleavable t-butyldithiomethyl moiety so as to thereby create a 3'-OH; and e) iteratively performing steps a) through d) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the structure:

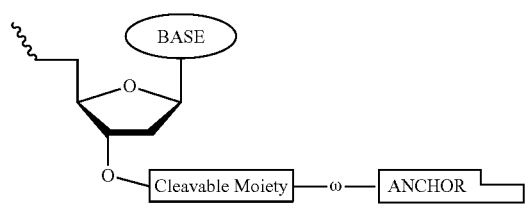

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

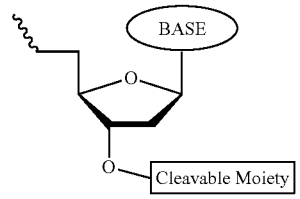

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) contact the single-stranded DNA of step a) with a first, second, and third type of binding molecule, each type of binding molecule having the structure:

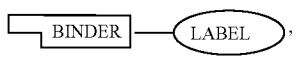

wherein binder is a small chemical group correlated to the identity of the type of binding molecule and that orthogonally and rapidly reacts with an anchor, and wherein Label is a detectable label, wherein the binder of each type of binding molecule is different from the binder of the remaining two types of binding molecule, wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue;

c) removing any nucleotide analogues from step a) not incorporated into the primer;

d) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

e) if a detectable label is detected in step d), contacting the single-stranded DNA with a means of cleaving the detectable label and/or the binding molecule from the first type of nucleotide analogue;

f) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

g) if a detectable label is detected in step f), contacting the single-stranded DNA with a means of cleaving the detectable label and/or the binding molecule from the second type of nucleotide analogue;

h) detecting whether there is an absence of detectable label bound to the incorporated nucleotide of step a), thereby determining the identity of the incorporated nucleotide analogue, and thereby the identity of the complementary nucleotide residue in the single-stranded DNA;

i) cleaving the cleavable t-butyldithiomethyl moiety so as to thereby create a 3'-OH; and j) iteratively performing steps a) through i) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first and second types of nucleotide analogue have the structure:

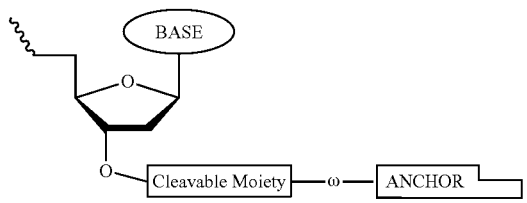

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first and second type of nucleotide analogue is independently different from the base of each of the three remaining types of nucleotide analogue, wherein the anchor of the first type of nucleotide analogue is different from the anchor of the second type of nucleotide analogue, wherein the third type of nucleotide analogue has the structure:

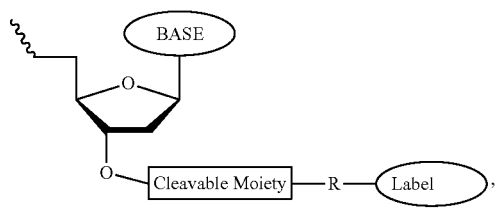

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the third type of nucleotide analogue is independently different from the base of each of the three remaining types of nucleotide analogue, wherein the fourth type of nucleotide analogue has the structure:

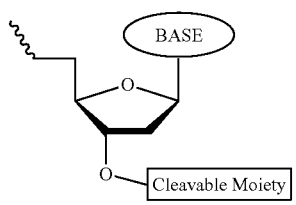

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing any nucleotide analogues from step a) not incorporated into the primer;

c) detecting whether there is a presence of detectable label bound to the incorporated nucleotide of step a), thereby determining that identity of the incorporated nucleotide is of the third type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first and second type of binding molecule, wherein the first and second type of binding molecule have the structure:

wherein binder is a small chemical group correlated to the identity of the type of binding molecule and that orthogonally and rapidly reacts with an anchor, and wherein Label is a detectable label, wherein the binder of each type of binding molecule is different one another, wherein the first type of binding molecule and the first type of nucleotide analogue, and the second type of binding molecule and second type of nucleotide analogue, respectively complementary and thereby orthogonally and rapidly react thereby binding each individual type of binding molecule with an individual type of nucleotide analogue;

e) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

f) if a detectable label is detected in step e), contacting the single-stranded DNA with a means of cleaving the detectable label and/or the binding molecule from the first type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the structure:

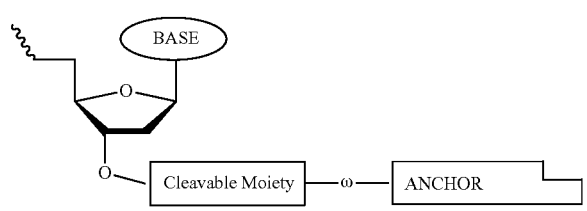

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

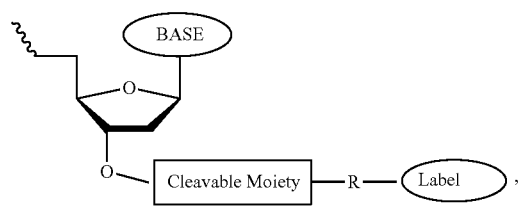

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the fourth type of nucleotide analogue is independently different from the base of each of the three remaining types of nucleotide analogue;

b) removing all unincorporated nucleotide analogues from step a);

c) detecting whether there is a presence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first, second, and third type of binding molecule, wherein the first, second, and third type of binding molecule have the structure:

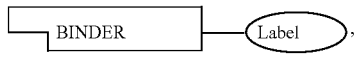

wherein binder is a small chemical group correlated to the identity of the type of binding molecule and that orthogonally and rapidly reacts with an anchor, and wherein Label is a detectable label, wherein the binder of each type of binding molecule is different from one another, wherein the first type of binding molecule and wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue;

e) detecting whether there is a presence of detectable label bound to the incorporated nucleotide of step a);

f) contacting the single-stranded DNA with a means of cleaving the detectable label and/or the binding molecule from the first type of nucleotide analogue;

g) detecting whether there is an absence of detectable label bound to the incorporated nucleotide of step a), thereby determining that the identity of the incorporated nucleotide is of the first type of nucleotide analogue, and thereby the identity of the complementary nucleotide residue in the single-stranded DNA;

h) if a detectable label is detected in step f), contacting the single-stranded DNA with a means of cleaving the detectable label and/or the binding molecule from the second type of nucleotide analogue;

i) detecting whether there is an absence of detectable label bound to the incorporated nucleotide of step a), thereby determining the identity of the incorporated nucleotide analogue, and thereby the identity of the complementary nucleotide residue in the single-stranded DNA;

j) cleaving the cleavable t-butyldithiomethyl moiety so as to thereby create a 3'-OH; and k) iteratively performing steps a) through j) for each nucleotide residue of the single-stranded DNA to be sequenced so as to thereby determine the sequence of the single-stranded DNA.

Herein is disclosed a further method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third types of nucleotide analogue have the structure:

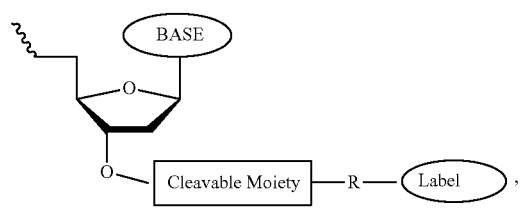

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the first, second, and third type of nucleotide analogue is independently different from the base of each of the three remaining types of nucleotide analogue, wherein the fourth type of nucleotide analogue has the structure:

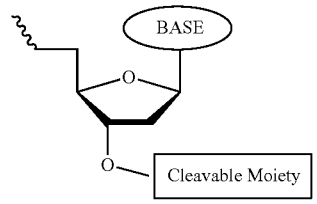

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing all unincorporated nucleotide analogues from step a);

c) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if a detectable label is detected in step c), contacting the single-stranded DNA with a means of cleaving the detectable label from the first type of nucleotide analogue;

e) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

f) if a detectable label is detected in step e), contacting the single-stranded DNA with a means of cleaving the detectable label from the second type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

In a further embodiment of the foregoing methods, the anchor of each type of nucleotide analogue having an anchor that forms a conjugate with a complementary binding molecule, each individually has the structure:

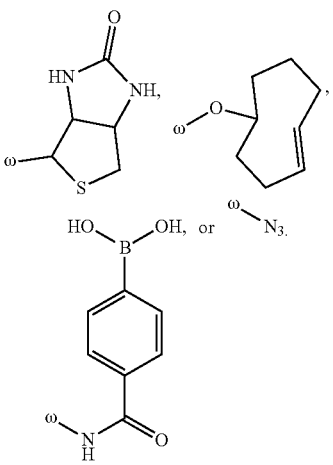

wherein ω represents one or more atoms through which a covalent connection is established to the cleavable t-butyldithiomethyl moiety.

In a further embodiment, the detectable label of the complementary binding molecule is selected from the group consisting of one or more dyes, fluorophores, combinatorial fluorescence energy transfer tags, chemiluminescent compounds, chromophores, mass tags, electrophores, mononucleotides, oligonucleotides, or combinations thereof.

In a further embodiment the detectable label of the complementary binding molecule comprises one or more fluorescence energy transfer tags.

In a further embodiment the complementary binding molecule further comprises one or more FRET cassettes. In a further embodiment the FRET cassettes comprise one or more dSpacer monomers.

In a further embodiment the complementary binding molecule has the structure:

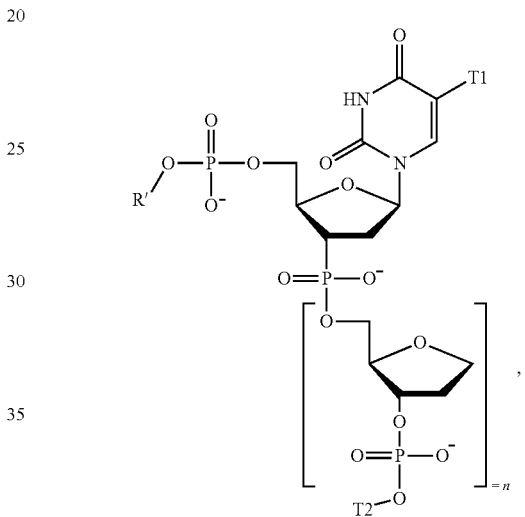

wherein T1 is a point of attachment for one or more fluorescent energy donor or acceptor, and T2 is a point of attachment for one or more of the complementary energy donor or acceptor to that in T1, wherein n is an integer between 1 and 20, and R represents the point of attachment to the binder of the binding molecule.

In a further embodiment the detectable label of the complementary binding molecule is one or more fluorophore. In a further embodiment the fluorophore of the detectable label of the complementary binding molecule is selected from the group consisting of BodipyFL, $R^6G$, ROX, Cy5, and Alexa488.

In certain embodiments of the invention, the label comprises a plurality of identical Raman-scattering moieties. In other embodiments, the tag comprises a plurality of different Raman-scattering moieties. In certain specific embodiments, the tag comprises 3, 9, or 27 Raman-scattering moieties. In an embodiment, the plurality of Raman-scattering moieties forms a linear tag. In another embodiment, the plurality of Raman-scattering moieties forms a non-linear tag. In a another embodiment, the non-linear tag is a dendrimer tag. In an embodiment, the tag has a Raman spectroscopy peak with wavenumber from 2125 $cm^{-1}$ to 2260 $cm^{-1}$.

In another embodiment the polymerase or polymerases are tethered to the noble metal nanoparticles. In another embodiment the noble metal nanoparticles are silver and/or gold nanoparticles. In another embodiment the polymerase or polymerases have 1 or more attached and/or conjugated noble metal nanoparticles, wherein the noble metal nanoparticles are a surface-enhanced Raman spectroscopy (SERS) substrates. In another embodiment the noble metal nanoparticles are either gold or silver nanoparticles. In another embodiment the metal nanoparticles of the polymerase or polymerases are between 3 nm and 10 nm. In another embodiment the polymerase or polymerases have 2, 3, 4, or 5 metal nanoparticles. In another embodiment the metal nanoparticles of the polymerase or polymerases are attached and/or conjugated to the polymerase 1 nm-3 nm from the active site of the polymerase. In another embodiment the metal nanoparticles of the polymerase or polymerases are attached and/or conjugated to the polymerase or polymerases 1 nm-3 nm from the active site of the polymerase, thereby creating a region of enhanced sensitivity for surface enhanced Raman spectroscopy (SERS) at the active site. In another embodiment the metal nanoparticles are attached and/or conjugated to the polymerase such that when a nucleoside and/or nucleotide are in the active site of the polymerase, and wherein the nucleoside and/or nucleotide are tagged with a Raman active molecule, the metal nanoparticles are located 1 nm-3 nm from the Raman active molecule. In another embodiment the attached and/or conjugated metal nanoparticles of the polymerase create a region of enhanced sensitivity for surface enhanced Raman spectroscopy (SERS) at the location of the Raman active molecule.

In some embodiments of the invention, vibrational spectroscopy is used to detect the presence of incorporated nucleotide analogs. Vibrational spectroscopy is a spectrographic analysis where the sample is illuminated with incident radiation in order to excite molecular vibrations. Vibrational excitation, caused by molecules of the sample absorbing, reflecting or scattering a particular discrete amount of energy, is detected and can be measured. The two major types of vibrational spectroscopy are infrared (usually FTIR) and Raman. If FTIR is employed, then the IR spectra of the nucleotide analogs are measured. If Raman is employed, then the Raman spectra of the nucleotide analogs is measured (for example of the nucleotide analogs and in the methods described herein).

Because of well-understood base-pairing rules, determining the wavenumber of the Raman spectroscopy peak of a dNTP analog incorporated into a primer or DNA extension product, and thereby the identity of the dNTP analog that was incorporated, permits identification of the complementary nucleotide residue in the single-stranded polynucleotide that the primer or DNA extension product is hybridized to. Thus, if the dNTP analog that was incorporated has a unique wavenumber in the Raman spectroscopy peak identifying it as comprising an adenine, a thymine, a cytosine, or a guanine, then the complementary nucleotide residue in the single-stranded polynucleotide is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analog that was incorporated comprises an adenine, a uracil, a cytosine, or a guanine, then the complementary nucleotide residue in the single-stranded RNA is identified as a uracil, an adenine, a guanine or a cytosine, respectively.

In a further embodiment the binder of the complementary binding molecule of each type of nucleotide analogue having an anchor comprises:
a) a compound comprising streptavidin having the structure:

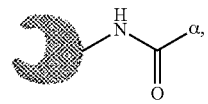

or b) a compound comprising the structure:

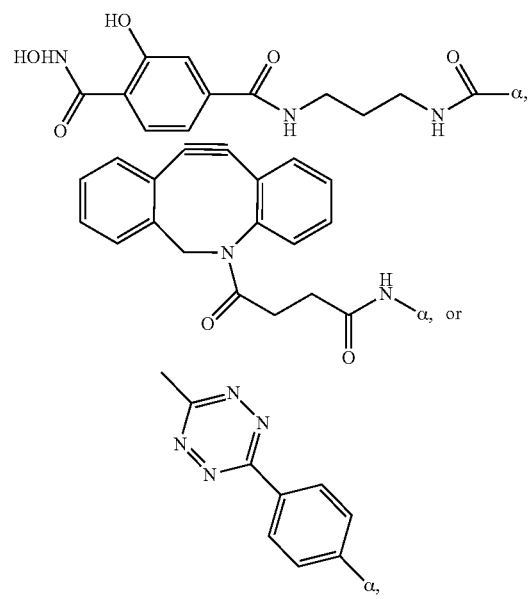

wherein α is one or more atoms through which a covalent connection is established to a detectable label.

In a further embodiment, if the anchor of a type of nucleotide analogue has the structure:

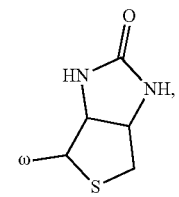

wherein ω represents one or more atoms through which a covalent connection is established to the cleavable t-butyl-dithiomethyl moiety, then the anchor orthogonally and rapidly reacts with a binder of a complimentary binding molecule, wherein said binder comprises streptavidin, and has the structure:

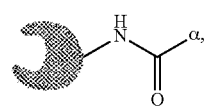

wherein α is one or more atoms through which a covalent connection is established to a detectable label, thereby forming a conjugate having the structure:

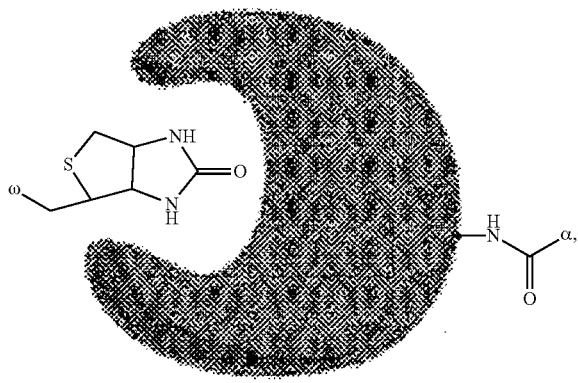

wherein α is one or more atoms through which a covalent connection is established to detectable label, and wherein ω is one or more atoms through which a covalent connection is established to the cleavable t-butyldithiomethyl moiety.

In a further embodiment the label is cleaved from the conjugate comprising the type of nucleotide analogue and the binding molecule with citric acid/Na₂HPO₄.

In a further embodiment the type of nucleotide analogue has the structure:

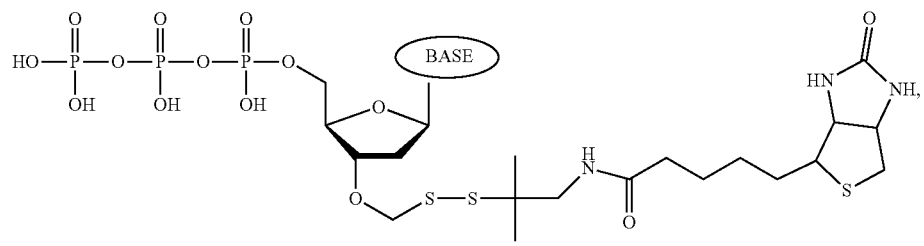 [SMILES: C[C@H]1C[C@@H](OCSSC(C)(C)CNC(=O)CCCCC2SCC3NC(=O)NC32)[C@@H](COP(=O)(O)OP(=O)(O)OP(=O)(O)O)O1]

wherein base is one of adenine, guanine, thymine, cytosine, uracil, or derivatives thereof.

In a further embodiment the complementary binding molecule comprises streptavidin, and wherein the complementary binding molecule has the structure:

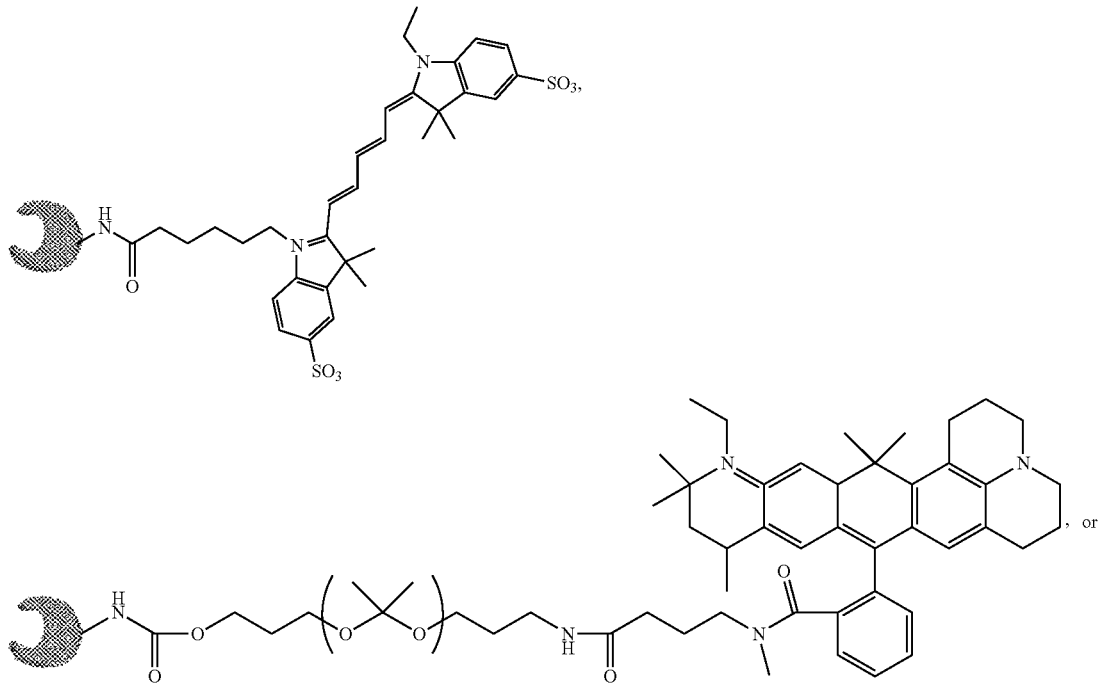

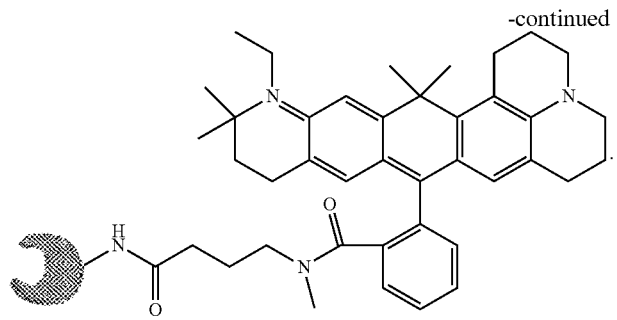

In a further embodiment the anchor of a type of nucleotide analogue has the structure:

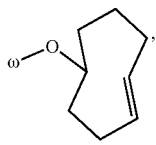

wherein ω represents one or more atoms through which a covalent connection is established to the cleavable t-butyldithiomethyl moiety, then the anchor orthogonally and rapidly reacts with a binder of a complimentary binding molecule, wherein said binder has the structure:

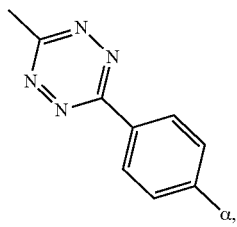

wherein α is one or more atoms through which a covalent connection is established to a detectable label, thereby forming a conjugate having the structure:

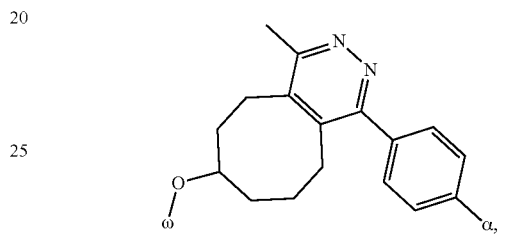

wherein α is one or more atoms through which a covalent connection is established to detectable label, and wherein ω is one or more atoms through which a covalent connection is established to the cleavable t-butyldithiomethyl moiety.

In a further embodiment the label is cleaved from the conjugate comprising the type of nucleotide analogue and binding molecule with $Na_2S_2O_4/H_2O$.

In a further embodiment the type of nucleotide analogue has the structure:

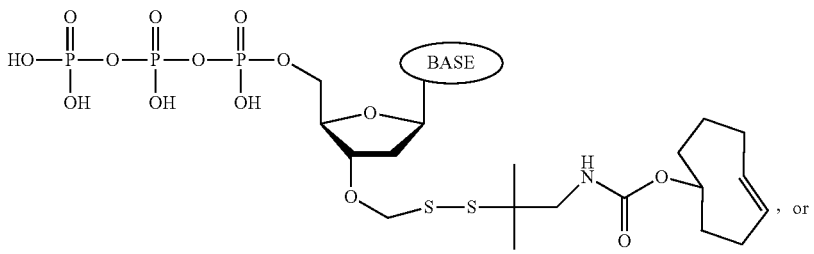, or

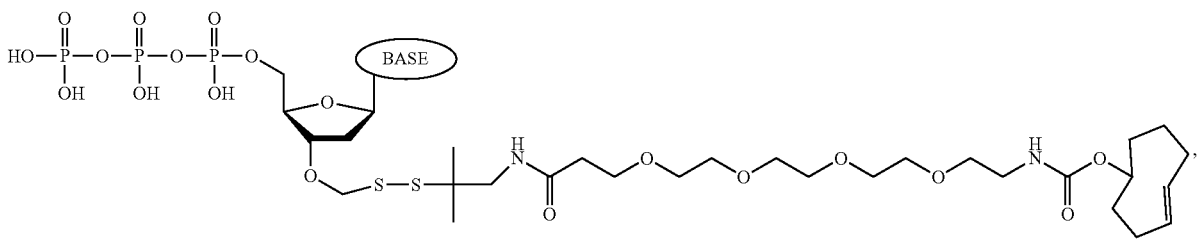, wherein base is one of adenine, guanine, thymine, cytosine, uracil, or derivatives thereof.

In a further embodiment, the complementary binding molecule has the structure:
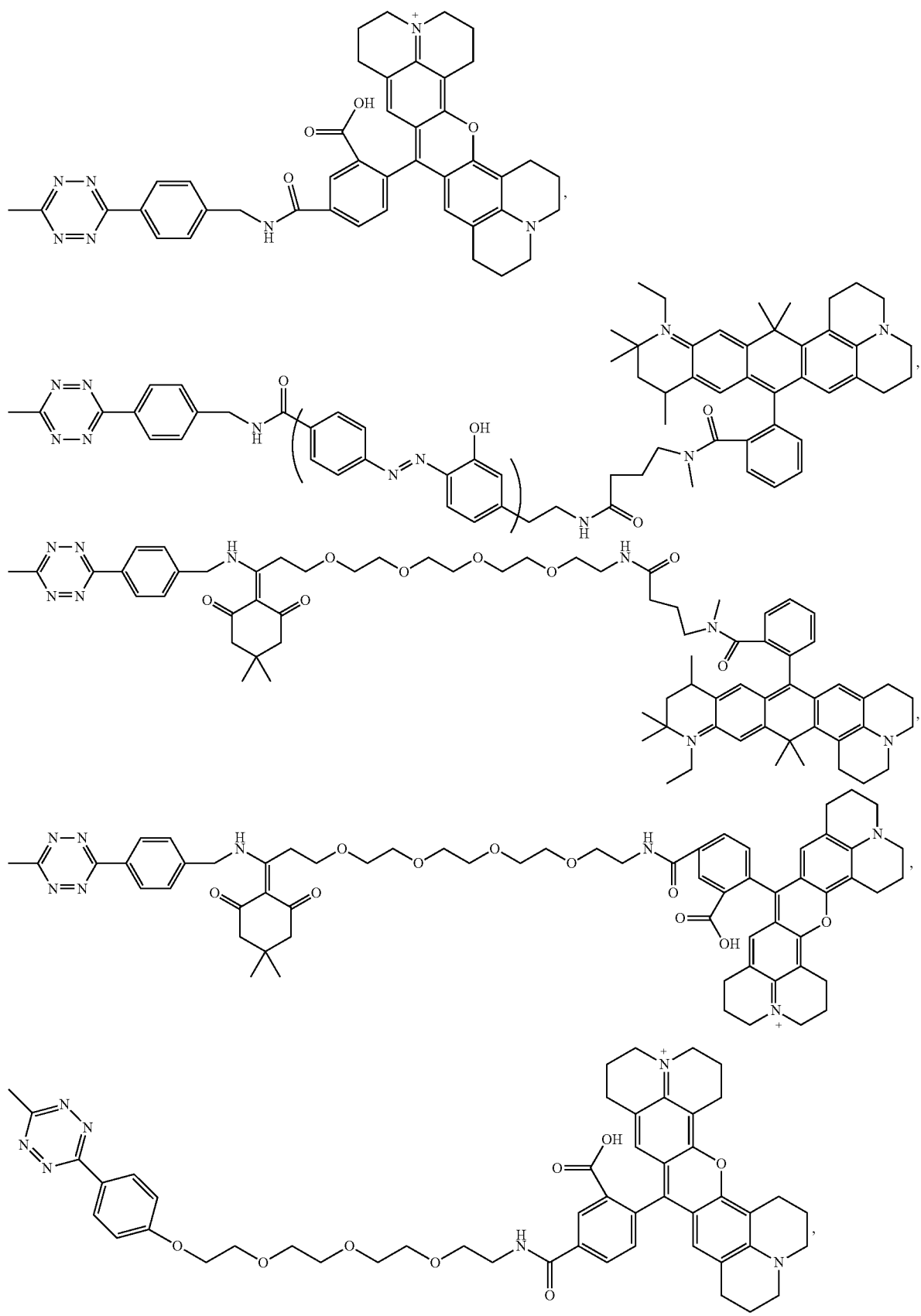

-continued

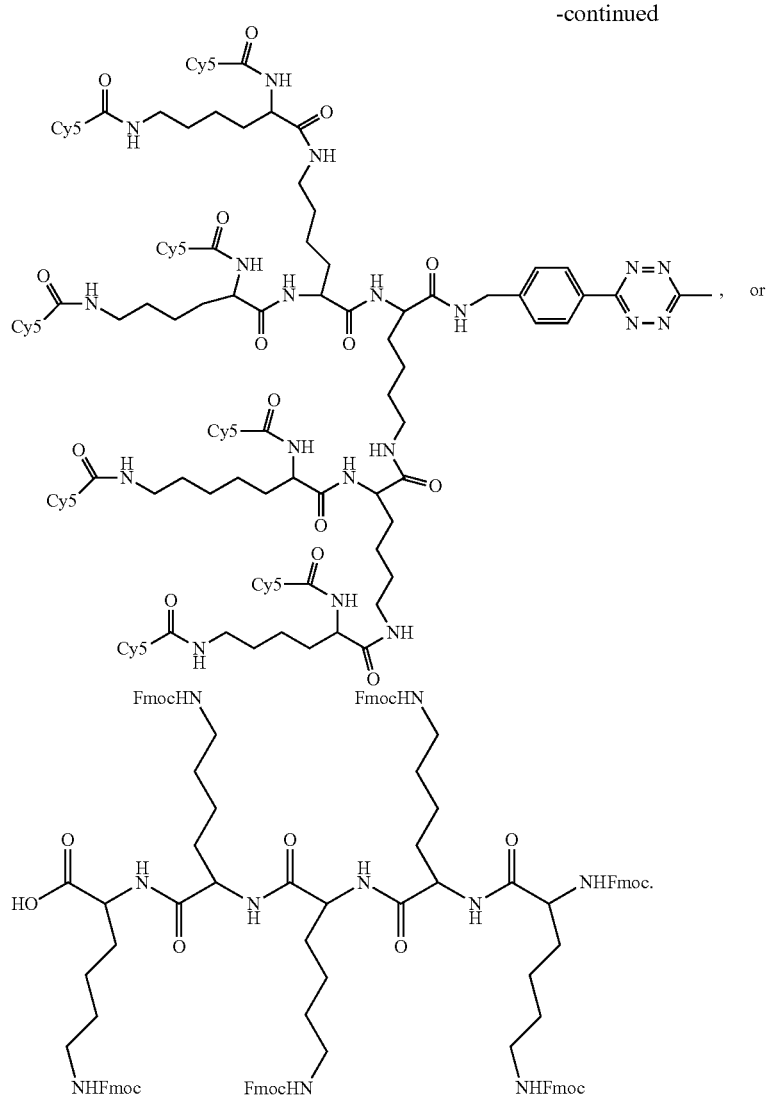

In a further embodiment, if the anchor of a type of nucleotide analogue has the structure:

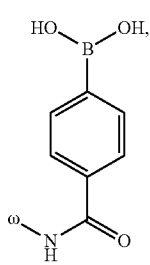

wherein ω represents one or more atoms through which a covalent connection is established to the cleavable t-butyldithiomethyl moiety, then the anchor orthogonally and rapidly reacts with a binder of a complimentary binding molecule, wherein said binder has the structure:

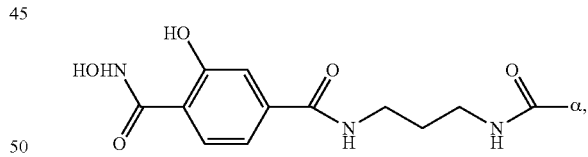

wherein α is one or more atoms through which a covalent connection is established to a detectable label, thereby forming a conjugate having the structure:

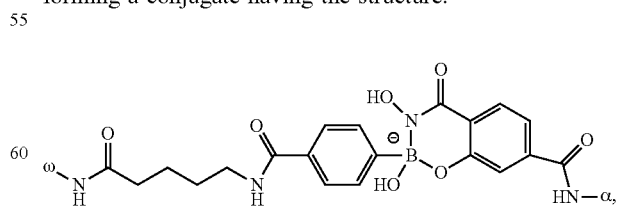

wherein α is one or more atoms through which a covalent connection is established to detectable label, and wherein ω is one or more atoms through which a covalent connection is established to the cleavable t-butyldithiomethyl moiety.

In a further embodiment the type of nucleotide analogue has the structure:

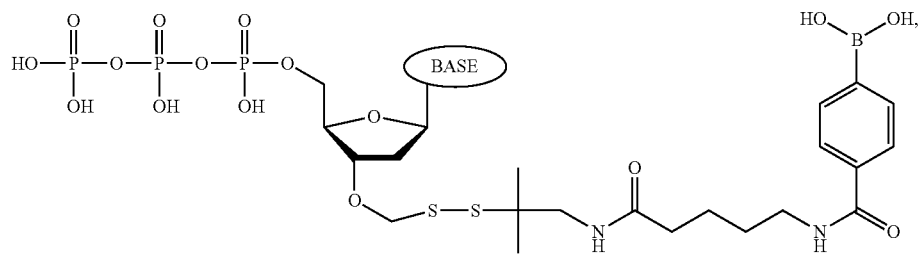 [SMILES: C[C@H]1C[C@@H](OCSSC(C)(C)CNC(=O)CCCCNC(=O)c2ccc(B(O)O)cc2)[C@@H](COP(=O)(O)OP(=O)(O)OP(=O)(O)O)O1]

wherein base is one of adenine, guanine, thymine, cytosine, uracil, or derivatives thereof.

In a further embodiment the complementary binding molecule has the structure:

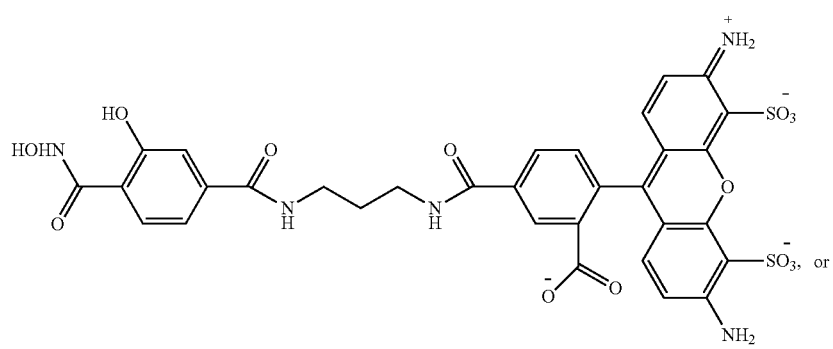

or

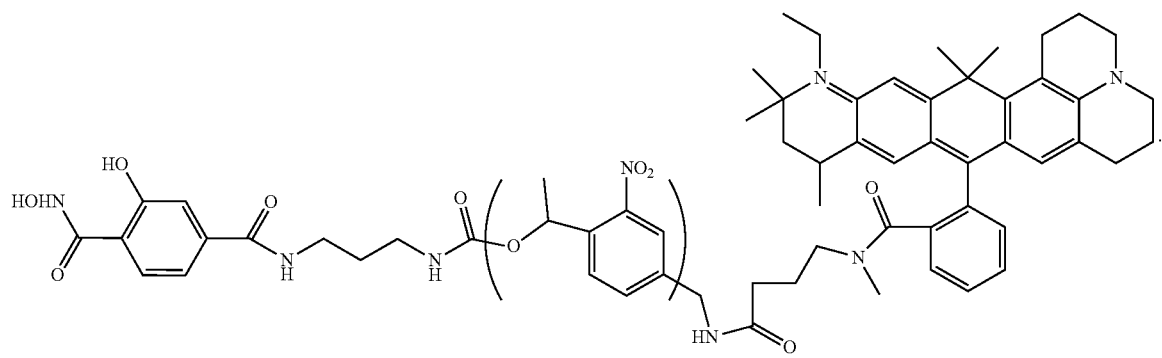

In a further embodiment if the anchor of a type of nucleotide analogue has the structure:

wherein ω represents one or more atoms through which a covalent connection is established to the cleavable t-butyl-dithiomethyl moiety, then the anchor orthogonally and rapidly reacts with a binder of a complimentary binding molecule, wherein said binder has the structure:

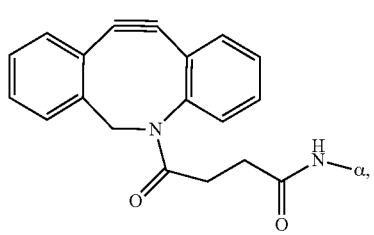

wherein α is one or more atoms through which a covalent connection is established to a detectable label, thereby forming a conjugate having the structure:

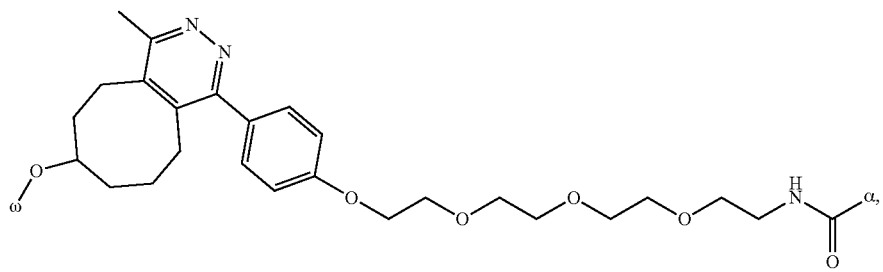

wherein α is one or more atoms through which a covalent connection is established to detectable label, and wherein ω is one or more atoms through which a covalent connection is established to the cleavable t-butyldithiomethyl moiety.

In a further embodiment, the label is cleaved from the conjugate comprising the type of nucleotide analogue and binding molecule with citric acid/$Na_2HPO_4$.

In a further embodiment the type of nucleotide analogue has the structure:

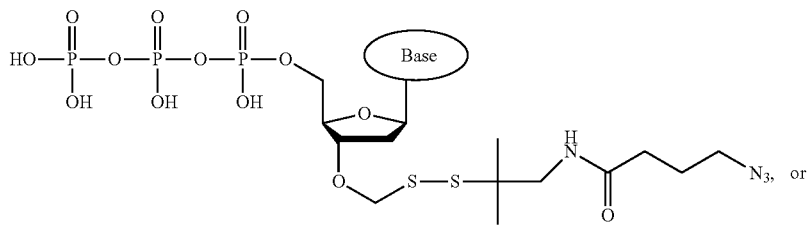

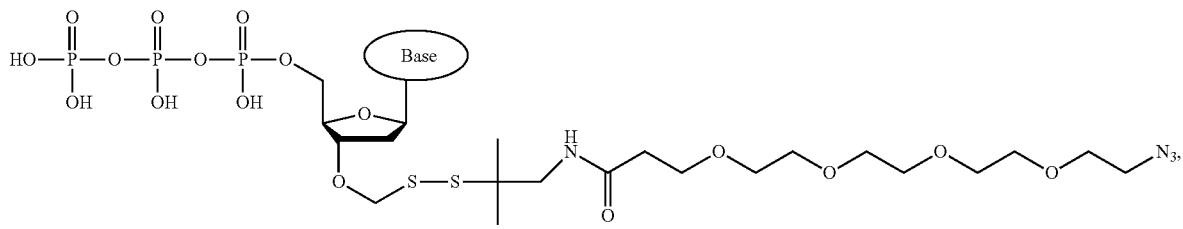

wherein base is one of adenine, guanine, thymine, cytosine, uracil, or derivatives thereof.

In a further embodiment, the complementary binding molecule has the structure:

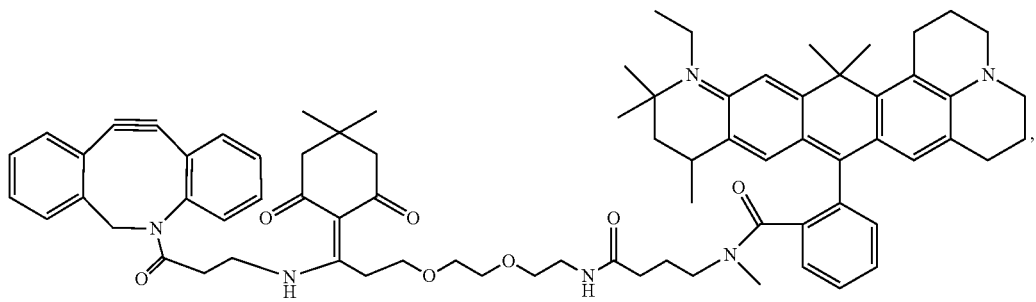

-continued

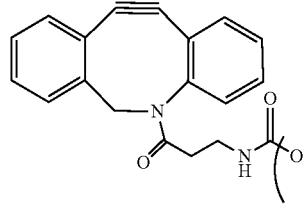
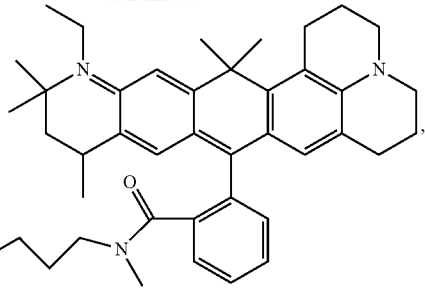

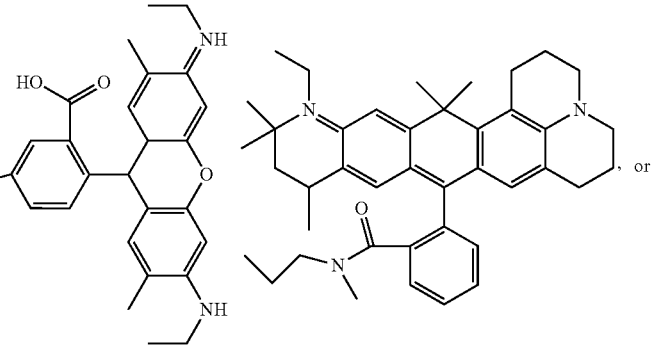, or

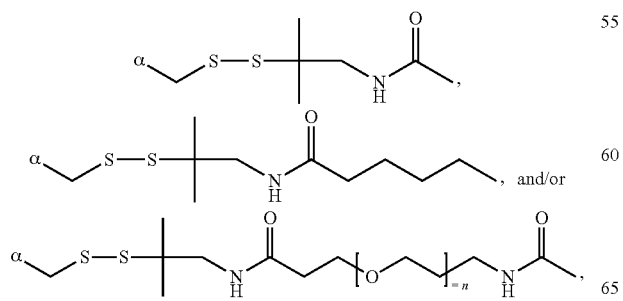

In a further embodiment the cleavable t-butyldithiomethyl moiety of each type of nucleotide analogue is a t-butyldithiomethyl linker, which has the structure:

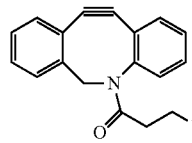

wherein α represents the point of connection to the 3'-oxygen.

In a further embodiment the cleavable t-butyldithiomethyl linker has the structure:

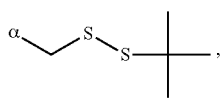

wherein α represents the point of connection to the 3'-oxygen; and wherein n is an integer which may be 1, 2, 3, 4, or 5.

In a further embodiment the cleavable t-butyldithiomethyl moiety may be cleaved by a water soluble phosphine, thereby resulting in a 3'-OH. In a further embodiment the water soluble phosphine is tris-(2-carboxyethyl)phosphine (TCEP) or tris(hydroxypropyl)phosphine (THP), wherein the cleavable t-butyldithiomethyl moiety may be cleaved by a water soluble phosphine, thereby resulting in a 3'-OH.

In further embodiments of the foregoing methods, the nucleotide analogues having the structure:

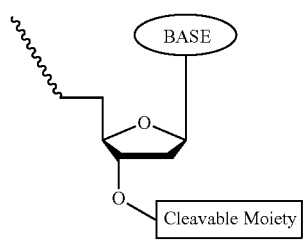

may be nucleotide analogues having the structure: and/or

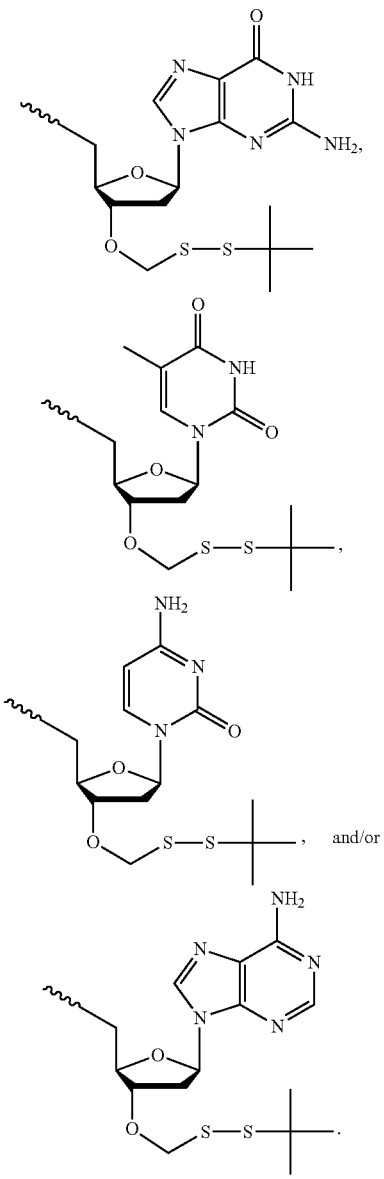

A further embodiment of the subject invention is a method for determining the identity of a nucleotide at a predetermined position in a nucleic acid of interest, comprising:
a) providing
1) the nucleic acid of interest,
2) a nucleic acid polymerase,
3) a primer capable of hybridizing to said nucleic acid immediately 3' of such predetermined position,
4) four different nucleotide analogues, wherein each nucleotide analogue comprises (i) a base (ii) a sugar, and (iii) a cleavable t-butyldithiomethyl moiety covalently attached to a 3'-oxygen of the sugar, and wherein the base of each analogue consists of one of adenine or an analogue of adenine, guanine or an analogue of guanine, cytosine or an analogue of cytosine, thiamine or an analogue of thiamine, and a unique detectable label;

b) incorporating one of said nucleotide analogues onto the end of said primer to form an extension strand;
c) detecting the unique detectable label of the incorporated nucleotide analogue so as to thereby identify the incorporated nucleotide analogue on the end of said extension strand; and
d) based on the identity of the incorporated nucleotide, determining the identity of the nucleotide at the predetermined position.

In a further embodiment, the extension strand of step (b) is treated so as to cleave the t-butyldithiomethyl moiety bound to the 3'-oxygen of the sugar and so as to produce a 3'-OH on the sugar and for producing an extension, remove the label from the extension strand to which another nucleotide analogue may be added. In a further method, the treatment comprises contacting the extension strand with tris-(2-carboxyethyl)phosphine (TCEP) or tris(hydroxypropyl)phosphine (THP).

In a further embodiment, the t-Butyldithiomethyl linker has the structure:

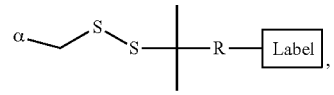

wherein α represents the point of connection to the 3'-oxygen; wherein R represents one or more atoms through which a covalent connection is established to the detectable label; and wherein Label is the detectable label.

In a further embodiment, the t-Butyldithiomethyl linker has the structure:

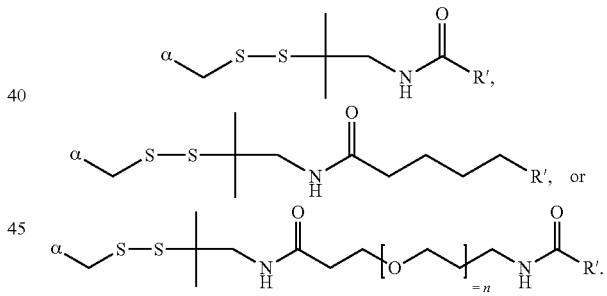

wherein α represents the point of connection to the 3'-oxygen; wherein n is 1, 2, 3, 4, or 5; and wherein R' represents one or more atoms through which a covalent connection is established to the detectable label.

In a further embodiment of each of the foregoing methods, nucleotide analogue is a nucleotide triphosphate, a nucleotide tetraphosphate, a nucleotide pentaphosphate, or a nucleotide hexaphosphate.

In a further embodiment of each of the foregoing methods, the nucleotide analogue(s) comprise a deoxyribose. In a further method the polymerase is a DNA polymerase and the nucleic acid is DNA. In a further method of each of the foregoing methods, the nucleotide analogue(s) comprise a ribose. In a further embodiment of each of the foregoing methods, the polymerase is a reverse transcriptase and the nucleic acid is RNA. In a further embodiment of each of the foregoing methods, the polymerase is a DNA-based RNA polymerase and the nucleic acid is DNA. In a further embodiment of each of the foregoing methods, the polymerase is an RNA-based RNA polymerase and the nucleic acid is RNA.

In a further embodiment, the t-Butyldithiomethyl linker has the structure:

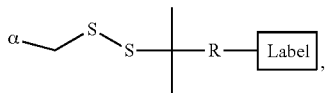

wherein α represents the point of connnection to the 3'-oxygen; wherein R represents one or more atoms through which a covalent connection is established to the detectable label; and wherein Label is the detectable label.

In a further embodiment, the detectable label is selected from the group consisting of a dye, a fluorophore, a combinatorial fluorescence energy transfer tag, a chemiluminescent compound, a chromophore, a mass tag, an electrophore, a mononucleotide, an oligonucleotide, or a combination thereof. In a further embodiment, the detectable label is a fluorophore. In a further embodiment, the fluorophore is selected from the group consisting of BodipyFL, R$^6$G, ROX, Cy5, and Alexa488.

In a further embodiment, each nucleotide analog is selected from the group consisting of 3'-O-Alexa488-t-Butyldithiomethyl-dCTP, 3'-O-Cy5-t-Butyldithiomethyl-dGTP, 3'-O-Rox-t-Butyldithiomethyl-dATP, 3'-O-RG6-t-Butyldithiomethyl-dTTP, 3'-O-Alexa488-PEG$_4$-t-Butyldithiomethyl-dCTP, 3'-O-RG6-PEG$_4$-t-Butyldithiomethyl-dTTP, 3'-O-Rox-PEG$_4$-t-Butyldithiomethyl-dATP, 3'-O-Cy5-PEG$_4$-t-Butyldithiomethyl-dGTP.

In a further embodiment, the structure of each labeled nucleotide analog is selected from:

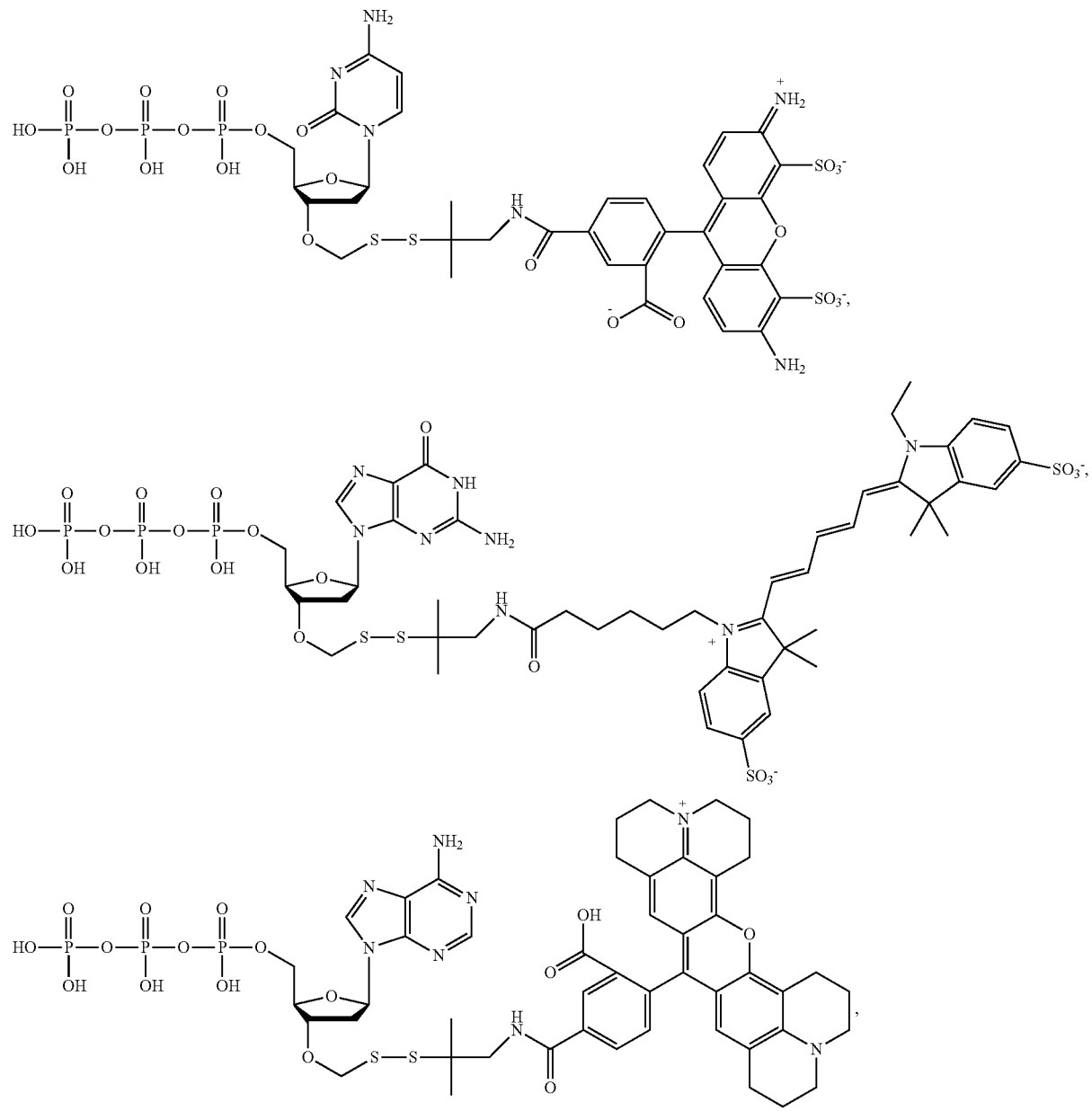

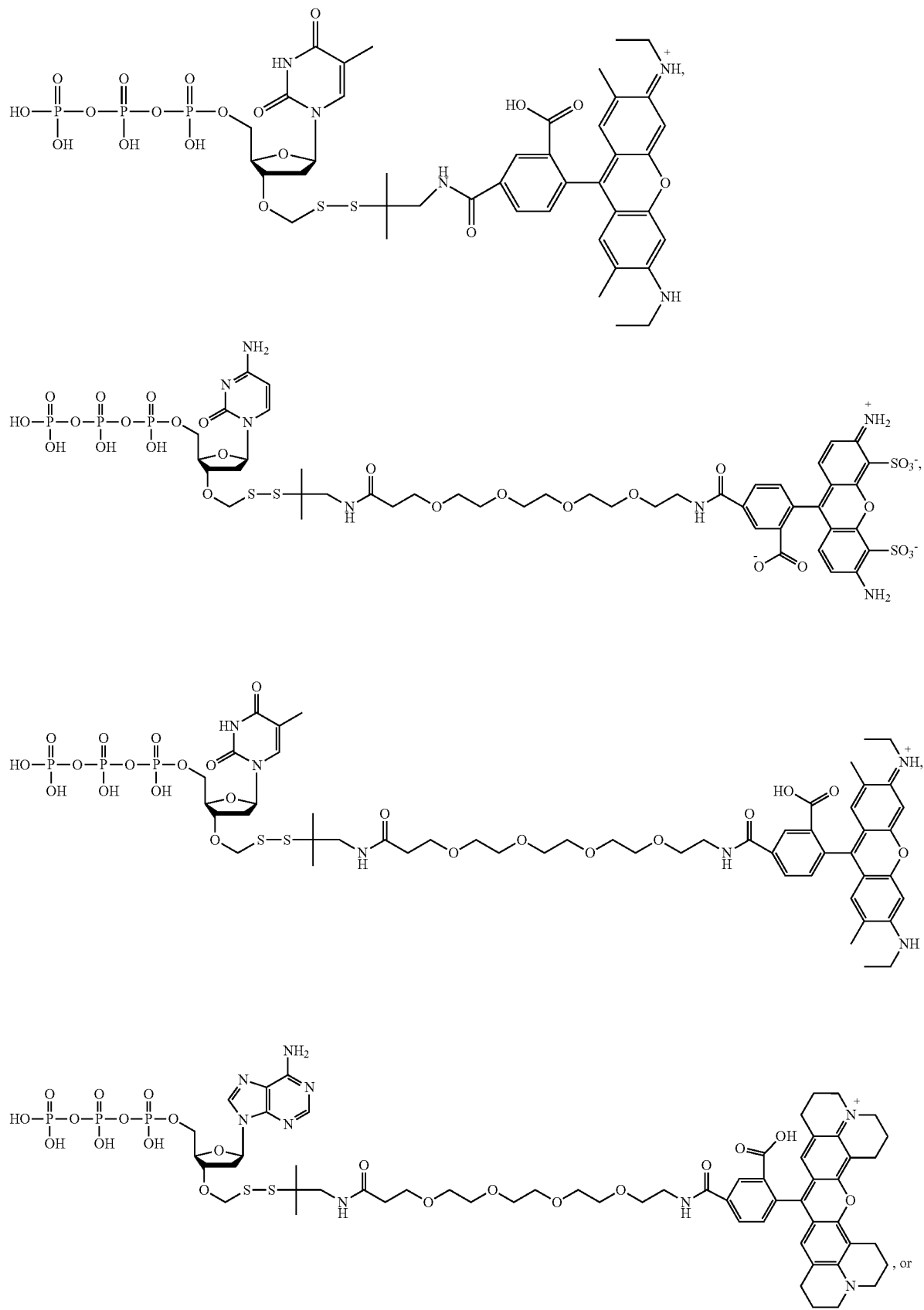

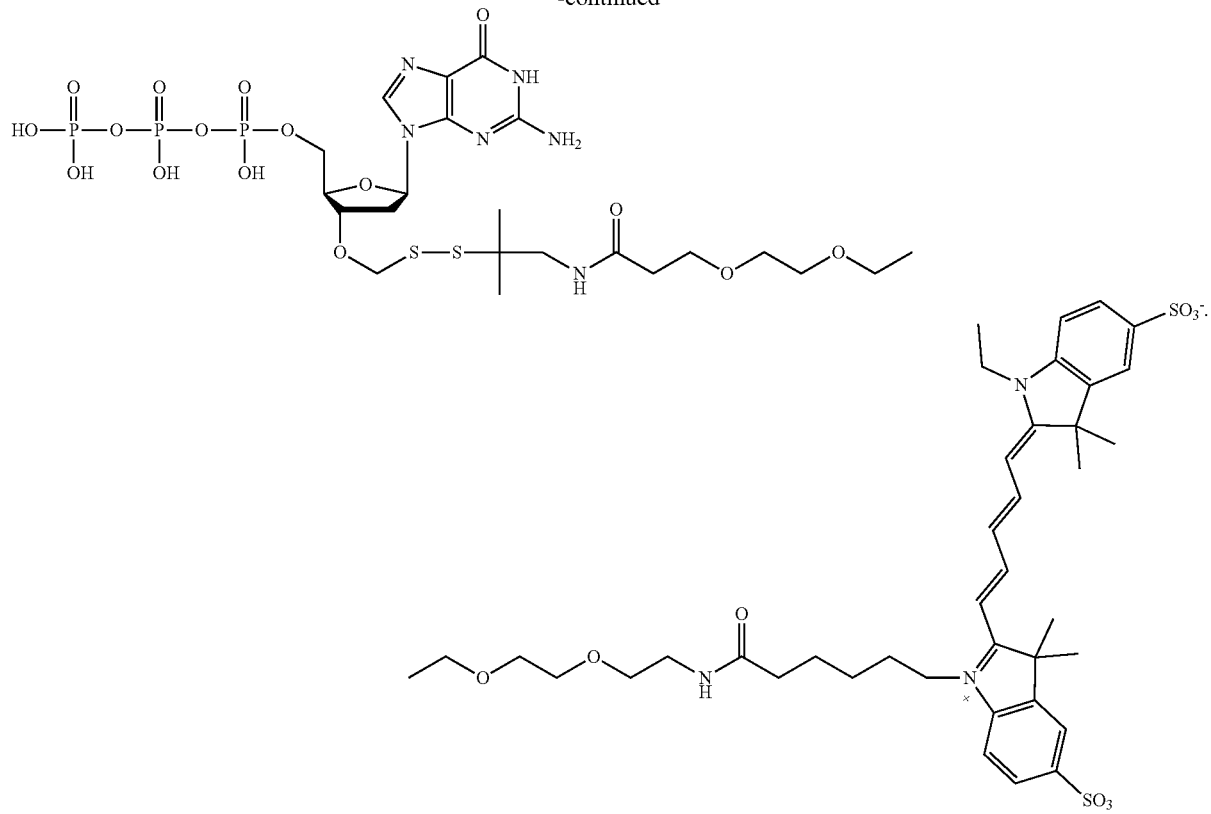

In a further embodiment, herein disclosed is a method of sequencing a nucleic acid of interest which comprises repeatedly determining the identity of each nucleotide present in the nucleic acid of interest according to any of the foregoing methods the method.

In a further embodiment of each of the foregoing sequencing methods, sequencing occurs simultaneously with a plurality of different nucleic acids of interest which comprises simultaneously sequencing each such nucleic acid.

In a further embodiment of each of the foregoing methods, nucleotide analogue is a nucleotide triphosphate, a nucleotide tetraphosphate, a nucleotide pentaphosphate, or a nucleotide hexaphosphate.

In a further embodiment of each of the foregoing methods, the nucleotide analogue(s) comprise a deoxyribose. In a further embodiment the polymerase is a DNA polymerase and the nucleic acid is DNA. In a further embodiment of each of the foregoing methods, the nucleotide analogue(s) comprise a ribose. In a further embodiment of each of the foregoing methods, the polymerase is a reverse transcriptase and the nucleic acid is RNA. In a further embodiment of each of the foregoing methods, the polymerase is a DNA-based RNA polymerase and the nucleic acid is DNA. In a further embodiment of each of the foregoing methods, the polymerase is an RNA-based RNA polymerase and the nucleic acid is RNA.

In a further embodiment of each of the foregoing methods, the nucleic acid of interest is immobilized on a solid support. In a further embodiment, the nucleic acid of interest is immobilized on the solid support via a 1,3-dipolar cycloaddition linkage, an amide bond or a biotin-streptavidin interaction. In a further embodiment, the solid support is in the form of a chip, a bead, a well, a capillary tube, or a slide.

In a further embodiment, the solid support comprises gold, quartz, silica, or a plastic. In a further method, the solid support is porous.

In certain embodiments, the polymerase, single-stranded polynucleotide, DNA, or primer is bound to a solid substrate via 1,3-dipolar azide-alkyne cycloaddition chemistry. In an embodiment the polymerase, DNA, RNA, or primer, is bound to the solid substrate via a polyethylene glycol molecule. In an embodiment the polymerase, DNA, RNA, or primer, is alkyne-labeled. In an embodiment the polymerase, DNA, RNA, or primer, is bound to the solid substrate via a polyethylene glycol molecule and the solid substrate is azide-functionalized. In an embodiment the polymerase, DNA, RNA, or primer, is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded polynucleotide. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the any of the foregoing methods, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In one embodiment, the surface or substrate is a SERS-prepared surface or substrate designed specifically for detection of a label nucleotide. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may include DNA functionalized sites, and may have a gap size range from 50 nm to 1 nm. In another embodiment, a nucleotide polymerase is immobilized within the gap.

In another embodiment the nucleotide polymerase SERS-prepared and designed specifically for detection of a labeled nucleotide and/or nucleoside. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may have a gap size range from 12 nm to 1 nm. In another embodiment, a nucleotide polymerase is immobilized within on a surface, substrate, or nanoplasmonic antenna on a surface.

In another embodiment, the surface comprises a DNA origami scaffold or an array of DNA origami scaffolds. It is also contemplated that the DNA origami scaffold further comprising a primer molecules positioned between Au and Ag nanoparticles and nanorods located at specified binding sites.

In a further embodiment, the surface comprises plasmonic crystals or an array of plasmonic structures. For example, the plasmonic structures may be periodic TiO—Au—TiO structures.

In various embodiments the polymerase, nucleic acid samples, DNA, RNA, or primer are separated in discrete compartments, wells or depressions on a surface.

In this invention methods are provided wherein about 1000 or fewer copies of the polymerase, nucleic acid sample, DNA, RNA, or primer are bound to the substrate. This invention also provides the instant methods wherein $2 \times 10^7$, $1 \times 10^7$, $1 \times 10^6$ or $1 \times 10^4$ or fewer copies of the polymerase, nucleic acid sample, DNA, RNA, or primer are bound to the substrate or surface.

In further embodiments of the foregoing methods, the nucleotide incorporation events may be detected in real-time (i.e., as they occur).

Further embodiments of the foregoing methods may be single-molecule methods. That is, the signal that is detected is generated by a single molecule (i.e., single nucleotide incorporation) and is not generated from a plurality of clonal molecules. The methods may not require DNA amplification.

In other embodiments of the foregoing methods, a plurality of identical single-stranded DNA or RNA molecules are sequenced simultaneously, thereby producing an aggregate signal.

In further embodiments of the foregoing methods, the signal generated by a nucleotide incorporation event is detected and/or generated through the use of a nanopore. Such nanopore devices and systems of the present disclosure may be combined with, or modified by other nanopore devices and methods such as those described in U.S. Pat. Nos. 7,005,264 B2; 7,846,738; 6,617,113; 6,746,594; 6,673,615; 6,627,067; 6,464,842; 6,362,002; 6,267,872; 6,6015,714; 5,795,782; and U.S. Publication Nos. 2015/0111759 and 2015/0368710, each of which is entirely incorporated herein by reference.

In some embodiments, the immobilized polymerase, nucleic acid sample, DNA, RNA, or primer, is immobilized at a high density. This invention also provides the instant methods wherein over or up to $1 \times 10^7$, $1 \times 10^8$, $1 \times 10^9$ copies of the polymerase, nucleic acid sample, DNA, RNA, or primer are bound to the substrate or surface.

In other embodiments of the methods and/or compositions of this invention, the DNA is single-stranded. In other embodiments of the methods or of the compositions described herein, the single-stranded polynucleotide is replaced with an RNA that is single-stranded.

Incorporation into an oligonucleotide or polynucleotide (such as a primer or DNA extension strand) of a nucleotide and/or nucleoside analog means the formation of a phosphodiester bond between the 3' carbon atom of the 3' terminal nucleotide residue of the polynucleotide and the 5' carbon atom of the dNTP analog resulting in the loss of pyrophosphate from the dNTP analog.

A Raman spectroscopy system, as can be used in the methods described herein, typically comprises an excitation source (such as a laser, including a laser diode in appropriate configuration, or two or more lasers), a sample illumination system and light collection optics, a wavelength selector (such as a filter or spectrophotometer), and a detection apparatus (such as a CCD, a photodiode array, or a photomultiplier). Interference (notch) filters with cut-off spectral range of $\pm 80$-$120$ cm$^{-1}$ from the laser line can be used for stray light elimination. Holographic gratings can be used. Double and triple spectrometers allow taking Raman spectra without use of notch filters. Photodiode Arrays (PDA) or a Charge-Coupled Devices (CCD) can be used to detect Raman scattered light.

In an embodiment, surface enhanced Raman spectroscopy (SERS) is used which employs a surface treated with one or more of certain metals known in the art to cause SERS effects. In an embodiment the surface is a surface to which the polymerase, polynucleotide, single-stranded polynucleotide, single-stranded DNA polynucleotide, single-stranded RNA, primer, DNA extension strand, or oligonucleotide probe of the methods described herein is attached. Many suitable metals are known in the art. In an embodiment the surface is electrochemically etched silver or treated with/comprises silver and/or gold colloids with average particle size below 20 nm. The wavenumber of the Raman spectroscopy peak of an entity is identified by irradiating the entity with the excitation source, such as a laser, and collecting the resulting Raman spectrum using a detection apparatus. The wavenumber of the Raman spectroscopy peak is determined from the Raman spectrum. In an embodiment, the spectrum measured is from 2000 cm$^{-1}$ to 2300 cm$^{-1}$ and the wavenumber of the Raman spectroscopy peak is the peak wavenumber within that spectrum. In an embodiment the spectrum measured is a sub-range of 2000 cm$^{-1}$ to 2300 cm$^{-1}$ and the Raman spectroscopy peak wavenumber is the peak wavenumber within that spectrum sub-range.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

Unless otherwise defined, all technical and scientific terms used herein have the same meaning as commonly understood by a one of ordinary skill in the art to which this invention belongs.

As used herein, unless otherwise stated, the singular forms 'a', 'an', and 'the' include plural referents unless the context clearly dictates otherwise. It is further noted that the claims may be drafted to exclude any optional element. As such, this statement is intended to serve as antecedent basis for use of such exclusive terminology as 'solely', 'only' and the like in connection with the recitation of claim elements, or use of a 'negative limitation'.

The methods described herein can be applied mutatis mutandis to sequencing RNA using the appropriate dNTPs and analogues thereof.

All combinations of the various elements described herein are within the scope of the invention. All sub-combinations of the various elements described herein are also within the scope of the invention. Each embodiment disclosed herein is contemplated as being applicable to each of the other disclosed embodiments. In addition, the elements recited in the compound embodiments can be used in the composition and method embodiments described herein and vice versa.

This invention will be better understood by reference to the Experimental Details which follow, but those skilled in the art will readily appreciate that the specific experiments detailed are only illustrative of the invention as described more fully in the claims which follow thereafter.

Embodiment P1. A nucleotide analog consisting of (i) a base, (ii) a sugar which may be a deoxyribose or a ribose, (iii) a t-butyldithiomethyl linker bound to the 3'-oxygen of the deoxyribose or ribose, and (iv) a detectable label bound to the t-butyldithiomethyl linker.

Embodiment P2. The nucleotide analog of embodiment P1, wherein the sugar is a deoxyribose.

Embodiment P3. The nucleotide analog of embodiment P1, wherein the sugar is a ribose.

Embodiment P4. The nucleotide analog of any one of embodiments P1-P3, wherein the nucleotide analog is a nucleotide monophosphate, a nucleotide diphosphate, a nucleotide triphosphate, a nucleotide tetraphosphate, a nucleotide pentaphosphate, or a nucleotide hexaphosphate.

Embodiment P5. The nucleotide analog of any one of embodiments P1-P4, wherein the base is adenine or an analog of adenine, guanine or an analog of guanine, cytosine or an analog of cytosine, thymine or an analog of thymine or uracil or an analog of uracil.

Embodiment P6. The nucleotide analog of any one of embodiments P1-P5, wherein the t-butyldithiomethyl linker has the structure:

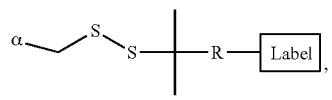

wherein α represents the point of connection to the 3'-oxygen; wherein R represents a structure consisting of one or more atoms one of which is covalently bound to the detectable label; and wherein Label represents the detectable label.

Embodiment P7. The nucleotide analog of embodiment P6, wherein the t-butyldithiomethyl linker has the structure:

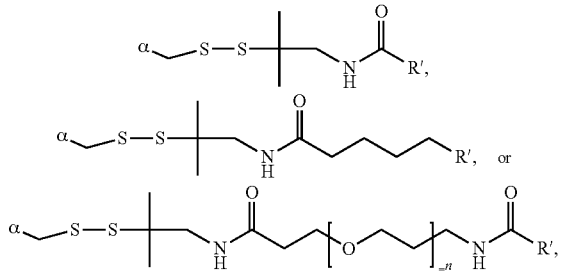

wherein α represents the point of connection to the 3'-oxygen; wherein n is an integer which may be 1, 2, 3, 4, or 5; and wherein R' represents a structure covalently attached to the detectable label.

Embodiment P8. The nucleotide analog of any one of embodiments P1-P7, wherein the detectable label is a dye, a fluorophore, a fluorescence energy transfer tag, a chemiluminescent compound, a chromophore, a mass tag, an electrophore, a mononucleotide, an oligonucleotide, or a combination thereof.

Embodiment P9. The nucleotide analog of embodiment P8, wherein the detectable label is a fluorophore.

Embodiment P10. The nucleotide analog of embodiment P9, wherein the fluorophore is BodipyFL, $R^6G$, ROX, Cy5, or Alexa488.

Embodiment P11. The nucleotide analog of embodiment P1, wherein the nucleotide analog is 3'-O-Alexa488-t-butyldithiomethyl-dCTP, 3'-O-Cy5-t-butyldithiomethyl-dGTP, 3'-O-Rox-t-butyldithiomethyl-dATP, 3'-O-RG6-t-butyldithiomethyl-dTTP, 3'-O-Alexa488-PEG$_4$-t-butyldithiomethyl-dCTP, 3'-O-RG6-PEG$_4$-t-butyldithiomethyl-dTTP, 3'-O-Rox-PEG$_4$-t-butyldithiomethyl-dATP, or 3'-O-Cy5-PEG$_4$-t-butyldithiomethyl-dGTP.

Embodiment P12. The nucleotide analog of embodiment P1, having the structure:
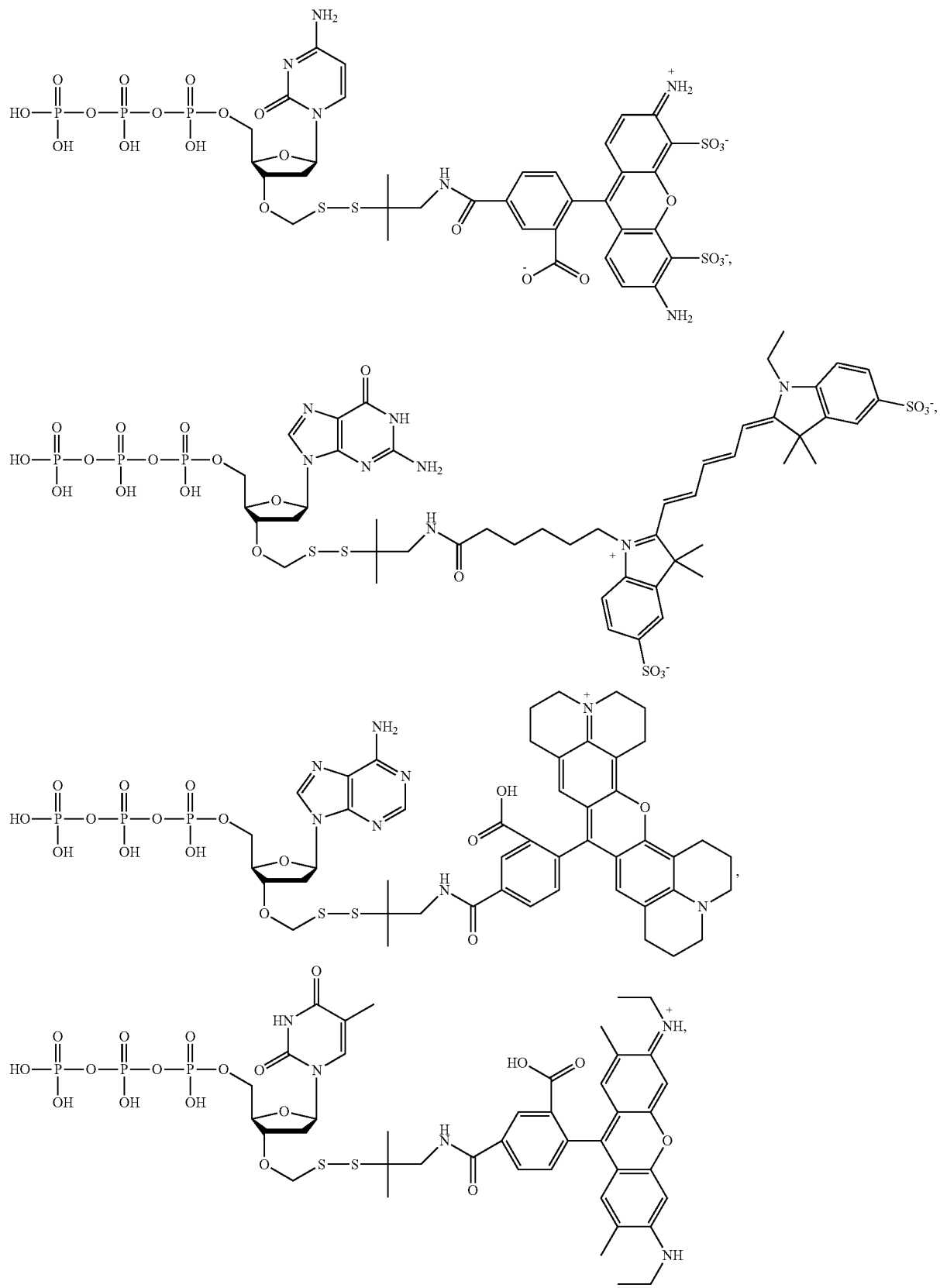

-continued
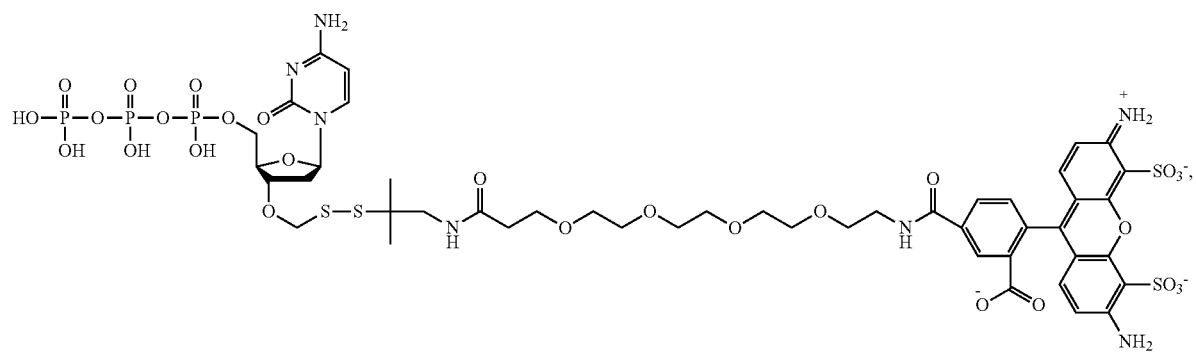
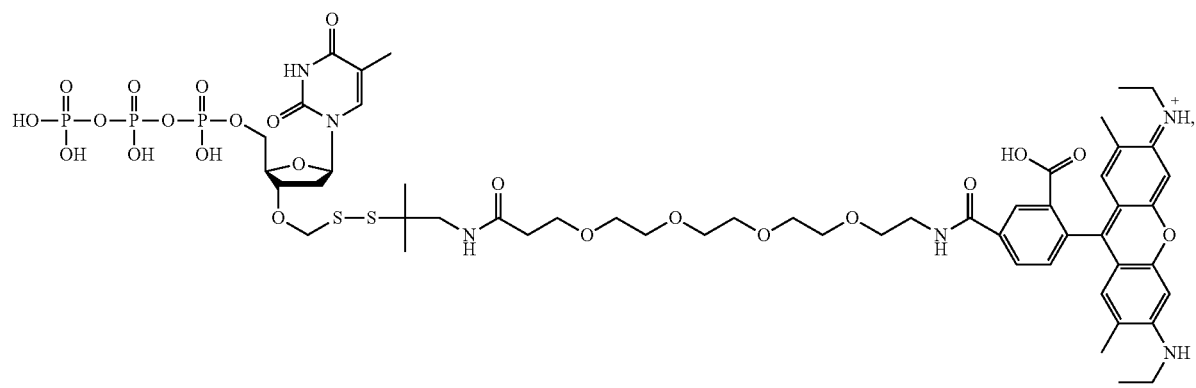
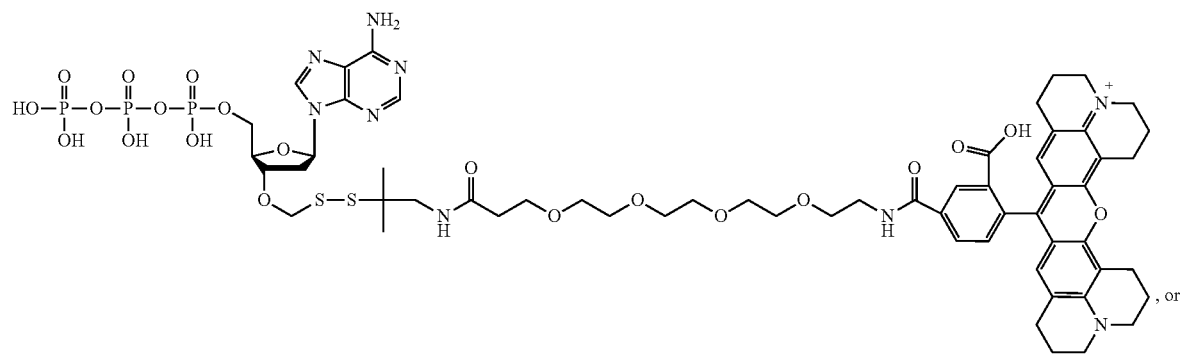
, or
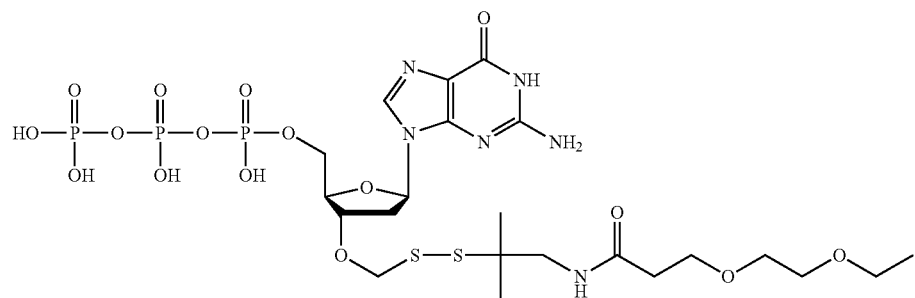

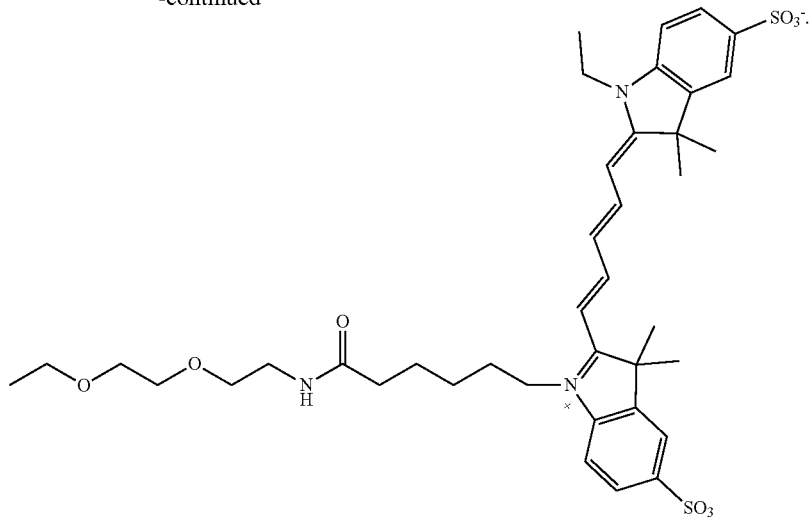

Embodiment P13. A composition comprising at least two different nucleotide analogs of any one of embodiments 1-12, wherein each nucleotide analog consists of a different base and a different detectable label from each other nucleotide analog present in the composition.

Embodiment P14. A method for determining the identity of a nucleotide at a predetermined position in a nucleic acid of interest, comprising:
 a) providing
  1) the nucleic acid of interest,
  2) a nucleic acid polymerase,
  3) a primer capable of hybridizing to said nucleic acid immediately 3' of such predetermined position,
  4) four different nucleotide analogs of embodiment 1, each of which consists of one of adenine or an analog of adenine, guanine or an analog of guanine, cytosine or an analog of cytosine, thiamine or an analog of thiamine, and a unique detectable label;
 b) incorporating one of said nucleotide analogs onto the end of said primer to form an extension strand;
 c) detecting the unique detectable label of the incorporated nucleotide analog so as to thereby identify the incorporated nucleotide analog on the end of said extension strand; and
 d) based on the identity of the incorporated nucleotide, determining the identity of the nucleotide at the predetermined position.

Embodiment P15. The method of embodiment P14 further comprising, treating the extension strand of step (b) so as to cleave the t-butyldithiomethyl linker bound to the 3'-oxygen of the sugar and so as to produce a 3'-OH on the sugar and for producing an extension, remove the label from the extension strand to which another nucleotide analog may be added.

Embodiment P16. The method of any one of embodiments P14-P15, wherein treatment comprises contacting the extension strand with tris-(2-carboxyethyl)phosphine (TCEP) or tris(hydroxypropyl)phosphine (THP).

Embodiment P17. The method of any one of embodiments P14-P16, wherein each nucleotide analog is a nucleotide triphosphate, a nucleotide tetraphosphate, a nucleotide pentaphosphate, or a nucleotide hexaphosphate.

Embodiment P18. The method of any one of embodiments P14-P17, wherein the nucleotide analog comprises a deoxyribose.

Embodiment P19. The method of embodiment P18, wherein the polymerase is a DNA polymerase and the nucleic acid is DNA.

Embodiment P20. The method of embodiment P18, wherein the polymerase is a reverse transcriptase and the nucleic acid is RNA.

Embodiment P21. The method of any one of embodiments P14-P20, wherein the nucleotide analog comprises a ribose.

Embodiment P22. The method of embodiment P21, wherein the polymerase is a DNA-based RNA polymerase and the nucleic acid is DNA.

Embodiment P23. The method of embodiment P21, wherein the polymerase is an RNA-based RNA polymerase and the nucleic acid is RNA.

Embodiment P24. The method of any one of embodiments P14-P23, wherein the t-Butyldithiomethyl linker has the structure:

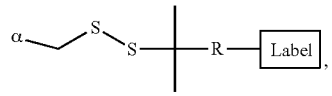

wherein α represents the point of connection to the 3'-oxygen; wherein R represents one or more atoms through which a covalent connection is established to the detectable label; and wherein Label is the detectable label.

Embodiment P25 The method of any one of embodiments P14-P24, wherein the t-Butyldithiomethyl linker has the structure:

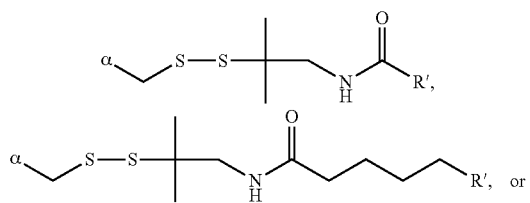

-continued

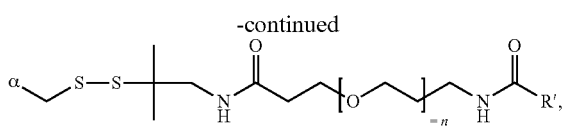

wherein α represents the point of connection to the 3'-oxygen; wherein n is 1, 2, 3, 4, or 5; and wherein R' represents one or more atoms through which a covalent connection is established to the detectable label.

Embodiment P26. The method of any one of embodiments P14-P25, wherein the detectable label is selected from the group consisting of a dye, a fluorophore, a combinatorial fluorescence energy transfer tag, a chemiluminescent compound, a chromophore, a mass tag, an electrophore, a mononucleotide, an oligonucleotide, or a combination thereof.

Embodiment P27. The method of embodiment P26, wherein the detectable label is a fluorophore.

Embodiment P28. The method of embodiment P27, wherein the fluorophore is selected from the group consisting of BodipyFL, $R^6G$, ROX, Cy5, and Alexa488.

Embodiment P29. The method of any one of embodiments P14-P23, wherein each nucleotide analog is selected from the group consisting of 3'-O-Alexa488-t-Butyldithiomethyl-dCTP, 3'-O-Cy5-t-Butyldithiomethyl-dGTP, 3'-O-Rox-t-Butyldithiomethyl-dATP, 3'-O-RG6-t-Butyldithiomethyl-dTTP, 3'-O-Alexa488-$PEG_4$-t-Butyldithiomethyl-dCTP, 3'-O-RG6-$PEG_4$-t-Butyldithiomethyl-dTTP, 3'-O-Rox-$PEG_4$-t-Butyldithiomethyl-dATP, 3'-O-Cy5-$PEG_4$-t-Butyldithiomethyl-dGTP.

Embodiment P30. The method of any one of embodiments P14-P23, wherein the structure of each labeled nucleotide analog is selected from:

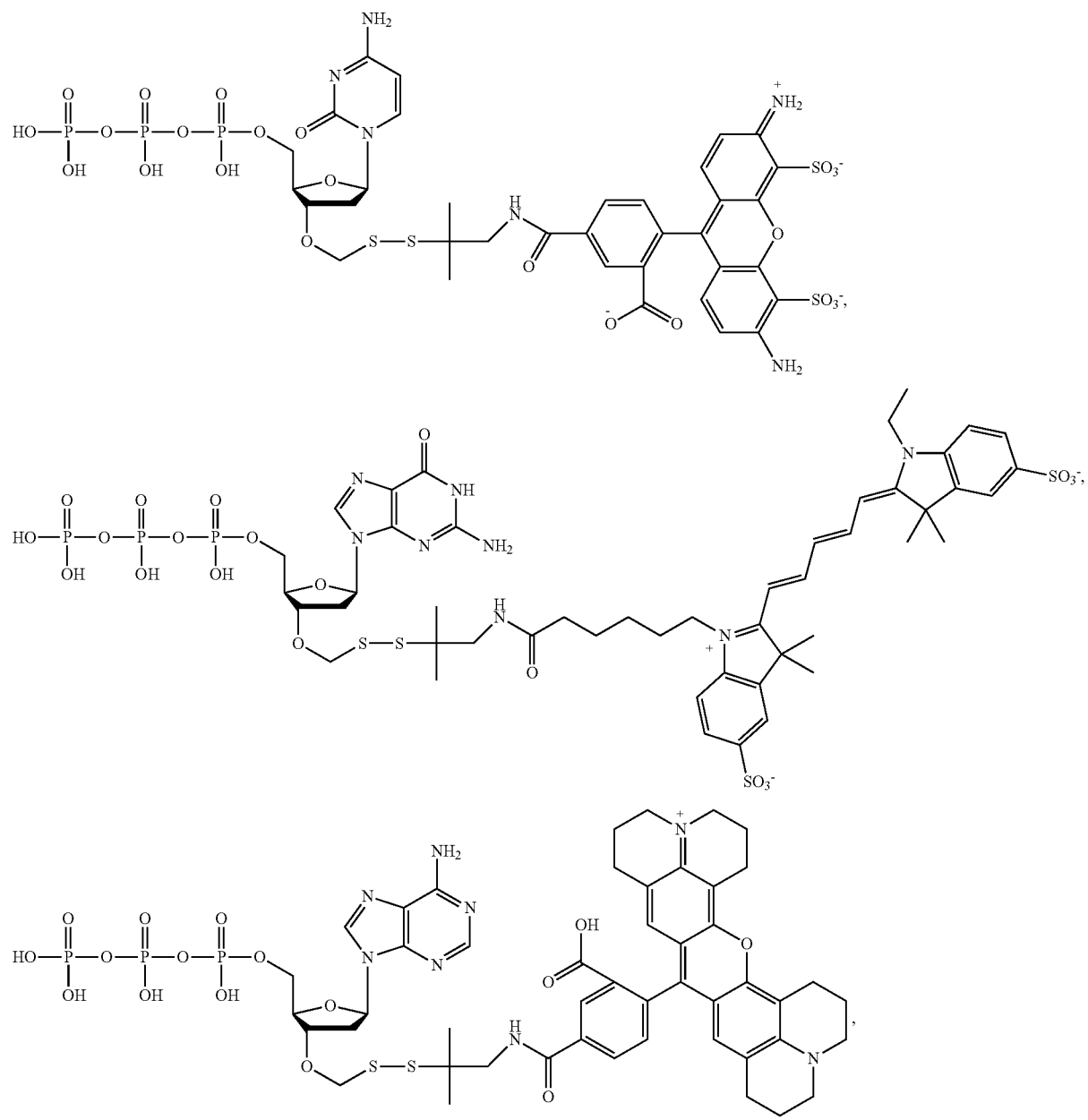

-continued
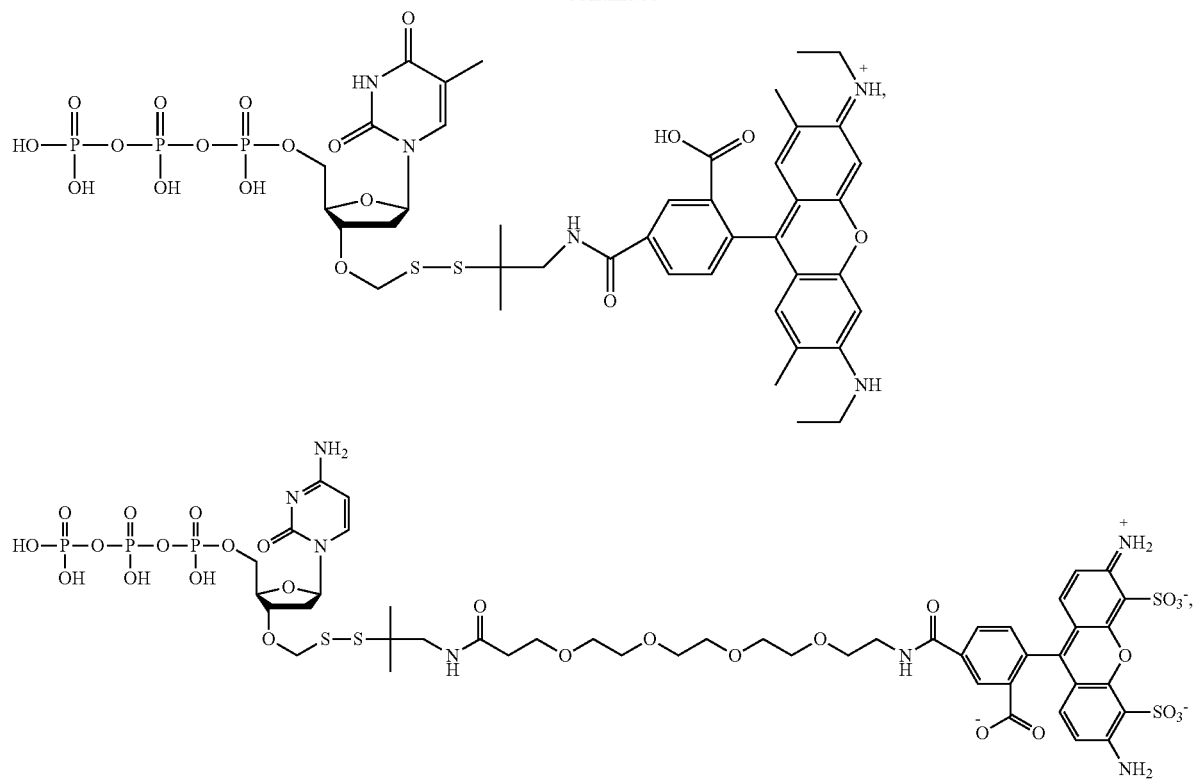
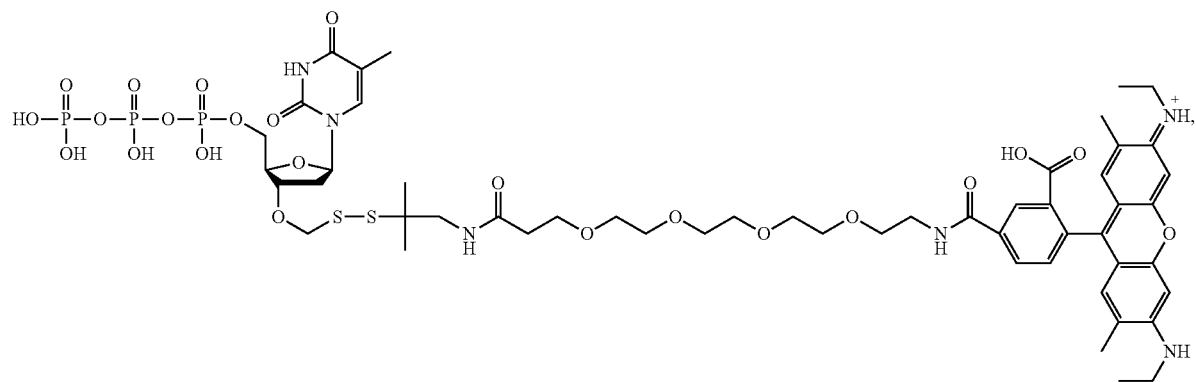
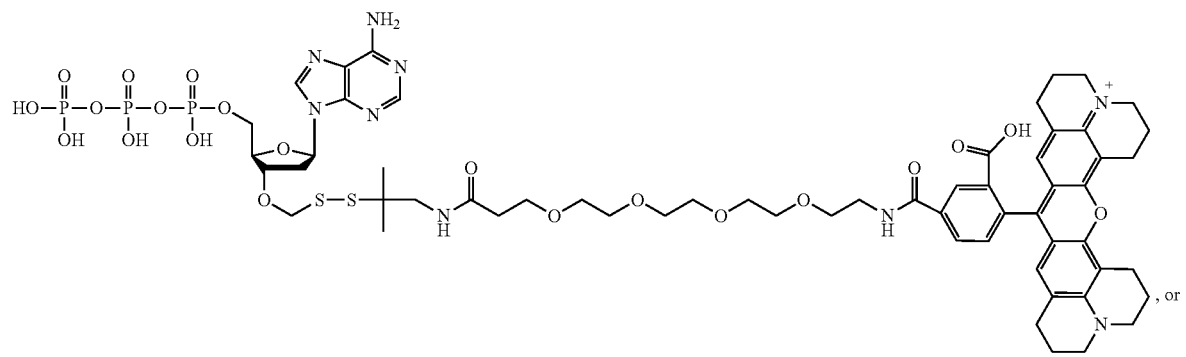

-continued

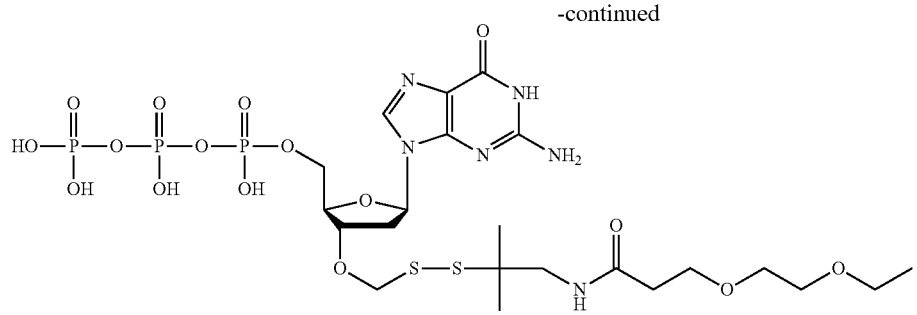

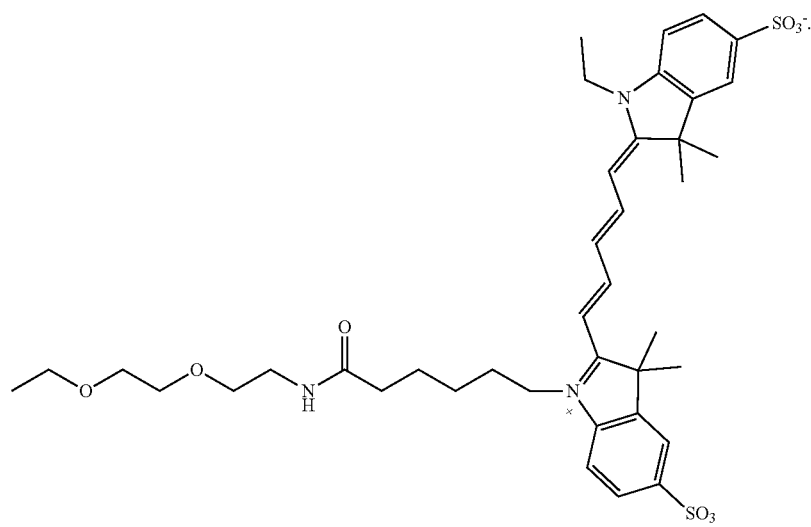

Embodiment P31. The method of any one of embodiments P14-P30, wherein the nucleic acid of interest is immobilized on a solid support.

Embodiment P32. The method of embodiment P31, wherein the nucleic acid of interest is immobilized on the solid support via an azido linkage, an alkynyl linkage, a 1,3-dipolar cycloaddition linkage, or a biotin-streptavidin interaction.

Embodiment P33. The method of any one of embodiments P31-P32, wherein the solid support is in the form of a chip, a bead, a well, a capillary tube, or a slide.

Embodiment P34. The method of any of embodiments P31-P33, wherein the solid support comprises gold, quartz, silica, or a plastic.

Embodiment P35. The method of any of embodiments P31-P34, wherein the solid support is porous.

Embodiment P36. A method of sequencing a nucleic acid of interest which comprises repeatedly determining the identity of each nucleotide present in the nucleic acid of interest according to the method of any one of embodiments P14-P35.

Embodiment P37. A method of simultaneously sequencing a plurality of different nucleic acids of interest which comprises simultaneously sequencing each such nucleic acid according to the method of embodiment P36.

Embodiment P38. A process for producing a 3'-O-Bodipy-t-Butyldithiomethyl-dNTP, comprising:
 a) reacting,
  1) a 5'-O-tert-Butyldimethylsilyl-nucleoside,
  2) acetic acid, and
  3) acetic anhydride, under conditions permitting the production of a 3'-O-methylthiomethyl-5'-O-tert-butyldimerthylsilyl-nucleoside;

b) contacting the 3'-O-methylthiomethyl-5'-O-tert-butyldimerthylsilyl-nucleoside produced in step a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

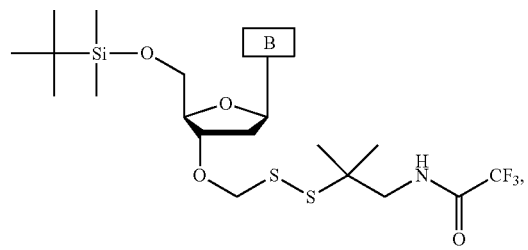

wherein B is a nucleobase;

c) contacting the product produced in step b) with tetra-butylammonium fluoride THF solution under conditions permitting the production of a product having the structure:

445

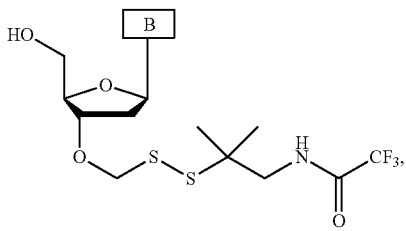

wherein B is a nucleobase;

d) contacting the product produced in step c) with tetra-butylammonium pyrophosphate, 2-chloro-4-H-1,3,2-benzodioxaphosphorin-4-one, and iodine solution under conditions permitting the production of a 3-O—NH$_2$-t-Butyldithiomethyl-dNTP;

e) contacting the 3-O—NH$_2$-t-Butyldithiomethyl-dNTP of step d) with Bodipy FL-NHS ester under conditions permitting the production of the 3'-O-Bodipy-t-Butyldithiomethyl-dNTP.

Embodiment P39. The process of embodiment P38, wherein the 3'-O-Bodipy-t-Butyldithiomethyl-dNTP is a 3'-O-Bodipy-t-Butyldithiomethyl-dATP or an analog thereof, 3'-O-Bodipy-t-Butyldithiomethyl-dTTP or an analog thereof, 3'-O-Bodipy-t-Butyldithiomethyl-dGTP or an analog thereof, or 3'-O-Bodipy-t-Butyldithiomethyl-dCTP.

Embodiment P40. The process of embodiment P39, wherein the 3'-O-Bodipy-t-Butyldithiomethyl-dNTP is 3'-O-Bodipy-t-Butyldithiomethyl-dTTP.

Embodiment P41. A process for producing a 3'-O-Bodipy-PEG$_4$-t-Butyldithiomethyl-dNTP, comprising:

a) reacting, 1) a 5'-O-tert-Butyldimethylsilyl-nucleoside, 2) acetic acid, and 3) acetic anhydride, under conditions permitting the production of a 3'-O-methylthiomethyl-5'-O-tert-butyldimerthylsilyl-nucleoside;

b) contacting the 3'-O-methylthiomethyl-5'-O-tert-butyldimerthylsilyl-nucleoside produced in part a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

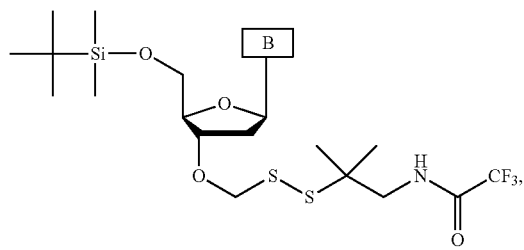

wherein B is a nucleobase;

c) contacting the product produced in step b) with tetra-butylammonium fluoride THF solution under conditions permitting the production of a product having the structure:

446

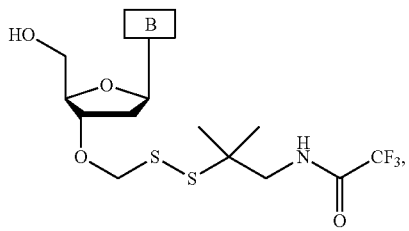

wherein B is a nucleobase;

d) contacting the product produced in step c) with tetra-butylammonium pyrophosphate, 2-chloro-4-H-1,3,2-benzodioxaphosphorin-4-one, and iodine solution under conditions permitting the production of a 3-O—NH$_2$-t-Butyldithiomethyl-dNTP;

e) contacting the 3-O—NH$_2$-t-Butyldithiomethyl-dNTP of step d) with Bodipy-PEG$_4$-Acid, N,N-disuccinimidyl carbonate, and 4-dimethylaminopyridine under conditions permitting the production of the 3'-O-PEG$_4$-Bodipy-t-Butyldithiomethyl-dNTP.

Embodiment P42. The process of embodiment 41, wherein the 3'-O-PEG$_4$-Bodipy-t-Butyldithiomethyl-dNTP is a 3'-O-PEG$_4$-Bodipy-t-Butyldithiomethyl-dATP or an analog thereof, 3'-O-PEG$_4$-Bodipy-t-Butyldithiomethyl-dTTP or an analog thereof, 3'-O-PEG$_4$-Bodipy-t-Butyldithiomethyl-dGTP or an analog thereof, or 3'-O-PEG$_4$-Bodipy-t-Butyldithiomethyl-dCTP.

Embodiment P43. The process of embodiment 42, wherein the 3'-O-PEG$_4$-Bodipy-t-Butyldithiomethyl-dNTP is 3'-O-PEG$_4$-Bodipy-t-Butyldithiomethyl-dTTP.

Embodiment P44. A process for producing a 3'-O-Rox-t-Butyldithiomethyl-dATP, comprising:

a) reacting, 1) a N$^4$-Benzoyl-5'-O-tert-butyldimethylsilyl-2'-deoxyadenosine, and 2) acetic acid and acetic anhydride under conditions permitting the formation of a N$^4$-Benzoyl-3'-O-methylthiomethyl-5'-O-tert-butyldimethylsilyl-2'-deoxyadenosine;

b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

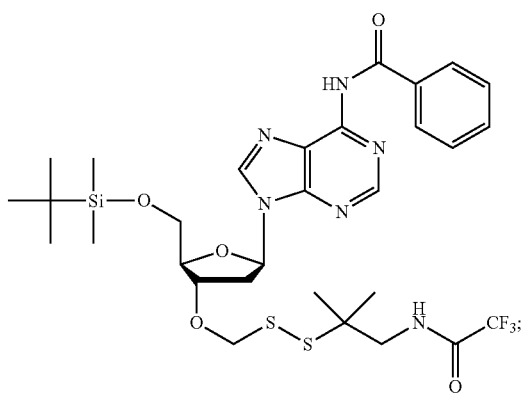

c) contacting the product of step b) with tetrabutylammonium fluoride THF solution under conditions permitting the production of a product having the structure:

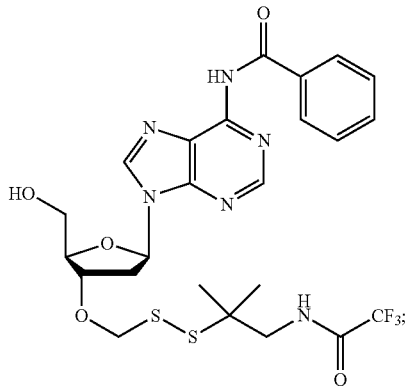

d) contacting product of step c) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dATP;

e) contacting the 3'-O—NH$_2$-t-Butyldithiomethyl-dATP produced in step d) with ROX—NHS ester under conditions permitting the production of the 3'-O-Rox-t-Butyldithiomethyl-dATP.

Embodiment P45. A process for producing a 3'-O-Rox-PEG$_4$-t-Butyldithiomethyl-dATP, comprising:

a) reacting,
   1) a N$^4$-Benzoyl-5'-O-tert-butyldimethylsilyl-2'-deoxyadenosine, and
   2) acetic acid and acetic anhydride under conditions permitting the formation of a N$^4$-Benzoyl-3'-O-methylthiomethyl-5'-O-tert-butyldimethylsilyl-2'-deoxyadenosine;

b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

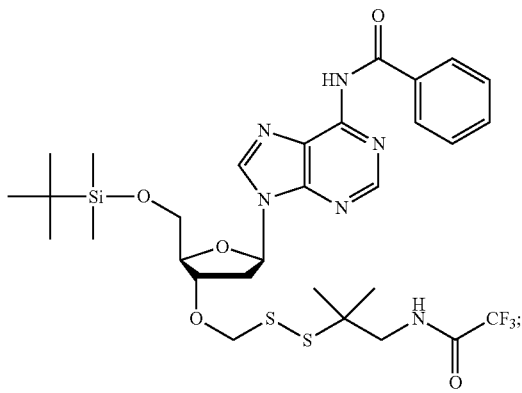

c) contacting the product of step b) with tetrabutylammonium fluoride THF solution under conditions permitting the production of a product having the structure:

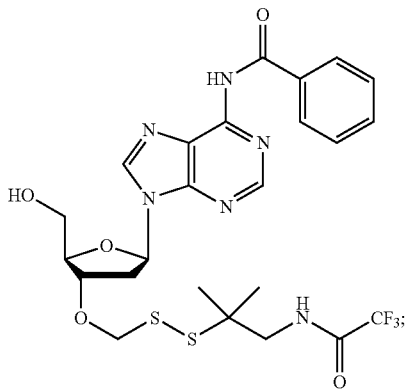

d) contacting product of step c) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dATP;

e) contacting the 3'-O—NH$_2$-t-Butyldithiomethyl-dATP produced in step d) with ROX-PEG$_4$-Acid, N,N-disuccinimidyl carbonate, and 4-dimethylaminopyridine under conditions permitting the production of the 3'-O-Rox-PEG$_4$t-Butyldithiomethyl-dATP.

Embodiment P46. A process for producing a 3'-O-Alexa488-t-Butyldithiomethyl-dCTP, comprising:

a) reacting
   1) a N -Benzoyl-5'-O-tert-butyldimethylsilyl-2'-deoxycytidine, and
   2) acetic acid and acetic anhydride under conditions permitting the formation of a N$^4$-Benzoyl-3'-O-methylthiomethyl-5'-O-tert-butyldimethylsilyl-2'-deoxycytidine;

b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

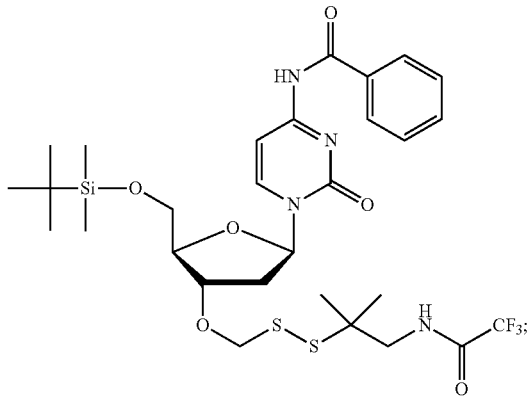

c) contacting the product of step b) with tetrabutylammonium fluoride THF solution under conditions permitting the production of a product having the structure:

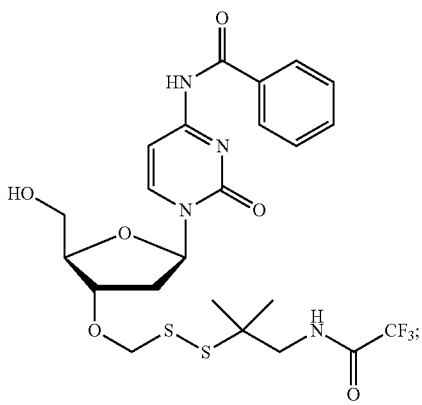

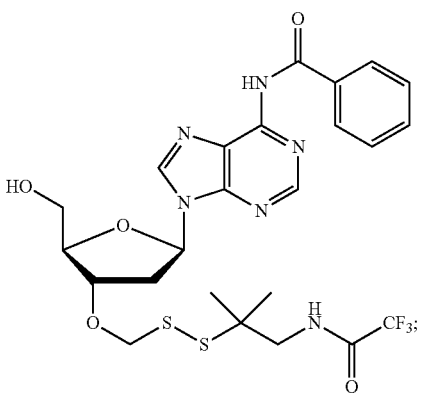

d) contacting product of step c) with tetrabutylammonium pyrophosphate, 1-chloro-4-H-1,3,2-benzodioxaphosphorin-4-one, tributylamine, and iodine solution under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-NHS ester under conditions permitting the production of the 3'-O-Alexa488-t-Butyldithiomethyl-dCTP.

Embodiment P47. A process for producing a 3'-O-Alexa488-PEG$_4$-t-Butyldithiomethyl-dCTP, comprising:

a) reacting
1) a N$^4$-Benzoyl-5'-O-tert-butyldimethylsilyl-2'-deoxycytidine, and
2) acetic acid and acetic anhydride under conditions permitting the formation of a N$^4$-Benzoyl-3'-O-methylthiomethyl-5'-O-tert-butyldimethylsilyl-2'-deoxycytidine;

b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

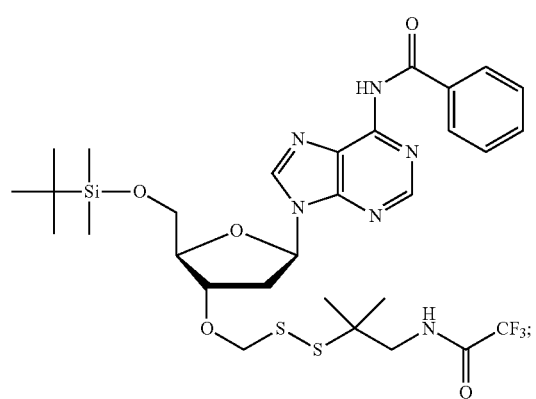

c) contacting the product of step b) with tetrabutylammonium fluoride THF solution under conditions permitting the production of a product having the structure:

d) contacting product of step c) with tetrabutylammonium pyrophosphate, 1-chloro-4-H-1,3,2-benzodioxaphosphorin-4-one, tributylamine, and iodine solution under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-PEG$_4$-NHS ester, N,N-disuccinimidyl carbonate, and 4-dimethylaminopyridine under conditions permitting the production of the 3'-O-Alexa488-PEG$_4$-t-Butyldithiomethyl-dCTP.

Embodiment P48. A process for producing a 3'-O-Cy5-t-Butyldithiomethyl-dGTP, comprising:

a) reacting
1) a 2'-deoxyguanosine, and
2) tert-butyldimethylsilyl chloride, imidazole, and N,N-dimethylformamide dimethyl acetal,
under conditions permitting the formation of a N$^4$-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid and acetic anhydride under conditions permitting the production of a product having the structure:

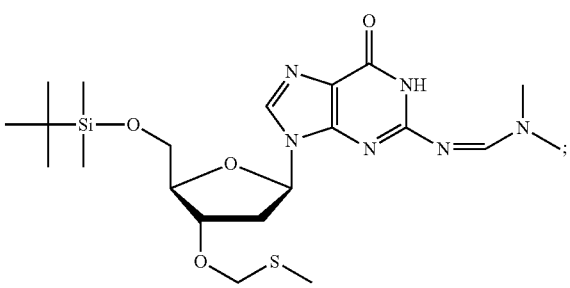

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

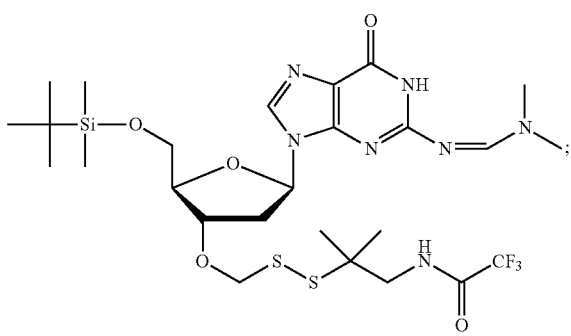

d) contacting the product of step c) with tetrabutylammonium fluoride THF solution under conditions permitting the production of a product having the structure:

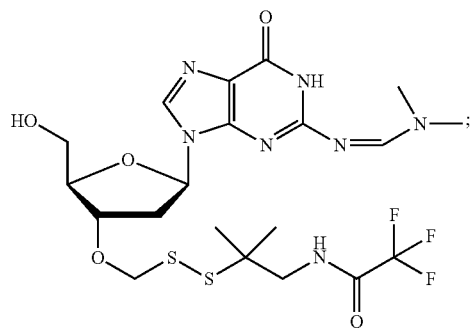

e) contacting product of step d) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dGTP;

f) contacting the 3'-O—NH$_2$-t-Butyldithiomethyl-dGTP produced in step e) with Cy5-NHS under conditions permitting the production of the 3'-O-Cy5-t-Butyldithiomethyl-dGTP.

Embodiment P49. A process for producing a 3'-O-Cy5-PEG$_4$-t-Butyldithiomethyl-dGTP, comprising:

a) reacting 1) a 2'-deoxyguanosine, and 2) tert-butyldimethylsilyl chloride, imidazole, and N,N-dimethylformamide dimethyl acetal, under conditions permitting the formation of a N$^4$-DMF-5'-O-tert-butyldimethylsilyl-2'-deoxyguanosine;

b) contacting the N$^4$-DMF-5'-O-tert-butyldimethylsilyl-2'-deoxyguanosine produced in step a) with acetic acid and acetic anhydride under conditions permitting the production of a product having the structure:

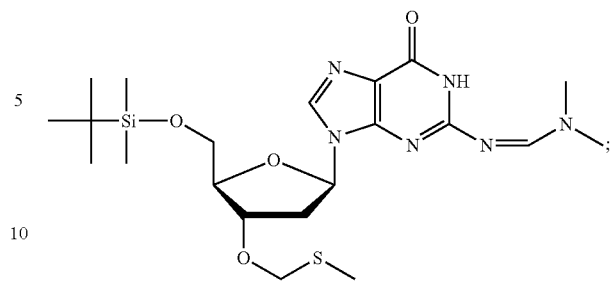

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

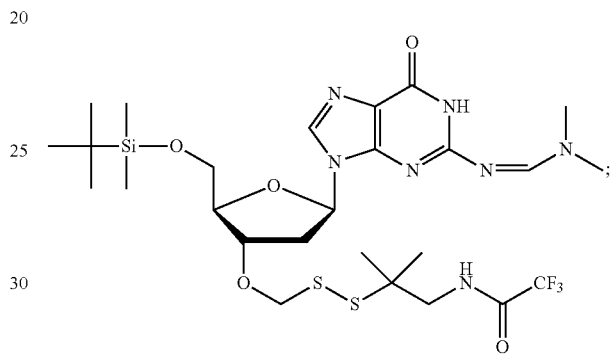

d) contacting the product of step c) with tetrabutylammonium fluoride THF solution under conditions permitting the production of a product having the structure:

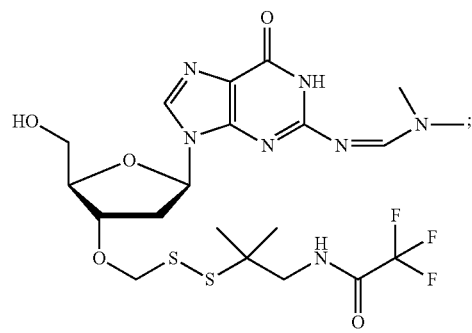

e) contacting product of step d) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dGTP;

f) contacting the 3'-O—NH$_2$-t-Butyldithiomethyl-dGTP produced in step e) with Cy5-PEG$_4$-NHS under conditions permitting the production of the 3'-O-Cy5-PEG$_4$-t-Butyldithiomethyl-dGTP.

Embodiment R1. A nucleotide analogue comprised of (i) a base (ii) a sugar, and (iii) a cleavable t-butyldithiomethyl moiety covalently attached to a 3'-oxygen of the sugar.

Embodiment R2. The nucleotide analog of embodiment R1, wherein the sugar is a deoxyribose.

Embodiment R3. The nucleotide analog of embodiment R1, wherein the sugar is a ribose.

Embodiment R4. The nucleotide analog of any one of embodiments R1-R3, wherein the nucleotide analog is a nucleotide monophosphate, a nucleotide diphosphate, a nucleotide triphosphate, a nucleotide tetraphosphate, a nucleotide pentaphosphate, or a nucleotide hexaphosphate.

Embodiment R5. The nucleotide analogue of any one of embodiments R1-R4, wherein the base is adenine or an analogue of adenine, guanine or an analogue of guanine, cytosine or an analogue of cytosine, thymine or an analogue of thymine, or uracil or an analogue of uracil.

Embodiment R6. The nucleotide analogue of any one of embodiments R1-R5, wherein the cleavable t-butyldithiomethyl moiety has the structure:

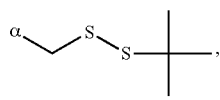

wherein α represents the point of connection to the 3'-oxygen.

Embodiment R7. The nucleotide analogue of embodiment R7, wherein the cleavable t-butyldithiomethyl moiety has the structure:

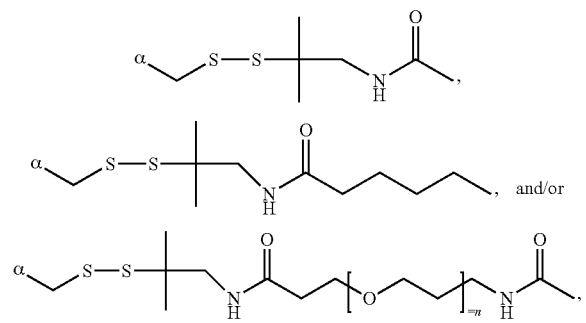

wherein α represents the point of connection to the 3'-oxygen; and wherein n is an integer which may be 1, 2, 3, 4, or 5.

Embodiment R8. The nucleotide analogue of embodiment 6, wherein the nucleotide analogue has the structure:

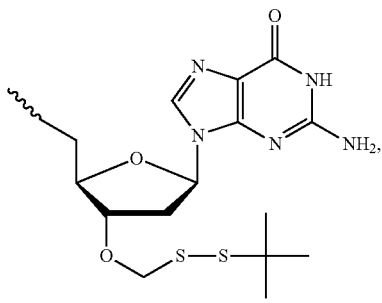

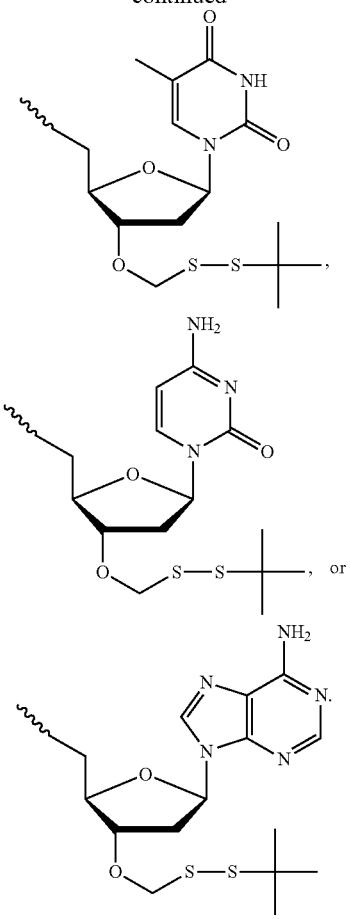

Embodiment R9. The nucleotide analogue of any one of embodiments R1-R8, further comprising a detectable label.

Embodiment R10. The nucleotide analogue of embodiment R9, wherein the cleavable t-butyldithiomethyl moiety has the structure:

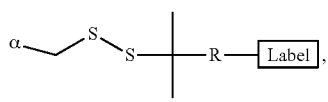

wherein α represents the point of connection to the 3'-oxygen;

wherein R represents a structure consisting of one or more atoms one of which is covalently bound to the detectable label; and wherein Label represents the detectable label.

Embodiment R11. The nucleotide analog of embodiment R10, wherein the cleavable t-butyldithiomethyl moiety has the structure:

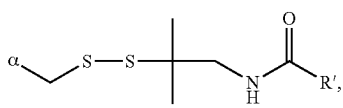

-continued

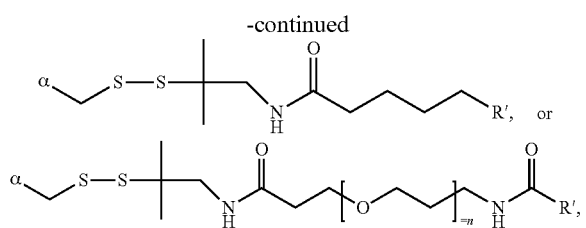

wherein α represents the point of connection to the 3'-oxygen;
wherein n is an integer which may be 1, 2, 3, 4, or 5; and
wherein R' represents one or more atoms through which a covalent connection is established to the detectable label.

Embodiment R12. The nucleotide analogue of any one of embodiments R9-R11, wherein the nucleotide analogue has the structure:

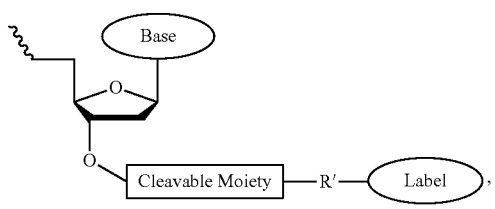

wherein Cleavable Moiety is the cleavable t-butyldithiomethyl moiety,
wherein Label represents the detectable label, and
wherein R' represents one or more atoms through which a covalent connection is established to the detectable label.

Embodiment R13. The nucleotide analog of any one of embodiments R9-R12, wherein the detectable label is a dye, a fluorophore, a fluorescence energy transfer tag, a chemiluminescent compound, a chromophore, a mass tag, an electrophore, a mononucleotide, an oligonucleotide, or a combination thereof.

Embodiment R14. The nucleotide analog of embodiment R13, wherein the detectable label is a fluorophore.

Embodiment R15. The nucleotide analog of embodiment R14, wherein the fluorophore is BodipyFL, R6G, ROX, Cy5, or Alexa488.

Embodiment R16. The nucleotide analog of embodiment R15, wherein the nucleotide analog is 3'-O-Alexa488-t-butyldithiomethyl-dCTP, 3'-O-Cy5-t-butyldithiomethyl-dGTP, 3'-O-Rox-t-butyldithiomethyl-dATP, 3'-O-RG6-t-butyldithiomethyl-dTTP, 3'-O-Alexa488-PEG$_4$-t-butyldithiomethyl-dCTP, 3'-O-RG6-PEG$_4$-t-butyldithiomethyl-dTTP, 3'-O-Rox-PEG$_4$-t-butyldithiomethyl-dATP, or 3'-O-Cy5-PEG$_4$-t-butyldithiomethyl-dGTP.

Embodiment R17. The nucleotide analog of embodiment R15, having the structure:

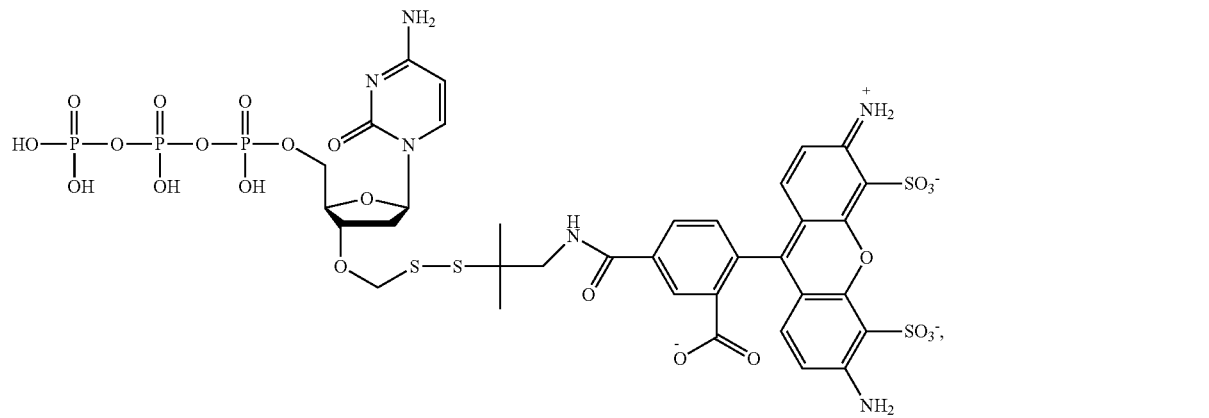

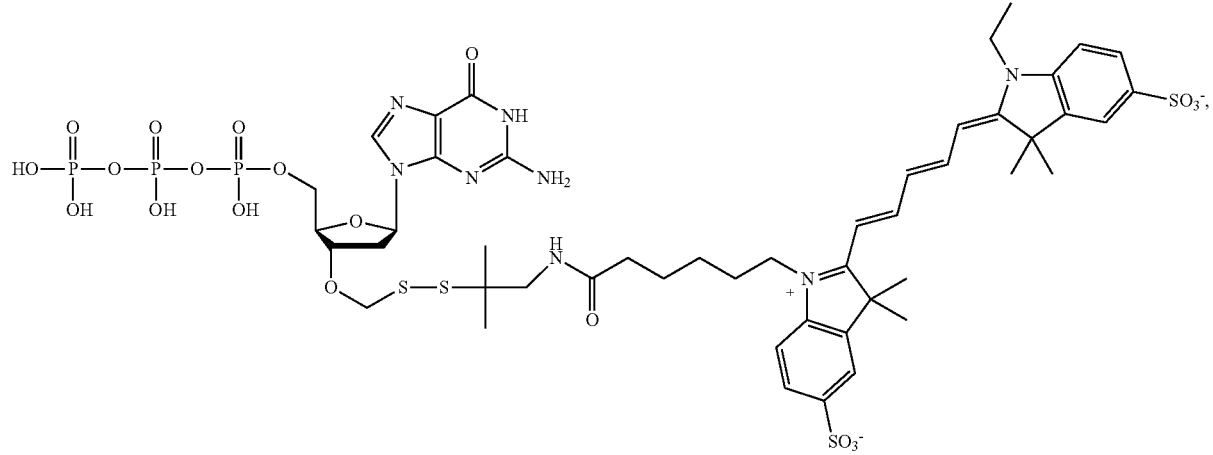

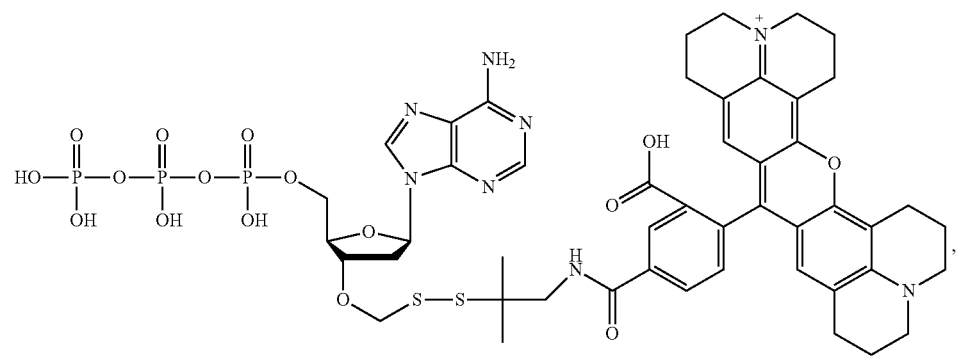
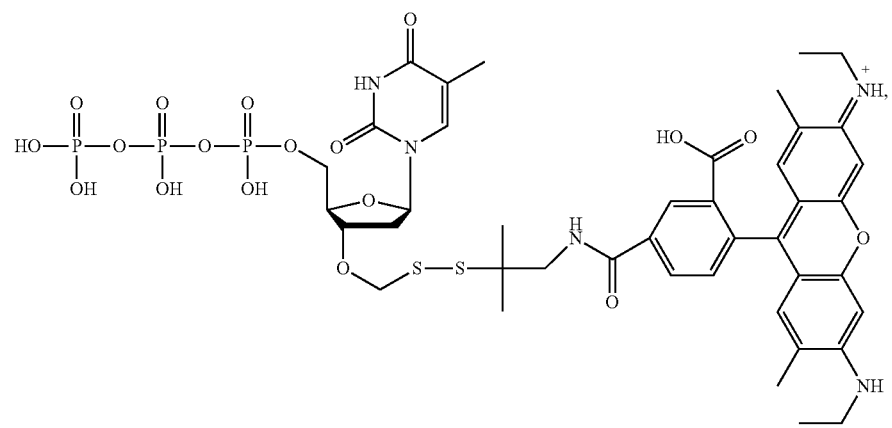
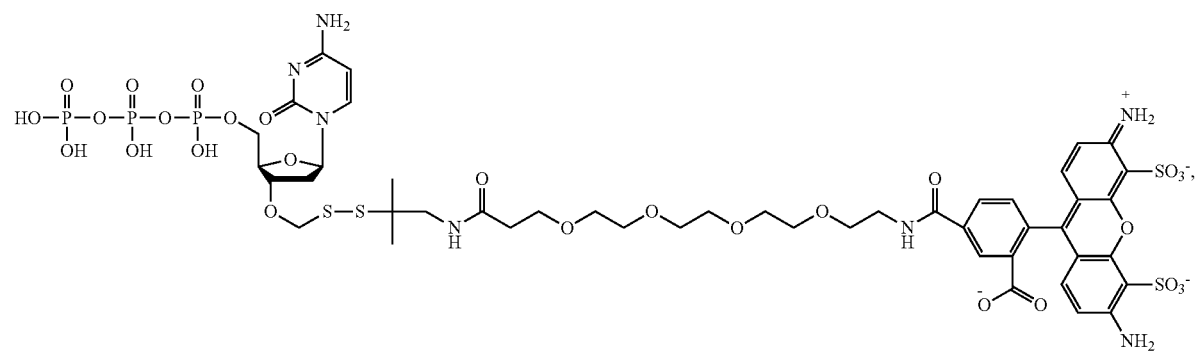
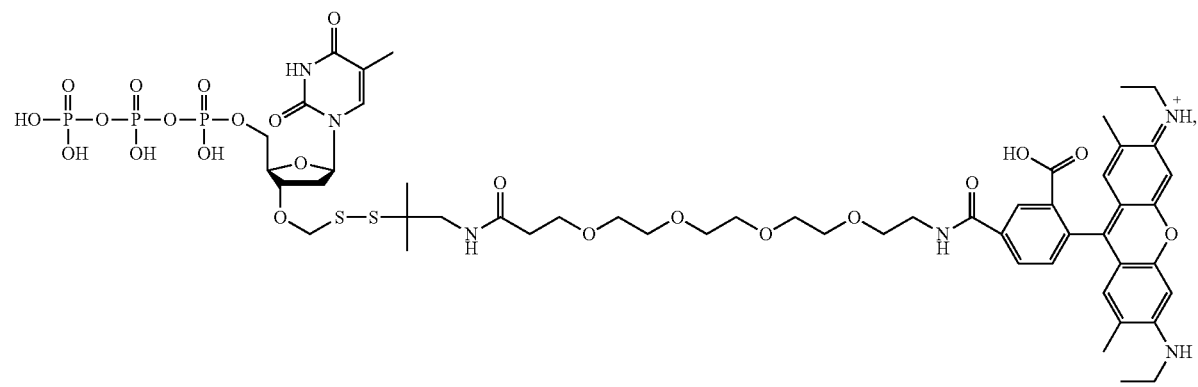

-continued

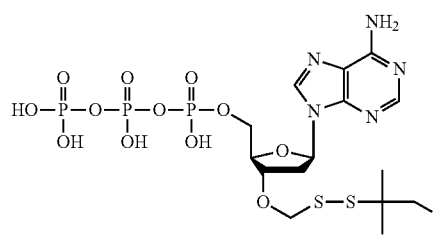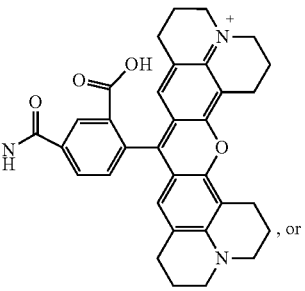

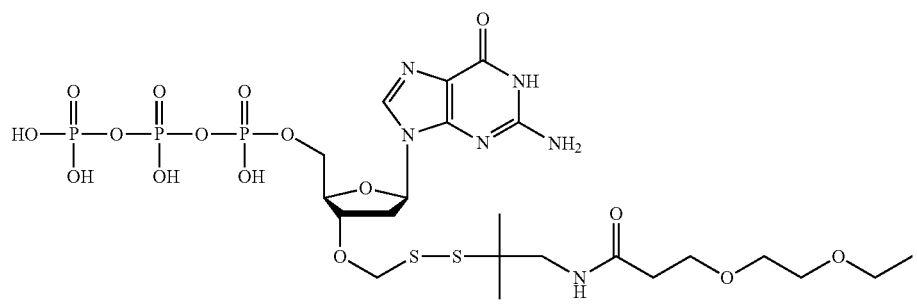

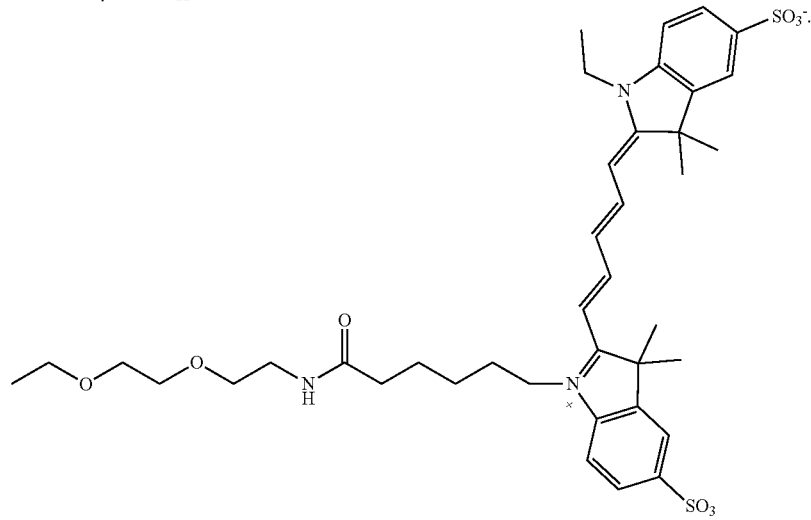

Embodiment R18. A composition comprising at least two different nucleotide analogues of any one of embodiments R11-R17, wherein each nucleotide analogue consists of a different base, and wherein each nucleotide analogue consists of a different detectable label from each other nucleotide analogue in the composition.

Embodiment R19. The nucleotide analogues of any one of embodiments R1-R9, further comprising an anchor moiety, wherein the anchor moiety is a predetermined small chemical moiety correlated to the identity of the base and that orthogonally and rapidly reacts with a complementary binding molecule thereby forming a conjugate of the anchor moiety and binding molecule.

Embodiment R20 The nucleotide of embodiment R19, having the structure:

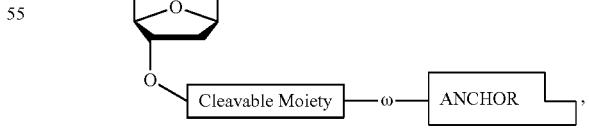

wherein base is one of adenine, guanine, thymine, cytosine, uracil, or analogues thereof, wherein Cleavable Moiety is the cleavable t-butyldithiomethyl moiety, wherein Anchor is the anchor moiety, and wherein ω represents a structure consisting of one or more atoms of which is covalently bound to both the t-butyldithiomethyl cleavable moiety and the anchor moiety.

Embodiment R21 The nucleotide analogue of embodiment R20 or embodiment R21, wherein the anchor moiety has the structure:

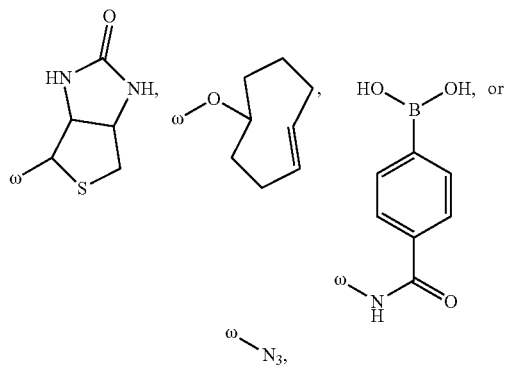

wherein ω represents one or more atoms through which a covalent connection is established to the cleavable t-butyldithiomethyl moiety.

Embodiment R22. The nucleotide analogue of any one of embodiments R19-R21, wherein the anchor orthogonally and rapidly reacts with a complementary binding molecule thereby binding the anchor and binding molecule so as to form a conjugate of the anchor moiety and the binding molecule, wherein the binding molecule has the structure:

wherein Label is a detectable label, and wherein binder is a small chemical group correlated to the identity of the detectable label and that orthogonally and rapidly reacts with an anchor moiety thereby forming a conjugate of the anchor moiety and binding molecule.

Embodiment R23. The nucleotide analogue of embodiment R22, wherein the detectable label of the complementary binding molecule is selected from the group consisting of one or more dyes, fluorophores, combinatorial fluorescence energy transfer tags, chemiluminescent compounds, chromophores, mass tags, electrophores, mononucleotides, oligonucleotides, or combinations thereof.

Embodiment R24. The nucleotide analogue of embodiment R23, wherein the detectable label of the complementary binding molecule comprises one or more fluorescence energy transfer tags.

Embodiment R25. The nucleotide analogue of embodiment R24, wherein the complementary binding molecule further comprises one or more FRET cassettes.

Embodiment R26. The nucleotide analogue of embodiment R25, wherein the FRET cassettes comprise one or more dSpacer monomers.

Embodiment R27 The nucleotide analogue of embodiment R26, wherein the complementary binding molecule has the structure:

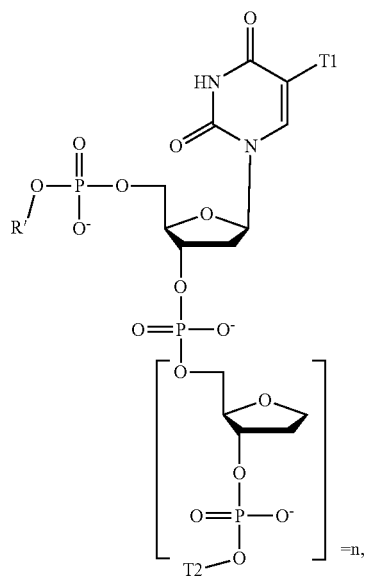

wherein T1 is a point of attachment for one or more fluorescent energy donor or acceptor, and T2 is a point of attachment for one or more of the complementary energy donor or acceptor to that in T1, wherein n is an integer between 1 and 20, and R represents the point of attachment to the binder of the binding molecule.

Embodiment R28 The nucleotide analogue of embodiment R24, wherein the detectable label of the complementary binding molecule is one or more fluorophore.

Embodiment R29 The nucleotide analogue of embodiment R28, wherein the fluorophore of the detectable label of the complementary binding molecule is selected from the group consisting of BodipyFL, R6G, ROX, Cy5, and Alexa488.

Embodiment R30 The nucleotide analogue of any one of embodiments R22-R29, wherein the binder of the complementary binding molecule comprises:

a) a compound comprising streptavidin having the structure:

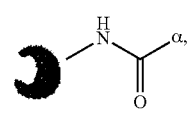

or b) a compound comprising the structure:

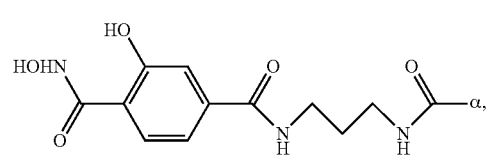

-continued

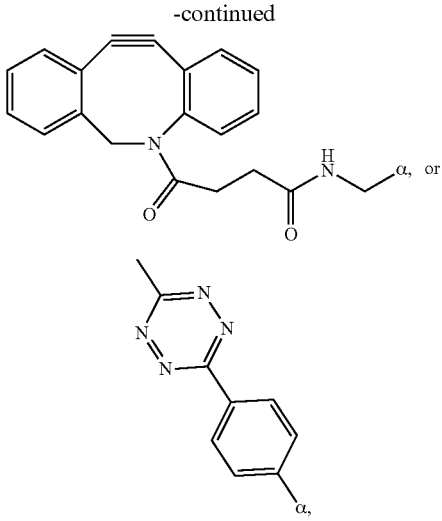

wherein α represents one or more atoms through which a covalent connection is established to the detectable label.

Embodiment R31. The nucleotide analogue of embodiment 30, wherein the anchor moiety has the structure:

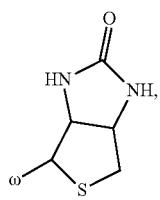

wherein ω represents one or more atoms through which a covalent connection is established to the cleavable t-butyldithiomethyl moiety, and the anchor moiety orthogonally and rapidly reacts with a binder of the complimentary binding molecule, wherein said binder comprises streptavidin, and has the structure:

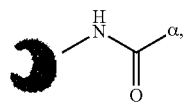

wherein α is one or more atoms through which a covalent connection is established to the detectable label, and thereby forms a conjugate having the structure:

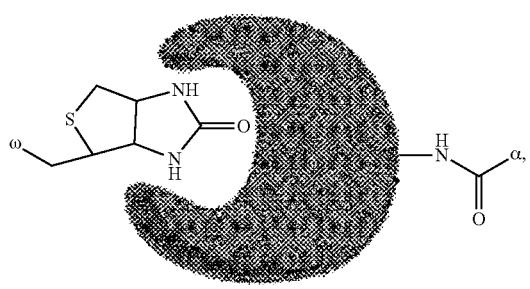

wherein α is one or more atoms through which a covalent connection is established to the detectable label, and wherein ω is one or more atoms through which a covalent connection is established to the cleavable t-butyldithiomethyl moiety.

Embodiment R32 The nucleotide analogue of embodiment R31 having the structure:

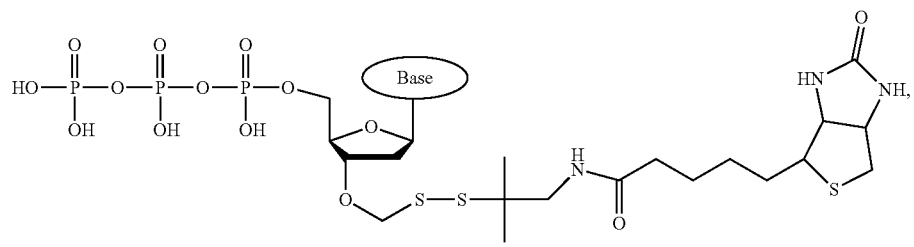

wherein base is one of adenine, guanine, thymine, cytosine, uracil, or analogues thereof.

Embodiment R33 The nucleotide analogue of embodiment R31 or R32, wherein the binder of the complementary binding molecule comprises streptavidin, and wherein the complementary binding molecule has the structure:

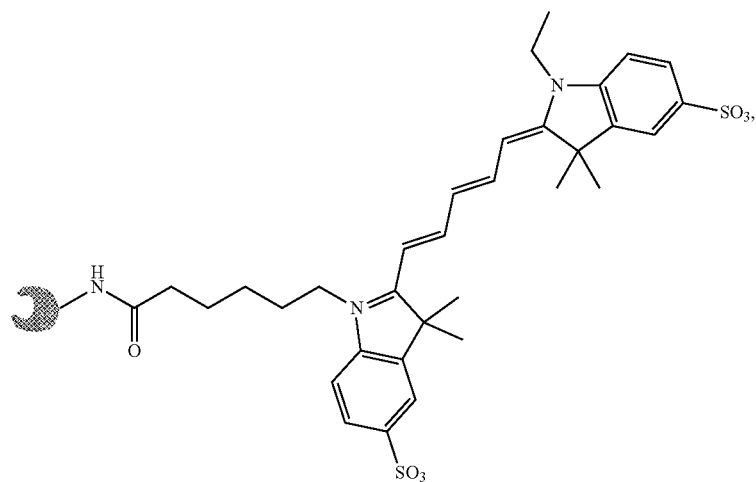

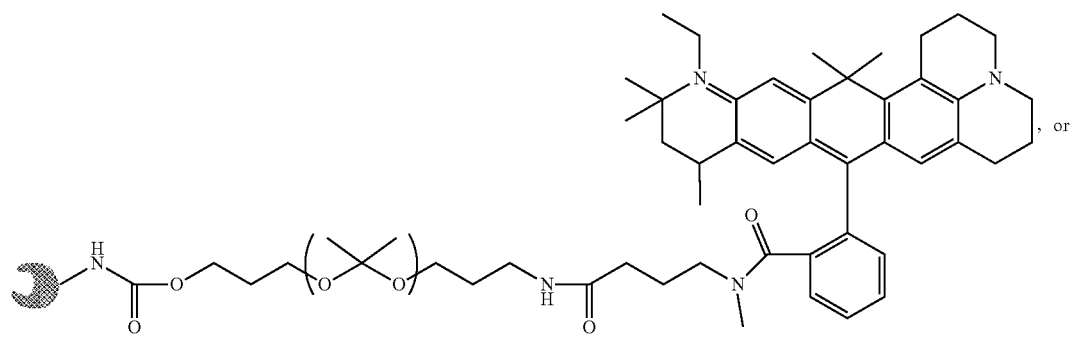

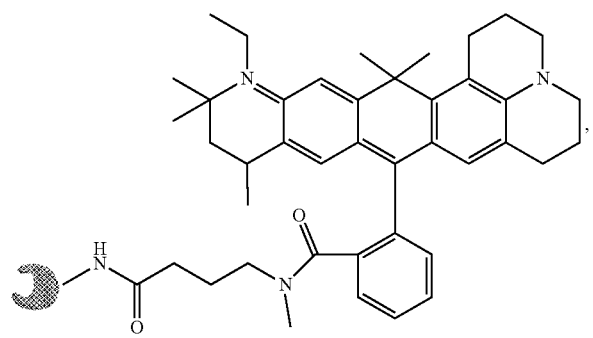

Embodiment R34 The nucleotide analogue embodiment R30, wherein the anchor moiety has the structure:

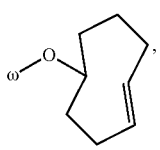

wherein ω represents one or more atoms through which a covalent connection is established to the cleavable t-butyl-dithiomethyl moiety, and the anchor moiety orthogonally and rapidly reacts with the binder of the complimentary binding molecule, wherein said binder has the structure:

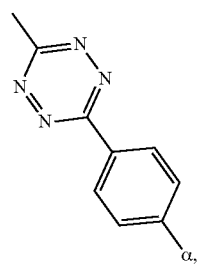

wherein α is one or more atoms through which a covalent connection is established to the detectable label, and thereby forms a conjugate having the structure:

467

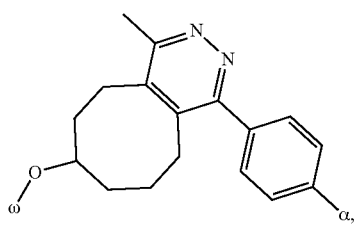

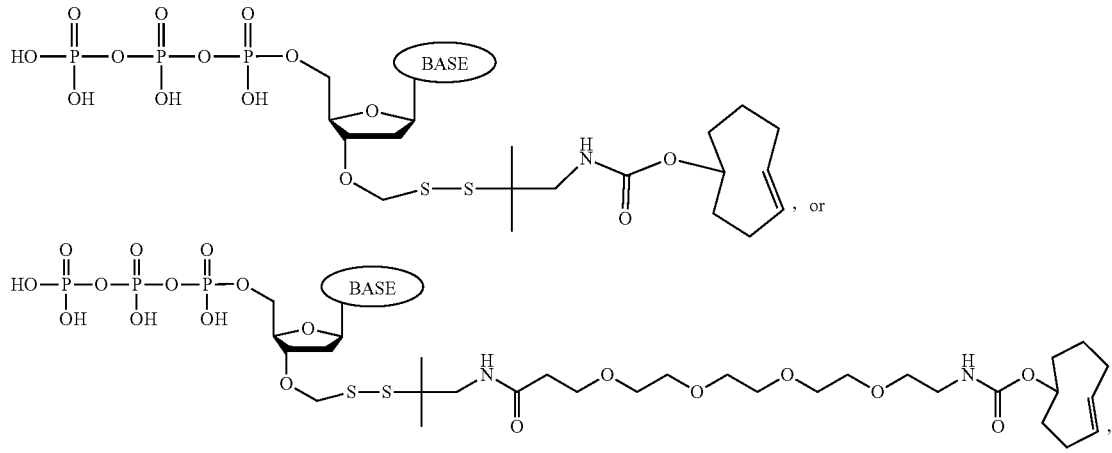

wherein α is one or more atoms through which a covalent connection is established to the detectable label, and wherein ω is one or more atoms through which a covalent connection is established to the cleavable t-butyldithiomethyl moiety.

Embodiment R35. The nucleotide analogue of embodiment R34 having the structure:

wherein base is one of adenine, guanine, thymine, cytosine, uracil, or an analogue thereof.

Embodiment R36 The nucleotide analogue of any one of embodiments R34-R35, wherein the complementary binding molecule has the structure:

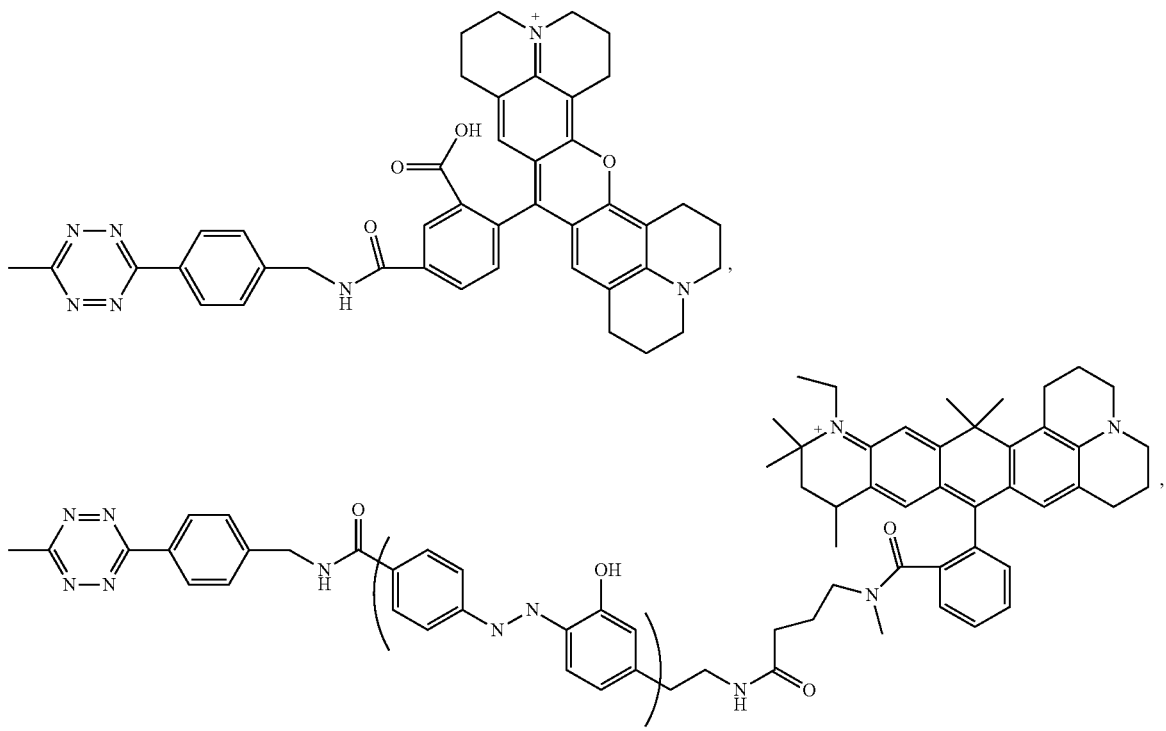

469
-continued
470
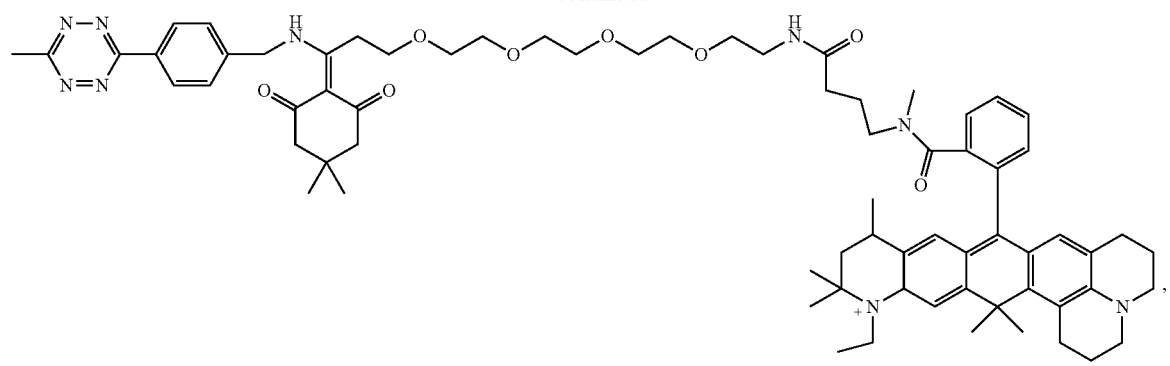
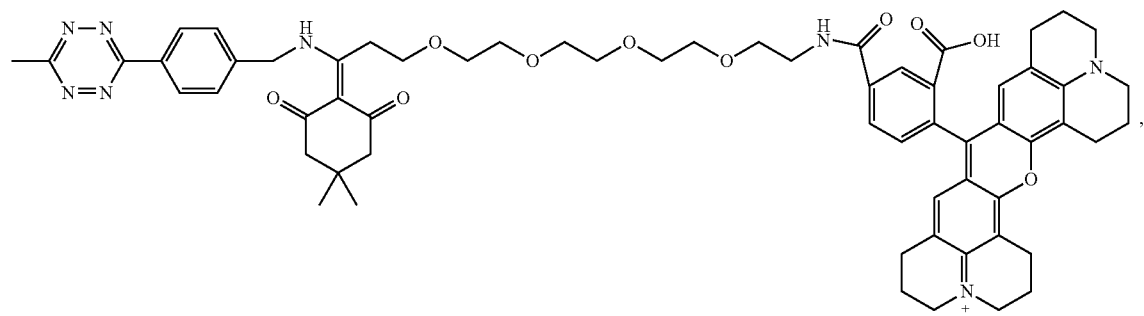
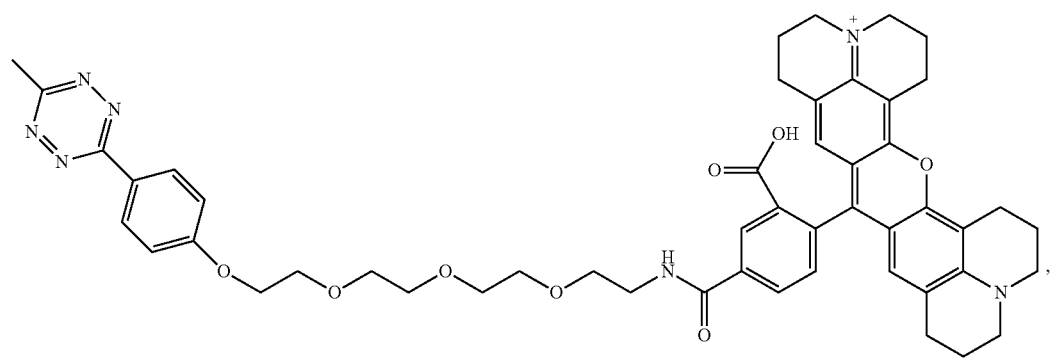

-continued
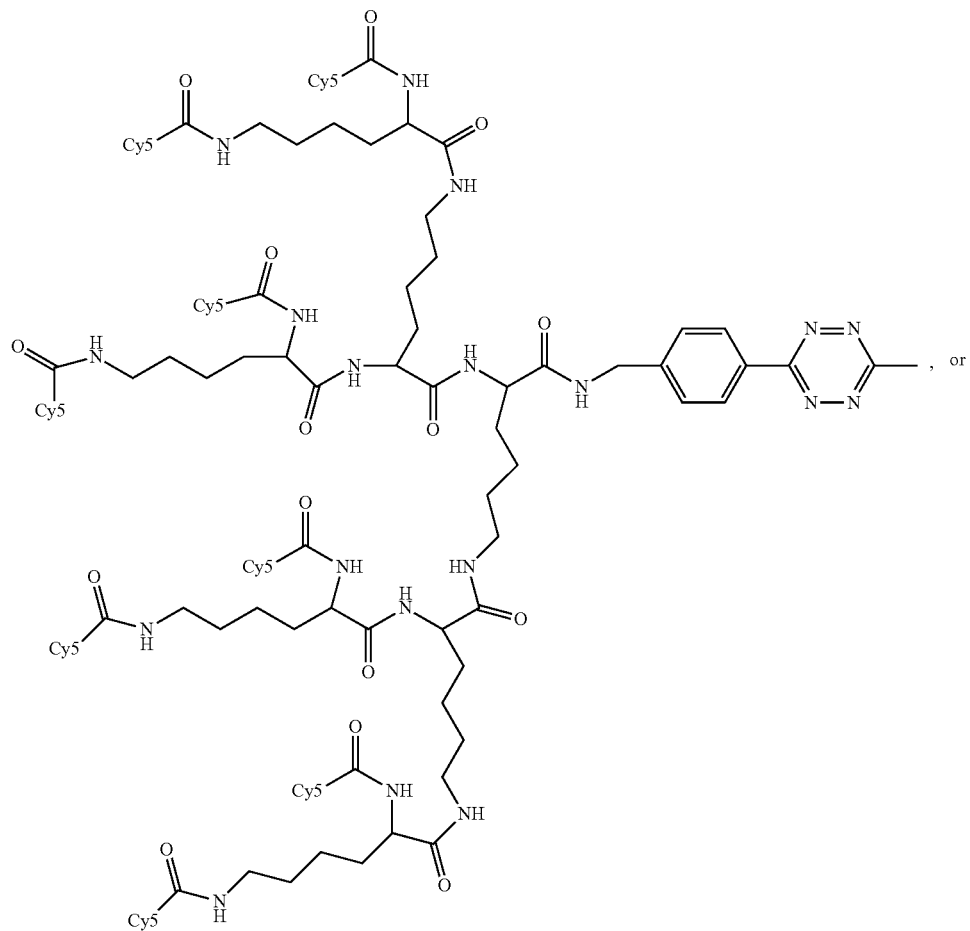
, or
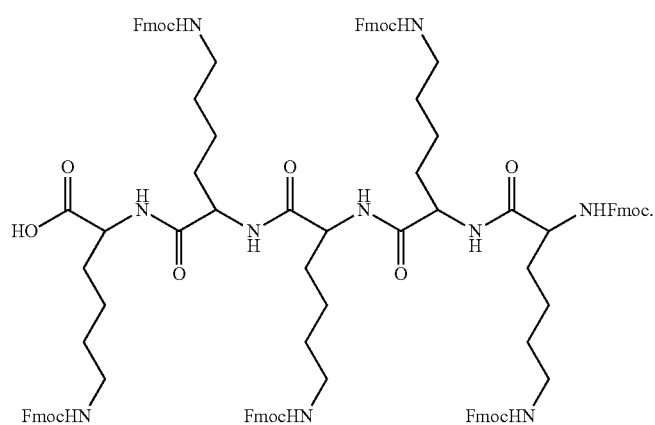
? indicates text missing or illegible when filed Embodiment R37 The nucleotide analogue of embodiment R30, wherein the anchor moiety has the structure:

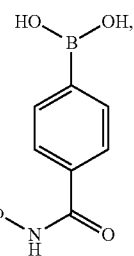

wherein ω represents one or more atoms through which a covalent connection is established to the cleavable t-butyldithiomethyl moiety, and
the anchor moiety orthogonally and rapidly reacts with the binder of the complimentary binding molecule, wherein said binder has the structure:

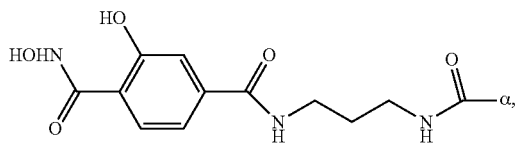

wherein α is one or more atoms through which a covalent connection is established to the detectable label, and thereby forms a conjugate having the structure:

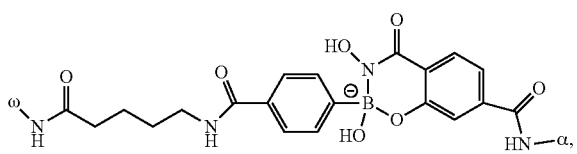

wherein α is one or more atoms through which a covalent connection is established to the detectable label, and wherein ω is one or more atoms through which a covalent connection is established to the cleavable t-butyldithiomethyl moiety.

Embodiment R38. The nucleotide analogue of embodiment R37 having the structure:

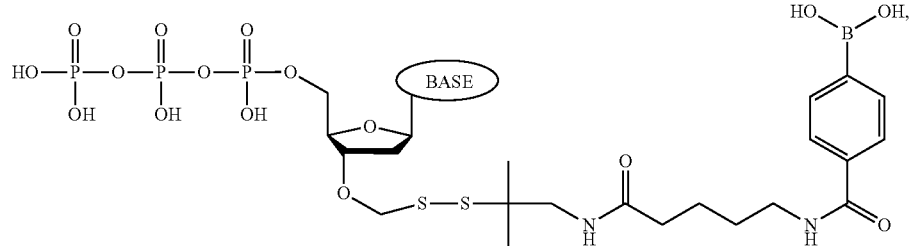

wherein base is one of adenine, guanine, thymine, cytosine, uracil, or derivatives thereof.

Embodiment R39. The nucleotide analogue of any one of embodiments R37-R38, wherein the complementary binding molecule has the structure:

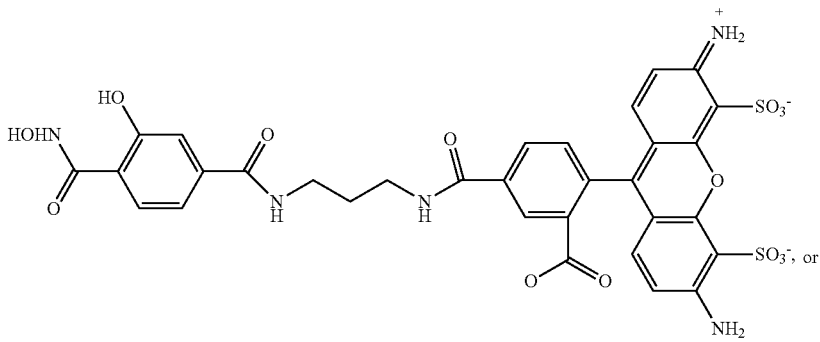

-continued

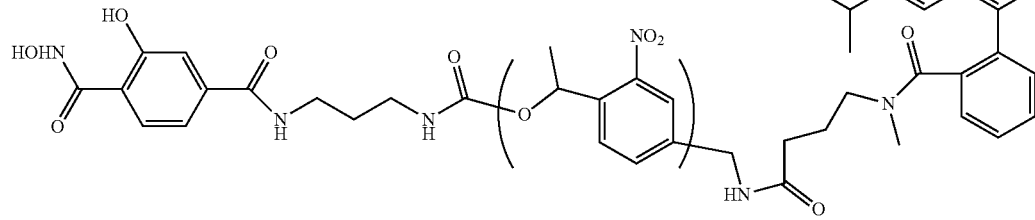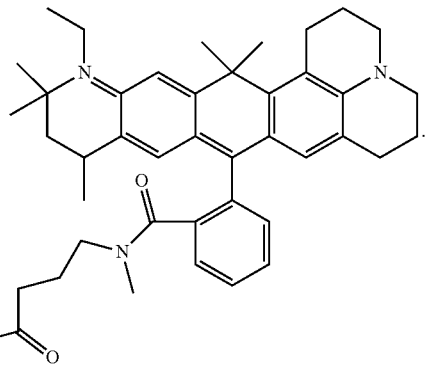

Embodiment R40. The nucleotide analogue of embodiment R30, wherein the anchor has the structure:

wherein ω represents one or more atoms through which a covalent connection is established to the cleavable t-butyldithiomethyl moiety, and the anchor orthogonally and rapidly reacts with a binder of a complimentary binding molecule, wherein said binder has the structure:

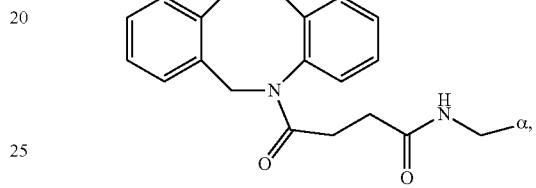

wherein α is one or more atoms through which a covalent connection is established to a detectable label, and thereby forms a conjugate having the structure:

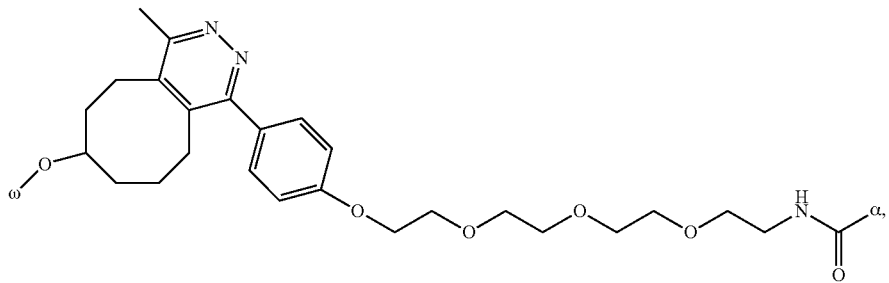

wherein α is one or more atoms through which a covalent connection is established to detectable label, and wherein ω is one or more atoms through which a covalent connection is established to the cleavable t-butyldithiomethyl moiety.

Embodiment R41. The nucleotide analogue of embodiment R40, wherein the nucleotide analogue has the structure:

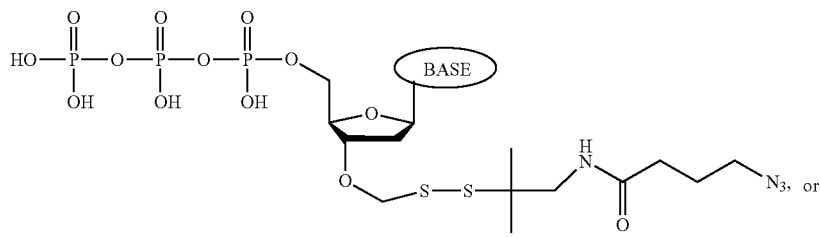

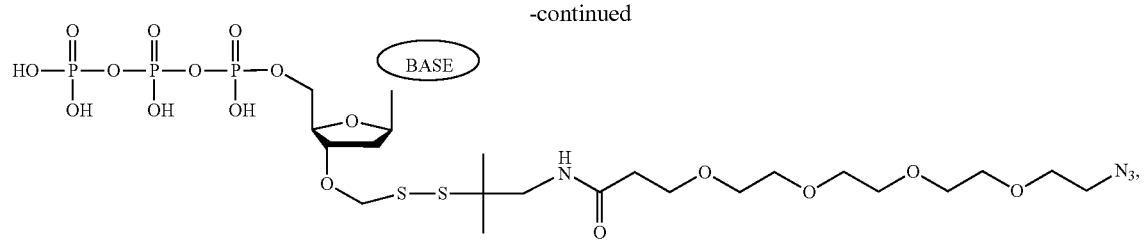
wherein base is one of adenine, guanine, thymine, cytosine, uracil, or an analogue thereof.
Embodiment R42 The nucleotide analogue of any one of embodiments R40-R41, wherein the complementary binding molecule has the structure:
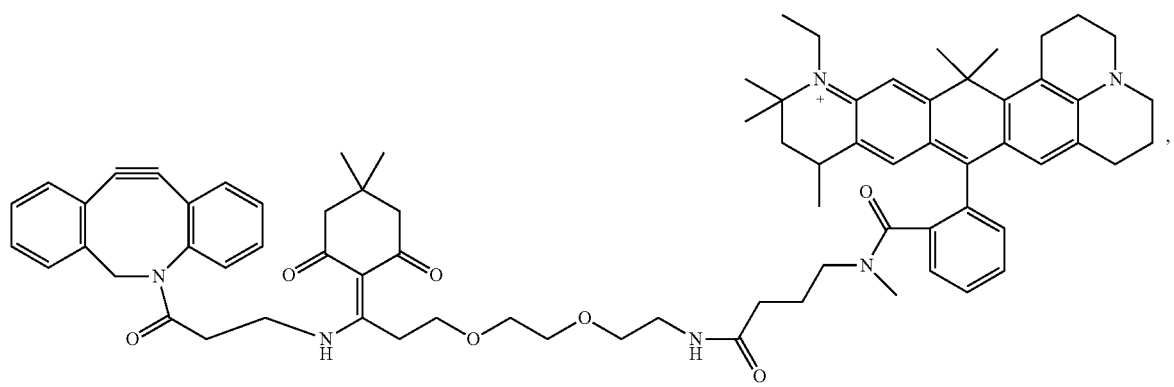
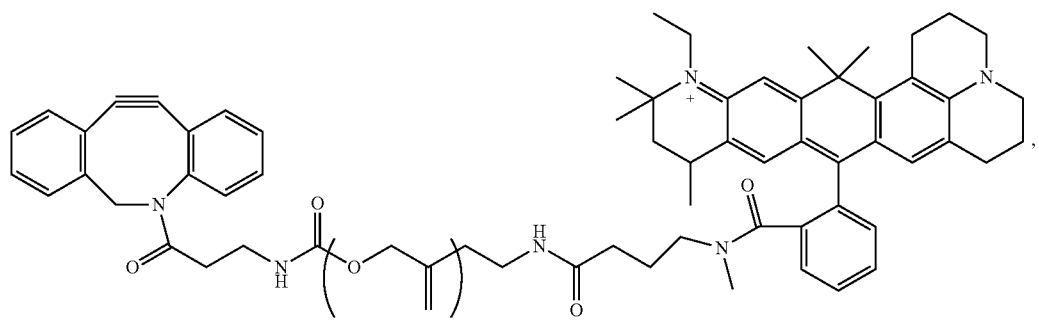
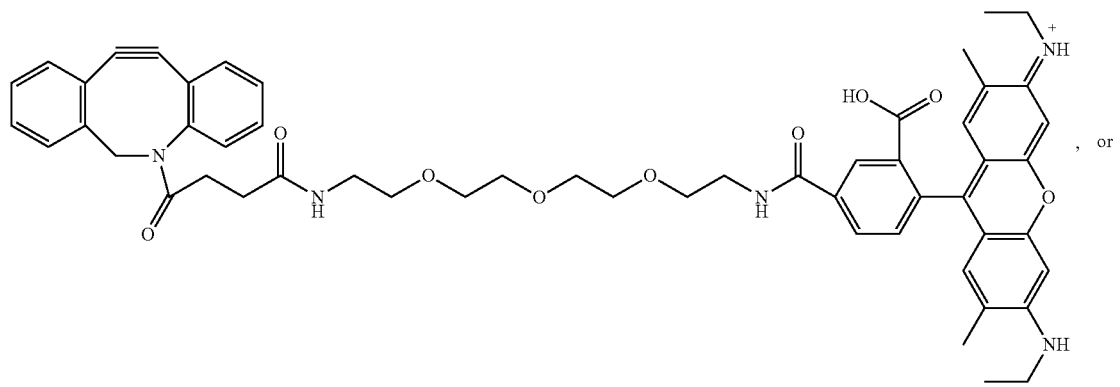
, or

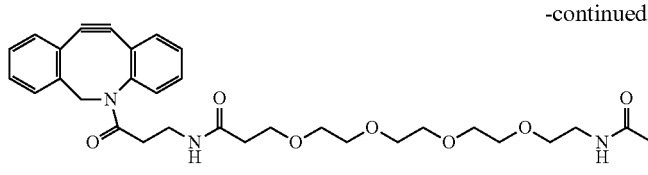

-continued

Embodiment R43 The nucleotide analogue of any one of embodiments R1-R42, wherein the cleavable t-butyldithiomethyl moiety may be cleaved by a water soluble phosphine, thereby resulting in a 3'-OH.

Embodiment R44 The nucleotide analogue of embodiment R43, wherein the water soluble phosphine is tris-(2-carboxyethyl)phosphine (TCEP) or tris(hydroxypropyl)phosphine (THP).

Embodiment R45. A composition comprising at least two nucleotide analogues of any one of embodiments R1-R44, wherein each nucleotide analogue has a different base.

Embodiment R46. A composition comprising at least two nucleotide analogues of any one of embodiments 19-44, wherein each nucleotide analogue has a different base, and wherein each nucleotide analogue has a different anchor moiety.

Embodiment R47. A process for producing a 3'-O-Bodipy-t-Butyldithiomethyl-dNTP, comprising:

a) reacting,
  1) a 5'-O-tert-Butyldimethylsilyl-nucleoside,
  2) acetic acid, and
  3) acetic anhydride,
    under conditions permitting the production of a 3'-O-methylthiomethyl-5'-O-tert-butyldimerthylsilyl-nucleoside;

b) contacting the 3'-O-methylthiomethyl-5'-O-tert-butyldimerthylsilyl-nucleoside produced in step a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

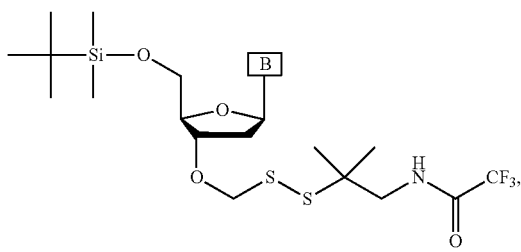

wherein B is a nucleobase;

c) contacting the product produced in step b) with tetra-butylammonium fluoride THE solution under conditions permitting the production of a product having the structure:

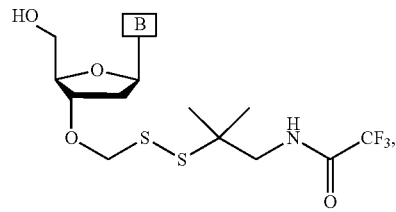

wherein B is a nucleobase;

d) contacting the product produced in step c) with tetra-butylammonium pyrophosphate, 2-chloro-4-H-1,3,2-benzodioxaphosphorin-4-one, and iodine solution under conditions permitting the production of a 3-O—NH$_2$-t-Bityldithiomethyl-dNTP;

e) contacting the 3-O—NH$_2$-t-Butyldithiomethyl-dNTP of step d) with Bodipy FL-NHS ester under conditions permitting the production of the 3'-O-Bodipy-t-Butyldithiomethyl-dNTP.

Embodiment R48. The process of embodiment R47, wherein the 3'-O-Bodipy-t-Butyldithiomethyl-dNTP is a 3'-O-Bodipy-t-Butyldithiomethyl-dATP or an analog thereof, 3'-O-Bodipy-t-Butyldithiomethyl-dTTP or an analog thereof, 3'-O-Bodipy-t-Butyldithiomethyl-dGTP or an analog thereof, or 3'-O-Bodipy-t-Butyldithiomethyl-dCTP.

Embodiment R49. The process of embodiment R48, wherein the 3'-O-Bodipy-t-Butyldithiomethyl-dNTP is 3'-O-Bodipy-t-Butyldithiomethyl-dTTP.

Embodiment R50. A process for producing a 3'-O-Bodipy-PEG$_4$-t-Butyldithiomethyl-dNTP, comprising:

a) reacting,
  1) a 5'-O-tert-Butyldimethylsilyl-nucleoside,
  2) acetic acid, and
  3) acetic anhydride,
    under conditions permitting the production of a 3'-O-methylthiomethyl-5'-O-tert-butyldimerthylsilyl-nucleoside;

b) contacting the 3'-O-methylthiomethyl-5'-O-tert-butyldimerthylsilyl-nucleoside produced in part a) with trimethylamine, molecular sieve, sulfuryl chloride, potassium p-toluenethiosulfonate, and 2,2,2,-trifluoro-N-(2-mercapto-2-methylpropyl)acetamide, under conditions permitting the production of a product having the structure:

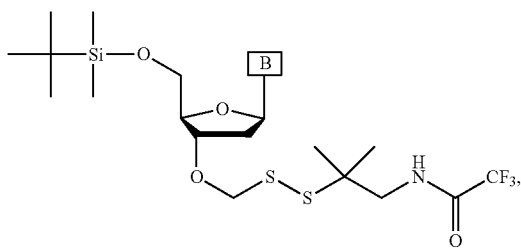

wherein B is a nucleobase;

c) contacting the product produced in step b) with tetrabutylammonium fluoride THF solution under conditions permitting the production of a product having the structure:

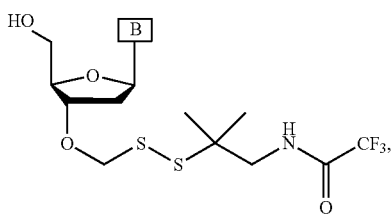

wherein B is a nucleobase;

d) contacting the product produced in step c) with tetrabutylammonium pyrophosphate, 2-chloro-4-H-1,3,2-benzodioxaphosphorin-4-one, and iodine solution under conditions permitting the production of a 3-O—NH$_2$-t-Butyldithiomethyl-dNTP;

e) contacting the 3-O—NH$_2$-t-Butyldithiomethyl-dNTP of step d) with Bodipy-PEG$_4$-Acid, N,N-disuccinimidyl carbonate, and 4-dimethylaminopyridine under conditions permitting the production of the 3'-O-PEG$_4$-Bodipy-t-Butyldithiomethyl-dNTP.

Embodiment R51. The process of embodiment 50, wherein the 3'-O-PEG$_4$-Bodipy-t-Butyldithiomethyl-dNTP is a 3'-O-PEG$_4$-Bodipy-t-Butyldithiomethyl-dATP or an analog thereof, 3'-O-PEG$_4$-Bodipy-t-Butyldithiomethyl-dTTP or an analog thereof, 3'-O-PEG$_4$-Bodipy-t-Butyldithiomethyl-dGTP or an analog thereof, or 3'-O-PEG$_4$-Bodipy-t-Butyldithiomethyl-dCTP.

Embodiment R52. The process of embodiment 51, wherein the 3'-O-PEG$_4$-Bodipy-t-Butyldithiomethyl-dNTP is 3'-O-PEG$_4$-Bodipy-t-Butyldithiomethyl-dTTP.

Embodiment R53. A process for producing a 3'-O-Rox-t-Butyldithiomethyl-dATP, comprising:

a) reacting,
1) a N$^4$-Benzoyl-5'-O-tert-butyldimethylsilyl-2'-deoxyadenosine, and
2) acetic acid and acetic anhydride under conditions permitting the formation of a N$^4$-Benzoyl-3'-O-methylthiomethyl-5'-O-tert-butyldimethylsilyl-2'-deoxyadenosine;

b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

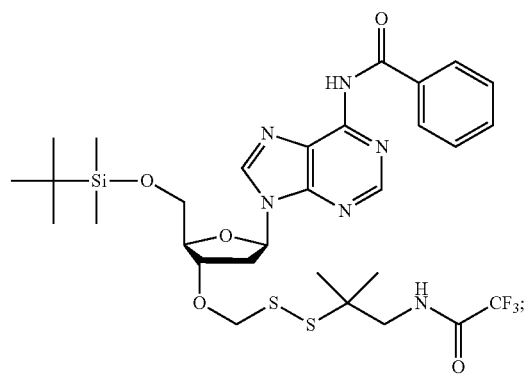

c) contacting the product of step b) with tetrabutylammonium fluoride THF solution under conditions permitting the production of a product having the structure:

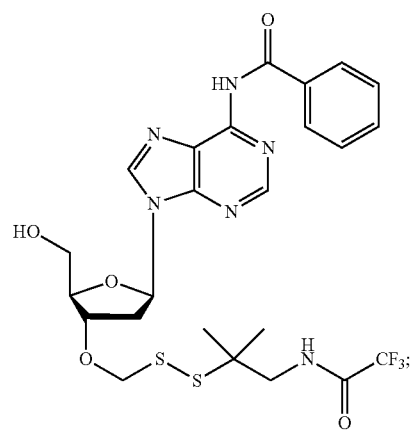

d) contacting product of step c) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dATP;

e) contacting the 3'-O—NH$_2$-t-Butyldithiomethyl-dATP produced in step d) with ROX—NHS ester under conditions permitting the production of the 3'-O-Rox-t-Butyldithiomethyl-dATP.

Embodiment R54 A process for producing a 3'-O-Rox-PEG$_4$-t-Butyldithiomethyl-dATP, comprising:

a) reacting,
1) a N$^4$-Benzoyl-5'-O-tert-butyldimethylsilyl-2'-deoxyadenosine, and
2) acetic acid and acetic anhydride under conditions permitting the formation of a N$^4$-Benzoyl-3'-O-methylthiomethyl-5'-O-tert-butyldimethylsilyl-2'-deoxyadenosine;

b) contacting the N$^4$-Benzoyl-3'-O-methylthiomethyl-5'-O-tert-butyldimethylsilyl-2'-deoxyadenosine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

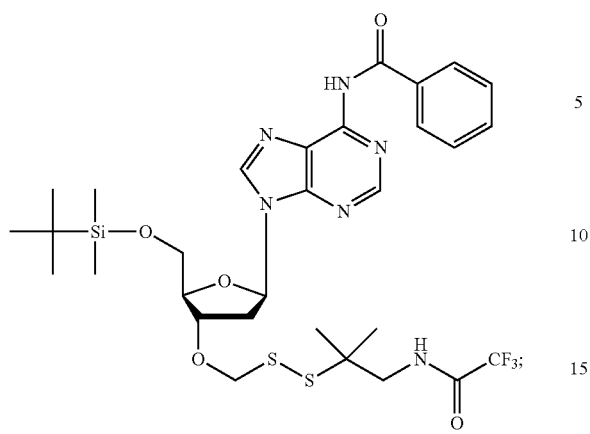

c) contacting the product of step b) with tetrabutylammonium fluoride THF solution under conditions permitting the production of a product having the structure:

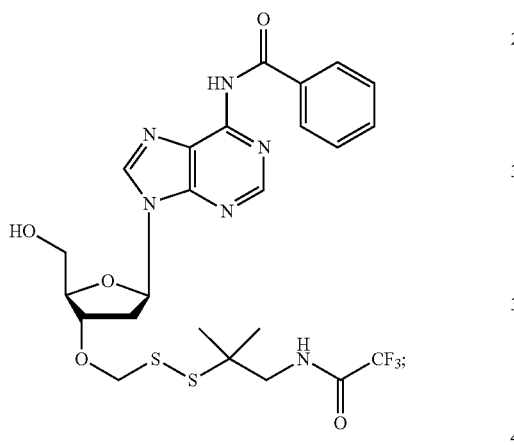

d) contacting product of step c) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dATP;
e) contacting the 3'-O—NH$_2$-t-Butyldithiomethyl-dATP produced in step d) with ROX-PEG$_4$-Acid, N,N-disuccinimidyl carbonate, and 4-dimethylaminopyridine under conditions permitting the production of the 3'-O-Rox-PEG$_4$t-Butyldithiomethyl-dATP.

Embodiment R55 A process for producing a 3'-O-Alexa488-t-Butyldithiomethyl-dCTP, comprising:
a) reacting
1) a N$^4$-Benzoyl-5'-O-tert-butyldimethylsilyl-2'-deoxycytidine, and
2) acetic acid and acetic anhydride
under conditions permitting the formation of a N$^4$-Benzoyl-3'-O-methylthiomethyl-5'-O-tert-butyldimethylsilyl-2'-deoxycytidine;
b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

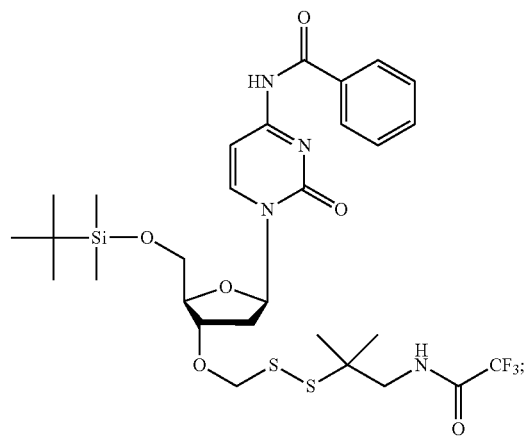

c) contacting the product of step b) with tetrabutylammonium fluoride THF solution under conditions permitting the production of a product having the structure:

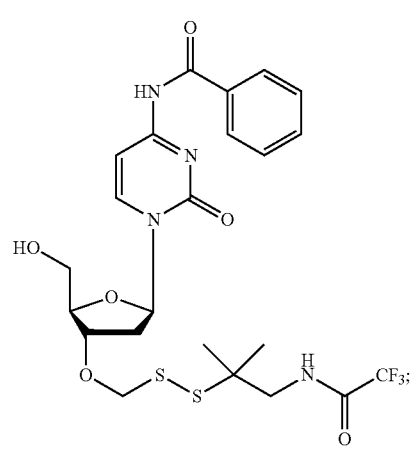

d) contacting product of step c) with tetrabutylammonium pyrophosphate, 1-chloro-4-H-1,3,2-benzodioxaphosphorin-4-one, tributylamine, and iodine solution under conditions permitting the production of a 3'-O—NH$_2$-t-Butyldithiomethyl-dCTP;
e) contacting the 3'-O—NH$_2$-t-Butyldithiomethyl-dCTP produced in step d) with Alexa488-NHS ester under conditions permitting the production of the 3'-O-Alexa488-t-Butyldithiomethyl-dCTP.

Embodiment R56 A process for producing a 3'-O-Alexa488-PEG$_4$-t-Butyldithiomethyl-dCTP, comprising:
a) reacting
1) a N-Benzoyl-5'-O-tert-butyldimethylsilyl-2'-deoxycytidine, and
2) acetic acid and acetic anhydride
under conditions permitting the formation of a N$^4$-Benzoyl-3'-O-methylthiomethyl-5'-O-tert-butyldimethylsilyl-2'-deoxycytidine;
b) contacting the N$^4$-Benzoyl-3'-O-methylthiomethyl-5'-O-tert-butyldimethylsilyl-2'-deoxycytidine produced in step a) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

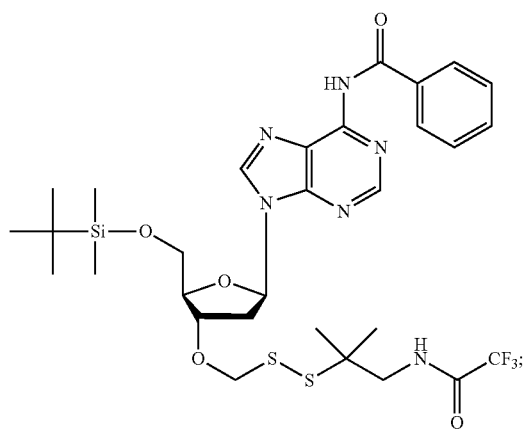

c) contacting the product of step b) with tetrabutylammonium fluoride THF solution under conditions permitting the production of a product having the structure:

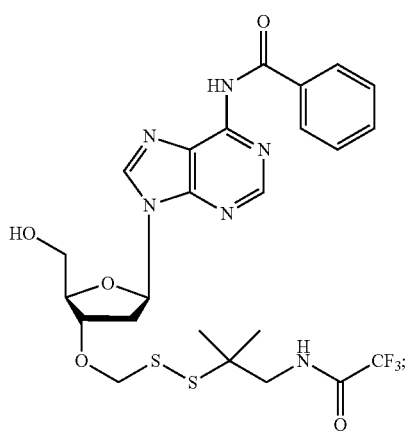

d) contacting product of step c) with tetrabutylammonium pyrophosphate, 1-chloro-4-H-1,3,2-benzodioxaphosphorin-4-one, tributylamine, and iodine solution under conditions permitting the production of a 3'-O—NH$_2$-t-Butyldithiomethyl-dCTP;

e) contacting the 3'-O—NH$_2$-t-Butyldithiomethyl-dCTP produced in step d) with Alexa488-PEG$_4$-NHS ester, N,N-disuccinimidyl carbonate, and 4-dimethylaminopyridine under conditions permitting the production of the 3'-O-Alexa488-PEG$_4$-t-Butyldithiomethyl-dCTP.

Embodiment R57 A process for producing a 3'-O-Cy5-t-Butyldithiomethyl-dGTP, comprising:

a) reacting
1) a 2'-deoxyguanosine, and
2) tert-butyldimethylsilyl chloride, imidazole, and N,N-dimethylformamide dimethyl acetal,
under conditions permitting the formation of a N$^4$-DMF-5'-O-tert-butyldimethylsilyl-2'-deoxyguanosine;
b) contacting the N$^4$-DMF-5'-O-tert-butyldimethylsilyl-2'-deoxyguanosine produced in step a) with acetic acid and acetic anhydride under conditions permitting the production of a product having the structure:

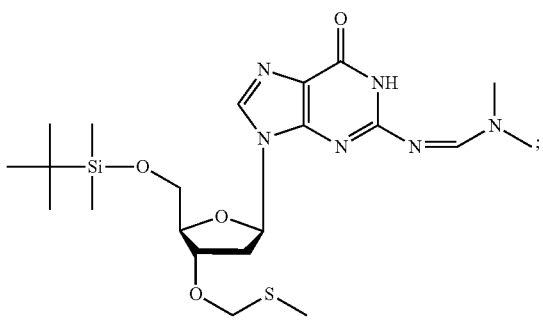

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

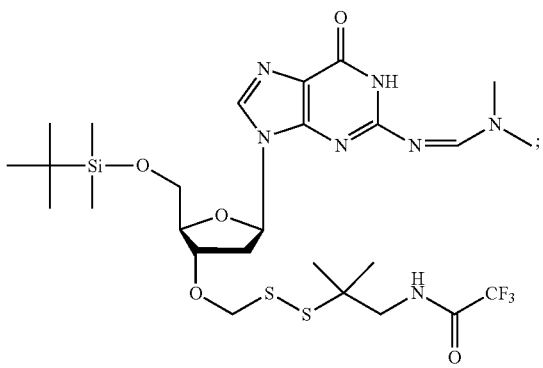

d) contacting the product of step c) with tetrabutylammonium fluoride THF solution under conditions permitting the production of a product having the structure:

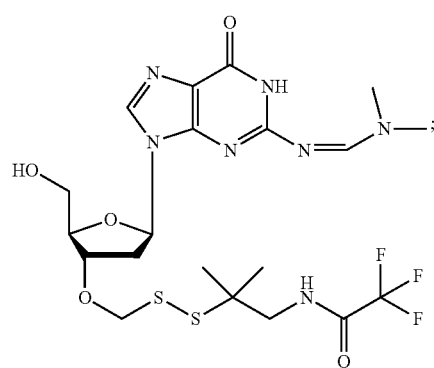

e) contacting product of step d) with tetrabutylammonium pyrophosphate, 1-chloro-4-H-1,3,2-benzodioxaphosphorin-4-one, tributylamine, and iodine solution under conditions permitting the production of 3'-O—NH$_2$-t-Butyldithiomethyl-dGTP;

f) contacting the 3'-O—NH$_2$-t-Butyldithiomethyl-dGTP produced in step e) with Cy5-NHS under conditions permitting the production of the 3'-O-Cy5-t-Butyldithiomethyl-dGTP.

Embodiment R58 A process for producing a 3'-O-Cy5-PEG$_4$-t-Butyldithiomethyl-dGTP, comprising:

a) reacting
  1) a 2'-deoxyguanosine, and
  2) tert-butyldimethylsilyl chloride, imidazole, and N,N-dimethylformamide dimethyl acetal,
  under conditions permitting the formation of a N⁴-DMF-5'-O-tert-butyldimethylsilyl-2'-deoxyguanosine;
b) contacting the N⁴-DMF-5'-O-tert-butyldimethylsilyl-2'-deoxyguanosine produced in step a) with acetic acid and acetic anhydride under conditions permitting the production of a product having the structure:

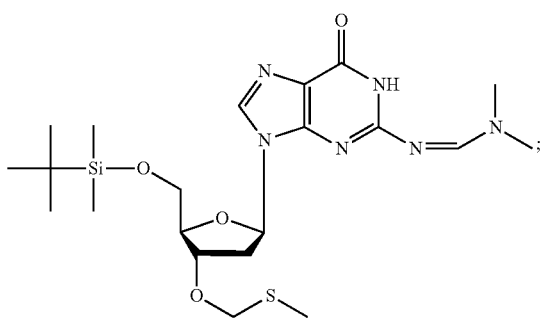

c) contacting the product of step b) with trimethylamine, molecular sieves, sufuryl chloride, p-toluenethiosulfonate, and 2,2,2,-trifluor-N-(2-mercapto-2-methylpropyl)acetamide under conditions permitting the production of a product having the structure:

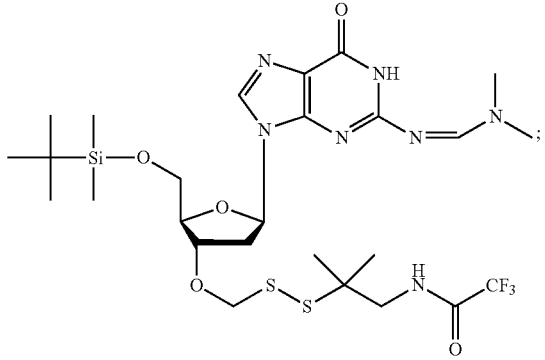

d) contacting the product of step c) with tetrabutylammonium fluoride THF solution under conditions permitting the production of a product having the structure:

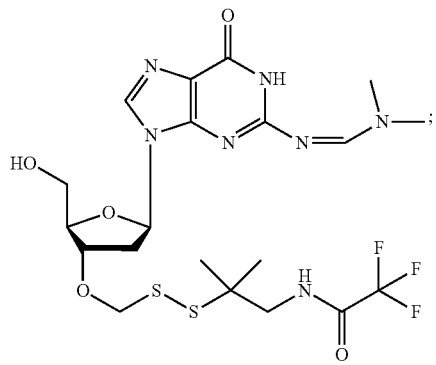

e) contacting product of step d) with tetrabutylammonium pyrophosphate, 1-chloro-4-H-1,3,2-benzodioxaphosphorin-4-one, tributylamine, and iodine solution under conditions permitting the production of 3'-O—NH₂-t-Butyldithiomethyl-dGTP;

f) contacting the 3'-O—NH₂-t-Butyldithiomethyl-dGTP produced in step e) with Cy5-PEG₄-NHS under conditions permitting the production of the 3'-O-Cy5-PEG₄-t-Butyldithiomethyl-dGTP.

Embodiment R59. A method for determining the nucleotide sequence of a single-stranded DNA, the method comprising:

a) contacting the single-stranded DNA having a primer hybridized to a portion thereof, with a nucleotide polymerase and a first type of nucleotide analogue under conditions permitting the nucleotide polymerase to catalyze incorporation of the nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the nucleotide analogue has the structure:

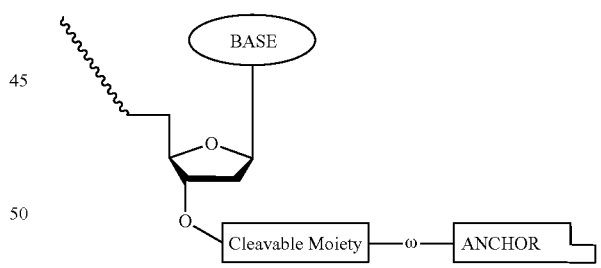

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein (ο represents a structure consisting of one or more atoms of which is covalently bound to both the cleavable t-butyldithiomethyl moiety and the anchor moiety, wherein the identity of the anchor moiety is predetermined and is correlated to the identity of the base, b) contacting the single-stranded DNA of step a) with a binding molecule complementary to the anchor moiety of the nucleotide analogue of step a), wherein the binding molecule has the structure:

wherein binder is a chemical group that orthogonally and rapidly reacts with the anchor moiety, thereby forming a conjugate of the binding molecule and the anchor moiety, and Label is a detectable label, c) removing any nucleotide analogue not incorporated into the primer in step a);

d) detecting the presence of any detectable label so as to thereby determine whether the nucleotide analogue of step a) was incorporated so as to thereby determine the identity of the complementary nucleotide residue in the single-stranded DNA, and wherein if the base of the nucleotide analogue a) is not complementary to the nucleotide residue of the single-stranded DNA which is immediately 5' to the nucleotide residue of the single-stranded DNA hybridized to the 3' terminal nucleotide residue of the primer, then iteratively repeating steps a) through c) with a second, third, and then fourth type of nucleotide analogue, wherein each different type of nucleotide analogue has a different base from each other type of nucleotide analogue, until the nucleotide analogue has a base that is complementary, e) cleaving the cleavable t-butyldithiomethyl moiety, so as to thereby create a 3'-OH; and f) iteratively performing steps a) through e) for each nucleotide residue of the single-stranded DNA to be sequenced so as to thereby determine the sequence of the single-stranded DNA.

Embodiment R60. The method of embodiment R59, wherein steps b) and c) can be performed simultaneously, or in the order step b) then step c) or in the order step c) then step b).

Embodiment R61. The method of embodiment R59 or embodiment R60, where the first, second, third, and fourth type of nucleotide analogue have different anchor moieties, and wherein each different anchor moiety is complementary to a different binding molecule.

Embodiment R62. The method of any one of embodiment R61, wherein the different binding molecules each have a different detectable label.

Embodiment R63. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein each type of nucleotide analogue has the structure:

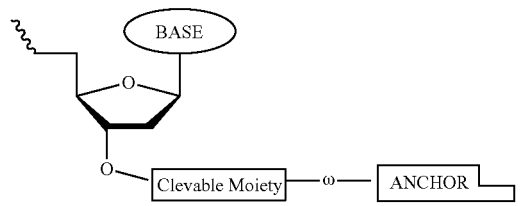

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of each type of nucleotide analogue is independently different from the base of the remaining three types of nucleotide analogue, wherein the anchor moiety of each type of nucleotide analogue is independently different from the anchor moiety of the remaining three types of nucleotide analogue, wherein the anchor moiety of each type of nucleotide analogue orthogonally and rapidly reacts with a different binding molecule from each of the remaining three types of nucleotide analogue;

b) contacting the single-stranded DNA of step a) with a first, second, third, and fourth type of binding molecule, under conditions permitting the anchor of the nucleotide analogue incorporated in step a) to orthogonally and rapidly react with a complementary binding molecule thereby forming a conjugate of the binding molecule and the anchor moiety, wherein the first, second, third, and fourth type of binding molecule each have the structure:

wherein binder is a small chemical group that orthogonally and rapidly reacts with an anchor moiety, and wherein Label is a predetermined detectable label correlated to the identity of the type of binding molecule, wherein the binder of each type of binding molecule is different from the binder of the remaining three types of binding molecule, wherein the first type of binding molecule and the first type of nucleotide analogue, the second type of binding molecule and second type of nucleotide analogue, the third type of binding molecule and third type of nucleotide analogue, and the fourth type of binding molecule and the fourth type of nucleotide analogue are respectively complementary and thereby orthogonally and rapidly react thereby forming a conjugate of an individual type of binding molecule with an individual type of nucleotide analogue;

c) determining the identity of the detectable label of the nucleotide analogue incorporated in step a) so as to thereby determine the identity of the incorporated nucleotide analogue and the identity of the complementary nucleotide residue in the single-stranded DNA;

d) cleaving the cleavable t-butyldithiomethyl moiety, so as to thereby create a 3'-OH; and e) iteratively performing steps a) through d) for each nucleotide residue of the single-stranded DNA to be sequenced so as to thereby determine the sequence of the single-stranded DNA.

Embodiment R64. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first and second types of nucleotide analogue have the structure:

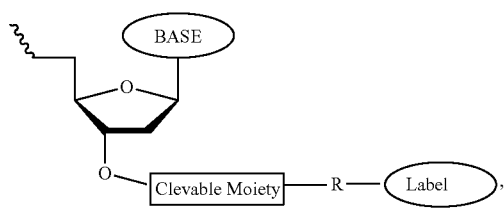

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the label of the first type of nucleotide analogue is different form the label of the second type of nucleotide analogue, wherein the base of each of the first and second type of nucleotide analogue is independently different from the base of each of the three remaining types of nucleotide analogue, wherein the third and fourth type of nucleotide analogue has the structure:

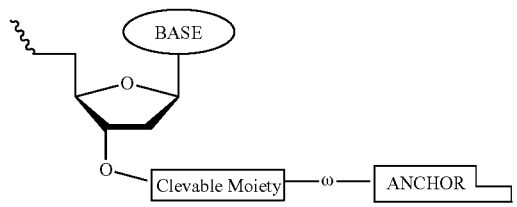

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ⍵ represents a structure consisting of one or more atoms of which is covalently bound to both the cleavable t-butyldithiomethyl moiety and the anchor moiety, wherein the base of the third and fourth type of nucleotide analogue is independently different from the base of each of the three remaining types of nucleotide analogue, wherein the anchor moiety of the third type of nucleotide analogue is different from the anchor moiety of the fourth type of nucleotide analogue;

b) removing any nucleotide analogues not incorporated in step a);

c) detecting the presence of either the detectable label of the first or second type of nucleotide analogue incorporated in step a) so as to thereby determine the identity of the incorporated nucleotide analogue and the identity of the complementary nucleotide residue in the single-stranded DNA, wherein if the base of the first and second type of nucleotide is not complementary, contacting the single-stranded DNA with a first and second type of binding molecule, wherein the first and second type of binding molecule have the structure:

wherein binder is a small chemical group that orthogonally and rapidly reacts with an anchor, and wherein Label is a predetermined detectable label correlated to the identity of the binding molecule, wherein the detectable label of the first type of binding molecule is the same as the detectable label of the first type of nucleotide analogue, wherein the detectable label of the second type of binding molecule is the same as the detectable label of the second type of nucleotide analogue, wherein the binder of the first type of binding molecule orthogonally and rapidly reacts with the anchor of the third type of nucleotide analogue, and wherein the second type of binding molecule orthogonally and rapidly reacts with the anchor of the fourth type of nucleotide analogue,

493 removing any unbound binding molecule, and detecting the presence of either the first or second binding molecule so as to thereby determine the identity of the nucleotide analogue incorporated in step a) and the identity of the complementary nucleotide residue in the single-stranded DNA;

d) cleaving the cleavable t-butyldithiomethyl moiety so as to thereby create a 3'-OH; and e) iteratively performing steps a) through d) for each nucleotide residue of the single-stranded DNA to be sequenced so as to thereby determine the sequence of the single-stranded DNA.

Embodiment R65. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the structure:

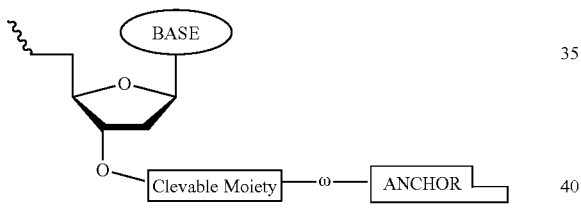

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

494

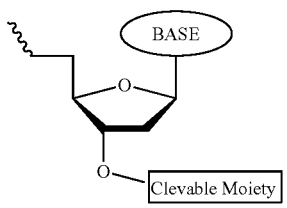

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) contacting the single-stranded DNA of step a) with a first, second, and third type of binding molecule, each type of binding molecule having the structure:

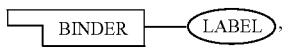

wherein binder is a small chemical group correlated to the identity of the type of binding molecule and that orthogonally and rapidly reacts with an anchor so as to form a conjugate, and wherein Label is a detectable label, wherein the binder of each type of binding molecule is different from the binder of the remaining two types of binding molecule, wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue;

c) removing any nucleotide analogues from step a) not incorporated into the primer;

d) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

e) if a detectable label is detected in step d), contacting the single-stranded DNA with a means of cleaving the detectable label and/or the binding molecule from the first type of nucleotide analogue;

f) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

g) if a detectable label is detected in step f), contacting the single-stranded DNA with a means of cleaving the detectable label and/or the binding molecule from the second type of nucleotide analogue;

h) detecting whether there is an absence of detectable label bound to the incorporated nucleotide of step a), thereby determining the identity of the incorporated nucleotide analogue, and thereby the identity of the complementary nucleotide residue in the single-stranded DNA;

i) cleaving the cleavable t-butyldithiomethyl moiety so as to thereby create a 3'-OH; and j) iteratively performing steps a) through i) for each nucleotide residue of the single-stranded DNA to be sequenced so as to thereby determine the sequence of the single-stranded DNA.

Embodiment R66. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first and second types of nucleotide analogue have the structure:

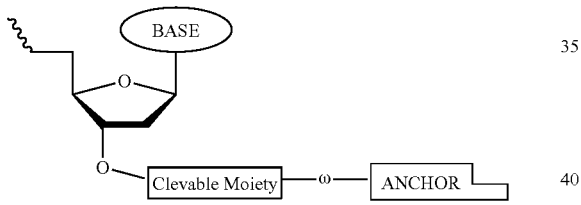

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein wo represents a structure consisting of one or more atoms of which is covalently bound to both the cleavable t-butyldithiomethyl moiety and the anchor moiety, wherein the base of the first and second type of nucleotide analogue is independently different from the base of each of the three remaining types of nucleotide analogue, wherein the anchor of the first type of nucleotide analogue is different from the anchor of the second type of nucleotide analogue, wherein the third type of nucleotide analogue has the structure:

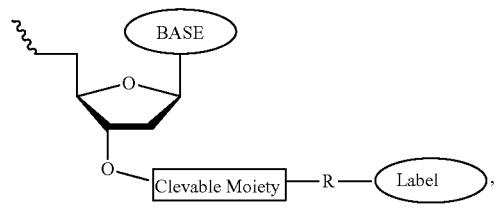

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the third type of nucleotide analogue is independently different from the base of each of the three remaining types of nucleotide analogue, wherein the fourth type of nucleotide analogue has the structure:

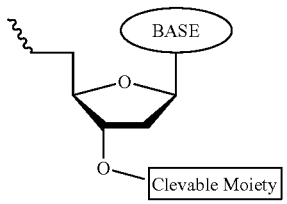

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing any nucleotide analogues from step a) not incorporated into the primer;

c) detecting whether there is a presence of detectable label bound to the incorporated nucleotide of step a), thereby determining that identity of the incorporated nucleotide is of the third type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first and second type of binding molecule, wherein the first and second type of binding molecule have the structure:

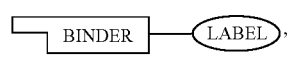

wherein binder is a small chemical group correlated to the identity of the type of binding molecule and that orthogonally and rapidly reacts with an anchor, and wherein Label is a detectable label, wherein the binder of each type of binding molecule is different one another, wherein the first type of binding molecule and the first type of nucleotide analogue, and the second type of binding molecule and second type of nucleotide analogue, respectively complementary and thereby orthogonally and rapidly react thereby binding each individual type of binding molecule with an individual type of nucleotide analogue so as to form a conjugate;

e) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

f) if a detectable label is detected in step e), contacting the single-stranded DNA with a means of cleaving the detectable label and/or the binding molecule from the first type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

Embodiment R67. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third type of nucleotide analogue have the

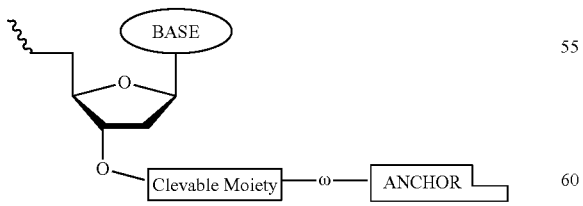

wherein base is any one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein Anchor is an anchor moiety that is a small chemical moiety that orthogonally and rapidly reacts with a complementary binding molecule thereby forming a conjugate of the anchor moiety and binding molecule, wherein ω represents a structure consisting of one or more atoms of which is covalently bound to both the cleavable t-butyldithiomethyl moiety and the anchor moiety, wherein the base of the first, second, and third type of nucleotide analogue is independently different from the base of each of the three remaining types of nucleotide analogue, wherein the first, second, and third type of nucleotide analogue each independently have a different anchor from one another, wherein the fourth type of nucleotide analogue has the structure:

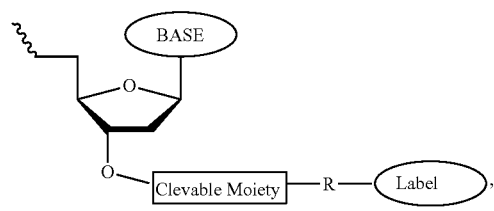

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the fourth type of nucleotide analogue is independently different from the base of each of the three remaining types of nucleotide analogue;

b) removing all unincorporated nucleotide analogues from step a);

c) detecting whether there is a presence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if an absence of detectable label bound to the incorporated nucleotide of step a) is detected in step c), contacting the single-stranded DNA with a first, second, and third type of binding molecule, wherein the first, second, and third type of binding molecule have the structure:

wherein binder is a small chemical group correlated to the identity of the type of binding molecule and that orthogonally and rapidly reacts with an anchor moiety so as to form a conjugate, and wherein Label is a detectable label, wherein the binder of each type of binding molecule is different from one another, wherein the first type of binding molecule and wherein the first type of binding molecule and the first type of nucleotide analogue, the second type of binding molecule and second type of nucleotide analogue, and third type of binding molecule and third type of nucleotide analogue are respectively complementary and thereby orthogonally and rapidly react thereby binding each individual type of binding molecule with an individual type of nucleotide analogue so as to form a conjugate;

e) detecting whether there is a presence of detectable label bound to the incorporated nucleotide of step a);

f) contacting the single-stranded DNA with a means of cleaving the detectable label and/or the binding molecule from the first type of nucleotide analogue;

g) detecting whether there is an absence of detectable label bound to the incorporated nucleotide of step a), thereby determining that the identity of the incorporated nucleotide is of the first type of nucleotide analogue, and thereby the identity of the complementary nucleotide residue in the single-stranded DNA;

h) if a detectable label is detected in step f), contacting the single-stranded DNA with a means of cleaving the detectable label and/or the binding molecule from the second type of nucleotide analogue;

i) detecting whether there is an absence of detectable label bound to the incorporated nucleotide of step a), thereby determining the identity of the incorporated nucleotide analogue, and thereby the identity of the complementary nucleotide residue in the single-stranded DNA;

j) cleaving the cleavable t-butyldithiomethyl moiety so as to thereby create a 3'-OH; and k) iteratively performing steps a) through j) for each nucleotide residue of the single-stranded DNA to be sequenced so as to thereby determine the sequence of the single-stranded DNA.

Embodiment R68. A method for determining the nucleotide sequence of a single-stranded DNA, the method comprising:

a) contacting the single-stranded DNA having a primer hybridized to a portion thereof, with a nucleotide polymerase and a first, second, third, and fourth type of nucleotide analogue under conditions permitting the nucleotide polymerase to catalyze incorporation of a nucleotide analogue into the primer if the nucleotide analogue is complementary to a nucleotide residue of the single-stranded DNA that is immediately 5' to a nucleotide residue of the single-stranded DNA hybridized to the 3' terminal nucleotide residue of the primer, so as to form a DNA extension product, wherein the first, second, and third types of nucleotide analogue have the structure:

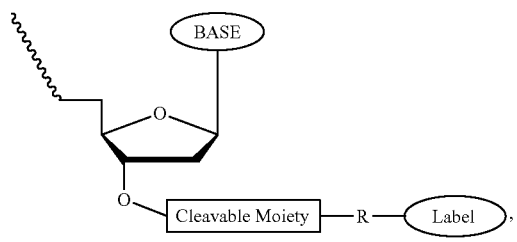

wherein base is one of adenine, guanine, thymine, cytosine, uracil, or an analogue thereof, wherein Linker is a cleavable t-butyldithiomethyl moiety that when bound to the 3'-O prevents a nucleotide polymerase from catalyzing a polymerase reaction with the 3'-O of the nucleotide analogue, wherein Label is a predetermined detectable label, and wherein R represents a structure consisting of one or more atoms of which is covalently bound to both the cleavable t-butyldithiomethyl moiety and the detectable label, wherein the base of the first, second, and third type of nucleotide analogue is independently different from the base of each of the three remaining types of nucleotide analogue, wherein the fourth type of nucleotide analogue has the structure:

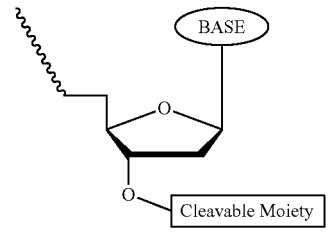

wherein base is one of adenine, guanine, thymine, cytosine, uracil, or an analogue thereof, wherein Cleavable Moiety is a cleavable t-butyldithiomethyl moiety that when bound to the 3'-O prevents a nucleotide polymerase from catalyzing a polymerase reaction with the 3'-O of the nucleotide analogue, wherein the base of the fourth type of nucleotide analogue is independently different from the base of each of the three remaining types of nucleotide analogue;

b) removing all unincorporated nucleotide analogues from step a);

c) detecting whether there is an absence of detectable label bound to the incorporated nucleotide of step a), thereby determining that identity of the incorporated nucleotide is of the fourth type of nucleotide analogue, and thereby the identity of the complementary nucleotide residue in the single-stranded DNA;

d) if a detectable label is detected in step c), contacting the single-stranded DNA with a means of cleaving the detectable label from the first type of nucleotide analogue;

e) detecting whether there is an absence of detectable label bound to the incorporated nucleotide of step a), thereby determining that identity of the incorporated nucleotide is of the first type of nucleotide analogue, and thereby the identity of the complementary nucleotide residue in the single-stranded DNA;

f) if a detectable label is detected in step e), contacting the single-stranded DNA with a means of cleaving the detectable label from the second type of nucleotide analogue;

g) detecting whether there is an absence of detectable label bound to the incorporated nucleotide of step a), thereby determining the identity of the incorporated nucleotide analogue, and thereby the identity of the complementary nucleotide residue in the single-stranded DNA;

h) cleaving the cleavable t-butyldithiomethyl moiety so as to thereby create a 3'-OH; and i) iteratively performing steps a) through h) for each nucleotide residue of the single-stranded DNA to be sequenced so as to thereby determine the sequence of the single-stranded DNA.

Embodiment R69 The method of any one of embodiments R59-R67, wherein the anchor of each type of nucleotide analogue having an anchor that forms a conjugate with a complementary binding molecule, each individually has the structure:

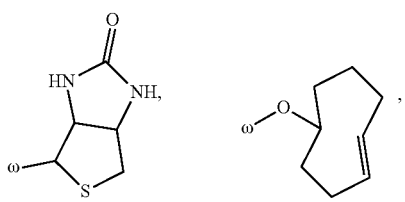

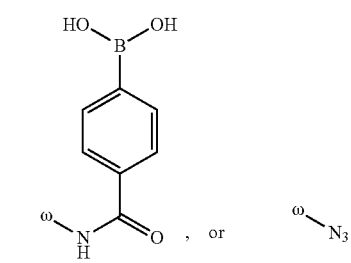

wherein ω represents one or more atoms through which a covalent connection is established to the cleavable t-butyldithiomethyl moiety.

Embodiment R70 The method of embodiment R69, wherein the detectable label of the complementary binding molecule is selected from the group consisting of one or more dyes, fluorophores, combinatorial fluorescence energy transfer tags, chemiluminescent compounds, chromophores, mass tags, electrophores, mononucleotides, oligonucleotides, or combinations thereof.

Embodiment R71. The method of embodiment R70, wherein the detectable label of the complementary binding molecule comprises one or more fluorescence energy transfer tags.

Embodiment R72. The method of embodiment R71, wherein the complementary binding molecule further comprises one or more FRET cassettes.

Embodiment R73. The method of embodiment R72, wherein the FRET cassettes comprise one or more dSpacer monomers.

Embodiment R74. The method of embodiment R73, wherein the complementary binding molecule has the structure:

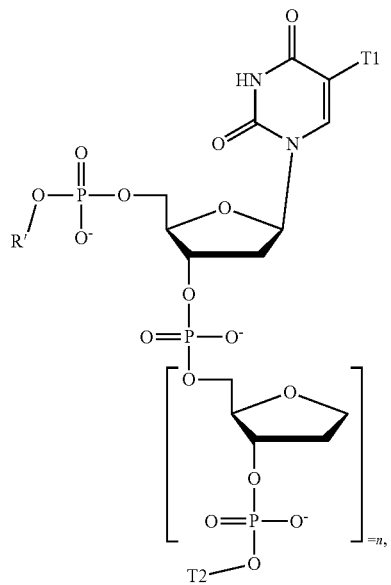

wherein T1 is a point of attachment for one or more fluorescent energy donor or acceptor, and T2 is a point of attachment for one or more of the complementary energy donor or acceptor to that in T1, wherein n is an integer between 1 and 20, and R represents the point of attachment to the binder of the binding molecule.

Embodiment R75. The method of embodiment R69, wherein the detectable label of the complementary binding molecule is one or more fluorophore.

Embodiment R76. The method of embodiment R75, wherein the fluorophore of the detectable label of the complementary binding molecule is selected from the group consisting of BodipyFL, R6G, ROX, Cy5, and Alexa488.

Embodiment R77. The method of any one of embodiments R69-R76, wherein the binder of the complementary binding molecule of each type of nucleotide analogue has an anchor comprising:

a) a compound comprising streptavidin having the structure:

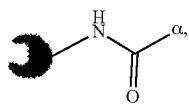

or b) a compound comprising the structure:

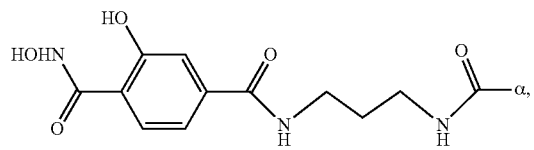

-continued

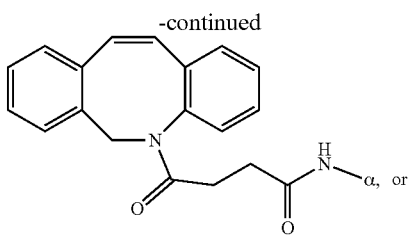

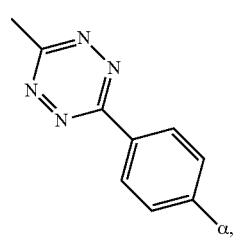

wherein α is one or more atoms through which a covalent connection is established to a detectable label.

Embodiment R78 The method of embodiment R77, wherein one type of nucleotide analogue has an anchor having the structure:

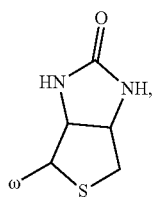

wherein ω represents one or more atoms through which a covalent connection is established to the cleavable t-butyldithiomethyl moiety, and the anchor orthogonally and rapidly reacts with a binder of a complimentary binding molecule, wherein said binder comprises streptavidin, and has the structure:

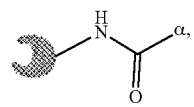

wherein α is one or more atoms through which a covalent connection is established to a detectable label, and thereby forms a conjugate having the structure:

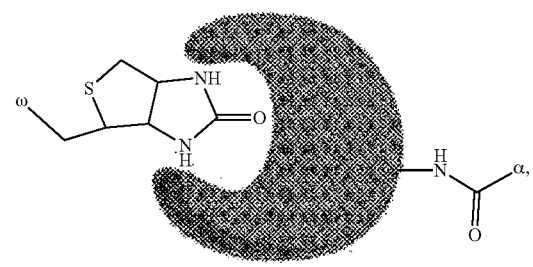

wherein α is one or more atoms through which a covalent connection is established to detectable label, and wherein ω is one or more atoms through which a covalent connection is established to the cleavable t-butyldithiomethyl moiety.

Embodiment R79. The method of embodiment R78, wherein the label is cleaved from the conjugate comprising the type of nucleotide analogue and binding molecule with citric acid/Na$_2$HPO$_4$.

Embodiment R80. The method of embodiment R78 or R79, wherein the type of nucleotide analogue has the structure:

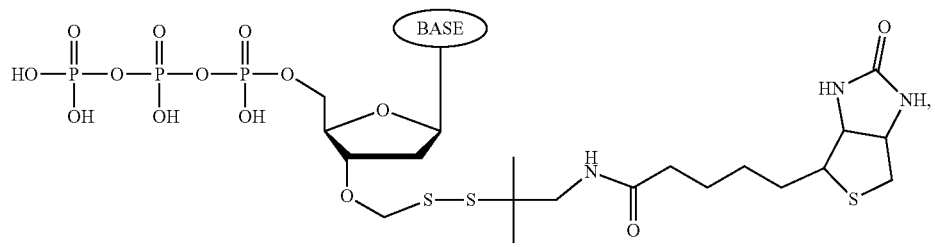 [SMILES: C[C@H]1C[C@@H](OCSSC(C)(C)CNC(=O)CCCCC2SCC3NC(=O)NC32)[C@@H](COP(=O)(O)OP(=O)(O)OP(=O)(O)O)O1]

wherein base is one of adenine, guanine, thymine, cytosine, uracil, or an analogue thereof.

Embodiment R81. The method of any one of embodiments R78-R80, wherein the complementary binding molecule comprises streptavidin, and wherein the complementary binding molecule has the structure:

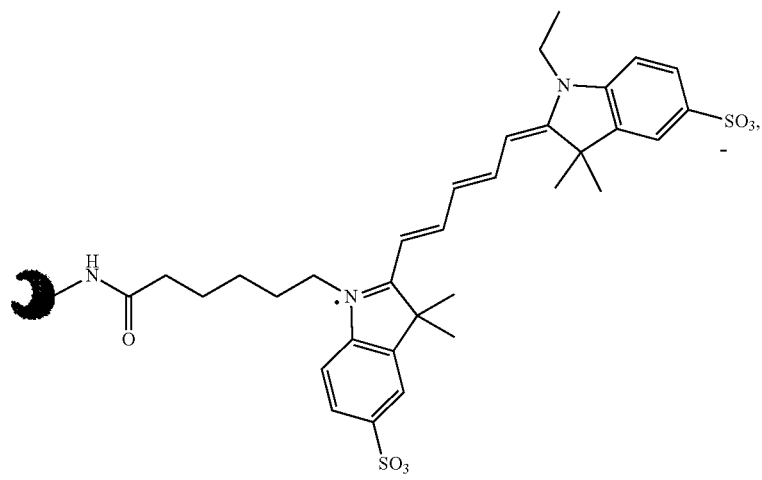

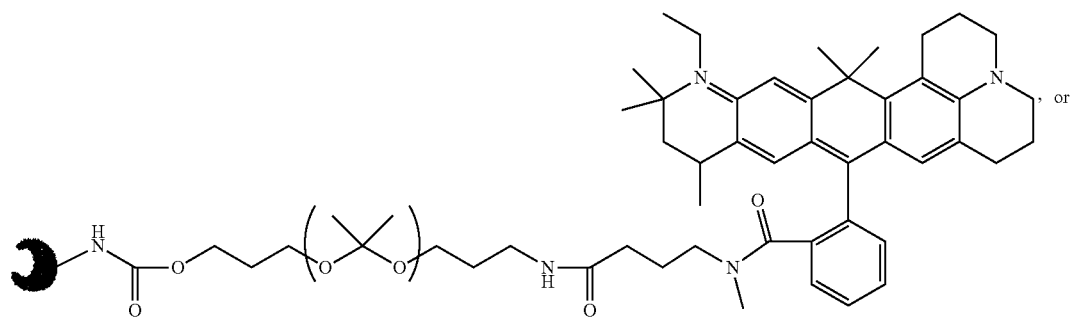

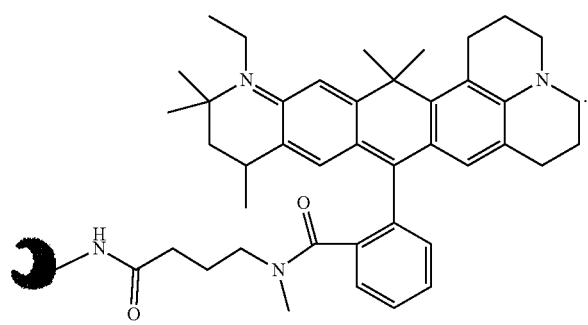

Embodiment R82 The method of embodiment R77, wherein one type of nucleotide analogue has an anchor moiety having the structure:

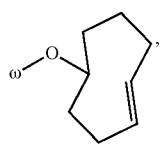

wherein ω represents one or more atoms through which a covalent connection is established to the cleavable t-butyldithiomethyl moiety, and the anchor orthogonally and rapidly reacts with a binder of a complimentary binding molecule, wherein said binder has the structure:

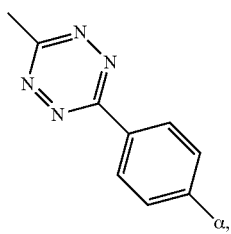

wherein α is one or more atoms through which a covalent connection is established to a detectable label, and
thereby forms a conjugate having the structure:

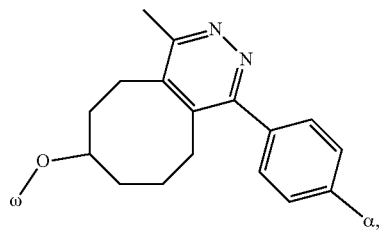

wherein α is one or more atoms through which a covalent connection is established to detectable label, and wherein ω is one or more atoms through which a covalent connection is established to the cleavable t-butyldithiomethyl moiety.

Embodiment R83. The method of embodiment R82, wherein the label is cleaved from the conjugate comprising the type of nucleotide analogue and binding molecule with $Na_2S_2O_4/H_2O$.

Embodiment R84. The method of embodiment R82 or R83, wherein the type of nucleotide analogue has the structure:

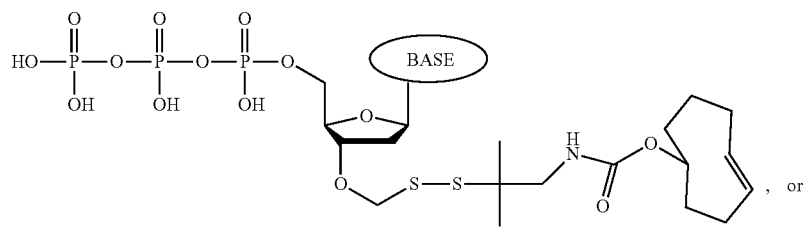

, or

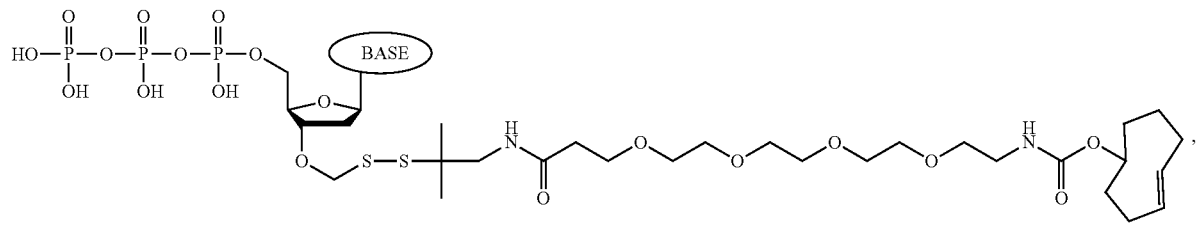

, wherein base is one of adenine, guanine, thymine, cytosine, uracil, or an analogue thereof.

Embodiment R85. The method of any one of embodiments R82-R84, wherein the complementary binding molecule has the structure:

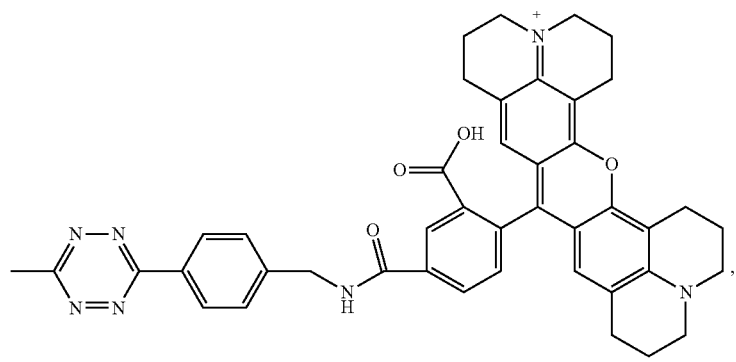

,

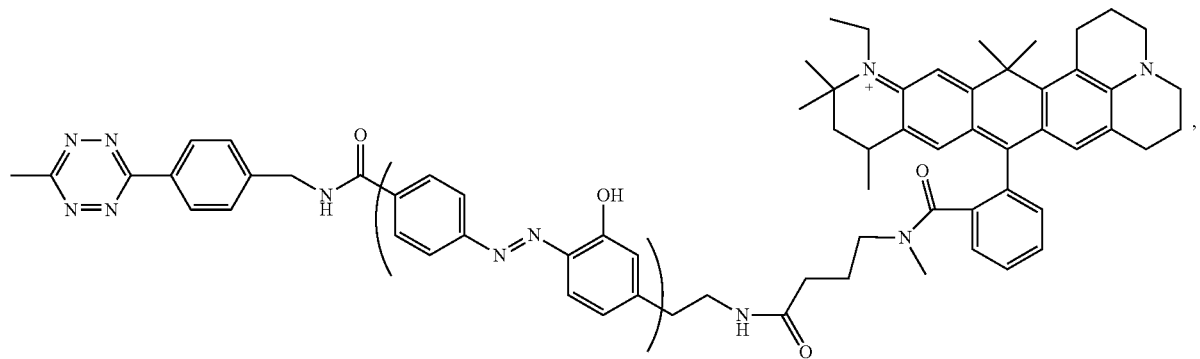
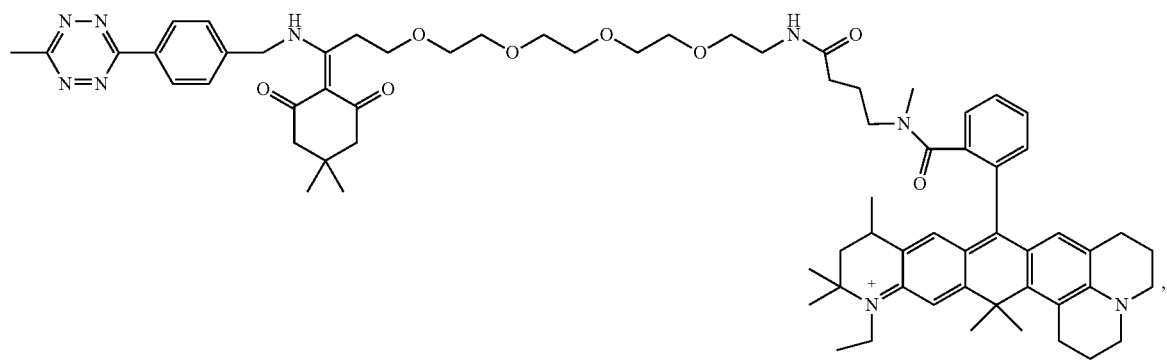
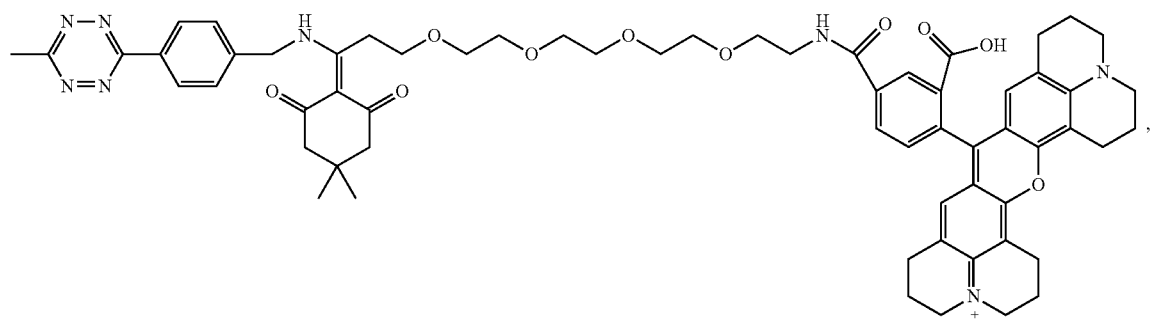
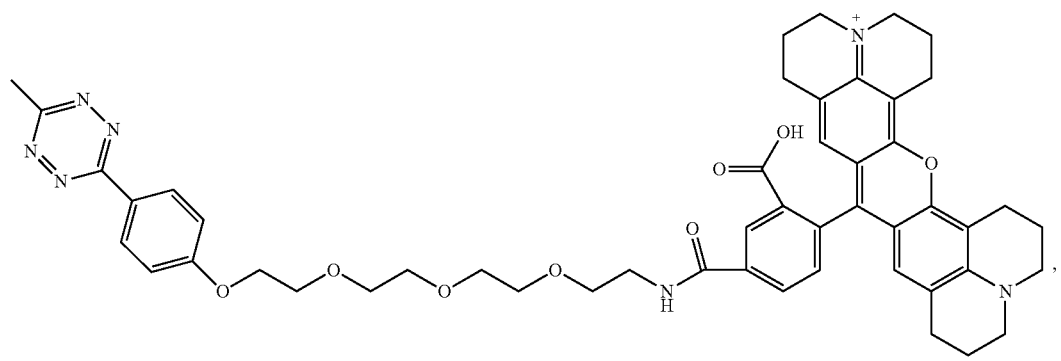

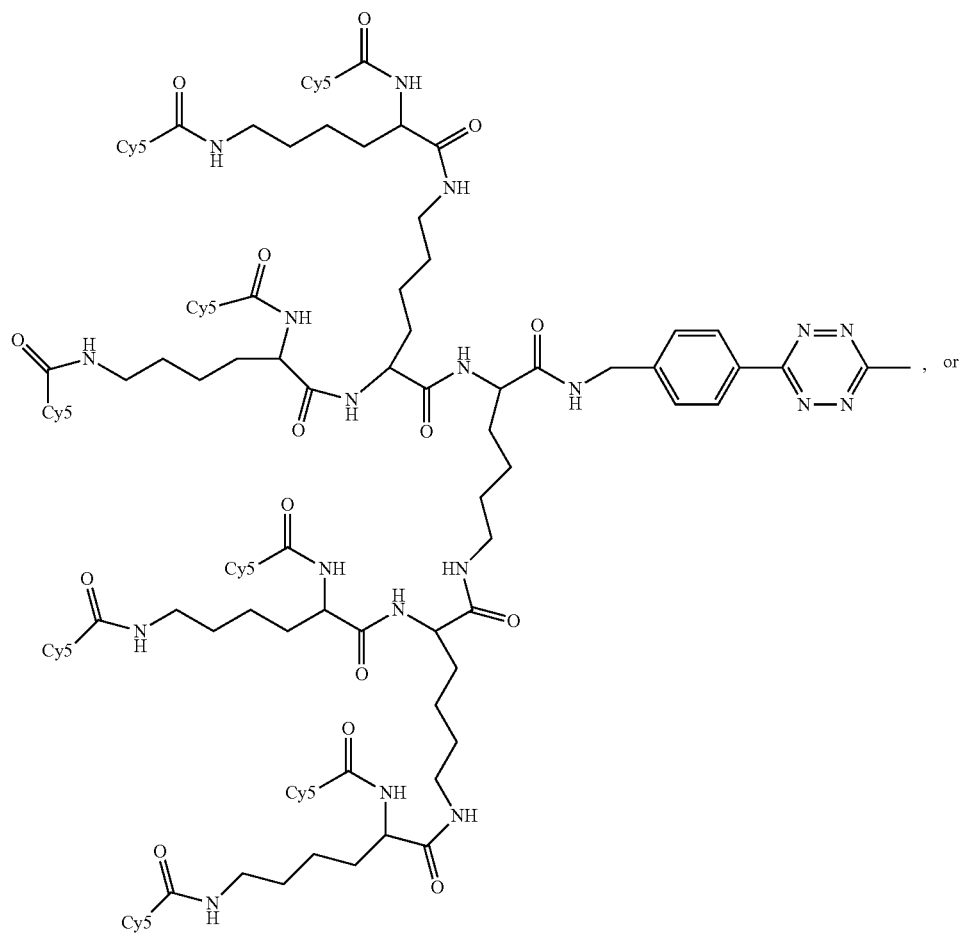
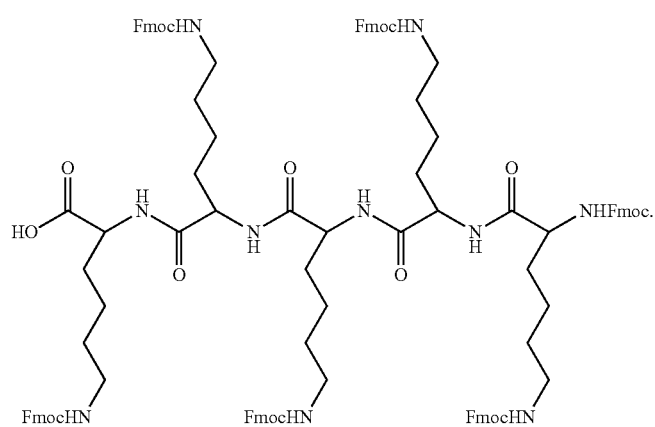

Embodiment R86. The method of embodiment R77, wherein one type of nucleotide analogue has an anchor moiety having the structure

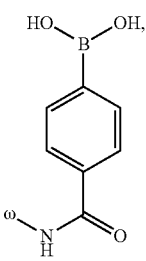

wherein ω represents one or more atoms through which a covalent connection is established to the cleavable t-butyldithiomethyl moiety, and
the anchor orthogonally and rapidly reacts with a binder of a complimentary binding molecule, wherein said binder has the structure:

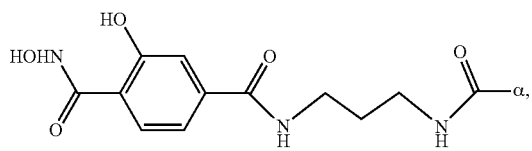

wherein α is one or more atoms through which a covalent connection is established to a detectable label, and thereby forms a conjugate having the structure:

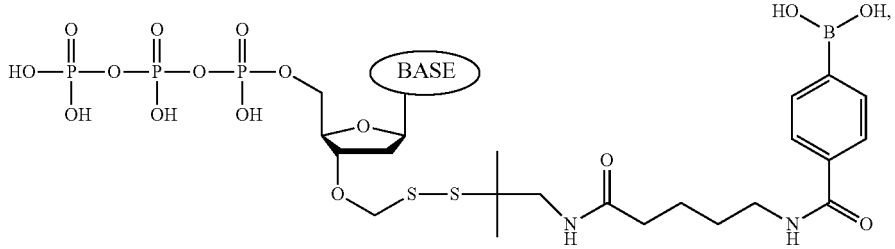

wherein α is one or more atoms through which a covalent connection is established to detectable label, and wherein ω is one or more atoms through which a covalent connection is established to the cleavable t-butyldithiomethyl moiety.

Embodiment R87. The method of embodiment R86, wherein the type of nucleotide analogue has the structure:

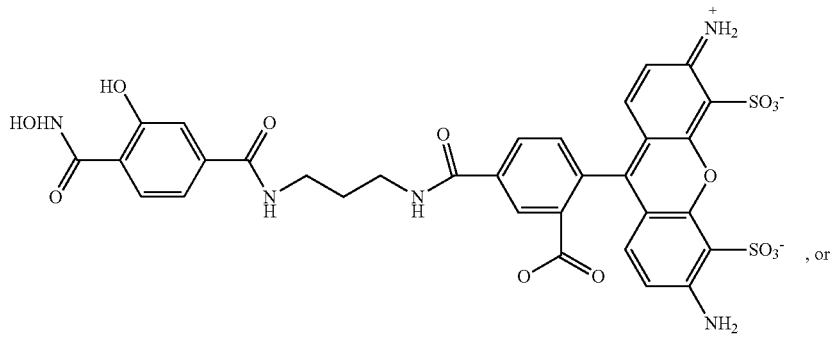

wherein base is one of adenine, guanine, thymine, cytosine, uracil, or an analogue thereof.

Embodiment R88. The method of embodiment R86 or R87, wherein the complementary binding molecule has the structure:

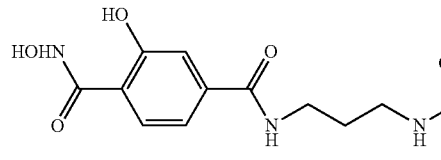
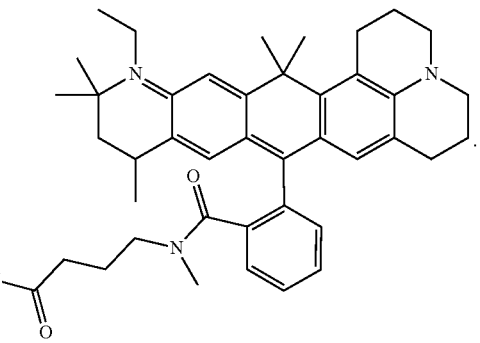

Embodiment R89. The method of embodiment R77, wherein one type of nucleotide analogue has an anchor having the structure:

wherein ω represents one or more atoms through which a covalent connection is established to the cleavable t-butyldithiomethyl moiety, and the anchor orthogonally and rapidly reacts with a binder of a complimentary binding molecule, wherein said binder has the structure:

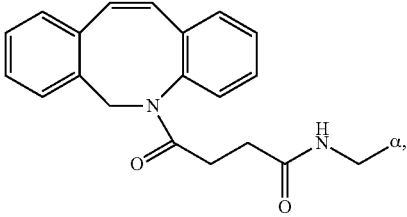

wherein α is one or more atoms through which a covalent connection is established to a detectable label, and thereby forms a conjugate having the structure:

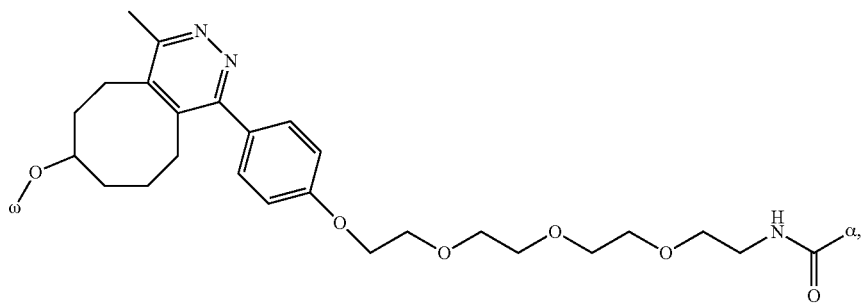

wherein α is one or more atoms through which a covalent connection is established to detectable label, and wherein ω is one or more atoms through which a covalent connection is established to the cleavable t-butyldithiomethyl moiety.

Embodiment R90. The method of embodiment R89, wherein the label is cleaved from the conjugate comprising the type of nucleotide analogue and binding molecule with citric acid/$Na_2HPO_4$.

Embodiment R91. The method of embodiment R89 or R90, wherein the type of nucleotide analogue has the structure:

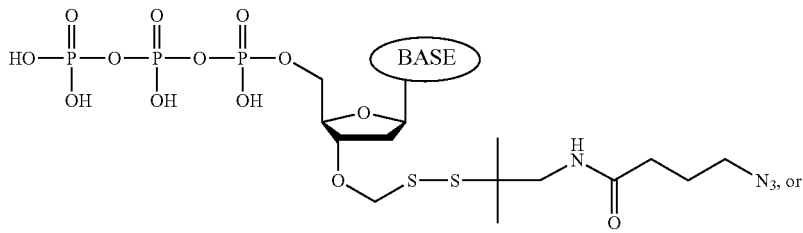

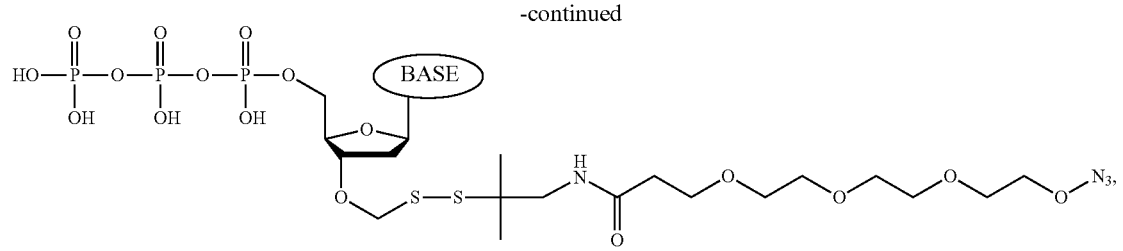
wherein base is one of adenine, guanine, thymine, cytosine, uracil, or a derivative thereof.
Embodiment R92. The method of any one of embodiments R89-R91, wherein the complementary binding molecule has the structure:
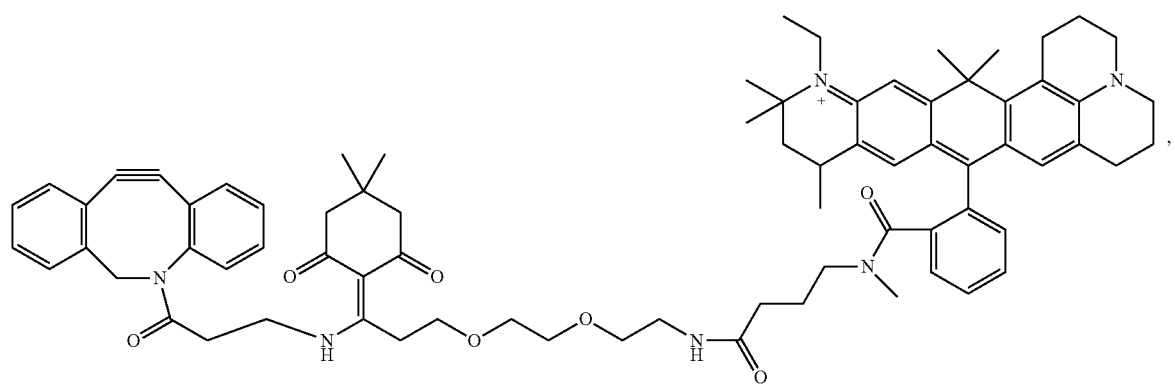
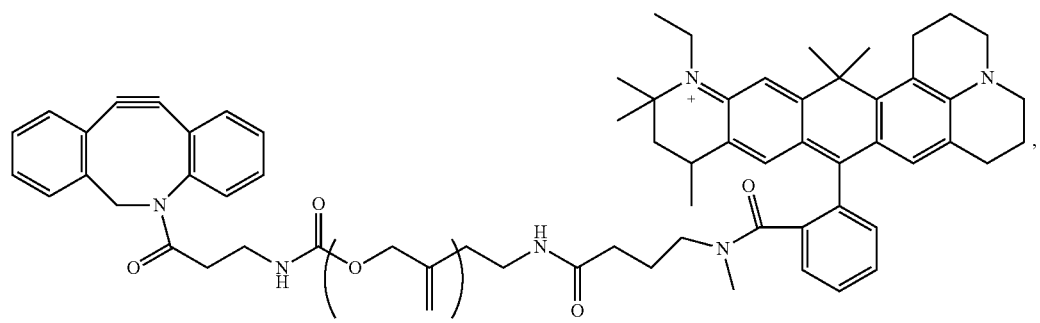
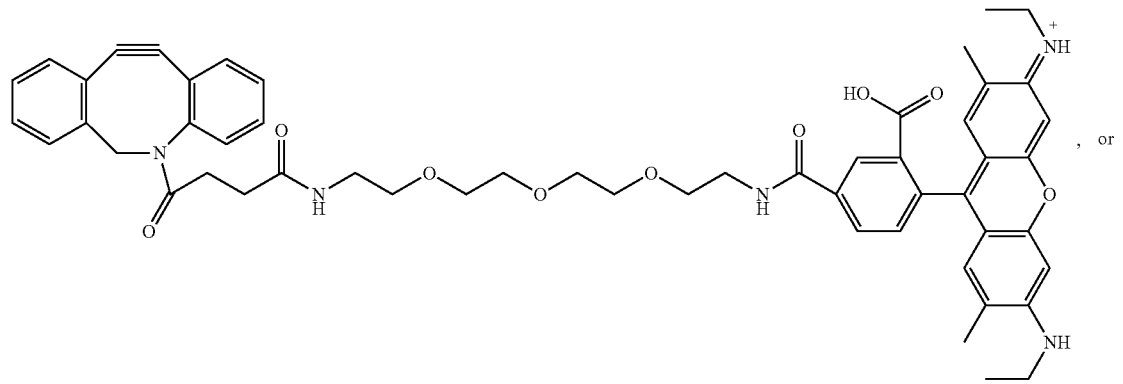

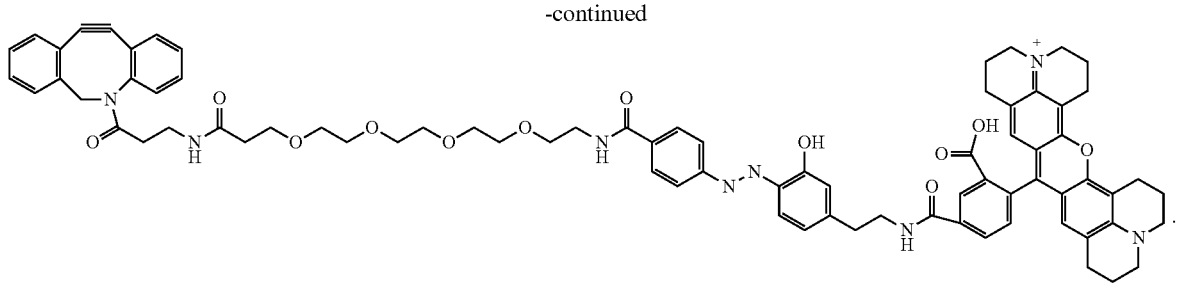

Embodiment R93. The method of any one of embodiments R58-R92, wherein the cleavable t-butyldithiomethyl moiety, has the structure:

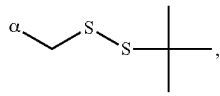

wherein α represents the point of connection to the 3'-oxygen.

Embodiment R94. The method of embodiment R93, wherein the cleavable t-butyldithiomethyl moiety has the structure:

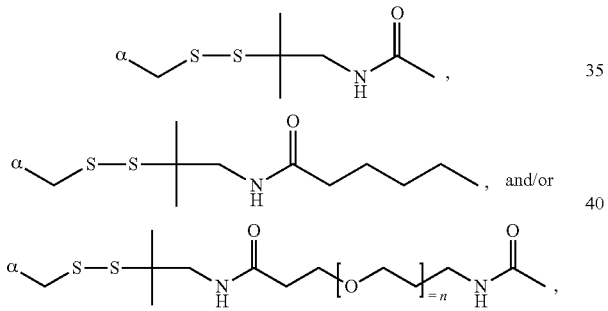

wherein α represents the point of connection to the 3'-oxygen; and wherein n is an integer which may be 1, 2, 3, 4, or 5.

Embodiment R95. The method of any one of embodiments R65-R66, or R68, wherein the fourth type of nucleotide analogue has the structure:

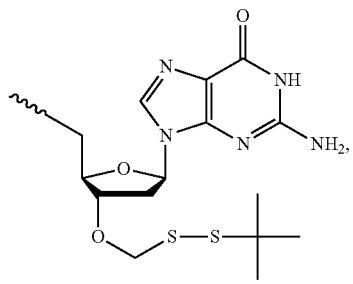

Embodiment R96. The method of any one of embodiments R68-R95, wherein the cleavable t-butyldithiomethyl moiety may be cleaved by a water soluble phosphine, thereby resulting in a 3'-OH.

Embodiment R97. The method of embodiment R96, wherein the water soluble phosphine is tris-(2-carboxyethyl)phosphine (TCEP) or tris(hydroxypropyl)phosphine (THP).

Embodiment R98. A method for determining the identity of a nucleotide at a predetermined position in a nucleic acid of interest, comprising:
  a) providing
    1) the nucleic acid of interest,
    2) a nucleic acid polymerase,
    3) a primer capable of hybridizing to said nucleic acid immediately 3' of such predetermined position,
    4) four different nucleotide analogues of embodiment 9, each of which consists of one of adenine or an analogue of adenine, guanine or an analogue of guanine, cytosine or an analogue of cytosine, thiamine or an analogue of thiamine, and a unique detectable label;

b) incorporating one of said nucleotide analogues onto the end of said primer to form an extension strand;

c) detecting the unique detectable label of the incorporated nucleotide analogue so as to thereby identify the incorporated nucleotide analogue on the end of said extension strand; and d) based on the identity of the incorporated nucleotide, determining the identity of the nucleotide at the predetermined position.

Embodiment R99 The method of embodiment R98 further comprising, treating the extension strand of step (b) so as to cleave the t-butyldithiomethyl moiety bound to the 3'-oxygen of the sugar and so as to produce a 3'-OH on the sugar and for producing an extension, remove the label from the extension strand to which another nucleotide analogue may be added.

Embodiment R100 The method of embodiment R99, wherein treatment comprises contacting the extension strand with tris-(2-carboxyethyl)phosphine (TCEP) or tris(hydroxypropyl)phosphine (THP).

Embodiment R101. The method of any one of embodiments R98-R100, wherein each nucleotide analogue is a nucleotide triphosphate, a nucleotide tetraphosphate, a nucleotide pentaphosphate, or a nucleotide hexaphosphate.

Embodiment R102. The method of any one of embodiments R98-R101, wherein the nucleotide analogues comprise a deoxyribose.

Embodiment R103. The method embodiment R102, wherein the polymerase is a DNA polymerase and the nucleic acid is DNA.

Embodiment R104. The method of any one of embodiments R98-R101, wherein the nucleotide analogues comprise a ribose.

Embodiment R105. The method of embodiment R104, wherein the polymerase is a reverse transcriptase and the nucleic acid is RNA.

Embodiment R106. The method of embodiment R102, wherein the polymerase is a DNA-based RNA polymerase and the nucleic acid is DNA.

Embodiment R107. The method of embodiment R104, wherein the polymerase is an RNA-based RNA polymerase and the nucleic acid is RNA.

Embodiment R108. The method of any one of embodiments R98-R108, wherein the t-Butyldithiomethyl linker has the structure:

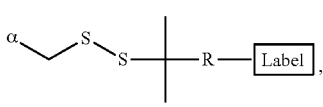

wherein α represents the point of connection to the 3'-oxygen;

wherein R represents one or more atoms through which a covalent connection is established to the detectable label; and wherein Label is the detectable label.

Embodiment R109. The method of any one of embodiments R98-R108, wherein the t-Butyldithiomethyl linker has the structure:

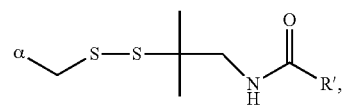

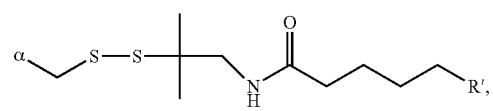

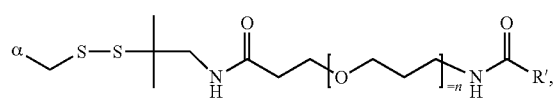

wherein α represents the point of connection to the 3'-oxygen;

wherein n is 1, 2, 3, 4, or 5; and wherein R' represents one or more atoms through which a covalent connection is established to the detectable label.

Embodiment R110. The method of any one of embodiments R98-R109, wherein the detectable label is selected from the group consisting of a dye, a fluorophore, a combinatorial fluorescence energy transfer tag, a chemiluminescent compound, a chromophore, a mass tag, an electrophore, a mononucleotide, an oligonucleotide, or a combination thereof.

Embodiment R111. The method of embodiment R110, wherein the detectable label is a fluorophore.

Embodiment R112. The method of embodiment R112, wherein the fluorophore is selected from the group consisting of BodipyFL, R6G, ROX, Cy5, and Alexa488.

Embodiment R113. The method of any one of embodiments R98-R112, wherein each nucleotide analog is selected from the group consisting of 3'-O-Alexa488-t-Butyldithiomethyl-dCTP, 3'-O-Cy5-t-Butyldithiomethyl-dGTP, 3'-O-Rox-t-Butyldithiomethyl-dATP, 3'-O-RG6-t-Butyldithiomethyl-dTTP, 3'-O-Alexa488-PEG$_4$-t-Butyldithiomethyl-dCTP, 3'-O-RG6-PEG$_4$-t-Butyldithiomethyl-dTTP, 3'-O-Rox-PEG$_4$-t-Butyldithiomethyl-dATP, 3'-O-Cy5-PEG$_4$-t-Butyldithiomethyl-dGTP.

Embodiment R114. The method of any one of embodiments R98-R110, wherein the structure of each labeled nucleotide analog is selected from:

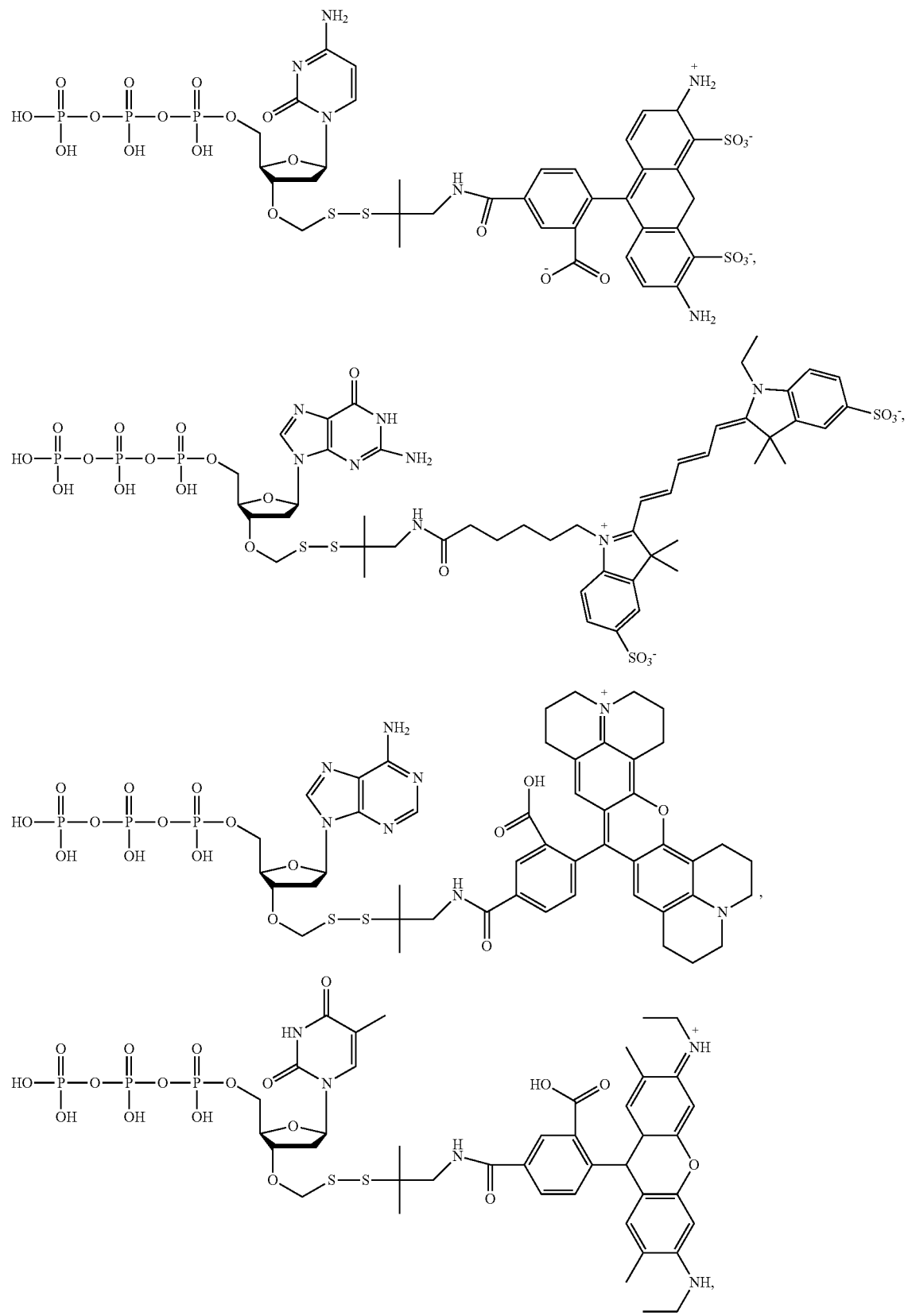

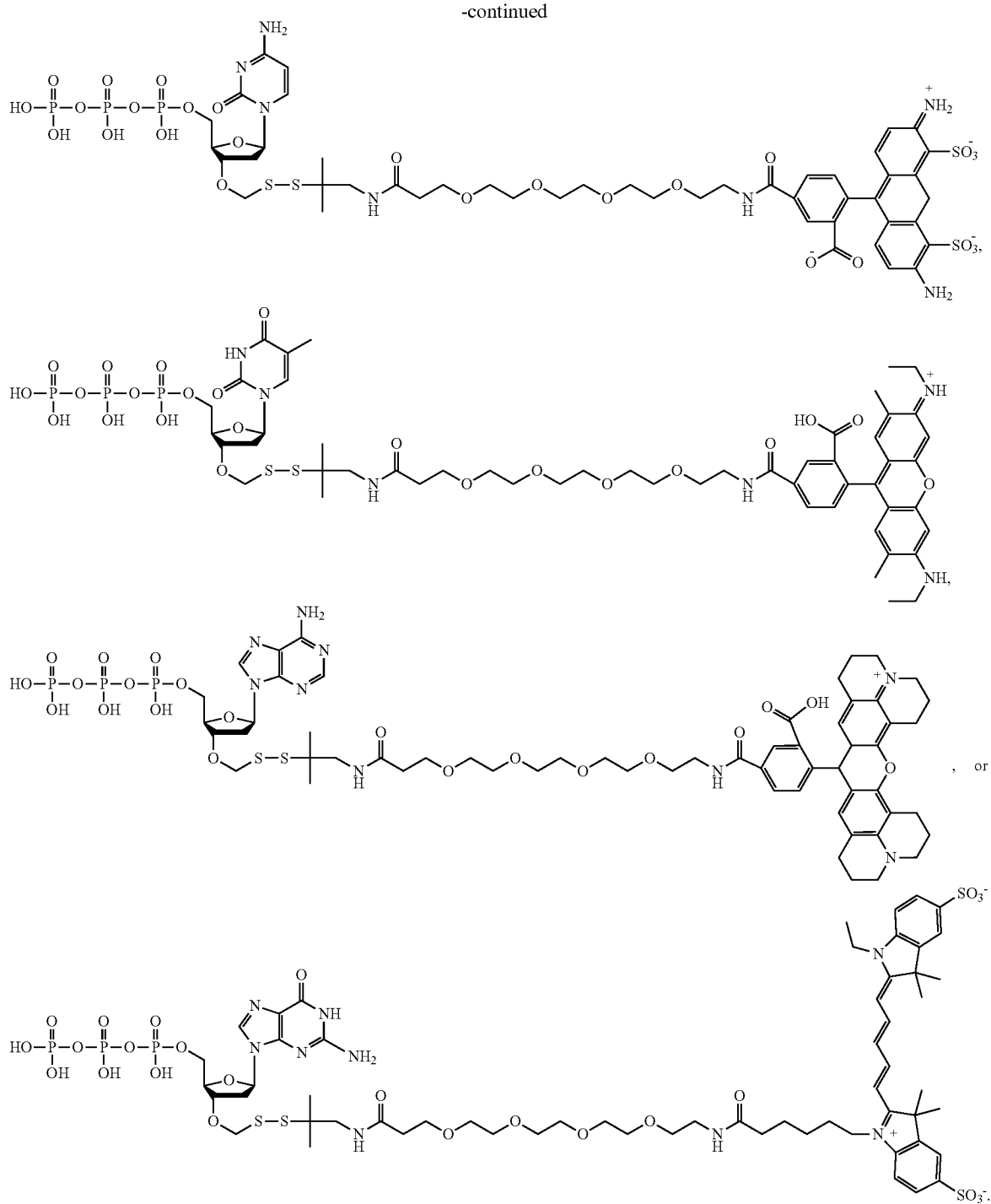

Embodiment R115. The method of any one of embodiments R98-R114, wherein the nucleic acid of interest is immobilized on a solid support.

Embodiment R116. The method of embodiment R115, wherein the nucleic acid of interest is immobilized on the solid support via an azido linkage, an alkynyl linkage, a 1,3-dipolar cycloaddition linkage, or a biotin-streptavidin interaction.

Embodiment R117. The method of any one of embodiments R115-R116, wherein the solid support is in the form of a chip, a bead, a well, a capillary tube, or a slide.

Embodiment R118. The method of any of embodiments R115-R117, wherein the solid support comprises gold, quartz, silica, or a plastic.

Embodiment R119. The method of any of embodiments R115-R117, wherein the solid support is porous.

Embodiment R120. A method of sequencing a nucleic acid of interest which comprises repeatedly determining the identity of each nucleotide present in the nucleic acid of interest according to the method of any one of embodiments R98-R119.

Embodiment R121. A method of simultaneously sequencing a plurality of different nucleic acids of interest which comprises simultaneously sequencing each such nucleic acid according to the method of embodiment R120.

Embodiments for 3' Anchor Tags for SBS:

Embodiment J1. A method for determining the nucleotide sequence of a single-stranded DNA including:
   contacting the single-stranded DNA, wherein the single-stranded DNA is bound to a polymerase which is in turn attached to a membrane-embedded nanopore in an electrolyte solution, wherein the single-stranded DNA has a primer hybridized to a portion thereof, and determining the sequence of the single stranded DNA template, following the steps of
   (a) addition of four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O-being blocked by a cleavable linker and anchor moiety, preventing further incorporation in this step;
   (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a);
   (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide;
   (d) cleavage of the 3'-O-cleavable linker-attached tag by treatment with an appropriate cleaving agent, thus generating a free 3'-OH ready for the next extension reaction.
   (e) Iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

Embodiment J2. The method of Embodiment J1 wherein each of the at least four 3'-O-Anchor-Cleavable Linker nucleotides includes a triphosphate or a polyphosphate, a base which is adenine, guanine, cytosine, thymine, or uracil, or a derivative of each thereof, and an anchor molecule covalently coupled to the 3'-O-position of the nucleotide-sugar moiety including a cleavable linker at the 3'-O-position;

Embodiment J3. The method of Embodiment J1 wherein the cleavable linker is dithiomethyl (SS(DTM)), Allyl, Azo, or 2-Nitrobenzyl-based linkers.

Embodiment J4. The method of Embodiment J1 wherein the cleavable linker is cleaved by DTT, THP, TCEP, Pd(0), sodium dithionite, or UV light of approximately 340 nm.

Embodiment J5. The method of Embodiment Ji wherein the anchor moiety includes biotin, azide, trans-cyclooctene (TCO), phenylboronic acid (PBA), quadricyclane, or norbornene.

Embodiment J6. The method of Embodiment J1 wherein the anchor binding partner molecule includes streptavidin, dibenzylcyclooctene (DBCO), tetrazine, salicylhydroxamic acid (SHA), bis(dithiobenzil)nickel(II) compounds, nitrile oxide containing compounds Embodiment J7. The method of Embodiment J1 wherein the nanopore tag is an oligonucleotide, peptide, PEG, carbohydrate or a combination thereof.

Embodiment J8. A method for determining the nucleotide sequence of a single-stranded DNA including:
   contacting the single-stranded DNA template, wherein the single-strand DNA to be sequenced hybridizes to the primer, wherein the single-stranded primer is conjugated to a membrane-embedded nanopore in an electrolyte solution, and determining the sequence of the single stranded DNA template, following the steps of
   (a) addition of polymerase and four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O-being blocked by a cleavable linker and anchor moiety, preventing further incorporation in this step;
   (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a);
   (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide;
   (d) cleavage of the 3'-O-cleavable linker-attached tag by treatment with an appropriate cleaving agent, thus generating a free 3'-OH ready for the next extension reaction.
   (e) Iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

Embodiment J9. The method of Embodiment J8 wherein each of the at least four 3'-O-Anchor-Cleavable Linker nucleotides includes a triphosphate or a polyphosphate, a base which is adenine, guanine, cytosine, thymine, or uracil, or a derivative of each thereof, and an anchor molecule covalently coupled to the 3'-O-position of the nucleotide sugar moiety including a cleavable linker at the 3'-O-position;

Embodiment J10. The method of Embodiment J8 wherein the cleavable linker is a dithiomethyl (SS(DTM)), Allyl, Azo, or 2-Nitrobenzyl-based linkers.

Embodiment J11. The method of Embodiment J8 wherein the cleavable linker is cleaved by DTT, THP, TCEP, Pd(0), sodium dithionite, or UV light of approximately 340 nm.

Embodiment J12. The method of Embodiment J8 wherein the anchor moiety includes biotin, azide, trans-cyclooctene (TCO), phenylboronic acid (PBA), quadricyclane, or norbornene.

Embodiment J13. The method of Embodiment J8 wherein the anchor binding partner molecule includes streptavidin, dibenzylcyclooctene (DBCO), tetrazine, salicylhydroxamic acid (SHA), bis(dithiobenzil)nickel(II) compounds, nitrile oxide containing compounds Embodiment J14. The method of Embodiment J8 wherein the nanopore tag is an oligonucleotide, peptide, PEG, carbohydrate or a combination thereof.

Embodiment J15. The methods of Embodiments J1 and J8, wherein 4 nucleotide analogs attached to a cleavable linker including 4 different anchor molecules are added, followed by the addition of 4 comparable anchor binding molecules attached to 4 different nanopore tags.

Embodiment J16. The methods of Embodiments J1 and J8, wherein 3 nucleotide analogs attached to a cleavable linker including 3 different anchor molecules and 1 nucleotide analog attached to a cleavable linker lacking an anchor molecule are added, followed by the addition of 3 comparable anchor binding molecules attached to 3 different nanopore tags;

Embodiment J17. The methods of Embodiments J1 and J8, wherein each of the 4 nucleotides has a different combination of anchor and cleavable linker, and 2 different binding molecules attached to 2 different nanopore tags.

Embodiment J18. The method of Embodiment J17, wherein one of the nucleotides is an azido anchor and a SS(DTM) cleavable linker, the second nucleotide is an TCO anchor and a SS(DTM) cleavable linker, the third nucleotide is an azido anchor and a 2-nitrobenzyl cleavable linker, and the fourth nucleotide is a TCO anchor and a 2-nitrobenzyl cleavable linker.

Embodiment J19. The method of Embodiment J17, wherein one of the nucleotides is an azido anchor and a SS(DTM) cleavable linker, the second nucleotide is an TCO anchor and a SS(DTM) cleavable linker, the third nucleotide is an azido anchor and a Azo cleavable linker, and the fourth nucleotide is a TCO anchor and a Azo cleavable linker.

Embodiment J20. The method of Embodiment J17, wherein one of the nucleotides is an azido anchor and a SS(DTM) cleavable linker, the second nucleotide is an TCO anchor and a SS(DTM) cleavable linker, the third nucleotide is an azido anchor and an allyl cleavable linker, and the fourth nucleotide is a TCO anchor and an allyl cleavable linker.

Embodiment J21. The methods of Embodiments J17-J20, wherein the anchor binding molecules include DBCO attached to one nanopore tag and tetrazine attached to a different nanopore tag.

Embodiment J22. The methods of Embodiments J17-J20, wherein the nanopore tag is an oligonucleotide, PEG, peptide, or carbohydrate chain.

Embodiment J23. The methods of Embodiments J1 and J8, wherein the four nucleotides include 3'-O-Anchor-Cleavable Linker (DTM) nucleotides;

Embodiment J24. The methods of Embodiments J1 and J8, wherein the anchor moiety attached to the 3'-O-DTM nucleotides is selected from azide, trans-cyclooctene (TCO), PBA, and quadricyclane (QC).

Embodiment J25. The methods of Embodiments J1 and J8, wherein the anchor binding molecule attached to the nanopore tags is selected from DBCO, tetrazine, SHA, and Ni-bis(dithioline) compounds.

Embodiment J26. The methods of Embodiments J1 and J8, wherein the cleavable linker (DTM) is cleaved by DTT, TCEP or THP.

For Mixture Of Nucleotide Analogs With Dyes On Base, And Label (Dye Or Anchor) On 3' Position (FIGS. 70-76)

Embodiment K1. A method of sequencing nucleic acid, including: a) extending a priming strand of DNA by incorporating a labeled nucleotide into the priming strand; and b) identifying the labeled nucleotide, so as to sequence the nucleic acid.

Embodiment K2. The method of embodiment K1, wherein the labeled nucleotide has the label linked to the base and a cleavable blocking group on the 3'-hydroxyl group.

Embodiment K3. The method of embodiment K1, wherein the labeled nucleotide has the label linked to the 3' OH through a cleavable linker.

Embodiment K4. The method of embodiment K2, wherein the label is attached to the base via a cleavable linker.

Embodiment K5. The method of embodiments K2 to K4, wherein the chemically cleavable linker is dithiomethyl SS(DTM), Azo, allyl or 2-nitrobenzyl.

Embodiment K6. The method of embodiments K2 to K3, wherein the 3' OH blocking group is SS(DTM), azidomethyl, Azo, allyl or 2-nitrobenzyl.

Embodiment K7. The method of embodiment K1, wherein the nucleotide analog includes a deazapurine base.

Embodiment K8. A method of sequencing nucleic acid including: a) providing a nucleic acid template hybridized to a primer; b) extending the primer hybridized to the nucleic acid template with a labeled nucleotide or nucleotide analog, wherein the labeled nucleotide or nucleotide analog includes nucleotide analogs with a label linked to the base and a blocking group on the 3-hydroxyl group, and nucleotides or nucleotide analogs with a cleavable label blocking the 3' OH; and c) identifying the labeled nucleotide, so as to sequence the nucleic acid.

Embodiment K9. The method of embodiment 8, wherein the labeled nucleotide or nucleotide analog includes nucleotide analogs with a label linked to the base and a blocking group on the 3-hydroxyl group, and nucleotides or nucleotide analogs with a cleavable label blocking the 3' OH.

Embodiment K10. The method of embodiment K9, wherein the label is attached to the base or blocking the 3' OH group with a cleavable linker.

Embodiment K11. The method of embodiment K10, wherein the cleavable linker is a chemically cleavable linkers.

Embodiment K12. The method of embodiment K10, wherein the chemically cleavable linker is dithiomethyl SS(DTM), Azo, allyl or 2-nitrobenzyl.

Embodiment K13. The method of embodiment K8, wherein the nucleotide analog includes a deazapurine base.

Embodiment K14. A method of simultaneously sequencing a plurality of different nucleic acids, including: a) extending a plurality of priming DNA strands hybridized to template DNAs, each of which includes one of the priming DNA strands, by incorporating a labeled nucleotide; and b) identifying each labeled nucleotide, so as to simultaneously sequence the plurality of different nucleic acids.

Embodiment K15. The method of embodiment K14, wherein the labeled nucleotide or nucleotide analog includes nucleotide analogs with a label linked to the base and a blocking group on the 3'-hydroxyl group, and nucleotides or nucleotide analogs with a cleavable label blocking the 3' OH.

Embodiment K16. The method of embodiment K15, wherein the label is attached to the base via a cleavable linker.

Embodiment K17. The method of embodiment K14, wherein the 3' OH blocking group is attached to the deoxyribose via a cleavable linker.

Embodiment K18. The method of embodiment K14, wherein the cleavable linker is chemically cleavable linkers.

Embodiment K19. The method of embodiment K18, wherein the chemically cleavable linker is dithiomethyl SS(DTM), Azo, allyl or 2-nitrobenzyl.

Embodiment $K_{20}$. The method of embodiment K14, wherein the 3' OH blocking group is SS(DTM), azidomethyl, Azo, allyl or 2-nitrobenzyl.

Embodiment K21. The method of embodiment K14, wherein the nucleotide analogue includes a deazapurine base.

EXAMPLES

Among various new DNA sequencing methods, sequencing by synthesis (SBS) is the leading method for realizing the goal of the $1,000 genome. Currently, the widely used high-throughput SBS technology (Bentley (2008)) determines DNA sequences during the polymerase reaction using cleavable fluorescently labeled nucleotide reversible terminator (NRT) sequencing chemistry that have been previously developed (Ju et al. (2003); Ju et al. (2006)). These cleavable fluorescent NRTs were designed such that each of the four nucleotides (A, C, G, T) is modified by attaching a unique cleavable fluorophore to the specific location of the base and capping the 3'-OH group with a small reversibly-blocking moiety so they are still recognized by DNA polymerase as substrates. Thus, the cleavable fluorescent NRTs involve two modifications in separate locations of the nucleotide (Ju et al. (2003); Ju et al. (2006)); Bentley et al. 2008): (1) a fluorescent dye to serve as a reporter group on the base; and (2) a small chemical moiety to cap the 3'-OH group to temporarily terminate the polymerase reaction after nucleotide incorporation for sequence determination. After incorporation and signal detection, the fluorophore is cleaved and the 3'-OH capping moiety removed to resume the polymerase reaction in the next cycle. These cleavable fluorescent NRTs have proved to be good substrates for re-engineered polymerases and have been used extensively in next generation DNA sequencing systems (Ju (2006); Bentley (2008)). Moreover, they enable accurate determination of homopolymer sequences, since only one base is identified in each cycle.

Fluorescence-based methods have many advantages in terms of detection sensitivity. However, because of the large size of the fluorophores, specific polymerase and reaction conditions need to be optimized for sequencing reactions. In addition, the current cleavable fluorescent NRTs used in SBS leave a modified group on the base of the growing DNA strand after cleavage of the fluorophore, limiting sequencing read length.

As an alternative to fluorescence-based DNA SBS, an approach has been previously reported, which uses an azido moiety ($N_3$) that has an intense, narrow and unique Raman shift at 2125 $cm^{-1}$, where virtually all biological molecules are transparent, as a label for SBS (Palla (2014)). The azido label is part of the moiety that also serves as a reversible blocking group for the 3'-OH group of the nucleotides. The extended DNA strand from these nucleotides is identical to natural DNA. This is unlike many, current SBS approaches, which require the use of modified nucleotides that leave short remnants of the linkers after cleavage of the fluorescent tags (Ju (2006); Bentley (2008); Harris (2008)); as these remnants build up in the extended DNA chains, they are increasingly likely to alter DNA structure and impede further nucleotide incorporation by polymerase.

Fluorescent NRTs with the following blocking groups at the 3'-OH have been reported: 3'-O-allyl-dNTP(Bentley (2008)), 3'-O-azidomethyl-dNTPs (Wu (2007); Guo (2008); Bentley (2008)), 3'-O—$NH_2$-dNTPs (Hunter (2010)), and 3'-O-cyanoethyl-dNTPs (Knapp (2011)), which can be cleaved by Pd(0), tris(2-carboxyethyl)phosphine (TCEP), dilute nitrous acid and fluoride, respectively, to generate the free 3'-OH group.

Various modifications based on 3'-O-alkyldithiomethyl (3'-O-DTM) for the nucleosides (Kwiatkowski (2007); Muller (2011); Semenyuk (2010)) were reported for the synthesis of oligonucleotides. The stability and reductive cleavage leading to hydroxyl production from the O-DTM group have been established (Kwiatkowski (2007); Muller (2011); Semenyuk (2010)), but their utility in DNA sequencing applications has not been reported. This is due to the fact that nucleotide analogs with a large fluorescent dye blocking the 3'-OH group were not reported to be incorporated by DNA polymerase in template-directed DNA synthesis.

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. SBS determines DNA sequences during the polymerase reaction. Currently, the widely used high-throughput SBS technology (Bentley (2008)) determines DNA sequences during the polymerase reaction using cleavable fluorescently labeled nucleotide reversible terminator (NRT) sequencing chemistry that has been previously developed (Ju et al. (2003); Ju et al. (2006)). These cleavable fluorescent NRTs were designed based on the rationale that each of the four nucleotides (A, C, G, T) is modified by attaching a unique cleavable fluorophore to the specific location of the base and capping the 3'-OH group with a small reversible-blocking moiety so they are still recognized by DNA polymerase as substrates. Thus, the cleavable fluorescent NRTs involve two modifications in separate locations of the nucleotide (Ju et al. (2003); Ju et al. (2006); Bentley et al. (2008)): (1) a fluorescent dye to serve as a reporter group on the base; and (2) a small chemical moiety to cap the 3'-OH group to temporarily terminate the polymerase reaction after nucleotide incorporation for sequence determination. After nucleotide incorporation and signal detection to identify the incorporated nucleotide, the fluorophore is cleaved and the 3'-OH capping moiety is removed, enabling the polymerase reaction to resume in the next cycle. These cleavable fluorescent NRTs have proved to be good substrates for re-engineered polymerases and have been used extensively in next generation DNA sequencing systems (Ju (2006); Bentley (2008)). Moreover, they enable accurate determination of homopolymer sequences, since only one base is identified in each cycle.

It is known that nucleotides modified with bulky groups such as energy transfer dyes at the 5-position of the pyrimidines (T and C) and the 7-position of purines (G and A) are still recognizable by engineered DNA polymerase as substrates (Rosenblum (1997); Zhu (1994). The ternary complexes of a rat DNA polymerase, a DNA template-primer, and dideoxycytidine triphosphate have been determined (Pelletier (1994)), which supports these findings. Thus, if a unique fluorescent dye is linked to the 5-position of the pyrimidines (T and C) and the 7-position of purines (G and A) via a cleavable linker, and a small chemical moiety is used to cap the 3'-OH group, the resulting nucleotide analogues should incorporate into the growing DNA strand as terminators. Based on this rationale, an SBS approach using cleavable fluorescent nucleotide analogues as reversible terminators to sequence surface-immobilized DNA was developed (Ju (2003); Ruparel (2005); Marguiles (2005); Ju (2006); Wu (2007); Guo (2008)). In this approach, the nucleotides are modified at two specific locations so that they are still recognized by DNA polymerase as substrates: (1) a different fluorophore with a distinct fluorescent emission is attached to the specific location of each of the four bases through a cleavable linker and (ii) the 3'-OH group is capped by a small chemically reversible moiety. DNA polymerase only incorporates a single nucleotide analogue complementary to the base on a DNA template covalently linked to a surface. After incorporation, the unique fluorescence emission is detected to identify the incorporated nucleotide. The fluorophore is subsequently removed and 3'-OH group is chemically regenerated, which allows the next cycle of the polymerase reaction to occur. Because a high density of different DNA templates can be spotted on the large surface of a DNA chip, each cycle can identify many bases in parallel, allowing the simultaneous sequencing of a large number of DNA molecules.

Fluorescence-based methods have many advantages in terms of detection sensitivity. However, because of the large size of the fluorophores, specific polymerase and reaction conditions need to be optimized for sequencing reactions. An additional disadvantage of the abovementioned SBS approach is the production of a small molecular "scar" (often a propargylamine or a modified propargylamino moiety) at the nucleotide base after cleavage of the fluorescent dye from the incorporated nucleotide in the polymerase reaction. The growing DNA chain accumulates these scars through each successive round of SBS. At some point, the residual scars may be significant enough to interfere with the DNA double helix structure, thereby negatively affecting DNA polymerase recognition and consequently limiting the read length.

Due to the desirability of increasing SBS read-length, SBS schemes have been explored in which the "reporter" dye is attached directly to the 3'-OH group of the nucleotide analogues via a cleavable linker that will allow scarless SBS to take place. In such a scarless SBS process, after nucleotide incorporation and imaging of the reporter moiety on the incorporated 3'-O modified nucleotide for sequence determination, the cleavage of the linker would generate a free 3'-OH group on the growing DNA strand for subsequent extension reactions. Earlier work was focused on designing and synthesizing a cleavable chemical moiety that was linked to a fluorescent dye to cap the 3'-OH group of the nucleotides using 3'-O-ester linkage (Cheeseman (1994); Canard (1994)). However, these nucleotide analogues were largely unsuccessful in SBS schemes because DNA polymerase had difficulty accepting these nucleotide analogues as a substrate. Aiming to create a high-throughput DNA sequencing platform, other groups also pursued modified nucleotides with a reversible 3'-O fluorescent dye (Welch (1999); Metzker (2005); Lu (2006)). Accumulated research efforts indicated that the major challenge for this approach is that DNA polymerase has difficulty accepting 3'-O bulky-dye-modified nucleotides as substrates, because the 3' position on the deoxyribose of the nucleotides is very close to the amino acid residues in the active site of the DNA polymerase while in the ternary complex formed by the polymerase with the complementary nucleotide and the primed template. Recently, Kim et. al. reported 3'-O-fluorescently modified nucleotides using an allyl linker to attach small fluorescent dyes (coumarin, Pacific Blue and BodipyFL), which are reasonably good substrates for a Therminator II DNA polymerase. However, nucleotides modified with bulky dyes or highly charged dyes (such as Alexa 488) using the same linker are not suitable substrates for DNA polymerase (Kim (2010); Kim (2014)).

To enable long read-length in SBS, it is essential for the cleavable linker to be stable during the sequencing reactions, with a minimal number of cycles and to leave no scars on the base after the cleavage reaction. Nucleotide analogues with reporter molecules attached to the 3'-O via a cleavable linker are ideal for this purpose; such modified nucleotides would generate naturally elongated DNA during the DNA synthesis. However the major challenge is designing and synthesizing this type of modified nucleotide analogue that is accepted by DNA polymerase as a substrate. The NRTs with the following blocking groups at the 3'-OH of the nucleotide have been reported and shown to be good substrates for DNA polymerases: 3'-O-(2-nitrobenzyl)-dNTPs (Wu (2007)), 3'-O-allyl-dNTPs (Ju (2003); Ju (2006)), 3'-O-azidomethyl-dNTPs (Guo (2008); Bentley (2008)), 3'-O—NH2 (Hutter (2010)), and 3'-O-cyanoethyl (Diana (2011)). The 3' blocking moieties in all these molecules can be readily cleaved to regenerate the 3'-OH group. This combined research indicates that 3'-O-NRTs with a small chemical moiety attached to the 3'-OH group are good substrates for DNA polymerases and are ideal for conducting DNA SBS. Various 3'-O-t-butyldithiomethyl (3'-O-DTM) based modifications on nucleosides (Kwiatkowski (2007); Muller (2011); Semenyuk (2006)) have been reported for the synthesis of oligonucleotides. The reductive cleavage leading to hydroxyl production from O-DTM group has been well established (Kwiatkowski (2007); Muller (2011); Semenyuk (2006)), but the utility of these types of molecules with the 3'-O-DTM modification in DNA SBS applications has not been reported. Accordingly, there is a need for the use in scarless SBS, and synthesis of, 3'-O modified nucleotides and nucleosides that are effectively recognized as substrates by DNA polymerases, are efficiently and accurately incorporated into growing DNA chains during SBS, have a 3'-O blocking group that is cleavable under mild conditions wherein cleavage results in a 3'-OH, and permit long SBS read-lengths.

Example 1: Synthesis and Characterization of 3'-O-Dye-DTM-dNTPs

Fluorescence-based DNA sequencing-by-synthesis methods have many advantages in terms of detection sensitivity.

However, because of the large size of the fluorophores, specific polymerase and reaction conditions need to be optimized for sequencing reactions. In addition, the current cleavable fluorescent nucleotide reversible terminators used in SBS leave a modified group, or scar, on the base of the growing DNA strand after cleavage of the fluorophore, which in turn limits read length.

Fluorescent NRTs with the following blocking groups at the 3'-OH have been reported: 3'-O-allyl-dNTP(Bentley (2008)), 3'-O-azidomethyl-dNTPs (Wu (2007); Guo (2008); Bentley (2008)), 3'-O—$NH_2$-dNTPs (Hunter (2010)), and 3'-O-cyanoethyl-dNTPs (Knapp (2011)), which can be cleaved by Pd(0), tris(2-carboxyethyl)phosphine (TCEP), dilute nitrous acid and fluoride, respectively, to generate the free 3'-OH group.

Various modifications based on 3'-O-alkyldithiomethyl (3'-O-DTM) for the nucleosides (Kwiatkowski (2007); Muller (2011); Semenyuk (2010)) have been reported for the synthesis of oligonucleotides. The stability and reductive cleavage leading to hydroxyl production from the O-DTM group has also been established (Kwiatkowski (2007); Muller (2011); Semenyuk (2010)), but their utility in DNA sequencing applications has not been reported. This is because nucleotide analogs with a large fluorescent dye blocking the 3'-OH group were reported to not be incorporated by DNA polymerase in template-directed DNA synthesis.

By the unique chemical design of the cleavable linker attached to a fluorescent dye to block the 3'-OH group of the nucleotide, coupled with specific polymerase reaction conditions, it is herein disclosed that the modified 3'-O-dithiomethyl (3'-O-DTM) is a successful reversible linkage group for attaching a fluorescent dye reporter to block the 3'-OH group of the nucleotide for DNA SBS. To this end, herein disclosed are novel 3' reversibly labeled nucleotides as traceless reversible terminators, which were designed and synthesized for DNA SBS. In these novel nucleotide analogs, only the 3'-OH group of the nucleotide is reversibly blocked with a DTM linker, which is attached to the fluorescent label, thus realizing the dual function of the 3'-O- modification of the nucleotide, serving as both the reversible terminator function and the cleavable fluorescence reporter.

It is further disclosed herein, that in SBS cycles, such 3'-O-Dye-DTM-dNTPs are well recognized by the DNA polymerase, Therminator (9° N DNA polymerase variant), as substrates and incorporated into the growing DNA strand. After determining the identity of the incorporated nucleotide by its fluorescent signal, TCEP or Tris(3-hydroxypropyl) phosphine (THP) treatment cleaves the disulfide bond in the DMT moiety leading to both the removal of the fluorescence reporter and the regeneration of the 3'-OH group to allow for continuous sequencing. After each incorporation and cleavage, an extended natural DNA strand is produced to allow for the seamless incorporation of incoming complementary 3'-O-Dye-DTM-dNTPs during SBS.

There are surprising advantages to using 3'-O-Dye-DTM-dNTPs for SBS. As disclosed herein, consecutive polymerase extension reaction using 3'-O-Dye-DTM-dNTPs with a synthetic template and primer have been carried out. After single base extension and cleavage of the DTM moiety and the removal of dye from the 3'-O of the DNA extension product, the resulting primer extension product can be further extended with an additional 3'-O-Dye-DTM-dNTP, leading to a high-yield incorporation with accurate sequence determination. Because these 3'-O-Dye-DTM-dNTPs do not require the attachment of fluorescent labels on the base, their synthesis is simpler and therefore more cost effective. In addition, the extended DNA strand is identical to natural DNA. The use of 3'-O-Dye-DTM-dNTPs will lead to very long, accurate read lengths for SBS.

The synthesis of 3'-O—Bodipy-DTM-dTTP and 3'-O—Bodipy-$PEG_4$-DTM-dTTP

3'-O-methylthiomethyl-5'-O-tert-butyldimethylsilyl thymidine (T2): To a solution of the 5'-O-tert-Butyldimethylsilyl thymidine (T1, 1.07 g, 3 mmol) in DMSO (10 mL) with stirring was added acetic acid (2.6 mL) and acetic anhydride (8.6 mL). The reaction mixture was stirred at room temperature until the reaction was complete (48 h), which was monitored by TLC. Then the mixture was added slowly to the solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the residue of the desired compound was purified by silica gel column chromatography (ethyl acetate/hexane: 1/2) to give pure product T2 (0.97 g, 74%). $^1$H NMR (400 MHz, $CDCl_3$) δ: 8.16 (s, 1H), 7.48 (s, 1H), 6.28 (m, 1H), 4.62 (m, 2H), 4.46 (m, 1H), 4.10 (m, 1H), 3.78-3.90 (m, 2H), 2.39 (m, 1H), 2.14 (s, 3H), 1.97 (m, 1H), 1.92 (s, 3H), 0.93 (s, 9H), 0.13 (s, 3H); HRMS ($Fab^+$) calc'd for $C_{18}H_{33}N_2O_5SSi$ [(M+H)+]: 417.1879, found: 417.1890.

Compound T3: 3'—O-methylthiomethyl-5'-O-tert-butyldimethylsilyl thymidine (T2, 625 mg, 1.50 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.12 mL, 1.50 mmol) in anhydrous dichloromethane (3 mL) was added dropwise during 2 minutes. The ice-bath was removed and the reaction mixture was stirred further for 0.5 hour. Then potassium p-toluenethiosulfonate (0.61 g, 2.25 mmol) in anhydrous DMF (3 mL) was added to the mixture. Stirring was continued at room temperature for additional 1 hour followed by addition of 2,2,2-trifluoro-N-(2-mercapto-2-methylpropyl)acetamide (403 mg, 2.01 mmol). The reaction mixture was stirred at room temperature for 0.5 hour and quickly filtered through celite. The filter was washed with dichloromethane and the organic fraction was concentrated to give the crude compound T3.

Compound T4: Without isolation, the crude compound T3 was dissolved in THF (10 mL) followed by the addition of tetrabutylammonium fluoride THF solution (1.0 M, 1.0 mL, 1.0 mmol). The mixture was stirring at room temperature until the reaction was complete, which was monitored by TLC. Then, the mixture was concentrated in vacuo, saturated $NaHCO_3$ solution (50 mL) was added and the mixture was extracted with dichloromethane. The organic layer was dried over anhydrous $Na_2SO_4$, filtered, concentrated and the obtained crude mixture was purified by flash column chromatography (dichloromethane/methanol: 20/1) to give compound T4 (199 mg, 27% from compound T2). $^1$H NMR (400 MHz, $CDCl_3$) δ 9.41 (s, 1H), 7.44 (s, 1H), 7.07 (t, J=6.6 Hz, 1H), 6.11 (t, J=7.0 Hz, 1H), 4.88-4.80 (m, 2H), 4.57 (m, 1H), 4.14 (q, J=2.9 Hz, 1H), 3.93 (m, 1H), 3.82 (m, 1H), 3.49 (d, J=6.2 Hz, 2H), 3.10 (t, J=6.2, 4.1 Hz, 1H), 2.42-2.39 (m, 2H), 1.91 (s, 3H), 1.31 (m, 6H). $^{13}$C NMR (75 MHz, $CDCl_3$) δ 164.39, 158.22, 150.95, 137.33, 111.61, 87.33, 85.30, 80.39, 78.65, 77.66, 62.84, 50.70, 48.24, 37.28, 25.74, 12.86; MS ($APCI^+$) calc'd for $C_{17}H_{24}F_3N_3O_6S_2$: 487.51, found: 487.6.

3'-O—$NH_2$-DTM-dTTP (T5): Compound T4 (50 mg, 103 μmol), tetrabutylammonium pyrophosphate (150 mg, 0.27 mmol) and 2-chloro-4-H-1,3,2-benzodioxaphosphorin-4- one (33 mg, 0.17 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-ethyldithiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. The resulting solution was extracted with ethyl acetate. The aqueous layer was concentrated in vacuo and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford T5, which was characterized by MALDI-TOF MS, calc'd for $C_{15}H_{28}N_3O_{14}P_3S_2$: 631.45, found: 631.0.

3'-O-Bodipy-DTM-dTTP (compound T6): To a stirred solution of Bodipy FL-NHS ester (1.5 mg, 3.9 μmol) in DMF (0.2 ml), 3'-O-DTM-dTTP (compound T5, 4.0 μmol) in $NaHCO_3/Na_2CO_3$ buffer (pH 8.9, 0.1 M, 0.3 ml). The reaction mixture was stirred at room temperature for 3 h with exclusion of light. The reaction mixture was purified by a preparative silica gel TLC plate (dichloromethane/methanol, 4:1). The crude product was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-Bodipy-dTTP T6, which was characterized by MALDI-TOF MS, calc'd for $C_{29}H_{41}BF_2N_5O_{15}P_3S_2$: 905.5, found: 904.1.

3'-O-Bodipy-PEG$_4$-DTM-dTTP (compound T7): To a stirred solution of Bodipy-PEG$_4$-Acid (2.1 mg, 3.8 μmol) in dry DMF (200 μl), N,N-disuccinimidyl carbonate (1.03 mg, 4.0 μmol) and 4-dimethylaminopyridine (0.48 mg, 4.0 μmol) were added. The reaction mixture was stirred at room temperature for 2 h. TLC indicated that Bodipy-PEG$_4$-Acid was completely converted to compound Bodipy-PEG$_4$-NHS ester, which was directly used to couple with amino-3'-O-DTM-dTTP (3.8 μmol) in $NaHCO_3/Na_2CO_3$ buffer (pH 8.9, 0.1 M) (300 μl). The reaction mixture was stirred at room temperature for 3 h with exclusion of light. The reaction mixture was purified by a preparative silica gel TLC plate (dichloromethane/methanol, 4:1). The crude mixture was purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-PEG$_4$-Bodipy-dTTP T7, which was characterized by MALDI-TOF MS calc'd for $C_{40}H_{62}BF_2N_6O_{20}P_3S_2$: 1152.8, found: 1151.4.

The synthesis of 3'-O-Rox-DTM-dATP and 3'-O-Rox-PEG$_4$-DTM-dATP

N$^4$-Benzoyl-3'-O-methylthiomethyl-5'-O-tert-butyldimethylsilyl-2'-deoxyadenosine (A2): To a solution of the N$^4$-Benzoyl-5'-O-tert-butyldimethylsilyl-2'-deoxyadenosine (A1, 1.41 g, 3 mmol) in DMSO (10 mL) with stirring was added acetic acid (3 mL) and acetic anhydride (9 mL). The reaction mixture was stirred at room temperature until the reaction was complete (48 h), which was monitored by TLC. Then the mixture was added slowly to the solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the residue of the desired compound was purified by silica gel column chromatography (dichloromethane/methanol: 30/1) to give pure product A2 (1.39 g, 88%). $^1$H NMR (400 MHz, CDCl$_3$) δ 9.12 (s, 1H), 8.81 (s, 1H), 8.35 (s, 1H), 8.10-8.01 (m, 2H), 7.68 (m, 1H), 7.49 (m, 2H), 6.53 (dd, J=7.5, 6.0 Hz, 1H), 4.78-4.65 (m, 3H), 4.24 (dt, J=4.3, 3.1 Hz, 1H), 3.98-3.81 (m, 2H), 2.80-2.60 (m, 2H), 2.21 (s, 3H), 0.94 (s, 10 H), 0.13 (s, 6H); MS (APCI$^+$) calc'd for $C_{25}H_{35}N_5O_4SSi$: 529.73, found: 529.4.

Compound A3: N$^4$—Benzoyl-3'-O-methylthiomethyl-5'-O-tert-butyldimethylsilyl-2'-deoxyadenosine (A2, 550 mg, 1.04 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.12 mL, 1.50 mmol) in anhydrous dichloromethane (3 mL) was added dropwise during 2 minutes. The ice-bath was removed and the reaction mixture was stirred further for 0.5 hour. Then potassium p-toluenethiosulfonate (0.61 g, 2.25 mmol) in anhydrous DMF (3 mL) was added to the mixture. Stirring was continued at room temperature for additional 1 hour followed by addition of 2,2,2-trifluoro-N-(2-mercapto-2-methylpropyl)acetamide (302 mg, 1.5 mmol). The reaction mixture was stirred at room temperature for 0.5 hour and quickly filtered through celite. The filter was washed with dichloromethane and the organic fraction was concentrated to give the crude compound A3: MS (APCI$^+$) calc'd for $C_{30}H_{41}F_3N_6O_5S_2Si$: 714.89, found: 714.6.

Compound A4: Without isolation, the crude compound A3 was dissolved in THF (10 mL) followed by the addition of tetrabutylammonium fluoride THF solution (1.0 M, 1.0 mL, 1.0 mmol). The mixture was stirred at room temperature until the reaction was complete, which was monitored by TLC. Then, the mixture was concentrated in vacuo, saturated NaHCO$_3$ solution (50 mL) was added and the mixture was extracted with dichloromethane. The organic layer was dried over anhydrous Na$_2$SO$_4$, filtered, concentrated and the obtained crude mixture was purified by flash column chromatography (dichloromethane/methanol: 20/1) to give compound A4 (128 mg, 20% from compound A2). $^1$H NMR (400 MHz, CDCl$_3$) δ 9.16 (s, 1H), 8.77 (s, 1H), 8.11 (s, 1H), 8.07-8.00 (m, 2H), 7.61 (m, 1H), 7.56-7.52 (m, 2H), 6.91 (m, 1H), 6.33 (dd, J=9.4, 5.5 Hz, 1H), 5.83 (d, J=10.7 Hz, 1H), 4.88 (d, J=2.6 Hz, 2H), 4.75 (dt, J=5.4, 1.2 Hz, 1H), 4.36 (q, J=1.7 Hz, 1H), 4.03 (dd, J=12.8, 1.8 Hz, 1H), 3.81 (t, J=10.9 Hz, 1H), 3.51 (d, J=6.2 Hz, 2H), 3.10 (m, 1 H), 2.56-2.46 (m, 1H), 1.36 (s, 6H); $^{13}$C NMR (75 MHz, CDCl$_3$) δ 164.91, 152.49, 151.03, 150.71, 142.95, 133.82, 133.33, 129.29, 128.29, 125.00, 118.23, 114.41, 88.01, 87.10, 80.37, 80.19, 63.91, 60.76, 50.66, 47.99, 38.17, 25.82, 25.75; MS (APCI$^+$) calc'd for $C_{24}H_{27}F3N_6O_5S_2$: 600.6, found: 600.7.

3'-NH2-DTM-dATP (A5): Compound A4 (50 mg, 103 μmol), tetrabutylammonium pyrophosphate (150 mg, 0.27 mmol) and 2-chloro-4-H-1,3,2-benzodioxaphosphorin-4-one (33 mg, 0.17 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-ethylthiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. The resulting solution was extracted with ethyl acetate. The aqueous layer was concentrated in vacuo to approximately 20 mL, then concentrated $NH_4OH$ (20 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford A5, which was characterized by MALDI-TOF MS, calc'd for $C_{15}H_{27}N_6O_{12}P_3S_2$: 640.45, found: 639.6.

3'-O-Rox-DTM-dATP (compound A6): To a stirred solution of ROX—NHS ester (2 mg, 3.2 µmol) in DMF (0.2 ml), amino 3'-O-DTM-dATP (compound A5, 3.0 µmol) in $NaHCO_3/Na_2CO_3$ buffer (pH 8.9, 0.1 M, 0.3 ml). The reaction mixture was stirred at room temperature for 3 h with exclusion of light. The reaction mixture was purified by a preparative silica gel TLC plate (dichloromethane/methanol, 4:1). The crude product was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-Rox-dATP A6, which was characterized by MALDI-TOF MS, calc'd for $C_{48}H_{55}N_8O_{16}P_3S_2$: 1157.0, found: 1155.4.

3'-O-Rox-PEG$_4$-DTM-dATP (compound A7): To a stirred solution of ROX-PEG$_4$-Acid (2.6 mg, 3.3 µmol) in dry DMF (200 µl), N,N-disuccinimidyl carbonate (0.90 mg, 3.5 µmol) and 4-dimethylaminopyridine (0.43 mg, 3.5 µmol) were added. The reaction mixture was stirred at room temperature for 2 h. TLC indicated that ROX-PEG$_4$-Acid was completely converted to compound ROX-PEG$_4$-NHS ester, which was directly used to couple with amino-3'-O-DTM-dATP (3.5 µmol) in $NaHCO_3/Na_2CO_3$ buffer (pH 8.9, 0.1 M) (300 µl). The reaction mixture was stirred at room temperature for 3 h with exclusion of light. The reaction mixture was purified by a preparative silica gel TLC plate (dichloromethane/methanol, 4:1). The crude mixture was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-PEG$_4$-Rox-dATP A7, which was characterized by MALDI-TOF MS, calc'd for $C_{59}H_{76}N_9O_{21}P_3S_2$: 1404.3, found: 1401.6.

The synthesis of 3'-O-Alexa488-DTM-dCTP and 3'-O-PEG$_4$-Alexa488-DTM-dCTP $N^4$-Benzoyl-3'-O-methylthiomethyl-5'-O-tert-butyldimethylsilyl-2'-deoxycytidine (C2): To a solution of the $N^4$-Benzoyl-5'-O-tert-butyldimethylsilyl-2'-deoxycytidine (C1, 2.25 g, 2.51 mmol) in DMSO (20 mL) with stirring was added acetic acid (8 mL) and acetic anhydride (20 mL). The reaction mixture was stirred at room temperature until the reaction was complete (24 h), which was monitored by TLC. Then the mixture was added slowly to the solution of sodium bicarbonate under vigorous stirring and extracted with ethyl acetate (3×50 mL). The combined organic layers were dried over $Na_2SO_4$ and filtered. The filtrate was concentrated to dryness under reduced pressure and the residue of the desired compound was purified by silica gel column chromatography (DCM/MeOH: 1/30) to give pure product C2 (2.13 g, 83%). $^1$H NMR (400 MHz, CDCl$_3$) δ: 8.43 (d, J=8.4 Hz, 1H), 7.92 (d, J=7.6 Hz, 2H), 7.66 (m, 1H), 7.53 (m, 3H), 6.30 (t, J=6.0 Hz, 1H), 4.69 (dd, J=32 Hz; 7.6 Hz, 2H), 4.50 (m, 1H), 4.18 (m, 1H), 3.98-3.83 (m, 2H), 2.74 (m, 1H), 2.21-2.12 (m, 4H), 0.93 (s, 9H), 0.15 (m, 6H). MS (APCI$^+$) calc'd for $C_{24}H_{35}N_3O_5SSi$: 505.70, found: 505.6.

Compound C3: $N^4$—Benzoyl-3'-O-methylthiomethyl-5'-O-tert-butyldimethylsilyl-2'-deoxycytidine (C2, 0.87 mg, 1.72 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.15 mL, 1.80 mmol) in anhydrous dichloromethane (3 mL) was added dropwise during 2 minutes. The ice-bath was removed and the reaction mixture was stirred further for 0.5 hour. Then potassium p-toluenethiosulfonate (0.68 g, 2.5 mmol) in anhydrous DMF (3 mL) was added to the mixture. Stirring was continued at room temperature for additional 1 hour followed by addition of 2,2,2-trifluoro-N-(2-mercapto-2-methylpropyl) acetamide (402 mg, 2.0 mmol). The reaction mixture was stirred at room temperature for 0.5 hour and quickly filtered through celite. The filter was washed with dichloromethane and the organic fraction was concentrated to give the crude compound C3: MS (APCI$^-$) calc'd for $C_{29}H_{41}F_3N_4O_6S_2Si$: 690.87, found: 689.8 [M−H].

Compound C4: Without the isolation, the crude compound C3 was dissolved in THF (10 mL) followed by the addition of tetrabutylammonium fluoride THF solution (1.0 M, 1.0 mL, 1.0 mmol). The mixture was stirring at room temperature until the reaction was complete, which was monitored by TLC. Then, the mixture was concentrated in vacuo, saturated $NaHCO_3$ solution (50 mL) was added and the mixture was extracted with dichloromethane. The organic layer was dried over anhydrous $Na_2SO_4$, filtered, concentrated and the obtained crude mixture was purified by flash column chromatography (dichloromethane/methanol: 20/1) to give compound C4 (171 mg, 17% from compound C2). $^1$H NMR (400 MHz, CDCl$_3$) δ 8.94 (br, 1H), 8.32 (d, J=7.5 Hz, 1H), 7.90-7.83 (m, 2H), 7.65-7.55 (m, 2H), 7.49 (dd, J=8.4, 7.1 Hz, 2H), 7.12 (t, J=6.3 Hz, 1H), 6.15 (t, J=6.4 Hz, 1H), 4.93-4.78 (m, 2H), 4.58 (dt, J=6.5, 3.3 Hz, 1H), 4.24 (q, J=3.0 Hz, 1H), 4.02 (dd, J=12.1, 3.0 Hz, 11H), 3.86 (dd, J=12.1, 2.9 Hz, 1H), 3.66 (br, 1H), 3.50 (d, J=6.2 Hz, 2H), 2.71 (m, 1H), 2.40 (m, 1H), 1.34 (s, 6H). $^{13}$C NMR (75 MHz, CDCl$_3$) δ 162.82, 158.20, 157.72, 155.45, 146.01, 133.63, 129.40, 127.98, 97.24, 89.14, 86.04, 80.46, 78.25, 62.47, 50.72, 48.04, 38.47, 25.78; MS (APCI$^+$) calc'd for $C_{23}H_{27}F_3N_4O_6S_2$: 576.61, found: 576.

3'-NH2-DTM-dCTP (C5): Compound C4 (50 mg, 87 µmol), tetrabutylammonium pyrophosphate (140 mg, 0.25 mmol) and 2-chloro-4-H-1,3,2-benzodioxaphosphorin-4-one (30 mg, 0.15 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-ethyldithiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. The resulting solution was extracted with ethyl acetate. The aqueous layer was concentrated in vacuo and the residue was diluted with 5 ml of water. The crude mixture was then purified with anion exchange chromatography on DEAE-Sephadex A-25 at 4° C. using a gradient of TEAB (pH 8.0; 0.1-1.0 M), and further purified by reverse-phase HPLC to afford C5, which was characterized by MALDI-TOF MS, calc'd for $C_{14}H_{29}N_4O_{13}P_3S_2$: 618.4, found: 616.7.

3'-O-Alexa488-DTM-dCTP and 3'-O-PEG$_4$-Alexa488-DTM-dCTP can be synthesized by coupling the 3'-NH$_2$-DTM-dCTP (C5) with the NHS ester of Alexa488.

The synthesis of 3'-O-Cy5-DTM-dGTP and 3'-O-Cy5-PEG$_4$-DTM-dGTP $N^4$-DMF-5'-O-tert-butyldimethylsilyl-2'-deoxyguanosine (G2): The mixture of 2'-deoxyguanosine (G1, 1.33 g, 5 mmol), tert-butyldimethylsilyl chloride (825 mg, 5.5 mmol) and imidazol (370 mg, 5.5 mmol) was dissolved in dry DMF (20 mL) and stirring at room temperature until the reaction was complete, which was monitored by TLC. Then the solvent was removed and the residue was added N,N-dimethylformamide dimethyl acetal (2.5 mL) in dry DMF (10 mL). Stirring was continued at room temperature for additional 10 hours, then the reaction mixture was poured into stirred ice-water (200 mL) and the precipitate was collected by suction filtration, washed with water and hexane. The obtained crude product was purified by column chromatography (dichloromethane/methanol: 20/1) to give $N^4$-DMF-5'-O-tert-butyldimethylsilyl-2'-deoxyguanosine (G2, 1.76 g, 81%). $^1$H NMR (400 MHz, CDCl$_3$) δ 9.52 (s, 1H), 8.60-8.55 (m, 1H), 7.91 (s, 1H), 6.43 (t, J=6.7 Hz, 1H), 4.68 (d, J=4.6 Hz, 1H), 4.16-4.08 (m, 1H), 3.94-3.87 (m, 1H), 3.87-3.77 (m, 2H), 3.16 (s, 3H), 3.07 (s, 3H), 2.63-2.49 (m, 2H), 0.91 (s, 9H), 0.09 (d, J=0.8 Hz, 6H). MS (APCI$^+$): MS (APCI$^+$) calc'd for $C_{19}H_{32}N_6O_4Si$: 436.58, found: 436.6.

$N^4$-DMF-3'-O-methylthiomethyl-5'-O-tert-butyldimethylsilyl-2'-deoxyguanosine (G3): To a solution of the $N^4$-Benzoyl-5'-O-tert-butyldimethylsilyl-2'-deoxyadenosine (G2, 1.31 g, 3 mmol) in DMSO (10 mL) with stirring was added acetic acid (3 mL) and acetic anhydride (9 mL). The reaction mixture was stirred at room temperature until the reaction was complete (48 h), which was monitored by TLC. Then the mixture was added slowly to the solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the residue of the desired compound was purified by silica gel column chromatography (dichloromethane/methanol: 30/1) to give pure product G3 (1.16 g, 78%). $^1$H NMR (400 MHz, CDCl$_3$) δ 9.76 (s, 1H), 8.61 (s, 1H), 7.85 (s, 1H), 6.33 (dd, J=7.4, 6.4 Hz, 1H), 4.74-4.63 (m, 2H), 4.63-4.58 (m, 1H), 4.13 (m, 1H), 3.84-3.71 (m, 2H), 3.19 (d, J=0.7 Hz, 3H), 3.10 (d, J=0.7 Hz, 3H), 2.58-2.46 (m, 2H), 2.17 (s, 3H), 0.91 (s, 9H), 0.09 (s, 6H); MS (APCI$^+$) calc'd for $C_{21}H_{36}N_6O_4SSi$: 496.7, found: 496.8. The target compounds 3'-O-Cy5-DTM-dGTP and 3'-O-Cy5-PEG$_4$-DTM-dGTP are produced.

Consecutive Polymerase Extension Using 3'-O-Rox-DTM-dATP Reversible Terminator and Characterization by MALDI-TOF Mass Spectrometry (Results are Shown in FIG. 33

The first extension reaction was carried out using 200 pmol of reversible terminator (3'-O-Rox-DTM-dATP), 2 units of Therminator™ IX DNA Polymerase (A$_9$° NT$^M$ DNA Polymerase variant from NEB), 100 pmol of DNA primer (5'-TAGATGACCCTGCCTTGTCG-3') (SEQ ID NO:2), 60 pmol of DNA template (5'-GAAGGA-GACACGCGGCCAGAGAGGGTCCTGTCCGTGTTTG TGCGTGGAGTTCGACA AGGCAGGGT-CATCTAATGGTGATGAGTCC-TATCCTTTTCTCTTCGTTCTCCGT-3') (SEQ ID NO:1) in a 20 μl buffer containing 20 mM Tris-HCl, 10 mM (NH$_4$)$_2$SO$_4$, 10 mM KCl, 2 mM MgSO$_4$, 0.1% Triton X-100, pH 8.8 @25° C., and 2 mM MnCl$_2$. The reaction was conducted in an ABI GeneAmp PCR System 9700 with initial incubation at 65° C. for 30 second, followed by 38 cycles of 65° C./30 sec, 45° C./30 sec, 65° C./30 sec. Multiple reactions were carried out and an aliquot of the reaction mixture was desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide and THP (Tris-hydroxypropyl-phosphine) was used to remove the Rox-tBu-SS group from the 3' end of the DNA extension product to regenerate the 3'-OH group in preparation for the next extension reaction. The cleavage reaction was carried out by incubating the extension reaction mixture with THP at 5 mM final concentration and incubating at 65° C. for 5 minutes.

The reaction mixture after THP treatment was purified by reverse phase HPLC on an XTerra MS C18, 2.5 μm 4.6 mm×50 mm column (Waters, MA) to obtain the pure cleavage product. Mobile phase: A, 8.6 mM triethylamine/100 mM1,1,1,3,3,3-hexafluoro-2-propanol in water (pH 8.1); B, methanol. Elution was performed at 40° C. with a 0.5 mL/min flow rate with a linear gradient from 88% A/12% B to 65.5% A/34.5% B for 90 min. The purified product was used in the subsequent extension reaction.

Since there are two consecutive Ts on the DNA template after the DNA primer binding site, the second extension reaction was carried out in the same way as the first extension reaction. The overall results are shown in FIG. 33 MALDI TOF MS of the primers after each step demonstrate accurate incorporation of 3'-Rox-SS-dATP, efficient cleavage of SS bond and recovering of 3'OH, and incorporation of another 3'-Rox-SS-dATP.

Figure 34A:
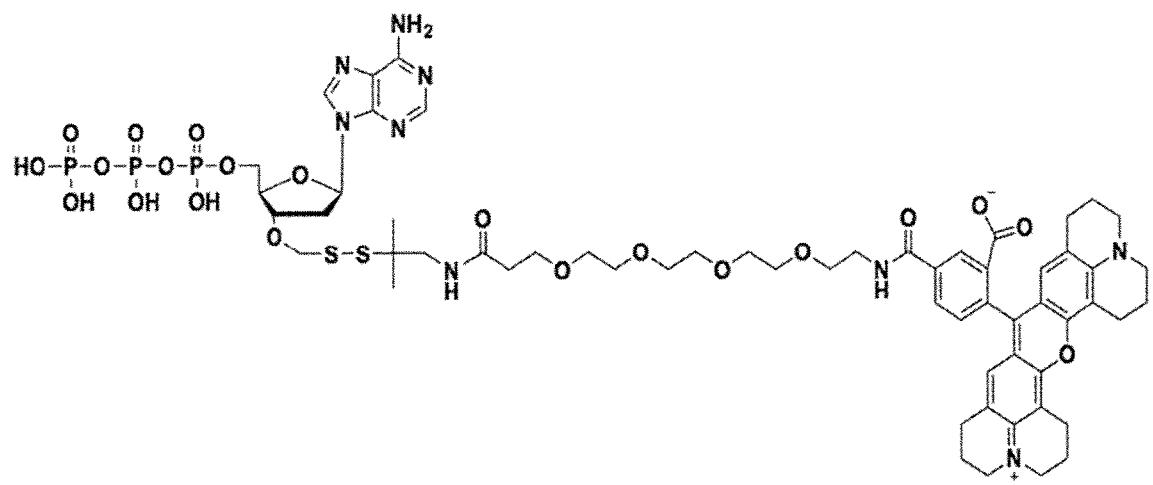
FIGS. 34A-34C. DNA polymerase extension and cleavage using 3'-O-Rox-PEG$_4$-DTM-dATP as a reversible terminator. MALDI-TOF MS spectra of the extension product and the cleavage product.
Figure 34B:
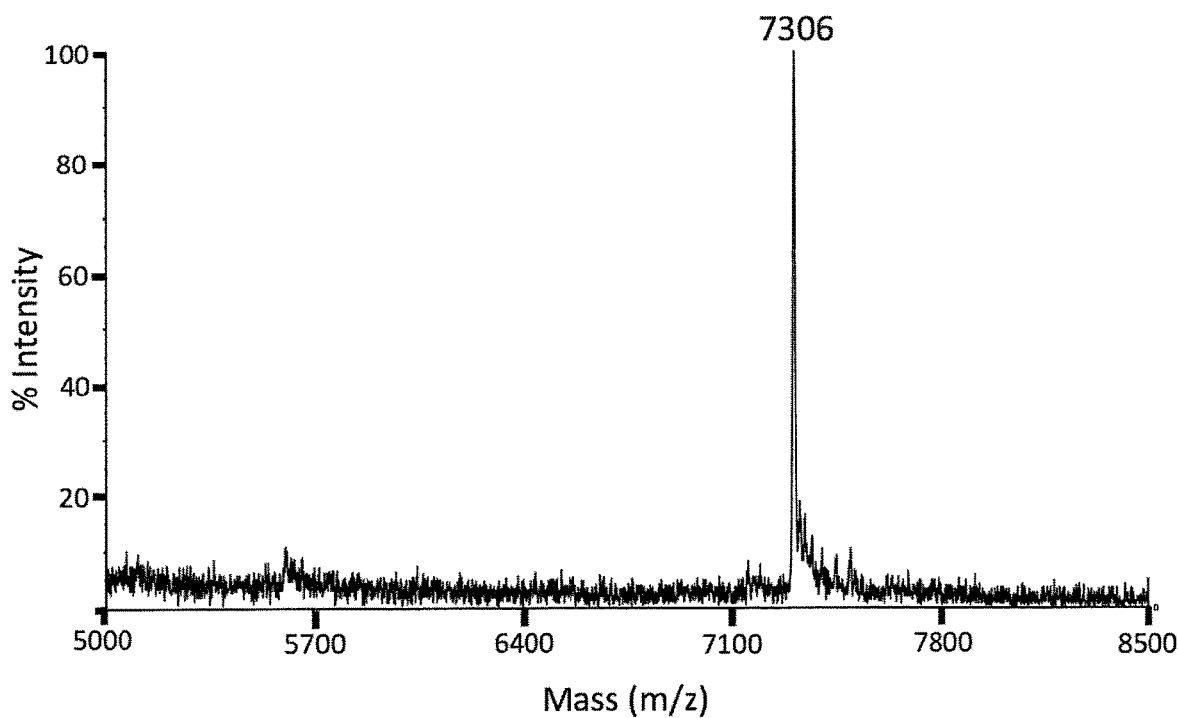
Figure 34C:
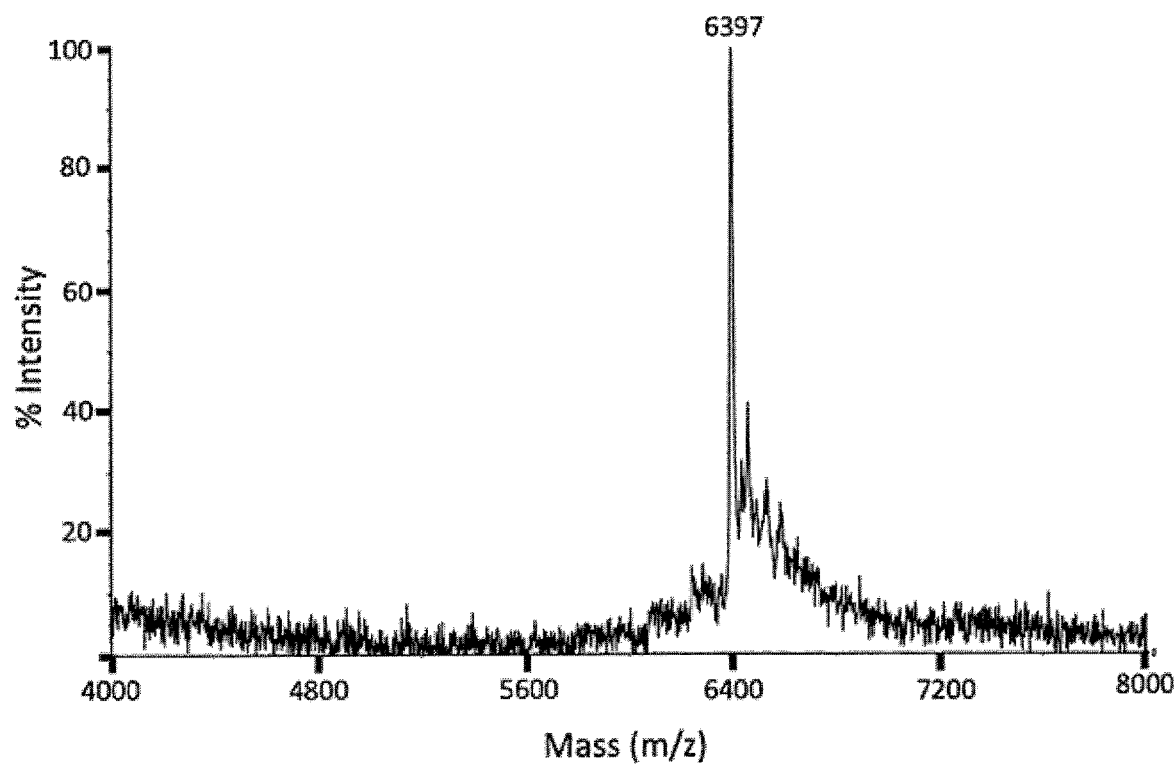

DNA Polymerase Extension Using 3'-O-Rox-PEG$_4$-DTM-dATP Reversible Terminator, Cleavage Reaction Using THP. And Characterization by MALDI-TOF Mass Spectrometry (Results are Shown in FIGS. 34A-34C.

The DNA Polymerase extension was carried out using 200 pmol of reversible terminator (3'-O-Rox-PEG$_4$-DTM-dATP), 2 units of Terminator™ IX DNA Polymerase (NEB), 100 pmol of primer (5'-TAGATGACCCTGCCTTGTCG-3') (SEQ ID NO:2), 60 pmol of DNA template (5'-GAAGGA-GACACGCGGCCAGAGAGGGTCCTGTCCGTGTTTG TGC GTGGAGTTCGACAAGGCAGGGT-CATCTAATGGTGATGAGTCCTATCCTTTTCTCTTC GTTCTCCGT-3') (SEQ ID NO:3) in a 20 μl buffer containing 20 mM Tris-HCl, 10 mM (NH$_4$)$_2$SO$_4$, 10 mM KCl, 2 mM MgSO$_4$, 0.1% Triton X-100, pH 8.8 @25° C., and 2 mM MnCl$_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixture was then desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide and THP was used to remove the blocking group from the 3' end of the DNA extension product to regenerate the 3'-OH group. The cleavage reaction was carried out by incubating the extension reaction mixture with THP at 5 mM final concentration and incubating at 65° C. for 5 minutes.

DNA Polymerase Extension Using Either 3'-O-Bodipy-DTM-dTTP, or 3'-O-Bodipy-PEG$_4$-DTM-dTTP Reversible Terminator, Cleavage Reaction Using THP, and Characterization by MALDI-TOF Mass Spectrometry (Results are Shown in FIGS. 35A-35C and FIGS. 36A-36C Binary structures of DNA bound to 9° N and the closely related KOD DNA polymerase from *Thermococcus kodakaraensis* have been published (Bergen K, Betz K, Welte W, Diederichs K, Marx A. Structures of KOD and 9oN DNA polymerases complexed with primer template duplex. *ChemBioChem*. 2013; 14(9):1058-1062.) and these authors have speculated on the reasons these enzymes may be more tolerant toward modified nucleotides. The minor groove appears to be relatively less sterically hindered than family A polymerases, perhaps explaining their relative ease of the former in utilizing nucleotides with small C4' modifications. Similarly, there may be a more accessible major groove, which could explain the ability of these enzymes to accept nucleotides with bulky modifications at the C5 position of pyrimidines and the C7 position of 7-deazapurines. Unfortunately, crystal structures of ternary complexes with the archaeal family B polymerases have yet to be obtained, so little can be said with certainty regarding the positions around an incoming nucleotide, and crystals of the mutated versions of the 9° N (e.g., Therminator III and IX) have not been published. We have successfully used several of the 9° N polymerase mutants to incorporate deoxynucleotide analogues with a wide variety of sometimes quite substantial modifications on the terminal phosphate (Therminator γ (Kumar S, Tao C, Chien M, et al. PEG-Labeled Nucleotides and Nanopore Detection for Single Molecule DNA Sequencing by Synthesis. Scientific Reports. 2012; 2:684. doi: 10.1038/srep00684., Fuller C W, Kumar S, Porel M, et al. Real-time single-molecule electronic DNA sequencing by synthesis using polymer-tagged nucleotides on a nanopore array. Proceedings of the National Academy of Sciences of the United States of America. 2016; 113(19):5233-5238. doi:10.1073/pnas.1601782113) and base (9° N polymerase (exo-) A485L/Y409V (Guo J, Xu N, Li Z, et al. Four-color DNA sequencing with 3'-O-modified nucleotide reversible terminators and chemically cleavable fluorescent dideoxynucleotides. Proceedings of the National Academy of Sciences of the United States of America. 2008; 105(27):9145-9150. doi:10.1073/pnas.0804023105, Ruparel et al 20105) and Therminator II) as well as a broad range of modifications at the 3' oxygen of the sugar (Therminator III and more recently Therminator IX).

The DNA Polymerase extension was carried out using 200 pmol of reversible terminator (3'-O-Bodipy-DTM-dTTP, or 3'-O-Bodipy-PEG$_4$-DTM-dTTP), 2 units of Terminator™ IX DNA Polymerase (NEB), 100 pmol of primer (5'-GATAGGACTCATCACCA-3'), (SEQ ID NO:4) 60 pmol of DNA template (5'-GAAGGAGACACGCGGCCAGAGAGGGTCCTGTCCGTGTTTGTGCGTGGAGTTCGACA AGGCAGGGTCATCTAATGGTGATGAGTCC-TATCCTTTTCTCTTCGTTCTCCGT-3') (SEQ ID NO:5) in a 20 µl buffer containing 20 mM Tris-HCl, 10 mM (NH$_4$)$_2$SO$_4$, 10 mM KCl, 2 mM MgSO$_4$, 0.1% Triton X-100, pH 8.8 @25° C., and 2 mM MnCl$_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixture was desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide in the extension reaction mixture and THP was used to remove the blocking group from the 3' end of the DNA extension product to regenerate the 3'-OH group. The cleavage reaction was carried out by incubating the extension reaction mixture with THP at 5 mM final concentration and incubating at 65° C. for 5 minutes. The reaction mixture was desalted using a C18 ZipTip column (Millipore, MA) and analyzed by MALDI-TOF MS (ABI Voyager DE).

References for Example 1: 1. Hyman E. D. (1988) A new method of sequencing DNA. Anal Biochem 174(2): 423-436., 2. Ronaghi M, Uhlén M, Nyré-n P (1998) A sequencing method based on real-time pyrophosphate. Science 281 (5375): 363-365., 3. Ju J, Li Z, Edwards J. R., Itagaki Y (2003) U.S. Pat. No. 6,664,079., 4. Li Z, et al. (2003) A photocleavable fluorescent nucleotide for DNA sequencing and analysis. Proc. Natl. Acad. Sci. USA, 100(2): 414-419., 5. Braslavsky I, Hebert B, Kartalov E, Quake S (2003) Sequence information can be obtained from single DNA molecules. Proc. Natl. Acad. Sci. USA 100(7): 3960-3964., 6. Ruparel H, et al. (2005) Design and synthesis of a 3'-O-allyl photocleavable fluorescent nucleotide as a reversible terminator for DNA sequencing by synthesis. Proc. Natl. Acad. Sci. USA 102(17): 5932-5937., 7. Margulies M, et al. (2005) Genome sequencing in microfabricated high-density picolitre reactors. Nature 437(7057): 376-380., 8. Ju J, et al. (2006) Four-color DNA sequencing by synthesis using cleavable fluorescent nucleotide reversible terminators. Proc. Natl. Acad. Sci. USA 103(52): 19635-19640., 9. Wu J, et al. (2007) 3'-O-modified nucleotides as reversible terminators for pyrosequencing. Proc. Natl. Acad. Sci. USA 104(104): 16462-16467., 10. Guo J, et al. (2008) Four-color DNA sequencing with 3'-O-modified nucleotide reversible terminators and chemically cleavable fluorescent dideoxynucleotides. Proc. Natl. Acad. Sci. USA 105(27): 9145-9150., 11. Bentley D. R., et al. (2008) Accurate whole human genome sequencing using reversible terminator chemistry. Nature 456(7218): 53-59., 12. Harris T. D., et al. (2008) Single-molecule DNA sequencing of a viral genome. Science 320(5872): 106-109., 13. Eid J, et al. (2009) Real-time DNA sequencing from single polymerase molecules. Science 323(5910): 133-138., 14. Rothberg J. M., et al. (2011) An integrated semiconductor device enabling non-optical genome sequencing. Nature 475(7356): 348-352., 15. Palla M, et al. (2014). DNA sequencing by synthesis using 3'-O-azidomethyl nucleotide reversible terminators and surface-enhanced Raman spectroscopic detection. RSC Adv. January 1; 4(90): 49342-49346., 16. Hutter D, et al. (2010) Labeled nucleoside triphosphates with reversibly terminating aminoalkoxy groups. Nucleosides Nucleotides & Nucleic Acids 29: 879-895., 17. Knapp D. C., et al. (2011) Fluoride-Cleavable, Fluorescently Labeled Reversible Terminators: Synthesis and Use in Primer Extension. Chem. Eur. J., 17, 2903-2915., 18. Kwiatkowski M. (2007) Compounds for protecting hydroxyls and methods for their use. U.S. Pat. No. 7,279,563., 19. Muller S, Matthaus J. (2011) Method for producing trinucleotides. Patent Application WO 2011061114., 20. Semenyuk A, et al. (2006) Synthesis of RNA using 2'-O-DTM protection. JACS, 128, 12356-12357; Ju J, et al (2016) Raman Cluster Tagged Molecules for Biological Imaging. US Patent 20160024570; Ju J, et al (2015) DNA Sequencing by Synthesis Using Raman and Infrared Spectroscopy Detection. US Patent Application 20150080232.

Example 2: Sequencing by Synthesis Methods Using 3'-O-Modified Nucleotide Analogues Fluorescence-based DNA sequencing-by-synthesis methods have many advantages in terms of detection sensitivity. However, because of the large size of the fluorophores, specific polymerase and reaction conditions need to be optimized for sequencing reactions. In addition, the current cleavable fluorescent nucleotide reversible terminators used in SBS leave a modified group, or scar, on the base of the growing DNA strand after cleavage of the fluorophore, which in turn limits read length.

Fluorescent NRTs with the following blocking groups at the 3'-OH have been reported: 3'-O-allyl-dNTP(Bentley (2008)), 3'-O-azidomethyl-dNTPs (Wu (2007); Guo (2008); Bentley (2008)), 3'-O—NH$_2$-dNTPs (Hunter (2010)), and 3'-O-cyanoethyl-dNTPs (Knapp (2011)), which can be cleaved by Pd(0), tris(2-carboxyethyl)phosphine (TCEP), dilute nitrous acid and fluoride, respectively, to generate the free 3'-OH group.

Various modifications based on 3'-O-alkyldithiomethyl (3'-O-DTM) for the nucleosides (Kwiatkowski (2007); Muller (2011); Semenyuk (2010)) have been reported for the synthesis of oligonucleotides. The stability and reductive cleavage leading to hydroxyl production from the O-DTM group has also been established (Kwiatkowski (2007); Muller (2011); Semenyuk (2010)), but their utility in DNA sequencing applications has not been reported. This is because nucleotide analogs with a large fluorescent dye blocking the 3'-OH group were reported to not be incorporated by DNA polymerase in template-directed DNA synthesis.

By the unique chemical design of the cleavable t-butyl-dithiomethyl moiety attached to a fluorescent dye to block the 3'-OH group of the nucleotide, coupled with specific polymerase reaction conditions, it is herein disclosed that the modified 3'-O-dithiomethyl (3'-O-DTM) is a successful reversible linkage group for attaching a fluorescent dye reporter to block the 3'-OH group of the nucleotide for DNA SBS. To this end, herein disclosed are novel 3' reversibly labeled nucleotides as traceless reversible terminators, which were designed and synthesized for DNA SBS. In these novel nucleotide analogs, only the 3'-OH group of the nucleotide is reversibly blocked with a DTM linker, which is attached to the fluorescent label, thus realizing the dual function of the 3'-O-modification of the nucleotide, serving as both the reversible terminator function and the cleavable fluorescence reporter (FIG. 1 and FIGS. 2A-2E).

It is further disclosed herein, that in SBS cycles, such 3'-O-Dye-DTM-dNTPs are well recognized by the DNA polymerase, Therminator (9° N DNA polymerase variant), as substrates and incorporated into the growing DNA strand. After determining the identity of the incorporated nucleotide by its fluorescent signal, TCEP or Tris(3-hydroxypropyl)phosphine (THP) treatment cleaves the disulfide bond in the DMT moiety leading to both the removal of the fluorescence reporter and the regeneration of the 3'-OH group (FIGS. 3A-3B) to allow for continuous sequencing. After each incorporation and cleavage, an extended natural DNA strand is produced to allow for the seamless incorporation of incoming complementary 3'-O-Dye-DTM-dNTPs during SBS.

There are surprising advantages to using 3'-O-Dye-DTM-dNTPs for SBS. As disclosed herein, consecutive polymerase extension reaction using 3'-O-Dye-DTM-dNTPs with a synthetic template and primer have been carried out. After single base extension and cleavage of the DTM moiety and the removal of dye from the 3'-O of the DNA extension product, the resulting primer extension product can be further extended with an additional 3'-O-Dye-DTM-dNTP, leading to a high-yield incorporation with accurate sequence determination. Because these 3'-O-Dye-DTM-dNTPs do not require the attachment of fluorescent labels on the base, their synthesis is simpler and therefore more cost effective. In addition, the extended DNA strand is identical to natural DNA. The use of 3'-O-Dye-DTM-dNTPs will lead to very long, accurate read lengths for SBS.

Disclosed herein, and explained in greater detail below, are a variety of new DNA sequencing methods based on the combinatorial use of 3'-O-CleavableLinker-Label-dNTPs, 3'-O-CleavableLinker-Anchor-dNTPs and 3'-O-Cleavable-Group-dNTPs and their orthogonal reporter dye labeled binding molecule counterparts or cleavable reporter. Use of 3'-O-Dye-SS(DTM)-dNTPs, 3'-O-anchor-SS(DTM)-dNTPs and 3'-O-SS(DTM)-dNTPs along with orthoganal binding molecules conjugated with fluoroscent dyes (or conjugated with fluoroscent dyes using different cleavable linkages) allows the construction of a wide spectrum of new methods for four-color, two-color and one-color DNA SBS at the single molecule level or the ensemble level.

Figure 3A:
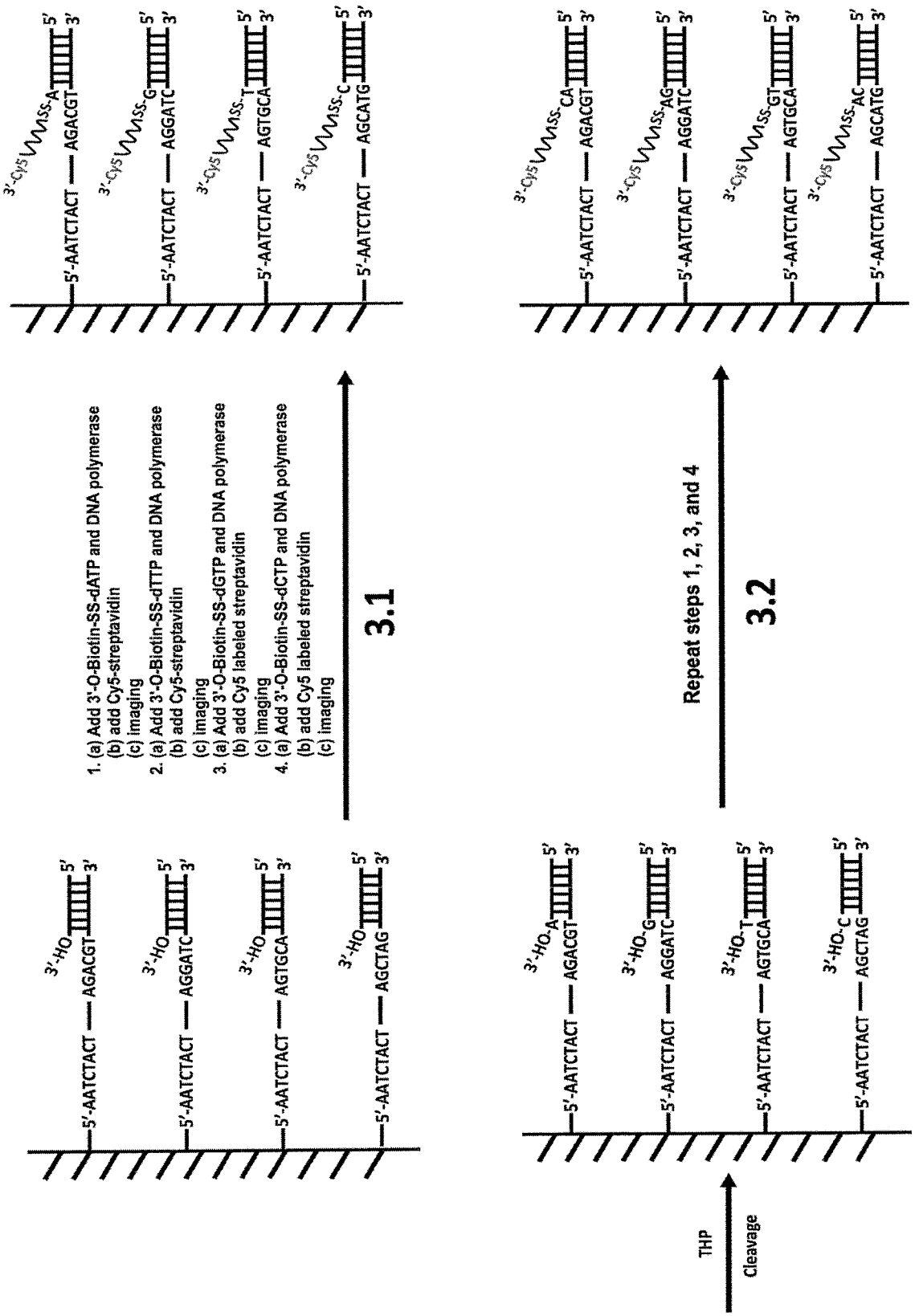
Figure 3B:
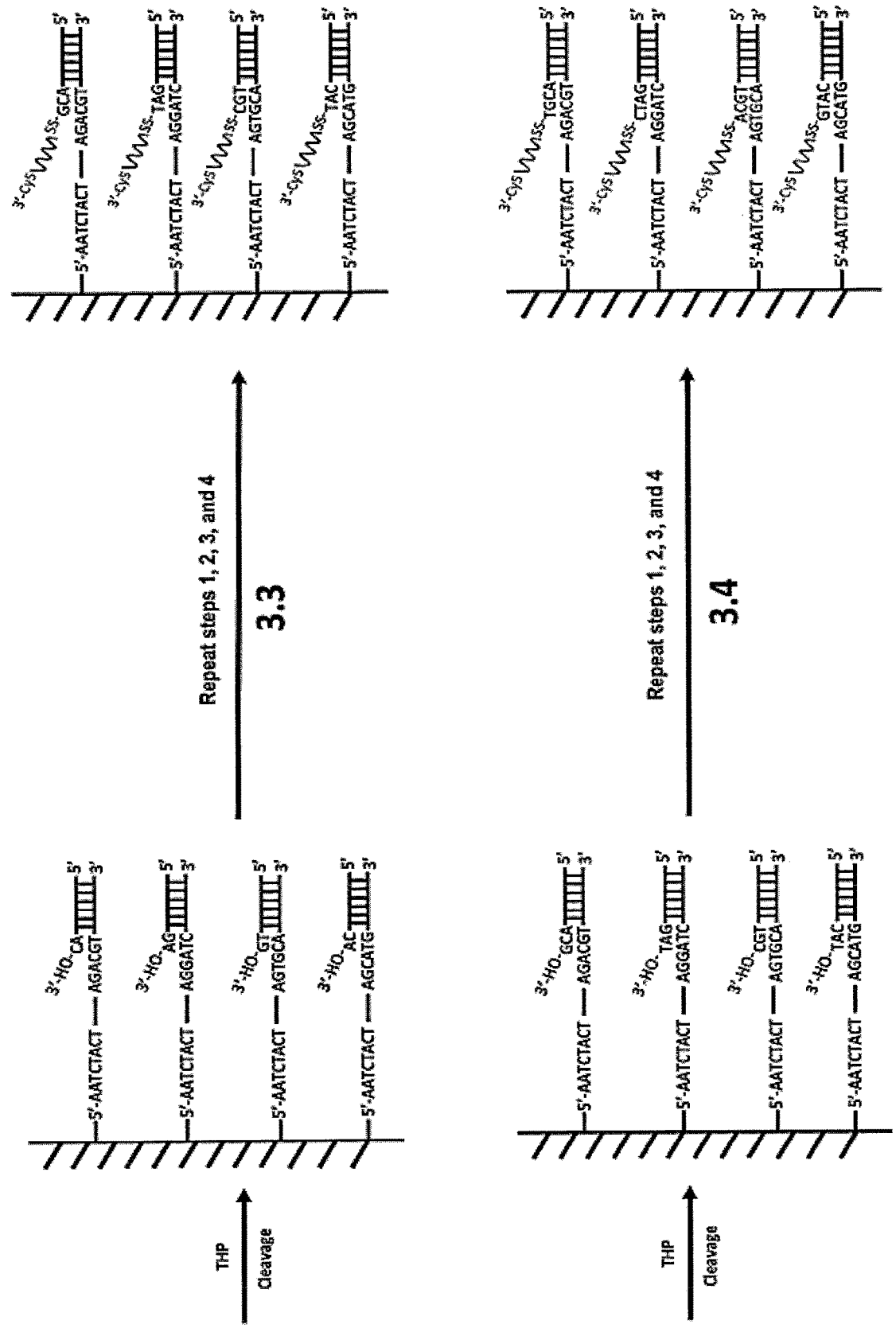

Example A: One-Color DNA SBS (FIGS. 3A-3B)

Scarless one-color SBS using 3'-O-Biotin-SS(DTM)-dNTPs and Cy5 labeled streptavidin (FIGS. 2A-2E). DNA polymerase incorporation reaction is conducted by using one of the four 3'-O-Biotin-SS-dNTPs, followed by the addition of the Cy5 labeled streptavidin and imaging to determine DNA sequences as described in STEP 1 through STEP 4 (as shown in FIGS. 3A-3B). Each step consists of three parts: (PART a) Polymerase and one of the four 3'-O-Biotin-SS-dNTPs are added followed by washing; if the added nucleotide is complementary to the nucleotide on the template immediately next to the 3' end of the primer, then the added nucleotide will incorporate into the primer to produce a DNA extension product that has a Biotin at the 3' end. (PART b) Cy5 labeled streptavidin is added, which will bond to the Biotin at the 3' end of the DNA extension product. (PART c) After washing away the unbound Cy5 labeled streptavidin, imaging is performed to detect the Cy5 signal for the identification of the incorporated nucleotide. Following STEP 4, addition of THP to the DNA extension products will cleave the disulfide bond and regenerate a free 3'-OH group on the 3' end of the DNA extension products. The process is sequentially repeated, consisting of STEP 1 through STEP 4, followed by THP cleavage, for continuing sequence determination.

Figure 7:
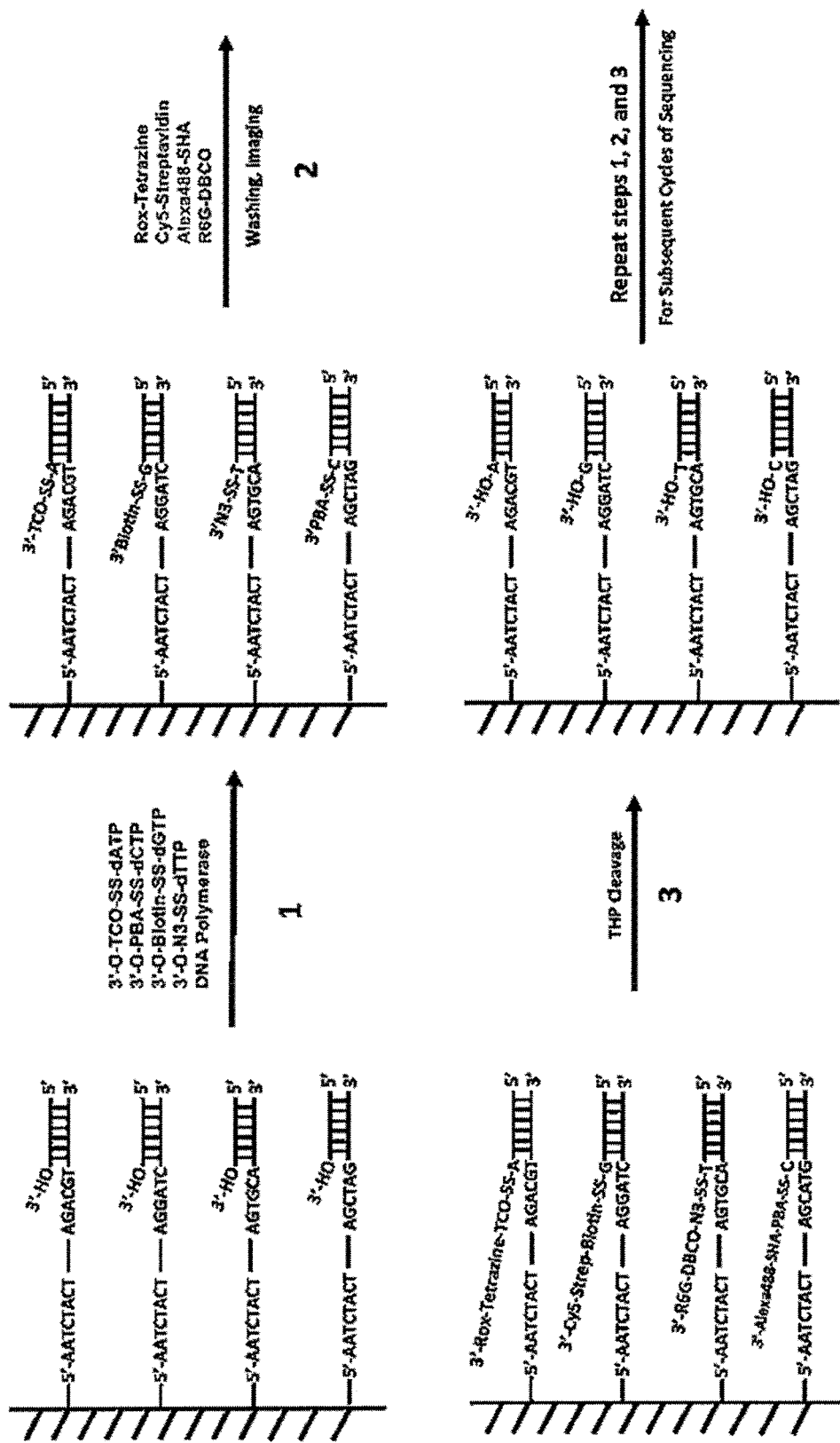
FIG. 7. Scarless SBS using 3'-O-"anchor"-SS(DTM)-dNTPs (3'-O-TCO-t-Butyldithiomethyl(SS)-dATP, 3'-O-PBA-t-Butyldithiomethyl(SS)-dCTP, 3'-O-Biotin-t-Butyldithiomethyl(SS)-dGTP, 3'-O-Azido-t-Butyldithiomethyl(SS)-dTTP) and four correspondingly-matched dye labeled binding molecules (Rox-Labeled Tetrazine, Alexa488-Labeled SHA, Cy5-Labeled Streptavidin, and R6G-Labeled Dibenzocyclooctyne). Addition of the DNA polymerase and the four 3'-O-"anchor"-SS(DTM)-dNTPs (3'-O-TCO-SSdATP, 3'-O-PBA-SS-dCTP, 3'-O-Biotin-SS-dGTP and 3'-O—N₃-SS-dTTP) to the immobilized primed DNA template enables the incorporation of the complementary nucleotide analogue to the growing DNA strand to terminate DNA synthesis. After washing away the unincorporated nucleotide analogues, add the dye labeled binding molecules, which will specifically connect with each of the four unique "anchor" moieties at the 3'-end of each DNA extension product to enable the labeling of each DNA product terminated with each of the four nucleotide analogues (A, C, G, T) with the four distinct fluorescent dyes. Detection of the unique fluorescence signal from each of the fluorescent dyes on the DNA products allows for the identification of the incorporated nucleotide. Next, treatment of the DNA products with THP cleaves the SS linker, leading to the removal of the fluorescent dye and the regeneration of a free 3'-OH group on the DNA extension product, which is ready for next cycle of DNA sequencing reaction (as shown in the subsequent steps of FIG. 7). The text over the arrows is as follows: 1. 3'-O-TCO-SS-dATP, 3'-O-PBA-SS-dCTP, 3'-O-Biotin-SS-dGTP, 3'-O-N3-SS-dTTP, DNA Polymerase. 2. Rox-Tetrazine, cy5-Streptavidin, Atexa488-SHA, R6G-DBCO, Washing, Imaging. 3. THP Cleavage. 4. Repeat steps 1, 2 and 3 For Subsequent Cycles of Sequencing.

Example B. Four-Color DNA SBS (FIG. 7)

Figure 4:
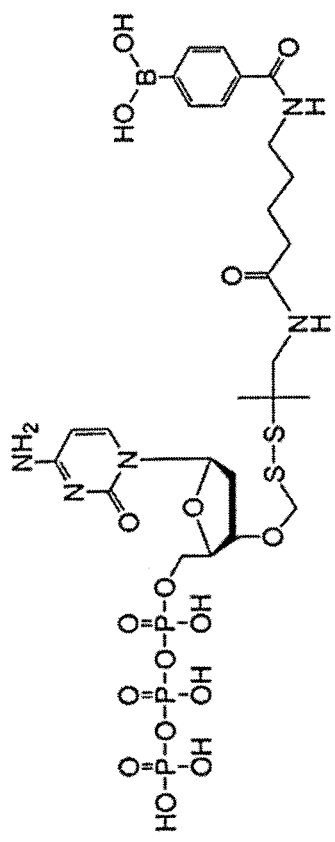
FIG. 4. Structures of 3'-O-"Anchor"-SS(DTM)-dNTPs (3'-O-TCO-t-Butyldithiomethyl-dATP, 3'-O-PBA-t-Butyldithiomethyl-dCTP, 3'-O-Biotin-t-Butyldithiomethyl-dGTP, 3'-O-Azido-t-Butyldithiomethyl-dTTP). In this set of nucleotide analogues, four different "anchor" moieties, TCO, PBA, Biotin and Azido groups, are attached to the 3'-O of dATP, dCTP, dGTP and dTTP, respectively, through the DTM linkage, as shown in this figure.
Figure 4:
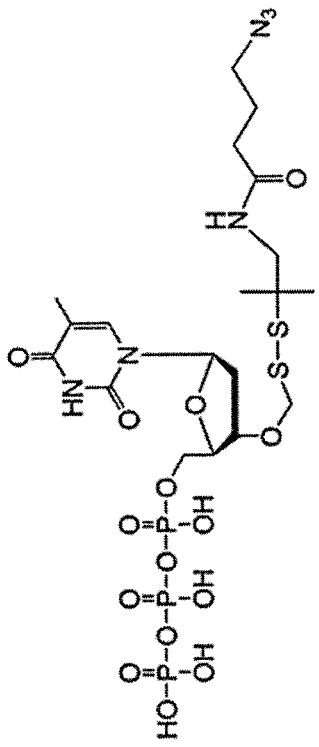
Figure 4:
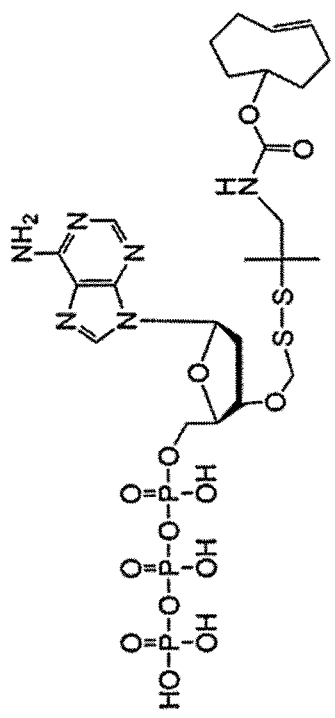
Figure 4:
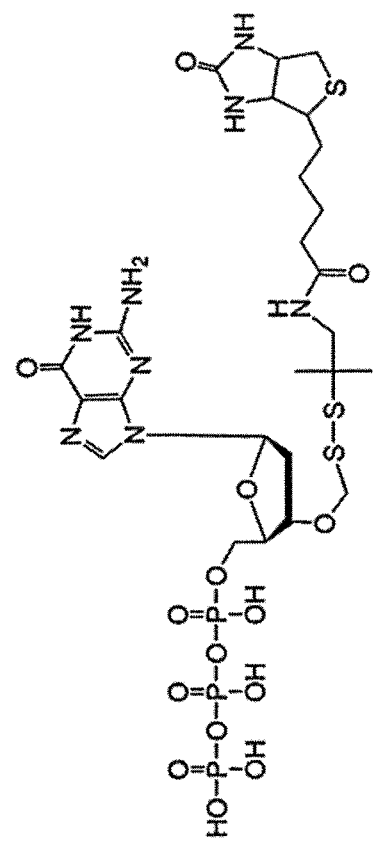
Figure 5:
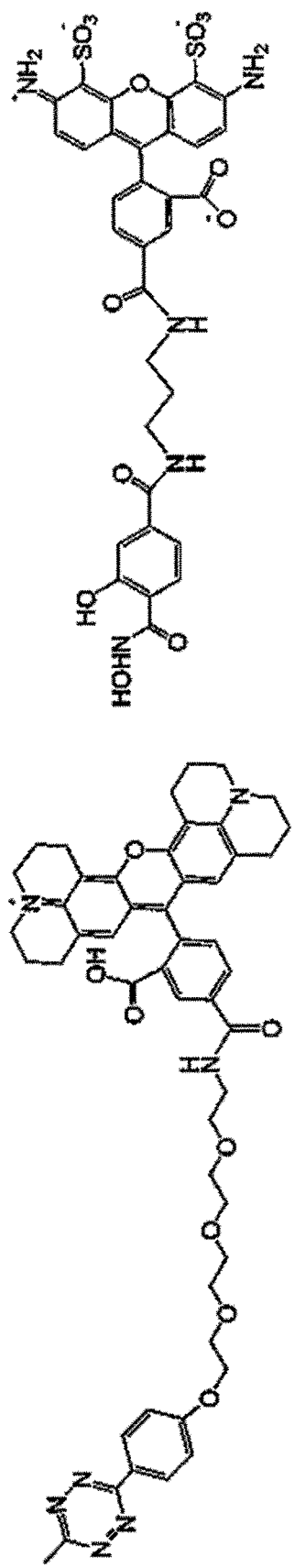
FIG. 5. Structures of four-color labeled orthogonal binding molecules (Rox-Labeled Tetrazine, Alexa488-Labeled SHA, Cy5-Labeled Streptavidin, and R6G-Labeled Dibenzocyclooctyne) that bond specifically with the four "anchor" moieties in the nucleotide analogues (3'-O-TCO-t-Butyldithiomethyl-dATP, 3'-O-PBA-t-Butyldithiomethyl-dCTP, 3'-O-Biotin-t-Butyldithiomethyl-dGTP, 3'-O-Azido-t-Butyldithiomethyl-dTTP) listed in FIG. 4, as follows: Rox is attached to the Tetrazine (which specifically reacts with TCO); Alexa488 is attached to the SHA (which forms a stable complex with PBA); Cy5 is attached to the Streptavidin (which forms a stable complex with Biotin); and R6G is attached to the Dibenzocyclooctyne (DBCO, which quickly forms a Triazole moiety with an $N_3$ group). Thus, each nucleotide analogue listed in FIG. 4 can be labeled by a unique fluorescent dye.
Figure 5:
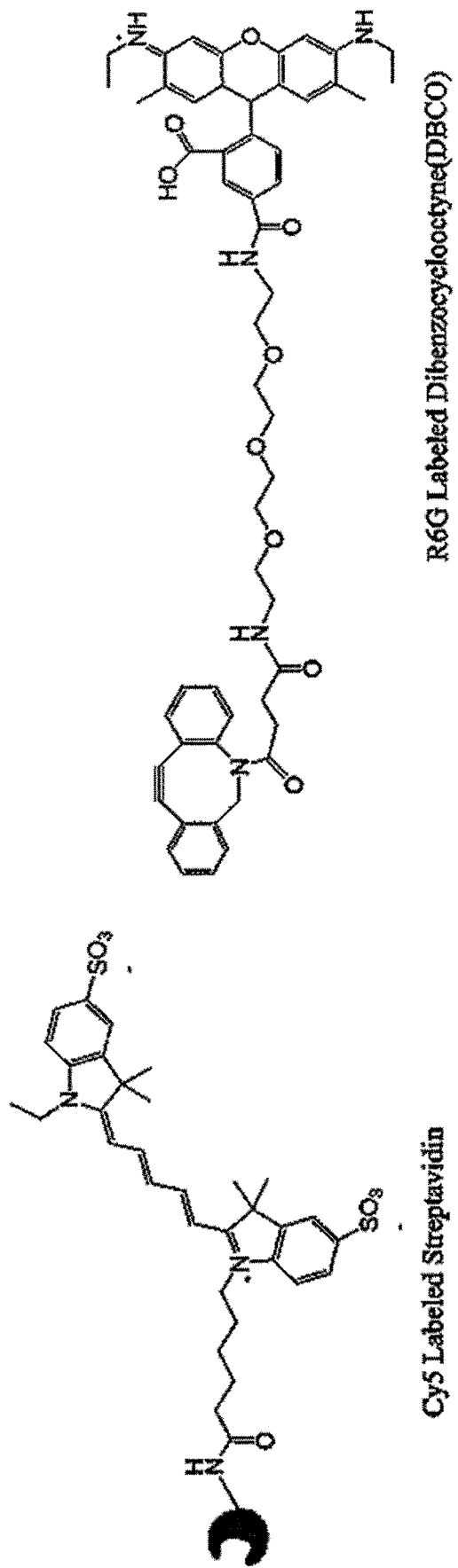
Figure 6C:
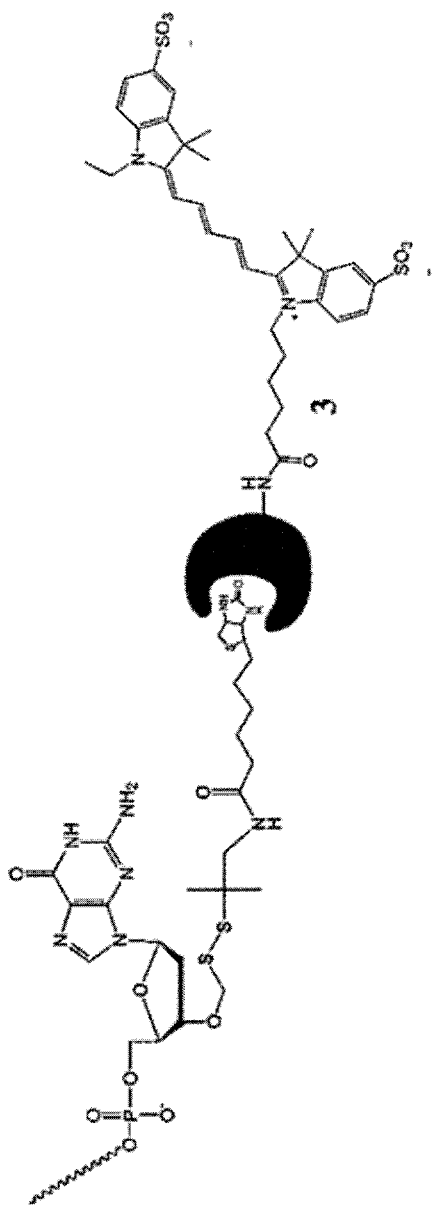
Figure 6D:
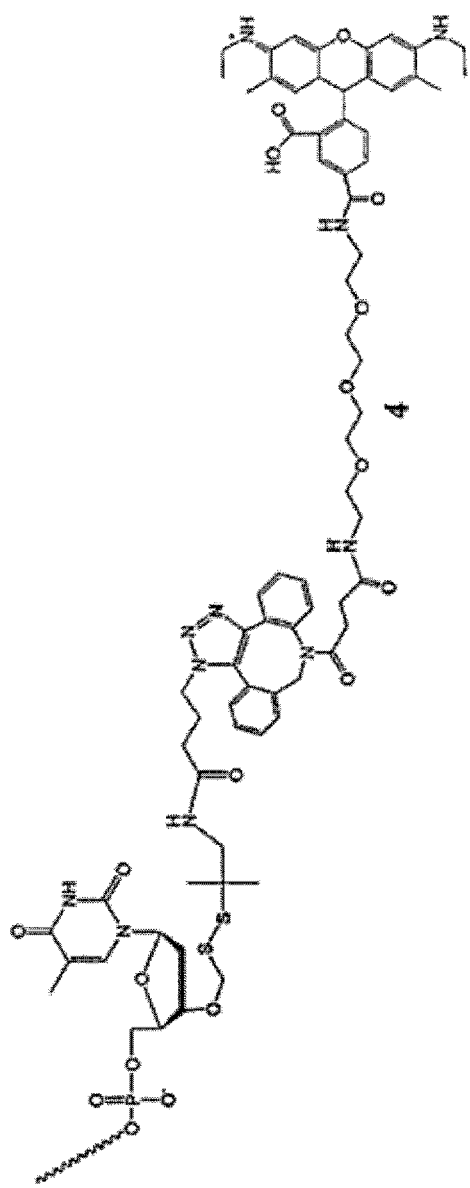

Scarless SBS using 3'-O-"anchor"-SS(DTM)-dNTPs (3'-O-TCO-t-Butyldithiomethyl(SS)-dATP, 3'-O-PBA-t-Butyldithiomethyl(SS)-dCTP, 3'-O-Biotin-t-Butyldithiomethyl(SS)-dGTP, 3'-O-Azido-t-Butyldithiomethyl(SS)-dTTP) (FIG. 4) and four correspondingly matched dye labeled binding molecules (Rox-Labeled Tetrazine, Alexa488-Labeled SHA, Cy5-Labeled Streptavidin, and R6G-Labeled Dibenzocyclooctyne) (FIG. 5). DNA polymerase and the four 3'-O-"anchor"-SS(DTM)-dNTPs (3'-O-TCO-SS-dATP, 3'-O-PBA-SS-dCTP, 3'-O-Biotin-SS-dGTP and 3'-O—N$_3$—SS-dTTP) are added to the immobilized primed DNA template, which enables the incorporation of the complementary nucleotide analogue to the growing DNA strand to terminate DNA synthesis. After washing away the unincorporated nucleotide analogues, the dye labeled binding molecules are added, which will specifically connect with each of the four unique "anchor" moieties at the 3'-end of each DNA extension product to enable the labeling of each DNA product terminated with each of the four nucleotide analogues (A, C, G, T) with the four distinct fluorescent dyes. Detetion of the unique fluorescence signal from each of the fluorescent dyes on the DNA products allows for the identification of the incorporated nucleotide. Next, treatment of the DNA products with THP cleaves the SS linker, leading to the removal of the fluorescent dye and the regeneration of a free 3'-OH group on the DNA extension product, which is ready for next cycle of DNA sequencing reaction (as shown in the subsequent steps of FIG. 7).

FIGS. 6A-6D shows that the formation of the conjugates or complexes between DNA products produced by incorporating 3'-O "anchor" labeled nucleotides (3'-O-TCO-t-Butyldithiomethyl-dATP, 3'-O-PBA-t-Butyldithiomethyl-dCTP, 3'-O-Biotin-t-Butyldithiomethyl-dGTP, 3'-O-Azido-t-Butyldithiomethyl-dTTP) with four correspondingly-matched labeled binding molecules (Rox-Labeled Tetrazine, Alexa488-Labeled SHA, Cy5-Labeled Streptavidin, and R6G-Labeled Dibenzocyclooctyne).

Figure 13A:
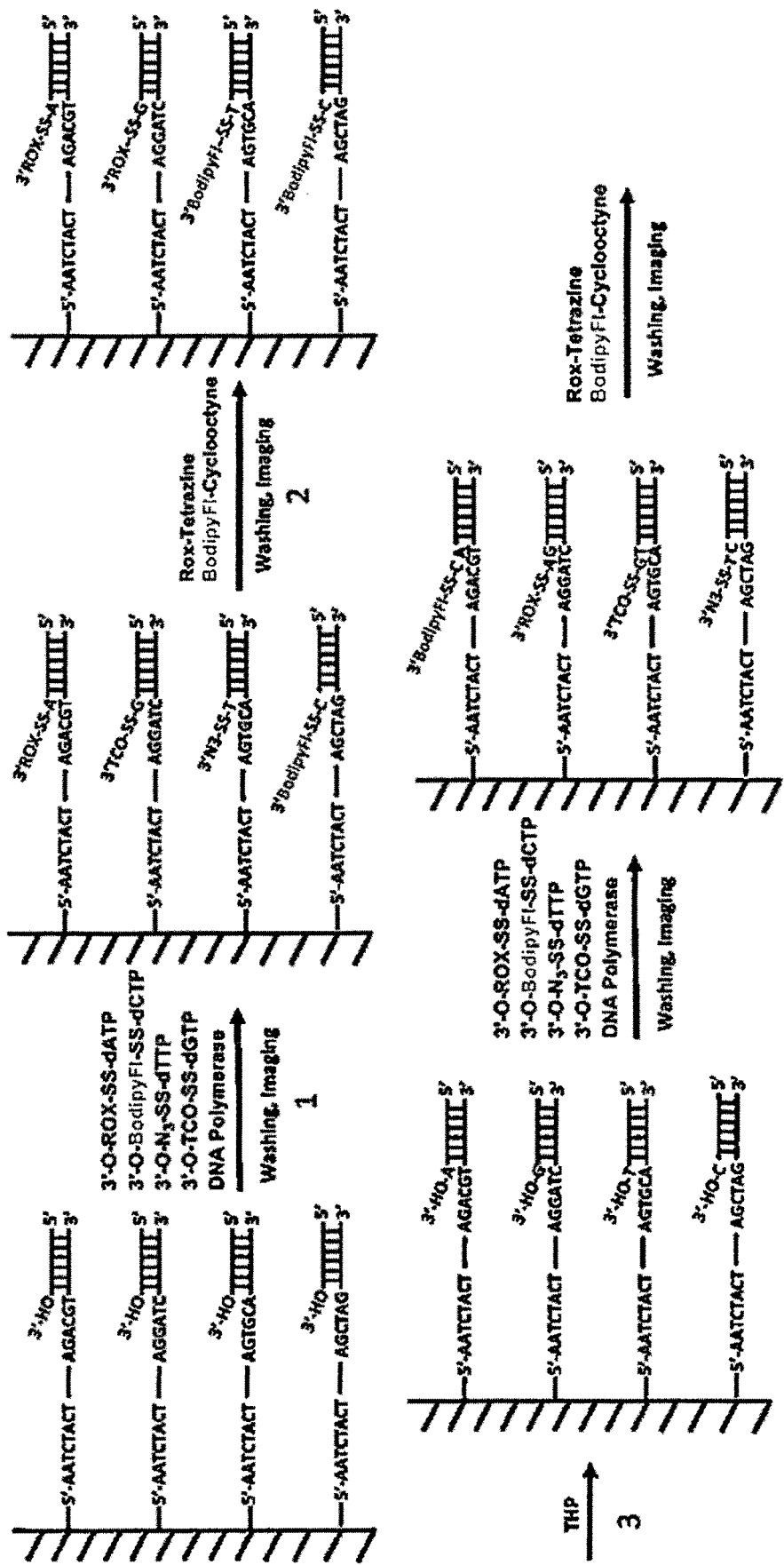
FIGS. 13A-13B. Use of 3'-O-Dye-SS(DTM)-dNTPs (3'-O-Rox-SS-dATP & 3'-O-BodipyFL-SS-dCTP), 3'-O-Anchor-SS(DTM)-dNTPs (3'-O—$N_3$-SS-dTTP & 3'-O-TCO-SS-dGTP) and their corresponding dye labeled binding molecules (Rox-Tetrazine & BodipyFL-Dibenzocyclooctyne) to perform 2-color DNA SBS. Addition of the DNA polymerase and the four nucleotide analogues (3'-O-Rox-SS-dATP, 3'-O-BodipyFL-SS-dCTP, 3'-O—$N_3$-SS-dTTP and 3'-O-TCO-SS-dGTP) to the immobilized primed DNA template enables the incorporation of the complementary nucleotide analogue to the growing DNA strand to terminate DNA synthesis (STEP 1). After washing away the unincorporated nucleotide analogues, detect the fluorescent signal from Rox and BodipyFL to identify the incorporate nucleotide as A (labeled with Rox) and C (labled with BodipyFL). Next, add the dye labeled binding molecules (Rox-Tetrazine & BodipyFL-Dibenzocyclooctyne) to the DNA extension products (STEP 2), which will specifically connect with the two unique "anchor" moieties (TCO and $N_3$) at the 3'-end of each DNA extension product, to enable the labeling of each DNA product terminated with each of the two nucleotide analogues (G and T) with two distinct fluorescent dyes (labeled with Rox for G and labeled with BodipyFL for T). Detection of the unique, newly produced florescence signal from Rox and BodipyFL on the DNA extension products (in addition to the signal from STEP 1), allows for the identification of the newly-incorporated nucleotides as G and T respectively. Next, treatment of the DNA products with THP cleaves the SS linker, leading to the removal of the fluorescent dye and the regeneration of a free 3'-OH group on the DNA extension product (STEP 3), which is ready for the next cycle of DNA sequencing reaction (as shown in the subsequent steps of FIGS. 13A-13B). The text in FIG. 13A is as follows: 3'-O—ROX-SS-dATP, 3'-O-BodipyFL-SS-dCTP, 3'-O—$N_3$-SS-dGTP,3'-O-TCO-SS-dGTP, DNA Polymerase. The text in FIG. 13B is as follows: Repeat steps 1, 2 and 3 For Subsequent Cycles of Sequencing.
Figure 13B:
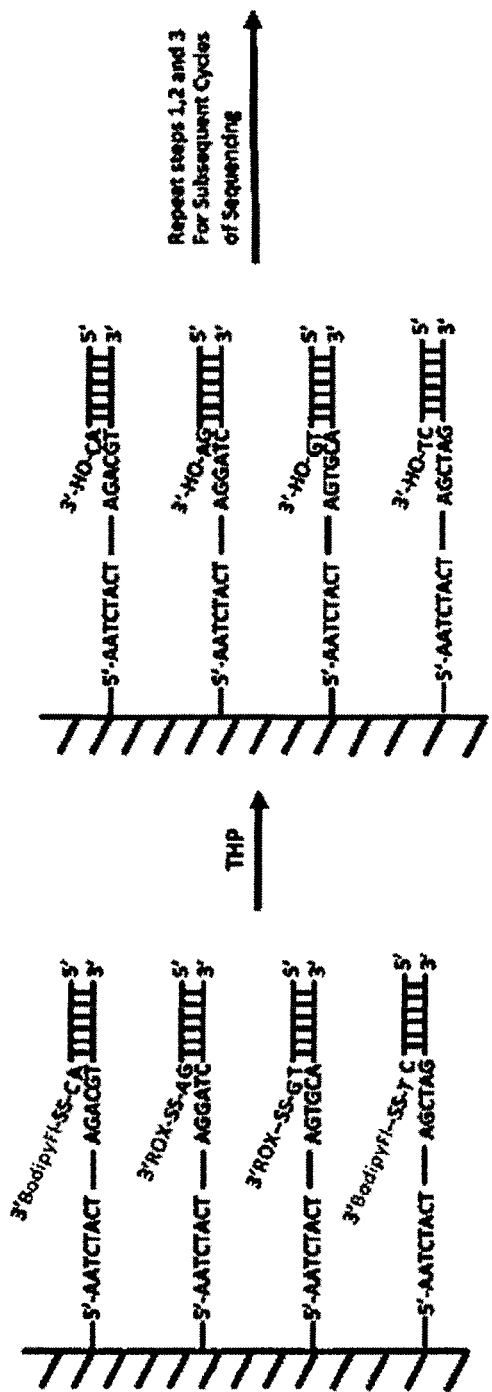

Example C. Two-Color DNA SBS (FIGS. 13A-13B)

Figure 12:
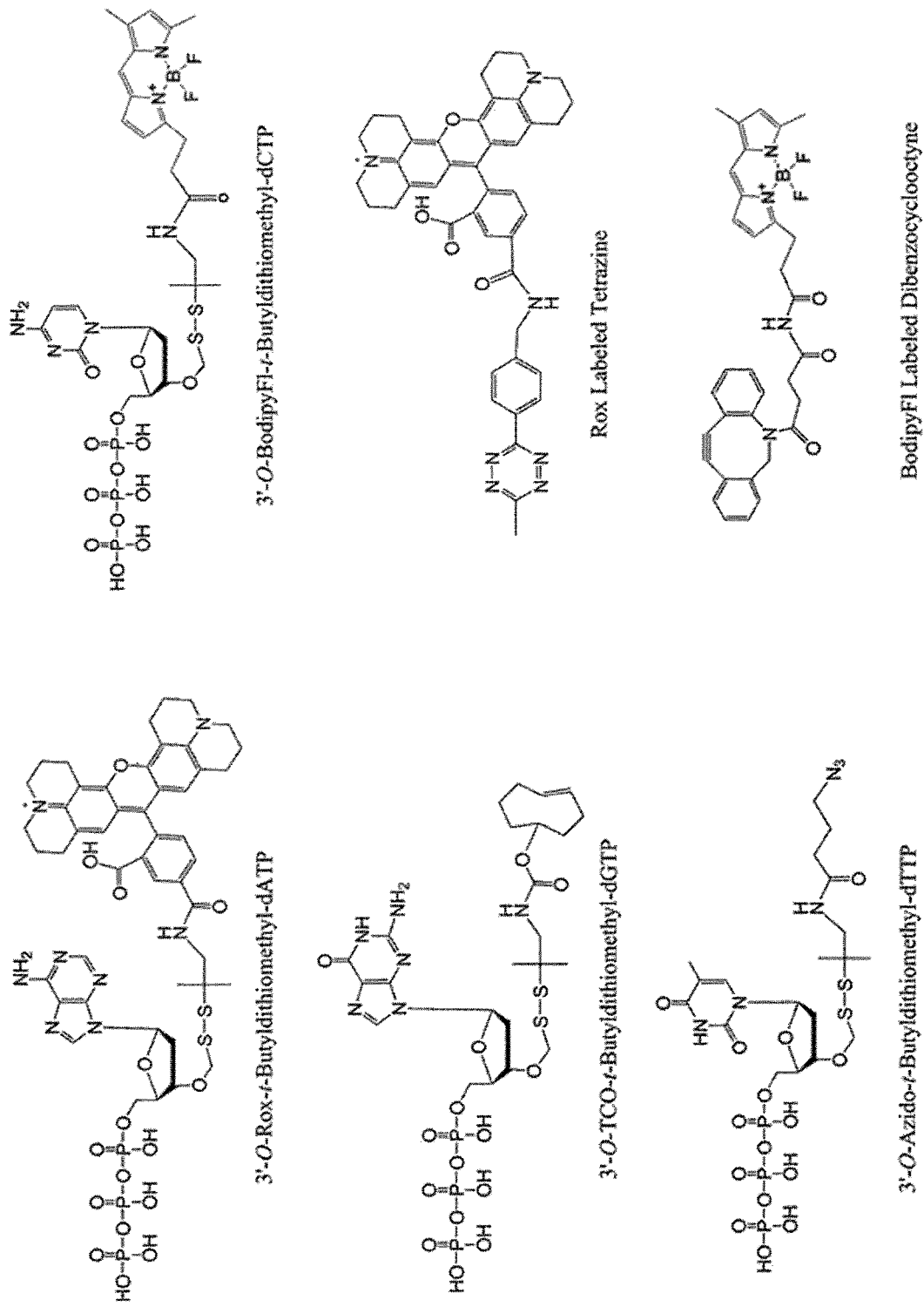
FIG. 12. Example Structures of 3'-O-Dye-SS(DTM)-dNTPs (3'-O-Rox-t-Butyldythiomethyl-dATP & 3'-O-BodipyFL-t-Butyldythiomethyl-dCTP); 3'-O-Anchor-SS(DTM)-dNTPs (3'-O-TCO-t-Butyldythiomethyl-dGTP & 3'-O-Azido-t-Butyldythiomethyl-dTTP), with their corresponding dye labeled binding molecules (Rox Labeled Tetrazine & BodipyFL Labeled Dibenzocyclooctyne).

Use of 3'-O-Dye-SS(DTM)-dNTPs (3'-O-Rox-SS-dATP & 3'-O-BodipyFL-SS-dCTP), 3'-O-Anchor-SS(DTM)-dNTPs (3'-O—N$_3$—SS-dTTP & 3'-O-TCO-SS-dGTP) and their corresponding dye labeled binding molecules (Rox-Tetrazine & BodipyFL-Dibenzocyclooctyne) to perform 2-color DNA SBS (FIG. 12). DNA polymerase and the four nucleotide analogues (3'-O-Rox-SS-dATP, 3'-O-BodipyFL-SS-dCTP, 3'-O—N$_3$—SS-dTTP and 3'-O-TCO-SS-dGTP) are added to the immobilized primed DNA template, which enables the incorporation of the complementary nucleotide analogue to the growing DNA strand to terminate DNA synthesis (STEP 1). After washing away the unincorporated nucleotide analogues, the fluorescent signal from Rox and BodipyFL is detected to identify the incorporated nucleotide as A (labeled with Rox) and C (labled with BodipyFL). Next, the dye labeled binding molecules (Rox-Tetrazine & BodipyFL-Dibenzocyclooctyne) are added to the DNA extension products (STEP 2), which will specifically connect with the two unique "anchor" moieties (TCO and N$_3$) at the 3'-end of each DNA extension product, to enable the labeling of each DNA product terminated with each of the two nucleotide analogues (G and T) with two distinct fluorescent dyes (labeled with Rox for G and labeled with BodipyFL for T). Detection of the unique, newly produced florescence signal from Rox and BodipyFL on the DNA extension products (in addition to the signal from STEP 1), allows for the identification of the newly-incorporated nucleotides as G and T respectively. Next, treatment of the DNA products with THP cleaves the SS linker, leading to the removal of the fluorescent dye and the regeneration of a free 3'-OH group on the DNA extension product (STEP 3), which is ready for the next cycle of DNA sequencing reaction (as shown in the subsequent steps of FIGS. 13A-13B).

Figure 14:
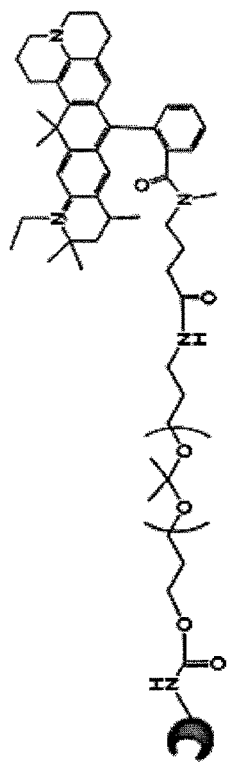
FIG. 14. Structures of Labeled Binding Molecules Conjugated with Fluorescent Dyes via Different Cleavable t-butyldithiomethyl moiety s (which are highlighted in parentheses in this figure). Tetrazine is tethered to ATTO647N via an azo linkage (Tetrazine-Azo(linker)-ATTO647N), which can be cleaved by sodium dithionite ($Na_2S_2O_4$); Streptavidin is tethered to ATTO647N via a dimethylketal linkage (Streptavidin-Dimethylketal(linker)-ATTO647N)), which can be cleaved under weak acidic conditions such as a citric acid buffer (pH 4); SHA is tethered to ATTO647N via a photocleavable nitrobenzyl linkage (SHA-2-Nitrobenzyl(linker)-ATTO647N), which can be cleaved by photoirradiation; DBCO is tethered to ATTO647N via an allyl linkage (Dibenzocyclooctyne-Allyl (linker)-ATTO647N), which can be cleaved by Pd(0); DBCO can also be tethered to ATTO647N via Dde linkage (Dibenzocyclooctyne-Dde(linker)-ATTO647N), which can be cleaved by hydrazine. ATTO647N labeled Streptavidin (Streptavidin-ATTO647N) can also be used in combination with three other binding molecules conjugated with fluoroscent dyes via different cleavable t-butyldithiomethyl moietys.
Figure 14:
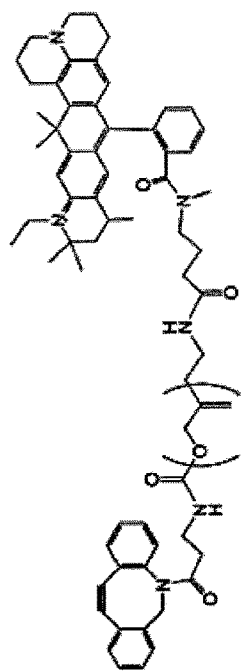
Figure 14:
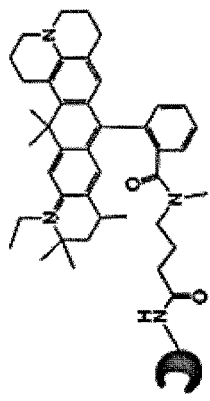
Figure 14:
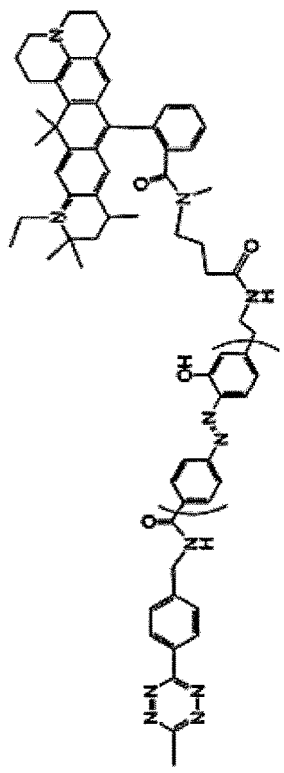
Figure 14:
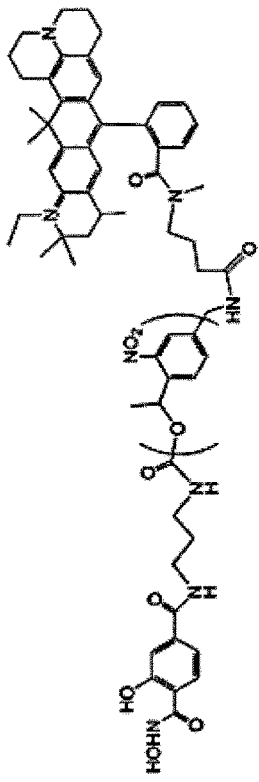
Figure 14:
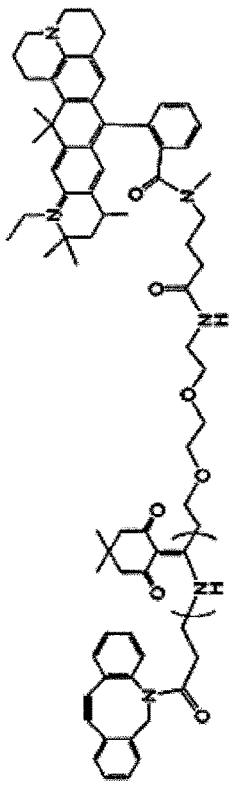

Use of 3'-O-CleavableLinker-Label-dNTPs, 3'-O-CleavableLinker-Anchor-dNTPs and 3'-O-CleavableGroup-dNTPs combined with labeled binding molecules that are conjugated with fluoroscence dyes via different cleavable linkage allows the construction of one-color SBS at the single molecule or the ensemble molecule levels. After incorporating the 3'-anchor-DTM-dNTPs and the 3'-DTM-dNTP, treatment with orthogonal labeled binding molecules conjugated with fluorescence dyes (ATTO647N, Cy5, Rox, etc.) via different cleavable linkages (Azo, Dde, Nitrobenzyl, Dimethylketal, etc.) (FIG. 14) results in the labeling of all incorporated 3'-anchor nucleotides at the 3'-end of the DNA extension products due to the specific anchor-binding molecule reaction. Sequential and specific cleavage, followed by imaging, are carried out to remove the dye from the 3'-end of the DNA extension products, allowing signal changes to be accurately detected. Each cleavage method only cleaves one type of the linkage which is uniquely attached to one of the labeled binding molecules, therefore each cleavage method can be used to encode one of the DNA bases on their corresponding 3'-O-anchor moiety for that particular nucleotide analogue. In general, only three of the four DNA bases (A, C, G, T) are required to have a label for selective detection. Once the first three of these bases are labeled, the fourth one does not require a label to be differentiated from the other three for sequence determination, as exemplified in the following schemes.

Figure 16A:
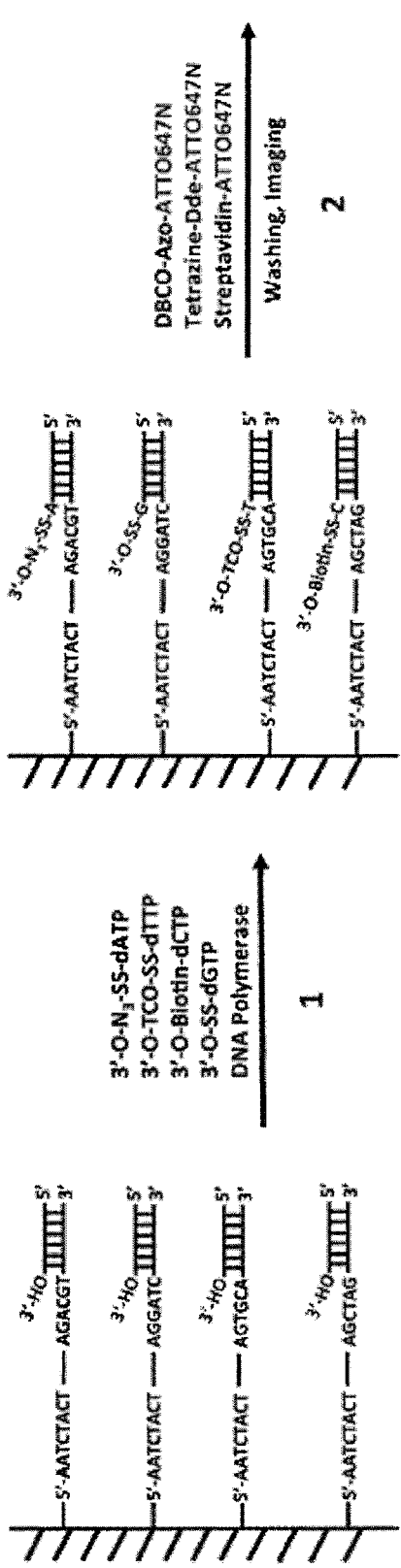
FIGS. 16A-16C. (1) In presence of DNA polymerase, three 3'-anchor nucleotides [3'-SS(DTM)N3-dATP, 3'-SS (DTM)TCO-dTTP, 3'-SS(DTM)Biotin-dCTP] and 3'-tButyl-SS(DTM)-dGTP, as shown in FIG. 15] are added to the primed DNA templates to allow incorporation into the primer; (2) Attach the fluorescent label (ATTO647N, for example) by adding DBCO-Azo-(-N=N-Linker)-ATTO647N, Tetrazine-Dde(Linker)-ATTO647N, Streptavidin-ATTO647N (as shown in FIG. 15) to the DNA extension products that contain the incorporated 3'-anchor nucleotide analogues, which leads to the labeling of all the incorporated nucleotides (except G) at their 3'-end due to specific anchor-binding molecule interaction; (3) After washing, the first round of imaging is performed, and the DNA products terminated with A, C and T all display the same color, while the DNA products that do not emit a signal is terminated by a nucleotide G; (4) The first cleavage (I) is conducted by treatment with sodium dithionite ($Na_2S_2O_4$), which only cleaves the azo linkage to remove the fluorescent dye from the DNA products terminated with the A nucleotide. The second round of imaging is performed. If the fluorescent signal disappears after the cleavage I, the DNA products are determined as having incorporated an A nucleotide; (5) The second cleavage (II) is conducted by treatment with hydrazine ($N_2H_4$), which will cleave the Dde linkage to remove the fluorescent dye from the DNA products terminated with the T nucleotide. The third round of imaging is performed. If the fluorescent signal disappears after the cleavage II, the DNA products are determined as having incorporated a T nucleotide. The DNA products with unchanged fluorescent signals are identified by inference as being terminated by a C nucleotide; (6) The third cleavage (III) is conducted with THP to cleave the disulfide bond and remove the dye on C, so the change of the signal after the THP treatment also determines the DNA products as being terminated by a C nucleotide. Meanwhile, the THP treatment will also claeve the DTM (SS) bond to regenerate free 3'-OH on all the DNA extension products, which are ready for subsequent cycles of single-color DNA SBS. (7) Repeat steps 1 to 6 to continue subsequent cycles of single-color DNA SBS. The text over the arrows is as follows.
Figure 16B:
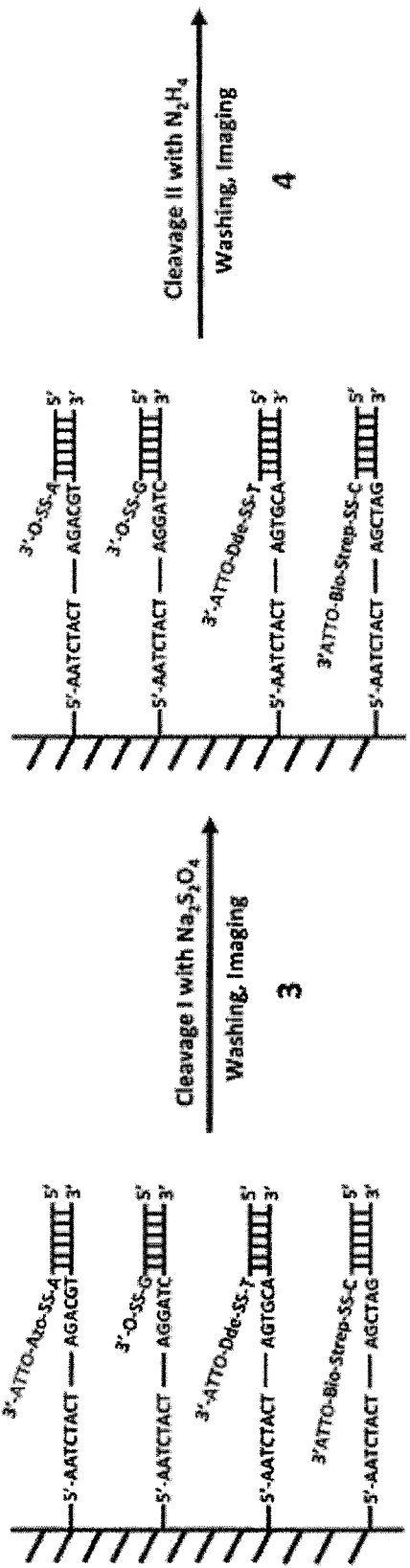
Figure 16C:
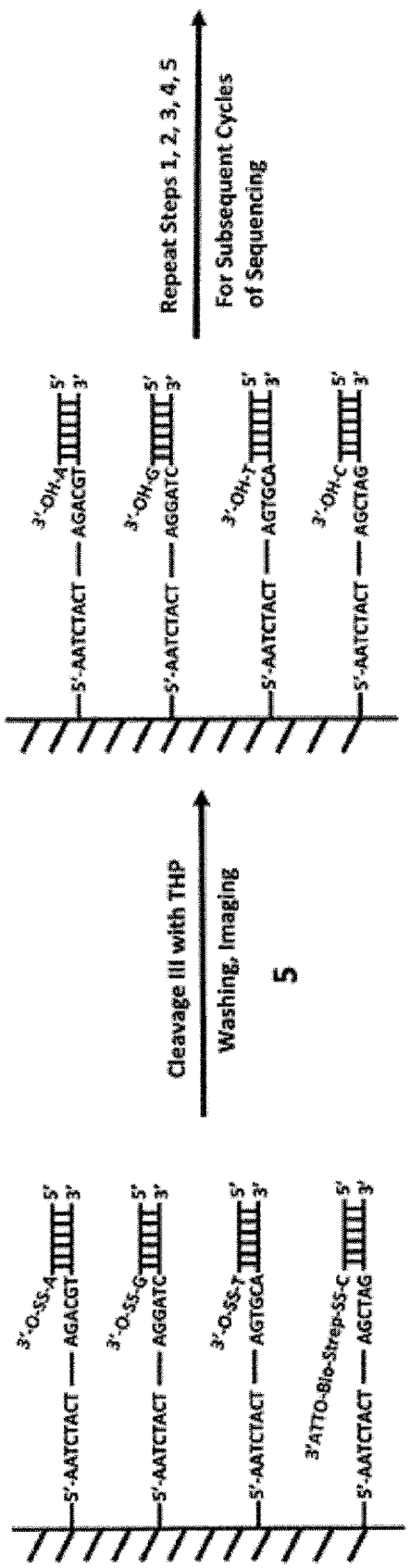

Example D. One-Color DNA SBS (FIGS. 16A-16C)

Figure 15:
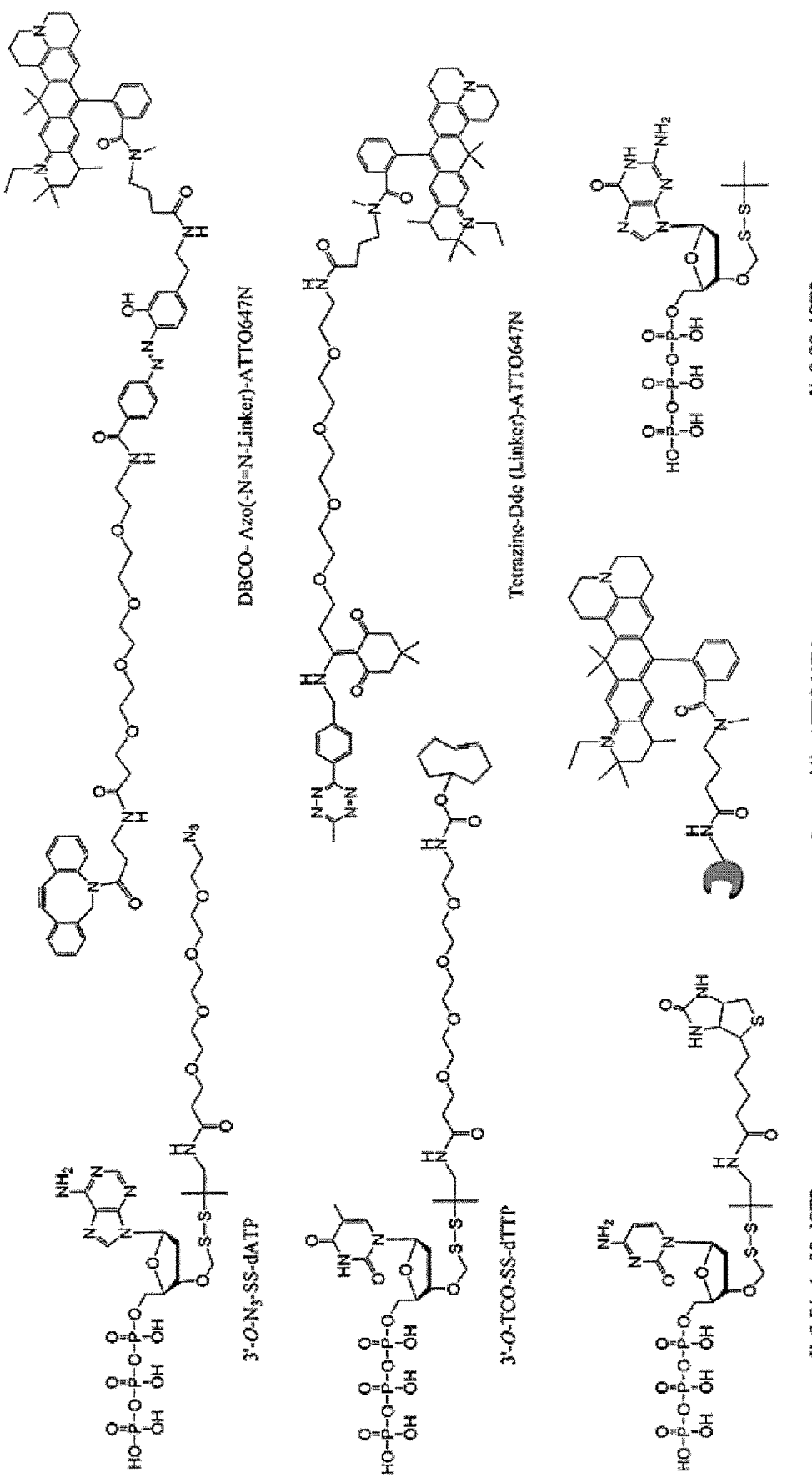
FIG. 15. Sample Structures of 3'-O-"anchor"-SS(DTM)-dNTPs (3'-O—$N_3$-SS-dATP, 3'-O-TCO-SS-dTTP, 3'-O-Biotin-SS-dCTP) along with their corresponding labeled binding molecules [DBCO-Azo(-N=N-Linker)-ATTO647N, Tetrazine-Dde(Linker)-ATTO647N, and Streptavidin-ATTO647N] conjugated with one florescent dye via different cleavable linkage in combination with 3'-O-t-Butyl-SS (DTM)-dGTP (3'-O-SS-dGTP) for performing one-color SBS at the single-molecule level or at the ensemble level.

1: In presence of DNA polymerase, three 3'-anchor nucleotides [3'-SS(DTM)N$_3$-dATP, 3'-SS(DTM)TCO-dTTP, 3'-SS(DTM)Biotin-dCTP] and 3'-tButyl-SS(DTM)-dGTP, as shown in FIG. 15 are added to the primed DNA templates to allow incorporation into the primer.

2: The fluorescent label (ATTO647N, for example) is attached by adding DBCO-Azo-(—N=N-Linker)-ATTO647N, Tetrazine-Dde(Linker)-ATTO647N, Streptavidin-ATTO647N (as shown in FIG. 15) to the DNA extension products that contain the incorporated 3'-anchor nucleotide analogues, which leads to the labeling of all the incorporated nucleotides (except G) at their 3'-end due to specific anchor-binding molecule interaction.

3: After washing, the first round of imaging is performed, and the DNA products terminated with A, C and T all display the same color, while the DNA products that do not emit a signal are terminated by a nucleotide G.

4: The first cleavage (I) is conducted by treatment with sodium dithionite (Na$_2$S$_2$O$_4$), which only cleaves the azo linkage to remove the fluorescent dye from the DNA products terminated with the A nucleotide. The second round of imaging is performed. If the fluorescent signal disappears after the cleavage I, the DNA products are determined as having incorporated an A nucleotide.

5: The second cleavage (II) is conducted by treatment with hydrazine (N$_2$H$_4$), which will cleave the Dde linkage to remove the fluorescent dye from the DNA products terminated with the T nucleotide. The third round of imaging is performed. If the fluorescent signal disappears after the cleavage II, the DNA products are determined as having incorporated a T nucleotide. The DNA products with unchanged fluorescent signals are identified by inference as being terminated by a C nucleotide.

6: The third cleavage (III) is conducted with THP to cleave the disulfide bond and remove the dye on C, so the change of the signal after the THP treatment also determines the DNA products as being terminated by a C nucleotide. Meanwhile, the THP treatment will also cleave the DTM (SS) bond to regenerate free 3'-OH on all the DNA extension products, which are ready for subsequent cycles of single-color DNA SBS.

7: Repeat steps 1 to 6 to continue subsequent cycles of single-color DNA SBS.

Figure 18A:
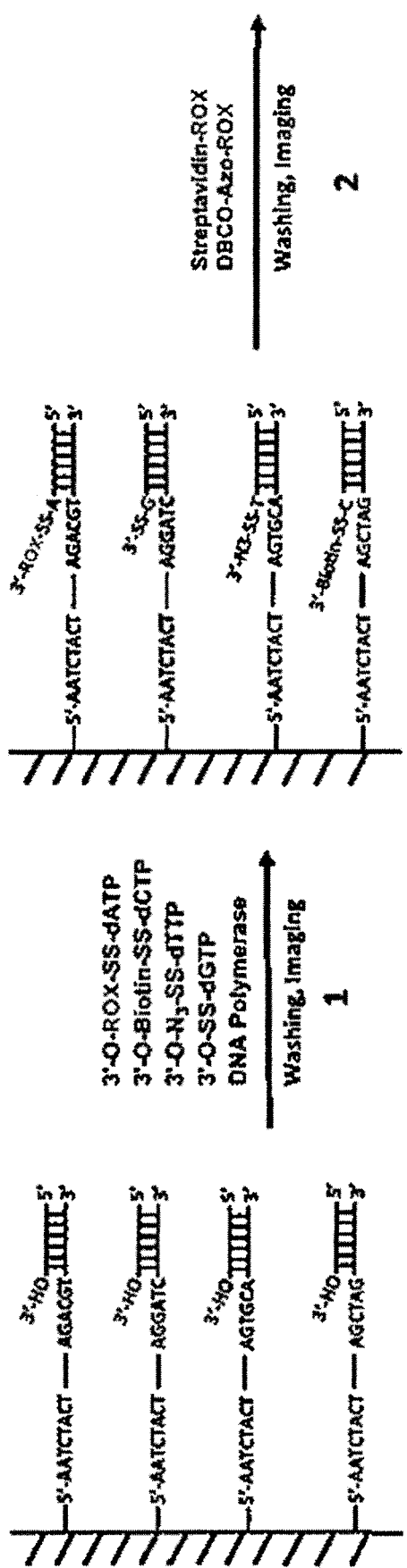
FIGS. 18A-18C. (1) In presence of DNA polymerase, two 3'-anchor nucleotides [(3'-O—$N_3$-SS(DTM)-dTTP, 3'-O-Biotin-SS(DTM)-dCTP)], 3'-O-Rox-SS(DTM)-dATP and 3'-O-tButyl-SS(DTM)-dGTP, as shown in FIG. 17] are added to the primed DNA templates to allow incorporation into the primer; (2) After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals; (3) Attach the fluorescent label (Rox, for example) by adding DBCO-Azo-(-N=N-Linker)-Rox, Streptavidin-Rox (as shown in FIG. 17) to the DNA extension products that contain the incorporated 3'-anchor nucleotide analogues, which leads to the labeling of all the incorporated nucleotides (except G) at their 3'-end due to specific anchor-binding molecule interaction; (4) After washing, the second round of imaging is performed, and the DNA products terminated with A, C and T all display the same Rox signal, while the DNA products that do not emit a signal is terminated by a nucleotide G; (5) The first cleavage (I) is conducted by treatment with sodium dithionite ($Na_2S_2O_4$), which only cleaves the azo linkage to remove the fluorescent dye Rox from the DNA products terminated with the T nucleotide. The second round of imaging is performed. If the Rox fluorescent signal disappears after the cleavage I, the DNA products are determined as having incorporated a T nucleotide; (6) The second cleavage (II) is conducted with THP to cleave the disulfide bond and remove the dye from the DNA extension products terminated with nucleotides A and C, so the change of the signal after the THP treatment determines the DNA products as being terminated by a C nucleotide, because DNA products as being terminated by an A nucleotide have already being determined in the first round of imaging described above. Meanwhile, the THP treatment will also claeve the DTM (SS) bond to regenerate free 3'-OH on all the DNA extension products, which are ready for subsequent cycles of single-color DNA SBS. Repeat steps 1 to 6 to continue subsequent cycles of single-color DNA SBS. The text over the arrows is as follows.
Figure 18B:
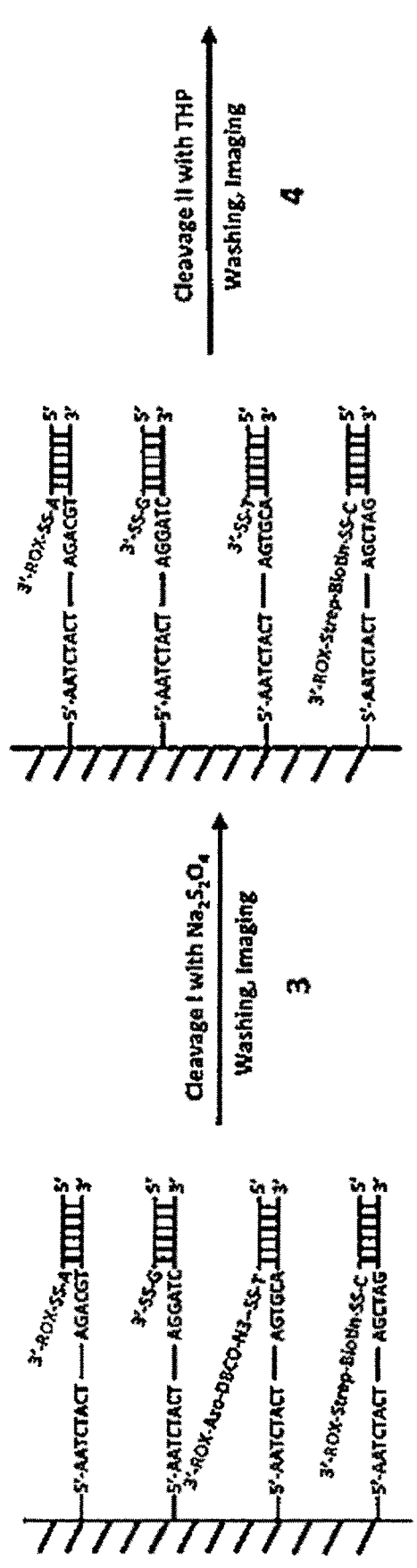
Figure 18C:
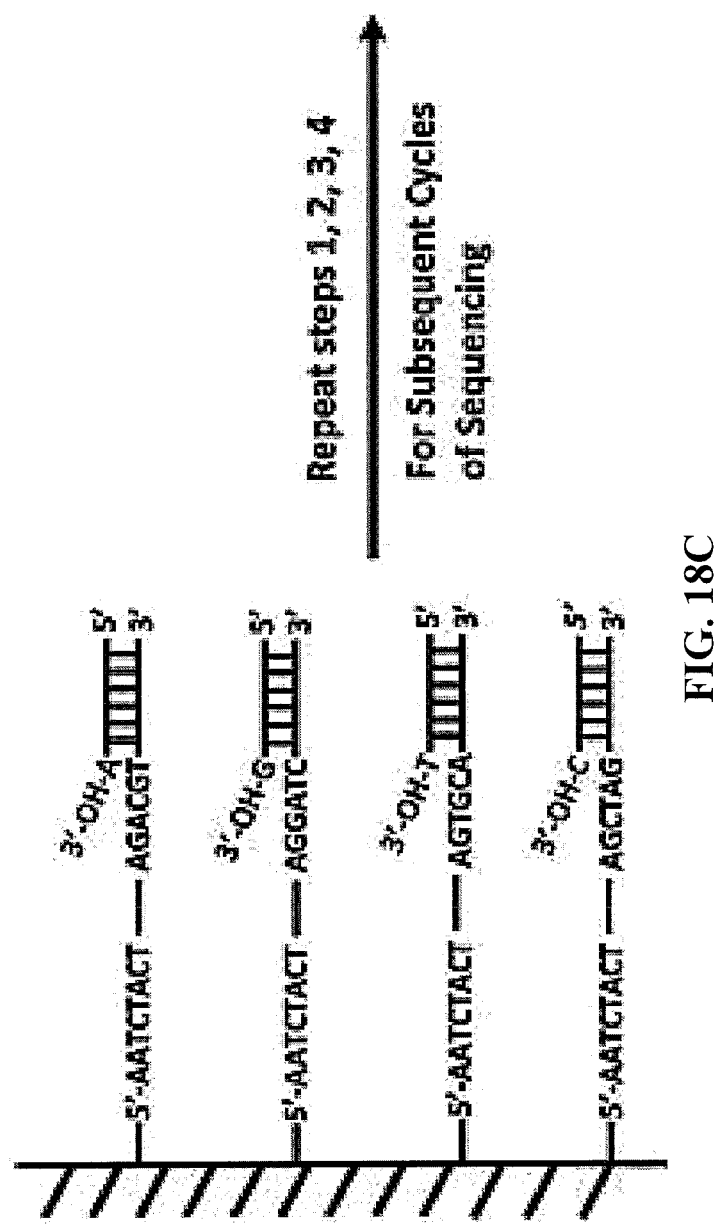

Example E. One-Color DNA SBS (FIGS. 18A-18C)

Figure 17:
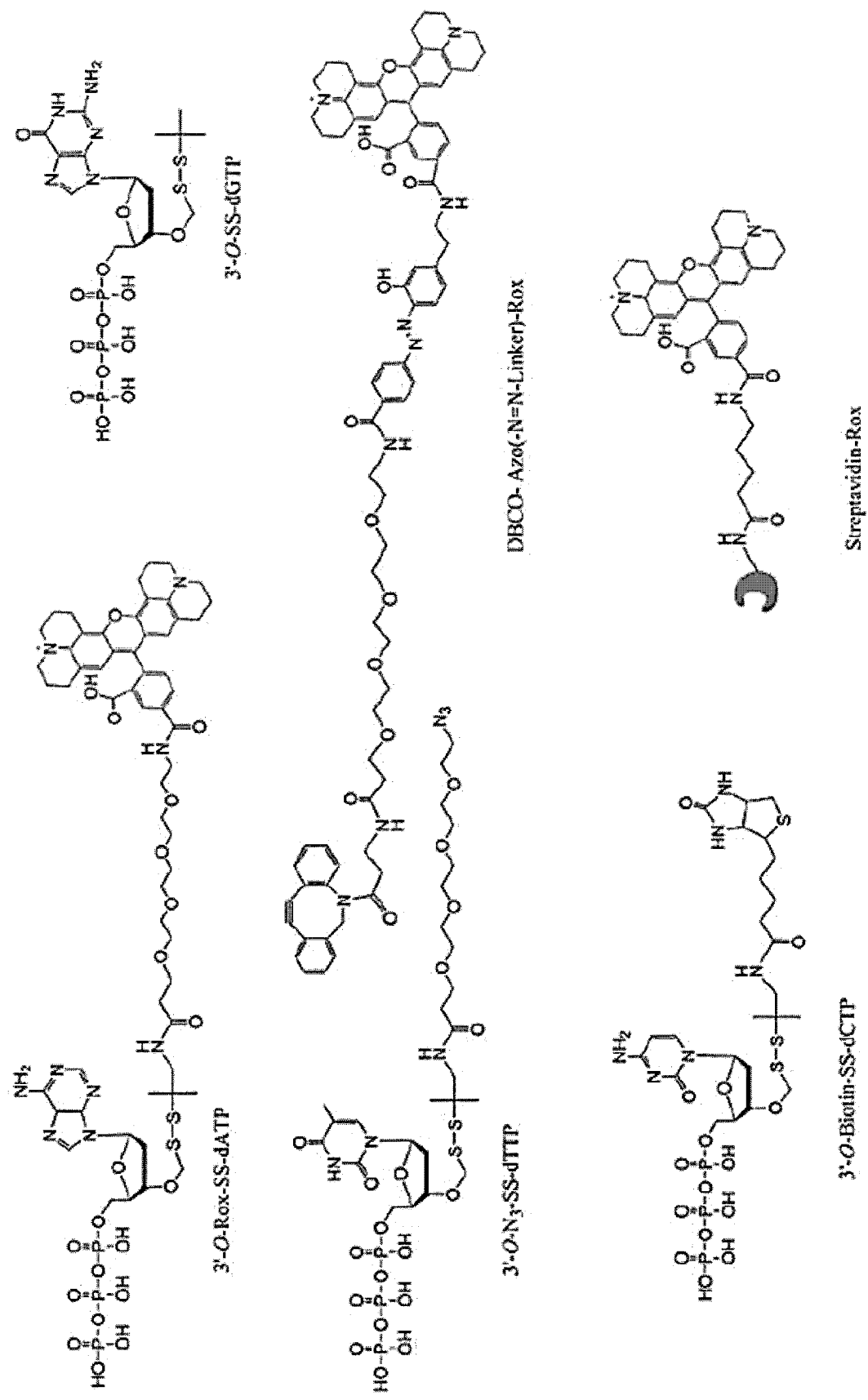
FIG. 17. Sample Structures of 3'-O-Dye-SS(DTM)-dNTP (3'-O-Rox-SS-dATP), 3'-O-"anchor"-SS(DTM)-dNTPs (3'-O—$N_3$-SS-dTTP and 3'-O-Biotin-SS-dCTP) along with their corresponding labeled binding molecules [DBCO-Azo (-N=N-Linker)-Rox and Streptavidin-Rox]conjugated with one floresent dye via different cleavable linkage in combination with 3'-O-t-Butyl-SS(DTM)-dGTP (3'-O-SS-dGTP) for performing one-color SBS at the single-molecule level or at the ensemble level.

1: In presence of DNA polymerase, two 3'-anchor nucleotides [(3'-O—N$_3$—SS(DTM)-dTTP, 3'-O-Biotin-SS(DTM)-dCTP)], 3'-O-Rox-SS(DTM)-dATP and 3'-O-tButyl-SS (DTM)-dGTP, as shown in FIG. 17] are added to the primed DNA templates to allow incorporation into the primer.

2: Attach the fluorescent label (Rox, for example) by adding DBCO-Azo-(—N=N-Linker)-Rox, Streptavidin-Rox (as shown in FIG. 17) to the DNA extension products that contain the incorporated 3'-anchor nucleotide analogues, which leads to the labeling of all the incorporated nucleotides (except G) at their 3'-end due to specific anchor-binding molecule interaction.

3: After washing, the second round of imaging is performed, and the DNA products terminated with A, C and T all display the same Rox signal, while the DNA products that do not emit a signal is terminated by a nucleotide G.

4: The first cleavage (I) is conducted by treatment with sodium dithionite ($Na_2S_2O_4$), which only cleaves the azo linkage to remove the fluorescent dye Rox from the DNA products terminated with the T nucleotide. The second round of imaging is performed. If the Rox fluorescent signal disappears after the cleavage I, the DNA products are determined as having incorporated a T nucleotide.

5: The second cleavage (II) is conducted with THP to cleave the disulfide bond and remove the dye from the DNA extension products terminated with nucleotides A and C, so the change of the signal after the THP treatment determines the DNA products as being terminated by a C nucleotide, because DNA products as being terminated by an A nucleotide have already being determined in the first round of imaging described above. Meanwhile, the THP treatment will also claeve the DTM (SS) bond to regenerate free 3'-OH on all the DNA extension products, which are ready for subsequent cycles of single-color DNA SBS. Repeat steps to continue subsequent cycles of single-color DNA SBS.

Figure 20C:
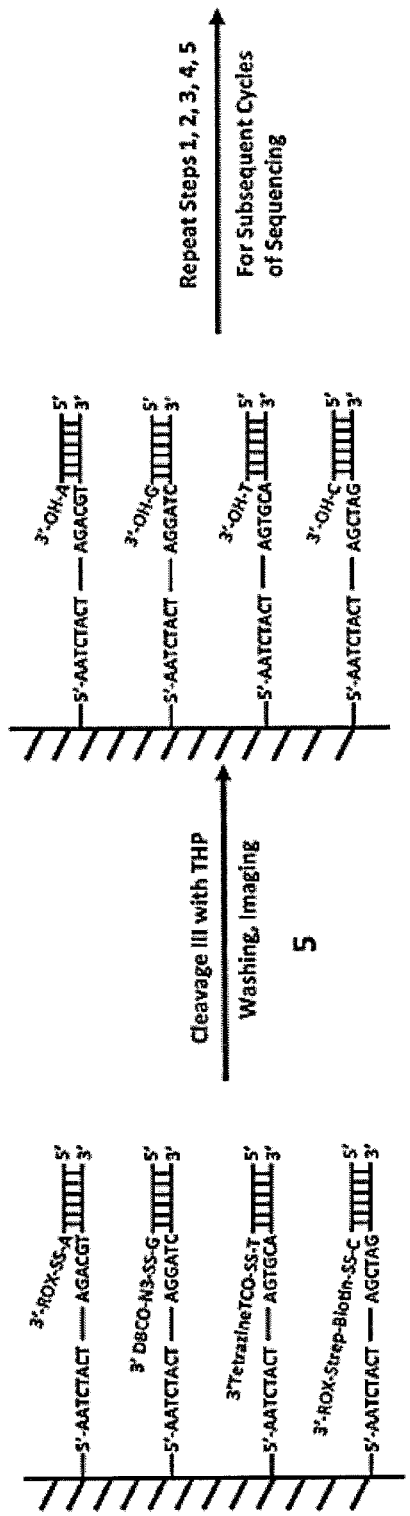

Example F. One-Color DNA SBS (FIGS. 20A-20C)

Figure 19A:
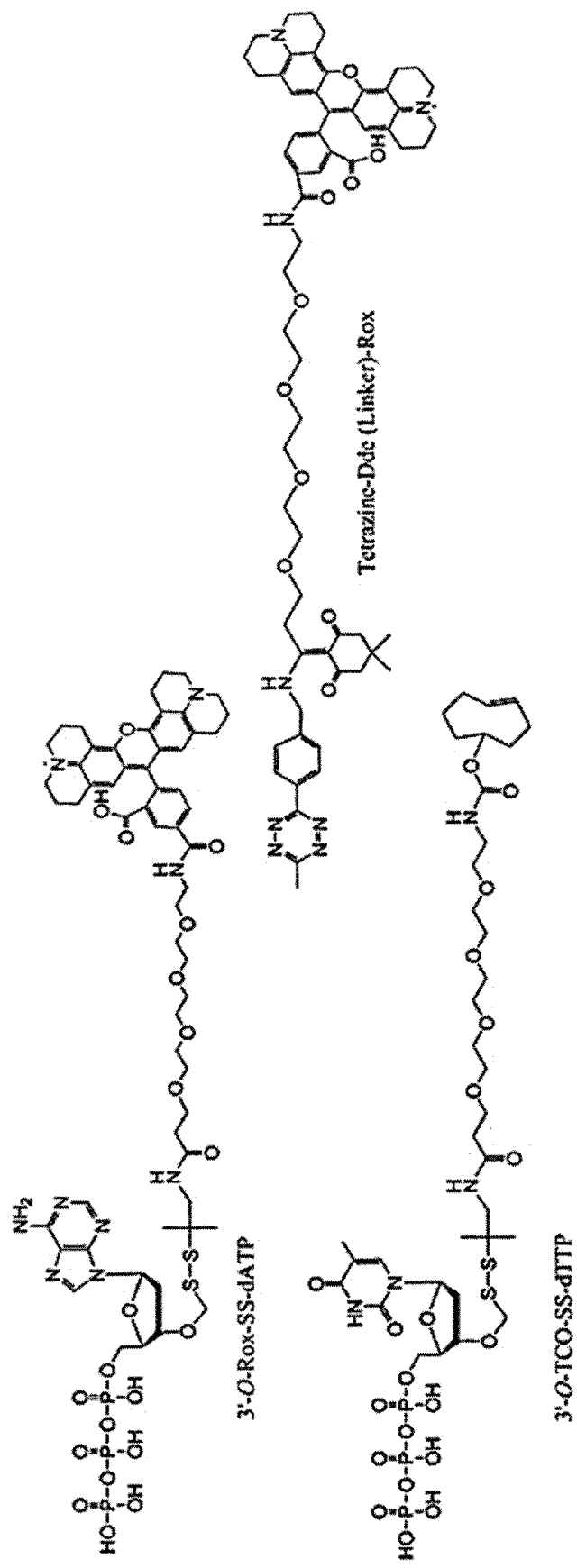
FIGS. 19A-19B. Sample Structures of 3'-O-Dye-SS (DTM)-dNTP (3'-O-Rox-SS-dATP), 3'-O-"anchor"-SS (DTM)-dNTPs (3'-O-TCO-SS-dTTP, 3'-O-Biotin-SS-dCTP and 3'-O—$N_3$-SS-dGTP) along with their corresponding labeled binding molecules [Tetrazine-Dde(Linker)-Rox, Streptavidin-Rox and DBCO-Azo(-N=N-Linker)-Rox] conjugated with one floroscent dye via different cleavable linkage for performing one-color SBS at the single-molecule level or at the ensemble level.
Figure 19B:
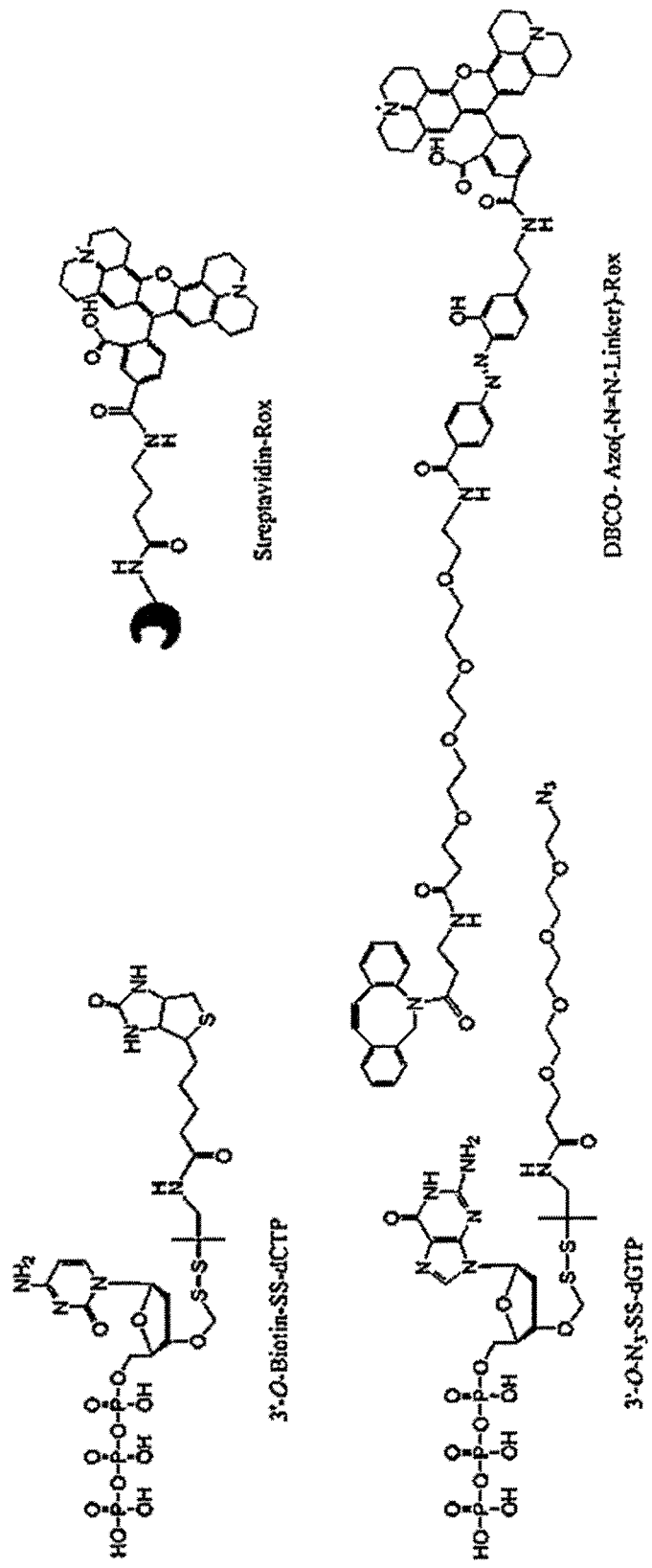

1: In presence of DNA polymerase, three 3'-anchor nucleotides [3'-O—$N_3$—SS(DTM)-dGTP, 3'-O-Biotin-SS(DTM)-dCTP, 3'-O-TCO-SS(DTM)-dTTP)] and 3'-O-Rox-SS(DTM)-dATP, as shown in FIGS. 19A-19B] are added to the primed DNA templates to allow incorporation into the primer.

2: After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals.

3: Attach the fluorescent label (Rox, for example) by adding DBCO-Azo-(—N=N-Linker)-Rox, Tetrazine-Dde-Rox and Streptavidin-Rox (as shown in FIGS. 19-19B) to the DNA extension products that contain the incorporated 3'-anchor nucleotide analogues, which leads to the labeling of all the incorporated nucleotides at their 3'-end due to specific anchor-binding molecule interaction.

4: After washing, the second round of imaging is performed, and the DNA products terminated with A, G, T, C all display the same Rox signal. Subtraction of the Rox signals from the DNA products determined in the first round of imaging as terminated at an A nucleotide reveals the DNA products terminated at G, T, C.

5: The first cleavage (I) is conducted by treatment with sodium dithionite ($Na_2S_2O_4$), which only cleaves the azo linkage to remove the fluorescent dye Rox from the DNA products terminated with the G nucleotide. The second round of imaging is performed. If the Rox fluorescent signal disappears after the cleavage I, the DNA products are determined as having incorporated a G nucleotide.

6: The second cleavage (II) is conducted with hydrazine ($N_2H_4$), which will cleave the Dde linkage to remove the fluorescent dye Rox from the DNA products terminated with the T nucleotide. The third round of imaging is performed. If the Rox fluorescent signal disappears after the cleavage II, the DNA products are determined as having incorporated a T nucleotide. If the Rox fluorescent signal stays after the cleavage II, the DNA products are determined as having incorporated a C nucleotide.

7: The third cleavage (III) is conducted with THP to cleave the disulfide bond and remove the Rox dye from the DNA extension products terminated with nucleotides A and C, so the change of the signal after the THP treatment also determines the DNA products as being terminated by a C nucleotide, because DNA products as being terminated by an A nucleotide have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Repeat steps 1 to 7 to continue subsequent cycles of single-color DNA SBS.

Figure 22:
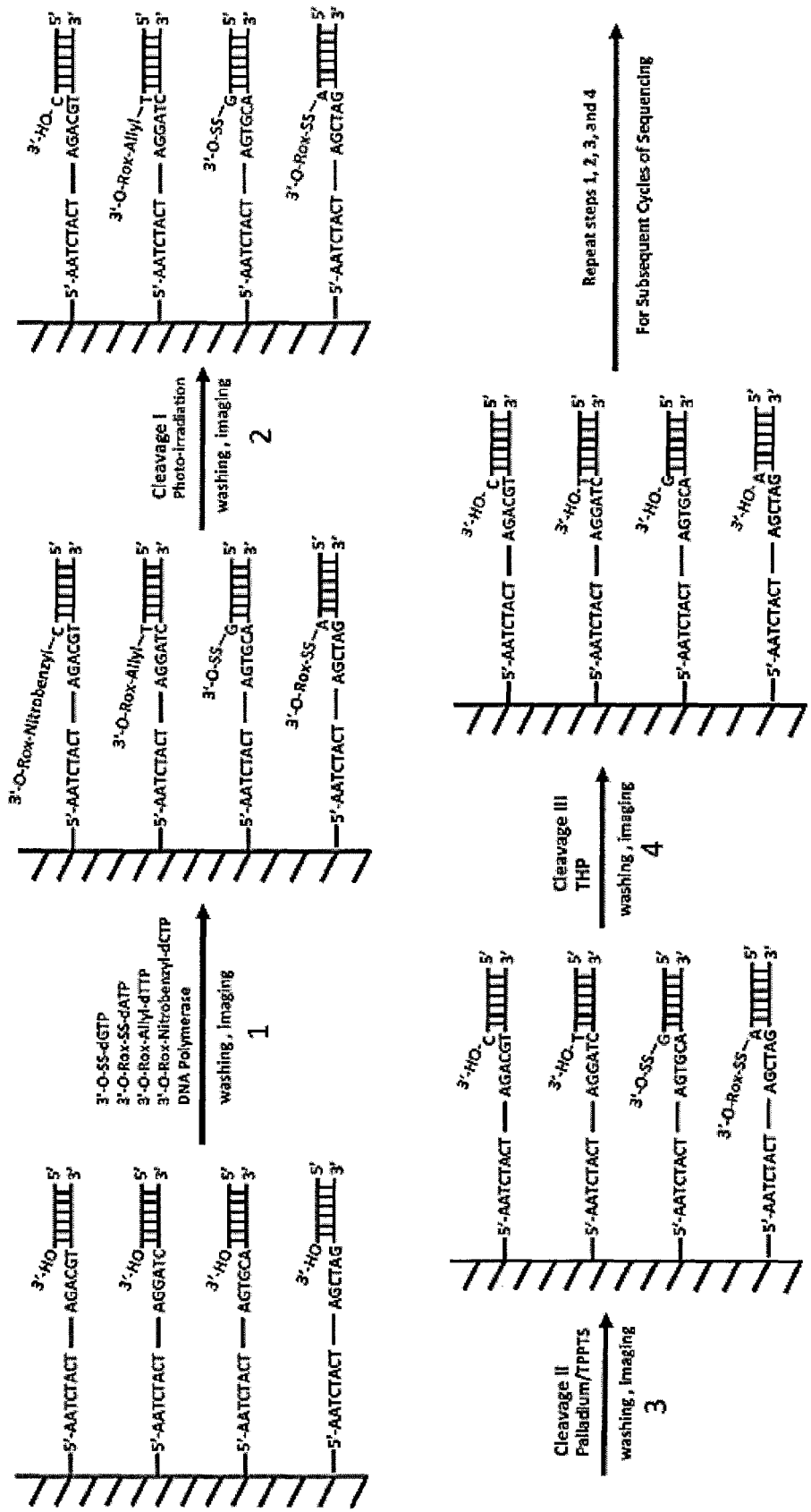
FIG. 22. (1) In presence of DNA polymerase, the three 3'-O-CleavableLinker-Label-dNTPs [3'-O-Rox-SS(DTM)-dATP, 3'-O-Rox-Allyl-dTTP, 3'-O-Rox-Nitrobenzyl-dCTP] and 3'-n-tButyl-SS-dGTP, as shown in FIG. 21] are added to the primed DNA templates to allow incorporation into the primer; (2) After washing, the first round of imaging is performed, and the DNA products terminated with C, T and A all display the same Rox signal, while the DNA products that do not emit a signal is terminated by a nucleotide G; (3) The first cleavage (I) is conducted by photo-irradiation at ~350 nm to remove the fluorescent dye Rox from the DNA products terminated with the C nucleotide. The second round of imaging is performed. If the Rox fluorescent signal disappears after the cleavage I, the DNA products are determined as having incorporated a C nucleotide; (4) The second cleavage (II) is conducted with Pd (0), which will cleave the allyl linkage to remove the fluorescent dye Rox from the DNA products terminated with the T nucleotide. The third round of imaging is performed. If the Rox fluorescent signal disappears after the cleavage II, the DNA products are determined as having incorporated a T nucleotide. If the Rox fluorescent signal stays after the cleavage II, the DNA products are determined as having incorporated an A nucleotide; (5) The third cleavage (III) is conducted with THP to cleave the disulfide bond and remove the Rox dye from the DNA extension products terminated with nucleotides A, so the change of the signal after the THP treatment also determines the DNA products as being terminated by an A nucleotide. Meanwhile, the THP treatment will also cleave the DTM (SS) bond to regenerate free 3'-OH on all the DNA extension products, which are ready for subsequent cycles of single-color DNA SBS. Repeat steps 1 to 5 to continue subsequent cycles of single-color DNA SBS. The text above the arrow is as follows: 1. 3'-O-SS-dGTP, 3'-O-Rox-SS-dATP, 3'-O-Rox-Allyl-dTTP, 3'-O-Rox-Nitrobenzyl-dCTP, DNA Polymerase, Washing, Imaging. 2. Cleavage I Photoirradiation, Washing, Imaging. 3. Cleavage II, Palladium/TPPTS, Washing, Imaging. 4. Cleavage III THP Washing, Imaging. Repeat steps 1, 2, 3 and 4 For Subsequent cycles of Sequencing.

Example G One color DNA SBS (FIG. 22)

Figure 21:
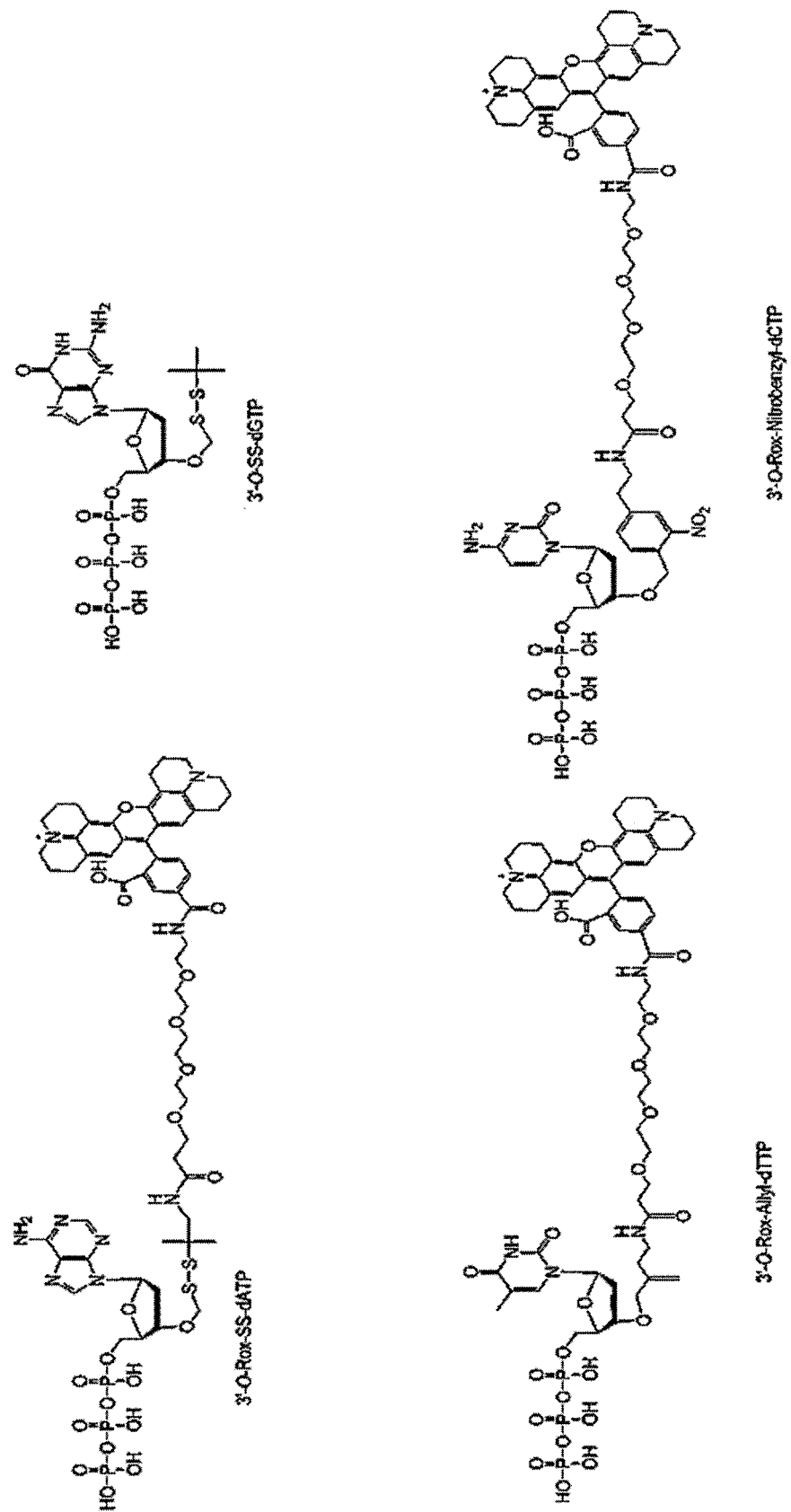
FIG. 21. Structures of 3'-O-Linker-Label-dNTPs [3'-O-Rox-SS(DTM)-dATP, 3'-O-Rox-Allyl-dTTP, 3'-O-Rox-Nitrobenzyl-dCTP] and 3'-O-SS(DTM)-dGTP.

(1) In presence of DNA polymerase, the three 3'-O-CleavableLinker-Label-dNTPs [3'-O-Rox-SS(DTM)-dATP, 3'-O-Rox-Allyl-dTTP, 3'-O-Rox-Nitrobenzyl-dCTP] and 3'-O-tButyl-SS-dGTP, as shown in FIG. 21] are added to the primed DNA templates to allow incorporation into the primer.

(2) After washing, the first round of imaging is performed, and the DNA products terminated with C, T and A all display the same Rox signal, while the DNA products that do not emit a signal is terminated by a nucleotide G.

(3) The first cleavage (I) is conducted by photo-irradiation at ~350 nm to remove the fluorescent dye Rox from the DNA products terminated with the C nucleotide. The second round of imaging is performed. If the Rox fluorescent signal disappears after the cleavage I, the DNA products are determined as having incorporated a C nucleotide.

(4) The second cleavage (II) is conducted with Pd (0), which will cleave the allyl linkage to remove the fluorescent dye Rox from the DNA products terminated with the T nucleotide. The third round of imaging is performed. If the Rox fluorescent signal disappears after the cleavage II, the DNA products are determined as having incorporated a T nucleotide. If the Rox fluorescent signal stays after the cleavage II, the DNA products are determined as having incorporated an A nucleotide.

(5) The third cleavage (III) is conducted with THP to cleave the disulfide bond and remove the Rox dye from the DNA extension products terminated with nucleotides A, so the change of the signal after the THP treatment also determines the DNA products as being terminated by an A nucleotide. Meanwhile, the THP treatment will also cleave the DTM (SS) bond to regenerate free 3'-OH on all the DNA extension products, which are ready for subsequent cycles of single-color DNA SBS. Repeat steps 1 to 5 to continue subsequent cycles of single-color DNA SBS.

All the above example sequencing methods (Examples A-G) can be modified with unlabeled nucleotide reversible terminator chasing extension (Ju (2006)) using 3'-O-t-Butyl-SS-dNTPs. In this procedure, 3'-O-t-Butyl-SS-dNTPs will be used to run polymerase extension after each steps of polymerase extension reaction using 3'-O-CleavableLinker- Label-dNTPs and 3'-O-CleavableLinker-Anchor-dNTPs to ensure the complete primer extension at the 3'-end for ensemble SBS.

MALDI-TOF mass spectra of the DNA extension products from polymerase reactions using some of the nucleotide analogues described above are performed and the results are described in FIGS. 23A-23B to FIGS. 28A-28C. The results indicate that 3'-O-tButyl-SS-dATP modified with a relatively smaller 3'-O blocking group is incorporated by polymerase with a much higher efficiency than 3'-O-Rox-SS-dATP labeled with a bulky Rox dye. Nucleotide analogue modified by a Rox through a $PEG_4$ linker is shown to be a better substrate for the DNA polymerase than the nucleotide analogue modified by Rox without a PEG linker.

Figure 23A:
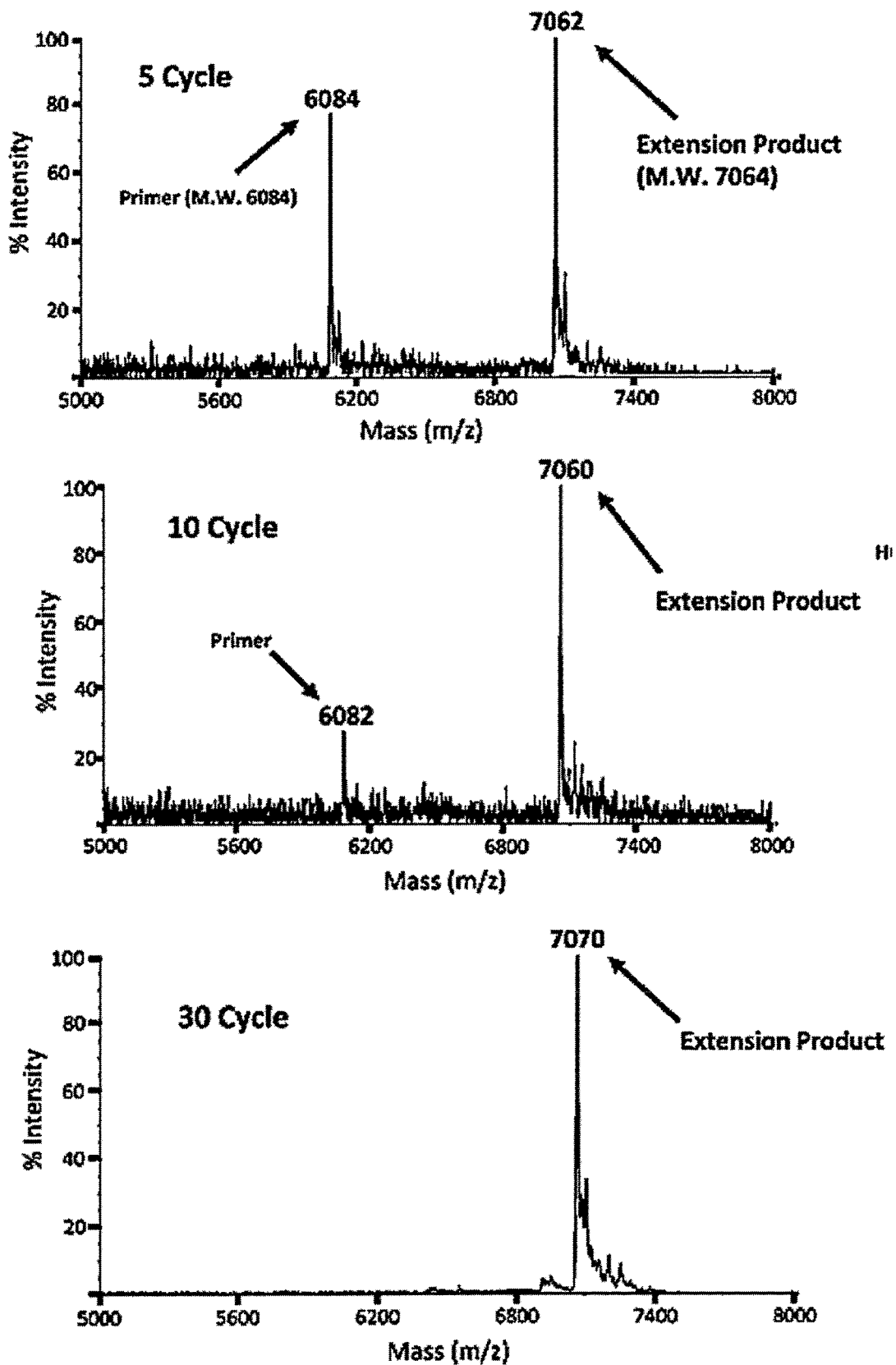
FIGS. 23A-23B. MALDI-TOF mass spectra of DNA extension products from polymerase reactions using 3'-O-Rox-SS-dATP for 5, 10, and 30 cycles. About 50% of the primers were extended with 3'-O-Rox-SS-dATP after 5 cycles. About 80% of the primers were extended after 10 cycles, and primer was completely extended after 30 cycles.
Figure 23B:
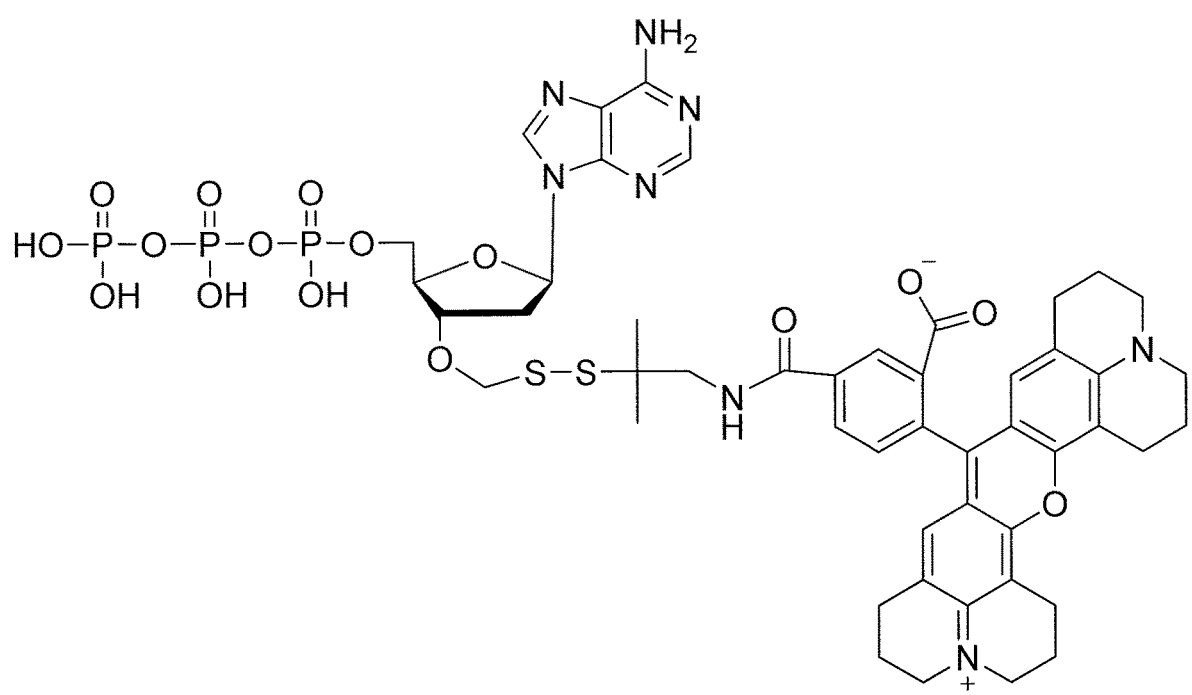

Polymerase Extension Using 3'-O-DTM-dNTPs, 3'-O-Anchor-DTM-dNTPs and 3'-O-Dye-DTM-dNTPs and Characterization by MALDI-TOF Mass Spectrometry Polymerase extension reaction using 3'-O—SS-Rox-dATP for 5, 10, and 30 cycles. The extension reaction was carried out using 200 pmol of reversible terminator 3'-O—SS-Rox-dATP, 2 units of Therminator IX DNA Polymerase (NEB), 20 pmol of DNA primer (M.W. 6084), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reactions were conducted in an ABI GeneAmp PCR System 9700 with initial incubation at 65° C. for 30 second, followed by 5, 10, or 30 cycles of 65° C./30 sec, 45° C./30 sec, 65° C./30 sec. The reaction mixtures were desalted using Oligo Clean & Concentrator™ (ZYMO Research) and analyzed by MALDI-TOF MS (ABI Voyager DE) and the results are shown in FIGS. 23A-23B. DNA template: 5'-GAAGGA-GACACGCGGCCAGAGAGGGTCCTGTCCGTGTTTG TCCGTGGAGTTCGAC AAGGCAGGGT-CATCTAATGGTGATGAGTCC-TATCCTTTTCTCTTCGTTCTCCGT-3' (SEQ ID NO:6). DNA Primer (M.W. 6084): 5'-TA-GATGACCCTGCCTTGTCG-3' (SEQ ID NO:7)

Figure 24:
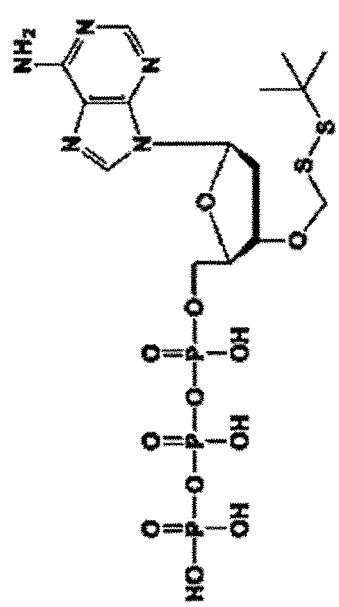
FIG. 24. MALDI-TOF mass spectrum of DNA extension product from polymerase reactions using 3'-O-tButyl-SS-dATP shows that extension is completed after 5 cycles of extension.
Figure 24:
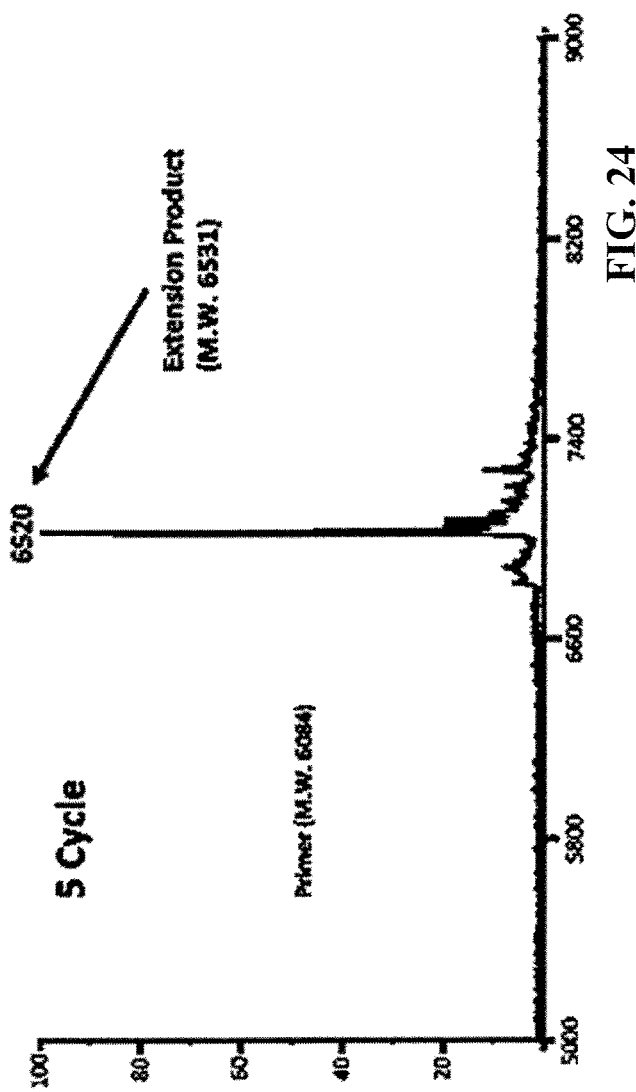

Polymerase extension reaction using 3'-O-tButyl-SS-dATP (5 cycles). The extension reaction was carried out using 200 pmol of reversible terminator 3'-O-tButyl-SS-dATP, 2 units of Therminator IX DNA Polymerase (NEB), 20 pmol of DNA primer (M.W. 6084), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 5 cycles of 65° C./30 sec, 45° C./30 sec, 65° C./30 sec. The reaction mixtures were desalted using Oligo Clean & Concentrator™ (ZYMO Research) and analyzed by MALDI-TOF MS (ABI Voyager DE) the result is shown in FIG. 24. DNA template: 5'-GAAGGA-GACACGCGGCCAGAGAGGGTCCTGTCCGTGTTTGT CCGTGGAGTTCGAC AAGGCAGGGT-CATCTAATGGTGATGAGTCC-TATCCTTTTCTCTTCGTTCTCCGT-3' (SEQ ID NO:8). DNA Primer (M.W. 6084): 5'-TA-GATGACCCTGCCTTGTCG-3' (SEQ ID NO:9)

Figure 25A:
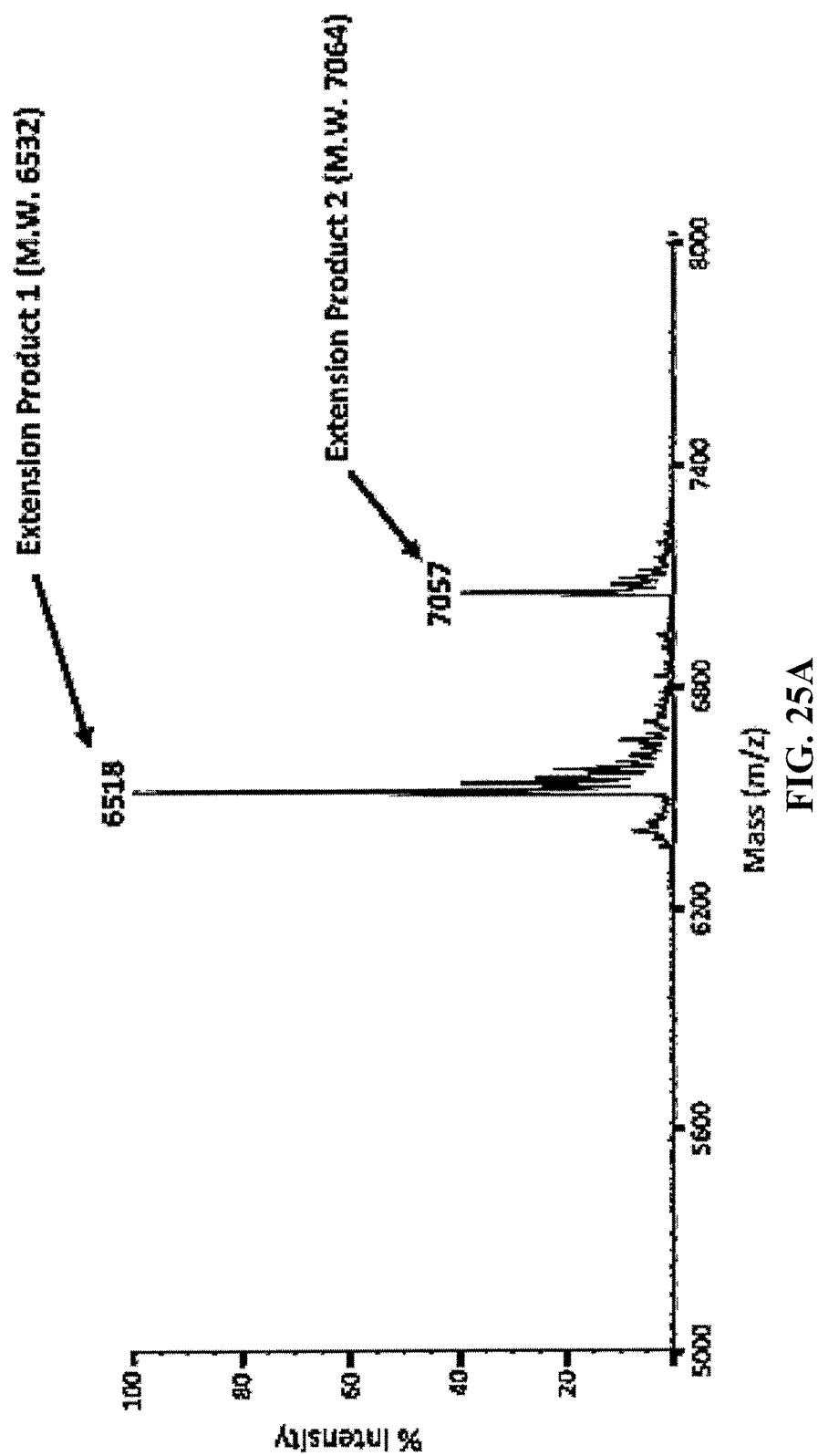
FIGS. 25A-25C. MALDI-TOF mass spectrum of DNA extension products from polymerase reactions using a mixture of 3'-O-tButyl-SS-dATP and 3'-O-Rox-SS-dATP at a 1:1 ratio. The extension reaction is completed after 5 cycles and the height of the extension product peak with 3'-O-tButyl-SS-dATP (Extension Product 1, M.W. 6532) is more than twice that of the height of the extension product with 3'-O-Rox-SS-dATP (Extension Product 2, M.W. 7064), indicating that 3'-O-tButyl-SS-dATP modified with a relatively smaller 3'-O blocking group is incorporated by polymerase with a much higher efficiency than 3'-O-Rox-SS-dATP labeled with a bulky Rox dye.
Figure 25B:
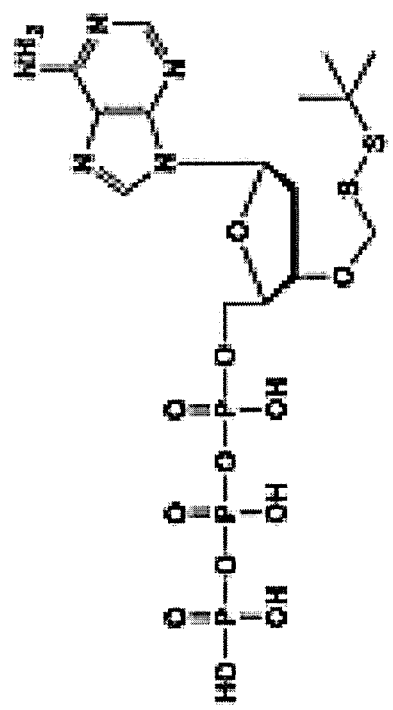
Figure 25C:
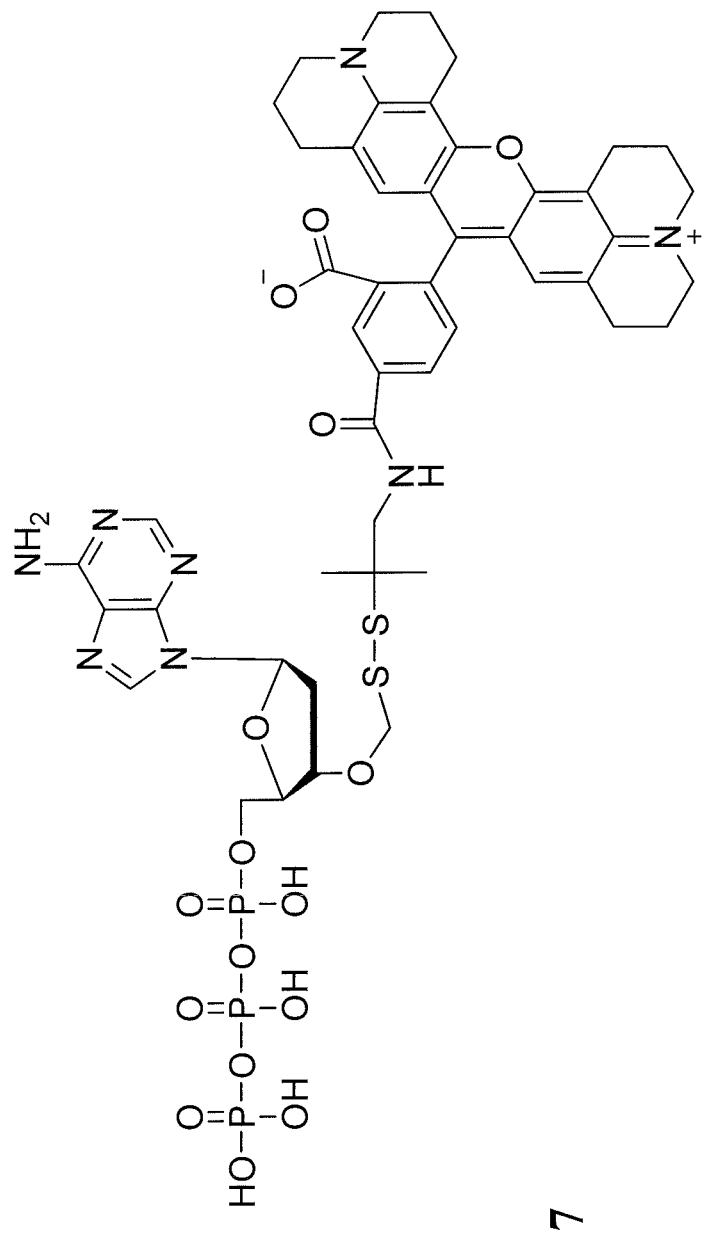

Polymerase extension reaction using 3'-O-tButyl-SS-dATP and 3'-O-Rox-SS-dATP at a ratio of 1:1. The extension reaction was carried out using 100 pmol of reversible terminator 3'-O-tButyl-SS-dATP, 100 pmol of reversible terminator 3'-O-Rox-SS-dATP, 2 unit of Therminator IX DNA Polymerase (NEB), 20 pmol of DNA primer (M.W. 6084), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixtures were desalted using Oligo Clean & Concentrator™ (ZYMO Research) and analyzed by MALDI-TOF MS (ABI Voyager DE) the result is shown in FIGS. 25A-25C. DNA template: 5'-GAAGGA-GACACGCGGCCAGAGAGGGTCCTGTCCGTGTTTGT CCGTGGAGTTCGAC AAGGCAGGGT-CATCTAATGGTGATGAGTCC-TATCCTTTTCTCTTCGTTCTCCGT-3' (SEQ ID NO:10). DNA Primer (M.W. 6084): 5'-TA-GATGACCCTGCCTTGTCG-3' (SEQ ID NO: 11).

Figure 26:
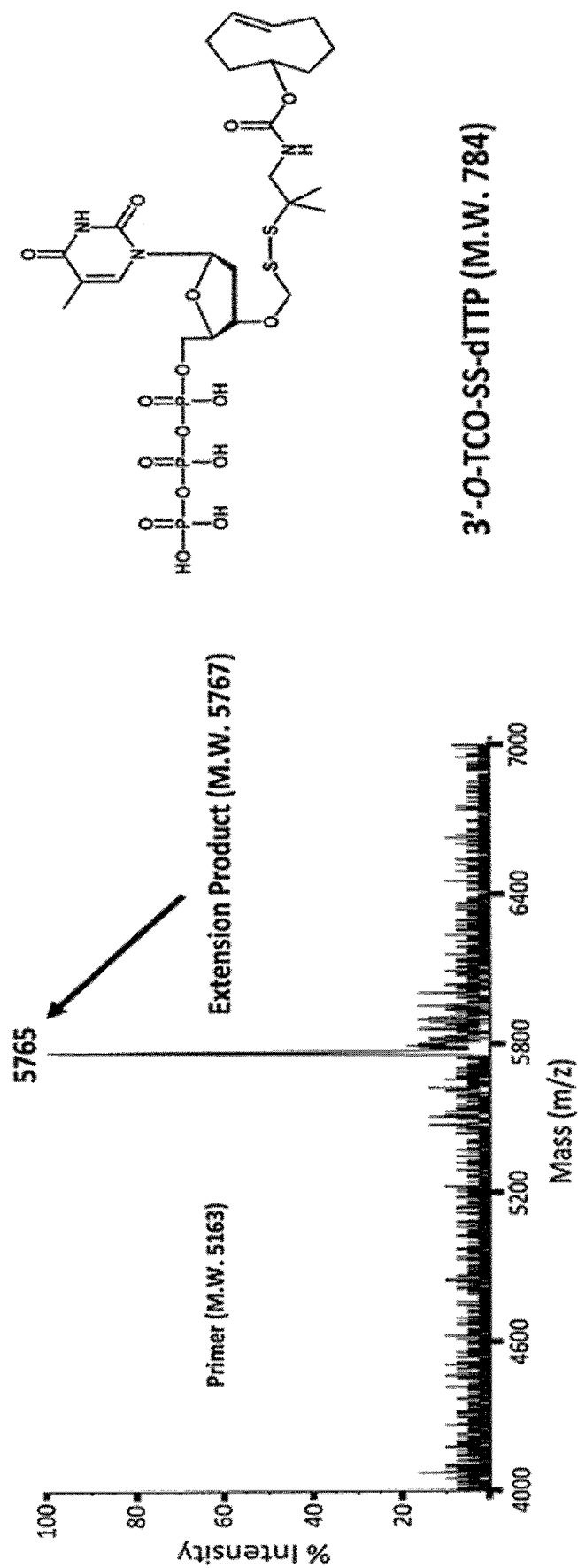
FIG. 26. MALDI-TOF mass spectrum of a DNA extension product from polymerase reaction using 3'-O-TCO-SS-dTTP. The result shows that primer is completed extended by the 3'-O-TCO-SS-dTTP after 38 cycles to yield an extension product at 5765 Daltons (calculated M.W. 5767).

Polymerase extension reaction using 3'-O-SS-TCO-dTTP. The extension reaction was carried out using 100 pmol of reversible terminator 3'-O-SS-TCO-dTTP, 2 units of Therminator IX DNA Polymerase (NEB), 20 pmol of DNA primer (M.W. 5163), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 see, 45° C./30 sec, 65° C./30 sec. The reaction mixtures were desalted using Oligo Clean & Concentrator™ (ZYMO Research) and analyzed by MALDI-TOF MS (ABI Voyager DE) the result is shown in FIG. 26. DNA template: 5'-GAAGGA-GACACGCGGCCAGAGAGGGTCCTGTCCGTGTTT GTCCGTGGAGTTCGAC AAGGCAGGGT-CATCTAATGGTGATGAGTCC-TATCCTTTTCTCTTCGTTCTCCGT-3' (SEQ ID NO:12). DNA Primer (M.W. 5163): 5'-GATAGGACTCATCACCA-3' (SEQ ID NO:13).

Figure 27A:
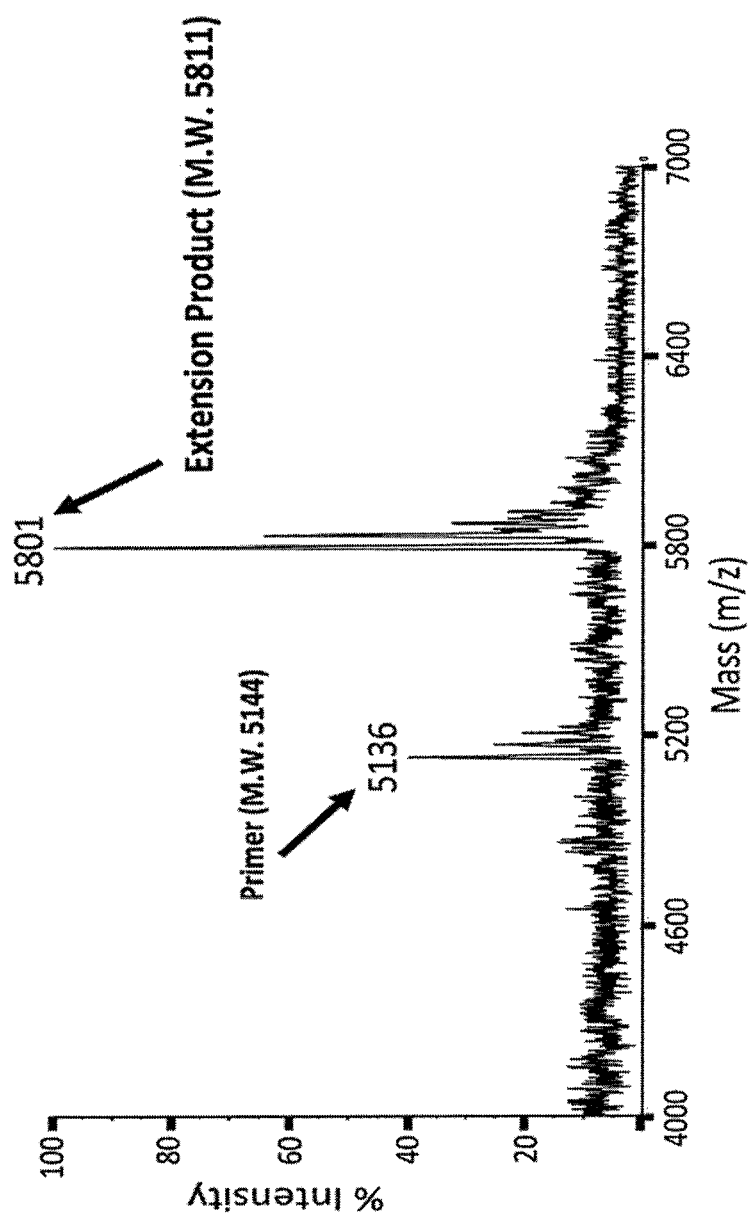

Polymerase extension reaction using 3'-O-Biotin-SS-dCTP. The extension reaction was carried out using 100 pmol of reversible terminator 3'-O-Biotin-dCTP, 2 units of Therminator IX DNA Polymerase (NEB), 20 pmol of DNA primer (M.W. 6131), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixtures were desalted using Oligo Clean & Concentrator™ (ZYMO Research) and analyzed by MALDI-TOF MS (ABI Voyager DE) the result is shown in FIGS. 27A-27B. DNA template: 5'-TACCCGGAGGC-CAAGTACGGCGGGTACGTCCTTGACAATGTGTA-CATCAACATCAC CTACCAC-CATGTCAGTCTCGGTTGGATCCTCTATTGTGTCCG GG-3' (SEQ ID NO:14). DNA primer (M.W. 6131): 5'-GTT-GATGTACACATTGTCAA-3' (SEQ ID NO:15).

Figure 28A:
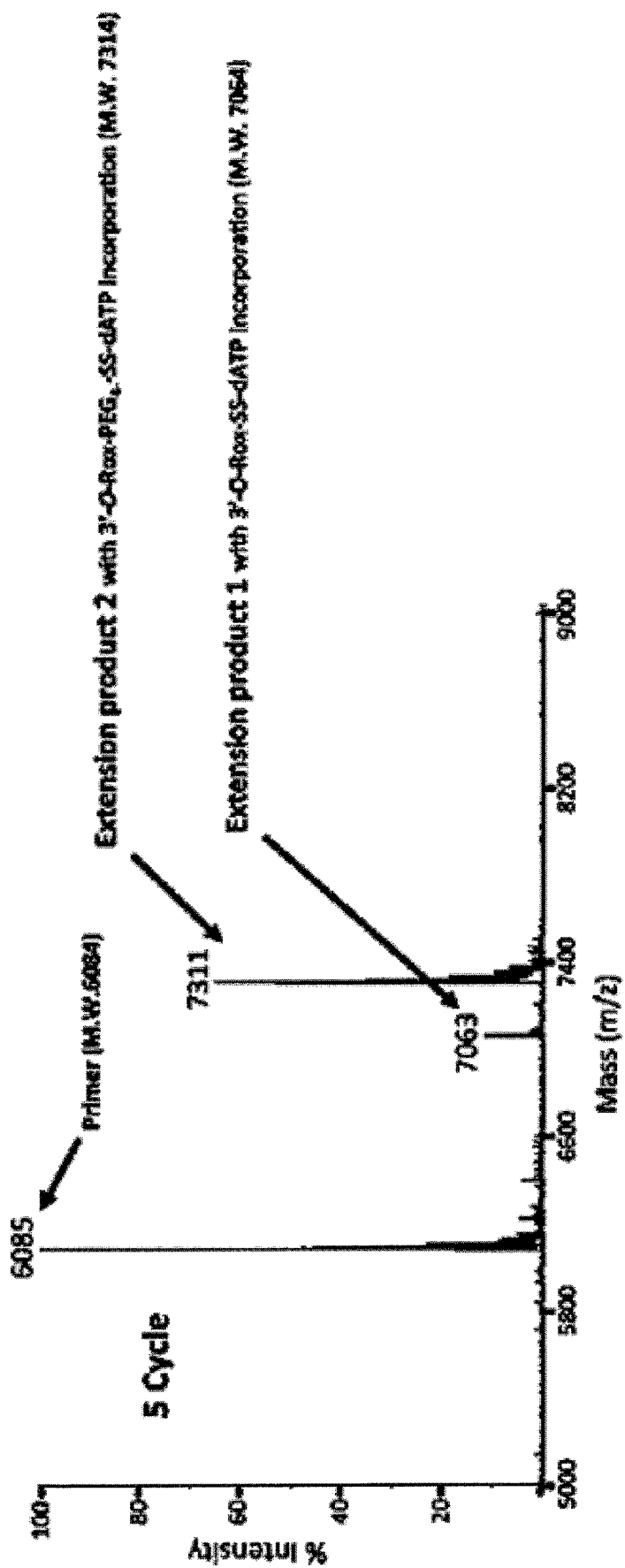

Polymerase extension reaction using a mixture of 3'-O-Rox-SS-dATP and 3'-O-Rox-$PEG_4$-SS-dATP at a ratio of 1:1 (5 cycles). The extension reaction was carried out using 100 pmol of reversible terminator 3'-O-Rox-SS-dATP, 100 pmol of reversible terminator (3'-O-Rox-$PEG_4$-SS-dATP), 2 units of Therminator IX DNA Polymerase (NEB), 20 pmol of DNA primer (M.W. 6084), 100 pmol of DNA template in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 5 cycles of 65° C./30 see, 45° C./30 sec, 65° C./30 sec. The reaction mixtures were desalted using Oligo Clean & Concentrator™ (ZYMO Research) and analyzed by MALDI-TOF MS (ABI Voyager DE) the result is shown in FIGS. 28A-28C. DNA template: 5'-GAAGGA-GACACGCGGCCAGAGAGGGTCCTGTCCGTGTTTG TCCGTGGAGTTCGAC AAGGCAGGGT-CATCTAATGGTGATGAGTCC-TATCCTTTTCTCTTCGTTCTCCGT-3' (SEQ ID NO:16). DNA Primer (M.W. 6084): 5'-TA-GATGACCCTGCCTTGTCG-3' (SEQ ID NO:17).

Figure 29:
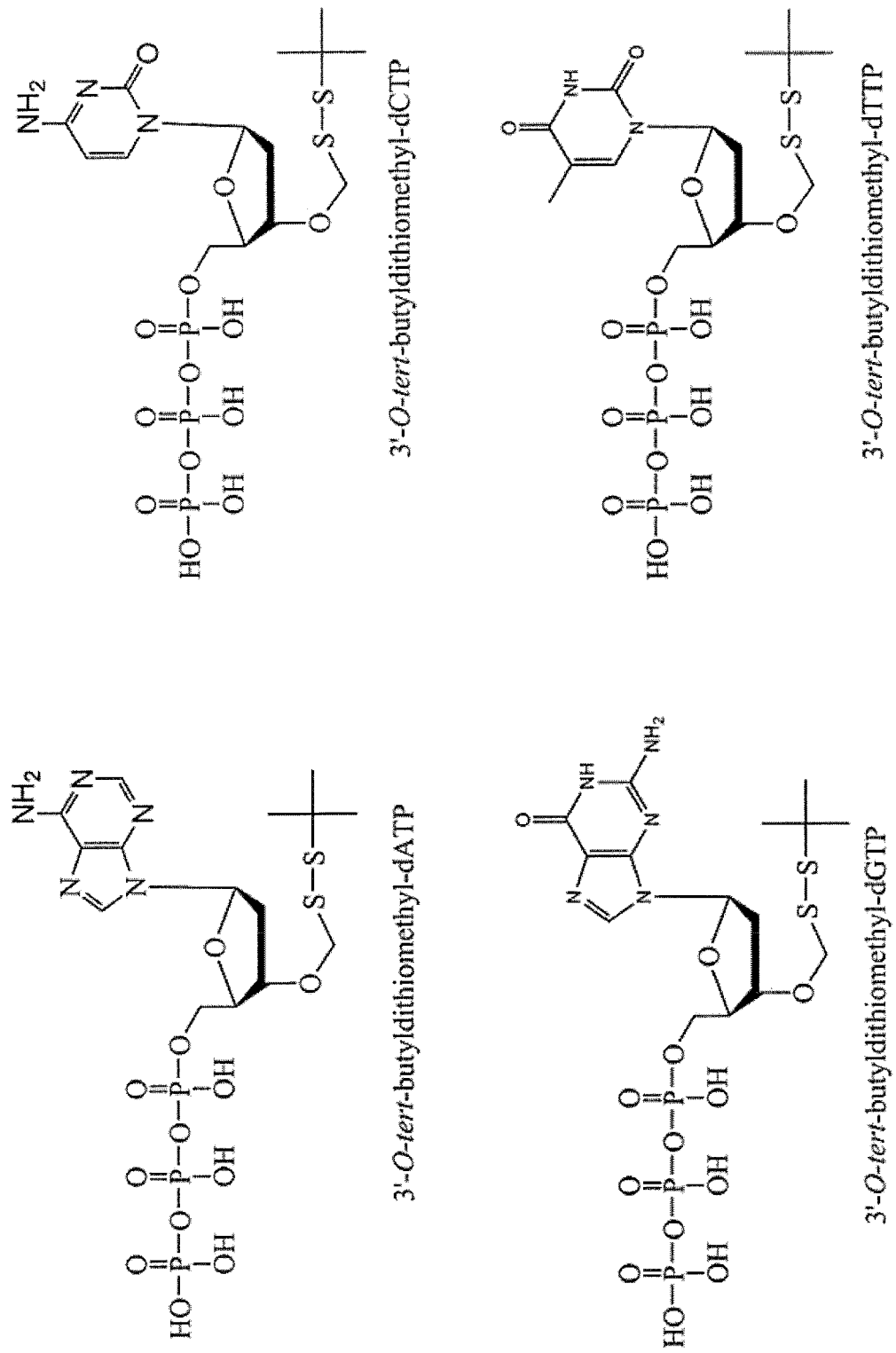
FIG. 29. Structures of 3'-O-t-Butyldithiomethyl-dNTPs.
Figure 30C:
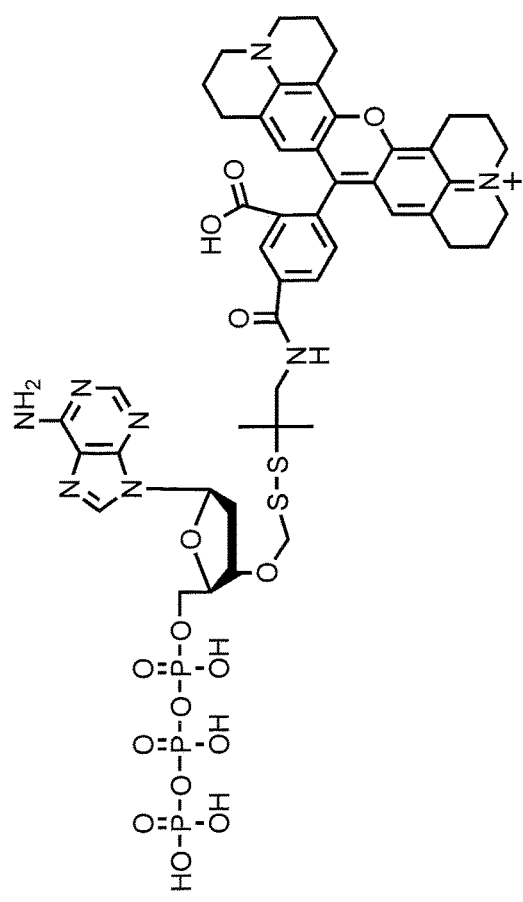
Figure 30D:
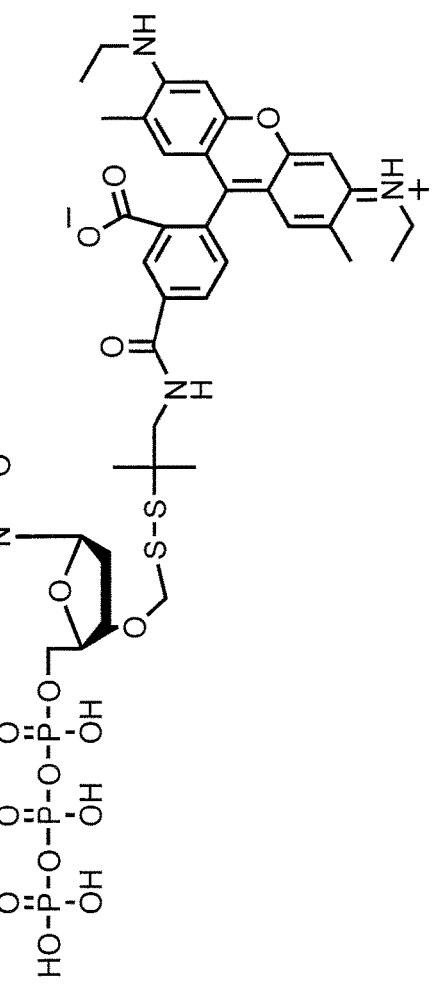
Figure 31A:
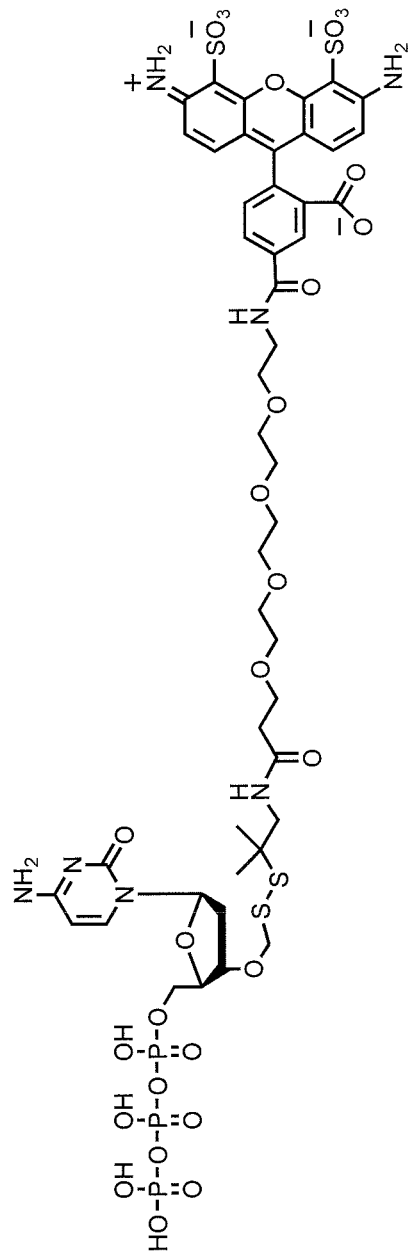
FIGS. 31A-31D. Structures of four 3'-O-Dye-DTM-dNTPs with PEG4 between dye and DTM.
Figure 31B:
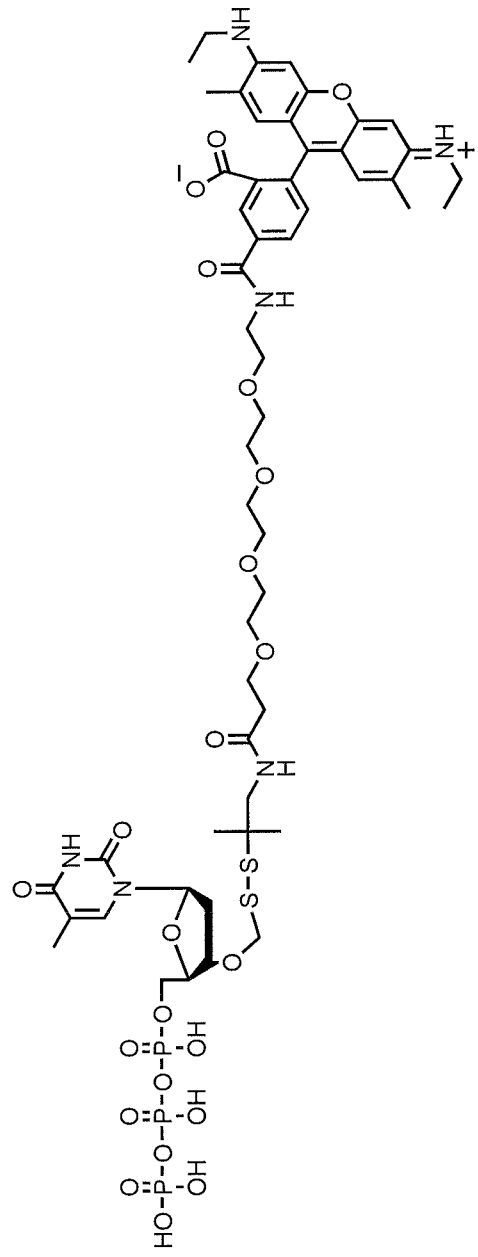
Figure 31C:
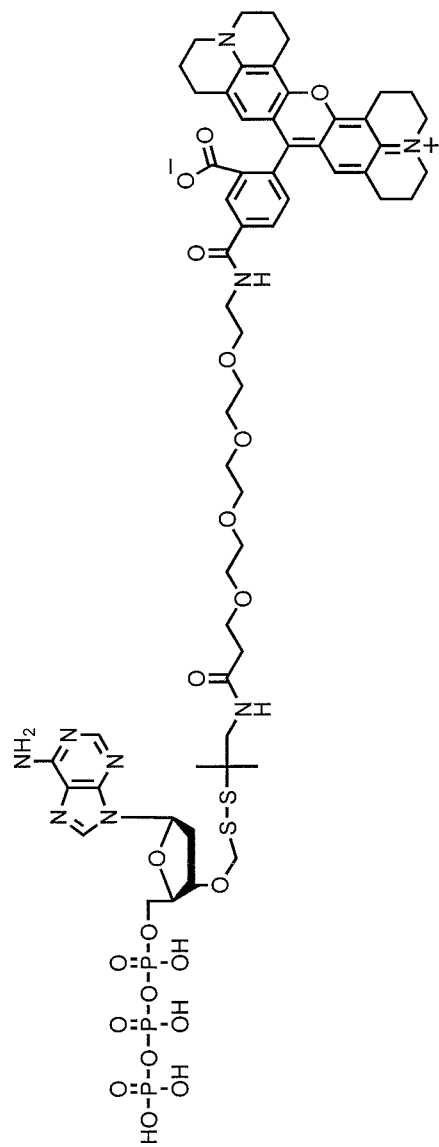
Figure 31D:
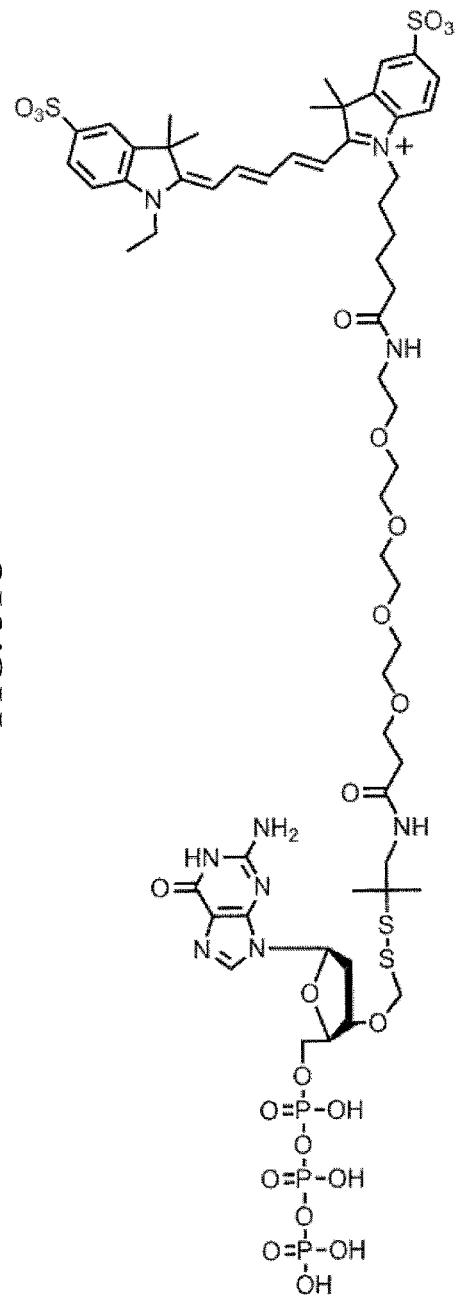
Figure 32:
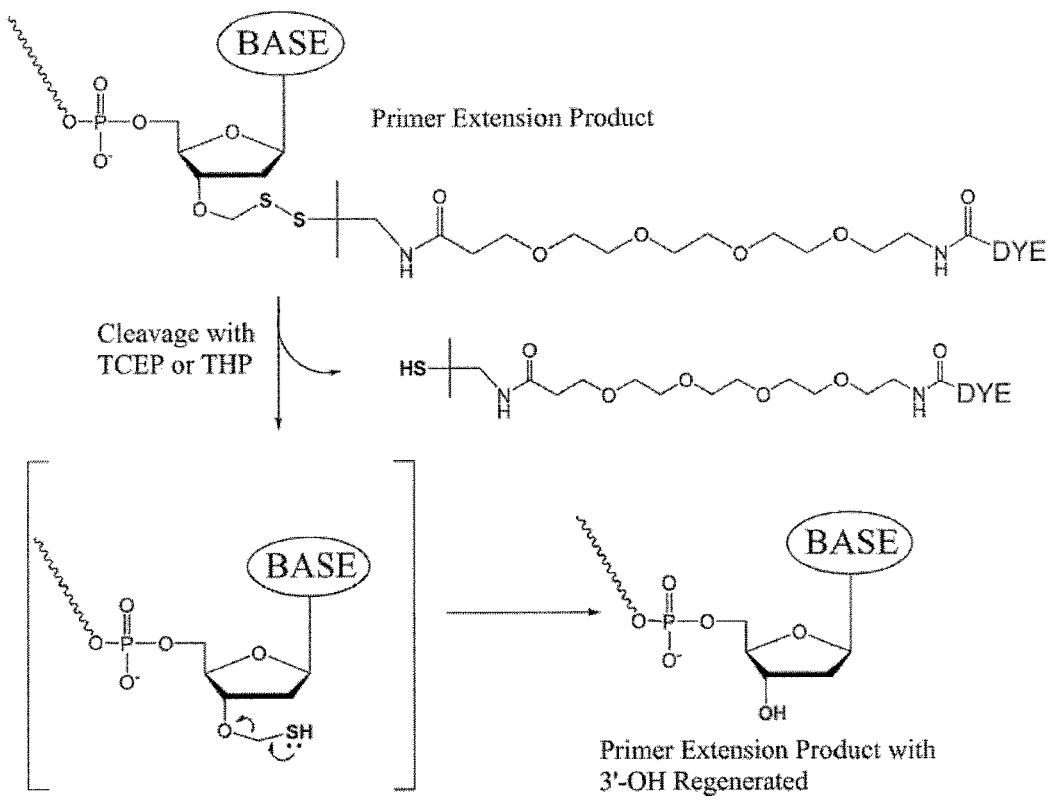
FIG. 32. Cleavage of DNA extension product incorporated with a 3'-O-Dye (Label)-DTM-dNTP generates a free 3'-OH group and an extended DNA strand without any modification.
Figure 32:
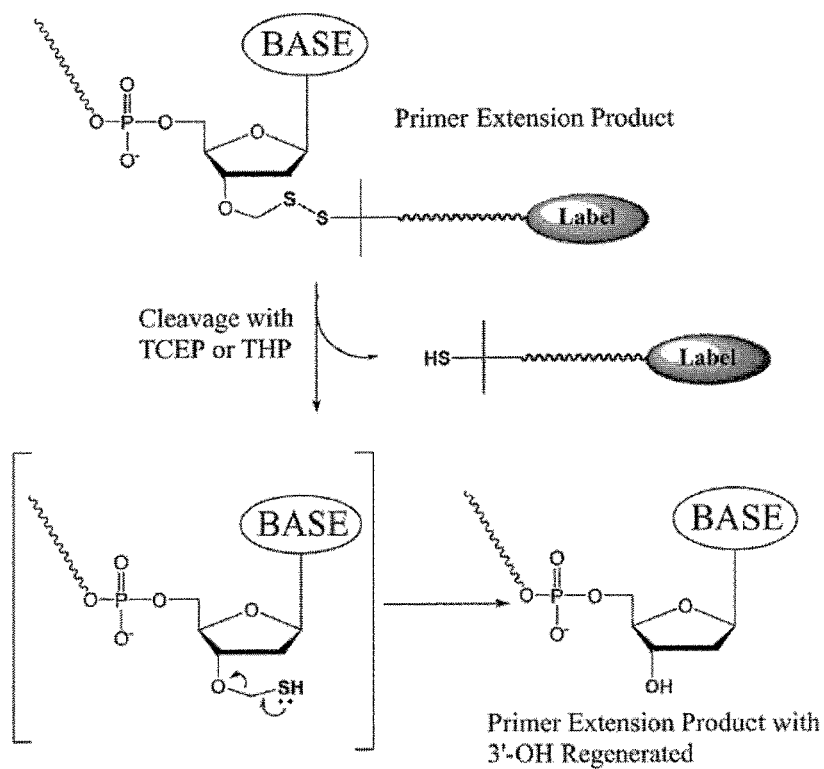
Figure 33A:
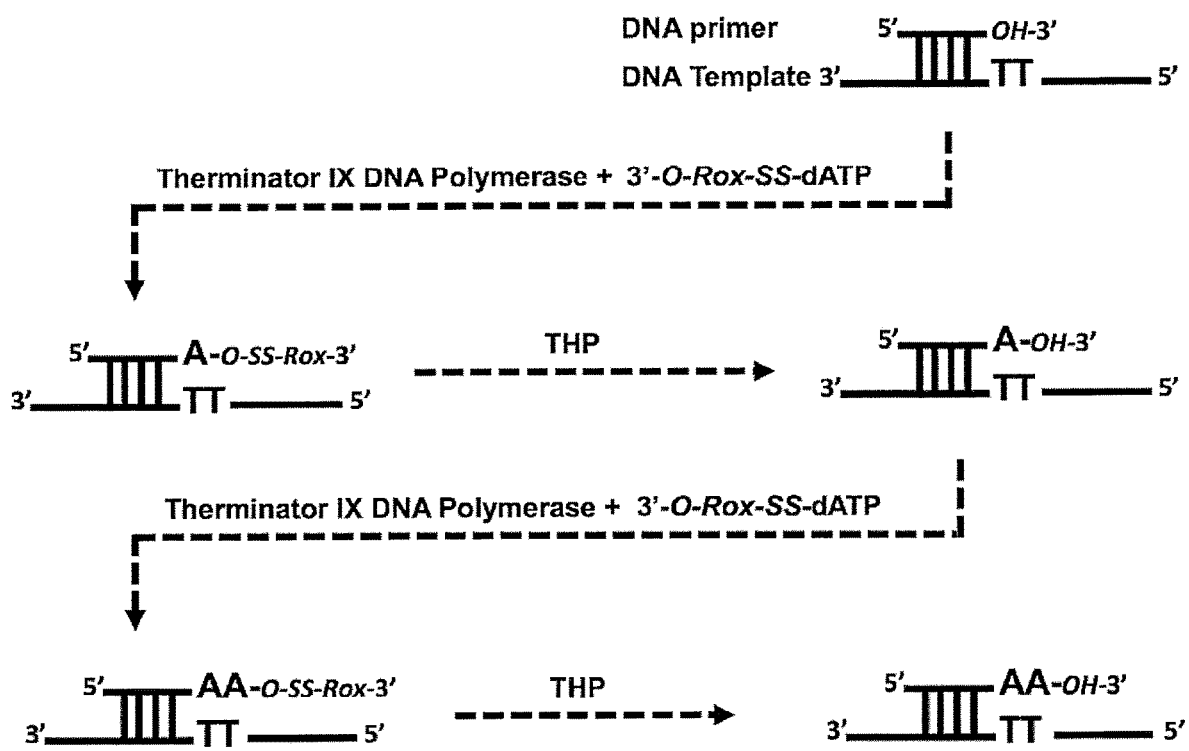
FIGS. 33A-33E. Experimental scheme of consecutive DNA polymerase extension and cleavage using 3'-O-Rox-DTM-dATP as a reversible terminator. MALDI-TOF MS spectra of the first extension (Product 1, calc. M.W. 7076), the first cleavage (Product 2, calc. M.W. 6400), and the second extension (Product 3, calc. M.W. 7382).
Figure 33B:
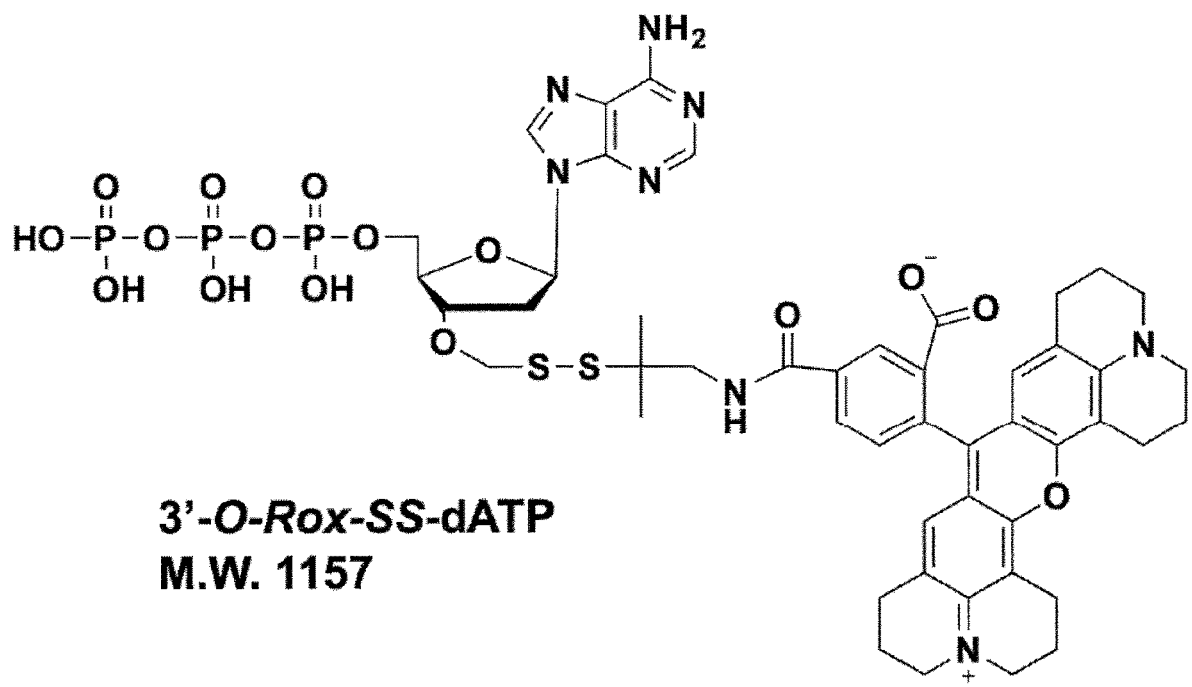
Figure 33B:
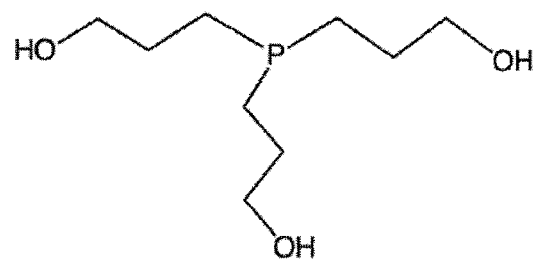
Figure 33C:
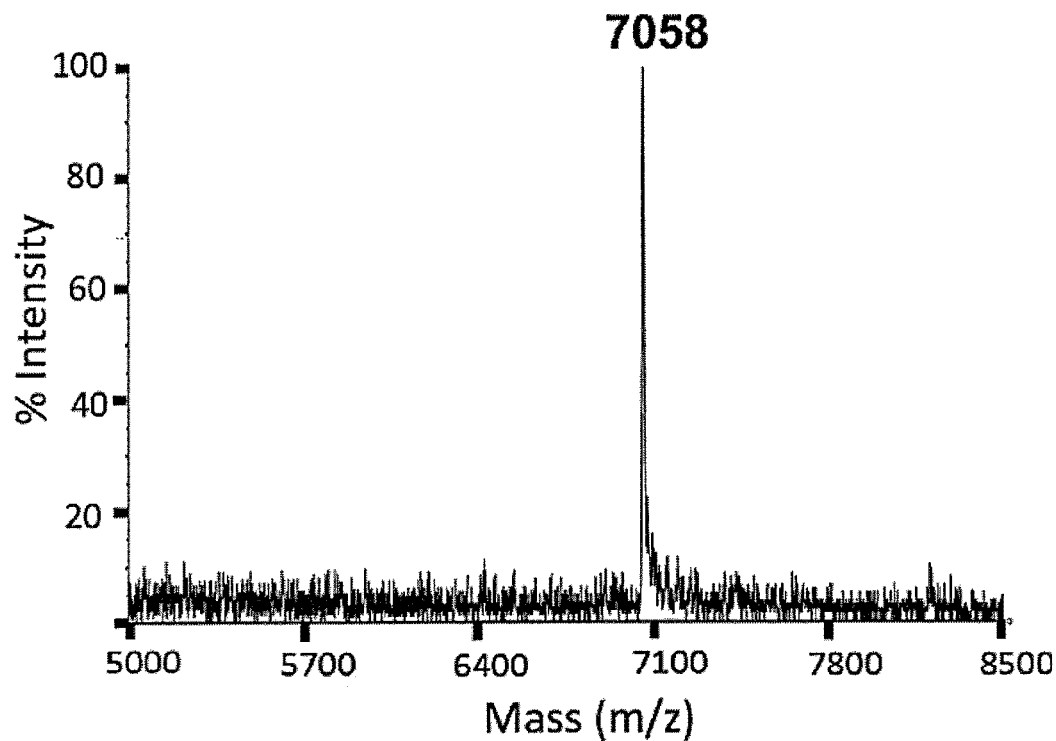
Figure 33D:
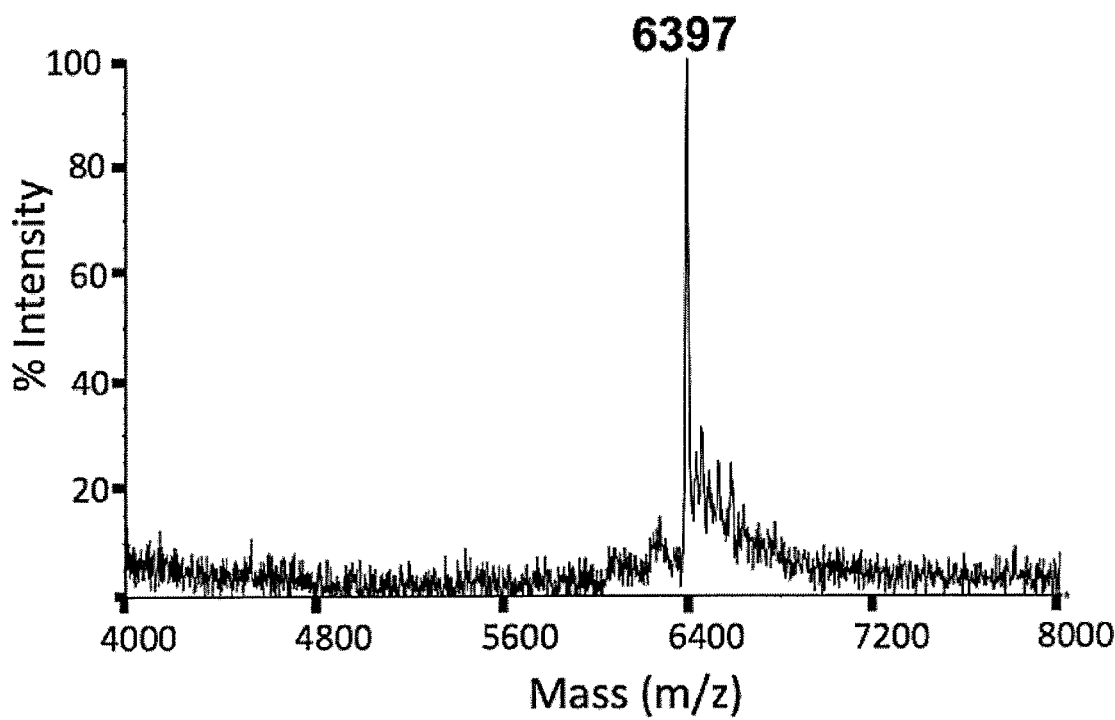
Figure 33E:
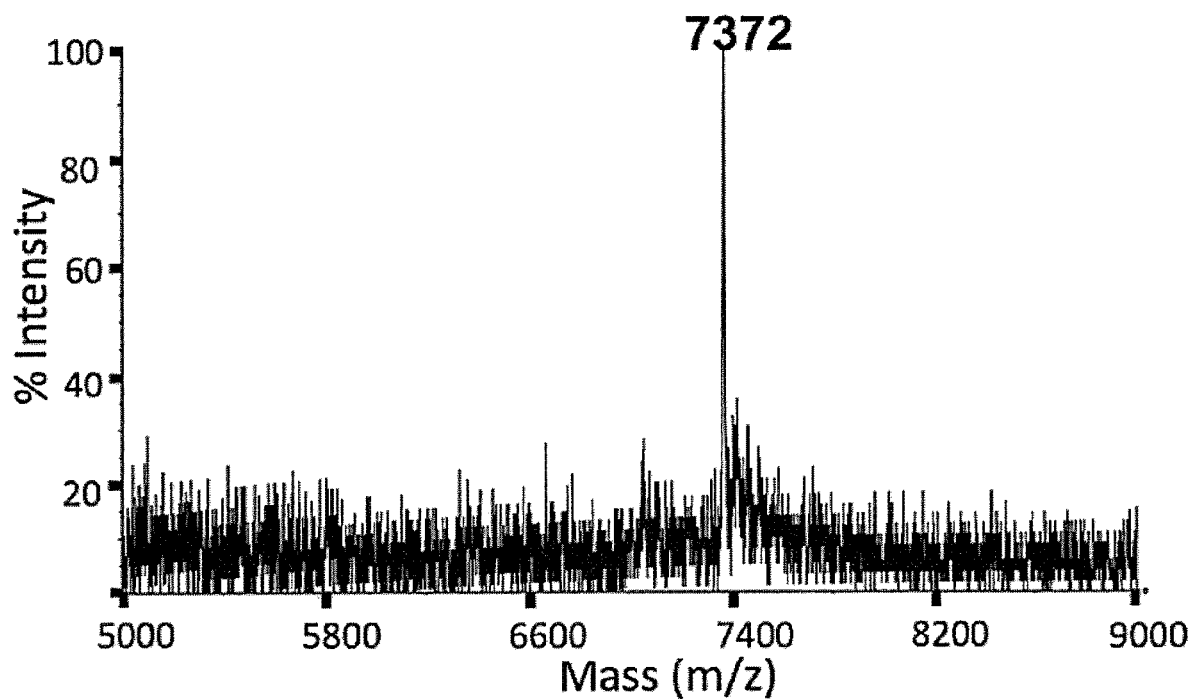

The structures of 3'-O-tBu-SS-dNTPs are shown in FIG. 29 and these molecules are synthesized according to the schemes described below.

Synthesis of 3'-O-modified Nucleotide Analogues

Disclosed herein, and in and explained in greater detail below, is the design and synthesis of the three groups of nucleotides with the following general structure 3'-O-CleavableLinker-Label-dNTPs, 3'-O-CleavableLinker-Anchor-dNTPs and 3'-O-CleavableGroup-dNTPs are described as follows: 3'-O-DTM-Dye-dNTPs, 3'-O-anchor-DTM-dNTPs (FIGS. 2A-2E and FIG. 4) and 3'-O-DTM-dNTPs in which fluorescent dye or a small anchor moiety is attached to the 3'-O-position of the nucleotide through a DTM cleavable linker. Each incorporated nucleotide analogue contains a 3'-O-DTM group that is cleaved after each cycle of sequence determination; the 3'-OH of the incorporated nucleotide is then regenerated for subsequent cycles of SBS. Using MALDI-TOF MS to analyze the DNA extension products resulting from the use of the abovementioned nucleotides in polymerase reactions, we established that these 3'-O modified nucleotide analogues are efficient substrates for DNA polymerase to terminate the DNA synthesis. These results also established that both the fluorophore (or anchor moiety) and the 3'-O-DTM group are removable with high efficiency in a single step in an aqueous solution and without any residual scars on the incorporated nucleotide. Thus, the natural nucleotides are restored after each nucleotide incorporation and cleavage, producing a growing DNA strand that bears no modifications and will not impede further polymerase reactions.

Synthesis of 3'-O-tert-butyldithiomethyl-dTTP (5a) (Scheme 30)

3'-O-methylthiomethyl-5'-O-tert-butyldimethylsilyl thymidine (T2): To a stirring solution of 5'-O-tert-butyldimethylsilyl thymidine (T1, 1.07 g, 3 mmol) in DMSO (10 mL) was added acetic acid (2.6 mL, 45 mmol) and acetic anhydride (8.6 mL, 90 mmol). The reaction mixture was stirred at room temperature until the reaction was complete, which was monitored by TLC. Then the mixture was added slowly to a saturated solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the compound was purified by silica gel column chromatography (ethyl acetate/hexane: 1:2) to give pure product T2 (0.97 g, 74%). $^1$H NMR (400 MHz, $CDCl_3$) δ:8.16 (s, 1H), 7.48 (s, 1H), 6.28 (m, 1H), 4.62 (m, 2H), 4.46 (m, 1H), 4.10 (m, 11H), 3.78-3.90 (m, 2H), 2.39 (m, 11H), 2.14 (s, 3H), 1.97 (m, 1H), 1.92 (s, 3H), 0.93 (s, 9H), 0.13 (s, 3H); HRMS (FAB$^+$) calc'd for $C_{18}H_{33}N_2O_5SSi$ [(M+H)+]: 417.1879, found: 417.1890.

3'-O-tert-butyldithiomethyl-5'-O-tert-butyldimethylsilyl thymidine (T3) 3'-O-methylthiomethyl-5'-O-tert-butyldimethylsilyl thymidine (T2, 420 mg, 1 mmol) was dissolved in anhydrous dichloromethane (20 mL), followed by addition of triethylamine (0.18 mL, 1.31 mmol, 1.2 eq.) and molecular sieve (3 Å, 2 g). The mixture was cooled in an ice-bath after stirring at room temperature for 30 min and then a solution of sulfuryl chloride (redistilled, 0.1 mL, 1.31 mmol, 1.2 eq.) in anhydrous dichloromethane (3 mL) was added dropwise over 2 minutes. The ice-bath was removed and the reaction mixture was stirred further for 30 min. Then potassium p-toluenethiosulfonate (375 mg, 1.65 mmol) in anhydrous DMF (2 mL) was added to the mixture. Stirring was continued at room temperature for additional hour followed by addition of tert-butyl mercaptan (1 mL). The reaction mixture was stirred at room temperature for 30 min and quickly filtered through celite. The filter was washed with dichloromethane and the organic fraction was concentrated to give crude product T3.

3'-O-tert-butyldithiomethyl-thymidine (T4): Without isolation, the crude compound T3 was dissolved in THF (10 mL) and a THF solution of tetrabutylammonium fluoride (1.0 M, 1.04 mL, 1.04 mmol) was added. The reaction mixture was stirred at room temperature for 4 hours. The reaction mixture was concentrated in vacuo, saturated $NaHCO_3$ solution (50 mL) was added and the mixture was extracted with dichloromethane (3×20 mL). The organic layer was dried over anhydrous $Na_2SO_4$, filtered, concentrated and the obtained crude mixture was purified by flash column chromatography (dichloromethane/methanol: 20/1) to give 3'-O-tert-butyldithiomethyl-thymidine T4 (132 mg, 35% from compound T2). $^1$H NMR (300 MHz, $CDCl_3$) δ: 7.41 (q, J=1.2 Hz, 1H), 6.15 (dd, J=7.4, 6.5 Hz, 1H), 4.89-4.82 (m, 2H), 4.62-4.54 (m, 1H), 4.15 (q, J=3.0 Hz, 1H), 3.97-3.86 (m, 2H), 2.42 (ddd, J=7.5, 4.8, 2.5 Hz, 2H), 1.95 (d, J=1.2 Hz, 3H), 1.36 (s, 8H).

3'-O-tert-butyldithiomethyl-dTTP (T5): 3'-O-tert-butyldithiomethyl-thymidine (T4, 50 mg, 0.13 mmol), tetrabutylammonium pyrophosphate (197 mg, 0.36 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of 3'-O-tert-butyldithiomethyl-thymidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for additional 2 hours. The resulting solution was extracted with ethyl acetate (2×30 mL). The aqueous layer was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford T5, which was characterized by MALDI-TOF MS calc'd for $C_{15}H_{27}N_2O_{14}P_3S_2$: 616.4, found: 615.4.

Synthesis of 3'-O-tert-butyldithiomethyl-dGTP (Scheme 31)

$N^2$-isobutyryl-3'-O-methylthiomethyl-5'-O-tert-butyldimethylsilyl-2'-deoxyguanosine (G2): To a stirring solution of the $N^2$-isobutyryl-5'-O-tert-butyldimethylsilyl-2'-deoxyguanosine (G1, 1.31 g, 3 mmol) in DMSO (10 mL) was added acetic acid (2.6 mL, 45 mmol) and acetic anhydride (8.6 mL, 90 mmol). The reaction mixture was stirred at room temperature until the reaction was complete, which was monitored by TLC. Then the mixture was added slowly to a saturated solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the compound was purified by silica gel column chromatography (DCM/methanol: 20:1) to give pure product G2 (75%, 1.15 g). $^1$H NMR (400 MHz, $CDCl_3$) δ 12.10 (d, J=2.9 Hz, 1H), 9.17 (d, J=3.0 Hz, 1H), 8.03 (m, 1H), 6.18 (td, J =6.9, 2.9 Hz, 1H), 4.74-4.60 (m, 3H), 4.13 (dq, J=6.8, 3.3 Hz, 1H), 3.84-3.75 (m, 2H), 2.78 (m, 1H), 2.54 (m, 2H), 2.16 (s, 3H), 1.33-1.22 (m, 6H), 0.96-0.87 (m, 9H), 0.09 (dd, J=6.7, 3.8 Hz, 6H).

$N^2$-isobutyryl-3'-O-tert-butyldithiomethyl-5'-O-tert-butyldimethylsilyl-2'-deoxyguanosine (G3): $N^2$-isobutyryl-3'-O-methylthiomethyl-5'-O-tert-butyldimethylsilyl-2'-deoxyguanosine (G2, 511 mg, 1.0 mmol) was dissolved in anhydrous dichloromethane (20 mL), followed by addition of triethylamine (0.17 mL, 1.2 mmol) and molecular sieve (3 Å, 2 g). The mixture was cooled in an ice-bath after stirring at room temperature for 30 min and then a solution of sulfuryl chloride (0.095 mL, 1.2 mmol) in anhydrous dichloromethane (3 mL) was added dropwise over 2 minutes. The ice-bath was removed and the reaction mixture was stirred further for 30 min. Then potassium 4-toluenethiosulfonate (341 mg, 1.5 mmol) in anhydrous DMF (2 mL) was added to the mixture. Stirring was continued at room temperature for an additional hour followed by addition of tert-butyl mercaptan (1 mL). The reaction mixture was stirred at room temperature for 30 min and quickly filtered through celite. The filter was washed with dichloromethane and the organic fraction was concentrated to give crude product G3.

$N^2$-isobutyryl-3'-O-tert-butyldithiomethyl-2'-deoxyguanosine (G4): Without the isolation, the crude compound G3 was dissolved in THF (10 mL) and a THF solution of tetrabutylammonium fluoride(1.OM, 1.04 mL, 1.04 mmol) was added. The reaction mixture was stirred at room temperature for 4 hours. The reaction mixture was concentrated in vacuo, saturated $NaHCO_3$ solution (50 mL) was added and the mixture was extracted with dichloromethane (3×20 mL). The organic layer was dried over anhydrous $Na_2SO_4$, filtered, concentrated and the obtained crude mixture was purified by flash column chromatography (dichloromethane/methanol: 20/1) to give $N^2$-isobutyryl-3'-O-tert-butyldithiomethyl-2'-deoxyguanosine G4 (155 mg, 33% from compound G2). $^1$H NMR (400 MHz, $CDCl_3$) δ 12.19 (s, 1H), 9.44 (s, 1H), 7.97 (s, 1H), 6.17 (dd, J=8.4, 5.9 Hz, 1H), 5.04 (s, 1H), 4.92-4.80 (m, 2H), 4.76-4.64 (m, 1H), 4.26 (q, J=2.6 Hz, 1H), 3.98 (dd, J=12.2, 2.8 Hz, 1H), 3.80 (d, J=12.3 Hz, 1H), 2.91-2.73 (m, 2H), 2.49 (m, 1H), 1.35 (s, 9H), 1.36-1.22 (m, 6H). $^{13}$C NMR (75 MHz, $CDCl_3$) δ 179.60, 155.80, 148.10, 147.96, 139.11, 122.30, 86.29, 81.22, 78.96, 63.21, 48.07, 38.18, 36.64, 30.29, 19.39, 19.34. [1159]3'—O-tert-butyldithiomethyl-dGTP (G5): $N^2$-isobutyryl-3'-O-tert-butyldithiomethyl-2'-deoxyguanosine (G4, 50 mg, 0.11 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of $N^2$-isobutyryl-3'-O-tert-butyldithiomethyl-2'-deoxyguanosine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for additional 2 hours. The resulting solution was extracted with ethyl acetate. The aqueous layer was concentrated in vacuo to approximately 20 mL, Then concentrated $NH_4OH$ (20 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford G5. HRMS ($ESI^-$) calc'd for $C_{15}H_{25}N_5O_{13}P_3S_2$ [(M–H)$^-$]: 640.0103, found: 640.0148.

Synthesis of 3'-O-tert-butyldithiomethyl-dATP (Scheme 32)

$N^6$-Benzoyl-5'-O-tert-butyldimethylsilyl-3'-O-methylthiolmethyl-2'-deoxyadenosine (A2): To a solution of the $N^6$-Benzoyl-5'-O-tert-butyldimethylsilyl-2'-deoxyadenosine (A1, 1.41 g, 3 mmol) in DMSO (10 mL) with stirring was added acetic acid (3 mL) and acetic anhydride (9 mL). The reaction mixture was stirred at room temperature until the reaction was complete, which was monitored by TLC. Then the mixture was added slowly to the solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the residue of the desired compound was purified by silica gel column chromatography (dichloromethane/methanol: 30/1) to give pure product A2 (1.39 g, 88%). $^1$H NMR (400 MHz, $CDCl_3$) δ 9.12 (s, 1H), 8.81 (s, 1H), 8.35 (s, 1H), 8.10-8.01 (m, 2H), 7.68 (m, 1H), 7.49 (m, 2H), 6.53 (dd, J=7.5, 6.0 Hz, 1H), 4.78-4.65 (m, 3H), 4.24 (dt, J=4.3, 3.1 Hz, 1H), 3.98-3.81 (m, 2H), 2.80-2.60 (m, 2H), 2.21 (s, 3H), 0.94 (s, 10H), 0.13 (s, 6H); MS ($APCI^+$) calc'd for $C_{26}H_{36}N_4O_4SSi$: 528.74, found: 529.4 $[M+H]^+$.

$N^6$-Benzoyl-5'-O-tert-butyldimethylsilyl-3'-O-tert-butyldithiomethyl-2'-deoxyadenosine (A3): N-Benzoyl-5'-O-tert-butyldimethylsilyl-3'-O-methylthiolmethyl-2'-deoxyadenosine (A2, 529 mg, 1.0 mmol) was dissolved in anhydrous dichloromethane (20 mL), followed by addition of triethylamine (0.17 mL, 1.2 mmol) and molecular sieve (3 Å, 2 g). The mixture was cooled in an ice-bath after stirring at room temperature for 30 min and then a solution of sulfuryl chloride (0.095 mL, 1.2 mmol) in anhydrous dichloromethane (3 mL) was added dropwise over 2 minutes. The ice-bath was removed and the reaction mixture was stirred further for 30 min. Then potassium 4-toluenethiosulfonate (341 mg, 1.5 mmol) in anhydrous DMF (2 mL) was added to the mixture. Stirring was continued at room temperature for an additional hour followed by addition of tert-butyl mercaptan (1 mL). The reaction mixture was stirred at room temperature for 30 min and quickly filtered through celite. The filter was washed with dichloromethane and the organic fraction was concentrated to give crude product A3.

$N^6$-Benzoyl-3'-O-tert-butyldithiomethyl-2'-deoxyadenosine (A4): Without the isolation, the crude compound A3 was dissolved in THF (10 mL) and a THF solution of tetrabutylammonium fluoride(1.OM, 1.04 mL, 1.04 mmol) was added. The reaction mixture was stirred at room temperature for 4 hours. The reaction mixture was concentrated in vacuo, saturated $NaHCO_3$ solution (50 mL) was added and the mixture was extracted with dichloromethane (3×20 mL). The organic layer was dried over anhydrous $Na_2SO_4$, filtered, concentrated and the obtained crude mixture was purified by flash column chromatography (dichloromethane/methanol: 20/1) to give $N^6$-Benzoyl-3'-O-tert-butyldithiomethyl-2'-deoxyadenosine A4 (128 mg, 26% from compound A2). $^1$H NMR (400 MHz, DMSO-d$_6$) δ 11.18 (s, 1H), 8.77 (s, 1H), 8.71 (s, 1H), 8.10-8.02 (m, 2H), 7.66 (t, J=7.6 Hz, 1H), 7.56 (t, J=7.6 Hz 2H), 6.47 (dd, J=8.0, 6.0 Hz, 1H), 5.15 (t, J=5.5 Hz, 1H), 5.00 (s, 2H), 4.65 (dt, J=5.4, 2.4 Hz, 1H), 4.12 (td, J=4.7, 2.2 Hz, 1H), 3.02-2.88 (m, 1H), 2.84 (q, J=7.3 Hz, 2H), 2.61 (m, 1H), 1.35 (s, 9H).

3'-O-tert-butyldithiomethyl-dATP (A5): N$^6$-Benzoyl-3'-O-tert-butyldithiomethyl-2'-deoxyadenosine (A4, 50 mg, 0.10 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of N$^6$-Benzoyl-3'-O-tert-butyldithiomethyl-2'-deoxyadenosine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for additional 2 hours. The resulting solution was extracted with ethyl acetate. The aqueous layer was concentrated in vacuo to approximately 20 mL, Then concentrated NH$_4$OH (20 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford A5, which was characterized by MALDI-TOF MS calc'd for C$_{15}$H$_{26}$N$_5$O$_{12}$P$_3$S$_2$: 625.4, found: 625.0.

Synthesis of 3'-O-tert-butyldithiomethyl-dCTP (Scheme 33)

N$^4$-Benzoyl-3'-O-methylthiomethyl-5'-O-tert-butyldimethylsilyl-2'-deoxycytidine(C2): To a solution of N$^6$-Benzoyl-5'-O-tert-butyldimethylsilyl-2'-deoxycytidine(C1, 1.5 g, 3.4 mmol) in DMSO (6.5 mL) with stirring was added acetic acid (2.91 mL) and acetic anhydride (9.29 mL). The reaction mixture was stirred at room temperature until the reaction for 2 days. Then the reaction mixture was added dropwise to solution of sodium bicarbonate and extracted by ethyl acetate(50 ml×3). The obtained crude product was purified by column chromatography (Ethyl Acetate/Hexane: 8/2) to give pure product 5 (1.26 g, 74%) as a white solid. $^1$H NMR (400 MHz, CDCl$_3$) δ 8.43 (d, J=7.4 Hz, 1H), 7.92 (d, J=7.6 Hz, 2H), 7.69-7.50 (m, 4H), 6.31 (t, J=6.1 Hz, 1H), 4.75-4.59 (m, 2H), 4.51 (dt, J=6.2, 3.9 Hz, 1H), 4.20 (dt, J=3.7, 2.6 Hz, 1H), 4.01 (dd, J=11.4, 2.9 Hz, 1H), 3.86 (dd, J=11.4, 2.4 Hz, 11H), 2.72 (ddd, J=13.8, 6.2, 4.1 Hz, 1H), 2.18 (s, 4H), 0.97 (s, 9H), 0.17 (d, J=3.9 Hz, 6H). HRMS (ESI$^+$) calc'd for C$_{24}$H$_{35}$N$_3$O$_5$SSi[(M+H)$^+$]: 506.2145, found: 506.2146.

N$^4$-Benzoyl-3'-O-tert-butyldithiomethyl-5'-O-tert-butyldimethylsilyl-2'-deoxycytidine (C3): N$^4$—Benzoyl-3'-O-methylthiomethyl-5'-O-tert-butyldimethylsilyl-2'-deoxycytidine (C2, 1.01 g, 2 mmol) was dissolved in anhydrous dichloromethane (8 mL, followed by addition of triethylamine (278 L, 2 mmol) and molecular sieves (3 Å, 1 g). The mixture was cooled in an ice-bath after stirring at room temperature for 0.5 hour and then a solution of sulfuryl chloride (161 L, 2.2 mmol) in anhydrous dichloromethane (8 mL) was added dropwise. The ice-bath was removed and the reaction mixture was stirred further for 0.5 hour. Then potassium p-toluenethiosulfonate (678 mg, 3 mmol) in anhydrous DMF (1 mL) was added to the mixture. Stirring was continued at room temperature for additional 1 hour followed by addition of tert-butyl mercaptan (1 mL). The reaction mixture was stirred at room temperature for 0.5 hour and quickly filtered. The solvent was removed under reduced pressure and the residue was dissolved in ethyl acetate and washed by brine(3×50 mL). The combined organic layers were dried over Na$_2$SO$_4$ and filtered. The filtrate was concentrated to dryness under reduced pressure and the residue of the desired compound was purified by silica gel column chromatography using a gradient of ethyl acetate-Hexane from 3:7(v/v) to 5:5(v/v), yielding 959 mg C3 as a white foam (83%). $^1$H NMR (400 MHz, CDCl$_3$) δ 8.43 (d, J=7.4 Hz, 1H), 7.92 (d, J=7.6 Hz, 2H), 7.69-7.50 (m, 4H), 6.31 (t, J=6.1 Hz, 1H), 4.75-4.59 (m, 2H), 4.51 (dt, J=6.2, 3.9 Hz, 1H), 4.20 (dt, J=3.7, 2.6 Hz, 1H), 4.01 (dd, J=11.4, 2.9 Hz, 1H), 3.86 (dd, J=11.4, 2.4 Hz, 1H), 2.72 (ddd, J=13.8, 6.2, 4.1 Hz, 1H), 2.18 (s, 4H), 0.97 (s, 9H), 0.17 (d, J=3.9 Hz, 6H), 0.10 (s, 2H). HRMS (ESI$^+$) calc'd for: C$_{27}$H$_{41}$N$_3$O$_5$S$_2$Si [(M+Na)$^+$]:602.2155, found: 602.2147.

N$^4$-Benzoyl-3'-O-tert-butyldithiomethyl-2'-deoxycytidine (C4): To a stirred solution of N$^4$-Benzoyl-3'-O-tert-butyldithiomethyl-5'-O-tert-butyldimethylsilyl-2'-deoxycytidine (C3, 958 mg, 1.66 mmol) in a mixture of Tetrahydrofuran (24 ml), tetrabutylammonium fluoride (1.OM, 2.48 mL) was added in small portion, stirred at room temperature for 3 hours. The reaction mixture was poured into saturated sodium bicarbonate solution (50 mL) and extracted by Ethyl Acetate (3×50 mL). The combined organic layers were dried over Na$_2$SO$_4$ and filtered. The filtrate was concentrated to dryness under reduced pressure and the residue of the desired compound was purified by silica gel column chromatography using a gradient of ethyl acetate-Hexane from 5:5(v/v), affording 435 mg C4 as white solid powder (56%). $^1$H NMR (400 MHz, Methanol-d$_4$) δ 8.52 (d, J=7.5 Hz, 1H), 8.04-7.96 (m, 2H), 7.71-7.60 (m, 2H), 7.61-7.51 (m, 2H), 6.28-6.19 (m, 1H), 4.95-4.86 (m, 2H), 4.54 (dt, J1=6.0, 3.0 Hz, 1H), 4.23 (q, J=3.4 Hz, 1H), 3.92-3.76 (m, 2H), 2.70 (ddd, J=13.9, 6.0, 2.9 Hz, 1H), 2.25 (ddd, J=13.6, 7.2, 6.2 Hz, 1H), 1.37 (s, 9H). HRMS (ESI$^+$) calc'd for C$_{21}$H$_{27}$N$_3$O$_5$S$_2$[(M+Na)$^+$]: 488.1290, found: 488.1297.

3'-O-tert-butyldithiomethyl-dCTP (C5): N$^4$—Benzoyl-3'-O-tert-butyldithiomethyl-2'-deoxycytidine (C4, 50 mg, 0.11 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 reaction mixture was added to the solution of N$^4$-Benzoyl-3'-O-tert-butyldithiomethyl-2'-deoxycytidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for additional 2 hours. The resulting solution was extracted with ethyl acetate. The aqueous layer was concentrated in vacuo to approximately 20 mL, Then concentrated NH$_4$OH (20 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford C5. HRMS (ESI$^-$) calc'd for $C_{14}H_{25}N_3O_{13}P_3S_2$ [(M-H)$^-$]: 600.0042, found: 600.0033.

The synthesis of 3'-O-Bodipy-DTM-dTTP and 3'-O-Bodipy-PEG$_4$-DTM-dTTP (Scheme 34)

3'-O-methylthiomethyl-5'-O-tert-butyldimethylsilyl thymidine (T2): To a solution of the 5'-O-tert-Butyldimethylsilyl thymidine (T1, 1.07 g, 3 mmol) in DMSO (10 mL) with stirring was added acetic acid (2.6 mL) and acetic anhydride (8.6 mL). The reaction mixture was stirred at room temperature until the reaction was complete (48 h), which was monitored by TLC. Then the mixture was added slowly to the solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the residue of the desired compound was purified by silica gel column chromatography (ethyl acetate/hexane: 1/2) to give pure product T2 (0.97 g, 74%). $^1$H NMR (400 MHz, CDCl$_3$) δ: 8.16 (s, 1H), 7.48 (s, 1H), 6.28 (m, 1H), 4.62 (m, 2H), 4.46 (m, 1H), 4.10 (m, 1H), 3.78-3.90 (m, 2H), 2.39 (m, 1H), 2.14 (s, 3H), 1.97 (m, 1H), 1.92 (s, 3H), 0.93 (s, 9H), 0.13 (s, 3H); HRMS (Fab$^+$) calc'd for $C_{18}H_{33}N_2O_5SSi$ [(M+H)+]: 417.1879, found: 417.1890.

Compound T6: 3'—O-methylthiomethyl-5'-O-tert-butyldimethylsilyl thymidine (T2, 625 mg, 1.50 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.12 mL, 1.50 mmol) in anhydrous dichloromethane (3 mL) was added dropwise during 2 minutes. The ice-bath was removed and the reaction mixture was stirred further for 0.5 hour. Then potassium p-toluenethiosulfonate (0.61 g, 2.25 mmol) in anhydrous DMF (3 mL) was added to the mixture. Stirring was continued at room temperature for additional 1 hour followed by addition of 2,2,2-trifluoro-N-(2-mercapto-2-methylpropyl)acetamide (403 mg, 2.01 mmol). The reaction mixture was stirred at room temperature for 0.5 hour and quickly filtered through celite. The filter was washed with dichloromethane and the organic fraction was concentrated to give the crude compound T6.

Compound T7: Without the isolation, the crude compound T6 was dissolved in THF (10 mL) followed by the addition of tetrabutylammonium fluoride THF solution (1.0 M, 1.0 mL, 1.0 mmol). The mixture was stirred at room temperature until the reaction was complete, which was monitored by TLC. Then, the mixture was concentrated in vacuo, saturated NaHCO$_3$ solution (50 mL) was added and the mixture was extracted with dichloromethane. The organic layer was dried over anhydrous Na$_2$SO$_4$, filtered, concentrated and the obtained crude mixture was purified by flash column chromatography (dichloromethane/methanol: 20/1) to give compound T7 (199 mg, 27% from compound T2). $^1$H NMR (400 MHz, CDCl$_3$) δ 9.41 (s, 1H), 7.44 (s, 1H), 7.07 (t, J=6.6 Hz, 11H), 6.11 (t, J=7.0 Hz, 1H), 4.88-4.80 (m, 2H), 4.57 (m, 1H), 4.14 (q, J=2.9 Hz, 1H), 3.93 (m, 1H), 3.82 (m, 1H), 3.49 (d, J=6.2 Hz, 2H), 3.10 (t, J=6.2, 4.1 Hz, 1H), 2.42-2.39 (m, 2H), 1.91 (s, 3H), 1.31 (m, 6H). $^{13}$C NMR (75 MHz, CDCl$_3$) δ 164.39, 158.22, 150.95, 137.33, 111.61, 85.30, 80.39, 78.65, 77.66, 62.84, 50.70, 48.24, 37.28, 25.74, 12.86; MS (APCI$^+$) calc'd for $C_{17}H_{24}F_3N_3O_6S_2$: 487.51, found: 487.6.

3'-O—NH$_2$-DTM-dTTP (T8): Compound T7 (50 mg, 103 μmol), tetrabutylammonium pyrophosphate (150 mg, 0.27 mmol) and 2-chloro-4-H-1,3,2-benzodioxaphosphorin-4-one (33 mg, 0.17 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-t-Butyl-dithiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. The resulting solution was extracted with ethyl acetate. Then concentrated NH$_4$OH (20 ml) was added and stirred overnight at room temperature. The aqueous layer was concentrated in vacuo and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford T8, which was characterized by MALDI-TOF MS, calc'd for $C_{15}H_{28}N_3O_{14}P_3S_2$: 631.45, found: 631.0.

3'-O-Bodipy-DTM-dTTP (compound T9): To a stirred solution of Bodipy FL-NHS ester (1.5 mg, 3.9 μmol) in DMF (0.2 ml), 3'-O-DTM-dTTP (compound T8, 4.0 μmol) in NaHCO$_3$/Na$_2$CO$_3$ buffer (pH 8.9, 0.1 M, 0.3 ml). The reaction mixture was stirred at room temperature for 3 h with exclusion of light. The reaction mixture was purified by a preparative silica gel TLC plate (dichloromethane/methanol, 4:1). The crude product was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-Bodipy-dTTP T9, which was characterized by MALDI-TOF MS, calc'd for $C_{29}H_{41}BF_2N_5O_{15}P_3S_2$: 905.5, found: 904.1.

3'-O-Bodipy-PEG$_4$-DTM-dTTP (compound T10): To a stirred solution of Bodipy-PEG$_4$-Acid (2.1 mg, 3.8 μmol) in dry DMF (200 μl), N,N-disuccinimidyl carbonate (1.03 mg, 4.0 μmol) and 4-dimethylaminopyridine (0.48 mg, 4.0 μmol) were added. The reaction mixture was stirred at room temperature for 2 h. TLC indicated that Bodipy-PEG$_4$-Acid was completely converted to compound Bodipy-PEG$_4$-NHS ester, which was directly used to couple with amino-3'-O-DTM-dTTP (3.8 mol) in NaHCO$_3$/Na$_2$CO$_3$ buffer (pH 8.9, 0.1 M) (300 μl). The reaction mixture was stirred at room temperature for 3 h with exclusion of light. The reaction mixture was purified by a preparative silica gel TLC plate (dichloromethane/methanol, 4:1). The crude mixture was purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-PEG$_4$-Bodipy-dTTP T10, which was characterized by MALDI-TOF MS calc'd for $C_{40}H_{62}BF_2N_6O_{20}P_3S_2$: 1152.8, found: 1151.4.

The synthesis of 3'-O-Rox-DTM-dATP and 3'-O-Rox-PEG$_4$-DTM-dATP (Scheme 35)

N$^4$-Benzoyl-3'-O-methylthiomethyl-5'-O-tert-butyldimethylsilyl-2'-deoxyadenosine (A2): To a solution of the N$^4$Benzoyl-5'-O-tert-butyldimethylsilyl-2'-deoxyadenosine (A1, 1.41 g, 3 mmol) in DMSO (10 mL) with stirring was added acetic acid (3 mL) and acetic anhydride (9 mL). The reaction mixture was stirred at room temperature until the reaction was complete (48 h), which was monitored by TLC. Then the mixture was added slowly to the solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the residue of the desired compound was purified by silica gel column chromatography (dichloromethane/methanol: 30/1) to give pure product A2 (1.39 g, 88%). $^1$H NMR (400 MHz, $CDCl_3$) δ 9.12 (s, 1H), 8.81 (s, 1H), 8.35 (s, 1H), 8.10-8.01 (m, 2H), 7.68 (m, 1H), 7.49 (m, 2H), 6.53 (dd, J=7.5, 6.0 Hz, 1H), 4.78-4.65 (m, 3H), 4.24 (dt, J=4.3, 3.1 Hz, 1H), 3.98-3.81 (m, 2H), 2.80-2.60 (m, 2H), 2.21 (s, 3H), 0.94 (s, 10H), 0.13 (s, 6H); MS ($APCI^+$) calc'd for $C_{25}H_{35}N_5O_4SSi$: 529.73, found:: 529.4.

Compound A6: N-Benzoyl-3'-O-methylthiomethyl-5'-O-tert-butyldimethylsilyl-2'-deoxyadenosine (A2, 550 mg, 1.04 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.12 mL, 1.50 mmol) in anhydrous dichloromethane (3 mL) was added dropwise during 2 minutes. The ice-bath was removed and the reaction mixture was stirred further for 0.5 hour. Then potassium p-toluenethiosulfonate (0.61 g, 2.25 mmol) in anhydrous DMF (3 mL) was added to the mixture. Stirring was continued at room temperature for additional 1 hour followed by addition of 2,2,2-trifluoro-N-(2-mercapto-2-methylpropyl)acetamide (302 mg, 1.5 mmol). The reaction mixture was stirred at room temperature for 0.5 hour and quickly filtered through celite. The filter was washed with dichloromethane and the organic fraction was concentrated to give the crude compound A6: MS ($APCI^+$) calc'd for $C_{30}H_{41}F_3N_6O_{15}S_2Si$: 714.89, found: 714.6.

Compound A7: Without the isolation, the crude compound A6 was dissolved in THF (10 mL) followed by the addition of tetrabutylammonium fluoride THF solution (1.0 M, 1.0 mL, 1.0 mmol). The mixture was stirring at room temperature until the reaction was complete, which was monitored by TLC. Then, the mixture was concentrated in vacuo, saturated $NaHCO_3$ solution (50 mL) was added and the mixture was extracted with dichloromethane. The organic layer was dried over anhydrous $Na_2SO_4$, filtered, concentrated and the obtained crude mixture was purified by flash column chromatography (dichloromethane/methanol: 20/1) to give compound A7 (128 mg, 20% from compound A2). $^1$H NMR (400 MHz, $CDCl_3$) δ 9.16 (s, 1H), 8.77 (s, 1H), 8.11 (s, 1H), 8.07-8.00 (m, 2H), 7.61 (m, 1H), 7.56-7.52 (m, 2H), 6.91 (m, 1H), 6.33 (dd, J=9.4, 5.5 Hz, 1H), 5.83 (d, J=10.7 Hz, 1H), 4.88 (d, J=2.6 Hz, 2H), 4.75 (dt, J=5.4, 1.2 Hz, 1H), 4.36 (q, J =1.7 Hz, 1H), 4.03 (dd, J=12.8, 1.8 Hz, 1H), 3.81 (t, J=10.9 Hz, 11H), 3.51 (d, J=6.2 Hz, 2H), 3.10 (m, 1H), 2.56-2.46 (m, 1H), 1.36 (s, 6H); $^{13}$C NMR (75 MHz, $CDCl_3$) δ 164.91, 152.49, 151.03, 150.71, 142.95, 133.82, 133.33, 129.29, 128.29, 125.00, 118.23, 114.41, 88.01, 87.10, 80.37, 80.19, 63.91, 60.76, 50.66, 47.99, 38.17, 25.82, 25.75; MS ($APCI^+$) calc'd for $C_{24}H_{27}F_3N_6O_5S_2$: 600.6, found: 600.7.

3'-NH2-DTM-dATP (A8: Compound A7 (50 mg, 103 µmol), tetrabutylammonium pyrophosphate (150 mg, 0.27 mmol) and 2-chloro-4-H-1,3,2-benzodioxaphosphorin-4-one (33 mg, 0.17 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-t-Butyldithiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. Then concentrated $NH_4OH$ (20 ml) was added and stirred overnight at room temperature. The resulting solution was extracted with ethyl acetate. The aqueous layer was concentrated in vacuo to approximately 20 mL, Then concentrated $NH_4OH$ (20 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford A8, which was characterized by MALDI-TOF MS, calc'd for $C_{15}H_{27}N_6O_2P_3S_2$: 640.45, found: 639.6.

3'-O-Rox-DTM-dATP (compound A9): To a stirred solution of ROX—NHS ester (2 mg, 3.2 µmol) in DMF (0.2 ml), amino 3'-O-DTM-dATP (compound A8, 3.0 µmol) in $NaHCO_3/Na_2CO_3$ buffer (pH 8.9, 0.1 M, 0.3 ml). The reaction mixture was stirred at room temperature for 3 h with exclusion of light. The reaction mixture was purified by a preparative silica gel TLC plate (dichloromethane/methanol, 4:1). The crude product was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-Rox-dATP A9, which was characterized by MALDI-TOF MS, calc'd for $C_{48}H_{55}N_8O_{16}P_3S_2$: 1157.0, found: 1155.4.

3'-O-Rox-$PEG_4$-DTM-dATP (compound A10): To a stirred solution of ROX-$PEG_4$-Acid (2.6 mg, 3.3 µmol) in dry DMF (200 µl), N,N-disuccinimidyl carbonate (0.90 mg, 3.5 µmol) and 4-dimethylaminopyridine (0.43 mg, 3.5 µmol) were added. The reaction mixture was stirred at room temperature for 2 h. TLC indicated that ROX-$PEG_4$-Acid was completely converted to compound ROX-$PEG_4$-NHS ester, which was directly used to couple with amino-3'-O-DTM-dATP (3.5 µmol) in $NaHCO_3/Na_2CO_3$ buffer (pH 8.9, 0.1 M) (300 µl). The reaction mixture was stirred at room temperature for 3 h with exclusion of light. The reaction mixture was purified by a preparative silica gel TLC plate (dichloromethane/methanol, 4:1). The crude mixture was then purified with anion exchange chromatography on DEAE-Sephadex A-25 at 4° C. using a gradient of TEAB (pH 8.0; 0.1-1.0 M), and further purified on reverse-phase HPLC to afford 3'-O-DTM-$PEG_4$-Rox-dATP A10, which was characterized by MALDI-TOF MS, calc'd for $C_{59}H_{76}N_9O_{21}P_3S_2$: 1404.3, found: 1401.6.

Synthesis of 3'-O-TCO-DTM-dTTP (Scheme 36): Compound T8 (1 mg, 1.6 µmol) was dissolved in 0.1 M $NaHCO_3/Na_2CO_3$ (500 µL, pH=8.8), followed by addition of trans-cyclooctenyl NHS ester (1 mg, 3.7 µmol) in anhydride DMF (500 µL), stirring at r.t. for 4 hours. The product was purified by reverse-phase HPLC to give pure T11, which was characterized by HRMS, calc'd for $C_{21}H3_3N6O_{16}P3[M-H]$: 717.1088, found: 717.1100.

Synthesis of 3'-O-Biotin-DTM-dCTP (Scheme 37)

$N^4$-Benzoyl-3'-O-methylthiomethyl-5'-O-tert-butyldimethylsilyl-2'-deoxycytidine (C2): To a solution of the $N^4$-Benzoyl-5'-O-tert-butyldimethylsilyl-2'-deoxycytidine (C1, 2.25 g, 2.51 mmol) in DMSO (20 mL) with stirring was added acetic acid (8 mL) and acetic anhydride (20 mL). The reaction mixture was stirred at room temperature until the reaction was complete (24 h), which was monitored by TLC. Then the mixture was added slowly to the solution of sodium bicarbonate under vigorous stirring and extracted with ethyl acetate (3×50 mL). The combined organic layers were dried over $Na_2SO_4$ and filtered. The filtrate was concentrated to dryness under reduced pressure and the residue of the desired compound was purified by silica gel column chromatography (DCM/MeOH: 1/30) to give pure product C2 (2.13 g, 83%). $^1H$ NMR (400 MHz, $CDCl_3$) δ: 8.43 (d, J=8.4 Hz, 1 H), 7.92 (d, J=7.6 Hz, 2H), 7.66 (m, 1H), 7.53 (m, 3H), 6.30 (t, J=6.0 Hz, 1H), 4.69 (dd, J=32 Hz; 7.6 Hz, 2H), 4.50 (m, 1H), 4.18 (m, 1H), 3.98-3.83 (m, 2H), 2.74 (m, 1H), 2.21-2.12 (m, 4H), 0.93 (s, 9H), 0.15 (m, 6H). MS (APCI$^+$) calc'd for $C_{24}H^{35}N^3O_5SSi$: 505.70, found: 505.6.

Compound C6: $N^4$-Benzoyl-3'-O-methylthiomethyl-5'-O-tert-butyldimethylsilyl-2'-deoxycytidine (C2, 0.87 mg, 1.72 mmol) was dissolved in anhydrous dichloromethane (20 mL), followed by addition of triethylamine (0.3 mL) and molecular sieves (3 Å, 2 g). The mixture was cooled in an ice-bath after stirring at room temperature for 0.5 hour and then a solution of sulfuryl chloride (0.15 mL, 1.80 mmol) in anhydrous dichloromethane (3 mL) was added dropwise during 2 minutes. The ice-bath was removed and the reaction mixture was stirred further for 0.5 hour. Then potassium p-toluenethiosulfonate (0.68 g, 2.5 mmol) in anhydrous DMF (3 mL) was added to the mixture. Stirring was continued at room temperature for additional 1 hour followed by addition of 2,2,2-trifluoro-N-(2-mercapto-2-methylpropyl)acetamide (402 mg, 2.0 mmol). The reaction mixture was stirred at room temperature for 0.5 hour and quickly filtered through celite. The filter was washed with dichloromethane and the organic fraction was concentrated to give the crude compound C6: MS (APCI$^-$) calc'd for $C_{29}H_{41}F_3N_4O_6S_2Si$: 690.87, found: 689.8 [M–H]$^-$.

Compound C7: Without the isolation, the crude compound C6 was dissolved in THF (10 mL) followed by the addition of tetrabutylammonium fluoride THF solution (1.0 M, 1.0 mL, 1.0 mmol). The mixture was stirring at room temperature until the reaction was complete, which was monitored by TLC. Then, the mixture was concentrated in vacuo, saturated $NaHCO_3$ solution (50 mL) was added and the mixture was extracted with dichloromethane. The organic layer was dried over anhydrous $Na_2SO_4$, filtered, concentrated and the obtained crude mixture was purified by flash column chromatography (dichloromethane/methanol: 20/1) to give compound C7 (171 mg, 17% from compound C2). $^1H$ NMR (400 MHz, $CDCl_3$) δ 8.94 (br, 1H), 8.32 (d, J=7.5 Hz, 1H), 7.90-7.83 (m, 2H), 7.65-7.55 (m, 2H), 7.49 (dd, J=8.4, 7.1 Hz, 2H), 7.12 (t, J=6.3 Hz, 1H), 6.15 (t, J=6.4 Hz, 1H), 4.93-4.78 (m, 2H), 4.58 (dt, J=6.5, 3.3 Hz, 1H), 4.24 (q, J=3.0 Hz, 1H), 4.02 (dd, J=12.1, 3.0 Hz, 1H), 3.86 (dd, J=12.1, 2.9 Hz, 1H), 3.66 (br, 1H), 3.50 (d, J=6.2 Hz, 2H), 2.71 (m, 1H), 2.40 (m, 1H), 1.34 (s, 6H). $^{13}C$ NMR (75 MHz, $CDCl_3$) δ 162.82, 158.20, 157.72, 155.45, 146.01, 133.63, 129.40, 127.98, 97.24, 89.14, 86.04, 80.46, 78.25, 62.47, 50.72, 48.04, 38.47, 25.78; MS (APCI$^+$) calc'd for $C_{23}H^{27}F^3N_4O_6S_2$: 576.61, found: 576.

3'-$NH_2$-DTM-dCTP (C8): Compound C7 (50 mg, 87 μmol), tetrabutylammonium pyrophosphate (140 mg, 0.25 mmol) and 2-chloro-4-H-1,3,2-benzodioxaphosphorin-4-one (30 mg, 0.15 mmol) were dried separately over night under high vacuum at ambient temperature. The tetrabutylammonium pyrophosphate was dissolved in dimethylformamide (DMF, 1 mL) under argon followed by addition of tributylamine (1.5 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-t-Butyl-dithiomethyl thymidine and stirred further for 1 hour at room temperature. Iodine solution (0.02 M iodine/pyridine/water) was then injected into the reaction mixture until a permanent brown color was observed. After 10 min, Water (30 mL) was added and the reaction mixture was stirred at room temperature for additional 2 hour. The resulting solution was extracted with ethyl acetate. The aqueous layer was concentrated in vacuo and the residue was diluted with 5 ml of water. The crude mixture was then purified with anion exchange chromatography on DEAE-Sephadex A-25 at 4° C. using a gradient of TEAB (pH 8.0; 0.1-1.0 M), and further purified by reverse-phase HPLC to afford C8, which was characterized by MALDI-TOF MS, calc'd for $C_{14}H_{29}N_4O_{13}P_3S_2$: 618.4, found: 616.7

3'--Biotin-DTM-dCTP (C9): To a stirred solution of Bio-NHS ester (2 mg, 3.2 μmol) in DMF (0.2 ml), amino 3'-O-DTM-dCTP (compound C8, 3.0 μmol) in $NaHCO_3$/$Na_2CO_3$ buffer (pH 8.9, 0.1 M, 0.3 ml). The reaction mixture was stirred at room temperature for 3 h with exclusion of light. The crude product was then purified with anion exchange chromatography on DEAE-Sephadex A-25 at 4° C. using a gradient of TEAB (pH 8.0; 0.1-1.0 M), and further purified on reverse-phase HPLC to afford 3'-O-Biotin-DTM-dATP C9, which was characterized by MALDI-TOF MS, calc'd: 842, found: 842.5.

The syntheses of 3'-O-DTM-Anchor-SS(DTM)-dNTPs (structures shown in FIG. 4) are described in Schemes below.

Synthesis of Dye Labeled Binding Molecules

Synthesis of Labeled Binding Molecules Conjugated with Fluorescent Dyes is conducted by coupling commercially available binding molecule starting materials with various activated Dyes. Example synthesis of Rox Labeled Tetrazine, Alexa488 Labeled SHA and R6G Labeled Dibenzocyclooctyne(DBCO) is shown in Scheme 42.

Synthesis of multiple-dye conjugated binding molecules (Cy5-tetrazine as an example) is shown in Schemes 43-45.

Figure 10A:
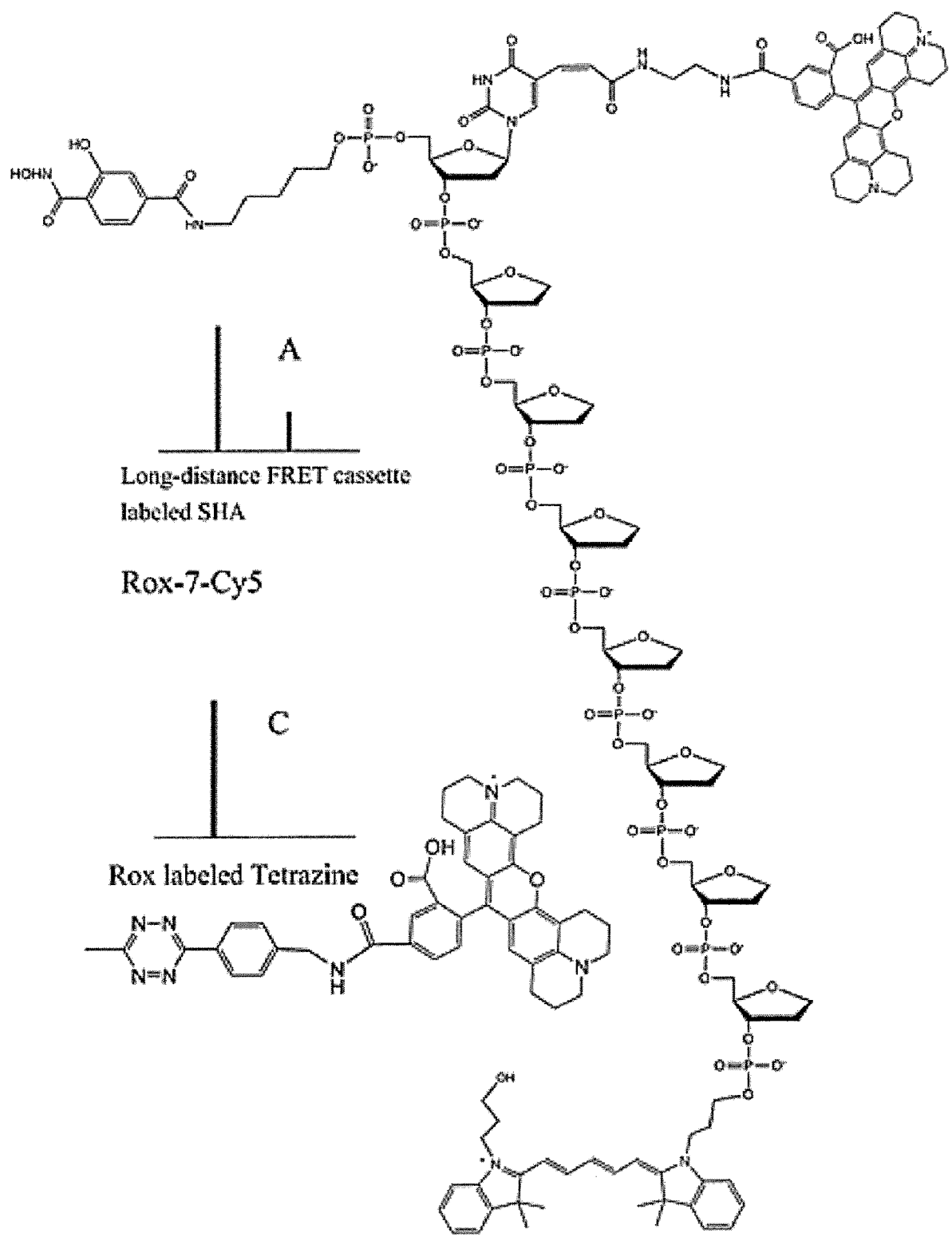
FIGS. 10A-10D. Examples of FRET Cassette Labeled Binding Molecules. FRET cassette provides numerous distinct FRET signal signatures by altering the distance between donor and accepter fluorophores. Binding molecules conjugated to such FRET cassette with four unique FRET signal signatures enables the coupling of such FRET cassette to 3'-end of the DNA extension product using "anchor" moiety coupling reaction; this allows for the use of two different fluorescent dyes with distinct emissions through FRET to perform scarless 2-color SBS to identify the four DNA bases. In the set of FRET cassette labeled binding molecules shown above, Rox and Cy5, serving as donor and accepter respectively, are attached with 7 or 3 dSpacer monomers to yield two different FRET cassettes: FRET Cassette A (Rox-7-Cy5 attached to SHA), which has a long separation distance of 7 dSpacer monomers between Rox and Cy5, will have a less efficient energy transfer from the donor (Rox) to the accepter (Cy5), thereby generating a weak Cy5 emission signal and a strong Rox emission signal. FRET Cassette B (Rox-3-Cy5 attached to trans-cyclooctene TCO), which has a short separation distance of 3 dSpacer monomers between Rox and Cy5, will have a more efficient energy transfer from the donor (Rox) to the accepter (Cy5), thereby generating a strong Cy5 signal and a weak Rox signal. In Labeling Molecule C, where the single Rox is attached to Tetrazine, only the Rox signal is detectable. In Labeling Molecule D, where the single Cy5 is attached to Streptavidin, only the Cy5 signal is detectable. Following a scheme similar to the one indicated in FIG. 7 to perform SBS by carrying out the following steps to sequence DNA: Addition of the DNA polymerase and the four 3'-O-"anchor"-SS(DTM)-dNTPs (3'-O-TCO-SS-dATP, 3'-O-PBA-SS-dCTP, 3'-O-Biotin-SS-dGTP and 3'-O—N₃-SS-dTTP) to the immobilized primed DNA template enables the incorporation of the complementary nucleotide analogue to the growing DNA strand to terminate DNA synthesis. After washing away the unincorporated nucleotide analogues, add the dye labeled binding molecules (A, B, C, D), which will specifically connect with each of the four unique "anchor" moieties at the 3'-end of each DNA extension product to enable the labeling of each DNA product terminated with each of the four nucleotide analogues (A, C, G, T) with four distinct fluorescent signatures. Detection of the unique fluorescent signatures from the labeled DNA products allows for the identification of the incorporated nucleotide. Next, treatment of the DNA products with THP cleaves the SS linker, leading to the removal of the fluorescent label and the regeneration of a free 3'-OH group on the DNA extension product, which is ready for next cycle of DNA sequencing reaction.
Figure 10B:
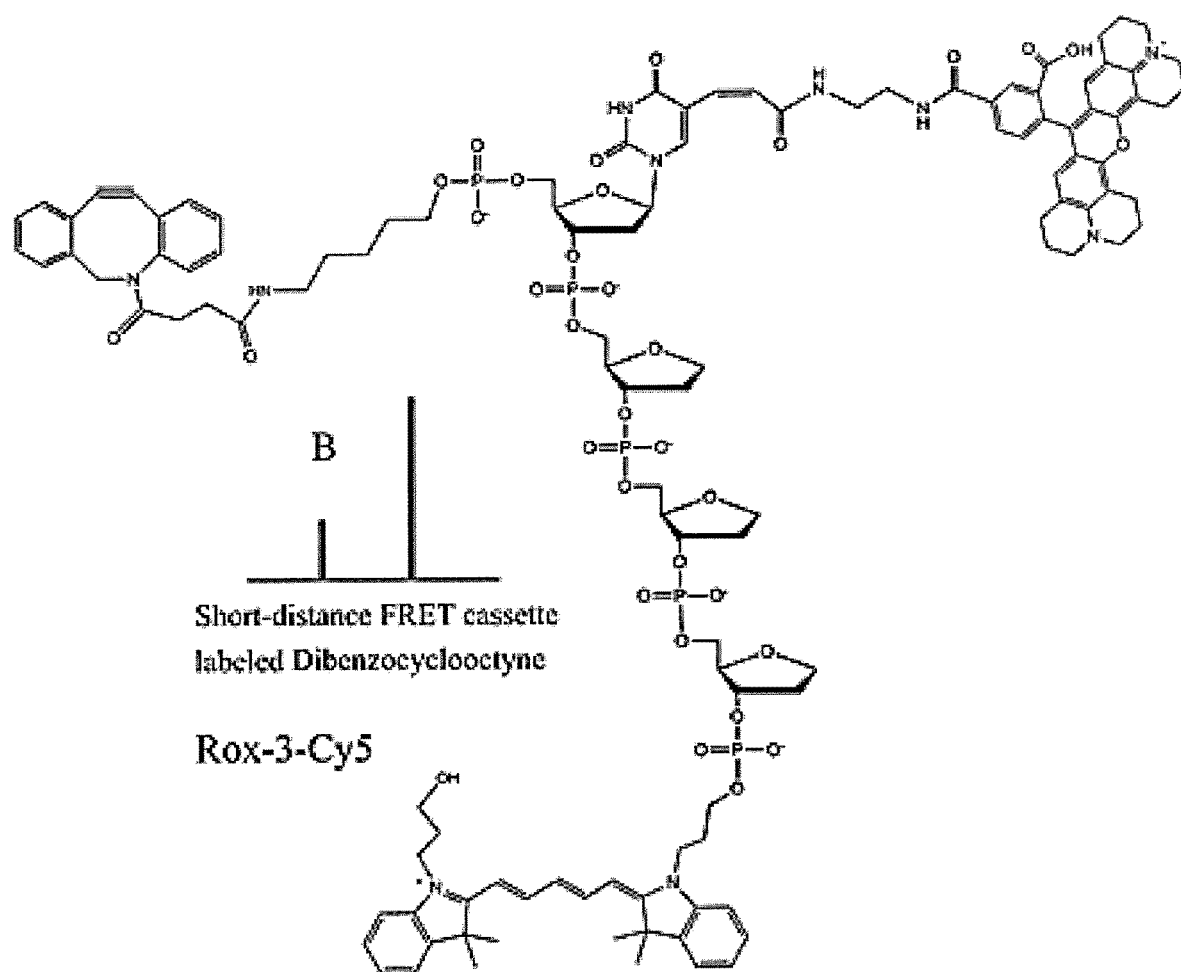
Figure 10C:
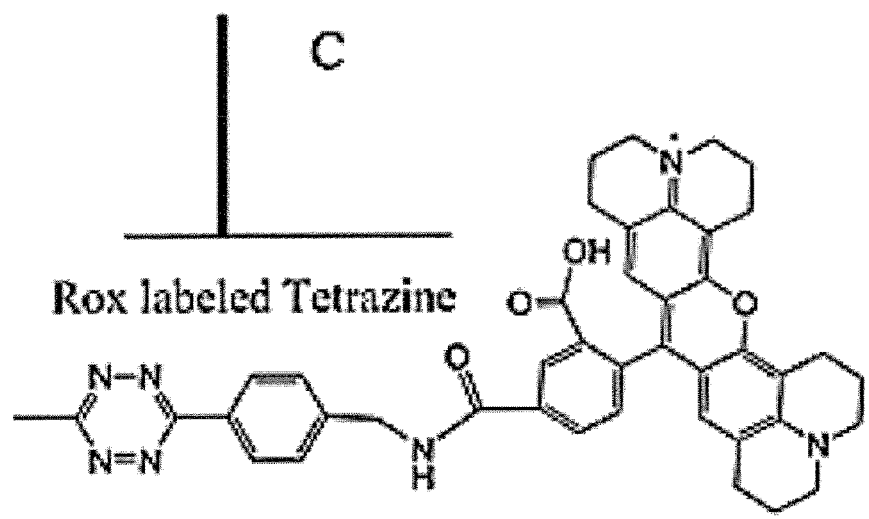
Figure 10D:
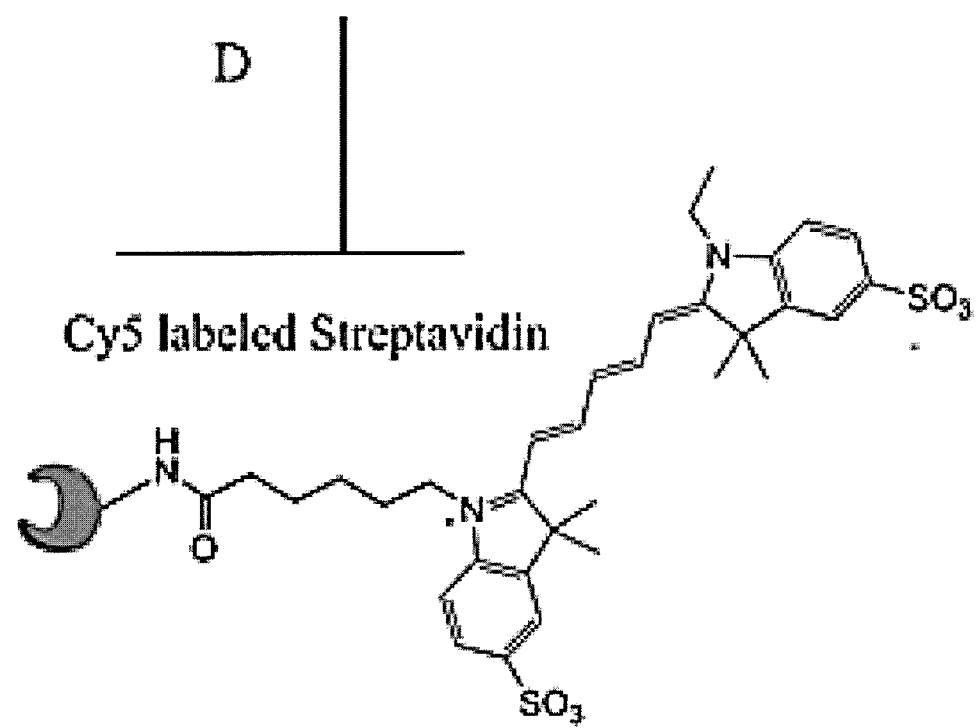
Figure 11:
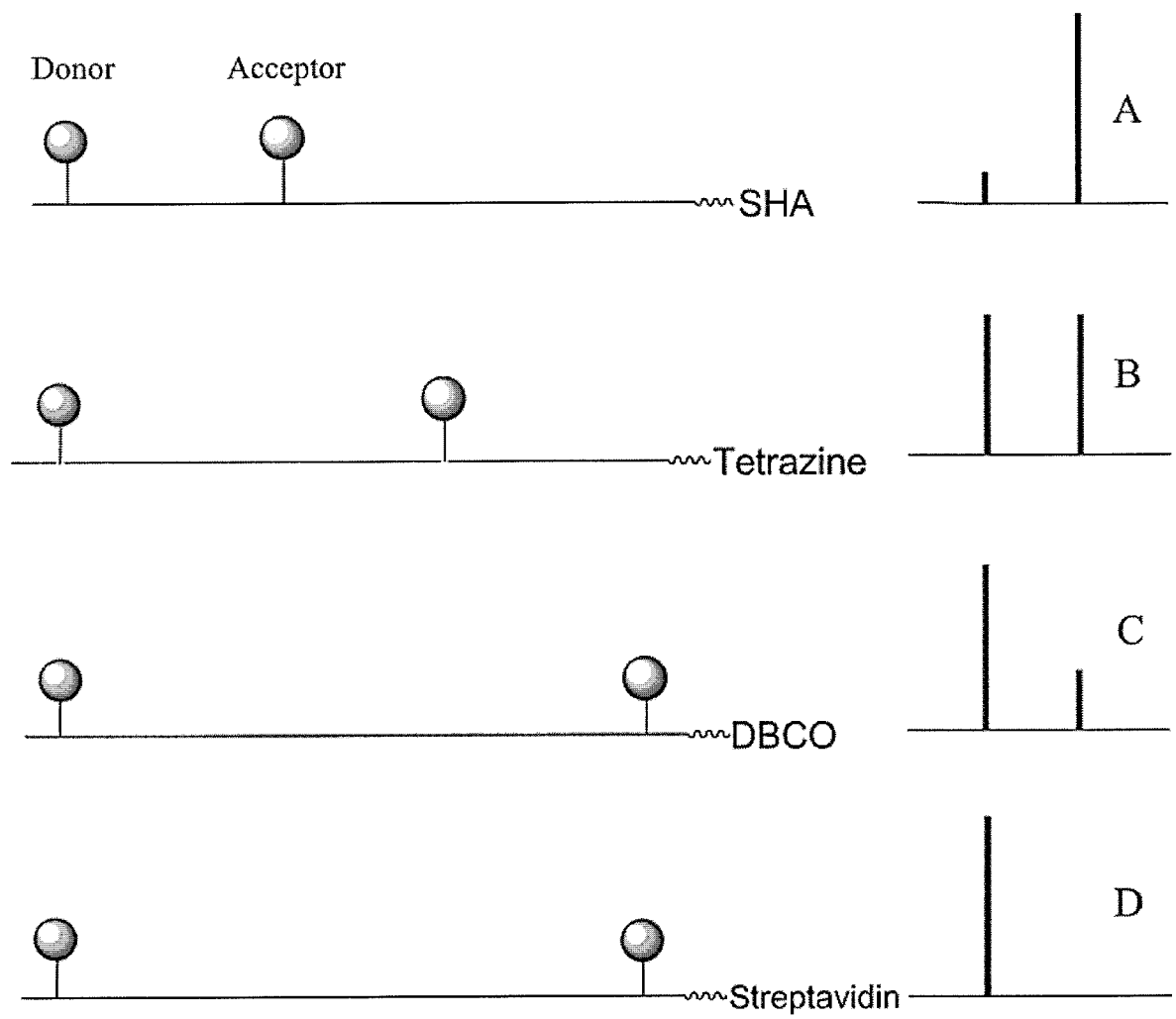
FIG. 11. General Scheme of FRET Cassette Labeled Binding Molecules (e.g., SHA, Tetrazine, DBCO, Streptavidin, etc.). The FRET Cassette provides numerous distinct FRET signal signatures (A, B, C, D) by altering the distance between the donor and the accepter fluorophores. Following a scheme similar to the one indicated in FIG. 7 to perform SBS by carrying out the following steps to sequence DNA: Addition of the DNA polymerase and the four 3'-O-"anchor"-SS(DTM)-dNTPs (3'-O-TCO-SS-dATP, 3'-O-PBA-SS-dCTP, 3'-O-Biotin-SS-dGTP and 3'-O—N₃-SS-dTTP) to the immobilized primed DNA template enables the incorporation of the complementary nucleotide analogue to the growing DNA strand to terminate DNA synthesis. After washing away the unincorporated nucleotide analogues, add the dye labeled binding molecules (A, B, C, D), which will specifically connect with each of the four unique "anchor" moieties at the 3'-end of each DNA extension product to enable the labeling of each DNA product terminated with each of the four nucleotide analogues (A, C, G, T) with four distinct fluorescent signatures. Detection of the unique fluorescent signatures from the labeled DNA products allows for the identification of the incorporated nucleotide. Next, treatment of the DNA products with THP cleaves the SS linker, leading to the removal of the fluorescent label and the regeneration of a free 3'-OH group on the DNA extension product, which is ready for next cycle of DNA sequencing reaction.

Synthesis of Rox-7-Cy5 labeled SHA (shown FIG. 10A).

Cy5 labeled CPG (Glen Research) is used to start solid phase oligonucleotide synthesis on a DNA synthesizer. dSpacer phosphoramidite is used as the building block for seven consecutive coupling cycles, then Rox labeled dT phosphoramidite is used in the next coupling cycle. C5 amino modifier phosphoramidite is used in the last coupling cycle. After cleavage under mild condition following the GlenResearch protocol, the amino modified Rox-7-Cy5 product is produced and purified by HPLC. Coupling of SHA NHS ester with amino modified Rox-7-Cy5 in DMSO/$NaCO_3$, $NaHCO_3$ buffer (pH 8.9) will afford Rox-7-Cy5 labeled SHA.

Synthesis of Rox-3-Cy5 labeled DBCO (shown in FIG. 10 B)

Cy5 labeled CPG (Glen Research) is used to start solid phase oligonucleotide synthesis on a DNA synthesizer. dSpacer phosphoramidite is used as the building block for three consecutive coupling cycles, then Rox labeled dT phosphoramidite is used in the next coupling cycle. C5 amino modifier phosphoramidite is used in the last coupling cycle. After cleavage under mild condition following the GlenResearch protocol, the amino modified Rox-3-Cy5 product is produced and purified by HPLC. Coupling of DBCO NHS ester with amino modified Rox-3-Cy5 in DMSO/$NaCO_3$, $NaHCO_3$ buffer (pH 8.9) will afford Rox-3-Cy5 labeled DBCO.

Syntheses of Labeled Binding Molecules Conjugated with Fluorescent Dye via Different Cleavable Linkers (the structures of these molecules are shown in FIG. 12) are shown in Schemes 46 to 52.

Synthesis of Labeled Binding Molecules Conjugated with Fluorescent Dyes is achieved by coupling commercially available activated Dyes with binding molecules containing cleavable linkage moieties, which are synthesized using commercially available materials.

The example synthesis of SHA-2-Nitrobenzyl (linker)-ATTO647N is shown in Scheme 46; The example synthesis of Tetrazine-Azo(linker)-ATTO647N is shown in Scheme 47 and the construction of the Azo linker moiety is accomplished using literature method;[41] The example synthesis of Streptavidin-Dimethylketal(linker)-ATTO647N is shown in Scheme 48 and the construction of the Dimethylketal linker moiety is accomplished using literature method; [42] The example synthesis of Dibenzocyclooctyne(DBCO)-Allyl (linker)-ATTO647N is shown in Scheme 49; The example synthesis of Dibenzocyclooctyne(DBCO)-Dde(linker)-ATTO647N is shown in Scheme 50 and the construction of the Dde linker moiety is accomplished using literature method. [43] The example synthesis of Terazine-Dde(linker)-ATTO647N and Terazine-Dde(linker)-ROX is shown in Scheme 51; The example synthesis of DBCO-Azo(-N=N-Linker)-ATTO647N and DBCO-Azo(-N=N-Linker)-ROX is shown in Scheme 52.

Detailed cleavage reaction and the cleaved products using linkers constructed from Azo, Dimethylketal and Dde under mild conditions (using $N_2S_2O_4$, Citric acid and $N_2H_4$ respectively) are shown in Scheme 55 using Tetrazine-Azo(linker)-ATTO647N, Streptavidin-Dimethylketal(linker)-ATTO647N) and Dibenzocyclooctyne-Dde(linker)-ATTO647N described above as examples.

Example Synthesis of 3'-O-Rox-Nitrobenzyl-dCTP and 3'-O-Rox-Allyl-dTTP are shown in Scheme 53 and Scheme 54 respectively.

Consecutive Polymerase Extension using 3'-O-Rox-DTM-dATP Reversible Terminator and Characterization by MALDI-TOF Mass Spectrometry (Results are shown in FIGS. 34A-34C)

This extension reaction was carried out using 200 pmol of reversible terminator (3'-O-Rox-DTM-dATP), 2 units of Therminator™ IX DNA Polymerase ($A_9°$ N™ DNA Polymerase variant from NEB), 100 pmol of DNA primer (5'-TAGATGACCCTGCCTTGTCG-3') (SEQ ID NO:18), 60 pmol of DNA template (5'-GAAGGA-GACACGCGGCCAGAGAGGGTCCTGTCCGTGTTTG TGCGTGGA GTTCGACAAGGCAGGGT-CATCTAATGGTGATGAGTCC-TATCCTTTTCTCTTCGTTCTC CGT-3') (SEQ ID NO:19) in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 sec, 45° C./30 sec, 65° C./30 sec. Multiple reactions were carried out and an aliquot of the reaction mixture was desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide and THP (Tris-hydroxypropyl-phosphine) was used to remove the Rox-tBu-SS group from the 3' end of the DNA extension product to regenerate the 3'-OH group in preparation for the next extension reaction. The cleavage reaction was carried out by incubating the extension reaction mixture with THP at 5 mM final concentration and incubating at 65° C. for 5 minutes.

The reaction mixture after THP treatment was purified by reverse phase HPLC on an XTerra MS C18, 2.5 µm 4.6 mm×50 mm column (Waters, MA) to obtain the pure cleavage product. Mobile phase: A, 8.6 mM triethylamine/100 mM1,1,1,3,3,3-hexafluoro-2-propanol in water (pH 8.1); B, methanol. Elution was performed at 40° C. with a 0.5 mL/min flow rate with a linear gradient from 88% A/12% B to 65.5% A/34.5% B for 90 min. The purified product was used in the subsequent extension reaction.

Since there are two consecutive Ts on the DNA template after the DNA primer binding site, the second extension reaction was carried out in the same way as the first extension reaction. The overall results are shown in FIGS. 34A-34C, MALDI TOF MS of the primers after each step demonstrate accurate incorporation of 3'-Rox-SS-dATP, efficient cleavage of SS bond and recovering of 3'OH, and incorporation of another 3'-Rox-SS-dATP.

Figure 35A:
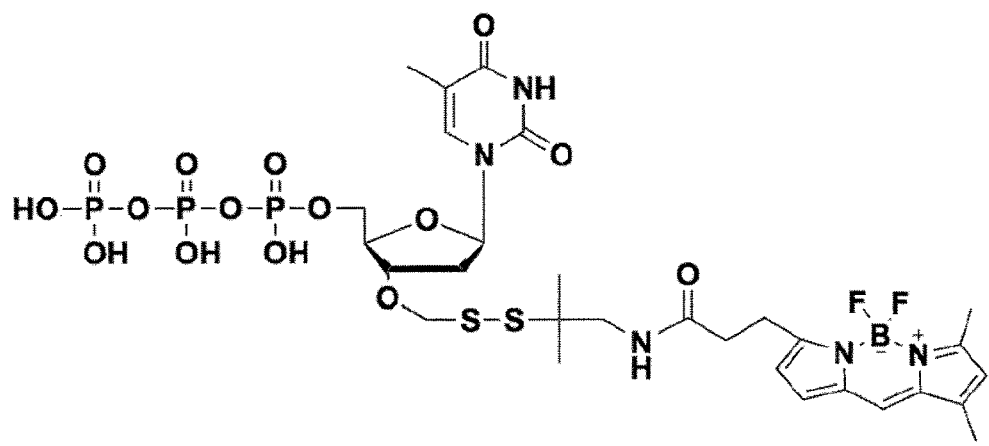
FIGS. 35A-35C. DNA polymerase extension and cleavage using 3'-O-Bodipy-DTM-dTTP as a reversible terminator. MALDI-TOF MS spectra of the extension product and the cleavage product.
Figure 35B:
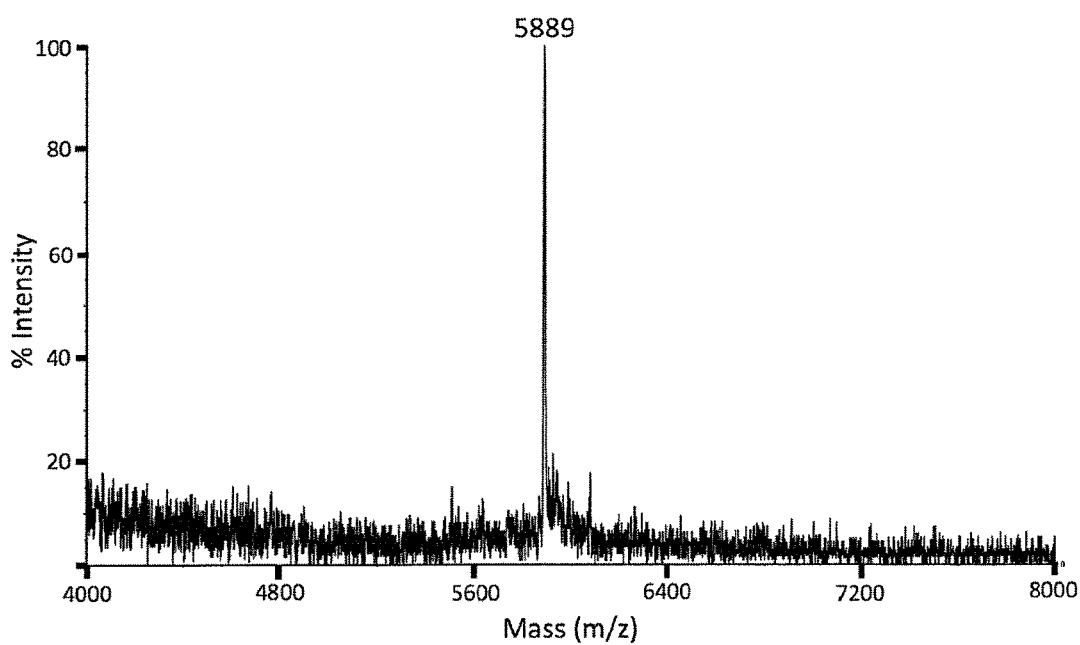
Figure 35C:
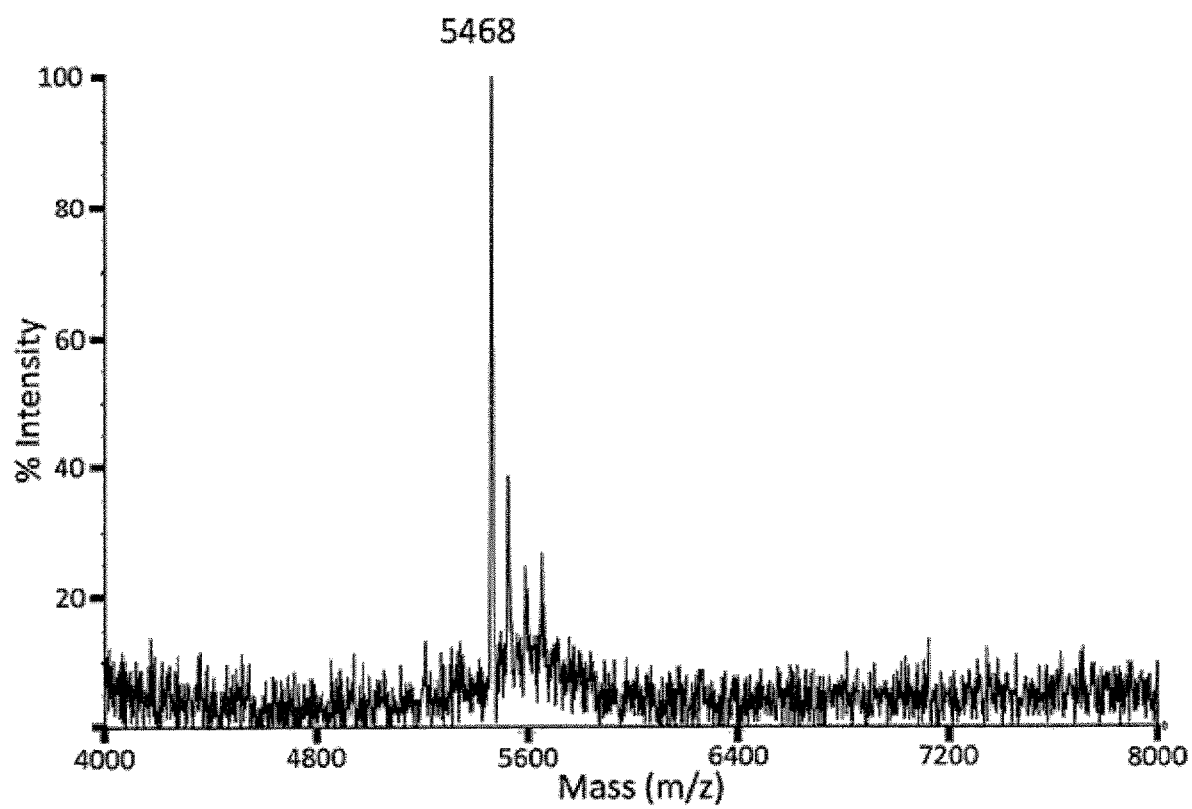
Figure 36A:
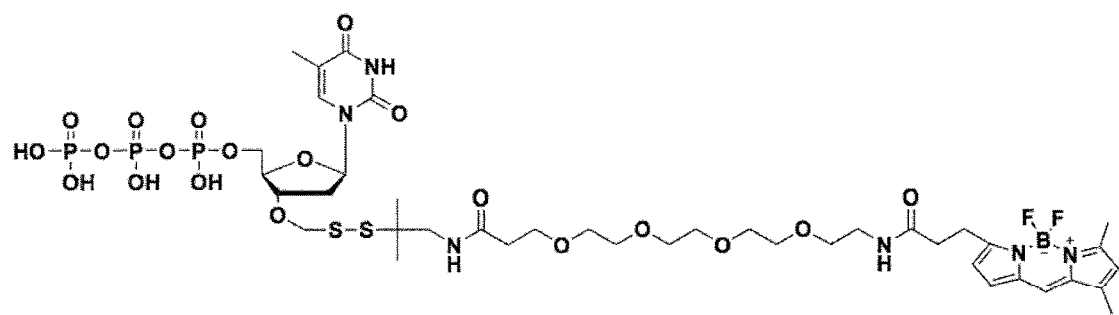
FIGS. 36A-36C. DNA polymerase extension and cleavage using 3'-O-Bodipy-PEG$_4$-DTM-dTTP as a reversible terminator. MALDI-TOF MS spectra of the extension product and the cleavage product.
Figure 36B:
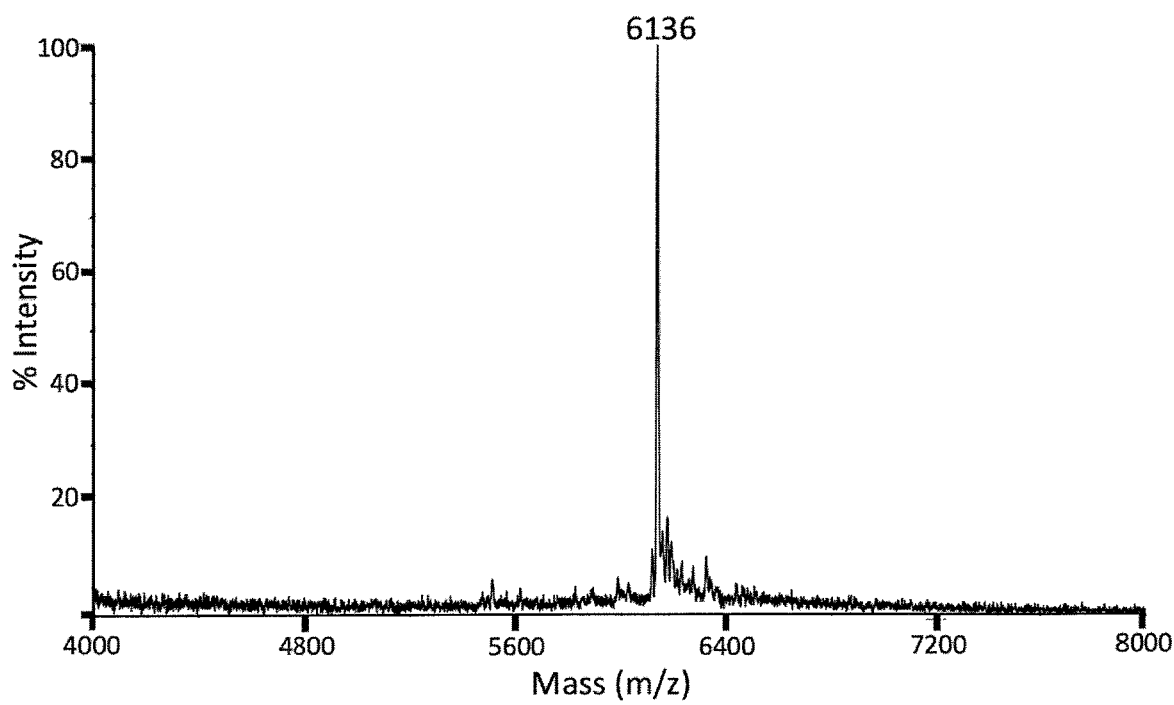
Figure 36C:
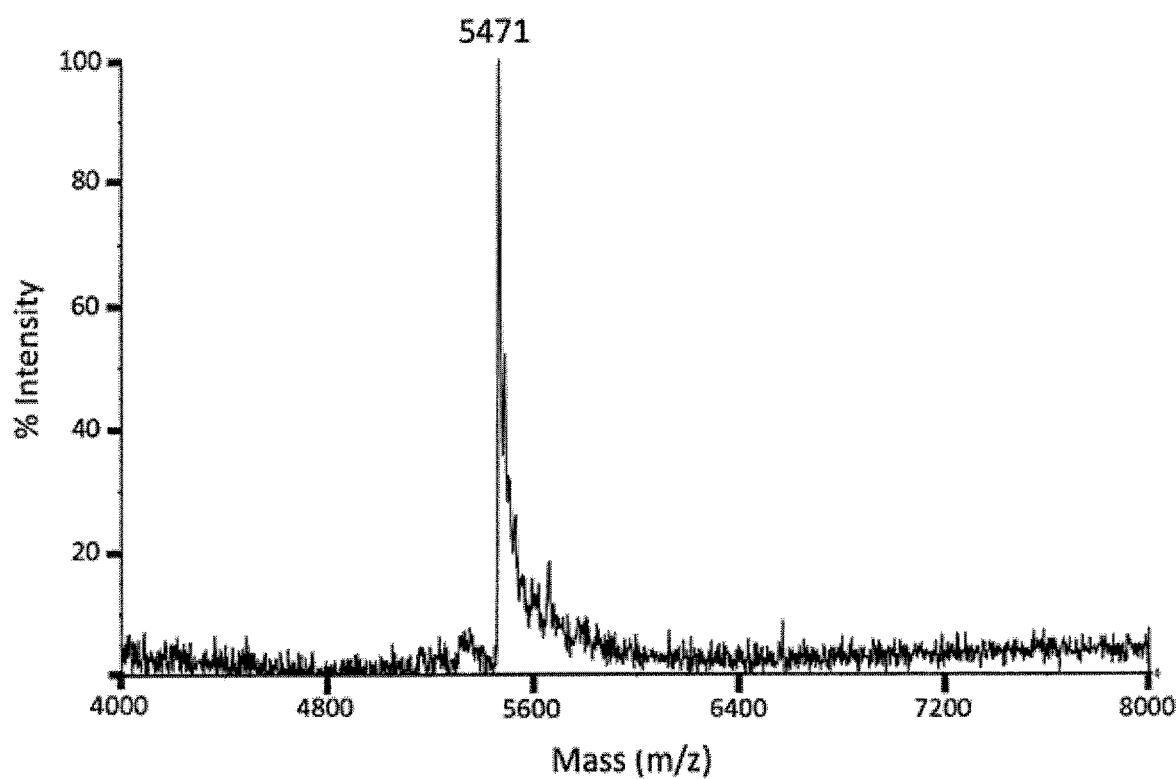

DNA Polymerase Extension using 3'-O-Rox-PEG$_4$-DTM-dATP Reversible Terminator, cleavage reaction using THP, and characterization by MALDI-TOF Mass Spectrometry (Results are shown in FIGS. 35A-35C)

The DNA Polymerase extension was carried out using 200 pmol of reversible terminator (3'-O-Rox-PEG$_4$-DTM-dATP), 2 units of Terminator™ IX DNA Polymerase (NEB), 100 pmol of primer (5'-TAGATGACCCTGCCTTGTCG-3') (SEQ ID NO:20), 60 pmol of DNA template (5'-GAAGGA-GACACGCGGCCAGAGAGGGTCCTGTCCGTGTTTG TGCGTGGAGTTCGACA AGGCAGGGT-CATCTAATGGTGATGAGTCC-TATCCTTTTCTCTTCGTTCTCCGT-3') (SEQ ID NO:21) in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixture was then desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide and THP was used to remove the blocking group from the 3' end of the DNA extension product to regenerate the 3'-OH group. The cleavage reaction was carried out by incubating the extension reaction mixture with THP at 5 mM final concentration and incubating at 65° C. for 5 minutes.

DNA Polymerase Extension using either 3'-O-Bodipy-DTM-dTTP, or 3'-O-Bodipy-PEG$_4$-DTM-dTTP Reversible Terminator, cleavage reaction using THP, and characterization by MALDI-TOF Mass Spectrometry (Results are shown in FIGS. 10A-10D and FIG. 11)

The DNA Polymerase extension was carried out using 200 pmol of reversible terminator (3'-O-Bodipy-DTM-dTTP, or 3'-O-Bodipy-PEG$_4$-DTM-dTTP), 2 units of Terminator™ IX DNA Polymerase (NEB), 100 pmol of primer (5'-GATAGGACTCATCACCA-3'), (SEQ ID NO:22) 60 pmol of DNA template (5'-GAAGGA-GACACGCGGCCAGAGAGGGTCCTGTCCGTGTTTG TGCGTGGAGTTCGACA AGGCAGGGT-CATCTAATGGTGATGAGTCC-TATCCTTTTCTCTTCGTTCTCCGT-3') (SEQ ID NO:23) in a 20 µl buffer containing 20 mM Tris-HCl, 10 mM $(NH_4)_2SO_4$, 10 mM KCl, 2 mM $MgSO_4$, 0.1% Triton X-100, pH 8.8 @25° C., and 2 mM $MnCl_2$. The reaction was conducted in an ABI GeneAmp PCR System 9700 with initial incubation at 65° C. for 30 second, followed by 38 cycles of 65° C./30 sec, 45° C./30 sec, 65° C./30 sec. The reaction mixture was desalted using a C18 ZipTip column (Millipore, MA) and analyzed by MALDI-TOF MS (ABI Voyager DE).

Calf Intestinal Alkaline Phosphatase (CIP) from NEB was used to inactivate residual reversible terminator nucleotide in the extension reaction mixture and THP was used to remove the blocking group from the 3' end of the DNA extension product to regenerate the 3'-OH group. The cleavage reaction was carried out by incubating the extension reaction mixture with THP at 5 mM final concentration and incubating at 65° C. for 5 minutes. The reaction mixture was desalted using a C18 ZipTip column (Millipore, MA) and analyzed by MALDI-TOF MS (ABI Voyager DE).

References for Example 2: 1. Hyman E. D., "A new method of sequencing DNA. Anal Biochem" 174(2): 423-436 (1988).; 2. Ronaghi M., Uhl6n M., Nyr6n P., "A sequencing method based on real-time pyrophosphate" Science 281(5375): 363-365 (1998).; 3. Ju J., Li Z., Edwards J. R., Itagaki Y., U.S. Pat. No. 6,664,079 (2003).; 4. Li Z. et al., "A photocleavable fluorescent nucleotide for DNA sequencing and analysis", Proc. Natl. Acad. Sci. USA, 100(2): 414-419 (2003).; 5. Braslavsky I., Hebert B., Kartalov E., Quake S., "Sequence information can be obtained from single DNA molecules", Proc. Natl. Acad. Sci. USA 100(7): 3960-3964 (2003).; 6. Ruparel H. et al., "Design and synthesis of a 3'-O-allyl photocleavable fluorescent nucleotide as a reversible terminator for DNA sequencing by synthesis", Proc. Natl. Acad. Sci. USA 102(17): 5932-5937 (2005).; 7. Margulies M. et al., "Genome sequencing in microfabricated high-density picolitre reactors", Nature 437(7057): 376-380 (2005).; 8. Ju J. et al., "Four-color DNA sequencing by synthesis using cleavable fluorescent nucleotide reversible terminators", Proc. Natl. Acad. Sci. USA 103(52): 19635-19640 (2006).; 9. Wu J. et al., "3'-O-modified nucleotides as reversible terminators for pyrosequencing", Proc. Natl. Acad. Sci. USA 104(104): 16462-16467 (2007).; 10. Guo J. et al., "Four-color DNA sequencing with 3'-O-modified nucleotide reversible terminators and chemically cleavable fluorescent dideoxynucleotides", Proc. Natl. Acad. Sci. USA 105(27): 9145-9150 (2008).; 11. Bentley D. R. et al., "Accurate whole human genome sequencing using reversible terminator chemistry", Nature 456(7218): 53-59 (2008).; 12. Harris T. D. et al., "Single-molecule DNA sequencing of a viral genome", Science 320(5872): 106-109 (2008).; 13. Eid J. et al., "Real-time DNA sequencing from single polymerase molecules", Science 323(5910): 133-138 (2009).; 14. Rothberg J. M. et al., "An integrated semiconductor device enabling non-optical genome sequencing", Nature 475(7356): 348-352 (2011).; 15. Rosenblum B. B. et al., "New dye-labeled terminators for improved DNA sequencing patterns", Nucleic Acids Res., 25, 4500-4504 (1997).; 16. Zhu Z. et al., "Directly labeled DNA probes using fluorescent nucleotides with different length linkers", Nucleic Acids Res., 22, 3418-3422 (1994).; 17. Pelletier H. et al., "Structures of ternary complexes of rat DNA polymerase beta, a DNA template-primer, and ddCTP", Science, 264, 189-1903 (1994).; 18. Cheeseman P., "Method for sequencing polynucleotides", U.S. Pat. No. 5,302,509 (1994).; 19. Canard B. et al., "DNA polymerase fluorescent substrates with reversible 3'-tags", Gene., 148, 1-6 (1994).; 20. Welch M. B. et al., "Synthesis of nucleosides designed for combinatorial DNA sequencing", Chem. Eur. J., 5, 951-960 (1999).; 21. Metzker M. L., "Emerging technologies in DNA sequencing", Genome Res., 15, 1767-1776 (2005).; 22. Lu G. et al., "A diversity oriented synthesis of 3'-O-modified nucleoside triphosphates for DNA sequencing by synthesis. Bioorg", Med. Chem. Lett., 16, 3902-3905 (2006).; 23. Kim T. S. et al., "Novel 3'-O-fluorescently modified nucleotides for reversible termination of DNA synthesis", ChemBiochem, 11, 75-78 (2010).; 24. Kim D. R. et al., "Synthesis of 3'-O-fluorescently mono-modified reversible terminators and their uses in sequencing-by-synthesis", Bioorg. Med. Chem. Lett., 24, 209-213 (2014).; 25. Hutter D. et al., "Labeled nucleoside triphosphates with reversibly terminating aminoalkoxy groups", Nucleos. Nucleot. Nucl., 29, 879-895 (2010).; 26. Diana C. et al., "Fluoride-Cleavable, Fluorescently Labelled Reversible Terminators: Synthesis and Use in Primer Extension", Chem. Eur. J., 17, 2903-2915 (2011).; 27. Kwiatkowski M., "Compounds for protecting hydroxyls and methods for their use", U.S. Pat. No. 7,279,563 (2007).; 28. Muller S. et al., "Method for producing trinucleotides", PCT International Application Publication No. WO 2011/061114 (2011).; 29. Semenyuk A. et al., "Synthesis of RNA using 2'-O-DTM protection", J. Am. Chem. Soc., 128, 12356-12357 (2006).; 30. John C. et al., "Rapid Cu-Free Click Chemistry with Readily Synthesized Biarylazacyclooctynones", J. Am. Chem. Soc., 132, 3688-3690 (2010).; 31. Shieha P. et al., "Design strategies for bioorthogonal smart probes", Org. Biomol. Chem., 12, 9307-9320 (2014).; 32. Melissa L. et al., "Tetrazine Ligation: Fast Bioconjugation Based on Inverse-Electron-Demand Diels-Alder Reactivity", J. Am. Chem. Soc., 130, 13518-13519 (2008).; 33. Marjoke F. et al., "Bioorthogonal labelling of biomolecules: new functional handles and ligation methods", Org. Biomol. Chem., 11, 6439-6455 (2013).; 34. Bergseid M. et al., "Small molecule-based chemical affinity system for the purification of proteins", BioTechniques, 29, 1126-1133 (2000).; 35. Anthony K. et al., "Triple Fluorescence Energy Transfer in Covalently Trichromophore-Labeled DNA", J. Am. Chem. Soc., 123, 12923-12924 (2001).; 36. Ju J., "Sets of labeled energy transfer fluorescent primers and their use in multi component analysis", U.S. Pat. No. 5,952,180 (1999).; 37. Leriche G. et al., "Optimization of the Azobenzene Scaffold for Reductive Cleavage by Dithionite; Development of an Azobenzene Cleavable Linker for Proteomic Applications", Eur. J. Org. Chem., 23, 4360-64 (2010).; 38. Budin G. et al., "Nondenaturing Chemical Proteomics for Protein Complex Isolation and Identification" ChemBioChem, 11, 2359-2361 (2010).; 39. Binaulda S. et al., "Acid-degradable polymers for drug delivery: a decade of innovation", Chem. Commun., 49, 2082-2102 (2013).; 40. Ellis R. A. et al., "Chemical constructs", European Patent No. EP 1119529 B1 (2003).; 41. Rathod K. M. et al., "Synthesis and antimicrobial activity of azo compounds containing m-cresol moiety", Chem. Sci. Tran., 2, 25-28 (2013).; 42. Shenoi R. A. et al., "Branched Multifunctional Polyether Polyketals: Variation of Ketal Group Structure Enables Unprecedented Control over Polymer Degradation in Solution and within Cells", J. Am. Chem. Soc., 134, 14945-14957 (2012).; 43. Chhabra S. R. et al., "An appraisal of new variants of Dde amine protecting group for solid phase peptide synthesis Tetra", Lett., 39, 1603-1606 (1998).

Example 3: Single-Molecule Electronic Sequencing by Synthesis Using 3'-O-Anchor-Cleavable Linker Nucleotides/Polymer Tags and Nanopore Detection Nanopore-based electronic single molecule real time DNA sequencing by synthesis approaches have been previously developed (Kumar et al Scientific Reports (2012) 2, 684; Fuller et al, PNAS USA (2016) 113, 5233-5238). A nanopore SBS sequencing method that combines SBS with nanopore-based identification of different-sized polymer tags attached to the terminal phosphate of the nucleotides has been reported. One of four different-length PEG tags was attached to the terminal phosphate of each nucleotide. Despite having long tags with 16-36 PEG monomer units, these tagged nucleotides were incorporated efficiently by DNA polymerase. During the phosphoryl transfer step of the DNA polymerase reaction, the tag is released as part of the polyphosphate byproduct, so only the natural nucleotide remains in the growing DNA strand. This tag was detected and identified by monitoring pore current as it passed through a single-protein nanopore (α-hemolysin) embedded in a lipid membrane under a voltage gradient. Depending on the length of the PEG tag, the pore current was reduced to different levels, and translocation required different times (Kumar et al Scientific Reports (2012) 2, 684), allowing discrimination of such tags and enabling the identification of each nucleotide incorporated in the SBS process.

To develop this nanopore SBS approach further and to optimize the tags, Fuller et al (PNAS USA (2016) 113, 5233-5238) have reported the design and synthesis of nucleotides tagged with modified oligonucleotides and their application for nanopore SBS. These tags have structural modifications that create distinct ionic current blockades, measured using an electronic chip-based array of nanopores embedded in lipid bilayer membranes. The tags are attached to the terminal phosphate of 2'-deoxynucleoside-5'-hexaphosphates using Huisgen cycloaddition azide/alkyne coupling chemistry (Fuller et al. US Patent Application US20150368710). With these tagged nucleotides, continuous single-molecule electronic DNA sequencing with single-base resolution by nanopore SBS was demonstrated. The measurement of current is made during the polymerase catalytic cycle when the complementary tagged nucleotide is bound within the complex of DNA polymerase, primer/template, and divalent metal cation and lasts until the completion of the polymerase catalytic step with the release of the tagged polyphosphate product. Once this product is released, the polymer tag is free to leave the pore, ending the blockade signal for that particular DNA synthesis step. To increase the likelihood that each tag will be measured in sequential order, a single polymerase molecule is covalently attached to the nanopore at an appropriate distance to allow fast capture of the tag by the nanopore. Each of the four tags has a distinctive structure that interacts with the narrowest constriction in the αHL channel, thereby reducing the ionic current across the channel to different extents (Fuller et al, PNAS USA (2016) 113, 5233-5238). In this approach, it is critical to control the relative rates of the polymerase reaction, the capture of tags by the nanopore, and the ionic current monitoring to ensure that each and every base is called in sequential order. Failure to do so will result in "insertion" or "deletion" artifacts.

We reason that the above obstacles can be overcome by purposely pausing the reactions by addition of a nucleotide with a cleavable 3'-OH blocking group (linker) containing an anchor to which a nanopore tag with an anchor binding molecule can be attached. The following electronic detection of such a tag would result in one base at a time being called, even in homopolymeric tracts (runs of nucleotides with the same base such as $A_n$ or $C_n$, where n>1). A few such 3'-O-cleavable linkers that still allow incorporation of the nucleotides bearing such linkers into a growing DNA strand exist, including the 3'-O-dithiomethyl linker described herein.

3'-O-cleavable linker (dithiomethyl, DTM) nucleotides having an anchor moiety attached to the cleavable linker described in this application can be used for such nanopore-based sequencing approaches. A binding molecule compatible with the anchor on the DTM linker would be attached to a nanopore tag specific for each of the four nucleotides (A, C, G and T/U). Briefly, after incorporation into a primer of one of the 3'-O-cleavable linker nucleotides bearing an anchor due to base pairing with the complementary nucleotide on the template strand, labeling with the nanopore tags containing anchor binding partners will reveal which nucleotide was added at that step; subsequent cleavage of the linker will release the tags in preparation for the next incorporation. In this process, the 3'-OH group will be restored so that the growing DNA strand will bear only natural nucleotides.

Single-Molecule SBS by a Nanopore Using 3'-O-Anchor-Cleavable Linker Nucleotides (General Approach)

Figure 37:
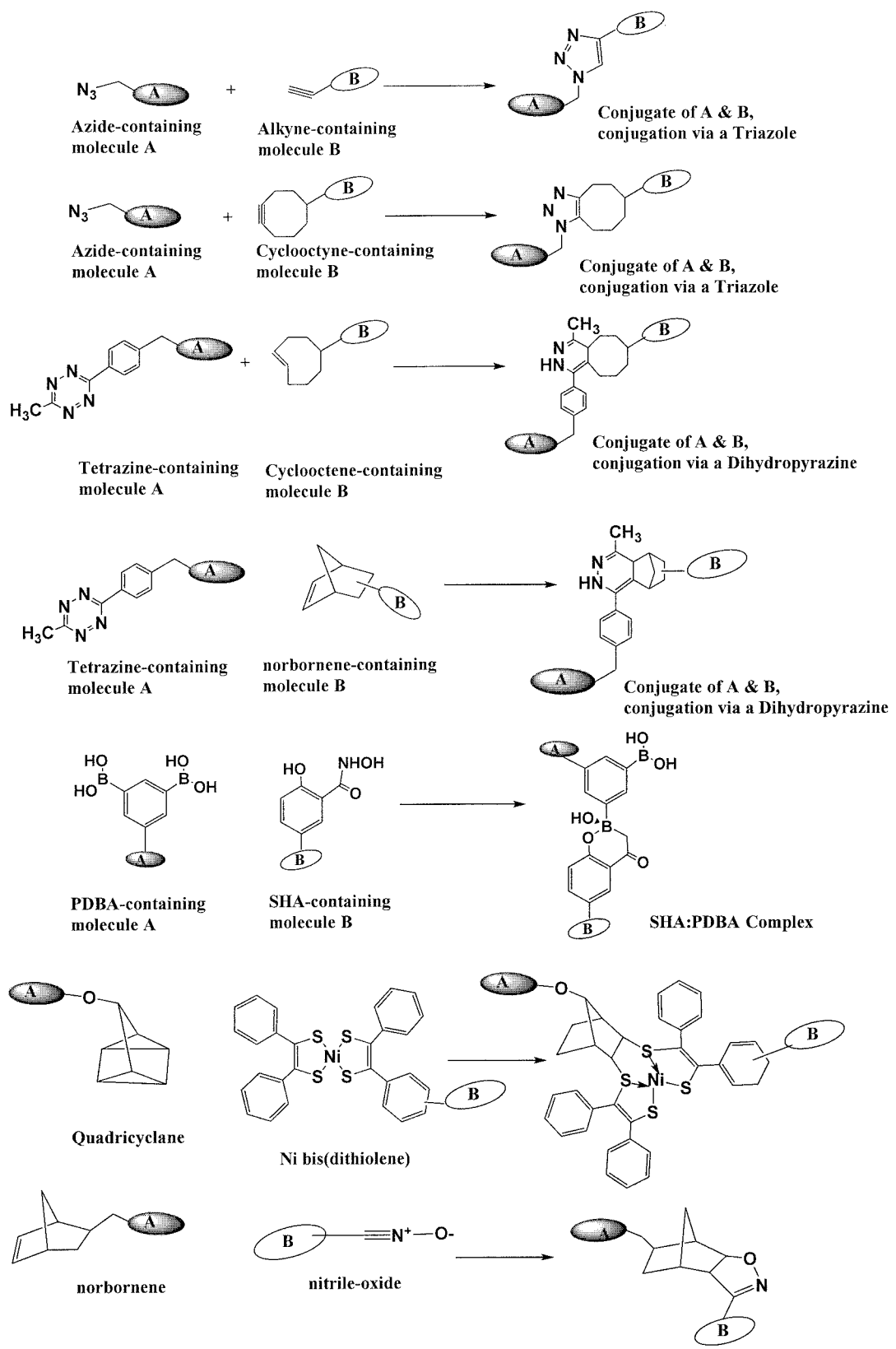
FIG. 37: Anchor and binding moieties which react covalently or form complexes with each other.
Figure 38:
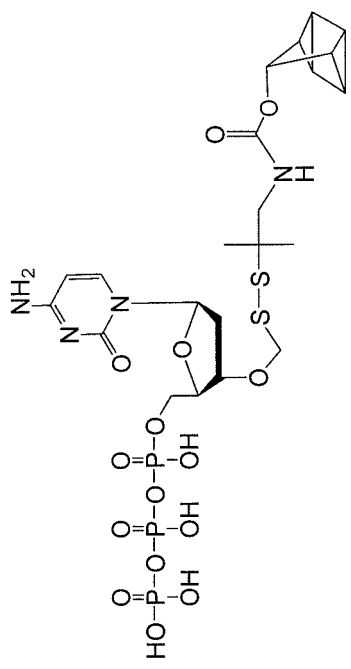
FIG. 38: Structures of four 3'-O-Anchor-SS(DTM)-dNTPs.
Figure 38:
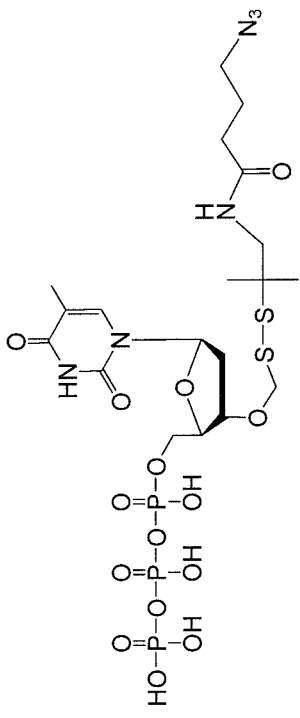
Figure 38:
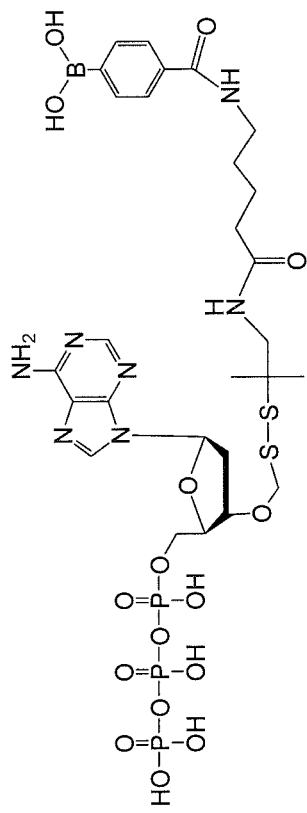
Figure 38:
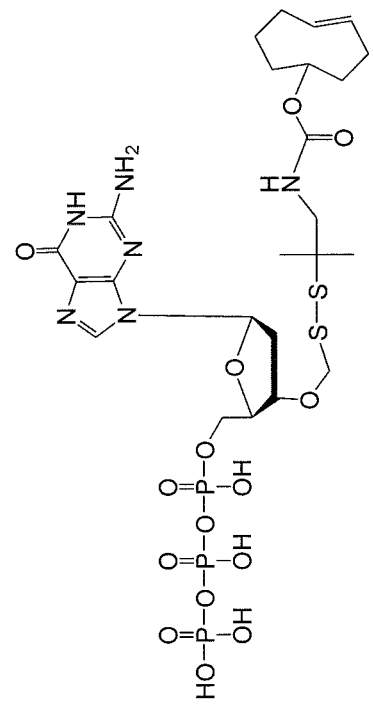
Figure 39:
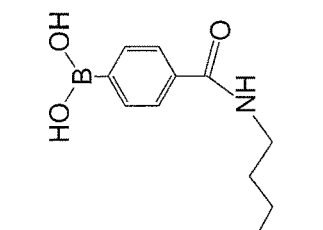
FIG. 39: Structures of three 3'-O-Anchor-SS (DTM)-dNTPs and 3'-O-SS(DTM)-dATP.
Figure 39:
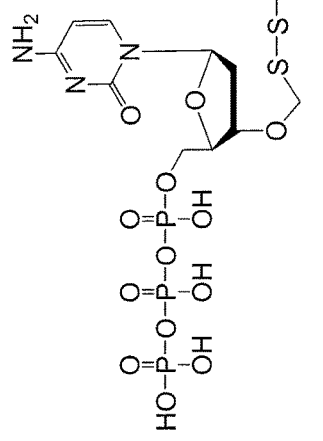
Figure 39:
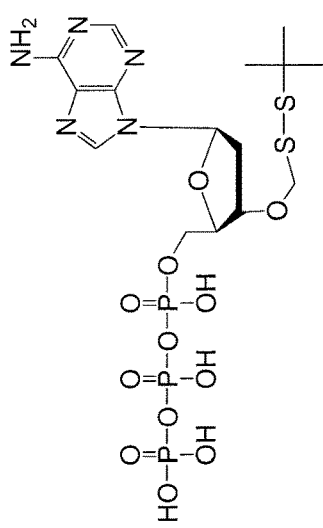
Figure 39:
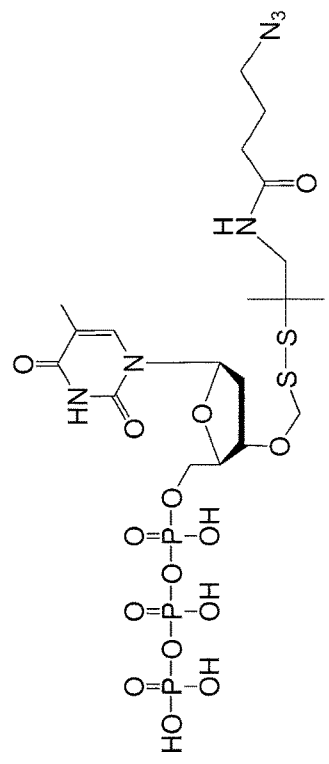
Figure 39:
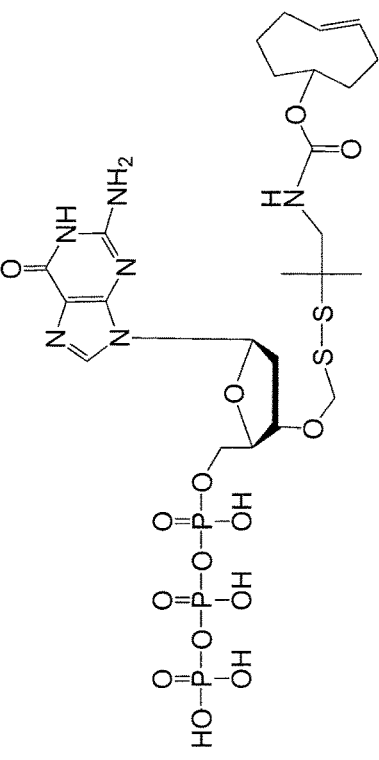
Figure 40:
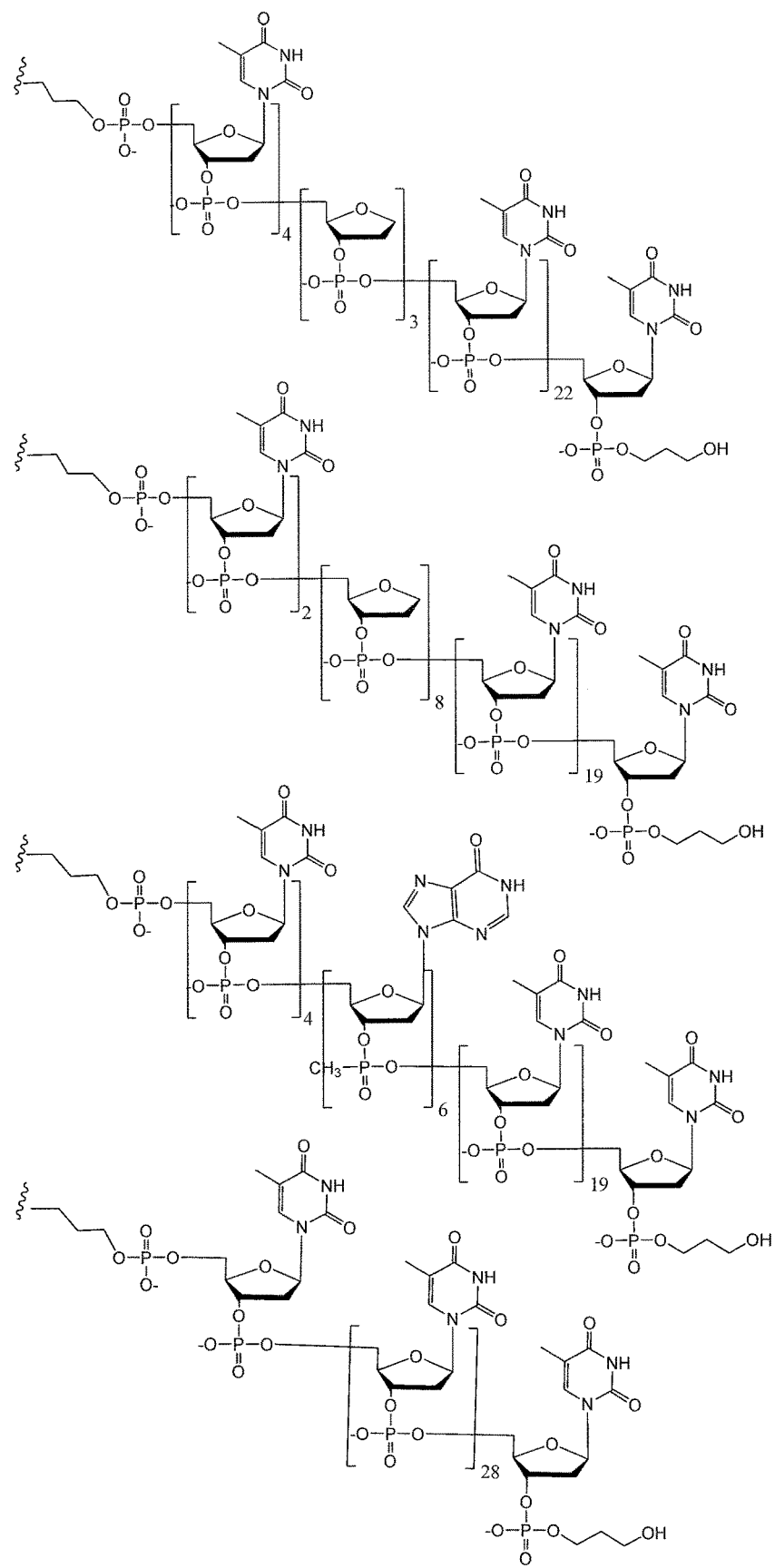
FIG. 40: Example structures of four nanotags tethered to binding molecules, which will give distinctive current blockade signals upon attaching to the anchor moieties in NanoSBS. The nanotags can be based on modified oligonucleotides, peptides, polyethylene glycols (PEG) or a combination thereof.
Figure 41:
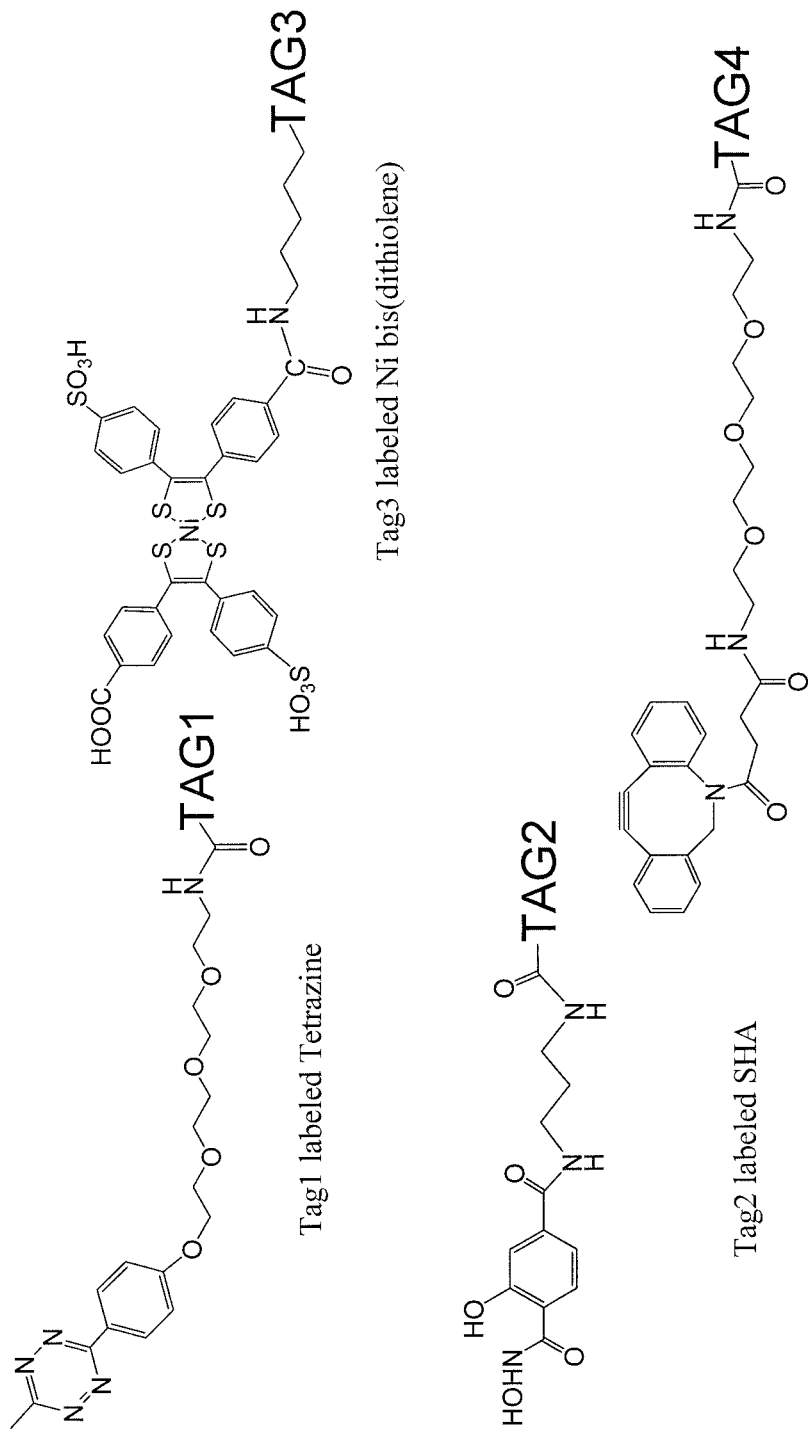
FIG. 41: Structures of nanotag conjugated binding molecules which will react with the anchor moieties attached to the 3'-O-SS-linker nucleotides.
Figure 42:
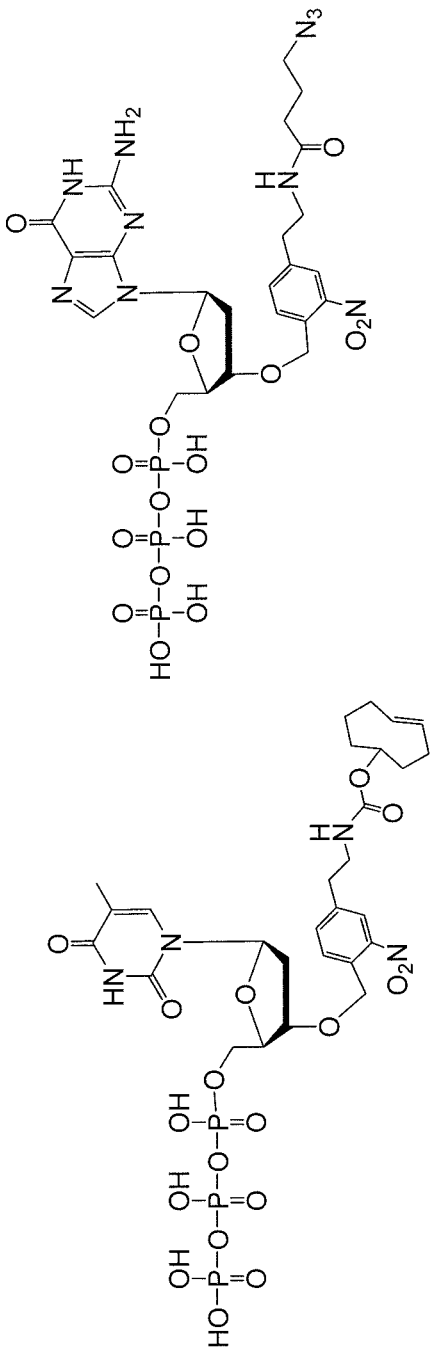
FIG. 42: Structures of two 3'-O-Anchor-2NB(2-Nitrobenzyl)-dNTPs (top) and two 3'-O-Anchor-SS(DTM)-dNTPs (bottom) used in 2-Tag nanopore SBS.
Figure 42:
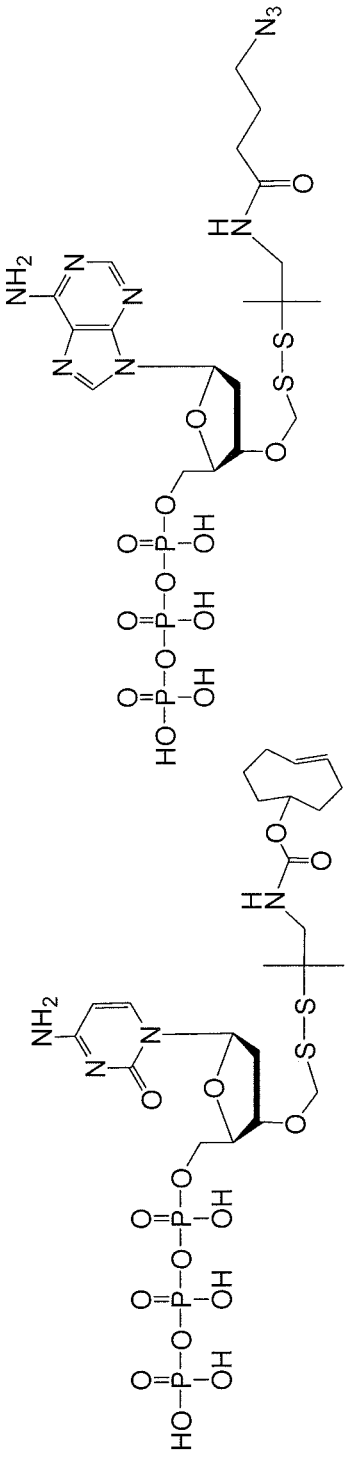
Figure 43:
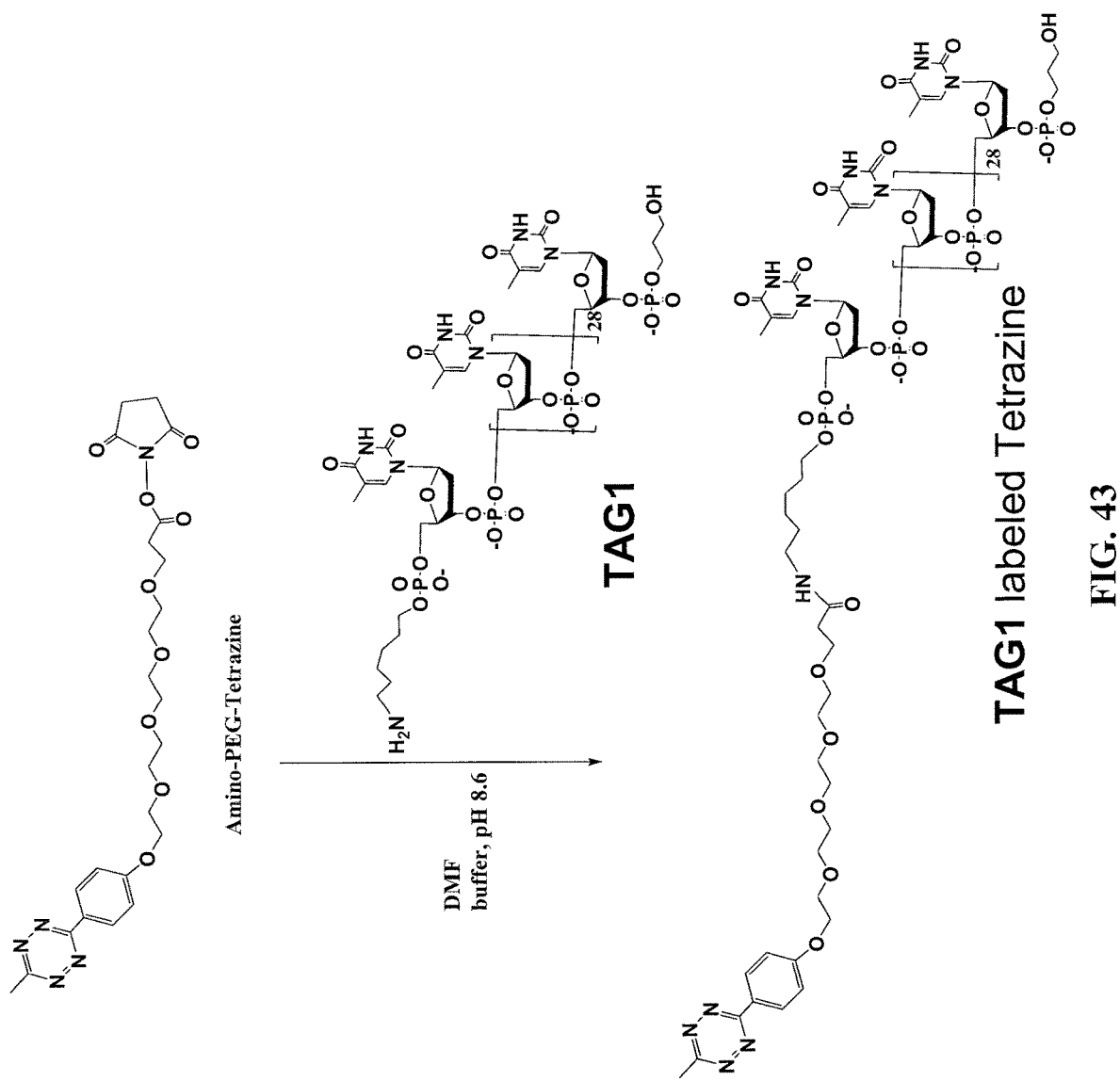
FIG. 43: Synthetic scheme for making Tetrazine labeled TAG1. Commercially available Tetrazine NHS ester is coupled with amino modified oligo Tag 1 yielding the Tag1-Tetrazine conjugate.
Figure 44:
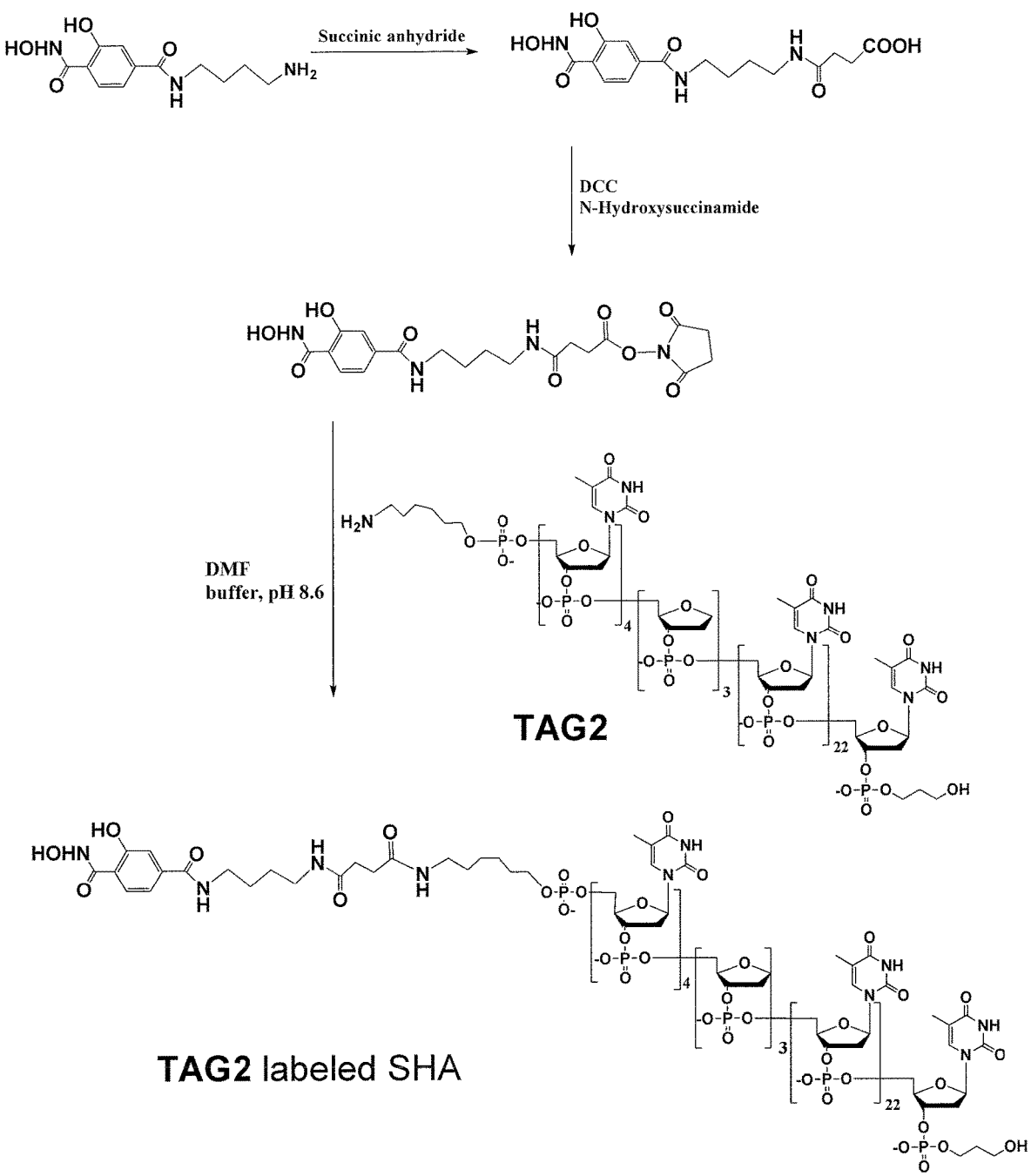
FIG. 44: Synthetic scheme for making SHA (Salicylhydroxamic acid) labeled TAG2. The amino derivative of SHA is reacted with succinic anhydride giving the acid derivative of SHA, which is converted to the NHS ester by reaction with N-hydroxysuccinimide and DCC. The SHA NHS ester can then be coupled to amino modified oligo Tag2 to yield the Tag2-SHA conjugate.
Figure 45:
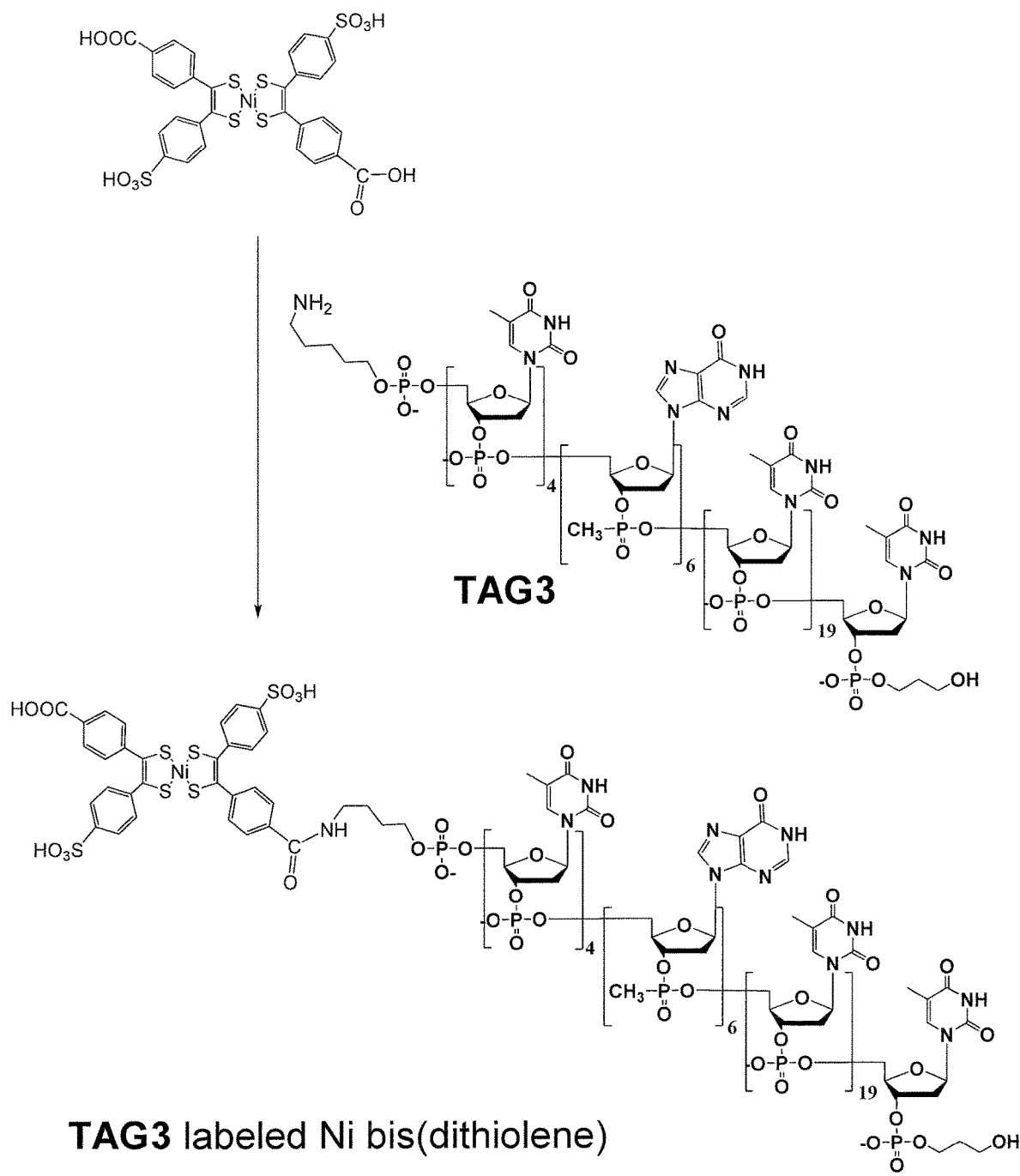
FIG. 45: Synthetic scheme for making Ni Bis(dithiolene) labeled TAG3. Incubating Ni Bis(dithiolene) acid with amino modified oligo Tag3 in presence of EDC gives the Tag3-Ni Bis(dithiolene) conjugate.
Figure 46:
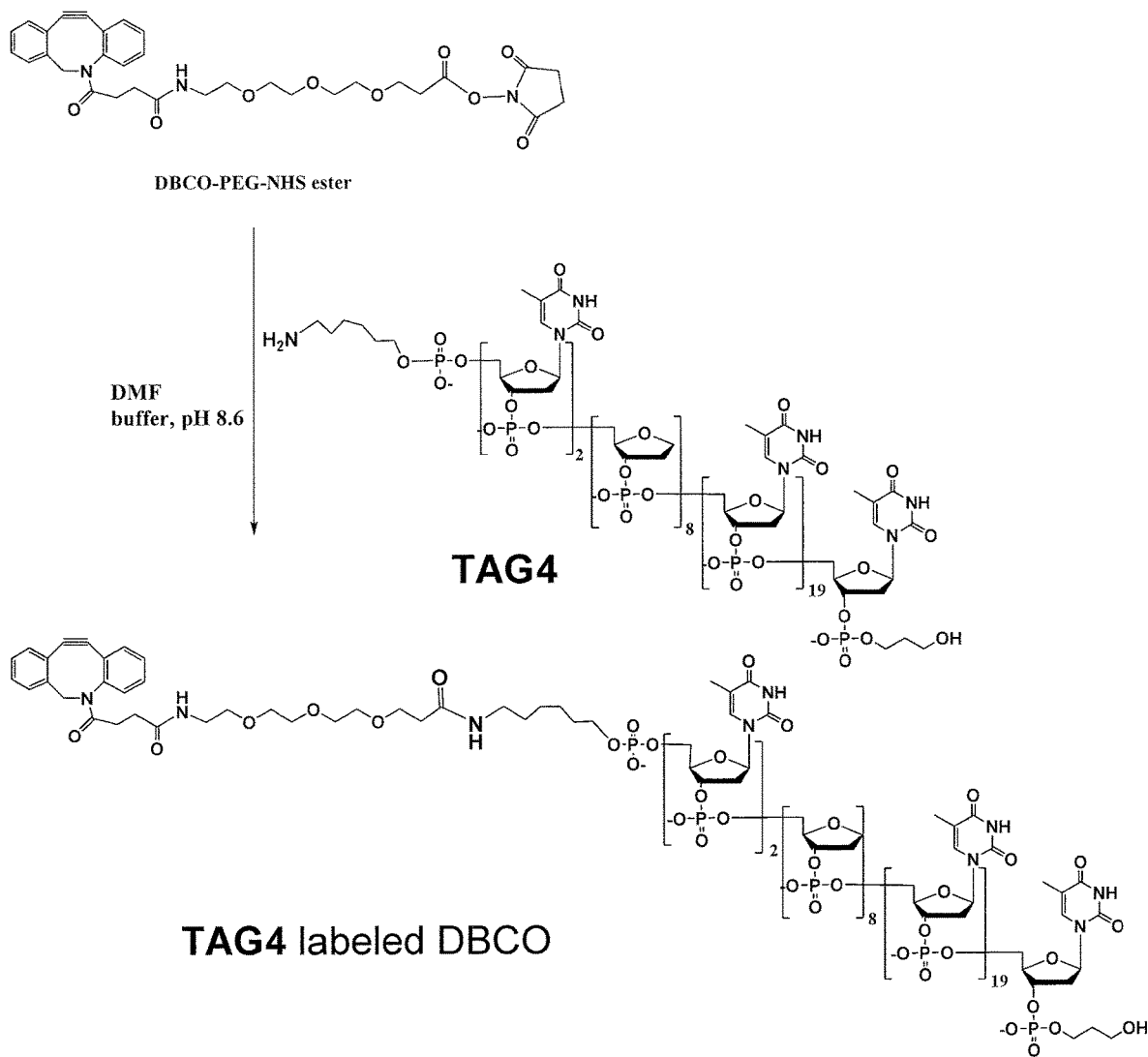
FIG. 46: Synthetic scheme for making DBCO labeled TAG4. Commercially available DBCO NHS ester is coupled with amino modified oligo Tag 4 yielding the Tag4-DBCO conjugate.
Figure 47:
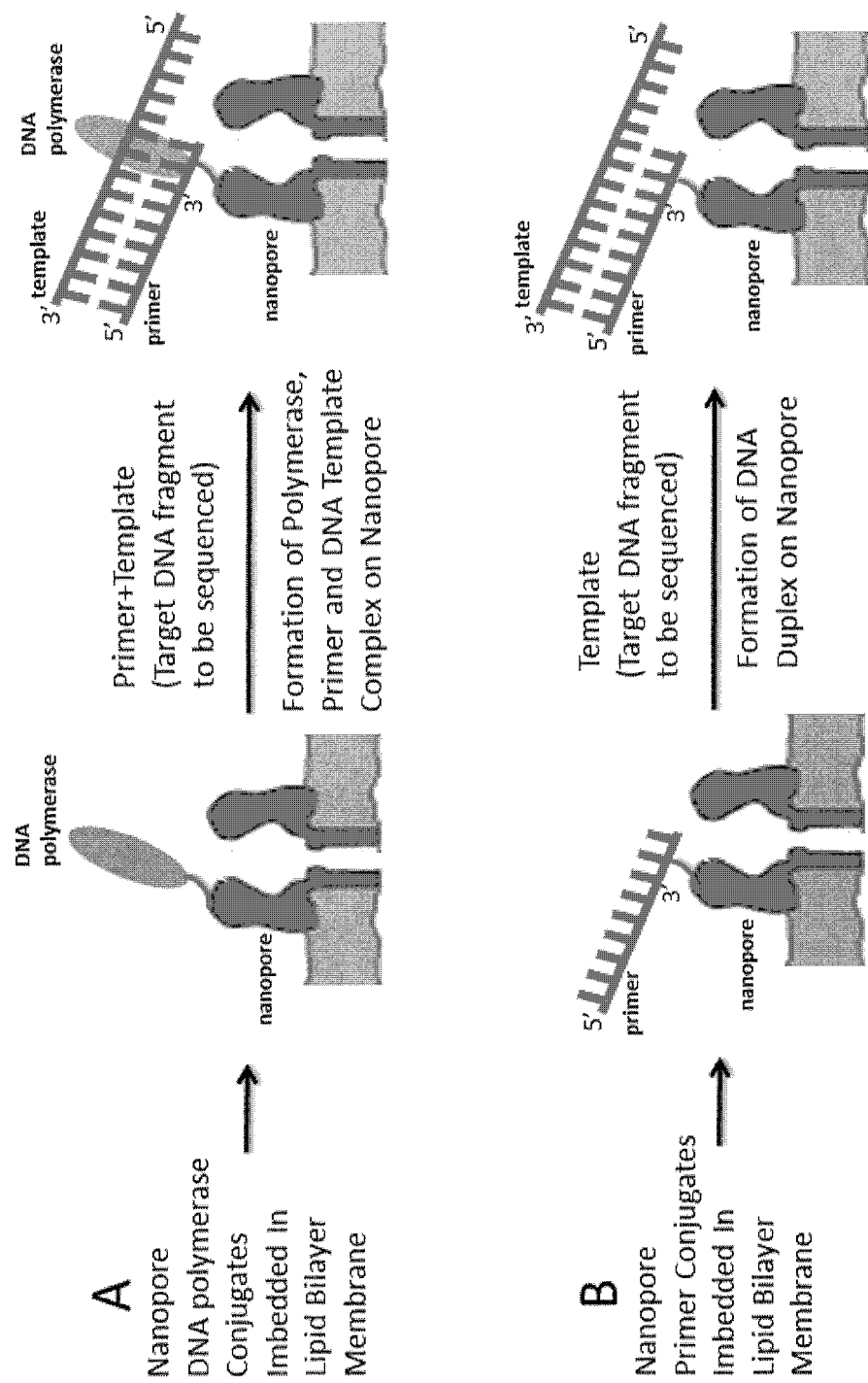
FIG. 47: Construction of nanopore-polymerase-DNA duplex complex (A) and nanopore-DNA duplex complex (B) for SBS on nanopore using 3'-O-anchor-DTM-dNTPs and labeled binding molecules. In (B), polymerase is added to the complex in solution (not shown).
Figure 48A:
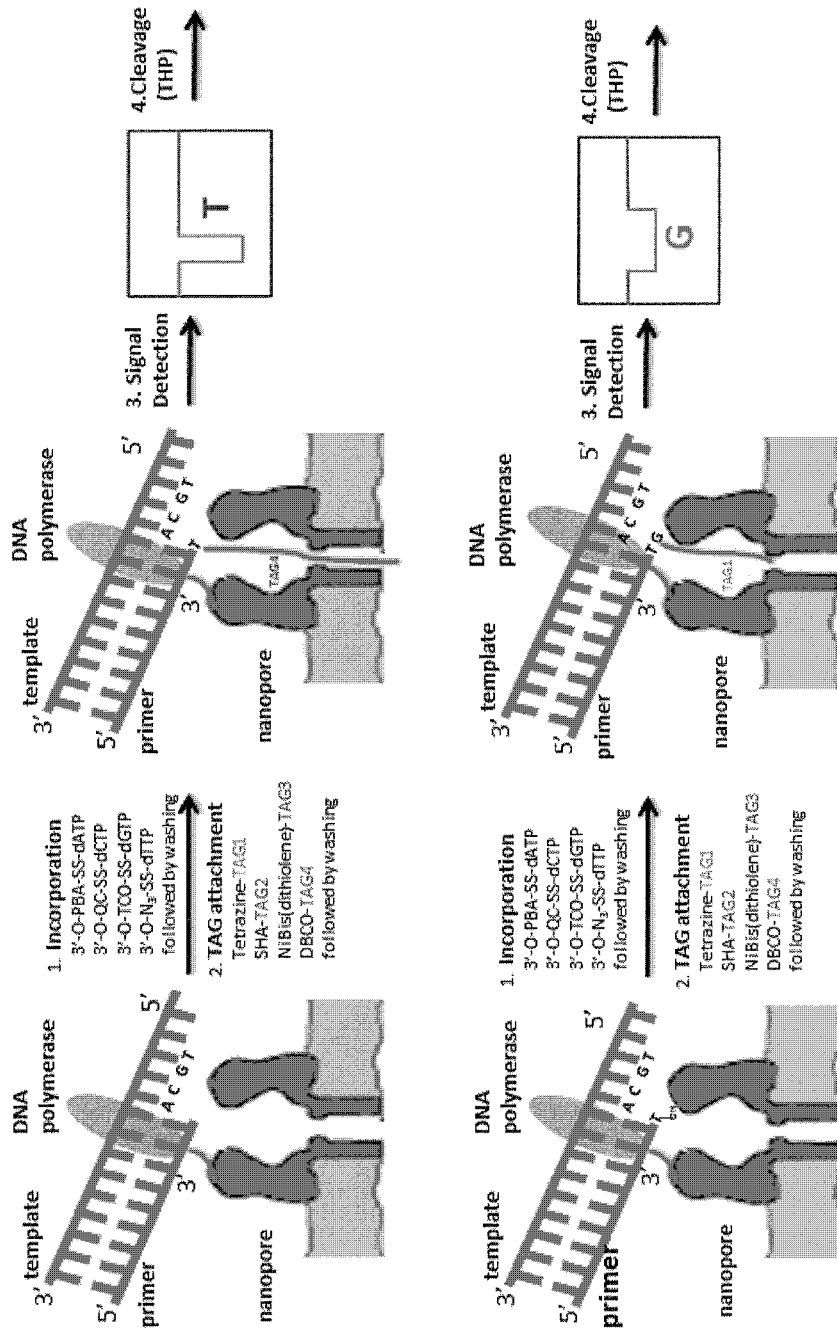
FIG. 48A-48B: Single-molecule SBS by a nanopore using 3'-O-Anchor-cleavable linker nucleotides; 4 anchor 4 tag scheme starting from DNA polymerase-nanopore conjugate. To the nanopore-polymerase-DNA duplex complex shown here as an example, 1) 3'-O-PBA-SS-dATP, 3'-O-quadricyclane(QC)-SS-dCTP, 3'-O-TCO-SS-dGTP and 3'-O—N$_3$-SS-dTTP are added, complementary 3'-O—N$_3$-SS-dTTP is incorporated by DNA polymerase, 2) Adding the 4 tag labeled binding molecules (Tetrazine-TAG1, SHA-TAG2, Ni-bis(dithiolene)-TAG3 and DBCO-TAG4). Only Tag4 is attached to the 3' end of T due to orthogonal interaction between N$_3$ and DBCO, 3) Subsequent nanopore electronic detection only shows the Tag4 signal, indicating incorporation of dTTP. 4) Cleavage using TCEP or THP removes the Tag from the 3'end, and at the same time regenerates the free 3'OH in preparation for the next cycle of sequencing. Washing steps are carried out after each step in the procedure. Steps 1) and 2) are repeated. Only 3'-O-TCO-SS-dGTP is incorporated and Tetrazine-TAG1 is attached, leading to 3) detection of the Tag1 signal, indicating incorporation of G. Cleavage using TCEP or THP removes Tag1 from the 3'end, again regenerating a free 3'OH. Steps 1) and 2) are repeated. 3'-O-QC-SS-dCTP is incorporated and Ni-bis(dithiolene)-TAG3 is attached, leading to 3) detection of the Tag3 signal, indicating incorporation of C. Steps 1) and 2) are repeated. 3'-O-PBA-SS-dATP is incorporated and SHA-TAG2 is attached to the 3'end, 3) nanopore electronic detection gives a Tag2 signal, indicating incorporation of A.
Figure 48B:
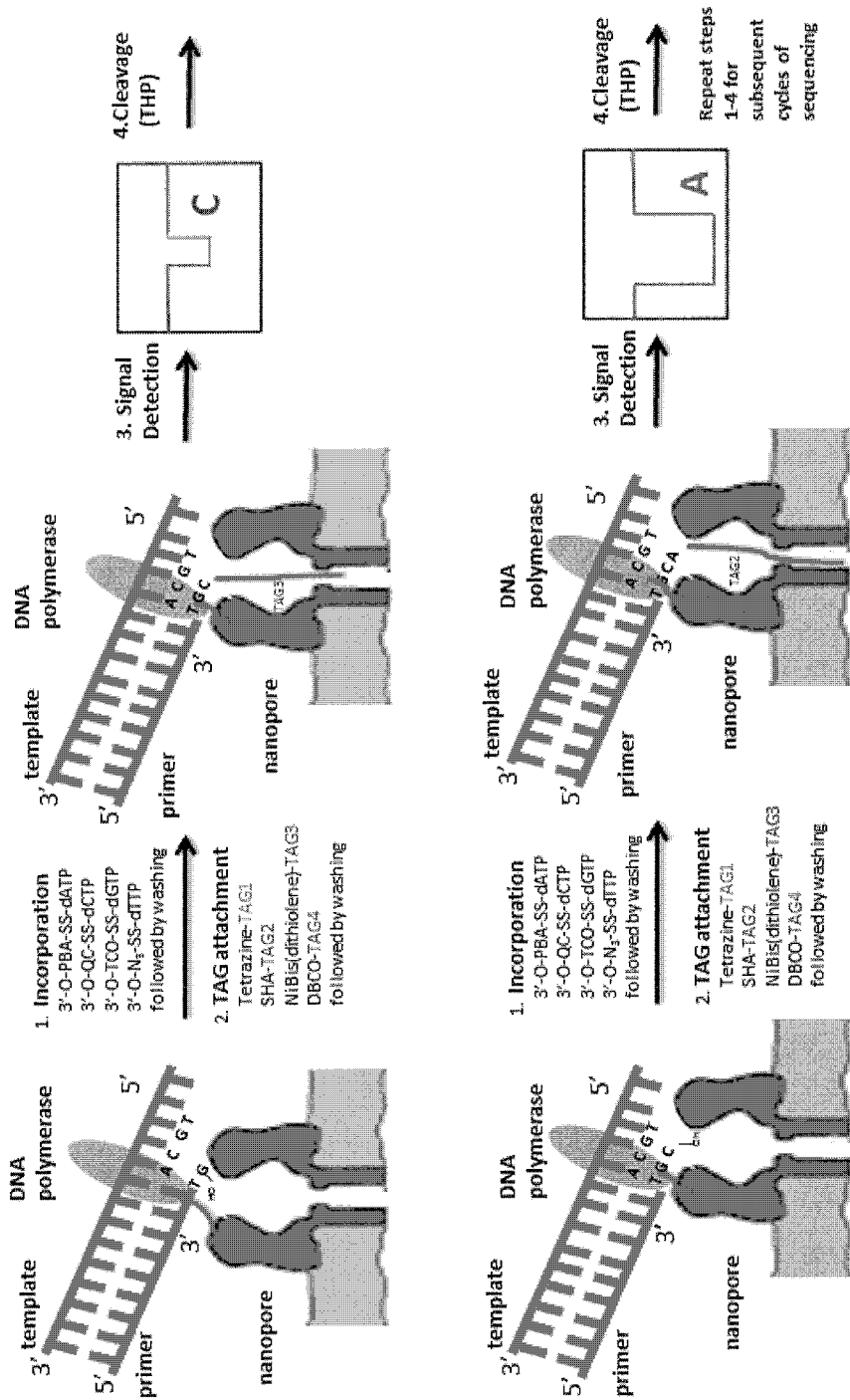
Figure 49A:
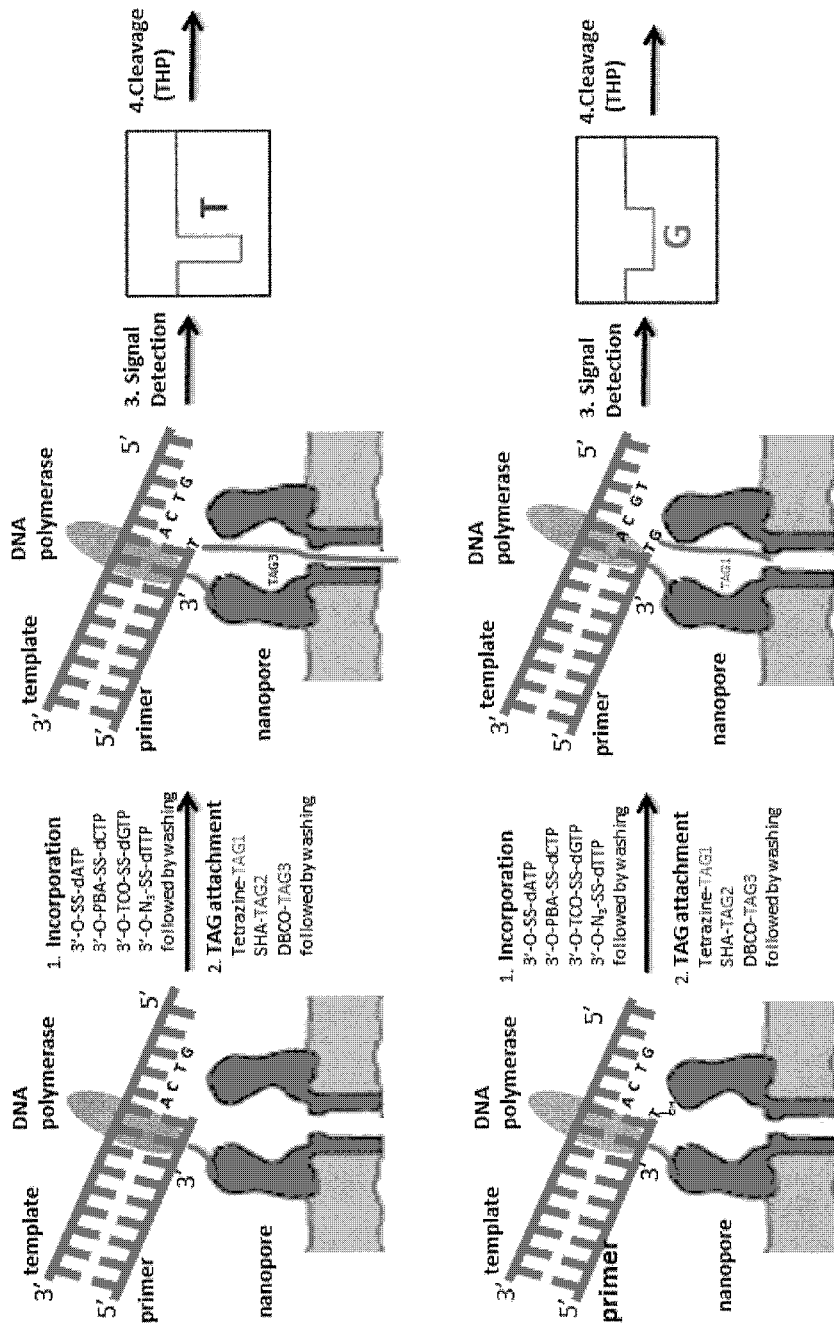
FIGS. 49A-49B. Single-molecule SBS by a nanopore using 3'-O-Anchor-cleavable linker nucleotides; 3 anchor 3 tag scheme starting from DNA polymerase-nanopore conjugate. To the nanopore-polymerase-DNA duplex complex shown here as an example, 1) 3'-O-SS-dATP, 3'-O-PBA-SS-dCTP, 3'-O-TCO-SS-dGTP and 3'-O—N$_3$-SS-dTTP are added. Complementary 3'-O—N$_3$-SS-dTTP is incorporated by DNA polymerase, 2) the 3 tag labeled binding molecules (Tetrazine-TAG1, SHA-TAG2 and DBCO-TAG3) are added. Only Tag3 is attached to the 3' end of T due to orthogonal interaction between N$_3$ and DBCO, 3) Subsequent nanopore electronic detection only shows the Tag3 signal, indicating incorporation of dTTP. 4) Cleavage using or TCEP or THP removes the Tag from the 3'end, and at the same time regenerates the free 3'OH in preparation for the next cycle of sequencing. Washing steps are carried out after each step in the procedure. Steps 1) and 2) are repeated. Only 3'-O-TCO-SS-dGTP is incorporated and Tetrazine-TAG1 is attached, leading to 3) detection of the Tag1 signal, indicating incorporation of G. Cleavage using TCEP or THP removes Tag1 from the 3'end, again regenerating a free 3'OH. Steps 1) and 2) are repeated. 3'-O-SS-dATP is incorporated and no tag should be attached to the 3'end of A, therefore 3) nanopore electronic detection shows no tag signal, indicating incorporation of A. Steps 1) and 2) are repeated. 3'-O-PBA-SS-dCTP is incorporated and SHA-TAG2 is attached, leading to 3) detection of the Tag2 signal, indicating incorporation of C.
Figure 49B:
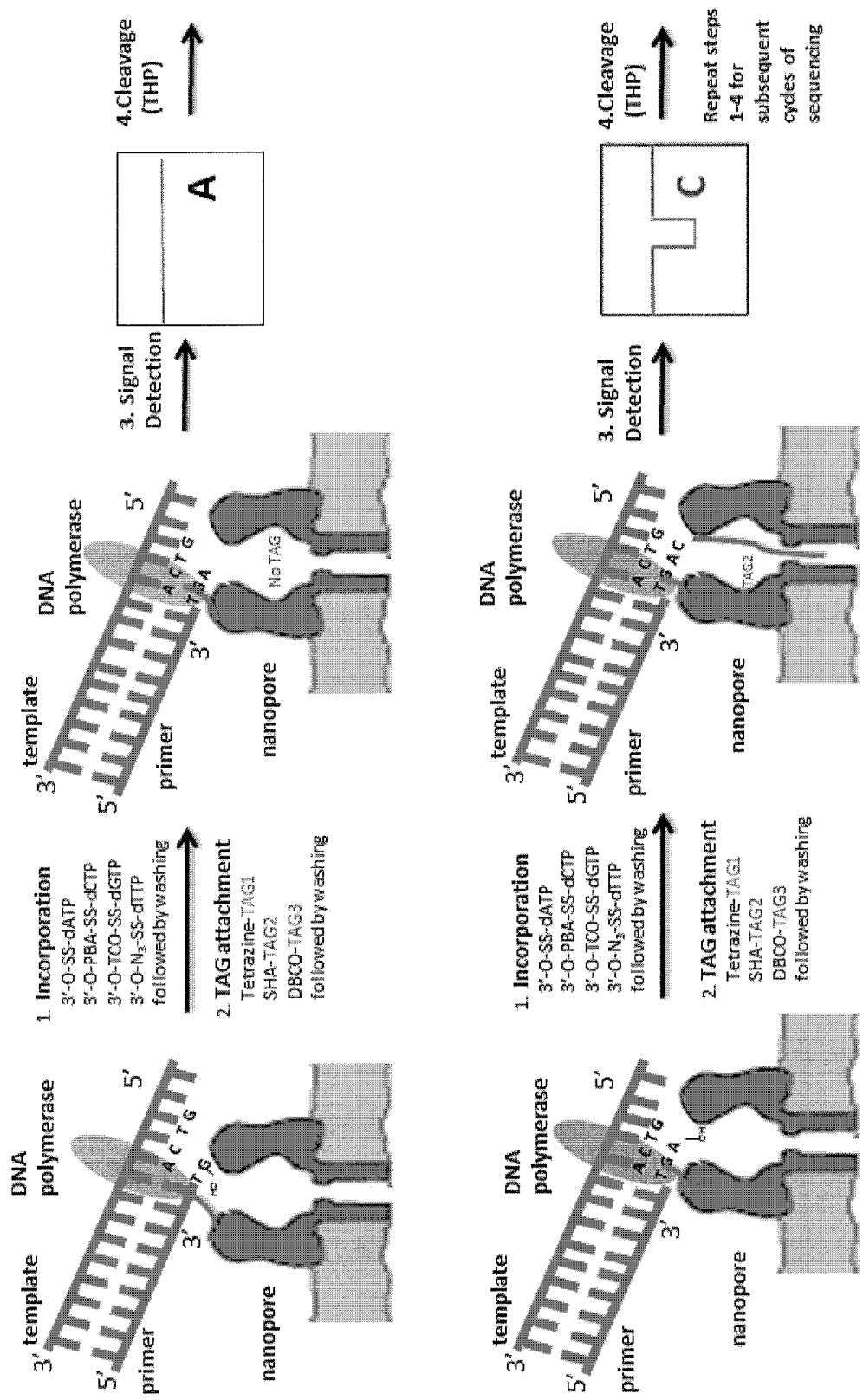
Figure 50A:
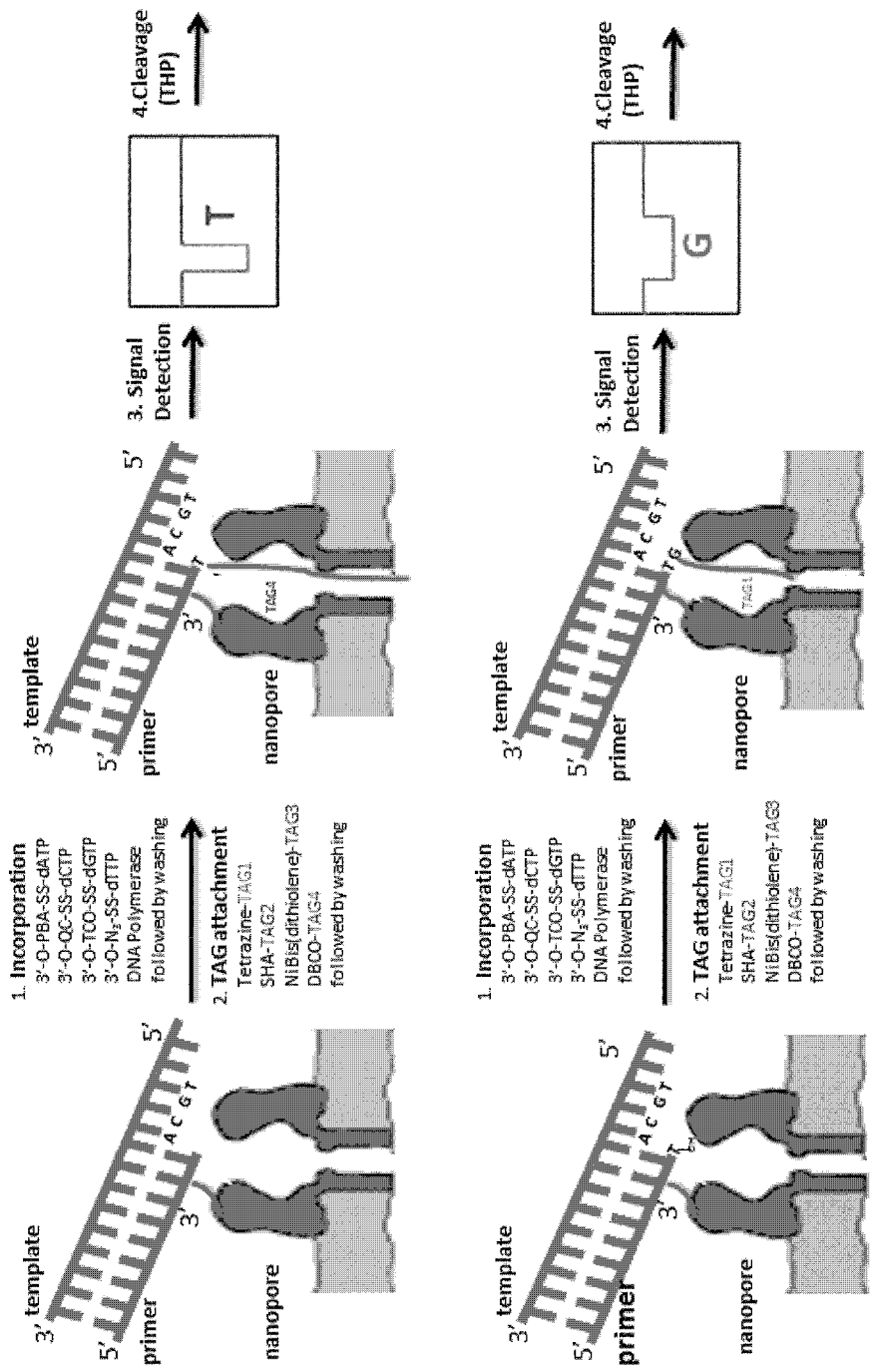
FIGS. 50A-50B. Single-molecule SBS by a nanopore using 3'-O-Anchor-cleavable linker nucleotides; 4 anchor 4 tag scheme starting from DNA primer-nanopore conjugate. To the nanopore-primer complex shown here as an example, 1) DNA polymerase, 3'-O-PBA-SS-dATP, 3'-O-QC-SS-dCTP, 3'-O-TCO-SS-dGTP and 3'-O—N$_3$-SS-dTTP are added. Complementary 3'-O—N$_3$-SS-dTTP is incorporated by DNA polymerase, 2) Adding the 4 tag labeled binding molecules (Tetrazine-TAG1, SHA-TAG2, Ni-bis(dithiolene)-TAG3 and DBCO-TAG4). Only Tag4 is attached to the 3' end of T due to orthogonal interaction between N$_3$ and DBCO, 3) Subsequent nanopore electronic detection only shows the Tag4 signal, indicating incorporation of dTTP. 4) Cleavage using TCEP or THP removes the Tag from the 3'end, and at the same time regenerates the free 3'OH in preparation for the next cycle of sequencing. Washing steps are carried out after each step in the procedure. Steps 1) and 2) are repeated. Only 3'-O-TCO-SS-dGTP is incorporated and Tetrazine-TAG1 is attached, leading to 3) detection of the Tag1 signal, indicating incorporation of G. Cleavage using TCEP or THP removes Tag1 from the 3'end, again regenerating a free 3'OH. Steps 1) and 2) are repeated. 3'-O-QC-SS-dCTP is incorporated and Ni-bis(dithiolene)-TAG3 is attached, leading to 3) detection of the Tag3 signal, indicating incorporation of C. Steps 1) and 2) are repeated. 3'-O-PBA-SS-dATP is incorporated and SHA-TAG2 is attached to the 3'end, 3) nanopore electronic detection gives a Tag2 signal, indicating incorporation of A FIGS. 51A-51B. Single-molecule SBS by a nanopore using 3'-O-Anchor-cleavable linker nucleotides; 3 anchor 3 tag scheme starting from DNA primer-nanopore conjugate. To the nanopore-primer complex shown here as an example, 1) DNA polymerase, 3'-O-SS-dATP, 3'-O-PBA-SS-dCTP, 3'-O-TCO-SS-dGTP and 3'-O—N$_3$-SS-dTTP are added, complementary 3'-O—N$_3$-SS-dTTP is incorporated by DNA polymerase, 2) the 3 tag labeled binding molecules (Tetrazine-TAG1, SHA-TAG2 and DBCO-TAG3) are added. Only Tag3 is attached to the 3' end of T due to orthogonal interaction between N$_3$ and DBCO, 3) Subsequent nanopore electronic detection only shows the Tag3 signal, indicating incorporation of dTTP. 4) Cleavage using TCEP or THP removes the Tag from the 3'end, and at the same time regenerates the free 3'OH in preparation for the next cycle of sequencing. Washing steps are carried out after each step in the procedure. Steps 1) and 2) are repeated. Only 3'-O-TCO-SS-dGTP is incorporated and Tetrazine-TAG1 is attached, leading to 3) detection of the Tag1 signal, indicating incorporation of G. Cleavage using TCEP or THP removes Tag1 from the 3'end, again regenerating a free 3'OH. Steps 1) and 2) are repeated. 3'-O-SS-dATP is incorporated and no tag should be attached to the 3'end of A, therefore 3) nanopore electronic detection shows no tag signal, indicating incorporation of A. Steps 1) and 2) are repeated. 3'-O-TBA-SS-dCTP is incorporated and SHA-TAG2 is attached, leading to 3) detection of the Tag2 signal, indicating incorporation of C.
Figure 50B:
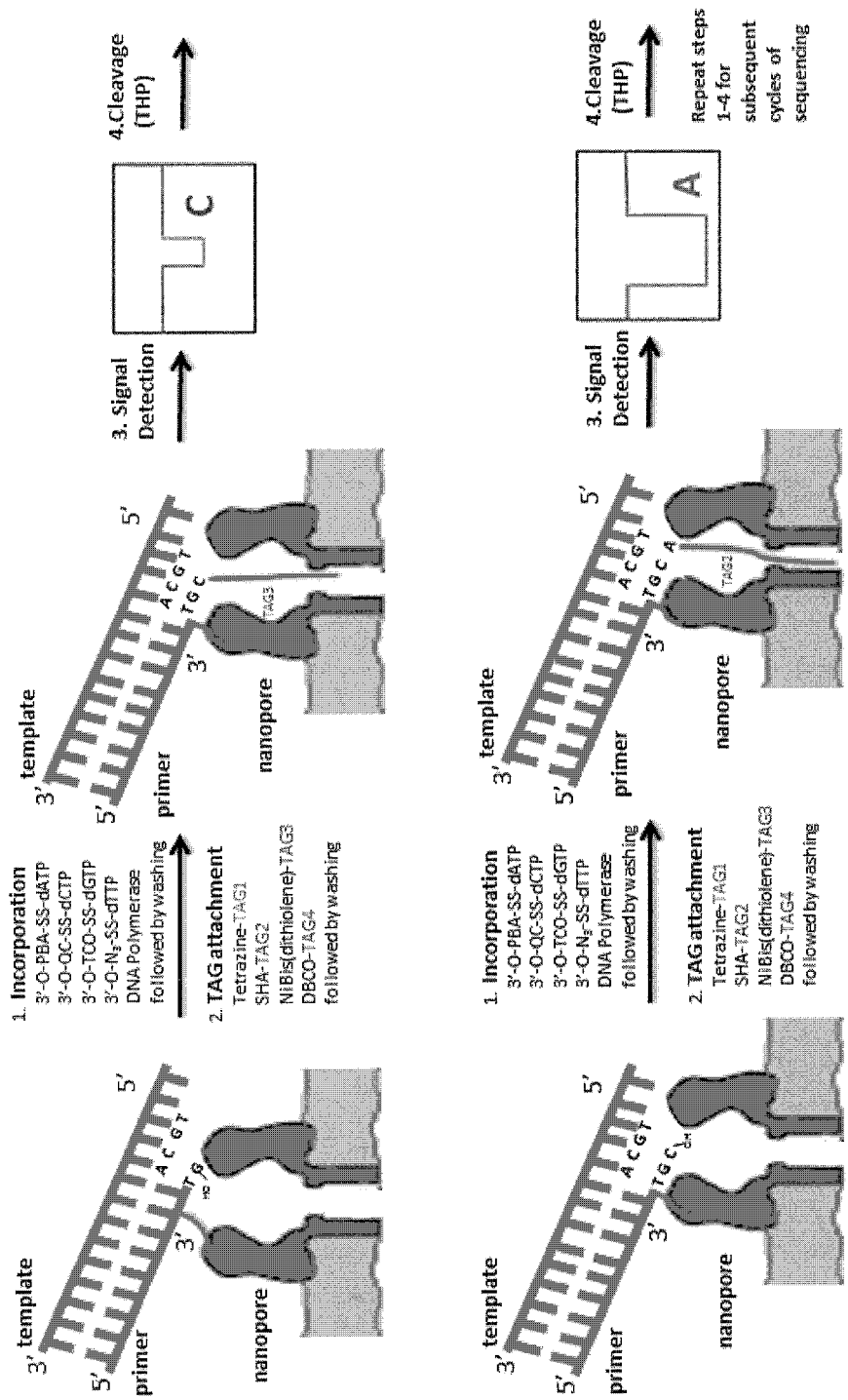
Figure 51A:
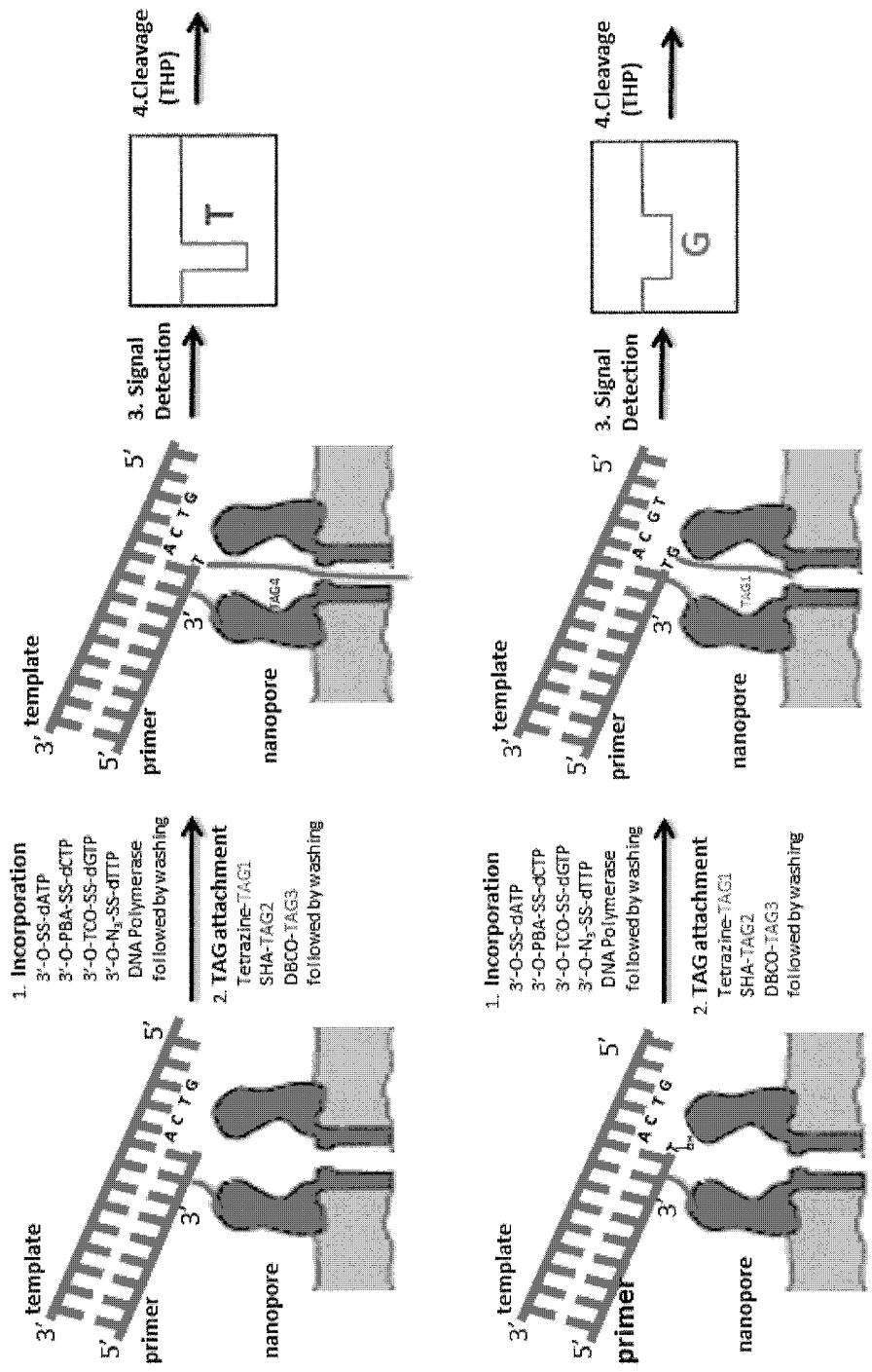
Figure 51B:
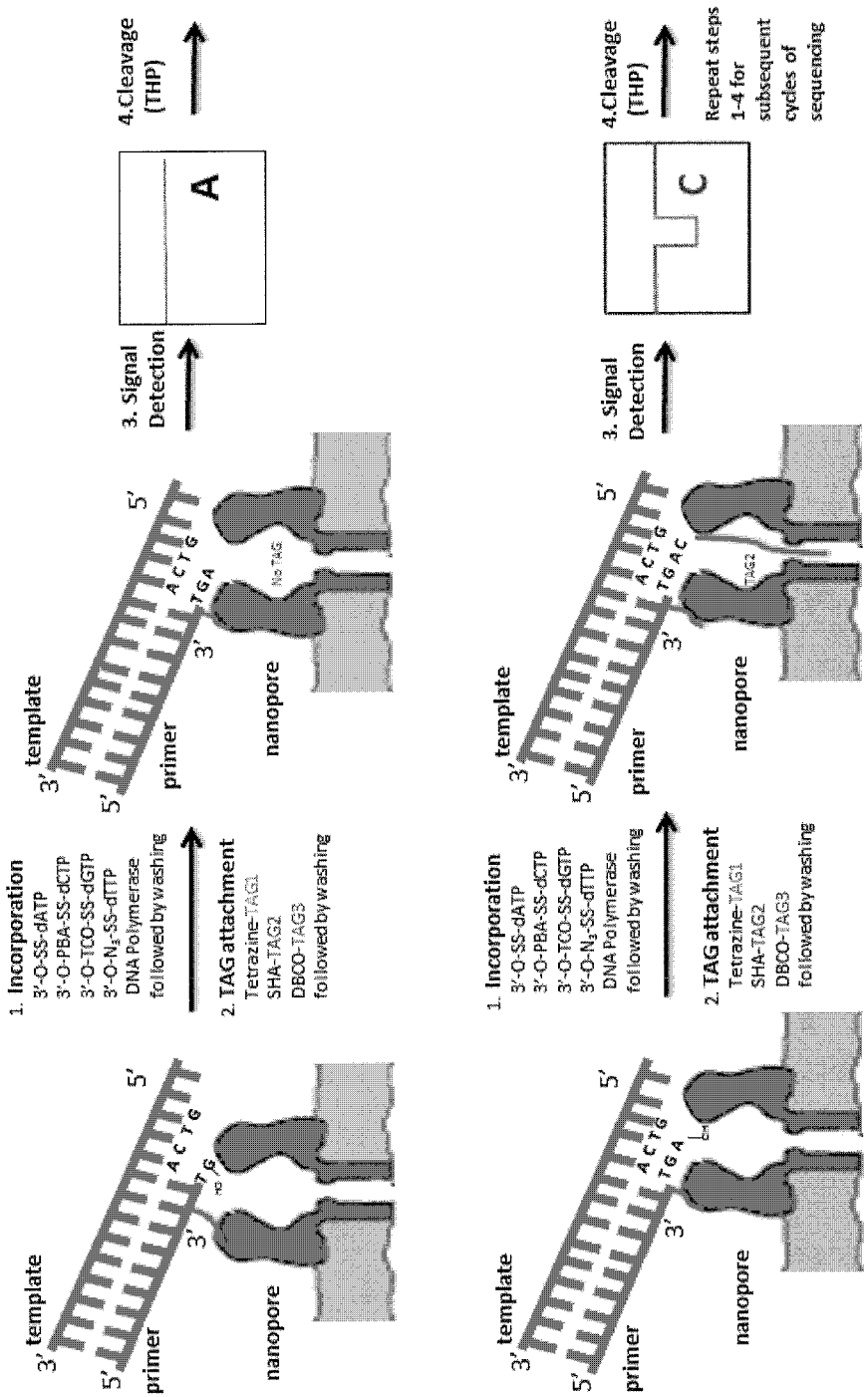

Thus, in an embodiment of the present invention, the nucleotide analogue comprising a cleavable linker (DTM) at the 3'-O-position of the nucleotide is covalently linked to the anchor moiety (e.g. biotin, azide, trans-cyclooctene (TCO), phenylboronic acid (PBA), quadricyclane, norbomene). These anchor moieties can react in biorthogonal fashion with their binding partner (e.g. streptavidin, dibenzylcyclooctene (DBCO), tetrazine, salicylhydroxamic acid (SHA), bis(dithiobenzil)nickel(II) compounds, nitrile oxide containing compounds (Zheng et al, Molecules (2015) 20, 3190-3205; Springer et al J. Biomol. Tech. (2003) 14, 183-190; Sletten and Bertozzi (2011) 133, 17570; Gutsmiedl et al, Org Lett (2009) 11, 2405)). Some of the above molecules can be placed either on the 3'-position of the nucleotide as anchors or on the tag as binding molecules. For instance, PBA or phenyldiboronic acid (PDBA) reacts with SHA molecules to form a complex under a variety of conditions; biotin complexes with streptavidin; the azido group reacts with DBCO; tetrazine reacts with trans-cyclooctene and norbornene in an efficient manner; quadricyclane complexes with bis(dithiobenzil)nickel(II) compounds, and norbornene conjugates with nitrile oxide (see examples in FIG. 37);

Wherein each of the at least four 3'-O-Anchor-DTM nucleotides comprises a triphosphate or a polyphosphate, a base which is adenine, guanine, cytosine, thymine, or uracil, or a derivative of each thereof, and an anchor molecule covalently coupled to the 3'-O-position of the nucleotide sugar moiety comprising a cleavable linker (DTM) at the 3'-O-position (examples in FIGS. 38, 39 and 42);

Wherein (i) the type of base in each anchor attached nucleotide is different from the type of base in each of the other three anchor tagged nucleotides, and (ii) determining which anchor nucleotide has been incorporated into the primer to form a DNA extension product in the first step is accomplished by adding the 4 different tags tethered with different binding partners which will either be covalently attached to or complexed with the corresponding anchor moieties attached via the 3'-O-cleavable linker (DTM) moiety;

Wherein the anchor and or binding moiety is selected from azido, dibenzocyclooctyne, tetrazine, cyclooctene, norbornene, biotin, SHA, PBA, quadricyclane, nitrile oxide, bis(dithiobenzil)nickel(II) compounds, or streptavidin (FIG. 37);

Wherein the nanopore tag is an oligonucleotide, peptide, PEG, carbohydrate or a combination thereof (Fuller et al U.S. Patent Application US20150368710) (examples in FIG. 40);

Wherein the nanopore tag is conjugated to the binding molecule (FIG. 41), using synthetic schemes such as those shown in FIGS. 43-46.

Variants of Single-Molecule SBS by a Nanopore Using 3'-O-Anchor-Cleavable Linker Nucleotides In the following four embodiments, either polymerase (FIGS. 47A, 48 and 49) or the primer (FIGS. 47B, 50 and 51) is attached to the nanopore. The advantage of the former is that capture of the tags by the nanopore should be fast and that there is essentially unlimited flexibility with regard to the length of the DNA to be sequenced, since the enzyme active site and thus the tag release site will always be positioned near the nanopore channel. Thus this approach will be ideal for long sequence reads. In the latter case, the approach will be adequate for short sequences including single-base genotyping assays. Also, in two of the following embodiments (FIGS. 48 and 50), 4 tags will be attached to 4 anchors which are in turn tethered to 4 distinct nucleotides; in the other two embodiments (FIGS. 49 and 51), 3 tags will be attached to 3 anchors which are in turn tethered to 3 of the nucleotides, while the $4^{th}$ nucleotide will only possess a reversible blocking group (linker) without an anchor or tag. All four sequencing schemes allow additions of mixtures of the four nucleotides and mixtures of the four or three tags, thus reducing the number of reaction steps. In the following embodiments washing steps are performed after each step of the procedure.

Single-Molecule SBS by a Nanopore Using 3'-O-Anchor-Cleavable Linker Nucleotides (4 Anchor 4 Tag Scheme Starting from DNA Polymerase-Nanopore Conjugate) (FIG. 48)

In an embodiment of the present invention, a single polymerase molecule is covalently attached to the nanopore at an appropriate distance to allow fast capture of the tag by the nanopore. To this polymerase-coupled nanopore embedded in a lipid bilayer, a template DNA to be sequenced along with the appropriate primer is added followed by 1) the addition of four nucleotides comprising 3'-O-cleavable linkers (DTM) attached with anchor moieties (example set in FIG. 38). The appropriate nucleotide analogue complementary to the nucleotide residue of the single-stranded DNA (template) which is immediately 5' to a nucleotide residue of said single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O being blocked by a cleavable linker and anchor moiety, preventing further incorporation in this step;
2) the addition to the extended primer of 4 different nanopore tags attached with different binding molecules corresponding to 4 anchors; the appropriate binding molecule with tag will either covalently bind or complex with the 3'-O-anchor nucleotide incorporated in step (1);
3) application of a voltage across the membrane and measuring an electronic (ionic current) change across the nanopore resulting from the tag attached thereto generated in step (2) translocating through the nanopore, wherein the electronic change is different for each different type of tag, thereby identifying the nucleotide residue in the single-stranded template DNA, which is complementary to the incorporated tagged nucleotide;
4) cleavage of the 3'-O-cleavable linker-attached tag by treatment with an appropriate cleaving agent, such as DTT, TCEP or THP, thus generating a free 3'-OH ready for the next extension reaction. Iteratively performing steps (1)-(4) for each nucleotide residue of the single-stranded DNA being sequenced, wherein in each iteration of step (1) the 3'-O-cleavable anchor nucleotide is incorporated into the DNA extension product resulting from the previous iteration of step (4) if it is complementary to the nucleotide residue of the single-stranded (template) DNA which is immediately 5' to a nucleotide residue of said single-stranded DNA hybridized to the 3' terminal nucleotide residue of the DNA extension product, thereby determining the nucleotide sequence of the single-stranded DNA.

Single-Molecule SBS by a Nanopore Using 3'-O-Anchor-Cleavable Linker Nucleotides (3 Anchor 3 Tag Scheme Starting from DNA Polymerase-Nanopore Conjugate) (FIG. 49)

In another embodiment of the present invention, a single polymerase molecule is covalently attached to the nanopore at an appropriate distance to allow fast capture of the tag by the nanopore. To this polymerase coupled nanopore embedded in a lipid bilayer, a template DNA to be sequenced along with the appropriate primer is added followed by 1) the addition of four nucleotides comprising one 3'-O-cleavable linker (DTM) nucleotide without anchor and three 3'-O-cleavable linker (DTM) nucleotides attached with anchor moieties via the cleavable linker (example set in FIG. 39). The appropriate nucleotide analog complementary to the nucleotide residue of the single-stranded (template) DNA which is immediately 5' to a nucleotide residue of said single-stranded DNA will be incorporated by DNA polymerase at the 3' terminal nucleotide residue of the primer, so as to form a DNA extension product. Only a single 3'-O-anchor-cleavable linker (DTM) nucleotide or one 3'-O-cleavable linker (DTM) nucleotide (without anchor) will be added to the primer due to the 3'-O being blocked by an anchorless cleavable linker or a cleavable linker with anchor moiety, preventing further incorporation in this step;
2) addition to the extended primer of 3 different nanopore tags conjugated with different binding molecules corresponding to the 3 anchors; the appropriate binding molecule with tag will either covalently bind or complex with the 3'-O-anchor nucleotide incorporated in step (1);
3) application of a voltage across the membrane and measuring an electronic (ionic current) change across the nanopore resulting from the tag attached thereto generated in step (2) translocating through the nanopore, wherein the electronic change is different for each different type of tag, thereby identifying the nucleotide residue in the single-stranded template DNA, which is complementary to the incorporated tagged nucleotide; if no electronic change across the nanopore can be measured after applying a voltage across the membrane, the incorporated nucleotide will be determined as the 3'-O-cleavable linker nucleotide without an anchor;
4) cleavage of the 3'-O-cleavable linker attached tag or 3'-O-cleavable linker by treatment with appropriate cleaving agent, such as DTT, TCEP or THP, thus generating a free 3'-OH ready for the next extension reaction.

Iteratively performing steps (1) to (4) for each nucleotide residue of the single-stranded DNA being sequenced, wherein in each iteration of step (1) the 3'-O-cleavable anchor nucleotide or 3'-O-cleavable linker nucleotide without anchor is incorporated into the DNA extension product resulting from the previous iteration of step (4) if it is complementary to the nucleotide residue of the single-stranded (template) DNA which is immediately 5' to a nucleotide residue of said single-stranded DNA hybridized to the 3' terminal nucleotide residue of the DNA extension product, thereby determining the nucleotide sequence of the single-stranded DNA.

Single-Molecule SBS by a Nanopore Using 3'-O-Anchor-Cleavable Linker Nucleotides (4 Anchor 4 Tag Scheme Starting from DNA Primer-Nanopore Conjugate) (FIG. 50)

In another embodiment of the present invention, a single stranded primer complementary to the single stranded DNA to be sequenced is covalently attached to the nanopore. To this primer coupled nanopore embedded in a lipid bilayer, a template DNA to be sequenced along with the DNA polymerase is added followed by 1) the addition of four nucleotides comprising 3'-O-cleavable linker (DTM) attached with anchor moieties (example set in FIG. 38). The appropriate nucleotide analog complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will be added to the primer due to the 3'-O being blocked by a cleavable linker and anchor moiety, preventing further incorporation in this step;

2) the addition to the extended primer of 4 different nanopore tags attached with different binding molecules corresponding to 4 anchors; the appropriate binding molecule with tag will either covalently bind or complex with the 3'-O-anchor nucleotide incorporated in step (1);

3) application of a voltage across the membrane and measuring an electronic (ionic current) change across the nanopore resulting from the tag attached thereto generated in step (2) translocating through the nanopore, wherein the electronic change is different for each different type of tag, thereby identifying the nucleotide residue in the single-stranded template DNA, which is complementary to the incorporated tagged nucleotide;

4) cleavage of the 3'-O-cleavable linker attached tag by treatment with an appropriate cleaving agent, such as DTT, TCEP or THP, thus generating a free 3'-OH ready for the next extension reaction.

Iteratively performing steps (1) to (4) for each nucleotide residue of the single-stranded DNA being sequenced, wherein in each iteration of step (1) the 3'-O-cleavable anchor nucleotide is incorporated into the DNA extension product resulting from the previous iteration of step (4) if it is complementary to the nucleotide residue of the single-stranded (template) DNA which is immediately 5' to a nucleotide residue of said single-stranded DNA hybridized to the 3' terminal nucleotide residue of the DNA extension product, thereby determining the nucleotide sequence of the single-stranded DNA.

Single-Molecule SBS by a Nanopore Using 3'-O-Anchor-Cleavable Linker Nucleotides (3 Anchor 3 Tag Scheme Starting from DNA Primer-Nanopore Conjugate) (FIG. 51)

In another embodiment of the present invention, a single stranded primer complementary to the single stranded DNA to be sequenced is covalently attached to the nanopore. To this primer coupled nanopore embedded in a lipid bilayer, a template DNA to be sequenced along with the DNA polymerase is added followed by 1) the addition of four nucleotides comprising one 3'-O-cleavable linker (DTM) nucleotide without anchor and three 3'-O-cleavable linker (DTM) nucleotides attached with anchor moieties via the cleavable linker (example set in FIG. 39). The appropriate nucleotide analog complementary to the nucleotide residue of the single-stranded (template) DNA which is immediately 5' to a nucleotide residue of said single-stranded DNA will be incorporated by DNA polymerase at the 3' terminal nucleotide residue of the primer, so as to form a DNA extension product. Only a single 3'-O-anchor-cleavable linker (DTM) nucleotide or one 3'-O-cleavable linker (DTM) nucleotide without anchor will be added to the primer due to the 3'-O being blocked by the anchorless cleavable linker or a cleavable linker with anchor moiety, preventing further incorporation;

2) addition to the extended primer of 3 different nanopore tags conjugated with different binding molecules corresponding to the 3 anchors; the appropriate binding molecule with tag will either covalently bind or complex with the 3'-O-anchor nucleotide incorporated in step (1);

3) application of a voltage across the membrane and measuring an electronic (ionic current) change across the nanopore resulting from the tag attached thereto generated in step (2) translocating through the nanopore, wherein the electronic change is different for each different type of tag, thereby identifying the nucleotide residue in the single-stranded template DNA, which is complementary to the incorporated tagged nucleotide; if no electronic change across the nanopore can be measured after applying a voltage across the membrane, the incorporated nucleotide will be determined as the 3'-O-cleavable linker nucleotide without an anchor;

4) cleavage of the 3'-O-cleavable linker attached tag or 3'-O-cleavable linker without tag by treatment with an appropriate cleaving agent, such as DTT, TCEP or THP; thus generating a free 3'-OH ready for the next extension reaction.

Figure 52A:
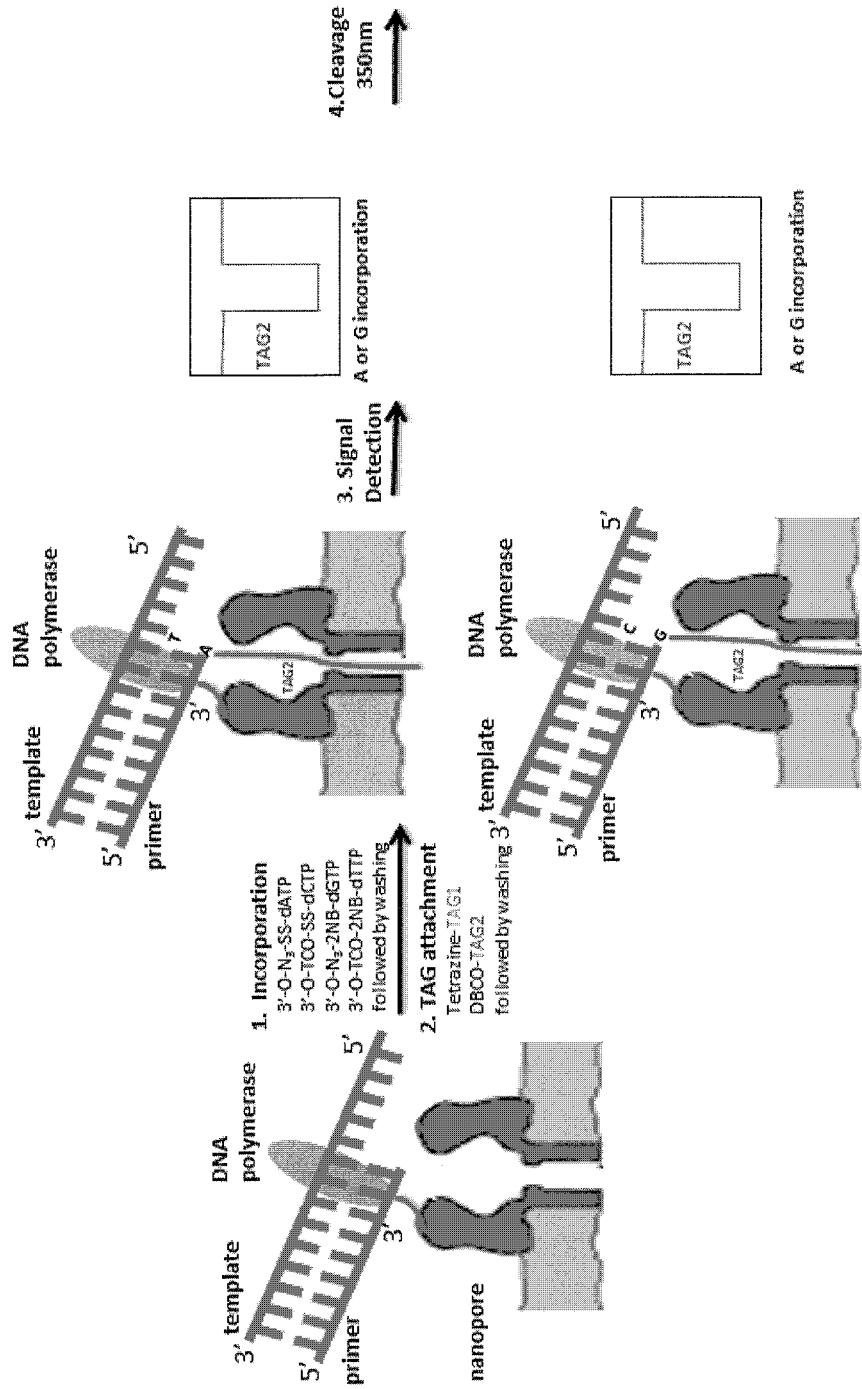
FIGS. 52A-52C. Single-molecule SBS by a nanopore using 3'-O-Anchor-cleavable linker nucleotides: 2 anchor 2 tag scheme starting from DNA primer-nanopore conjugate. To the nanopore-polymerase complex shown here as an example, 1) 3'-O—N$_3$-SS-dATP, 3'-O-TCO-SS-dCTP, 3'-O-TCO-2NB-dTTP and 3'-O—N$_3$-2NB-dGTP are added, complementary 3'-O—N$_3$-SS-dATP (top) or 3'-O—N$_3$-2NB-dGTP (bottom) are incorporated by DNA polymerase; 2) the two tag labeled binding molecules Tetrazine-TAG1 and DBCO-TAG2 are added. TAG2 is attached to the 3' end of A or G due to orthologous interaction between N$_3$ and DBCO. 3) Subsequent nanopore electronic detection shows only the Tag2 signal, indicating incorporation of dATP or dGTP into the growing primer strand. 4) Photocleavage using 340 nm light removes the tag from the G and restores its 3'-OH group due to its having a 2-nitrobenzyl (2NB) cleavable group. 5) Signal detection indicates either a loss of the Tag2 signal, indicating that dGTP was incorporated, or a remaining Tag2 signal, indicating incorporation of dATP. 6) Cleavage of the SS group with THP restores the 3'-OH on the A in preparation for the second cycle. Washes are carried out after each step. Steps 1)-6) are repeated for the second cycle of sequencing. In this case, 1) incorporation of 3'-O-TCO-SS-dCTP (top) or 3'-O-TCO-2NB-dTTP (bottom) will take place. 2) the two tag labeled binding molecules Tetrazine-TAG1 and DBCO-TAG2 are added; only TAG2 is attached to the 3' end of C or T due to orthologous interaction between TCO and tetrazine.3) Subsequent nanopore electronic detection shows only the Tag1 signal, indicating incorporation of dCTP or dTTP into the growing primer strand. 4) Photocleavage using 340 nm light removes the tag from the T and restores its 3'-OH group due to its having a 2NB cleavable group. 5) Signal detection indicates either a loss of the Tag1 signal, indicating that dTTP was incorporated or a remaining Tag1 signal, indicating incorporation of dCTP. 6) Cleavage of the SS group with THP restores the 3'-OH on the dCTP. Steps 1)-6) are repeated for additional cycles of sequencing.
Figure 52B:
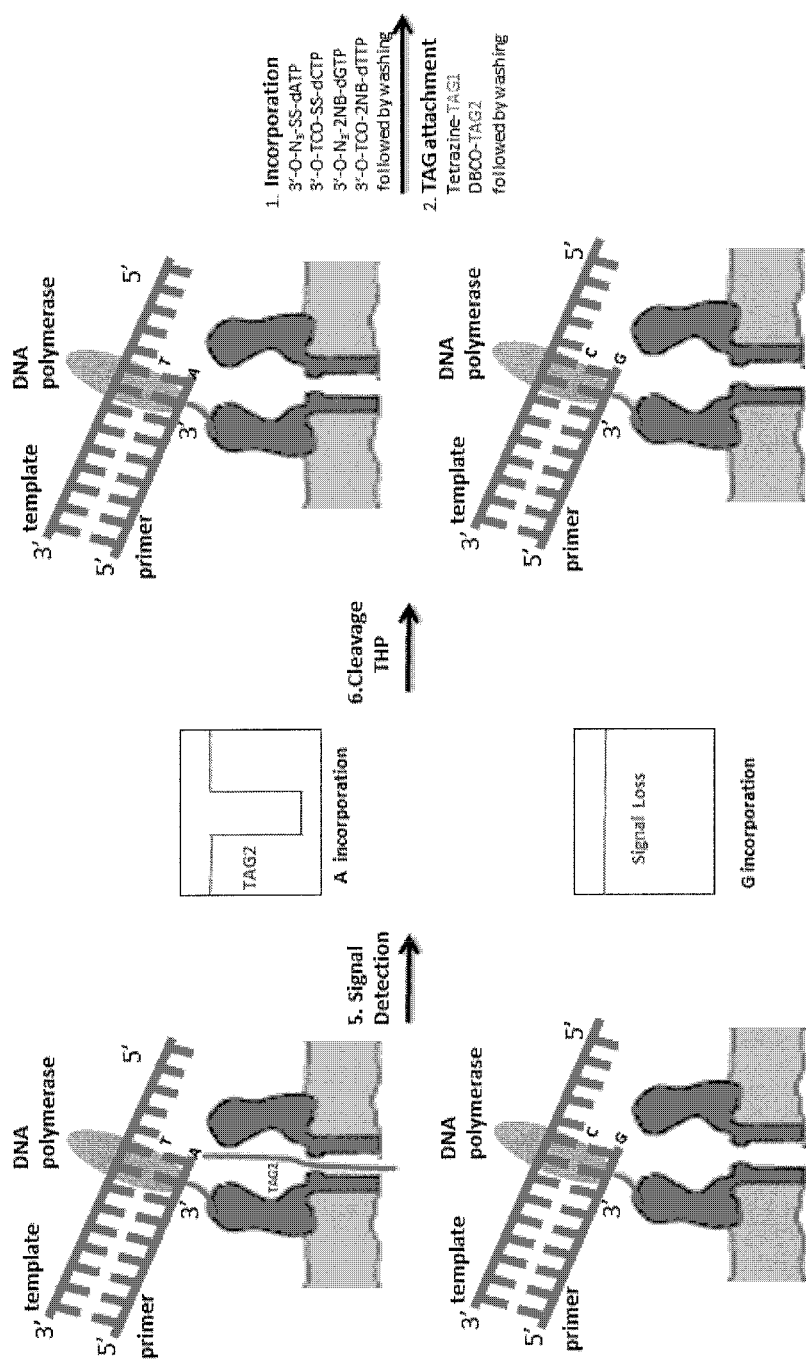
Figure 52C:
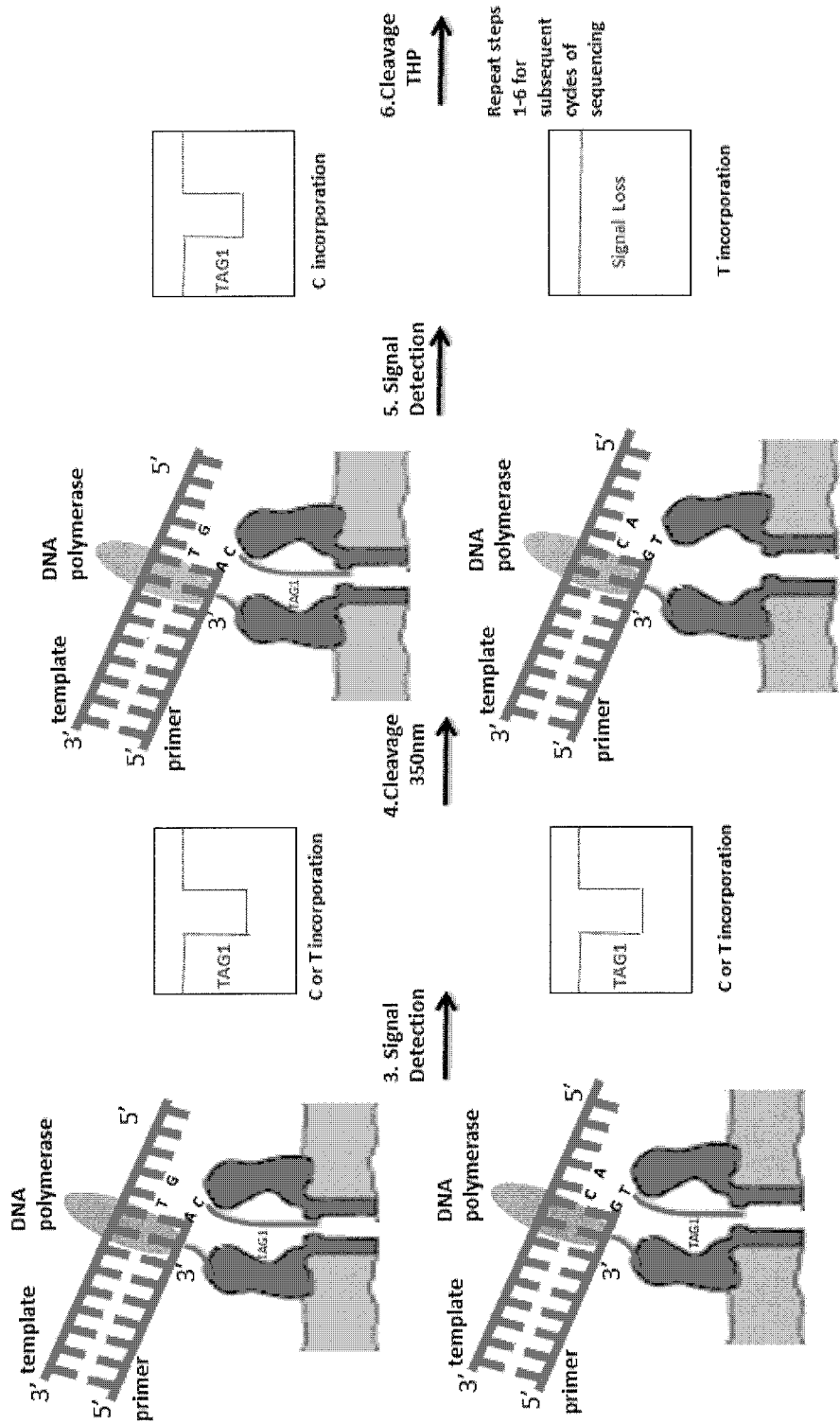

Iteratively performing steps (1) to (4) for each nucleotide residue of the single-stranded DNA being sequenced, wherein in each iteration of step (1) the 3'-O-cleavable anchor nucleotide or 3'-O-cleavable linker nucleotide without anchor is incorporated into the DNA extension product resulting from the previous iteration of step (4) if it is complementary to the nucleotide residue of the single-stranded (template) DNA which is immediately 5' to a nucleotide residue of said single-stranded DNA hybridized to the 3' terminal nucleotide residue of the DNA extension product, thereby determining the nucleotide sequence of the single-stranded DNA Single-Molecule SBS by a Nanopore Using 3'-O-Anchor-Cleavable Linker Nucleotides (2 Anchor 2 Tag 2 Cleavable Linker Scheme Starting from DNA Polymerase-Nanopore Conjugate) (FIGS. 52A-52C)

In addition to the above four embodiments for four-tag and three-tag single-molecule SBS by a nanopore, we propose a two-tag approach (FIG. 52) involving the use of two pairs of 3'-O-Anchor-Cleavable Linker Nucleotides, one pair bearing a DTM(SS) cleavable linker and the other pair an orthogonal cleavable linker (2-nitrobenzyl (2NB) version presented here (FIG. 42) but other possibilities include allyl and azo versions). Another aspect of this approach is that two nucleotides bear one type of anchor molecule attached to the linker and the other two nucleotides bear a second type of anchor molecule (here we show $N_3$ and TCO anchors, but other possible anchors comprise biotin, PBA, quadricyclane and norbornene). Finally two different tags are used that produce different nanopore electronic (ionic current) signals (here we show TAG1 attached to DBCO and TAG2 attached to Tetrazine, but other possible anchor binding molecules comprise streptavidin, SHA, bis(dithiobenzil)nickel(II) compounds and nitrile oxide). The DBCO group on TAG1 conjugates with the $N_3$ anchor and the Tetrazine group on TAG2 conjugates with the TCO anchor. Importantly, each nucleotide will have a unique combination of cleavable linker and anchor: in the example presented, we use a $N_3$ anchor and SS cleavable linker on dATP, a TCO anchor and SS cleavable linker on dCTP, a $N_3$ anchor and 2NB cleavable linker on dGTP, and a TCO anchor and 2NB cleavable linker on dTTP. Finally, while the following embodiment is illustrated with a polymerase molecule covalently attached to the nanopore as in FIG. 47a, it can also be performed with the primer attached to the nanopore as in FIG. 47b. In the following embodiment washing steps are performed after each step of the procedure.

In an embodiment of the present invention, a single polymerase molecule is covalently attached to the nanopore at an appropriate distance to allow fast capture of the tag by the nanopore. To this polymerase-coupled nanopore embedded in a lipid bilayer, a template DNA to be sequenced along with the appropriate primer is added followed by 1) the addition of four nucleotides comprising cleavable linkers and anchor moieties as follows (3'-O—$N_3$—SS-dATP, 3'-O-TCO-SS-dCTP, 3'-O—$N_3$-2NB-dGTP and 3'-O-TCO-2NB-dTTP) (example set in FIG. 42). The appropriate nucleotide analogue complementary to the nucleotide residue of the single-stranded DNA (template) which is immediately 5' to a nucleotide residue of said single-stranded DNA will be incorporated by DNA polymerase at the 3' terminal nucleotide residue of the primer, so as to form a DNA extension product. Only a single 3'-O-anchor-cleavable linker nucleotide will add to the primer due to the 3'-O being blocked by a cleavable linker and anchor moiety, preventing further incorporation in this step;
2) the addition to the extended primer of 2 different nanopore tags attached with different binding molecules corresponding to 2 anchors (DBCO-TAG1 and Tetrazine-TAG2); the appropriate binding molecule with tag will either covalently bind or complex with the 3'-O-anchor nucleotide incorporated in step (1); thus, A and G will receive TAG1, C and T will receive TAG2.
3) application of a voltage across the membrane and measuring an electronic (ionic current) change across the nanopore resulting from the tag attached thereto generated in step (2) translocating through the nanopore, wherein the electronic change is different for the two different tags, thereby partially identifying the nucleotide residue in the single-stranded template DNA, which is complementary to the incorporated tagged nucleotide; thus a TAG1 signal will indicate that either A or G was incorporated, a TAG2 signal will indicate that either C or T was incorporated.
4) cleavage of the 3'-O-2-nitrobenzyl linker-attached tags by treatment with light at −340 nm, thus generating a free 3'-OH ready for the next extension reaction on primers that were extended with G or T, while leaving tags on A and C.
5) application of a voltage across the membrane and measuring an electronic (ionic current) change across the nanopore resulting from any tag still attached thereto generated in step (2) translocating through the nanopore, wherein the electronic change is different for the two different tags, thereby identifying the nucleotide residue in the single-stranded template DNA, which is complementary to the incorporated tagged nucleotide; thus loss of a TAG1 signal seen in step (3) will indicate that a G was incorporated while a remaining TAG1 signal will indicate that an A was incorporated; loss of a TAG2 signal seen in step (3) will indicate that T was incorporated while a remaining TAG2 signal will indicate that C was incorporated.
6) cleavage of the 3'-O-SS(DTM) linkers from any remaining tags by treatment with DTT or TCEP or THP to restore the 3'-OH group in readiness for the next cycle of SBS sequencing.

Iteratively performing steps (1)-(6) for each nucleotide residue of the single-stranded DNA being sequenced, wherein in each iteration of step (1) the 3'-O-cleavable anchor nucleotide is incorporated into the DNA extension product resulting from the previous iteration of step (4) if it is complementary to the nucleotide residue of the single-stranded (template) DNA which is immediately 5' to a nucleotide residue of said single-stranded DNA hybridized to the 3' terminal nucleotide residue of the DNA extension product, thereby determining the nucleotide sequence of the single-stranded DNA.

References for Example 3 include: Kumar et al. PEG-labeled nucleotides and nanopore detection for single molecule DNA sequencing by synthesis. Scientific Reports (2012) 2, 684. Fuller et al. Real-time single-molecule electronic DNA sequencing by synthesis using polymer-tagged nucleotides on a nanopore array. Proceedings of the National Academy of Sciences U,S,A, (2016) 113, 5233-5238. Fuller et al. Chemical methods for producing tagged nucleotides. US Patent Application US20150368710. Zheng et al. Development of bioorthogonal reactions and their applications in bioconjugation. Molecules (2015) 20, 3190-3205. Springer et al. Salicylhydroxamic acid functionalized affinity membranes for specific immobilization of proteins and oligonucleotides. Journal of Biomolecular Techniques (2003) 14, 183-190. Sletten E M, Bertozzi C R. A bioorthogonal quadricyclane ligation. Journal of the American Chemical Society (2011) 133, 17570-17573. Gutsmiedl K et al. Copper-free "click" modification of DNA via nitrile oxide-norbornene 1,3-dipolar cycloaddition. Organic Letters (2009) 11, 2405-2408.

Figure 53:
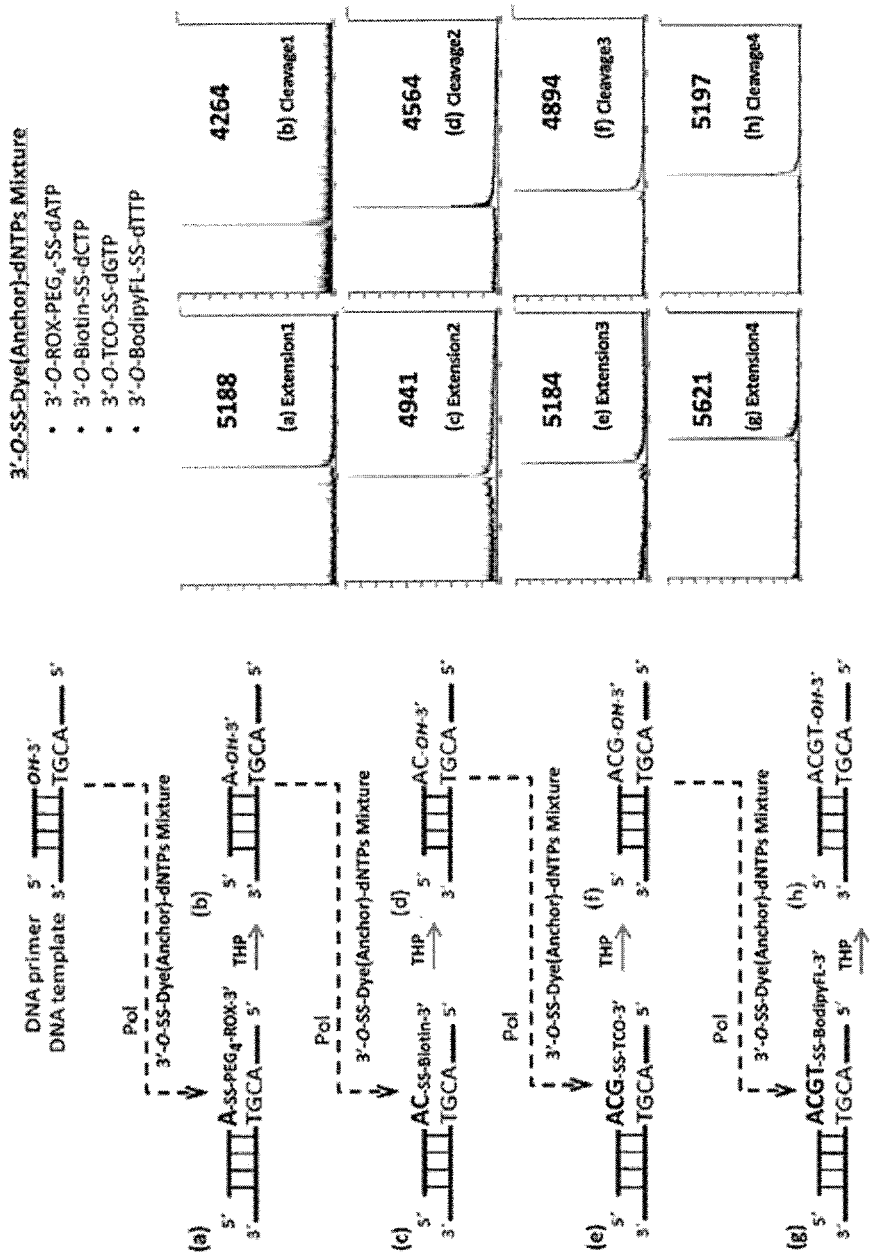
FIG. 53: Use of 3'-O-Dye-SS(DTM)-dNTPs (3'-O-Rox-PEG$_4$-SS-dATP and 3'-O-BodipyFL-SS-dTTP), 3'-O-Anchor-SS(DTM)-dNTPs (3'-O-TCO-SS-dGTP and 3'-O-Biotin-SS-dCTP) for continuous SBS with MALDI-TOF MS detection of intermediate products. Reactions were carried out in solution with mixtures of two 3'-dye modified nucleotides (3'-SS-Rox-dATP and 3'-SS-BodipyFL-dTTP) and two 3'-anchor modified nucleotides (3'-SS-Biotin-dCTP and 3'-SS-TCO-dGTP). Replicate reactions consisted of 20 pmol of the 51mer template shown below, 100 pmol primer or base-extended primers (13-16mer), 150 pmol 3'-O-Dye(Anchor)-dNTPs mixture, 2 units Therminator IX DNA polymerase and 2 mM manganese in 20 µl 1X Thermo Pol buffer subjected to 38 cycles of 30 sec at 65° C. and 30 sec at 45° C. Reactions from multiple replicate tubes were pooled and HPLC was used to remove unused 3'-Dye(Anchor)-dNTPs and salt and obtain pure incorporation products as verified by MALDI-TOF MS. Cleavage with 100 pmol tris-hydroxypropyl phosphine (THP) for 5 min at 65° C. led to recovery of the 3' OH. The samples were treated with OligoClean & Concentrator™ kit (ZymoResearch, USA) to remove salt and cleaved groups and sizes of products checked by MALDI-TOF MS. The 13-mer shown below was used in the initial reaction. In subsequent cycles, primers extended at the 3' end with the base from the previous cycle were used. As shown in the scheme at the left, 4 cycles of extension (a, c, e, g) and cleavage (b, d, f, g) were conducted to add A, C, G and T to the 3' ends of these primers (complementary to the 4 bases 5' to the underlined primer binding site shown in bold letters in the template). The results of MALDI-TOF MS analysis confirmed that the correct nucleotides were added and then converted to natural nucleotides containing a free 3'-OH group in each cycle. Addition of the nucleotide mixture to the 13-mer primer annealed to a DNA template resulted in complete incorporation of 3'-SS-PEG$_4$-Rox-dATP into the primer as evidenced by the single observed peak in the mass spectrum (MS) of 5188 Da (5188 Da expected) (a). After treatment with THP to cleave the 3'-SS-PEG4-Rox group, a single MS peak was observed at 4264 Da (4272 Da expected). (b). Extension of the 14-mer primer in the second cycle revealed incorporation of 3'-SS-Biotin-dCTP into the growing primer strand (single MS peak at 4941 Da observed, 4939 Da expected) (c). After treatment with THP, a single cleavage peak at 4564 Da was found (4561 Da expected) (d). In the third cycle, incorporation of 3'-SS-TCO-dGTP generated a MS peak of 5184 Da (5194 Da expected) (e) and complete cleavage of the anchor and restoration of the 3'-OH group (MS peak at 4894 Da (4890 Da expected) was shown by MS (f). Finally, in the fourth cycle, the newly formed 16-mer DNA strand was used as a primer for 3'-SS-BodipyFL-dTTP incorporation. The MS results (g and h) demonstrated a single peak with molecular weight of 5621 Da (5620 Da expected) for 3'-SS-BodipyFL-dTTP incorporation and 5197 Da (5195 Da expected) after cleavage.

Example 4: Fluorescence-Based SBS Sequencing with 3'-O-Dye-SS(DTM)-dNTPs and 3'-O-Anchor-SS(DTM)-dNTPs We present results for two of the above described schemes involving pairs of 3'-O-Dye-SS(DTM)-dNTPs for two of the four bases (for example, A and T (or U)) and 3'-O-Anchor-SS(DTM)-dNTPs for the other two bases (for example, C and G). First, we demonstrate the ability to incorporate all four of these in succession using solution-based assays and a MALDI-TOF MS readout (FIG. 53). Next we present the ability to obtain a 4-base read (FIG. 54) for a four-color SBS protocol (FIG. 70) with templates immobilized on glass slides and fluorescence scanning using four dyes that have distinct emission spectra. Then we demonstrate 4 and 6-base reads (FIG. 56) obtained using a set of dyes that generates only two color signals (FIG. 71).

We also propose seven new schemes in this document taking advantage of the use of the following types of nucleotide analogues in various combinations: (1) those with dyes attached to the 5 position of pyrimidine bases or 7 position of purine bases via azo linkages and having dithiomethyl blocking groups with attached dyes at the 3'-O-position (3'-O-DTM-dNTP-SS-Dyes and 3'-O-DTM-dNTP-Azo-Dyes); (2) those with dyes directly attached to the 3'-O-group on the sugar via dithiomethyl-based linkers (3'-O-Dye-SS(DTM)-dNTPs); (3) those with anchors for subsequent attachment of dyes attached to the 3'-O-position via dithiomethyl groups, allyl, or 2-nitrobenzyl groups (3'-O-Anchor-SS(DTM)-dNTPs, 3'-O-Anchor-Allyl-dNTPs, 3'-O-Anchor-2-Nitrobenzyl-dNTPs). Both 4-color and 2-color variants of SBS sequencing reactions are described using sets of these nucleotides: For four color versions, the use of either two from group (1) and two from group (2) (FIG. 72) or two from group (1) and two from group (3) (FIG. 73) are described. For two color versions, the use of two from group (1) and two from group (3) (FIG. 74), two from group (1) and two from group (2) (FIG. 75), or four from group (3), two of which have SS and two of which have 2NB (or other) linkages (FIG. 76) are given as examples. Demonstration of Incorporation of Two 3'-O-Dye-SS (DTM)-dNTPs and Two 3'-O-Anchor-SS(DTM)-dNTPs to Obtain a Continuous Four Base Sequence in Solution:

FIG. 53. Use of 3'-O-Dye-SS(DTM)-dNTPs (3'-O—Rox-PEG$_4$-SS-dATP and 3'-O-BodipyFL-SS-dTTP), 3'-O-Anchor-SS(DTM)-dNTPs (3'-O-TCO-SS-dGTP and 3'-O-Biotin-SS-dCTP) for continuous SBS with MALDI-TOF MS detection of intermediate products. Reactions were carried out in solution with mixtures of two 3'-dye modified nucleotides (3'-SS-Rox-dATP and 3'-SS-BodipyFL-dTTP) and two 3'-anchor modified nucleotides (3'-SS-Biotin-dCTP and 3'-SS-TCO-dGTP). Replicate reactions consisted of 20 pmol of the 51mer template shown below, 100 pmol primer or base-extended primers (13-16mer), 150 pmol 3'-O-Dye(Anchor)-dNTPs mixture, 2 units Therminator IX DNA polymerase and 2 mM manganese in 20 µl 1X Thermo Pol buffer subjected to 38 cycles of 30 sec at 65° C. and 30 sec at 45° C. Reactions from multiple replicate tubes were pooled and HPLC was used to remove unused 3'-Dye(Anchor)-dNTPs and salt and obtain pure incorporation products as verified by MALDI-TOF MS. Cleavage with 100 pmol tris-hydroxypropyl phosphine (THP) for 5 min at 65° C. led to recovery of the 3' OH. The samples were treated with OligoClean & Concentrator™ kit (ZymoResearch, USA) to remove salt and cleaved groups and sizes of products checked by MALDI-TOF MS. The 13-mer shown below was used in the initial reaction. In subsequent cycles, primers extended at the 3' end with the base from the previous cycle were used.

As shown in the scheme at the left, 4 cycles of extension (a, c, e, g) and cleavage (b, d, f, g) were conducted to add A, C, G and T to the 3' ends of these primers (complementary to the 4 bases 5' to the underlined primer binding site shown in bold letters in the template). The results of MALDI-TOF MS analysis confirmed that the correct nucleotides were added and then converted to natural nucleotides containing a free 3'-OH group in each cycle. Addition of the nucleotide mixture to the 13-mer primer annealed to a DNA template resulted in complete incorporation of 3'-SS-PEG$_4$-Rox-dATP into the primer as evidenced by the single observed peak in the mass spectrum (MS) of 5188 Da (5188 Da expected) (a). After treatment with THP to cleave the 3'-SS-PEG$_4$-Rox group, a single MS peak was observed at 4264 Da (4272 Da expected) (b). Extension of the 14-mer primer in the second cycle revealed incorporation of 3'-SS-Biotin-dCTP into the growing primer strand (single MS peak at 4941 Da observed, 4939 Da expected) (c). After treatment with THP, a single cleavage peak at 4564 Da was found (4561 Da expected) (d). In the third cycle, incorporation of 3'-SS-TCO-dGTP generated a MS peak of 5184 Da (5194 Da expected) (e) and complete cleavage of the anchor and restoration of the 3'-OH group (MS peak at 4894 Da, 4890 Da expected) was shown by MS (f). Finally, in the fourth cycle, the newly formed 16-mer DNA strand was used as a primer for 3'-SS-BodipyFL-dTTP incorporation. The MS results (g and h) demonstrated a single peak with molecular weight of 5621 Da (5620 Da expected) for 3'-SS-BodipyFL-dTTP incorporation and 5197 Da (5195 Da expected) after cleavage.

```
51 mer template:
5'-TACATCAACTACCCGGAGGCCAAGTACGGCGGGTACGTCCTTGACA
ATGTG-3'

13 mer primer:
5'-CACATTGTCAAGG-3' MW:3959
```

After each incorporation, the expected size of the product should be the sum of the starting primer plus the incoming nucleotide minus the MW (175) of the pyrophosphate group, yielding MWs of 5188 Da, 4939 Da, 5194 Da and 5620 Da. Demonstration of 4-Color Sequencing Using a Combination of 3'-O-Dye-SS(DTM)-dNTPs and 3'-O-Anchor-SS(DTM)-dNTPs with their Corresponding Dye Labeled Binding Molecules on a DNA Primer-Loop Template Immobilized on Glass Slides (FIG. 70 and FIG. 54)

Scheme 1. Use of 3'-O-Dye-SS(DTM)-dNTPs (3'-O-Rox-PEG$_4$-SS-dATP and 3'-O-BodipyFL-SS-dTTP), 3'-O-Anchor-SS(DTM)-dNTPs (3'-O-TCO-SS-dGTP and 3'-O-Biotin-SS-dCTP) with their corresponding Dye Labeled Binding Molecules (TAMRA Labeled Tetrazine and Cy5 Labeled Streptavidin) to perform 4-color DNA SBS. Step 1, addition of DNA polymerase and the four nucleotide analogues (3'-O-Rox-PEG$_4$-SS-dATP, 3'-O-BodipyFL-SS-dTTP, 3'-O-TCO-SS-dGTP and 3'-O-Biotin-SS-dCTP) to the immobilized primed DNA template enables the incorporation of the complementary nucleotide analogue to the growing DNA strand to terminate DNA synthesis. Step 2, Chase: addition of the DNA polymerase and four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to the growing DNA strands that were not extended with one of the dye or anchor labeled dNTPs in step 1. The growing DNA strands are terminated with one of the four dye or anchor labeled nucleotide analogues (A, C, G, T) or the same one of the four nucleotide analogues (A, C, G, T) without dye or anchor. Step 3, Next, the dye labeled binding molecules (TAMRA labeled tetrazine and Cy5 labeled streptavidin) are added to the DNA extension products, which will specifically connect with the two unique "anchor" moieties (TCO and biotin) on each DNA extension product, to enable the labeling of each DNA product terminated with each of the two nucleotide analogues (G and C) with two distinct fluorescent dyes (labeled with TAMRA for G and labeled with Cy5 for C). Step 4, after washing away the unbound dye labeled binding molecules, detection of the unique fluorescence signal from each of the fluorescent dyes on the DNA products allows the identification of the incorporated nucleotide for sequence determination. Next, in Step 5, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 55.

FIG. 56: Four base read for SBS of DNA immobilized on slides using four-color approach. Using the primer-loop template shown at the top of the figure, in which the next four bases to be added are C, A, T, C, reactions were carried out as in the protocol for FIG. 70. 5'—NH$_2$-modified template was immobilized on NHS ester-modified slides from Surmodics. Each cycle was carried out as follows: (1) extension with 60 µl of 0.02 µM 3'-O-Rox-PEG$_4$-SS-dATP, 0.05 µM 3'-O-BodipyFL-SS-dTTP, 0.5 µM 3'-O-Biotin-PEG$_4$-SS-dCTP, 0.5 µM 3'-O-TCO-SS-dGTP, 1X Thermo Pol Reaction Buffer (NEB), 2 mM MnCl$_2$, 6 U Terminator IX DNA polymerase for 15 min at 65° C.; (2) washing with 1X Thermo Pol Reaction Buffer; (3) chase with 60 µl of 4 µM each of the four 3'-O-SS(DTM)-dNTPs, 1X Thermo Pol Reaction Buffer, 2 mM MnCl$_2$, 6 U Terminator IX DNA polymerase for 10 min at 65° C.; (4) washing with 1X Thermo Pol Reaction Buffer; (5) labeling with 60 µl of 10 µM Tetrazine-PEG$_4$-TAMRA, 4 µM Streptavidin-Cy5, 1X PBS, pH 7.4 for 10 min at 37° C.; (6) washing with 1X Thermo Pol Reaction Buffer, 1X SPSC buffer (1X PBS, pH 7.4, 0.5M NaCl, 0.1% Tween-20) and water; (7) scanning air dried slides with excitation at 488 nm, 543 nm, 594 nm and 633 nm, and emission settings at appropriate wavelengths for each dye, to record fluorescence intensity of spots; (8) cleavage with 10 mM THP for 10 min at 65° C.; (9) washing with water, 1X SPSC, and water again; (9) scanning air dried slides to determine background (repeating washes as necessary to minimize the background). The above was carried out 4 times to obtain the raw image intensity readings shown in the bar graph at the bottom for the first four bases of the extended primer.

FIG. 55: Structures of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG$_4$-SS-dGTP and 3'-O-Biotin-SS-dCTP) with their corresponding Dye Labeled Binding Molecules (TAMRA or Cy3 Labeled Tetrazine and Cy5 Labeled Streptavidin) to perform 4-color DNA SBS using approach delineated in FIG. 70.

Demonstration of Successful 2-Color Continuous Sequencing Using a Combination of 3'-O-Dye-SS(DTM)-dNTPs and 3'-O-Anchor-SS(DTM)-dNTPs with their Corresponding Dye Labeled Binding Molecules on Immobilized DNA Templates (FIG. 71 and FIG. 56):

FIG. 71. Use of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG$_4$-SS-dGTP and 3'-O-Biotin-PEG$_4$-SS-dCTP) with their corresponding Dye Labeled Binding Molecules (Alexa488-PEG$_4$ Labeled Tetrazine and Alexa594 Labeled Streptavidin) to perform 2-color DNA SBS. Although 4 different dyes have been used in this experiment, Rox and Alexa594 have very similar absorption and emission spectra, as do BodipyFL and Alexa488. Hence this is described as a 2-color experiment. Step 1, addition of DNA polymerase and the four nucleotide analogues (3'-O-Rox-SS-dATP, 3'-O-BodipyFL-SS-dTTP, 3'-O-TCO-PEG$_4$-SS-dGTP and 3'-O-Biotin-PEG$_4$-SS-dCTP) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the growing DNA strands that were not extended with one of the dye or anchor labeled dNTPs in step 1. The growing DNA strands are terminated with one of the four dye or anchor labeled nucleotide analogues (A, C, G, T) or the same one of the four nucleotide analogues (A, C, G, T) without dye or anchor. Imaging is performed to identify incorporation of 3'-O-Rox-SS-dATP and 3'-O-BodipyFL-SS-dTTP. Step 3, Next, the dye labeled binding molecules (Alexa488-PEG$_4$ labeled tetrazine and Alexa594 labeled streptavidin) are added to the DNA extension products, which will specifically connect with the two unique "anchor" moieties (TCO and biotin) on each DNA extension product, to enable the labeling of each DNA product terminated with each of the two nucleotide analogues (G and C) with two distinct fluorescent dyes (labeled with Alexa488 for G and labeled with Alexa594 for C). Step 4, after washing away the unbound dye labeled binding molecules, detection of the unique fluorescence signal from each of the fluorescent dyes on the DNA products allows the identification of the incorporated nucleotide for sequence determination. Next, in Step 5, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 71.

FIG. 56: Four and six base reads for SBS of primer-loop template DNA immobilized on slides using two-color approach. Using the looped priming template shown at the top of the figure, in which the next four bases to be added are T, A, G, A, or the looped priming template shown in the middle of the figure, in which the next six bases are C, A, T, C, A, A, reactions were carried out as in the protocol for FIG. 71. 5'—NH$_2$-modified template was immobilized on NHS ester-modified slides from Surmodics. Each cycle was carried out as follows: (1) extension with 60 µl of 0.02 µM 3'-O-Rox-PEG$_4$-SS-dATP, 0.05 µM 3'-O-BodipyFL-SS-dTTP, 0.5 µM 3'-O-Biotin-SS-dCTP, 0.2 M 3'-O-TCO-SS-dGTP, 1X Thermo Pol Reaction Buffer (NEB), 2 mM MnCl$_2$, 6 U Terminator IX DNA polymerase for 15 min at 65° C.; (2) washing with 1X Thermo Pol Reaction Buffer; (3) chase with 60 µl of 4 µM each of the four 3'-O-SS(DTM)-dNTPs, 1X Thermo Pol Reaction Buffer, 2 mM MnCl$_2$, 6 U Terminator IX DNA polymerase for 10 min at 65° C.; (4) washing with 1X Thermo Pol Reaction Buffer; (5) scanning air dried slides at 488 nm and 594 nm excitation with appropriate emission settings to record fluorescence intensity of spots; (6) labeling with 60 µl of 0.5 µM Tetrazine-PEG$_4$-Alexa488, 0.5 µM Streptavidin-Alexa594, 1X PBS, pH 7.4 for 10 min at 37° C.; (7) washing with 1X Thermo Pol Reaction Buffer, 1X SPSC buffer and water; (8) scanning air dried slides at 488 nm and 594 mn excitation with appropriate emission settings to record fluorescence intensity of spots; (9) cleavage with 5 mM THP for 10 min at 65° C.; (10) washing with water, 1X SPSC, and water again; (11) scanning air dried slides to determine background (repeating washes as necessary to obtain minimal background). The above was carried out 4-6 times to obtain the raw image intensity readings shown in the bar graphs below the template structures. In each cycle, E represents the imaging results after the extension and L represents the imaging results after the labeling. So in the top graph, the T is determined after the initial extension due to the presence of the BodipyFL dye directly attached to the 3'-O-of the dTTP, as are the A's in the second and fourth cycle; however the G in the third cycle is not seen until the labeling reaction in which the Alexa488-tetrazine is conjugated to the anchoring molecule (TCO) on the 3'-O-of the dGTP. Similarly in the lower bar graph, the A's and T's are visualized immediately after extension, but the C's are not observed until the labeling reaction is performed.

FIG. 57: Structures of 3'-O-Dye-SS(DTM)-dNTPs (3'-O-Rox-SS-dATP and 3'-O-BodipyFL-SS-dTTP), 3'-O-Anchor-SS(DTM)-dNTPs (3'-O-TCO-PEG$_4$-SS-dGTP and 3'-O-Biotin-SS-dCTP) with their corresponding Dye Labeled Binding Molecules (Alexa488 Labeled Tetrazine and Alexa594 Labeled Streptavidin) to perform 2-color DNA SBS using approach delineated in FIG. 71.

FIG. 72: Use of 3'-O-SS(DTM)-dNTP-SS-Dyes (3'-O-SS-dGTP-7-SS-Cy5, 3'-O-SS-dCTP-5-SS-R6G); 3'-O-Dye-SS(DTM)-dNTPs (3'-O-Rox-PEG$_4$-SS-dATP and 3'-O-BodipyFL-SS-dTTP) for 4-color DNA SBS. Step 1, Addition of DNA polymerase and the four nucleotide analogues (3'-O-SS-dGTP-7-SS-Cy5, 3'-O-SS-dCTP-5-SS-R6G, 3'-O-Rox-PEG$_4$-SS-dATP and 3'-O-BodipyFL-SS-dTTP) to the immobilized primed DNA template enables the incorporation of the complementary dye labeled nucleotide analogue to the growing DNA strand. The growing DNA strand is terminated with one of the four nucleotide analogues (A, C, G, T) with the four distinct fluorescent dyes. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four nucleotide analogues (A, C, G, T) with the four distinct fluorescent dyes or the same one of the four nucleotide analogues (A, C, G, T) without dye. Step 3, after washing away the unincorporated nucleotide analogues, detection of the unique fluorescence signal from each of the fluorescent dyes on the DNA products allows the identification of the incorporated nucleotide for sequence determination. Next, in Step 4, treatment of the DNA products with THP cleaves the SS linker, leading to the removal of the fluorescent dye and the regeneration of a free 3'-OH group on the DNA extension product, which is ready for the next cycle of the DNA sequencing reaction. Structures of modified nucleotides used in this scheme are shown in FIG. 58.

FIG. 58: Structures of 3'-O-Dye-SS(DTM)-dNTPs (3'-O-Rox-SS-dATP and 3'-O-BodipyFL-SS-dTTP) and 3'-O-SS(DTM)-dNTP-SS-Dyes (3'-O-SS-dGTP-7-SS-Cy5 and 3'-O-SS-dCTP-5-SS-R6G) for 4-color sequencing using approach delineated in FIG. 72.

FIG. 73: Use of 3'-O-SS(DTM)-dNTP-SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Rox Labeled Tetrazine and BodipyFL Labeled Streptavidin) to perform 4-color DNA SBS. Step 1, addition of DNA polymerase and the four nucleotide analogues (3'-O-SS-dGTP-7-SS-Cy5, 3'-O-SS-dCTP-5-SS-R6G, 3'-O-TCO-SS-dATP and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye or anchor labeled nucleotide analogues (A, C, G, T) or the same one of the four nucleotide analogues (A, C, G, T) without dye or anchor. Step 3, next, the dye labeled binding molecules (Rox labeled tetrazine and BodipyFL labeled streptavidin) are added to the DNA extension products, which will specifically connect with the two unique "anchor" moieties (TCO and biotin) on each DNA extension product, to enable the labeling of each DNA product terminated with each of the two nucleotide analogues (A and T) with two distinct fluorescent dyes (labeled with Rox for A and labeled with BodipyFL for T). Step 4, after washing away the unbound dye-labeled binding molecules, detection of the unique fluorescence signal from each of the fluorescent dyes on the DNA products allows identification of the incorporated nucleotides for sequence determination. A Rox signal indicates incorporation of A, a BodipyFL signal indicates incorporation of T, a Cy5 signal indicates incorporation of G and an R6G signal indicates incorporation of C. Next, in Step 5, treatment of the DNA products with THP cleaves the SS linker, leading to the removal of the remaining fluorescent dye and the regeneration of a free 3'-OH group on the DNA extension product, which is ready for the next cycle of the DNA sequencing reaction. Structures of modified nucleotides used in this scheme are shown in FIG. 59.

FIG. 59: Structures of 3'-O-Anchor-SS(DTM)-dNTPs (3'-O-TCO-SS-dATP and 3'-O-Biotin-SS-dTTP), 3'-O-SS(DTM)-dNTP-SS-Dyes (3'-O-SS-dGTP-7-SS-Cy5 and 3'-O-SS-dCTP-5-SS-R6G) and the corresponding Dye Labeled Binding Molecules (Rox Labeled Tetrazine and BodipyFL Labeled Streptavidin) to perform 4-color DNA SBS using approach delineated in FIG. 73.

FIG. 74: Use of 3'-O-SS(DTM)-dNTP-SS-Dyes (3'-O-SS-dGTP-7-SS-Cy5, 3'-O-SS-dCTP-5-SS-R6G); 3'-O-Anchor-SS(DTM)-dNTPs (3'-O-TCO-SS-dATP, 3'-O-Biotin-SS-dTTP) with their corresponding Dye Labeled Binding Molecules (Cy5 Labeled Tetrazine and R6G Labeled Streptavidin) to perform 2-color DNA SBS. Step 1, addition of DNA polymerase and the four nucleotide analogues (3'-O-SS-dGTP-7-SS-Cy5, 3'-O-SS-dCTP-5-SS-R6G, 3'-O-TCO-SS-dATP and 3'-O-Biotin-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye or anchor labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows identification of the incorporated nucleotide for sequence determination, Cy5 signal indicates incorporation of G, R6G signal indicates incorporation of C. Step 4, next, the dye labeled binding molecules (Cy5 labeled tetrazine and R6G labeled streptavidin) are added to the DNA extension products, which will specifically connect with the two unique "anchor" moieties (TCO and biotin) on each DNA extension product, to enable the labeling of each DNA products terminated with one of the two nucleotide analogues (A and T) with two distinct fluorescent dyes (labeled with Cy5 for A and labeled with R6G for T). Step 5, after washing away the unattached labels, a second round of detection of the unique fluorescence signal from each of the fluorescent dyes on the DNA products allows the identification of the incorporated nucleotide for sequence determination. Appearance of a Cy5 signal indicates incorporation of A, R6G signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. Structures of modified nucleotides used in this scheme are shown in FIG. 60.

FIG. 60: Structures of 3'-O-Anchor-SS(DTM)-dNTPs (3'-O-TCO-SS-dATP and 3'-O-Biotin-SS-dTTP), 3'-O-SS (DTM)-dNTP-SS-Dyes (3'-O-SS-dGTP-7-SS-Cy5 and 3'-O-SS-dCTP-5-SS-R6G) and the corresponding Dye Labeled Binding Molecules (Cy5 Labeled Tetrazine and R6G Labeled Streptavidin) to perform 2-color DNA SBS using approach delineated in FIG. 74.

FIG. 75: Use of 3'-O-SS(DTM)-dNTP-Azo-Dyes (3'-O-SS-dGTP-7-Azo-Rox, 3'-O-SS-dCTP-5-Azo-BodipyFL); 3'-O-Dye-SS(DTM)-dNTPs (3'-O-Rox-SS-dATP, 3'-O-BodipyFL-SS-dTTP) to perform 2-color DNA SBS. Step 1, addition of DNA polymerase and the four nucleotide analogues (3'-O-SS-dGTP-7-Azo-Rox, 3'-O-SS-dCTP-5-Azo-BodipyFL, 3'-O-Rox-SS-dATP and 3'-O-BodipyFL-SS-dTTP) to the immobilized primed DNA template enables the incorporation of the complementary nucleotide analogue to the growing DNA strand to terminate DNA synthesis. Step 2, Chase: addition of DNA polymerase and four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl (SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands in the ensemble that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows the identification of the incorporated nucleotide for sequence determination. Rox signal indicates incorporation of A or G, BodipyFL signal indicates incorporation of C or T. Step 4, cleavage of Azo linker by adding sodium dithionite ($Na_2S_2O_4$) to the elongated DNA strands results in removal of Rox from incorporated G and BodipyFL from incorporated C. Step 5, after washing away the cleaved dyes, a second round of detection of the unique fluorescence signal from each of the fluorescent dyes on the DNA products allows the identification of the incorporated nucleotide for sequence determination. Disappearance of Rox signal indicates incorporation of G, and disappearance of BodipyFL signal indicates incorporation of C. Remaining Rox signal indicates incorporation of A, and remaining BodipyFL signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. The presence of an additional SS linkage between the Azo group and the base results in the production of a shorter scar on the incorporated nucleotide after THP treatment which should result in longer reads. Structures of modified nucleotides used in this scheme are shown in FIG. 61.

FIG. 61: Structures of 3'-O-Dye-SS(DTM)-dNTPs (3'-O-Rox-SS-dATP and 3'-O-BodipyFL-SS-dTTP) and 3'-O-DTM(SS)-dNTP-Azo-Dyes (3'-O-SS-dGTP-7-Azo-Rox or 3'-O-SS-dGTP-7-SS-Azo-Rox and 3'-O-SS-dCTP-5-Azo-BodipyFL or3'-O-SS-dCTP-5-SS-Azo-BodipyFL) for 2-color DNA SBS using approach delineated in FIG. 75.

Two Color SBS Scheme Involving Two Different Anchors and Two Different Cleavable Linkers for Dye Attachment on the 3'-O—Position of the Deoxynucleotide:

A number of different cleavable linkers can be used in this scenario. Two of the nucleotides will bear an SS(DTM) linker and the other two will include a 2-nitrobenzyl (2NB) linker (or azo linker or allyl linker). The two linkers will be used in cross combination with two anchor/binding molecule pairs (TCO anchor on the 3'-OH of the nucleotide with its binding partner Tetrazine attached to one fluorescent dye; $N_3$ anchor with its partner binding molecule attached to a second dye. The key is that each of the four nucleotides will have a different anchor and linker combination: for instance dATP could have $N_3$ anchor and SS linker; dCTP could have TCO anchor and SS linker; dGTP could have $N_3$ anchor and 2NB linker; dTTP could have TCO anchor and 2NB linker. Though we use SS (cleaved with DTT, TCEP or THP) and 2-nitrobenzyl linkers (cleaved with ~340 nm light) in the following scheme (FIG. 76), other possible choices are SS and azo linkers (cleaved with sodium dithionite) or SS and allyl linkers (cleaved with Pd(0)).

FIG. 76: Use of 3'-O-Anchor-SS(DTM)-dNTPs (3'-O—$N_3$—SS-dATP and 3'-O-TCO-SS-dCTP) and 3'-O-Anchor-2-Nitrobenzyl-dNTPs (3'-O—$N_3$-2-Nitrobenzyl-dGTP and 3'-O-TCO-2-Nitrobenzyl-dTTP) with their corresponding Dye Labeled Binding Molecules (BodipyFL Labeled DBCO and Rox labeled Tetrazine) to perform 2-color DNA SBS. Step 1, addition of DNA polymerase and the four nucleotide analogues (3'-O—$N_3$—SS-dATP, 3'-O-TCO-SS-dCTP, 3'-O—$N_3$-2-Nitrobenzyl-dGTP and 3'-O-TCO-2-Nitrobenzyl-dTTP) to the immobilized primed DNA template enables the incorporation of the complementary nucleotide analogue to the growing DNA strand to terminate DNA synthesis. Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to the subset of growing DNA strands in the ensemble that were not extended with any of the anchor labeled dNTPs in step 1. The growing DNA strands are terminated with one of the four anchor labeled nucleotide analogues (A, C, G, T) or the same one of the four nucleotide analogues (A, C, G, T) without dye or anchor. Step3, next, the dye labeled binding molecules (Rox labeled Tetrazine and BodipyFL labeled DBCO) are added to the DNA extension products, which will specifically connect with the two unique "anchor" moieties (TCO and $N_3$) on each DNA extension product, to enable the labeling of each DNA product terminated with one of the four nucleotide analogues with one of the two dyes (A and G with BodipyFL and C and T with Rox). Step 4, after washing away the unbound dye-labeled binding molecules, detection of the fluorescence signals from each of the fluorescent dyes on the DNA products allows partial identification of the incorporated nucleotides for sequence determination. A BodipyFL signal indicates incorporation of A or G, a Rox signal indicates incorporation of T or C. Next, in Step 5, treatment of the DNA products with 340 nm light cleaves the 2-Nitrobenzyl linker, leading to the removal of the fluorescent dye and the regeneration of a free 3'-OH group on the DNA extension products extended with either a G or T. After washing, in Step 6 imaging is carried out a second time to detect remaining fluorescent signals. Loss of a BodipyFL signal indicates that the incorporated nucleotide was a G, a remaining Bodipy FL signal indicates that the incorporated nucleotide was an A; similarly loss of a Rox signal indicates that the incorporated nucleotide was a T, a remaining Rox signal indicates that the incorporated nucleotide was a C. Finally, in Step 7, treatment with THP cleaves any dye remaining on incorporated A or C, and restores the 3'-OH on those nucleotides as well. At this point, the extension products are ready for the next cycle of the DNA sequencing reaction. Structures of modified nucleotides used in this scheme are shown in FIG. 63.

FIG. 63: 3'—O-Anchor-SS(DTM)-dNTP (3'-O-TCO-SS-dCTP and 3'-O-N3-SS-dATP), 3'-O-Anchor-2NB-dNTPs (3'-O-TCO-2NB-dTTP and 3'-O-N3-2NB-dGTP) and their corresponding Dye-labeled binding molecules (Rox labeled tetrazine and BodipyF1 labeled DBCO) for 2-color DNA SBS using approach delineated in FIG. 76.

FIG. 64: Structures of 3'-O-Anchor-SS(DTM)-dNTP, 3'-O-Anchor-Allyl-dNTPs, and 3'-O-Anchor-2NB-dNTPs. Combinatorial use of two from one category with the same anchor, two from another category with another anchor and their corresponding two Dye-labeled binding molecules results in 2-color DNA SBS. One specific approach is shown in FIG. 76 as an example.

FIG. 66: Example synthesis of 3'-O-SS(DTM)-dGTP-SS-Azo-Rox and 3'-O-SS(DTM)-dTTP-SS-Azo-BodipyFL. Rox and BodipyFL labeled Azo Linker NHS esters are coupled with 3'-O-SS(DTM)-dGTP-SS—NH$_2$ and 3'-O-SS(DTM)-dTTP-SS—NH$_2$ giving 3'-O-SS(DTM)-dGTP-SS-Azo-Rox and 3'-O-SS(DTM)-dTTP-SS-Azo-BodipyFL.

FIG. 67: Synthesis of 3'-O-SS(DTM)-dATP-SS-Rox.

FIG. 68: Synthesis of 3'-O-SS(DTM)-dUTP-SS-BodipyFL.

FIG. 69: Example syntheses of 3'-O-Anchor-2NB-dNTP (3'-O-TCO-2-Nitrobenzyl-dTTP and 3'-O-Azido-2-Nitrobenzyl-dGTP).

Synthetic Schemes

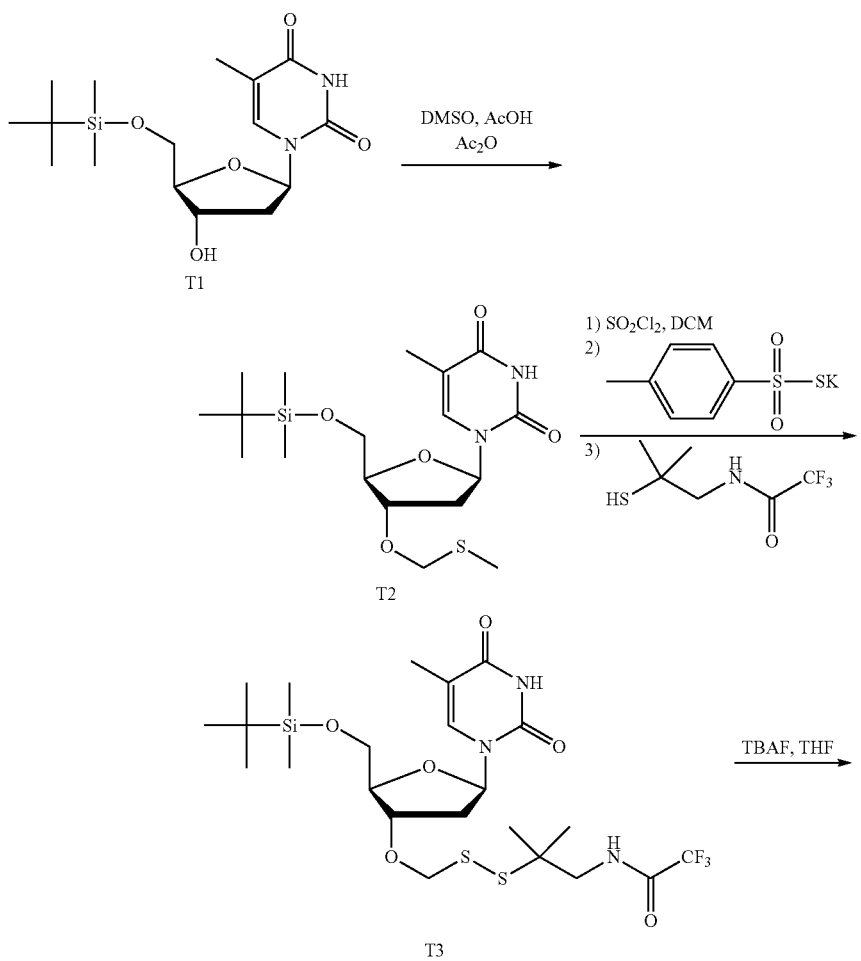

Scheme 1. The synthesis of 3'-O-Bodipy-DTM-dTTP and 3'-O-Bodipy-PEG$_4$-DTM-dTTP.

-continued
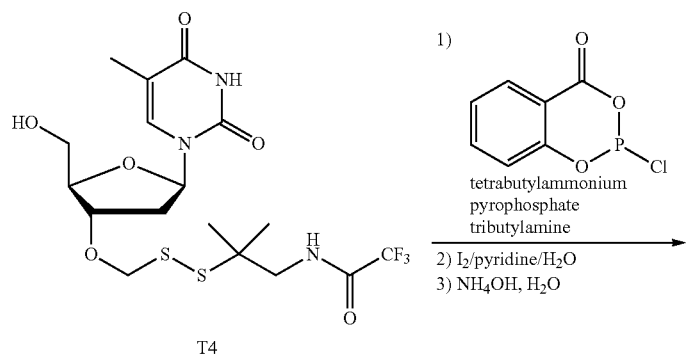
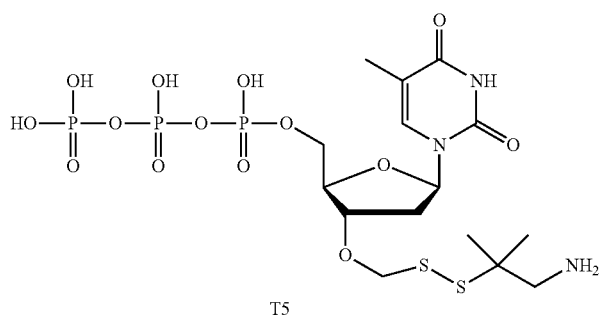
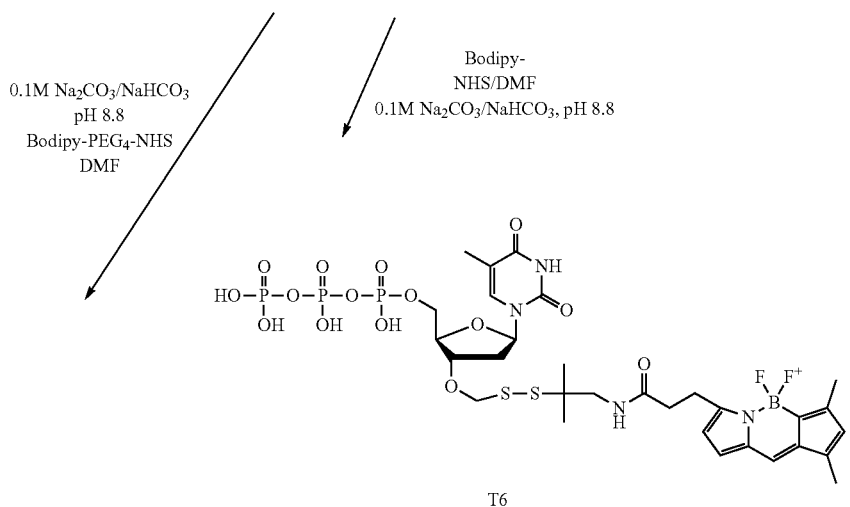
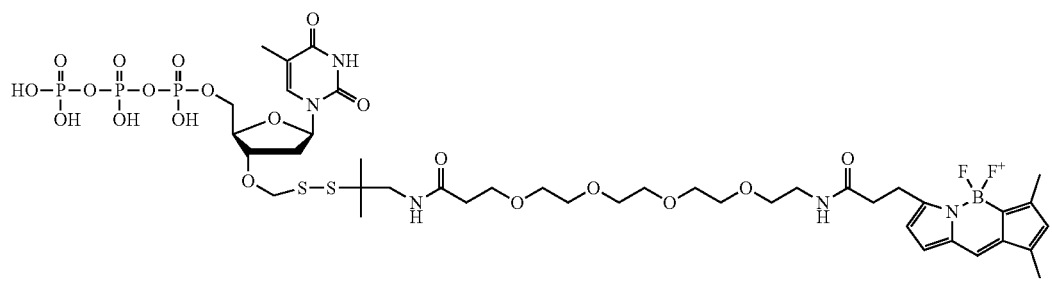

Scheme 2. The synthesis of 3′-O-Rox-DTM-dATP and 3′-O-Rox-PEG₄-DTM-dATP.
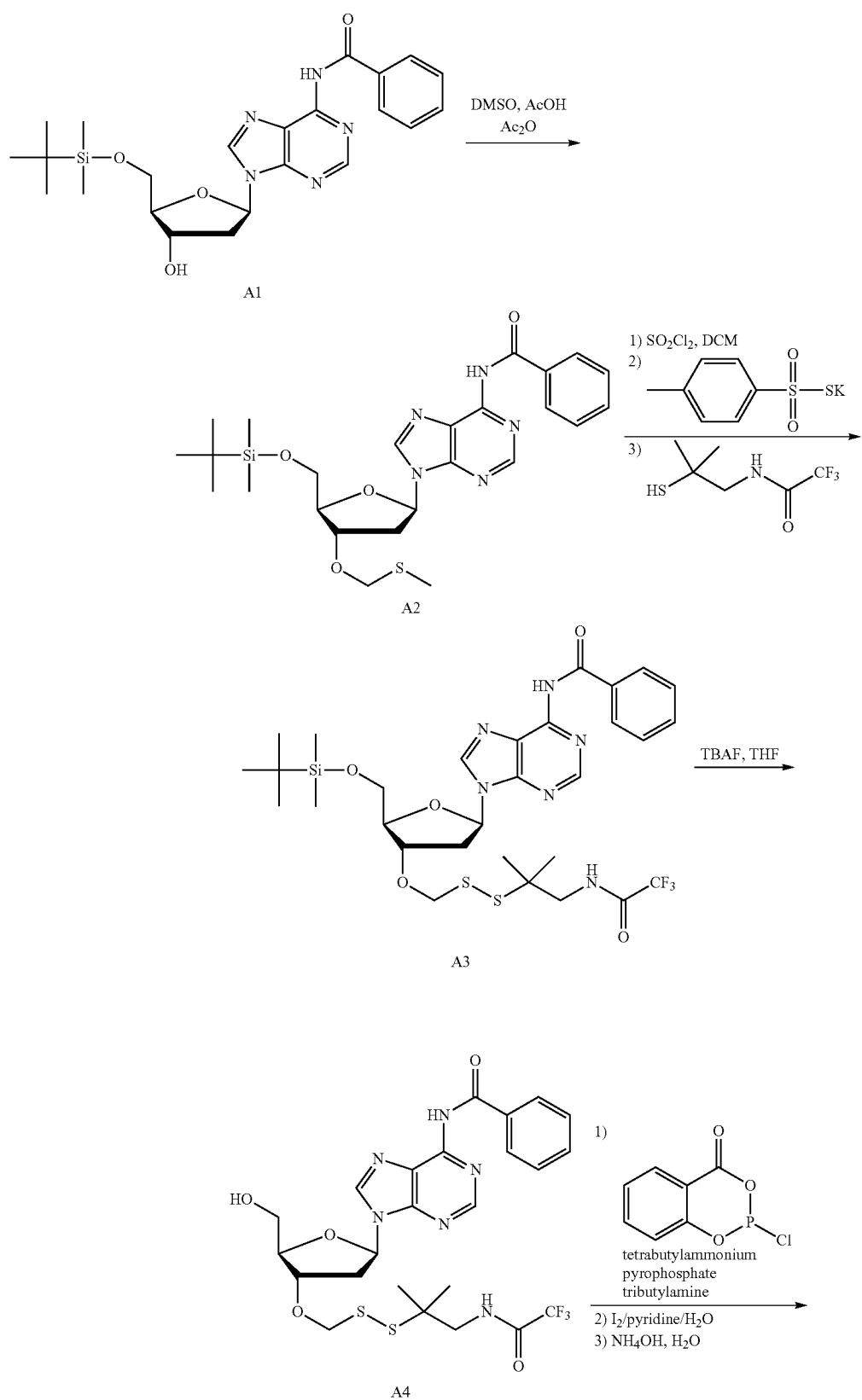

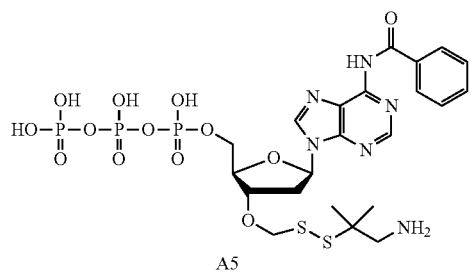
A5
0.1M Na₂CO₃/NaHCO₃  ROX-PEG4-NHS
pH 8.9                DMF
ROX-NHS/DMF
0.1M Na₂CO₃/NaHCO₃, pH 8.9
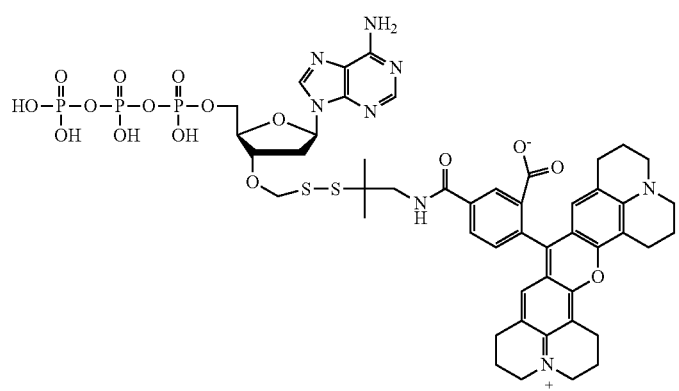
A6
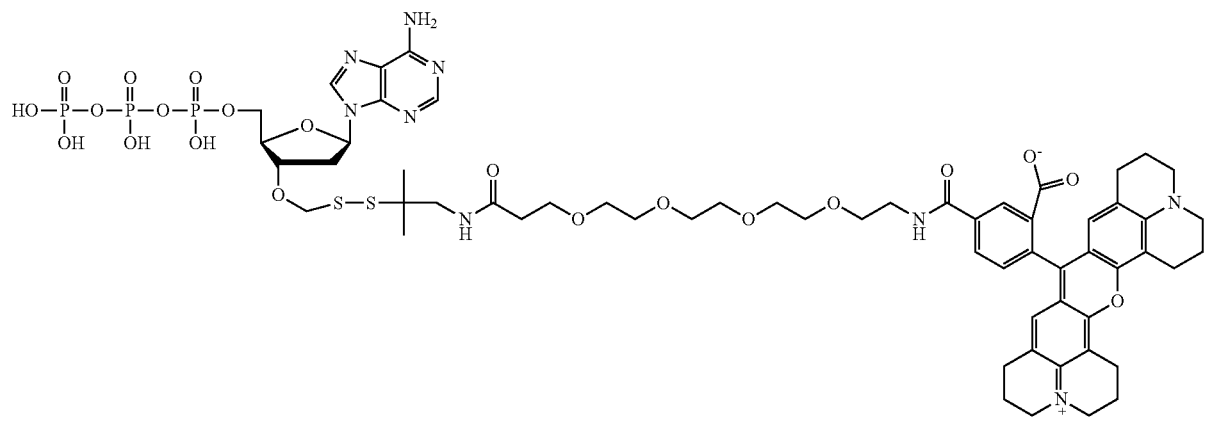
A7

Scheme 3. The synthesis of 3′-O-Alexa488-DTM-dCTP and 3′-O-PEG₄-Alexa488-DTM-dCTP.
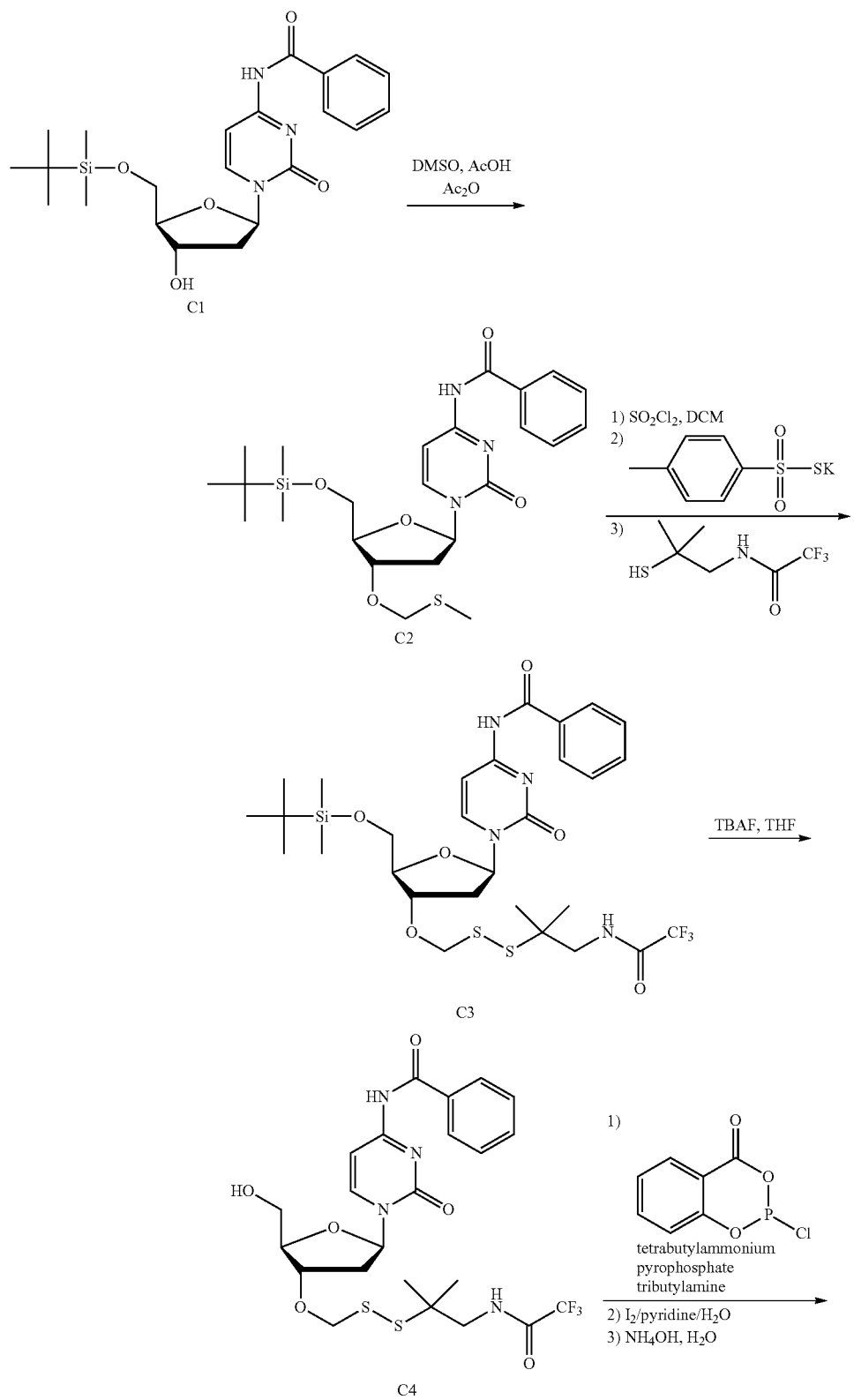

-continued
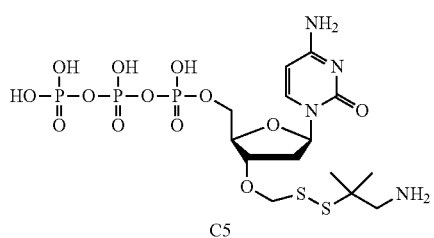
C5
0.1M Na₂CO₃/NaHCO₃   |   0.1M Na₂CO₃/
pH 8.9                              NaHCO₃,
Alexa488-PEG₄-NHS       pH 8.9
Alexa488-NHS
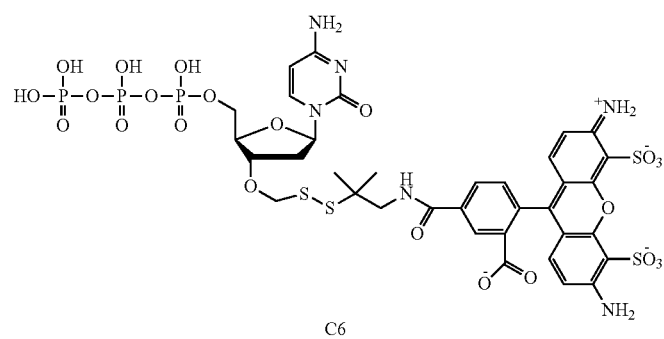
C6
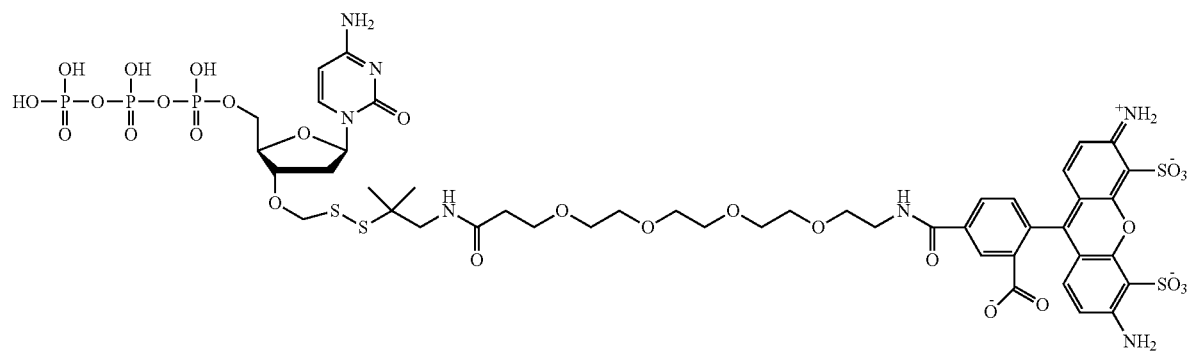
C7
Scheme 4. The synthesis of 3′-O-Cy5-DTM-dGTP and 3′-O-Cy5-PEG₄-DTM-dGTP.
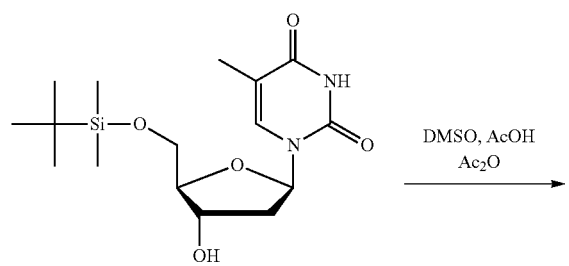
DMSO, AcOH
Ac₂O -continued
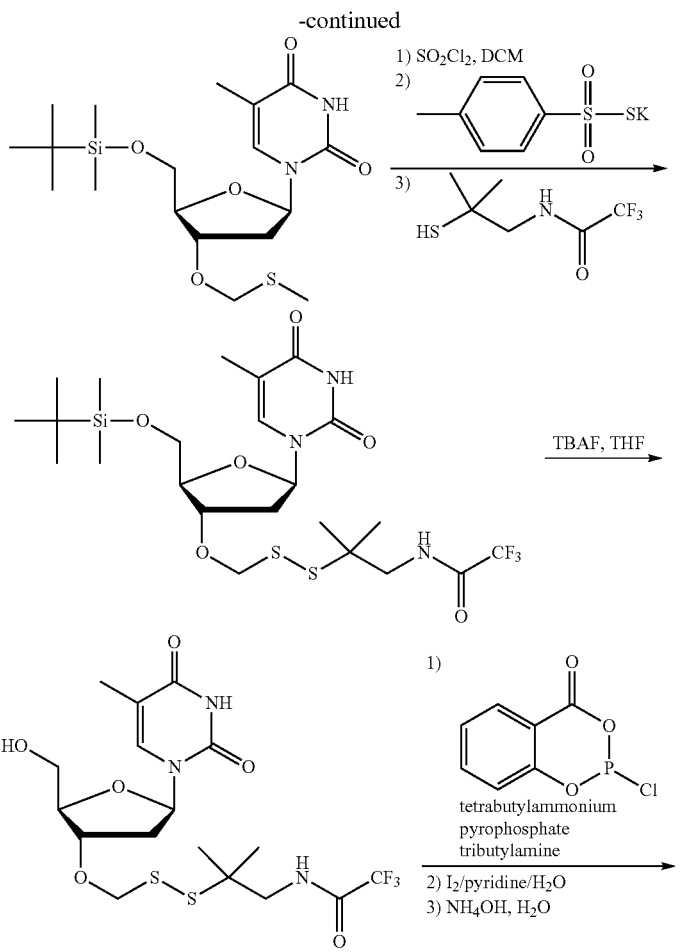
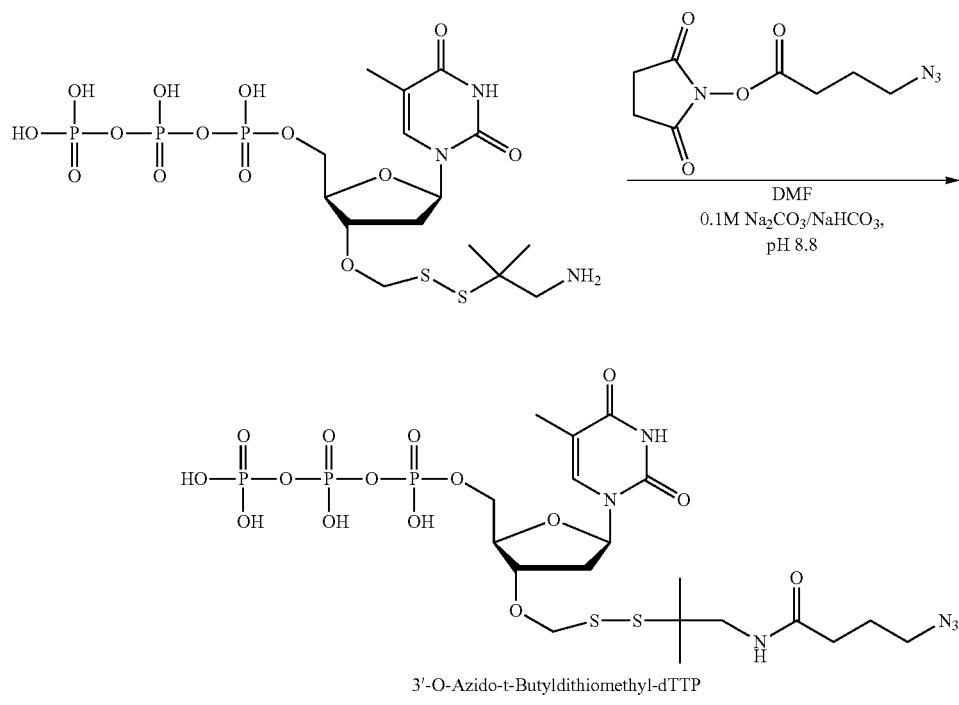
3'-O-Azido-t-Butyldithiomethyl-dTTP Scheme 30. Synthesis of 3'-O-t-Butyldithiomethyl-dTTP (5a).
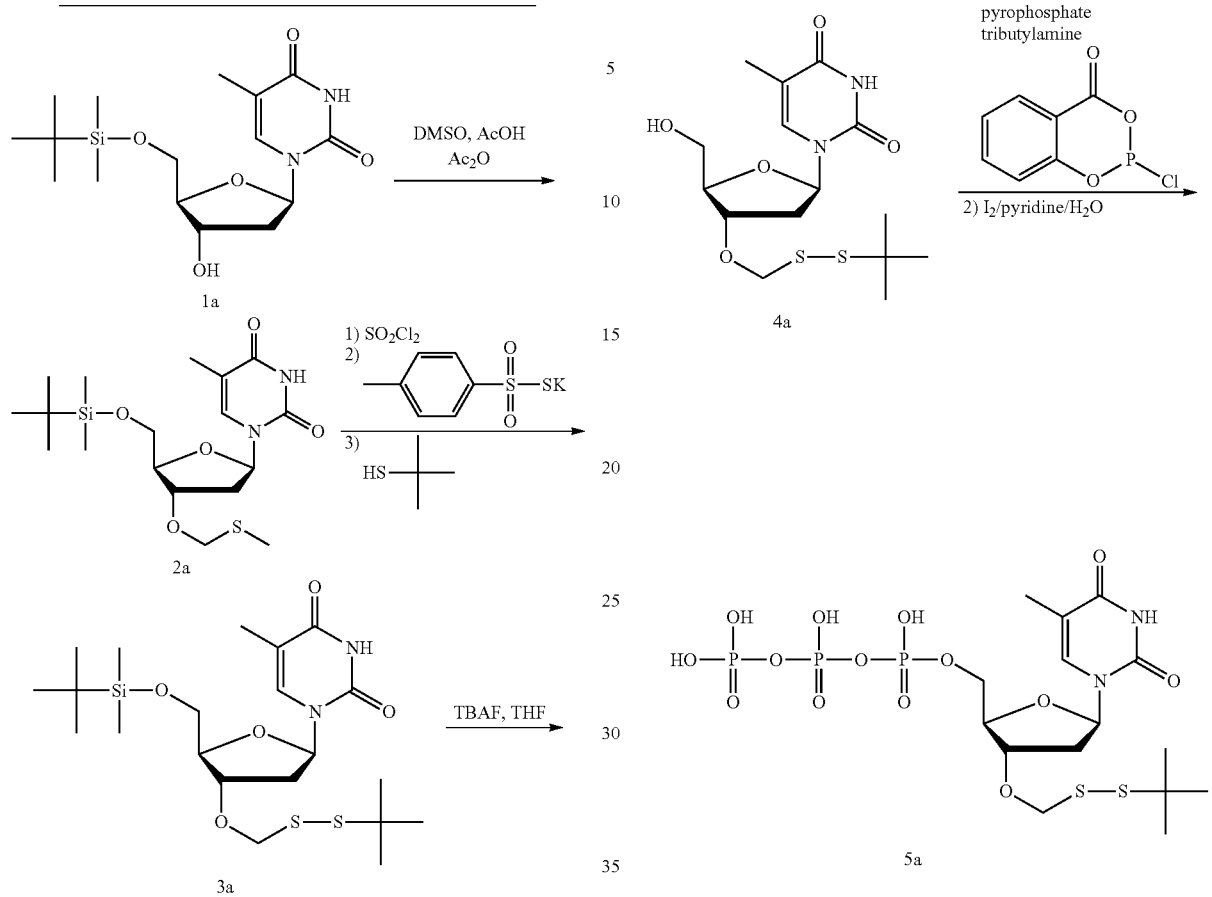
Scheme 31 - Synthesis of 3'-O-t-Butyldithiomethyl-dGTP (G5).
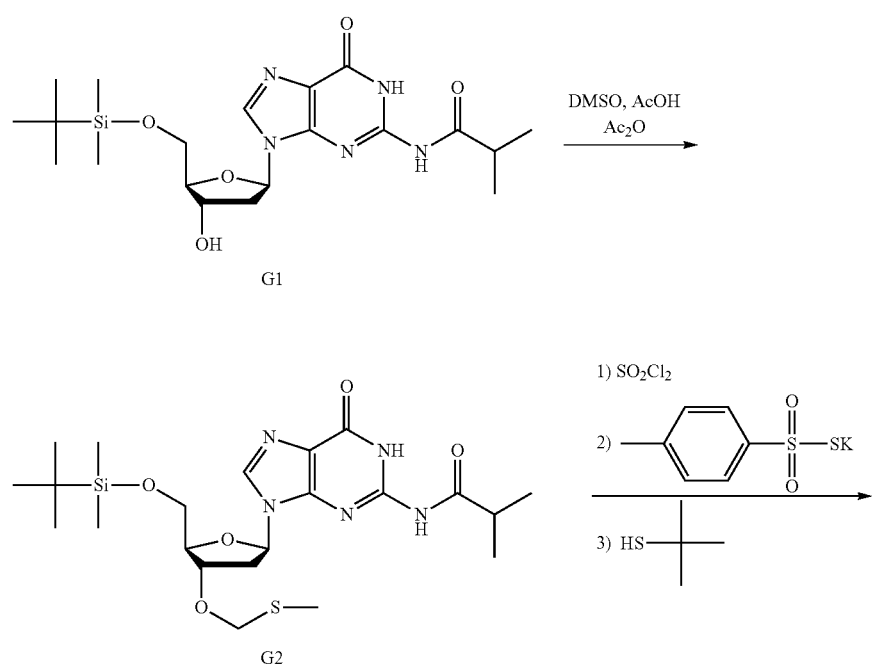

-continued
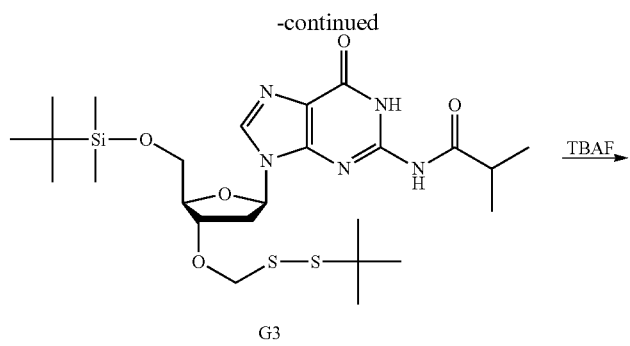
G3
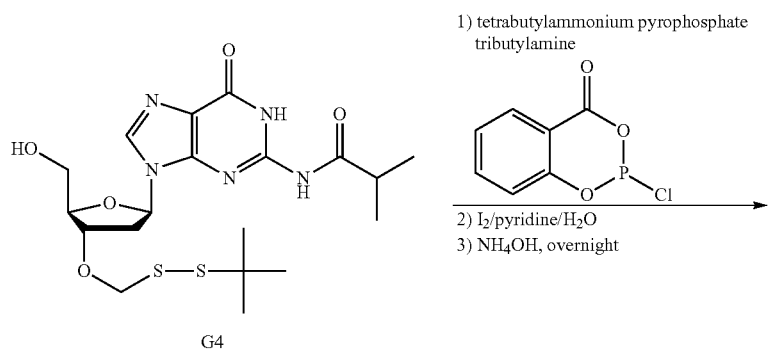
G4
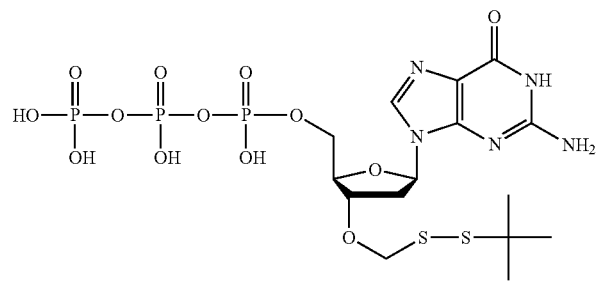
G5
Scheme 32 - The synthesis of 3'-O-t-Butyldithiomethyl-dATP (A5).
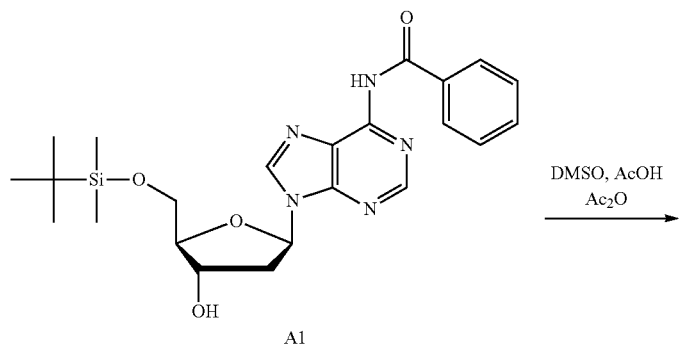
A1

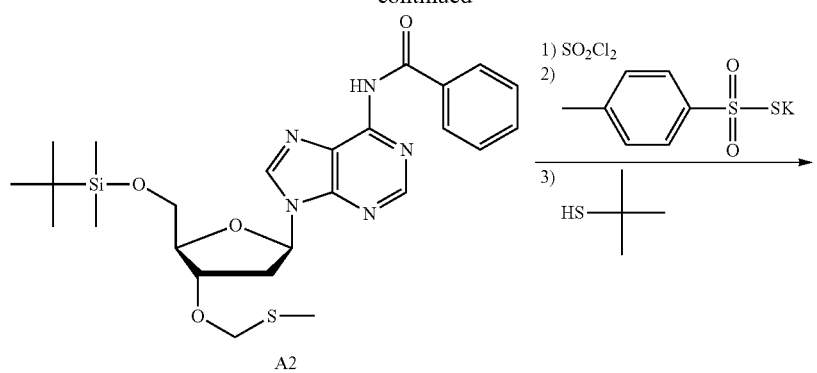
A2
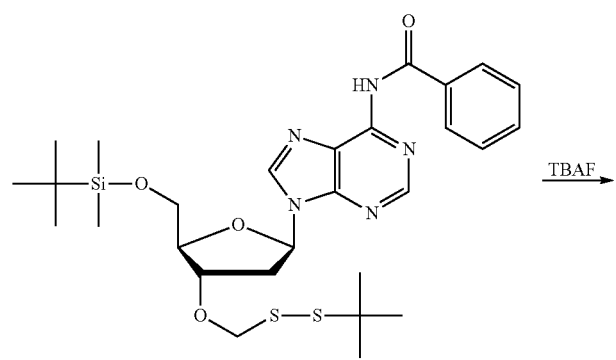
A3
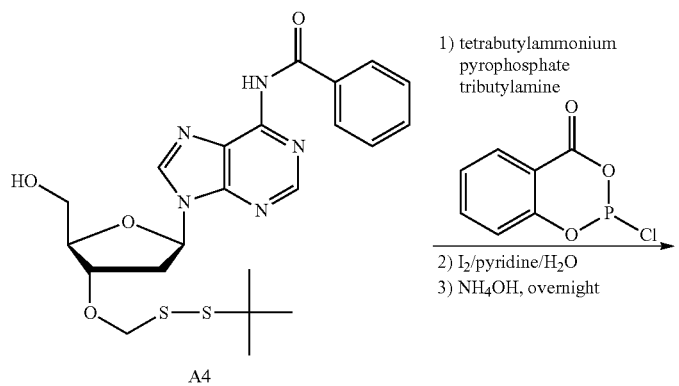
A4
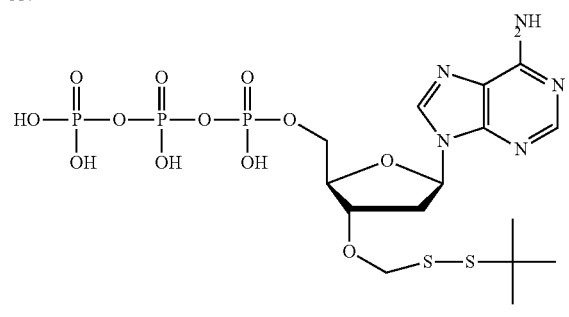
A5

Scheme 33 - Synthesis of 3'-O-t-Butyldithiomethyl-dCTP (C5).
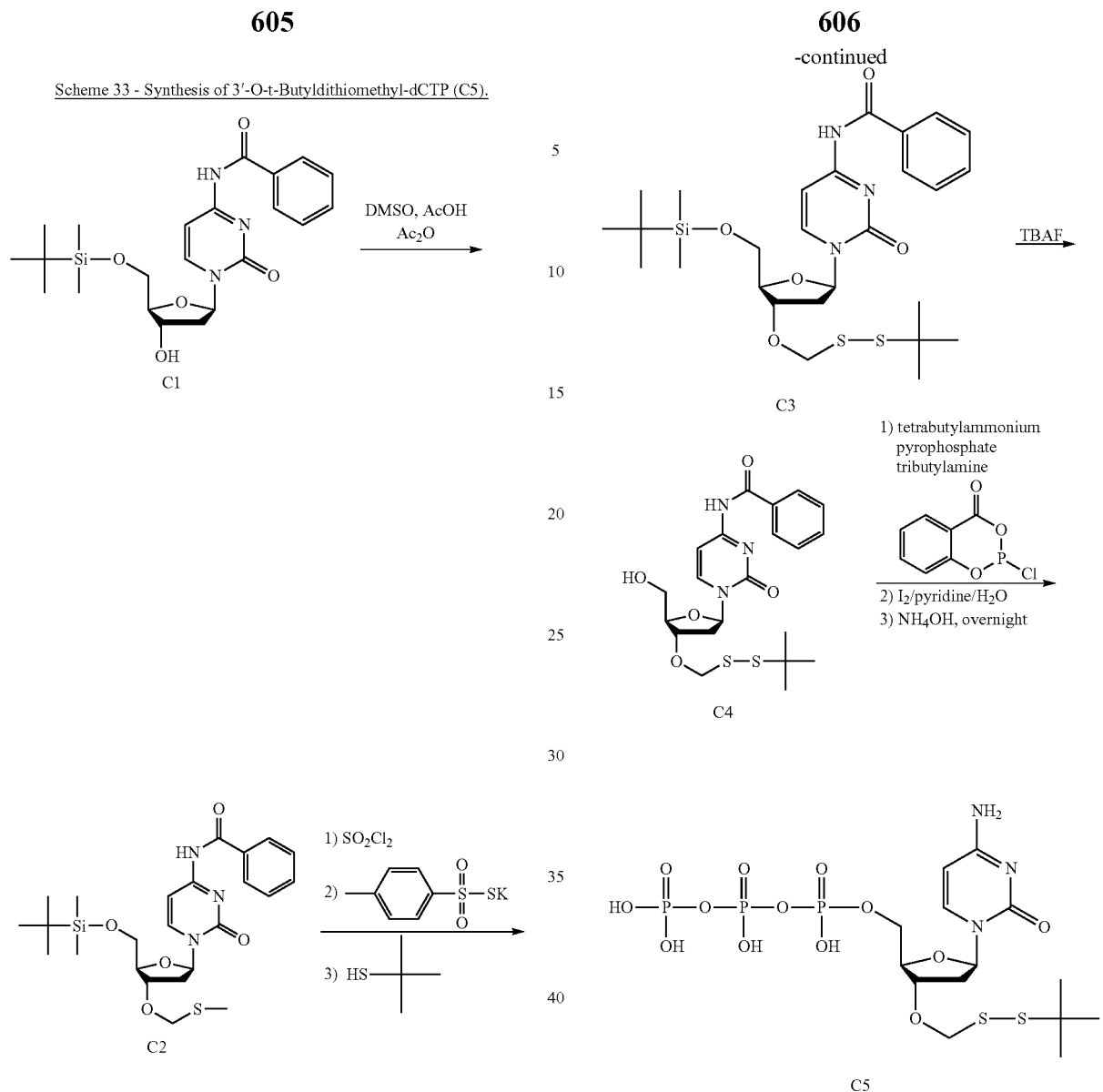
Scheme 34.
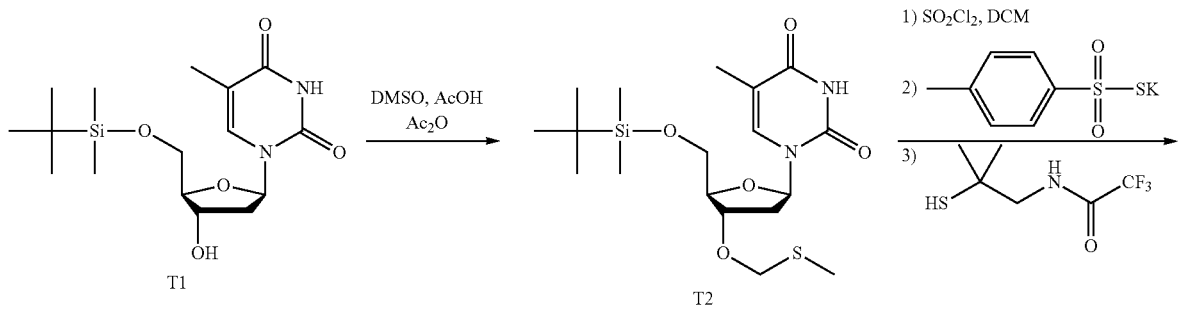

-continued
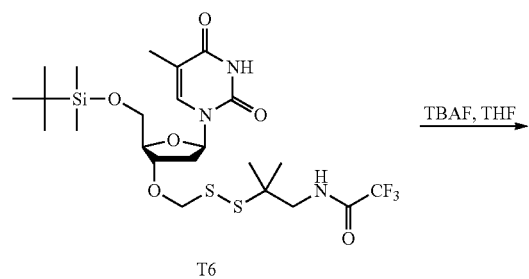
T6
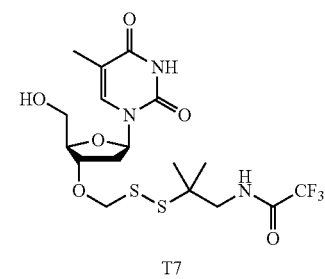
T7
TBAF, THF →
1) 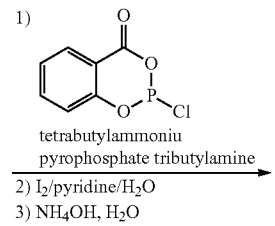
tetrabutylammoniu pyrophosphate tributylamine
2) I₂/pyridine/H₂O
3) NH₄OH, H₂O
→
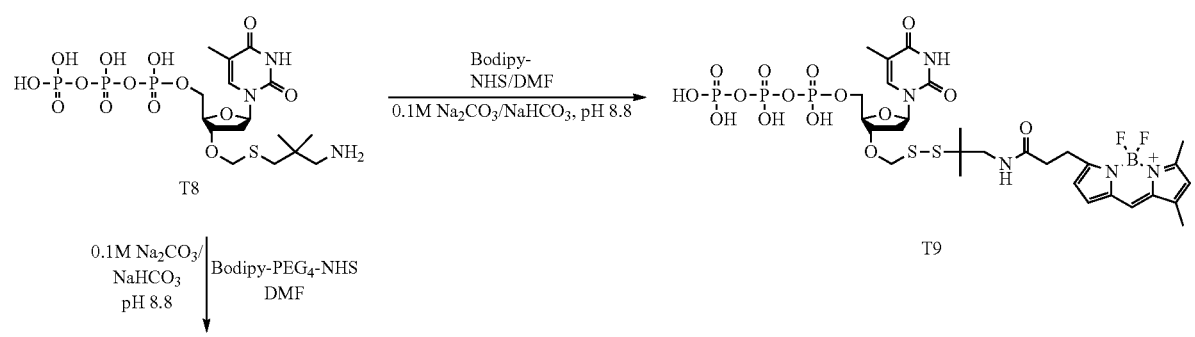
T8 → Bodipy-NHS/DMF, 0.1M Na₂CO₃/NaHCO₃, pH 8.8 → T9
0.1M Na₂CO₃/NaHCO₃ pH 8.8 | Bodipy-PEG₄-NHS DMF ↓
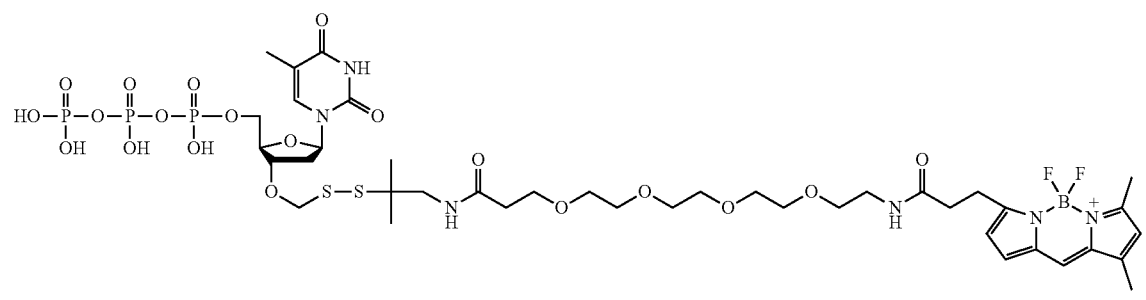
T10
Scheme 35.
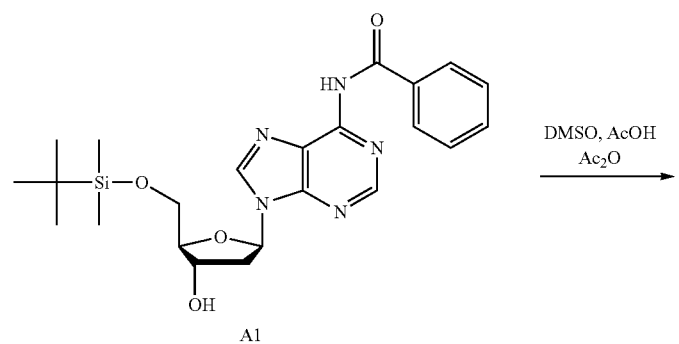
A1
DMSO, AcOH
Ac₂O
→

-continued
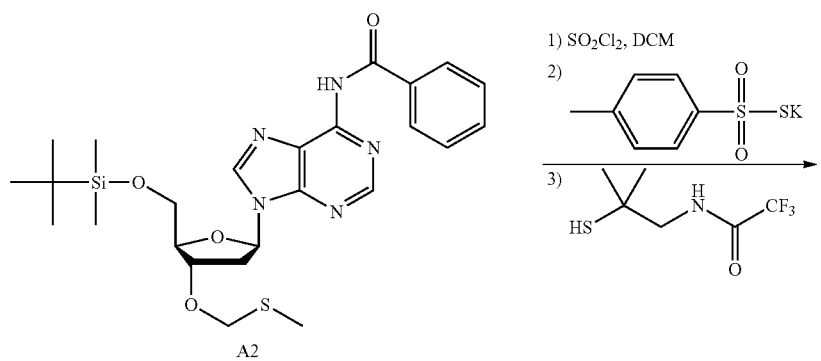
A2
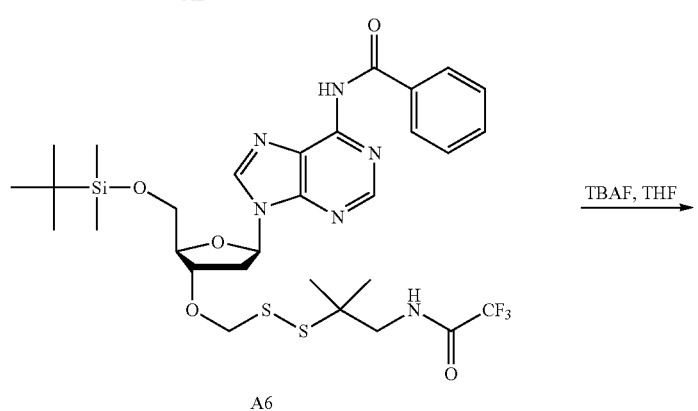
A6
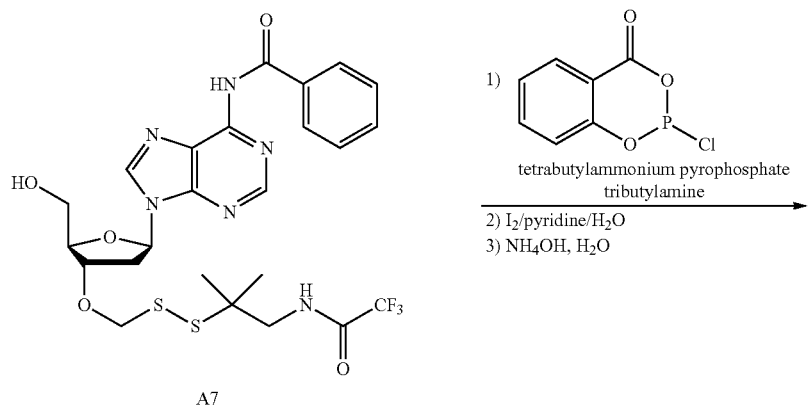
A7
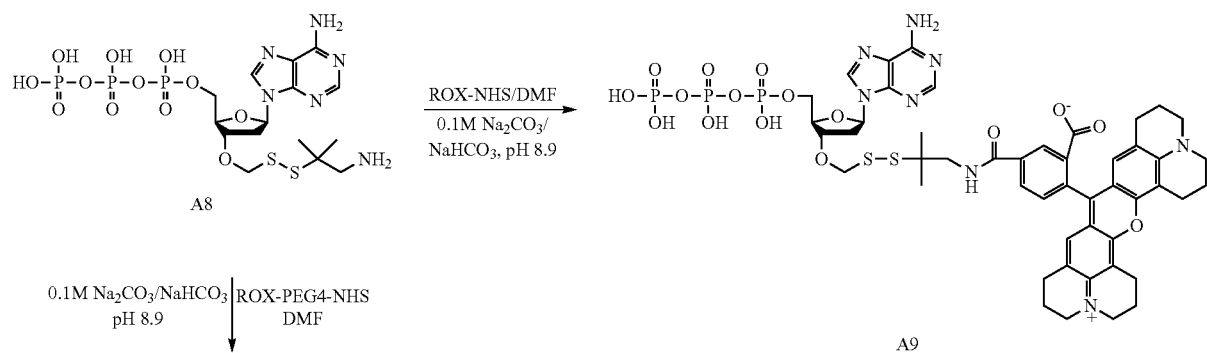
A8
A9

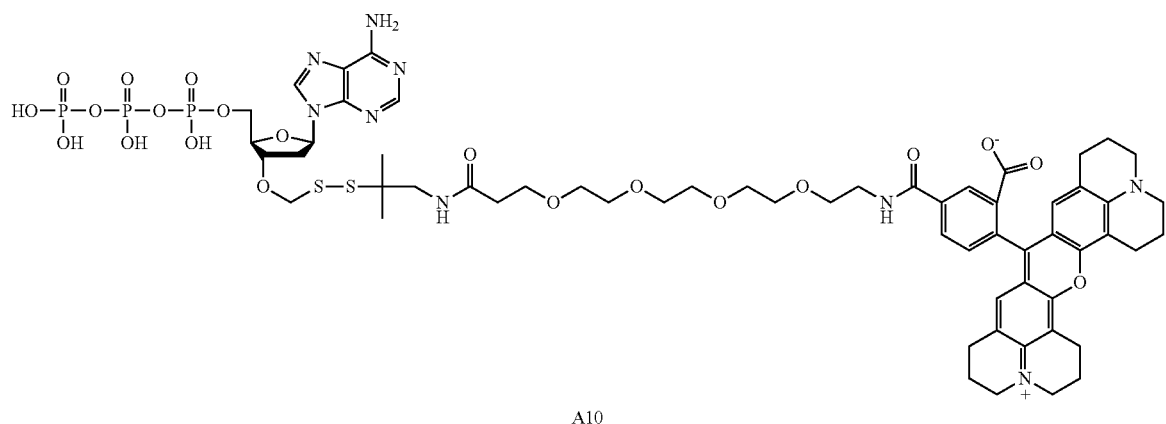
A10
Scheme 36 - Synthesis of 3'-O-TCO-SS(DTM)-dTTP (T11).
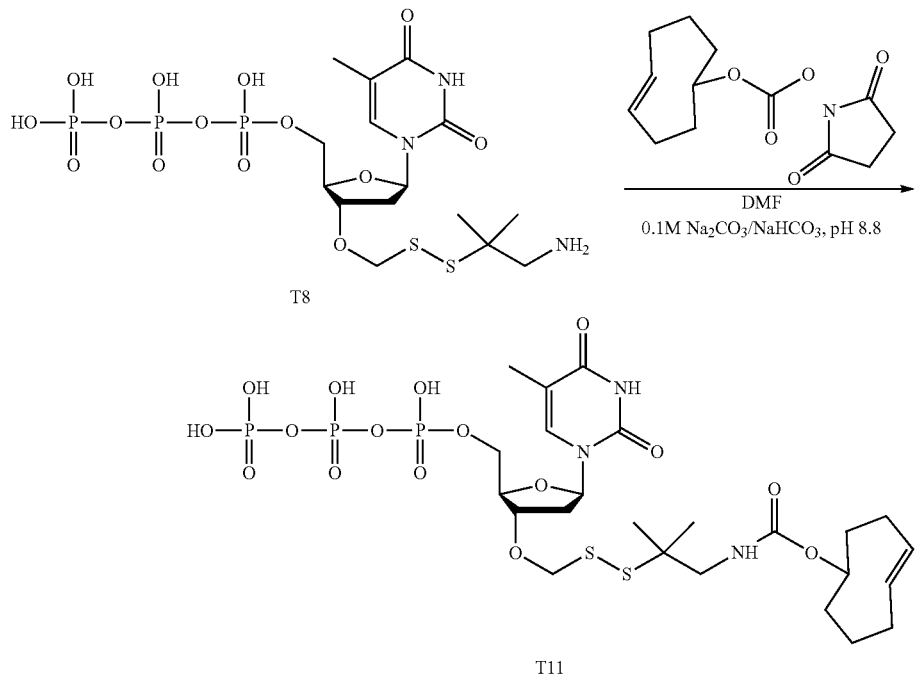
Scheme 37 - Synthesis of 3'-O-Biotin-SS(DTM)-dCTP.
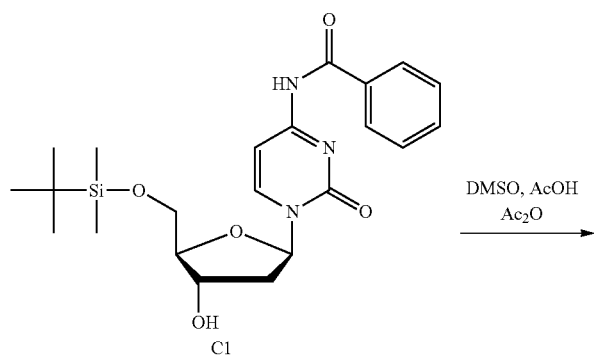

-continued
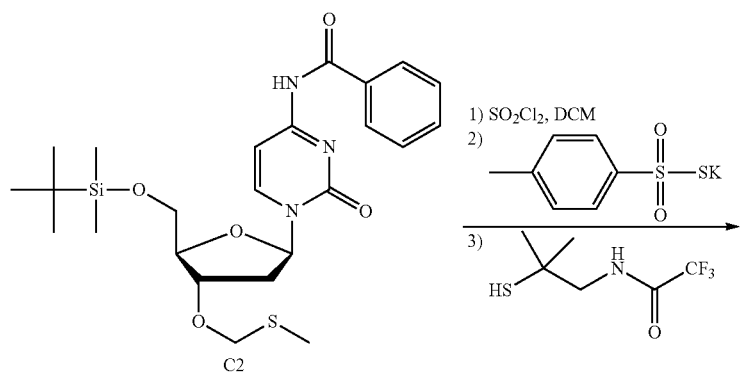
C2
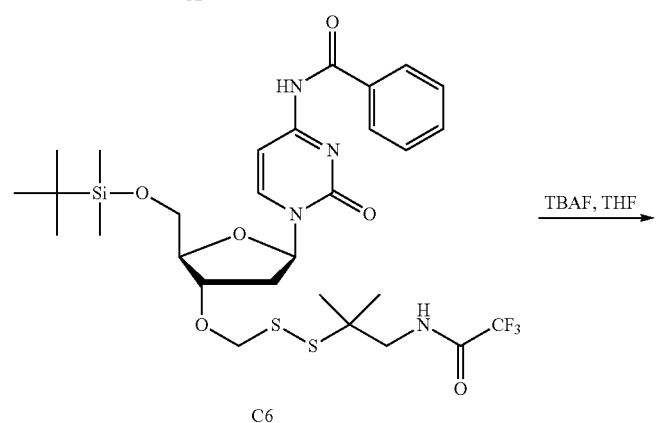
C6
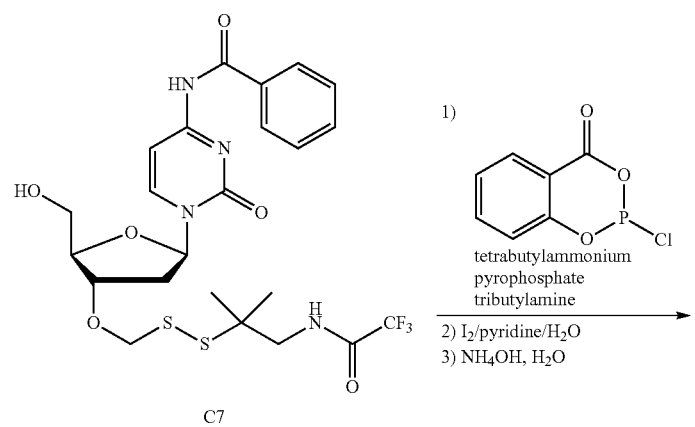
C7
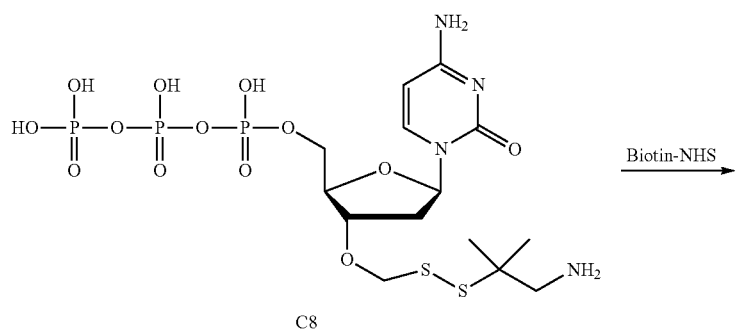
C8

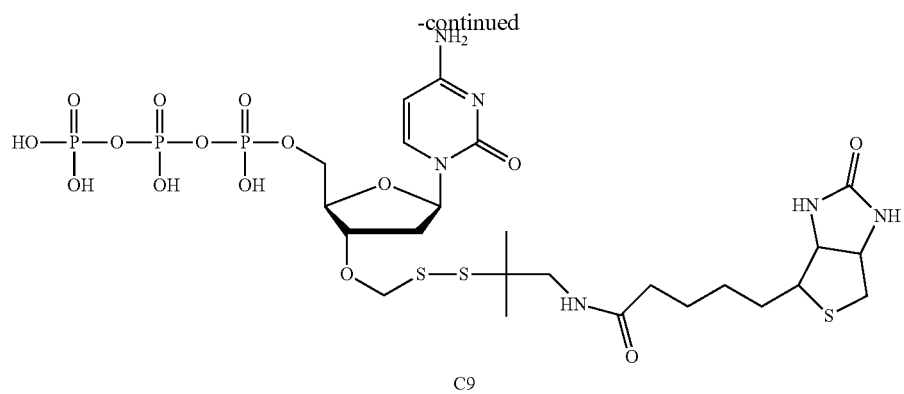
C9
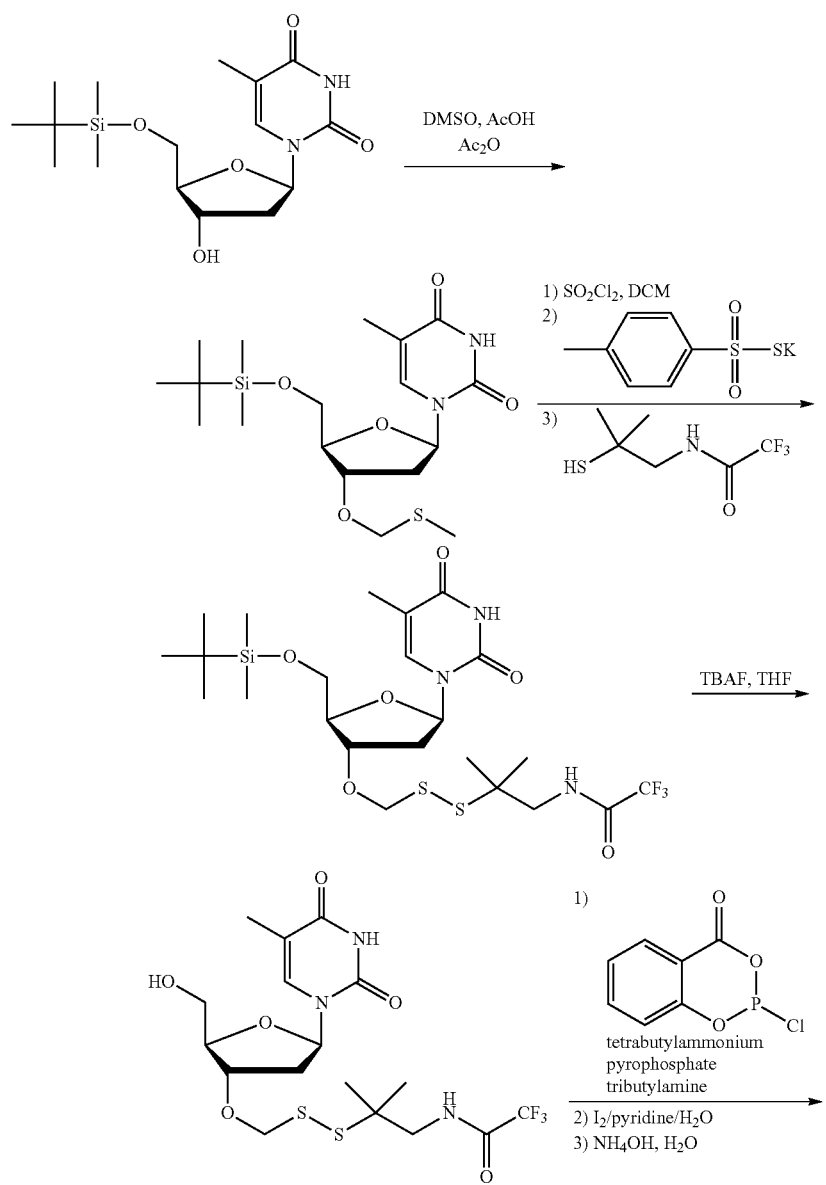
Scheme 38 - Synthesis of 3'-O-Azido-SS(DTM)-dTTP (3'-O-Azido-t-Buyldithiomethyl-dTTP).

-continued
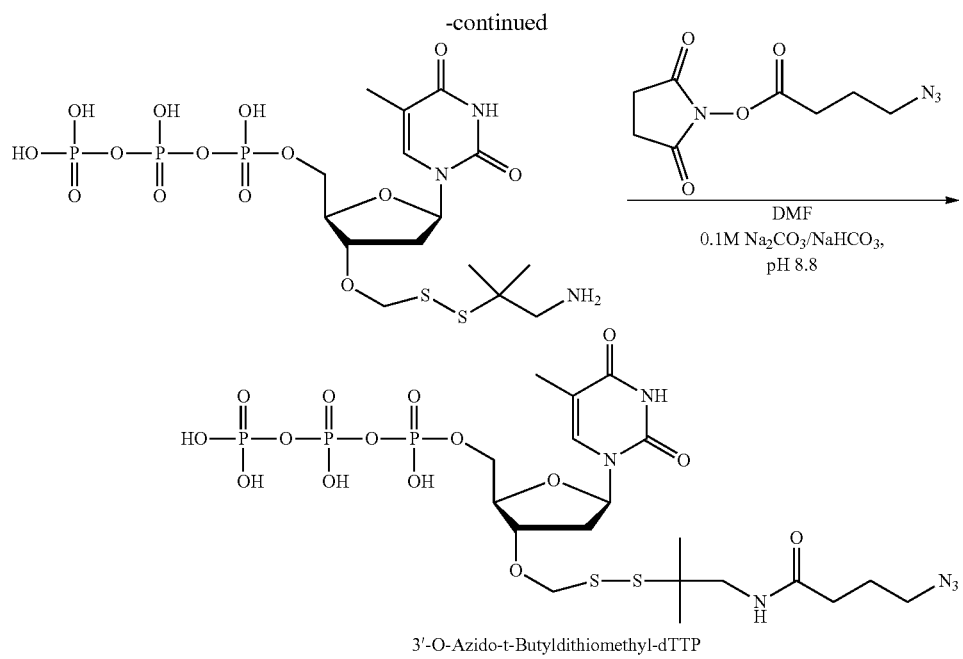
3'-O-Azido-t-Butyldithiomethyl-dTTP
Scheme 39 - Synthesis of 3'-O-Biotin-SS(DTM)-dGTP (3'-O-Biotin-t-Buyldithiomethyl-dGTP).
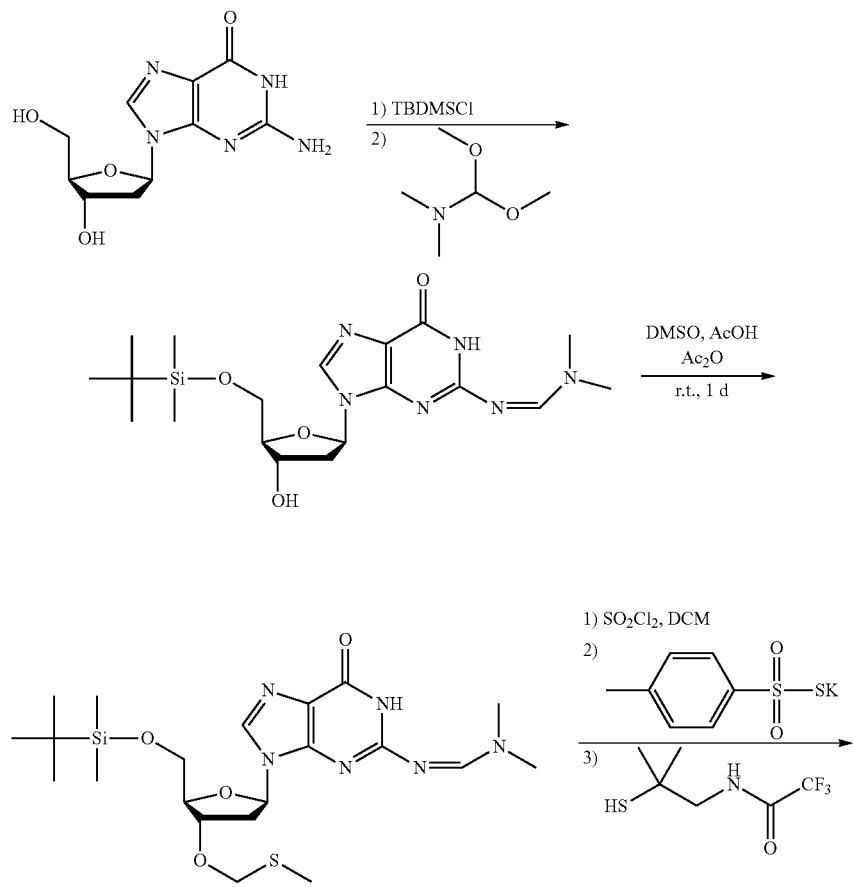

-continued
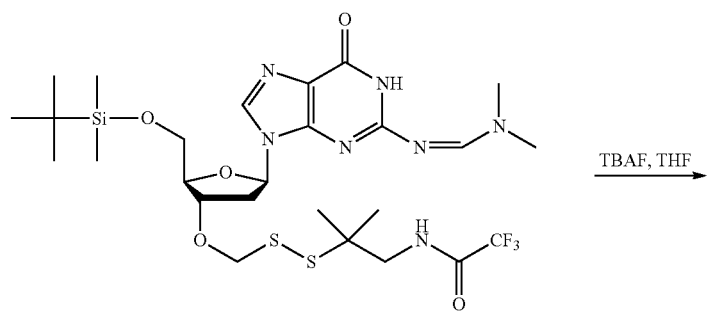
TBAF, THF →
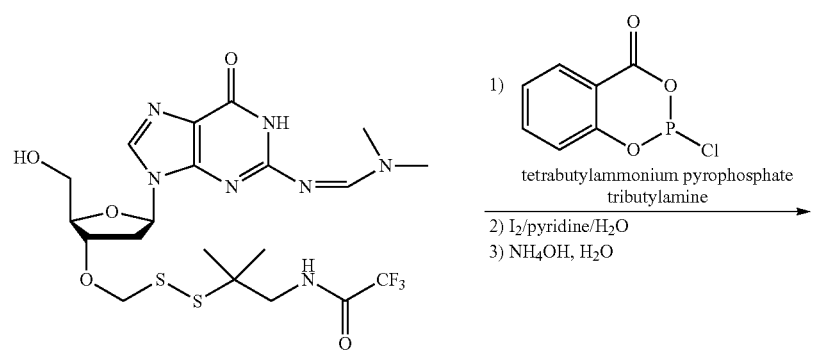
1) <chemical structure: 2-chloro-4H-benzo[d][1,3,2]dioxaphosphinin-4-one>
tetrabutylammonium pyrophosphate
tributylamine
2) I₂/pyridine/H₂O
3) NH₄OH, H₂O
→
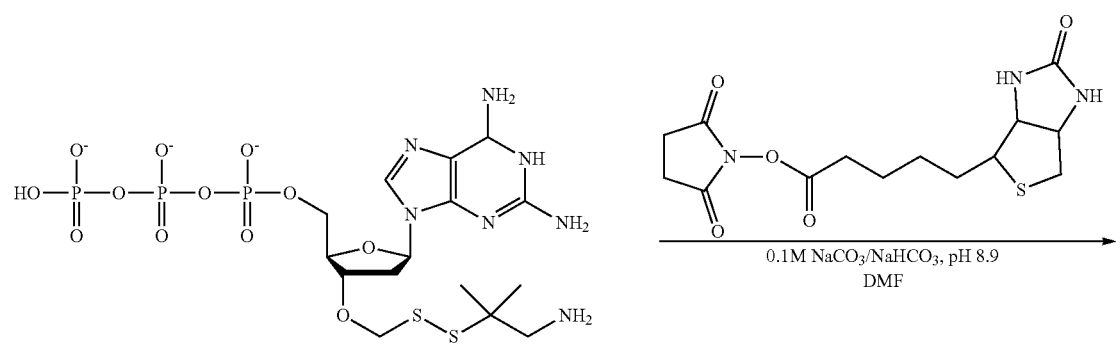
0.1M NaCO₃/NaHCO₃, pH 8.9
DMF
→
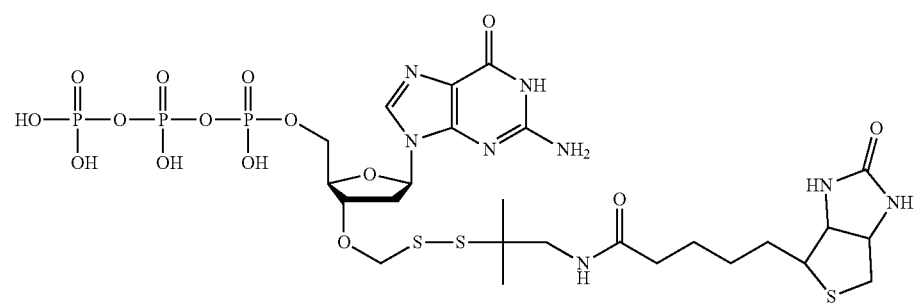
3'-O-Biotin-t-Butyldithiomethyl-dGTP Scheme 40 - Synthesis of 3'-O-PBA-SS(DTM)-dCTP (3'-O-PBA-t-Buyldithiomethyl-dCTP).
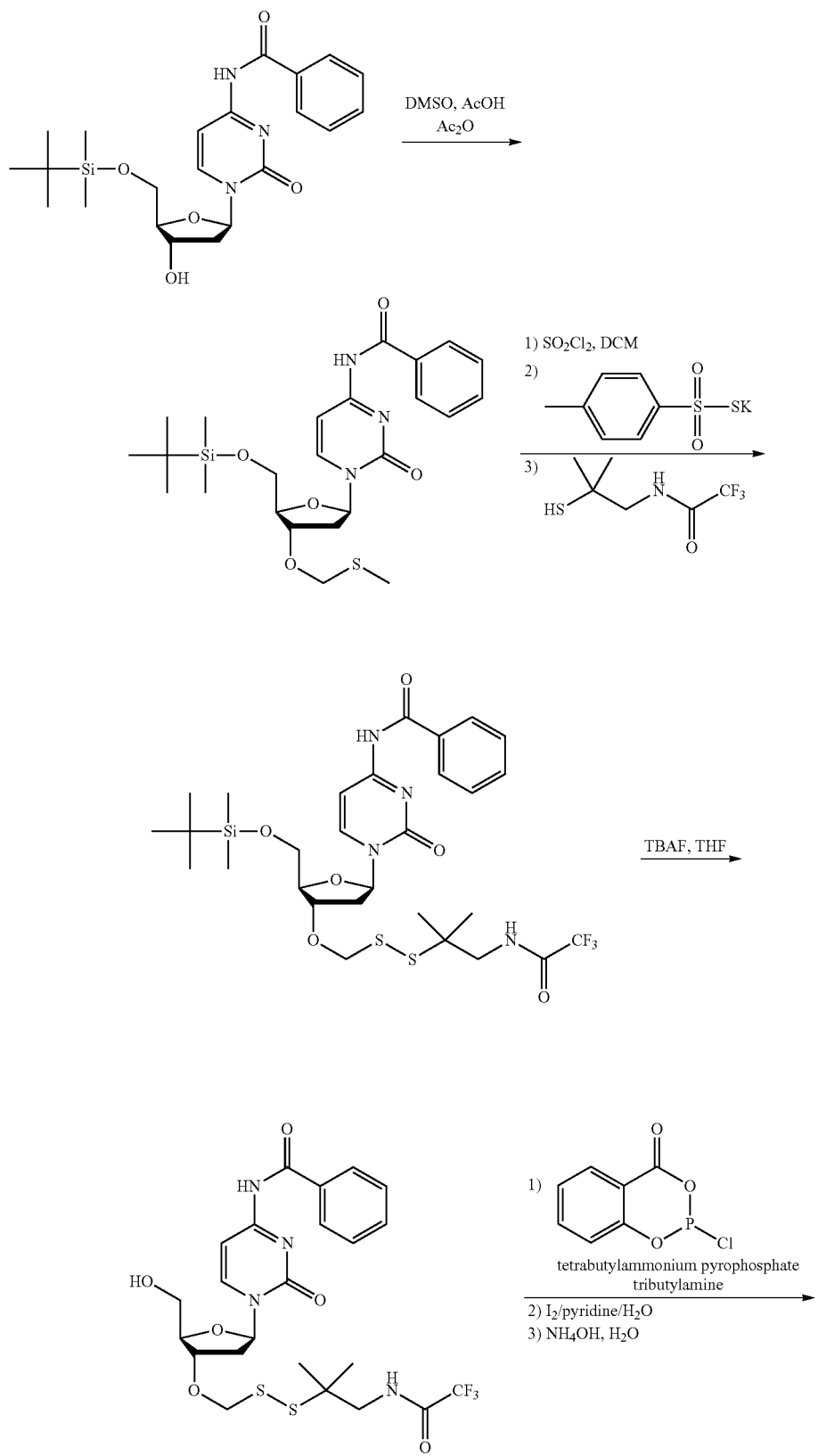

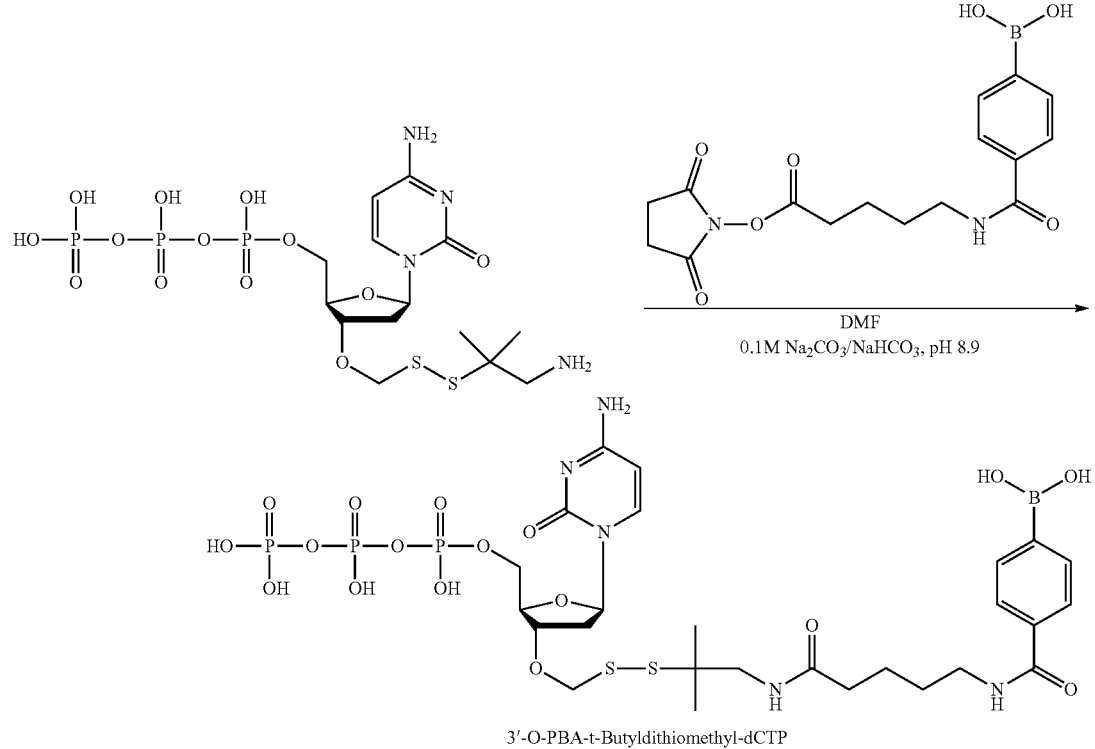
3'-O-PBA-t-Butyldithiomethyl-dCTP
Scheme 41 - Synthesis of 3'-O-TCO-SS(DTM)-dATP (3'-O-TCO-t-Buyldithiomethyl-dATP).
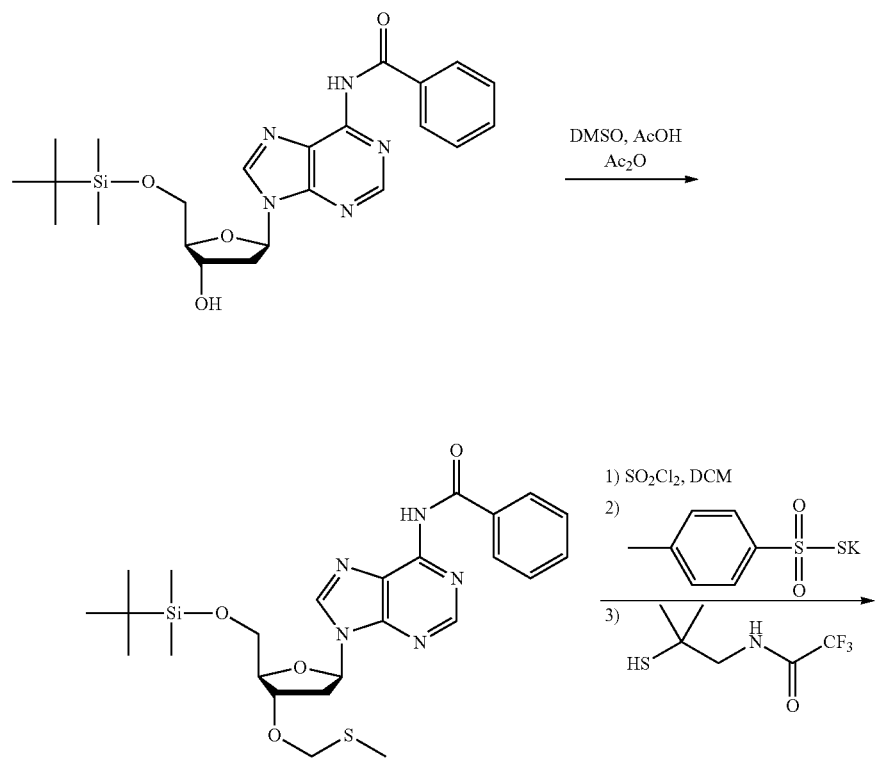

-continued
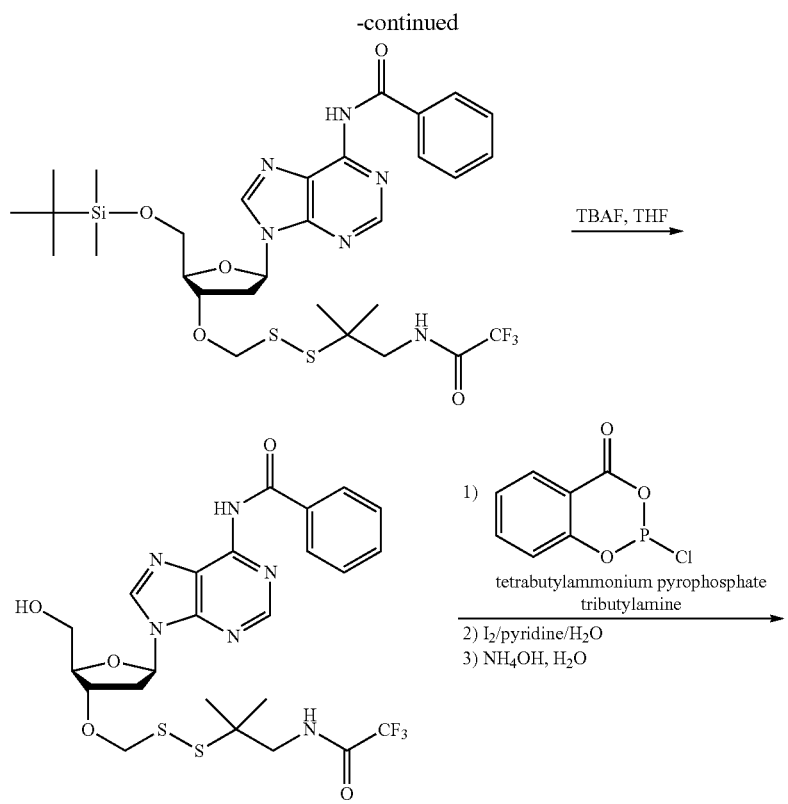
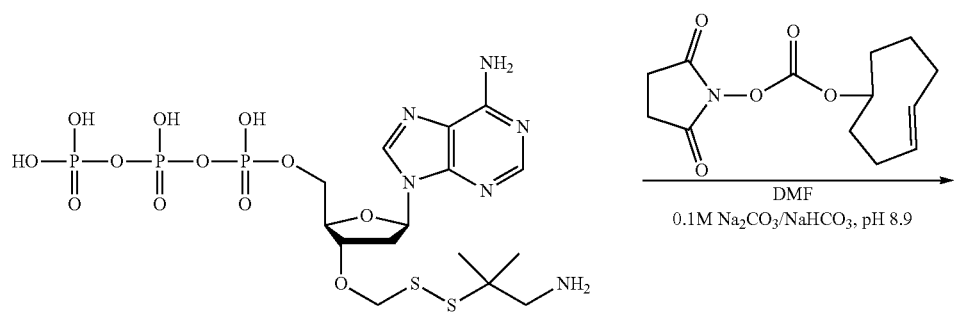
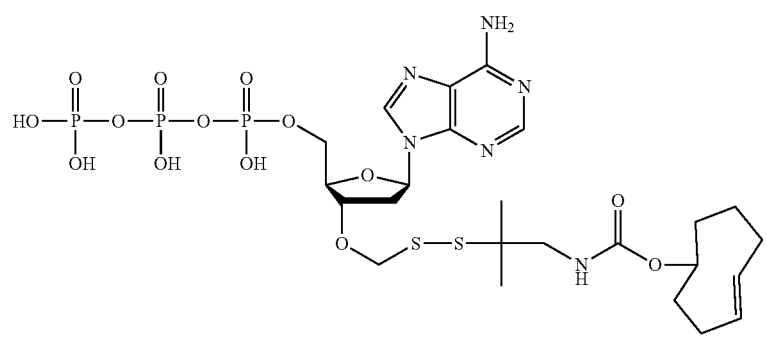
3'-O-TCO-t-Butyldithiomethyl-dATP Scheme 42 - Synthesis of Labeled Binding Molecules Conjugated with Fluorescent Dyes. Shows in the synthesis of Rox Labeled Tetrazine, Alexa488 Labeled SHA and R6G Labeled Dibenzocyclooctyen (DBCO) using commerciallly available starting materials.
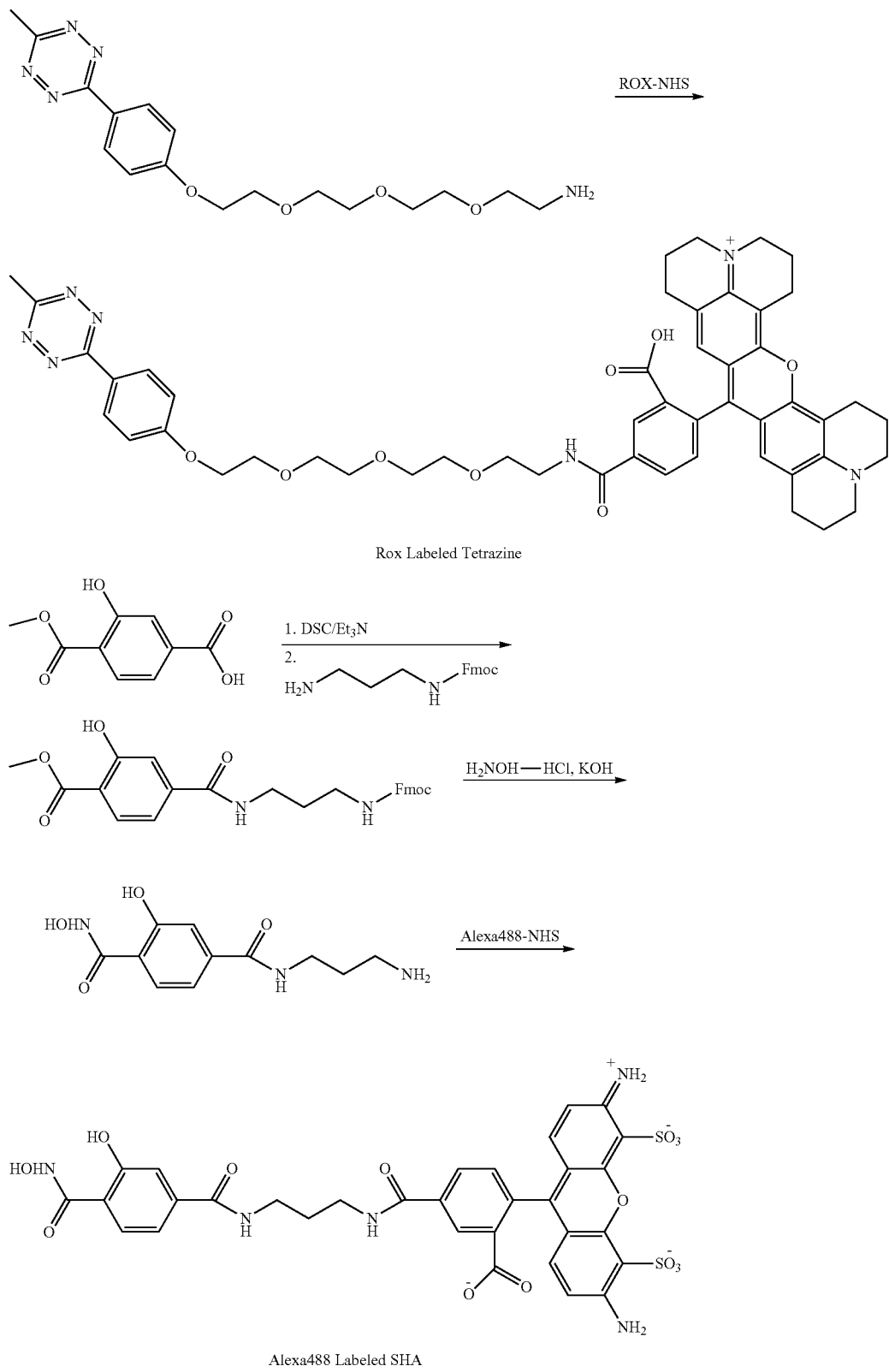

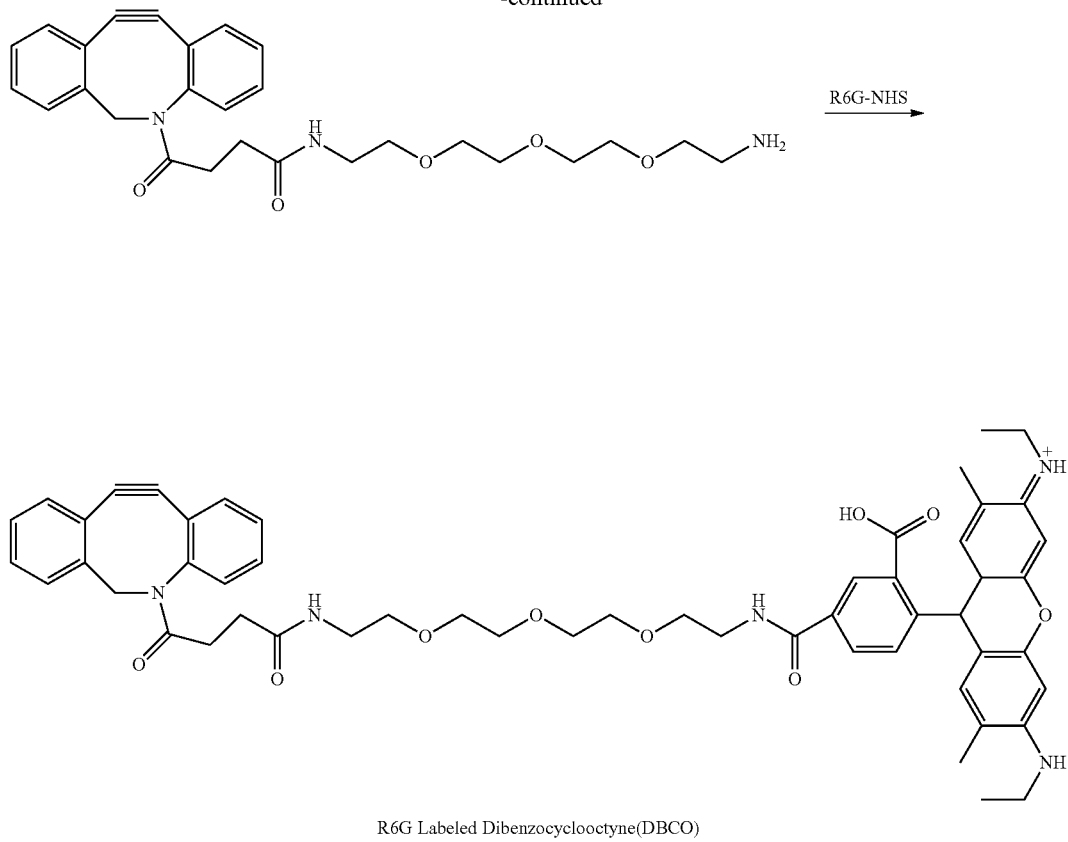

R6G Labeled Dibenzocyclooctyne(DBCO)

Figure 8:
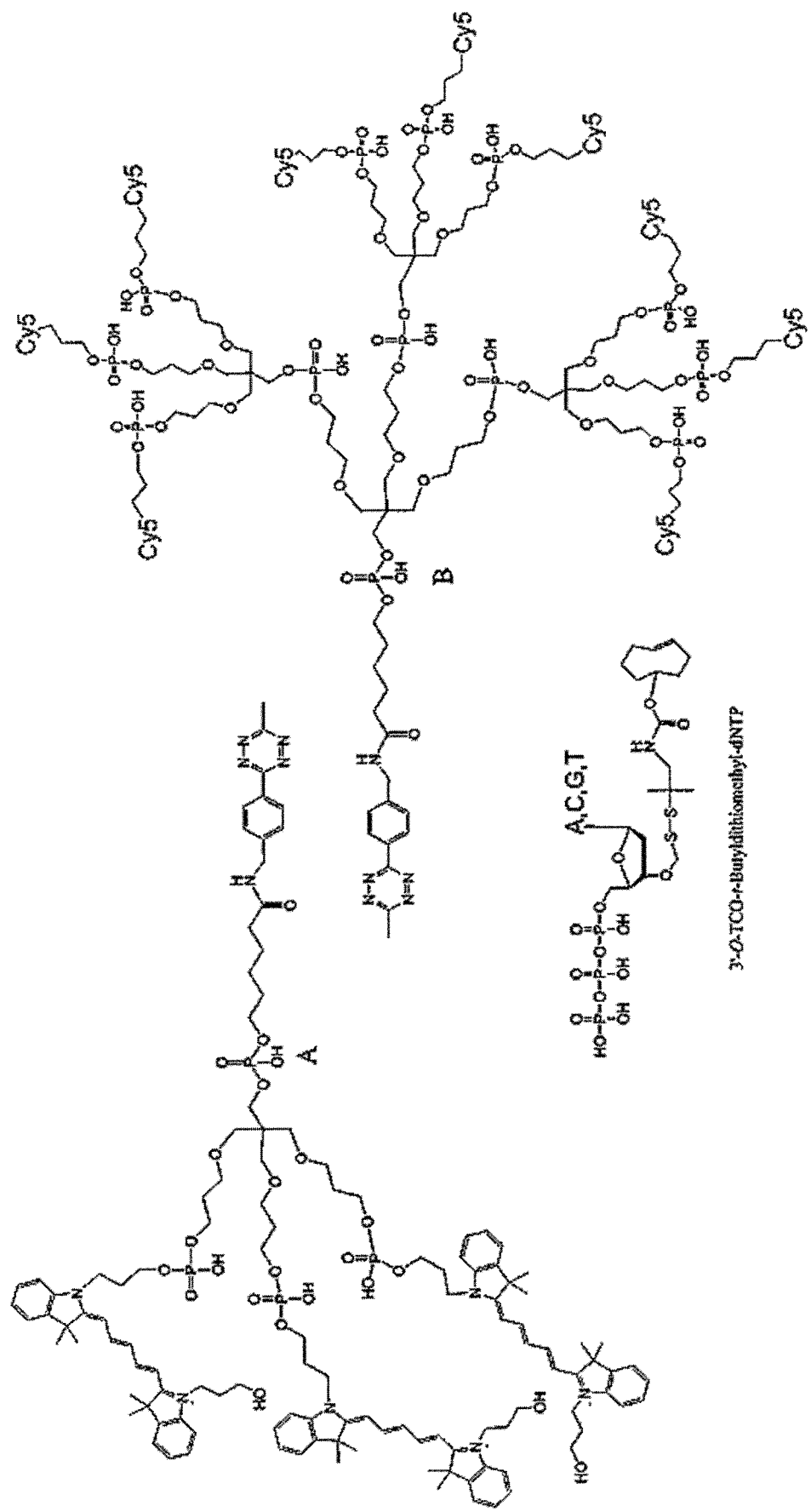
FIG. 8. Structures of Fluorescent (Cy5) Dendrimer Conjugated Tetrazine (A and B) and 3'-O-TCO-SS(DTM)-dNTPs. Incorporation of each of the four 3'-O-TCO-SS(DTM)-dNTPs into the growing DNA strand in the polymerase reaction terminates the DNA synthesis, leading to the DNA products that have a TCO group as a 3' end. Coupling of the DNA products that have a TCO group as a 3' end with either Molecule A or Molecule B (shown above) that has the Tetrazine moiety through the TCO-Tetrazine ligation allows the DNA product to be labeled with multiple fluorescent dyes, thereby facilitating signal amplification for detection to perform either SBS at the single-molecule level or at an ensemble level (following a schema similar to the one shown in FIGS. 3A-3B).

Scheme 43 - Synthesis of Fluorescent (Cy5) Dendrimer Conjugated Tetrazine (A in FIG. 8) from commercially available starting materials. Trebler phosphoramidiate and Cy5 phosphoramidite are from GlenResearch. First, use trebler phosphoramidite to couple with Tetrazine to produce Tetrazine-Trebler. After DMT deprotection, the coupling of Cy5 phosphoramidite with Tetrazine-Trebler will afford Cy5 labeled dendrimer A. For the synthesis of Cy5 labeled dendrimer B shown in FIG. 8, coupling 2nd trebler phosphoramidite to the Tetrazine-Trebler, followed by DMT deprotection and coupling with Cy5 phosphoramidite will yield the desired product.

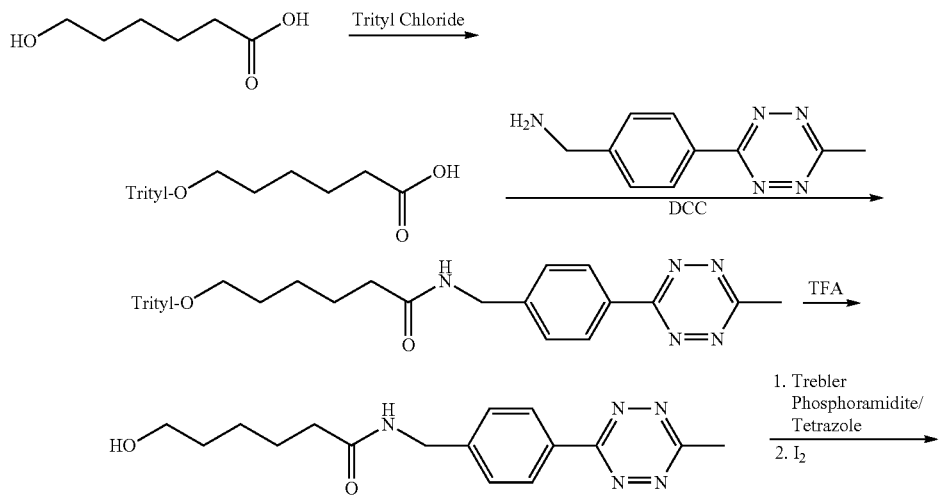

Figure 9:
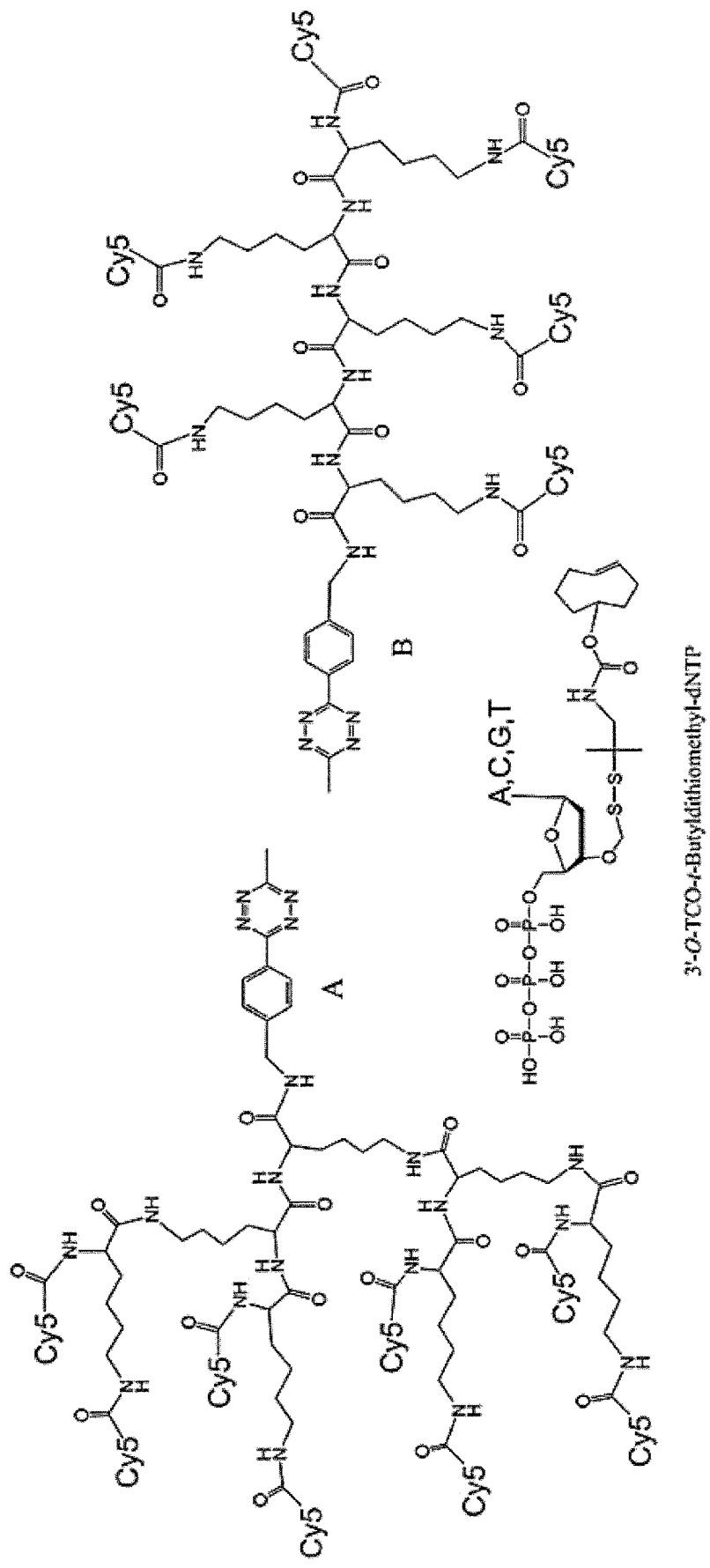
FIG. 9. Example of a Peptide-Based Fluorescent (Cy5) Dendrimer Conjugated Tetrazine (Molecule A) and Polymer Conjugated Tetrazine (Molecule B). Incorporation of each of the four 3'-O-TCO-SS(DTM)-dNTPs into the growing DNA strand in the polymerase reaction terminates the DNA synthesis, leading to the DNA products that have a TCO group as a 3' end. Coupling of the DNA products that have a TCO group as a 3' end with either Molecule A or Molecule B (shown above) that has the Tetrazine moiety through the TCO-Tetrazine ligation allows the DNA product to be labeled with multiple fluorescent dyes, thereby facilitating signal amplification for detection to perform either SBS at the single-molecule level or at an ensemble level (following a schema similar to the one shown in FIGS. 3A-3B).

631 632
-continued
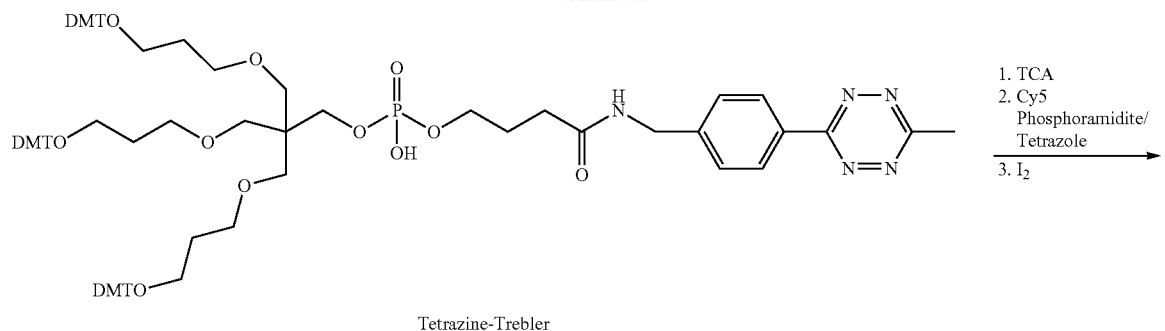
Tetrazine-Trebler
1. TCA
2. Cy5 Phosphoramidite/ Tetrazole
3. I₂
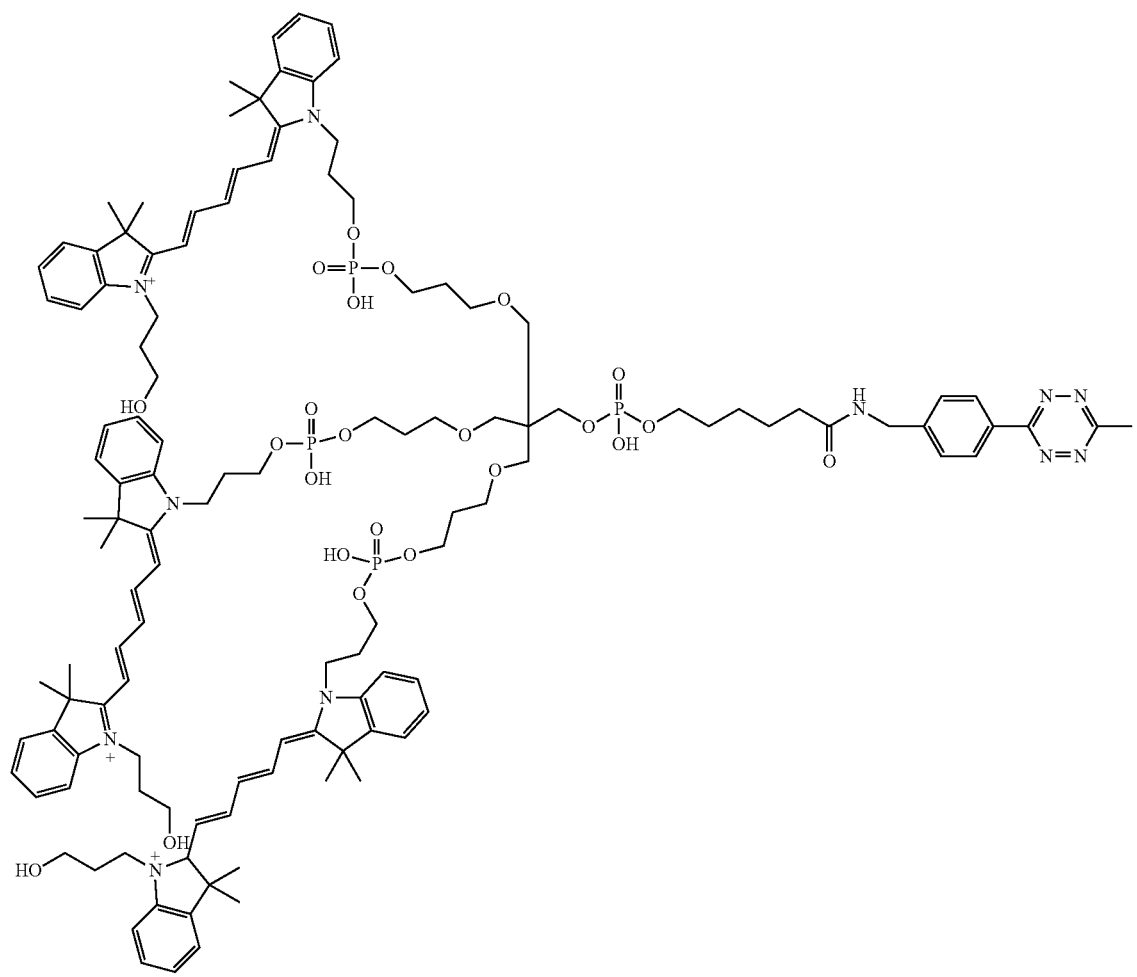
A Scheme 44 - Synthesis of Peptide-Based Fluorescent (Cy5) Dendrimer Conjugated with Tetrazine (molecule A in FIG. 9).
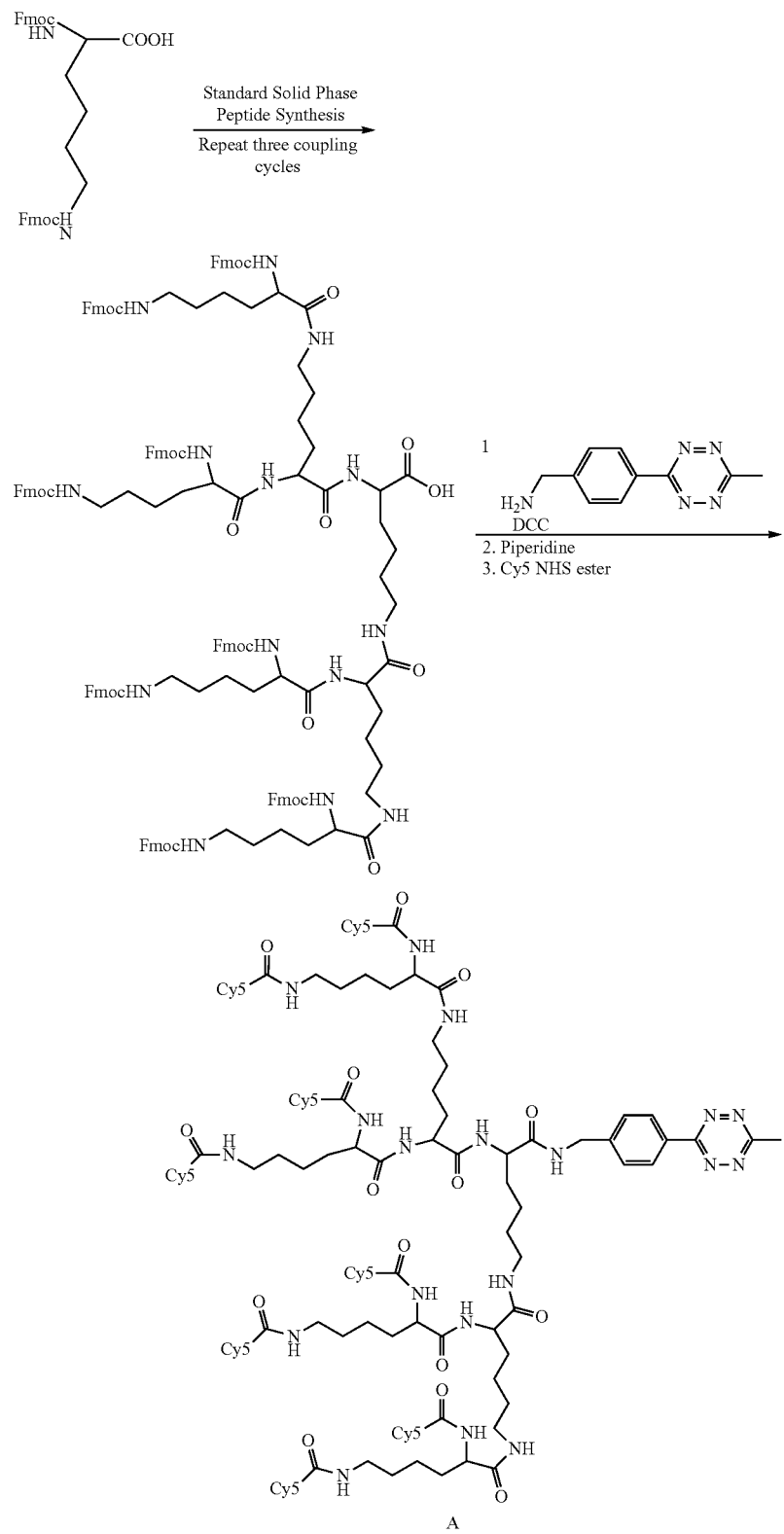
A Scheme 45 - Synthesis of Peptide-Based Multi-Fluorescent Dye (Cy5) Conjugated with Tetrazine (molecule B in FIG. 9).
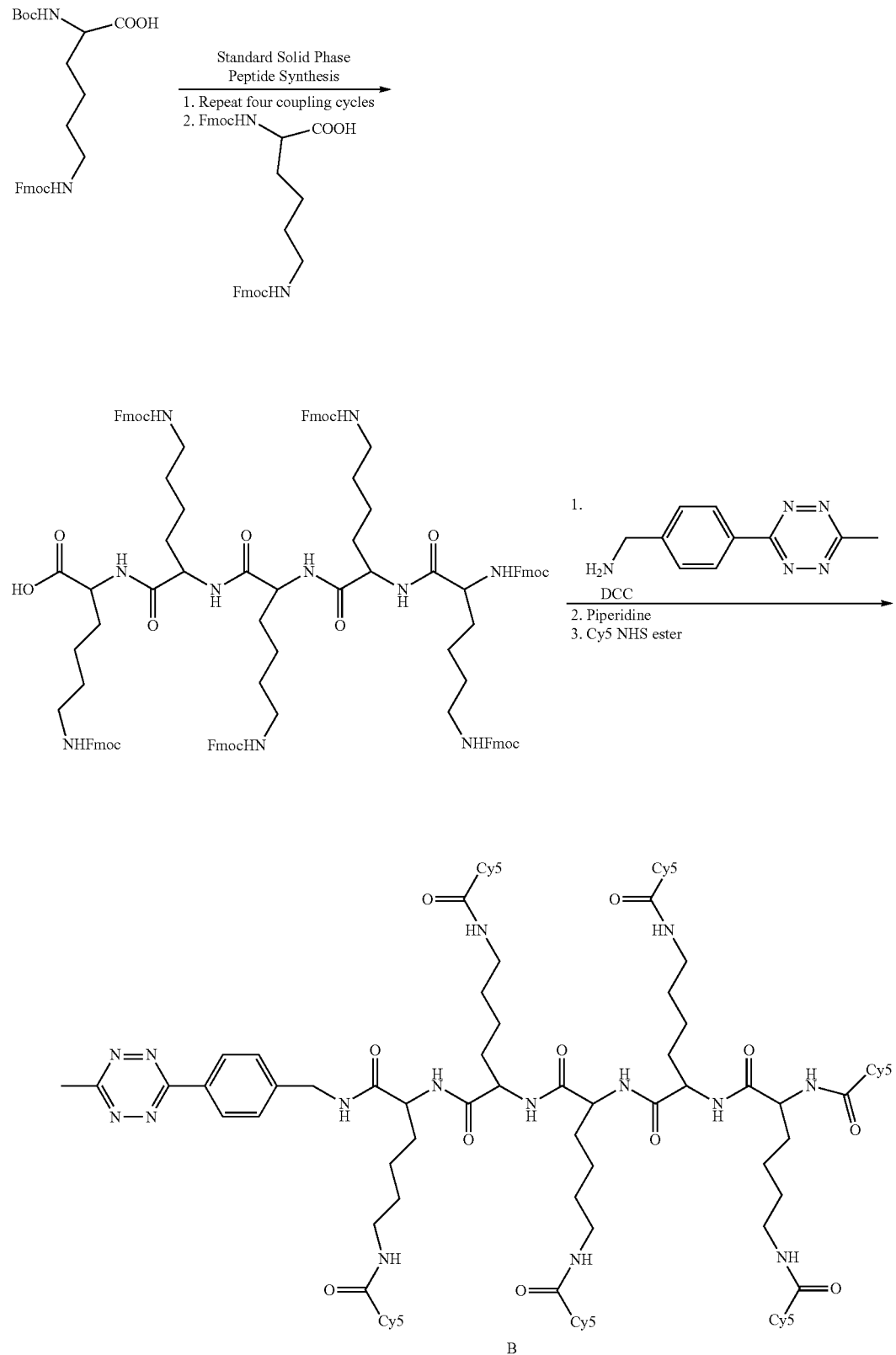

Scheme 46 - Synthesis of Labeled Binding Molecules Conjugated with Fluorescent Dye via Different Cleavable t-butyldithiomethyl moiety s (which are highlighted in parentheses in this scheme). The synthesis of SHA-2-Nitrobenzyl (linker)-ATTO647N from commercially available starting materials.
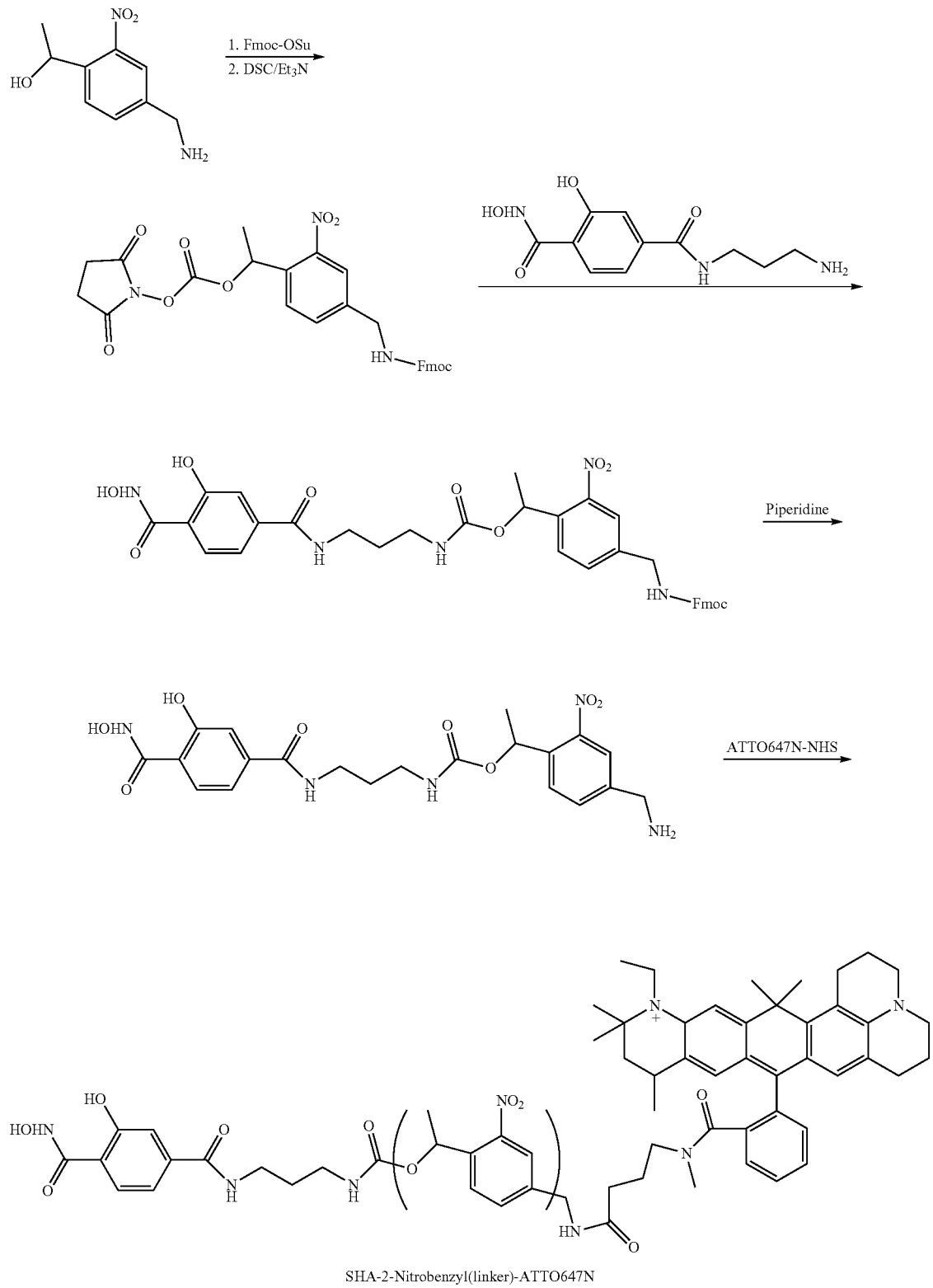
SHA-2-Nitrobenzyl(linker)-ATTO647N Scheme 47. Synthesis of Labeled Binding Molecules Conjugated with Fluorescent Dyes via Different Cleavable Linkers. The synthesis of Tetrazine-Azo(linker)-ATTO647N using commercially available starting materials.
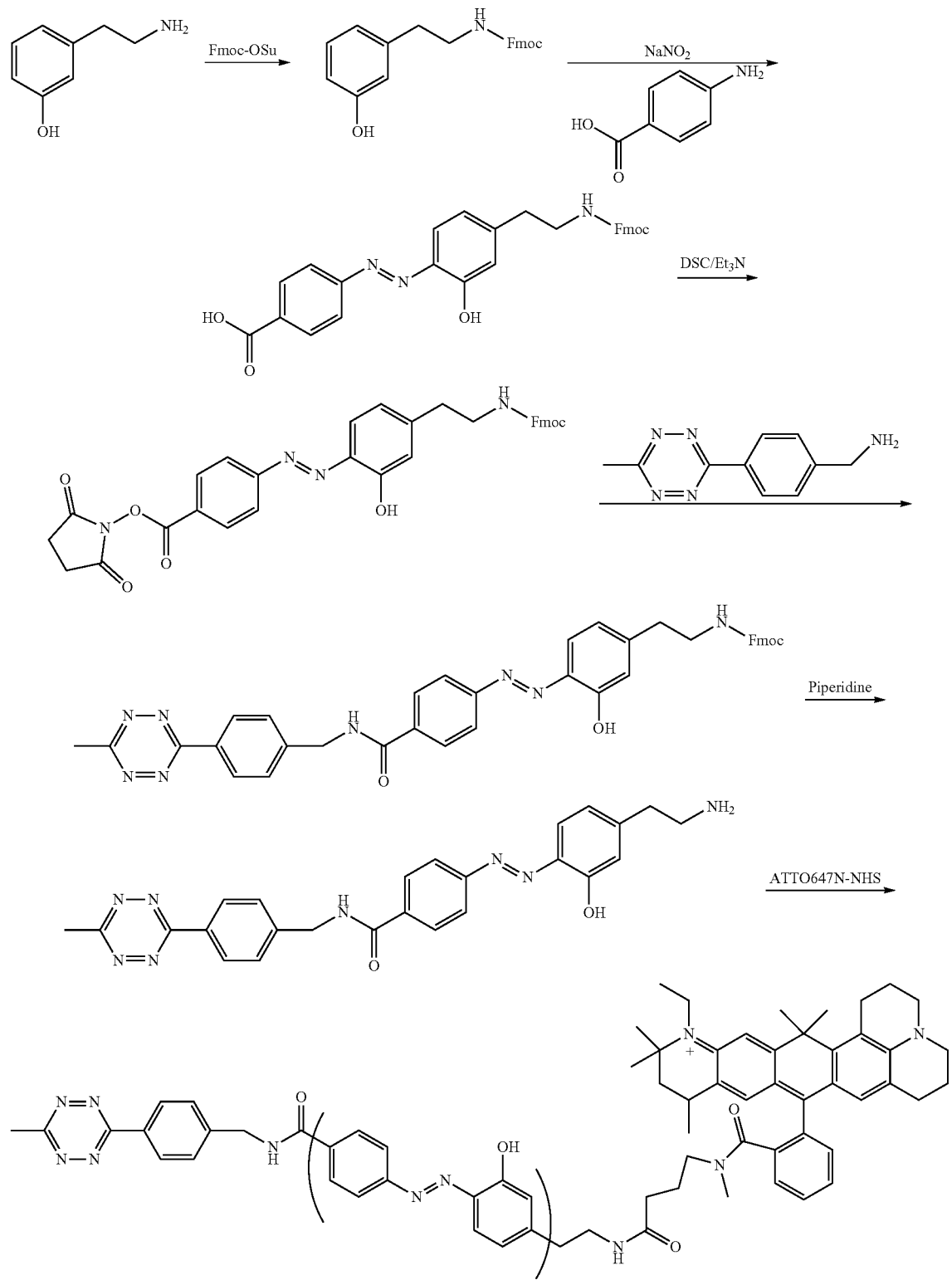
Tetrazine-Azo(linker)-ATTO647N Scheme 48 - The synthesis of Streptavidin-Dimethylketal(linker)-ATTO647N using commercially available starting materials.
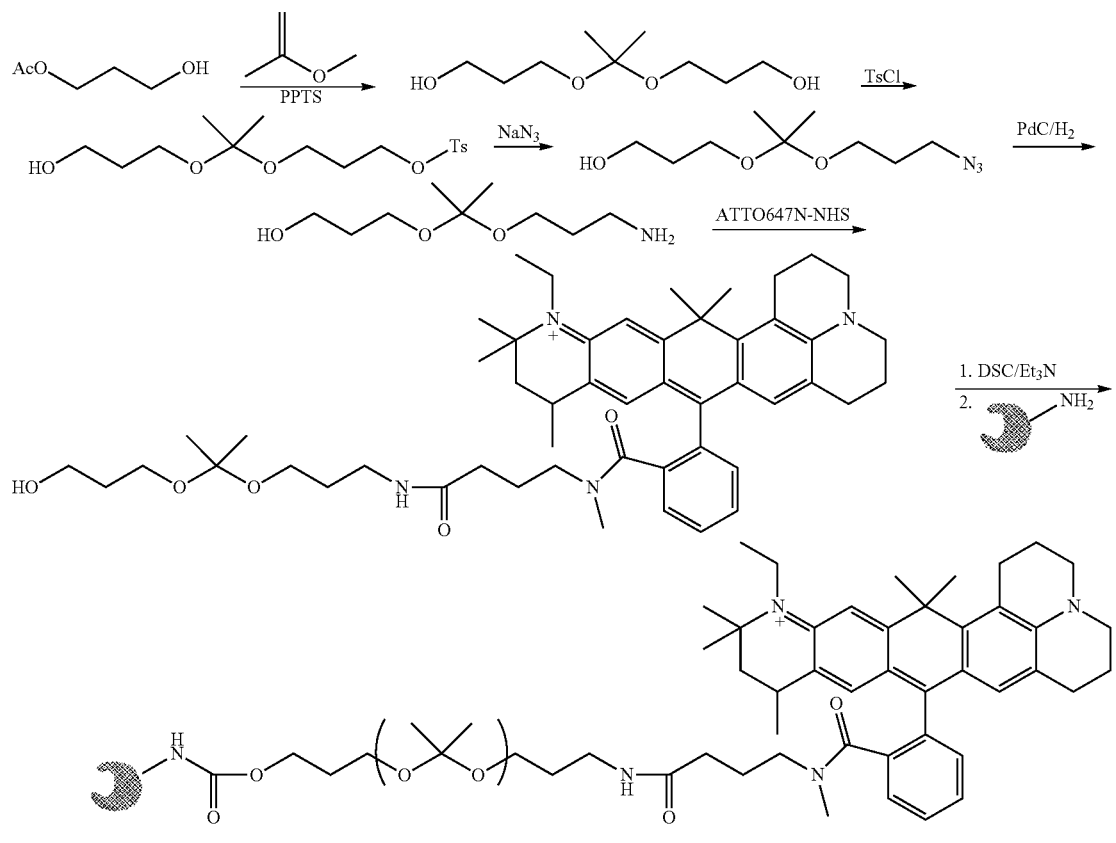
Scheme 49 - The synthesis of Dibenzocylooctyne(DBCO)-Allyl(linker)-ATTO647N using commercially available starting materials.
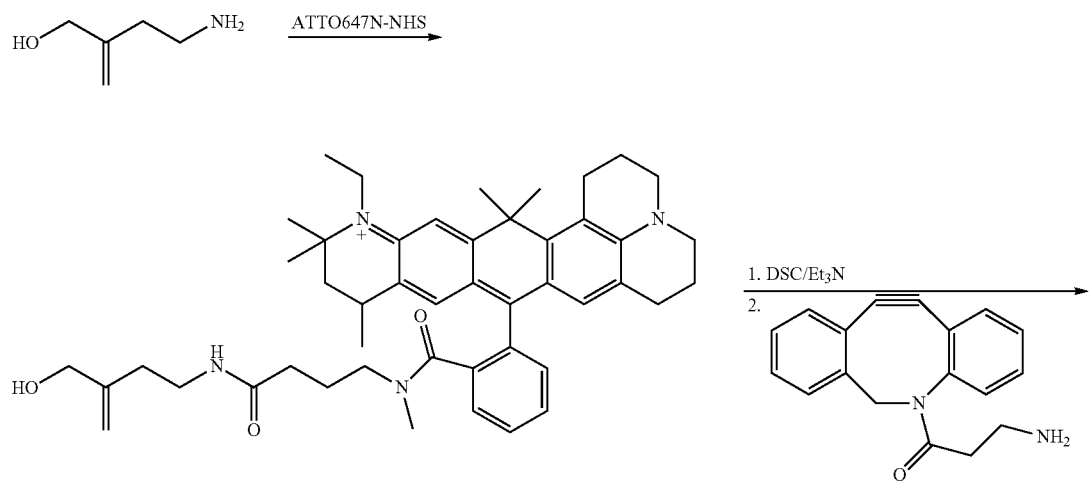

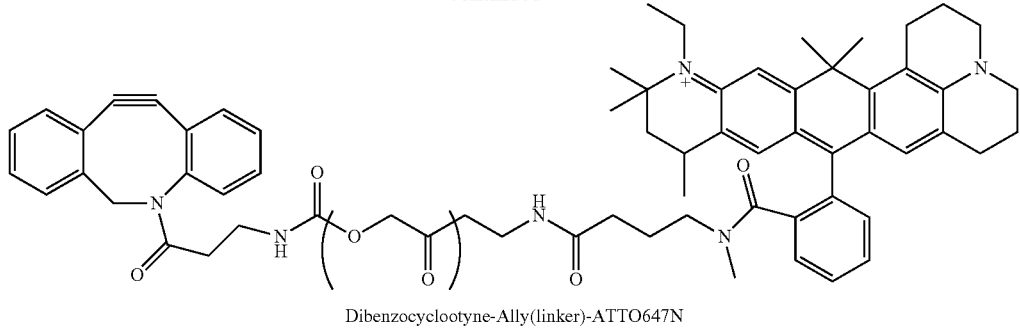
Dibenzocyclootyne-Ally(linker)-ATTO647N
Scheme 50. The synthesis of Dibenzocyclooctyne(DBCO)-Dde(linker)-ATT0647N using commercially available starting materials.
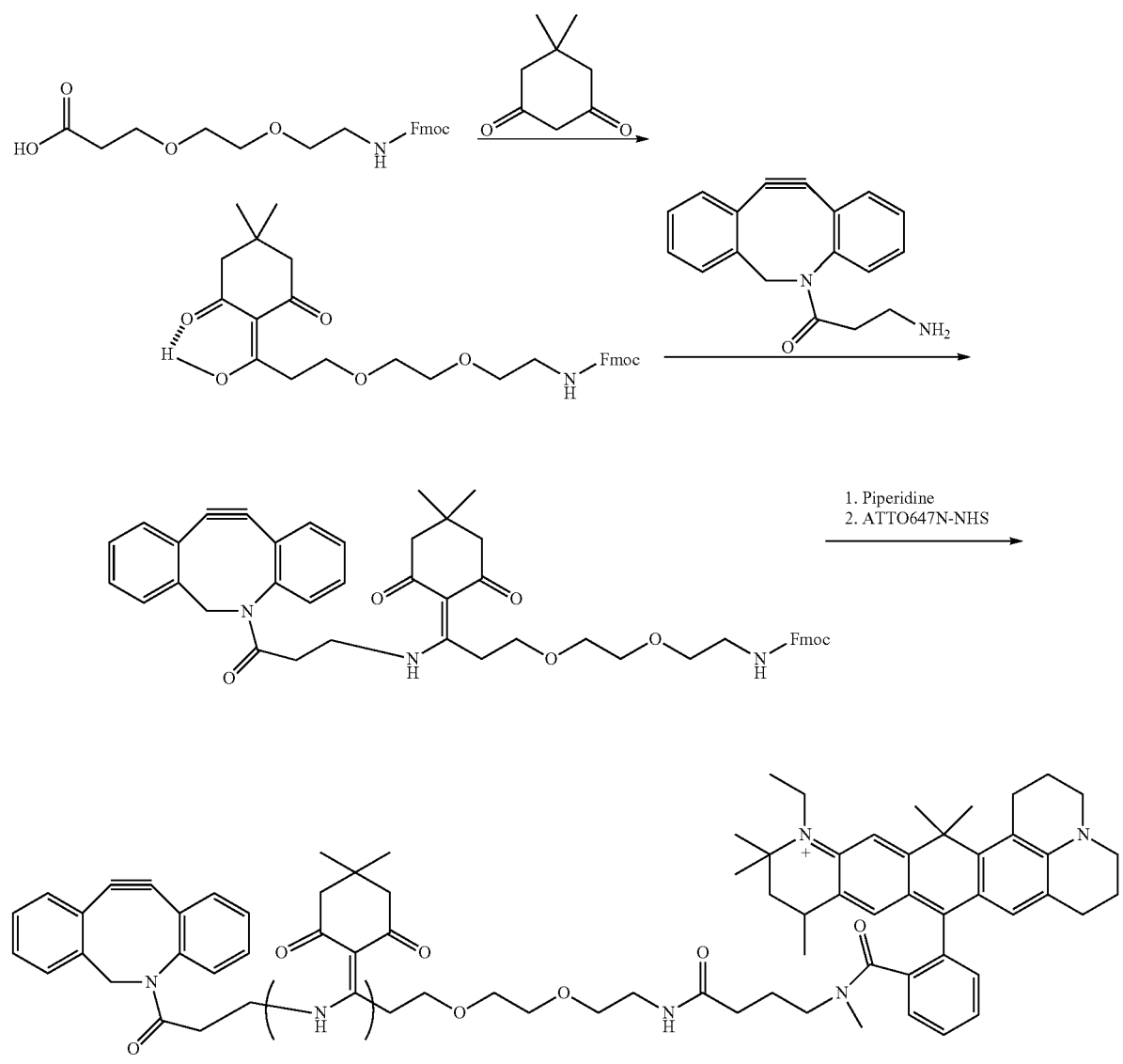
Dibenzocylootyne-Dde(linker)-ATTO647N Scheme 51. Synthesis of Terazine-Dde(linker)-ATTO0647N and Terazine-Dde(linker) - ROX using commerically available starting materials.
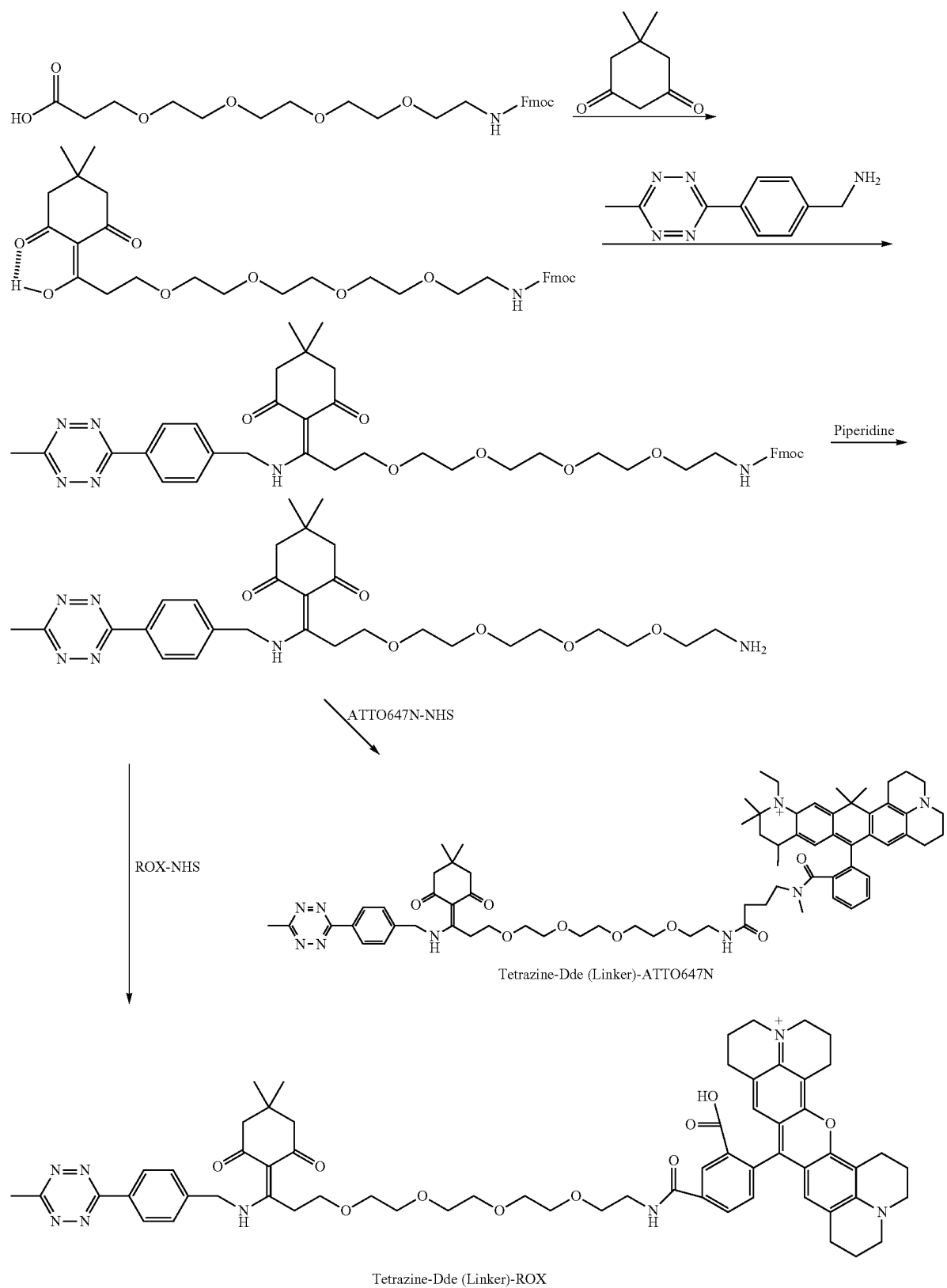

Scheme 52 - Synthsis of DBCO-Azo(-N═N-Linker)-ATTO647N and DBCO-Azo(-N═N-Linker)-ROX using commercially available starting materials.
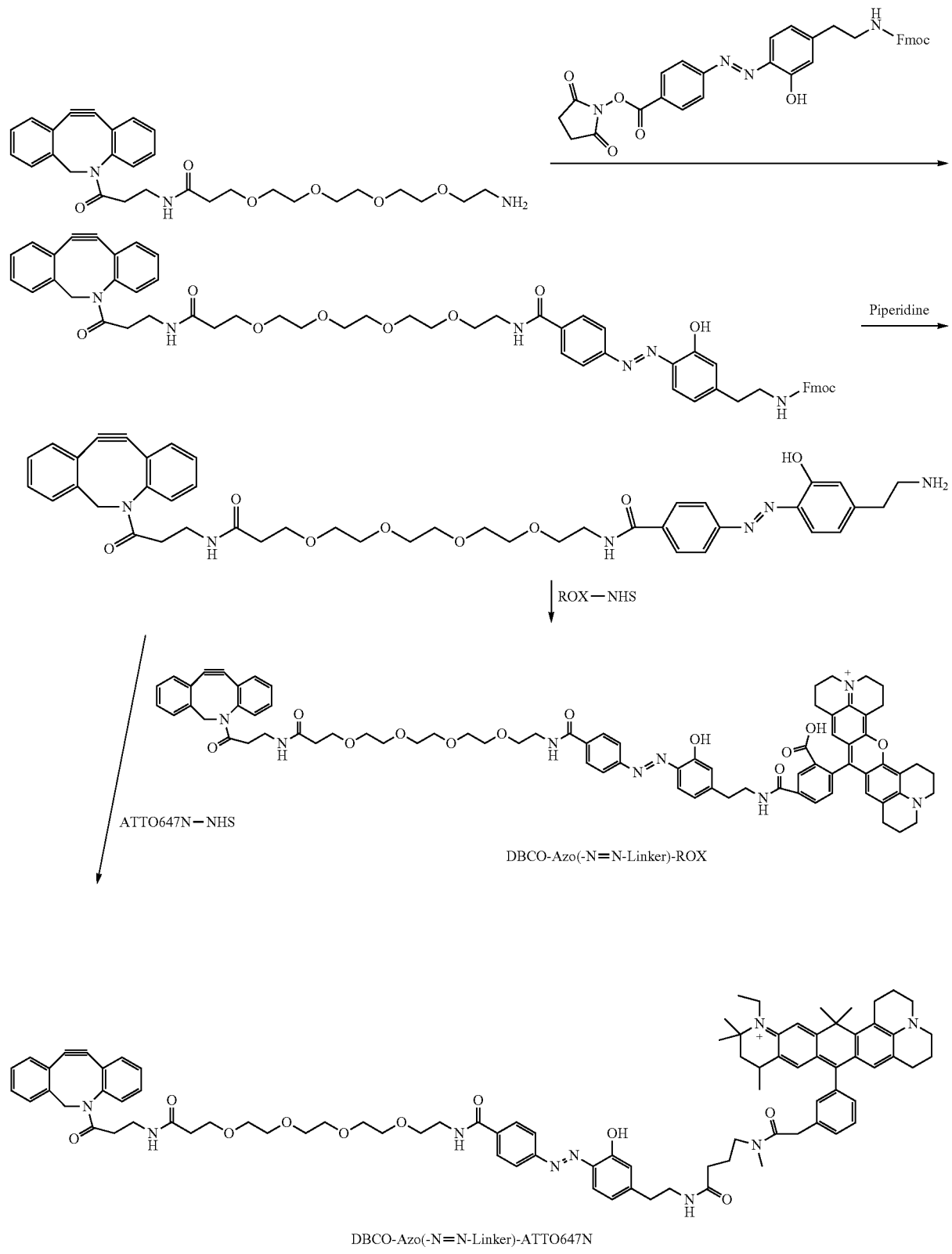

Scheme 53. Synthesis of 3'-O-Rox-Nitrobenzyl-dCTP.
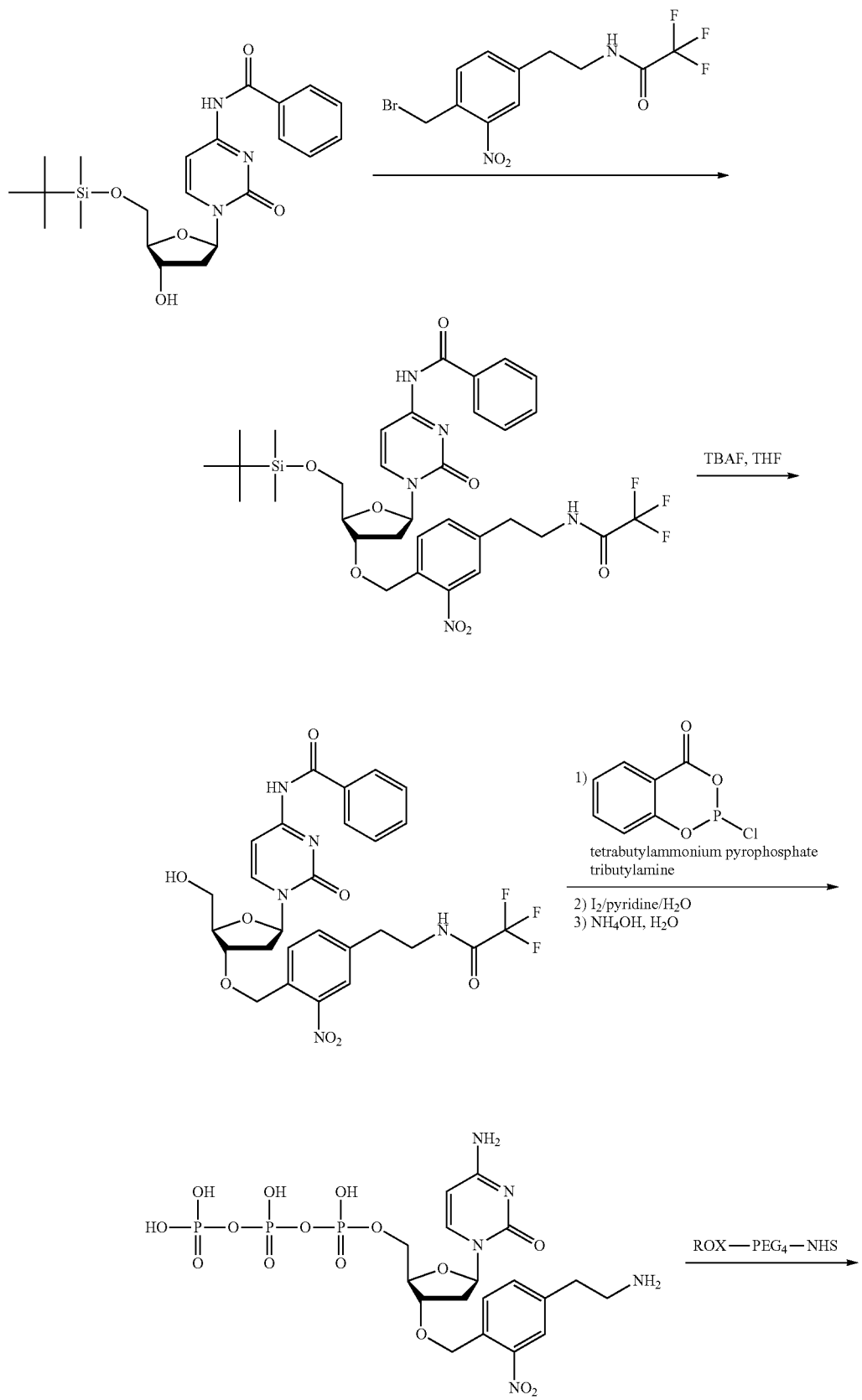

-continued
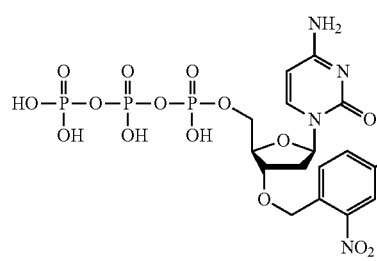 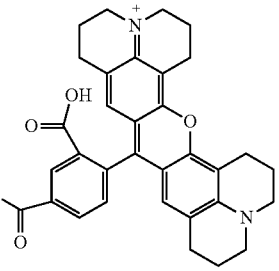
3′-O-Rox-Nitrobenzyl-dCTP
Scheme 54 - Synthesis of 3′-O-Rox-Allyl-dTTP.
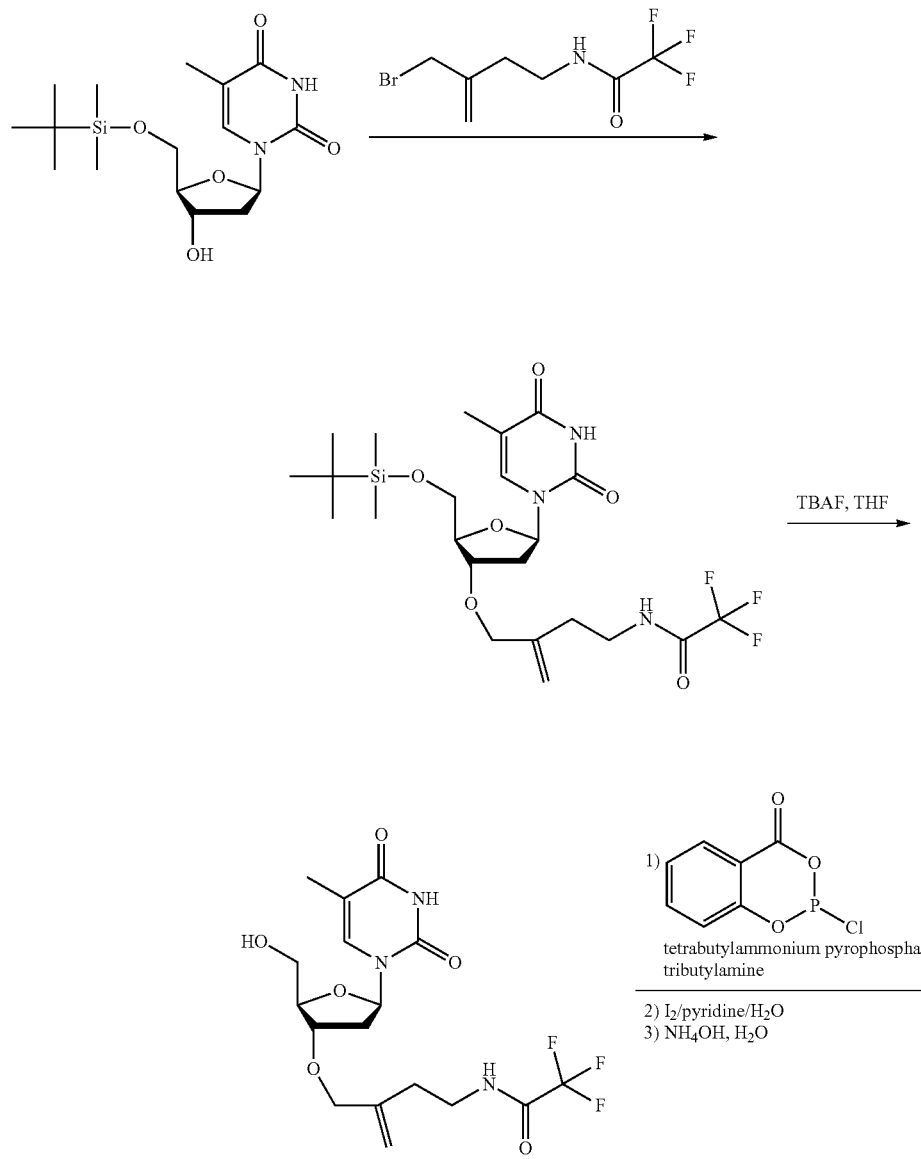

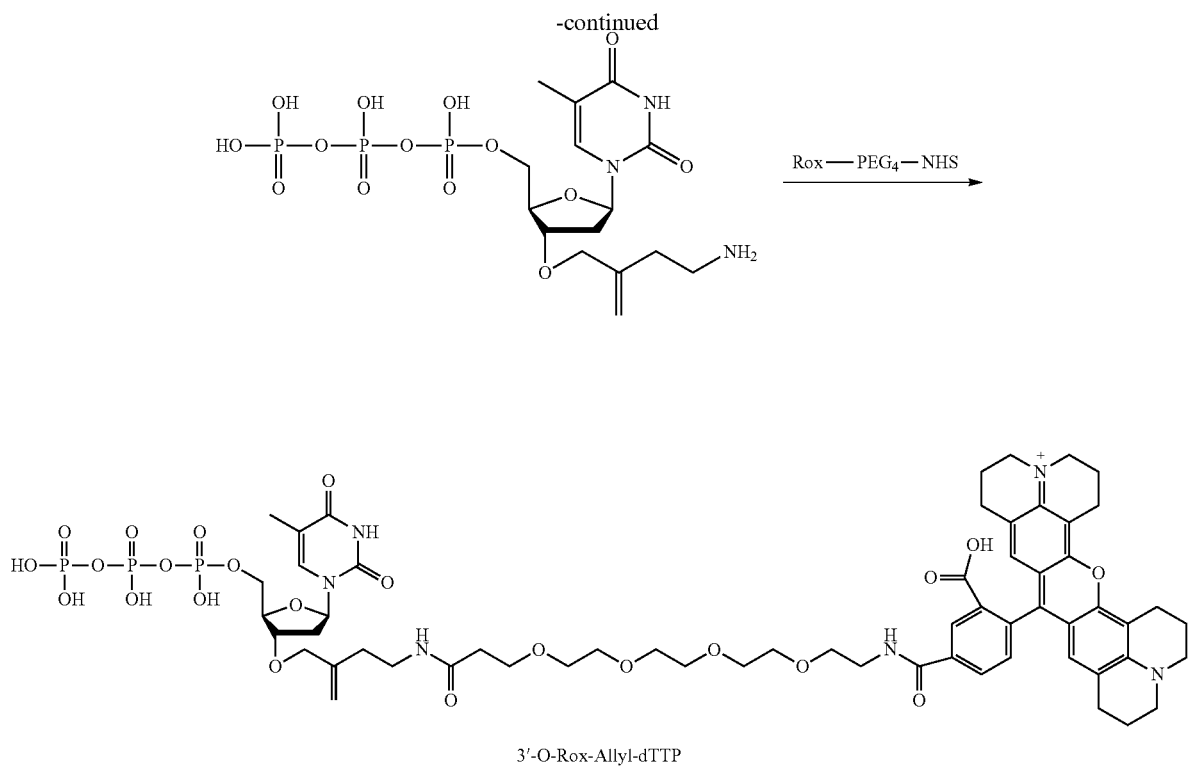

3'-O-Rox-Allyl-dTTP

Scheme 55 - Examples of specific cleavage reactions to cleave the Azo, Dimethylketal and Dde linkers. The Azo linker compound (Tetrazine-Azo(linker)-ATTO647N) is reduced into two aniline moieties by treatment with sodium dithionite. Treatment with citric acid/$Na_2HPO_4$ buffer (pH 4.1), the acid-sensitive dimethylketal linker compound (Streptavidin-Dimethylketal(linker)-ATTO647N) is hydrolyzed into two alcohol moieties and acetone. The Dde linker in the Dibenzocyclooctyne-Dde(linker)-ATTO647N is rapidly cleaved by treatment with 2% $N_2H_4$, yielding an amine containing fragment and the dye containing fragments.

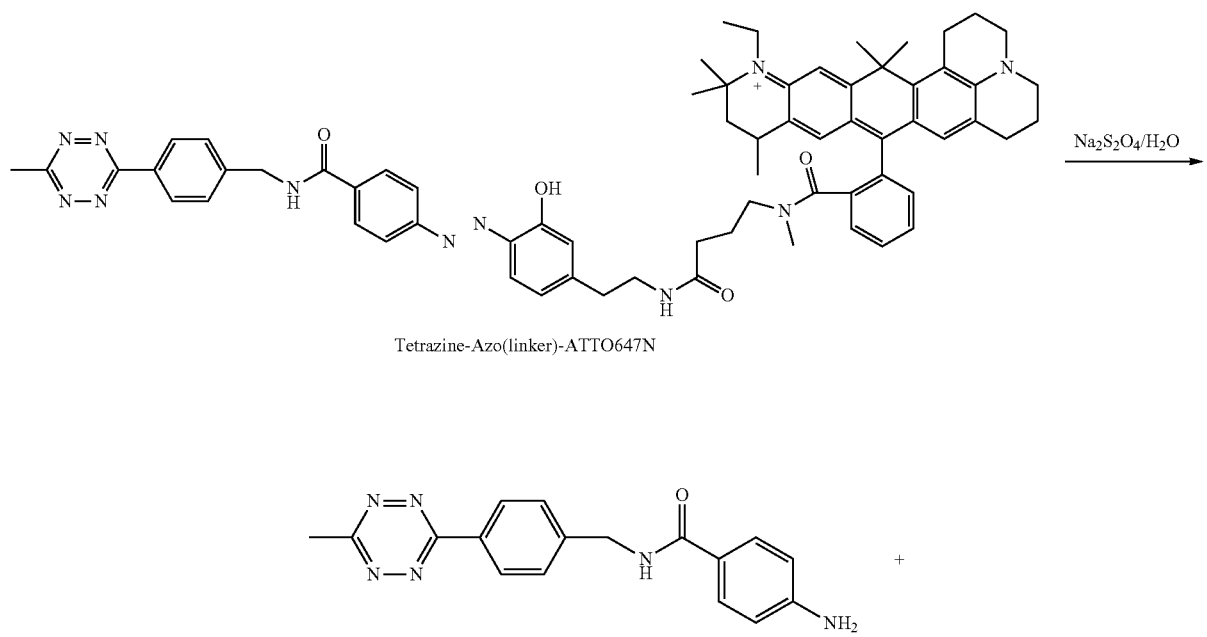

Tetrazine-Azo(linker)-ATTO647N 655 656
-continued
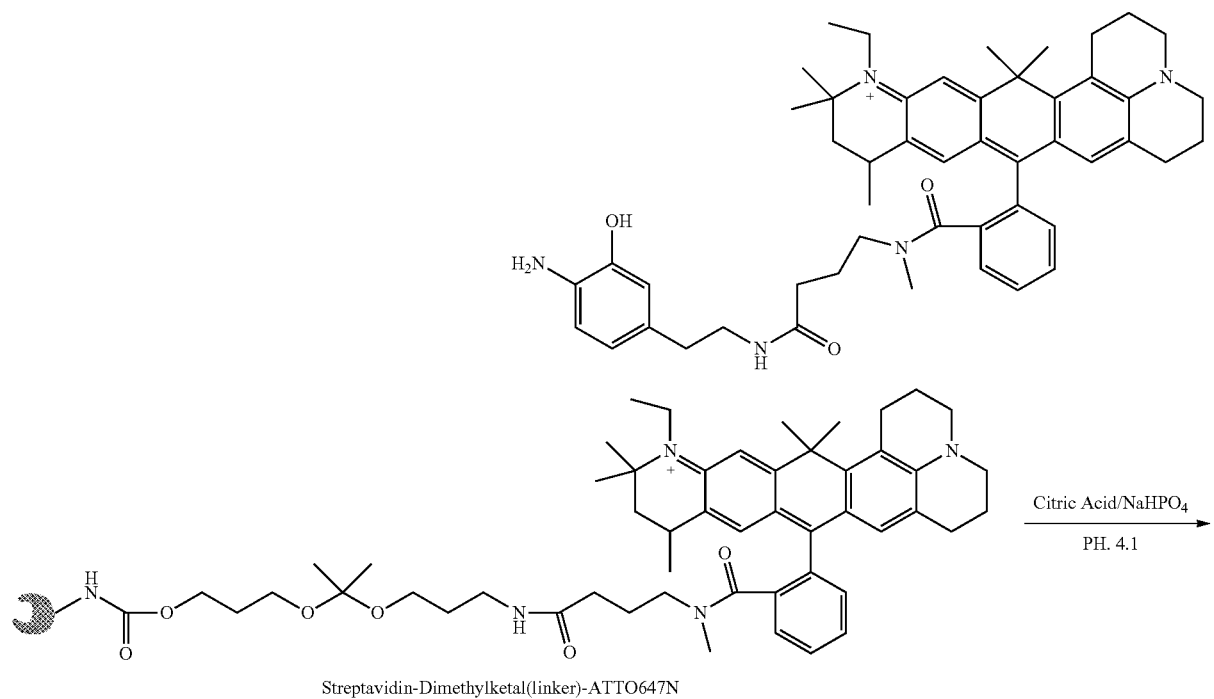
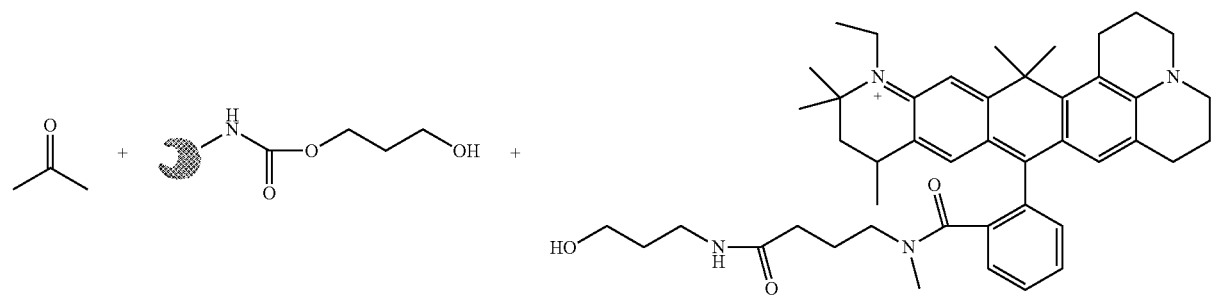
Streptavidin-Dimethylketal(linker)-ATTO647N
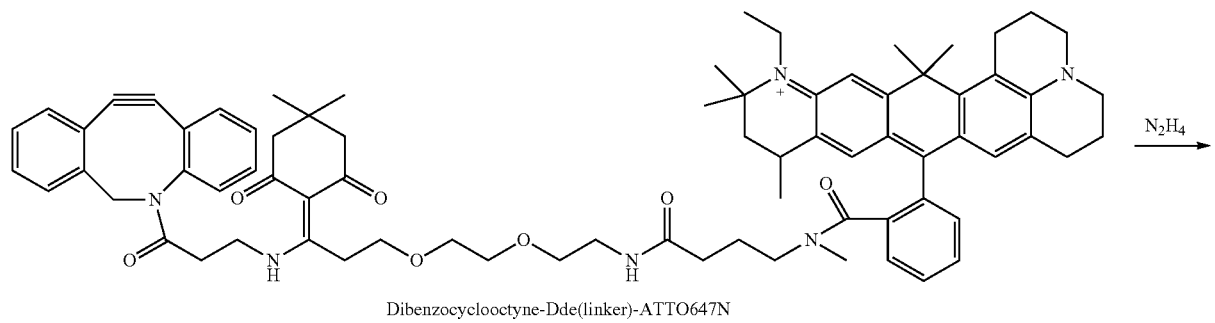
Dibenzocyclooctyne-Dde(linker)-ATTO647N
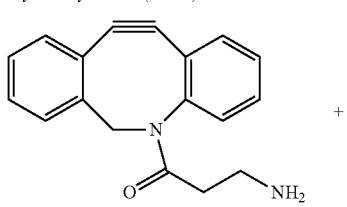

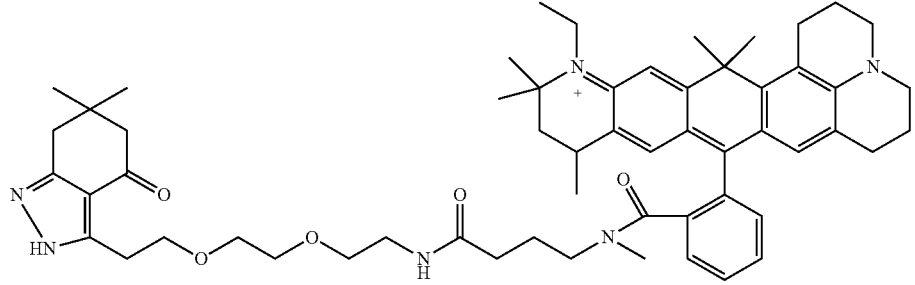

Additional Examples with Nucleotide Analogues that have Modifications on Both 3' Position and Base Here are provided 8 additional SBS schemes using nucleotide analogues that include 3' modifications (dyes or anchors) along with base modifications (anchors or directly attached dyes). Included are two examples aimed mainly at single molecule sequencing in which clusters of dyes are placed at these positions (via anchors at 3' position or directly on the base). The dye clusters include multiple dyes placed in various positions on linear polymers as well as branched polymers (dendrimers).

In the schemes described, even if the 3' position of the nucleotide analogues is not further modified, it will be blocked by a dithiomethyl (DTM) moiety which can be cleaved specifically with THP. In the following schemes Azo, Allyl and 2-nitrobenzyl groups are used as examples of non-DTM cleavable linkers; sodium dithionite, Pd(0) and 340 nm light, respectively, are shown as examples of means of cleavage; ATTO647N, Rox, Alexa488, BodipyFL and Cy5 are used as examples of fluorophores; biotin or TCO are provided as examples of the anchors; and streptavidin or tetrazine are used as examples of the anchor binding molecules. However, a variety of other cleavable groups in the linker, cleavage agents, fluorophores, anchors (e.g., DBCO, $N_3$, tetrazine), and anchor binding molecules (e.g., $N_3$, DBCO, TCO) are also feasible.

The first four schemes (A-D) are two color SBS schemes that require two fluorescence detection steps; schemes E-H are single color fluorescence schemes that require three fluorescence detection steps to determine the incorporated nucleotide. Optional confirmatory imaging steps are included in some of these schemes. As with all the previously described schemes, chasing is performed after adding the nucleotide analogues to guarantee that every primer has been extended so as to avoid asynchronous reactions, and washing is required between every step to remove the previous set of reagents and/or released dyes.

Scheme A: Two color SBS: imaging after incorporation and labeling (FIG. 77). In Scheme A, a set of nucleotide analogues, one with Anchor1 attached to the 3' position of the sugar via a dithiomethyl (DTM) cleavable linker, one with Anchor2 attached to the 3' position via a DTM cleavable linker, one with Dye1 attached to the base via a DTM linker, and one with Dye2 attached to the base via a DTM linker, is used. Imaging after addition of the four nucleotide analogues will indicate incorporation by either of two nucleotide analogues specifically. After labeling with both Dye1 labeled Anchor1 binding molecule and Dye2 labeled Anchor2 binding molecule, imaging will reveal specifically incorporation by one of the other two nucleotide analogues. Cleavage with THP will then remove the remaining dyes and restore the 3'-OH group for subsequent sequencing cycles. In the example shown, Dye1 is Alexa488, Dye2 is Rox, Anchor1 is biotin, and Anchor2 is TCO. Other combinations of dyes and anchors can also be used.

Scheme B: Two color SBS: imaging after incorporation and cleavage (FIG. 79). In Scheme B, a set of nucleotide analogues, one with Dye1 attached to the 3' position of the sugar via a DTM cleavable linker, one with Dye2 attached to the base via a DTM linker, one with Dye1 attached to the base via an Azo cleavable linker, and one with Dye2 attached to the base via an Azo cleavable linker, is used. In contrast to some previous schemes, here three of the nucleotide analogues have dyes on the base with only one nucleotide analogue having a dye at the 3' position. After incorporation, a Dye1 signal will indicate incorporation by either of two of the nucleotide analogues, while a Dye2 signal will indicate incorporation by either of the other two nucleotide analogues. Next, specific cleavage of the Azo linkers will reveal specifically which of either pair was incorporated. Cleavage with THP will then remove the remaining dyes and restore the 3'-OH group for subsequent sequencing cycles. In the example shown, Dye1 is Rox and Dye2 is BodipyFL. Other dyes can also be used.

Scheme C: Two color SBS with dye clusters: imaging after incorporation and labeling (FIG. 81). In Scheme C, a different set of nucleotide analogues is used: one with a DTM cleavable linker at the 3' position attached to Anchor1, one with a DTM cleavable linker at the 3' position attached to Anchor2, one with a Dye1 cluster attached to the base via a DTM cleavable linker, and one with a Dye2 cluster attached to the base via a DTM cleavable linker. Imaging immediately after incorporation will reveal specifically two of the nucleotide analogues. Next, labeling is carried out with an Anchor1 binding molecule attached to a Dye1 cluster and an Anchor2 binding molecule attached to a Dye2 cluster. Appearance of Dye1 or Dye2 fluorescence after this step will specifically identify incorporation by the remaining two nucleotide analogues. The use of dye clusters consisting of multiple dyes, such as 4, 5 or potentially 8 or more identical fluorophores, arranged so as to avoid quenching, will enable both ensemble and single molecule sequencing. Cleavage with THP will then remove the remaining dyes and restore the 3'-OH group for subsequent sequencing cycles. In the example shown, the Dye1 cluster is a Rox cluster, the Dye2 cluster is an Alexa488 cluster, Anchor1 is TCO, and Anchor2 is biotin. Other combinations of dyes and anchors can also be used.

Scheme D: Two color SBS with energy transfer dyes: imaging after incorporation and labeling (FIG. 83). In Scheme D, the set of nucleotide analogues consists of one with a DTM cleavable linker at the 3' position attached to Anchor1, one with a DTM cleavable linker at the 3' position attached to Anchor2, one a fluorophore attached to the base via an DTM cleavable linker, and one with a donor plus acceptor energy transfer pair of fluorophores attached to the base via a DTM cleavable linker. Excitation of the donor dye after incorporation will reveal specifically two of the bases, one if donor emission is detected and the other if acceptor emission predominates. Next, labeling is carried out with Anchor1 binding molecule attached to the donor dye, and Anchor2 binding molecule attached to the energy transfer dye pair cassette. Illumination at the donor absorbance wavelength will reveal specifically incorporation of the remaining two nucleotide analogues. Cleavage with THP will then remove the remaining dyes and restore the 3'-OH group for subsequent sequencing cycles. In the example shown, Anchor1 is biotin, Anchor2 is TCO, Dye1 is Rox, and the dye pair cassette has Rox as the donor and Cy5 as the acceptor. Other combinations of dyes and anchors can also be used.

Scheme E: One color SBS: imaging after 2 labeling steps and cleavage (FIG. 85). In Scheme E, a set of nucleotide analogues with orthogonal cleavable linker-anchor combinations is used: one with Anchor1 attached to the 3' position via a DTM cleavable linker, one with Anchor2 attached to the 3' position via a DTM cleavable linker, one with Anchor1 attached to the base via an Azo cleavable linker, and one with Anchor2 attached to the base via an Azo cleavable linker. After labeling with Anchor1 binding molecule attached to Dye1, imaging reveals two possible incorporated bases. Next, after labeling with Anchor2 binding molecule attached to Dye1, imaging confirms incorporation of the other two possible incorporated bases. Finally, treatment with sodium dithionite will cleave the Azo linkers, specifically revealing which nucleotide was added. Cleavage with THP will then remove the remaining dyes and restore the 3'-OH group for subsequent sequencing cycles. In the example shown, Dye1 is ATTO647N, Anchor1 is TCO, and Anchor2 is biotin. Other combinations of dyes and anchors can also be used.

Scheme F: One color SBS: imaging after incorporation, labeling and cleavage (FIG. 87). In Scheme F, the set of nucleotide analogues consists of one with Dye1 attached to the 3' position via a DTM cleavable linker, one with Anchor1 attached to the 3' position via a DTM cleavable linker, one with Dye1 attached to the base via an Azo cleavable linker, and one with Anchor1 attached to the base via an Azo cleavable linker. Dye1 detection after incorporation reveals either of two of the possible incorporated nucleotide analogues. After labeling with Anchor1 binding molecules attached to Dye1, imaging confirms incorporation of either of the other two possible nucleotide analogues. Finally, treatment with sodium dithionite will cleave the Azo linkers, specifically revealing which nucleotide was added. Cleavage with THP will then remove the remaining dyes and restore the 3'-OH group for subsequent sequencing cycles. In the example shown, Dye1 is Rox and Anchor1 is TCO. Other dyes and anchors can also be used.

Scheme G: One color SBS: imaging after labeling and 2 cleavage steps (FIG. 89). In Scheme G, three of the nucleotide analogues have the same Anchor1 molecule attached to the 3' position via either of three different cleavable linkers (Allyl, 2-nitrobenzyl and DTM); the fourth nucleotide has Dye1 attached to the base via a DTM linker. After incorporation, imaging reveals specifically one of the nucleotide analogues. Imaging following labeling with the Anchor1 binding molecule attached to Dye1 indicates the possibility of any of the remaining three nucleotide analogues having been incorporated. Next, specific cleavage reactions are carried out, one by one, with Pd(0) to cleave the allyl linkage, with 340 nm light to cleave the 2-nitrobenzyl linkage, and finally with THP to cleave the DTM linkage, remove the remaining dye and restore the 3'-OH group for subsequent sequencing cycles. Loss of fluorescence at any one of these steps will reveal specifically which nucleotide was incorporated. In the example shown, Dye1 is ATTO647N and Anchor1 is biotin. Other dyes and anchors can also be used.

Scheme H: One color SBS: imaging after incorporation, labeling and cleavage (FIG. 91). In Scheme H, a set of nucleotide analogues with orthogonal cleavable linker-anchor-dye cluster combinations is used: one with a Dye1 cluster attached to the base via a DTM cleavable linker, one with a Dye1 cluster attached to the base via an Azo cleavable linker, one with Anchor1 attached to the 3' position via a DTM cleavable linker, and one with Anchor2 attached to the 3' position via a DTM cleavable linker. After incorporation, fluorescence indicates the possibility of either of two nucleotide analogues. Imaging after labeling with a Dye1 cluster attached to an Anchor1 binding molecule will specifically reveal one of the remaining two nucleotide analogues, and imaging after subsequent labeling with a Dye1 cluster attached to Anchor2 binding molecule will specifically reveal the other of the remaining two nucleotide analogues. Imaging following cleavage with sodium dithionite to remove dyes with Azo linkers will specifically reveal either of the first two nucleotide analogues having been incorporated. Finally, cleavage with THP will remove the remaining dyes and restore the 3'-OH group for subsequent sequencing cycles. As with Scheme C, the use of dye clusters with multiple dyes, such as of 4, 5 or potentially 8 or more identical fluorophores will enable ensemble and single molecule sequencing. In the example shown, the Dye1 cluster is a Rox cluster, Anchor1 is biotin, and Anchor2 is TCO. Other combinations of dyes and anchors can also be used.

What is claimed is:

1. A thermophilic nucleic acid polymerase complex comprising a thermophilic nucleic acid polymerase bound to a nucleotide analogue having the formula:

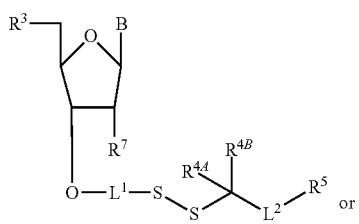

(III)

or

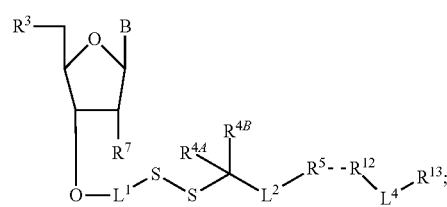

(IV)

wherein the symbol "----" is a non-covalent bond;

B is a base or analogue thereof;

$L^1$ is a substituted or unsubstituted methylene, and wherein if $L^1$ is a substituted methylene, $L^1$ is substituted with a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene;

$L^2$ is a cleavable linker or a non-cleavable linker;

$R^3$ is triphosphate;

$R^{4A}$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, or substituted or unsubstituted heteroalkyl;

$R^{4B}$ is hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —X—$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein $R^6$ is —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, or substituted or unsubstituted heteroalkyl; and wherein X is a bond, O, $NR^{6A}$, or S;

wherein $R^{6A}$ is —OH, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, substituted or unsubstituted alkyl, or unsubstituted heteroalkyl;

$R^5$ is a detectable label or a biotin moiety;

$R^7$ is hydrogen;

$R^{12}$ is a streptavidin moiety;

$L^4$ is an orthogonally cleavable linker; and $R^{13}$ is a fluorescent dye.

2. The complex of claim 1, wherein $L^2$ is a chemically cleavable linker, a photocleavable linker, an acid-cleavable linker, a base-cleavable linker, an oxidant-cleavable linker, a reductant-cleavable linker, or a fluoride-cleavable linker;

$R^{4A}$ is substituted or unsubstituted $C_1$-$C_6$ alkyl, or substituted or unsubstituted 2 to 6 membered heteroalkyl;

$R^5$ is a biotin moiety; and $L^4$ is a photocleavable linker, an acid-cleavable linker, a base-cleavable linker, an oxidant-cleavable linker, a reductant-cleavable linker, or a fluoride-cleavable linker.

3. The complex of claim 1, wherein $R^5$ is a biotin moiety.

4. The complex of claim 1, wherein $L^1$ is an unsubstituted methylene.

5. The complex of claim 1, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene;

wherein at least one of $L^{2A}$, $L^{2B}$, $L^{2C}$, $L^{2D}$, and $L^{2E}$ is not a bond.

$R^{4A}$ is unsubstituted methyl;

$R^6$ is unsubstituted methyl $R^{6A}$ is unsubstituted methyl; and $L^4$ is $L^{4A}$-$L^{4B}$-$L^{4C}$-$L^{4D}$-$L^{4E}$; and $L^{4A}$ is a bond, —NN—, —NHC(O)—, —C(O)NH—, substituted or unsubstituted alkylene, substituted or unsubstituted heteroalkylene;

$L^{4B}$ is a bond, —NN—, —NHC(O)—, —C(O)NH—, substituted or unsubstituted cycloalkylene, substituted or unsubstituted heterocycloalkylene, substituted or unsubstituted arylene, or substituted or unsubstituted heteroarylene;

$L^{4C}$ is a bond, —NN—, —NHC(O)—, —C(O)NH—, substituted or unsubstituted cycloalkylene, substituted or unsubstituted heterocycloalkylene, substituted or unsubstituted arylene, or substituted or unsubstituted heteroarylene;

$L^{4D}$ is a bond, —NN—, —NHC(O)—, —C(O)NH—, substituted or unsubstituted alkylene, substituted or unsubstituted heteroalkylene; and $L^{4E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein at least one of $L^{4A}$, $L^{4B}$, $L^{4C}$, $L^{4D}$, and $L^{4E}$ is not a bond.

6. The complex of claim 1, wherein $L^2$ is $L^{2A}$-$L^{2B}$-$L^{2C}$-$L^{2D}$-$L^{2E}$; and $L^{2A}$ is a bond, substituted or unsubstituted alkylene, substituted or unsubstituted heteroalkylene;

$L^{2B}$ is a bond, substituted or unsubstituted cycloalkylene, substituted or unsubstituted heterocycloalkylene, substituted or unsubstituted arylene, or substituted or unsubstituted heteroarylene;

$L^{2C}$ is a bond, substituted or unsubstituted cycloalkylene, substituted or unsubstituted heterocycloalkylene, substituted or unsubstituted arylene, or substituted or unsubstituted heteroarylene;

$L^{2D}$ is a bond, substituted or unsubstituted alkylene, substituted or unsubstituted heteroalkylene; and $L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein at least one of $L^{2A}$, $L^{2B}$, $L^{2C}$, $L^{2D}$, and $L^{2E}$ is not a bond.

7. The complex of claim 1, wherein $L^2$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

8. The complex of claim 1, wherein $L^2$ is a substituted or unsubstituted 4 to 8 membered heteroalkylene.

9. The complex of claim 1, wherein $L^2$ is —$C(CH_3)_2$ $CH_2NHC(O)$—,

671
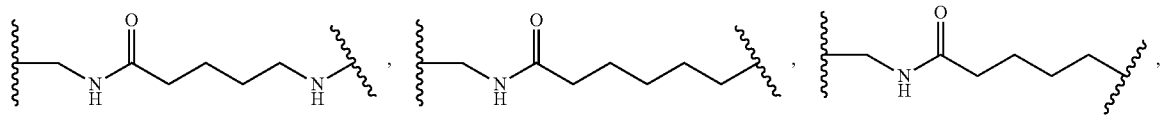
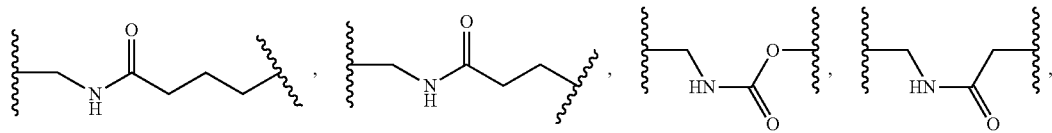
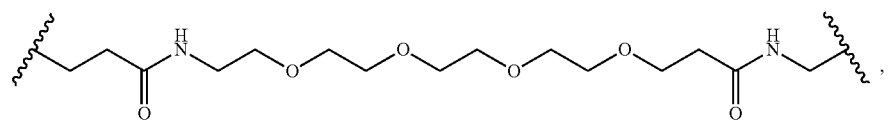
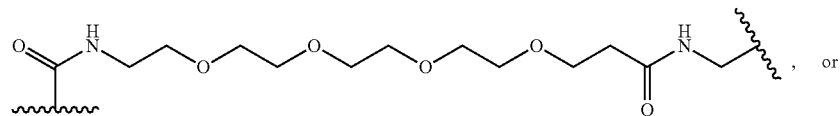
672
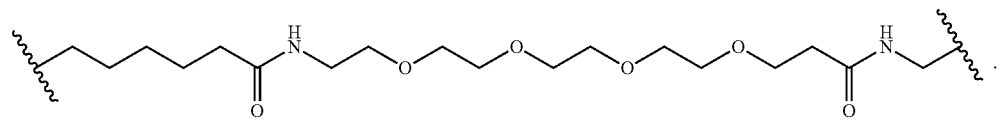
, or
10. A thermophilic nucleic acid polymerase complex comprising a thermophilic nucleic acid polymerase bound to a nucleotide analogue, wherein the nucleotide analogue has the formula:
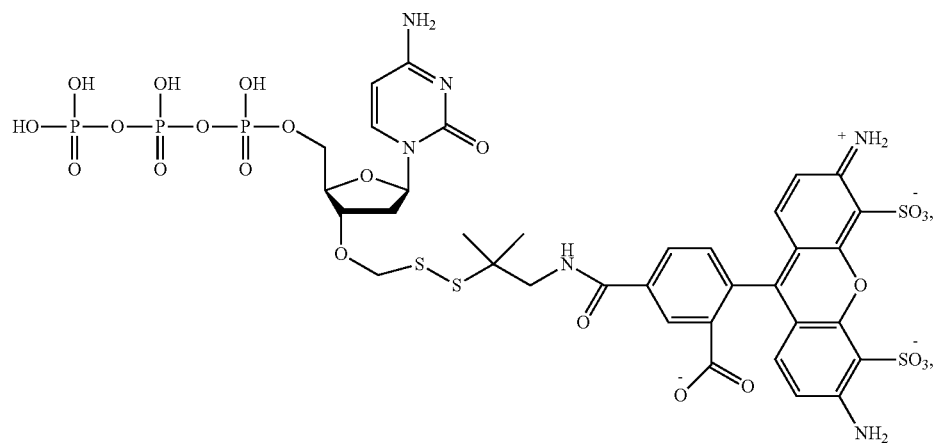

-continued
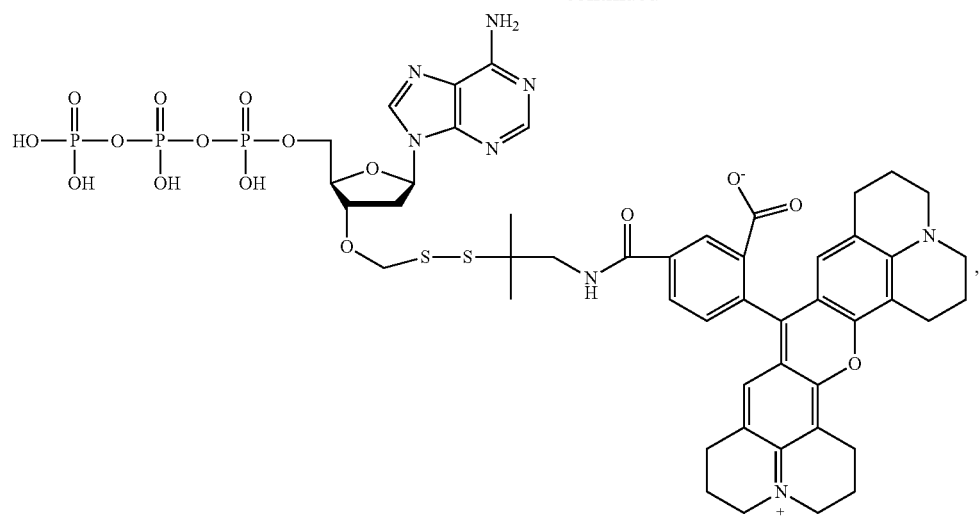
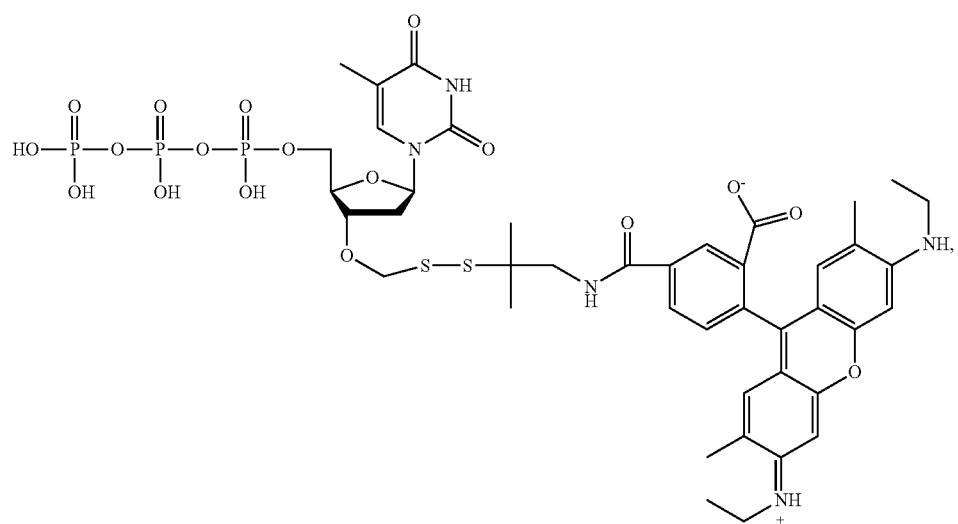
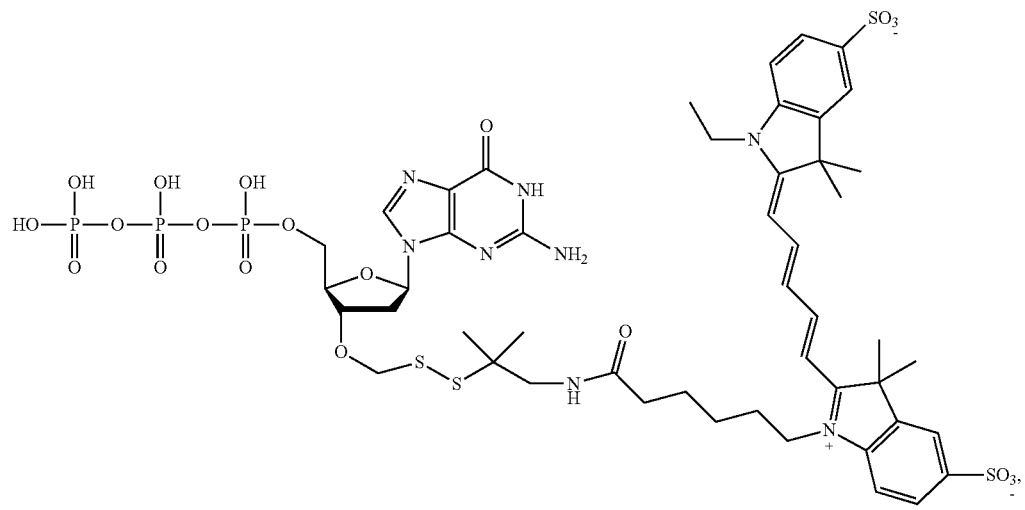

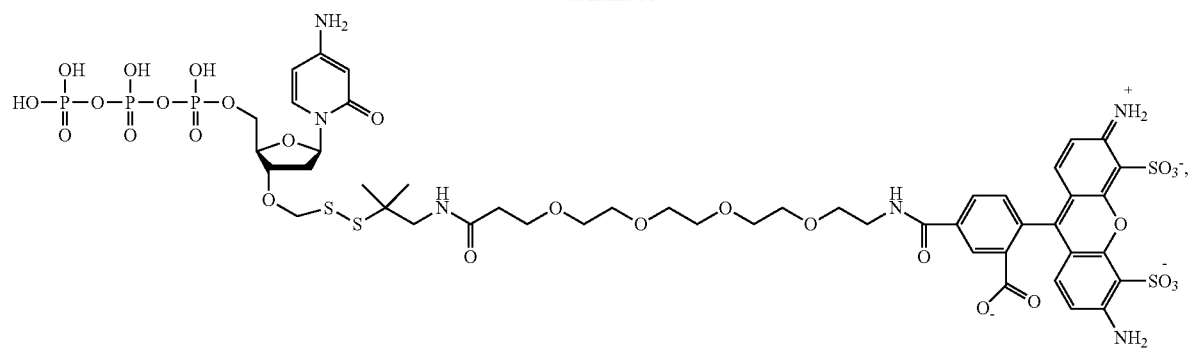
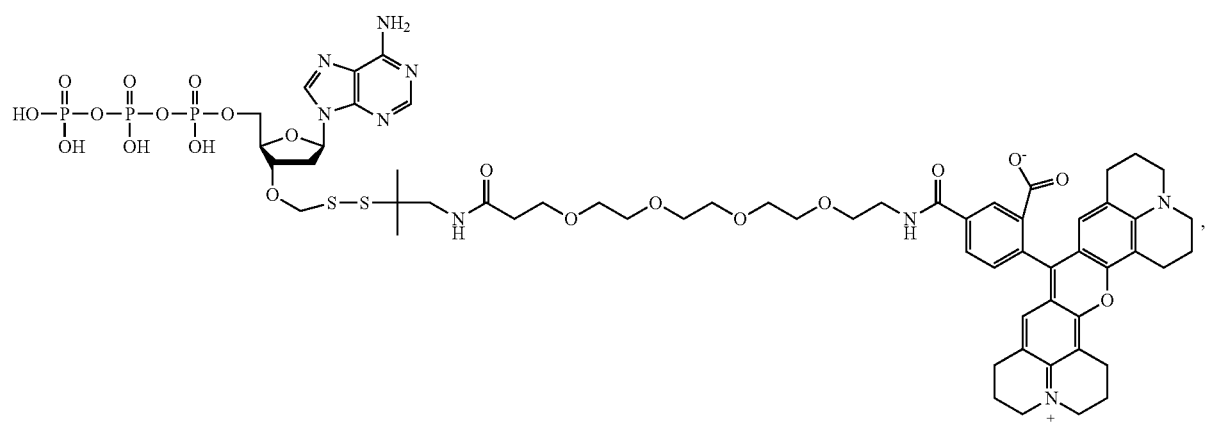
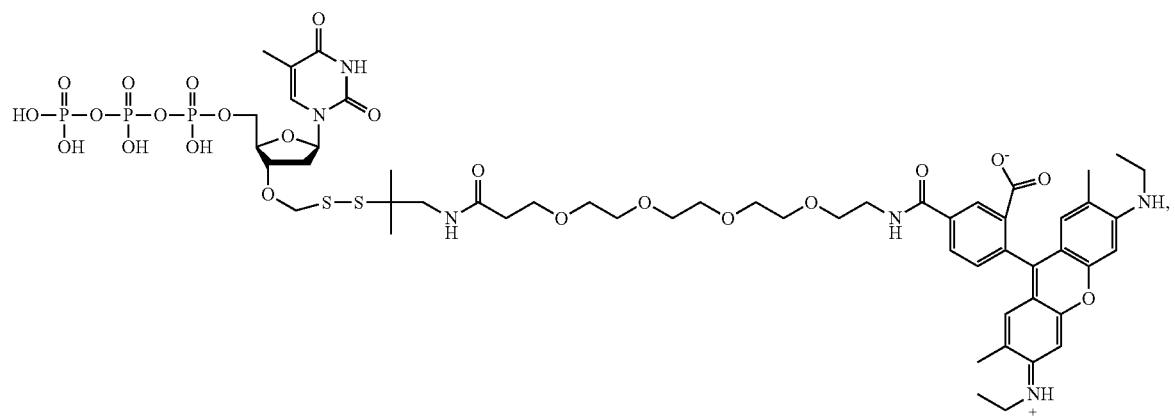

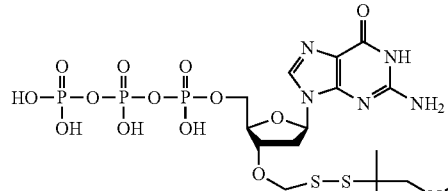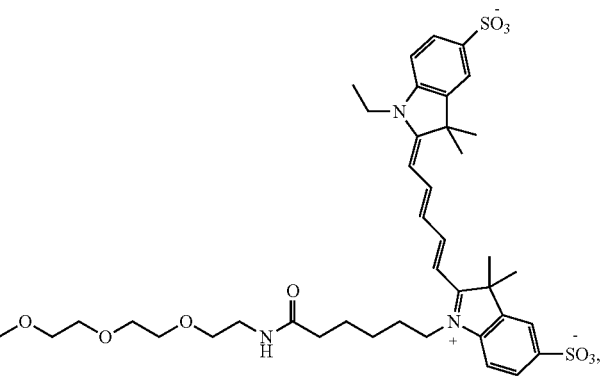

or

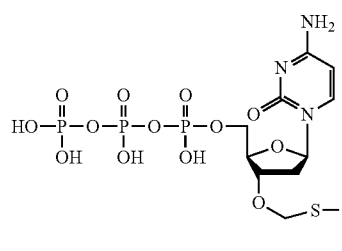

11. The complex of claim 1, wherein B is:

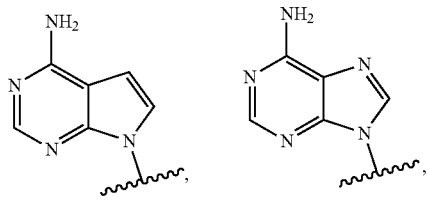

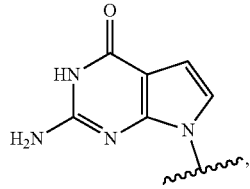

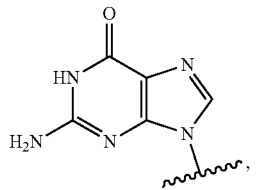

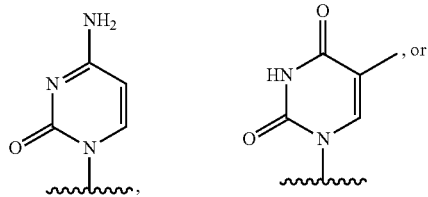, or

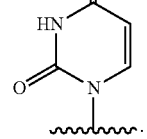

12. The complex of claim 1, wherein $L^1$ is a substituted or unsubstituted methylene, and wherein if $L^1$ is a substituted methylene, $L^1$ is substituted with a substituted or unsubstituted $C_1$-$C_6$ alkylene or substituted or unsubstituted 2 to 6 membered heteroalkylene; or wherein $L^2$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

13. The complex of claim 12, wherein $L^1$ is a substituted or unsubstituted methylene.

14. The complex of claim 13, wherein $L^1$ is substituted with a substituted or unsubstituted $C_1$-$C_6$ alkylene.

15. The complex of claim 1, wherein $R^{4A}$ is substituted or unsubstituted $C_1$-$C_6$ alkyl.

16. The complex of claim 1, wherein $R^6$ is substituted or unsubstituted $C_1$-$C_6$ alkyl, or substituted or unsubstituted 2 to 6 membered heteroalkyl; or wherein $R^{6A}$ is substituted or unsubstituted $C_1$-$C_6$ alkyl, or substituted or unsubstituted 2 to 6 membered heteroalkyl.

17. The complex of claim 16, wherein $R^6$ is substituted or unsubstituted $C_1$-$C_6$ alkyl; or wherein $R^{6A}$ is substituted or unsubstituted $C_1$-$C_6$ alkyl.

18. The complex of claim 1, wherein $R^{12}$-$L^4$-$R^{13}$ has the formula:

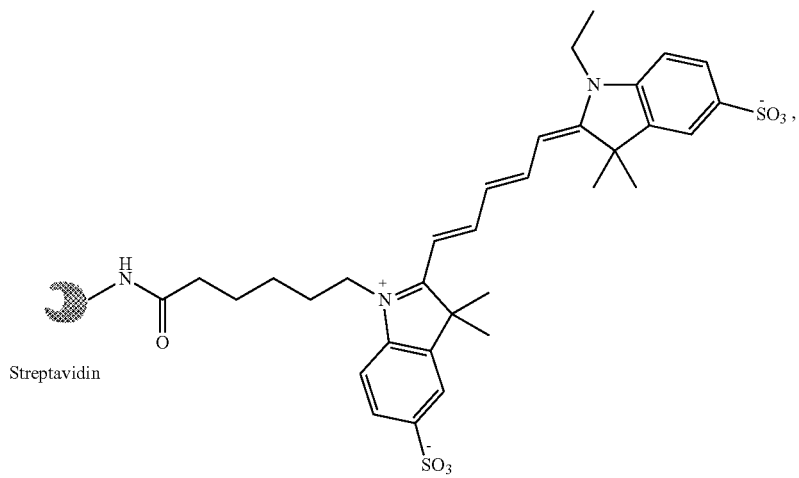

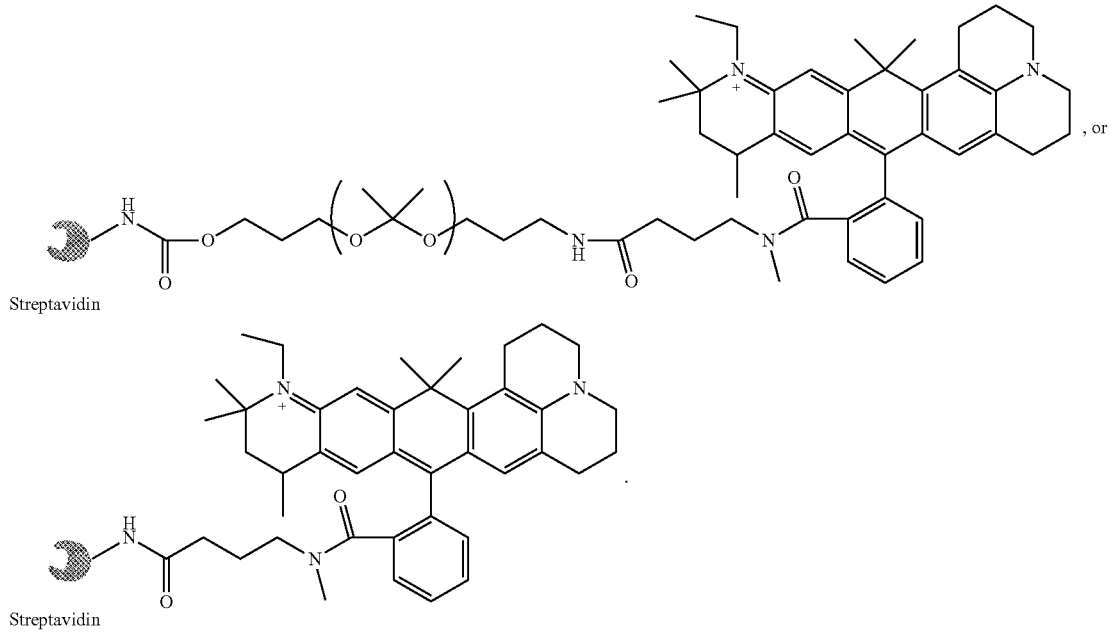

19. The thermophilic nucleic acid polymerase complex of claim 1, comprising a thermophilic nucleic acid polymerase bound to a nucleotide analogue having the formula:

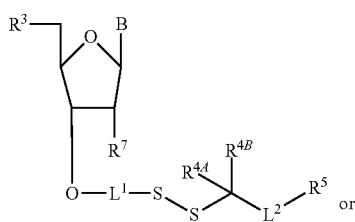

(III)

-continued

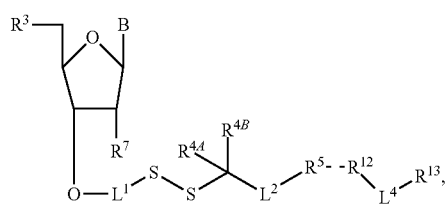

(IV)

wherein said polymerase is bound to the nucleotide analogue, wherein said nucleotide analogue is bound to a streptavidin; and wherein said streptavidin is bound to two or more fluorophores.

20. The polymerase complex of claim 19, wherein each of the two or more fluorophores comprises a cyanine moiety.

\* \* \* \* \*